(12) United States Patent
Bacon et al.

(10) Patent No.: US 9,815,818 B2
(45) Date of Patent: Nov. 14, 2017

(54) COT MODULATORS AND METHODS OF USE THEREOF

(71) Applicant: Gilead Sciences, Inc., Foster City, CA (US)

(72) Inventors: Elizabeth M. Bacon, Burlingame, CA (US); Gayatri Balan, Bellevue, WA (US); Chien-Hung Chou, Dublin, CA (US); Christopher T. Clark, Seattle, WA (US); Jeromy J. Cottell, Foster City, CA (US); Musong Kim, Bellevue, WA (US); Thorsten A. Kirschberg, Redwood City, CA (US); John O. Link, San Francisco, CA (US); Gary Phillips, Issaquah, WA (US); Scott D. Schroeder, Foster City, CA (US); Neil H. Squires, San Francisco, CA (US); Kirk L. Stevens, Bothell, WA (US); James G. Taylor, Burlingame, CA (US); William J. Watkins, Saratoga, CA (US); Nathan E. Wright, Foster City, CA (US); Sheila M. Zipfel, San Mateo, CA (US)

(73) Assignee: GILEAD SCIENCES, INC., Foster City, CA (US)

(*) Notice: Subject to any disclaimer, the term of this patent is extended or adjusted under 35 U.S.C. 154(b) by 0 days.

(21) Appl. No.: 15/199,779

(22) Filed: Jun. 30, 2016

(65) Prior Publication Data

US 2017/0008873 A1 Jan. 12, 2017

Related U.S. Application Data

(60) Provisional application No. 62/269,061, filed on Dec. 17, 2015, provisional application No. 62/189,155, filed on Jul. 6, 2015.

(51) Int. Cl.
| | | |
|---|---|---|
| C07D 401/12 | (2006.01) | |
| C07D 401/14 | (2006.01) | |
| C07D 405/14 | (2006.01) | |
| C07D 413/12 | (2006.01) | |
| C07D 453/02 | (2006.01) | |
| C07D 409/14 | (2006.01) | |
| C07D 413/14 | (2006.01) | |
| C07D 417/14 | (2006.01) | |
| C07F 7/08 | (2006.01) | |

(52) U.S. Cl.
CPC ......... *C07D 401/12* (2013.01); *C07D 401/14* (2013.01); *C07D 405/14* (2013.01); *C07D 409/14* (2013.01); *C07D 413/12* (2013.01); *C07D 413/14* (2013.01); *C07D 417/14* (2013.01); *C07D 453/02* (2013.01); *C07F 7/0814* (2013.01)

(58) Field of Classification Search
CPC .. C07D 401/12; C07D 401/14; C07D 405/14; C07D 409/14; C07D 413/12; C07D 413/14; C07D 417/14; C07D 453/02; C07F 7/0814

See application file for complete search history.

(56) References Cited

U.S. PATENT DOCUMENTS

| | | |
|---|---|---|
| 7,297,795 B2 | 11/2007 | Sutherland et al. |
| 2005/0043537 A1 | 2/2005 | Sutherland et al. |
| 2006/0264460 A1 | 11/2006 | Green et al. |

FOREIGN PATENT DOCUMENTS

| | | |
|---|---|---|
| WO | WO-2005/019201 A2 | 3/2005 |
| WO | WO-2006/124692 A2 | 11/2006 |

OTHER PUBLICATIONS

Cusack, K. et al. (2009) "Identification of a selective thieno[2,3-c]pyridine inhibitor of COT kinase and TNF-α production" Bioorganic & Medicinal Chemistry Letters 19:1722-1725.

Detz, R. et al. (2008) "Enantioselective Copper-Catalyzed Propargylic Amination" Angew. Chem. Int. Ed. 47:3777-3780.

Garofalo, A. et al.(2013) "Discovery of 4-alkylamino-7-aryl-3-cyanoquinoline LRRK2 kinase inhibitors" Bioorganic & Medicianl Chemistry Letters 23:1974-1977.

Gavrin et al. (2005) "Inhibition of Tpl2 kinase and TNF-oα production with 1,7-naphthyridine-3-carbonitriles: Synthesis and structure-activity relationships" Bioorganic & Medicinal Chemistry Letters 15:5288-5292.

George, D. et al. (2008) "Discovery of thieno[2,3-c]pyridines as potent COT inhibitors" Bioorganic & Medicinal Chemistry Letters 18:4952-4955.

George, D. et al. (2009) "Cot/Tpl-2 Protein Kinase as a Target for the Treatment of Inflammatory Disease" Current Topics in Medicinal Chemistry 9:611-622.

Gianatassio, R. et al. (2016) "Strain Release Amination" Science 351(6270):241-246.

Glatthar, R. et al. (2016) "Discovery of lmidazoquinolines as a Novel Class of Potent, Selective, and in Vivo Efficacious Cancer Osaka Thyroid (COT) Kinase Inhibitors" Journal of Medicinal Chemistry 59:7544-7560.

Green, N. et al. (2007) "Inhibitors of Tumor Progression Loci-2 (Tpl2) Kinase and Tumor Necrosis Factor α (TNF-α) Production: Selectivity and in Vivo Antiinflammatory Activity of Novel 8-Substituted-4-anilino-6-aminoquinoline-3-carbonitriles" J. Med. Chem. 50:4728-4745.

Hall, J. Perry et al. (2007) "Pharmacologic Inhibition of Tpl2 Blocks Inflammatory Responses in Primary Human Monocytes, Synoviocytes, and Blood" The Journal of Biological Chemistry 282:46:33295-33304.

(Continued)

*Primary Examiner* — Savitha Rao
(74) *Attorney, Agent, or Firm* — Kevin J. Capps

(57) ABSTRACT

The present disclosure relates generally to modulators of Cot (cancer Osaka thyroid) and methods of use and manufacture thereof.

32 Claims, No Drawings

(56) References Cited

OTHER PUBLICATIONS

Hu et al. (2006) "Inhibition of Tpl2 kinase and TNFa production with quinoline-3-carbonitriles for the treatment of rheumatoid arthritis" Bioorganic & Medicinal Chemistry Letters 16:6067-6072.

Hu, Y. et al. (2011) "Discovery of indazoles as inhibitors of Tpl2 kinase" Bioorganic & Medicinal Chemistry Letters 1-4 (article in press; doi: 10.1016).

Int'l Search Report—Written Opinion dated Aug. 16, 2016 for PCT Apppl. No. PCT/US2016/040520.

Int'l Search Report—Written Opinion dated Sep. 23, 2016 for PCT/US2016/040552.

Kaila, N. et al. (2007) "Identification of a novel class of selective Tpl2 kinase inhibitors: 4-Alkylamino-[1,7]naphthyridine-3-carbonitriles" Bioorganic & Medicinal Chemistry 15:6425-6442.

Kitamura, M. et al. (2014) "A reagent for safe and efficient diazo-transfer to primary amines: 2-azido-1,3-dimethylimidazolinium hexafluorophosphate" Org. Biomol. Chem. 12:4397-4406.

Restriction Requirement dated Feb. 16, 2017 for U.S. Appl. No. 15/199,534.

Teli. M. et al. (2011) "Pharmacophore generation and atom-based 3D-QSAR of novel quinoline-3-carbonitrile derivatives as Tpl2 kinase inhibitors" Journal of Enzyme Inhibition and Medicinal Chemistry, 1-13.

Wu, J. et al. (2009) "Selective inhibitors of tumor progression loci-2 (Tpl2) kinase with potent inhibition of TNF-$\alpha$ production in human whole blood" Bioorganic & Medicinal Chemistry Letters 19:3485-3488.

COT MODULATORS AND METHODS OF USE THEREOF

CROSS REFERENCE TO RELATED APPLICATIONS

This application claims the benefit under 35 U.S.C. 119(e) to U.S. Provisional Application No. 62/189,155, filed Jul. 6, 2015, and U.S. Provisional Application No. 62/269,061, filed Dec. 17, 2015, where the contents of each is incorporated herein by reference in its entirety.

FIELD

The present disclosure relates generally to modulators of Cot (cancer Osaka thyroid) and methods of use and manufacture thereof.

BACKGROUND

Cot (cancer Osaka thyroid) protein is a serine/threonine kinase that is a member of the MAP kinase kinase kinase (MAP3K) family. It is also known as "Tpl2" (tumor progression locus), "MAP3K8" (mitogen-activated protein kinase kinase kinase 8) or "EST" (Ewing sarcoma transformant). Cot was identified by its oncogenic transforming activity in cells and has been shown to regulate oncogenic and inflammatory pathways.

Cot is known to be upstream in the MEK-ERK pathway and is essential for LPS induced tumor necrosis factor-α (TNF-α) production. Cot has been shown to be involved in both production and signaling of TNFα. TNFα is a pro-inflammatory cytokine and plays an important role in inflammatory diseases, such as rheumatoid arthritis (RA), multiple sclerosis (MS), inflammatory bowel disease (IBD), diabetes, sepsis, psoriasis, misregulated TNFα expression and graft rejection.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g. renal cell carcinoma carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic mueloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lymphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections {e.g. influenza) and wound healing.

Agents and methods that modulate the expression or activity of Cot, therefore, may be useful for preventing or treating such diseases.

SUMMARY

The present disclosure provides compounds that modulate the expression or activity of Cot. The disclosure also provides compositions, including pharmaceutical compositions, kits that include the compounds, and methods of using (or administering) and making the compounds. The compounds provided herein are useful in treating diseases, disorders, or conditions that are mediated by Cot. The disclosure also provides compounds for use in therapy. The disclosure further provides compounds for use in a method of treating a disease, disorder, or condition that is mediated by Cot. Moreover, the disclosure provides uses of the compounds in the manufacture of a medicament for the treatment of a disease, disorder or condition that is mediated by (or mediated, at least in part, by) Cot.

In one aspect, provided is a compound having the structure of Formula I:

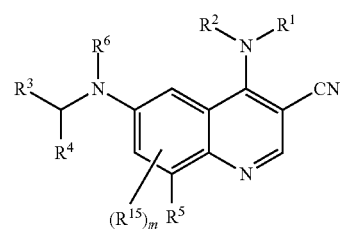

wherein
$R^1$ is hydrogen, —O—$R^7$, —N($R^8$)($R^9$), —C(O)—$R^7$, —S(O)$_2$—$R^7$, —$C_{1-9}$ alkyl, $C_{2-6}$ alkenyl, $C_{2-6}$ alkynyl, $C_{3-15}$ cycloalkyl, heterocyclyl, aryl, or heteroaryl;
  wherein each $C_{1-9}$ alkyl, $C_{2-6}$ alkenyl, $C_{2-6}$ alkynyl, $C_{3-15}$ cycloalkyl, heterocyclyl, aryl, and heteroaryl may be optionally substituted with one to four $Z^1$;
$R^2$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^2$;
or $R^1$ and $R^2$ together with the nitrogen to which they are attached to form a heterocyclyl or heteroaryl, wherein each heterocyclyl or heteroaryl is optionally substituted with one to four $Z^2$;
$R^3$ is heterocyclyl or heteroaryl, wherein each heterocyclyl or heteroaryl is optionally substituted with one to four $Z^3$;

R⁴ is aryl, wherein said aryl is optionally substituted with one to four $Z^4$;

R⁵ is hydrogen, halo, —CN, —NO₂, —O—R⁷, —N(R⁸)(R⁹), —S(O)—R⁷, —S(O)₂R⁷, —S(O)₂N(R⁷)₂, —C(O)R⁷, —OC(O)—R⁷, —C(O)O—R⁷, —OC(O)O—R⁷, —OC(O)N(R¹⁰)(R¹¹), —C(O)N(R⁷)₂, —N(R⁷)C(O)(R⁷), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;

R⁶ is hydrogen, —C(O)—R⁷, —C(O)O—R⁷, —C(O)N(R⁷)₂, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;

each R⁷ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

R⁸ and R⁹ at each occurrence are independently hydrogen, —S(O)₂R¹⁰, —C(O)—R¹⁰, —C(O)O—R¹⁰, —C(O)N(R¹⁰)(R¹¹), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;

R¹⁰ and R¹¹ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl,
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^2$, $Z^3$, $Z^4$, $Z^5$, $Z^6$, $Z^7$ and $Z^8$ is independently hydrogen, oxo, halo, —NO₂, —N₃, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R¹², —C(O)—R¹², —C(O)O—R¹², —C(O)—N(R¹³)(R¹⁴), —N(R¹³)(R¹⁴), —N(R¹³)₂(R¹⁴)⁺, —N(R¹²)C(O)—R¹², —N(R¹²)C(O)O—R¹², —N(R¹²)C(O)N(R¹³)(R¹⁴), —N(R¹²)S(O)₂(R¹²), —NR¹²S(O)₂N(R¹³)(R¹⁴), —NR¹²S(O)₂O(R¹²), —OC(O)R¹², —OC(O)—N(R¹³)(R¹⁴), —P(O)(OR¹²)₂, —OP(O(OR¹²)₂, —CH₂P(O)(OR¹²)₂, —OCH₂P(O)(OR¹²)₂, —C(O)OCH₂P(O)(OR¹²)₂, —P(O)(R¹²)(OR¹²), —OP(O)(R¹²)(OR¹²), —CH₂P(O)(R¹²)(OR¹²), OCH₂P(O)(R¹²)(OR¹²), —C(O)OCH₂P(O)(R¹²)(OR¹²), —P(O)(N(R¹²)₂)₂, —OP(O)(N(R¹²)₂)₂, —CH₂P(O)(N(R¹²)₂)₂, —OCH₂P(O)(N(R¹²)₂)₂, —C(O)OCH₂P(O)(N(R¹²)₂)₂, —P(O)(N(R¹²)₂)(OR¹²), —OP(O)(N(R¹²)₂)(OR¹²), —CH₂P(O)(N(R¹²)₂)(OR¹²), —OCH₂P(O)(N(R¹²)₂)(OR¹²), —C(O)OCH₂P(O)(N(R¹²)₂)(OR¹²), —P(O)(R¹²)(N(R¹²)₂), —OP(O)(R¹²)(N(R¹²)₂), —CH₂P(O)(R¹²)(N(R¹²)₂), —OCH₂P(O)(R¹²)(N(R¹²)₂) C(O)OCH₂P(O)(R¹²)(N(R¹²)₂), —Si(R¹²)₃, —S—R¹², —S(O)R¹², —S(O)(NH)R¹², —S(O)₂R¹² or —S(O)₂N(R¹³)(R¹⁴);
  wherein any alkyl, alkenyl, alkynyl, cycloalkyl, haloalkyl aryl, heteroaryl or heterocyclyl is optionally substituted with one to four $Z^{1a}$ groups;

each $Z^{1a}$ is independently oxo, halo, thioxo, —NO₂, —CN, —N₃, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R¹², —C(O)R¹², —C(O)O—R¹², —C(O)N(R¹³)(R¹⁴), —N(R¹³)(R¹⁴), —N(R¹³)₂(R¹⁴)⁺, —N(R¹²)—C(O)R¹², —N(R¹²)C(O)O(R¹²), —N(R¹²)C(O)N(R¹³)(R¹⁴), —N(R¹²)S(O)₂(R¹²), —N(R¹²)S(O)₂—N(R¹³)(R¹⁴), —N(R¹²)S(O)₂O(R¹²), —OC(O)R¹², —OC(O)OR¹², —OC(O)—N(R¹³)(R¹⁴), —Si(R¹²)₃, —S—R¹², —S(O)R¹², —S(O)(NH)R¹², —S(O)₂R¹² or —S(O)₂N(R¹³)(R¹⁴);
  wherein any alkenyl, alkynyl, cycloalkyl, aryl, heteroaryl or heterocyclyl is optionally substituted with one to four $Z^{1b}$ groups;

each R¹² is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl,
  wherein any alkyl, alkenyl, alkynyl, cycloalkyl, aryl, heteroaryl or heterocyclyl is optionally substituted with one to four $Z^{1b}$ groups;

R¹³ and R¹⁴ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four $Z^{1b}$ groups, or R¹³ and R¹⁴ together with the nitrogen to which they are attached form a heterocyclyl, wherein said heterocyclyl is optionally substituted with one to four $Z^{1b}$ groups;

each R¹⁵ is independently halo, —CN, —NO₂, —O—R⁷, —N(R⁸)(R⁹), —S(O)—R⁷, —S(O)₂R⁷, —S(O)₂N(R)₂, —C(O)R⁷, —OC(O)—R⁷, —C(O)O—R⁷, —OC(O)O—R⁷, —OC(O)N(R¹)(R¹¹), —C(O)N(R⁷)₂, —N(R)C(O)(R⁷), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl; and each $Z^{1b}$ is independently oxo, thioxo, hydroxy, halo, —NO₂, —N₃, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH₂, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)₂, —N($C_{3-15}$ cycloalkyl)₂, —N($C_{2-6}$ alkenyl)₂, —N($C_{2-6}$ alkynyl)₂, —N($C_{3-15}$ cycloalkyl)₂, —N($C_{1-8}$ haloalkyl)₂, —N(aryl)₂, —N(heteroaryl)₂, —N(heterocyclyl)₂, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH₂, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)₂, —C(O)N($C_{3-15}$ cycloalkyl)₂, —C(O)N($C_{2-6}$ alkenyl)₂, —C(O)N($C_{2-6}$ alkynyl)₂, —C(O)N($C_{3-15}$ cycloalkyl)₂, —C(O)N($C_{1-8}$ haloalkyl)₂, —C(O)N(aryl)₂, —C(O)N(heteroaryl)₂, —C(O)N(heterocyclyl)₂, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

m is 0, 1, or 2;

or a pharmaceutically acceptable salt, tautomer, stereoisomer, mixture of stereoisomers, prodrug, or deuterated analog thereof.

Some embodiments provide a method of using (or administering) the compounds of Formula I, or additional Formula(s) described throughout, in the treatment of a disease or condition in a mammal, particularly a human, that is amenable to treatment by an Cot modulator.

In certain embodiments, the disclosure provides pharmaceutical compositions comprising a therapeutically effective amount of a compound of the disclosure (e.g. a compound of Formula I or additional Formulas described throughout), and at least one pharmaceutically acceptable excipient.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH(CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an alkyl group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., C$_{2-20}$ alkynyl), 2 to 8 carbon atoms (i.e., C$_{2-6}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Amidino" refers to —C(NH)(NH$_2$).

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl the resulting ring system is heterocyclyl.

"Azido" refers to —N$_3$.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Guanidino" refers to —NHC(NH)(NH$_2$).

"Hydrazino" refers to —NHNH$_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or L ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro [3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system, "Hydroxy" or "hydroxyl" refers to the group —OH.

"Oxo" refers to the group (=O) or (O).

"Nitro" refers to the group —$NO_2$.

"Sulfonyl" refers to the group —$S(O)_2R$, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl. "Alkylsulfonyl" refers to the group —$S(O)_2R$, where R is alkyl.

"Alkylsulfinyl" refers to the group —S(O)R, where R is alkyl.

"Thiocyanate"-SCN.

"Thiol" refers to the group —SR, where R is alkyl, haloalkyl, heterocyclyl, cycloalkyl, heteroaryl, or aryl.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^8F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2(alkyl)$), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

LIST OF ABBREVIATIONS AND ACRONYMS

| Abbreviation | Meaning |
| --- | --- |
| ° C. | Degree Celsius |
| Ac | Acetyl |
| aq. | Aqueous |
| ATP | Adenosine triphosphate |
| BOC | tert-Butoxycarbonyl |
| br | Broad |
| BSA | Bovine serum albumin |
| Cbz | Carboxybenzyl |
| COD | Cyclooctadiene |
| COPD | Chronic obstructive pulmonary disease |
| Cot | Cancer Osaka Thyroid |
| Cp | Cyclopentadienyl |
| d | Doublet |
| DABCO | 1,4-Diazabicyclo[2.2.2]octane |
| DBU | 1,8-Diazabicyclo[5.4.0]undec-7-ene |
| DCE | Dichloroethene |
| DCM | Dichloromethane |
| dd | Doublet of doublets |

-continued

| Abbreviation | Meaning |
|---|---|
| DEF | N, N-Diethylformamide |
| DMF | Dimethylformamide |
| DMSO | Dimethylsulfoxide |
| dppf | 1,1'-Bis(diphenylphosphino)ferrocene |
| dt | Doublet-triplet |
| DTT | Dithiothreitol |
| $EC_{50}$ | The half maximal effective concentration |
| EGFR | Epidermal growth factor receptor |
| eq | Equivalents |
| ES/MS | Electrospray mass spectrometry |
| Et | Ethyl |
| FBS | Fetal bovine serum |
| g | Grams |
| HEPES | 2-[4-(2-hydroxyethyl)piperazin-1-yl]ethanesulfonic acid |
| HPLC | High pressure liquid chromatography |
| hrs | Hours |
| Hz | Hertz |
| IBD | Inflammatory bowel disease |
| i-pr | Isopropyl |
| J | Coupling constant (MHz) |
| Kg/kg | Kilogram |
| LCMS | Liquid chromatography-mass spectrometry |
| LPS | Lipopolysaccharide |
| M | Molar |
| m | multiplet |
| M+ | Mass peak |
| M + H+ | Mass peak plus hydrogen |
| Me | Methyl |
| mg | Milligram |
| MHz | Megahertz |
| min | Minute |
| ml/mL | Milliliter |
| mM | Millimolar |
| mmol | Millimole |
| MOPS | 3-Morpholinopropane-1-sulfonic acid |
| MS | Mass spectroscopy |
| Ms | Mesyl |
| nBu/Bu | Butyl |
| nL | Nanoliter |
| nm | Nanometer |
| NMR | Nuclear magnetic resonance |
| NP-40 | Nonyl phenoxypolyethoxylethanol |
| Ns | Nosyl |
| Pd—C/Pd/C | Palladium on Carbon |
| pg | Pictogram |
| Ph | Phenyl |
| PPTS | Pyridinium p-toluenesulfonate |
| PS | Polystyrene |
| p-TSOH/pTSA | p-Toluenesulfonic acid |
| q | Quartet |
| q.s. | Quantity sufficient to achieve a stated function |
| RBF | Round bottom flask |
| RP | Reverse phase |
| RPMI | Roswell Park Memorial Institute medium |
| rt | Room temperature |
| s | Singlet |
| sat. | Saturated |
| t | Triplet |
| TBAF | Tetra-n-butylammonium fluoride |
| TBS | tert-Butyldimethylsilyl |
| t-Bu | tert-Butyl |
| TC | Thiophene-2-carboxylate |
| TEA | Triethanolamine |
| Tf | Trifluoromethanesulfonyl |
| TFA | Trifluoroacetic acid |
| THF | Tetrahydrofuran |
| Tpl2 | Tumor Progression Locus 2 |
| TR-FRET | Time-resolved fluorescence energy transfer |
| Ts | Tosyl |
| δ | Chemical shift (ppm) |
| μL/μl | Microliter |
| μM | Micromolar |

Compounds

Provided herein are compounds that function as modulators of Cot. In one aspect, provided is a compound having structure of Formula I:

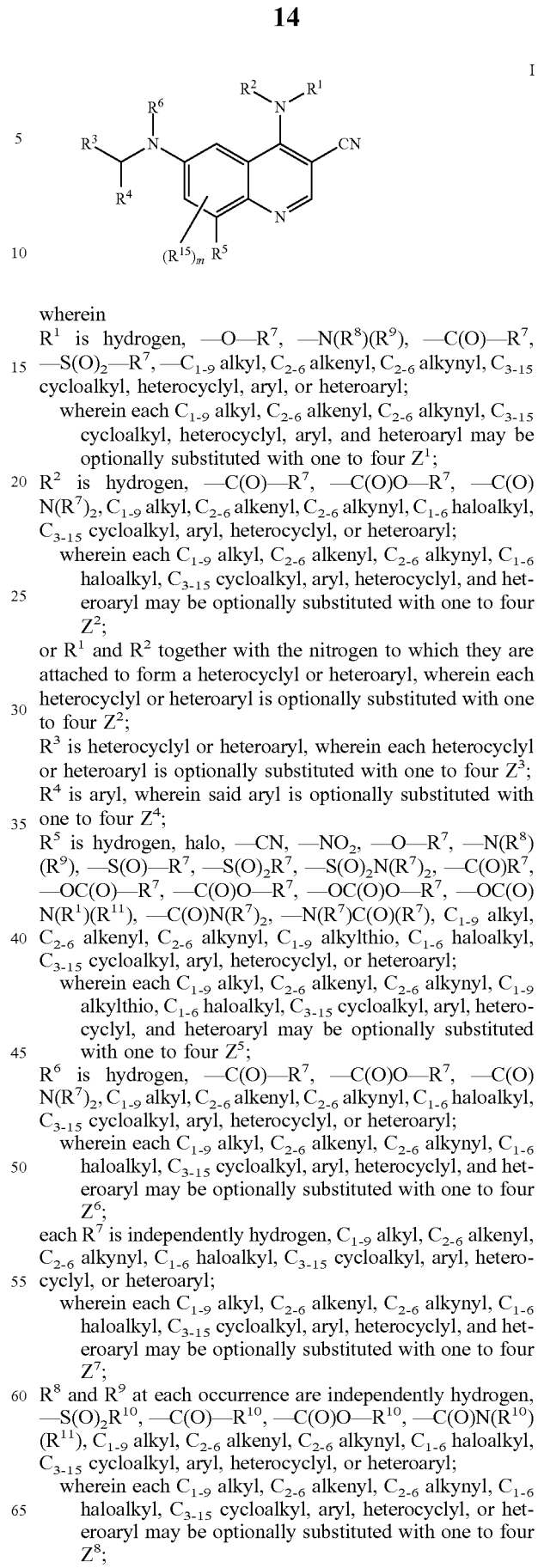

wherein $R^1$ is hydrogen, —O—$R^7$, —N($R^8$)($R^9$), —C(O)—$R^7$, —S(O)$_2$—$R^7$, $C_{1-9}$ alkyl, $C_{2-6}$ alkenyl, $C_{2-6}$ alkynyl, $C_{3-15}$ cycloalkyl, heterocyclyl, aryl, or heteroaryl;
  wherein each $C_{1-9}$ alkyl, $C_{2-6}$ alkenyl, $C_{2-6}$ alkynyl, $C_{3-15}$ cycloalkyl, heterocyclyl, aryl, and heteroaryl may be optionally substituted with one to four $Z^1$;

$R^2$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^2$;

or $R^1$ and $R^2$ together with the nitrogen to which they are attached to form a heterocyclyl or heteroaryl, wherein each heterocyclyl or heteroaryl is optionally substituted with one to four $Z^2$;

$R^3$ is heterocyclyl or heteroaryl, wherein each heterocyclyl or heteroaryl is optionally substituted with one to four $Z^3$;

$R^4$ is aryl, wherein said aryl is optionally substituted with one to four $Z^4$;

$R^5$ is hydrogen, halo, —CN, —NO$_2$, —O—$R^7$, —N($R^8$)($R^9$), —S(O)—$R^7$, —S(O)$_2$$R^7$, —S(O)$_2$N($R^7$)$_2$, —C(O)$R^7$, —OC(O)—$R^7$, —C(O)O—$R^7$, —OC(O)O—$R^7$, —OC(O)N($R^1$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;

$R^6$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;

each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

$R^8$ and $R^9$ at each occurrence are independently hydrogen, —S(O)$_2$$R^{10}$, —C(O)—$R^{10}$, —C(O)O—$R^{10}$, —C(O)N($R^{10}$)($R^{11}$), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;

$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl, wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^2$, $Z^3$, $Z^4$, $Z^5$, $Z^6$, $Z^7$ and $Z^8$ is independently hydrogen, oxo, halo, —$NO_2$, —$N_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$—N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^{12}$)$_2$, —$CH_2$P(O)(O$R^{12}$)$_2$, —$OCH_2$P(O)(O$R^{12}$)$_2$, —C(O)O$CH_2$P(O)(O$R^{12}$)$_2$, —P(O)($R^{12}$)(O$R^{12}$), —OP(O)($R^{12}$)(O$R^{12}$), —$CH_2$P(O)($R^{12}$)(O$R^{12}$), —$OCH_2$P(O)($R^{12}$)(O$R^{12}$), —C(O)O$CH_2$P(O)($R^{12}$)(O$R^{12}$), —P(O)(N($R^{12}$)$_2$)$_2$, —OP(O)(N($R^{12}$)$_2$)$_2$, —$CH_2$P(O)(N($R^{12}$)$_2$)$_2$, —$OCH_2$P(O)(N($R^{12}$)$_2$)$_2$, —C(O)O$CH_2$P(O)(N($R^{12}$)$_2$)$_2$, —P(O)(N($R^{12}$)$_2$)(O$R^{12}$), —OP(O)(N($R^{12}$)$_2$)(O$R^{12}$), —$CH_2$P(O)(N($R^{12}$)$_2$)(O$R^{12}$), —$OCH_2$P(O)(N($R^{12}$)$_2$)(O$R^{12}$), —C(O)O$CH_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —$CH_2$P(O)($R^{12}$)(N($R^{12}$)$_2$), —$OCH_2$P(O)($R^{12}$)(N($R^{12}$)$_2$), —C(O)O$CH_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkyl, alkenyl, alkynyl, cycloalkyl, haloalkyl aryl, heteroaryl or heterocyclyl is optionally substituted with one to four $Z^{1a}$ groups;

each $Z^{1a}$ is independently oxo, halo, thioxo, —$NO_2$, —CN, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

each $R^{15}$ is independently halo, —CN, —$NO_2$, —O—$R^7$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl; and each $Z^{1b}$ is independently oxo, thioxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)₂(C₃₋₁₅ cycloalkyl), —S(O)₂(C₁₋₈ haloalkyl), —S(O)₂(aryl), —S(O)₂(heteroaryl), —S(O)₂(heterocyclyl), —S(O)₂NH(C₁₋₉ alkyl), —S(O)₂N(C₁₋₉ alkyl)₂, —O(C₃₋₁₅ cycloalkyl), —O(C₁₋₈ haloalkyl), —O(aryl), —O(heteroaryl), —O(heterocyclyl), or —O(C₁₋₉ alkyl);

m is 0, 1, or 2;

or a pharmaceutically acceptable salt, tautomer, stereoisomer, mixture of stereoisomers, prodrug, or deuterated analog thereof.

In certain embodiments, the compound of Formula I is represented by Formula IA:

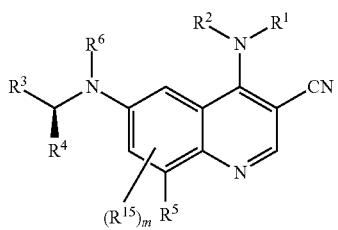

IA wherein R¹-R⁶, R¹⁵ and m are as described herein.

In certain embodiments, the compound of Formula I is represented by Formula IB:

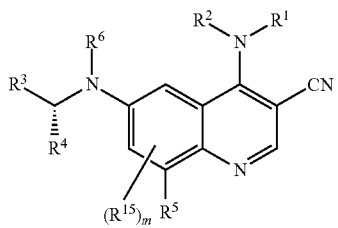

IB wherein R¹-R⁶, R¹⁵ and in are as described herein.

In certain embodiments, m is 0. In certain embodiments, R² is hydrogen.

In certain embodiments, provided is a compound of Formula II:

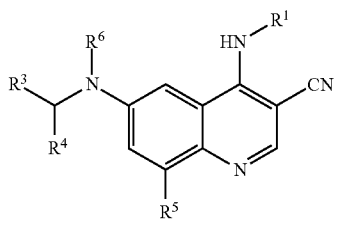

II wherein R¹, R³, R⁴, R⁵ and R⁶ are as defined herein.

In certain embodiments, provided is a compound of Formula IIA:

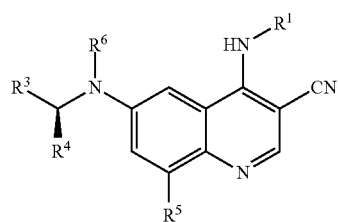

IIA wherein R¹, R³, R⁴, R⁵ and R⁶ are as defined herein.

In certain embodiments, the compound of Formula I is represented by Formula III:

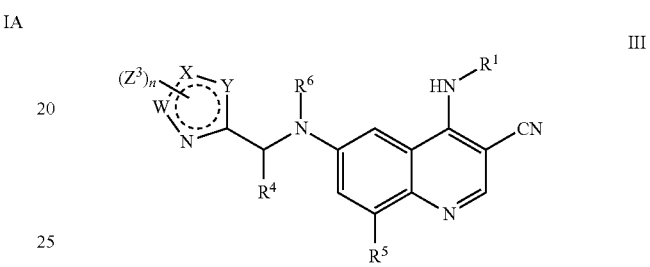

III wherein R¹, R⁴, R⁵ and R⁶ are as defined herein,
W, X and Y are each independently N or C;
n is 1, 2, or 3;
each Z³ is independently hydrogen, oxo, halo, —NO₂, —N₃, —CN, thioxo, C₁₋₉ alkyl, C₂₋₆ alkenyl, C₂₋₆ alkynyl, C₃₋₁₅ cycloalkyl, C₁₋₈ haloalkyl, aryl, heteroaryl, heterocyclyl, —O—R¹², —C(O)—R¹², —C(O)O—R¹², —C(O)—N(R¹³)(R¹⁴), —N(R¹³)(R¹⁴), —N(R¹³)₂(R¹⁴)⁺, —N(R¹²)C(O)—R¹², —N(R¹²)C(O)O—R², —N(R¹²)C(O)N(R¹³)(R¹⁴), —N(R¹²)S(O)₂(R¹²), —NR¹²S(O)₂N(R¹³)(R¹⁴), —NR¹²S(O)₂O(R¹²), —OC(O)R¹², —OC(O)—N(R¹³)(R¹⁴), —P(O)(OR¹²)₂, —OP(O)(OR¹²)₂, —CH₂P(O)(OR²)₂, —OCH₂P(O)(OR¹²)₂, —C(O)OCH₂P(O)(OR¹²)₂, —P(O)(R¹²)(OR¹²), —OP(O)(R¹²)(OR¹²), —CH₂P(O)(R¹²)(OR¹²), —OCH₂P(O)(R¹²)(OR¹²), —C(O)OCH₂P(O)(R¹²)(OR¹²), —P(O)(N(R¹²)₂)₂, —OP(O)(N(R¹²)₂)₂, —CH₂P(O)(N(R¹²)₂)₂, —OCH₂P(O)(N(R¹²)₂)₂, —C(O)OCH₂P(O)(N(R¹²)₂)₂, —P(O)(N(R¹²)₂)(OR¹²), —OP(O)(N(R¹²)₂)(OR¹²), —CH₂P(O)(N(R¹²)₂)(OR¹²), —OCH₂P(O)(N(R¹²)₂)(OR¹²), —C(O)OCH₂P(O)(N(R¹²)₂)(OR¹²), —P(O)(R¹²)(N(R¹²)₂), —OP(O)(R¹²)(N(R¹²)₂), —CH₂P(O)(R¹²)(N(R¹)₂), —OCH₂P(O)(R¹²)(N(R¹²)₂), —C(O)OCH₂P(O)(R¹²)(N(R¹²)₂), —Si(R¹²)₃, —S—R¹², —S(O)R¹², —S(O)(NH)R¹², —S(O)₂R¹² or —S(O)₂N(R¹³)(R¹⁴);
wherein any alkyl, alkenyl, alkynyl, cycloalkyl, haloalkyl aryl, heteroaryl or heterocyclyl is optionally substituted with one to four Z¹ᵃ groups;
each Z¹ᵃ is independently oxo, halo, thioxo, —NO₂, —CN, —N₃, C₁₋₉ alkyl, C₂₋₆ alkenyl, C₂₋₆ alkynyl, C₃₋₁₅ cycloalkyl, C₁₋₈ haloalkyl, aryl, heteroaryl, heterocyclyl, —O—R¹², —C(O)R¹², —C(O)O—R¹², —C(O)N(R¹³)(R¹⁴), —N(R¹³)(R¹⁴), —N(R¹³)₂(R¹⁴)⁺, —N(R¹²)—C(O)R¹², —N(R¹²)C(O)O(R¹²), —N(R¹²)C(O)N(R¹³)(R¹⁴), —N(R¹²)S(O)₂(R¹²), —N(R¹²)S(O)₂—N(R¹³)(R¹⁴), —N(R¹²)S(O)₂O(R¹²), —OC(O)R¹², —OC(O)OR¹², —OC(O)—N(R¹³)(R¹⁴), —Si(R¹²)₃, —S—R¹², —S(O)R¹², —S(O)(NH)R¹², —S(O)₂R¹² or —S(O)₂N(R¹³)(R¹⁴);
wherein any alkenyl, alkynyl, cycloalkyl, aryl, heteroaryl or heterocyclyl is optionally substituted with one to four Z¹ᵇ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four $Z^{1b}$ groups;
$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups; and
each $Z^{1b}$ is independently oxo, thioxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;
  wherein any alkyl, cycloalkyl, aryl, heteroaryl, or heterocyclyl is optionally substituted with one to four halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

or a pharmaceutically acceptable salt, tautomer, stereoisomer, mixture of stereoisomers, prodrug, or deuterated analog thereof.

In certain embodiments, the compound of Formula I is represented by Formula IIIA:

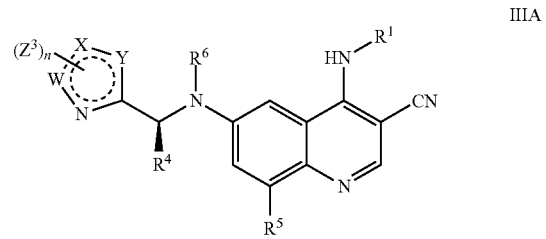

IIIA wherein $R^1$, $R^4$, $R^5$ and $R^6$ are as defined herein,
W, X and Y are each independently N or C;
n is 1, 2, or 3;
each $Z^3$ is independently hydrogen, oxo, halo, —$NO_2$, —$N_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^1$)$_2$, —$CH_2$P(O)(O$R^{12}$)$_2$, —O$CH_2$P(O)(O$R^{12}$)$_2$, —C(O)O$CH_2$P(O)(O$R^{12}$)$_2$, —P(O)($R^{12}$)(O$R^{12}$), —OP(O)($R^{12}$)(O$R^{12}$), —$CH_2$P(O)($R^{12}$)(O$R^{12}$), —O$CH_2$P(O)($R^{12}$)(O$R^{12}$), —C(O)O$CH_2$P(O)($R^{12}$)(O$R^{12}$), —P(O)(N($R^{12}$)$_2$)$_2$, —OP(O)(N($R^{12}$)$_2$)$_2$, —$CH_2$P(O)(N($R^{12}$)$_2$)$_2$, —O$CH_2$P(O)(N($R^{12}$)$_2$)$_2$, —C(O)O$CH_2$P(O)(N($R^{12}$)$_2$)$_2$, —P(O)(N($R^{12}$)$_2$)(O$R^{12}$), —OP(O)(N($R^{12}$)$_2$)(O$R^{12}$), —$CH_2$P(O)(N($R^{12}$)$_2$)(O$R^{12}$), —O$CH_2$P(O)(N($R^{12}$)$_2$)(O$R^{12}$), —C(O)O$CH_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —$CH_2$P(O)($R^{12}$)(N($R^{12}$)$_2$), —O$CH_2$P(O)($R^{12}$)(N($R^{12}$)$_2$), —C(O)O$CH_2$P(O)($R^1$)(N($R^{12}$)$_2$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);
wherein any alkyl, alkenyl, alkynyl, cycloalkyl, haloalkyl aryl, heteroaryl or heterocyclyl is optionally substituted with one to four $Z^{1a}$ groups;

each $Z^{1a}$ is independently oxo, halo, thioxo, —$NO_2$, —CN, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);

wherein any alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups; and each $Z^{1b}$ is independently oxo, thioxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

or a pharmaceutically acceptable salt, tautomer, stereoisomer, mixture of stereoisomers, prodrug, or deuterated analog thereof.

In certain embodiments, W is N, X is N—$Z^3$, and Y is C—$Z^3$. In certain embodiments, W is C—$Z^3$, X is N—$Z^3$, and Y is C—$Z^3$.

In certain embodiments, the compound of Formula I is represented by Formula IV or V:

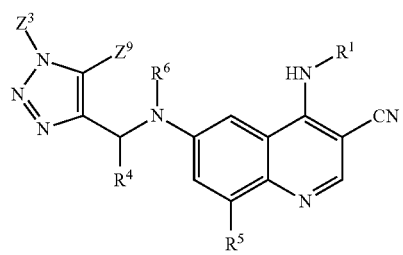

IV

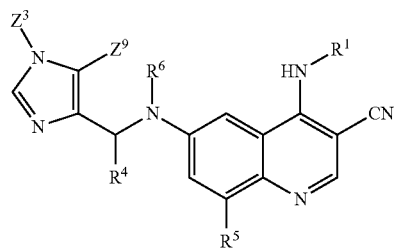

V wherein $Z^3$, $R^1$, $R^4$, $R^5$ and $R^6$ are as defined herein and $Z^9$ is hydrogen, halo, —CN, or —O—$R^{12}$.

In certain embodiments, the compound of Formula I is represented by Formula IVA or VA:

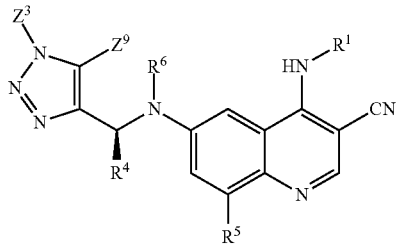

IVA

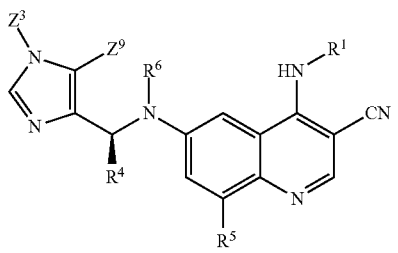

VA wherein $Z^3$, $R^1$, $R^4$, $R^5$ and $R^6$ are as defined herein and $Z^9$ is hydrogen, halo, —CN, or —O—$R^{12}$.

In certain embodiments, the compound of Formula I is represented by Formula VI or VII:

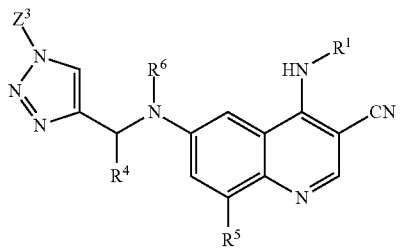

VI

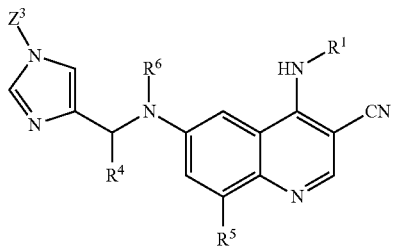

VII wherein $Z^3$, $R^1$, $R^4$, $R^5$ and $R^6$ are as defined herein.

In certain embodiments, the compound of Formula I is represented by Formula VIA or VIIA:

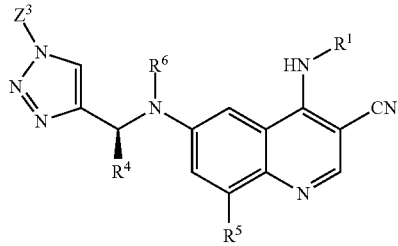

VIA

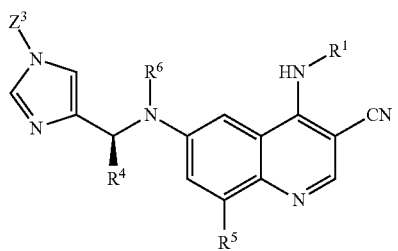

VIIA wherein $Z^3$, $R^1$, $R^4$, $R^5$ and $R^6$ are as defined herein.

In certain embodiments, $R^6$ is hydrogen.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, heterocyclyl, aryl, or heteroaryl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si(R)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, heterocyclyl, aryl, or heteroaryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, heterocyclyl, aryl, or heteroaryl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
  wherein said $C_{1-9}$ alkyl, $C_{3-15}$ cycloalkyl, heterocyclyl, aryl, or heteroaryl may be optionally substituted with one to three substituents independently selected from the group consisting of halo, hydroxyl, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, aryl, or heterocyclyl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen, $C_{1-9}$ alkyl, $C_{3-15}$ cycloalkyl, heterocyclyl, aryl, or heteroaryl;
wherein said $C_{1-9}$ alkyl, $C_{3-15}$ cycloalkyl, aryl, or heterocyclyl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, heterocyclyl, or aryl may be optionally substituted with one to three substituents independently selected from the group consisting of halo, hydroxyl, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl;
wherein said $C_{1-9}$ alkyl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl.

In certain embodiments, $Z^3$ is $C_{3-15}$ cycloalkyl, heterocyclyl, aryl, or heteroaryl;
wherein said $C_{3-15}$ cycloalkyl, heterocyclyl, aryl, or heteroaryl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, aryl, heterocyclyl, or heteroaryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is $C_{3-15}$ cycloalkyl, heterocyclyl, aryl, or heteroaryl;
wherein said $C_{3-15}$ cycloalkyl, heterocyclyl, or aryl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, heterocyclyl, or aryl may be optionally substituted with one to three substituents independently selected from the group consisting of halo, hydroxy, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl.

In certain embodiments, $Z^3$ is $C_{3-15}$ cycloalkyl, heterocyclyl, aryl, or heteroaryl; and said $C_{3-15}$ cycloalkyl, heterocyclyl, aryl, or heteroaryl may be optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl.

In certain embodiments, $Z^3$ is hydrogen, $C_{1-9}$ alkyl, $C_{3-15}$ cycloalkyl, heterocyclyl, aryl, or heteroaryl;
wherein said $C_{1-9}$ alkyl, $C_{3-15}$ cycloalkyl, aryl, or heterocyclyl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl;
wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl;

$R^1$ is hydrogen, —O—$R^7$, —N($R^8$)($R^9$), —C(O)—$R^7$, —S(O)$_2$—$R^7$, $C_{1-9}$ alkyl, $C_{3-15}$ cycloalkyl, heterocyclyl, aryl, or heteroaryl;
wherein said $C_{1-9}$ alkyl, $C_{3-15}$ cycloalkyl, heterocyclyl, aryl, or heteroaryl may be optionally substituted with one to three substituents independently selected from the group consisting of —CN, halo, —O—$R^{12}$, —N($R^{13}$)($R^{14}$), —N($R^{12}$)C(O)O—$R^{12}$, —S(O)$_2$—$R^{12}$, —Si($R^{12}$)$_3$, $C_{1-9}$ alkyl, heterocyclyl, aryl, and heteroaryl;
wherein said $C_{1-9}$ alkyl, $C_{3-15}$ cycloalkyl, aryl, or heteroaryl may be optionally substituted with one to three substituents independently selected from the group consisting of —CN, halo, —O—$R^{12}$, —N($R^{13}$)($R^{14}$), $C_{1-9}$ alkyl, $C_{3-15}$ cycloalkyl, and aryl;

$R^4$ is aryl;
wherein said aryl is optionally substituted with one to three substituents independently selected from the group consisting of —CN, halo, —O—$R^{12}$, —C(O)—$R^{12}$, —C(O)O—$R^{12}$, —S(O)$_2$—$R^{12}$, —N($R^{12}$)C(O)—

$R^{12}$, —N($R^{12}$)S(O)$_2R^{12}$, —C(O)N($R^{13}$)($R^{14}$), —N($R^{13}$)($R^{14}$), $C_{1-9}$ alkyl, heterocyclyl, aryl, and heteroaryl;
  wherein said $C_{1-9}$ alkyl, or heteroaryl may be optionally substituted with one to three substituents independently selected from the group consisting of halo, —O—$R^{12}$, —N($R^{13}$)($R^{14}$), $C_{1-9}$ alkyl, and heterocyclyl;
$R^5$ is —CN, halo, —O—$R^7$, —C(O)$R^7$, —N($R^8$)C(O)($R^7$), —C(O)N(R)($R^9$), $C_{1-9}$ alkyl, $C_{2-6}$ alkynyl, $C_{3-15}$ cycloalkyl, aryl, or heteroaryl;
  wherein said $C_{1-9}$ alkyl, aryl, or heteroaryl may be optionally substituted with one to three substituents independently selected from the group consisting of halo, —O—$R^{12}$, and $C_{1-9}$ alkyl;
each $R^7$ is independently hydrogen, $C_{1-9}$ alkyl, $C_{3-15}$ cycloalkyl, heterocyclyl, or aryl;
  wherein said $C_{1-9}$ alkyl, or heterocyclyl may be optionally substituted with one to three substituents independently selected from the group consisting of halo, —O—$R^{12}$, —N($R^{13}$)($R^{14}$), $C_{1-9}$ alkyl, aryl, and heteroaryl;
each $R^{12}$ is independently hydrogen, $C_{1-9}$ alkyl, $C_{3-15}$ cycloalkyl, heterocyclyl, or aryl;
  wherein said $C_{1-9}$ alkyl, or heterocyclyl may be optionally substituted with one to three substituents independently selected from the group consisting of halo, hydroxy, —O($C_{1-9}$ alkyl), —N($C_{1-9}$ alkyl)$_2$, $C_{1-9}$ alkyl, aryl, and heteroaryl; and
each $R^{13}$ and $R^{14}$ are independently hydrogen, $C_{1-9}$ alkyl, $C_{3-15}$ cycloalkyl, heterocyclyl, or aryl;
  wherein said $C_{1-9}$ alkyl, or heterocyclyl may be optionally substituted with one to three substituents independently selected from the group consisting of halo, hydroxy, —O($C_{1-9}$ alkyl), —N($C_{1-9}$ alkyl)$_2$, $C_{1-9}$ alkyl, aryl, and heteroaryl;
or a pharmaceutically acceptable salt, tautomer, stereoisomer, mixture of stereoisomers, prodrug, or deuterated analog thereof.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, aryl, or heterocyclyl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl;
  wherein said $C_{1-9}$ alkyl, $C_{3-15}$ cycloalkyl, heterocyclyl, or aryl may be optionally substituted with one to three substituents independently selected from the group consisting of halo, hydroxy, —O($C_{1-9}$ alkyl), —C(O)—N($C_{1-9}$ alkyl)$_2$, $C_{1-9}$ alkyl, and heterocyclyl;
$R^1$ is hydrogen, —O—$R^7$, —N($R^8$)($R^9$), —C(O)—$R^7$, —S(O)$_2$—$R^7$, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, heterocyclyl, aryl, or heteroaryl may be optionally substituted with one to three substituents independently selected from the group consisting of —CN, halo, —O—$R^{12}$, —N($R^{13}$)($R^{14}$), —N($R^{12}$)C(O)O—$R^{12}$, —S(O)$_2$—$R^{12}$, —Si($R^{12}$)$_3$, $C_{1-9}$ alkyl, $C_{3-15}$ cycloalkyl, heterocyclyl, aryl, and heteroaryl;
    wherein said $C_{1-9}$ alkyl, $C_{3-15}$ cycloalkyl, aryl, or heteroaryl may be optionally substituted with one to three substituents independently selected from the group consisting of —CN, halo, —O—$R^{12}$, —N($R^{13}$)($R^{14}$), $C_{1-9}$ alkyl, $C_{3-15}$ cycloalkyl, and aryl;
$R^4$ is aryl;
  wherein said aryl is optionally substituted with one to three substituents independently selected from the group consisting of —CN, halo, —O—$R^{12}$, —C(O)—$R^{12}$, —C(O)O—$R^{12}$, —S(O)$_2$—$R^{12}$, —N($R^{12}$)C(O)—$R^{12}$, —N($R^{12}$)S(O)$_2R^{12}$, —C(O)N($R^{13}$)($R^{14}$), —N($R^{13}$)($R^{14}$), $C_{1-9}$ alkyl, heterocyclyl, aryl, and heteroaryl;
    wherein said $C_{1-9}$ alkyl, or heteroaryl may be optionally substituted with one to three substituents independently selected from the group consisting of halo, —O—$R^{12}$, —N($R^{13}$)($R^{14}$), $C_{1-9}$ alkyl, and heterocyclyl;
$R^5$ is —CN, halo, —O—$R^7$, —C(O)$R^7$, —N($R^8$)C(O)($R^7$), —C(O)N($R^8$)($R^9$), —S(O)$_2R^7$, $C_{1-9}$ alkyl, $C_{2-6}$ alkynyl, $C_{3-15}$ cycloalkyl, aryl, or heteroaryl;
  wherein said $C_{1-9}$ alkyl, aryl, or heteroaryl may be optionally substituted with one to three substituents independently selected from the group consisting of halo, —O—$R^{12}$, and $C_{1-9}$ alkyl;
each $R^7$ is independently hydrogen, $C_{1-9}$ alkyl, $C_{3-15}$ cycloalkyl, heterocyclyl, or aryl;
  wherein said $C_{1-9}$ alkyl, or heterocyclyl may be optionally substituted with one to three substituents independently selected from the group consisting of halo, —O—$R^{12}$, —N($R^{13}$)($R^{14}$), $C_{1-9}$ alkyl, aryl, and heteroaryl;
each $R^{12}$ is independently hydrogen, $C_{1-9}$ alkyl, $C_{3-15}$ cycloalkyl, heterocyclyl, or aryl;
  wherein said $C_{1-9}$ alkyl, or heterocyclyl may be optionally substituted with one to three substituents independently selected from the group consisting of halo, hydroxy, —O($C_{1-9}$ alkyl), —N($C_{1-9}$ alkyl)$_2$, $C_{1-9}$ alkyl, aryl, and heteroaryl; and
each $R^{13}$ and $R^{14}$ are independently hydrogen, $C_{1-9}$ alkyl, $C_{3-15}$ cycloalkyl, heterocyclyl, or aryl;
  wherein said $C_{1-9}$ alkyl, or heterocyclyl may be optionally substituted with one to three substituents independently selected from the group consisting of halo, hydroxy, —O($C_{1-9}$ alkyl), —N($C_{1-9}$ alkyl)$_2$, $C_{1-9}$ alkyl, aryl, and heteroaryl;
or a pharmaceutically acceptable salt, tautomer, stereoisomer, mixture of stereoisomers, prodrug, or deuterated analog thereof.

In certain embodiments, $Z^3$ is hydrogen, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, aryl, or heterocyclyl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl;
    wherein said $C_{1-9}$ alkyl, $C_{3-15}$ cycloalkyl, heterocyclyl, or aryl may be optionally substituted with one to three substituents independently selected from the group consisting of halo, hydroxy, —O($C_{1-9}$ alkyl), —C(O)—N($C_{1-9}$ alkyl)$_2$, $C_{1-9}$ alkyl, and heterocyclyl;
$R^1$ is hydrogen, —O—$R^7$, —N($R^8$)($R^9$), —C(O)—$R^7$, —S(O)$_2$—$R^7$, $C_{1-9}$ alkyl, $C_{3-15}$ cycloalkyl, heterocyclyl, aryl, or heteroaryl;
  wherein said $C_{1-9}$ alkyl, $C_{3-15}$ cycloalkyl, heterocyclyl, aryl, or heteroaryl may be optionally substituted with one to four substituents independently selected from the group consisting of —CN, halo, —O—R$^{12}$, —C(O)—R$^{12}$, —C(O)O—R$^{12}$, —N(R$^{13}$)(R$^{14}$), —N(R$^{12}$)C(O)O—R$^{12}$, —S(O)$_2$—R$^{12}$, —Si(R$^{12}$)$_3$, C$_{1-9}$ alkyl, C$_{3-15}$ cycloalkyl, heterocyclyl, aryl, and heteroaryl;
  wherein said C$_{1-9}$ alkyl, C$_{3-15}$ cycloalkyl, aryl, or heteroaryl may be optionally substituted with one to three substituents independently selected from the group consisting of —CN, halo, —O—R$^{12}$, —N(R$^{13}$)(R$^{14}$), C$_{1-9}$ alkyl, C$_{3-15}$ cycloalkyl, and aryl;

R$^4$ is aryl;
  wherein said aryl is optionally substituted with one to three substituents independently selected from the group consisting of —CN, halo, —O—R$^{12}$, —C(O)—R$^{12}$, —C(O)O—R$^{12}$, —S(O)$_2$—R$^{12}$, —N(R$^{12}$)C(O)—R$^{12}$, —N(R$^{12}$)S(O)$_2$R$^{12}$, —C(O)N(R$^{13}$)(R$^{14}$), —N(R$^{13}$)(R$^{14}$), C$_{1-9}$ alkyl, C$_{3-15}$ cycloalkyl, heterocyclyl, aryl, and heteroaryl;
    wherein said C$_{1-9}$ alkyl, C$_{3-15}$ cycloalkyl, or heteroaryl may be optionally substituted with one to three substituents independently selected from the group consisting of halo, —CN, —O—R$^{12}$, —N(R$^{13}$)(R$^{14}$), C$_{1-9}$ alkyl, and heterocyclyl;

R$^5$ is —CN, halo, —O—R$^7$, —C(O)R$^7$, —N(R$^8$)C(O)(R$^7$), —C(O)N(R$^8$)(R$^9$), —S(O)$_2$R$^7$, C$_{1-9}$ alkyl, C$_{2-6}$ alkynyl, C$_{3-15}$ cycloalkyl, aryl, or heteroaryl;
  wherein said C$_{1-9}$ alkyl, aryl, or heteroaryl may be optionally substituted with one to three substituents independently selected from the group consisting of halo, —O—R$^{12}$, and C$_{1-9}$ alkyl;

each R$^7$ is independently hydrogen, C$_{1-9}$ alkyl, C$_{3-15}$ cycloalkyl, heterocyclyl, or aryl;
  wherein said C$_{1-9}$ alkyl, or heterocyclyl may be optionally substituted with one to three substituents independently selected from the group consisting of halo, —O—R$^{12}$, —N(R$^{13}$)(R$^{14}$), C$_{1-9}$ alkyl, aryl, and heteroaryl;

each R$^{12}$ is independently hydrogen, C$_{1-9}$ alkyl, C$_{3-15}$ cycloalkyl, heterocyclyl, or aryl;
  wherein said C$_{1-9}$ alkyl, or heterocyclyl may be optionally substituted with one to three substituents independently selected from the group consisting of halo, hydroxy, —O(C$_{1-9}$ alkyl), —N(C$_{1-9}$ alkyl)$_2$, C$_{1-9}$ alkyl, aryl, and heteroaryl; and each R$^{13}$ and R$^{14}$ are independently hydrogen, C$_{1-9}$ alkyl, C$_{3-15}$ cycloalkyl, heterocyclyl, or aryl;
  wherein said C$_{1-9}$ alkyl, or heterocyclyl may be optionally substituted with one to three substituents independently selected from the group consisting of halo, hydroxy, —O(C$_{1-9}$ alkyl), —N(C$_{1-9}$ alkyl)$_2$, C$_{1-9}$ alkyl, aryl, and heteroaryl;

or a pharmaceutically acceptable salt, tautomer, stereoisomer, mixture of stereoisomers, prodrug, or deuterated analog thereof.

In certain embodiments, R$^1$ is C$_{1-9}$ alkyl, C$_{3-15}$ cycloalkyl, heterocyclyl, aryl, or heteroaryl; and said C$_{1-9}$ alkyl, C$_{3-15}$ cycloalkyl, heterocyclyl, aryl, or heteroaryl may be optionally substituted with one to four substituents independently selected the group consisting of halo, —CN, —O—R$^{12}$, —C(O)—R$^{12}$, —C(O)O—R$^{12}$, C$_{1-9}$ alkyl, and aryl. In certain embodiments, R$^1$ is C$_{1-9}$ alkyl, C$_{3-15}$ cycloalkyl, heterocyclyl, aryl, or heteroaryl; and said C$_{1-9}$ alkyl, C$_{3-15}$ cycloalkyl, heterocyclyl, aryl, or heteroaryl may be optionally substituted with one to four substituents independently selected the group consisting of halo, —CN, —O—R$^{12}$, C$_{1-9}$ alkyl, and aryl.

In certain embodiments, R$^1$ is C$_{1-9}$ alkyl, optionally substituted with one to four substituents independently selected the group consisting of halo, —CN, —O—R$^{12}$, —C(O)O—R$^{12}$, C$_{1-9}$ alkyl, and aryl. In certain embodiments, R$^1$ is C$_{1-9}$ alkyl, optionally substituted with one to three substituents independently selected the group consisting of halo, —CN, —O—R$^{12}$, C$_{1-9}$ alkyl, and aryl.

In certain embodiments, R$^1$ is C$_{3-15}$ cycloalkyl, heterocyclyl, or heteroaryl;
  wherein said C$_{3-15}$ cycloalkyl, heterocyclyl, or heteroaryl may be optionally substituted with one to four substituents independently selected from the group consisting of —CN, halo, —O—R$^{12}$, —N(R$^{13}$)(R$^{14}$), —NH—C(O)O—R$^{12}$, —S(O)$_2$—R$^{12}$, —Si(R$^{12}$)$_3$, C$_{1-9}$ alkyl, C$_{3-15}$ cycloalkyl, heterocyclyl, aryl, and heteroaryl; and
  wherein said C$_{1-9}$ alkyl, C$_{3-15}$ cycloalkyl, aryl, or heteroaryl may be optionally substituted with one to three substituents independently selected from the group consisting of —CN, halo, —O—R$^{12}$, —N(R$^{13}$)(R$^{14}$), C$_{1-9}$ alkyl, C$_{3-15}$ cycloalkyl, and aryl.

In certain embodiments, R$^1$ is C$_{3-15}$ cycloalkyl, heterocyclyl or heteroaryl, wherein said C$_{3-15}$ cycloalkyl, heterocyclyl or heteroaryl is optionally substituted with one to four substituents independently selected the group consisting of halo, —CN, —O—R$^{12}$, C$_{1-9}$ alkyl, and aryl.

In certain embodiments, R$^1$ is aryl;
  wherein said aryl may be optionally substituted with one to four substituents independently selected from the group consisting of —CN, halo, —O—R$^{12}$, —C(O)—R$^{12}$, —N(R$^{13}$)(R$^{14}$), —NH—C(O)O—R$^{12}$, —S(O)$_2$—R$^{12}$, —Si(R$^{12}$)$_3$, C$_{1-9}$ alkyl, C$_{3-15}$ cycloalkyl, heterocyclyl, aryl, and heteroaryl; and
  wherein said C$_{1-9}$ alkyl, C$_{3-15}$ cycloalkyl, aryl, or heteroaryl may be optionally substituted with one to three substituents independently selected from the group consisting of —CN, halo, —O—R$^{12}$, —N(R$^{13}$)(R$^{14}$), C$_{1-9}$ alkyl, C$_{3-15}$ cycloalkyl, and aryl.

In certain embodiments, R$^1$ is aryl;
  wherein said aryl may be optionally substituted with one to three substituents independently selected from the group consisting of —CN, halo, —O—R$^{12}$, —N(R$^{13}$)(R$^{14}$), —NH—C(O)O—R$^{12}$, —S(O)$_2$—R$^{12}$, —Si(R$^{12}$)$_3$, C$_{1-9}$ alkyl, C$_{3-15}$ cycloalkyl, heterocyclyl, aryl, and heteroaryl; and
  wherein said C$_{1-9}$ alkyl, C$_{3-15}$ cycloalkyl, aryl, or heteroaryl may be optionally substituted with one to three substituents independently selected from the group consisting of —CN, halo, —O—R$^{12}$, —N(R$^{13}$)(R$^{14}$), C$_{1-9}$ alkyl, C$_{3-15}$ cycloalkyl, and aryl.

In certain embodiments, R$^1$ is aryl, optionally substituted with one to four substituents independently selected the group consisting of halo, —CN, —O—R$^{12}$, —C(O)—R$^{12}$, C$_{1-9}$ alkyl, and aryl. In certain embodiments, R$^1$ is aryl, optionally substituted with one to three substituents independently selected the group consisting of halo, —CN, —O—R$^{12}$, C$_{1-9}$ alkyl, and aryl.

In one embodiment, R$^1$ is ((1R,2R)-2-(hydroxymethyl)cyclohexyl, ((1R,2S)-2-(tert-butoxycarbonylamino)cyclohex-1-yl)amino, ((1S,2R)-2-(tert-butoxycarbonylamino)cyclohex-1-yl)amino, ((1S,2S)-2-(hydroxymethyl)cyclohexyl, (1-(difluoromethyl)cyclobutyl)methyl, (1-(difluoromethyl)cyclopropyl)methyl, (1-(trifluoromethyl)cyclopropyl)methyl, (1-cyclopropylcyclobutyl)methyl, (1-ethylcyclobutyl)methyl, (1-methyl-H-pyrazol-3-yl)

methyl, (1-methyl-1H-pyrazol-4-yl)methyl, (1-methyl-1H-pyrazol-5-yl)ethyl, (1-methyl-1H-pyrazol-5-yl)methyl, (1-methylcyclobutyl)methyl, (1-methylcyclopropyl)methyl, (1R,2R)-2-(trifluoromethyl)cyclopropyl, (1R,2R)-2-ethylcyclopropyl, (1R,2S)-2-aminocyclohexyl, (1R,3R)-3-hydroxycyclohexyl, (1R,3R,6S,8S)-tricyclo[4.3.1.1 3,8]undecan-3-yl, (1R,3S)-3-hydroxycyclohexyl, (1r,4S)-4-hydroxycyclohexyl, (1R,5S)-3-oxabicyclo[3.1.0]hexan-6-yl, (1R,5S)-bicyclo[3.1.0]hexan-6-yl, (1R,5S)-bicyclo[3.3.1]nonan-3-yl, (1R,5S,6s)-bicyclo[3.1.0]hexan-6-yl, (1S,2R)-2-aminocyclohexyl, (1S,2S)-2-hydroxycyclohexyl, (1S,3R)-3-hydroxycyclohexyl, (1S,3S)-3-hydroxycyclohexyl, (1S,3S,5S,7S)-adamantan-2-yl, (1s,4s)-bicyclo[2.2.2]octan-2-yl, (2-(methylsulfonyl)-1-phenylethyl, (2-(trimethylsilyl)ethyl, (3-(trifluoromethyl)phenyl, (3,3-difluoro-1-methylcyclobutyl)methyl, (3-chloro-4-(pyridin-2-ylmethoxy)phenyl, (3-methyloxetan-3-yl)methyl, (3R,4R)-1-ethyl-3-hydroxypiperidin-4-yl, (3R,4R)-3-hydroxypiperidin-4-yl, (3R,5R,7R)-adamantan-1-yl, (4-((dimethylamino)methyl)phenyl, (4-fluorophenyl)methyl, (4-methyltetrahydro-2H-pyran-4-yl)methyl, (R)-((1R,2R)-2-cyanocyclopropyl)(phenyl)methyl, (R)-((1S,2S)-2-cyanocyclopropyl)(phenyl)methyl, (R)-1-(2-fluorophenyl)ethyl, (R)-1-(3-fluorophenyl)ethyl, (R)-1-(3-fluorophenyl)propyl, (R)-1-(4-fluorophenyl)ethyl, (R)-1-(m-tolyl)propyl, (R)-1-(o-tolyl)ethyl, (R)-1-(o-tolyl)propyl, (R)-1-(p-tolyl)propyl, (R)-1-(tetrahydro-2H-pyran-4-yl)ethyl, (R)-1,2,3,4-tetrahydronaphthalen-1-yl, (R)-1-cyano-3,3-dimethylbutan-2-yl, (R)-1-cyclohexylethyl, (R)-1-hydroxy-3,3-dimethylbutan-2-yl, (R)-1-methoxypropan-2-yl, (R)-1-phenyl-3-(piperidin-1-yl)propyl, (R)-1-phenyl-3-(pyrrolidin-1-yl)propyl, (R)-1-phenylbutyl, (R)-1-phenylethyl, (R)-1-phenylpropyl, (R)-2-(methylsulfonyl)-1-phenylethyl, (R)-2,2,2-trifluoro-1-phenylethyl, (R)-2,2-dimethylcyclohexyl, (R)-2,3-dihydro-1H-inden-1-yl, (R)-2-cyano-1-phenylethyl, (R)-2-cyano-1-phenylethyl, (R)-2-methyl-1-phenylpropyl, (R)-2-phenylpropyl, (R)-3,3-dimethylbutan-2-yl, (R)-3,3-dimethyltetrahydro-2H-pyran-4-yl, (R)-3-cyano-1-phenylpropyl, (R)-3-fluoro-1-phenylpropyl, (R)-3-hydroxy-1-phenylpropyl, (R)-3-morpholino-1-phenylpropyl, (R)-chroman-4-yl, (R)-cyclopropyl(phenyl)methyl, (R)-sec-butyl, (R)-tetrahydro-2H-pyran-3-yl, (S)-((1R,2R)-2-cyanocyclopropyl)(phenyl)methyl, (S)-((1S,2S)-2-cyanocyclopropyl)(phenyl)methyl, (S)-1-(tetrahydro-2H-pyran-4-yl)ethyl, (S)-1,2,3,4-tetrahydronaphthalen-1-yl, (S)-1-hydroxy-3,3-dimethylbutan-2-yl, (S)-1-methoxypropan-2-yl, (S)-1-phenylethyl, (S)-2-(methylsulfonyl)-1-phenylethyl, (S)-2,2,2-trifluoro-1-phenylethyl, (S)-2,2-dimethylcyclohexyl, (S)-2,3-dihydro-1H-inden-1-yl, (S)-2-cyano-1-phenylethyl, (S)-2-hydroxy-1-phenylethyl, (S)-2-methoxy-1-phenylethyl, (S)-2-phenylpropyl, (S)-3,3-dimethylbutan-2-yl, (S)-3,3-dimethyltetrahydro-2H-pyran-4-yl, (S)-3-cyano-1-phenylpropyl, (S)-3-hydroxy-1-phenylpropyl, (S)-chroman-4-yl, (S)-sec-butyl, (S)-tetrahydro-2H-pyran-3-yl, (tetrahydro-2H-pyran-2-yl)methyl, (tetrahydro-2H-pyran-3-yl)methyl, (tetrahydrofuran-3-yl)methyl, (trimethylsilyl)methyl, [1,1'-bi(cyclopropan)]-1H-yl, 1-((3R,4R)-3-hydroxy-1-(oxetan-3-yl)piperidin-4-yl, 1-(2,2,2-trifluoroethyl)-1H-pyrazol-3-yl, 1-(5,6-difluoropyridin-3-yl)propyl, 1-(pyridin-2-yl)ethyl, 1-(pyridin-3-yl)ethyl, 1-(tert-butyl)cyclopropyl, 1-(tert-butyl)piperidin-4-yl, 1-(tetrahydro-2H-pyran-4-yl)propyl, 1,1-dioxidothietan-3-yl, 1-benzyl-1H-indazol-5-yl, 1-cyanocyclopropyl, 1-ethylcyclobutyl, 1-ethylcyclopropyl, 1-hydroxy-2-methylpropan-2-yl, 1-methyl-1H-pyrazol-4-yl, 1-methyl-6-oxo-1,6-dihydropyridin-3-yl, 1-methylcyclobutyl, (1-methylcyclobutyl)methyl, 1-methylcycloheptyl, 1-methylcyclohexyl, 1-methylcyclopropyl, 1-methylcyclopropyl, 1-methylpiperidin-4-yl, 1-phenylbutan-2-yl, 1-phenylcyclopropyl, 2-(1H-imidazol-2-yl)ethyl, 2-(1-methyl-1H-imidazol-2-yl)ethyl, 2-2-yl)ethyl, 2-(trifluoromethoxy)phenyl, 2,2,2-trichloroethyl, 2,2,2-trifluoroethyl, 2,2,3-trimethylbutyl, 2,2-difluoropropyl, 2,2-dimethyl-1-phenylpropyl, 2,2-dimethylbutyl, 2,2-dimethylcyclopentyl, 2,2-dimethylcyclopropyl, 2,2-dimethylpropyl-1,1-d2, 2,3,4-trifluorophenyl, 2,3-dichloro-4-fluorophenyl, 2,3-dichlorophenyl, 2,3-difluorobenzyl, 2,3-dimethylbutan-2-yl, 2,4,5-trifluorophenyl, 2,4,6-trifluorophenyl, 2,4-dichloro-5-methoxyphenyl, 2,4-difluorophenyl, 2,5-dichlorophenyl, 2,6-difluorophenyl, 2,6-dimethylcyclohexyl, 2,6-dimethyl-tetrahydro-2H-pyran-4-yl, 2-chlorobenzyl, 2-chlorothiophen-3-yl, 2-cyano-1-phenylethyl, 2-cyano-2-methylpropyl, 2-cyano-4-fluorophenyl, 2-cyanoethyl, 2-cyclopropylethyl, 2-fluoro-2-methylpropyl, 2-fluorobenzyl, 2-fluorophenyl, 2-fluoropyridin-3-yl, 2-hydroxy-2-methylpropyl, 2-methoxy-2-methylpropyl, 2-methoxybenzyl, 2-methoxyethyl, 2-methoxyphenyl, 2-methoxypyridin-3-yl, 2-methyl-2-phenylpropyl, 2-methylbenzyl, 2-methylcyclohexyl, 2-morpholino-1-phenylethyl, 2-oxo-2,3-dihydro-1H-benzol imidazol-4-yl, 3-(2H-1,2,3-triazol-2-yl)phenyl, 3-(difluoromethyl)phenyl, 3-(dimethylamino)propyl, 3,3,3-trifluoro-1-phenylpropyl, 3,3-difluoro-1-methylcyclobutyl, 3,3-difluorocyclobutyl, 3,3-dimethylbutyl, 3,3-dimethylcyclobutyl, 3,3-dimethyltetrahydro-2H-pyran-4-yl, 3,4-dichloro-2-fluorophenyl, 3,4-dichlorophenyl, 3,4-difluorophenyl, 3,5-dichlorophenyl, 3,5-difluorophenyl, 3-bromo-4-fluorophenyl, 3-bromophenyl, 3-chloro-2,2-dimethylpropyl, 3-chloro-2,4-difluorophenyl, 3-chloro-2,6-difluorophenyl, 3-chloro-2-cyclopropoxyphenyl, 3-chloro-2-fluorophenyl, 3-chloro-2-methoxyphenyl, 3-chloro-2-methylphenyl, 3-chloro-4,5-difluorophenyl, 3-chloro-4-cyanophenyl, 3-chloro-4-ethoxyphenyl, 3-chloro-4-fluorophenyl, 3-chloro-4-hydroxyphenyl, 3-chloro-5-fluorophenyl, 3-chlorophenyl, 3-cyano-1-phenylpropyl, 3-cyano-2,2-dimethylpropyl, 3-cyano-2,4-difluorophenyl, 3-cyanophenyl, 3-fluorophenyl, 3-hydroxy-2,2-dimethylpropyl, 3-hydroxycyclohexyl, 3-methoxy-2,2-dimethylpropyl, 3-methylbenzyl), 3-methyloxetan-3-yl, 3-phenylpropyl, 4-(benzyloxy)-3-chlorophenyl, 4-(trifluoromethoxy)phenyl, 4,5-dichloro-2-fluorophenyl, 4-chloro-3-fluorophenyl, 4-chlorophenyl, 4-chlorothiophen-3-yl, 4-fluoro-3-(methylsulfonyl)phenyl, 4-fluoro-3-(trifluoromethoxy)phenyl, 4-fluoro-3-(trifluoromethyl)phenyl, 4-fluorophenyl, 4-hydroxybutan-2-yl, 4-methylbenzyl, 5,6-difluoropyridin-3-yl, 5-chloro-2,4-difluorophenyl, 5-chloro-2-fluorophenyl, 5-chloro-6-fluoropyridin-3-yl, 5-chloropyridin-3-yl, 5-chlorothiophen-3-yl, 5-fluoropyridin-3-yl, 6-(trifluoromethyl)pyridin-3-yl, 6-chloro-5-fluoropyridin-3-yl, 6-fluoro-5-methylpyridin-3-yl, 6-fluoropyridin-3-yl, 6-methoxypyridin-3-yl, azepan-1-yl, benzyl, bicyclo[1.1.1]pentan-1-yl, bicyclo[2.2.1]heptan-2-yl, bicyclo[3.1.0]hexan-2-yl, bicyclo[3.1.0]hexan-6-yl, bicyclo[4.1.0]heptan-2-yl, cyclobutyl, cyclobutylmethyl, cycloheptyl, cyclohexyl, cyclopentyl, cyclopropyl, cyclopropylmethyl, H, isobutyl, isopentyl, isopropyl, morpholino, m-tolyl, N-cyclohexylamino, neopentyl, N-ethyl-N-phenylamino, oxetan-3-yl, oxetan-3-ylmethyl, phenethyl, phenyl, phenylcarbonyl, phenylsulfonyl, piperidin-1-yl, p-tolyl, pyridin-3-yl, pyrrolidin-1-yl, quinuclidin-3-yl, spiro[2.5]octan-1-yl, tert-butoxy, tert-butyl, tert-butylamino, tert-butylcarbonyl, tert-pentyl, tetrahydro-2H-pyran-4-yl, tetrahydro-2H-pyran-4-yl)methyl, thiazol-2-ylmethyl, thiazol-4-ylmethyl, thiazol-5-ylmethyl, thiophen-2-ylmethyl, or thiophen-3-ylmethyl.

In one embodiment, R¹ is (1R,2R)-2-(hydroxymethyl)cyclohexyl, (1R,2S)-2-(tert-butoxycarbonylamino)cyclohex-1-yl)amino, (1S,2R)-2-(tert-butoxycarbonylamino)cyclohex-1-yl)amino, (1S,2S)-2-(hydroxymethyl)cyclohexyl, (1-(difluoromethyl)cyclobutyl)methyl, (1-(difluoromethyl)cyclopropyl)methyl, (1-(trifluoromethyl)cyclopropyl)methyl, (1-cyclopropylcyclobutyl)methyl, (1-ethylcyclobutyl)methyl, (1-methyl-1H-pyrazol-3-yl)methyl, (1-methyl-1H-pyrazol-4-yl)methyl, (1-methyl-1H-pyrazol-5-yl)ethyl, (1-methyl-1H-pyrazol-5-yl)methyl, (1-methylcyclobutyl)methyl, (1-methylcyclopropyl)methyl, (1R,2R)-2-(trifluoromethyl)cyclopropyl, (1R,2R)-2-ethylcyclopropyl, (1R,2S)-2-aminocyclohexyl, (1R,3R)-3-hydroxycyclohexyl, (1R,3R,6S,8S)-tricyclo[4.3.1.13,8]undecan-3-yl, (1R,3S)-3-hydroxycyclohexyl, (1r,4S)-4-hydroxycyclohexyl, (1R,5S)-3-oxabicyclo[3.1.0]hexan-6-yl, (1R,5S)-bicyclo[3.1.0]hexan-6-yl, (1R,5S)-bicyclo[3.3.1]nonan-3-yl, (1R,5S,6s)-bicyclo[3.1.0]hexan-6-yl, (1S,2R)-2-aminocyclohexyl, (1S,2S)-2-hydroxycyclohexyl, (1S,3R)-3-hydroxycyclohexyl, (1S,3S)-3-hydroxycyclohexyl, (1S,3S,5S,7S)-adamantan-2-yl, (1s,4s)-bicyclo[2.2.2]octan-2-yl, (2-(methylsulfonyl)-1-phenylethyl, (2-(trimethylsilyl)ethyl, (3-(trifluoromethyl)phenyl, (3,3-difluoro-1-methylcyclobutyl)methyl, (3-chloro-4-(pyridin-2-ylmethoxy)phenyl, (3-methyloxetan-3-yl)methyl, (3R,4R)-1-ethyl-3-hydroxypiperidin-4-yl, (3R,4R)-3-hydroxypiperidin-4-yl, (3R,5R,7R)-adamantan-1-yl, (4-((dimethylamino)methyl)phenyl, (4-fluorophenyl)methyl, (4-methyltetrahydro-2H-pyran-4-yl)methyl, (R)-(1R,2R)-2-cyanocyclopropyl)(phenyl)methyl, (R)-(1S,2S)-2-cyanocyclopropyl)(phenyl)methyl, (R)-1-(2-fluorophenyl)ethyl, (R)-1-(3-fluorophenyl)ethyl, (R)-1-(3-fluorophenyl)propyl, (R)-1-(4-fluorophenyl)ethyl, (R)-1-(m-tolyl)propyl, (R)-1-(o-tolyl)ethyl, (R)-1-(o-tolyl)propyl, (R)-1-(p-tolyl)propyl, (R)-1-(tetrahydro-2H-pyran-4-yl)ethyl, (R)-1,2,3,4-tetrahydronaphthalen-1-yl, (R)-1-cyano-3,3-dimethylbutan-2-yl, (R)-1-cyclohexylethyl, (R)-1-hydroxy-3,3-dimethylbutan-2-yl, (R)-1-methoxypropan-2-yl, (R)-1-phenyl-3-(piperidin-1-yl)propyl, (R)-1-phenyl-3-(pyrrolidin-1-yl)propyl, (R)-1-phenylbutyl, (R)-1-phenylethyl, (R)-1-phenylpropyl, (R)-2-(methylsulfonyl)-1-phenylethyl, (R)-2,2,2-trifluoro-1-phenylethyl, (R)-2,2-dimethylcyclohexyl, (R)-2,3-dihydro-1H-inden-1-yl, (R)-2-cyano-1-phenylethyl, (R)-2-cyano-1-phenylethyl, (R)-2-methyl-1-phenylpropyl, (R)-2-phenylpropyl, (R)-3,3-dimethylbutan-2-yl, (R)-3,3-dimethyltetrahydro-2H-pyran-4-yl, (R)-3-(methylsulfonyl)-1-phenylpropyl, (R)-3-carboxy-1-phenylpropyl, (R)-3-cyano-1-phenylpropyl, (R)-3-fluoro-1-phenylpropyl, (R)-3-hydroxy-1-phenylpropyl, (R)-3-methoxy-1-phenylpropyl, (R)-3-morpholino-1-phenylpropyl, (R)-chroman-4-yl, (R)-cyclopropyl(phenyl)methyl, (R)-sec-butyl, (R)-tetrahydro-2H-pyran-3-yl, (S)-(1R,2R)-2-cyanocyclopropyl)(phenyl)methyl, (S)-(1S,2S)-2-cyanocyclopropyl)(phenyl)methyl, (S)-1-(tetrahydro-2H-pyran-4-yl)ethyl, (S)-1,2,3,4-tetrahydronaphthalen-1-yl, (S)-1-hydroxy-3,3-dimethylbutan-2-yl, (S)-1-methoxypropan-2-yl, (S)-1-phenylethyl, (S)-2-(methylsulfonyl)-1-phenyl ethyl, (S)-2,2,2-trifluoro-1-phenylethyl, (S)-2,2-difluoro-3-hydroxy-1-phenylpropyl, (S)-2,2-dimethylcyclohexyl, (S)-2,3-dihydro-1H-inden-1-yl, (S)-2-cyano-1-phenylethyl, (S)-2-hydroxy-1-phenyl ethyl, (S)-2-methoxy-1-phenylethyl, (S)-2-phenylpropyl, (S)-3,3-dimethylbutan-2-yl, (S)-3,3-dimethyltetrahydro-2H-pyran-4-yl, (S)-3-cyano-1-phenylpropyl, (S)-3-hydroxy-1-phenylpropyl, (S)-chroman-4-yl, (S)-sec-butyl, (S)-tetrahydro-2H-pyran-3-yl, (tetrahydro-2H-pyran-2-yl)methyl, (tetrahydro-2H-pyran-4-yl)methyl, (tetrahydrofuran-3-yl)methyl, (trimethylsilyl)methyl, [1,1'-bi(cyclopropan)]-1-yl, 1-((3R,4R)-3-hydroxy-1-(oxetan-3-yl)piperidin-4-yl, 1-(2,2,2-trifluoroethyl)-1H-pyrazol-3-yl, 1-(5,6-difluoropyridin-3-yl)propyl, 1-(difluoromethyl)cyclopropyl, 1-(pyridin-2-yl)ethyl, 1-(pyridin-3-yl)ethyl, 1-(tert-butyl)cyclopropyl, 1-(tert-butyl)piperidin-4-yl, 1-(tetrahydro-2H-pyran-4-yl)propyl, 1,1-dioxidothietan-3-yl, 1-benzyl-1H-indazol-5-yl, 1-cyanocyclopropyl, 1-ethylcyclobutyl, 1-ethylcyclopropyl, 1-hydroxy-2-methylpropan-2-yl, 1-methyl-1H-pyrazol-4-yl, 1-methyl-6-oxo-1,6-dihydropyridin-3-yl, 1-methylcyclobutyl, (1-methylcyclobutyl)methyl, 1-methylcycloheptyl, 1-methylcyclohexyl, 1-methylcyclopropyl, 1-methylcyclopropyl, 1-methylpiperidin-4-yl, 1-phenylbutan-2-yl, 1-phenylcyclopropyl, 2-(1H-imidazol-2-yl)ethyl, 2-(1-methyl-1H-imidazol-2-yl)ethyl, 2-(1-methyl-1H-pyrazol-3-yl)ethyl, 2-(pyridin-2-yl)ethyl, 2-(pyridin-3-yl)ethyl, 2-(thiazol-2-yl)ethyl, 2-(trifluoromethoxy)phenyl, 2,2,2-trichloroethyl, 2,2,2-trifluoroethyl, 2,2,3-trimethylbutyl, 2,2-difluoropropyl, 2,2-dimethyl-1-phenylpropyl, 2,2-dimethylbutyl, 2,2-dimethylcyclopentyl, 2,2-dimethylcyclopropyl, 2,2-dimethylpropyl-1,1-d2, 2,3,4-trifluorophenyl, 2,3-dichloro-4-fluorophenyl, 2,3-dichlorophenyl, 2,3-difluorobenzyl, 2,3-dimethylbutan-2-yl, 2,4,5-trifluorophenyl, 2,4,6-trifluorophenyl, 2,4-dichloro-5-methoxyphenyl, 2,4-difluorophenyl, 2,5-dichlorophenyl, 2,6-difluorophenyl, 2,6-dimethylcyclohexyl, 2,6-dimethyltetrahydro-2H-pyran-4-yl, 2-acetyl-3-chlorophenyl, 2-chlorobenzyl, 2-chlorothiophen-3-yl, 2-cyano-1-phenylethyl, 2-cyano-2-methylpropyl, 2-cyano-4-fluorophenyl, 2-cyanoethyl, 2-cyclopropylethyl, 2-fluoro-2-methylpropyl, 2-fluorobenzyl, 2-fluorophenyl, 2-fluoropyridin-3-yl, 2-hydroxy-2-methylpropyl, 2-methoxy-2-methylpropyl, 2-methoxybenzyl, 2-methoxyethyl, 2-methoxyphenyl, 2-methoxypyridin-3-yl, 2-methyl-2-phenylpropyl, 2-methylbenzyl, 2-methylcyclohexyl, 2-methyl-2-(pyridin-2-yl)propyl, 2-morpholino-1-phenylethyl, 2-oxo-2,3-dihydro-1H-benzo[d]imidazo-4-yl, 3-(2H-1,2,3-triazol-2-yl)phenyl, 3-(difluoromethyl)phenyl, 3-(dimethylamino)propyl, 3,3,3-trifluoro-1-phenylpropyl, 3,3-difluoro-1-methylcyclobutyl, 3,3-difluorocyclobutyl, 3,3-dimethylbutyl, 3,3-dimethylcyclobutyl, 3,3-dimethyltetrahydro-2H-pyran-4-yl, 3,4-dichloro-2-fluorophenyl, 3,4-dichlorophenyl, 3,4-difluorophenyl, 3,5-dichlorophenyl, 3,5-difluorophenyl, 3-bromo-4-fluorophenyl, 3-bromophenyl, 3-chloro-2,2-dimethylpropyl, 3-chloro-2,4-difluorophenyl, 3-chloro-2,6-difluorophenyl, 3-chloro-2-cyclopropoxyphenyl, 3-chloro-2-fluorophenyl, 3-chloro-2-methoxyphenyl, 3-chloro-2-methylphenyl, 3-chloro-4,5-difluorophenyl, 3-chloro-2-cyanophenyl, 3-chloro-4-cyanophenyl, 3-chloro-4-ethoxyphenyl, 3-chloro-4-fluorophenyl, 3-chloro-4-hydroxyphenyl, 3-chloro-5-fluorophenyl, 3-chlorophenyl, 3-chloro-2-(methylsulfonyl)phenyl, 3-chloro-2-(trifluoromethoxy)phenyl, 3-cyano-1-phenylpropyl, 3-cyano-2,2-dimethylpropyl, 3-cyano-2,4-difluorophenyl, 3-cyanophenyl, 3-fluorophenyl, 3-hydroxy-2,2-dimethylpropyl, 3-hydroxycyclohexyl, 3-methoxy-2,2-dimethylpropyl, 3-methylbenzyl), 3-methyloxetan-3-yl, 3-phenylpropyl, 4-(benzyloxy)-3-chlorophenyl, 4-(trifluoromethoxy)phenyl, 4,5-dichloro-2-fluorophenyl, 4-chloro-3-fluorophenyl, 4-chlorophenyl, 4-chlorothiophen-3-yl, 4-cyano-1-phenylbutyl, 4-fluoro-3-(methylsulfonyl)phenyl, 4-fluoro-3-(trifluoromethoxy)phenyl, 4-fluoro-3-(trifluoromethyl)phenyl, 4-fluorophenyl, 4-hydroxybutan-2-yl, 4-methylbenzyl, 5,6-difluoropyridin-3-yl, 5-chloro-2,4-difluorophenyl, 5-chloro-2-fluorophenyl, 5-chloro-6-fluoropyridin-3-yl, 5-chloropyridin-3-yl, 5-chlorothiophen-3-yl, 5-fluoropyridin-3-yl, 6-(trifluoromethyl)pyridin-3-yl, 6-chloro-5-fluoropyridin-3-yl, 6-fluoro-5- methylpyridin-3-yl, 6-fluoropyridin-3-yl, 6-methoxypyridin-3-yl, azepan-1-yl, benzyl, bicyclo[1.1.1]pentan-1-yl, bicyclo[1.1.1]pentan-1-ylmethyl, bicyclo[2.2.1]heptan-2-yl, bicyclo[3.1.0]hexan-2-yl, bicyclo[3.1.0]hexan-6-yl, bicyclo[4.1.0]heptan-2-yl, cyclobutyl, cyclobutylmethyl, cycloheptyl, cyclohexyl, cyclopentyl, cyclopropyl, cyclopropylmethyl, H, isobutyl, isopentyl, isopropyl, morpholino, m-tolyl, naphthalen-1-yl, N-cyclohexylamino, neopentyl, N-ethyl-N-phenylamino, oxetan-3-yl, oxetan-3-ylmethyl, phenethyl, phenyl, phenylcarbonyl, phenylsulfonyl, piperidin-1-yl, p-tolyl, pyridin-3-yl, pyrrolidin-1-yl, quinuclidin-3-yl, spiro[2.5]octan-1-yl, tert-butoxy, tert-butyl, tert-butylamino, tert-butylcarbonyl, tert-pentyl, tetrahydro-2H-pyran-4-yl, tetrahydro-2H-pyran-4-yl)methyl, thiazol-2-ylmethyl, thiazol-4-ylmethyl, thiazol-5-ylmethyl, thiophen-2-ylmethyl, or thiophen-3-ylmethyl.

In certain embodiments, $R^1$ is (R)-1-phenylethyl, (R)-1-phenylpropyl, 3,4-dichloro-2-fluorophenyl, 3-chloro-4-fluorophenyl, 5,6-difluoropyridin-3-yl, or neopentyl.

In one embodiment, $R^2$ is hydrogen. In one embodiment, $R^2$ is $C_{1-6}$ alkyl. In one embodiment, $R^2$ is methyl.

In one embodiment, $R^1$ and $R^2$ together with the nitrogen atom to which they are attached form a heterocyclyl or heterocyclyl. In certain embodiments, $R^1$ and $R^2$ together with the nitrogen to which they are attached form a heterocyclyl or heteroaryl, wherein said heterocyclyl may be optionally substituted with one to three $C_{1-9}$ alkyl. In certain embodiments, $R^1$ and $R^2$ together with the nitrogen atom to which they are attached form an optionally substituted pyrazolyl. In certain embodiments, $R^1$ and $R^2$ together with the nitrogen atom to which they are attached form 3,3-dimethylpiperidin-1-yl.

In one embodiment, $R^3$ is heterocyclyl or heteroaryl, wherein each heterocyclyl or heteroaryl is optionally substituted with one or more substituents (i.e., $Z^3$) selected from the group consisting of ((2-hydroxycarbonyl)-2,2-dimethyl)ethyl, ((R)-pyrrolidin-2-yl)methyl, ((S)-1-ethylpyrrolidin-3-yl, (1-(trifluoromethyl)cyclopropyl, (1-ethylazetidin-3-yl)methyl, (1-hydroxycyclopropyl)methyl, (1-methylcyclobutyl)methyl, (1-methylcyclopropyl)methyl, (1R,2S)-2-(trifluoromethyl)cyclopropyl, (1R,5S,6R)-3-(oxetan-3-yl)-3-azabicyclo[3.1.0]hexan-6-yl, (1R,5S,6S)-3-azabicyclo[3.1.0]hexan-6-yl, (2R)-1-(dimethylaminocarbonyl)pyrrolidin-2-yl, (3-(pyrrolidin-1-yl)oxetan-3-yl)methyl, (3-fluorooxetan-3-yl)methyl, (3R)-1-(benzyloxycarbonyl)pyrrolidin-3-yl, (3R,4R)-1-ethyl-3-fluoropiperidin-4-yl, (3R,4R)-1-ethyl-3-hydroxypiperidin-4-yl, (3R,4R)-3-fluoropiperidin-4-yl, (3R,4R)-3-hydroxy-1-(oxetan-3-yl)piperidin-4-yl, (3R,4R)-3-hydroxypiperidin-4-yl, (3S)-1-(benzyloxycarbonyl)pyrrolidin-4-yl, (3S,4R)-3-fluoropiperidin-4-yl, (oxetan-3-yl)piperidin-4-yl, (R)-1,1,1-trifluoropropan-2-yl, (R)-1-ethylpyrrolidin-3-yl, (R)-2,2-dimethylpiperidin-4-yl, (R)-pyrrolidin-3-yl, (S)-1-ethylpyrrolidin-3-yl, (S)-1-fluoropropan-2-yl, (S)-pyrrolidin-3-yl, (trimethylsilyl)methyl, 1-(2,2,2-trifluoroethyl, 1-(2,2,2-trifluoroethyl)piperidin-4-yl, 1-(2,2-difluoroethyl)piperidin-4-yl, 1-(2-methoxyethyl)piperidin-4-yl, 1-(3,3-difluorocyclobutyl)piperidin-4-yl, 1-(benzyloxycarbonyl)2,2-dimethylpiperidin-1-yl, 1-(benzyloxycarbonyl)piperidin-4-yl, 1-(dimethylaminocarbonyl)methylpiperidin-4-yl, 1-(methylsulfonyl)piperidin-4-yl, 1-(oxetan-3-yl)piperidin-4-yl, 1-(tert-butyl)piperidin-4-yl, 1-(tert-butyloxycarbonyl)piperidin-4-yl, 1-(trifluoromethyl)cyclopropyl, 1,1-difluoro-2-hydroxyethyl, 1,1-difluoropropan-2-yl, 1,1-dioxidothietan-3-yl, 1-acetylpiperidin-4-yl, 1-cyanocyclopropyl, 1-cyclopropylpiperidin-4-yl, 1-ethyl-2,2-dimethylpiperidin-4-yl, 1-ethyl-5,5-difluoropiperidin-3-yl, 1-ethylazetidin-3-yl, 1-ethylpiperidin-4-yl, 1-isopropylpiperidin-4-yl, 1-methylcyclopropyl, 1-methylpiperidin-4-yl, 2-(2-methoxyethoxy)ethyl, 2-(diethyl(methyl)ammonio)ethyl, 2-(dimethylamino)ethyl, 2-(trifluoromethyl)phenyl, 2,2,2-trifluoroethyl, 2,2,6,6-tetramethylpiperidin-4-yl, 2,2-difluorocyclopropyl, 2,2-difluoroethyl, 2,2-dimethylpiperidin-4-yl, 2,6-difluorobenzyl, 2-aminoethyl, 2-azaspiro[3.3]heptan-6-yl, 2-ethyl-2-azaspiro[3.3]heptan-6-yl, 2-fluoroethyl, 2-hydroxy-2-methylpropyl, 2-hydroxyethyl, 2-methoxyethyl, 2-morpholino-2-oxoethyl, 2-morpholinoethyl, 3-(dimethylamino)propyl, 3-(oxetan-3-yl)-3-azabicyclo[3.1.0]hexan-6-yl, 3-(pyrrolidin-1-yl)propyl, 3,3,3-trifluoro-2-hydroxypropyl, 3,3-dimethylpiperidin-4-yl, 3-azabicyclo[3.1.0]hexan-6-yl, 3-ethyl-3-azabicyclo[3.1.0]hexan-6-yl, 3-fluorooxetan-3-yl)methyl, 3-fluoropropyl, 3-hydroxyoxetan-3-yl, 3-hydroxypropyl, 3-methyloxetan-3-yl, 4-fluorophenyl, 5,5-difluoro-1-methylpiperidin-3-yl, 5,5-difluoropiperidin-3-yl, 5-methyl-1H-1,2,3-triazol-4-yl, aminocarbonylmethyl, azetidin-3-yl, benzyl, bicyclo[1.1.1]pentan-1-yl, cyanomethyl, cyclopentyl, cyclopropyl, difluoromethyl, fluoromethyl, hydroxycarbonylmethyl, isopropyl, methyl, neopentyl, oxazol-2-yl, oxetan-2-ylmethyl, oxetan-3-yl, phenyl, piperidin-4-yl, pivalylmethyl, pyridin-2-ylmethyl, pyridin-3-yl, pyridin-4-yl, pyrimidin-2-yl, pyrrolidin-1-yl)ethyl, quinuclidin-3-yl, tert-butyl, and tetrahydro-2H-pyran-4-yl.

In one embodiment, $R^3$ is heterocyclyl or heteroaryl, wherein the heterocyclyl or heteroaryl is optionally substituted with one or more substituents (i.e., $Z^3$) selected from the group consisting of ((2-hydroxycarbonyl)-2,2-dimethyl)ethyl, ((R)-pyrrolidin-2-yl)methyl, (S)-1-ethylpyrrolidin-3-yl, (1-(trifluoromethyl)cyclopropyl, (1-ethylazetidin-3-yl)methyl, (1-hydroxycyclopropyl)methyl, (1-methylcyclobutyl)methyl, (1-methylcyclopropyl)methyl, (1R,2S)-2-(trifluoromethyl)cyclopropyl, (1R,5S,6R)-3-(oxetan-3-yl)-3-azabicyclo[3.1.0]hexan-6-yl, (1R,5S,6S)-3-azabicyclo[3.1.0]hexan-6-yl, (1R,5S,6s)-3-cyclopropyl-3-azabicyclo[3.1.0]hexan-6-yl, (2R)-1-(dimethylaminocarbonyl)pyrrolidin-2-yl, (3-(pyrrolidin-1-yl)oxetan-3-yl)methyl, (3-fluorooxetan-3-yl)methyl, (3R)-1-(benzyloxycarbonyl)pyrrolidin-3-yl, (3R,4R)-1-ethyl-3-fluoropiperidin-4-yl, (3R,4R)-1-ethyl-3-hydroxypiperidin-4-yl, (3R,4R)-3-fluoropiperidin-4-yl, (3R,4R)-3-hydroxy-1-(oxetan-3-yl)piperidin-4-yl, (3R,4R)-3-hydroxypiperidin-4-yl, (3S)-1-(benzyloxycarbonyl)pyrrolidin-4-yl, (3S,4R)-3-fluoropiperidin-4-yl, (oxetan-3-yl)piperidin-4-yl, (R)-1,1,1-trifluoropropan-2-yl, (R)-1-ethylpyrrolidin-3-yl, (R)-2,2-dimethylpiperidin-4-yl, (R)-pyrrolidin-3-yl, (S)-1-ethylpyrrolidin-3-yl, (S)-1-fluoropropan-2-yl, (S)-pyrrolidin-3-yl, (trimethylsilyl)methyl, [1,1'-bi(cyclopropan)]-1-yl, 1-(1-(trifluoromethyl)cyclopropyl)-1H-1,2,3-triazol-4-yl)methyl, 1-(1-methylcyclopropyl)-1H-1,2,3-triazol-4-yl)methyl, 1-(2,2,2-trifluoroethyl, 1-(2,2,2-trifluoroethyl)piperidin-4-yl, 1-(2,2-difluoroethyl)piperidin-4-yl, 1-(2-methoxyethyl)piperidin-4-yl, 1-(3-(hydroxymethyl)oxetan-3-yl, 1-(3,3-difluorocyclobutyl)piperidin-4-yl, 1-(benzyloxycarbonyl)2,2-dimethylpiperidin-4-yl, 1-(benzyloxycarbonyl)piperidin-4-yl, 1-(difluoromethyl)cyclopropyl, 1-(dimethylaminocarbonyl)methylpiperidin-4-yl, 1-(fluoromethyl)cyclopropyl, 1-(hydroxymethyl)cyclopropyl, 1-(methylsulfonyl)piperidin-4-yl, 1-(oxetan-3-yl)piperidin-4-yl, 1-(pyrazin-2-yl)cyclopropyl, 1-(pyridazin-3-yl)cyclopropyl, 1-(pyridin-2-yl)cyclopropyl, 1-(pyridin-3-yl)cyclopropyl, 1-(pyridin-4-yl)cyclopropyl, quinuclidin-4-yl, 1-(tert-butyl)aziridin-2-yl)ethyl, 1-(tert-butyl)piperidin-4-yl, 1-(tert-butyloxycarbonyl)piperidin-4-yl, 1-(trifluoromethyl)cyclobutyl, 1-(trifluoromethyl)cyclopropyl, 1,1-difluoro-2-hydroxyethyl, 1,1-difluoropropan-2-yl, 1,1-dioxidothietan-3-yl, 1-acetylpiperidin-4-yl, 1-carbamoylcyclobut-1-yl, 1-carbamoylcyclopent-1-yl, 1-cyanocyclobutyl, 1-cyanocyclopropyl, 1-cyclopropyl-1H-1,2,3-triazol-4-yl, 1-cyclopropylpiperidin-4-yl, 1-ethyl-2,2-dimethylpiperidin-4-yl, 1-ethyl-5,5-difluoropiperidin-3-yl, 1-ethylazetidin-3-yl, 1-ethylpiperidin-4-yl, 1-isopropylpiperidin-4-yl, 1-methylcyclopropyl, 1-methylpiperidin-4-yl, 2-(2-methoxyethoxy)ethyl, 2-(diethyl(methyl)ammonio)ethyl, 2-(dimethylamino)ethyl, 2-(trifluoromethyl)phenyl, 2,2,2-trifluoroethyl, 2,2,6,6-tetramethylpiperidin-4-yl, 2,2-difluorocyclopropyl, 2,2-difluoroethyl, 2,2-dimethylpiperidin-4-yl, 2,6-difluorobenzyl, 2-amino-1,1-difluoro-2-oxoeth-1-yl, 2-amino-1,1-dimethyl-2-oxoethyl, 2-amino-2-oxoeth-1-yl, 2-aminoethyl, 2-azaspiro[3.3]heptan-6-yl, 2-ethyl-2-azaspiro[3.3]heptan-6-yl, 2-fluoroethyl, 2-hydroxy-2-methylpropyl, 2-hydroxyethyl, 2-methoxyethyl, 2-morpholino-2-oxoethyl, 2-morpholinoethyl, 3-(dimethylamino)propyl, 3-(oxetan-3-yl)-3-azabicyclo[3.1.0]hexan-6-yl, 3-(pyrrolidin-1-yl)propyl, 3-(tert-butylamino)-2-hydroxypropyl, 3,3,3-trifluoro-2-hydroxypropyl, 3,3-dimethylpiperidin-4-yl, 3-azabicyclo[3.1.0]hexan-6-yl, 3-carbamoyltetrahydrofuran-3-yl, 3-ethyl-3-azabicyclo[3.1.0]hexan-6-yl, 3-fluorooxetan-3-yl)methyl, 3-fluoropropyl, 3-hydroxyoxetan-3-yl, 3-hydroxypropyl, 3-methyloxetan-3-yl, 4-carbamoyltetrahydropyran-4-yl, 4-fluorophenyl, 5,5-difluoro-1-methylpiperidin-3-yl, 5,5-difluoropiperidin-3-yl, 5-methyl-1H-1,2,3-triazol-4-yl, aminocarbonylmethyl, azetidin-3-yl, benzyl, bicyclo[1.1.1]pentan-1-yl, cyanomethyl, cyclopentyl, cyclopropyl, difluoromethyl, fluoromethyl, hydroxycarbonylmethyl isopropyl, methyl, neopentyl, oxazol-2-yl, oxetan-2-ylmethyl, oxetan-3-yl, phenyl, piperidin-4-yl, pivalylmethyl, pyridin-2-ylmethyl, pyridin-3-yl, pyridin-4-yl, pyrimidin-2-yl, pyrrolidin-1-yl)ethyl, quinuclidin-3-yl, tert-butyl, and tetrahydro-2H-pyran-4-yl.

In one embodiment, R³ is triazolyl, pyrazolyl, isoxazolyl, isoxazolyl, oxazolyl, pyrazinyl, pyridinyl, pyrimidinyl, imidazolyl, thiadiazolyl, tetrazolyl, or oxadiazolyl, wherein each is optionally substituted by one or more Z³ groups as described herein. In one embodiment, R³ is optionally substituted triazolyl (e.g., 1H-1,2,3-triazolyl).

In certain embodiments, R³ is triazolyl substituted with one or more substituents selected from the group consisting of 1-(benzyloxycarbonyl)piperidin-4-yl, 1-(tert-butyl)piperidin-4-yl, 1-ethylpiperidin-4-yl, cyclopropyl, isopropyl, methyl, and piperidin-4-yl.

In one embodiment, R³ is

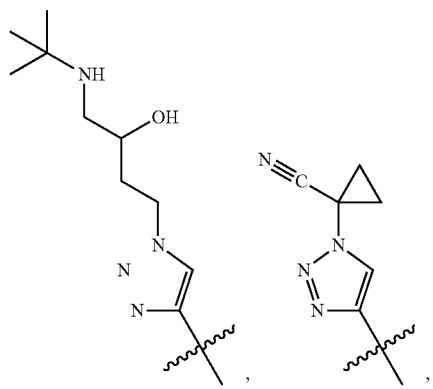

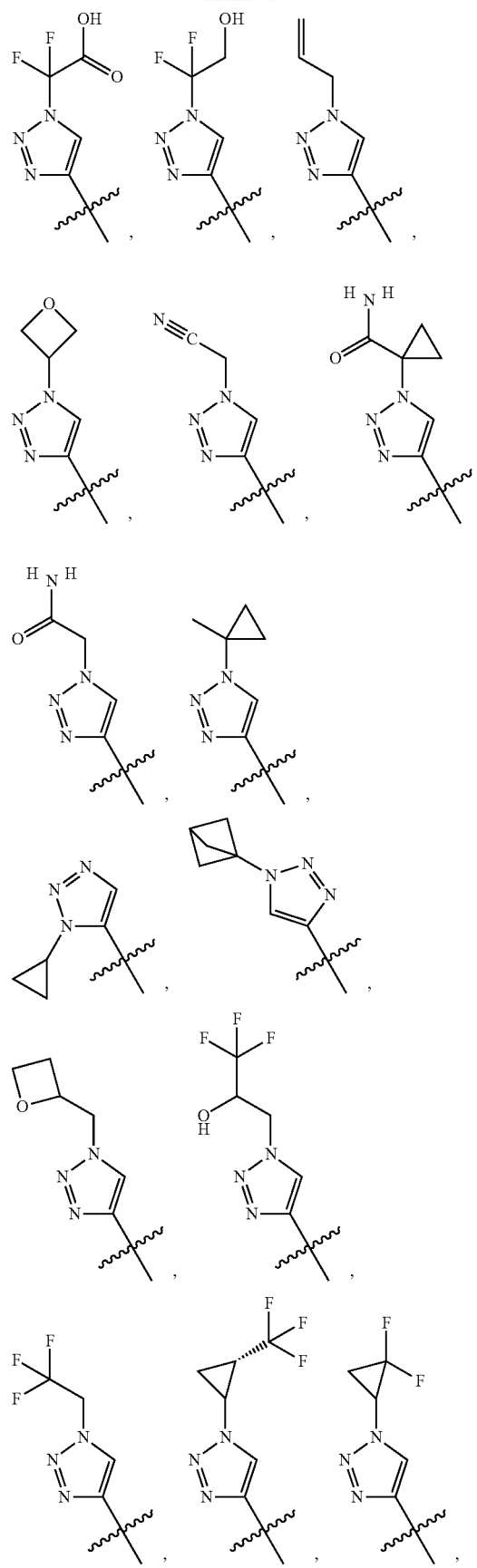

-continued
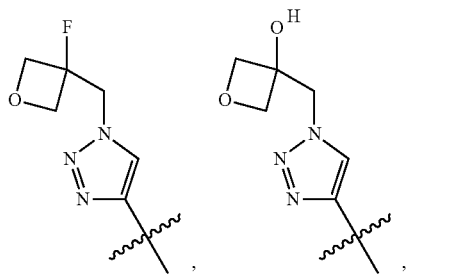
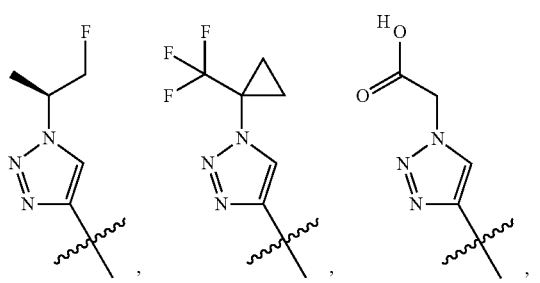
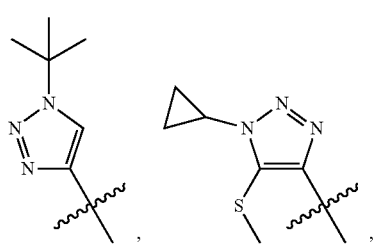
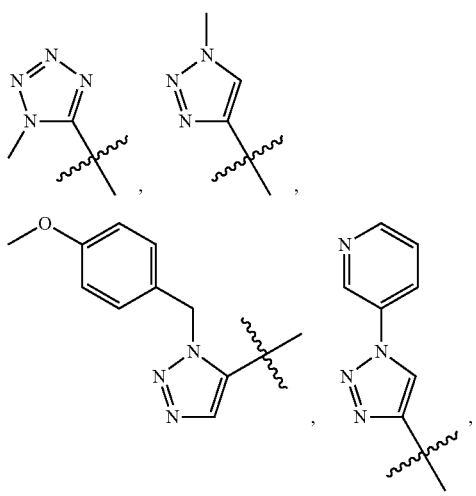
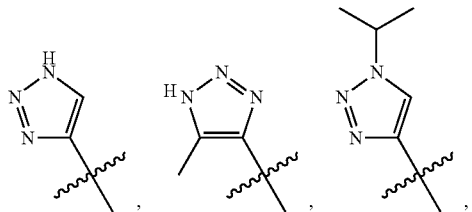
-continued
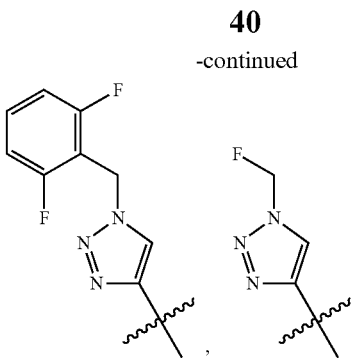
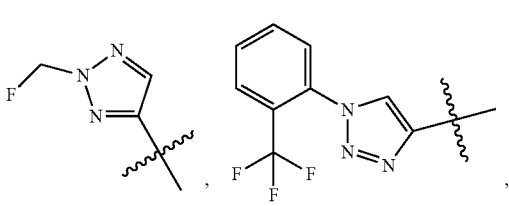
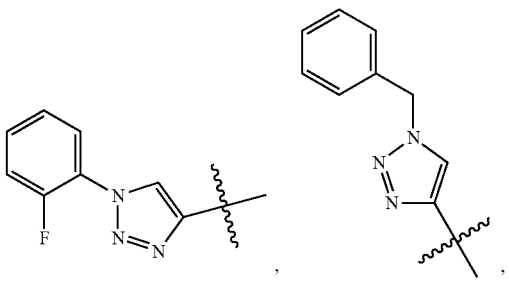
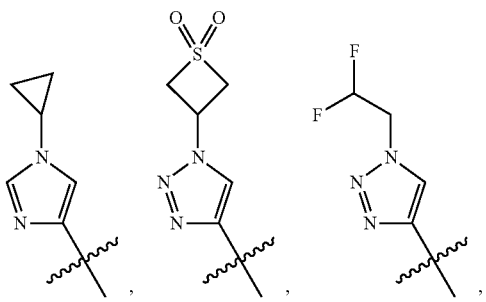
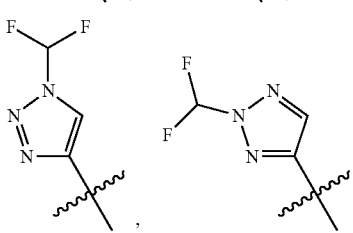
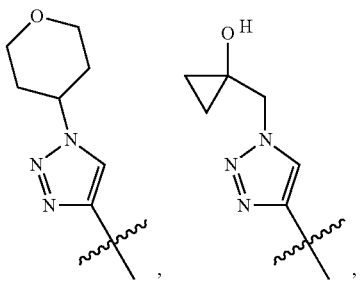

-continued
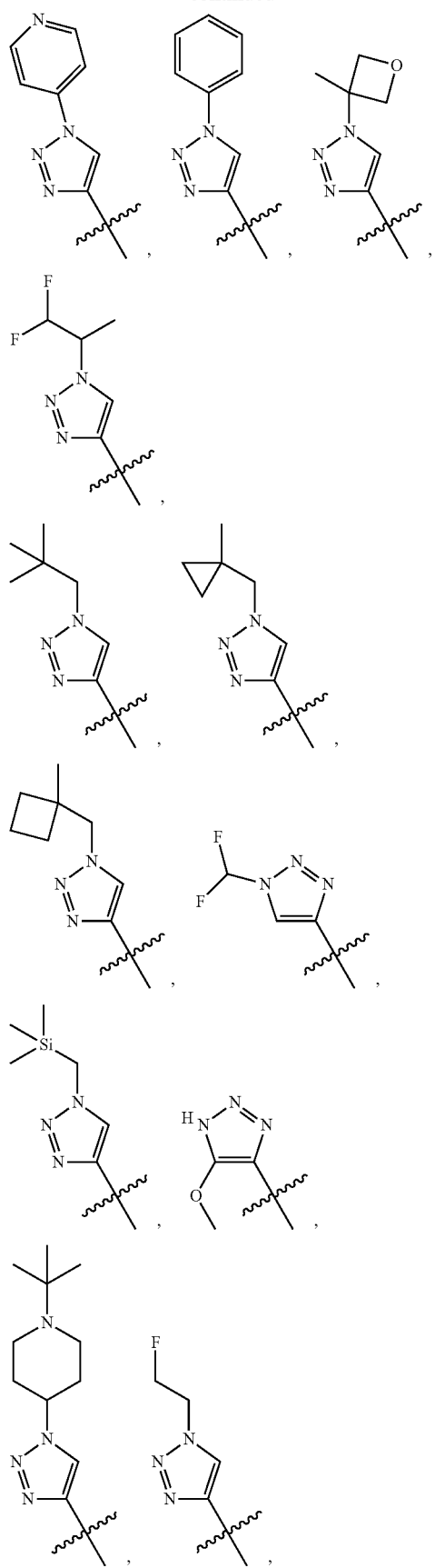
-continued
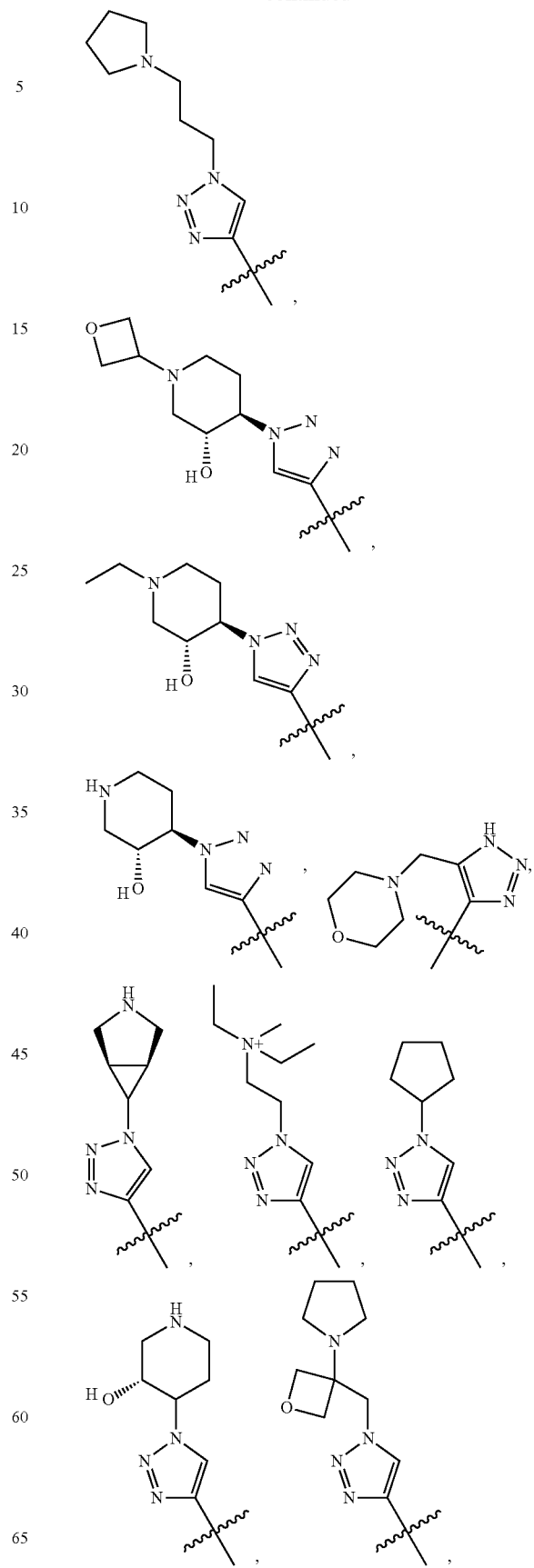

-continued
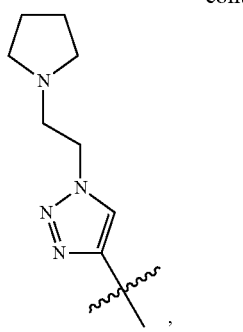
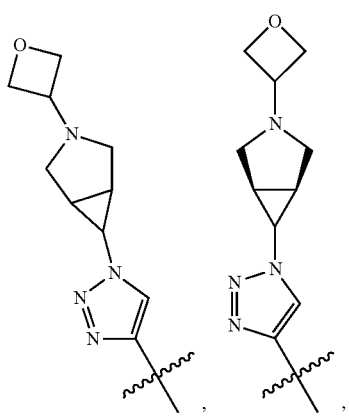
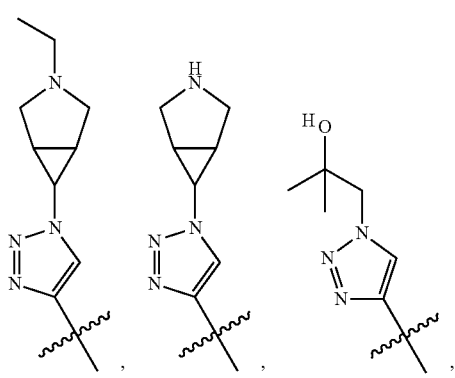
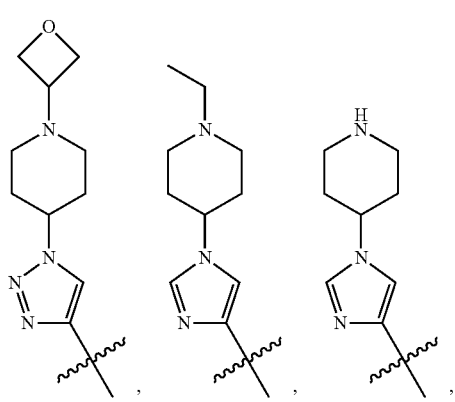
-continued
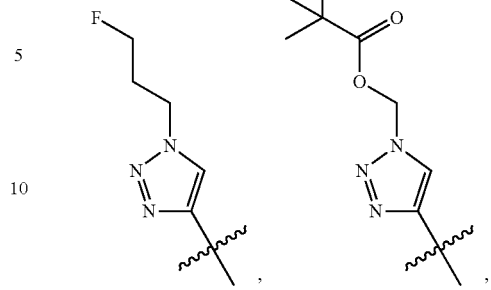
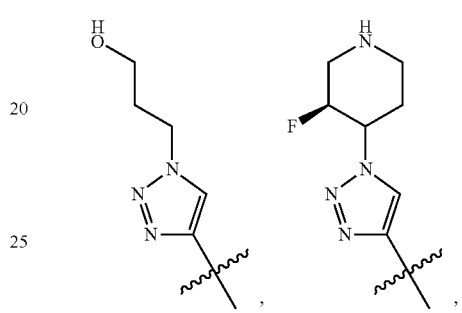
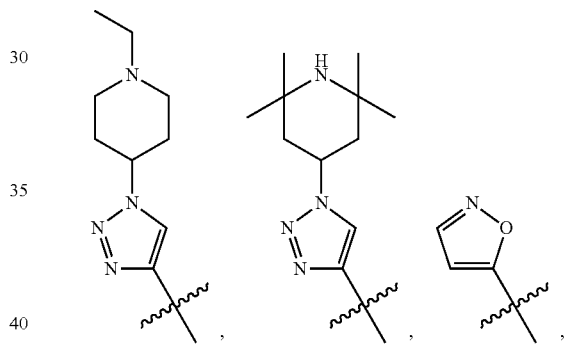
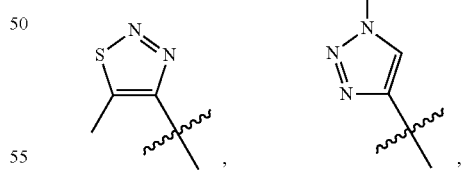
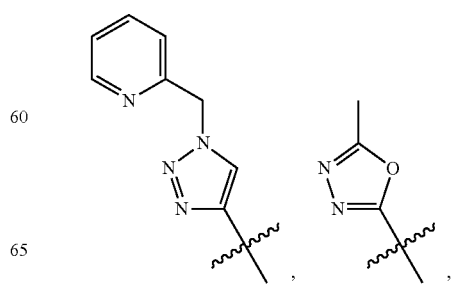

-continued
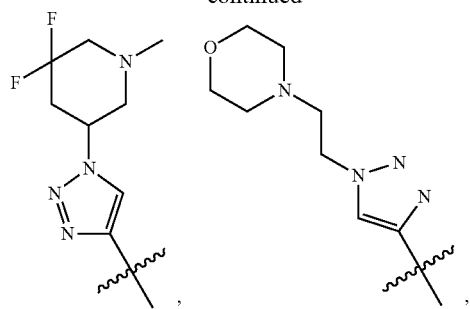
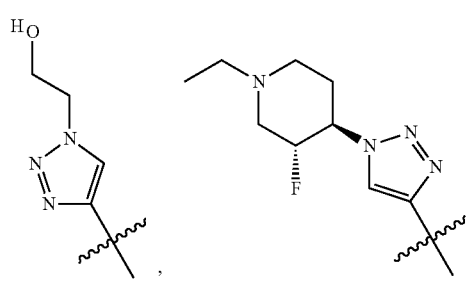
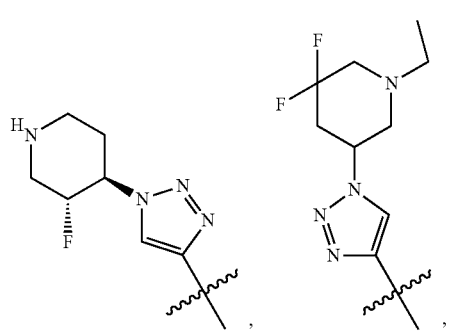
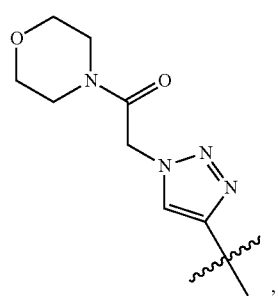
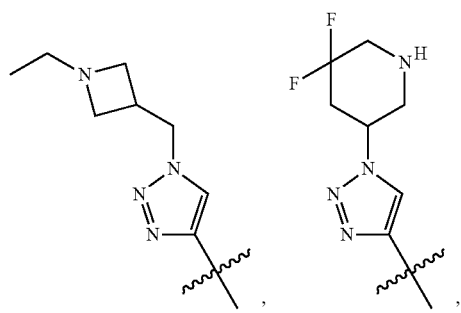
-continued
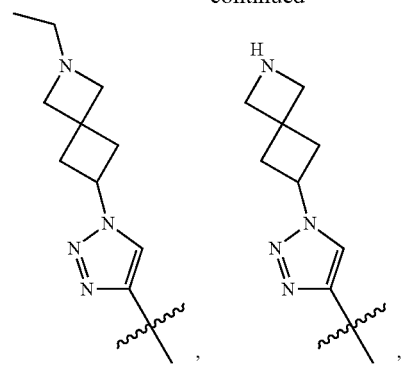
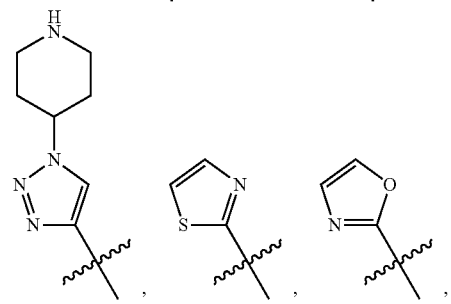
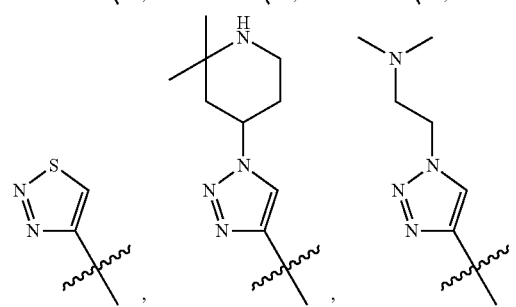
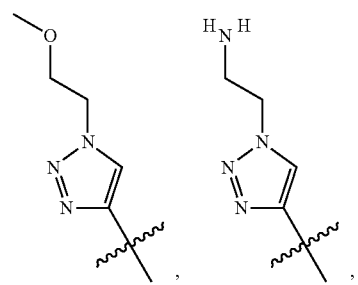
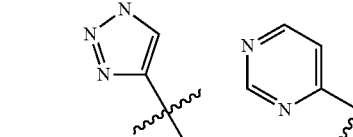
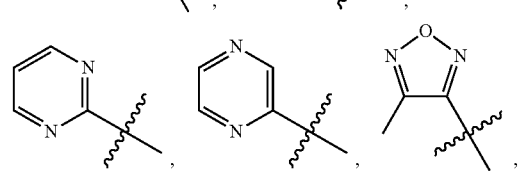

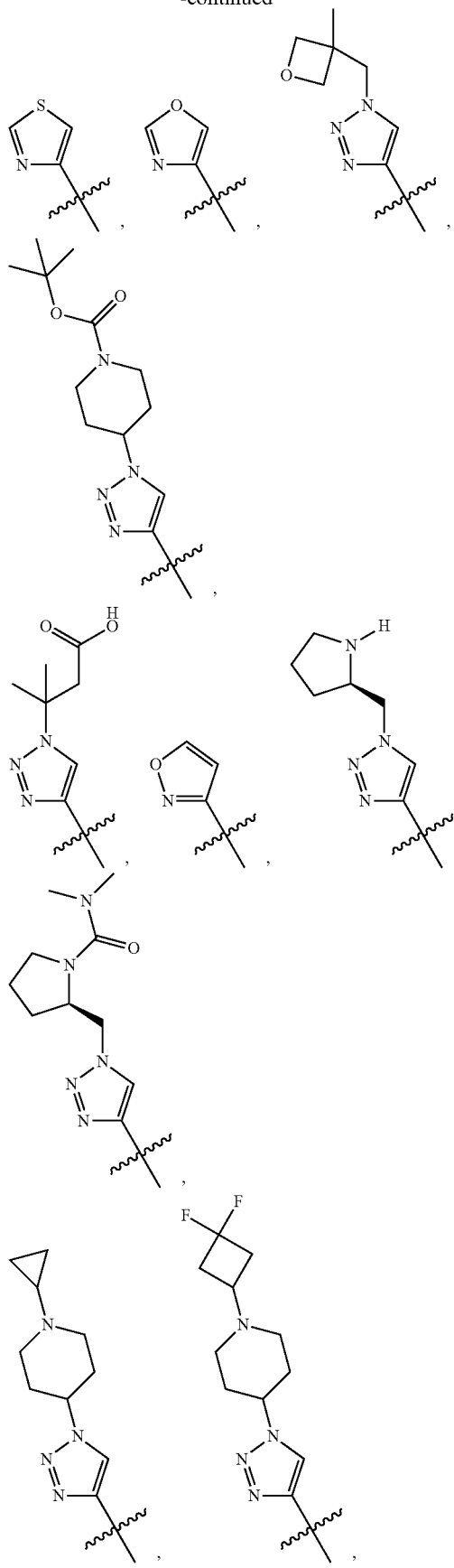
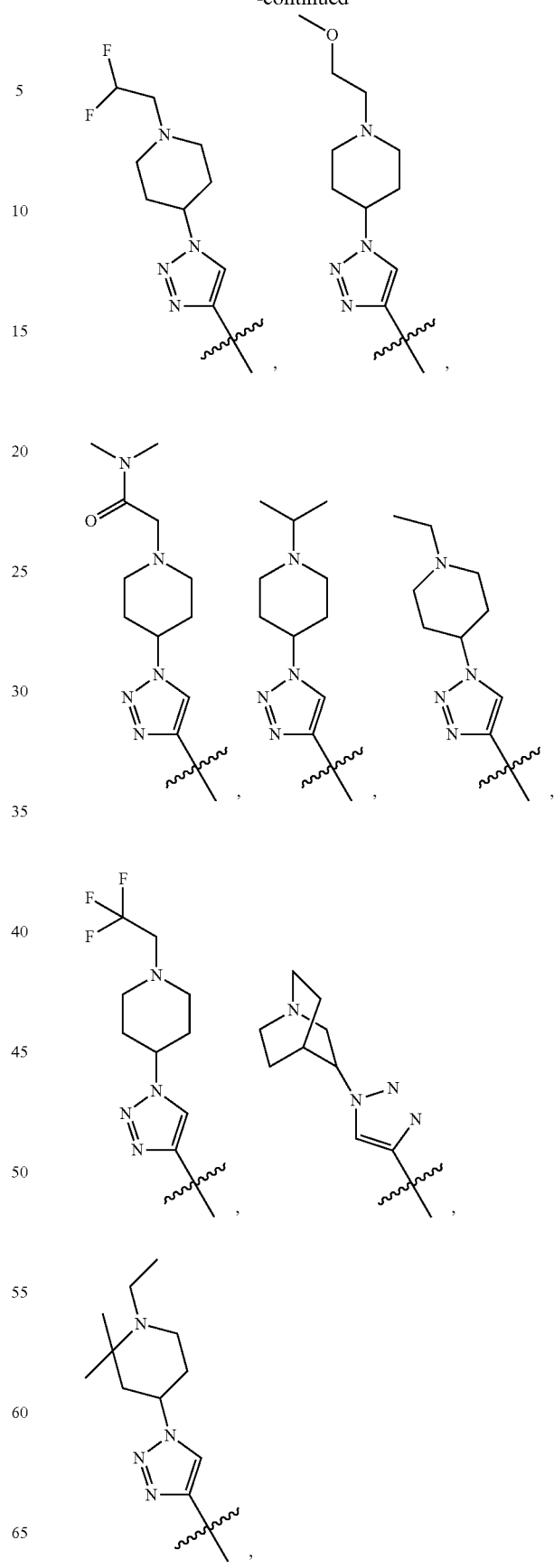

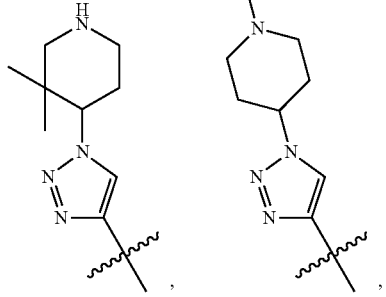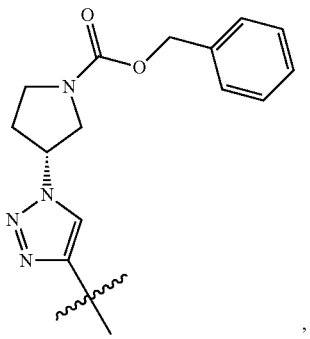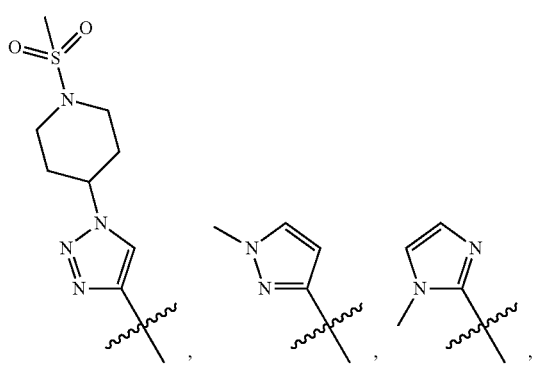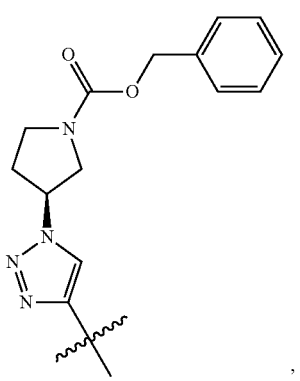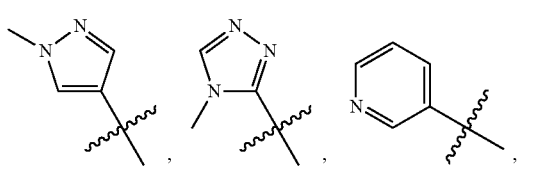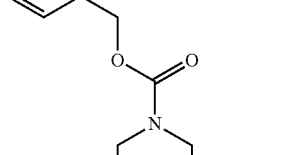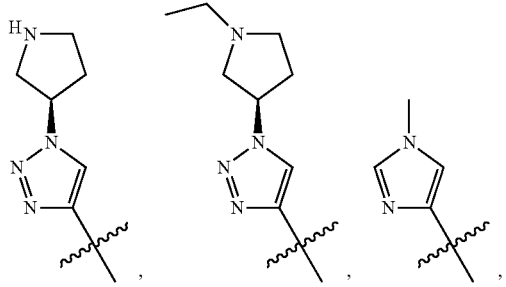
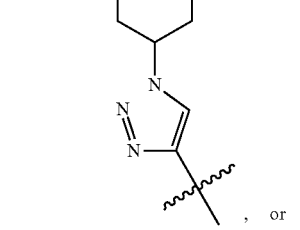, or 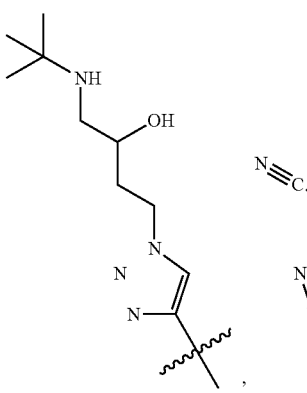.
In one embodiment, $R^3$ is
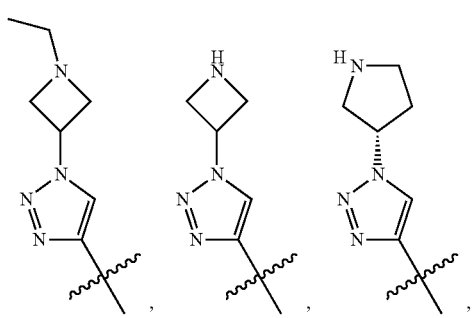

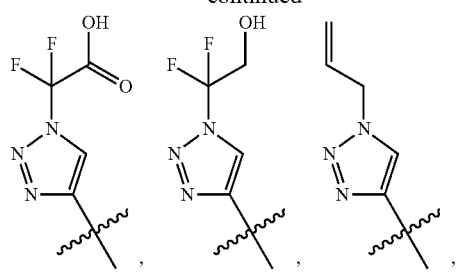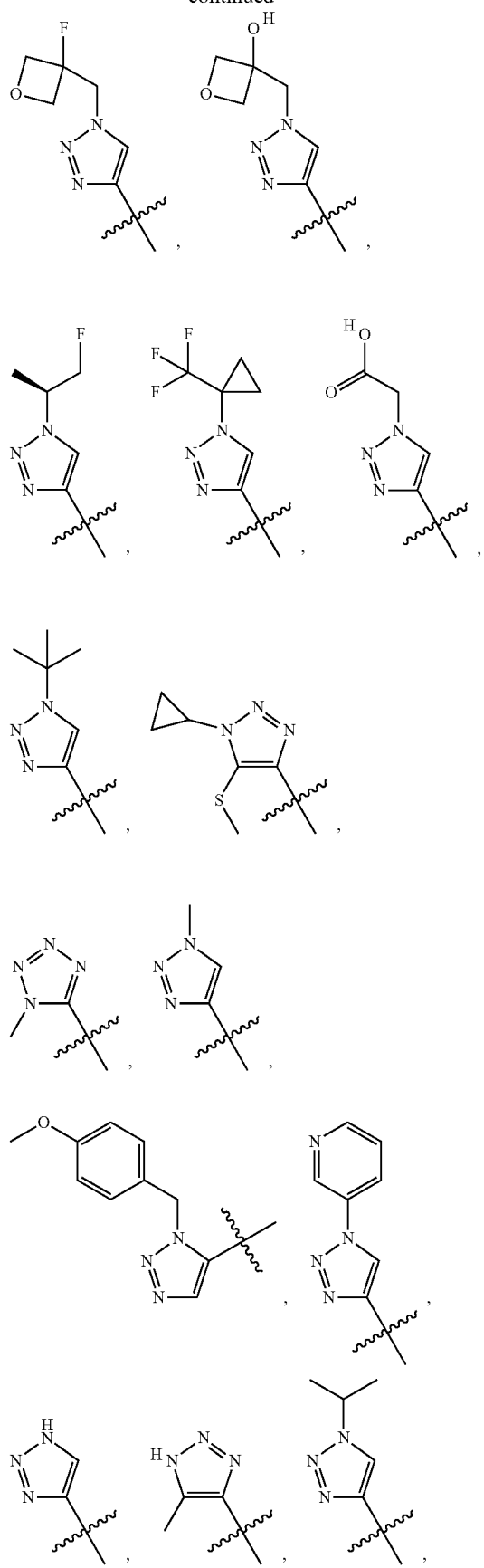

53
-continued
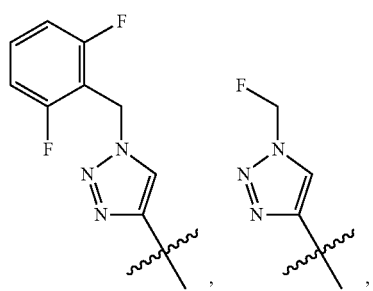
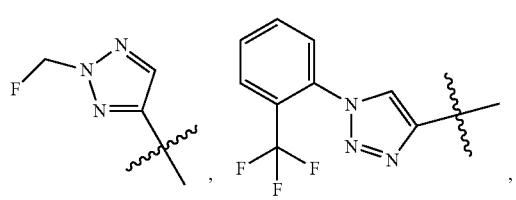
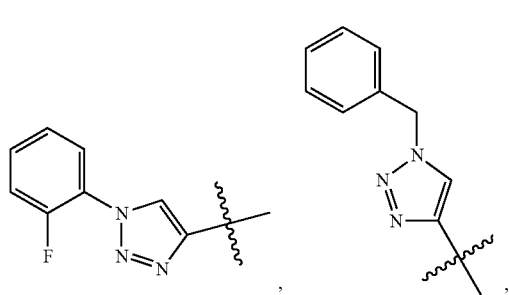
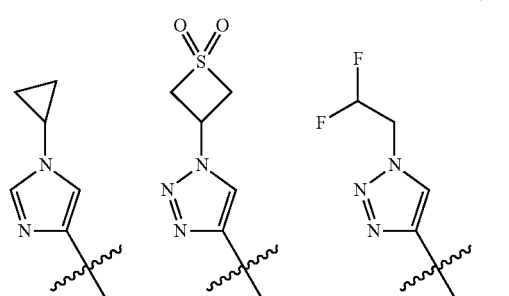
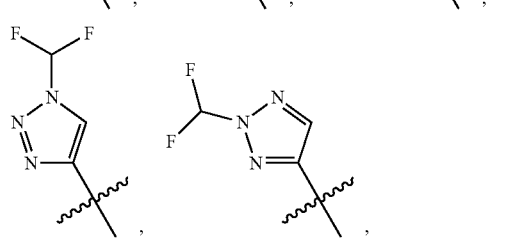
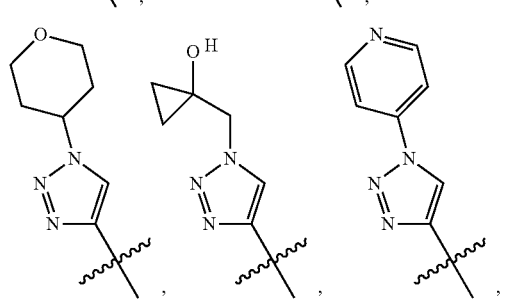
54
-continued
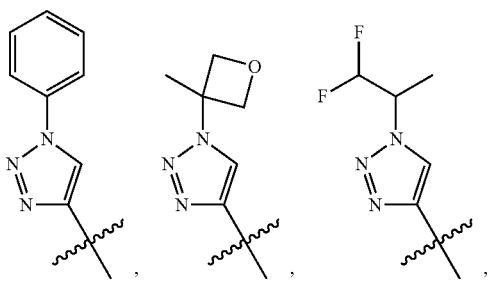
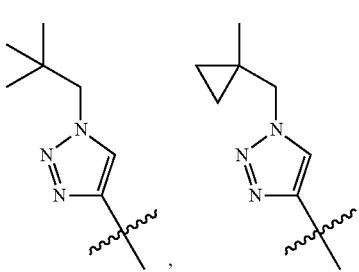
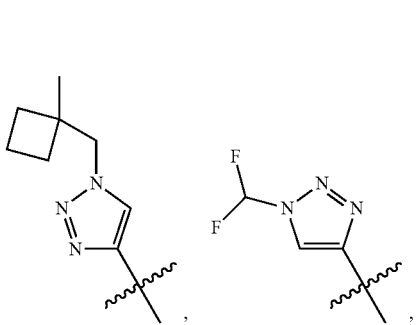
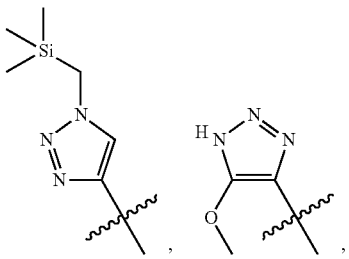
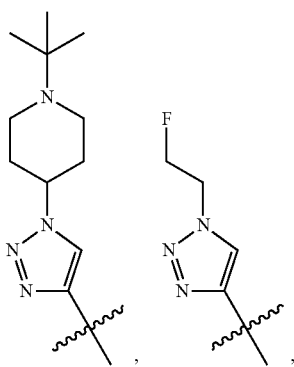

55
-continued
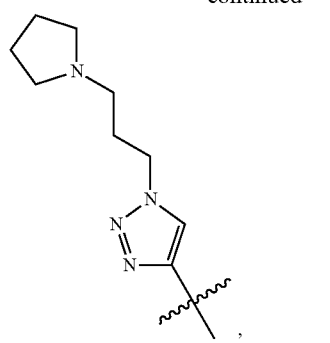
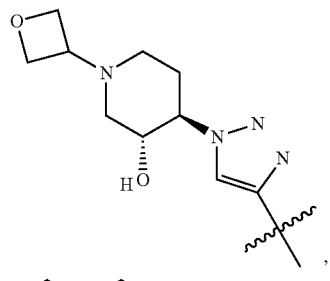
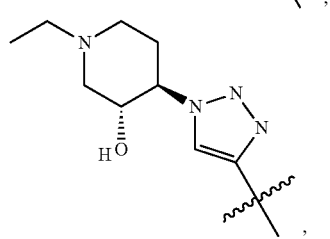
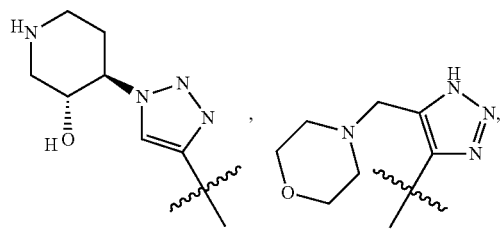
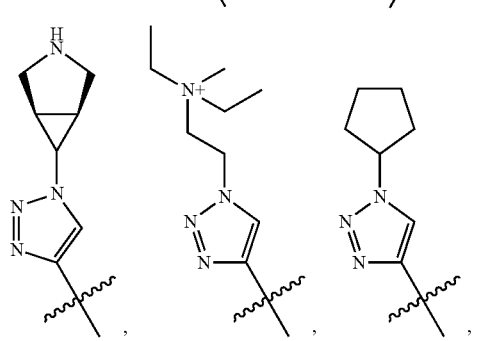
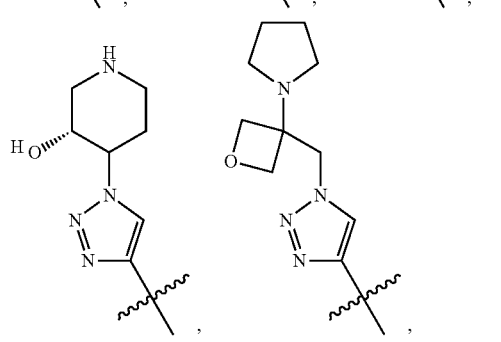
56
-continued
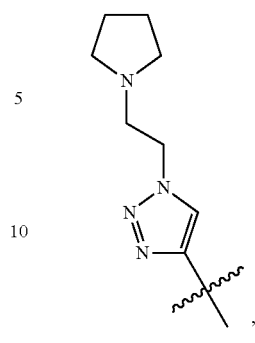
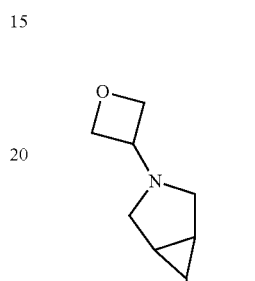
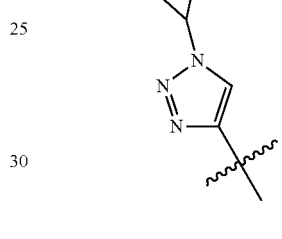
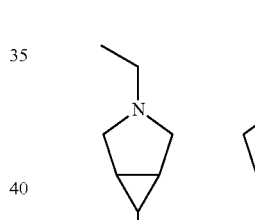
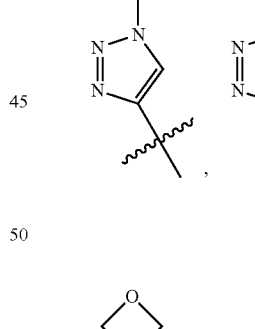
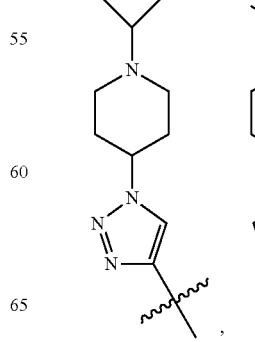
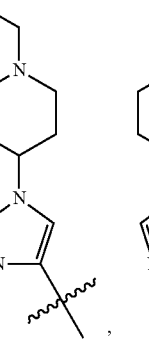

57
-continued
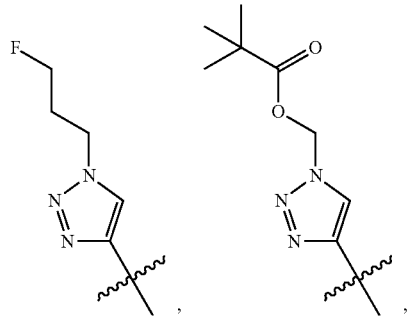
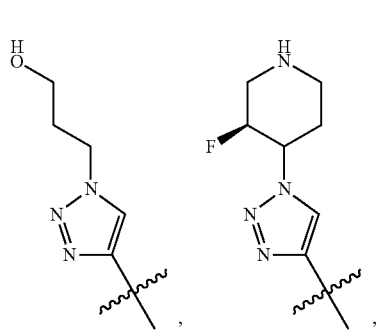
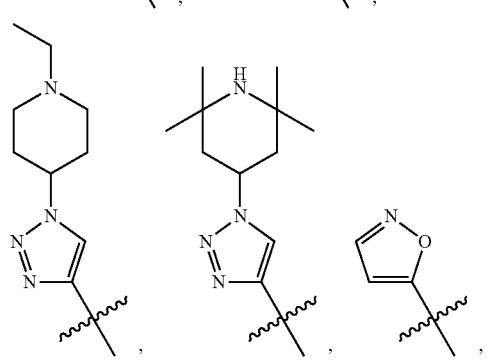
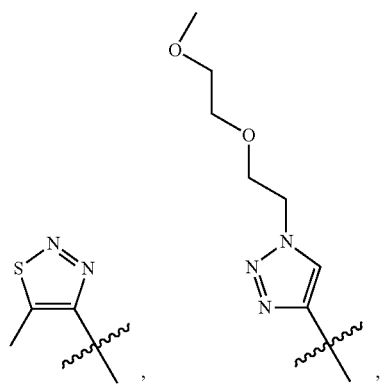
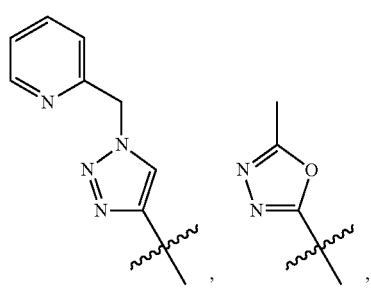
58
-continued
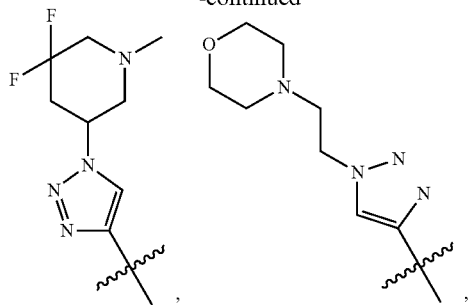
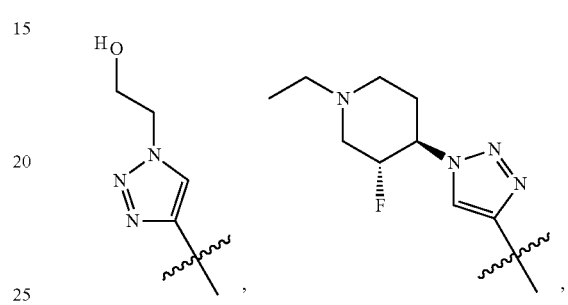
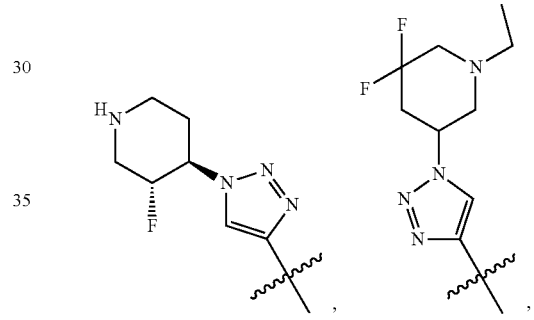
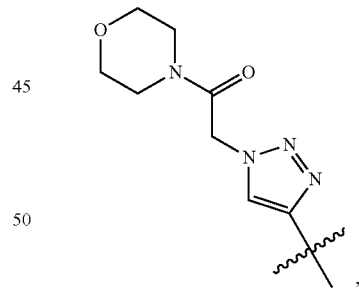
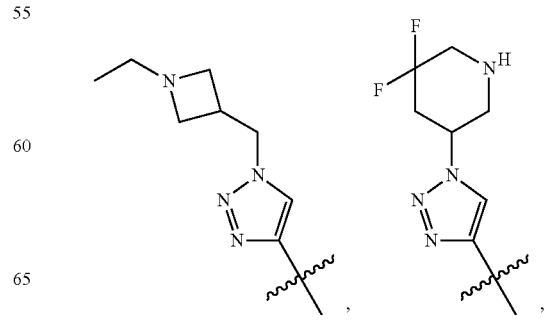

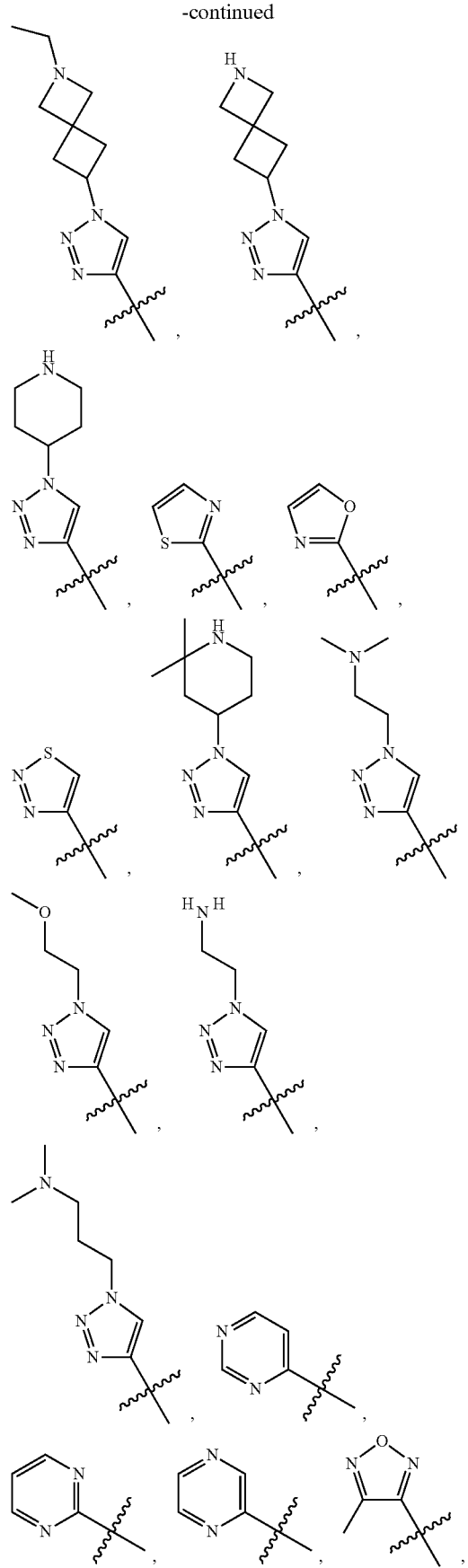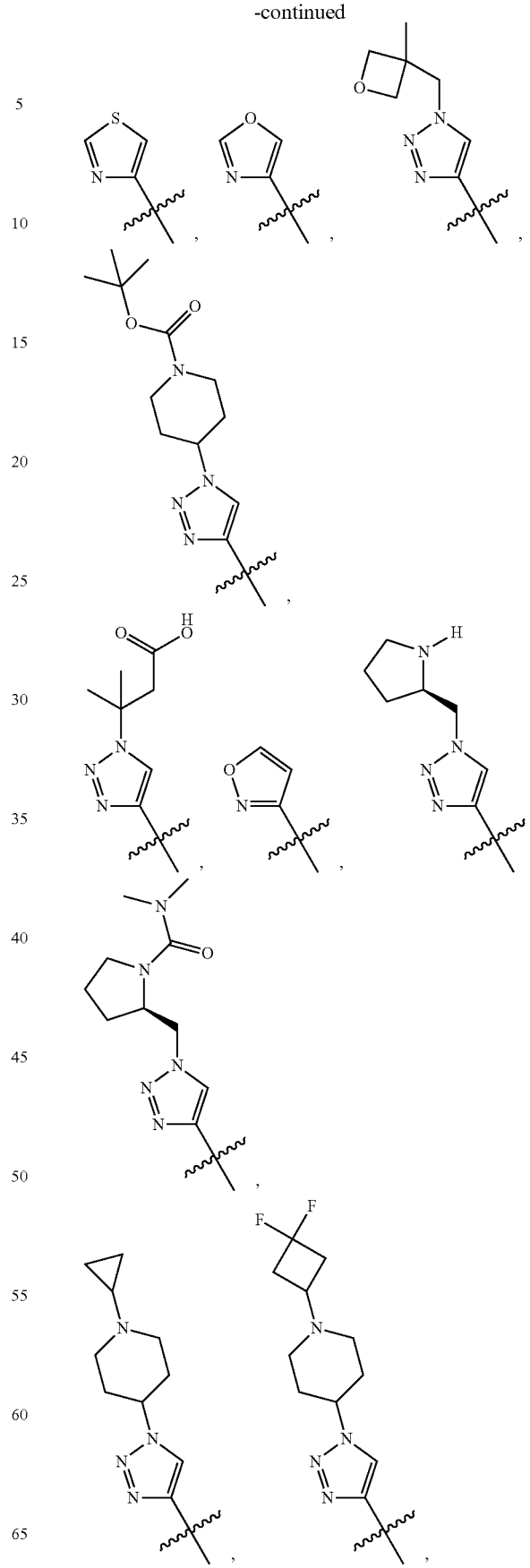

61
-continued
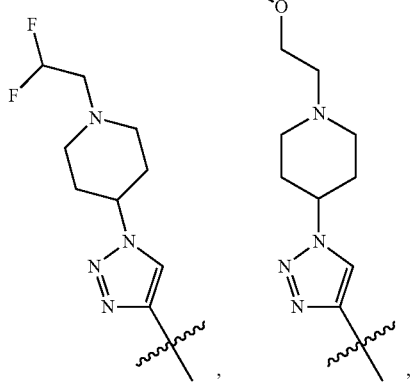
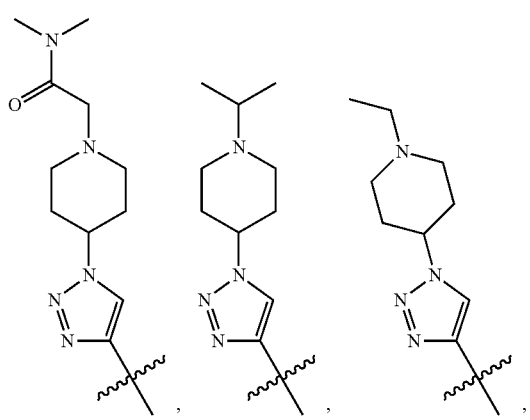
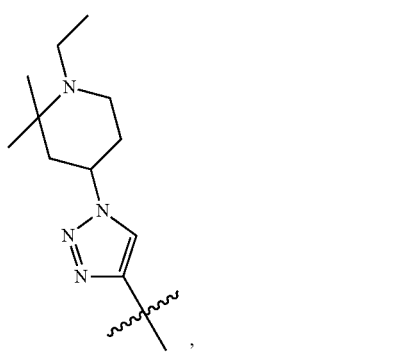
62
-continued
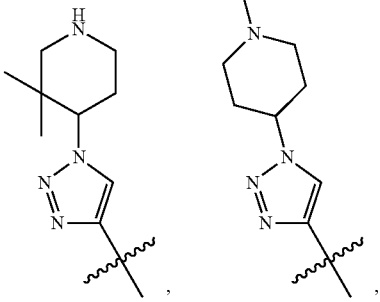
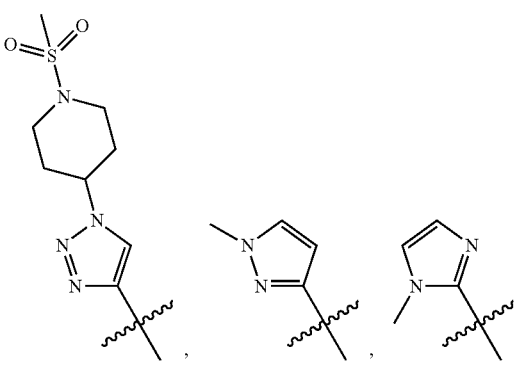
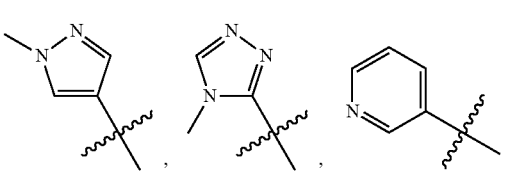
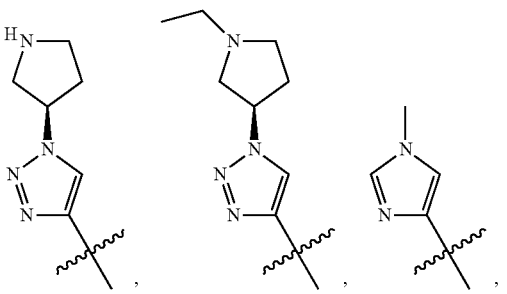
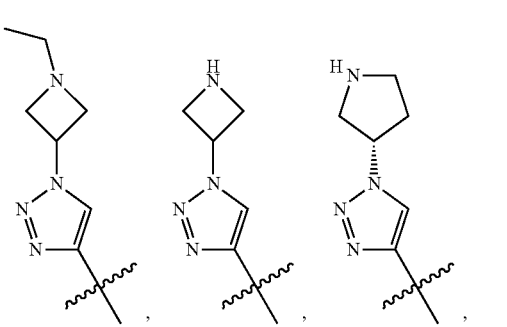

63
-continued
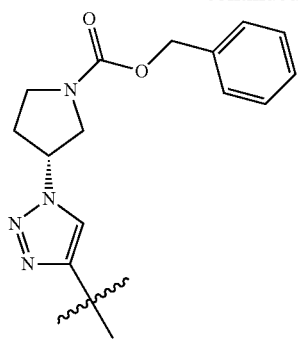
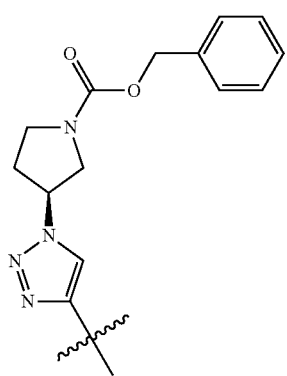
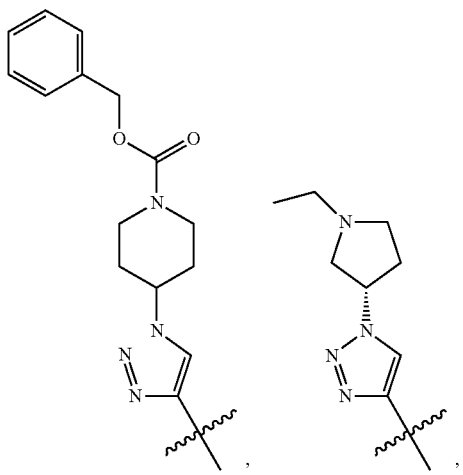
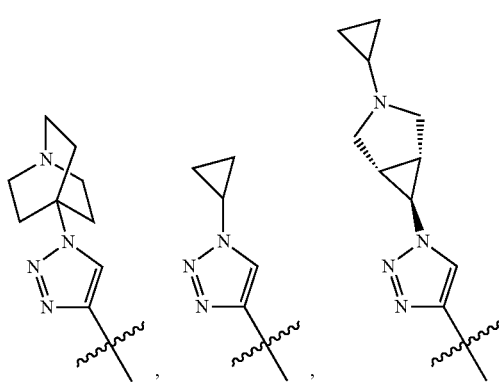
64
-continued
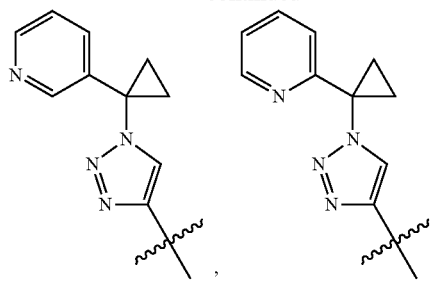
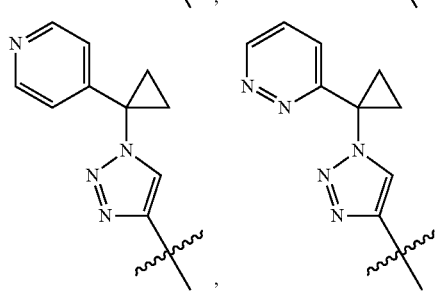
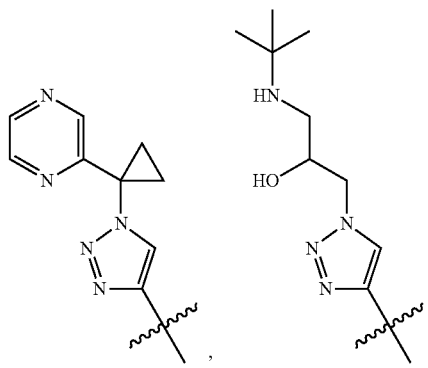
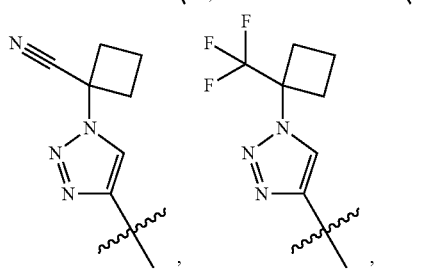
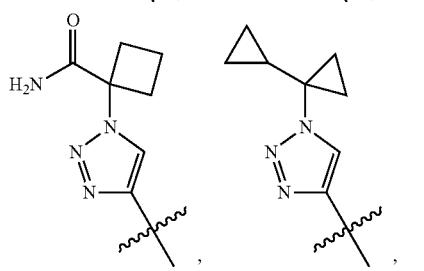
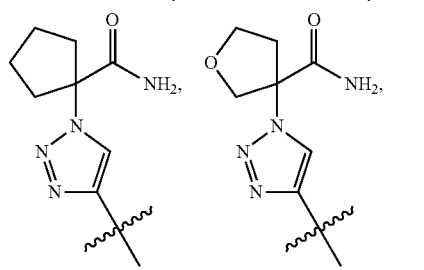

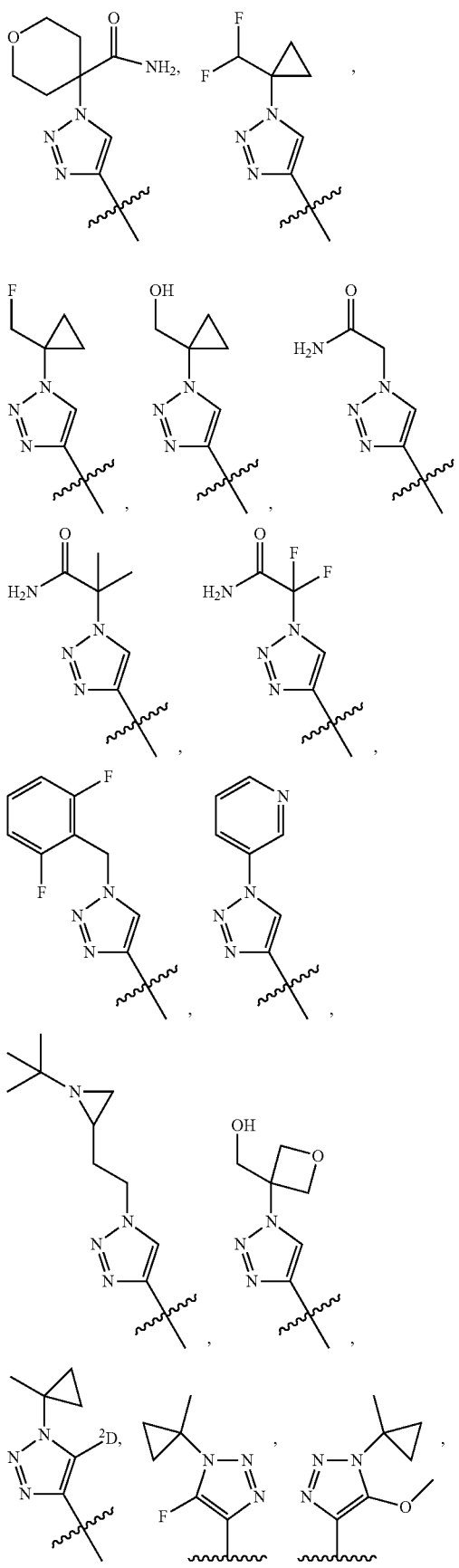
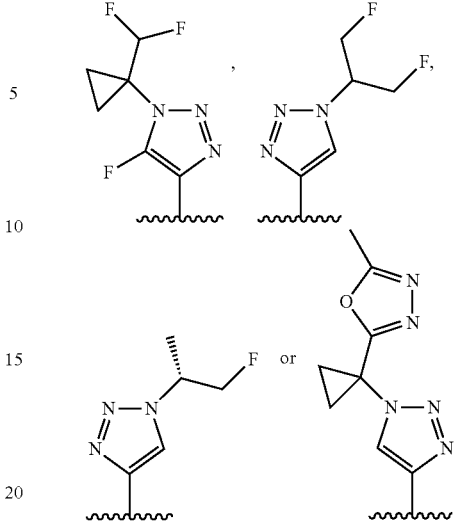

In certain embodiments, $R^4$ is aryl optionally substituted with one to three substituents independently selected from the group consisting of —CN, halo, —O—$R^{12}$, —C(O)—$R^{12}$, $C_{1-9}$ alkyl, $C_{1-9}$ haloalkyl, and heterocyclyl.

(2-(difluoromethyl)phenyl, (2-(hydroxymethyl)phenyl, [1,1'-biphenyl]-2-yl, [1,1'-biphenyl]-3-yl, 1-methylphenyl, 2-((dimethylamino)methyl)phenyl, 2-(difluoromethyl)phenyl, 2-(hydroxycarbonyl)phenyl, 2-(hydroxymethyl)phenyl, 2-(morpholinomethyl)phenyl, 2-(trifluoromethoxy)phenyl, 2-(trifluoromethyl)phenyl, 2,3-dichlorophenyl, 2,3-difluorophenyl, 2,4,6-trifluorophenyl, 2,4-difluorophenyl, 2-chloro-3-cyanophenyl, 2-chloro-4-fluorophenyl, 2-chloro-5-cyanophenyl, 2-chloro-6-fluorophenyl, 2-chlorophenyl, 2-cyanophenyl, 2-fluorophenyl, 2-methylphenyl, 2-methyl-3-(1H-1,2,3-triazol-1-yl)phenyl, 2-methyl-3-(1H-1,2,4-triazol-1-yl)phenyl, 2-methyl-3-(1H-pyrazol-1-yl)phenyl, 2-methyl-3-(1H-tetrazol-1-yl)phenyl, 2-methyl-3-(2H-1,2,3-triazol-2-yl)phenyl, 2-methyl-3-(4H-1,2,4-triazol-4-yl)phenyl, 2-methyl-3-(oxazol-2-yl)phenyl, 3-(((2-(dimethylamino)ethyl)(methyl)amino)methyl)phenyl, 3-(((2-(dimethylamino)ethyl)amino)methyl)phenyl, 3-((2-(dimethylamino)ethoxy)methyl)phenyl, 3-((3,3-difluoroazetidin-1-yl)methyl)phenyl, 3-((dimethylamino)methyl)phenyl, 3-(1,1-dioxidoisothiazolidin-2-yl)phenyl, 3-(1,3-dioxolan-2-yl)phenyl, 3-(1H-1,2,4-triazol-1-yl)phenyl, 3-(1H-imidazol-1-yl)-2-methylphenyl, 3-(1H-imidazol-1-yl)phenyl, 3-(1H-pyrazol-1-yl)phenyl, 3-(1-hydroxy-2,2-dimethylpropyl)phenyl, 3-(1-hydroxyethyl)phenyl, 3-(1-methyl-1H-imidazol-2-yl)phenyl, 3-(2-hydroxypropan-2-yl)phenyl, 3-(2-methylazetidine-1-carbonyl)phenyl, 3-(2-oxoazetidin-1-yl)phenyl, 3-(2-oxopiperidin-1-yl)phenyl, 3-(2-oxopyrrolidin-1-yl)phenyl, 3-(3-(dimethylamino)azetidine-1-carbonyl)phenyl, 3-(3,3-difluoroazetidine-1-carbonyl)phenyl, 3-(3-fluoroazetidine-1-carbonyl)phenyl, 3-(3-hydroxyazetidine-1-carbonyl)phenyl, 3-(3-methoxyazetidine-1-carbonyl)phenyl, 3-(azetidine-1-carbonyl)phenyl, 3-(dimethylamino)phenyl, 3-(dimethylcarbamoyl)phenyl, 3-(ethyl(methyl)carbamoyl)phenyl, 3-(hydroxycarbonyl)phenyl, 3-(hydroxymethyl)phenyl, 3-(methoxycarbonyl)phenyl, 3-(methoxymethyl)phenyl, 3-(methylamino)phenyl, 3-(methylcarbamoyl)phenyl, 3-(methylsulfonamido)phenyl, 3-(methylsulfonyl)phenyl, 3-(morpholinomethyl)phenyl, 3-(N,N-dimethylaminosulfonyl)phenyl, 3-(N-methylacetamido)

phenyl, 3-(N-methylmethylsulfonamido)phenyl, 3-(oxazol-2-yl)phenyl, 3-(piperidine-1-carbonyl)phenyl, 3-(pyrrolidin-1-ylmethyl)phenyl, 3-(pyrrolidine-1-carbonyl)phenyl, 3-(thiazol-2-yl)phenyl, 3-(trifluoromethyl)phenyl, 3,4,5-trifluorophenyl, 3,4-dichlorophenyl, 3,4-difluorophenyl, 3,5-bis(trifluoromethyl)phenyl, 3-acetamidophenyl, 3-acetylphenyl, 3-aminophenyl, 3-carbamoylphenyl, 3-chlorophenyl, 3-cyano-2-methylphenyl, 3-cyano-4-fluorophenyl, 3-cyanophenyl, 3-fluorophenyl, 3-formylphenyl, 3-iodophenyl, 3-methoxyphenyl, 3-tert-butylcarbonylphenyl, 4-((dimethylamino)methyl)phenyl, 4-(trifluoromethoxy)phenyl, 4-chlorophenyl, 4-cyanophenyl, 4-fluoro-2-methylphenyl, 4-fluorophenyl, 4-methylphenyl, naphthalen-1-yl, naphthalen-2-yl, N-methyl-3-carbamoylphenyl, or phenyl.

In one embodiment, $R^4$ is

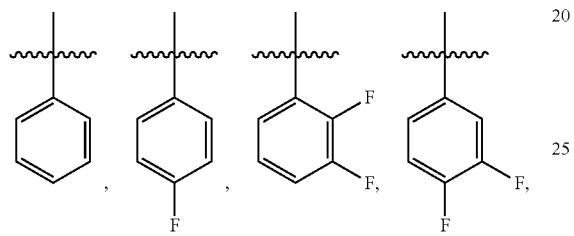

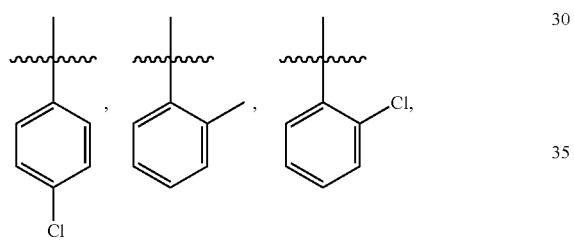

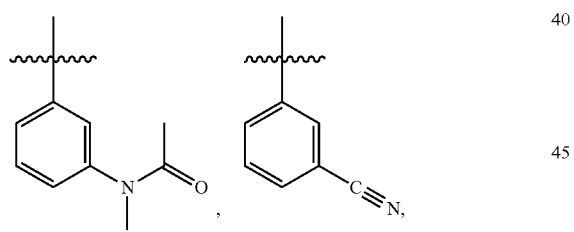

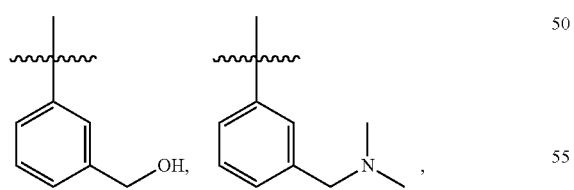

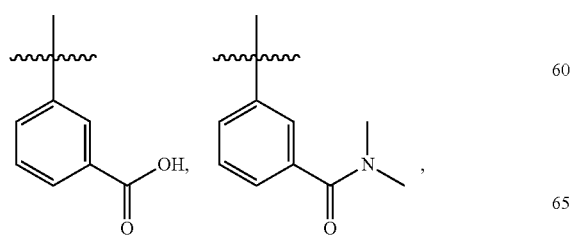

-continued

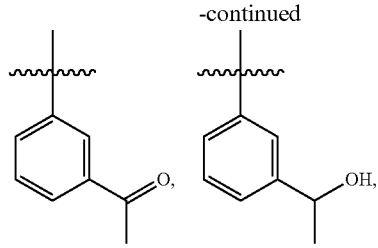

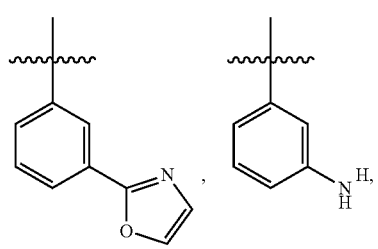

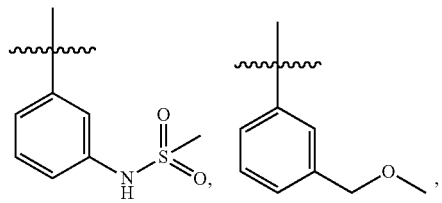

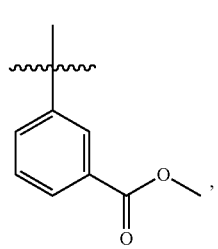

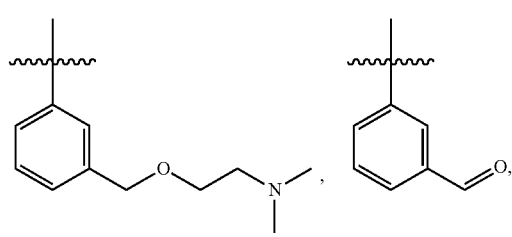

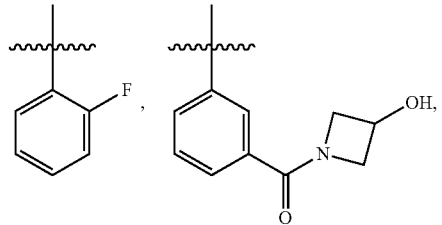

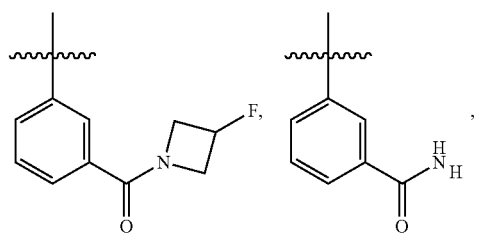

-continued
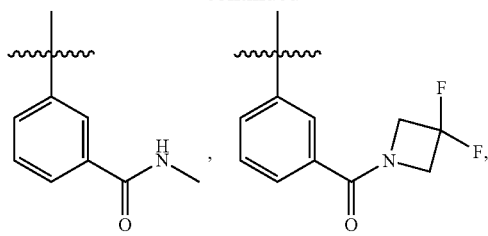
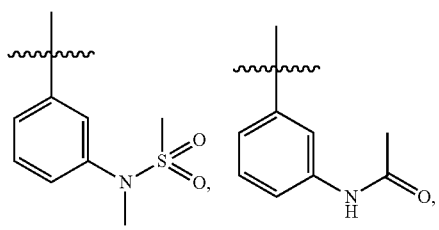
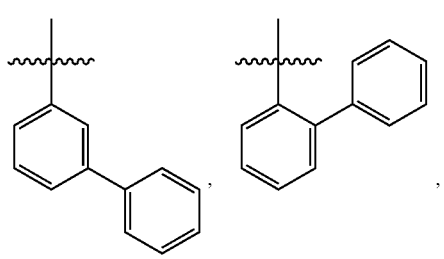
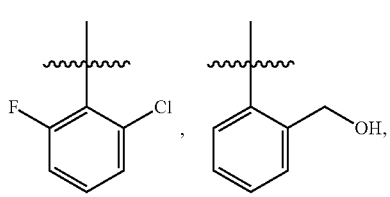
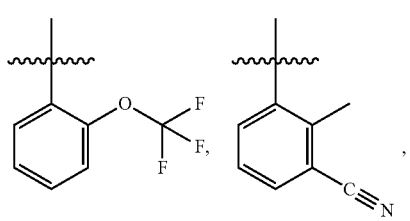
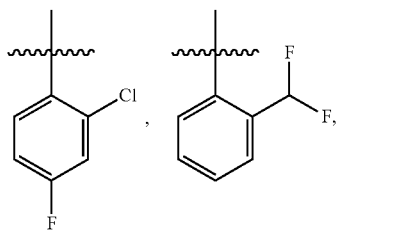
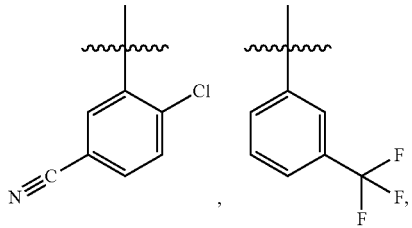
-continued
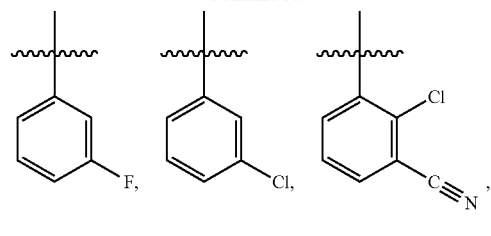
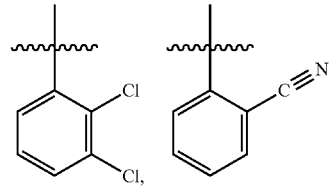
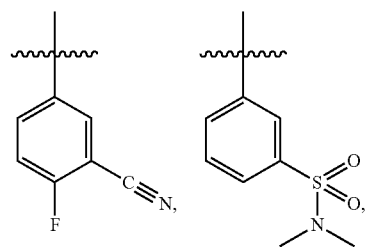
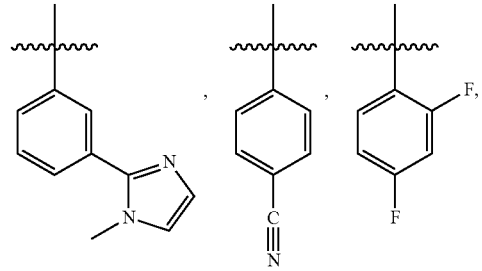
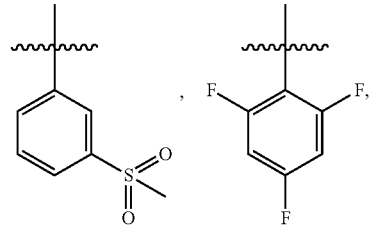
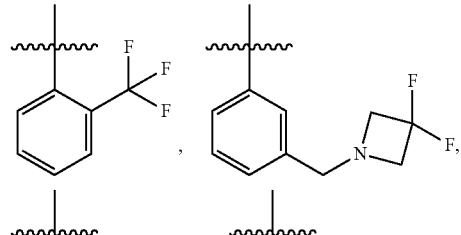
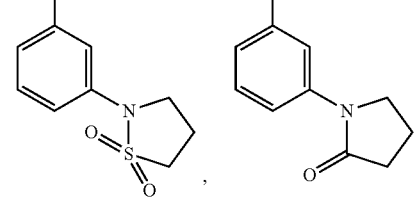

71
-continued
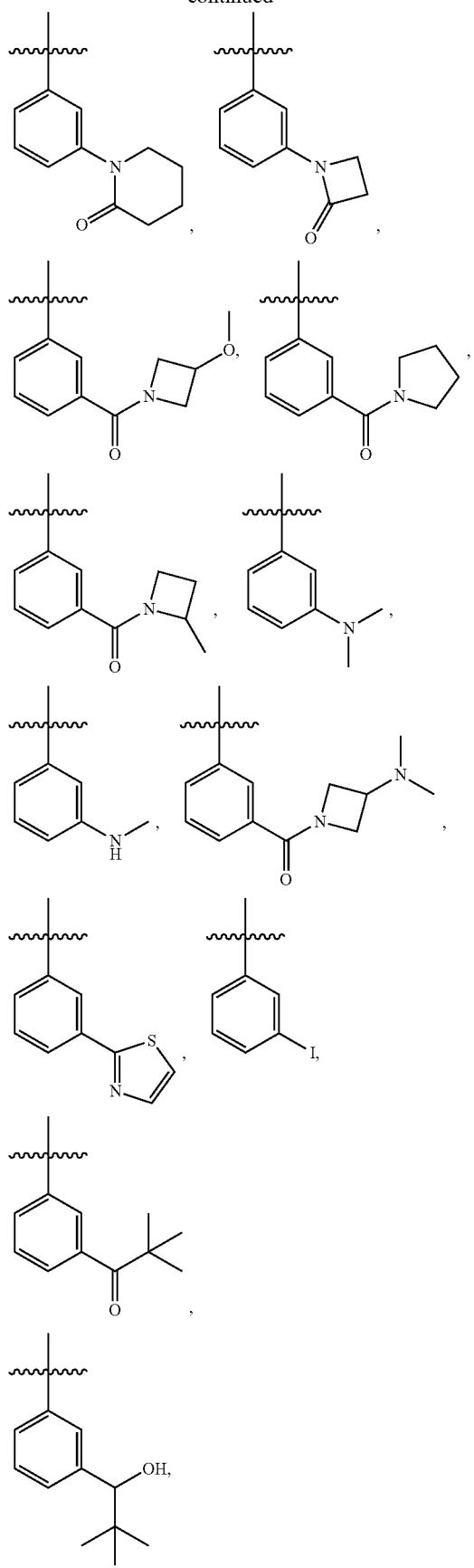
72
-continued
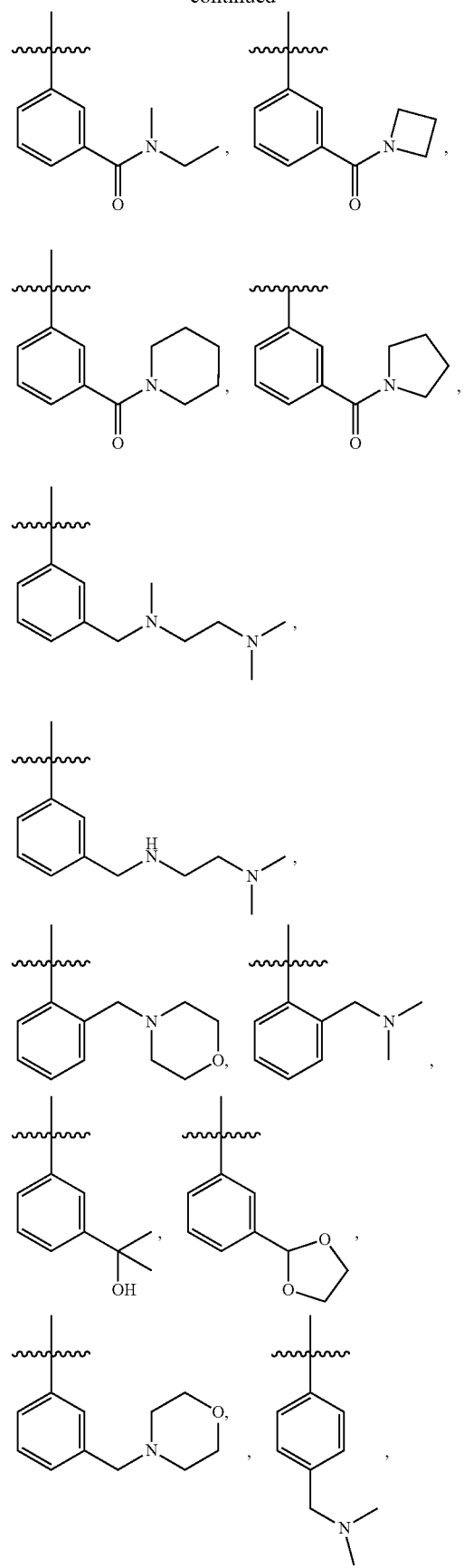

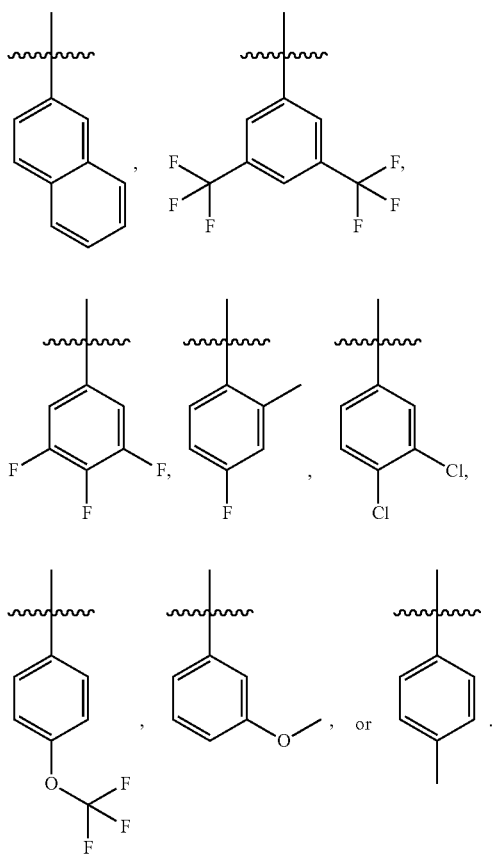
In one embodiment, R⁴ is
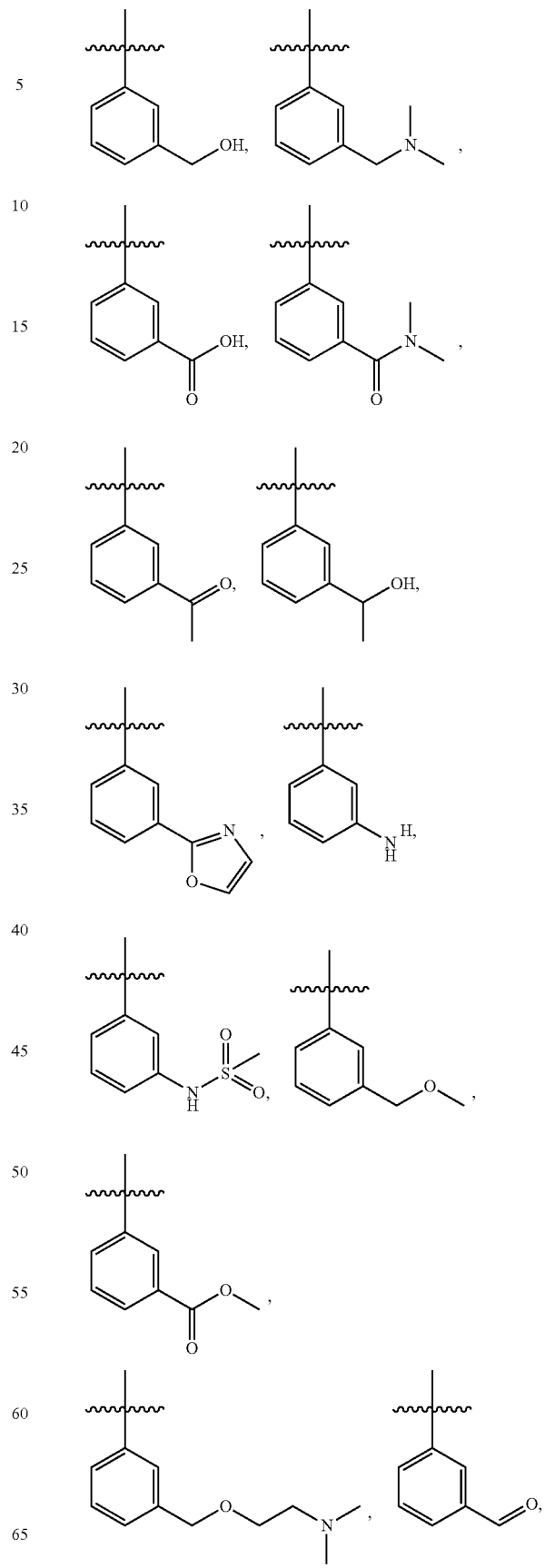

-continued
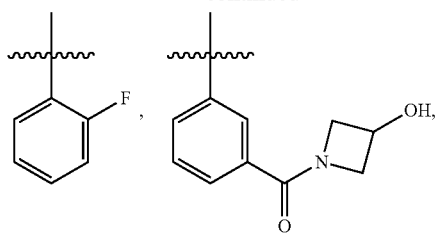
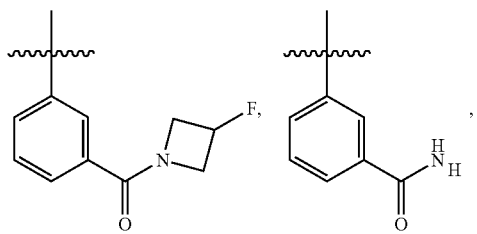
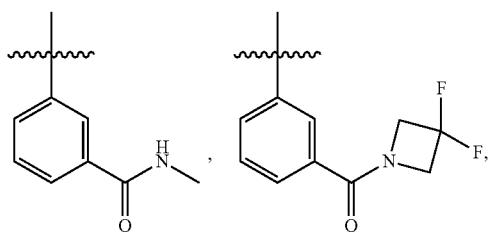
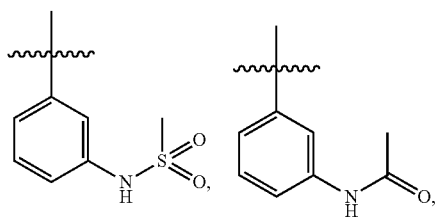
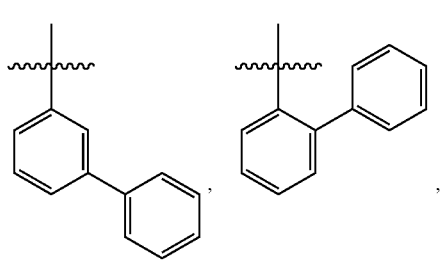
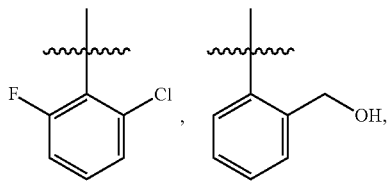
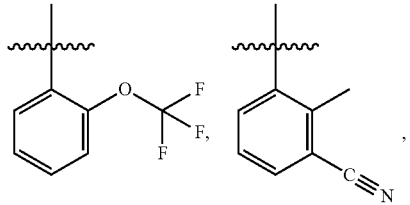
-continued
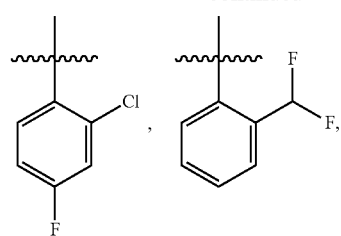
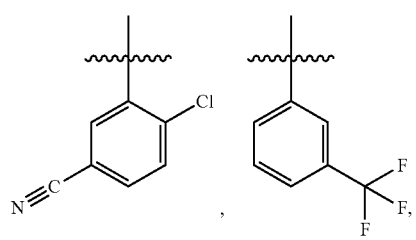
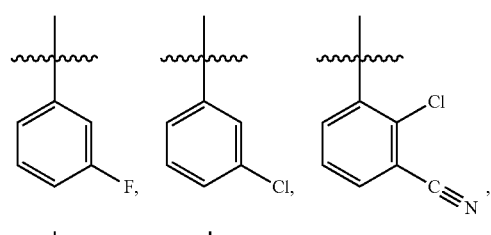
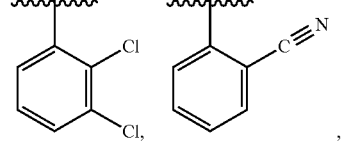
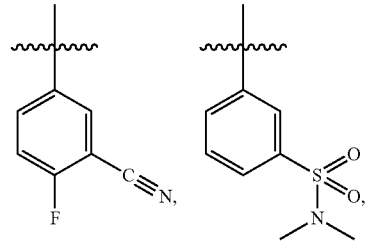
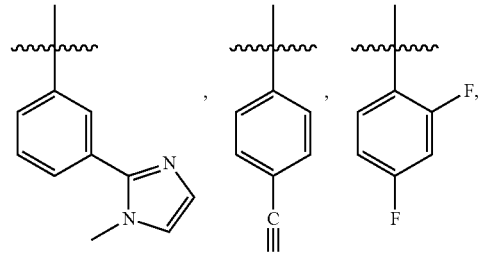
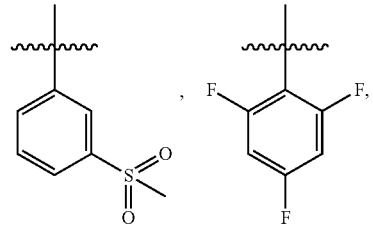

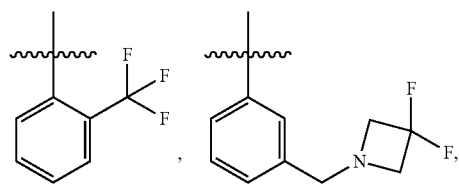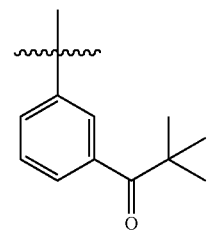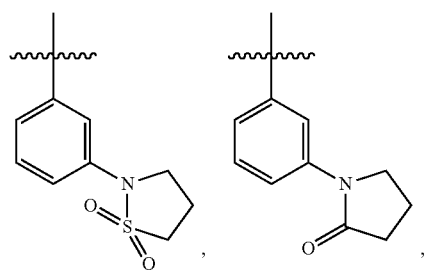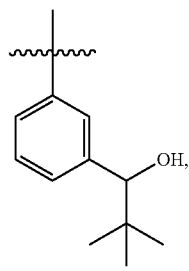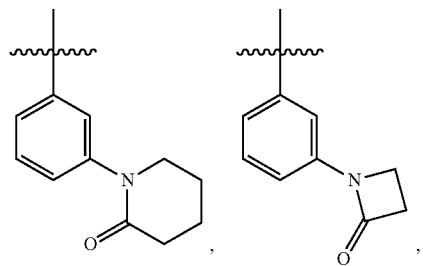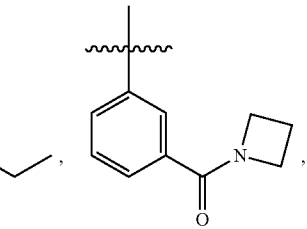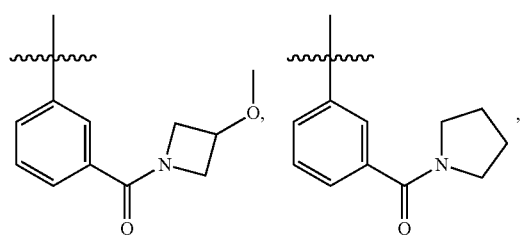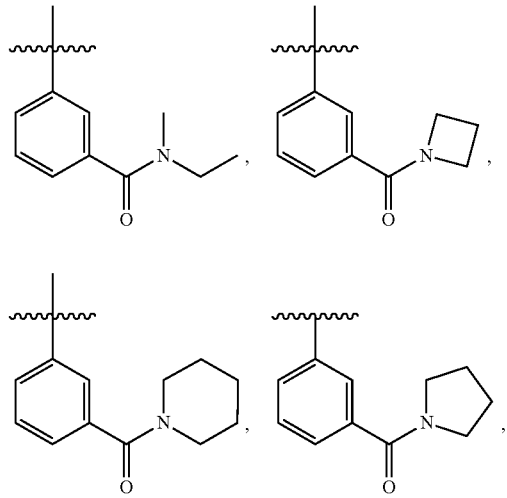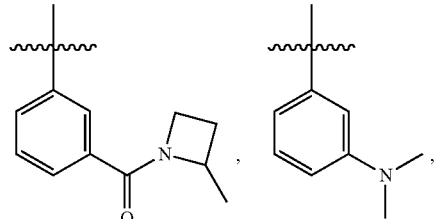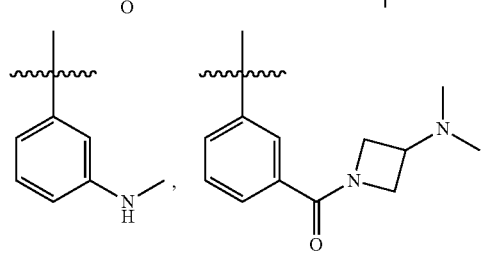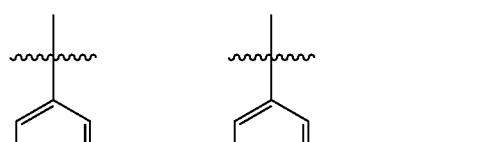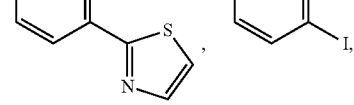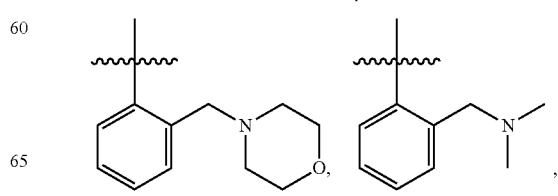

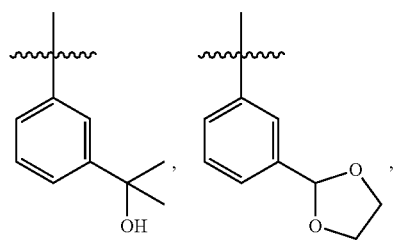
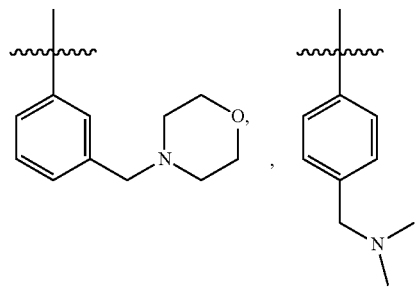
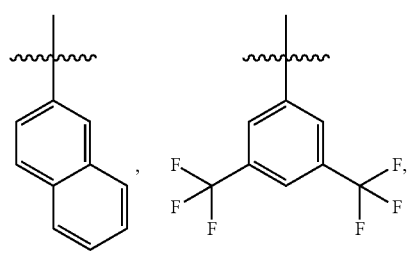
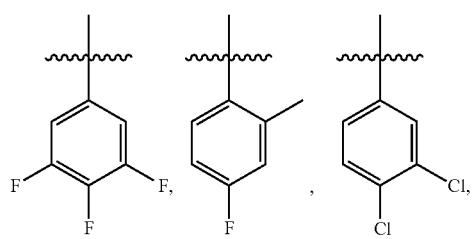
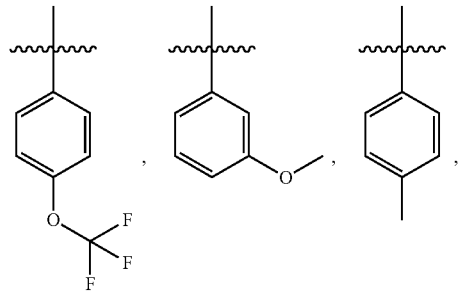
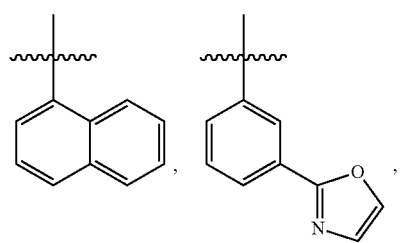
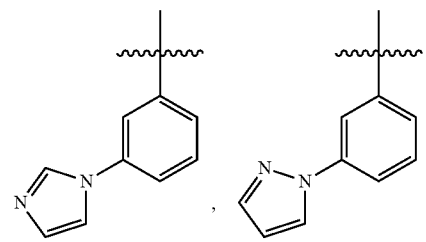
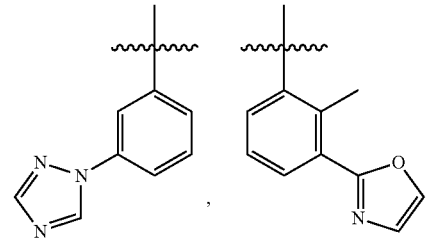
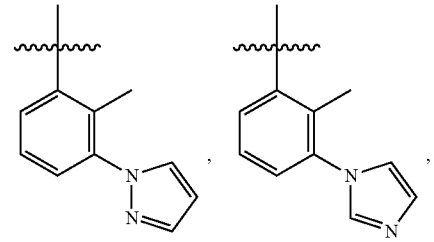
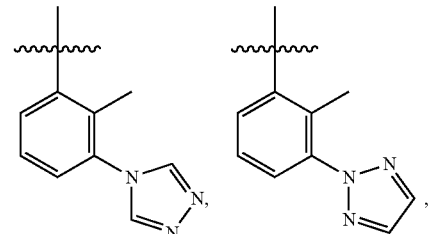
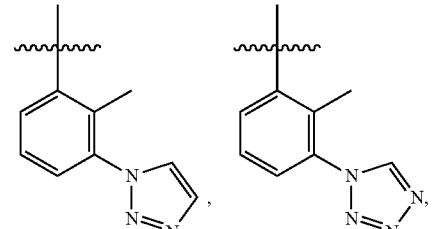
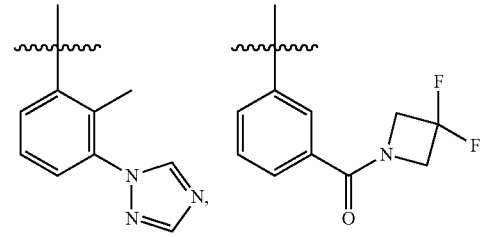
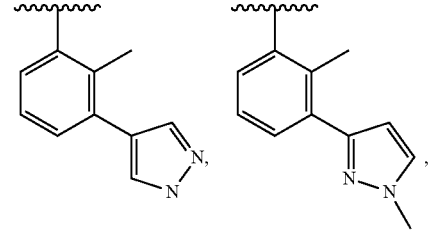

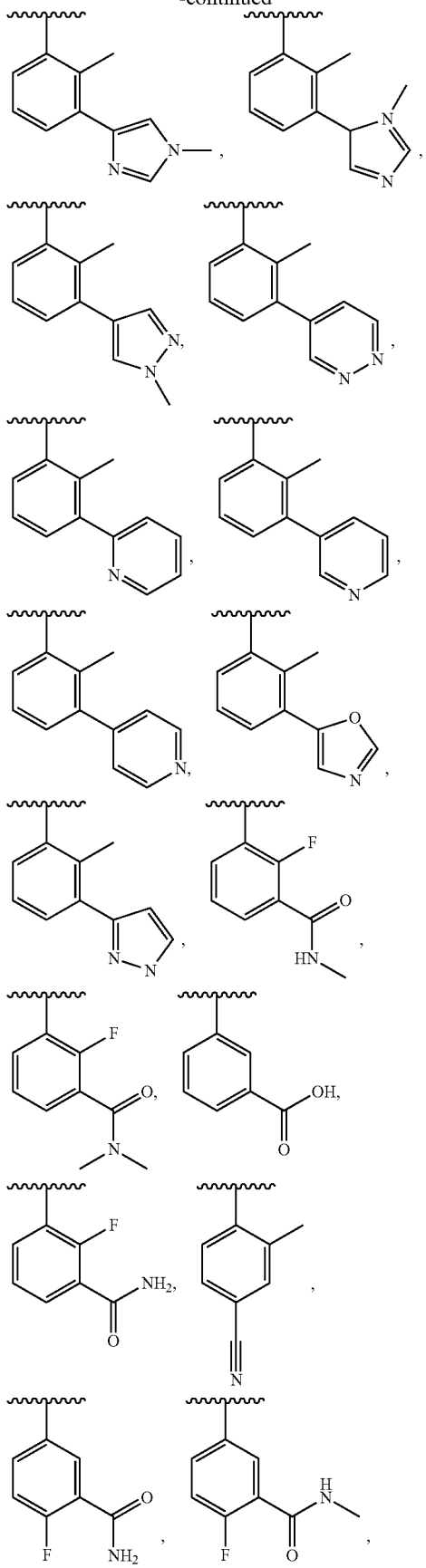
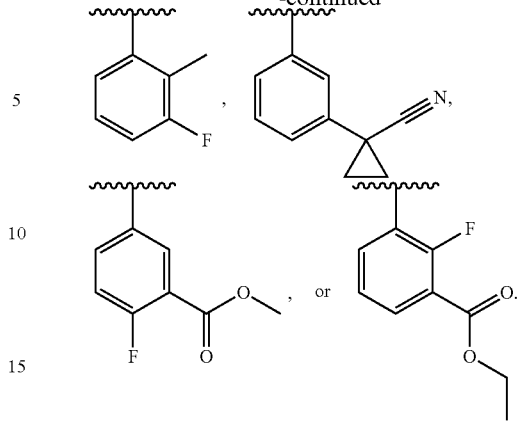

In one embodiment, R⁴ is 2-chlorophenyl, 3-(dimethylcarbamoyl)phenyl, 3-cyanophenyl, 4-chlorophenyl, 4-fluorophenyl, or phenyl.

In certain embodiments, $R^5$ is hydrogen, halo, —CN, —S(O)—R⁷, —S(O)₂R⁷, —SO₂N(R⁷)₂, —C(O)R⁷, —C(O)N(R⁷)₂, $C_{1-9}$ alkyl, $C_{2-6}$ alkenyl, $C_{2-6}$ alkynyl, $C_{3-15}$ cycloalkyl, aryl, heterocyclyl, or heteroaryl; wherein each $C_{1-9}$ alkyl, $C_{2-6}$ alkenyl, $C_{2-6}$ alkynyl, $C_{3-15}$ cycloalkyl, aryl, heterocyclyl, and heteroaryl may be optionally substituted with one to four $Z^5$.

In one embodiment, $R^5$ is hydrogen, halo, —CN, —C(O)R⁷, —S(O)₂R⁷, or heteroaryl. In one embodiment, $R^5$ is hydrogen, halo, —CN, —C(O)R⁷, or heteroaryl. In another embodiment, $R^5$ is halo.

In certain embodiments, $R^5$ is 1H-pyrazol-4-yl, 1-hydroxyethyl, 1-methyl-1H-pyrazol-4-yl, 4-(acetylamino)phenyl, 6-fluoropyridin-3-yl, acetyl, bromo, chloro, cyano, cyclopropyl, dimethylaminocarbonyl, ethynyl, fluoro, iodo, methoxy, methyl, hydroxyl, phenyl, pyridin-3-yl, pyridin-4-yl, pyrimidin-5-yl, or trifluoromethyl. In one embodiment, $R^5$ is chloro. In certain embodiments, $R^5$ is 1H-pyrazol-4-yl, 1-hydroxyethyl, 1-methyl-1H-pyrazol-4-yl, 4-(acetylamino)phenyl, 6-fluoropyridin-3-yl, acetyl, bromo, chloro, cyano, cyclopropyl, dimethylaminocarbonyl, ethynyl, fluoro, iodo, methoxy, methyl, methylsulfonyl, hydroxyl, phenyl, pyridin-3-yl, pyridin-4-yl, pyrimidin-5-yl, or trifluoromethyl. In one embodiment, $R^5$ is chloro.

In one embodiment, m is 0. In another embodiment, m is 1.

In general, the specific compounds exemplified herein are named using ChemBioDraw Ultra. However, it is understood that other names may be used to identify compounds of the same structure. In particular, the compounds may also be named using other nomenclature systems and symbols that are commonly recognized in the art of chemistry including, for example, Chemical Abstract Service (CAS) and International Union of Pure and Applied Chemistry (IUPAC). Other compounds or radicals may be named with common names, or systematic or non-systematic names.

In certain embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

Compositions provided herein that include a compound described herein or pharmaceutically acceptable salts, iso-

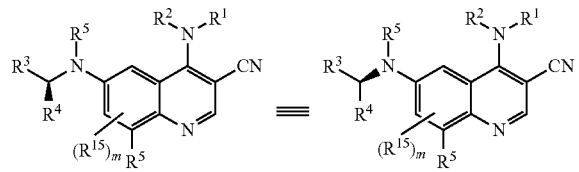 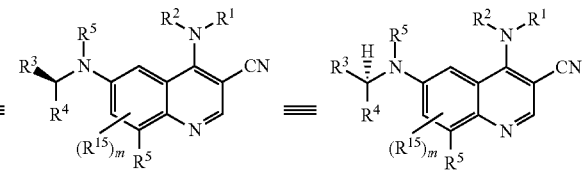

mer, or a mixture thereof may include racemic mixtures, or mixtures containing an enantiomeric excess of one enantiomer or single diastereomers or diastereomeric mixtures. All such isomeric forms of these compounds are expressly included herein as if each and every isomeric form were specifically and individually listed.

A composition comprising a mixture of enantiomers (or diastereomers) of a compound described herein or a pharmaceutically acceptable salt thereof, is also provided herein. In some embodiments, the composition comprises a single enantiomer of the compound and is substantially free of the other enantiomer. In certain embodiments, the compound of Formula I (or another Formula as described herein) contains one or more additional stereogenic atom(s) (e.g., at $R^1$ and/or $R^3$). In such instances, the composition may contain a mixture of diastereomers. In some embodiments, the composition comprises a single enantiomer of the compound and is substantially free (i.e., having less than or about 40%, 30%, 25%, 20%, 15%, 10%, 5%, 1%, 0.05%, or 0.01%) of one or more diastereomers.

In certain embodiments, provided is a composition comprising a mixture of Formula IA, or a pharmaceutically acceptable salt thereof, and Formula IB, or a pharmaceutically acceptable salt thereof.

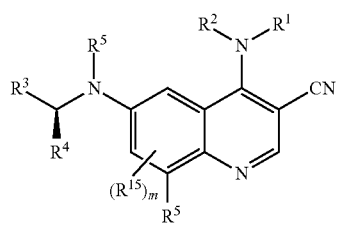

IA

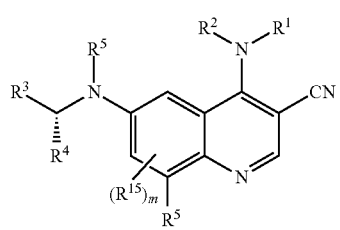

IB wherein m, $R^1$, $R^2$, $R^3$, $R^4$, $R^5$, $R^6$ and $R^{15}$ are as defined herein.

The stereochemistry of the $R^4$ group depicted in Formula IA may be represented in an alternative way, provided that the configuration of the carbon atom to which it is attached is not altered. For example, compounds of Formula 1A may be depicted in any one of the equivalent representations of Formula IA shown below.

In one embodiment, the mixture is a racemic mixture. In other embodiments, the composition comprises a mixture of Formula IA, or a pharmaceutically acceptable salt thereof, and Formula IB, or a pharmaceutically acceptable salt thereof, wherein Formula IA is present in excess of over Formula IB, or a pharmaceutically acceptable salt thereof. In certain embodiments, provided is a composition substantially free of Formula IB, having less than or about 40%, 30%, 25%, 20%, 15%, 10%, 5%, 1%, 0.05%, or 0.01% of compounds of Formula IB.

In certain embodiments, provided here in is a composition comprising a mixture of stereoisomers of a compound of Formula I:

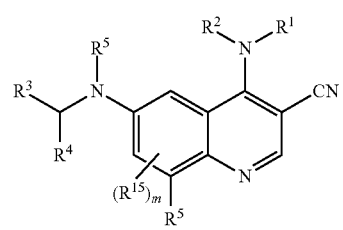

I wherein the mixture comprises compounds of Formula IA and IB in a ratio of at least about 3:1:

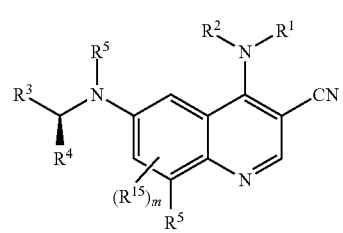

IA

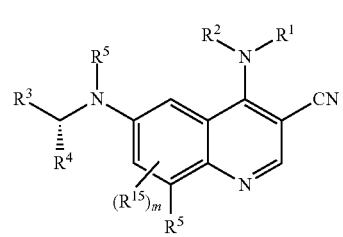

IB wherein m, $R^1$, $R^2$, $R^3$, $R^4$, $R^5$, $R^6$ and $R^{15}$ are as defined herein.

In other embodiments, the mixture comprises compounds of Formula IA and IB in a molar ratio of at least or about 3:1, at least or about 4:1, at least or about 5:1, at least or about 6:1, at least or about 7:1, at least or about 8:1, at least or about 9:1, at least or about 10:1, at least or about 11:1, at least or about 12:1, at least or about 20:1, at least or about 30:1, at least or about 40:1, at least or about 80:1, at least or about 160:1, or at least or about 320:1, respectively.

In certain embodiments, provided are also chelates, non-covalent complexes, and mixtures thereof, of the compounds described herein or a pharmaceutically acceptable salt, tautomer, stereoisomer, mixture of stereoisomers, prodrug, or deuterated analog thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

In certain embodiments, provided are prodrugs of the compounds described herein. "Prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

In certain embodiments, provided is a compound of Formula I, IA, IB, II, IIA, III, IIIA, IV, IVA, V, VA, VI, VIA, VII, VIIA, VIII or VIIIA, wherein $R^6$ is

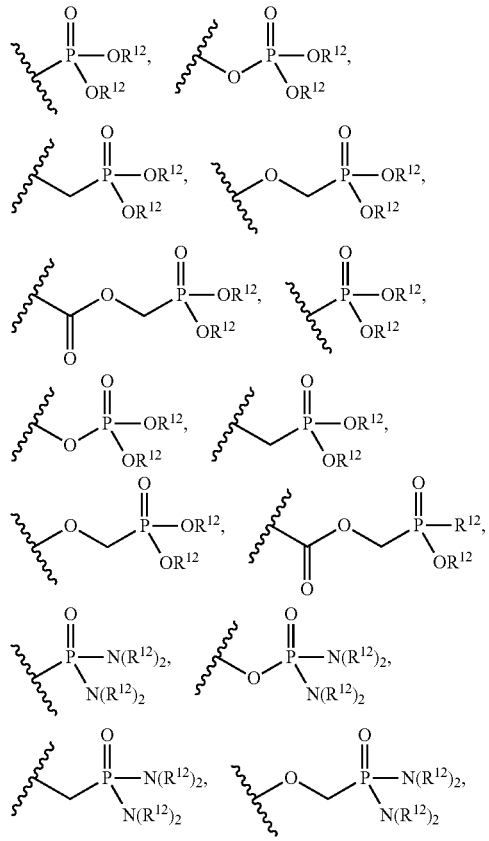

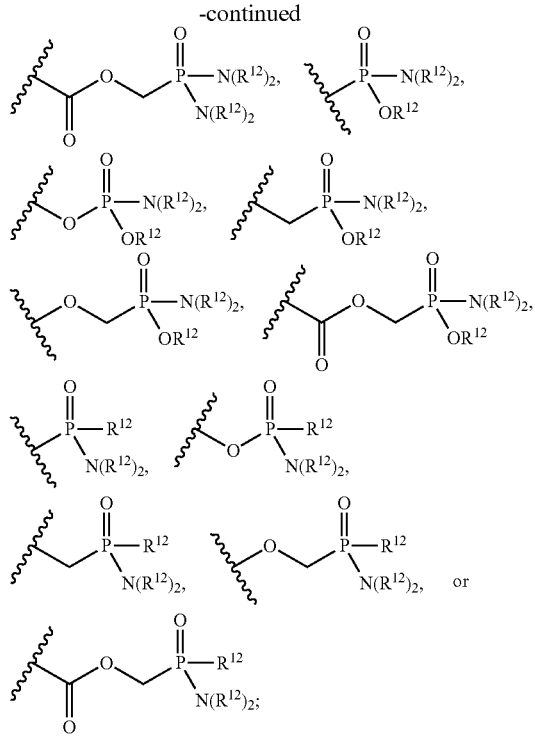

where each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups; and each $Z^{1b}$ is independently oxo, thioxo, hydroxy, halo, $-NO_2$, $-N_3$, $-CN$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O(C_{1-9}$ alkyl), $-O(C_{2-6}$ alkenyl), $-O(C_{2-6}$ alkynyl), $-O(C_{3-15}$ cycloalkyl), $-O(C_{1-8}$ haloalkyl), $-O$(aryl), $-O$(heteroaryl), $-O$(heterocyclyl), $-NH_2$, $-NH(C_{1-9}$ alkyl), $-NH(C_{2-6}$ alkenyl), $-NH(C_{2-6}$ alkynyl), $-NH(C_{3-15}$ cycloalkyl), $-NH(C_{1-8}$ haloalkyl), $-NH$(aryl), $-NH$(heteroaryl), $-NH$(heterocyclyl), $-N(C_{1-9}$ alkyl)$_2$, $-N(C_{3-15}$ cycloalkyl)$_2$, $-N(C_{2-6}$ alkenyl)$_2$, $-N(C_{2-6}$ alkynyl)$_2$, $-N(C_{3-15}$ cycloalkyl)$_2$, $-N(C_{1-8}$ haloalkyl)$_2$, $-N$(aryl)$_2$, $-N$(heteroaryl)$_2$, $-N$(heterocyclyl)$_2$, $-N(C_{1-9}$ alkyl)($C_{3-15}$ cycloalkyl), $-N(C_{1-9}$ alkyl)($C_{2-6}$ alkenyl), $-N(C_{1-9}$ alkyl)($C_{2-6}$ alkynyl), $-N(C_{1-9}$ alkyl)($C_{3-15}$ cycloalkyl), $-N(C_{1-9}$ alkyl)($C_{1-8}$ haloalkyl), $-N(C_{1-9}$ alkyl)(aryl), $-N(C_{1-9}$ alkyl)(heteroaryl), $-N(C_{1-9}$ alkyl)heterocyclyl), $-C(O)(C_{1-9}$ alkyl), $-C(O)(C_{2-6}$ alkenyl), $-C(O)(C_2$ alkynyl), $-C(O)(C_{3-15}$ cycloalkyl), $-C(O)(C_{1-8}$ haloalkyl), $-C(O)$(aryl), $-C(O)$(heteroaryl), $-C(O)$(heterocyclyl), $-C(O)O(C_{1-9}$ alkyl), $-C(O)O(C_{2-6}$ alkenyl), $-C(O)O(C_{2-6}$ alkynyl), $-C(O)O(C_{3-15}$ cycloalkyl), $-C(O)O(C_{1-8}$ haloalkyl), $-C(O)O$(aryl), $-C(O)O$(heteroaryl), $-C(O)O$(heterocyclyl), $-C(O)NH_2$, $-C(O)NH(C_{1-9}$ alkyl), $-C(O)NH(C_{2-6}$alkenyl), $-C(O)NH(C_{2-6}$ alkynyl), $-C(O)NH(C_{3-15}$ cycloalkyl), $-C(O)NH(C_{1-8}$ haloalkyl), $-C(O)NH$(aryl), $-C(O)NH$(heteroaryl), $-C(O)NH$(heterocyclyl), $-C(O)N(C_{1-9}$ alkyl)$_2$, $-C(O)N(C_{3-15}$ cycloalkyl)$_2$, $-C(O)N(C_{2-6}$ alkenyl)$_2$, $-C(O)N(C_{2-6}$alkynyl)$_2$, $-C(O)N(C_{3-15}$ cycloalkyl)$_2$, $-C(O)N(C_{1-8}$ haloalkyl)$_2$, $-C(O)N$(aryl)$_2$, $-C(O)N$(heteroaryl)$_2$, $-C(O)N$(heterocyclyl)$_2$, $-NHC$ (O)(C$_{1-9}$ alkyl), —NHC(O)(C$_{2-6}$alkenyl), —NHC(O)(C$_{2-6}$alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)((NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl).

In certain embodiments, R$^6$ is

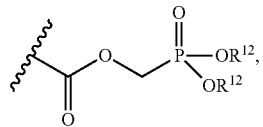

and each R$^{12}$ is independently as defined herein.

In certain embodiments, R$^6$ is

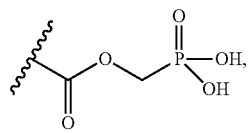 [SMILES: *C(=O)OCP(=O)(O)O]

R$^6$ also includes all individual stereoisomers, and mixtures thereof, including but not limited to, chirality at the phosphorous atom such as in the exemplary moieties shown above.

Also provided herein are the in vivo metabolic products of the compounds described herein. Such products may result, for example, from the oxidation, reduction, hydrolysis, amidation, esterification, and the like, of the administered compound, primarily due to enzymatic processes.

Therapeutic Uses of the Compounds

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Cot activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of Cot" or variants thereof refers to a decrease in activity in Cot as a direct or indirect response to the presence of a compound of the present application relative to the activity Cot in the absence of the compound of the present application. "Inhibition of Cot" refers to a decrease in Cot activity as a direct or indirect response to the presence of a compound described herein relative to the activity of Cot in the absence of the compound described herein. In some embodiments, the inhibition of Cot activity may be compared in the same subject prior to treatment, or other subjects not receiving the treatment.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds and compositions described herein may be used for a variety of purposes, including therapeutic and experimental purposes. For example, the compounds and compositions described herein may be used ex vivo to determine the optimal schedule and/or dosing of administration of a Cot inhibitor for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The compounds disclosed herein are useful for the treatment of diseases or conditions mediated by Cot. Non-limiting examples of diseases or conditions mediated by Cot include, without limitation, cancer, diabetes, and inflammatory diseases such as rheumatoid arthritis (RA), multiple sclerosis (MS), inflammatory bowel disease (IBD), sepsis, psoriasis, misregulated TNF expression and graft rejection.

In further embodiments, the methods are provided for alleviating a symptom of a disease or disorder mediated by Cot. In some embodiments, the methods include identifying a mammal having a symptom of a disease or disorder mediated by Cot, and providing to the mammal an amount of a compound as described herein effective to ameliorate (i.e., lessen the severity of) the symptom.

In some embodiments, the disease or condition mediated by Cot is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease or condition mediated by Cot is diabetes, which includes any metabolic disorder characterized by impaired insulin production and glucose tolerance. In some embodiments, diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). Type 2 is also known as Non-Insulin-Dependent Diabetes Mellitus (NIDDM).

In some embodiments, the disease or condition mediated by Cot is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated by Cot is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods are generally applicable to a subject having IBD of any level or degree of disease activity.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In certain embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) Improvements in any of the foregoing response criteria are specifically provided by the methods of the present disclosure.

Combination Therapies

In one embodiment, the compounds disclosed herein may be used in combination with one or more additional therapeutic agent that are being used and/or developed to treat inflammatory disorders (e.g., IBD). The one or more additional therapeutic agent may be a α4β7 inhibitor, a steroid, a MMP-9 antibody, a S1P1 agonist, a TNF biologic, or any combination thereof.

In some embodiments, the one or more additional therapeutic agent may be a α4β7 integrin inhibitor, or an agent that inhibits the expression and/or activity of α4β7 integrin. The inhibitor can be small molecule or biologic. For example, the α4β7 integrin inhibitor can be natalizumab or vedolizumab.

In some embodiments, the one or more additional therapeutic agent may be a steroid, including but not limited to, corticosteroids. Corticosteroids may be administered by various routes, including intravenously (i.e., methylprednisolone, hydrocortisone), orally (i.e., prednisone, prednisolone, budesonide, dexamethasone), or topically (i.e., enema, suppository, or foam preparations).

In some embodiments, the one or more additional therapeutic agent may be an MMP9 inhibitor, or an agent that inhibits the expression and/or activity of MMP9. A representative protein sequence for MMP9 is GenBank Accession No. NP_004985. The inhibitor can be small molecule or biologic. For instance, Gu et al., *The Journal of Neuroscience*. 25(27): 6401-6408 (2005) discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

In some embodiments, the one or more additional therapeutic agent may be a Sphingosine 1-Phosphate Receptor (SP 1) inhibitor, or an agent that inhibits the expression and/or activity of S1P1. The inhibitor can be small molecule or biologic. For example, the S1P inhibitor can be RPC1063.

In some embodiments, the one or more additional therapeutic agent may be a TNF inhibitor, or an agent that inhibits the expression and/or activity of TNF. The inhibitor can be small molecule or biologic. For example, the TNF inhibitor can be golimumab.

In some embodiments, the one or more additional therapeutic agent is being used and/or developed to treat ulcerative colitis (UC) and/or Crohn disease (CD). The agent can be a biologic or small molecule. In some embodiments, the agent is a modulator (e.g., agonist or antagonist) of S1P1, IL-6, CX3CL1, DHODH, α4, β7, JAK, TNF, CB, IL-12/IL-23, CCL20, TLR9, MAdCAM, CCR9, CXCL10, Smad7, PDE4, MC, VLA-1, GC, GATA-3, Eotaxin, FFA2, LIGHT, FMS, MMP9, CD40, Steroid, 5-ASA, Immunomod, STAT3, and/or EP4.

Non-limiting examples of agents being used and/or developed to treat ulcerative colitis (UC) include GSK3050002 (CCL20 modulator, by GSK), GS-5745 (MMP9 modulator, by Gilead), AVX-470 (TNF modulator, by Avaxia), Bertilimumab (Eotaxin modulator, by Immune Pharma), Simponi (TNF modulator, by Johnson & Johnson and Merck), RX-10001 (by Resolvyx), IBD-98 (5-ASA modulator, by Holy Stone), SP-333 (GC modulator, by Synergy), KAG-308 (EP4 modulator, by Kaken), SB012 (GATA-3 modulator, by Sterna), AJM300 (α4 modulator, by Ajinomoto), BL-7040 (TLR9 modulator, by BiolineRx), TAK-114 (SAT3 modulator, by Takeda), CyCol (by Sigmoid), GWP-42003 (CB modulator, by GW Pharma), ASP3291 (MC modulator, by Drais), GLPG0974 (FFA2 modulator, by Galapagos), Ozanimod (S1P1 modulator, by Receptos), ASP015K (JAK modulator, by Astellas), Apremilast (PDE4 modulator, by Celgene), Zoenasa (by Altheus), Kappaproct (TLR9 modulator, by InDex), Phosphatidylcholine (by Dr Falk/Lipid Tx), Tofacitinib (JAk modulator, by Pfizer), Cortment (Steroid modulator, by Ferring), Uceris (Steroid modulator, by Salix), and 5-ASA modulators such as Delzicol (by Actavis), Canasa (by Aptalis), Asacol (by Actavis), Pentasa (by Shire/Ferring), Lialda (by Shire), Mezavant (by Shire), Apriso (by Salix), Colazal (by Salix), Giazo (by Salix), and Salofalk (by Dr Falk). Non-limiting examples of agents being used and/or developed to treat Crohn disease (CD) include FFP102 (CD40 modulator, by Fast Forward), E6011 (CX3CL1 modulator, by Eisai), PF-06480605 (by Pfizer), QBECO SSI (Immunomod modulator, by Qu Biologics), PDA-001 (by Celgene), BI 655066 (IL-12/IL-23 modulator, by Boehringer), TNFα kinoid (TNF modulator, by Neovacs), AMG 139/MEDI-2070 (IL-12/IL-23 modulator, by AstraZeneca), PF-04236921 (IL-6 modulator, by Pfizer), Tysabri (β7 modulator, marketed by Biogen Idec in the U.S.), Cimzia (marketed by UCB in the U.S.), JNJ-40346527 (FMS modulator, by J&J), SGX-203 (Steroid modulator, by Solgenix), CyCron (by Sigmoid), CCX507 (CCR9 modulator, by ChemoCentryx), MT1303 (S1P1 modulator, by Mitsubishi), 6-MP (by Teva), ABT-494 (JAk modulator, by Abbvie), Tofacitinib (JAk modulator, by Pfizer), GLPG0634 (JAk modulator, by Galapagos), TRK-170 (β7 modulator, by Toray), Mongersen (Smad7 modulator, by Celgene), RHB-104 (by Redhill), Rifaxmin EIR (by Salix), Budenofalk (by Dr Falk), and Entocort (by AstraZeneca).

Non-limiting examples of agents being used and/or developed to treat ulcerative colitis (UC) and Crohn disease (CD) include PF-06410293 (by Pfizer), SAN-300 (VLA-1 modulator, by Salix), SAR252067 (LIGHT modulator, by Sanofi), PF-00547659 (MAdCAM modulator, by Pfizer), Eldelumab (Smad7 modulator, by BMS), AMG 181/MEDI-7183 (β7 modulator, by Amgen/AstraZeneca), Etrolizumab (37 modulator, by Roche), Ustekinumab (IL-12/IL-23 modulator, by J&J), Remicade (TNF modulator, by J&J and Merck), Entyvio (β7 modulator, by Takeda), Humira (TNF modulator, by Abbvie), Infliximab (by Celtrion), PF-06651600 (by Pfizer), GSK2982772 (by GSK), GLPG1205 (FFA2 modulator, by Galapagos), AG014 (by Intrexon) and Vidofludimus (DHODH modulator, by 4SC).

In some embodiments, the one or more additional therapeutic agent may be a JAK inhibitor, particularly a JAK-1 selective inhibitor. The inhibitor can be small molecule or biologic. For example, the JAK inhibitor can be Filgotinib, GLPG0634 (JAK modulator, by Galápagos).

Kits

Provided herein are also kits that include a compound of Formula I, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of Formula I (or any other Formula described herein), or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See. e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See. e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula I

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The term "solvent" generally refers to a solvent inert under the conditions of the reaction being described in conjunction therewith (including, for example, benzene, toluene, acetonitrile, tetrahydrofuran (THF), dimethylformamide (DMF), chloroform, methylene chloride (or dichloromethane), diethyl ether, methanol, and the like). Unless specified to the contrary, the solvents used in the reactions are inert organic solvents, and the reactions may carried out under an inert gas, preferably argon or nitrogen.

The term "q.s." means adding a quantity sufficient to achieve a stated function, e.g., to bring a solution to the desired volume (i.e., 100%).

The compounds of Formula I may prepared by first providing the substituted quinoline core, and optionally further modifying the core as desired to provide the substituents disclosed herein. Scheme 1 shows the preparation of the quinoline core to provide compounds of Formula 1-e, where m, $R^5$ and $R^{15}$ are as defined herein, or is a functional group that may be converted thereto using standard reaction conditions.

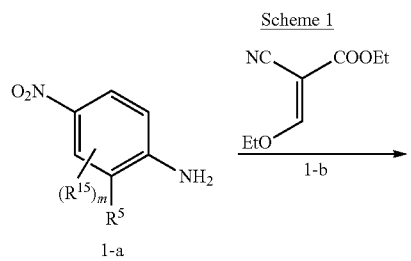

Scheme 1

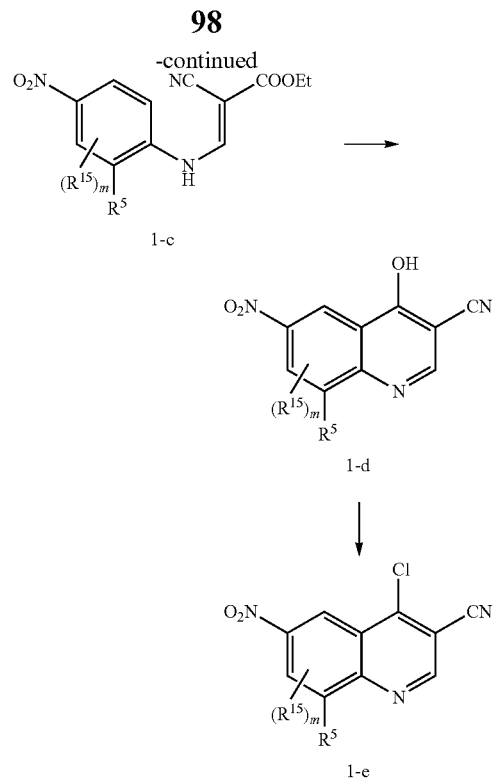

In Scheme 1, suitably substituted 1-a and 1-b are condensed in a suitable solvent (e.g., DMF, etc.) in the presence of catalyst (e.g., $Cs_2CO_3$, etc.) at an elevated temperature (e.g., about 40-50° C.) to provide 1-c. Compound 1-c is then converted to 1-d under thermal cyclization conditions (i.e., about 250° C.) or under microwave conditions. Chlorination of 1-d to provide 1-e is achieved using a suitable chlorinating agent (e.g., $POCl_3$, $SOCl_2$, etc.) at an elevated temperature (e.g., about 110-120° C.) in the presence of a base (e.g. pyridine, dimethylaniline, diethylaniline, etc.) or a catalyst (e.g., DMF, DEF, etc.) and in a suitable solvent (e.g. chlorobenzene, $CH_3CN$, etc.) or solvent-free conditions (i.e., neat).

Scheme 2 shows the synthesis of compounds of Formula 2-c and 2-d where m, $R^1$, $R^2$, $R^5$ and $R^{15}$ are as defined herein.

Scheme 2

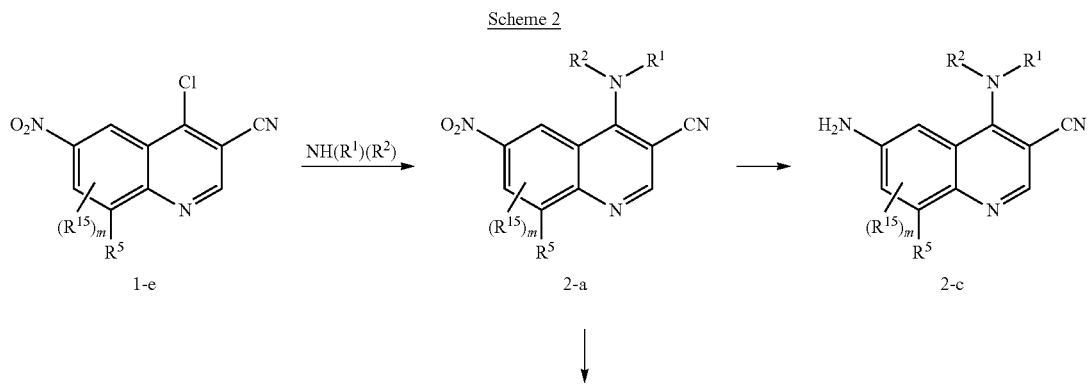

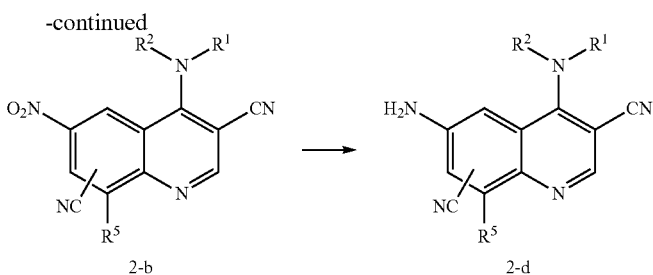

In Scheme 2, 1-e is reacted with a suitable amine under standard nucleophilic aromatic substitution conditions in the presence of a base (e.g., NEt$_3$, etc.) and at elevated temperature (e.g., 150° C.) to obtain 2-a. Compounds of Formula I where R$^5$ and/or R$^{15}$ is cyano are provided by reacting 2-a with a suitable cyanating agent (e.g., CuCN, Zn(CN)$_2$, etc.) in the presence of a catalyst (e.g., palladium, nickel, copper, etc.). Compounds 2-c and 2-d are then provided via reduction of the nitro group of compounds 2-a or 2-b, respectively (using e.g., Fe, SnCl$_2$, etc.).

Scheme 3 shows the synthesis of compounds 3-d and 3-e, where R$^4$ is as defined herein.

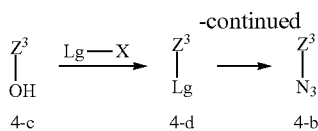

In Scheme 4, suitably substituted amine 4-a is treated with a diazo transfer agent (e.g., imidazole-1-sulfonyl azide hydrochloride) to afford corresponding 4-b. Alternatively, 4-b may be obtained in two steps from alcohol 4-c by conversion of the hydroxyl moiety to a suitable leaving

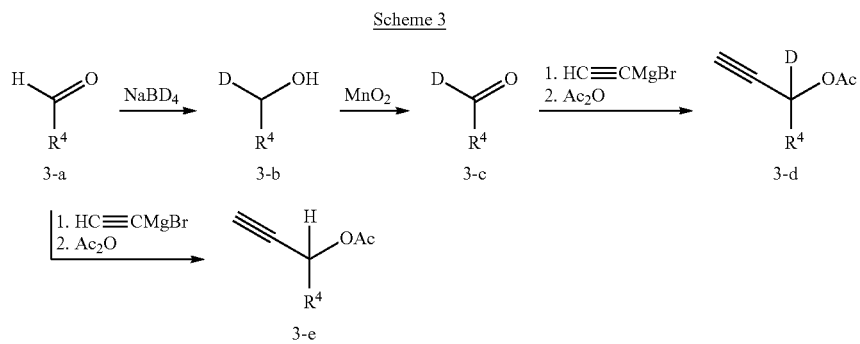

In Scheme 3, deuterated 3-c is provided by reducing suitably substituted aldehyde 3-a with a deuteride-containing reducing agent (e.g., NaBD$_4$), followed by oxidation of 3-b to the corresponding aldehyde 3-c under standard oxidizing conditions (e.g., MnO$_2$, Fe$_2$O$_3$, NiO, CuO, ZnO, ZrO$_2$, La$_2$O$_3$, Sm$_2$O$_3$, Eu$_2$O$_3$, Yb$_2$O$_3$, etc.). Compound 3-d is obtained in two steps by reaction of 3-c with ethynyl Grignard, followed by acylation of the resulting alcohol with acetic anhydride in the presence of a base (e.g., pyridine, TEA, etc.). Compound 3-e is provided in a similar two-step process by reacting suitably substituted aldehyde 3-a with ethynyl Grignard, followed by acylation of the resulting alcohol with acetic anhydride.

Scheme 4 shows the synthesis of suitably protected azide compounds of Formula 4-b, where Lg is a leaving group and Z$^3$ is as defined herein.

group (Lg) (e.g., TsO—, MsO—, NsO—, TfO—, etc.) followed by nucleophilic displacement with azide.

Scheme 5 shows the synthesis of intermediate compounds of Formula 5-c, where R$^{50}$ is alkyl and Z$^3$ is as defined herein.

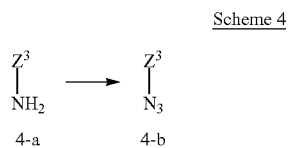

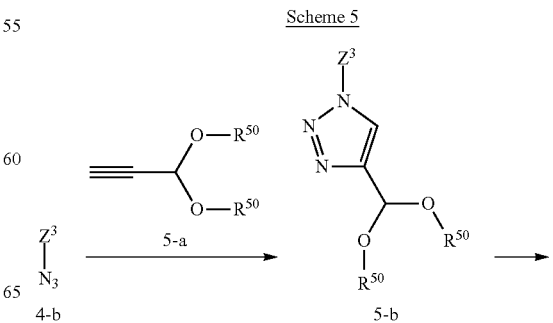

-continued

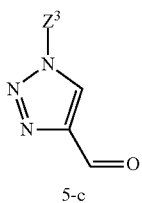

5-c

In Scheme 5, suitably substituted triazole 5-b is obtained by reaction of 4-b with 5-a using standard 1,3-dipolar cycloaddition conditions. Acetal 5-b is converted to the corresponding aldehyde 5-c under standard carbonyl deprotection conditions (e.g., aqueous acid).

Scheme 6 shows a general synthesis of exemplary compounds of Formula I, where $Z^3$, m, $R^1$, $R^2$, $R^4$, $R^5$ and $R^{15}$ and are as defined herein.

cyclization with azide 4-b under standard 1,3-dipolar cycloaddition conditions. Separation of the isomers of Formula 6-a to give compounds of Formula 6-b can be performed using standard chiral separation/resolution techniques (e.g., chiral chromatography, crystallization, etc.). Alternatively, compounds of Formula 6-b can be provided via enantioselective N-alkylation of 2-d with 3-d (or 3-e) using a chiral metal complex (e.g., $[Cu(CH_3CN)_4]PF_6$, CuOTf.benzene, $Cu(OAc)_2$, or Cu(I)I, etc., with a chiral ligand). Suitable reaction conditions and exemplary chiral ligands/complexes can be found in the literature (see, e.g., Detz, et al. Angew. Chem. Int. Ed. 2008, 47, 3777-3780). Contacting compound 6-c with azide 4-b under standard 1,3-dipolar cycloaddition conditions provides compound 6-b. 6-c may or may not be isolated prior to the addition of compound 4-b.

Scheme 7 shows an alternate synthesis of compounds of Formula I via imine formation and subsequent nucleophilic

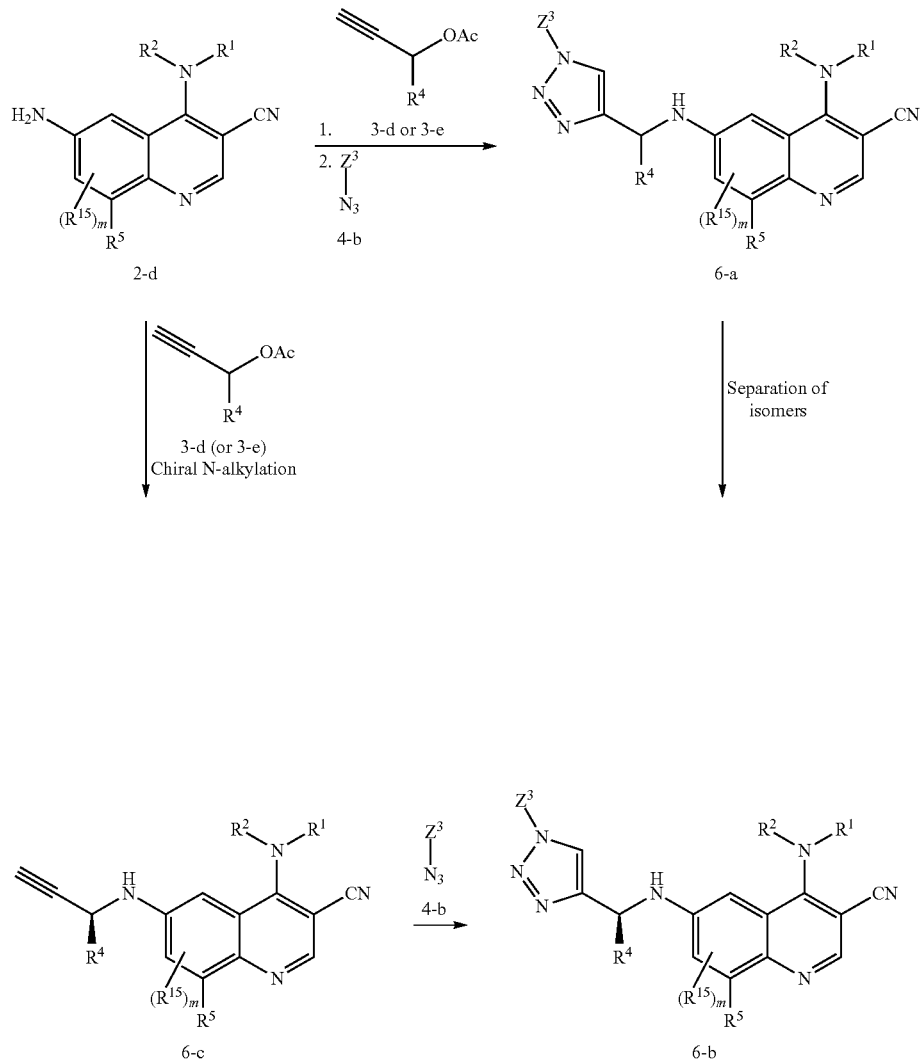

In Scheme 6, compounds of Formula 6-c can be provided via N-alkylation of amine 2-d with 3-d (or 3-e), followed by addition, where $Z^3$, m, $R^1$, $R^2$, $R^3$, $R^4$, $R^5$ and $R^{15}$ are as defined herein.

Scheme 7

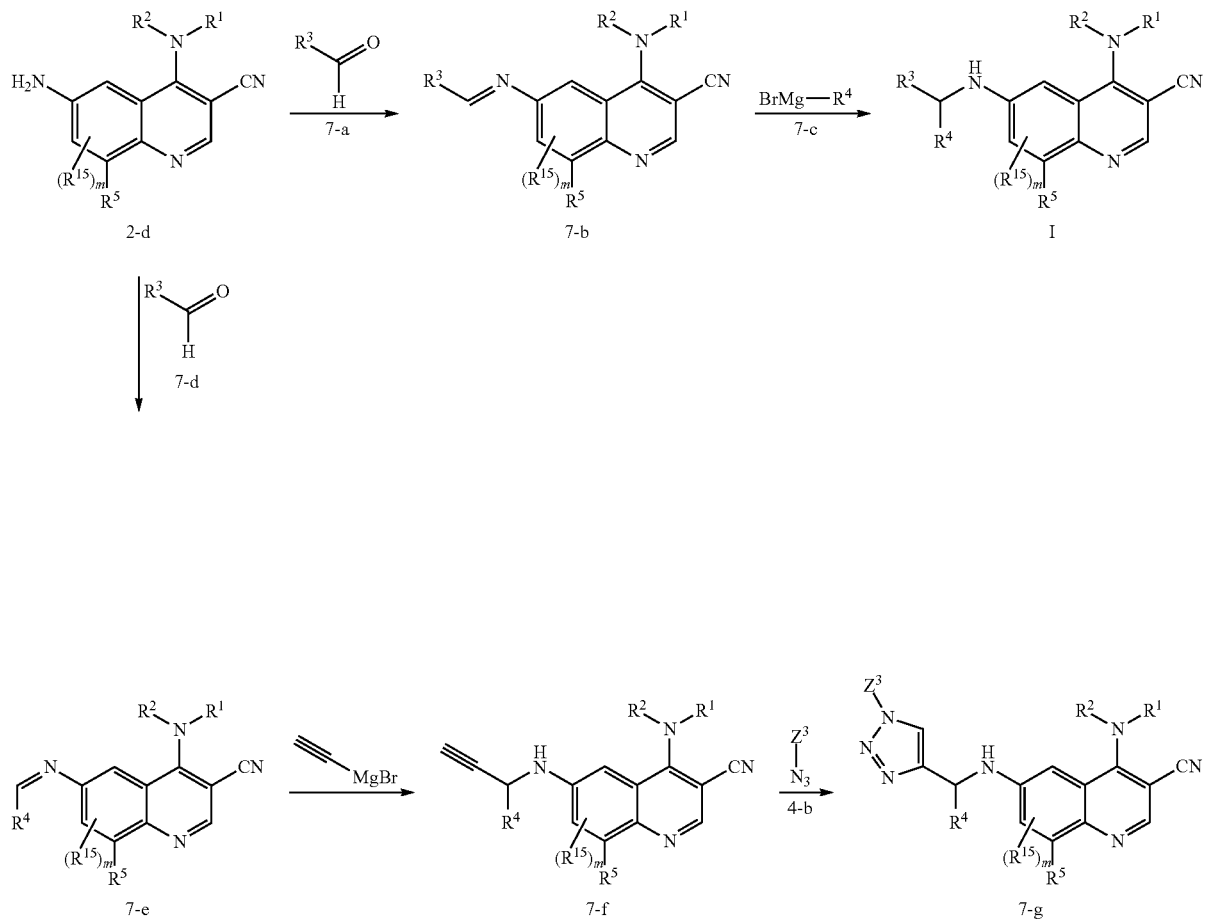

In Scheme 7, amine 2-d is reacted with aldehyde 7-a to afford the corresponding imine 7-b under standard imine-forming conditions. Compound 7-b is then reacted with Grignard reagent 7-c to provide Formula I. Alternatively, 2-d can be reacted with aldehyde 7-d to afford imine 7-e, which is then reacted with ethynyl Grignard to provide compound 7-f. Compound 7-f can then be converted to compound 7-g under standard 1,3-dipolar cycloaddition conditions with 4-b as shown in Scheme 6. Further, resolution of the isomers of Formula I or compound 7-g can be performed using standard chiral separation/resolution conditions (e.g., chiral chromatography, crystallization, etc.).

Scheme 8 shows another alternate general synthesis of compounds of Formula I, where m, $R^1$, $R^2$, $R^3$, $R^4$, $R^5$ and $R^{15}$ are as defined herein.

Scheme 8

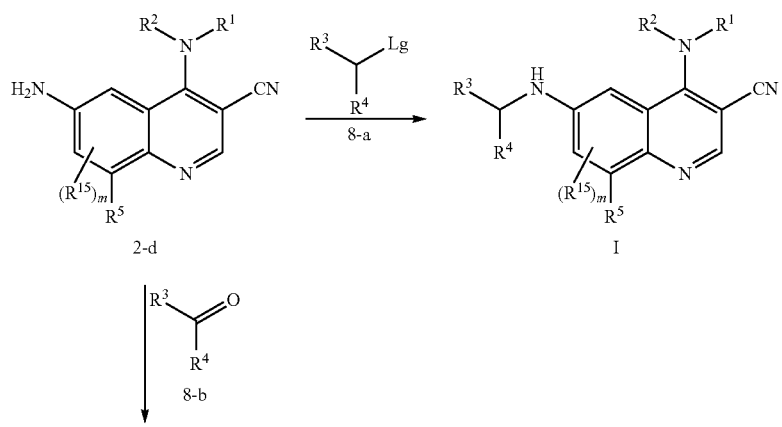

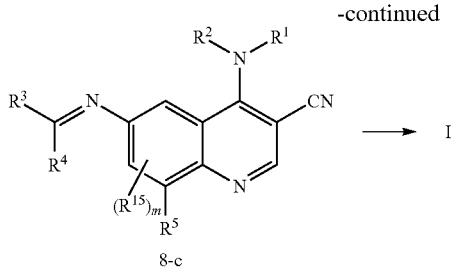

In Scheme 8, amine 2-d is reacted with appropriately substituted 8-a under nucleophilic substitution conditions, where Lg is a suitable leaving group, such as a halide (e.g., fluoro, chloro, bromo, iodo) or an activated alcohol (e.g., AcO—, TsO—, TfO—, MsO—, etc.) in the presence of a base, to provide compound of Formula I. Alternatively, amine 2-d is reacted with ketone 8-b to provide 8-c, which is subsequently reduced to provide compound of Formula I. Resolution of the isomers of Formula I can be performed using standard chiral separation/resolution conditions (e.g., chiral chromatography, crystallization, etc.).

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Intermediate Preparation

Example Synthesis of a Cyanoquinoline Core:

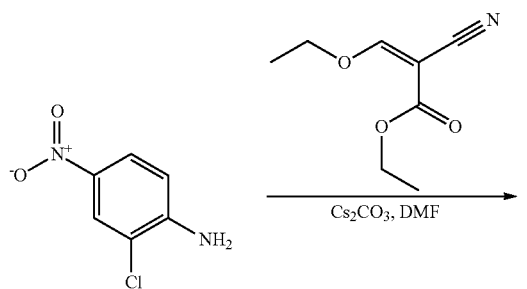

A mixture of 2-chloro-4-nitroaniline (1 eq), (Z)-ethyl 2-cyano-3-ethoxyacrylate (1.3 eq) and Cs$_2$CO$_3$ (1.3 eq) in DMF was heated at 45° C. overnight. After being cooled to room temperature, the mixture was poured into water. The formed solid was filtered, and washed with water and dried to give the title compound as a solid which was used for the next step without further purification.

$^1$H NMR (DMSO-d$_6$, 300 MHz): δ 11.28 (d, J=12.9 Hz, 1H), 8.84 (d, J=12.9 Hz, 1H), 8.42 (d, J=2.4 Hz, 1H), 8.26-8.22 (m, 1H), 8.02 (d, J=9.3 Hz, 1H), 4.27 (q, J=7.2 Hz, 2H), 1.27 (t, J=7.2 Hz, 3H).

Synthesis of 8-Chloro-6-nitro-4-oxo-1,4-dihydroquinoline-3-carbonitrile

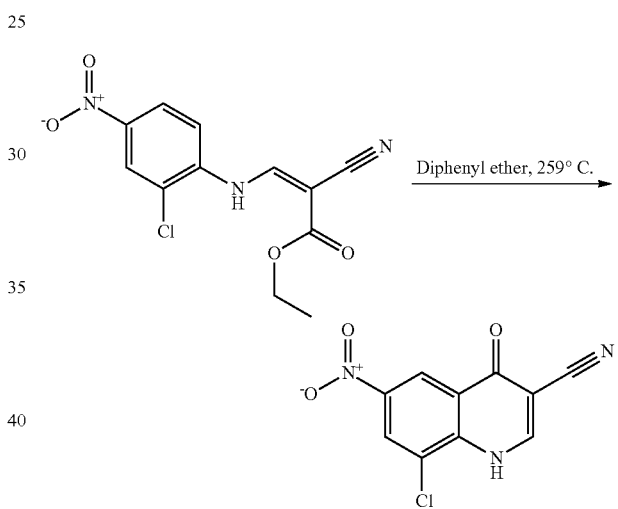

A suspension of (Z)-ethyl 3-((2-chloro-4-nitrophenyl)amino)-2-cyanoacrylate in diphenyl ether under nitrogen was heated to reflux with a sand bath in a heating mantle for 24 hours. After cooling to room temperature, the reaction mixture was poured into hexane and stirred for 2 hours. The mixture was filtered and the filter cake was washed with hexane twice to give title compound as a brown solid.

$^1$H NMR (DMSO-d$_6$, 300 MHz): δ 12.86 (br s, 1H), 8.73-8.71 (m, 3H).

Synthesis of 4,8-Dichloro-6-nitroquinoline-3-carbonitrile

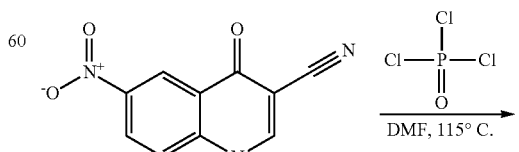

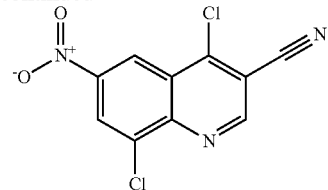

A suspension of 8-chloro-6-nitro-4-oxo-1,4-dihydroquinoline-3-carbonitrile and five drops of DMF in POCl$_3$ was heated at 115° C. overnight. The brown clear solution was cooled down to room temperature and excess of POCl$_3$ was removed. The residue was dissolved in DCM, washed with sat. NaHCO$_3$, brine and dried over Na$_2$SO$_4$. The solution was filtered and concentrated to give a crude product. The residue was triturated with hexane and EtOAc to afford the title compound as a brown solid.

$^1$H NMR (DMSO-d$_6$, 300 MHz): δ 9.50 (s, 1H), 8.98 (d, J=2.4 Hz, 1H), 8.89 (d, J=2.4 Hz, 1H).

Example Synthesis of an Alkynylacetate

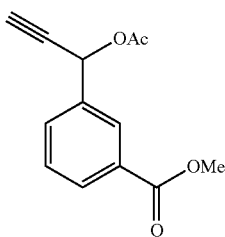 [SMILES: C#CC(OC(C)=O)c1cccc(C(=O)OC)c1]

Methyl 3-(1-acetoxyprop-2-yn-1-yl)benzoate methyl 3-formylbenzoate (1.00 g, 6.09 mmol) was dissolved in THF (30 mL) and brought to 0° C. Ethynylmagnesium bromide (0.5 M in THF, 12.8 mL, 6.40 mmol) was added slowly and the resulting solution allowed to stir for 30 minutes. Acetic anhydride (1.15 mL, 12.2 mmol) was then added, the cold bath removed, and the reaction mixture allowed to warm to room temperature over 2 hours. The reaction contents were quenched by the addition of saturated aqueous NH$_4$Cl (10 mL), poured into water (10 mL), and extract with EtOAc (3×30 mL). The combined organic phase was washed with brine (15 mL), dried over MgSO$_4$ and concentrated. The crude residue was purified by flash chromatography (eluent: EtOAc/hexanes) to give the desired product.

Synthesis of Selected Aldehydes

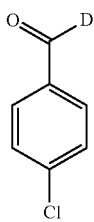

4-chlorobenzaldehyde-α-d 4-chlorobenzaldehyde (250 mg, 1.78 mmol) was dissolved in MeOH (8 mL) at room temperature. NaBD$_4$ (89 mg, 2.13 mmol) was then added as a single portion and the reaction mixture stirred for 20 minutes. The reaction mixture was carefully quenched with water (5 mL) and extracted with EtOAc (3×15 mL). The combined organic layers were washed with brine (5 mL), dried over MgSO$_4$ and concentrated to give crude alcohol which was carried forward without further purification. The crude alcohol was redissolved in DCM (10 mL) and manganese(IV) oxide (1.54 g, 17.8 mmol) was added at room temperature. After 2 hours the reaction mixture was filtered through a pad of celite rinsing with DCM and EtOAc. The filtrate was then concentrated to give the desired product with approximately 95% deuterium incorporation. Synthesis of the alkynyl acetate as outlined above.

3-(((tert-butyldimethylsilyl)oxy)methyl)benzaldehyde

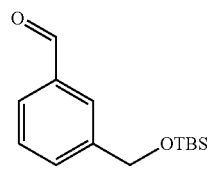 [SMILES: CC(C)(C)[Si](C)(C)OCc1cccc(C=O)c1]

(3-(((tert-butyldimethylsilyl)oxy)methyl)phenyl)methanol 1,3-phenylenedimethanol (3.00 g, 21.7 mmol) and imidazole (2.22 g, 32.6 mmol) were dissolved in DMF (40 mL) at room temperature. Tert-butyldimethylsilyl chloride (3.27 g, 21.7 mmol) was then added and the reaction stirred overnight. The DMF was removed under reduced pressure, the crude material partitioned between water (30 mL) and EtOAc (50 mL). The aqueous phase was extracted once more with EtOAc (50 mL). The organic layers were then combined, washed with brine (30 mL), dried over MgSO$_4$ and concentrated. The residue was subjected to flash chromatography (eluent: ethyl acetate/hexanes) to give (3-(((tert-butyldimethylsilyl)oxy)methyl)phenyl)methanol.

3-(((tert-butyldimethylsilyl)oxy)methyl)benzaldehyde (3-(((tert-butyldimethylsilyl)oxy)methyl)phenyl)methanol (2.57 g, 10.2 mmol) was dissolved in DCM (50 mL) at room temperature. Manganese(IV) oxide (2.66 g, 30.6 mmol) was then added and the reaction stirred for 2 hours. Additional manganese(IV) oxide (2.66 g, 30.6 mmol) was then added and the reaction stirred overnight. The reaction mixture was filtered through a pad of celite and the filtrate then concentrated to give 3-(((tert-butyldimethylsilyl)oxy)methyl)benzaldehyde which was used without further purification.

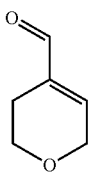

3,6-dihydro-2H-pyran-4-carbaldehyde

Prepared as described in: Z. S. Han et al *Org. Lett.* 2014, 16, 4142-4145.

N-(3-formylphenyl)-N-methylacetamide

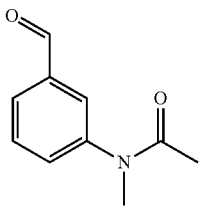

N-(3-(((tert-butyldimethylsilyl)oxy)methyl)phenyl) acetamide

N-(3-(hydroxymethyl)phenyl)acetamide (250 mg, 1.51 mmol) and imidazole (155 mg, 2.27 mmol) were dissolved in DMF (6 mL) at room temperature. Tert-butyldimethylsilyl chloride (240 mg, 1.59 mmol) was then added and the reaction stirred overnight. The DMF was removed under reduced pressure, the crude material partitioned between water (10 mL) and EtOAc (30 mL). The aqueous phase was extracted once more with EtOAc (20 mL). The organic layers were then combined, washed with brine (10 mL), dried over MgSO$_4$ and concentrated. The residue was subjected to flash chromatography (eluent: ethyl acetate/hexanes) to give (3-(((tert-butyldimethylsilyl)oxy)methyl) phenyl)methanol.

N-(3-(((tert-butyldimethylsilyl)oxy)methyl)phenyl)-N-methylacetamide

N-(3-(((tert-butyldimethylsilyl)oxy)methyl)phenyl)acetamide (353 mg, 1.26 mmol) was dissolved in THF (10 mL) and brought to 0° C. NaH (60% dispersion in mineral oil, 152 mg, 3.79 mmol) was added and the reaction mixture allowed to stir for 20 minutes after which iodomethane (0.39 mL, 6.3 mmol) was added. The reaction mixture was allowed to warm to room temperature over 1 hour after which it was quenched by water (5 mL) and extracted with EtOAc (3×15 mL). The combined organic phases were washed with brine (10 mL), dried over MgSO$_4$, and concentrated to give crude product which was carried forward without further purification.

N-(3-(hydroxymethyl)phenyl)-N-methylacetamide

N-(3-(((tert-butyldimethylsilyl)oxy)methyl)phenyl)-N-methylacetamide (370 mg, 1.26 mmol) was dissolved in THF (8 mL) and treated with tetrabutylammonium fluoride (1.0M in THF, 2.52 mL, 2.52 mmol) at room temperature for 30 minutes. The reaction contents were quenched by the addition of saturated aqueous NH$_4$Cl (5 mL), poured into water (5 mL) and extracted with EtOAc (3×15 mL). The combined organic phases were washed with brine, dried over MgSO$_4$ and concentrated. The crude residue was purified by flash chromatography (eluent: MeOH/ethyl acetate/hexanes) to give the desired product.

N-(3-formylphenyl)-N-methylacetamide

N-(3-(hydroxymethyl)phenyl)-N-methylacetamide (159 mg, 0.89 mmol) was dissolved in DCM (8 mL) and manganese(IV) oxide (1.54 g, 17.7 mmol) was added and the resulting mixture stirred at room temperature. After 2 hours the reaction mixture was filtered through celite and the filtrate concentrated to give the desired aldehyde product which was used without further purification.

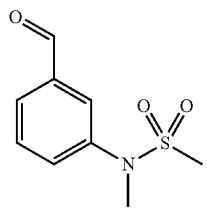

N-(3-formylphenyl)-N-methylmethanesulfonamide

N-(3-formylphenyl)methanesulfonamide (465 mg, 2.33 mmol) was dissolved in acetone (10 mL) at room temperature. Powdered K$_2$CO$_3$ (968 mg, 7.00 mmol) and iodomethane (0.29 mL, 4.67 mmol) were then added and the reaction mixture allowed to stir overnight. The reaction mixture was poured into water (5 mL) and extracted with EtOAc (3×15 mL). The combined organic phases were washed with brine (5 mL), dried over MgSO$_4$ and concentrated to give crude product which was carried on without further purification.

3-(2-oxoazetidin-1-yl)benzaldehyde

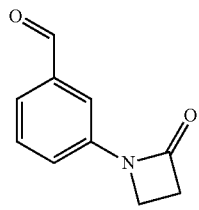 [SMILES: O=Cc1cccc(N2CCC2=O)c1]

1-(3-(hydroxymethyl)phenyl)azetidin-2-one

CuI (19 mg, 0.10 mmol) and K$_3$PO$_4$ (849 mg, 4.00 mmol) were added to a vial which was purged with argon. N,N'-dimethylethylenediamine (0.022 mL, 0.2 mmol), 3-(iodophenyl)methanol (468 mg, 2.00 mmol) and 2-azetidinone (171 mg, 2.4 mmol) were then added followed by toluene (2 mL). The reaction mixture was heated to 80° C. for 90 minutes after which it was cooled to room temperature, passed through a short silica plug washing with EtOAc and MeOH, and concentrated. The crude residue was then purified by flash chromatography (eluent: MeOH/DCM) to give the desired product.

3-(2-oxoazetidin-1-yl)benzaldehyde 1-(3-(hydroxymethyl)phenyl)azetidin-2-one (350 mg, 1.98 mmol) was dissolved in DCM (8 mL) and manganese (IV) oxide (2.61 g, 30.0 mmol) was added and the resulting mixture stirred at room temperature. After 2 hours the reaction mixture was filtered through celite and the filtrate concentrated to give the desired aldehyde product which was used without further purification.

3-(oxazol-2-yl)benzaldehyde

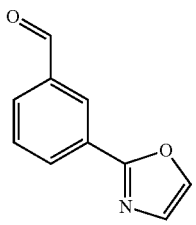 [SMILES: O=Cc1cccc(-c2ncco2)c1]

(3-(oxazol-2-yl)phenyl)methanol 3-(iodophenyl)methanol (0.13 mL, 1.04 mmol), 2-(tri-n-butylstannyl)oxazole (1.27 mL, 4.15 mmol), tetrakis(triphenylphosphine)palladium(0) (240 mg, 0.21 mmol), and lithium chloride (88 mg, 2.08 mmol) were all combined in DMF (5 mL) and purged with argon. The reaction mixture was then heated overnight at 90° C. after which it was passed through a silica-thiol plug, washing with MeOH and MeCN, and concentrated. The crude residue was purified by flash chromatography (eluent: EtOAc/hexanes) to give the desired product.

3-(oxazol-2-yl)benzaldehyde (3-(oxazol-2-yl)phenyl)methanol (174 mg, 0.99 mmol) was dissolved in DCM (8 mL) and manganese(IV) oxide (1.30 g, 14.9 mmol) was added and the resulting mixture stirred at room temperature. After 2 hours the reaction mixture was filtered through celite and the filtrate concentrated to give the desired aldehyde product which was used without further purification.

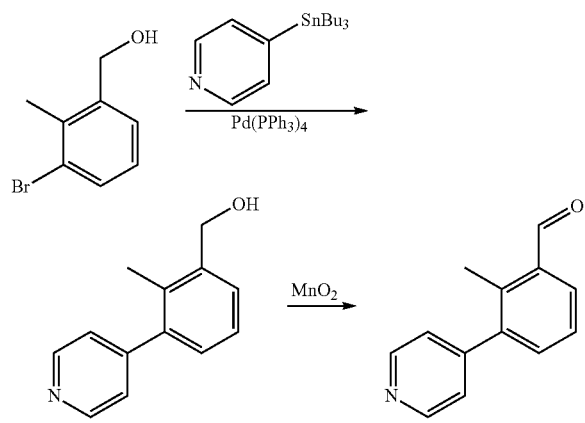

2-methyl-3-(pyridin-4-yl)benzaldehyde 3-bromo-2-methylbenzyl alcohol (200 mg, 1.0 mmol), tetrakis(triphenylphosphine)palladium(0) (115 mg, 0.10 mmol) and 4-tributyltinpyradine (439 mg, 1.2 mmol) were combined in DMF (2.0 mL) and purged with argon. The reaction mixture was heated to 200° C. for 45 minutes in a microwave reactor. Solids were filtered and resulting filtrate was diluted with dichloromethane (10 mL). Manganese(IV) oxide (2.2 g, 25 mmol) was then added as a single portion under ambient atmosphere and stirred for 1 hour at 25° C. at which point an addition portion of manganese(IV) oxide (2.2 g, 25 mmol) was added. After 1 hour of additional stirring the manganese(IV) oxide was removed via filtration through a pad of celite. The filtrate was concentrated then purified by via silica gel chromatography (eluent: EtOAc/hexanes) to give the product aldehyde.

Note: This protocol was employed successfully for other heteroaryl stannane coupling partners.

Synthesis of Selected Amines

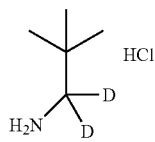

(2,2-dimethylpropyl-1,1-d2)amine HCl

LiAlD$_4$ (252 mg, 6.02 mmol) was suspended in Et$_2$O (10 mL) at room temperature. Trimethylacetonitrile (0.67 mL, 6.02 mmol) was then added slowly as a solution in Et$_2$O (6 mL) keeping the temperature below reflux. After 30 minutes the reaction mixture was quenched by careful, slow addition of water until gas evolution ceased. Saturated aqueous Rochelle's salt solution (50 mL) was then added and the resulting solution stirred vigorously for 2 hours. The phases were then separated and the aqueous extracted with Et$_2$O (3×30 mL). The combined organic phases were washed with brine (15 mL), dried over MgSO$_4$ and filtered. To the product solution in ether was added HCl (1.0M in ether, 15 mL, 15 mmol) after which the newly formed HCl salt was collected by filtration.

(R)-1-phenylpropan-1-amine-d7

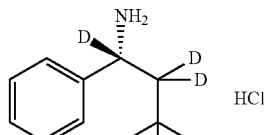

Ellman Auxiliary Condensation:
(S)-(−)-2-methyl-2-propanesulfinamide (862 mg, 7.12 mmol) was dissolved in DCM (15 mL). PPTS (81 mg, 0.32 mmol), MgSO$_4$ (3.89 g, 32.3 mmol), and benzaldehyde-d were then added and the resulting mixture allowed to stir at room temperature for 4 hours. The reaction mixture was filtered through celite rinsing with DCM, concentrated and purified by flash chromatography (eluent: EtOAc/hexanes) to give the desired product.

Grignard Formation and Addition to Sulfinimine:

Ethylbromide-d5 (1.00 g, 8.77 mmol) as a solution in dry THF (2 mL) was added to a suspension of magnesium turnings (426 mg, 17.5 mmol) in dry THF (7 mL) and stirred at room temperature for 2 hours. Heat generation and discoloration indicate successful Grignard reagent formation to give an approximately 1.0M solution of EtMgBr-d5 in THF. EtMgBr-d5 (1.0M in THF, 7.2 mL, 7.2 mmol) was added dropwise to a solution of sulfinimine (752 mg, 3.58 mmol) in DCM (10 mL) at −78° C. After stirring for 3 hours at −78° C., the reaction mixture was allowed to warm to room temperature overnight. The reaction contents were quenched by the addition of saturated aqueous NH4Cl (5 mL), poured into water (5 mL) and extracted with EtOAc (3×30 mL). The combined organic phases were washed with brine (15 mL), dried over MgSO4 and concentrated. The crude residue was purified by flash chromatography (eluent: EtOAc/hexanes) to give the desired product.

Auxiliary Removal:

Starting material (451 mg, 1.84 mmol) was dissolved in MeOH (0.9 mL) at room temperature. HCl (4.0M in dioxane, 0.92 mL, 3.69 mmol) was added and the solution stirred for 30 minutes. Reaction mixture was diluted with Et2O (20 mL) and the resulting precipitate collected by filtration to give the desired product as an HCl salt.

(1R,2R)-2-((S)-amino(phenyl)methyl)cyclopropanecarbonitrile

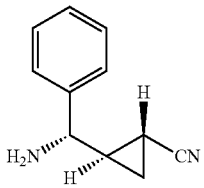

2-benzoylcylopropanecarbonitrile

Phenacyl chloride (10.0 g, 64.7 mmol) and DABCO (7.26 g, 64.7 mmol) were dissolved in THF (200 mL) and DMSO (50 mL) at room temperature and stirred for 30 minutes. Na2CO3 (10.3 g, 97.0 mmol) and acrylonitrile (8.48 mL, 129.4 mmol) were then added and the resulting mixture heated to 90° C. overnight. The reaction contents were quenched by the addition of saturated aqueous NH4Cl (40 mL), poured into water (20 mL) and extracted with EtOAc (3×150 mL). The combined organic phases were washed with brine (40 mL), dried over MgSO4 and concentrated. The crude residue was purified by flash chromatography (eluent: EtOAc/hexanes) to give trans-2-benzoylcyclopropanecarbonitrile and cis-2-benzoylcyclopropanecarbonitrile separately and both as racemic mixtures.

(R)—N-(((1S,2S)-2-cyanocyclopropyl)(phenyl)methylene)-2-methylpropane-2-sulfinamide and (R)—N-(((1R,2R)-2-cyanocyclopropyl)(phenyl)methylene)-2-methylpropane-2-sulfinamide Racemic trans-2-benzoylcyclopropanecarbonitrile (1.00 g, 5.84 mmol), (R)-(+)-2-methyl-2-propanesulfinamide (2.12 g, 17.5 mmol) and titanium(IV) ethoxide (7.35 mL, 35.1 mmol) were combined and heated to 85° C. for 3 hours. The reaction mixture was cooled to room temperature, diluted with EtOAc (100 mL) followed by water (5 mL) and allowed to stir for 30 minutes. The white precipitate was removed via filtration and the filtrate was washed with brine and concentrated. The crude residue was purified by flash chromatography (eluent: EtOAc/hexanes) to give (R)—N-(((1R,2R)-2-cyanocyclopropyl)(phenyl)methylene)-2-methylpropane-2-sulfinamide and (R)—N-(((1S,2S)-2-cyanocyclopropyl)(phenyl)methylene)-2-methylpropane-2-sulfinamide as pure enantiomers.

(R)—N—((S)(1R,2R)-2-cyanocyclopropyl)(phenyl)methyl)-2-methylpropane-2-sulfinamide (R)—N-(((1R,2R)-2-cyanocyclopropyl)(phenyl)methylene)-2-methylpropane-2-sulfinamide (250 mg, 0.91 mmol) was dissolved in THF and brought to −78° C. NaBH4 (70.0 mg, 1.85 mmol) was added as a single portion and the reaction mixture allowed to warm slowly to room temperature. Upon reaching room temperature the reaction contents were quenched with water (2 mL) and extracted with EtOAc (3×8 mL). The combined organic phases were washed with brine (5 mL), dried over MgSO4 and concentrated. The crude residue was purified by flash chromatography (eluent: EtOAc/hexanes) to give (R)—N—((R)-((1R,2R)-2-cyanocyclopropyl)(phenyl)methyl)-2-methylpropane-2-sulfinamide and (R)—N—((S)-((R,2R)-2-cyanocyclopropyl)(phenyl)methyl)-2-methylpropane-2-sulfinamide as pure enantiomers.

(1R,2R)-2-((S)-amino(phenyl)methyl)cyclopropanecarbonitrile (R)—N—((S)-((1R,2R)-2-cyanocyclopropyl)(phenyl)methyl)-2-methylpropane-2-sulfinamide (143 mg, 0.52 mmol) was dissolved in MeOH (0.5 mL) at room temperature. HCl (4.0M in dioxane, 0.26 mL, 1.04 mmol) was added and the solution stirred for 30 minutes. Reaction mixture was diluted with Et2O (20 mL) and the resulting precipitate collected by filtration to give the desired product as an HCl salt.

3-chloro-2-cycloproropoxyaniline

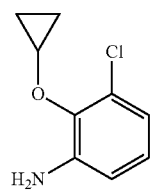

1-chloro-2-cyclopropoxy-3-nitrobenzene

To a solution of NaH (60% dispersion in mineral oil, 319 mg, 7.98 mmol) in THF (10 mL) was slowly added cyclopropyl alcohol (0.35 mL, 5.58 mmol). After 15 minutes of stirring, 1-chloro-2-fluoro-3-nitrobenzene (700 mg, 3.99 mmol) was added and the resulting solution heated to 75° C. for 1 hour. The reaction mixture was cooled to room temperature, quenched with water (5 mL) and extracted with EtOAc (3×15 mL). The combined organic phases were washed with brine (5 mL), dried over MgSO₄ and concentrated. The crude residue was purified by flash chromatography (eluent: EtOAc/hexanes) to give the desired product.

3-chloro-2-cycloproropoxyaniline 1-chloro-2-cyclopropoxy-3-nitrobenzene (420 mg, 1.97 mmol) was dissolved in EtOH (8 mL) at room temperature. Iron (549 mg, 9.83 mmol), CaCl₂ (327 mg, 2.95 mmol) and water (1 mL) were then added and the resulting mixture heated to 75° C. for 3 hours. The solids were removed by filtration washing with MeOH and EtOAc, the filtrate concentrated, and then redissolved in EtOAc (100 mL). The organic phase was washed with saturated aqueous NaHCO₃ (2×20 mL), brine (20 mL), dried over MgSO₄ and concentrated to give the crude product which was used without further purification.

Diazotransfer Reaction and Generation of Azides

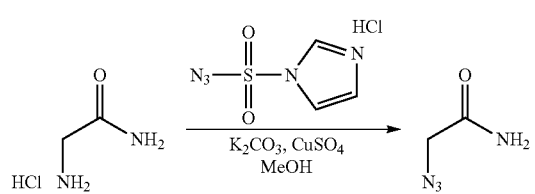

Glycinamide hydrochloride (50 mg, 0.45 mmol) was added to a suspension of 1H-imidazole-1-sulfonyl azide hydrochloride (118.5 mg, 0.56 mmol), potassium carbonate (125 mg, 0.90 mmol), and copper (II) sulfate pentahydrate (11.2 mg, 0.045 mmol) in methanol (1.0 mL). The blue mixture was stirred at room temperature for 16 hrs and was used without workup in the Click chemistry (Procedure 4). Reference: E. D. Goddard, et. al., Org. Lett., 2007, p. 3797.

Piperidine-Triazole Aldehyde

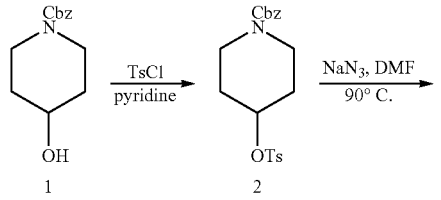

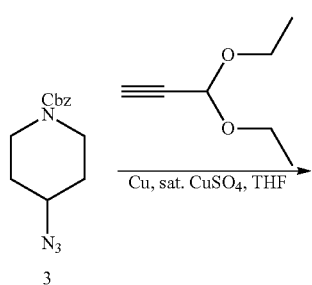

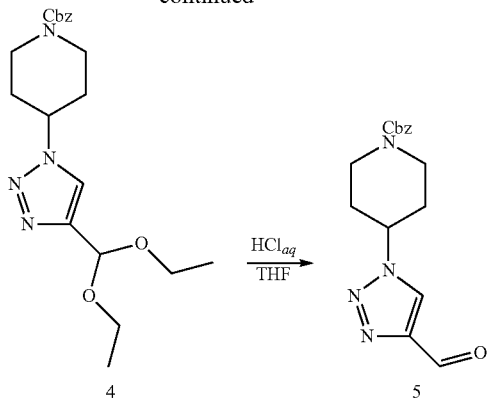

Benzyl 4-(tosyloxy)piperidine-1-carboxylate (2)

Benzyl 4-hydroxypiperidine-1-carboxylate (1) (17.2 g, 73.1 mmol) and p-toluenesulfonyl chloride (15.3 g, 80.4 mmol) were dissolved in pyridine (50 mL) and stirred at room temperature. After 23 hrs, the pyridine was removed under reduced pressure and the residue was dissolved in EtOAc (300 mL). The organic phase was washed with water (2×150 mL) and saturated ammonium chloride (100 mL), dried over sodium sulfate and the solvent was removed under reduced pressure. The residue was subjected to flash chromatography (eluent: ethyl acetate/hexanes). The fractions containing product were combined and the solvent was removed under reduced pressure, providing benzyl 4-(tosyloxy)piperidine-1-carboxylate (2).

Benzyl 4-azidopiperidine-1-carboxylate (3)

Sodium azide (2.48 g, 38.2 mmol) was added to a solution of benzyl 4-(tosyloxy)piperidine-1-carboxylate (2) (12.4 g, 31.8 mmol) in dimethylformamide (100 mL). The mixture was heated at 90° C. for 30 minutes. The mixture was cooled and diluted with ethyl acetate (250 mL) and washed with water (2×15 mL), 5% aqueous lithium chloride (10 mL) and brine (10 mL). The organic phase was dried over sodium sulfate and concentrated (not to dryness) providing the desired material. The yield was assumed to 100% and all material was used in the next step.

Benzyl 4-(4-(diethoxymethyl)-1H-1,2,3-triazol-1-yl)piperidine-1-carboxylate (4)

Copper powder (2.0 g, 31.5 mmol), was added to a solution of benzyl 4-azidopiperidine-1-carboxylate (3) (8.2 g, 31.5 mmol) 3,3-diethoxyprop-1-yne (4.44 g, 34.6 mmol) and saturated copper (II) sulfate (8 mL) in tetrahydrofuran (100 mL). After 17 hrs, the mixture was filtered through a pad of celite. The solvent was removed under reduced pressure and the residue was taken up in ethyl acetate (200 mL). The organic phase was washed with brine (3×100 mL), dried over sodium sulfate and concentrated. The residue was subjected to flash chromatography on silica gel (eluent: ethyl acetate/hexanes). The fractions containing product were combined and the solvent was removed under reduced pressure providing benzyl 4-(4-(diethoxymethyl)-1H-1,2,3-triazol-1-yl)piperidine-1-carboxylate (4).

Benzyl 4-(4-formyl-1H-1,2,3-triazol-1-yl)piperidine-1-carboxylate (5)

Aqueous hydrochloric acid (1 M, 2.2 mL, 2.2 mmol) was added to a solution of benzyl 4-(4-(diethoxymethyl)-1H-1,2,3-triazol-1-yl)piperidine-1-carboxylate (4) (429 mg, 1.1 mmol) in tetrahydrofuran (4 mL) and water (2 mL). The organic solvent was removed under reduced pressure. The aqueous mixture was diluted with acetonitrile (2 mL) and subjected to lyophilization. The yield was assumed to be 100%.

COMPOUND EXAMPLES

Example 1 Procedure 1

Water was added and the resulting precipitate was collected via filtration. The crude product was used in the next step without further purification.

ES/MS (M+H$^+$) 319.1.

Alternative Reaction Conditions for this Transformation:

4,8-dichloro-6-nitroquinoline-3-carbonitrile (3000 mg, 11.2 mmol), neopentylamine (1073 mg, 12.3 mmol) and triethylamine (1246 mg, 12.3 mmol) in iso-propanol (60 mL) were heated at 80° C. for 4 hrs. The reaction was cooled to room temperature. Removed the solvents and purified the crude reaction product via chromatography on silica gel (eluent: EtOAc/hexanes) yielding the product.

ES/MS (M+H$^+$) 319.1.

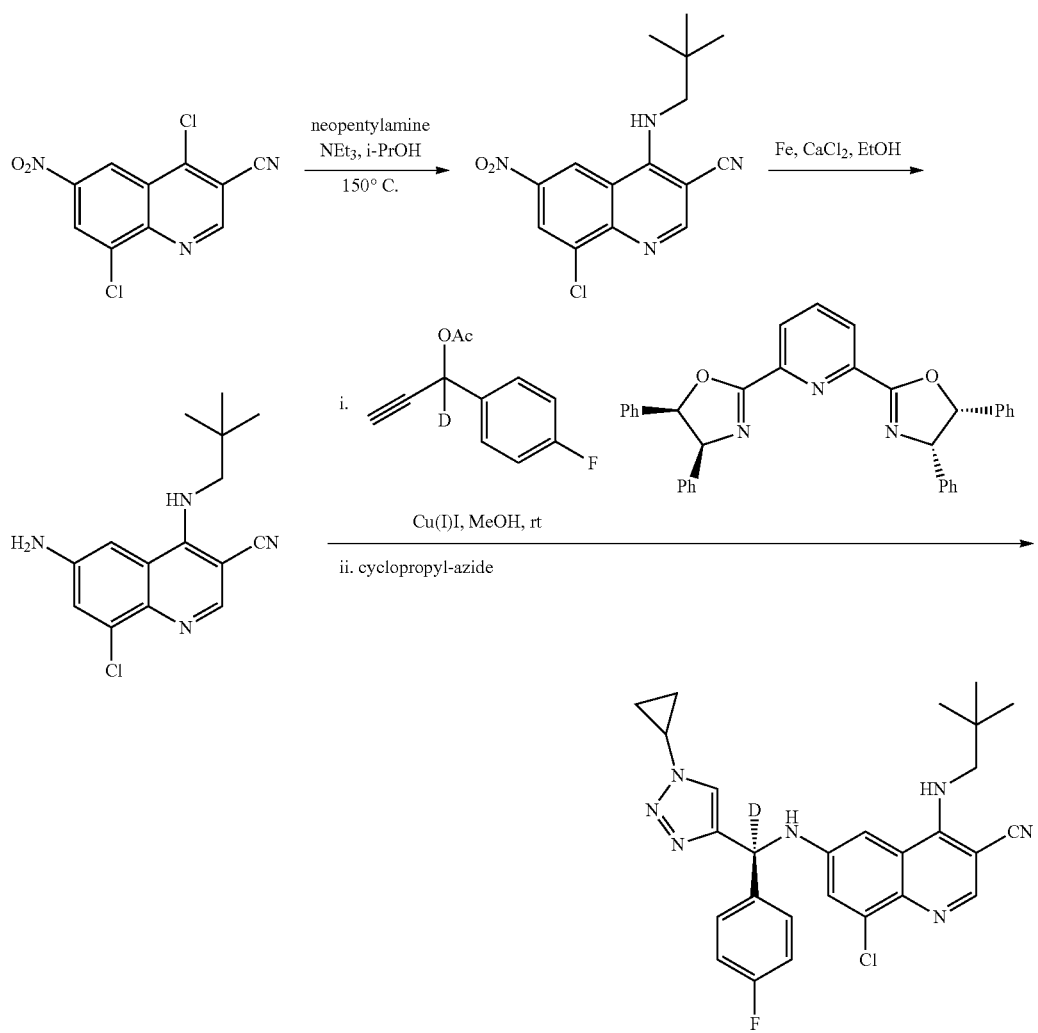

8-chlor-4(neopentylamino)-6-nitroquinoline-3-carbonitrile 6-amino-8-chloro-4-(neopentylamino)quinoline-3-carbonitrile 4,8-dichloro-6-nitroquinoline-3-carbonitrile (615 mg, 2.29 mmol), neopentylamine (220 mg, 0.25 mmol) and triethylamine (278 mg, 2.75 mmol) in iso-propanol (4 mL) were heated under microwave conditions at 150° C. for 45 minutes. The reaction was cooled to room temperature.

8-chloro-4-(neopentylamino)-6-nitroquinoline-3-carbonitrile (699 mg, 2.2 mmol), calcium chloride (483.6 mg, 3.28 mmol), iron powder (612.3 mg, 10.96 mmol) were heated in ethanol (22 mL)/water (2.2 mL) at 60° C. for 1 hour. The reaction was cooled to room temperature and solids were removed via filtration. The solids were washed with EtOAc and the combined organic layers were washed with aqueous sodium bicarbonate solution, brine, and were dried over sodium sulfate. Filtration and evaporation of all volatiles yielded the product.

ES/MS 289.1 (M+H$^+$).

Alternative Reduction Conditions with Tin Chloride:

8-chloro-4-(neopentylamino)-6-nitroquinoline-3-carbonitrile (2,000 mg, 6.2 mmol) and tin chloride (7079 mg, 31.3 mmol) heated at 70° C. for 4 hrs at which point more tin chloride (2832 mg, 12.6 mmol) was added. After 5 hrs, the reaction was complete. The reaction was cooled to room temperature. Half of the ethanol was removed under reduced pressure. The mixture was added to NaHCO$_3$ (200 mL) and diluted with EtOAc (500 mL). The organic phase was washed with brine (200 mL) and dried over sodium sulfate. The solvent was removed under reduced pressure, providing the desired material crude.

1H NMR (400 MHz, DMSO-d6) δ 8.19 (s, 1H), 7.32 (d, J=2.1 Hz, 1H), 7.29 (t, J=7.3 Hz, 1H), 7.18 (d, J=2.3 Hz, 1H), 5.74 (s, 2H), 3.66 (d, J=6.6 Hz, 2H), 0.96 (s, 9H).

ES/MS 289.1 (M+H$^+$).

(S)-8-chloro-6-(((1-cyclopropyl-1H-1,2,3-triazol-4-yl)(4-fluorophenyl)-methyl-d)amino)-4-(neopentylamino)quinoline-3-carbonitrile 6-amino-8-chloro-4-(neopentylamino)quinoline-3-carbonitrile (75 mg, 0.26 mmol), CuI (5 mg, 0.026 mmol) and 2,6-bis((4S,5R)-4,5-diphenyl-4,5-dihydrooxazol-2-yl)pyridine [oxazoline ligand](13.6 mg, 0.026 mmol) were sonicated in MeOH (3.5 mL) for about 1 minute. Alkynyl acetate (60.2 mg, 0.31 mmol) and di-isopropyl ethyl amine (40.3 mg, 0.31 mmol) were added and the reaction was stirred overnight. Cyclopropylazide (26 mg, 0.31 mmol) was added and the reaction was stirred or additional 2 hrs at room temperature. Solvents were removed in vacuo and the crude material was purified via silica gel chromatography (eluent: EtOAc/hexanes) and RP-HPLC (eluent: water/MeCN*0.1% TFA) to yield the product as trifluoro acetate salt.

1H NMR (400 MHz, DMSO-d6) δ 8.34 (d, J=1.2 Hz, 1H), 8.01 (s, 1H), 7.72 (s, 1H), 7.59 (d, J=2.2 Hz, 1H), 7.52 (m, 2H), 7.40 (s, 1H), 7.12 (m, 4H), 3.96 (m, 2H), 3.46 (dd, J=13.9/5.5 Hz, 1H), 1.11 (m, 4H), 0.88 (s, 9H). ES/MS 505.3 (M+H$^+$).

Example 2 Procedure 2

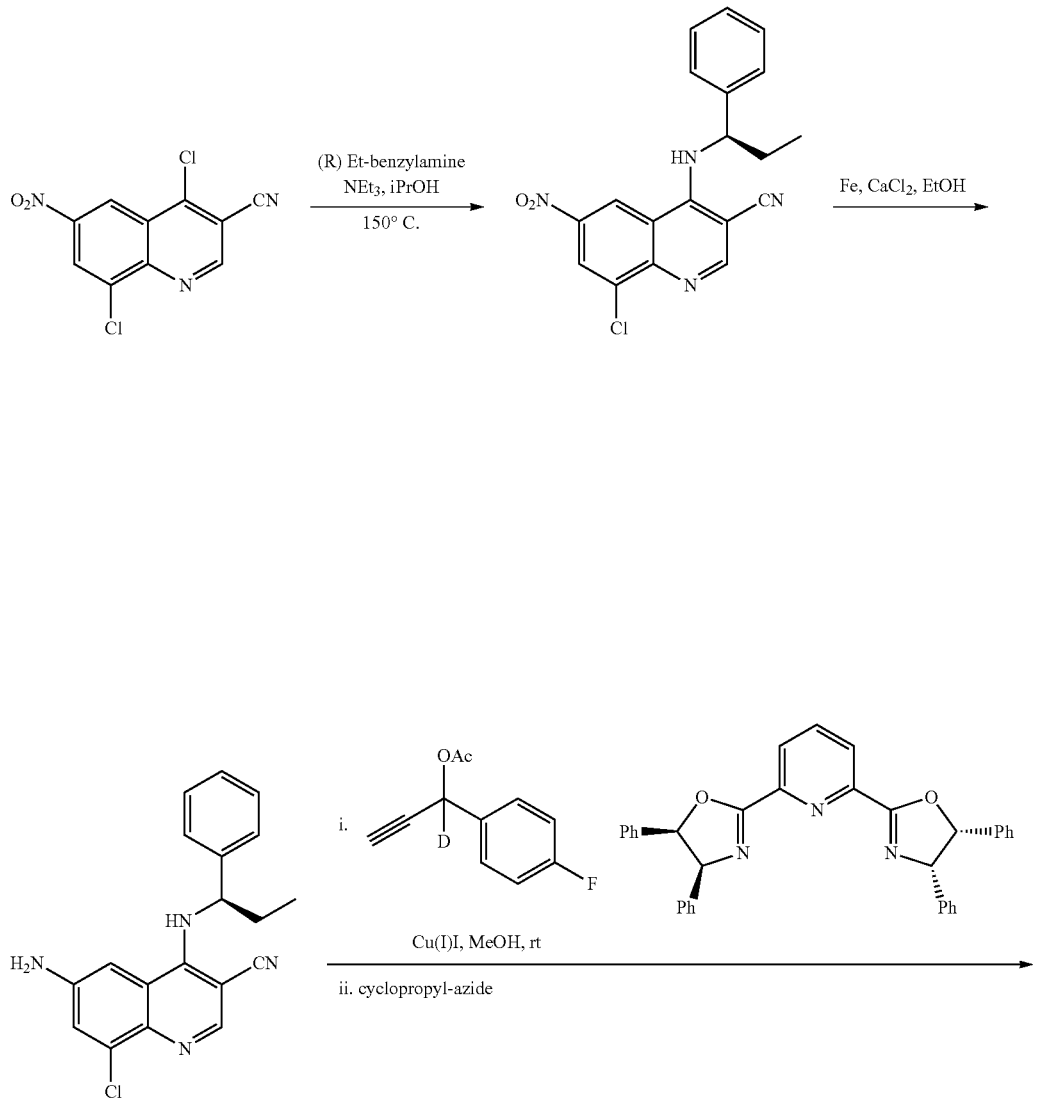

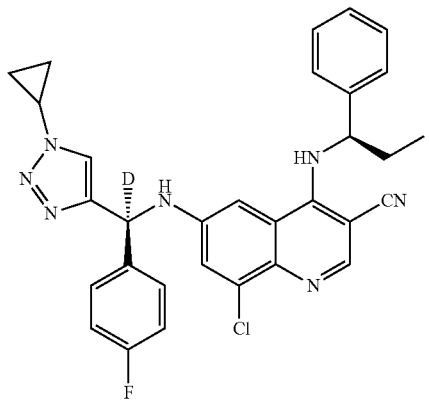

(R)-8-chloro-nitro-4-((1-phenylpropyl)amino)quinoline-3-carbonitrile 4,8-dichloro-6-nitroquinoline-3-carbonitrile (200 mg, 0.75 mmol), (R)-ethyl benzylamine (121 mg, 0.895 mmol) in iso-propanol (3 mL) were heated under microwave conditions at 150° C. for 45 minutes. The reaction was cooled to room temperature. Water and EtOAc were added. The aqueous layer was extracted with EtOAc and the combined organic layers were dried over sodium sulfate. Filtration and evaporation of solvents yielded the crude product which was used in the next step without further purification.
ES/MS 367.1 (M+H+).

6-amino-8-chloro-4-((1-phenylpropyl)amino)quinoline-3-carbonitrile (R)-6-amino-8-chloro-4-((1-phenylpropyl)amino)quinoline-3-carbonitrile (287 mg, 0.78 mmol), calcium chloride (172.6 mg, 1.17 mmol), iron powder (218.5 mg, 3.91 mmol) were heated in ethanol (5 mL)/water (0.5 mL) at 60° C. for 1 hour. The reaction was cooled to room temperature and solids were removed via filtration. The solids were washed with EtOAc and the combined organic layers were washed with aqueous sodium bicarbonate solution, brine, and were dried over sodium sulfate. Filtration and evaporation of all volatiles yielded the product.
ES/MS 337.1 (M+H+).

(S)-8-chloro-6-(((1-cyclopropyl-1H-1,2,3-triazol-4-yl)(4-fluorophenyl)-methyl-d)amino)-4-((1-phenyl-propyl)amino)quinoline-3-carbonitrile ((R)-6-amino-8-chloro-4-((1-phenylpropyl)amino)quinoline-3-carbonitrile (55 mg, 0.16 mmol), CuI (3.1 mg, 0.016 mmol) and 2,6-bis((4S,5R)-4,5-diphenyl-4,5-dihydrooxazol-2-yl)pyridine [oxazoline ligand] (8.5 mg, 0.016 mmol) were sonicated in MeOH (2.0 mL) for about 1 minute. Alkynyl acetate (34.1 mg, 0.18 mmol) and di-isopropyl ethyl amine (25.3 mg, 0.2 mmol) were added and the reaction was stirred overnight. Cyclopropylazide (17 mg, 0.2 mmol) in MeOH (1 mL) was added and the reaction was stirred for additional 24 hrs at room temperature. Solvents were removed in vacuo and the crude material was purified RP-HPLC (eluent: water/MeCN*0.1% TFA) to yield the product as trifluoro acetate salt.

$^1$H NMR (400 MHz, DMSO-d$_6$) δ 8.26 (s, 1H), 8.03 (s, 1H), 7.62-7.51 (m, 3H), 7.45-7.29 (m, 3H), 7.29-7.20 (m, 4H), 7.20-7.12 (m, 2H), 5.52-5.36 (m, 1H), 4.00-3.94 (m, 1H), 2.19-2.09 (m, 1H), 1.98-1.89 (m, 1H), 1.19-1.12 (m, 2H), 1.13-1.06 (m, 2H), 0.99-0.88 (m, 3H).
ES/MS 553.2 (M+H+).

Example 3 Procedure 3

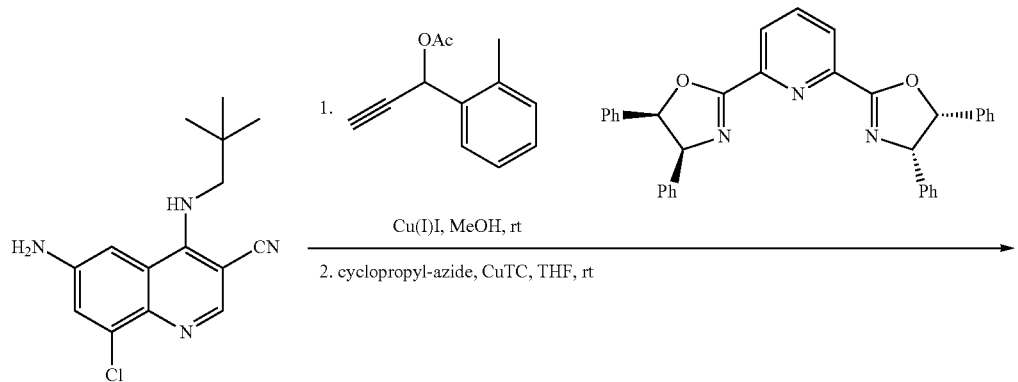

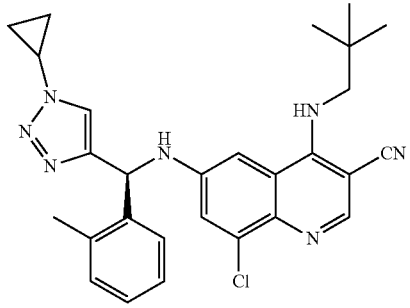

(S)-8-chloro-6-(((1-cyclopropyl-1H-1,2,3-triazol-4-yl)(4-fluorophenyl)-methyl)amino)-4-(neopentyl)quinoline-3-carbonitrile CuI (2.0 mg, 0.01 mmol) and 2,6-bis((4S,5R)-4,5-diphenyl-4,5-dihydrooxazol-2-yl)pyridine [oxazoline ligand] (6.5 mg, 0.012 mmol) were sonicated in MeOH (5.0 mL) for about 5 minutes. Alkynyl acetate (23.5 mg, 0.13 mmol) in MeOH (2 mL), 6-amino-8-chloro-4-(neopentylamino)quinoline-3-carbonitrile (30 mg, 0.104 mmol), and di-isopropyl ethyl amine (16.1 mg, 0.13 mmol) were added and the reaction was stirred for 1 hour. The crude reaction product was filtered over silica gel (eluent: EtOAc/hexanes) and this product was used in the next step.

ES/MS 417.3 (M+H$^+$).

The product from the N-alkylation was dissolved in THF (1 mL) at room temperature and copper (I) thiophene carboxylate (7.8 mg, 0.041 mmol) was added. Cyclopropylazide (8.5 mg, 0.014 mmol) in THF (1 mL) was added and the reaction was stirred for 30 minutes at room temperature. The reaction was partitioned between aqueous sodium bicarbonate solution and EtOAc. The aqueous layer was extracted with EtOAc and the combined layers were washed with brine and dried over sodium sulfate. Filtration and evaporation of solvents gives crude material. The crude material was purified RP-HPLC (eluent: water/MeCN*0.1% TFA) to yield the product as trifluoro acetate salt.

$^1$H NMR (400 MHz, Methanol-d$_4$) δ 8.48 (s, 1H), 7.75 (s, 1H), 7.61 (s, 1H), 7.28-7.13 (m, 4H), 6.90 (s, 1H), 6.17 (s, 1H), 3.99 (d, J=13.8 Hz, 1H), 3.92-3.83 (m, 2H), 2.38 (s, 3H), 1.25-1.08 (m, 4H), 0.94 (s, 9H).

ES/MS 500.2 (M+H$^+$).

Example 4 Procedure 4

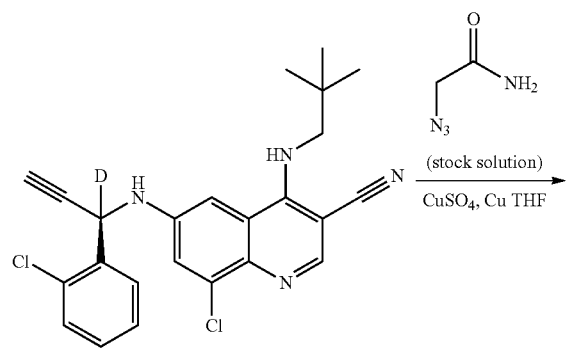

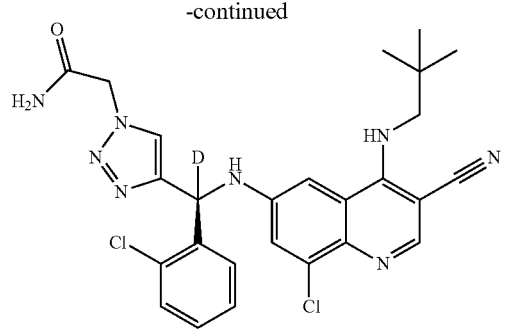

(S)-2-(4-(((8-chloro-3-cyano-4-(neopentylamino)quinolin-6-yl)amino)(2-chlorophenyl) methyl-d)-1H-1,2,3-triazol-1-yl)acetamide 2-Deutero (R)-8-chloro-6-((1-(2-chlorophenyl)prop-2-yn-1-yl)amino)-4-(neopentylamino)quinoline-3-carbonitrile (20 mg, 0.046 mmol), copper powder (15 mg, 0.23 mmol), acetic acid (108 μL, 1.8 mmol) and saturated aqueous copper (II) sulfate (0.1 mL) were added to the stock solution of 2-azidoacetamide (45 mg, 0.045 mmol). After 2 hrs, the reaction was complete. The solids were removed by filtration. The solution was diluted with ethyl acetate (15 mL) and washed with saturated sodium bicarbonate (8 mL), brine (8 mL), dried over Na$_2$SO$_4$ and concentrated. The residue was taken up in water (1 mL) and MeOH (1 mL) with 2 drops of TFA and subjected to RP-HPLC (eluent: water/MeCN*0.1% TFA). The fractions containing the desired product were combined and subjected to lyophilization, providing the desired compound.

$^1$H NMR (400 MHz, Methanol-d4) δ 8.52 (s, 1H), 7.83 (s, 1H), 7.63 (t, J=1.5 Hz, 1H), 7.50 (d, J=7.3 Hz, 2H), 7.40-7.30 (m, 2H), 7.02 (d, J=2.3 Hz, 1H), 5.25-5.12 (m, 2H), 4.11 (d, J=13.8 Hz, 1H), 3.84 (d, J=13.8 Hz, 1H), 1.00 (s, 9H).

125
Example 5 Procedure 5
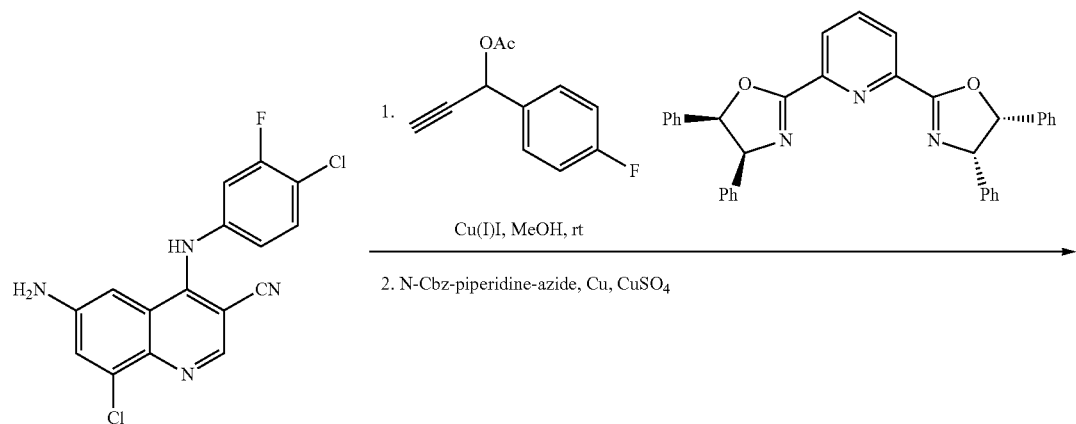
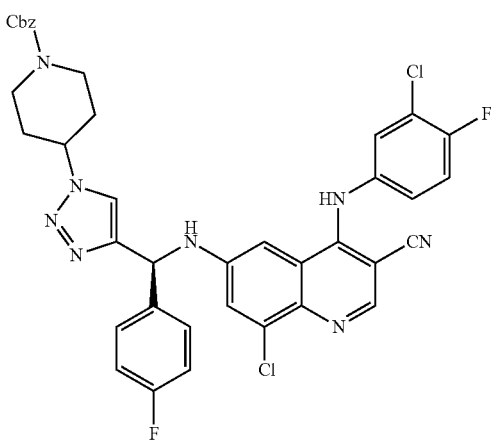
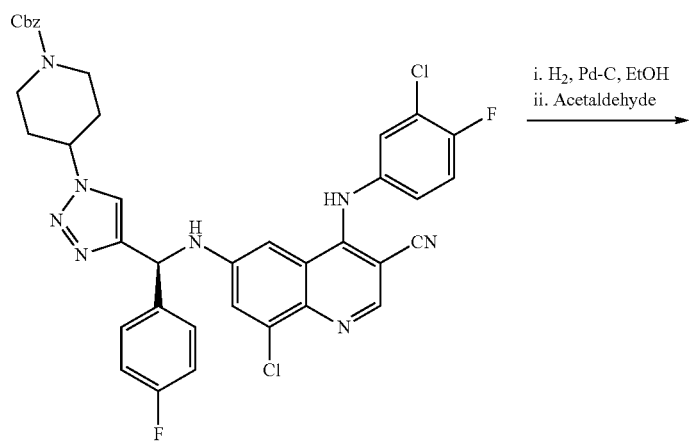
i. H$_2$, Pd-C, EtOH
ii. Acetaldehyde

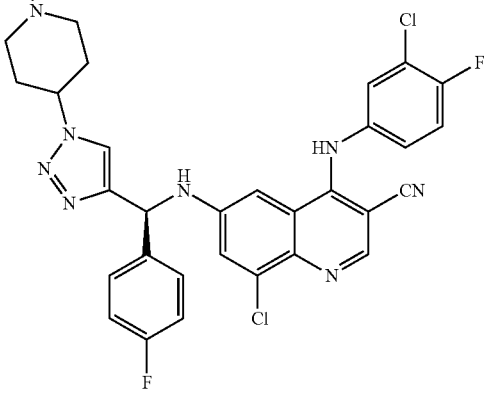

(R)-8-cloro-4-((3-cloro-4-fluorophenyl)amino-(1-(4-fluorophenyl)prop-2-yn-1-yl)amino)quinoline-3-carbonitrile CuI (27.0 mg, 0.144 mmol) and 2,6-bis((4S,5R)-4,5-diphenyl-4,5-dihydrooxazol-2-yl)pyridine [oxazoline ligand] (90.1 mg, 3.46 mmol) were sonicated in MeOH (10 mL) for about 5 minutes. Additional MeOH (40 mL) was added. Alkynyl acetate (23.5 mg, 0.13 mmol) in MeOH (2 mL), 6-amino-8-chloro-4-((4-chloro-3-fluorophenyl)amino)quinoline-3-carbonitrile (1000 mg, 2.88 mmol), and di-isopropyl ethyl amine (484 mg, 3.75 mmol) were added and the reaction was stirred at −15° C. for 23 hour. The crude reaction product was purified via silica gel chromatography (eluent: EtOAc/hexanes) to yield the product.

$^1$H NMR (400 MHz, DMSO-d6) δ 9.42 (s, 1H), 8.42 (d, J=0.9 Hz, 1H), 7.65-7.56 (m, 4H), 7.53 (dt, J=6.6, 1.9 Hz, 1H), 7.48-7.39 (m, 3H), 7.32-7.26 (m, 2H), 7.26-7.20 (m, 3H), 7.18 (d, J=9.0 Hz, 1H), 5.64 (dd, J=9.1, 2.3 Hz, 1H), 3.49 (d, J=2.2 Hz, 1H).

ES/MS 479.2 (M+H$^+$).

(S)-benzyl 4-(4-(((8-chloro-4-((3-chloro-4-fluorophenyl)amino)-3-cyanoquinolin-6-yl)amino)(4-fluorophenyl)methyl)-1H-1,2,3-triazol-1-yl)piperidine-1-carboxylate (R)-8-chloro-4-((3-chloro-4-fluorophenyl)amino)-6-((1-(4-fluorophenyl)prop-2-yn-1-yl)amino)quinoline-3-carbonitrile (1000 mg, 2.086 mmol) and N-Cbz piperidine 4 azide (543 mg, 2.086 mmol) were dissolved in THF (20 mL). Copper metal (132 mg, 2.086 mmol) was added followed by saturated aqueous copper sulfate solution (1 mL). After 16 hrs, the reaction was complete. The solids were removed by filtration through a pad of celite. The volatiles were removed under reduced pressure and the residue was purified by chromatography on silica gel (eluent: EtOAc/hexanes). The fractions containing product were combined and the solvent was removed under reduced pressure, providing the product.

ES/MS 739.1 (M+H$^+$).

Alternatively, the cycloaddition can be performed with Cu(I)thiophenecarboxylate catalyst or using the Cu(I) present from the N-alkylation.

Increase of the ee via recrystallization: 1.08 g of (S)-benzyl 4-(4-(((8-chloro-4-((3-chloro-4-fluorophenyl)amino)-3-cyanoquinolin-6-yl)amino(4-fluorophenyl)methyl)-1H-1,2,3-triazol-1-yl)piperidine-1-carboxylate (83% ee) was dissolved in THF (15 mL). The solvent was removed under reduced pressure. The residue was stirred with EtOH (30 mL). A fine solid formed and was isolated by filtration. Repeated the cycle two more time, providing the title compound with >95% ee.

(S)-8-chloro-4-((3-chloro-4-fluorophenyl)amino)-6-(((1-(1-ethylpiperidin-4-yl)-1H-1,2,3-triazol-4-yl)(4-fluorophenyl)methyl)amino)quinoline-3-carbonitrile (S)-benzyl 4-(4-(((8-chloro-4-((3-chloro-4-fluorophenyl)amino)-3-cyanoquinolin-6-yl)amino)(4-fluorophenyl)methyl)-1H-1,2,3-triazol-1-yl)piperidine-1-carboxylate (130 mg, 0.176 mmol) was dissolved in EtOAc (12 mL). Pd—C (37.3 mg; 10%) was added and the atmosphere was replaced with hydrogen. Acetaldehyde (77.4 mg, 1.75 mmol) was added and the reaction was stirred for 2.5 hrs at room temperature. The Pd/C was removed by filtration and the solvent was removed under reduced pressure. The residue was subjected to flash chromatography (eluent: (20% MeOH in EtOAc)/hexanes). The fractions containing product were combined and the solvent was removed under reduced pressure. The residue was taken up in DMF (0.4 ml) and MeOH (2 mL) with 2 drops of TFA and subjected to RP-HPLC (eluent: water/MeCN*0.1 TFA). The product fractions were combined and lyophilized, providing the product as trifluoro acetate salt.

$^1$H NMR (400 MHz, DMSO-d6) δ 9.40 (s, 1H), 9.31 (s, 1H), 8.40 (s, 1H), 8.11 (s, 0H), 7.98 (s, 1H), 7.66 (d, J=2.2 Hz, 1H), 7.51-7.43 (m, 4H), 7.42-7.32 (m, 2H), 7.21 (qd, J=4.3, 2.7 Hz, 3H), 7.14 (t, J=8.8 Hz, 3H), 6.14-6.01 (m, 1H), 4.85 (d, J=7.6 Hz, 0H), 4.72 (ddd, J=11.8, 7.7, 4.1 Hz, 1H), 3.60 (d, J=13.7 Hz, 4H), 3.41 (m, 0H), 3.25-3.10 (m, 3H), 3.06 (dt, J=13.3, 10.2 Hz, 1H), 2.41-2.25 (m, 2H), 2.24-2.07 (m, 2H), 1.22 (t, J=7.3 Hz, 3H).

ES/MS 633.1 (M+H$^+$).

Removal of the protecting group in the absence of a reaction partner yields the corresponding un-alkylated amine derivatives.

Example 6 Procedure 6

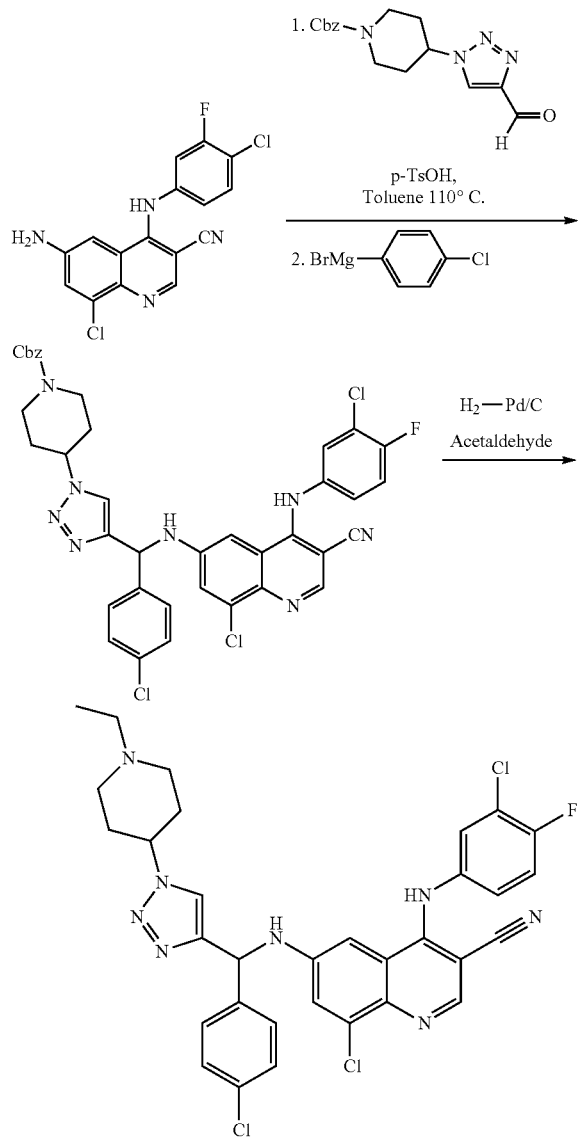

Benzyl 4-(4-(((8-chloro-4-((3-chloro-4-fluorophenyl)amino)-3-cyanoquinolin-6-yl)amino)(4-chlorophenyl)methyl)-1H-1,2,3-triazol-1-yl)piperidine-1-carboxylate A suspension of the 6-amino-8-chloro-4-((4-chloro-3-fluorophenyl)amino)quinoline-3-carbonitrile (204 mg, 0.65 mmol), aldehyde (225 mg, 0.65 mmol) and pTSA (12.4 mg, 0.065 mmol) in toluene (15 mL) was heated at reflux (50 mL RBF equipped with a Hickman still). After 4 hrs, the solvent was removed under reduced pressure. The solid was dissolved in methyl-THF and 4-Cl-phenylmagnesium bromide (2.6 mmol; 2.6 mL 1-M THF) was added dropwise at −10 C. After 30 min, the reaction was quenched with sat $NH_4Cl$ (3 mL). The layers were separated and the aqueous phase was extracted with EtOAc (15 mL). The combined organic layers were washed with brine (5 mL), dried over sodium sulfate and concentrated. The residue was subjected to flash chromatography on silica gel (eluent: EtOAc/hexanes). The fractions containing product were combined and the solvent was removed providing the product.

ES/MS 753.5 (M+H$^+$).

8-chloro-4-((3-chloro-4-fluorophenyl)amino)-6-(((4-chlorophenyl)(1-(1-ethylpiperidin-4-yl)-1H-1,2,3-triazol-4-yl)methyl)amino)quinoline-3-carbonitrile The starting material (94 mg, 0.124 mmol) and Pd—C (39 mg, 10%) in EtOH (3 mL)/EtOAc (2 mL) were stirred under an atmosphere of hydrogen. After 18 hrs, the reaction was filtered and the volatiles were removed in vacuo and the crude was purified via RP-HPLC (eluent: water/MeCN 0.1% TFA) to yield the product as trifluoro acetate salt.

1H NMR (400 MHz, DMSO-d6) δ 9.42-9.32 (m, 2H), 8.40 (s, 1H), 8.13 (s) & 8.00 (s, 1H), 7.66 (d, J=2.2 Hz, 1H), 7.48-7.20 (m, 13H), 6.07 (m, 1H), 4.84 (m) & 4.73 (m, 1H), 3.67-3.56 (m, 3H), 3.25-2.98 (m, 6H), 2.42-2.25 (m, 2H), 2.24-2.08 (m, 2H), 1.21 (t, J=7.3 Hz, 3H).

ES/MS 648. (M+H$^+$).

Removal of the protecting group in the absence of a reaction partner yields the corresponding un-alkylated amine derivatives.

Example 7 Procedure 7

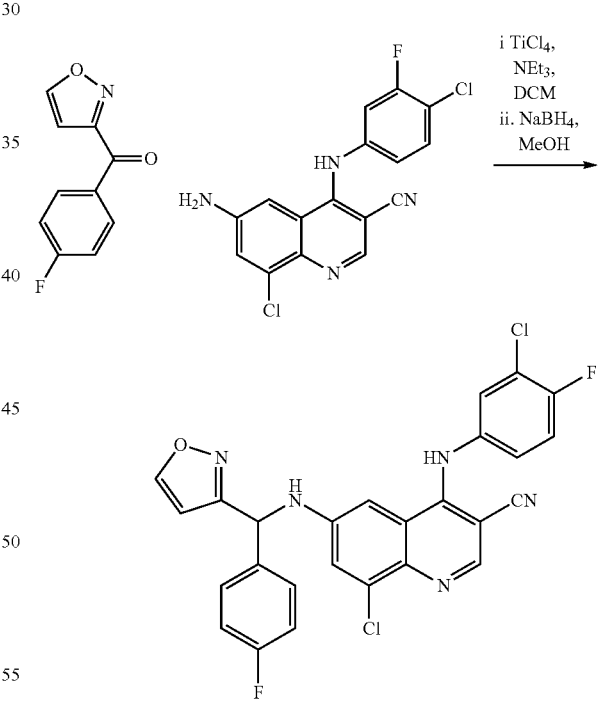

8-chloro-4-((3-chloro-4-fluorophenyl)amino)-6-(((4-fluorophenyl)(isoxazol-3-yl)methyl)amino)quinoline-3-carbonitrile To a suspension of the 6-amino-8-chloro-4-((4-chloro-3-fluorophenyl)amino)quinoline-3-carbonitrile (50 mg, 0.144 mmol) and (4-fluorophenyl)isoxazol-3-yl)methanone (28 mg, 0.144 mmol) in DCM (2 mL) was added triethylamine (35 mg, 0144 mmol) followed by $TiCl_4$ in DCM (0.86 mmol/0.086 mL). The reaction was stirred overnight at room temperature. It was diluted with MeOH (2 mL) and sodium borohydride (16 mg, 0.43 mmol) was added. The reaction was stirred for 2 hours, then was diluted with water and treated with 1M NaOH until a pH of about 13 was reached. It was extracted with DCM three times, and the combined organic layers were dried over sodium sulfate, filtered, and concentrated. The product was purified by chromatography on silica gel (eluent: EtOAc/hexanes) to yield the material as an oil, which was lyophilized from MeCN/water to yield the product as a solid.

1H NMR (400 MHz, DMSO-d6) δ 9.44 (s, 1H), 8.89 (dd, J=1.7, 0.5 Hz, 1H), 8.42 (s, 1H), 7.69 (d, J=2.3 Hz, 1H), 7.58-7.41 (m, 5H), 7.34 (d, J=2.4 Hz, 1H), 7.27 (ddd, J=8.9, 4.2, 2.7 Hz, 1H), 7.25-7.17 (m, 2H), 6.62 (d, J=1.7 Hz, 1H), 6.21 (d, J=9.4 Hz, 1H).

ES/MS 522.1 (M+H⁺).

Example 8 Procedure 8

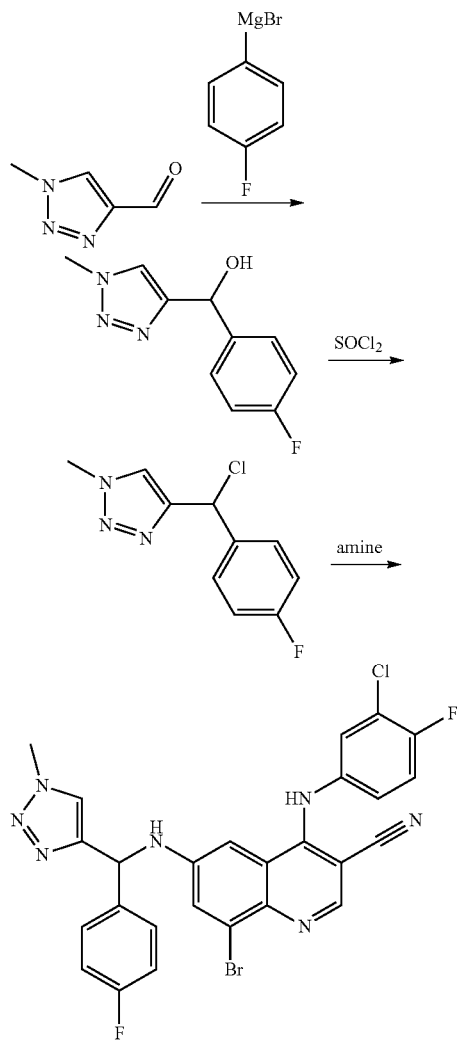

(4-fluorophenyl)(1-methyl-1H-1,2,3-triazol-4-yl) methanol 1.0 M (THF) of (4-fluorophenyl)magnesium bromide (4.9 mL, 4.9 mmol) was added to a stirring solution of 1-methyl-1H-1,2,3-triazole-4-carbaldehyde (500 mg, 4.5 mmol) in THF (30 mL) at 0° C. The resulting solution was allowed to warm to room temperature then stirred for additional 16 hrs. The reaction mixture was quenched with satd. aqueous NH₄Cl (30 mL) and the aqueous layer was extracted with EtOAc (3×30 mL). The combined organic layer was washed with brine, dried over Na₂SO₄, and concentrated to give crude alcohol. Chromatography afforded the title compound. ES/MS 208.0 (M+H⁺).

4-(chloro(4-fluorophenyl)methyl)-1-methyl-1H-1,2, 3-triazole

SOCl₂ (0.9 mL, 12 mmol) was added to a stirring solution of (4-fluorophenyl)(1-methyl-1H-1,2,3-triazol-4-yl)methanol (520 mg, 2.5 mmol) in DCM (50 mL). The reaction mixture was stirred for 16 hrs then concentrated to give crude chloride. The resulting compound was used in the next step with no further purification.

8-bromo-4-((3-chloro-4-fluorophenyl)amino)-6-(((4-fluorophenyl)(1-methyl-1H-1,2,3-triazol-4-yl) methyl)amino)quinoline-3-carbonitrile 4-(chloro(4-fluorophenyl)methyl)-1-methyl-1H-1,2,3-triazole (86 mg, 0.38 mmol) and di-isopropyl ethyl amine (0.2 mL, 1.28 mmol) were added to a stirring solution of 6-amino-8-bromo-4-((3-chloro-4-fluorophenyl)amino)quinoline-3-carbonitrile (100 mg, 0.25 mmol) in ACN (10 mL). The reaction mixture was heated at 90° C. for 16 hrs. The solution was cooled to room temperature then concentrated to give crude product. RP-HPLC (eluent: water/MeCN*0.1% TFA) afforded the title compound.

¹H NMR (400 MHz, DMSO-d6) δ 9.85 (s, 1H), 9.42 (s, 1H), 8.38 (s, 1H), 7.88-7.81 (m, 2H), 7.57-7.31 (m, 5H), 7.28-7.06 (m, 3H), 6.05 (s, 1H), 3.97 (s, 3H).

ES/MS 580.1 (M+H⁺).

Example 9 Procedure 9

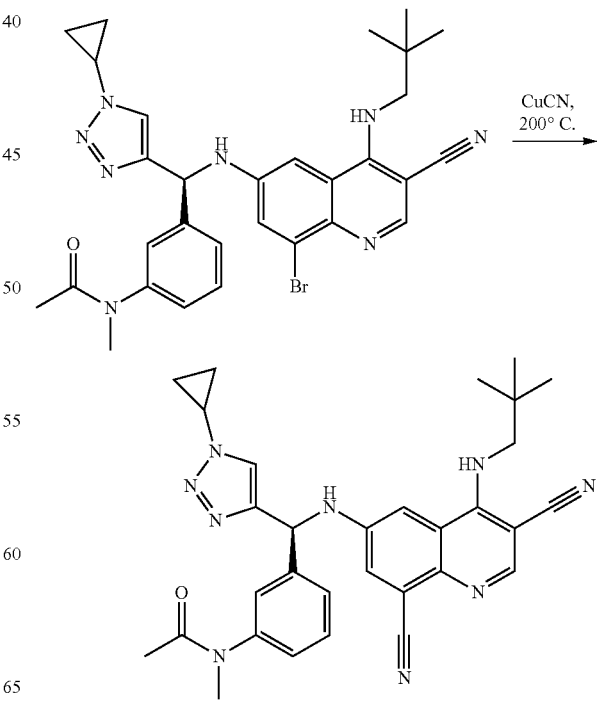

(S)—N-(3-((1-cyclopropyl-1H-1,2,3-triazol-4-yl)((3,8-dicyano-4-(neopentylamino)quinolin-6-yl)amino)methyl)phenyl)-N-methylacetamide DMF (2 mL) was added to (S)—N-(3-(((8-bromo-3-cyano-4-(neopentylamino)quinolin-6-yl)amino)(1-cyclopropyl-1H-1,2,3-triazol-4-yl)methyl)phenyl)-N-methylacetamide (92 mg, 0.15 mmol) and CuCN (41 mg, 0.46 mmol) in a microwave vial. The vial was heated to 200° C. for 15 minutes in a microwave and allowed to cool to room temperature. The reaction mixture was poured into water (4 mL) and extracted with EtOAc (3×8 mL). The combined organic phases were washed with brine (5 mL), dried over MgSO$_4$ and concentrated. The crude residue was purified by RP-HPLC (eluent: water/MeCN*0.1% TFA) to yield the product as trifluoro acetate salt.

ES/MS 548.1 (M+H$^+$).

Alternative Access to the 8-Cyano Core

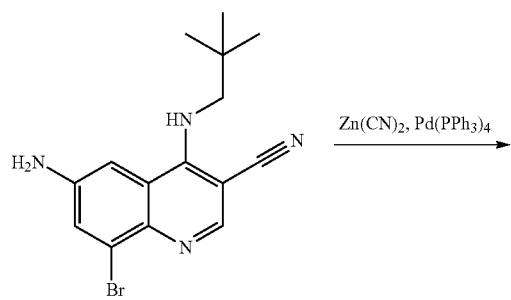

6-amino-4-(neopentylamino)quinoline-3,8-dicarbonitrile

Solid Zn(CN)$_2$ (211 mg, 1.8 mmol) and Pd(PPh)$_4$ (35 mg, 0.03 mmol) were added to a solution of 6-amino-8-bromo-4-(neopentylamino)quinoline-3-carbonitrile (500 mg, 1.5 mmol) in NMP (20 mL). The resulting mixture was degassed by bubbling argon gas through for 5 min. The reaction vessel was sealed then heated to 120° C. for 16 hrs. The reaction mixture was cooled then loaded directly to silica column to afford the pure nitrile. ES/MS 280.3 (M+H$^+$).

Further elaboration to the final compound can be performed according to procedures outlined herein.

Example 10 Procedure 10

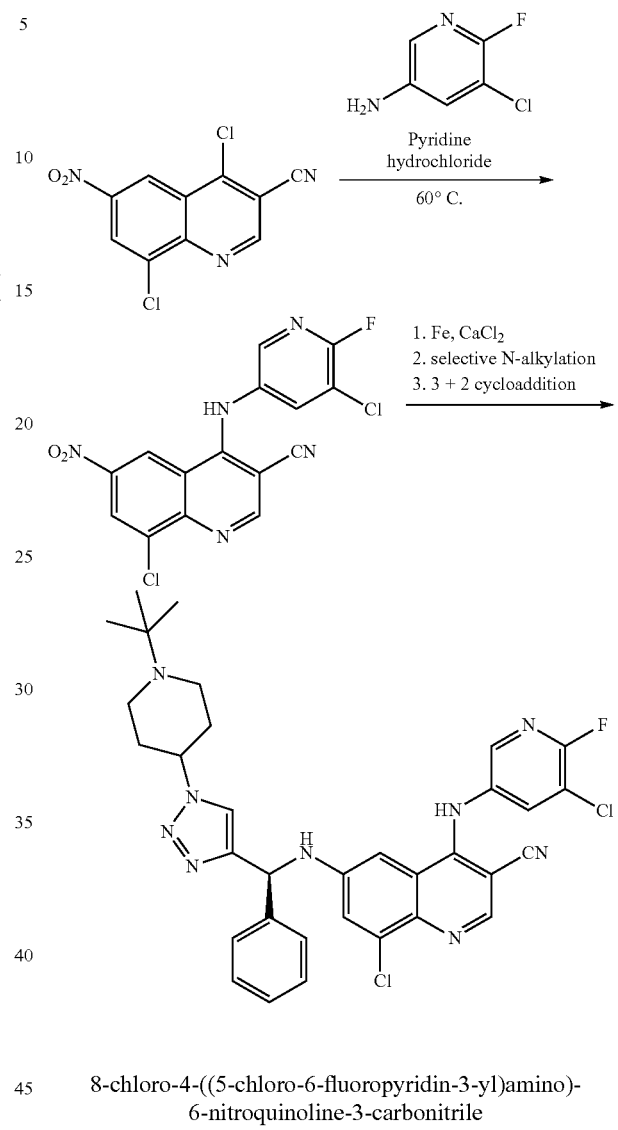

8-chloro-4-((5-chloro-6-fluoropyridin-3-yl)amino)-6-nitroquinoline-3-carbonitrile 4,8-dichloro-6-nitroquinoline-3-carbonitrile (300 mg, 1.12 mmol), 5-chloro-6-fluoropyridin-3-amine (180 mg, 1.23 mmol) and pyridine hydrochloride (388 mg, 3.36 mmol) in iso-propanol (7 mL) was heated at 60° C. overnight. The reaction was cooled to room temperature. Water was added and the resulting precipitate was collected via filtration. The crude product was used in the next step without further purification. ES/MS 377.9 (M+H$^+$).

6-amino-8-chloro-4-((5-chloro-6-fluoropyridin-3-yl)amino)quinoline-3-carbonitrile 8-chloro-4-((5-chloro-6-fluoropyridin-3-yl)amino)-6-nitroquinoline-3-carbonitrile (405 mg, 1.07 mmol), calcium chloride (178 mg, 1.61 mmol), iron powder (179 mg, 3.21 mmol) were heated in ethanol (10 mL)/water (1 mL) at 60° C. overnight. The reaction was cooled to room temperature and solids were removed via filtration. The solids were washed with EtOAc and the combined organic layers were washed with aqueous sodium bicarbonate solution, brine,

(S)-6-(((1-(1-(tert-butyl)piperidin-4-yl)-1H-1,2,3-triazol-4-yl)(phenyl)methyl)amino)-8-chloro-4-((5-chloro-6-fluoropyridin-3-yl)amino)quinoline-3-carbonitrile 6-amino-8-chloro-4-((5-chloro-6-fluoropyridin-3-yl) amino)quinoline-3-carbonitrile (242 mg, 0.69 mmol), CuI (13 mg, 0.07 mmol) and 2,6-bis((4S,5R)-4,5-diphenyl-4,5-dihydrooxazol-2-yl)pyridine [oxazoline ligand] (36 mg, 0.07 mmol) were sonicated in MeOH (9 mL) for about 1 minute. Alkynyl acetate (145 mg, 0.83 mmol) and di-isopropyl ethyl amine (108 mg, 0.83 mmol) were added and the reaction was stirred overnight. 4-azido-1-(tert-butyl) piperidine (152 mg, 0.83 mmol) was added and the reaction was stirred for two days at room temperature. Solvents were removed in vacuo and the crude material was purified via silica gel chromatography (eluent: EtOAc/hexanes) and RP-HPLC (eluent: water/MeCN*0.1% TFA) to yield the product as the trifluoroacetate salt.

$^1$H NMR (400 MHz, DMSO-d$_6$) δ 9.61 (s, 1H), 9.22 (m, 1H), 8.46 (s, 1H), 8.18-8.09 (m, 2H), 7.99 (s, 1H), 7.72 (d, J=2.2 Hz, 1H), 7.53-7.42 (m, 3H), 7.38-7.19 (m, 4H), 6.12-6.04 (m, 1H), 4.87-4.73 (m, 1H), 3.65 (d, J=11.7 Hz, 2H), 3.12 (dt, J=13.1, 10.2 Hz, 2H), 2.43-2.17 (m, 4H), 1.36 (s, 9H). ES/MS 644.2 (M+H$^+$).

Example 11 Procedure 11

(S)-8-acetyl-6-(((1-cyclopropyl-1H-1,2,3-triazol-4-yl)(4-fluorophenyl)methyl-d)amino)-4-(neopentylamino)quinoline-3-carbonitrile To (S)-8-bromo-6-(((1-cyclopropyl-1H-1,2,3-triazol-4-yl)(4-fluorophenyl)methyl-d)amino)-4-(neopentylamino) quinoline-3-carbonitrile (85 mg, 0.16 mmol) in DMF (1 mL) and water (0.1 mL) was added 4-(vinyloxy)butan-1-ol (72 mg, 0.62 mmol), palladium (II) acetate (1 mg, 0.005 mmol), 1,3-bis(diphenylphosphino)propane (3 mg, 0.009 mmol) and potassium carbonate (32 mg, 0.23 mmol). Reaction mixture was flushed with nitrogen and then heated at 100° C. overnight. After cooling to room temperature, 1N HCl (1 mL) was added and the mixture stirred for 10 hours. Reaction was diluted with water and extracted thrice with EtOAc. Combined organics were washed with water and brine and dried (Na$_2$SO$_4$). Filtrate was concentrated to yield the crude title compound material which was purified by HPLC (eluent: water/MeCN*0.1% TFA). Product was obtained as a solid.

ES/MS 513.3 (M+H$^+$).

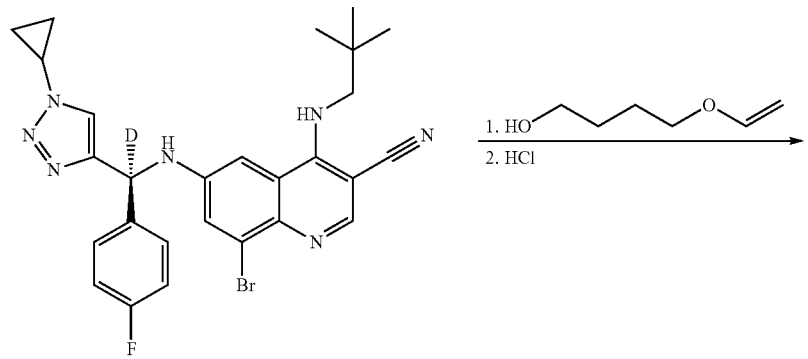

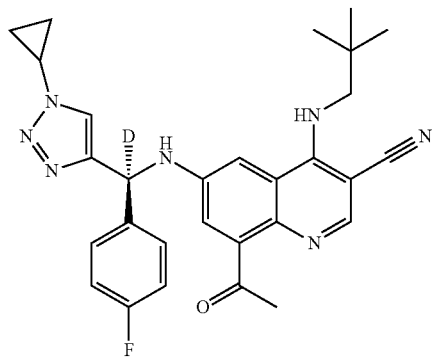

Example 12 Procedure 12

Example 13 Procedure 13

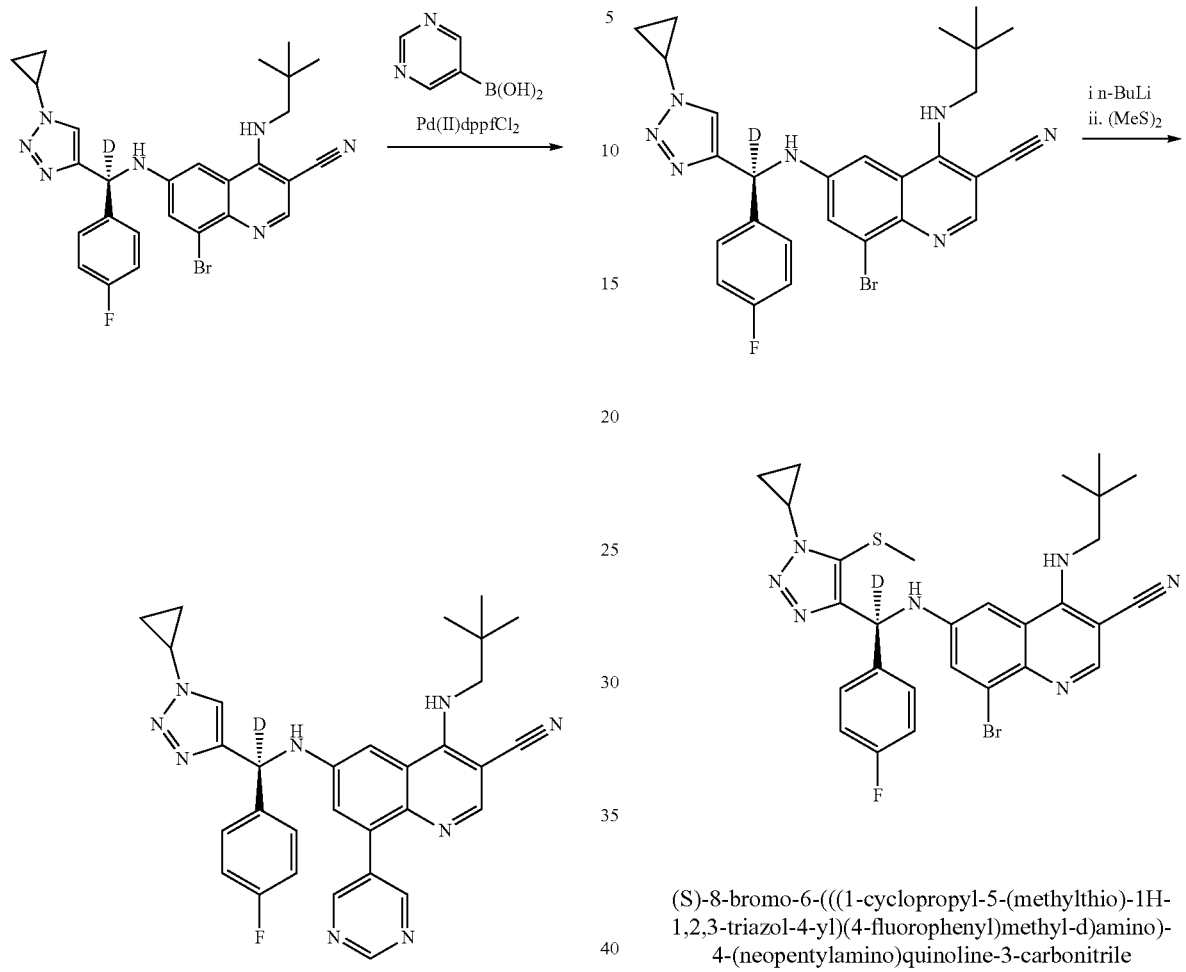

(S)-6-(((1-cyclopropyl-1H-1,2,3-triazol-4-yl)(4-fluorophenyl)methyl-d)amino)-4-(neopentylamino)-8-(pyrimidin-5-yl)quinoline-3-carbonitrile To (S)-8-bromo-6-(((1-cyclopropyl-1H-1,2,3-triazol-4-yl)(4-fluorophenyl)methyl-d)amino)-4-(neopentylamino)quinoline-3-carbonitrile (35 mg, 0.06 mmol), pyrimidin-5-ylboronic acid (9 mg, 0.08 mmol) and [1,1'-Bis(diphenylphosphino)ferrocene]dichloropalladium(II), complex with dichloromethane (2 mg, 0.003 mmol) was added dioxane (0.5 mL) and 1.5 M aqueous cesium carbonate (0.13 mL). Reaction mixture was flushed with nitrogen and heated at 80° C. overnight. Reaction was diluted with water and extracted twice with EtOAc. Combined organics were washed with water, brine, dried (Na$_2$SO$_4$), filtered and concentrated. Crude material was purified by HPLC (eluent: water/MeCN*0.1% TFA) to yield the product. ES/MS 549.3 (M+H$^+$).

(S)-8-bromo-6-(((1-cyclopropyl-5-(methylthio)-1H-1,2,3-triazol-4-yl)(4-fluorophenyl)methyl-d)amino)-4-(neopentylamino)quinoline-3-carbonitrile To (S)-8-bromo-6-(((1-cyclopropyl-1H-1,2,3-triazol-4-yl)(4-fluorophenyl)methyl-d)amino)-4-(neopentylamino)quinoline-3-carbonitrile (55 mg, 0.10 mmol) in THF (1 mL) at −78° C. was added, under nitrogen atmosphere, n-butyllithium (0.2 mL, 1.6 M). The mixture was stirred for 15 minutes after which a solution of dimethyldisulfide (11 mg, 0.12 mmol) in THF (0.5 mL) was added drop wise. The reaction mixture was allowed to warm to room temperature overnight and carefully quenched with water. Product was extracted with EtOAc and combined organics were washed with water, brine and dried (Na$_2$SO$_4$). Filtration and removal of solvent in vacuo furnished the crude which was purified by HPLC (eluent: water/MeCN*0.1% TFA) to give the product as a solid.

$^1$H NMR (400 MHz, DMSO-d$_6$) δ 8.33 (s, 1H), 7.88 (d, J=2.1 Hz, 1H), 7.73 (s, 1H), 7.58-7.50 (m, 2H), 7.39 (s, 1H), 7.15-7.07 (m, 3H), 4.03 (dd, J=13.9, 8.1 Hz, 1H), 3.98-3.88 (m, 1H), 3.41 (dd, J=13.9, 5.3 Hz, 1H), 2.26 (d, J=0.5 Hz, 3H), 1.28-1.14 (m, 4H), 0.85 (s, 9H).

ES/MS 595.2 (M+H$^+$).

Example 14 Procedure 14

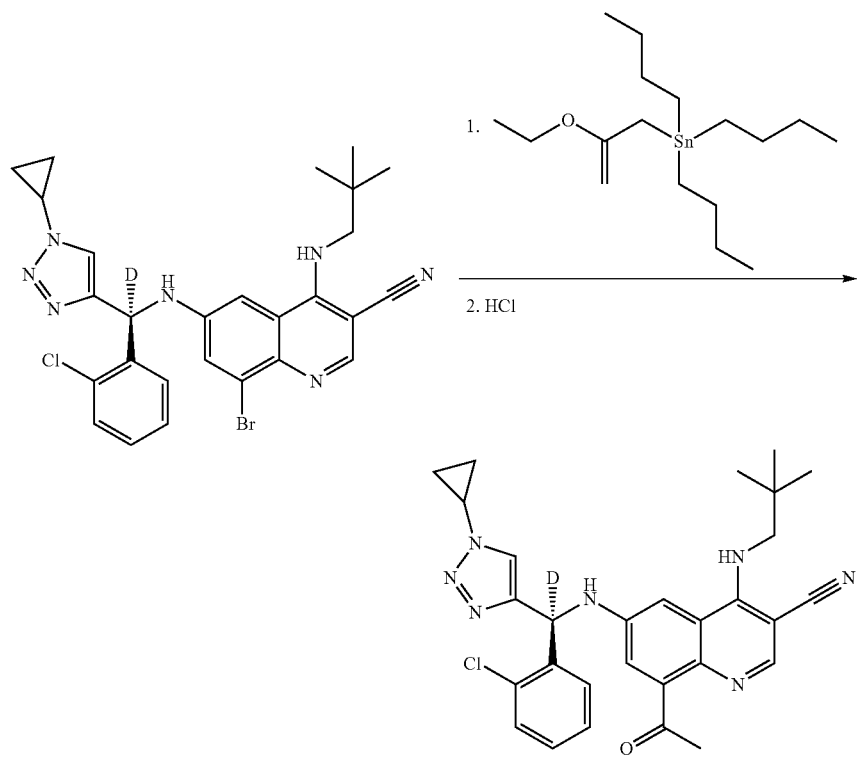

(S)-8-acetyl-6-(((2-chlorophenyl)(1-cyclopropyl-1H-1,2,3-triazol-4-yl)methyl-d)amino)-4-(neopentylamino)quinoline-3-carbonitrile To (S)-8-bromo-6-(((1-cyclopropyl-1H-1,2,3-triazol-4-yl)(4-fluorophenyl)methyl-d)amino)-4-(neopentylamino)quinoline-3-carbonitrile (65 mg, 0.12 mmol) and bis(triphenylphosphine)palladium(II) dichloride (8 mg, 0.01 mmol) in toluene (1 mL) was added tributyl(2-ethoxyallyl)stannane (47 mg, 0.13 mmol). The reaction mixture was flushed with nitrogen and heated at 100° C. overnight. After cooling to room temperature, 2N HCl (1 mL) was added and the mixture stirred for 2 hours. Reaction was diluted with water and extracted thrice with EtOAc. Combined organics were washed with water and brine and dried (Na$_2$SO$_4$). Filtrate was concentrated to yield the crude material which was purified twice by HPLC (eluent: water/MeCN*0.1% TFA) to give the product. ES/MS 529.2 (M+H$^+$).

Example 15 Procedure 15

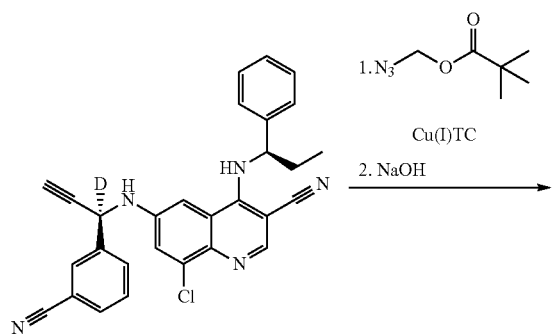

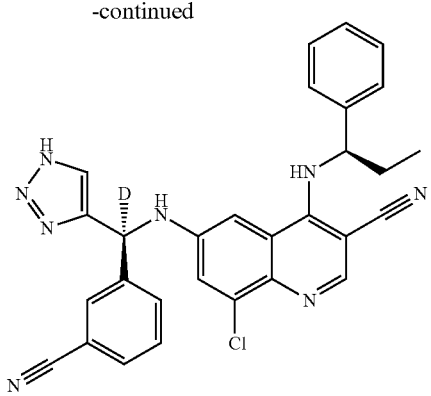

8-chloro-6-(((S)-(3-cyanophenyl)(1H-1,2,3-triazol-4-yl)methyl-d)amino)-4-(((R)-1-phenylpropyl)amino)quinoline-3-carbonitrile Starting alkyne (133 mg, 0.28 mmol) was dissolved in THF (2 mL). Cu(I)-thiophene-2-carboxylate (11 mg, 0.084 mmol) and azidomethyloxy pivalate (0.056 mL, 0.36 mmol) were added and the resulting solution stirred at room temperature for 30 minutes. The reaction contents were poured into saturated aqueous NaHCO$_3$ solution (5 mL) and extracted with EtOAc (3×8 mL). The combined organic layers were washed with brine (5 mL), dried over MgSO$_4$ and concentrated. The resulting crude residue was then dissolved in MeOH (2 mL). NaOH (1.0M in water, 0.61 mL, 0.61 mmol) was added and the reaction allowed to stir at room temperature for 30 min. HCl (1.0M in water, 0.61 mL, 0.61 mmol) was then added, the resulting solution poured into water (5 mL) and extracted with EtOAc (3×15 mL). The combined organic layers were washed with brine (5 mL), dried over MgSO$_4$ and concentrated. The resulting crude residue was purified by RP-HPLC (eluent: water/MeCN*0.1% TFA) to yield the product as trifluoro acetate salt.

ES/MS 520.0 (M+H$^+$).

Example 16 Procedure 16

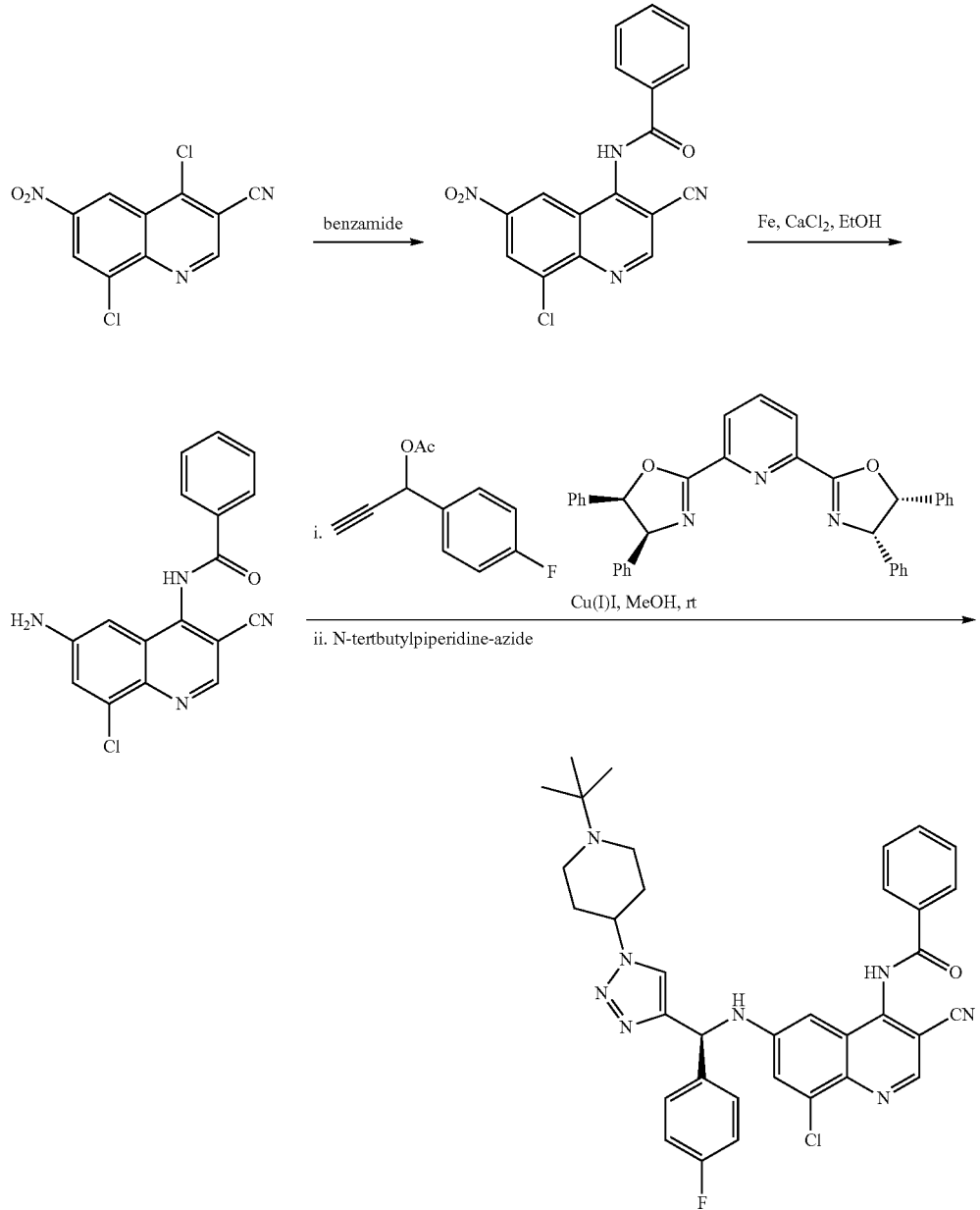

N-(8-chloro-3-cyano-6-nitroquinolin-4-yl)benzamide

To 4,8-dichloro-6-nitroquinoline-3-carbonitrile (300 mg, 1.12 mmol), benzamide (163 mg, 1.34 mmol), tris(dibenzylideneacetone) dipalladium (51 mg, 0.06 mmol), 4,5-bis(diphenylphosphino)-9,9-dimethylxanthene (65 mg, 0.11 mmol) and cesium carbonate (1.1 g, 3.36 mmol) was added dioxane and the reaction flushed with nitrogen. The mixture was then heated at 65° C. overnight. After cooling, solvent was removed in vacuo and the crude material purified by silica chromatography (MeOH/EtOAc) to yield a yellow solid. ES/MS 553.3 (M+H$^+$).

N-(6-amino-8-chloro-3-cyanoquinolin-4-yl)benzamide

N-(8-chloro-3-cyano-6-nitroquinolin-4-yl)benzamide (216 mg, 0.61 mmol), calcium chloride (102 mg, 0.92 mmol), iron powder (102 mg, 1.8 mmol) were heated in ethanol (10 mL) and water (1 mL) at 60° C. for 4 hours. The reaction was cooled to room temperature and solids were removed via filtration. The solids were washed with EtOAc and the combined organic layers were washed with water, brine, and dried (Na$_2$SO$_4$). Filtration and evaporation of all volatiles yielded the crude product which was carried forward as is. ES/MS 323.05 (M+H$^+$).

(S)—N-(6-(((1-(1-(tert-butyl)piperidin-4-yl)-1H-1,2,3-triazol-4-yl)(4-fluorophenyl)methyl)amino)-8-chloro-3-cyanoquinolin-4-yl)benzamide Starting with N-(6-amino-8-chloro-3-cyanoquinolin-4-yl)benzamide title compound was prepared following final steps of example 2. ES/MS 637.2 (M+H⁺).

Example 17 Procedure 17

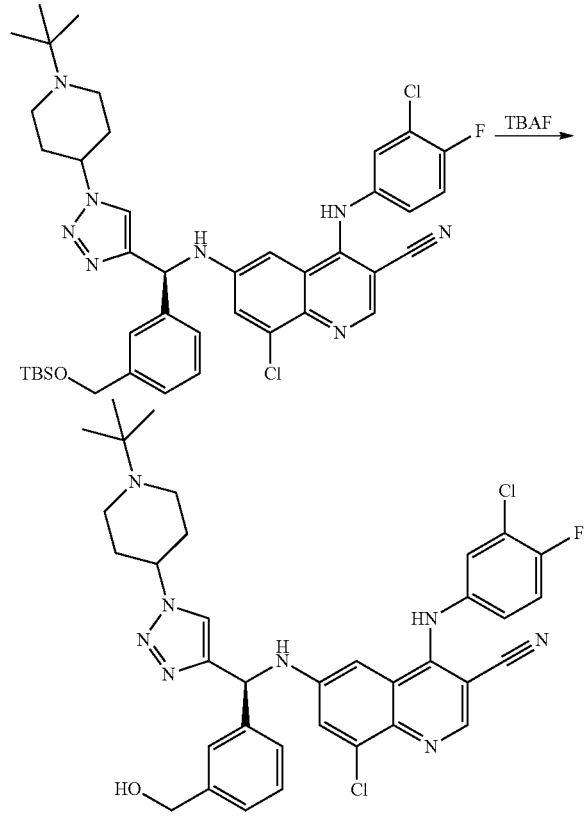

(S)-6-(((1-(1-(tert-butyl)piperidin-4-yl)-1H-1,2,3-triazol-4-yl)(3-(hydroxymethyl)phenyl)methyl)amino)-8-chloro-4-((3-chloro-4-fluorophenyl)amino)quinoline-3-carbonitrile (S)-6-(((1-(1-(tert-butyl)piperidin-4-yl)-1H-1,2,3-triazol-4-yl)(3-(((tert-butyldimethylsilyl)oxy)methyl)phenyl)methyl)amino)-8-chloro-4-((3-chloro-4-fluorophenyl)amino)quinoline-3-carbonitrile (247 mg, 0.31 mmol) was dissolved in THF (10 mL) at room temperature. Tetrabutylammonium fluoride (1.0M in THF, 0.38 mL, 0.38 mmol) was added and the resulting solution stirred for 30 minutes. Saturated aqueous NH₄Cl solution (3 mL) was added to the reaction mixture and the resulting solution extracted with EtOAc (3×15 mL). The organic phase was washed with brine (5 mL), dried over MgSO₄ and concentrated. The residue was purified by and RP-HPLC (eluent: water/MeCN*0.1% TFA) to yield the product as trifluoro acetate salt.

¹H NMR (400 MHz, Methanol-d₄) δ 8.44 (s, 1H), 7.78 (s, 1H), 7.65 (d, J=2.4 Hz, 1H), 7.47 (d, J=4.8 Hz, 2H), 7.38-7.23 (m, 5H), 7.18 (d, J=2.4 Hz, 1H), 6.02 (s, 1H), 4.89-4.71 (m, 1H), 4.58 (s, 2H), 3.79 (d, J=12.8 Hz, 2H), 3.21 (t, J=13.0 Hz, 2H), 2.42 (d, J=25.2 Hz, 4H), 1.46 (s, 9H). ES/MS 673.1 (M+H⁺).

Example 18 Procedure 18

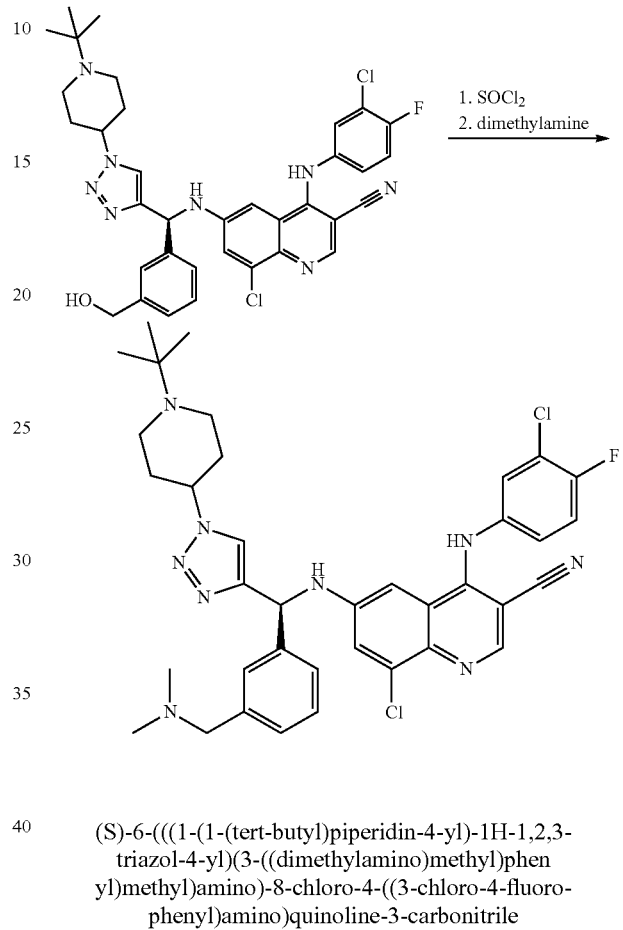

(S)-6-(((1-(1-(tert-butyl)piperidin-4-yl)-1H-1,2,3-triazol-4-yl)(3-((dimethylamino)methyl)phenyl)methyl)amino)-8-chloro-4-((3-chloro-4-fluorophenyl)amino)quinoline-3-carbonitrile (S)-6-(((1-(1-(tert-butyl)piperidin-4-yl)-1H-1,2,3-triazol-4-yl)(3-(hydroxymethyl)phenyl)methyl)amino)-8-chloro-4-((3-chloro-4-fluorophenyl)amino)quinoline-3-carbonitrile (30.0 mg, 0.045 mmol) was dissolved in DCM (2 mL) at room temperature. Thionyl chloride (0.13 mL, 1.78 mmol) was added and the resulting solution stirred for 10 minutes after it was concentrated to dryness. To the crude residue was added DCM (2 mL) followed by dimethylamine (40% aqueous solution, 1 mL). After 4 hours the solvents were removed and the crude residue was purified by RP-HPLC (eluent: water/MeCN*0.1% TFA) to yield the product as trifluoro acetate salt.

¹H NMR (400 MHz, Methanol-d₄) δ 8.45 (s, 1H), 8.00 (s, 1H), 7.67 (d, J=2.4 Hz, 1H), 7.65 (s, 1H), 7.56 (d, J=7.8 Hz, 1H), 7.53-7.40 (m, 3H), 7.36-7.23 (m, 2H), 7.21 (d, J=2.3 Hz, 1H), 6.09 (s, 1H), 4.80 (d, J=5.1 Hz, 1H), 4.35-4.21 (m, 2H), 3.79 (d, J=12.7 Hz, 2H), 3.28-3.16 (m, 2H), 2.80 (s, 6H), 2.45 (m, 4H), 1.46 (s, 9H).

ES/MS 700.2 (M+H⁺).

Example 19 Procedure 19

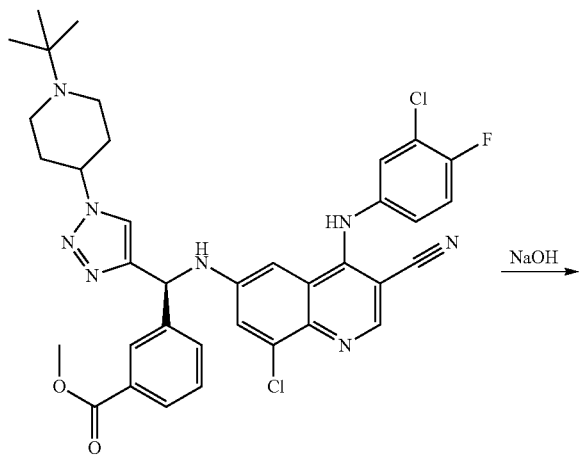

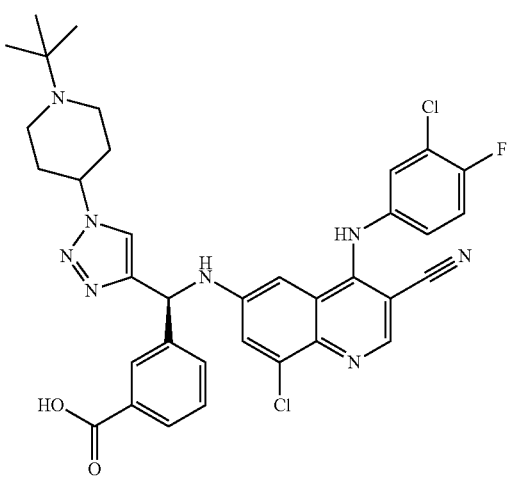

(S)-3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)amino)methyl)benzoic acid methyl (S)-3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)amino)methyl)benzoate (50.0 mg, 0.071 mmol) was dissolved in MeOH (2 mL) and water (0.5 mL) after which solid NaOH (14.3 mg, 0.36 mmol) was added and the reaction mixture allowed to stir at room temperature overnight. The mixture was diluted with EtOAc (30 mL), dried over MgSO₄, and concentrated. The crude residue was purified by and RP-HPLC (eluent: water/MeCN*0.1% TFA) to yield the product as trifluoro acetate salt.

ES/MS 687.0 (M+H⁺).

Example 20 Procedure 20

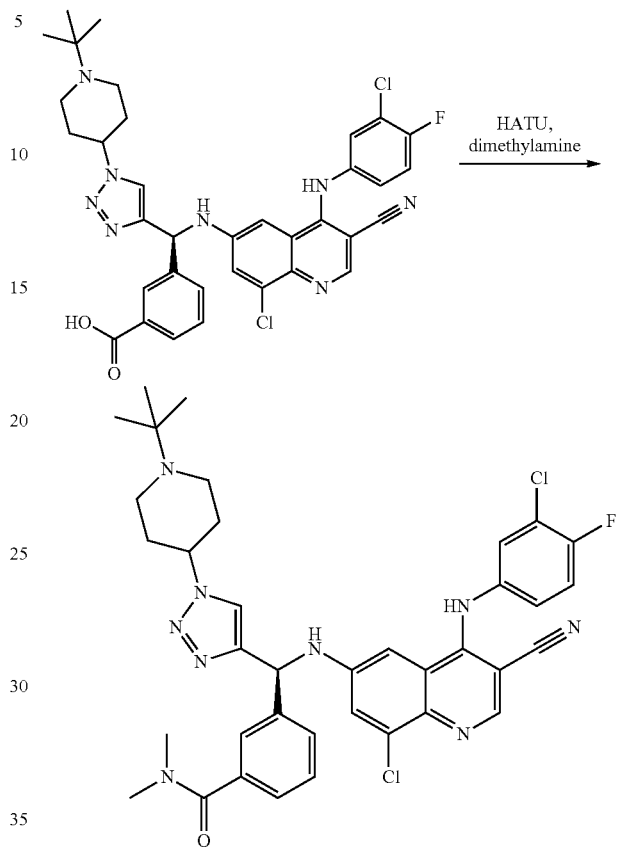

(S)-3((1-(1-(tert-butyl)piperidin-4-yl)-1H-1,2,3-triazol-4-yl(8-chloro-4-((3-chloro-4-fluorophenyl)amino)-3-cyanoquinolin-6-yl)amino)methyl)-N,N-dimethylbenzamide (S)-3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)benzoic acid (30.0 mg, 0.044 mmol) was dissolved in DMF (2 mL) at room temperature. Dimethylamine (2.0M in MeOH, 0.22 mL, 0.44 mmol), diisopropylethylamine (0.023 mL, 0.131 mmol) and HATU (25 mg, 0.065 mmol) were then added and the reaction mixture stirred for 12 hours. The reaction mixture was poured into water (3 mL) and extracted with EtOAc (3×8 mL). The organic phase was washed with brine (5 mL), dried over MgSO₄ and concentrated. The crude residue was then purified by RP-HPLC (eluent: water/MeCN*0.1% TFA) to yield the product as trifluoro acetate salt.

¹H NMR (400 MHz, Methanol-d₄) δ 8.43 (s, 1H), 7.84 (s, 1H), 7.65 (d, J=2.3 Hz, 1H), 7.56 (d, J=7.8 Hz, 1H), 7.51 (s, 1H), 7.46 (t, J=7.7 Hz, 2H), 7.37 (d, J=7.6 Hz, 1H), 7.32 (t, J=8.8 Hz, 1H), 7.25 (d, J=2.9 Hz, 1H), 7.15 (d, J=2.4 Hz, 1H), 6.07 (s, 1H), 4.82-4.72 (m, 1H), 3.81 (d, J=13.0 Hz, 2H), 3.21 (d, J=12.3 Hz, 2H), 3.06 (s, 3H), 2.88 (s, 3H), 2.54-2.32 (m, 4H), 1.46 (s, 9H). ES/MS 714.0 (M+H⁺).

Example 21 Procedure 21

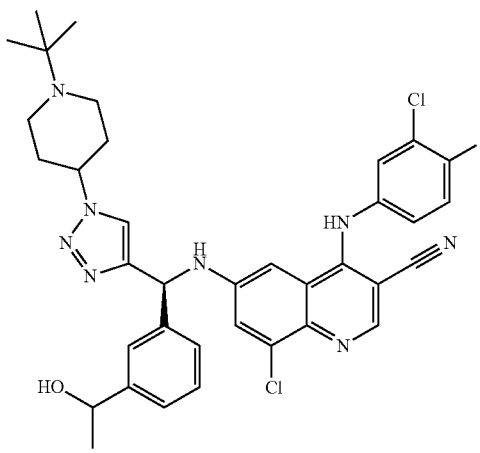

(S)-6-(((3-acetylphenyl)(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile 6-(((1S)-(1-(1-(tert-butyl)piperidin-4-yl)-1H-1,2,3-triazol-4-yl)(3-(1-hydroxyethyl)phenyl)methyl)amino)-8-chloro-4-((3-chloro-4-fluorophenyl)amino)quinoline-3-carbonitrile (41 mg, 0.060 mmol) was dissolved in DCM (2 mL) after which Dess-Martin periodinane (30.4 mg, 0.072 mmol) was added at room temperature. After 30 minutes the reaction contents were quenched by the addition of saturated aqueous $Na_2SO_3$ (3 mL) and stirred vigorously for 5 minutes. The reaction mixture was then poured into saturated aqueous $NaHCO_3$ (5 mL) and extracted with EtOAc (2×15 mL). The combined organic phase was washed with brine (5 mL), dried over $MgSO_4$ and concentrated. The crude residue was purified by and RP-HPLC (eluent: water/MeCN*0.1% TFA) to yield the product as trifluoro acetate salt.

Example 22 Procedure 22

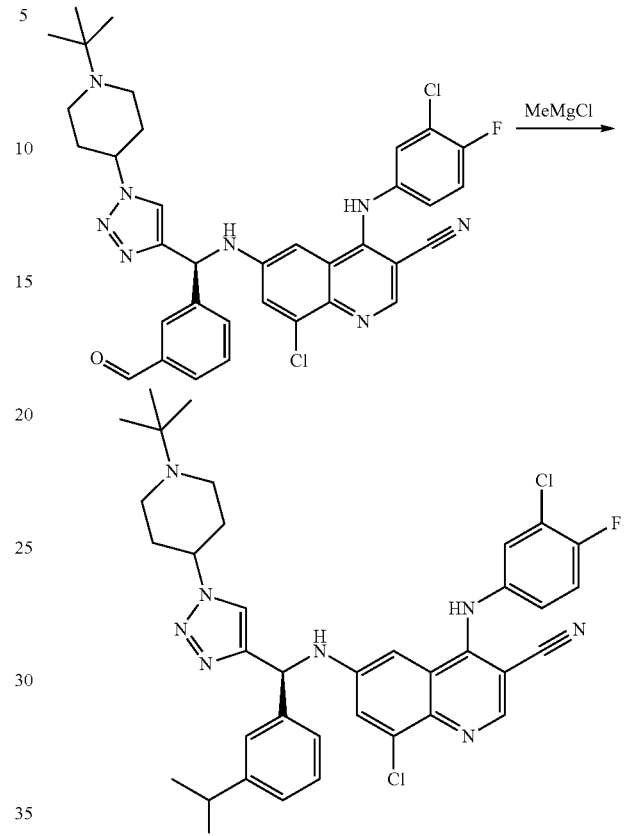

6-(((1S)-(1-(1-(tert-butyl)piperidin-4-yl)-1H-1,2,3-triazol-4-yl)(3-(1-hydroxyethyl)phenyl)methyl)amino)-8-chloro-4-((3-chloro-4-fluorophenyl)amino)quinoline-3-carbonitrile (S)-6-(((1-(1-(tert-butyl)piperidin-4-yl)-1H-1,2,3-triazol-4-yl)(3-formylphenyl)methyl)amino)-8-chloro-4-((3-chloro-4-fluorophenyl)amino)quinoline-3-carbonitrile (78 mg, 0.12 mmol) was dissolved in THF (5 mL) and brought to 0° C. Methylmagnesium chloride (3.0M in THF, 0.077 mL, 0.23 mmol) was added dropwise. After 5 minutes the reaction contents were quenched by the addition of water and the aqueous phase extracted with EtOAc (3×8 mL). The organic phase was washed with brine (5 mL), dried over $MgSO_4$ and concentrated. The crude residue was then purified by and RP-HPLC (eluent: water/MeCN*0.1% TFA) to yield the product as trifluoro acetate salt.

$^1$H NMR (400 MHz, Methanol-$d_4$) δ 8.47 (s, 1H), 7.81 (d, J=3.4 Hz, 1H), 7.68 (d, J=2.3 Hz, 1H), 7.53 (dd, J=11.1, 4.7 Hz, 2H), 7.41-7.24 (m, 6H), 6.06 (s, 1H), 4.80 (m, 2H), 3.79 (d, J=12.6 Hz, 2H), 3.23 (d, J=12.6 Hz, 2H), 2.43 (m, 4H), 1.46 (s, 9H), 1.37 (d, J=6.4 Hz, 3H). ES/MS 687.2 (M+H$^+$).

149
Example 23 Procedure 23

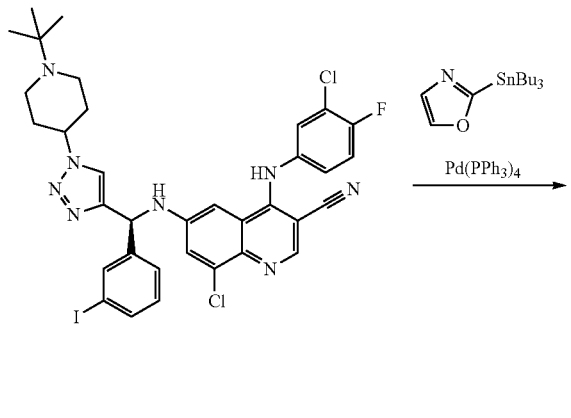

(S)-6-(((1-(1-(tert-butyl)piperidin-4-yl)-1H-1,2,3-triazol-4-yl)(3-(oxazol-2-yl)phenyl)methyl)amino)-8-chloro-4-((3-chloro-4-fluorophenyl)amino)quinoline-3-carbonitrile (S)-6-(((1-(1-(tert-butyl)piperidin-4-yl)-1H-1,2,3-triazol-4-yl)(3-iodophenyl)methyl)amino)-8-chloro-4-((3-chloro-4-fluorophenyl)amino)quinoline-3-carbonitrile (93 mg, 0.26 mmol), tetrakis(triphenylphosphine)palladium(0) (15 mg, 0.013 mmol), 2-tributyltinoxazole (21 mg, 0.065 mmol) and lithium chloride (5.5 mg, 0.13 mmol) were combined in DMF (1.5 mL) and purged with argon. The reaction mixture was heated to 90° C. overnight. After passing the reaction mixture through a silica-thiol plug the solvents were removed and the crude residue purified by RP-HPLC (eluent: water/MeCN*0.1% TFA) to yield the product as trifluoro acetate salt.

ES/MS 710.1 (M+H$^+$).

150
Example 24 Procedure 24

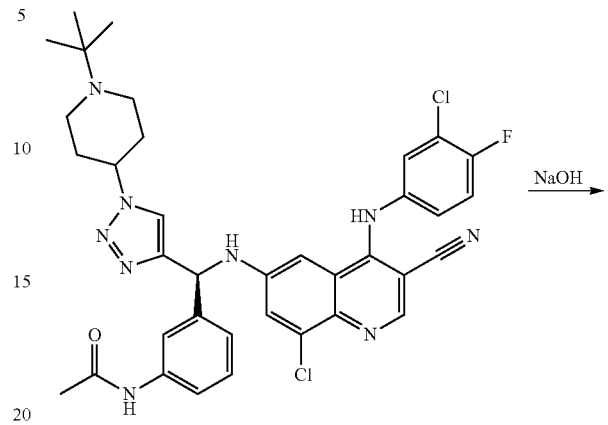

(S)-6-(((3-aminophenyl)(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile (S)—N-(3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)amino)methyl)phenyl)acetamide (20.0 mg, 0.029 mmol) was dissolved in EtOH (5 mL) after which NaOH (3.0M aq, 2.5 mL, 7.5 mmol) was added and the resulting solution heated to 70° C. for 24 hours. The reaction contents were poured into water (5 mL) and extracted with EtOAc (3×15 mL). The combined organic phases were washed with brine (5 mL), dried over MgSO$_4$ and concentrated. The crude residue was purified by RP-HPLC (eluent: water/MeCN*0.1% TFA) to yield the product as trifluoro acetate salt.

ES/MS 658.0 (M+H$^+$).

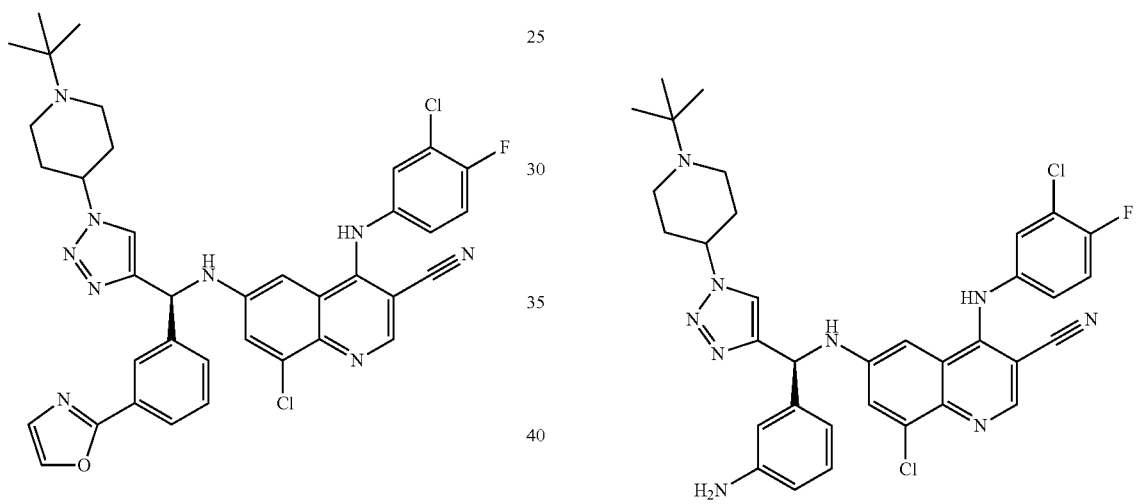

Example 25 Procedure 25

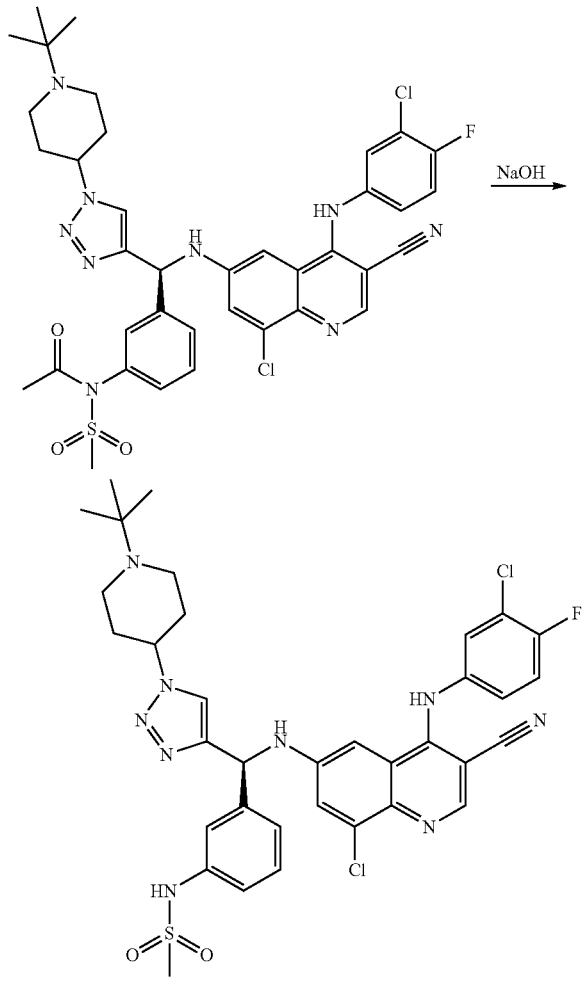

(S)—N-(3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)phenyl)methanesulfonamide (S)—N-(3-((1-(1-(tert-butyl)piperidin-4-yl)-1H-1,2,3-triazol-4-yl)(((8-chloro-4-((3-chloro-4-fluorophenyl)amino)-3-cyanoquinolin-6-yl)amino)methyl)phenyl)-N-(methylsulfonyl)acetamide (47 mg, 0.061 mmol) was dissolved in MeOH (2 mL) at room temperature. NaOH (1.0M aq, 0.30 mL, 0.30 mmol) was added and the reaction stirred for 30 minutes. HCl ((1.0M aq, 0.30 mL, 0.30 mmol) was added after which the reaction mixture was poured into water (3 mL) and extracted with EtOAc (3×8 mL). The combined organic phases were washed with brine (5 mL), dried over MgSO₄ and concentrated. The crude residue was purified by RP-HPLC (eluent: water/MeCN*0.1% TFA) to yield the product as trifluoro acetate salt.

ES/MS 736.0 (M+H$^+$).

Example 26 Procedure 26 GS-713242

(S) 8-chloro-6-(((2-chlorophenyl)(1-(1,1-difluoro-2-hydroxyethyl)-1H-1,2,3-triazol-4-yl)methyl-d)amino)-4-(neopentylamino)quinoline-3-carbonitrile

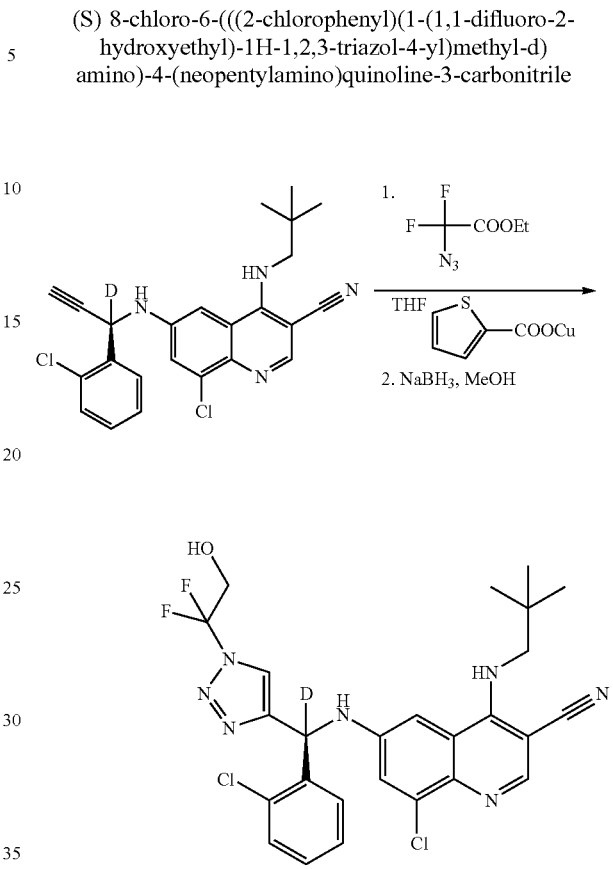

Ethyl 2-azido-2,2-difluoroacetate (11.2 mg, 0.068 mmol) was added to a solution of 8-chloro-6-((1-(2-chlorophenyl)prop-2-yn-1-yl-1-d)amino)-4-(neopentylamino)quinoline-3-carbonitrile (20 mg, 0.046 mmol) and Copper(I) thiophene-2-carboxylate (0.9 mg, 0.005 mmol) in THF (2 mL). After 45 minutes, the reaction was diluted with EtOAc (10 mL). The organic phase was washed with saturated sodium bicarbonate (5 mL) and brine (5 mL). The organic phase was dried over sodium sulfate and the solvent was removed under reduced pressure. The residue was taken up in MeOH (3 mL) and sodium borohydride (35 mg, 0.91 mmol). After 15 minutes the mixture was diluted with EtOAc (20 ml) and washed with saturated sodium bicarbonate (5 mL) and brine (5 mL). The organic phase was dried over sodium sulfate and the solvent was removed under reduced pressure. The residue was subjected to flash chromatography. The fractions containing product were combined and the solvent was removed under reduced pressure. The product was subjected to further purification via RP-HPLC. The fractions containing product were combined and subjected to lyophilization, providing (S) 8-chloro-6-(((2-chlorophenyl)(1-(1,1-difluoro-2-hydroxyethyl)-1H-1,2,3-triazol-4-yl)methyl-d)amino)-4-(neopentylamino)quinoline-3-carbonitrile.

ES/MS 561.1 (M+H$^+$).

Example 27 Procedure 27

8-chloro-4-((3-cloro-4-fluorophenyl)amino)-6-(((1-(1-ethylpiperidin-4-yl)-1H-imidazol-4-yl)(phenyl)methyl)amino)quinoline-3-carbonitrile

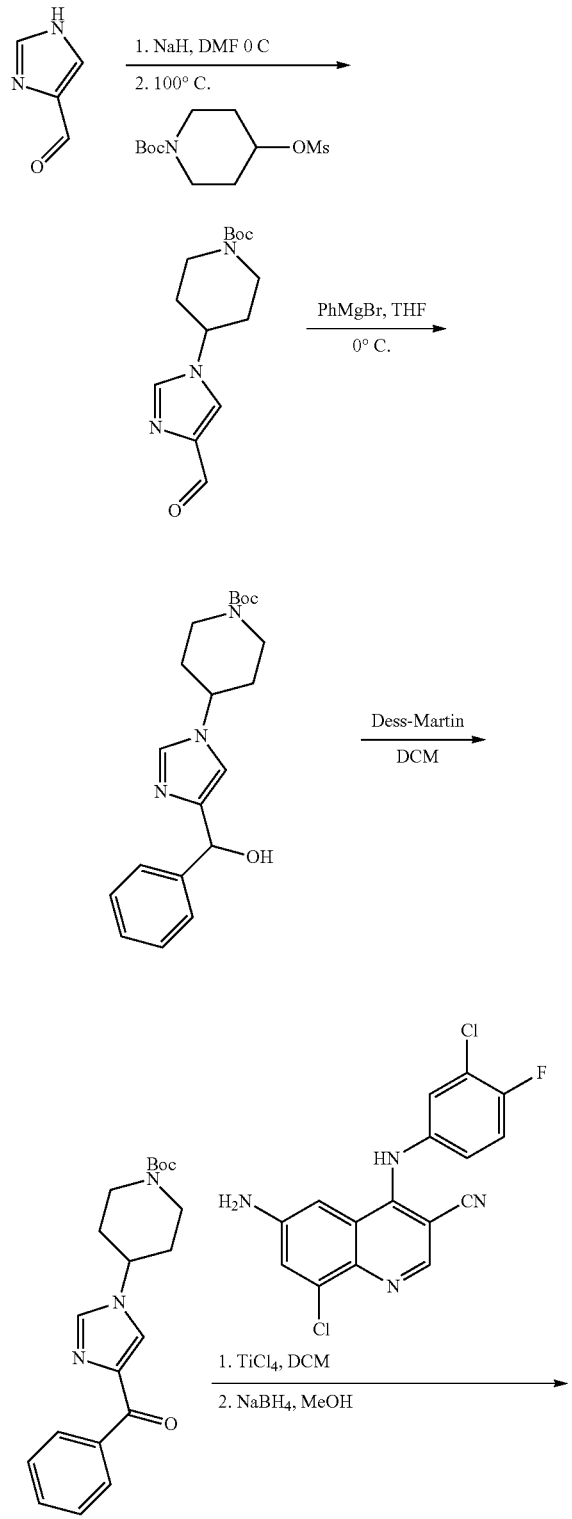

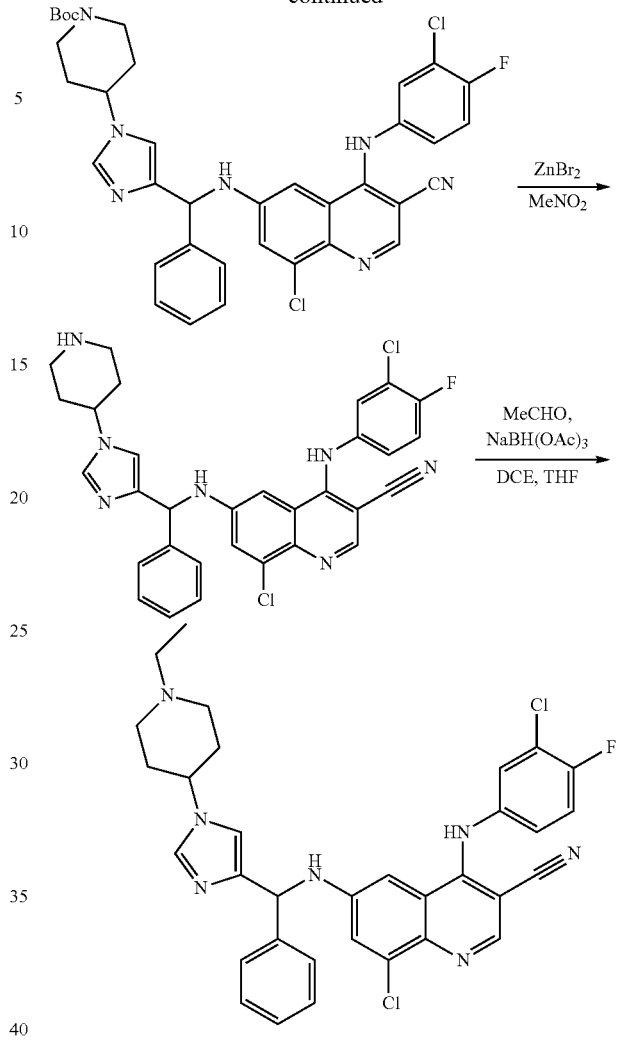

tert-butyl 4-(4-formyl-1H-imidazol-1-yl)piperidine-1-carboxylate

Sodium hydride (60% suspension in mineral oil) (458 mg, 11.5 mmol) was added in portions to a solution of 1H-imidazole-4-carbaldehyde (1 g, 10.4 mmol) in dimethylformamide (16 mL) at 0° C. After 30 min at 0° C. the mixture was allowed to warm to RT and tert-butyl 4-((methylsulfonyl)oxy)piperidine-1-carboxylate (2.9 g, 10.5 mmol) was added. The mixture was heated at 100° C. for 16 h. The reaction was cooled and diluted with ethyl acetate (75 mL). The organic phase was washed with water (2×25 mL) and brine (25 mL) and dried over sodium sulfate. The solvent was removed under reduced pressure and the residue was subjected to flash chromatography (0-100% ethyl acetate/hexane) to remove side products and undesired regioisomer. The solvent was removed under reduced pressure providing tert-butyl 4-(4-formyl-1H-imidazol-1-yl)piperidine-1-carboxylate.

tert-butyl 4-(4-(hydroxy(phenyl)methyl)-1H-imidazol-1-yl)piperidine-1-carboxylate Phenyl magnesiumbromide (1M in tetrahydrofuran) (1.3 mL, 1.28 mmol) was added to a solution of tert-butyl 4-(4-formyl-1H-imidazol-1-yl)piperidine-1-carboxylate (325 mg, 1.16 mmol) in tetrahydrofuran (10 mL). After 2 h the reaction was quenched with saturated ammonium chloride (10 mL) and diluted with ethyl acetate (25 mL). The organic phase was washed with brine (10 mL) and dried over sodium sulfate. The solvent was removed under reduced pressure, providing tert-butyl 4-(4-(hydroxy(phenyl)methyl)-1H-imidazol-1-yl)piperidine-1-carboxylate.

tert-butyl 4-(4-benzoyl-1H-imidazol-1-yl)piperidine-1-carboxylate

A solution of tert-butyl 4-(4-(hydroxy(phenyl)methyl)-1H-imidazol-1-yl)piperidine-1-carboxylate (408 mg, 1.1 mmol) and Dess-Martin periodinane (515 mg, 1.4 mmol) in dichloromethane (10 mL was stirred at room temperature for 2 h. The solvent was removed under reduced pressure and the residue was taken up in ethyl acetate (25 mL). The organic phase was washed with saturated sodium bicarbonate (10 mL). A solid formed which was removed by filtration. The organic phase was washed again with saturated sodium bicarbonate (10 mL) and brine (10 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure providing tert-butyl 4-(4-benzoyl-11H-imidazol-1-yl)piperidine-1-carboxylate.

tert-butyl 4-(4-(((8-chloro-4-((3-chloro-4-fluorophenyl)amino)-3-cyanoquinolin-6-yl)amino)(phenyl)methyl)-1H-imidazol-1-yl)piperidine-1-carboxylate A solution of 6-amino-8-chloro-4-((3-chloro-4-fluorophenyl)amino)quinoline-3-carbonitrile (98 mg, 0.28 mmol) and tert-butyl 4-(4-benzoyl-1H-imidazol-1-yl)piperidine-1-carboxylate (100 mg, 0.28 mmol) in dichloromethane (2 mL) was cooled to 0° C. under Argon. Triethylamine (125 µL, 0.90 mmol) was added followed by titanium (IV) tetrachloride (0.21 mL, 0.21 mmol-1M in DCM). After 20 h the reaction was diluted with methanol (1 mL) and sodium borohydride (43 mg, 1.1 mmol) was added. After 40 h the reaction was quenched with saturated sodium bicarbonate (5 mL) and partitioned with ethyl acetate (15 mL). The organic phase was washed with saturated sodium bicarbonate (10 mL), brine (10 mL), and dried over sodium sulfate. The solvent was removed under reduced pressure and the residue was subjected to flash chromatography (0-100% ethyl acetate/hexanes). The fractions containing product were combined and the solvent was removed under reduced pressure, providing tert-butyl 4-(4-(((8-chloro-4-((3-chloro-4-fluorophenyl)amino)-3-cyanoquinolin-6-yl)amino)(phenyl)methyl)-1H-imidazol-1-yl)piperidine-1-carboxylate.

8-chloro-4-((3-chloro-4-fluorophenyl)amino)-6-((phenyl(1-(piperidin-4-yl)-1H-imidazol-4-yl)methyl)amino)quinoline-3-carbonitrile Zinc bromide (105 mg, 0.47 mmol) was added to a solution of tert-butyl 4-(4-(((8-chloro-4-((3-chloro-4-fluorophenyl)amino)-3-cyanoquinolin-6-yl)amino)(phenyl)methyl)-1H-imidazol-1-yl)piperidine-1-carboxylate (64 mg, 0.094 mmol) in nitromethane (1 mL). After 3 h the solvent was removed under reduced pressure. The residue was partitioned between ethyl acetate (20 mL) and saturated sodium bicarbonate (10 mL). Solid formed which was removed by filtration. The organic phase was washed with saturated sodium bicarbonate (10 mL) and brine (10 mL). The organic phase was dried over sodium sulfate and the solvent was removed under reduced pressure, providing 8-chloro-4-((3-chloro-4-fluorophenyl)amino)-6-((phenyl(1-(piperidin-4-yl)-1H-imidazol-4-yl)methyl)amino)quinoline-3-carbonitrile.

ES/MS 585.9 (M+H+).

8-chloro-4-((3-chloro-4-fluorophenyl)amino)-6-(((1-(1-ethylpiperidin-4-yl)-1H-imidazol-4-yl)phenyl)methyl)amino)quinoline-3-carbonitrile 8-Chloro-4-((3-chloro-4-fluorophenyl)amino)-6-((phenyl(1-(piperidin-4-yl)-1H-imidazol-4-yl)methyl)amino)quino)quinoline-3-carbonitrile (41 mg, 0.070 mmol), acetaldehyde (9.7 µL, 0.17 mmol) and sodium triacetoxyborohydride (59 mg, 0.28 mmol) were dissolved in tetrahydrofuran (1 mL) and 1,1-dichloroethane (1 mL) and stirred at room temperature for 30 minutes. The mixture was diluted with ethyl acetate (10 mL) and washed twice with saturated sodium bicarbonate (5 mL) and brine (5 mL). The organic phase was dried over sodium sulfate and the solvent was removed under reduced pressure. The residue was subjected to flash chromatography. The fractions containing product were combined and the solvent was removed under reduced pressure. The residue was taken up in methanol and water with two drops of trifluoroacetic acid and subjected to preparative HPLC. The cleaner fractions were combined and subjected to lyophilization, providing 8-chloro-4-((3-chloro-4-fluorophenyl)amino)-6-(((1-(1-ethylpiperidin-4-yl)-1H-imidazol-4-yl)(phenyl)methyl)amino)quinoline-3-carbonitrile.

$^1$H NMR D$_2$O exchange (400 MHz, DMSO-d6) δ 9.05 (s, 1H), 8.97 (s, 1H), 8.42 (s, 1H), 7.64 (d, J=2.4 Hz, 1H), 7.55 (s, 0H), 7.47-7.42 (m, 4H), 7.42-7.36 (m, 4H), 7.36-7.30 (m, 2H), 7.19 (qd, J=4.1, 2.8 Hz, 3H), 5.96 (s, 1H), 4.51-4.38 (m, 1H), 3.58 (d, J=13.0 Hz, 4H), 3.25 (d, J=12.2 Hz, 1H), 3.12 (q, J=7.3 Hz, 2H), 3.06-2.93 (m, 2H), 2.35-2.25 (m, 3H), 2.05-1.91 (m, 2H), 1.20 (t, J=7.3 Hz, 3H).

ES/MS 613.9 (M+H+).

Example 28 Procedure 28

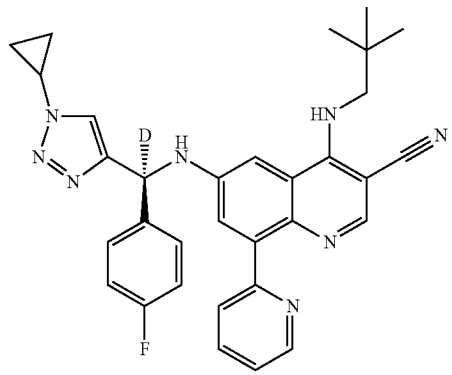

(S)-6-(((1-cyclopropyl-1H-1,2,3-triazol-4-yl)(4-fluorophenyl)methyl-d)amino)-4-(neopentylamino)-8-(pyridin-2-yl)quinoline-3-carbonitrile To (S)-6-(((1-cyclopropyl-1H-1,2,3-triazol-4-yl)(4-fluorophenyl)methyl-d)amino)-8-iodo-4-(neopentylamino)quinoline-3-carbonitrile (55 mg, 0.09 mmol), 6-methyl-2-(pyridin-2-yl)-1,3,6,2-dioxazaborocane-4,8-dione (32 mg, 0.13 mmol), [1,1'-bis(diphenylphosphino)ferrocene]dichloropalladium(II), complex with dichloromethane (6 mg, 0.009 mmol), diethanolamine (10 mg, 0.09 mmol), cupric acetate (8 mg, 0.046 mmol) and potassium phosphate tribasic (98 mg, 0.46 mmol) was added DMF (1 mL) and the reaction mixture degassed with nitrogen. The reaction mixture was then heated at 85° C. overnight. After filtering the solids through a pad of celite, the crude filtrate was concentrated and purified by HPLC (eluent: water/MeCN*0.1% TFA) to give the title compound. ES/MS 548.2 (M+H+).

Example 29 Procedure 29

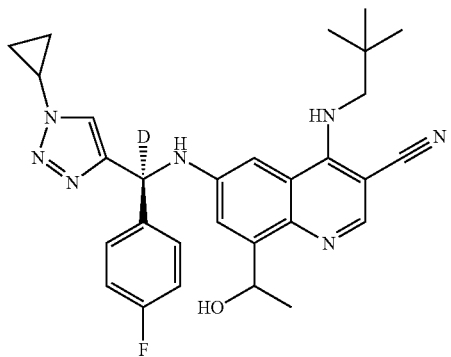

6-(((S)-(1-cyclopropyl-1H-1,2,3-triazol-4-yl)(4-fluorophenyl)methyl-d)amino)-8-(1-hydroxyethyl)-4-(neopentylamino)quinoline-3-carbonitrile Made by reduction of (S)-8-acetyl-6-(((2-chlorophenyl)(1-cyclopropyl-1H-1,2,3-triazol-4-yl)methyl-d)amino)-4-(neopentylamino)quinoline-3-carbonitrile with sodium triacetoxyborohydride. ES/MS 515.3 (M+H+).

Example 30 Procedure 30

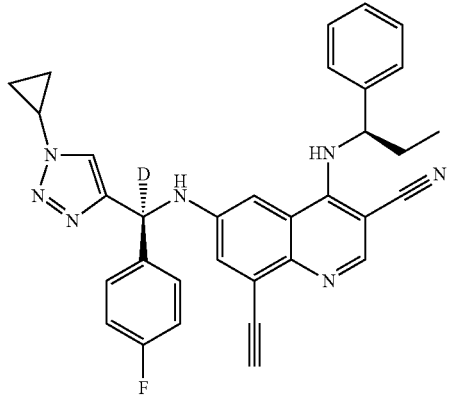

6-(((S)-(1-cyclopropyl-1H-1,2,3-triazol-4-yl)(4-fluorophenyl)methyl-d)amino)-8-ethynyl-4-(((R)-1-phenylpropyl)amino)quinoline-3-carbonitrile To 8-bromo-6-(((S)-(1-cyclopropyl-1H-1,2,3-triazol-4-yl)(4-fluorophenyl)methyl-d)amino)-4-(((R)-1-phenylpropyl)amino)quinoline-3-carbonitrile (80 mg, 0.13 mmol) in DMF (0.5 mL) was added ethynyltrimethylsilane (40 mg, 0.4 mmol), bis(triphenylphosphine) palladium (II) dichloride (9 mg, 0.013 mmol), copper (I) iodide (3 mg, 0.013 mmol) and triethylamine (0.3 mL). The reaction mixture was flushed with nitrogen and heated at 95° C. for 3 hours. After removing most of the solvent in vacuo, the crude residue was purified by HPLC (eluent: water/MeCN*0.1% TFA) to give the title compound.

ES/MS 543.3 (M+H+).

Example 31 Procedure 31

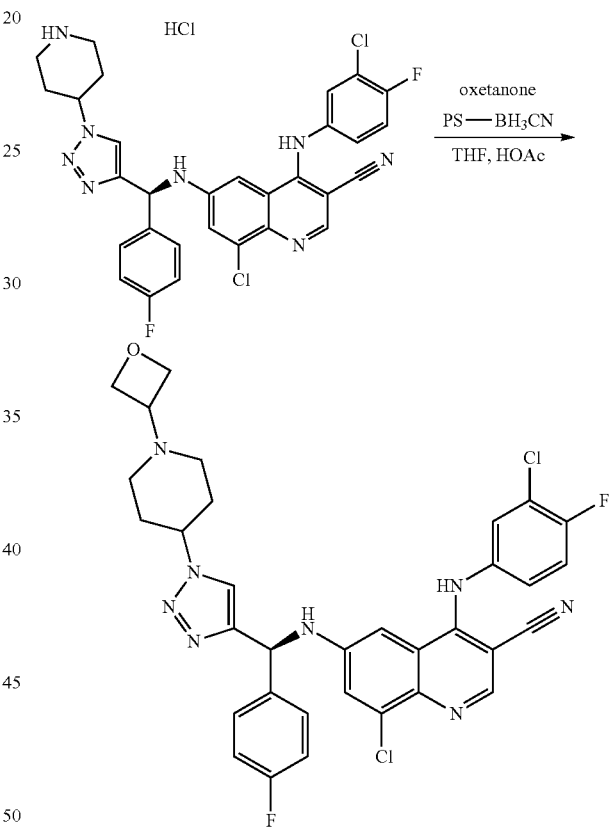

(S)-8-chloro-4-((3-chloro-4-fluorophenyl)amino)-6-(((4-fluorophenyl)(1-(piperidin-4-yl)-1H-1,2,3-triazol-4-yl)methyl)amino)quinoline-3-carbonitrile hydrochloride (30 mg, 0.05 mmol) was dissolved in 0.50 mL of 3:1 2-methyltetrahyrdofuran:acetic acid and treated with oxetanone (10 mg, 0.14 mmol) and PS—BH₃CN (polystyrene supported cyanoborohydride, 22 mg, 2.17 mmol/g). The mixture was stirred overnight. The resin was filtered and the resulting filtrate was concentrated. Purification using RP-HPLC (eluent: water/MeCN*0.1% TFA) provided the product as trifluoroacetate salt.

ES/MS 661.1 (M+H+)

Example 32 Procedure 32

8-chloro-6-(((S)-(1-cyclopropyl-1H-1,2,3-triazol-4-yl)(4-fluorophenyl)methyl)amino)-4-(((R)-3-fluoro-1-phenylpropyl)amino)quinoline-3-carbonitrile

Step 2. (R)-8-chloro-4-((3-fluoro-1-phenylpropyl)amino)-6-nitroquinoline-3-carbonitrile (R)-8-chloro-4-((3-hydroxy-1-phenylpropyl)amino)-6-nitroquinoline-3-carbonitrile (100 mg, 0.26 mmol) was treated

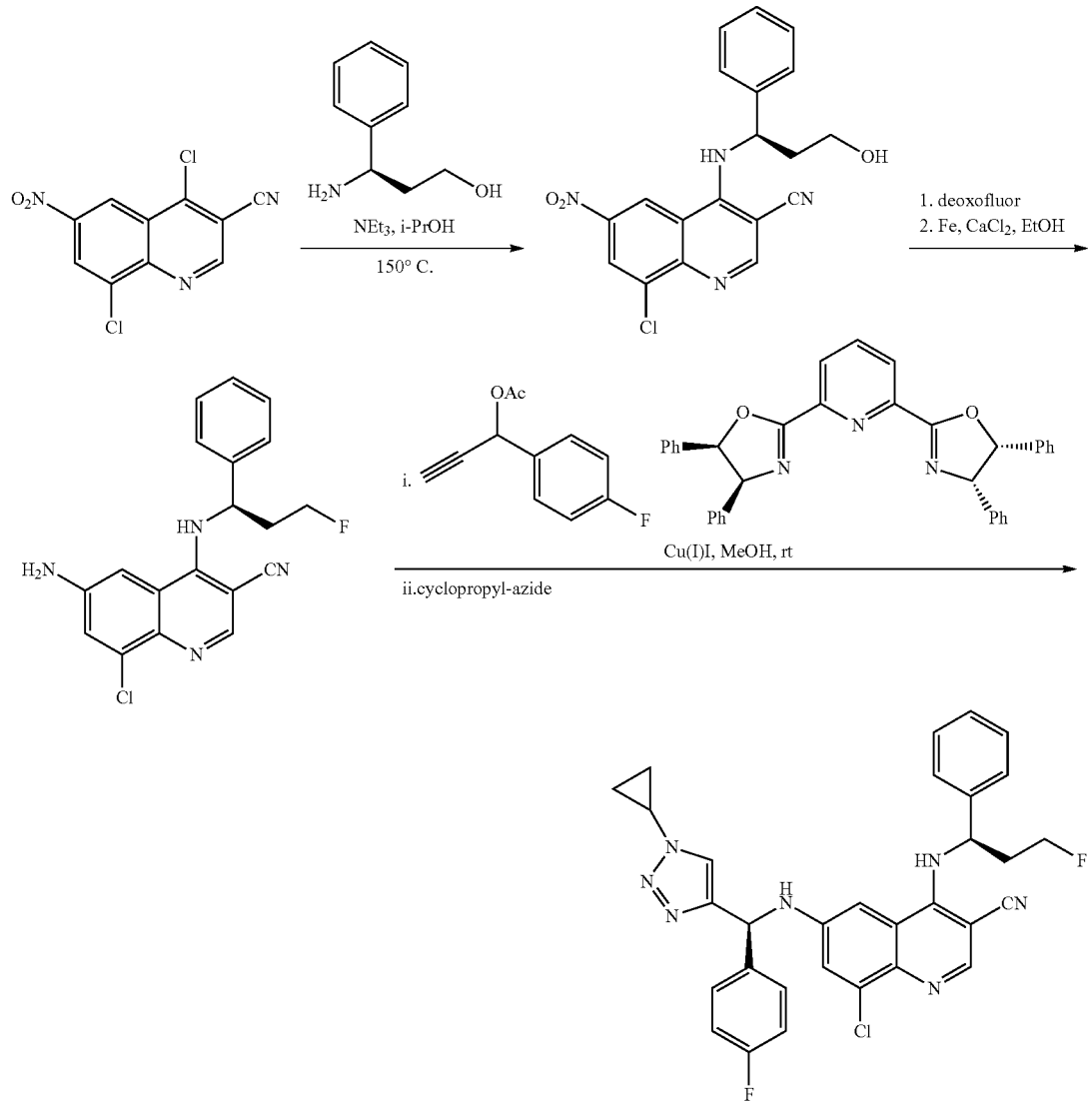

Step 1. (R)-8-chloro-4-((3-hydroxy-1-phenylpropyl)amino)-6-nitroquinoline-3-carbonitrile 4,8-dichloro-6-nitroquinoline-3-carbonitrile (400 mg, 1.49 mmol), (R)-3-amino-3-phenylpropan-1-ol (270.76 mg, 1.79 mmol) in iso-propanol (1.5 mL) were heated under microwave conditions at 150° C. for 45 minutes. The reaction was cooled to room temperature. Water and Et$_2$O were added. The aqueous layer was extracted with Et$_2$O and the combined organic layers were dried over sodium sulfate. Filtration and evaporation of solvents yielded the crude product which was used in the next step without further purification.

ES/MS 383.1 (M+H$^+$).

with deoxofluor (0.6 mL) at room temperature for 16 hours. The reaction mixture was cooled in an ice bath and carefully quenched with saturated sodium bicarbonate solution, then extracted with ethyl acetate. The organic phase was dried over sodium sulfate, filtered and concentrated to give the crude product which was used without further purification.

ES/MS 385.1 (M+H$^+$).

Step 3. (R)-6-amino-8-chloro-4-((3-fluoro-1-phenylpropyl)amino)quinoline-3-carbonitrile (R)-8-chloro-4-((3-fluoro-1-phenylpropyl)amino)-6-nitroquinoline-3-carbonitrile (115 mg, 0.3 mmol), Calcium chloride dihydrate (65.91 mg, 0.45 mmol), and iron powder (83.5 mg, 1.49 mmol) were heated in ethanol (3 mL)/water (0.3 mL) at 60° C. for 12 hours. The reaction was cooled to room temperature and solids were removed via filtration.

The solids were washed with EtOAc and the combined organic layers were washed with aqueous sodium bicarbonate solution, brine, and were dried over sodium sulfate. Filtration and evaporation of all volatiles yielded the product.

ES/MS 355.0 (M+H$^+$).

Step 4. 8-chloro-6-(((S)-(1-cyclopropyl-1H-1,2,3-triazol-4-yl)(4-fluorophenyl)methyl)amino)-4-(((R)-3-fluoro-1-phenylpropyl)amino)quinoline-3-carbonitrile (R)-6-amino-8-chloro-4-((3-fluoro-1-phenylpropyl)amino)quinoline-3-carbonitrile (45 mg, 0.13 mmol), CuI (1.2 mg, 0.05 mmol) and 2,6-bis((4S,5R)-4,5-diphenyl-4,5-dihydrooxazol-2-yl)pyridine [oxazoline ligand] (3.9 mg, 0.06 mmol) were sonicated in MeOH (2.0 mL) for about 1 minute. Alkynyl acetate (29 mg, 0.15 mmol) and di-isopropyl ethyl amine (19.7 mg, 0.15 mmol) were added and the reaction was stirred overnight. Cyclopropylazide (43 mg, 0.52 mmol) was added and the reaction was stirred for additional 16 hrs at room temperature. The material was partitioned between ethyl acetate and water and the organic phase was dried over sodium sulfate and filtered. Solvents were removed in vacuo and the crude material was purified by RP-HPLC (eluent: water/MeCN*0.1% TFA) to yield the product as trifluoroacetate salt.

1H NMR (400 MHz, Methanol-d4) δ 8.41 (s, 1H), 7.83 (m, 1H), 7.65 (m, 1H), 7.54-7.18 (m, 8H), 7.16-7.03 (m, 2H), 6.17-6.05 (m, 2H), 4.93-4.76 (m, 2H), 4.67-4.58 (m, 1H), 4.51 (m, 1H), 3.93-3.82 (m, 1H), 1.26-1.09 (m, 4H).
ES/MS 570.1 (M+H$^+$).

Example 33 Procedure 33

N-(8-chloro-3-cyano-6-((1-cyclopropyl-1H-1,2,3-triazol-4-yl)(4-fluorophenyl)methyl-d)amino)quinolin-4-yl)pivalamide

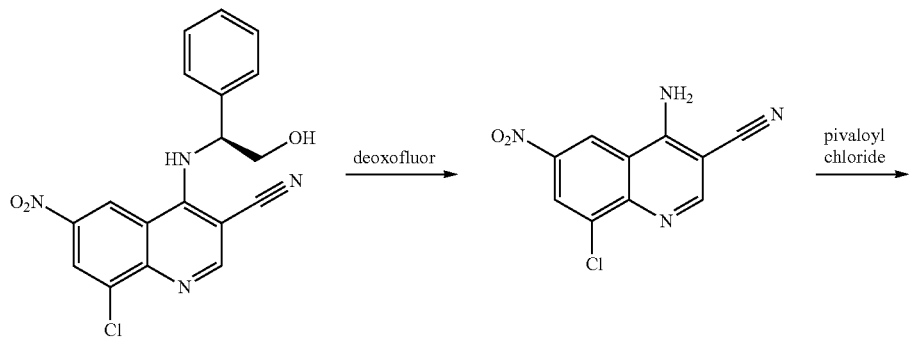

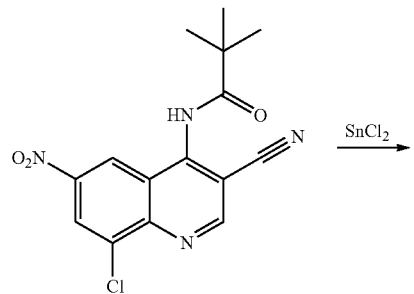

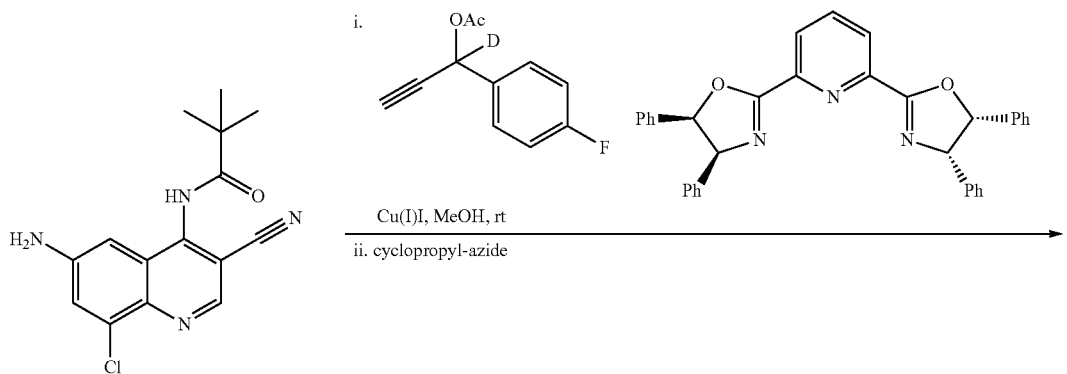

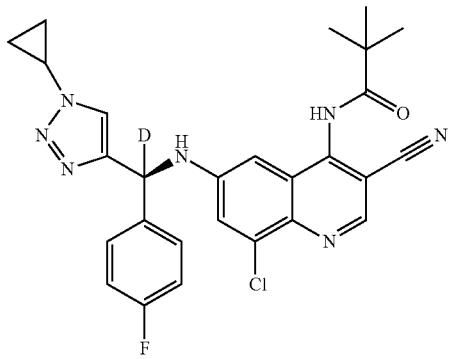

Step 1. 4-amino-8-chloro-6-nitroquinoline-3-carbonitrile (S)-8-chloro-4-((2-hydroxy-1-phenylethyl)amino)-6-nitroquinoline-3-carbonitrile (256 mg, 0.69 mmol) was treated with deoxofluor (0.6 mL) at room temperature for 16 hours. The reaction mixture was cooled in an ice bath and carefully quenched with saturated sodium bicarbonate solution, then extracted with ethyl acetate. The organic phase was dried over sodium sulfate, filtered and concentrated to give the crude product which was used without further purification.
ES/MS 249.1 (M+H$^+$).

Step 2. N-(8-chloro-3-cyano-6-nitroquinolin-4-yl)pivalamide 4-amino-8-chloro-6-nitroquinoline-3-carbonitrile (163 mg, 0.66 mmol), pivaloyl chloride (0.32 ml, 2.62 mmol), triethylamine, 99% (398.04 mg, 3.93 mmol), and DCM (6 ml) were combined and stirred for 2 days. The reaction mixture was concentrated, then taken up in ethyl acetate and washed with 1N HCl, saturated sodium bicarbonate and brine, then dried over sodium sulfate. Filtration and evaporation of all volatiles yielded the product.
ES/MS 333.0 (M+H$^+$).

Step 3. N-(6-amino-8-chloro-3-cyanoquinolin-4-yl)pivalamide

To a suspension of N-(8-chloro-3-cyano-6-nitroquinolin-4-yl)pivalamide (48 mg, 0.14 mmol) in EtOH (1.4 ml) was added stannous chloride, dihydrate (65.1 mg, 0.29 mmol). The resulting suspension was heated at 60° C. for 16 hours. The mixture was cooled to room temperature and quenched carefully with saturated sodium bicarbonate. Extraction with ethyl acetate, drying over anhydrous sodium sulfate, filtration and concentration gave the product.
ES/MS 303.2 (M+H$^+$).

Step 4. N-(8-chloro-3-cyano-6-((1-cyclopropyl-1H-1,2,3-triazol-4-yl)(4-fluorophenyl)methyl-d)amino)quinolin-4-yl)pivalamide CuI (1.3 mg, 0.007 mmol) and 2,6-bis((4S,5R)-4,5-diphenyl-4,5-dihydrooxazol-2-yl)pyridine [oxazoline ligand](4.1 mg, 0.06 mmol) were sonicated in MeOH (2.0 mL) for about 1 minute. Alkynyl acetate (29 mg, 0.15 mmol), N-(6-amino-8-chloro-3-cyanoquinolin-4-yl)pivalamide (40 mg, 0.13 mmol) and di-isopropyl ethyl amine (19.7 mg, 0.15 mmol) were added and the reaction was stirred for 1 hour. Cyclopropylazide (20 mg, 0.50 mmol) was added and the reaction was stirred at room temperature until complete. The crude reaction mixture was passed through a syringe filtered directly, and was purified by RP-HPLC (eluent: water/MeCN*0.1% TFA) to yield the product as trifluoroacetate salt.
1H NMR (400 MHz, Methanol-d4) δ 9.11 (s, 1H), 7.84 (s, 1H), 7.70 (m, 2H), 7.56 (m, 2H), 7.10 (m, 2H), 4.96-4.86 (m, 1H), 3.93-3.82 (m, 1H), 1.46 (s, 9H), 1.25-1.09 (m, 4H).
ES/MS 519.3 (M+H$^+$).

Example 34 Procedure 34

8-chloro-6-((1-cyclopropyl-1H-1,2,3-triazol-4-yl)(4-fluorophenyl)methyl-d)amino)-4-(((R)-3-morpholino-1-phenylpropyl)amino)quinoline-3-carbonitrile

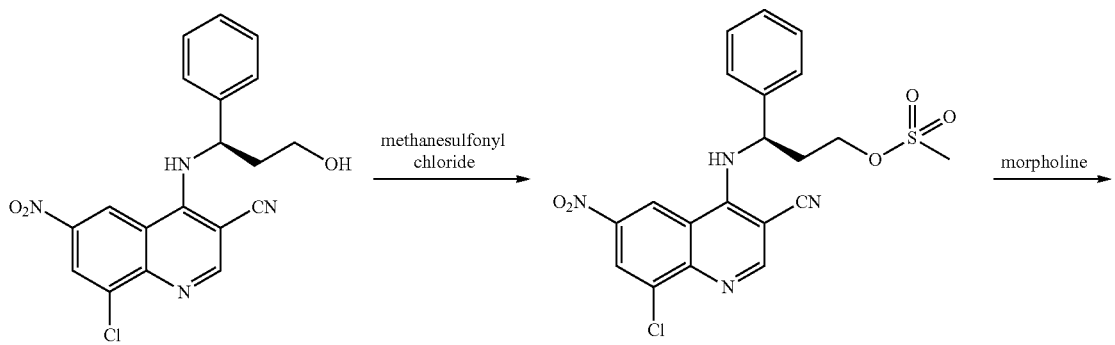

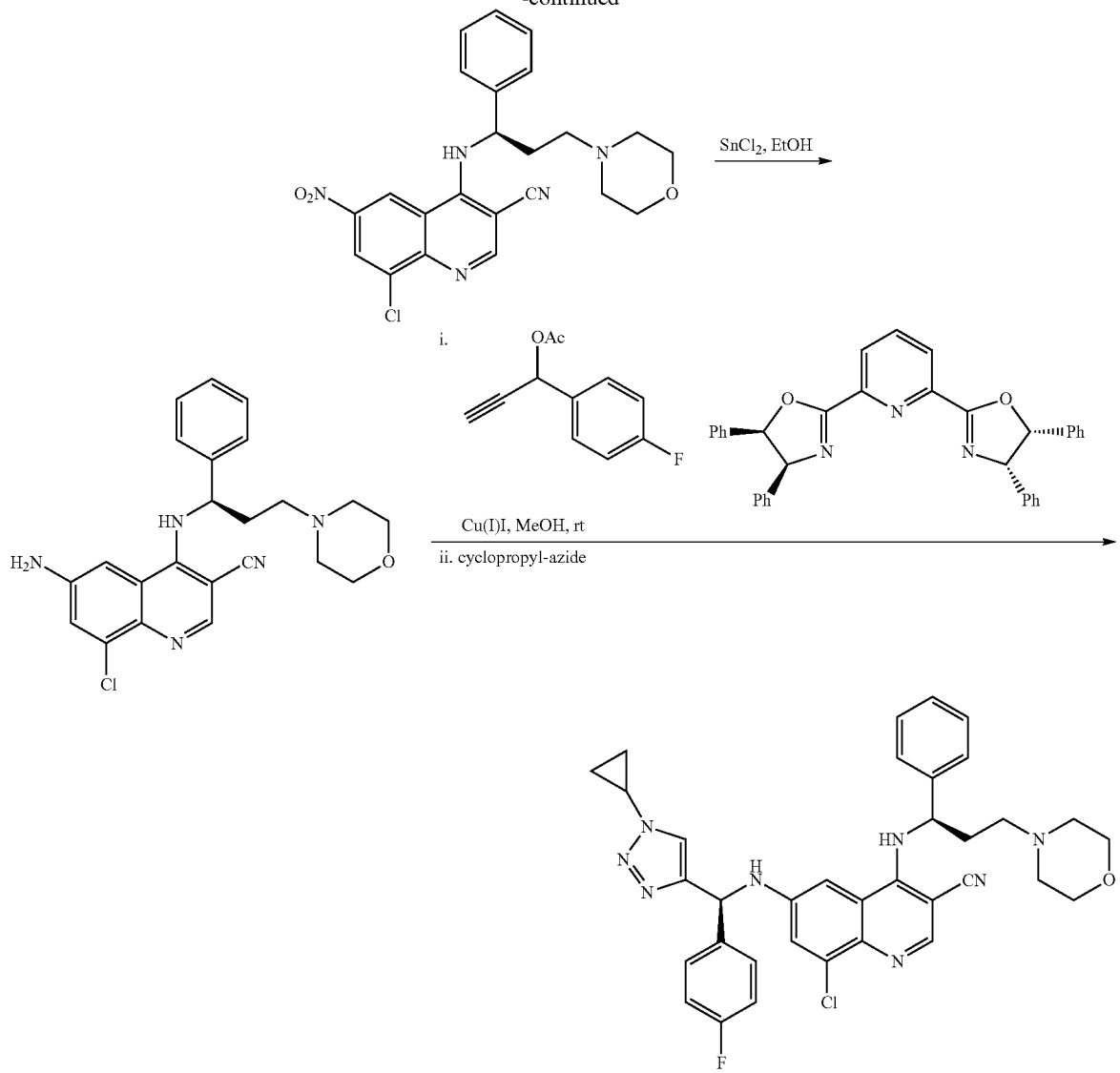

(R)-3-((8-chloro-3-cyano-6-nitroquinolin-4-yl)amino)-3-phenylpropyl methanesulfonate To a solution of (R)-8-chloro-4-((3-hydroxy-1-phenylpropyl)amino)-6-nitroquinoline-3-carbonitrile (1000 mg, 2.61 mmol) and triethylamine, 99% (0.62 ml, 4.44 mmol) in DCM (12 ml) was added methanesulfonyl chloride (0.3 ml, 3.92 mmol). After 1 hour, an additional portion of both methanesulfonyl chloride and triethylamine were added. After 15 minutes, ice was added and the product was extracted into ethyl acetate and washed with brine. Drying over sodium sulfate, filtration and concentration gave the crude product which was used without further purification.

ES/MS 461.0 (M+H$^+$).

(R)-8-chloro-4-((3-morpholino-1-phenylpropyl)amino)-6-nitroquinoline-3-carbonitrile (R)-3-((8-chloro-3-cyano-6-nitroquinolin-4-yl)amino)-3-phenylpropyl methanesulfonate (100 mg, 0.22 mmol) and morpholine (0.19 ml, 2.17 mmol) were heated together at 70° C. for 1 hour. Water was added and the product was extracted into ethyl acetate, washed water and brine, and dried over sodium sulfate. Filtration and evaporation of all volatiles yielded the crude product.

ES/MS 452.1 (M+H$^+$).

(R)-6-amino-8-chloro-4-((3-morpholino-1-phenylpropyl)amino)quinoline-3-carbonitrile To a suspension of (R)-8-chloro-4-((3-morpholino-1-phenylpropyl)amino)-6-nitroquinoline-3-carbonitrile (106 mg, 0.23 mmol) in EtOH (2.3 ml) was added stannous chloride dihydrate (89.0 mg, 0.47 mmol). The resulting suspension was heated at 70° C. for 16 hours. The mixture was cooled to room temperature and quenched carefully with saturated sodium bicarbonate. Extraction with ethyl acetate, drying over anhydrous sodium sulfate, filtration and concentration gave the crude product which was carried on to the next step without purification.

ES/MS 422.0 (M+H$^+$).

8-chloro-6-(((1-cyclopropyl-1H-1,2,3-triazol-4-yl)(4-fluorophenyl)methyl-d)amino)-4-(((R)-3-morpholino-1-phenylpropyl)amino)quinoline-3-carbonitrile CuI (1.3 mg, 0.007 mmol) and 2,6-bis((4S,5R)-4,5-diphenyl-4,5-dihydrooxazol-2-yl)pyridine [oxazoline ligand] (4.1 mg, 0.06 mmol) were sonicated in MeOH (2.0 mL) for about 1 minute. Alkynyl acetate (45 mg, 0.24 mmol), (R)-6-amino-8-chloro-4-((3-morpholino-1-phenylpropyl)amino)quinoline-3-carbonitrile (50 mg, 0.12 mmol), and di-isopropyl ethyl amine (18.3 mg, 0.14 mmol) were added and the reaction was stirred for 16 hours. Cyclopropylazide (20 mg, 0.50 mmol) was added and the reaction was stirred at room temperature until complete. The crude reaction mixture was passed through a syringe filtered directly, and was purified by RP-HPLC (eluent: water/MeCN*0.1% TFA) to yield the product as trifluoroacetate salt.

ES/MS 638.0 (M+H$^+$)

Example 35 Procedure 35

(S)-8-chloro-4-((3-chloro-4-fluorophenyl)amino)-6-(((4-fluorophenyl)(1-(1-(2-methoxyethyl)piperidin-4-yl)-1H-1,2,3-triazol-4-yl)methyl)amino)quinoline-3-carbonitrile

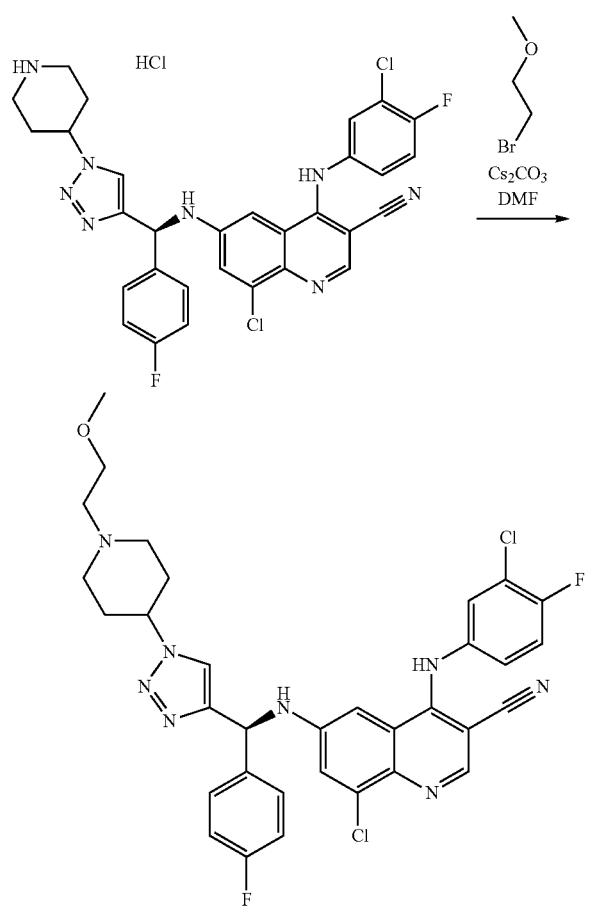

A solution of (S)-8-chloro-4-((3-chloro-4-fluorophenyl)amino)-6-(((4-fluorophenyl)(1-(piperidin-4-yl)-1H-1,2,3-triazol-4-yl)methyl)amino)quinoline-3-carbonitrile hydrochloride (30 mg, 0.05 mmol) in 0.5 mL of acetonitrile was treated with cesium carbonate (45.7 mg, 0.14 mmol) and 2-Bromoethyl methyl ether (0.005 ml, 0.05 mmol) and stirred overnight, then heated at 50° C. for 3 hours. A drop of 2-bromoethyl methyl ether was added and the reaction was continued at 50° C. for 12 hours. Purification by RP-HPLC (eluent: water/MeCN*0.1% TFA) gave the product.

ES/MS 663.3 (M+H$^+$)

Example 36 Procedure 36

8-chloro-6-(((3-cyanophenyl)(1-cyclopropyl-1H-1,2,3-triazol-4-yl)methyl-d)amino)-5-fluoro-4-(((R)-1-phenylpropyl)amino)quinoline-3-carbonitrile

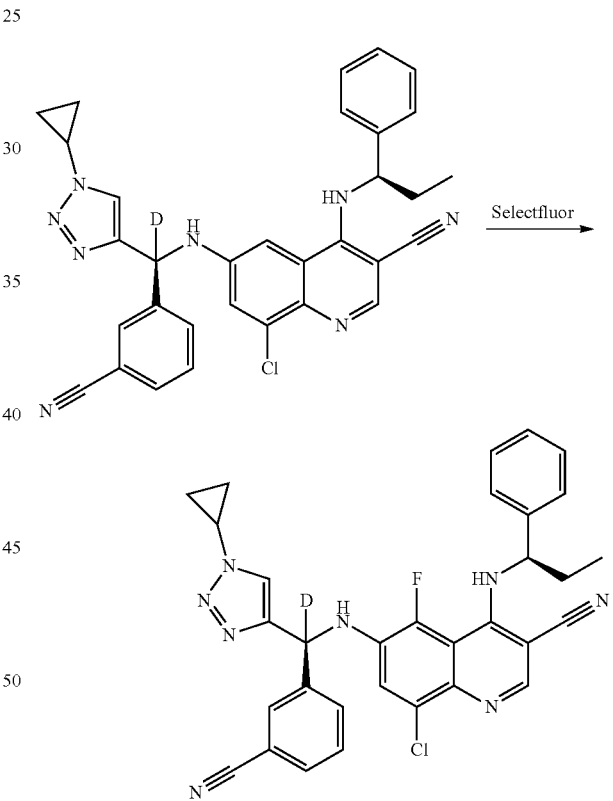

To a solution of 8-chloro-6-(((S)-(3-cyanophenyl)(1-cyclopropyl-1H-1,2,3-triazol-4-yl)methyl-d)amino)-4-(((R)-1-phenylpropyl)amino)quinoline-3-carbonitrile (23.9 mg, 0.043 mmol) in acetonitrile (0.8 ml) was added Selectfluor® II reagent (16.38 mg, 0.05 mmol). The reaction was monitored by LCMS. Once complete, it was passed through a syringe filter and purified by RP-HPLC (eluent: water/MeCN*0.1% TFA) to give the product as trifluoroacetate salt.

169

Example 37 Procedure 37

8-chloro-6-(((S)-(3-cyanophenyl)(1-cyclopropyl-1H-1,2,3-triazol-5-yl)methyl-d)amino)-4-(((R)-1-phenylpropyl)amino)quinoline-3-carbonitrile

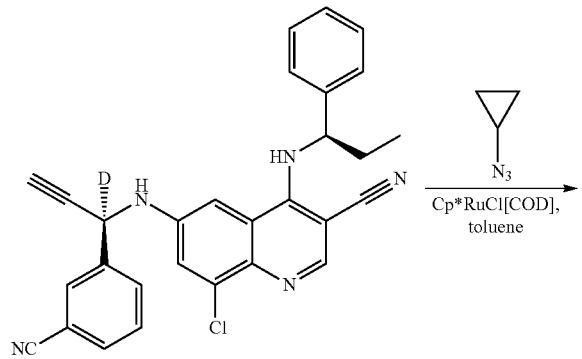

Cyclopropyl azide (15.6 mg, 0.068 mmol) was added to a solution of the 8-chloro-6-(((R)-1-(3-cyanophenyl)prop-2-yn-1-yl-1-d)amino)-4-(((R)-1-phenylpropyl)amino)quinoline-3-carbonitrile (25 mg, 0.052 mmol) and chloro(pentamethylcyclopentadienyl)cyclooctadiene)ruthenium(II) (4.5 mg, 0.010 mmol) in toluene (degassed with Argon for 20 minutes) (2 mL) under an atmosphere of Argon in an oven dried vial. After stirring for 1 h at room temperature the solvent was removed under reduced pressure. The residue was subjected to flash chromatography (0-100% (20% methanol in ethyl acetate)/hexanes). The fractions containing product were combined and the solvent was removed under reduced pressure. The residue was taken up in water and methanol with 2 drops of trifluoroacetic acid and subjected to preparative HPLC. The clean fractions were combined and subjected to lyophilization, providing 8-chloro-6-(((S)-(3-cyanophenyl)(1-cyclopropyl-1H-1,2,3-triazol-5-yl)methyl-d)amino)-4-(((R)-1-phenylpropyl)amino)quinoline-3-carbonitril [catalyst: J. Am. Chem. Soc., 2008 p. 8923]

170

Example 38 Procedure 38

(S)-6-(((1-(1-(tert-butyl)piperidin-4-yl)-1H-1,2,3-triazol-4-yl)(3-(methoxymethyl)phenyl)methyl)amino)-8-chloro-4-((3-chloro-4-fluorophenyl)amino)quinoline-3-carbonitrile

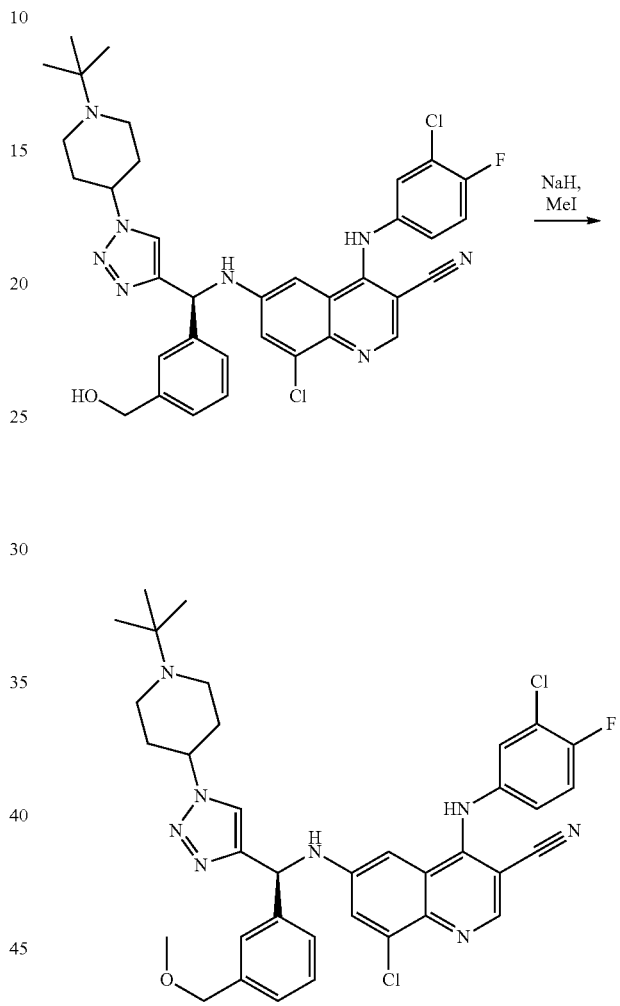

(S)-6-(((1-(1-(tert-butyl)piperidin-4-yl)-1H-1,2,3-triazol-4-yl)(3-(hydroxymethyl)phenyl)methyl)amino)-8-chloro-4-((3-chloro-4-fluorophenyl)amino)quinoline-3-carbonitrile (20.0 mg, 0.030 mmol) was dissolved in DMF (2 mL) and brought to 0° C. NaH (60% dispersion in mineral oil, 1.5 mg, 0.060 mmol) was then added and the resulting mixture stirred for 30 minutes. Iodomethane (0.007 mL, 0.12 mmol) was then added, the cold bath removed, and the reaction mixture allowed to warm to room temperature over 1 hour. The reaction contents were quenched by the addition of water (3 mL) which was extracted with EtOAc (3×8 mL). The organic phase was washed with brine (5 mL), dried over MgSO$_4$, and concentrated. The residue was purified by and RP-HPLC (eluent: water/MeCN*0.1% TFA) to yield the product as trifluoro acetate salt.

Example 39 Procedure 39

(S)-methyl 3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)(methyl)amino)methyl)benzoate

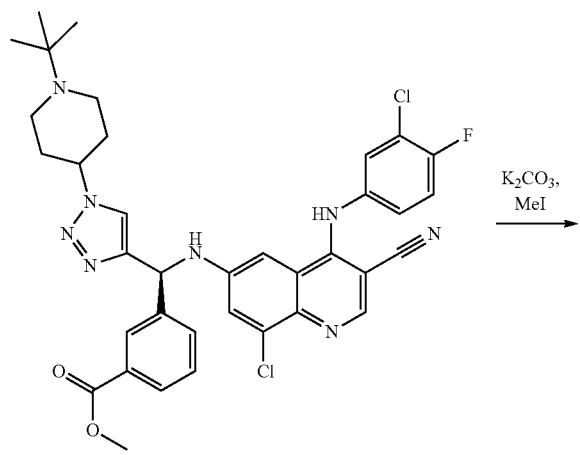

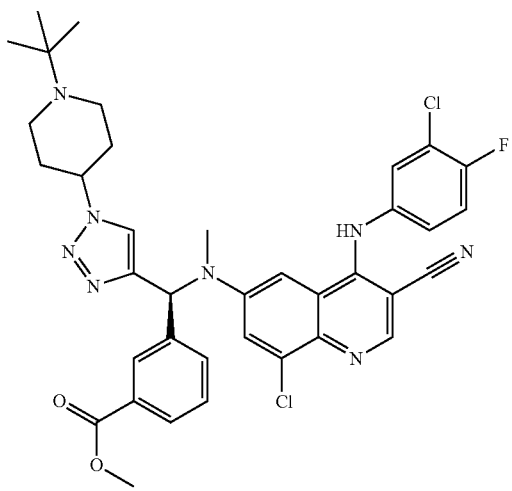

(S)-3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)benzoic acid (30.0 mg, 0.044 mmol), potassium carbonate (60.3 mg, 0.44 mmol) and iodomethane (0.011 mL, 0.18 mmol) were combined in acetone (2 mL) and stirred at room temperature for 4 hours. The reaction mixture was poured into water (3 mL) and extracted with EtOAc (3×8 mL). The organic phase was washed with brine (5 mL), dried over MgSO$_4$, and concentrated. The residue was purified by and RP-HPLC (eluent: water/MeCN*0.1% TFA) to yield the product as trifluoro acetate salt.

Example 40 Procedure 40

(S)-8-chloro-4-((3-chloro-4-fluorophenyl)amino)-6-(((3-((2-(dimethylamino)ethoxy)methyl)phenyl)(1-isopropyl-1H-1,2,3-triazol-4-yl)methyl)amino)quinoline-3-carbonitrile

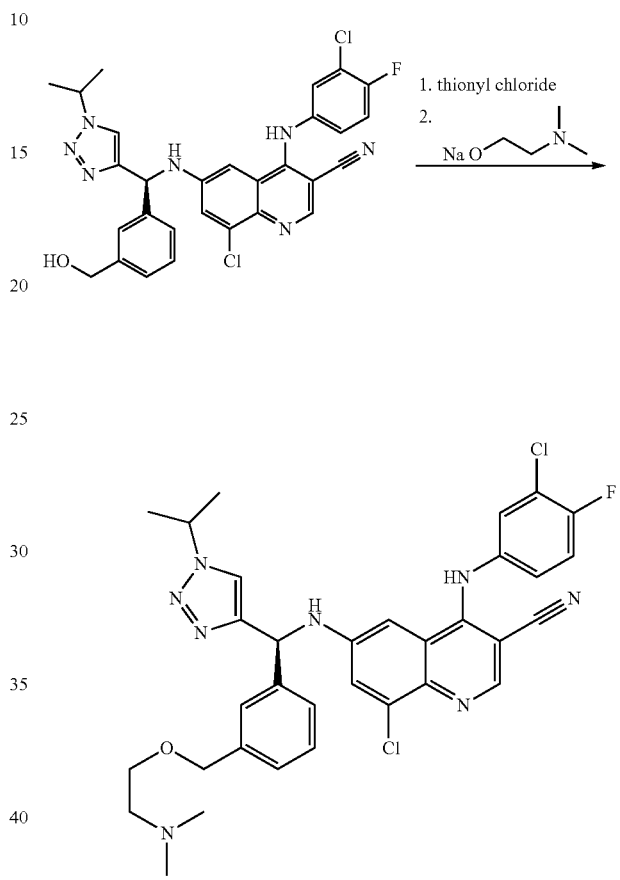

(S)-8-chloro-4-((3-chloro-4-fluorophenyl)amino)-6-(((3-(hydroxymethyl)phenyl)(1-isopropyl-1H-1,2,3-triazol-4-yl)methyl)amino)quinoline-3-carbonitrile (15.0 mg, 0.026 mmol) was dissolved in DCM (2 mL) at room temperature. Thionyl chloride (0.13 mL, 1.78 mmol) was added and the resulting solution stirred for 10 minutes after it was concentrated to dryness. In a separated flask, a solution of dimethylethanolamine (0.13 mL, 1.3 mmol) in DMF (2 mL) was treated with NaH (60% dispersion in mineral oil, 28 mg, 1.2 mmol) at 0° C. for 30 minutes. The newly formed chloride was taken up in DMF (1 mL) and added to the alkoxide solution at 0° C. after which the cold bath was removed and the reaction mixture allowed to warm to room temperature over 1 hour. The reaction contents were quenched by the addition of water and extracted with EtOAc (3×8 mL). The organic phase was washed with brine (5 mL), dried over MgSO$_4$ and concentrated. The crude residue was purified by RP-HPLC (eluent: water/MeCN*0.1% TFA) to yield the product as trifluoro acetate salt.

Example 41 Procedure 41

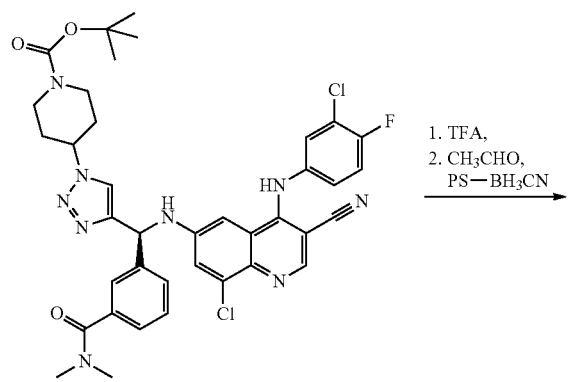

(S)-3-(((8-chloro-4-((3-chloro-4-fluorophenyl)amino)-3-cyanoquinolin-6-yl)amino)(1-(1-ethylpiperidin-4-yl)-1H-1,2,3-triazol-4-yl)methyl)-N,N-dimethylbenzamide (S)-tert-butyl 4-(4-(((8-chloro-4-((3-chloro-4-fluorophenyl)amino)-3-cyanoquinolin-6-yl)amino)(3-(dimethylcarbamoyl)phenyl)methyl)-1H-1,2,3-triazol-1-yl)piperidine-1-carboxylate (123 mg, 0.12 mmol) was dissolved in DCM (4 mL) and TFA (1 mL) and stirred at room temperature for 30 minutes. The reaction mixture was then concentrated to dryness and dissolved in MeOH (4.5 mL) and AcOH (1.5 mL). Acetaldehyde (0.068 mL, 1.2 mmol) and PS—CNBH$_3$ (polystyrene supported cyanoborohydride, 480 mg, 2.17 mmol/g) were then added and the resulting mixture stirred at room temperature for 2 hours. The resin was filtered and the resulting filtrate concentrated and purified by RP-HPLC (eluent: water/MeCN*0.1% TFA) to yield the product as trifluoro acetate salt.

Example 42 Procedure 42

(S)-6-(((1-(1-(tert-butyl)piperidin-4-yl)-1H-1,2,3-triazol-4-yl)(3-formylphenyl)methyl)amino)-8-chloro-4-((3-chloro-4-fluorophenyl)amino)quinoline-3-carbonitrile

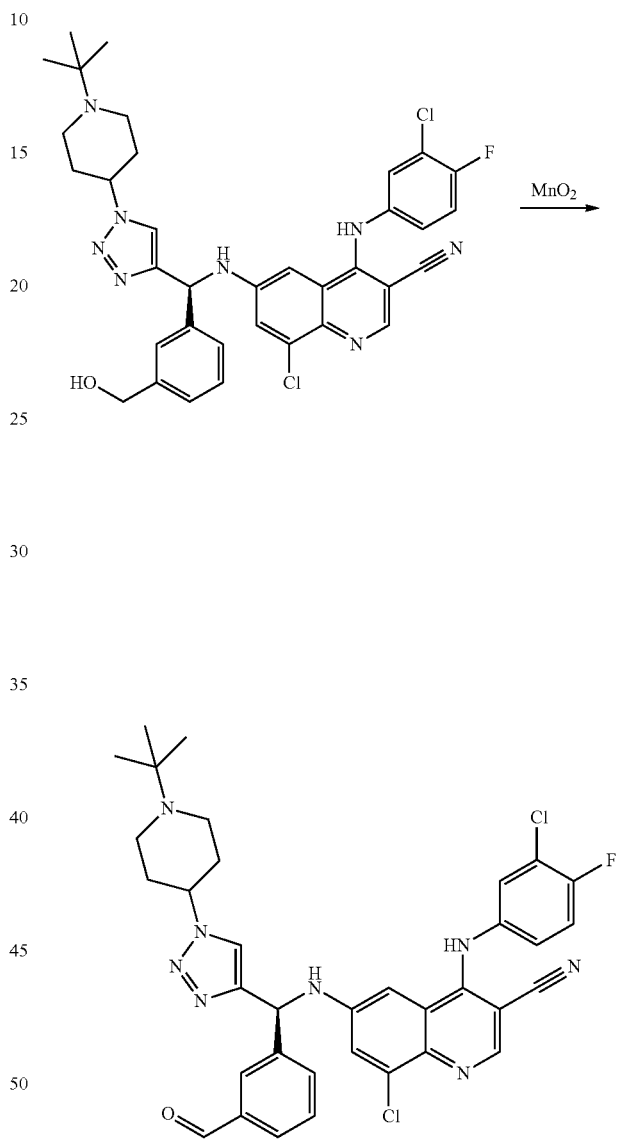

(S)-6-(((1-(1-(tert-butyl)piperidin-4-yl)-1H-1,2,3-triazol-4-yl)(3-(hydroxymethyl)phenyl)methyl)amino)-8-chloro-4-((3-chloro-4-fluorophenyl)amino)quinoline-3-carbonitrile (15.0 mg, 0.022 mmol) was dissolved in DCM (2 mL) and manganese(IV) oxide (58 mg, 0.67 mmol) was added and the resulting mixture stirred at room temperature. After 12 hours the reaction mixture was filtered through celite and the filtrate concentrated. The residue was then purified by and RP-HPLC (eluent: water/MeCN*0.1% TFA) to yield the product as trifluoro acetate salt.

Example 43 Procedure 43

(S)-6-(((1-cyclopropyl-1H-1,2,3-triazol-4-yl)(4-fluorophenyl)methyl-d)amino)-8-hydroxy-4-(neopentylamino)quinoline-3-carbonitrile

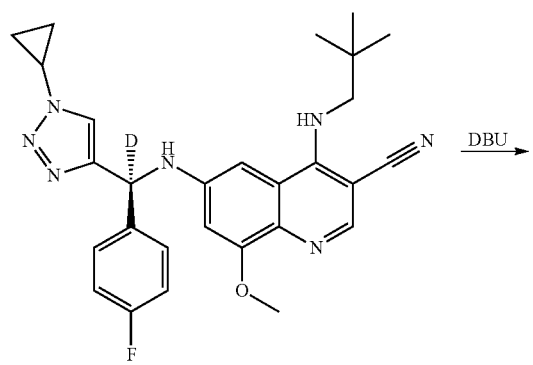

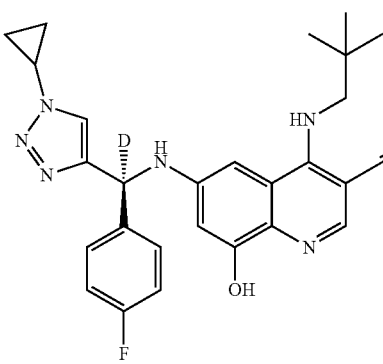

The starting material (30 mg, 0.06 mmol) was dissolved in DBN (2 mL) and heated at 150° C. for 20 hrs and 170° C. for additional 20 hrs. The mixture was cooled to room temperature and partitioned between EtOAc and water. The organic layer was washed with brine and dried over Na$_2$SO$_4$. Filtration and evaporation of the solvent yielded the crude product. Purification via RP-HPLC (eluent: water/MeCN*0.1% TFA) yielded the product as a trifluoro acetate salt.

1H NMR (400 MHz, DMSO-d6) δ 8.35 (s, 1H), 7.97 (s, 1H), 7.49 (dd, J=8.6, 5.6 Hz, 2H), 7.10 (t, J=8.8 Hz, 2H), 6.91 (s, 1H), 6.70 (s, 1H), 6.05 (d, J=7.6 Hz, 1H), 4.08 (s, 1H), 4.00-3.86 (m, 1H), 3.51 (s, 1H), 1.16-1.00 (m, 4H), 0.89 (s, 9H).

Example 44 Procedure 44

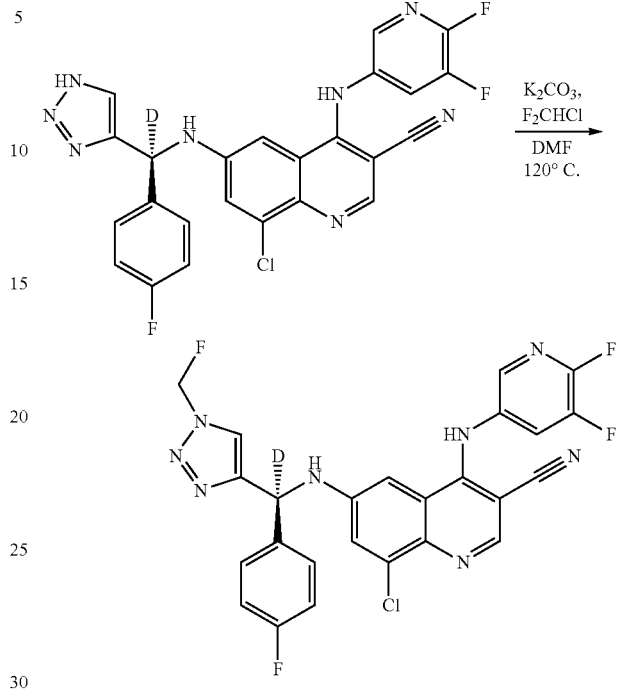

(S)-chloro-4-((5,6-difluoropyridin-3-yl)amino)-6-((f (1-(fluoromethyl)-1H-1,2,3-triazol-4-yl)(4-fluorophenyl)methyl-d)amino)quinoline-3-carbonitrile Solid K$_2$CO$_3$ (145 mg, 1.05 mmol) was added to a string solution of(S)-8-chloro-4-((5,6-difluoropyridin-3-yl)amino)-6-(((4-fluorophenyl)(1H-1,2,3-triazol-4-yl)methyl-d)amino)quinoline-3-carbonitrile (133 mg, 0.26 mmol) in DMF (10 mL). The resulting suspension was heated to 120° C. then F$_2$CHCl was bubbled through (10 bubbles/sec) for 15 min. The reaction mixture was cooled to rt then diluted with EtOAc (20 mL). The organic layer was washed with saturated NaHCO$_3$ (20 mL), brine (20 mL), dried over Na$_2$SO$_4$, and concentrated to give the crude product. HPLC afforded the title compound and regioisomers. 1H NMR (400 MHz, DMSO-d6) δ 9.56 (s, 1H), 8.44 (s, 1H), 8.25 (s, 1H), 8.04-7.94 (m, 2H), 7.70-7.60 (m, 1H), 7.55-7.42 (m, 3H), 7.25-7.11 (m, 3H), 6.51-6.39 (m, 1H), 6.32 (s, 1H). ES/MS 540.1 (M+H$^+$).

Example 45 Procedure 45

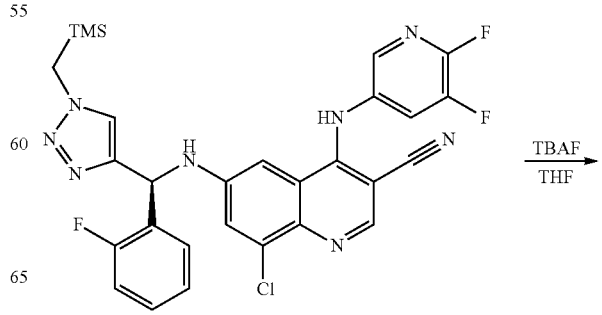

-continued

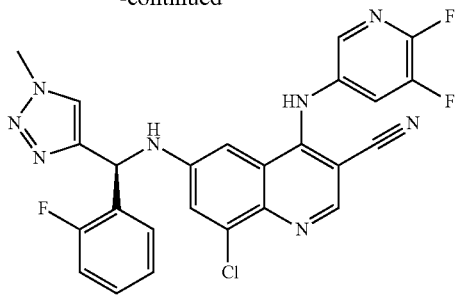

(S)-8-chloro-4-((5,6-difluoropyridin-3-yl)amino)-6-(((2-fluorophenyl)(1-methyl-1H-1,2,3-triazol-4-yl)methyl)amino)quinoline-3-carbonitrile 1.0 M TBAF in THF (0.15 mL, 0.15 mmol) was added to a stirring solution of (S)-8-chloro-4-((5,6-difluoropyridin-3-yl)amino)-6-(((2-fluorophenyl)(1-((trimethylsilyl)methyl)-1H-1,2,3-triazol-4-yl)methyl)amino)quinoline-3-carbonitrile (60 mg, 0.1 mmol, obtained per example 10) in THF (2 mL). The reaction mixture was stirred for 1 h then concentrated to give crude methyl triazole. HPLC purification afforded the title compound. 1H NMR (400 MHz, DMSO-d$_6$) δ 9.70 (s, 1H), 8.49 (s, 1H), 8.05-7.89 (m, 3H), 7.73 (d, J=2.2 Hz, 1H), 7.46 (td, J=7.9, 1.9 Hz, 1H), 7.41-7.28 (m, 2H), 7.24-7.11 (m, 3H), 6.25 (s, 1H), 4.00 (s, 3H). ES/MS 521.1 (M+H$^+$).

Example 46 Procedure 46

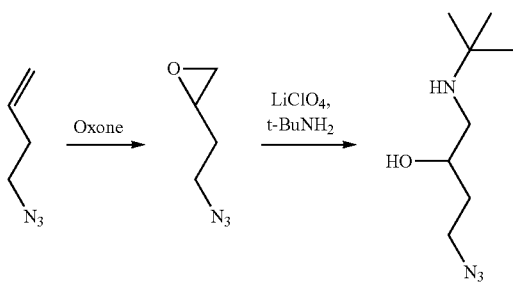

Oxone (1.5 g, 5.1 mmol) and acetone (3.7 mL, 51 mmol) were added to a stirring solution of 1-butene azide (0.1 g, 1 mmol) in DCM/NaHCO$_3$ (3 mL/5 mL) at 0° C. The resulting mixture was allowed to warm to rt and stirred for 1.5 hrs. The solution was extracted with DCM and the combined organic layers were dried and concentrated to give crude epoxide. The crude was redissolved in t-BuNH$_2$ (2.1 mL, 20 mmol). Lithium perchlorate (21 mg, 0.2 mmol) was added to the solution and stirred over night at rt. The resulting solution was used as is for the next step.

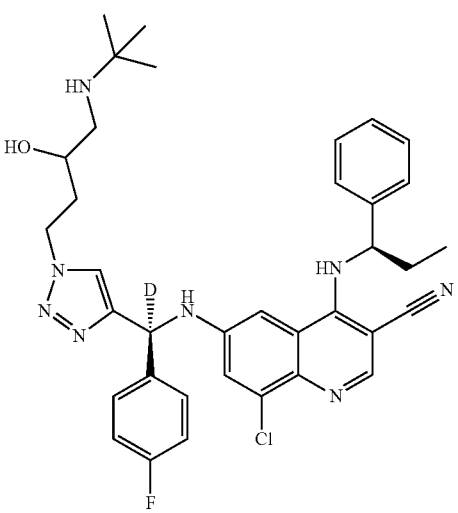

6-(((1S)-(1-(4-(tert-butylamino)-3-hydroxybutyl)-1H-1,2,3-triazol-4-yl)(4-fluorophenyl)methyl-d)amino)-8-chloro-4-(((R)-1-phenylpropyl)amino)quinoline-3-carbonitrile Synthesized according to example 2 with the azide synthesized in the previous step; 1H NMR (400 MHz, DMSO-d6) δ 8.30-8.18 (m, 2H), 8.00-7.94 (m, 1H), 7.63-7.53 (m, 3H), 7.44-7.12 (m, 10H), 5.52-5.31 (m, 1H), 4.84 (brs), 4.57-4.40 (m, 2H), 3.81-3.66 (m, 1H), 2.96 (t, J=11.0 Hz, 1H), 2.74 (d, J=11.4 Hz, 1H), 2.19-2.00 (m, 2H), 1.98-1.85 (m, 2H), 1.24 (s, 9H), 0.99-0.86 (m, 3H). ES/MS 656.3 (M+H+).

Example 47 Procedure 47

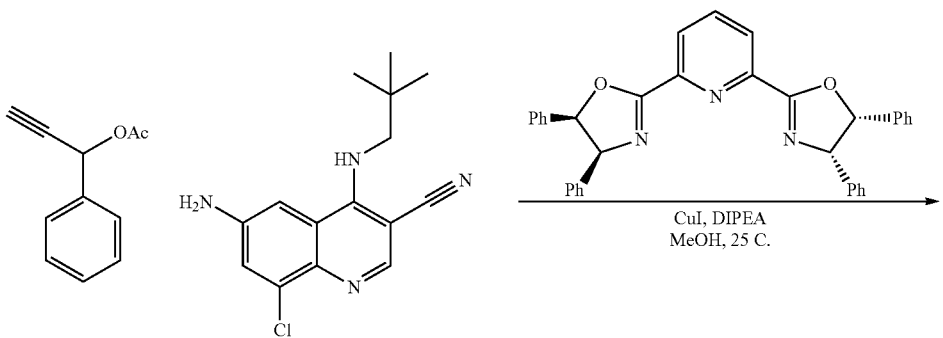

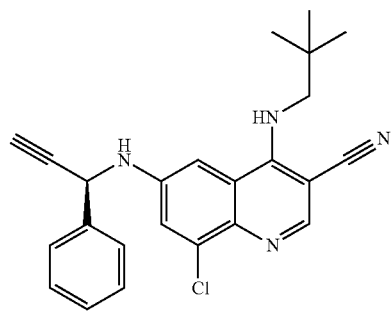 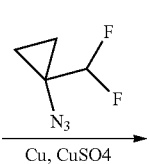 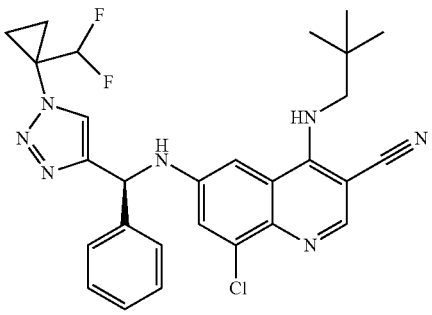

The CuI (6.6 mg, 0.035 mmol) and ligand (22 mg, 0.042 mmol) were suspended in MeOH (5 mL) and sonicated under argon for 5 min. The acetate (72 mg, 0.42 mmol) was added followed by the amine (100 mg, 0.35 mmol) and DIPEA (54 mg, 0.42 mmol) in that order at room temperature. After 1 h the N-alkylation reactions was complete. Evaporation and purification on silica get (eluent: EtOAc in hexanes) yielded 96 mg of N-alkylated product. 48 mg of the material was taken into THF (2 mL). Azide stock (1 mL/1 eq.), Cu and CuSO4 were added. Stirring at room temperature for 30 min. Diluted with EtOAc, washed with water, brine and dried over magnesium sulfate. Filtration, evaporation, and purification via RP-HPLC (eluent: water/MeCN*0.1 TFA) yielded the product as TFA salt.

$^1$H NMR (400 MHz, Methanol-d4) δ 8.45 (s, 1H), 7.84 (s, 1H), 7.65 (d, J=2.3 Hz, 1H), 7.47 (d, J=7.2 Hz, 2H), 7.41-7.32 (m, 2H), 7.35-7.26 (m, 1H), 7.07 (d, J=2.3 Hz, 1H), 6.08 (s, 1H), 5.93 (t, J=54.7 Hz, 1H), 4.15 (d, J=13.9 Hz, 1H), 3.74 (d, J=14.0 Hz, 1H), 1.51 (s, 4H), 0.97 (s, 9H).

Example 48 Procedure 48

The starting material (43 mg, 0.08 mmol), Zn (0.7 mg, 0.01 mmol), PddppfCl$_2$ (1.2 mg, 0.002 mmol) and Zn(CN)$_2$ (11.4 mg, 0.097 mmol) were combined in dimethylacetamide (1 mL) and degassed for 2 min. The mixture was heated in a microwave reactor at 200° C. for 20 min. The mixture was filtered and purified via RP-HPLC. The product fractions were combined and subjected to lyophilization, providing the desired compound as TFA salt. (Note: in some cases partial conversion was observed. Addition of more catalyst and resubmission to the reaction conditions gave further conversion.)

$^1$H NMR (400 MHz, Methanol-d4) δ 8.35 (s, 1H), 7.86 (s, 1H), 7.80 (d, J=2.5 Hz, 1H), 7.52-7.45 (m, 2H), 7.36 (dd, J=8.5, 6.6 Hz, 2H), 7.33-7.27 (m, 1H), 7.26 (d, J=2.5 Hz, 1H), 6.08 (s, 1H), 5.93 (t, J=54.7 Hz, 1H), 4.03 (d, J=13.8 Hz, 1H), 3.63 (d, J=13.9 Hz, 1H), 1.51 (s, 4H), 0.94 (s, 9H).

Example 49 Procedure 49

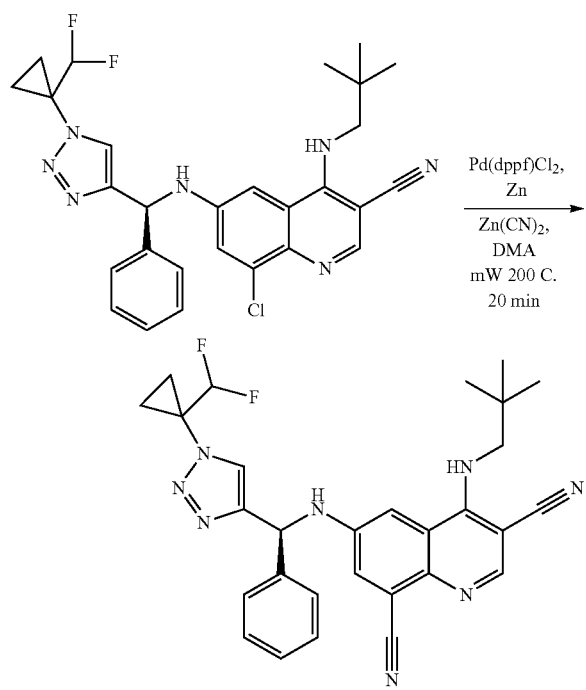

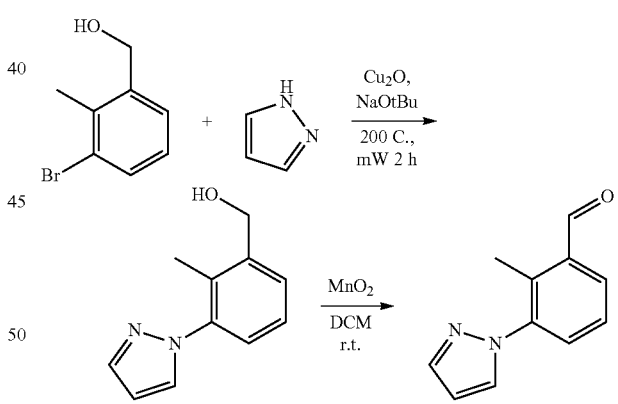

Bromide starting material (200 mg, 1.0 mmol), pyrazole (271 mg, 3.98 mmol), cuprous oxide (14.2 mg, 0.10 mmol), and sodium tert-butoxide (195 mg, 1.99 mmol) were combined in N-methyl pyrrolidinone (4 mL) and heated in a microwave reactor at 200° C. for 2 h. The reaction contents were diluted with EtOAc, washed with water, brine and dried over magnesium sulfate. After filtration and concentration the crude product was taken up in dichloromethane (10 mL) and Manganese (IV) oxide (2.16 g, 25 mmol) was added and the reaction stirred for 1 h at room temperature. The reaction contents were filtered through a pad of celite, concentrated, and was purified via silica gel chromatography (eluent: EtOAc/hexanes) to yield the product.

Example 50 Procedure 50

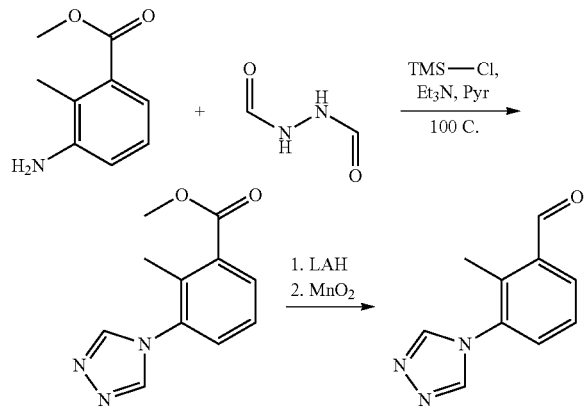

Aniline (1.5 g, 9.1 mmol) was dissolved in pyridine (45 mL) and diformylhydrazine (2.4 g, 27.2 mmol) was added as a single portion. Chlorotrimethylsilane (17.3 mL, 136.2 mmol) was added dropwise followed by triethylamine (8.9 mL, 63.6 mmol) dropwise. The reaction as heated overnight to 100° C. after which is was cooled to room temperature, diluted with EtOAc, washed with water, brine and dried over magnesium sulfate. Filtration and concentration was followed by silica gel chromatography (eluent: EtOAc/hexanes) to yield the product.

Ester (900 mg, 4.1 mmol) was dissolved in THF (15 mL) and brought to 0° C. after which lithium aluminum hydride (1.0M in Et$_2$O, 4.1 mL, 4.1 mmol) was added dropwise. After 30 minutes the reaction contents were carefully quenched by the addition of water and extracted with EtOAc. The organic extract was washed with brine, dried over magnesium sulfate, filtered and concentrated. The newly formed alcohol was then taken up in DCM (20 mL) and manganese (IV) oxide (4.6 g, 53 mmol) was added and the reaction stirred for 1 h at room temperature. The reaction contents were filtered through a pad of celite and concentrated to yield the aldehyde product.

Example 51 Procedure 51

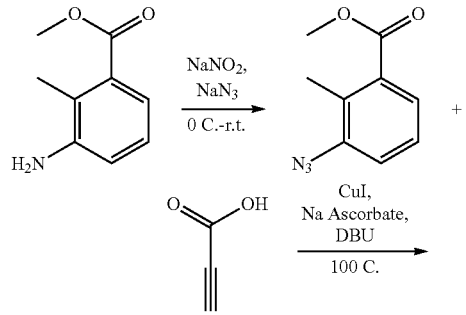

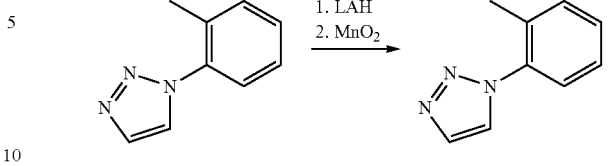

Dissolved aniline SM (1.0 g, 6.1 mmol) in 6N HCl solution (20 mL), brought to 0 deg in ice/water bath. Treated with aqueous solution of NaNO2 (418 mg, 6.1 mmol) in 1 mL water dropwise. Let stir 10 minutes at 0 deg then added NaN3 (472 mg, 7.3 mmol) as an aqueous solution in 2 mL water. The cold bath was removed and the reaction mixture allowed to warm to r.t. After 30 min full conversion observed. Reaction mixture was poured into water and extracted with EtOAct. The organic layer was dried over magnesium sulfate, filtered and concentrated to give crude azide product.

Newly formed azide (338 mg, 1.78 mmol), propiolic acid (186 mg, 2.65 mmol), cuprous iodide (67 mg, 0.35 mmol), sodium ascorbate (140 mg, 0.71 mmol), 1,8-Diazabicyclo[5.4.0]undec-7-ene 1,8-Diazabicyclo[5.4.0]undec-7-ene (0.13 mL, 0.88 mmol) were all combined in DMF (5 mL) and degassed with argon. The reaction mixture was heated to 100° C. for 15 h after which it was diluted with EtOAc, washed with water, brine and dried over magnesium sulfate. The crude product was purified via silica gel chromatography (eluent: EtOAc/hexanes) to yield the product.

Ester (79 mg, 0.36 mmol) was dissolved in THF (5 mL) and brought to 0° C. after which lithium aluminum hydride (1.0M in Et$_2$O, 0.36 mL, 0.36 mmol) was added dropwise. After 30 minutes the reaction contents were carefully quenched by the addition of water and extracted with EtOAc. The organic extract was washed with brine, dried over magnesium sulfate, filtered and concentrated. The newly formed alcohol was then taken up in DCM (5 mL) and manganese (IV) oxide (790 mg, 9.1 mmol) was added and the reaction stirred for 1 h at room temperature. The reaction contents were filtered through a pad of celite and concentrated to yield the aldehyde product.

Example 52 Procedure 52

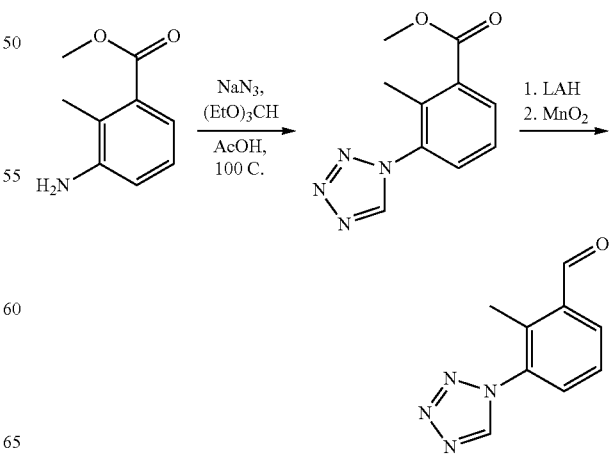

Aniline (500 mg, 3.03 mmol) and sodium azide (364 mg, 5.6 mmol) were dissolved in acetic acid (10 mL) followed by triethyl orthoformate (2.4 mL, 14.5 mmol). The reaction mixture was stirred at room temperature for 15 h then at 100° C. for 3 h. The reaction contents were concentrated directly and purified via silica gel chromatography (eluent: EtOAc/hexanes) to yield the product.

Ester (290 mg, 1.3 mmol) was dissolved in THF (10 mL) and brought to 0° C. after which lithium aluminum hydride (1.0M in Et$_2$O, 1.3 mL, 1.3 mmol) was added dropwise. After 30 minutes the reaction contents were carefully quenched by the addition of water and extracted with EtOAc. The organic extract was washed with brine, dried over magnesium sulfate, filtered and concentrated. The newly formed alcohol was then taken up in DCM (10 mL) and DMF (2 mL) and manganese (IV) oxide (2.65 g, 30 mmol) was added and the reaction stirred for 1 h at room temperature. The reaction contents were filtered through a pad of celite and concentrated to yield the aldehyde product.

Example 53 Procedure 53

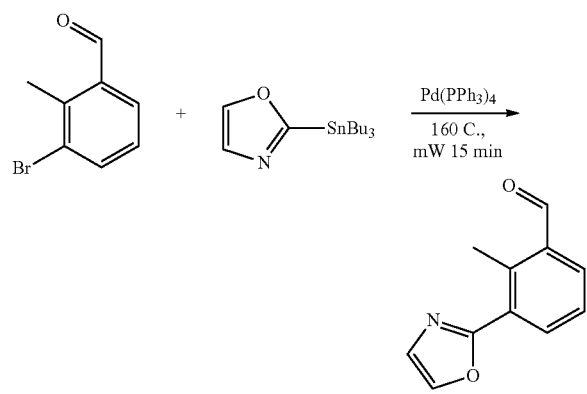

Bromide (300 mg, 1.5 mmol), stannane (0.46 mL, 1.5 mmol) and Pd(PPh$_3$)$_4$ were combined in DMF(4 mL) and heated to 160° C. for 15 minutes. The reaction contents were then diluted with EtOAc, washed with water, brine and dried over magnesium sulfate. The crude product was purified via silica gel chromatography (eluent: EtOAc/hexanes) to yield the desired aldehyde.

Example 54 Procedure 54

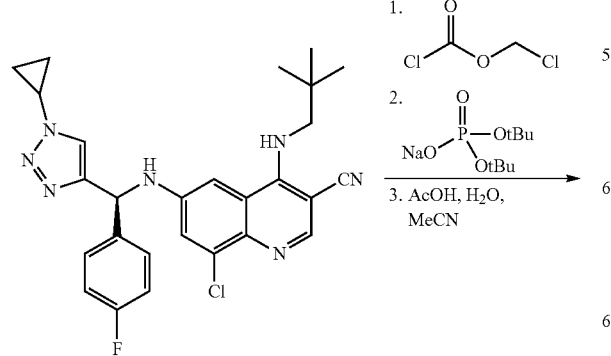

-continued

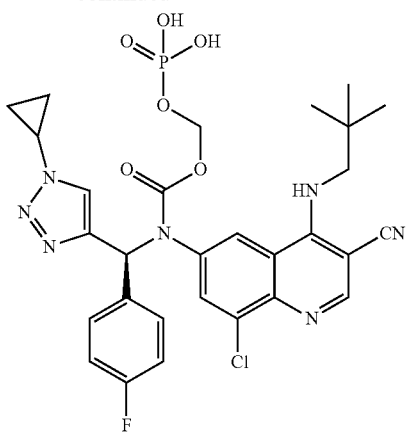

Starting material (30 mg, 0.06 mmol) was dissolved in DCM (1.5 mL) after which diisopropylethylamine (0.03 mL, 0.18 mmol) and chloromethyl chloroformate (9.2 mg, 0.07 mmol) were added and the resulting mixture stirred for 30 min. Chloromethyl chloroformate (154 mg, 1.2 mmol) was then added and the reaction mixture stirred for an additional 1 h. Upon completion the reaction was concentrated directly and purified via silica gel chromatography (eluent: EtOAc/hexanes) to yield the desired chloride.

The resulting chloride (34 mg, 0.057 mmol) was combined with ditert-butyl phosphate, potassium salt (28 mg, 0.11 mmol) and tetrabutylammonium iodide (2.0 mg, 0.006 mmol) and stirred at 60° C. for 12 h. The reaction contents were then diluted with EtOAc, washed with water, brine and dried over magnesium sulfate. The crude product was purified via silica gel chromatography (eluent: EtOAc/hexanes) to yield the desired product.

Starting material (28 mg, 0.036 mmol) was dissolved in acetic acid (0.5 mL), water (0.5 mL), acetonitrile (0.5 mL) and heated to 50° C. for 6 h. Upon completion the reaction mixture was directly purified via RP-HPLC. The product fractions were combined and subjected to lyophilization, providing the desired compound as TFA salt.

Example 55 Procedure 55

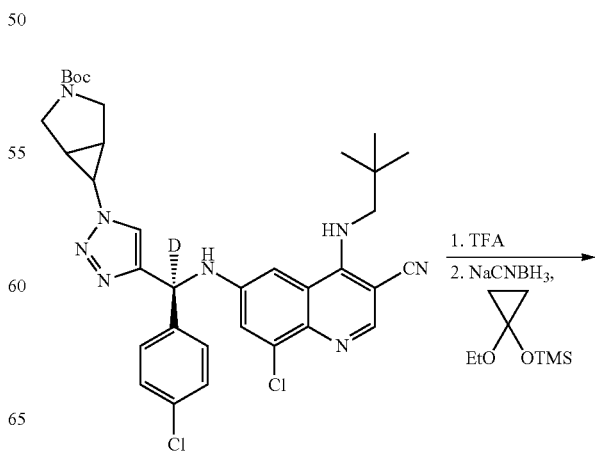

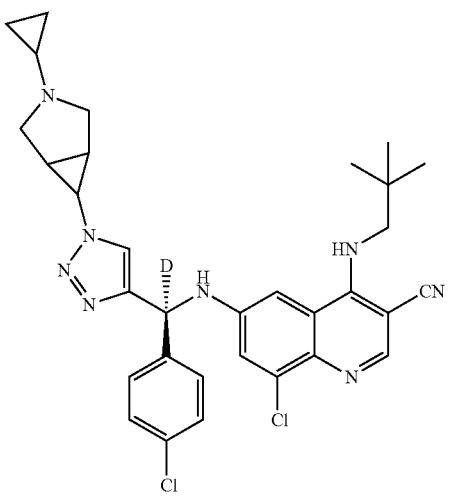

Boc amine (39 mg, 0.059 mmol) was taken up in DCM (1 mL) and trifluoroacetic acid (1 mL) and stirred for 2 h at room temperature. The reaction mixture was concentrated to dryness, taken up in THF (1 mL) and treated with sodium cyanoborohydride (37 mg, 0.59 mmol) and cyclopropyl mixed ketal (102 mg, 0.59 mmol) at room temperature overnight. The reaction contents were then diluted with EtOAc, washed with water, brine, dried over magnesium sulfate and purified by RP-HPLC. The product fractions were combined and subjected to lyophilization, providing the desired compound as TFA salt.

Example 56 Procedure 56

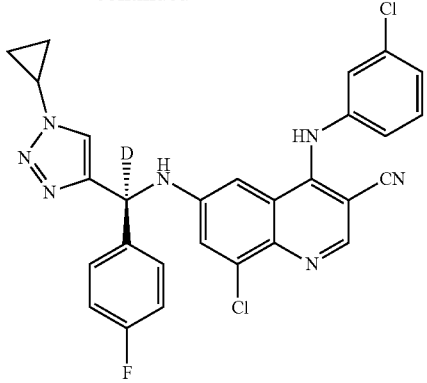

Iodide (50 mg, 0.074 mmol), stannane (269 mg, 0.74 mmol), and catalyst (27 mg, 0.037 mmol) were combined in DMF (1 mL), degassed with argon, and heated to 100° C. for 12 h. The reaction contents were then filtered through a pad of celite, rinsing with EtOAc, and concentrated. The crude product mixture was taken up in methanol (1 mL) and 1N HCl (1 mL) and stirred at room temperature for 15 h. The reaction contents were poured into saturated aqueous NaHCO₃ solution and extracted with EtOAc. The organic layers were dried over magnesium sulfate, filtered, concentrated and purified by RP-HPLC. The product fractions were combined and subjected to lyophilization, providing the desired ketone as TFA salt (4.9 mg, 11%) as well as the dehalogenated product.

Example 57 Procedure 57

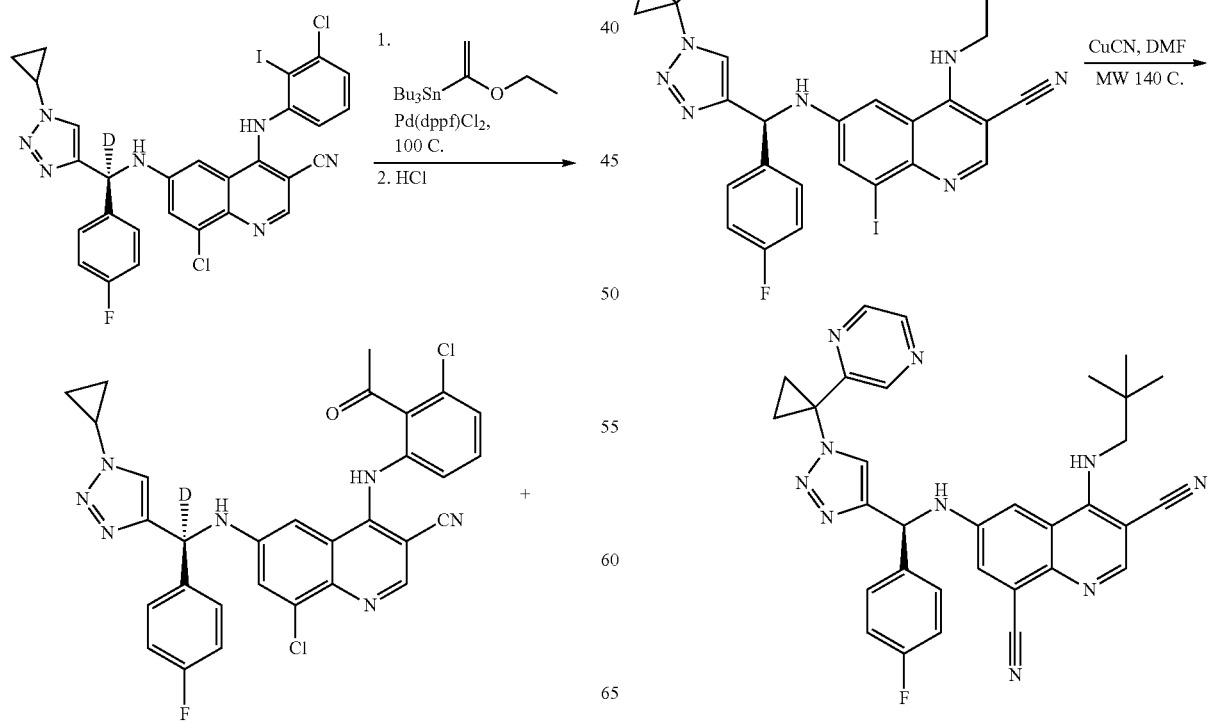

A solution of (S)-6-(((4-fluorophenyl)(1-(1-(pyrazin-2-yl)cyclopropyl)-1H-1,2,3-triazol-4-yl)methyl)amino)-8-iodo-4-(neopentylamino)quinoline-3-carbonitrile (26.9 mg, 0.040 mmol), copper (I) cyanide (10.7 mg, 0.12 mmol) in dimethylformamide (1 mL) was heated in a microwave reactor at 140 C. for 15 min. The mixture was diluted with ethyl acetate (10 ml) and washed with 5% lithium chloride (2×5 mL) and brine (5 mL). The organic phase was dried over sodium sulfate and the solvent was removed under reduced pressure. The residue was taken up in water (0.5 ml) and MeOH (1 mL) with 2 drops of TFA and subjected to prep HPLC. The clean fractions combined and subjected to lyophilization, providing the desired material.

Example 58 Procedure 58

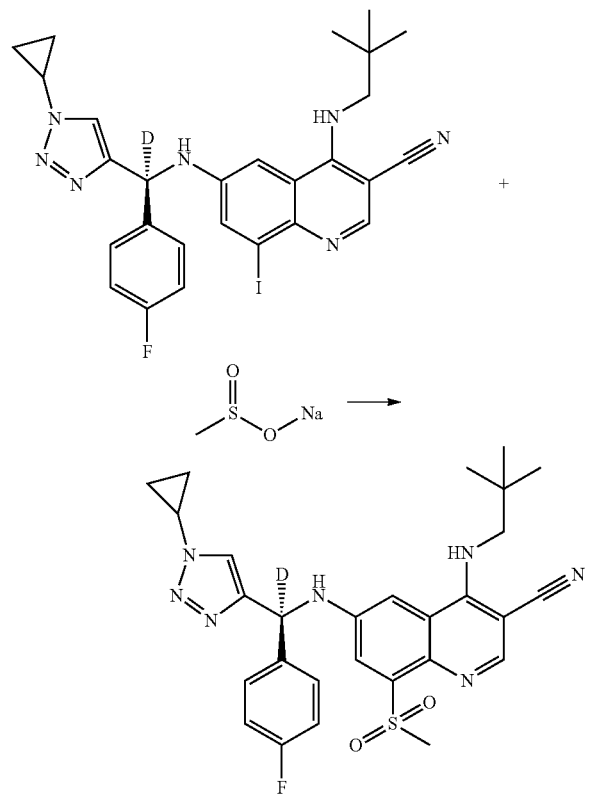

(S)-6-(((1-cyclopropyl-1H-1,2,3-triazol-4-yl)(4-fluorophenyl)methyl-d)amino)-8-(methylsulfonyl)-4-(neopentylamino)quinoline-3-carbonitrile To (S)-6-(((1-cyclopropyl-1H-1,2,3-triazol-4-yl)(4-fluorophenyl)methyl-d)amino)-8-iodo-4-(neopentylamino)quinoline-3-carbonitrile (50 mg, 0.084 mmol) was added L-proline (1.9 mg, 0.017 mmol), Cu(I) iodide (1.6 mg, 0.008 mmol), sodium methanesulfinate (10 mg, 0.101 mmol), cesium carbonate (27 mg, 0.084 mmol) and DMSO (0.5 mL). The reaction mixture was flushed with nitrogen and heated to 83° C. overnight. Reaction was then cooled to room temperature and diluted with water and EtOAc. Aqueous layer was extracted once more with EtOAc. Combined organics were washed with water, brine, dried (Na₂SO₄) and concentrated to give the crude product which was purified by HPLC (eluent: water/MeCN*0.1% TFA) to yield the title product. ES/MS 549.43 (M+H⁺).

Example 59 Procedure 59

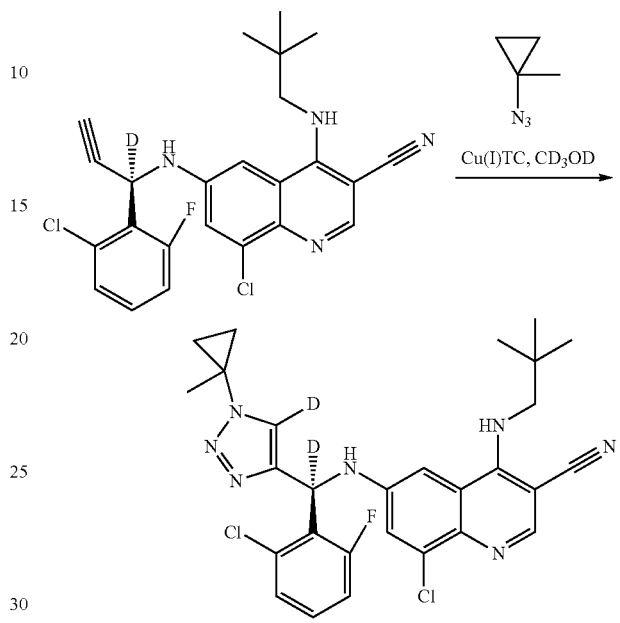

(S)-8-chloro-6-(((2-chloro-6-fluorophenyl)(1-(1-methylcyclopropyl)-1H-1,2,3-triazol-4-yl-5-d)methyl-d)amino)-(neopentylamino)quinoline-3-carbonitrile A solution of (R)-8-chloro-6-((1-(2-chloro-6-fluorophenyl)prop-2-yn-1-yl-1-d)amino)-4-(neopentylamino)quinoline-3-carbonitrile (55 mg, 0.121 mmol) in deuterated methanol (CD₃OD, 2.5 mL) was treated with the azide (14 mg, 0.145 mmol) and copper(I)thiophenecarboxylate (0.7 mg, 0.006 mmol) at room temperature. After 12 hours, the reaction was diluted with EtOAc and filtered through celite. The crude was purified by silica gel chromatography (eluent: EtOAc:hexanes) followed by HPLC purification(eluent: water/MeCN*0.1% TFA) to yield the title product. ES/MS 554.32 (M+H⁺).

Example 60 Procedure 60

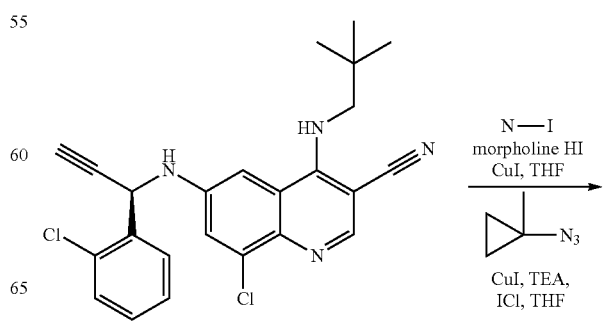

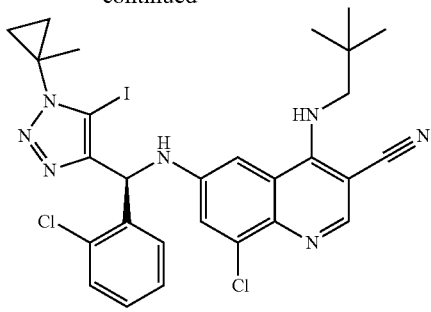

(S)-8-chloro-6-(((2-chlorophenyl)(5-iodo-1-(1-methylcyclopropyl)-1H-1,2,3-triazol-4-yl)methyl)amino)-4-(neopentylamino)quinoline-3-carbonitrile To a solution of (S)-8-chloro-6-(((2-chlorophenyl)(5-methoxy-1-(1-methylcyclopropyl)-1H-1,2,3-triazol-4-yl)methyl)amino)-4-(neopentylamino)quinoline-3-carbonitrile (430 mg, 0.98 mmol) in THF were added copper (I) iodide (37.4.5 mg, 0.906 mmol) and N-iodo morpholine hydroiodide (402 mg, 1.2 mmol). After 14 hrs, the reaction was diluted with EtOAc, washed with sodium bicarbonate solution and dried over sodium sulfate. Filtration and removal of volatiles yielded crude solid, which was used in the next step without further purification. To a solution of the starting material and copper iodide (20 mg, 0.1 mmol) in DMF (3 mL) was added cyclopropyl azide (97 mg 1.0 mmol), and triethylamine (101 mg, 1.0 mmol). After 16 h the reaction was diluted with ethyl acetate (5 mL). The product 190 mg) was isolated as a precipitate via filtration.

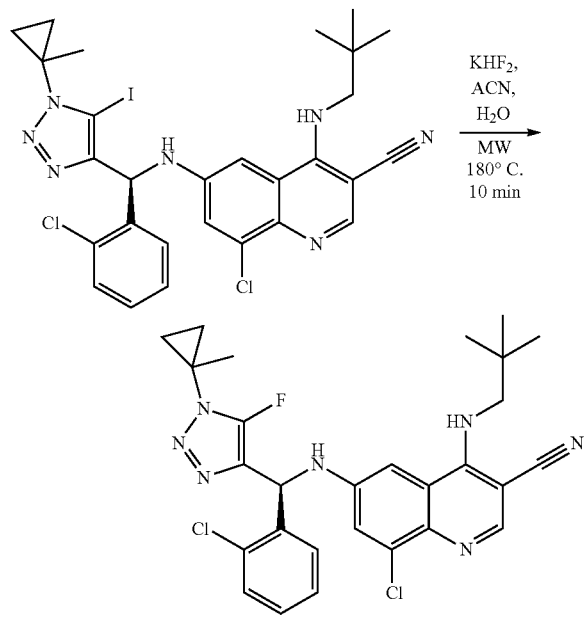

(S)-8-chloro-6-(((2-chlorophenyl)(5-fluoro-1-(1-methylcyclopropyl)-1H-1,2,3-triazol-4-yl)methyl)amino)-4-(neopentylamino)quinoline-3-carbonitrile Acetonitrile (4.0 mL) and water (4.0 mL) were added to (S)-8-chloro-6-(((2-chlorophenyl)(5-iodo-1-(1-methylcyclopropyl)-1H-1,2,3-triazol-4-yl)methyl)amino)-4-(neopentylamino)quinoline-3-carbonitrile (190 mg, 0.288 mmol) and KHF$_2$ (157.3 mg, 2.014 mmol) in a microwave vial. The vial was sealed and the reaction was heated in a microwave reactor at 180° C. for 10 minutes. The reaction was diluted with ethyl acetate (10 mL) and washed with brine (5 mL). The organic phase was dried over sodium sulfate and the solvent was removed under reduced pressure. The residue was subjected to flash chromatography (0-100% ethyl acetate/hexanes). The fractions containing product were combined and the solvent was removed under reduced pressure. The residue was taken up in methanol and water and subjected to preparative HPLC. The clean fractions were combined and subjected to lyophilization, providing (S)-8-chloro-6-(((2-chlorophenyl)(5-fluoro-1-(1-methylcyclopropyl)-1H-1,2,3-triazol-4-yl)methyl)amino)-4-(neopentylamino)quinoline-3-carbonitrile.

Example 61 Procedure 61

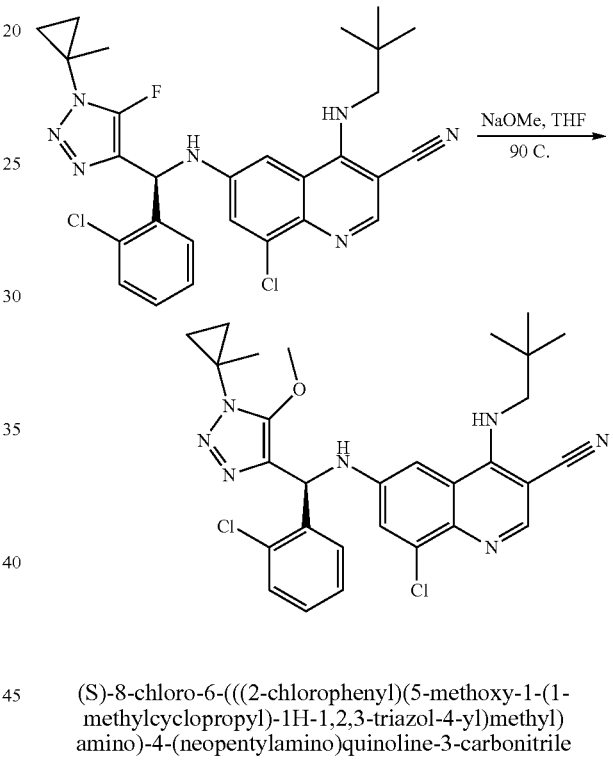

(S)-8-chloro-6-(((2-chlorophenyl)(5-methoxy-1-(1-methylcyclopropyl)-1H-1,2,3-triazol-4-yl)methyl)amino)-4-(neopentylamino)quinoline-3-carbonitrile Sodium methoxide (28 uL, 25% MeOH) was added to a solution of (S)-8-chloro-6-(((2-chlorophenyl)(5-fluoro-1-(1-methylcyclopropyl)-1H-1,2,3-triazol-4-yl)methyl)amino)-4-(neopentylamino)quinoline-3-carbonitrile (72 mg, 0.13 mmol) in tetrahydrofuran (3.0 mL). The solution was heated at 90° C. for 3 hours and the reaction was quenched with 2 drops of acetic acid. The solution was diluted with ethyl acetate and washed with saturated sodium bicarbonate) and brine. The organic phase was dried over sodium sulfate and the solvent was removed under reduced pressure. The residue was subjected to flash chromatography (0-100% ethyl acetate/hexanes). The fractions containing product were combined and the solvent was removed under reduced pressure. The residue was taken up in methanol/water and was subjected to preparative HPLC. The clean fractions containing product were combined and subjected to lyophilization, providing (S)-8-chloro-6-(((2-chlorophenyl)(5-methoxy-1-(1-methylcyclopropyl)-1H-1,2,3-triazol-4-yl)methyl)amino)-4-(neopentylamino)quinoline-3-carbonitrile.

Example 62 Procedure 62

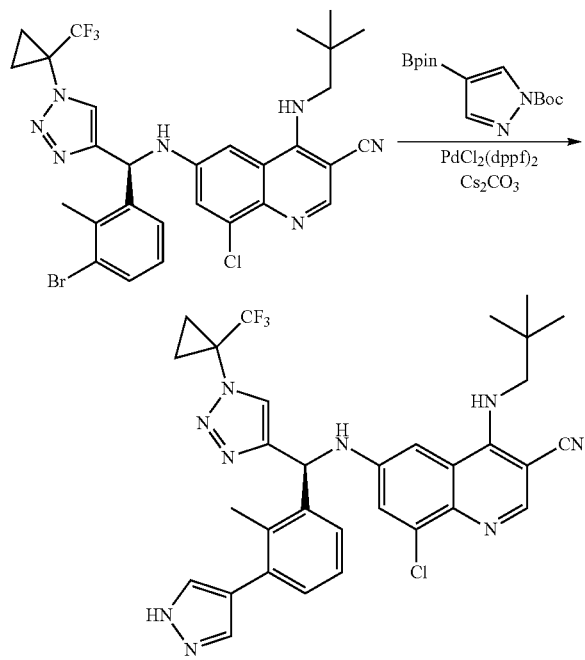

(S)-8-chloro-6-(((2-methyl-3-(1H-pyrazol-4-yl)phenyl)(1-(1-(trifluoromethyl)cyclopropyl)-1H-1,2,3-triazol-4-yl)methyl)amino)-4-(neopentylamino)quinoline-3-carbonitrile (S)-6-(((3-bromo-2-methylphenyl)(1-(1-(trifluoromethyl)cyclopropyl)-1H-1,2,3-triazol-4-yl)methyl)amino)-8-chloro-4-(neopentylamino)quinoline-3-carbonitrile (50 mg, 0.077 mmol), [11'-bis(diphenylphosphino)ferrocene]dichloropalladium(II) (9.4 mg, 0.015 mmol), 1-Boc-pyrazole-4-boronic acid pinacol ester (27 mg, 0.093 mmol) and cesium carbonate (76 mg, 0.23 mmol) were combined in DMF (1.5 mL) and purged with argon. The reaction mixture was heated to 180° C. for 20 minutes in a microwave reactor. After passing the reaction mixture through a silica-thiol plug the solvents were removed and the crude residue purified by RP-HPLC (eluent: water/MeCN*0.1% TFA) to yield the product as trifluoro acetate salt. Note: This procedure can be carried out with an iodide in place of the bromide.

The following compounds were prepared according to the Examples and Procedures described herein (and indicated in Table 1 under Example/Procedure) using the appropriate starting material(s) and appropriate protecting group chemistry as needed.

TABLE 1

| Compd | Structure | Name | Example/Procedure | ES/MS m/z |
|---|---|---|---|---|
| 1 | 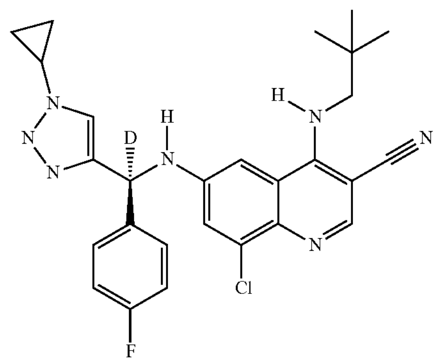 | (S)-8-chloro-6-(((1-cyclopropyl-1H-1,2,3-triazol-4-yl)(4-fluorophenyl)methyl-d)amino)-4-(neopentylamino)quinoline-3-carbonitrile | 1 | ES/MS 505.1 (M + H+) |
| 2 | 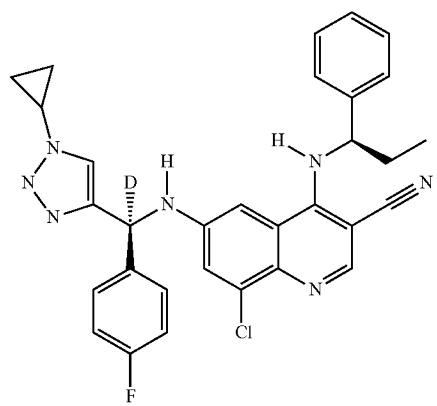 | 8-chloro-6-(((S)-(1-cyclopropyl-1H-1,2,3-triazol-4-yl)(4-fluorophenyl)methyl-d)amino)-4-(((R)-1-phenylpropyl)amino)quinoline-3-carbonitrile | 2 | ES/MS 553.2 (M + H+) |

TABLE 1-continued

| Compd | Structure | Name | Example/Procedure | ES/MS m/z |
|---|---|---|---|---|
| 3 | 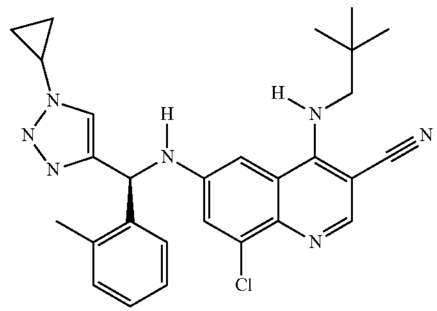 [SMILES: Cc1ccccc1[C@H](Nc1cc(Cl)c2ncc(C#N)c(NCC(C)(C)C)c2c1)C1=CN(C2CC2)NN1] | (S)-8-chloro-6-(((1-cyclopropyl-1H-1,2,3-triazol-4-yl)(o-tolyl)methyl)amino)-4-(neopentylamino)quinoline-3-carbonitrile | 3 | ES/MS 500.2 (M + H+) |
| 4 | 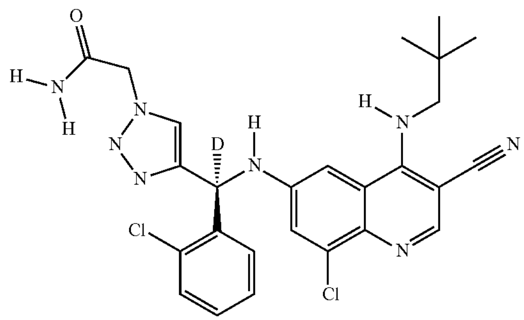 | 2-(4-(((8-chloro-3-cyano-4-(neopentylamino)quinolin-6-yl)amino)(2-chlorophenyl)methyl-d)-1H-1,2,3-triazol-1-yl)acetamide | 4 | ES/MS 538.2 (M + H+) |
| 5 | 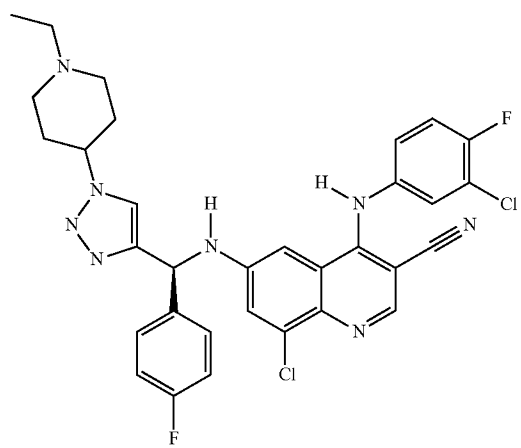 [SMILES: CCN1CCC(N2C=C([C@@H](Nc3cc(Cl)c4ncc(C#N)c(Nc5ccc(F)c(Cl)c5)c4c3)c3ccc(F)cc3)NN2)CC1] | (S)-8-chloro-4-((3-chloro-4-fluorophenyl)amino)-6-(((1-(1-ethylpiperidin-4-yl)-1H-1,2,3-triazol-4-yl)(4-fluorophenyl)methyl)amino)-quinoline-3-carbonitrile | 5 | ES/MS 633.1 (M + H+) |

TABLE 1-continued

| Compd | Structure | Name | Example/Procedure | ES/MS m/z |
|---|---|---|---|---|
| 6 | 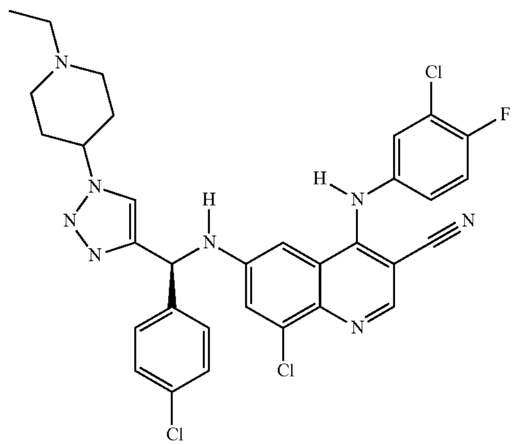 [SMILES: CCN1CCC(N2C=C([C@@H](Nc3cc(Cl)c4ncc(C#N)c(Nc5ccc(F)c(Cl)c5)c4c3)c3ccc(Cl)cc3)NN2)CC1] | 8-chloro-4-((3-chloro-4-fluorophenyl)amino)-6-(((4-chlorophenyl)(1-(1-ethylpiperidin-4-yl)-1H-1,2,3-triazol-4-yl)methyl)amino)quinoline-3-carbonitrile | 6 | |
| 7 | 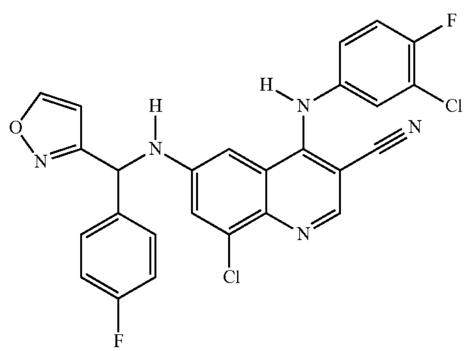 | 8-chloro-4-((3-chloro-4-fluorophenyl)amino)-6-(((4-fluorophenyl)(isoxazol-3-yl)methyl)amino)quinoline-3-carbonitrile | 7 | ES/MS 522.1 (M + H+) |

TABLE 1-continued

| Compd | Structure | Name | Example/Procedure | ES/MS m/z |
|---|---|---|---|---|
| 8 | 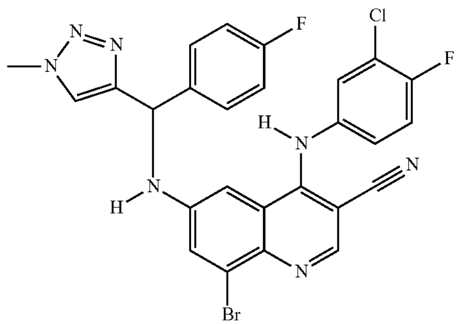 [SMILES: Cn1cc(C(Nc2cc(Br)c3ncc(C#N)c(Nc4ccc(F)c(Cl)c4)c3c2)c2ccc(F)cc2)nn1] | 8-bromo-4-((3-chloro-4-fluorophenyl)amino)-6-(((4-fluorophenyl)(1-methyl-1H-1,2,3-triazol-4-yl)methyl)amino)quinoline-3-carbonitrile | 8 | ES/MS 580.1 (M + H+) |
| 9 | 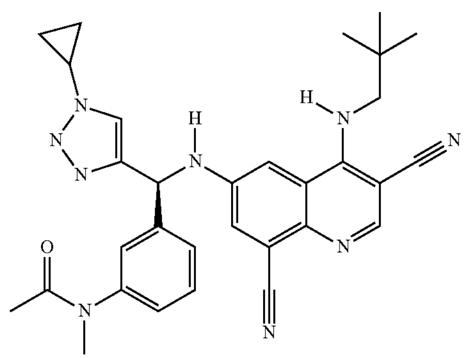 [SMILES: CC(=O)N(C)c1cccc([C@H](Nc2cc(C#N)c3ncc(C#N)c(NCC(C)(C)C)c3c2)C2=CN(C3CC3)NN2)c1] | (S)-N-(3-((1-cyclopropyl-1H-1,2,3-triazol-4-yl)(3,8-dicyano-4-(neopentylamino)quinolin-6-yl)amino)methyl)phenyl)-N-methylacetamide | 9a | ES/MS 548.1 (M + H+) |

TABLE 1-continued

| Compd | Structure | Name | Example/Procedure | ES/MS m/z |
|---|---|---|---|---|
| 10 | 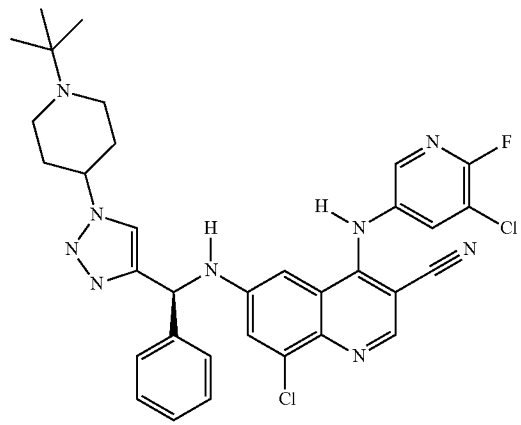 [SMILES: CC(C)(C)N1CCC(N2C=C([C@@H](Nc3cc(Cl)c4ncc(C#N)c(Nc5cnc(F)c(Cl)c5)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((5-chloro-6-fluoropyridin-3-yl)amino)quinoline-3-carbonitrile | 10 | ES/MS 644.2 (M + H+) |
| 11 | 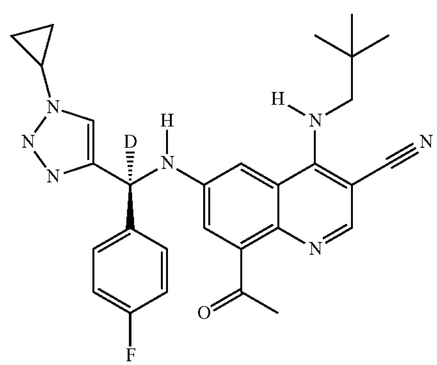 | (S)-8-acetyl-6-((((1-cyclopropyl-1H-1,2,3-triazol-4-yl)(4-fluorophenyl)methyl-d)amino)-4-(neopentylamino)quinoline-3-carbonitrile | 11 | ES/MS 513.3 (M + H+) |

TABLE 1-continued

| Compd | Structure | Name | Example/Procedure | ES/MS m/z |
|---|---|---|---|---|
| 12 | 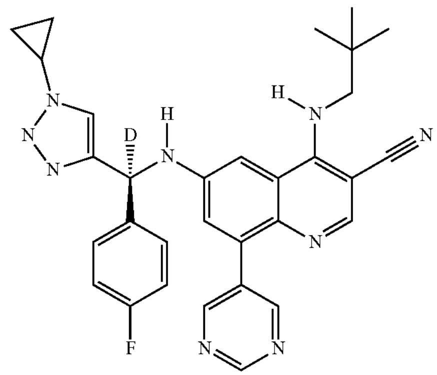 | (S)-6-((((1-cyclopropyl-1H-1,2,3-triazol-4-yl)(4-fluorophenyl)methyl-d)amino)-4-(neopentylamino)-8-(pyrimidin-5-yl)quinoline-3-carbonitrile | 12 | ES/MS 549.3 (M + H+) |
| 13 | 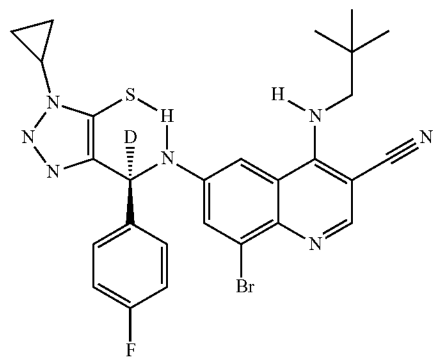 | (S)-8-bromo-6-((((1-cyclopropyl-5-(methylthio)-1H-1,2,3-triazol-4-yl)(4-fluorophenyl)methyl-d)amino)-4-(neopentylamino)quinoline-3-carbonitrile | 13 | ES/MS 595.2 (M + H+) |
| 14 | 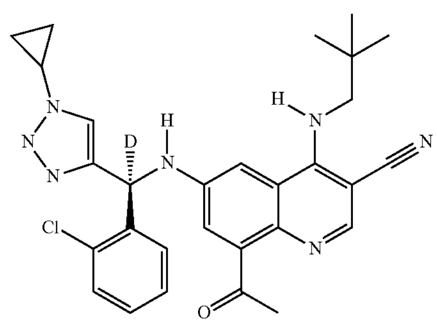 | (S)-8-acetyl-6-(((2-chlorophenyl)(1-cyclopropyl-1H-1,2,3-triazol-4-yl)methyl-d)amino)-4-(neopentylamino)quinoline-3-carbonitrile | 14 | ES/MS 529.2 (M + H+) |

TABLE 1-continued

| Compd | Structure | Name | Example/Procedure | ES/MS m/z |
|---|---|---|---|---|
| 15 | 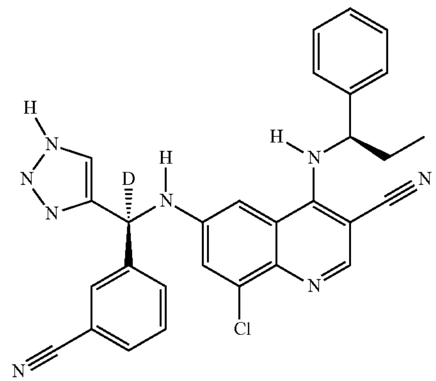 | 8-chloro-6-(((S)-(3-cyanophenyl)(1H-1,2,3-triazol-4-yl)methyl-d)amino)-4-(((R)-1-phenylpropyl)amino)quinoline-3-carbonitrile | 15 | ES/MS 520.0 (M + H+) |
| 16 | 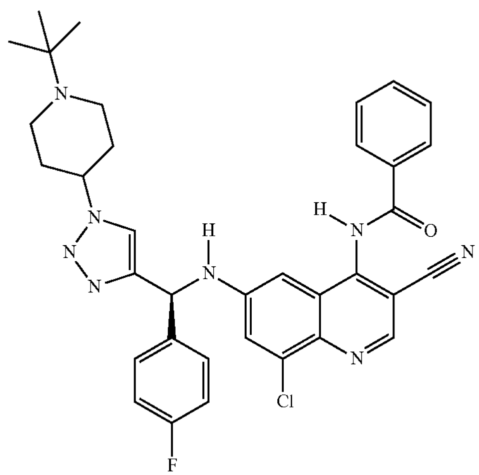 [SMILES: CC(C)(C)N1CCC(N2C=C([C@@H](Nc3cc(Cl)c4ncc(C#N)c(NC(=O)c5ccccc5)c4c3)c3ccc(F)cc3)NN2)CC1] | (S)-N-(6-(((1-(1-(tert-butyl)piperidin-4-yl)-1H-1,2,3-triazol-4-yl)(4-fluorophenyl)methyl)amino)-8-chloro-3-cyanoquinolin-4-yl)benzamide | 16 | ES/MS 637.2 (M + H+) |

TABLE 1-continued

| Compd | Structure | Name | Example/Procedure | ES/MS m/z |
|---|---|---|---|---|
| 17 | 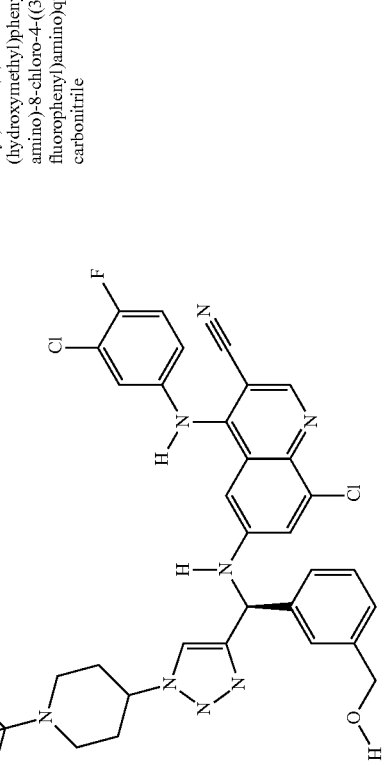 | (S)-6-((((1-(1-(tert-butyl)piperidin-4-yl)-1H-1,2,3-triazol-4-yl)(3-(hydroxymethyl)phenyl)methyl)amino)-8-chloro-4-((3-chloro-4-fluorophenyl)amino)quinoline-3-carbonitrile | 17 | ES/MS 673.1 (M + H+) |
| 18 | 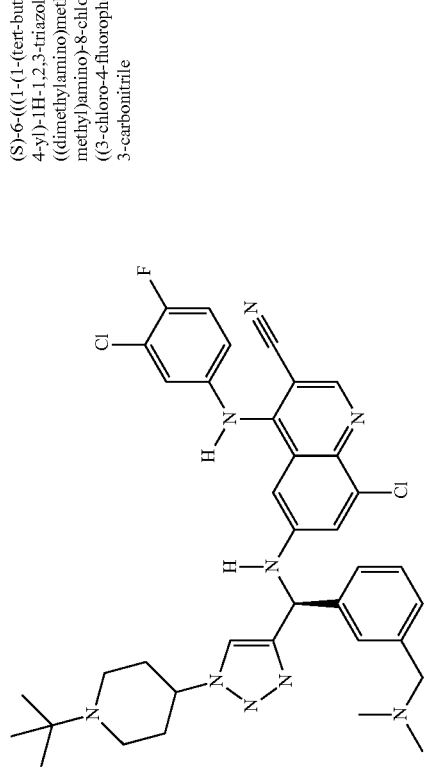 | (S)-6-((((1-(1-(tert-butyl)piperidin-4-yl)-1H-1,2,3-triazol-4-yl)(3-((dimethylamino)methyl)phenyl)methyl)amino)-8-chloro-4-((3-chloro-4-fluorophenyl)amino)quinoline-3-carbonitrile | 18 | ES/MS 700.2 (M + H+) |

TABLE 1-continued

| Compd | Structure | Name | Example/Procedure | ES/MS m/z |
|---|---|---|---|---|
| 19 | 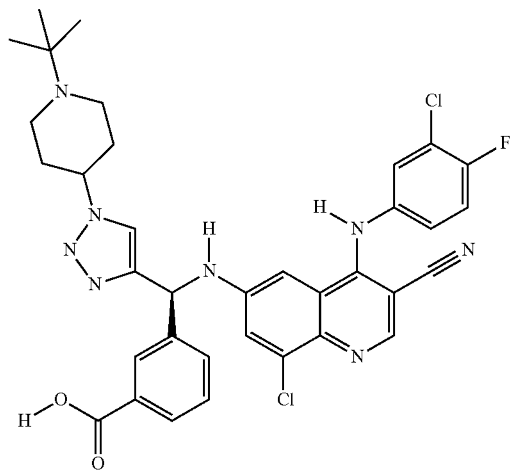 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)O)c3)NN2)CC1] | (S)-3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)amino)methyl)benzoic acid | 19 | ES/MS 687.0 (M + H+) |
| 20 | 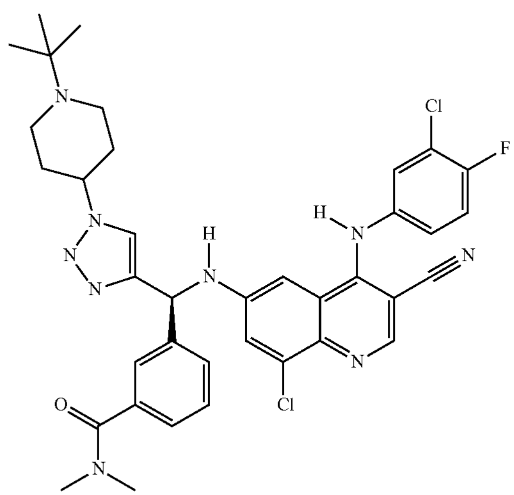 [SMILES: CN(C)C(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)amino)methyl)-N,N-dimethylbenzamide | 20 | ES/MS 714.0 (M + H+) |

TABLE 1-continued

| Compd | Structure | Name | Example/Procedure | ES/MS m/z |
|---|---|---|---|---|
| 21 | 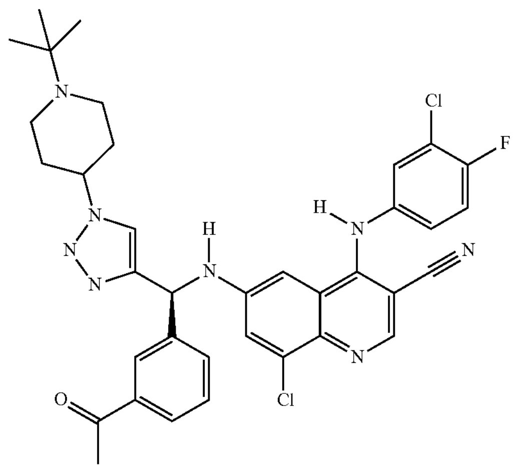 [SMILES: CC(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-6-(((3-acetylphenyl)(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile | 21 | ES/MS 685.1 (M + H+) |
| 22 | 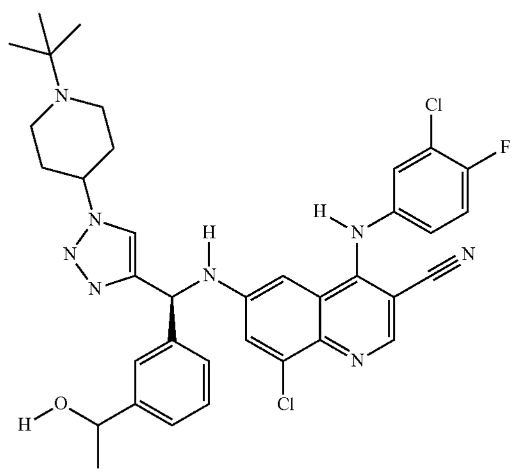 [SMILES: CC(O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | 6-(((1S)-(1-(1-(tert-butyl)piperidin-4-yl)-1H-1,2,3-triazol-4-yl)(3-(1-hydroxyethyl)phenyl)methyl)amino)-8-chloro-4-((3-chloro-4-fluorophenyl)amino)quinoline-3-carbonitrile | 22 | ES/MS 687.2 (M + H+) |

TABLE 1-continued

| Compd | Structure | Name | Example/Procedure | ES/MS m/z |
|---|---|---|---|---|
| 23 | 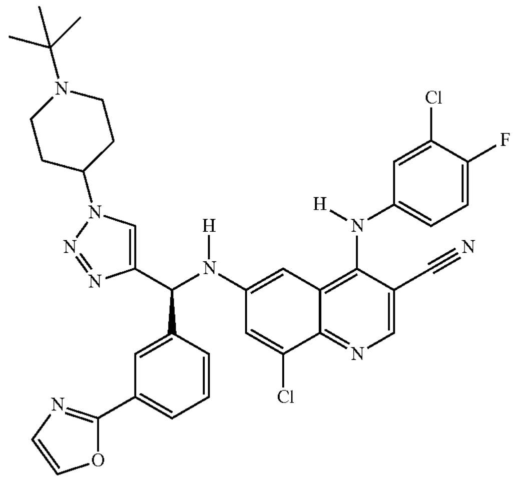 [SMILES: CC(C)(C)N1CCC(n2cc([C@@H](Nc3cc(Cl)c4ncc(C#N)c(Nc5ccc(F)c(Cl)c5)c4c3)c3cccc(-c4ncco4)c3)nn2)CC1] | (S)-6-((((1-(1-(tert-butyl)piperidin-4-yl)-1H-1,2,3-triazol-4-yl)(3-(oxazol-2-yl)phenyl)methyl)amino)-8-chloro-4-((3-chloro-4-fluorophenyl)amino)quinoline-3-carbonitrile | 23 | ES/MS 710.1 (M + H+) |
| 24 | 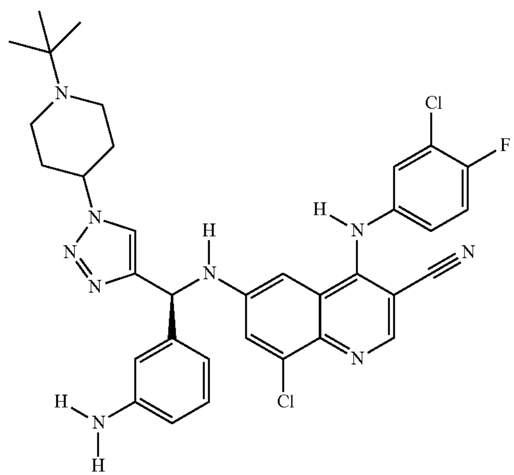 [SMILES: CC(C)(C)N1CCC(n2cc([C@@H](Nc3cc(Cl)c4ncc(C#N)c(Nc5ccc(F)c(Cl)c5)c4c3)c3cccc(N)c3)nn2)CC1] | (S)-6-(((3-aminophenyl)(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile | 24 | ES/MS 658.0 (M + H+) |

TABLE 1-continued

| Compd | Structure | Name | Example/Procedure | ES/MS m/z |
|---|---|---|---|---|
| 25 | 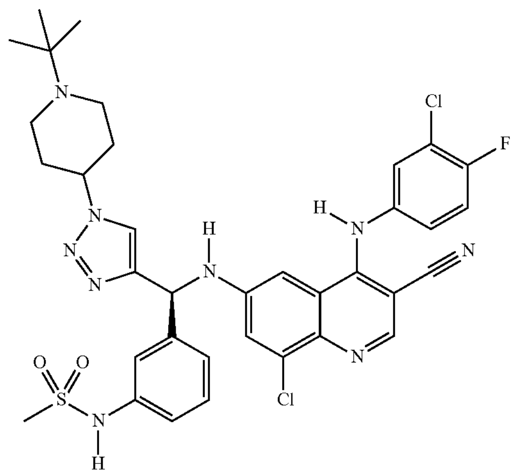 [SMILES: CC(C)(C)N1CCC(n2cc([C@@H](Nc3cc(Cl)c4ncc(C#N)c(Nc5ccc(F)c(Cl)c5)c4c3)c3cccc(NS(C)(=O)=O)c3)nn2)CC1] | (S)-N-(3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)phenyl)methane-sulfonamide | 25 | ES/MS 736.0 (M + H+) |
| 26 | 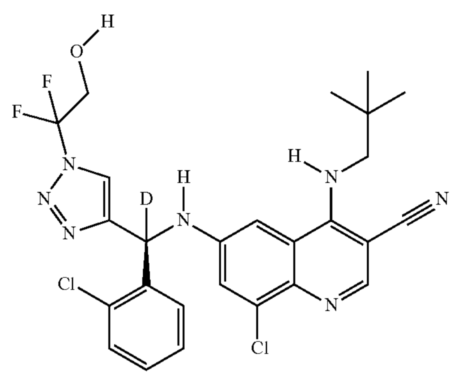 [SMILES: [2H][C@](Nc1cc(Cl)c2ncc(C#N)c(NCC(C)(C)C)c2c1)(c1cn(C(F)(F)CO)nn1)c1ccccc1Cl] | 8-chloro-6-(((2-chlorophenyl)(1-(1,1-difluoro-2-hydroxyethyl)-1H-1,2,3-triazol-4-yl)methyl-d)amino)-4-(neopentylamino)quinoline-3-carbonitrile | 26 | ES/MS 561.1 (M + H+) |

TABLE 1-continued

| Compd | Structure | Name | Example/Procedure | ES/MS m/z |
|---|---|---|---|---|
| 27 | 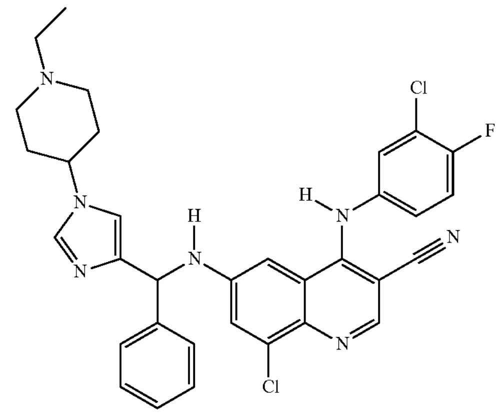 [SMILES: CCN1CCC(n2cnc(C(Nc3cc(Cl)c4ncc(C#N)c(Nc5ccc(F)c(Cl)c5)c4c3)c3ccccc3)c2)CC1] | 8-chloro-4-((3-chloro-4-fluorophenyl)amino)-6-(((1-(1-ethylpiperidin-4-yl)-1H-imidazol-4-yl)(phenyl)methyl)amino)quinoline-3-carbonitrile | 27 | ES/MS 613.9 (M + H+) |
| 28 | 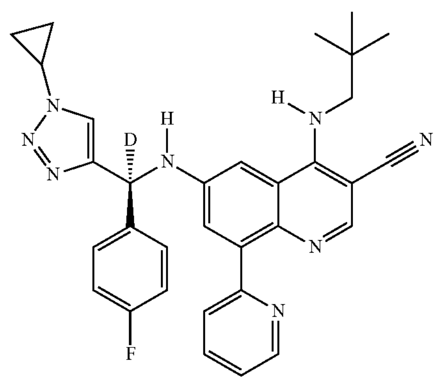 | (S)-6-(((1-cyclopropyl-1H-1,2,3-triazol-4-yl)(4-fluorophenyl)methyl-d)amino)-4-(neopentylamino)-8-(pyridin-2-yl)quinoline-3-carbonitrile | 28 | ES/MS 548.2 (M + H+) |

TABLE 1-continued

| Compd | Structure | Name | Example/Procedure | ES/MS m/z |
|---|---|---|---|---|
| 29 | 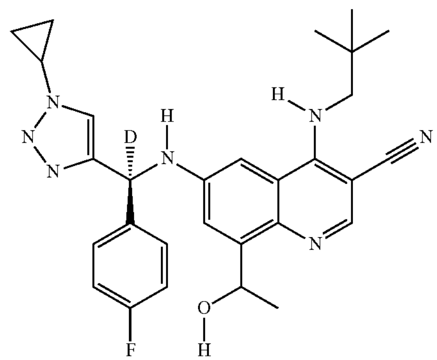 | 6-(((S)-(1-cyclopropyl-1H-1,2,3-triazol-4-yl)(4-fluorophenyl)methyl-d)amino)-8-(1-hydroxyethyl)-4-(neopentylamino)quinoline-3-carbonitrile | 29 | ES/MS 515.3 (M + H+) |
| 30 | 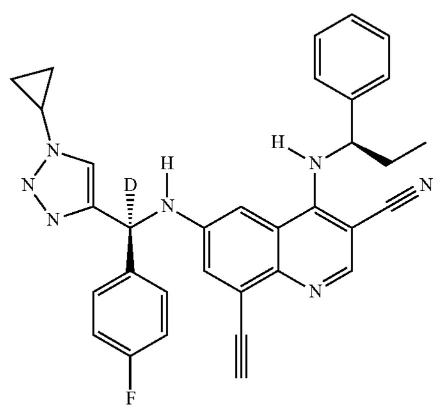 | 6-(((S)-(1-cyclopropyl-1H-1,2,3-triazol-4-yl)(4-fluorophenyl)methyl-d)amino)-8-ethynyl-4-(((R)-1-phenylpropyl)amino)quinoline-3-carbonitrile | 30 | ES/MS 543.3 (M + H+) |

TABLE 1-continued

| Compd | Structure | Name | Example/Procedure | ES/MS m/z |
|---|---|---|---|---|
| 31 | 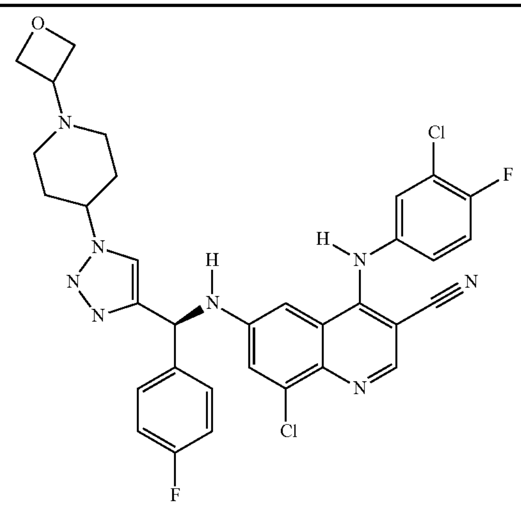 | (S)-8-chloro-4-((3-chloro-4-fluorophenyl)amino)-6-(((4-fluorophenyl)(1-(1-(oxetan-3-yl)piperidin-4-yl)-1H-1,2,3-triazol-4-yl)methyl)amino)quinoline-3-carbonitrile | 31 | ES/MS 661.1 (M + H+) |
| 32 | 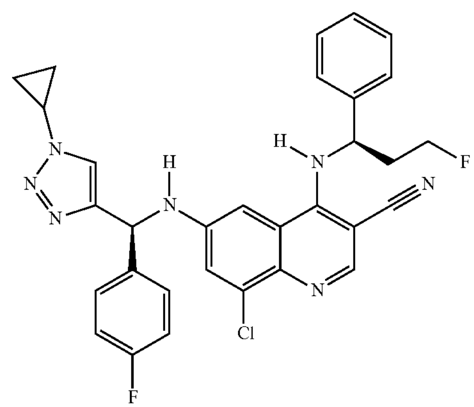 [SMILES: N#Cc1cnc2c(Cl)cc(N[C@@H](c3ccc(F)cc3)c3cn(C4CC4)nn3)cc2c1N[C@H](CCF)c1ccccc1] | 8-chloro-6-(((S)-(1-cyclopropyl-1H-1,2,3-triazol-4-yl)(4-fluorophenyl)methyl)amino)-4-(((R)-3-fluoro-1-phenylpropyl)amino)quinoline-3-carbonitrile | 32 | ES/MS 570.1 (M + H+) |

TABLE 1-continued

| Compd | Structure | Name | Example/Procedure | ES/MS m/z |
|---|---|---|---|---|
| 33 | 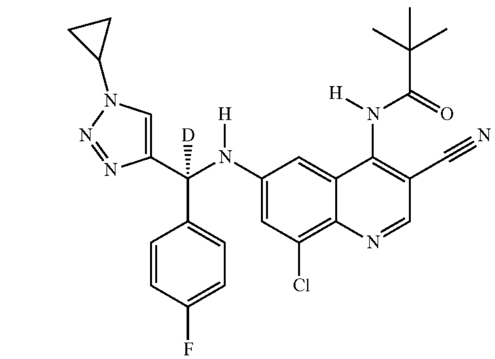 [SMILES: [2H][C@](Nc1cc(Cl)c2ncc(C#N)c(NC(=O)C(C)(C)C)c2c1)(c1ccc(F)cc1)c1cn(C2CC2)nn1] | N-(8-chloro-3-cyano-6-(((1-cyclopropyl-1H-1,2,3-triazol-4-yl)(4-fluorophenyl)methyl-d)amino)quinolin-4-yl)pivalamide | 33 | ES/MS 519.3 (M + H+) |
| 34 | 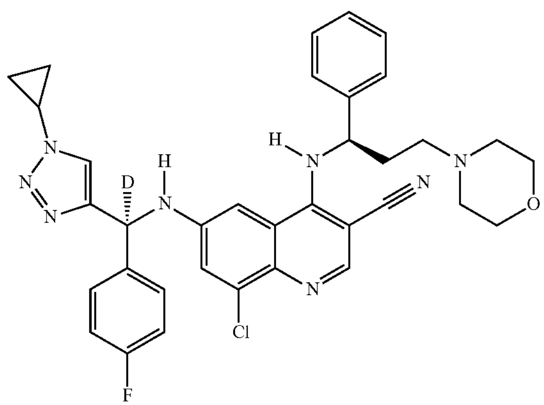 [SMILES: [2H][C@](Nc1cc(Cl)c2ncc(C#N)c(N[C@H](CCN3CCOCC3)c3ccccc3)c2c1)(c1ccc(F)cc1)c1cn(C2CC2)nn1] | 8-chloro-6-(((1-cyclopropyl-1H-1,2,3-triazol-4-yl)(4-fluorophenyl)methyl-d)amino)-4-(((R)-3-morpholino-1-phenylpropyl)amino)quinoline-3-carbonitrile | 34 | ES/MS 638.0 (M + H+) |

TABLE 1-continued

| Compd | Structure | Name | Example/Procedure | ES/MS m/z |
|---|---|---|---|---|
| 35 | 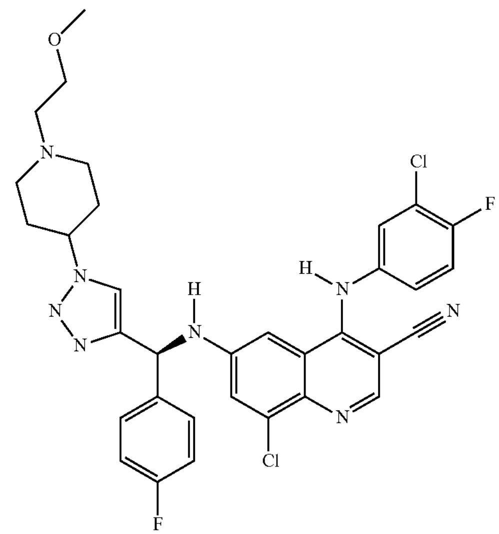 [SMILES: COCCN1CCC(N2C=C([C@@H](Nc3cc(Cl)c4ncc(C#N)c(Nc5ccc(F)c(Cl)c5)c4c3)c3ccc(F)cc3)NN2)CC1] | (S)-8-chloro-4-((3-chloro-4-fluorophenyl)amino)-6-(((4-fluorophenyl)(1-(1-(2-methoxyethyl)piperidin-4-yl)-1H-1,2,3-triazol-4-yl)methyl)amino)quinoline-3-carbonitrile | 35 | ES/MS 663.3 (M + H+) |
| 36 | 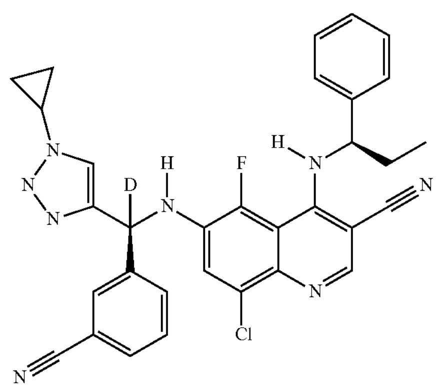 [SMILES: [2H][C@](Nc1cc(Cl)c2ncc(C#N)c(N[C@H](CC)c3ccccc3)c2c1F)(C1=CN(C2CC2)NN1)c1cccc(C#N)c1] | 8-chloro-6-(((3-cyanophenyl)(1-cyclopropyl-1H-1,2,3-triazol-4-yl)methyl-d)amino)-5-fluoro-4-(((R)-1-phenylpropyl)amino)quinoline-3-carbonitrile | 36 | ES/MS 578.0 (M + H+) |

TABLE 1-continued
| Compd | Structure | Name | Example/Procedure | ES/MS m/z |
|---|---|---|---|---|
| 37 | 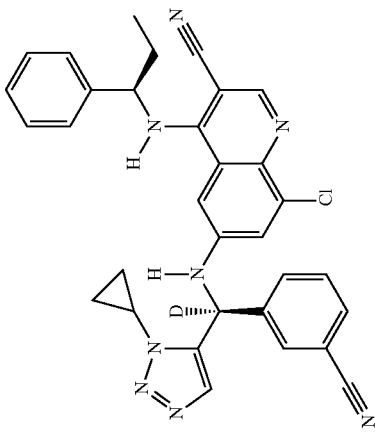 | 8-chloro-6-(((S)-(3-cyanophenyl)((1-cyclopropyl-1H-1,2,3-triazol-5-yl)methyl-d)amino)-4-(((R)-1-phenylpropyl)amino)quinoline-3-carbonitrile | 37 | ES/MS 560.1 (M + H+) |
| 38 | 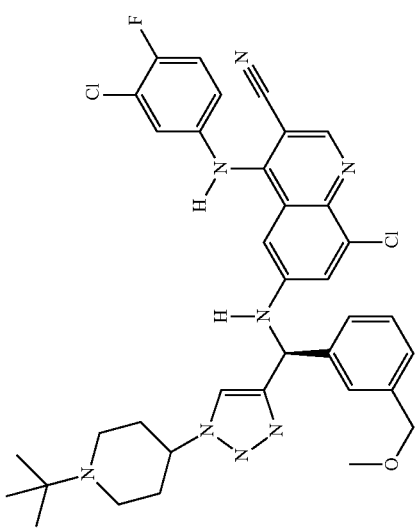 | (S)-6-((((1-(1-(tert-butyl)piperidin-4-yl)-1H-1,2,3-triazol-4-yl)(3-(methoxymethyl)phenyl)methyl)amino)-8-chloro-4-((3-chloro-4-fluorophenyl)amino)quinoline-3-carbonitrile | 38 | ES/MS 687.2 (M + H+) |

TABLE 1-continued

| Compd | Structure | Name | Example/Procedure | ES/MS m/z |
|---|---|---|---|---|
| 39 | 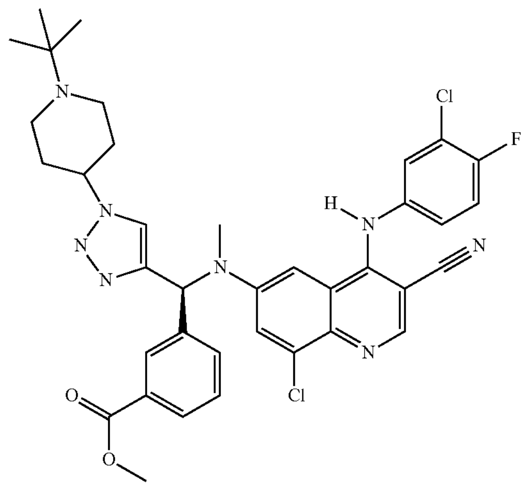 [SMILES: COC(=O)c1cccc([C@@H](C2=CN(C3CCN(C(C)(C)C)CC3)NN2)N(C)c2cc(Cl)c3ncc(C#N)c(Nc4ccc(F)c(Cl)c4)c3c2)c1] | methyl (S)-3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)(methyl)amino)methyl)benzoate | 39 | ES/MS 715.1 (M + H+) |
| 40 | 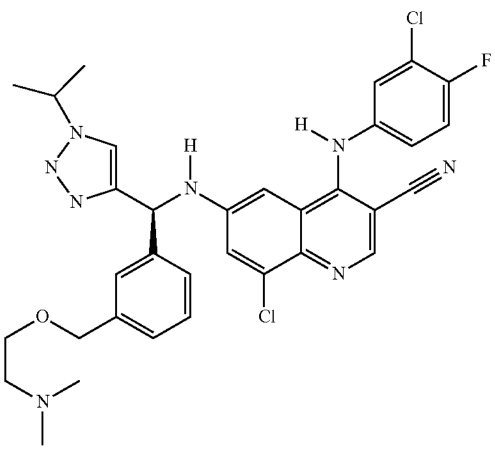 [SMILES: CC(C)N1C=C([C@@H](Nc2cc(Cl)c3ncc(C#N)c(Nc4ccc(F)c(Cl)c4)c3c2)c2cccc(COCCN(C)C)c2)NN1] | (S)-8-chloro-4-((3-chloro-4-fluorophenyl)amino)-6-(((3-((2-(dimethylamino)ethoxy)methyl)phenyl)(1-isopropyl-1H-1,2,3-triazol-4-yl)methyl)amino)quinoline-3-carbonitrile | 40 | ES/MS 647.0 (M + H+) |

TABLE 1-continued

| Compd | Structure | Name | Example/Procedure | ES/MS m/z |
|---|---|---|---|---|
| 41 | 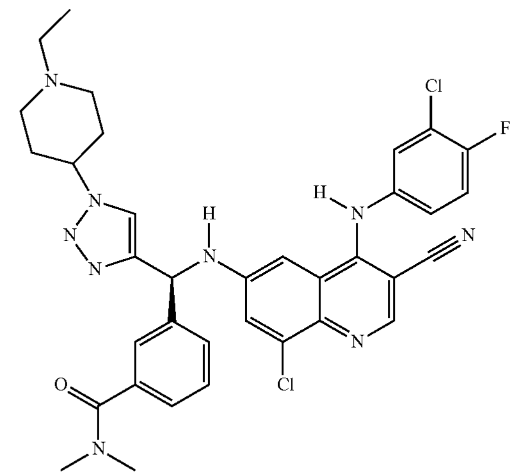 [SMILES: CCN1CCC(N2C=C([C@@H](Nc3cc(Cl)c4ncc(C#N)c(Nc5ccc(F)c(Cl)c5)c4c3)c3cccc(C(=O)N(C)C)c3)NN2)CC1] | (S)-3-(((8-chloro-4-((3-chloro-4-fluorophenyl)amino)-3-cyanoquinolin-6-yl)amino)(1-(1-ethylpiperidin-4-yl)-1H-1,2,3-triazol-4-yl)methyl)-N,N-dimethylbenzamide | 41 | ES/MS 685.9 (M + H+) |
| 42 | 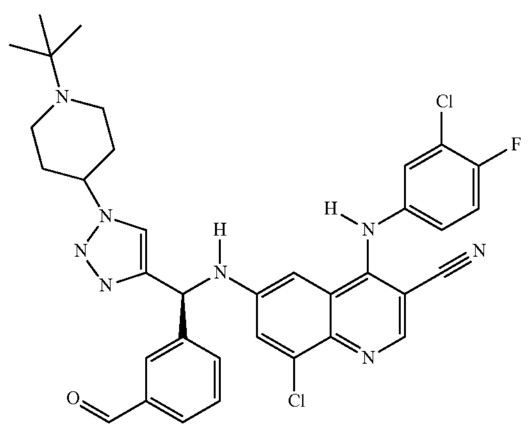 [SMILES: CC(C)(C)N1CCC(N2C=C([C@@H](Nc3cc(Cl)c4ncc(C#N)c(Nc5ccc(F)c(Cl)c5)c4c3)c3cccc(C=O)c3)NN2)CC1] | (S)-6-((((1-(1-(tert-butyl)piperidin-4-yl)-1H-1,2,3-triazol-4-yl)(3-formylphenyl)methyl)amino)-8-chloro-4-((3-chloro-4-fluorophenyl)amino)quinoline-3-carbonitrile | 42 | ES/MS 671.4 (M + H+) |

TABLE 1-continued

| Compd | Structure | Name | Example/Procedure | ES/MS m/z |
|---|---|---|---|---|
| 43 | 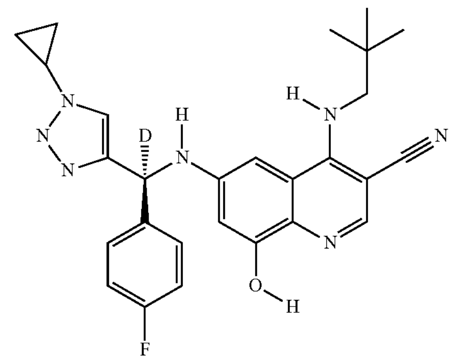 | (S)-6-((((1-cyclopropyl-1H-1,2,3-triazol-4-yl)(4-fluorophenyl)methyl-d)amino)-8-hydroxy-4-(neopentylamino)quinoline-3-carbonitrile | 43 | |
| 44 | 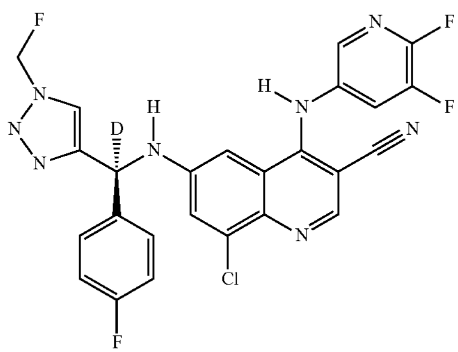 | (S)-8-chloro-4-((5,6-difluoropyridin-3-yl)amino)-6-(((1-(fluoromethyl)-1H-1,2,3-triazol-4-yl)(4-fluorophenyl)methyl-d)amino)quinoline-3-carbonitrile | 44 | ES/MS 540.1 (M + H+). |
| 45 | 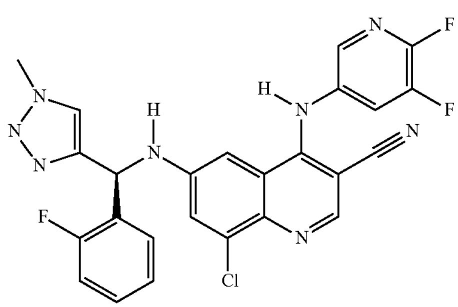 [SMILES: CN1C=C([C@@H](Nc2cc(Cl)c3ncc(C#N)c(Nc4cnc(F)c(F)c4)c3c2)c2ccccc2F)NN1] | (S)-8-chloro-4-((5,6-difluoropyridin-3-yl)amino)-6-(((2-fluorophenyl)(1-methyl-1H-1,2,3-triazol-4-yl)methyl)amino)quinoline-3-carbonitrile | 45 | ES/MS 521.1 (M + H+) |

TABLE 1-continued

| Compd | Structure | Name | Example/Procedure | ES/MS m/z |
|---|---|---|---|---|
| 46 | 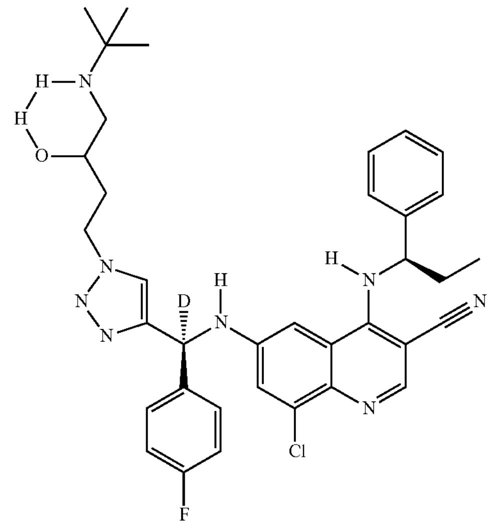 | 6-(((1S)-(1-(4-(tert-butylamino)-3-hydroxybutyl)-1H-1,2,3-triazol-4-yl)(4-fluorophenyl)methyl-d)amino)-8-chloro-4-(((R)-1-phenylpropyl)amino)quinoline-3-carbonitrile | 46 | ES/MS 656.3 (M + H+). |
| 47 | 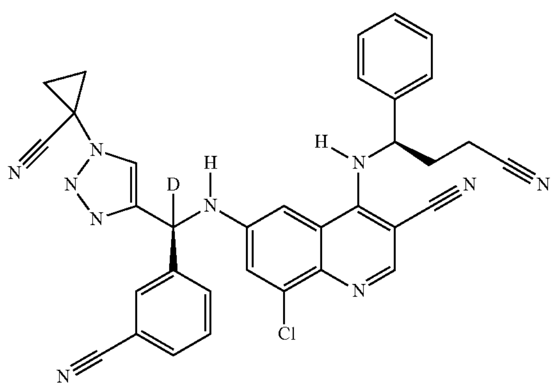 [SMILES: [2H][C@](Nc1cc(Cl)c2ncc(C#N)c(N[C@H](CCC#N)c3ccccc3)c2c1)(C1=CN(C2(C#N)CC2)NN1)c1cccc(C#N)c1] | 8-chloro-4-(((R)-3-cyano-1-phenylpropyl)amino)-6-(((1-(1-cyanocyclopropyl)-1H-1,2,3-triazol-4-yl)(3-cyanophenyl)methyl-d)amino)quinoline-3-carbonitrile | 4 | ES/MS 610.2 (M + H+). |

TABLE 1-continued

| Compd | Structure | Name | Example/Procedure | ES/MS m/z |
|---|---|---|---|---|
| 48 | 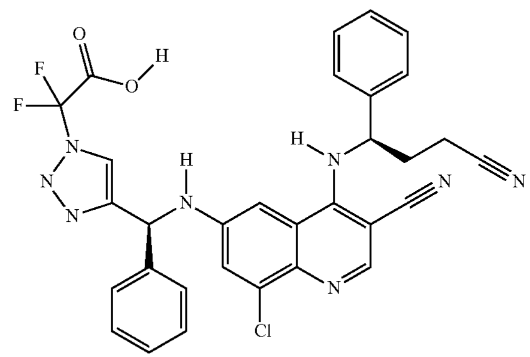 [SMILES: N#CCC[C@@H](Nc1c(C#N)cnc2c(Cl)cc(N[C@H](C3=CN(C(F)(F)C(=O)O)NN3)c3ccccc3)cc12)c1ccccc1] | 2-(4-(((S)-((8-chloro-3-cyano-4-(((R)-3-cyano-1-phenylpropyl)amino)quinolin-6-yl)amino)(phenyl)methyl)-1H-1,2,3-triazol-1-yl)-2,2-difluoroacetic acid | 2 | |
| 49 | 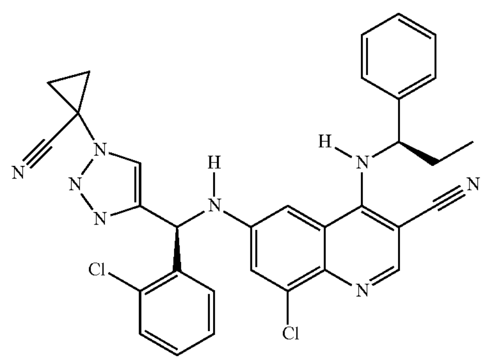 [SMILES: CC[C@@H](Nc1c(C#N)cnc2c(Cl)cc(N[C@H](C3=CN(C4(C#N)CC4)NN3)c3ccccc3Cl)cc12)c1ccccc1] | 8-chloro-6-(((S)-(2-chlorophenyl)(1-(1-cyanocyclopropyl)-1H-1,2,3-triazol-4-yl)methyl)amino)-4-(((R)-1-phenylpropyl)amino)quinoline-3-carbonitrile | 4 | ES/MS 593.1 (M + H+) |
| 50 | 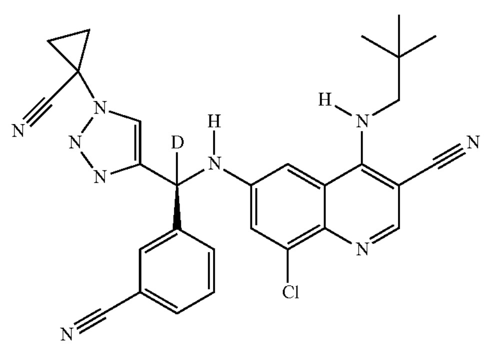 [SMILES: [2H][C@](Nc1cc(Cl)c2ncc(C#N)c(NCC(C)(C)C)c2c1)(C1=CN(C2(C#N)CC2)NN1)c1cccc(C#N)c1] | 8-chloro-6-(((1-(1-cyanocyclopropyl)-1H-1,2,3-triazol-4-yl)(3-cyanophenyl)methyl-d)amino)-4-(neopentylamino)quinoline-3-carbonitrile | 4 | ES/MS 537.2 (M + H+). |

TABLE 1-continued

| Compd | Structure | Name | Example/Procedure | ES/MS m/z |
|---|---|---|---|---|
| 51 | 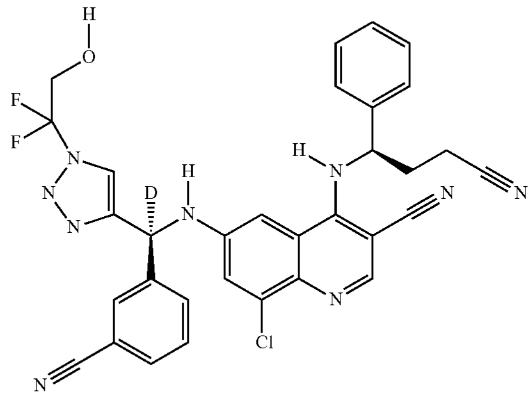 | 8-chloro-4-(((R)-3-cyano-1-phenylpropyl)amino)-6-(((S)-(3-cyanophenyl)(1-(1,1-difluoro-2-hydroxyethyl)-1H-1,2,3-trazol-4-yl)methyl-d)amino)quinoline-3-carbonitrile | 26 | 625.2 |
| 52 | 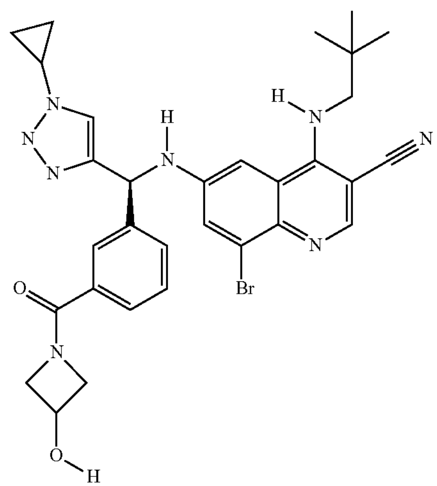 | (S)-8-bromo-6-(((1-cyclopropyl-1H-1,2,3-triazol-4-yl)(3-(3-hydroxyazetidine-1-carbonyl)phenyl)methyl)amino)-4-(neopentylamino)quinoline-3-carbonitrile | 20 | ES/MS 692.2 (M + H+) |

TABLE 1-continued

| Compd | Structure | Name | Example/Procedure | ES/MS m/z |
|---|---|---|---|---|
| 53 | 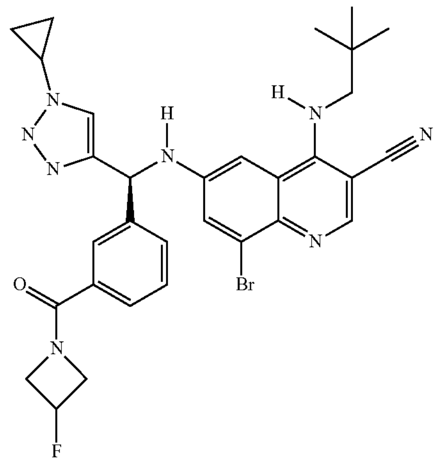 [SMILES: CC(C)(C)CNc1c(C#N)cnc2c(Br)cc(N[C@H](C3=CN(C4CC4)NN3)c3cccc(C(=O)N4CC(F)C4)c3)cc12] | (S)-8-bromo-6-((((1-cyclopropyl-1H-1,2,3-triazol-4-yl)(3-(3-fluoroazetidine-1-carbonyl)phenyl)methyl)amino)-4-(neopentylamino)quinoline-3-carbonitrile | 20 | ES/MS 631.2 (M + H+) |
| 54 | 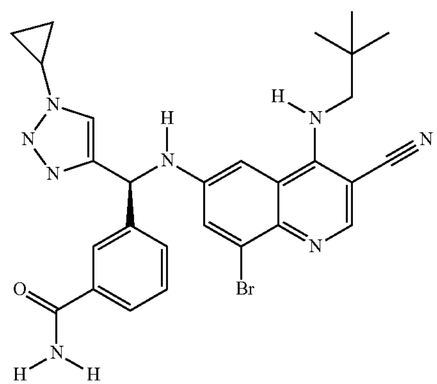 [SMILES: CC(C)(C)CNc1c(C#N)cnc2c(Br)cc(N[C@H](C3=CN(C4CC4)NN3)c3cccc(C(N)=O)c3)cc12] | (S)-3-(((8-bromo-3-cyano-4-(neopentylamino)quinolin-6-yl)amino)(1-cyclopropyl-1H-1,2,3-triazol-4-yl)methyl)benzamide | 20 | ES/MS 573.1 (M + H+) |

TABLE 1-continued

| Compd | Structure | Name | Example/Procedure | ES/MS m/z |
|---|---|---|---|---|
| 55 | 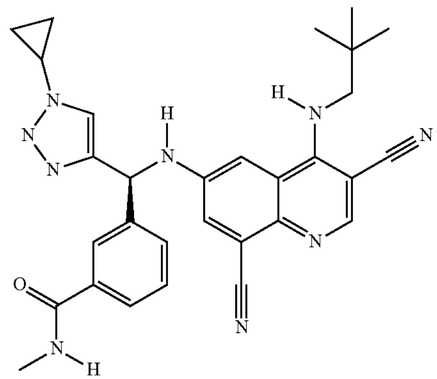 [SMILES: CNC(=O)c1cccc([C@H](Nc2cc(C#N)c3ncc(C#N)c(NCC(C)(C)C)c3c2)C2=CN(C3CC3)NN2)c1] | (S)-3-((1-cyclopropyl-1H-1,2,3-triazol-4-yl)(3,8-dicyano-4-(neopentylamino)quinolin-6-yl)amino)methyl)-N-methylbenzamide | 20 | ES/MS 534.1 (M + H+) |
| 56 | 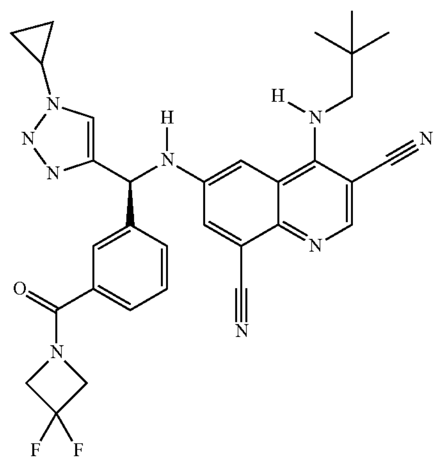 [SMILES: CC(C)(C)CNc1c(C#N)cnc2c(C#N)cc(N[C@H](C3=CN(C4CC4)NN3)c3cccc(C(=O)N4CC(F)(F)C4)c3)cc12] | (S)-6-(((1-cyclopropyl-1H-1,2,3-triazol-4-yl)(3-(3,3-difluoroazetidine-1-carbonyl)phenyl)methyl)amino)-4-(neopentylamino)quinoline-3,8-dicarbonitrile | 20 | ES/MS 596.1 (M + H+) |

TABLE 1-continued

| Compd | Structure | Name | Example/Procedure | ES/MS m/z |
|---|---|---|---|---|
| 57 | 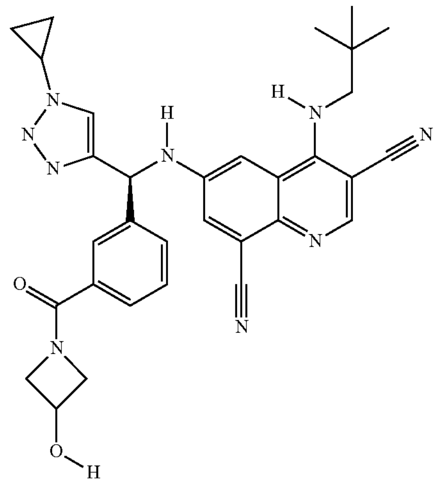 [SMILES: CC(C)(C)CNc1c(C#N)cnc2c(C#N)cc(N[C@H](C3=CN(C4CC4)NN3)c3cccc(C(=O)N4CC(O)C4)c3)cc12] | (S)-6-(((1-cyclopropyl-1H-1,2,3-triazol-4-yl)(3-(3-hydroxyazetidine-1-carbonyl)phenyl)methyl)amino)-4-(neopentylamino)quinoline-3,8-dicarbonitrile | 20 | ES/MS 576.0 (M + H+) |
| 58 | 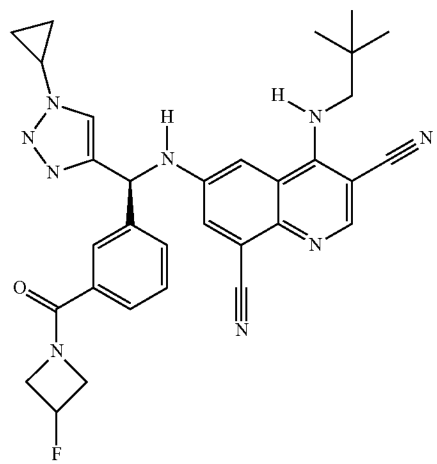 [SMILES: CC(C)(C)CNc1c(C#N)cnc2c(C#N)cc(N[C@H](C3=CN(C4CC4)NN3)c3cccc(C(=O)N4CC(F)C4)c3)cc12] | (S)-6-(((1-cyclopropyl-1H-1,2,3-triazol-4-yl)(3-(3-fluoroazetidine-1-carbonyl)phenyl)methyl)amino)-4-(neopentylamino)quinoline-3,8-dicarbonitrile | 20 | ES/MS 578.1 (M + H+) |

TABLE 1-continued

| Compd | Structure | Name | Example/Procedure | ES/MS m/z |
|---|---|---|---|---|
| 59 | 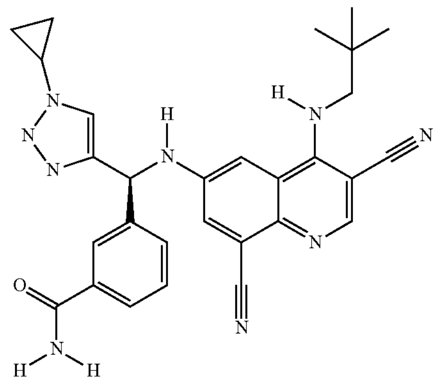 [SMILES: CC(C)(C)CNc1c(C#N)cnc2c(C#N)cc(N[C@H](C3=CN(C4CC4)NN3)c3cccc(C(N)=O)c3)cc12] | (S)-3-((1-cyclopropyl-1H-1,2,3-triazol-4-yl)(3,8-dicyano-4-(neopentylamino)quinolin-6-yl)amino)methyl)benzamide | 20 | ES/MS 520.1 (M + H+) |
| 60 | 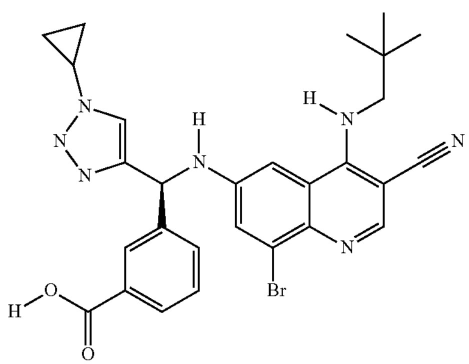 [SMILES: CC(C)(C)CNc1c(C#N)cnc2c(Br)cc(N[C@H](C3=CN(C4CC4)NN3)c3cccc(C(=O)O)c3)cc12] | (S)-3-(((8-bromo-3-cyano-4-(neopentylamino)quinolin-6-yl)amino)(1-cyclopropyl-1H-1,2,3-triazol-4-yl)methyl)benzoic acid | 19 | ES/MS 574.6 (M + H+) |

TABLE 1-continued

| Compd | Structure | Name | Example/Procedure | ES/MS m/z |
|---|---|---|---|---|
| 61 | 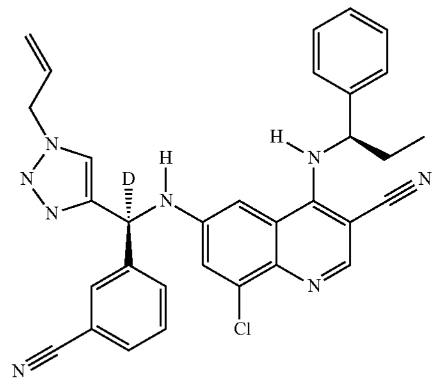 | 6-(((S)-(1-allyl-1H-1,2,3-triazol-4-yl)(3-cyanophenyl)methyl-d)amino)-8-chloro-4-(((R)-1-phenylpropyl)amino)quinoline-3-carbonitrile | 1 | ES/MS 560.2 (M + H+) |
| 62 | 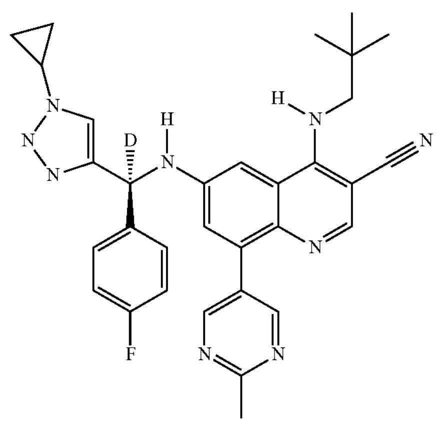 | (S)-6-((((1-cyclopropyl-1H-1,2,3-triazol-4-yl)(4-fluorophenyl)methyl-d)amino)-8-(2-methylpyrimidin-5-yl)-4-(neopentylamino)quinoline-3-carbonitrile | 12 | ES/MS 563.3 (M + H+) |

TABLE 1-continued

| Compd | Structure | Name | Example/Procedure | ES/MS m/z |
|---|---|---|---|---|
| 63 | 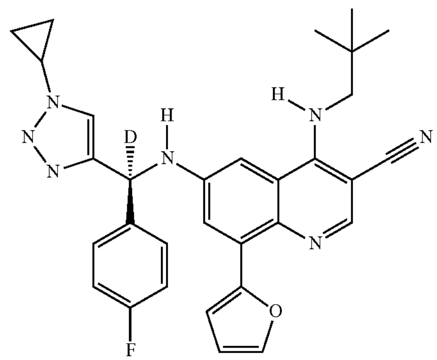 | (S)-6-(((1-cyclopropyl-1H-1,2,3-triazol-4-yl)(4-fluorophenyl)methyl-d)amino)-4-(neopentylamino)-8-(oxazol-5-yl)quinoline-3-carbonitrile | 12 | ES/MS 538.3 (M + H)+ |
| 64 | 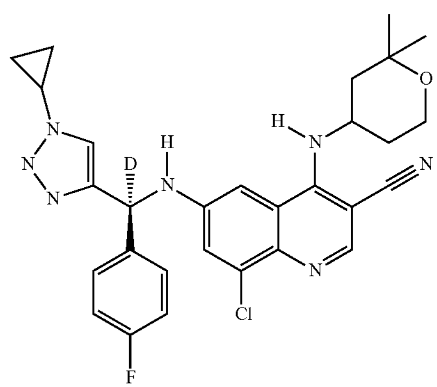 | 8-chloro-6-(((S)-(1-cyclopropyl-1H-1,2,3-triazol-4-yl)(4-fluorophenyl)methyl-d)amino)-4-((2,2-dimethyltetrahydro-2H-pyran-4-yl)amino)quinoline-3-carbonitrile | 3 | ES/MS 547.2 (M + H)+ |

TABLE 1-continued

| Compd | Structure | Name | Example/Procedure | ES/MS m/z |
|---|---|---|---|---|
| 65 | 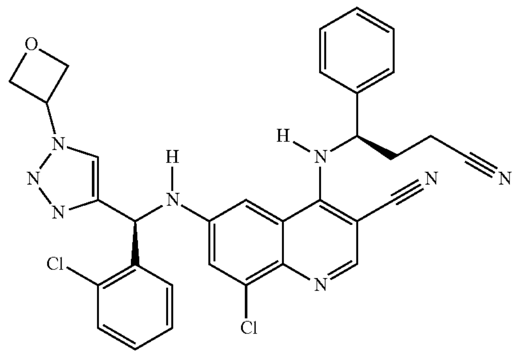 [SMILES: N#CCC[C@@H](Nc1c(C#N)cnc2c(Cl)cc(N[C@H](C3=CN(C4COC4)NN3)c3ccccc3Cl)cc12)c1ccccc1] | 8-chloro-6-(((S)-(2-chlorophenyl)(1-(oxetan-3-yl)-1H-1,2,3-triazol-4-yl)methyl)amino)-4-(((R)-3-cyano-1-phenylpropyl)amino)quinoline-3-carbonitrile | 3 | ES/MS 609.1 (M + H+) |
| 66 | 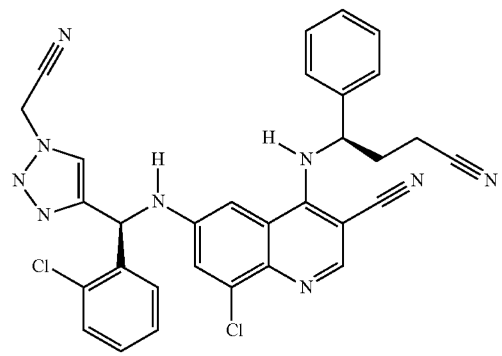 | 8-chloro-6-(((S)-(2-chlorophenyl)(1-(cyanomethyl)-1H-1,2,3-triazol-4-yl)methyl)amino)-4-(((R)-3-cyano-1-phenylpropyl)amino)quinoline-3-carbonitrile | 3 | ES/MS 592.1 (M + H+) |

TABLE 1-continued

| Compd | Structure | Name | Example/Procedure | ES/MS m/z |
|---|---|---|---|---|
| 67 | 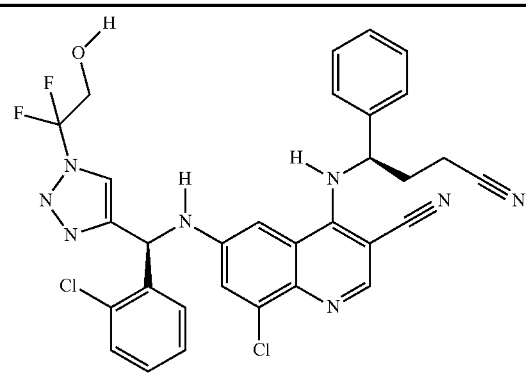 | 8-chloro-6-(((S)-(2-chlorophenyl)(1-(1,1-difluoro-2-hydroxyethyl)-1H-1,2,3-triazol-4-yl)methyl)amino)-4-(((R)-3-cyano-1-phenylpropyl)amino)quinoline-3-carbonitrile | 26 | ES/MS 633.1 (M + H+) |
| 68 | 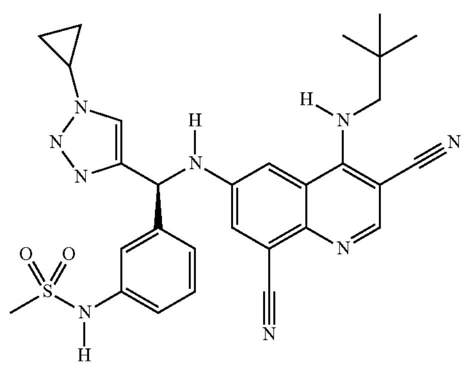 [SMILES: CC(C)(C)CNc1c(C#N)cnc2c(C#N)cc(N[C@H](C3=CN(C4CC4)NN3)c3cccc(NS(C)(=O)=O)c3)cc12] | (S)-N-(3-((1-cyclopropyl-1H-1,2,3-triazol-4-yl)(3,8-dicyano-4-(neopentylamino)quinolin-6-yl)amino)methyl)phenyl)-methanesulfonamide | 25 | ES/MS 570.1 (M + H+) |

TABLE 1-continued

| Compd | Structure | Name | Example/Procedure | ES/MS m/z |
|---|---|---|---|---|
| 69 | 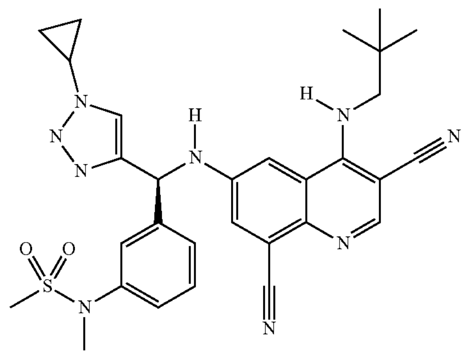 [SMILES: CN(c1cccc([C@H](Nc2cc(C#N)c3ncc(C#N)c(NCC(C)(C)C)c3c2)C2=CN(C3CC3)NN2)c1)S(C)(=O)=O] | (S)-N-(3-((1-cyclopropyl-1H-1,2,3-triazol-4-yl)(3,8-dicyano-4-(neopentylamino)quinolin-6-yl)aminolmethyl)phenyl)-N-methylmethanesulfonamide | 9a | ES/MS 584.1 (M + H+) |
| 70 | 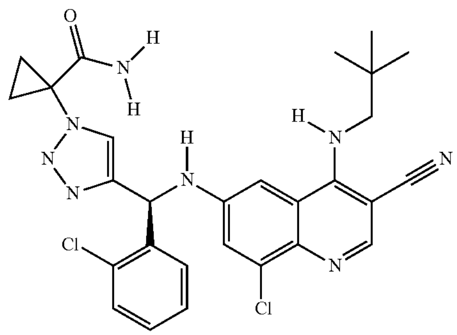 [SMILES: CC(C)(C)CNc1c(C#N)cnc2c(Cl)cc(N[C@H](C3=CN(C4(C(N)=O)CC4)NN3)c3ccccc3Cl)cc12] | (S)-1-(4-(((8-chloro-3-cyano-4-(neopentylamino)quinolin-6-yl)amino)(2-chlorophenyl)methyl)-1H-1,2,3-triazol-1-yl)cyclopropane-1-carboxamide | 4 | ES/MS 564.2 (M + H+) |
| 71 | 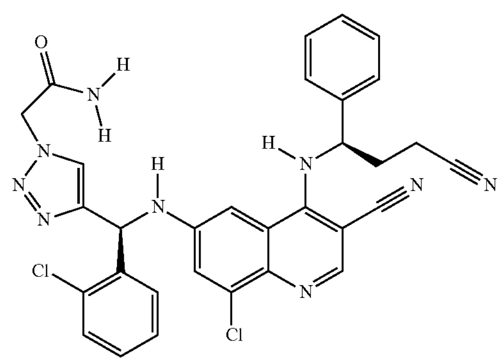 [SMILES: N#CCC[C@@H](Nc1c(C#N)cnc2c(Cl)cc(N[C@H](c3cn(CC(N)=O)nn3)c3ccccc3Cl)cc12)c1ccccc1] | 2-(4-((S)-((8-chloro-3-cyano-4-(((R)-3-cyano-1-phenylpropyl)amino)quinolin-6-yl)amino)(2-chlorophenyl)methyl)-1H-1,2,3-triazol-1-yl)acetamide | 4 | ES/MS 610.2 (M + H+) |

TABLE 1-continued

| Compd | Structure | Name | Example/Procedure | ES/MS m/z |
|---|---|---|---|---|
| 72 | 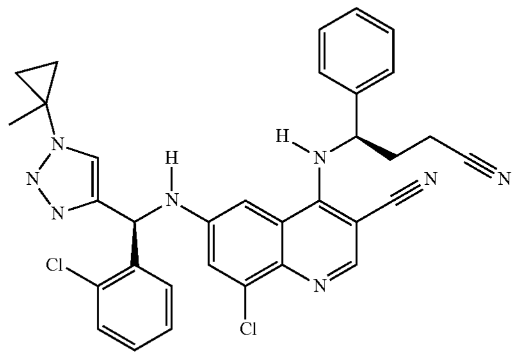 [SMILES: CC1(N2C=C([C@@H](Nc3cc(Cl)c4ncc(C#N)c(N[C@H](CCC#N)c5ccccc5)c4c3)c3ccccc3Cl)NN2)CC1] | 8-chloro-6-(((S)-(2-chlorophenyl)(1-(1-methylcyclopropyl)-1H-1,2,3-triazol-4-yl)methyl)amino)-4-(((R)-3-cyano-1-phenylpropyl)amino)quinoline-3-carbonitrile | 4 | ES/MS 607.2 (M + H+) |
| 73 | 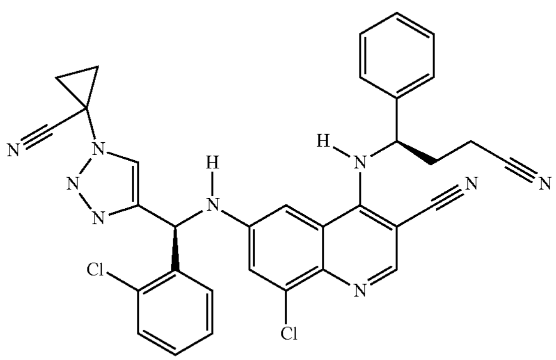 [SMILES: N#CCC[C@@H](Nc1c(C#N)cnc2c(Cl)cc(N[C@H](C3=CN(C4(C#N)CC4)NN3)c3ccccc3Cl)cc12)c1ccccc1] | 8-chloro-6-(((S)-(2-chlorophenyl)(1-(1-cyanocyclopropyl)-1H-1,2,3-triazol-4-yl)methyl)amino)-4-(((R)-3-cyano-1-phenylpropyl)amino)quinoline-3-carbonitrile | 4 | ES/MS 618.1 (M + H+) |

TABLE 1-continued
| Compd | Structure | Name | Example/Procedure | ES/MS m/z |
|---|---|---|---|---|
| 74 | 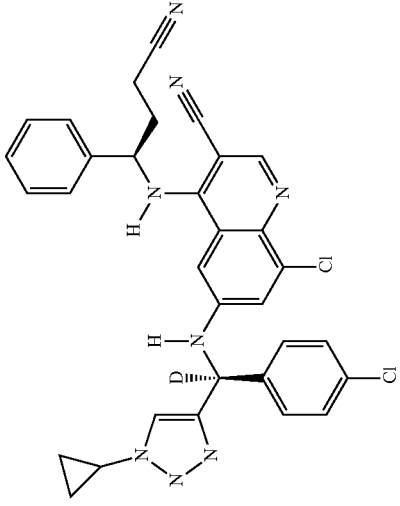 | 8-chloro-6-(((S)-(4-chlorophenyl)(1-cyclopropyl-1H-1,2,3-triazol-4-yl)methyl-d)amino)-4-(((R)-3-cyano-1-phenylpropyl)amino)quinoline-3-carbonitrile | 3 | ES/MS 594.1 (M + H+) |
| 75 | 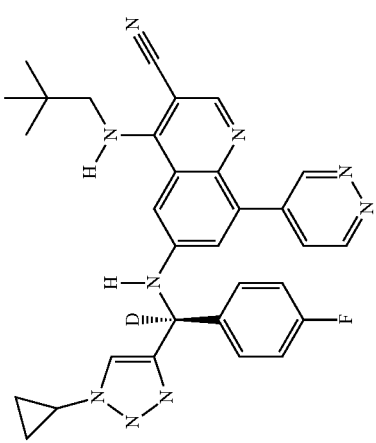 | (S)-6-(((1-cyclopropyl-1H-1,2,3-triazol-4-yl)(4-fluorophenyl)methyl-d)amino)-4-(neopentyl)amino)-8-(pyridazin-4-yl)quinoline-3-carbonitrile | 12 | ES/MS 549.5 (M + H+) |

TABLE 1-continued

| Compd | Structure | Name | Example/Procedure | ES/MS m/z |
|---|---|---|---|---|
| 76 | 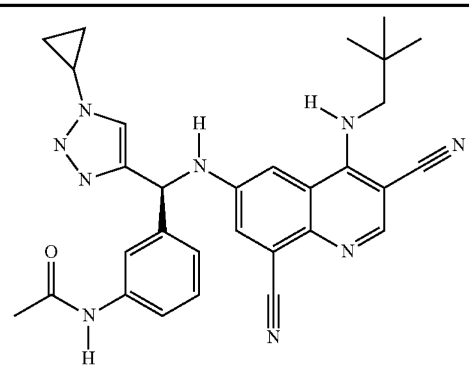 | (S)-N-(3-((1-cyclopropyl-1H-1,2,3-triazol-4-yl)(3,8-dicyano-4-(neopentylamino)quinolin-6-yl)amino)methyl)phenyl)acetamide | 9a | ES/MS 534.1 (M + H+) |
| 77 | 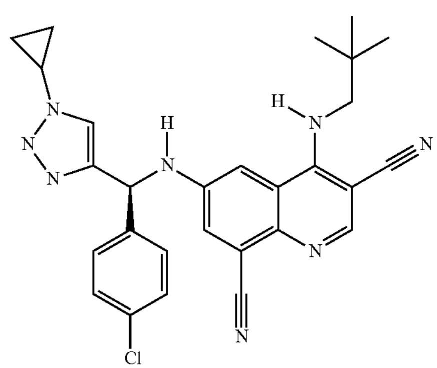 [SMILES: CC(C)(C)CNc1c(C#N)cnc2c(C#N)cc(N[C@H](C3=CN(C4CC4)NN3)c3ccc(Cl)cc3)cc12] | (S)-6-(((4-chlorophenyl)(1-cyclopropyl-1H-1,2,3-triazol-4-yl)methyl)amino)-4-(neopentylamino)quinoline-3,8-dicarbonitrile | 9a | ES/MS 512.2 (M + H+) |

TABLE 1-continued

| Compd | Structure | Name | Example/Procedure | ES/MS m/z |
|---|---|---|---|---|
| 78 | 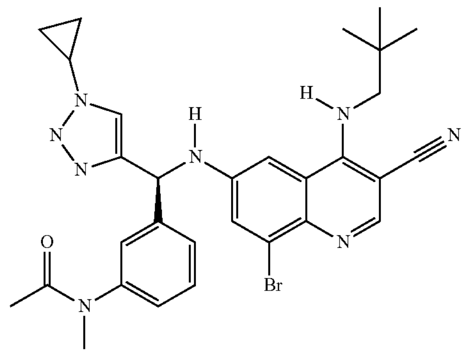 [SMILES: CC(=O)N(C)c1cccc([C@H](Nc2cc(Br)c3ncc(C#N)c(NCC(C)(C)C)c3c2)C2=CN(C3CC3)NN2)c1] | (S)-N-(3-(((8-bromo-3-cyano-4-(neopentylamino)quinolin-6-yl)amino)(1-cyclopropyl-1H-1,2,3-triazol-4-yl)methyl)phenyl)-N-methylacetamide | 3 | ES/MS 601.1 (M + H+) |
| 79 | 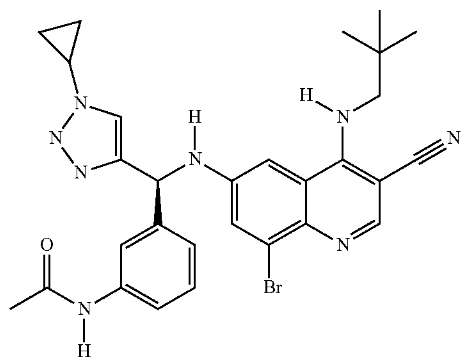 [SMILES: CC(=O)Nc1cccc([C@H](Nc2cc(Br)c3ncc(C#N)c(NCC(C)(C)C)c3c2)C2=CN(C3CC3)NN2)c1] | (S)-N-(3-(((8-bromo-3-cyano-4-(neopentylamino)quinolin-6-yl)amino)(1-cyclopropyl-1H-1,2,3-triazol-4-yl)methyl)phenyl)acetamide | 3 | ES/MS 587.9 (M + H+) |
| 80 | 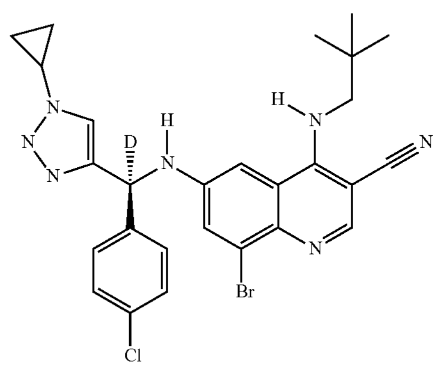 | (S)-8-bromo-6-(((4-chlorophenyl)(1-cyclopropyl-1H-1,2,3-triazol-4-yl)methyl-d)amino)-4-(neopentylamino)quinoline-3-carbonitrile | 3 | ES/MS 565.3 (M + H+) |

TABLE 1-continued

| Compd | Structure | Name | Example/Procedure | ES/MS m/z |
|---|---|---|---|---|
| 81 | 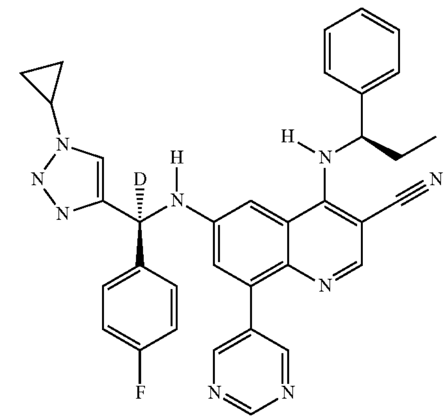 | 6-(((S)-(1-cyclopropyl-1H-1,2,3-triazol-4-yl)(4-fluorophenyl)methyl)amino)-4-(((R)-1-phenylpropyl)amino)-8-(pyrimidin-5-yl)quinoline-3-carbonitrile | 12 | ES/MS 597.3 (M + H+) |
| 82 | 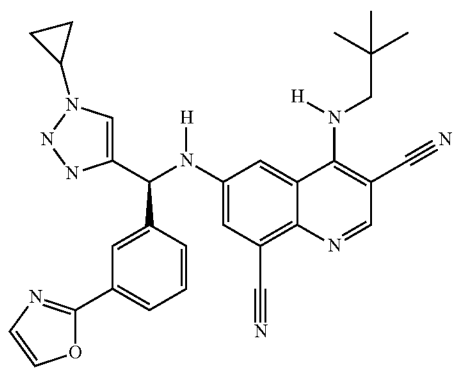 [SMILES: CC(C)(C)CNc1c(C#N)cnc2c(C#N)cc(N[C@H](C3=CN(C4CC4)NN3)c3cccc(-c4ncco4)c3)cc12] | (S)-6-(((1-cyclopropyl-1H-1,2,3-triazol-4-yl)(3-(oxazol-2-yl)phenyl)methyl)amino)-4-(neopentylamino)quinoline-3,8-dicarbonitrile | 9a | ES/MS 544.1 (M + H+) |

TABLE 1-continued

| Compd | Structure | Name | Example/Procedure | ES/MS m/z |
|---|---|---|---|---|
| 83 | 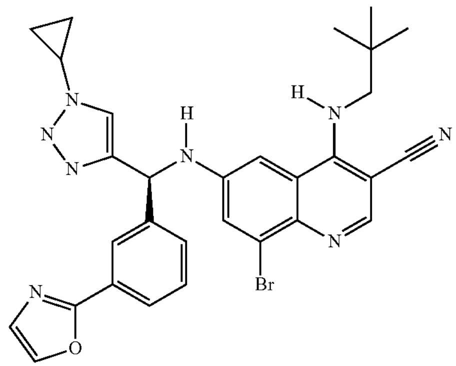 [SMILES: CC(C)(C)CNc1c(C#N)cnc2c(Br)cc(N[C@H](C3=CN(C4CC4)NN3)c3cccc(-c4ncco4)c3)cc12] | (S)-8-bromo-6-(((1-cyclopropyl-1H-1,2,3-triazol-4-yl)(3-(oxazol-2-yl)phenyl)methyl)amino)-4-(neopentylamino)quinoline-3-carbonitrile | 3 | ES/MS 597.2 (M + H+) |
| 84 | 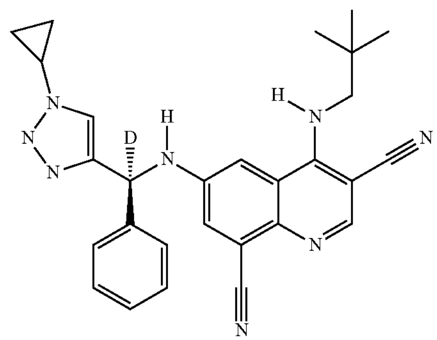 | (S)-6-(((1-cyclopropyl-1H-1,2,3-triazol-4-yl)(phenyl)methyl-d)amino)-4-(neopentylamino)quinoline-3,8-dicarbonitrile | 9a | ES/MS 578.2 (M + H+) |
| 85 | 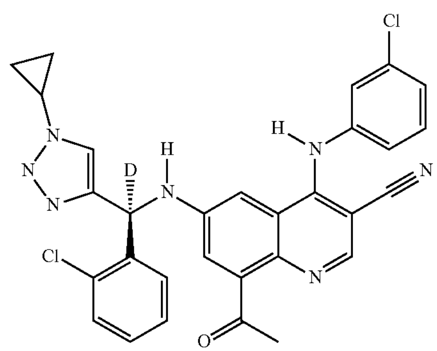 | (S)-8-acetyl-6-(((2-chlorophenyl)(1-cyclopropyl-1H-1,2,3-triazol-4-yl)methyl-d)amino)-4-((3-chlorophenyl)amino)quinoline-3-carbonitrile | 14 | ES/MS 569.2 (M + H+) |

TABLE 1-continued

| Compd | Structure | Name | Example/Procedure | ES/MS m/z |
|---|---|---|---|---|
| 86 | 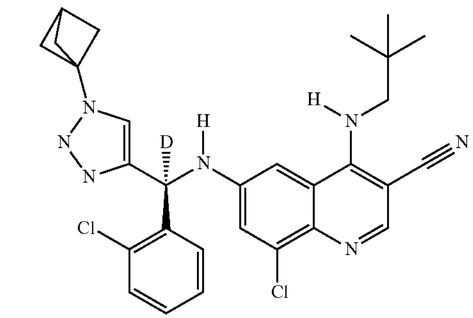 | (S)-6-(((1-(bicyclo[1.1.1]pentan-1-yl)-1H-1,2,3-triazol-4-yl)(2-chlorophenyl)methyl-d)amino)-8-chloro-4-(neopentylamino)quinoline-3-carbonitrile | 4 | ES/MS 547.4 (M + H+) |
| 87 | 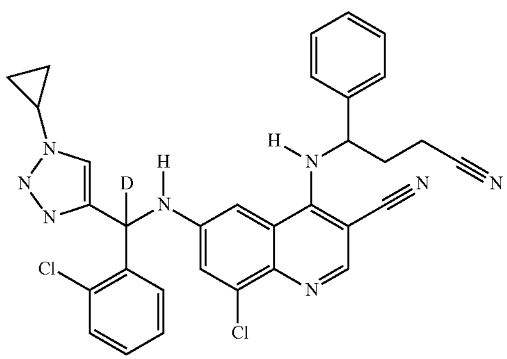 [SMILES: [2H]C(Nc1cc(Cl)c2ncc(C#N)c(NC(CCC#N)c3ccccc3)c2c1)(C1=CN(C2CC2)NN1)c1ccccc1Cl] | 8-chloro-6-(((2-chlorophenyl)(1-cyclopropyl-1H-1,2,3-triazol-4-yl)methyl-d)amino)-4-((3-cyano-1-phenylpropyl)amino)quinoline-3-carbonitrile | 4 | ES/MS 594.1 (M + H+) |
| 88 | 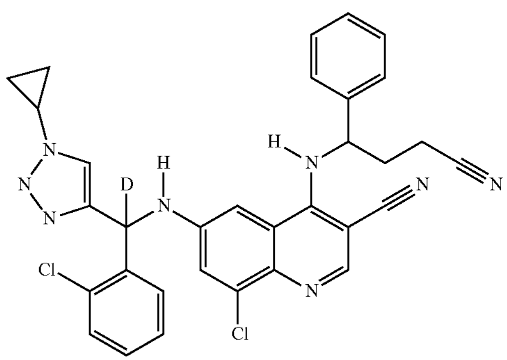 [SMILES: [2H]C(Nc1cc(Cl)c2ncc(C#N)c(NC(CCC#N)c3ccccc3)c2c1)(C1=CN(C2CC2)NN1)c1ccccc1Cl] | 8-chloro-6-(((2-chlorophenyl)(1-cyclopropyl-1H-1,2,3-triazol-4-yl)methyl-d)amino)-4-((3-cyano-1-phenylpropyl)amino)quinoline-3-carbonitrile | 4 | ES/MS 594.1 (M + H+) |

TABLE 1-continued

| Compd | Structure | Name | Example/Procedure | ES/MS m/z |
|---|---|---|---|---|
| 89 | 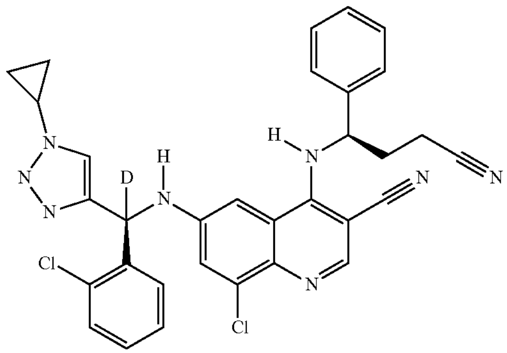 [SMILES: [2H][C@](Nc1cc(Cl)c2ncc(C#N)c(N[C@H](CCC#N)c3ccccc3)c2c1)(C1=CN(C2CC2)NN1)c1ccccc1Cl] | 8-chloro-6-(((2-chlorophenyl)(1-cyclopropyl-1H-1,2,3-triazol-4-yl)methyl-d)amino)-4-(((R)-3-cyano-1-phenylpropyl)amino)quinoline-3-carbonitrile | 4 | ES/MS 594.2 (M + H+) |
| 90 | 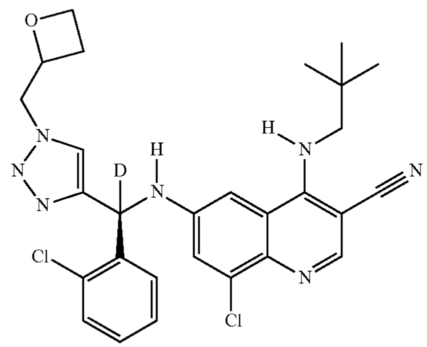 [SMILES: [2H][C@](Nc1cc(Cl)c2ncc(C#N)c(NCC(C)(C)C)c2c1)(C1=CN(CC2CCO2)NN1)c1ccccc1Cl] | 8-chloro-6-(((2-chlorophenyl)(1-(oxetan-2-ylmethyl)-1H-1,2,3-triazol-4-yl)methyl-d)amino)-4-(neopentylamino)quinoline-3-carbonitrile | 4 | ES/MS 551.2 (M + H+) |
| 91 | 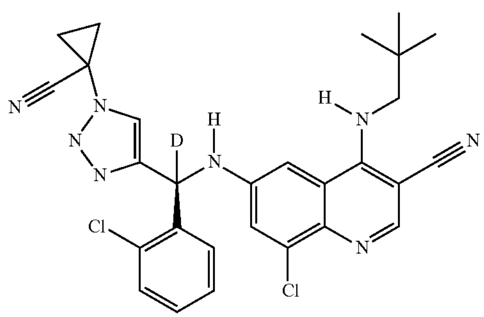 [SMILES: [2H][C@](Nc1cc(Cl)c2ncc(C#N)c(NCC(C)(C)C)c2c1)(C1=CN(C2(C#N)CC2)NN1)c1ccccc1Cl] | 8-chloro-6-(((2-chlorophenyl)(1-(1-cyanocyclopropyl)-1H-1,2,3-triazol-4-yl)methyl-d)amino)-4-(neopentylamino)quinoline-3-carbonitrile | 4 | ES/MS 546.2 (M + H+) |

TABLE 1-continued

| Compd | Structure | Name | Example/Procedure | ES/MS m/z |
|---|---|---|---|---|
| 92 | 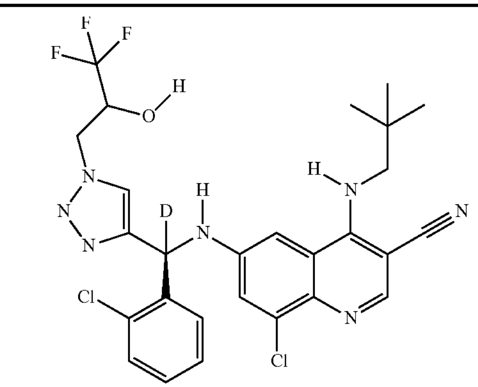 | 8-chloro-6-(((2-chlorophenyl)(1-(3,3,3-trifluoro-2-hydroxypropyl)-1H-1,2,3-triazol-4-yl)methyl-d)amino)-4-(neopentylamino)quinoline-3-carbonitrile | 4 | ES/MS 593.2 (M + H+) |
| 93 | 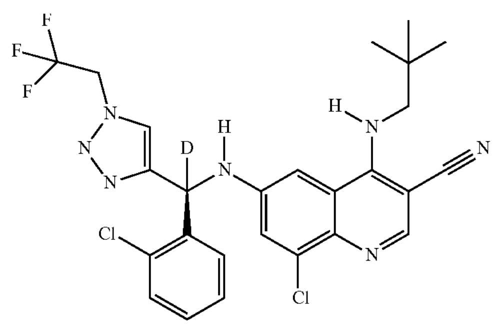 [SMILES: [2H][C@](Nc1cc(Cl)c2ncc(C#N)c(NCC(C)(C)C)c2c1)(C1=CN(CC(F)(F)F)NN1)c1ccccc1Cl] | 8-chloro-6-(((2-chlorophenyl)(1-(2,2,2-trifluoroethyl)-1H-1,2,3-triazol-4-yl)methyl-d)amino)-4-(neopentylamino)quinoline-3-carbonitrile | 4 | ES/MS 563.2 (M + H+) |

TABLE 1-continued
| Compd | Structure | Name | Example/Procedure | ES/MS m/z |
|---|---|---|---|---|
| 94 | 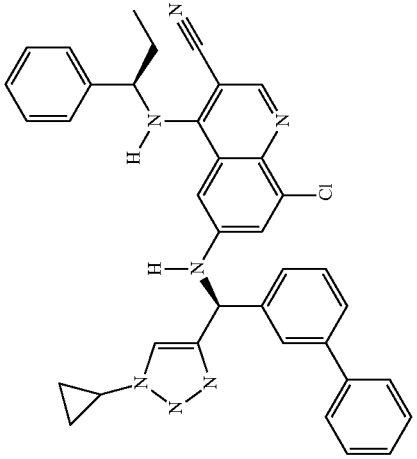 | 6-(((S)-[1,1'-biphenyl]-3-yl(1-cyclopropyl-1H-1,2,3-triazol-4-yl)methyl)amino)-8-chloro-4-(((R)-1-phenylpropyl)amino)quinoline-3-carbonitrile | 2 | ES/MS 610.4 (M + H+) |
| 95 | 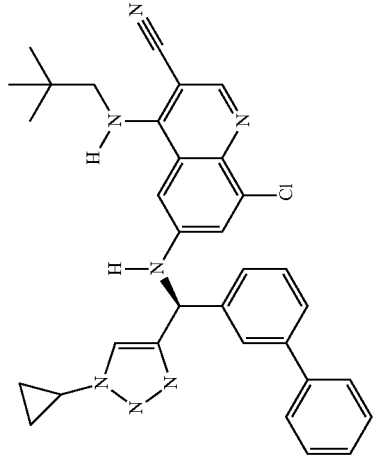 | (S)-6-(([1,1'-biphenyl]-3-yl(1-cyclopropyl-1H-1,2,3-triazol-4-yl)methyl)amino)-8-chloro-4-(neopentylamino)quinoline-3-carbonitrile | 1 | ES/MS 562.4 (M + H+) |

TABLE 1-continued

| Compd | Structure | Name | Example/Procedure | ES/MS m/z |
|---|---|---|---|---|
| 96 | 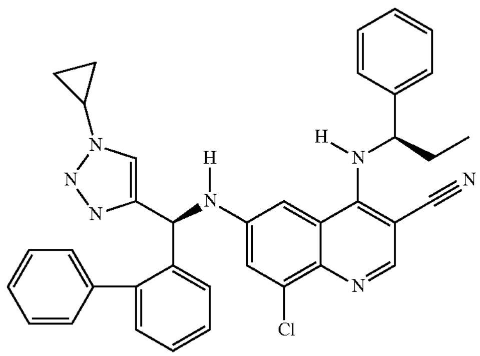 [SMILES: CC[C@@H](Nc1c(C#N)cnc2c(Cl)cc(N[C@H](C3=CN(C4CC4)NN3)c3ccccc3-c3ccccc3)cc12)c1ccccc1] | 6-(((S)-[1,1'-biphenyl]-2-yl(1-cyclopropyl-1H-1,2,3-triazol-4-yl)methyl)amino)-8-chloro-4-(((R)-1-phenylpropyl)amino)quinoline-3-carbonitrile | 2 | ES/MS 610.7 (M + H+) |
| 97 | 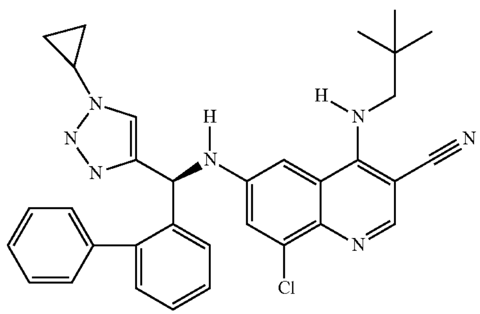 [SMILES: CC(C)(C)CNc1c(C#N)cnc2c(Cl)cc(N[C@H](C3=CN(C4CC4)NN3)c3ccccc3-c3ccccc3)cc12] | (S)-6-(([1,1'-biphenyl]-2-yl(1-cyclopropyl-1H-1,2,3-triazol-4-yl)methyl)amino)-8-chloro-4-(neopentylamino)quinoline-3-carbonitrile | 1 | ES/MS 562.3 (M + H+) |
| 98 | 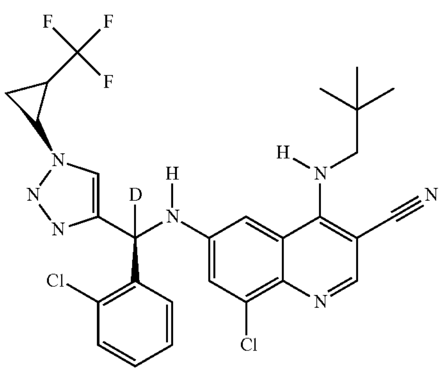 | 8-chloro-6-(((2-chlorophenyl)(1-((1R,2S)-2-(trifluoromethyl)cyclopropyl)-1H-1,2,3-triazol-4-yl)methyl-d)amino)-4-(neopentylamino)quinoline-3-carbonitrile | 4 | ES/MS 589.2 (M + H+) |

TABLE 1-continued

| Compd | Structure | Name | Example/Procedure | ES/MS m/z |
|---|---|---|---|---|
| 99 | 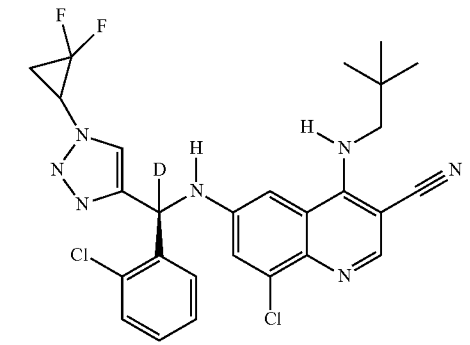 [SMILES: [2H][C@](Nc1cc(Cl)c2ncc(C#N)c(NCC(C)(C)C)c2c1)(C1=CN(C2CC2(F)F)NN1)c1ccccc1Cl] | 8-chloro-6-(((2-chlorophenyl)(1-(2,2-difluorocyclopropyl)-1H-1,2,3-triazol-4-yl)methyl-d)amino)-4-(neopentylamino)quinoline-3-carbonitrile | 4 | ES/MS 557.2 (M + H+) |
| 100 | 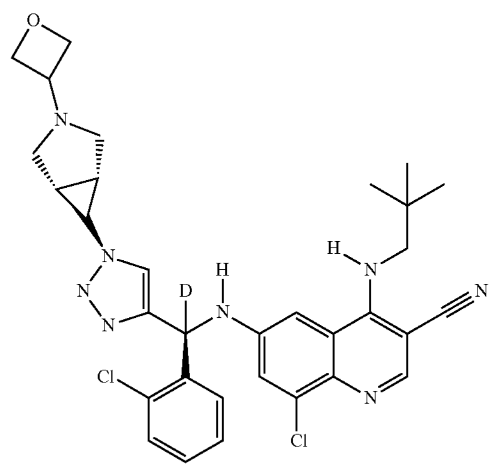 | 8-chloro-6-(((2-chlorophenyl)(1-((1R,5S,6r)-3-(oxetan-3-yl)-3-azabicyclo[3.1.0]hexan-6-yl)-1H-1,2,3-triazol-4-yl)methyl-d)amino)-4-(neopentylamino)quinoline-3-carbonitrile | 4 | ES/MS 618.3 (M + H+) |

TABLE 1-continued

| Compd | Structure | Name | Example/Procedure | ES/MS m/z |
|---|---|---|---|---|
| 101 | 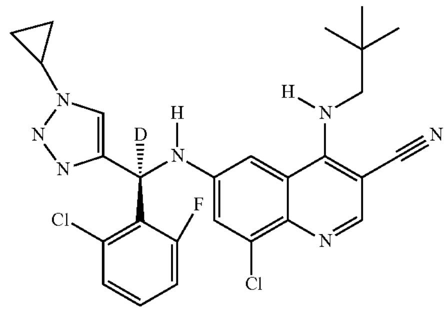 | (S)-8-chloro-6-(((2-chloro-6-fluorophenyl)(1-cyclopropyl-1H-1,2,3-triazol-4-yl)methyl-d)amino)-4-(neopentylamino)quinoline-3-carbonitrile | 1 | ES/MS 539.2 (M + H+) |
| 102 | 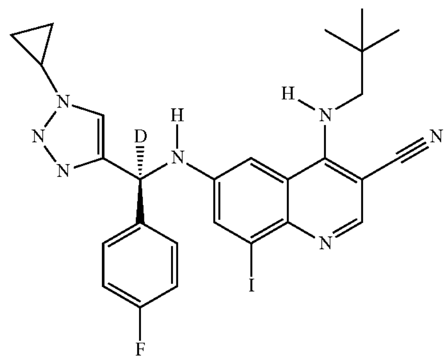 | (S)-6-(((1-cyclopropyl-1H-1,2,3-triazol-4-yl)(4-fluorophenyl)methyl-d)amino)-8-iodo-4-(neopentylamino)quinoline-3-carbonitrile | 1 | ES/MS 597.3 (M + H+) |
| 103 | 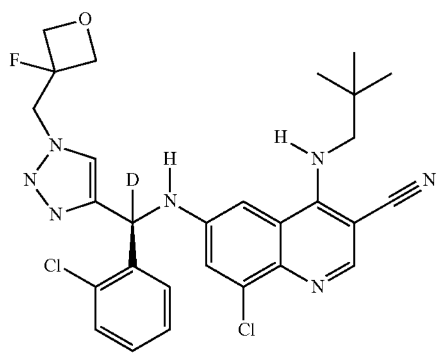 [SMILES: [2H][C@](Nc1cc(Cl)c2ncc(C#N)c(NCC(C)(C)C)c2c1)(C1=CN(CC2(F)COC2)NN1)c1ccccc1Cl] | 8-chloro-6-(((2-chlorophenyl)(1-((3-fluorooxetan-3-yl)methyl)-1H-1,2,3-triazol-4-yl)methyl-d)amino)-4-(neopentylamino)quinoline-3-carbonitrile | 4 | ES/MS 569.2 (M + H+) |

TABLE 1-continued

| Compd | Structure | Name | Example/Procedure | ES/MS m/z |
|---|---|---|---|---|
| 104 | 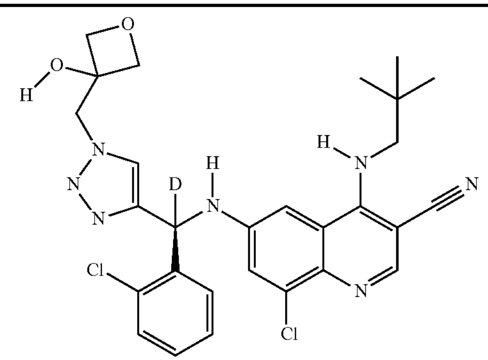 | 8-chloro-6-(((2-chlorophenyl)(1-((3-hydroxyoxetan-3-yl)methyl)-1H-1,2,3-triazol-4-yl)methyl-d)amino)-4-(neopentylamino)quinoline-3-carbonitrile | 4 | ES/MS 567.2 (M + H+) |
| 105 | 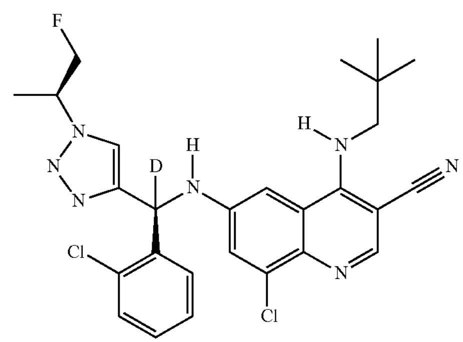 [SMILES: [2H][C@](Nc1cc(Cl)c2ncc(C#N)c(NCC(C)(C)C)c2c1)(C1=CN([C@@H](C)CF)NN1)c1ccccc1Cl] | 8-chloro-6-(((2-chlorophenyl)(1-((S)-1-fluoropropan-2-yl)-1H-1,2,3-triazol-4-yl)methyl-d)amino)-4-(neopentylamino)quinoline-3-carbonitrile | 4 | ES/MS 541.2 (M + H+) |
| 106 | 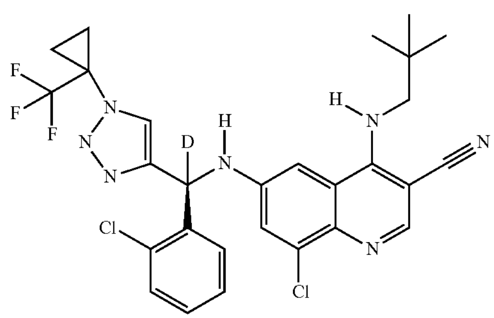 | 8-chloro-6-(((2-chlorophenyl)(1-(1-(trifluoromethyl)cyclopropyl)-1H-1,2,3-triazol-4-yl)methyl-d)amino)-4-(neopentylamino)quinoline-3-carbonitrile | 4 | ES/MS 5889.2 (M + H+) |

TABLE 1-continued

| Compd | Structure | Name | Example/Procedure | ES/MS m/z |
|---|---|---|---|---|
| 107 | 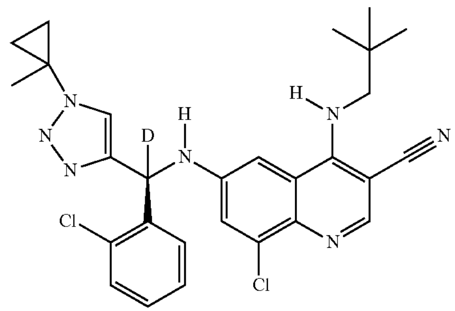 [SMILES: [2H][C@](Nc1cc(Cl)c2ncc(C#N)c(NCC(C)(C)C)c2c1)(C1=CN(C2(C)CC2)NN1)c1ccccc1Cl] | 8-chloro-6-(((2-chlorophenyl)(1-(1-methylcyclopropyl)-1H-1,2,3-triazol-4-yl)methyl-d)amino)-4-(neopentylamino)quinoline-3-carbonitrile | 4 | ES/MS 535.2 (M + H+) |
| 108 | 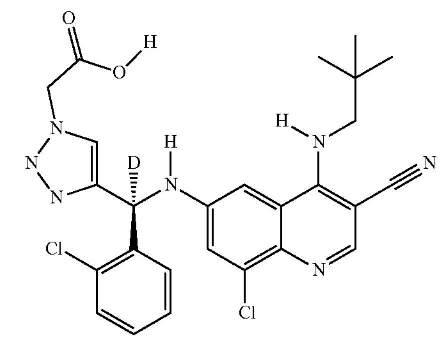 | (S)-2-(4-(((8-chloro-3-cyano-4-(neopentylamino)quinolin-6-yl)amino)(2-chlorophenyl)methyl-d)-1H-1,2,3-triazol-1-yl)acetic acid | 1 | ES/MS 539.1 (M + H+) |
| 109 | 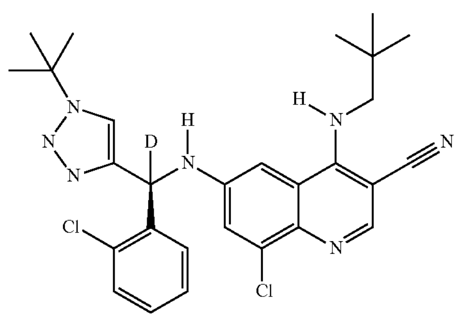 [SMILES: [2H][C@](Nc1cc(Cl)c2ncc(C#N)c(NCC(C)(C)C)c2c1)(C1=CN(C(C)(C)C)NN1)c1ccccc1Cl] | 6-(((1-(tert-butyl)-1H-1,2,3-triazol-4-yl)(2-chlorophenyl)methyl-d)amino)-8-chloro-4-(neopentylamino)quinoline-3-carbonitrile | 3 | ES/MS 537.2 (M + H+) |

TABLE 1-continued

| Compd | Structure | Name | Example/Procedure | ES/MS m/z |
|---|---|---|---|---|
| 110 | 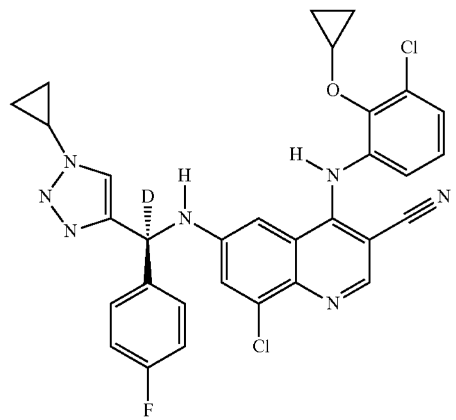 | (S)-8-chloro-4-((3-chloro-2-cyclopropoxyphenyl)amino)-6-(((1-cyclopropyl-1H-1,2,3-triazol-4-yl)(4-fluorophenyl)methyl-d)amino)quinoline-3-carbonitrile | 10 | ES/MS 601.0 (M + H+) |
| 111 | 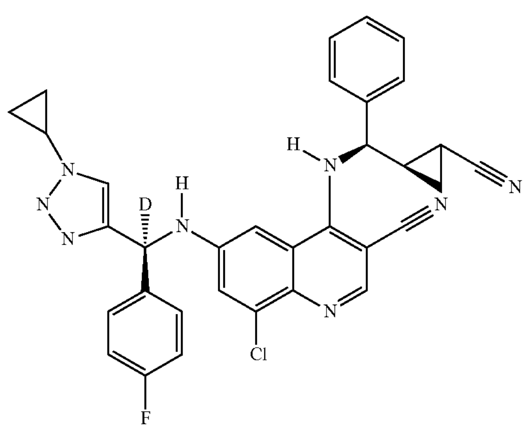 | 8-chloro-4-(((R)-((1R,2R)-2-cyanocyclopropyl)(phenyl)methyl)amino)-6-(((S)-(1-cyclopropyl-1H-1,2,3-triazol-4-yl)(4-fluorophenyl)methyl-d)amino)quinoline-3-carbonitrile | 3 | ES/MS 590.2 (M + H+) |

TABLE 1-continued
| Compd | Structure | Name | Example/Procedure | ES/MS m/z |
|---|---|---|---|---|
| 112 | 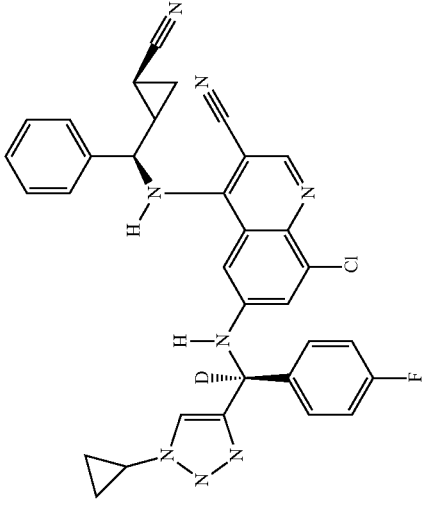 | 8-chloro-4-(((R)-((1S,2S)-2-cyanocyclopropyl)(phenyl)methyl)amino)-6-(((S)-(1-cyclopropyl-1H-1,2,3-triazol-4-yl)(4-fluorophenyl)methyl-d)amino)quinoline-3-carbonitrile | 3 | ES/MS 590.1 (M + H+) |
| 113 | 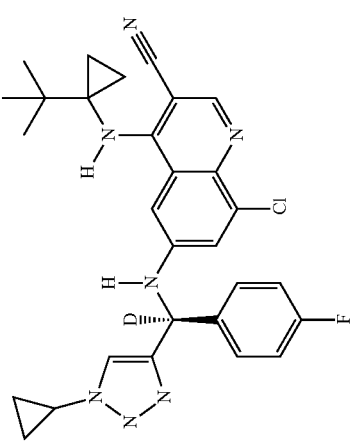 | (S)-4-((1-(tert-butyl)cyclopropyl)amino)-8-chloro-6-(((1-cyclopropyl-1H-1,2,3-triazol-4-yl)(4-fluorophenyl)methyl-d)amino)quinoline-3-carbonitrile | 3 | ES/MS 531.1 (M + H+) |

TABLE 1-continued

| Compd | Structure | Name | Example/Procedure | ES/MS m/z |
|---|---|---|---|---|
| 114 | 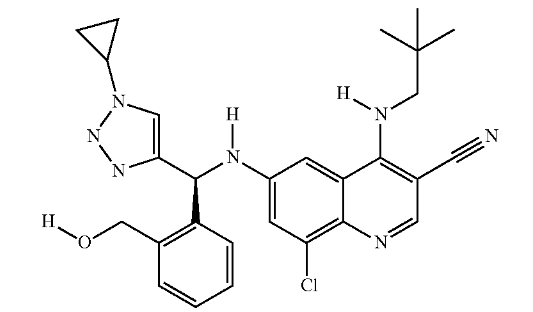 [SMILES: CC(C)(C)CNc1c(C#N)cnc2c(Cl)cc(N[C@H](C3=CN(C4CC4)NN3)c3ccccc3CO)cc12] | (S)-8-chloro-6-(((1-cyclopropyl-1H-1,2,3-triazol-4-yl)(2-(hydroxymethyl)phenyl)methyl)amino)-4-(neopentylamino)quinoline-3-carbonitrile | 17 | ES/MS 516.2 (M + H+) |
| 115 | 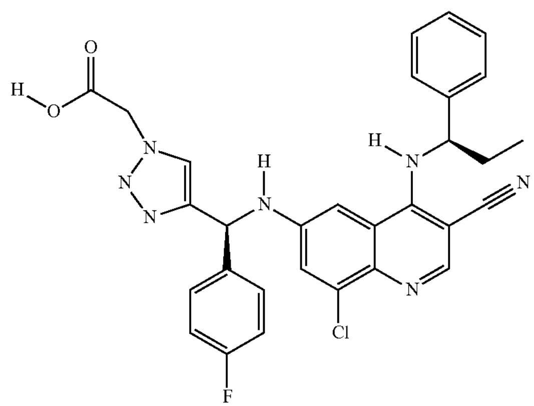 [SMILES: CC[C@@H](Nc1c(C#N)cnc2c(Cl)cc(N[C@H](C3=CN(CC(=O)O)NN3)c3ccc(F)cc3)cc12)c1ccccc1] | 2-(4-((S)-((8-chloro-3-cyano-4-(((R)-1-phenylpropyl)amino)quinolin-6-yl)amino)(4-fluorophenyl)methyl)-1H-1,2,3-triazol-1-yl)acetic acid | 19 | |

TABLE 1-continued

| Compd | Structure | Name | Example/Procedure | ES/MS m/z |
|---|---|---|---|---|
| 116 | 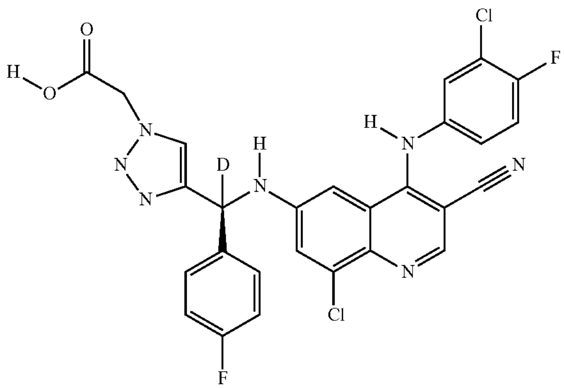 [SMILES: [2H][C@](Nc1cc(Cl)c2ncc(C#N)c(Nc3ccc(F)c(Cl)c3)c2c1)(C1=CN(CC(=O)O)NN1)c1ccc(F)cc1] | (S)-2-(4-(4-(((8-chloro-4-((3-chloro-4-fluorophenyl)amino)-3-cyanoquinolin-6-yl)amino)(4-fluorophenyl)methyl-d)-1H-1,2,3-triazol-1-yl)acetic acid | 19 | |
| 117 | 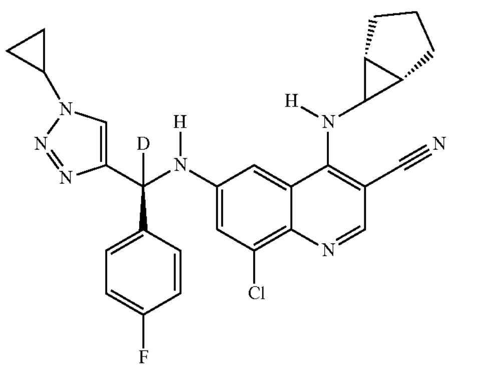 | 4-(((1R,5S)-bicyclo[3.1.0]hexan-6-yl)amino)-8-chloro-6-(((S)-(1-cyclopropyl-1H-1,2,3-triazol-4-yl)(4-fluorophenyl)methyl-d)amino)quinoline-3-carbonitrile | 1 | ES/MS 515.2 (M + H+) |
| 118 | 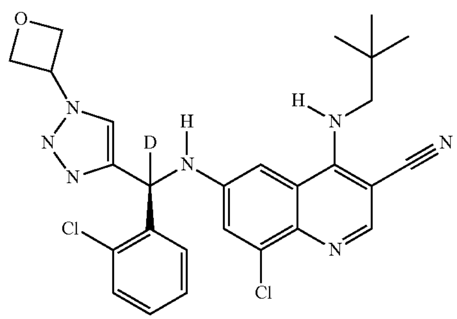 [SMILES: [2H][C@](Nc1cc(Cl)c2ncc(C#N)c(NCC(C)(C)C)c2c1)(C1=CN(C2COC2)NN1)c1ccccc1Cl] | 8-chloro-6-(((2-chlorophenyl)(1-(oxetan-3-yl)-1H-1,2,3-triazol-4-yl)methyl-d)amino)-4-(neopentylamino)quinoline-3-carbonitrile | 3 | ES/MS 537.2 (M + H+) |

TABLE 1-continued

| Compd | Structure | Name | Example/Procedure | ES/MS m/z |
|---|---|---|---|---|
| 119 | 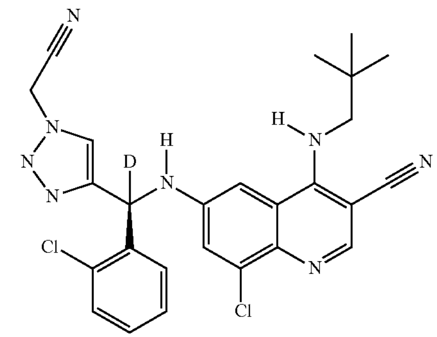 [SMILES: [2H][C@](Nc1cc(Cl)c2ncc(C#N)c(NCC(C)(C)C)c2c1)(C1=CN(CC#N)NN1)c1ccccc1Cl] | 8-chloro-6-(((2-chlorophenyl)(1-(cyanomethyl)-1H-1,2,3-triazol-4-yl)methyl-d)amino)-4-(neopentylamino)quinoline-3-carbonitrile | 3 | ES/MS 520.2 (M + H+) |
| 120 | 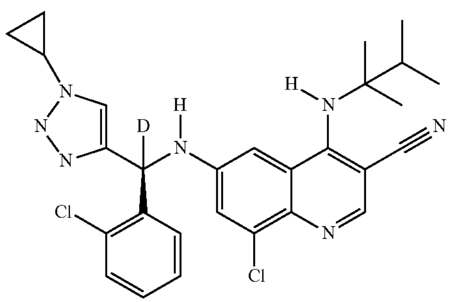 [SMILES: [2H][C@](Nc1cc(Cl)c2ncc(C#N)c(NC(C)(C)C(C)C)c2c1)(C1=CN(C2CC2)NN1)c1ccccc1Cl] | 8-chloro-6-(((2-chlorophenyl)(1-cyclopropyl-1H-1,2,3-triazol-4-yl)methyl-d)amino)-4-((2,3-dimethylbutan-2-yl)amino)quinoline-3-carbonitrile | 3 | ES/MS 535.0 (M + H+) |
| 121 | 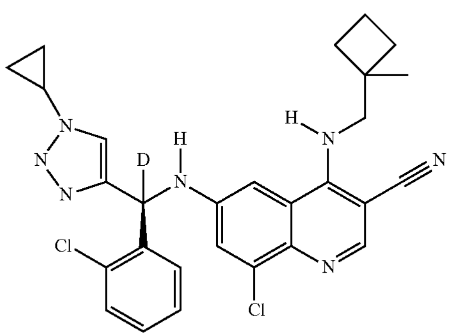 [SMILES: [2H][C@](Nc1cc(Cl)c2ncc(C#N)c(NCC3(C)CCC3)c2c1)(C1=CN(C2CC2)NN1)c1ccccc1Cl] | 8-chloro-6-(((2-chlorophenyl)(1-cyclopropyl-1H-1,2,3-triazol-4-yl)methyl-d)amino)-4-(((1-methylcyclobutyl)methyl)amino)-quinoline-3-carbonitrile | 3 | ES/MS 533.2 (M + H+) |

TABLE 1-continued

| Compd | Structure | Name | Example/Procedure | ES/MS m/z |
|---|---|---|---|---|
| 122 | 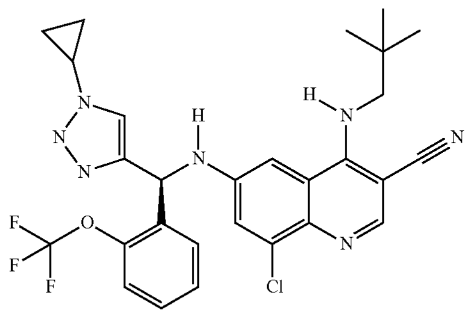 [SMILES: CC(C)(C)CNc1c(C#N)cnc2c(Cl)cc(N[C@H](C3=CN(C4CC4)NN3)c3ccccc3OC(F)(F)F)cc12] | (S)-8-chloro-6-(((1-cyclopropyl-1H-1,2,3-triazol-4-yl)(2-(trifluoromethoxy)phenyl)methyl)amino)-4-(neopentylamino)quinoline-3-carbonitrile | 3 | ES/MS 572.4 (M + H+) |
| 123 | 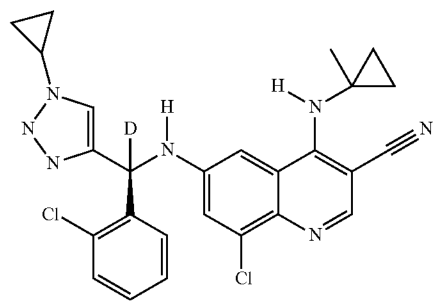 [SMILES: [2H][C@](Nc1cc(Cl)c2ncc(C#N)c(NC3(C)CC3)c2c1)(C1=CN(C2CC2)NN1)c1ccccc1Cl] | 8-chloro-6-(((2-chlorophenyl)(1-cyclopropyl-1H-1,2,3-triazol-4-yl)methyl-d)amino)-4-((1-methylcyclopropyl)amino)quinoline-3-carbonitrile | 3 | ES/MS 505.2 (M + H+) |
| 124 | 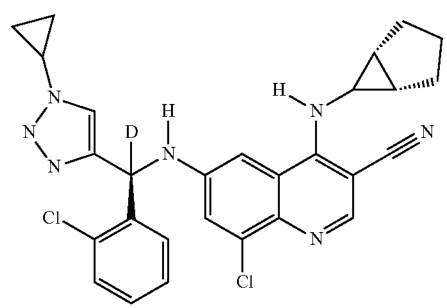 [SMILES: [2H][C@](Nc1cc(Cl)c2ncc(C#N)c(NC3[C@H]4CCC[C@@H]34)c2c1)(C1=CN(C2CC2)NN1)c1ccccc1Cl] | 4-(((1R,5S,6s)-bicyclo[3.1.0]hexan-6-yl)amino)-8-chloro-6-(((2-chlorophenyl)(1-cyclopropyl-1H-1,2,3-triazol-4-yl)methyl-d)amino)quinoline-3-carbonitrile | 3 | ES/MS 531.1 (M + H+) |

TABLE 1-continued
| Compd | Structure | Name | Example/Procedure | ES/MS m/z |
|---|---|---|---|---|
| 125 | 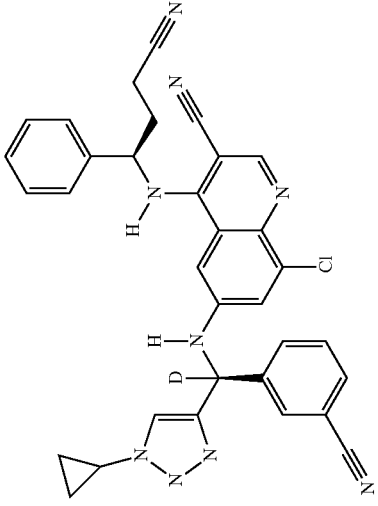 | 8-chloro-4-(((R)-3-cyano-1-phenylpropyl)amino)-6-(((S)-(3-cyanophenyl)(1-cyclopropyl-1H-1,2,3-triazol-4-yl)methyl-d)amino)quinoline-3-carbonitrile | 3 | ES/MS 585.0 (M + H+) |
| 126 | 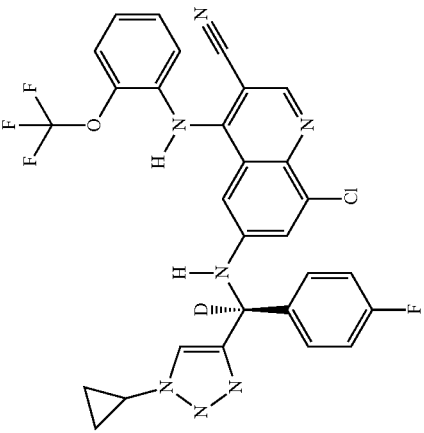 | (S)-8-chloro-6-(((1-cyclopropyl-1H-1,2,3-triazol-4-yl)(4-fluorophenyl)methyl-d)amino)-4-((2-(trifluoromethoxy)phenyl)amino)quinoline-3-carbonitrile | 10 | ES/MS 595.1 (M + H+) |

TABLE 1-continued

| Compd | Structure | Name | Example/Procedure | ES/MS m/z |
|---|---|---|---|---|
| 127 | 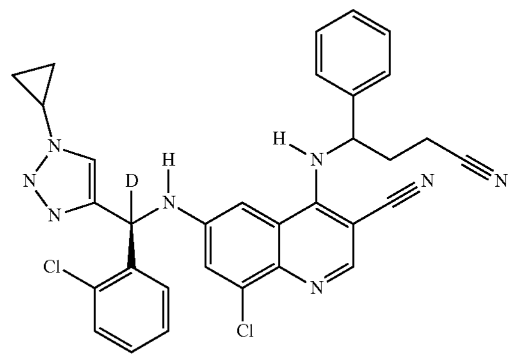 [SMILES: [2H][C@](Nc1cc(Cl)c2ncc(C#N)c(NC(CCC#N)c3ccccc3)c2c1)(C1=CN(C2CC2)NN1)c1ccccc1Cl] | 8-chloro-6-(((2-chlorophenyl)(1-cyclopropyl-1H-1,2,3-triazol-4-yl)methyl-d)amino)-4-((3-cyano-1-phenylpropyl)amino)quinoline-3-carbonitrile | 3 | ES/MS 594.1 (M + H+) |
| 128 | 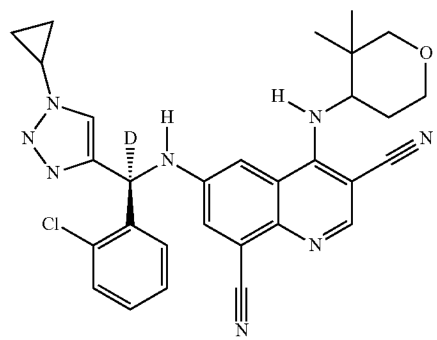 | 6-(((S)-(2-chlorophenyl)(1-cyclopropyl-1H-1,2,3-triazol-4-yl)methyl-d)amino)-4-((3,3-dimethyltetrahydro-2H-pyran-4-yl)amino)quinoline-3,8-dicarbonitrile | 1 | ES/MS 554.3 (M + H+) |
| 129 | 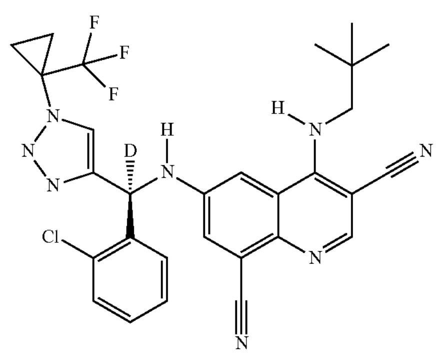 | (S)-6-(((2-chlorophenyl)(1-(trifluoromethyl)cyclopropyl)-1H-1,2,3-triazol-4-yl)methyl-d)amino)-4-(neopentylamino)quinoline-3,8-dicarbonitrile | 1 | ES/MS 580.2 (M + H+) |

TABLE 1-continued

| Compd | Structure | Name | Example/Procedure | ES/MS m/z |
|---|---|---|---|---|
| 130 | 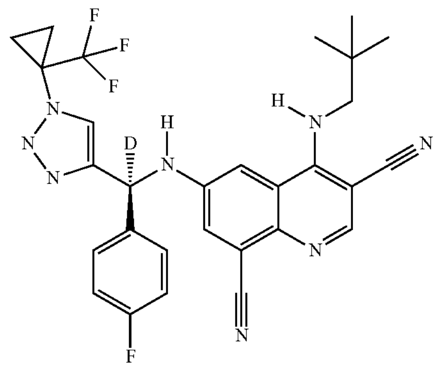 | (S)-6-(((4-fluorophenyl)(1-(1-(trifluoromethyl)cyclopropyl)-1H-1,2,3-triazol-4-yl)methyl)amino)-4-(neopentylamino)quinoline-3,8-dicarbonitrile | 1 | ES/MS 564.2 (M + H+) |
| 131 | 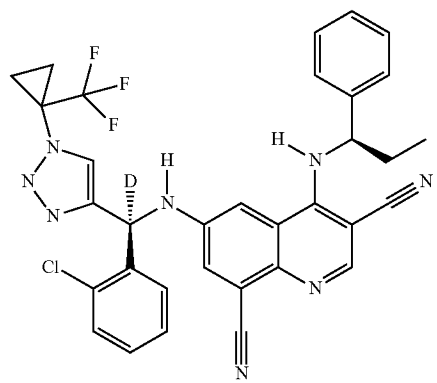 | 6-(((S)-(2-chlorophenyl)(1-(1-(trifluoromethyl)cyclopropyl)-1H-1,2,3-triazol-4-yl)methyl)amino)-4-(((R)-1-phenylpropyl)amino)quinoline-3,8-dicarbonitrile | 1 | ES/MS 628.2 (M + H+) |

TABLE 1-continued
| Compd | Structure | Name | Example/Procedure | ES/MS m/z |
|---|---|---|---|---|
| 132 | 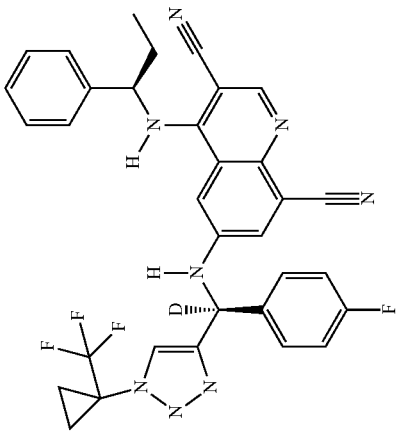 | 6-(((S)-(4-fluorophenyl)(1-(1-(trifluoromethyl)cyclopropyl)-1H-1,2,3-triazol-4-yl)methyl-d)amino)-4-(((R)-1-phenylpropyl)amino)quinoline-3,8-dicarbonitrile | 1 | ES/MS 612.2 (M + H+) |
| 133 | 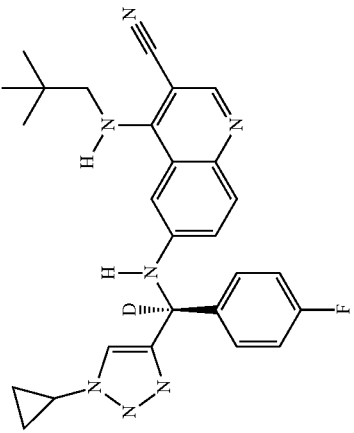 | 6-(((1-cyclopropyl-1H-1,2,3-triazol-4-yl)(4-fluorophenyl)methyl-d)amino)-4-(neopentylamino)quinoline-3-carbonitrile | 1 | ES/MS 471.1 (M + H+) |

TABLE 1-continued

| Compd | Structure | Name | Example/Procedure | ES/MS m/z |
|---|---|---|---|---|
| 134 | 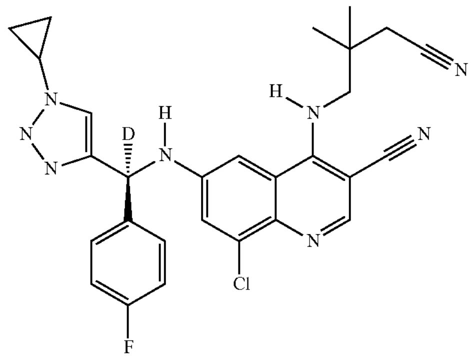 | (S)-8-chloro-4-((3-cyano-2,2-dimethylpropyl)amino)-6-(((1-cyclopropyl-1H-1,2,3-triazol-4-yl)(4-fluorophenyl)methyl-d)amino)quinoline-3-carbonitrile | 1 | ES/MS 530.3 (M + H+) |
| 135 | 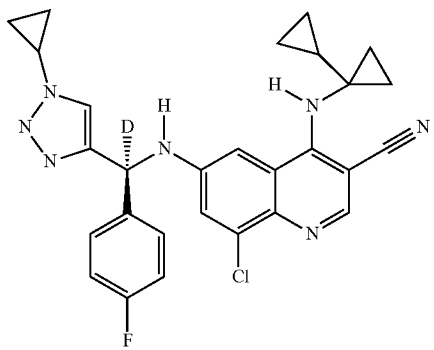 | (S)-4-([1,1'-bi(cyclopropan)]-1-ylamino)-8-chloro-6-(((1-cyclopropyl-1H-1,2,3-triazol-4-yl)(4-fluorophenyl)methyl-d)amino)quinoline-3-carbonitrile | 1 | ES/MS 515.3 (M + H+) |

TABLE 1-continued
| Compd | Structure | Name | Example/Procedure | ES/MS m/z |
|---|---|---|---|---|
| 136 | 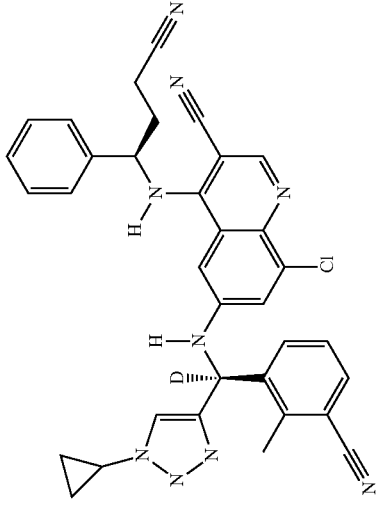 | 8-chloro-4-(((R)-3-cyano-1-phenylpropyl)amino)-6-(((S)-(3-cyano-2-methylphenyl)(1-cyclopropyl-1H-1,2,3-triazol-4-yl)methyl-d)amino)quinoline-3-carbonitrile | 3 | ES/MS 599.2 (M + H+) |
| 137 | 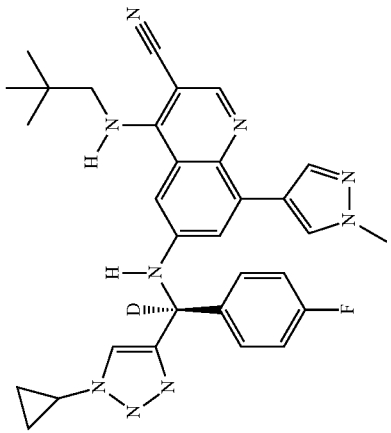 | (S)-6-(((1-cyclopropyl-1H-1,2,3-triazol-4-yl)(4-fluorophenyl)methyl-d)amino)-8-(1-methyl-1H-pyrazol-4-yl)-4-(neopentylamino)quinoline-3-carbonitrile | 12 | ES/MS 551.4 (M + H+) |

TABLE 1-continued

| Compd | Structure | Name | Example/Procedure | ES/MS m/z |
|---|---|---|---|---|
| 138 | 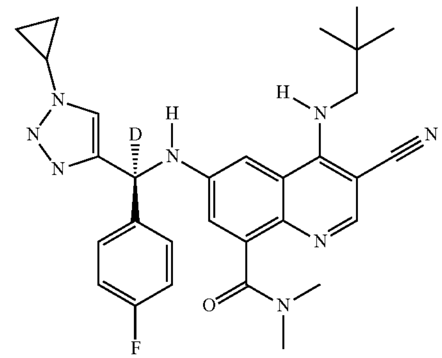 | (S)-3-cyano-6-(((1-cyclopropyl-1H-1,2,3-triazol-4-yl)(4-fluorophenyl)methyl-d)amino)-N,N-dimethyl-4-(neopentylamino)quinoline-8-carboxamide | 1 | ES/MS 542.2 (M + H+) |
| 139 | 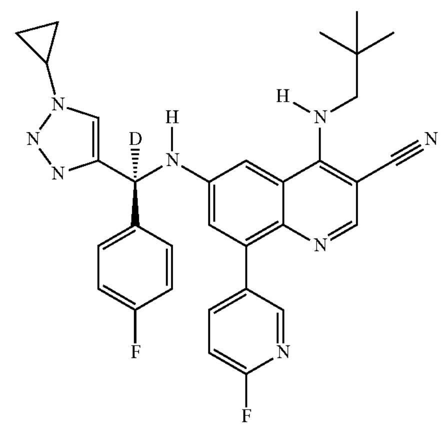 | (S)-6-(((1-cyclopropyl-1H-1,2,3-triazol-4-yl)(4-fluorophenyl)methyl-d)amino)-8-(6-fluoropyridin-3-yl)-4-(neopentylamino)quinoline-3-carbonitrile | 12 | ES/MS 566.2 (M + H+) |

TABLE 1-continued

| Compd | Structure | Name | Example/Procedure | ES/MS m/z |
|---|---|---|---|---|
| 140 | 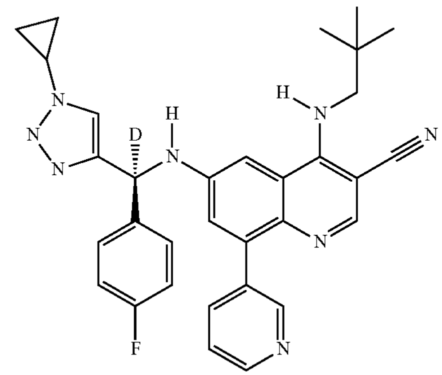 | (S)-6-(((1-cyclopropyl-1H-1,2,3-triazol-4-yl)(4-fluorophenyl)methyl-d)amino)-4-(neopentylamino)-8-(pyridin-4-yl)quinoline-3-carbonitrile | 12 | ES/MS 548.2 (M + H+) |
| 141 | 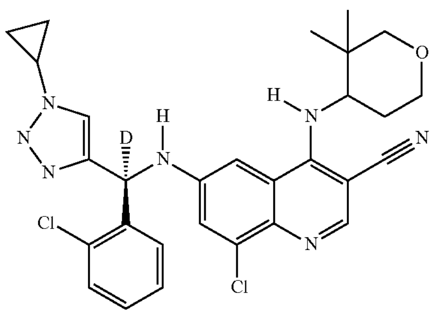 | 8-chloro-6-(((S)-(2-chlorophenyl)(1-cyclopropyl-1H-1,2,3-triazol-4-yl)methyl-d)amino)-4-((3,3-dimethyltetrahydro-2H-pyran-4-yl)amino)quinoline-3-carbonitrile | 1 | ES/MS 563.2 (M + H+) |
| 142 | 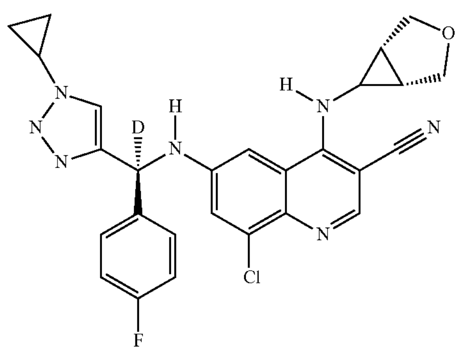 | 4-(((1R,5S)-3-oxabicyclo[3.1.0]hexan-6-yl)amino)-8-chloro-6-(((S)-(1-cyclopropyl-1H-1,2,3-triazol-4-yl)(4-fluorophenyl)methyl-d)amino)quinoline-3-carbonitrile | 1 | ES/MS 517.1 (M + H+) |

TABLE 1-continued
| Compd | Structure | Name | Example/Procedure | ES/MS m/z |
|---|---|---|---|---|
| 143 | 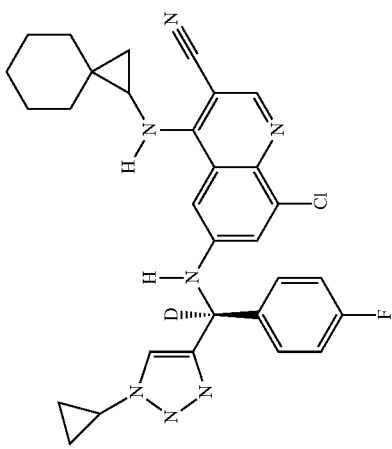 | 8-chloro-6-(((S)-(1-cyclopropyl-1H-1,2,3-triazol-4-yl)(4-fluorophenyl)methyl-d)amino)-4-(spiro[2.5]octan-1-ylamino)quinoline-3-carbonitrile | 1 | ES/MS 543.2 (M + H+) |
| 144 | 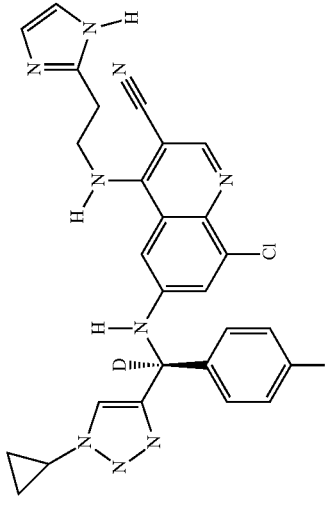 | (S)-4-((2-(1H-imidazol-2-yl)ethyl)amino)-8-chloro-6-(((1-cyclopropyl-1H-1,2,3-triazol-4-yl)(4-fluorophenyl)methyl-d)amino)quinoline-3-carbonitrile | 1 | ES/MS 529.2 (M + H+) |

TABLE 1-continued

| Compd | Structure | Name | Example/Procedure | ES/MS m/z |
|---|---|---|---|---|
| 145 | 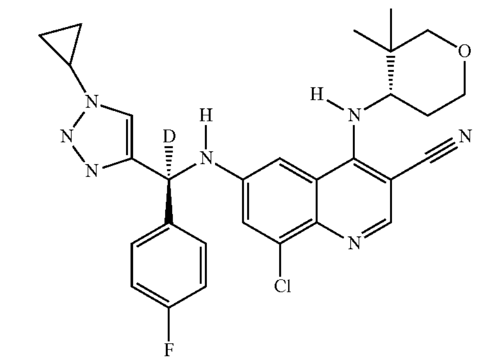 | 8-chloro-6-(((S)-(1-cyclopropyl-1H-1,2,3-triazol-4-yl)(4-fluorophenyl)methyl-d)amino)-4-(((S)-3,3-dimethyltetrahydro-2H-pyran-4-yl)amino)quinoline-3-carbonitrile | 1 | ES/MS 547.2 (M + H+) |
| 146 | 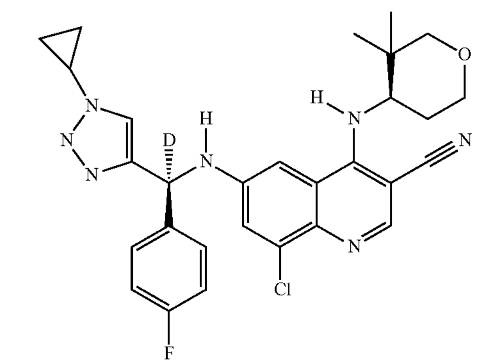 | 8-chloro-6-(((S)-(1-cyclopropyl-1H-1,2,3-triazol-4-yl)(4-fluorophenyl)methyl-d)amino)-4-(((R)-3,3-dimethyltetrahydro-2H-pyran-4-yl)amino)quinoline-3-carbonitrile | 1 | ES/MS 547.3 (M + H+) |
| 147 | 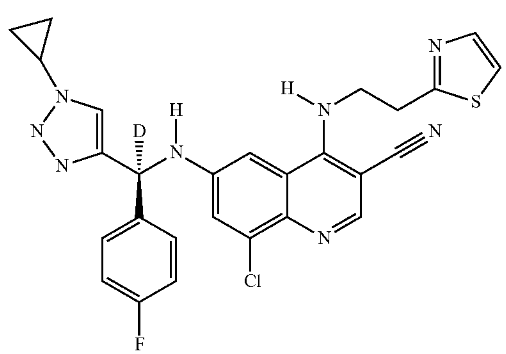 | (S)-8-chloro-6-(((1-cyclopropyl-1H-1,2,3-triazol-4-yl)(4-fluorophenyl)methyl-d)amino)-4-((2-(thiazol-2-yl)ethyl)amino)quinoline-3-carbonitrile | 1 | ES/MS 546.3 (M + H+) |

TABLE 1-continued

| Compd | Structure | Name | Example/Procedure | ES/MS m/z |
|---|---|---|---|---|
| 148 | 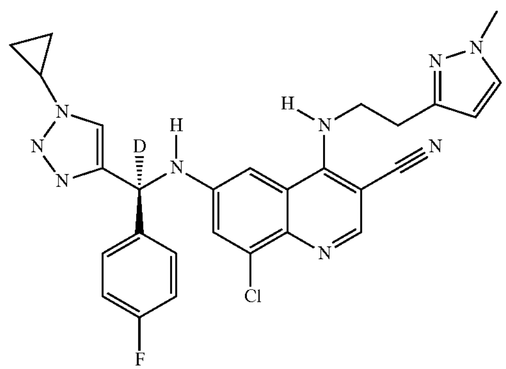 | (S)-8-chloro-6-(((1-cyclopropyl-1H-1,2,3-triazol-4-yl)(4-fluorophenyl)methyl-d)amino)-4-((2-(1-methyl-1H-pyrazol-3-yl)ethyl)amino)quinoline-3-carbonitrile | 1 | ES/MS 543.2 (M + H+) |
| 149 | 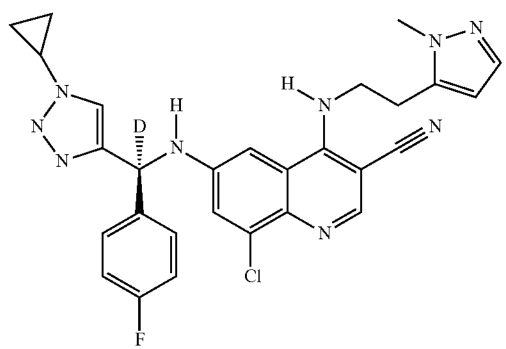 | (S)-8-chloro-6-(((1-cyclopropyl-1H-1,2,3-triazol-4-yl)(4-fluorophenyl)methyl-d)amino)-4-((2-(1-methyl-1H-pyrazol-5-yl)ethyl)amino)quinoline-3-carbonitrile | 1 | ES/MS 543.3 (M + H+) |

TABLE 1-continued

| Compd | Structure | Name | Example/Procedure | ES/MS m/z |
|---|---|---|---|---|
| 150 | 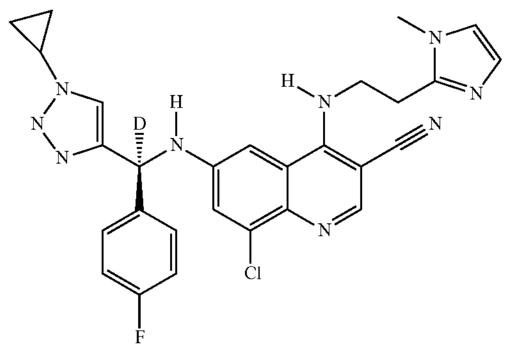 | (S)-8-chloro-6-(((1-cyclopropyl-1H-1,2,3-triazol-4-yl)(4-fluorophenyl)methyl-d)amino)-4-((2-(1-methyl-1H-imidazol-2-yl)ethyl)amino)quinoline-3-carbonitrile | 1 | ES/MS 543.2 (M + H+) |
| 151 | 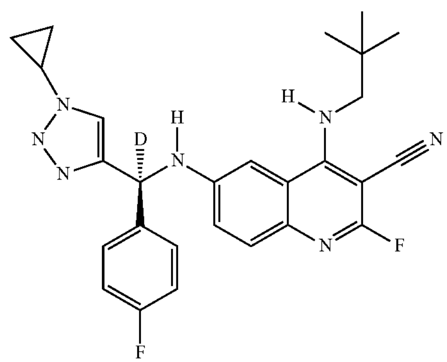 | (S)-6-(((1-cyclopropyl-1H-1,2,3-triazol-4-yl)(4-fluorophenyl)methyl-d)amino)-2-fluoro-4-(neopentylamino)quinoline-3-carbonitrile | 1 | ES/MS 489.2 (M + H+) |
| 152 | 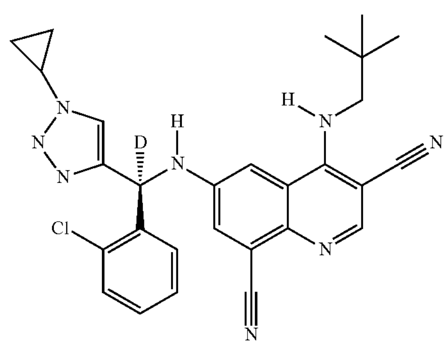 | (S)-6-(((2-chlorophenyl)(1-cyclopropyl-1H-1,2,3-triazol-4-yl)methyl-d)amino)-4-(neopentylamino)quinoline-3,8-dicarbonitrile | 1 | ES/MS 512.2 (M + H+) |

TABLE 1-continued

| Compd | Structure | Name | Example/Procedure | ES/MS m/z |
|---|---|---|---|---|
| 153 | 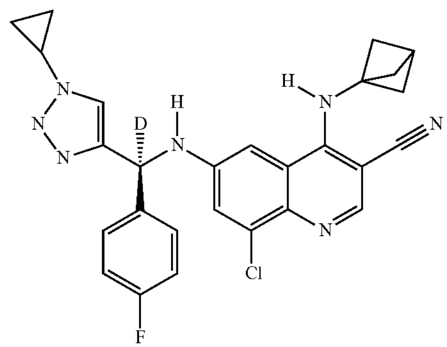 | (S)-4-(bicyclo[1.1.1]pentan-1-ylamino)-8-chloro-6-(((1-cyclopropyl-1H-1,2,3-triazol-4-yl)(4-fluorophenyl)methyl-d)amino)quinoline-3-carbonitrile | 3 | ES/MS 501.1 (M + H+) |
| 154 | 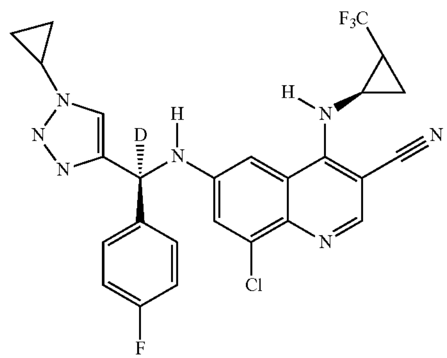 | 8-chloro-6-(((S)-(1-cyclopropyl-1H-1,2,3-triazol-4-yl)(4-fluorophenyl)methyl-d)amino)-4-(((1R,2R)-2-(trifluoromethyl)cyclopropyl)amino)-quinoline-3-carbonitrile | 3 | ES/MS 543.0 (M + H+) |

TABLE 1-continued

| Compd | Structure | Name | Example/Procedure | ES/MS m/z |
|---|---|---|---|---|
| 155 | 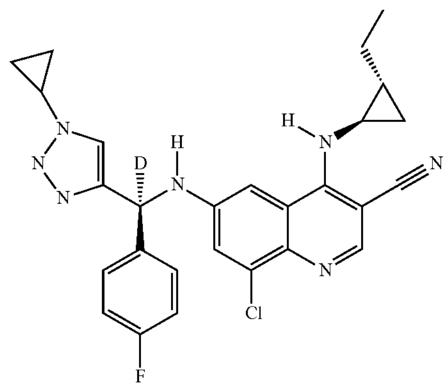 | 8-chloro-6-(((S)-(1-cyclopropyl-1H-1,2,3-triazol-4-yl)(4-florophenyl)methyl-d)amino)-4-(((1R,2R)-2-ethylcyclopropyl)amino)quinoline-3-carbonitrile | 3 | ES/MS 503.1 (M + H+) |
| 156 | 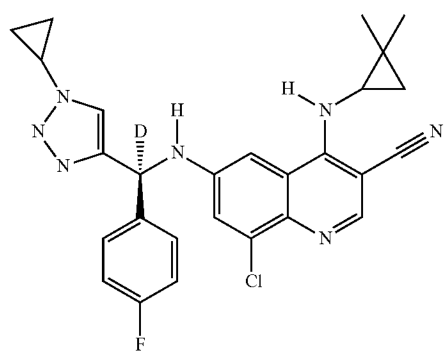 | 8-chloro-6-(((S)-(1-cyclopropyl-1H-1,2,3-triazol-4-yl)(4-fluorophenyl)methyl-d)amino)-4-((2-2-dimethylcyclopropyl)amino)-quinoline-3-carbonitrile | 3 | ES/MS 503.2 (M + H+) |

TABLE 1-continued

| Compd | Structure | Name | Example/Procedure | ES/MS m/z |
|---|---|---|---|---|
| 157 | 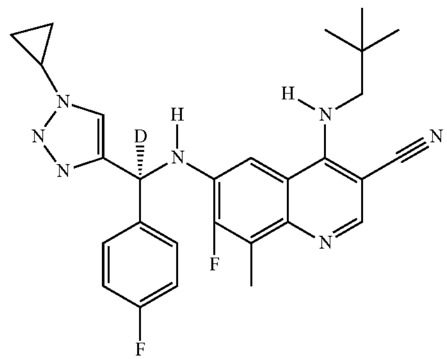 [SMILES: [2H][C@@](Nc1cc2c(NCC(C)(C)C)c(C#N)cnc2c(C)c1F)(C1=CN(C2CC2)NN1)c1ccc(F)cc1] | 6-(((1-cyclopropyl-1H-1,2,3-triazol-4-yl)(4-fluorophenyl)methyl-d)amino)-7-fluoro-8-methyl-4-(neopentylamino)quinoline-3-carbonitrile | 1 | ES/MS 503.2 (M + H+) |
| 158 | 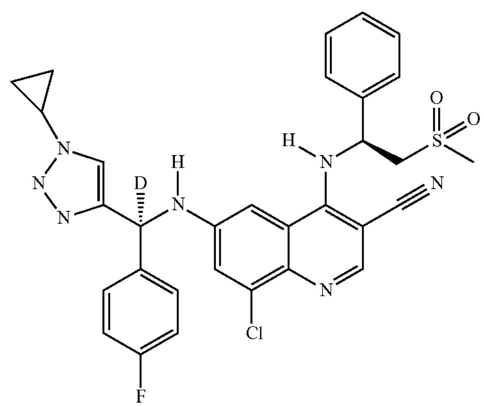 [SMILES: [2H][C@@](Nc1cc(Cl)c2ncc(C#N)c(N[C@H](CS(C)(=O)=O)c3ccccc3)c2c1)(C1=CN(C2CC2)NN1)c1ccc(F)cc1] | 8-chloro-6-(((1-cyclopropyl-1H-1,2,3-triazol-4-yl)(4-fluorophenyl)methyl-d)amino)-4-(((S)-2-(methylsulfonyl)-1-phenylethyl)amino)quinoline-3-carbonitrile | 2 | |

TABLE 1-continued

| Compd | Structure | Name | Example/Procedure | ES/MS m/z |
|---|---|---|---|---|
| 159 | 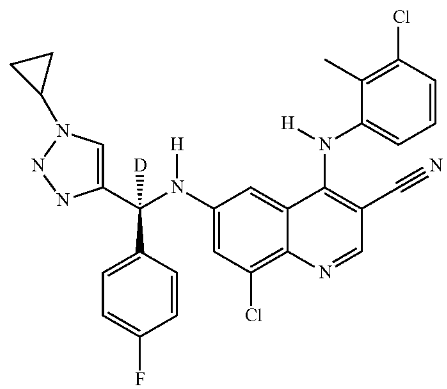 | (S)-8-chloro-4-((3-chloro-2-methylphenyl)amino)-6-(((1-cyclopropyl-1H-1,2,3-triazol-4-yl)(4-fluorophenyl)methyl-d)amino)quinoline-3-carbonitrile | 10 | ES/MS 559.2 (M + H+) |
| 160 | 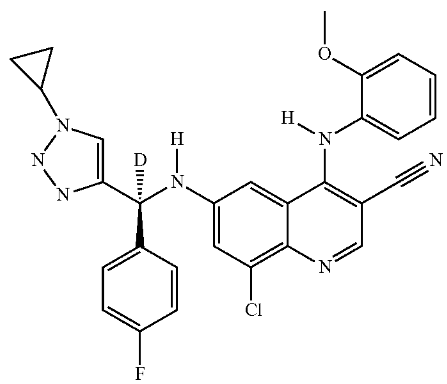 | (S)-8-chloro-6-(((1-cyclopropyl-1H-1,2,3-triazol-4-yl)(4-fluorophenyl)methyl-d)amino)-4-((2-methoxyphenyl)amino)quinoline-3-carbonitrile | 10 | ES/MS 541.2 (M + H+) |

TABLE 1-continued
| Compd | Structure | Name | Example/Procedure | ES/MS m/z |
|---|---|---|---|---|
| 161 | 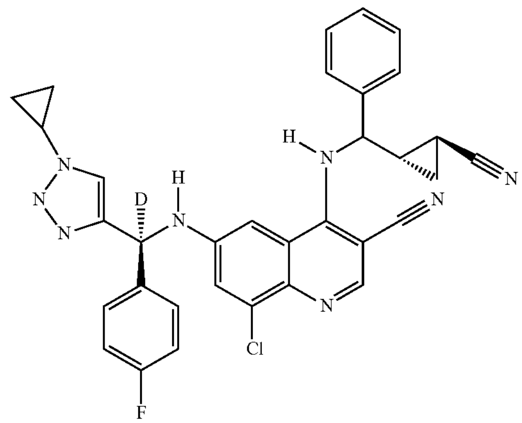 | 8-chloro-4-(((S)-((1S,2S)-2-cyanocyclopropyl)(phenyl)methyl)amino)-6-(((S)-(1-cyclopropyl-1H-1,2,3-triazol-4-yl)(4-fluorophenyl)methyl-d)amino)quinoline-3-carbonitrile | 3 | ES/MS 590.2 (M + H+) |
| 162 | 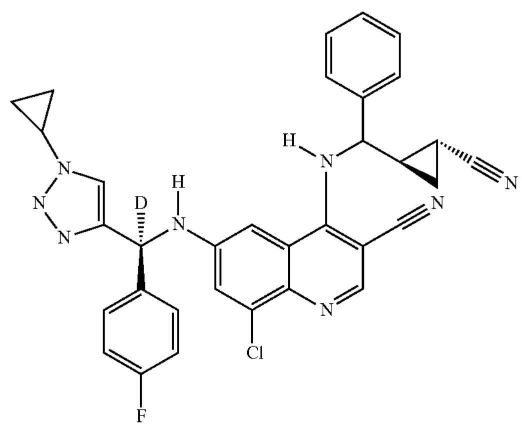 | 8-chloro-4-(((S)-((1R,2R)-2-cyanocyclopropyl)(phenyl)methyl)amino)-6-(((S)-(1-cyclopropyl-1H-1,2,3-triazol-4-yl)(4-fluorophenyl)methyl-d)amino)quinoline-3-carbonitrile | 3 | ES/MS 590.1 (M + H+) |

TABLE 1-continued

| Compd | Structure | Name | Example/Procedure | ES/MS m/z |
|---|---|---|---|---|
| 163 | 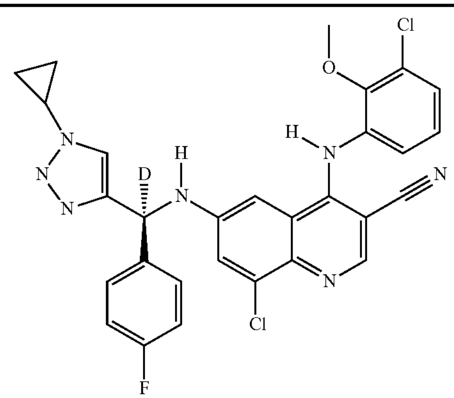 | (S)-8-chloro-4-((3-chloro-2-methoxyphenyl)amino)-6-(((1-cyclopropyl-1H-1,2,3-triazol-4-yl)(4-fluorophenyl)methyl-d)amino)quinoline-3-carbonitrile | 10 | ES/MS 575.0 (M + H+) |
| 164 | 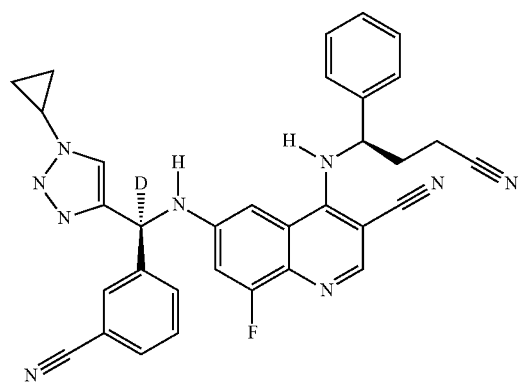 | 4-(((R)-3-cyano-1-phenylpropyl)amino)-6-(((S)-(3-cyanophenyl)(1-cyclopropyl-1H-1,2,3-triazol-4-yl)methyl-d)amino)-8-fluoroquinoline-3-carbonitrile | 1 | ES/MS 569.2 (M + H+) |

TABLE 1-continued
| Compd | Structure | Name | Example/Procedure | ES/MS m/z |
|---|---|---|---|---|
| 165 | 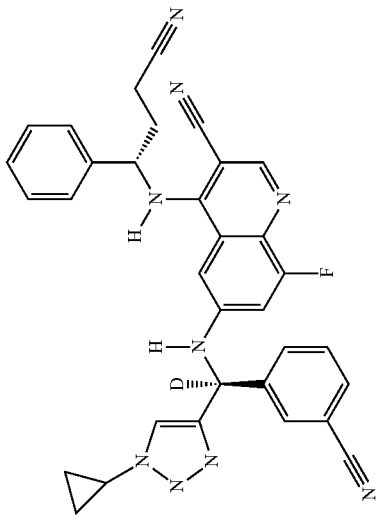 | 4-(((S)-3-cyano-1-phenylpropyl)amino)-6-(((S)-(3-cyanophenyl)(1-cyclopropyl-1H-1,2,3-triazol-4-yl)methyl-d)amino)-8-fluoroquinoline-3-carbonitrile | 1 | ES/MS 569.2 (M + H+) |
| 166 | 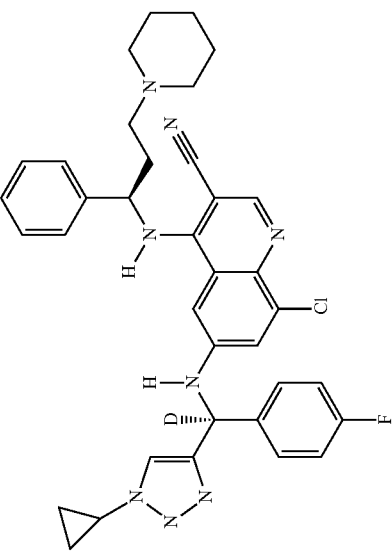 | 8-chloro-6-(((1-cyclopropyl-1H-1,2,3-triazol-4-yl)(4-fluorophenyl)methyl-d)amino)-4-(((R)-1-phenyl-3-(piperidin-1-yl)propyl)amino)quinoline-3-carbonitrile | 34 | ES/MS 636.4 (M + H+) |

TABLE 1-continued
| Compd | Structure | Name | Example/Procedure | ES/MS m/z |
|---|---|---|---|---|
| 167 | 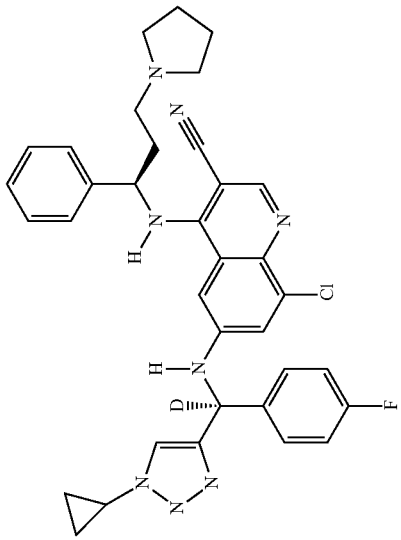 | 8-chloro-6-(((1-cyclopropyl-1H-1,2,3-triazol-4-yl)(4-fluorophenyl)methyl-d)amino)-4-(((R)-1-phenyl-3-(pyrrolidin-1-yl)propyl)amino)quinoline-3-carbonitrile | 34 | ES/MS 622.3 (M + H+) |
| 168 | 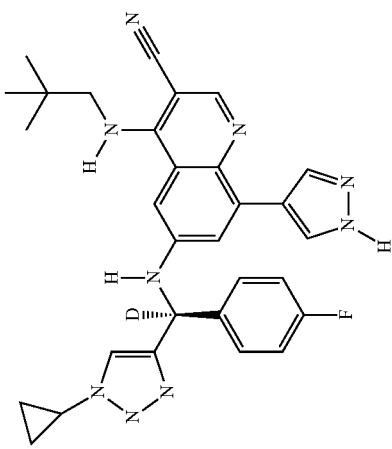 | (S)-6-(((1-cyclopropyl-1H-1,2,3-triazol-4-yl)(4-fluorophenyl)methyl-d)amino)-4-(neopentylamino)-8-(1H-pyrazol-4-yl)quinoline-3-carbonitrile | 12 | ES/MS 537.2 (M + H+) |

TABLE 1-continued

| Compd | Structure | Name | Example/Procedure | ES/MS m/z |
|---|---|---|---|---|
| 169 | 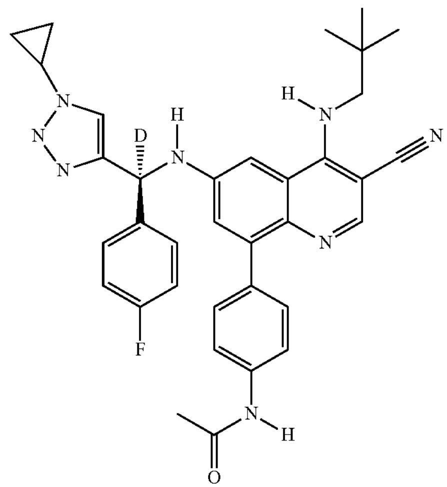 | (S)-N-(4-(3-cyano-6-(((1-cyclopropyl-1H-1,2,3-triazol-4-yl)(4-fluorophenyl)methyl-d)amino)-4-(neopentylamino)quinolin-8-yl)phenyl)acetamide | 12 | ES/MS 604.3 (M + H+) |
| 170 | 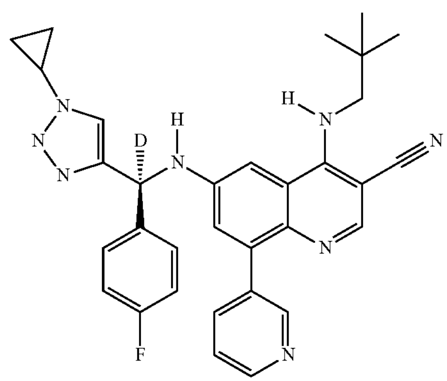 | (S)-6-(((1-cyclopropyl-1H-1,2,3-triazol-4-yl)(4-fluorophenyl)methyl-d)amino)-4-(neopentylamino)-8-(pyridin-3-yl)quinoline-3-carbonitrile | 12 | ES/MS 548.2 (M + H+) |

TABLE 1-continued

| Compd | Structure | Name | Example/Procedure | ES/MS m/z |
|---|---|---|---|---|
| 171 | 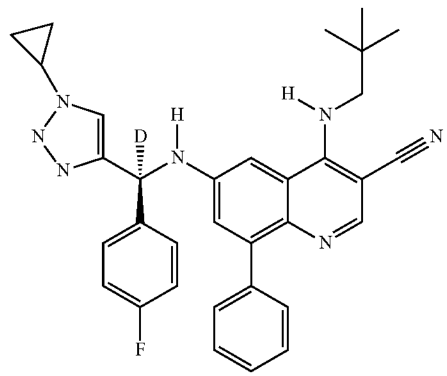 | (S)-6-(((1-cyclopropyl-1H-1,2,3-triazol-4-yl)(4-fluorophenyl)methyl-d)amino)-4-(neopentylamino)-8-phenylquinoline-3-carbonitrile | 12 | ES/MS 547.2 (M + H+) |
| 172 | 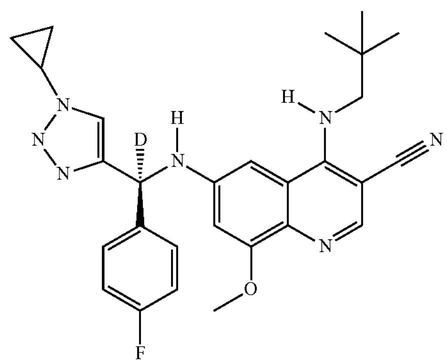 | (S)-6-(((1-cyclopropyl-1H-1,2,3-triazol-4-yl)(4-fluorophenyl)methyl-d)amino)-8-methoxy-4-(neopentylamino)quinoline-3-carbonitrile | 1 | |

TABLE 1-continued

| Compd | Structure | Name | Example/Procedure | ES/MS m/z |
|---|---|---|---|---|
| 173 | 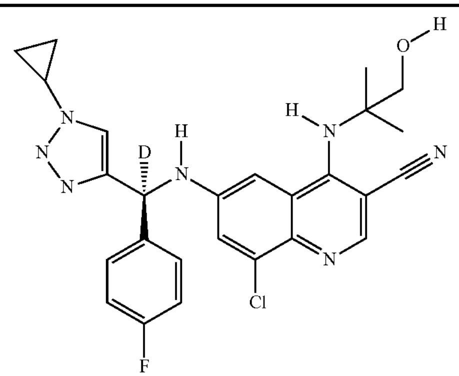 | (S)-8-chloro-6-(((1-cyclopropyl-1H-1,2,3-triazol-4-yl)(4-fluorophenyl)methyl-d)amino)-4-(((1-hydroxy-2-methylpropan-2-yl)amino)quinoline-3-carbonitrile | 3 | ES/MS 507.0 (M + H+) |
| 174 | 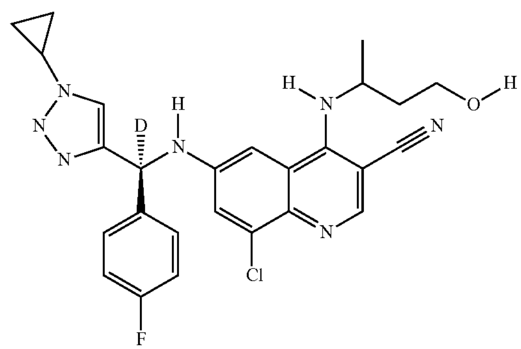 | 8-chloro-6-(((S)-(1-cyclopropyl-1H-1,2,3-triazol-4-yl)(4-fluorophenyl)methyl-d)amino)-4-(((4-hydroxybutan-2-yl)amino)quinoline-3-carbonitrile | 3 | ES/MS 507.2 (M + H+) |
| 175 | 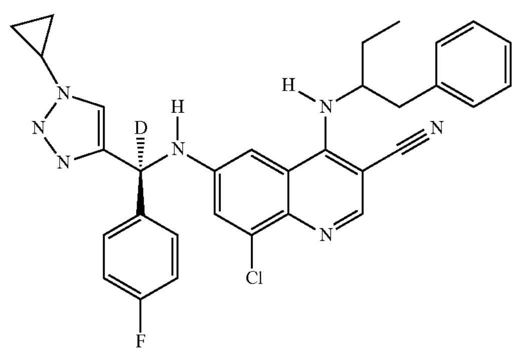 | 8-chloro-6-(((S)-(1-cyclopropyl-1H-1,2,3-triazol-4-yl)(4-fluorophenyl)methyl-d)amino)-4-(((1-phenylbutan-2-yl)amino)quinoline-3-carbonitrile | 1 | ES/MS 567.4 (M + H+) |

TABLE 1-continued

| Compd | Structure | Name | Example/Procedure | ES/MS m/z |
|---|---|---|---|---|
| 176 | 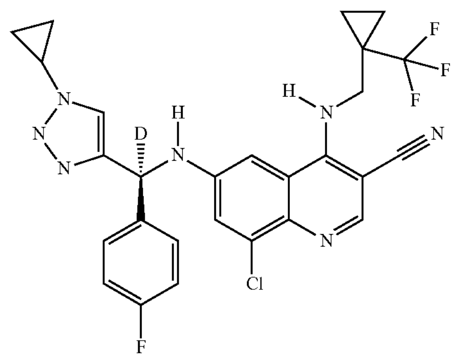 | (S)-8-chloro-6-(((1-cyclopropyl-1H-1,2,3-triazol-4-yl)(4-fluorophenyl)methyl-d)amino)-4-(((1-(trifluoromethyl)cyclopropyl)methyl)amino)quinoline-3-carbonitrile | 1 | ES/MS 557.1 (M + H+) |
| 177 | 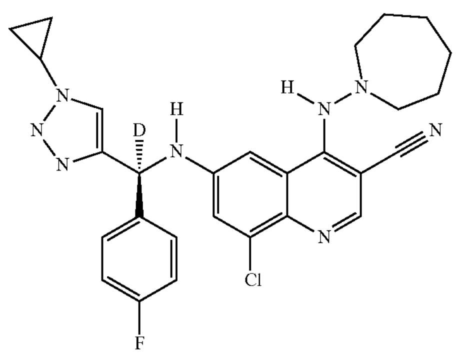 | (S)-4-(azepan-1-ylamino)-8-chloro-6-(((1-cyclopropyl-1H-1,2,3-triazol-4-yl)(4-fluorophenyl)methyl-d)amino)quinoline-3-carbonitrile | 1 | ES/MS 532.2 (M + H+) |

TABLE 1-continued

| Compd | Structure | Name | Example/Procedure | ES/MS m/z |
|---|---|---|---|---|
| 178 | 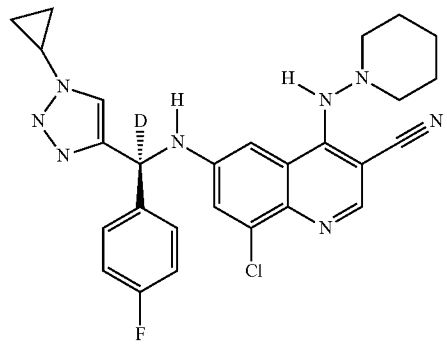 | (S)-8-chloro-6-(((1-cyclopropyl-1H-1,2,3-triazol-4-yl)(4-fluorophenyl)methyl-d)amino)-4-(piperidin-1-ylamino)quinoline-3-carbonitrile | 1 | ES/MS 518.3 (M + H+) |
| 179 | 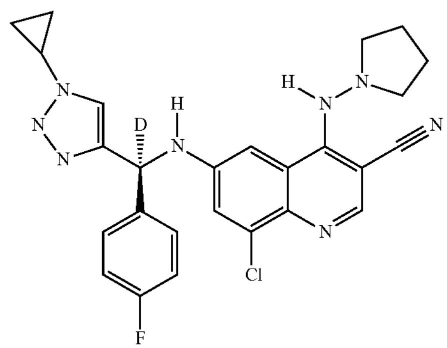 | (S)-8-chloro-6-(((1-cyclopropyl-1H-1,2,3-triazol-4-yl)(4-fluorophenyl)methyl-d)amino)-4-(pyrrolidin-1-ylamino)quinoline-3-carbonitrile | 1 | ES/MS 504.1 (M + H+) |

TABLE 1-continued
| Compd | Structure | Name | Example/Procedure | ES/MS m/z |
|---|---|---|---|---|
| 180 | 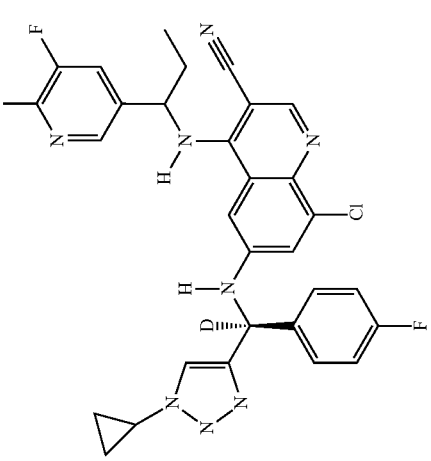 | 8-chloro-6-(((S)-(1-cyclopropyl-1H-1,2,3-triazol-4-yl)(4-fluorophenyl)methyl-d)amino)-4-(((1-(5,6-difluoropyridin-3-yl)propyl)amino)quinoline-3-carbonitrile | 2 | ES/MS 590.2 (M + H+) |
| 181 | 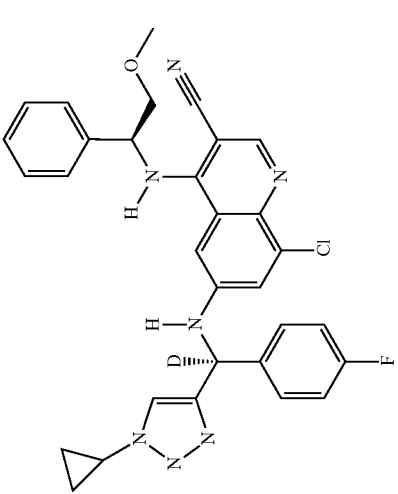 | 8-chloro-6-(((1-cyclopropyl-1H-1,2,3-triazol-4-yl)(4-fluorophenyl)methyl-d)amino)-4-(((S)-2-methoxy-1-phenylethyl)amino)quinoline-3-carbonitrile | 2 | ES/MS 569.2 (M + H+) |

TABLE 1-continued

| Compd | Structure | Name | Example/Procedure | ES/MS m/z |
|---|---|---|---|---|
| 182 | 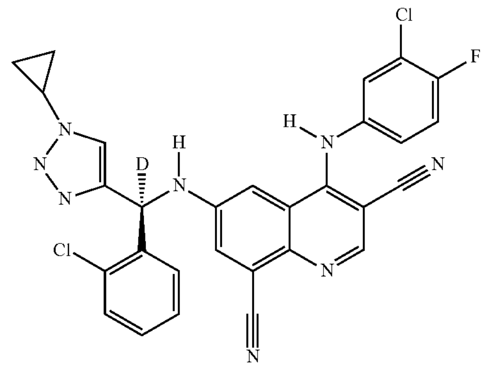 | (S)-4-((3-chloro-4-fluorophenyl)amino)-6-(((2-chlorophenyl)(1-cyclopropyl-1H-1,2,3-triazol-4-yl)methyl-d)amino)quinoline-3,8-dicarbonitrile | 1 | ES/MS 570.1 (M + H+) |
| 183 | 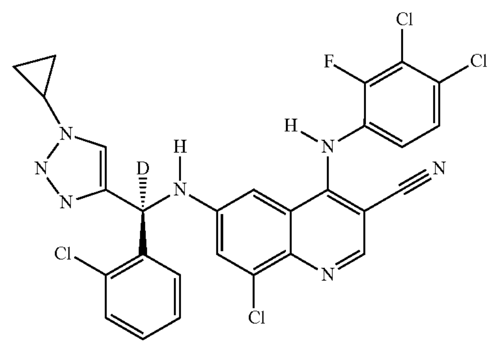 | (S)-8-chloro-6-(((2-chlorophenyl)(1-cyclopropyl-1H-1,2,3-triazol-4-yl)methyl-d)amino)-4-((3,4-dichloro-2-fluorophenyl)amino)quinoline-3-carbonitrile | 1 | ES/MS 613.1 (M + H+) |
| 184 | 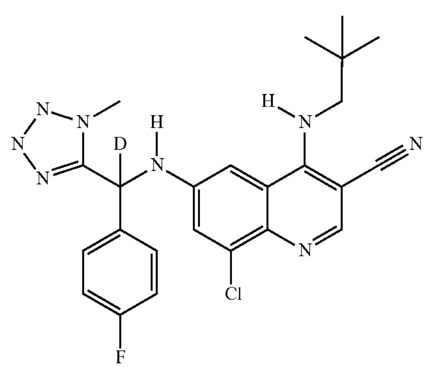 [SMILES: [2H]C(Nc1cc(Cl)c2ncc(C#N)c(NCC(C)(C)C)c2c1)(C1=NNNN1C)c1ccc(F)cc1] | 8-chloro-6-(((4-fluorophenyl)(1-methyl-1H-tetrazol-5-yl)methyl-d)amino)-4-(neopentylamino)quinoline-3-carbonitrile | 7 | ES/MS 480.2 (M + H+) |

TABLE 1-continued
| Compd | Structure | Name | Example/Procedure | ES/MS m/z |
|---|---|---|---|---|
| 185 | 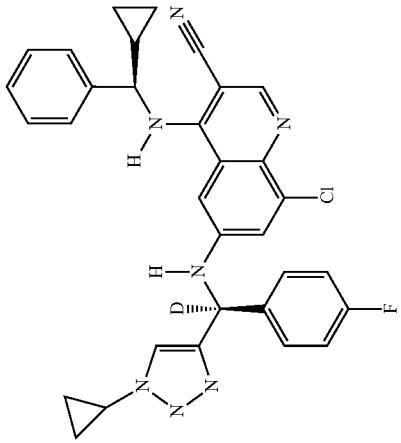 | 8-chloro-4-(((R)-cyclopropyl(phenyl)methyl)amino)-6-(((S)-(1-cyclopropyl-1H-1,2,3-triazol-4-yl)(4-fluorophenyl)methyl-d)amino)quinoline-3-carbonitrile | 1 | ES/MS 565.2 (M + H+) |
| 186 | 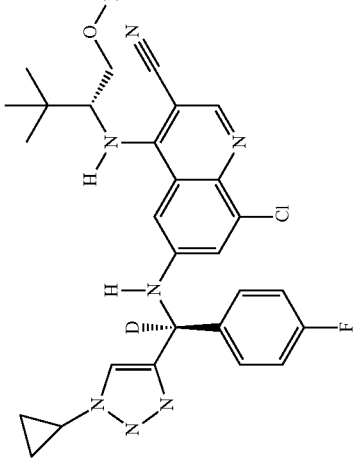 | 8-chloro-6-(((S)-(1-cyclopropyl-1H-1,2,3-triazol-4-yl)(4-fluorophenyl)methyl-d)amino)-4-(((R)-1-hydroxy-3,3-dimethylbutan-2-yl)amino)quinoline-3-carbonitrile | 1 | ES/MS 535.3 (M + H+) |

TABLE 1-continued
| Compd | Structure | Name | Example/Procedure | ES/MS m/z |
|---|---|---|---|---|
| 187 | 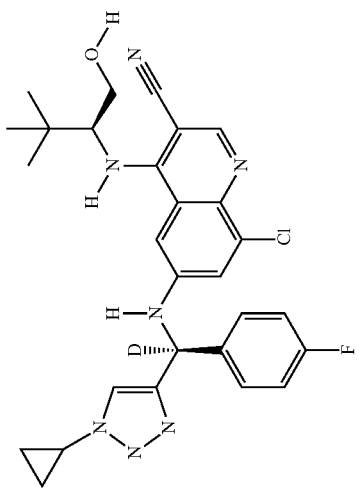 | 8-chloro-6-(((S)-(1-cyclopropyl-H-1,2,3-triazol-4-yl)(4-fluorophenyl)methyl-d)amino)-4-(((S)-1-hydroxy-3,3-dimethylbutan-2-yl)amino)quinoline-3-carbonitrile | 1 | ES/MS 535.4 (M + H+) |
| 188 | 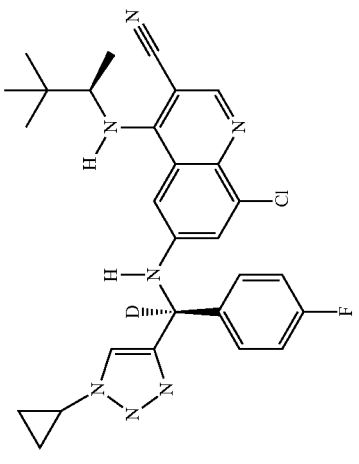 | 8-chloro-6-(((S)-(1-cyclopropyl-1H-1,2,3-triazol-4-yl)(4-fluorophenyl)methyl-d)amino)-4-(((R)-3,3-dimethylbutan-2-yl)amino)quinoline-3-carbonitrile | 1 | ES/MS 519.2 (M + H+) |

TABLE 1-continued

| Compd | Structure | Name | Example/Procedure | ES/MS m/z |
|---|---|---|---|---|
| 189 | 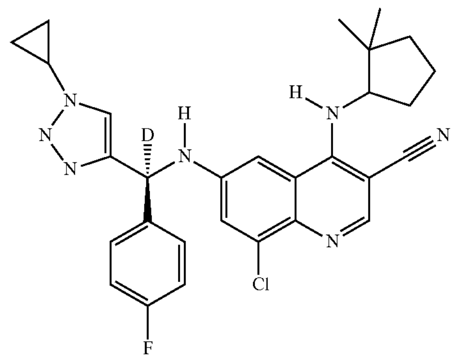 | 8-chloro-6-(((S)-(1-cyclopropyl-1H-1,2,3-triazol-4-yl)(4-fluorophenyl)methyl-d)amino)-4-(((2,2-dimethylcyclopentyl)amino)quinoline-3-carbonitrile | 1 | ES/MS 531.3 (M + H+) |
| 190 | 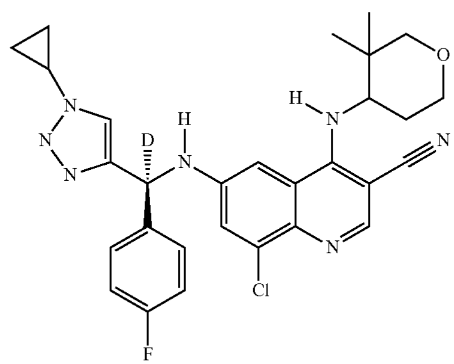 | 8-chloro-6-(((S)-(1-cyclopropyl-1H-1,2,3-triazol-4-yl)(4-fluorophenyl)methyl-d)amino)-4-(((3,3-dimethyltetrahydro-2H-pyran-4-yl)amino)quinoline-3-carbonitrile | 1 | ES/MS 547.5 (M + H+) |

TABLE 1-continued

| Compd | Structure | Name | Example/Procedure | ES/MS m/z |
|---|---|---|---|---|
| 191 | 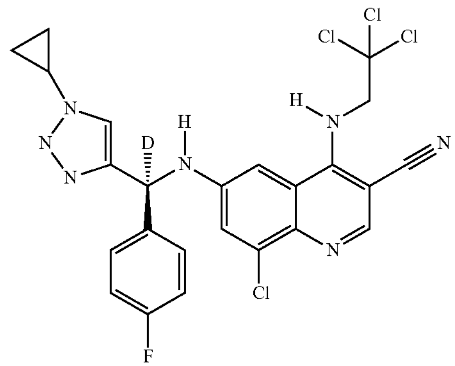 | (S)-8-chloro-6-(((1-cyclopropyl-1H-1,2,3-triazol-4-yl)(4-fluorophenyl)methyl-d)amino)-4-(((2,2,2-trichloroethyl)amino)quinoline-3-carbonitrile | 1 | ES/MS 565.3 (M + H+) |
| 192 | 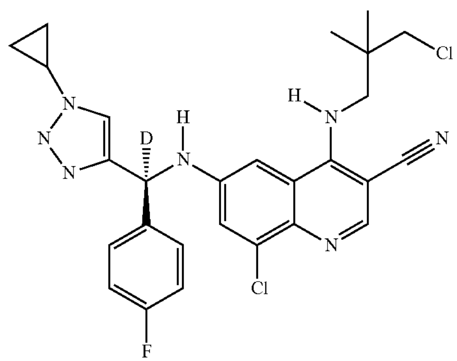 | (S)-8-chloro-4-((3-chloro-2,2-dimethylpropyl)amino)-6-(((1-cyclopropyl-1H-1,2,3-triazol-4-yl)(4-fluorophenyl)methyl-d)amino)quinoline-3-carbonitrile | 1 | ES/MS 539.3 (M + H+) |

TABLE 1-continued
| Compd | Structure | Name | Example/Procedure | ES/MS m/z |
|---|---|---|---|---|
| 193 | 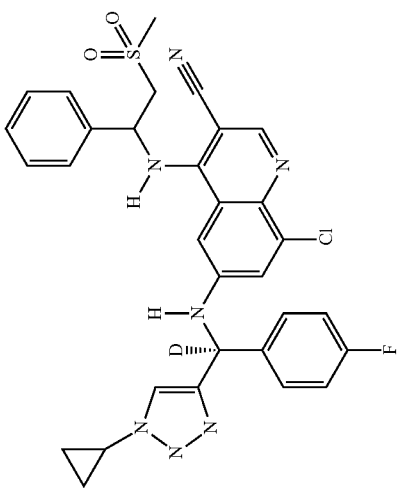 | 8-chloro-6-(((1-cyclopropyl-1H-1,2,3-triazol-4-yl)(4-fluorophenyl)methyl-d)amino)-4-((2-(methylsulfonyl)-1-phenylethyl)amino)quinoline-3-carbonitrile | 2 | ES/MS 617.0 (M + H+) |
| 194 | 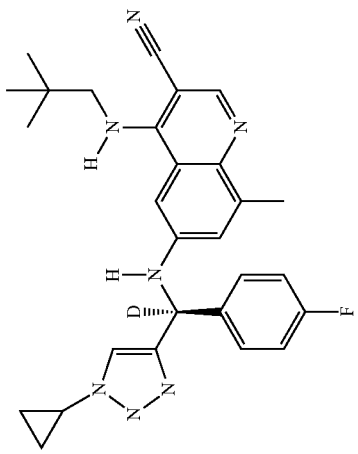 | (S)-6-(((1-cyclopropyl-1H-1,2,3-triazol-4-yl)(4-fluorophenyl)methyl-d)amino)-8-methyl-4-(neopentylamino)quinoline-3-carbonitrile | 1 | ES/MS 485.3 (M + H+) |

TABLE 1-continued

| Compd | Structure | Name | Example/Procedure | ES/MS m/z |
|---|---|---|---|---|
| 195 | 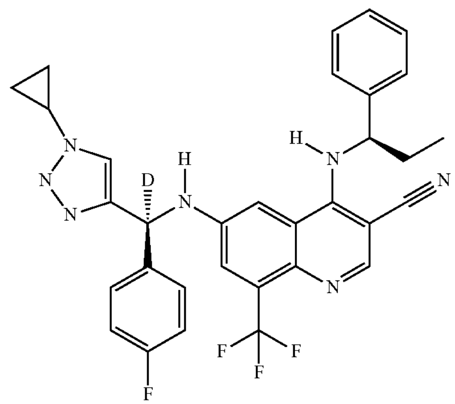 | 6-(((S)-(1-cyclopropyl-1H-1,2,3-triazol-4-yl)(4-fluorophenyl)methyl-d)amino)-4-(((R)-1-phenylpropyl)amino)-8-(trifluoromethyl)quinoline-3-carbonitrile | 2 | ES/MS 587.3 (M + H+) |
| 196 | 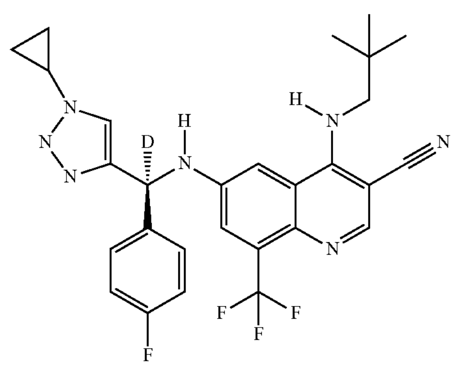 | (S)-6-(((1-cyclopropyl-1H-1,2,3-triazol-4-yl)(4-fluorophenyl)methyl-d)amino)-4-(neopentylamino)-8-(trifluoromethyl)quinoline-3-carbonitrile | 1 | ES/MS 539.2 (M + H+) |

TABLE 1-continued

| Compd | Structure | Name | Example/Procedure | ES/MS m/z |
|---|---|---|---|---|
| 197 | 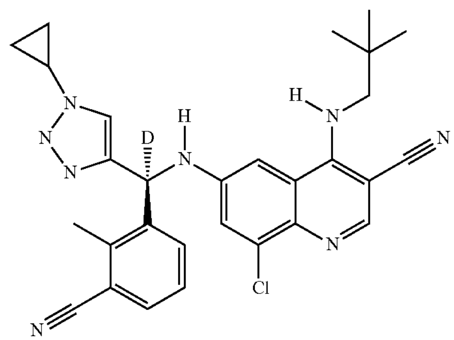 | (S)-8-chloro-6-(((3-cyano-2-methylphenyl)(1-cyclopropyl-1H-1,2,3-triazol-4-yl)methyl-d)amino)-4-(neopentylamino)quinoline-3-carbonitrile | 3 | ES/MS 526.4 (M + H+) |
| 198 | 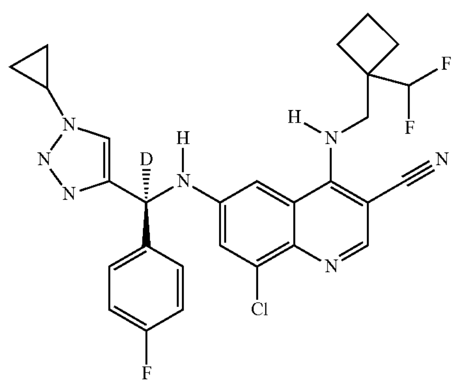 | (S)-8-chloro-6-(((1-cyclopropyl-1H-1,2,3-triazol-4-yl)(4-fluorophenyl)methyl-d)amino)-4-(((1-(difluoromethyl)cyclobutyl)methyl)amino)quinoline-3-carbonitrile | 3 | ES/MS 553.4 (M + H+) |

TABLE 1-continued

| Compd | Structure | Name | Example/Procedure | ES/MS m/z |
|---|---|---|---|---|
| 199 | 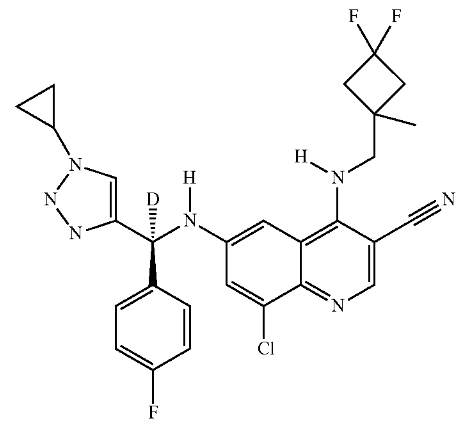 | (S)-8-chloro-6-(((1-cyclopropyl-1H-1,2,3-triazol-4-yl)(4-fluorophenyl)methyl-d)amino)-4-(((3,3-difluoro-1-methylcyclobutyl)methyl)amino)quinoline-3-carbonitrile | 3 | ES/MS 553.3 (M + H+) |
| 200 | 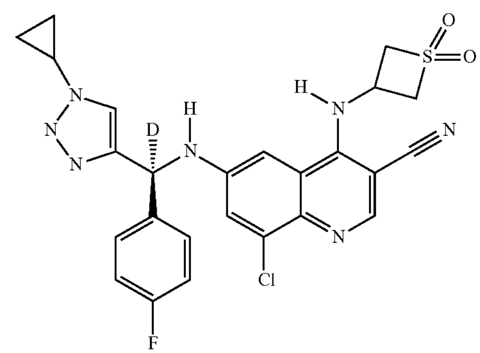 | (S)-8-chloro-6-(((1-cyclopropyl-1H-1,2,3-triazol-4-yl)(4-fluorophenyl)methyl-d)amino)-4-(((1,1-dioxidothietan-3-yl)amino)quinoline-3-carbonitrile | 3 | ES/MS 538.9 (M + H+) |

TABLE 1-continued

| Compd | Structure | Name | Example/Procedure | ES/MS m/z |
|---|---|---|---|---|
| 201 | 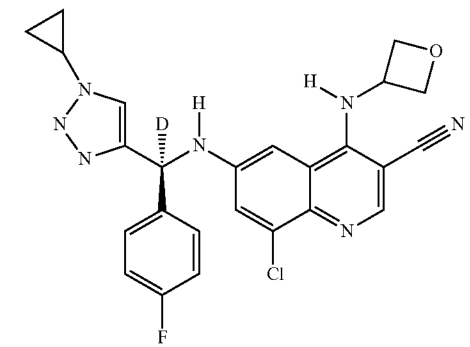 | (S)-8-chloro-6-(((1-cyclopropyl-1H-1,2,3-triazol-4-yl)(4-fluorophenyl)methyl-d)amino)-4-(oxetan-3-ylamino)quinoline-3-carbonitrile | 3 | ES/MS 491.1 (M + H+) |
| 202 | 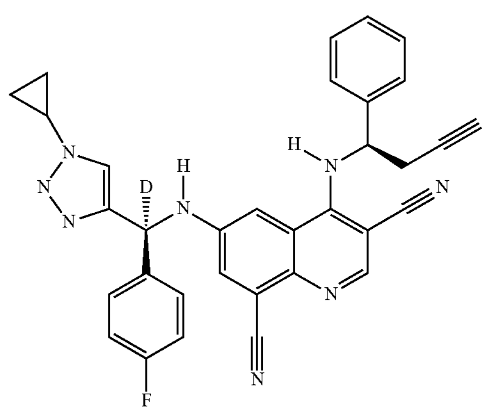 | 4-(((R)-2-cyano-1-phenylethyl)amino)-6-(((S)-(1-cyclopropyl-1H-1,2,3-triazol-4-yl)(4-fluorophenyl)methyl-d)amino)quinoline-3,8-dicarbonitrile | 1 | |

TABLE 1-continued

| Compd | Structure | Name | Example/Procedure | ES/MS m/z |
|---|---|---|---|---|
| 203 | 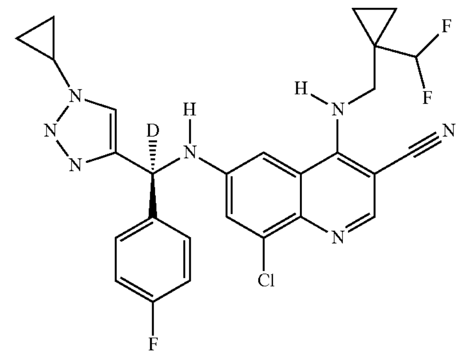 | (S)-8-chloro-6-(((1-cyclopropyl-1H-1,2,3-triazol-4-yl)(4-fluorophenyl)methyl-d)amino)-4-(((1-(difluoromethyl)cyclopropyl)methyl)amino)quinoline-3-carbonitrile | 1 | ES/MS 539.3 (M + H+) |
| 204 | 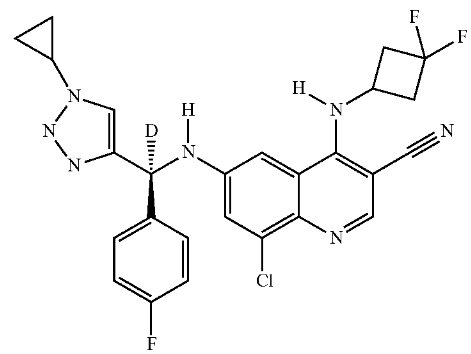 | (S)-8-chloro-6-(((1-cyclopropyl-1H-1,2,3-triazol-4-yl)(4-fluorophenyl)methyl-d)amino)-4-((3,3-difluorocyclobutyl)amino)quinoline-3-carbonitrile | 1 | ES/MS 526.2 (M + H+) |
| 205 | 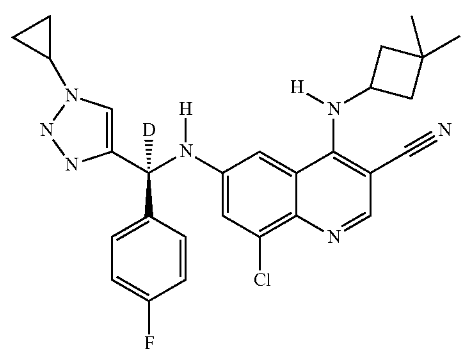 | (S)-8-chloro-6-(((1-cyclopropyl-1H-1,2,3-triazol-4-yl)(4-fluorophenyl)methyl-d)amino)-4-((3,3-dimethylcyclobutyl)amino)quinoline-3-carbonitrile | 1 | ES/MS 517.3 (M + H+) |

TABLE 1-continued

| Compd | Structure | Name | Example/Procedure | ES/MS m/z |
|---|---|---|---|---|
| 206 | 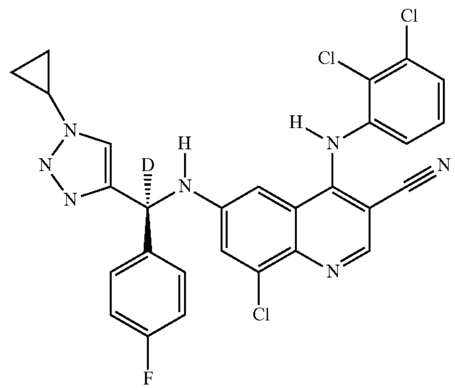 | (S)-8-chloro-6-(((1-cyclopropyl-1H-1,2,3-triazol-4-yl)(4-fluorophenyl)methyl-d)amino)-4-((2,3-dichlorophenyl)amino)quinoline-3-carbonitrile | 10 | ES/MS 579.3 (M + H+) |
| 207 | 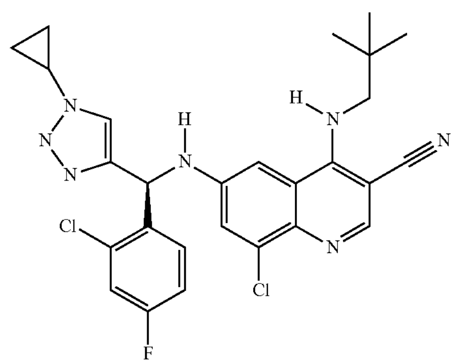 [SMILES: CC(C)(C)CNc1c(C#N)cnc2c(Cl)cc(N[C@H](C3=CN(C4CC4)NN3)c3ccc(F)cc3Cl)cc12] | (S)-8-chloro-6-(((2-chloro-4-fluorophenyl)(1-cyclopropyl-1H-1,2,3-triazol-4-yl)methyl)amino)-4-(neopentylamino)quinoline-3-carbonitrile | 1 | ES/MS 538.3 (M + H+) |

TABLE 1-continued

| Compd | Structure | Name | Example/Procedure | ES/MS m/z |
|---|---|---|---|---|
| 208 | 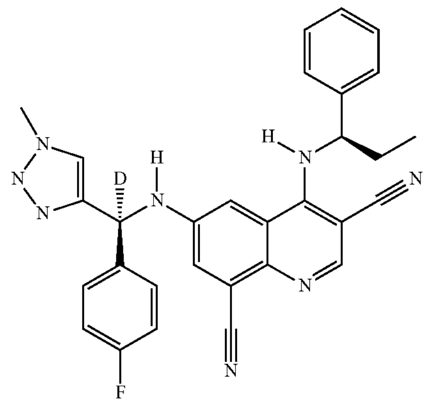 | 6-(((S)-(4-fluorophenyl)(1-methyl-1H-1,2,3-triazol-4-yl)methyl)amino)-4-(((R)-1-phenylpropyl)amino)quinoline-3,8-dicarbonitrile | 45 | ES/MS 518.2 (M + H+) |
| 209 | 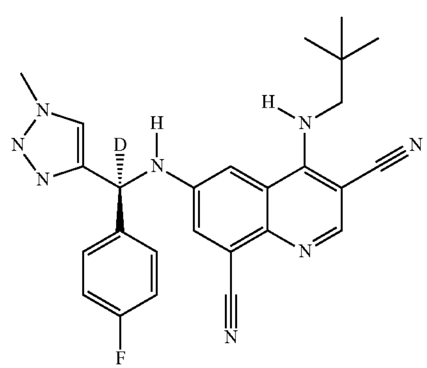 | (S)-6-(((4-fluorophenyl)(1-methyl-1H-1,2,3-triazol-4-yl)methyl)amino)-4-(neopentylamino)quinoline-3,8-dicarbonitrile | 45 | ES/MS 470.3 (M + H+) |

TABLE 1-continued

| Compd | Structure | Name | Example/Procedure | ES/MS m/z |
|---|---|---|---|---|
| 210 | 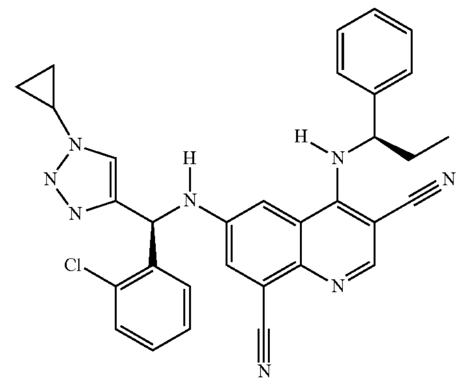 [SMILES: CC[C@@H](Nc1c(C#N)cnc2c(C#N)cc(N[C@H](C3=CN(C4CC4)NN3)c3ccccc3Cl)cc12)c1ccccc1] | 6-(((S)-(2-chlorophenyl)(1-cyclopropyl-1H-1,2,3-triazol-4-yl)methyl)amino)-4-(((R)-1-phenylpropyl)amino)quinoline-3,8-dicarbonitrile | 1 | ES/MS 559.2 (M + H+) |
| 211 | 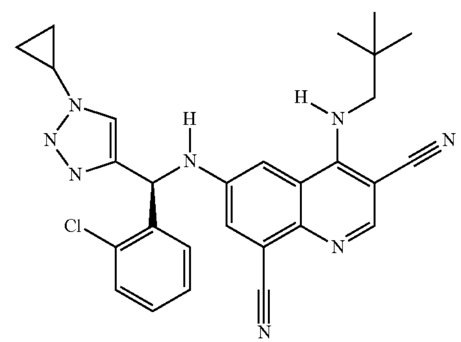 [SMILES: CC(C)(C)CNc1c(C#N)cnc2c(C#N)cc(N[C@H](C3=CN(C4CC4)NN3)c3ccccc3Cl)cc12] | (S)-6-(((2-chlorophenyl)(1-cyclopropyl-1H-1,2,3-triazol-4-yl)methyl)amino)-4-(neopentylamino)quinoline-3,8-dicarbonitrile | 1 | ES/MS 511.2 (M + H+) |
| 212 | 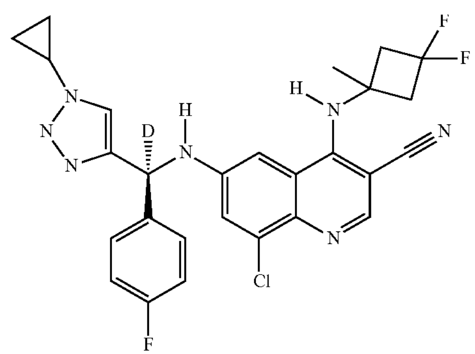 | (S)-8-chloro-6-(((1-cyclopropyl-1H-1,2,3-triazol-4-yl)(4-fluorophenyl)methyl-d)amino)-4-((3,3-difluoro-1-methylcyclobutyl)amino)quinoline-3-carbonitrile | 3 | ES/MS 539.1 (M + H+) |

TABLE 1-continued

| Compd | Structure | Name | Example/Procedure | ES/MS m/z |
|---|---|---|---|---|
| 213 | 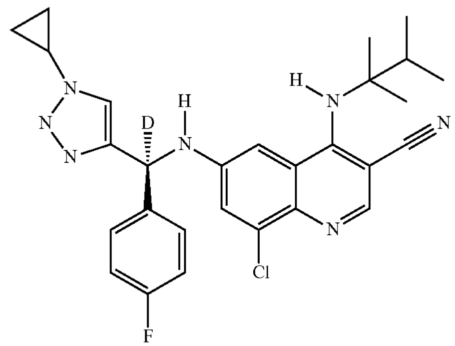 | (S)-8-chloro-6-(((1-cyclopropyl-1H-1,2,3-triazol-4-yl)(4-fluorophenyl)methyl-d)amino)-4-((2,3-dimethylbutan-2-yl)amino)quinoline-3-carbonitrile | 3 | ES/MS 519.2 (M + H+) |
| 214 | 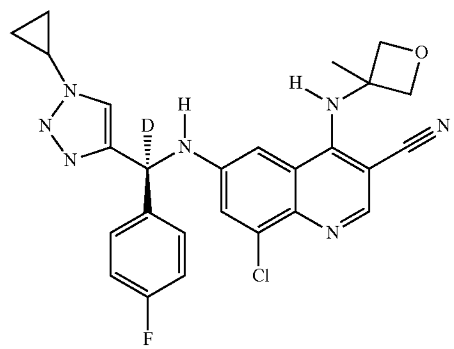 | (S)-8-chloro-6-(((1-cyclopropyl-1H-1,2,3-triazol-4-yl)(4-fluorophenyl)methyl-d)amino)-4-((3-methyloxetan-3-yl)amino)quinoline-3-carbonitrile | 3 | ES/MS 505.2 (M + H+) |
| 215 | 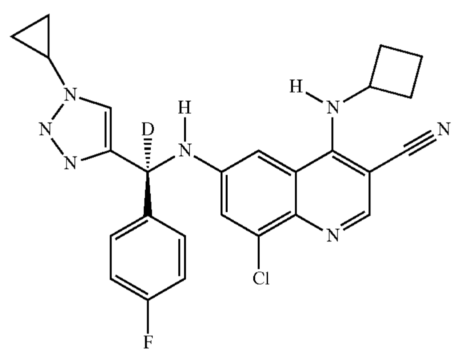 | (S)-8-chloro-4-(cyclobutylamino)-6-(((1-cyclopropyl-1H-1,2,3-triazol-4-yl)(4-fluorophenyl)methyl-d)amino)quinoline-3-carbonitrile | 3 | ES/MS 489.1 (M + H+) |

TABLE 1-continued

| Compd | Structure | Name | Example/Procedure | ES/MS m/z |
|---|---|---|---|---|
| 216 | 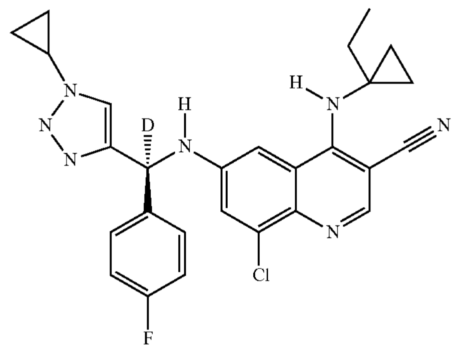 | (S)-8-chloro-6-(((1-cyclopropyl-1H-1,2,3-triazol-4-yl)(4-fluorophenyl)methyl)amino)-4-((1-ethylcyclopropyl)amino)quinoline-3-carbonitrile | 3 | ES/MS 503.3 (M + H+) |
| 217 | 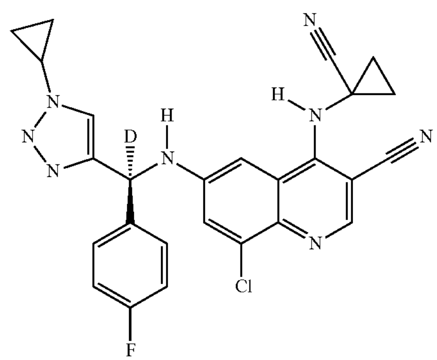 | (S)-8-chloro-4-((1-cyanocyclopropyl)amino)-6-(((1-cyclopropyl-1H-1,2,3-triazol-4-yl)(4-fluorophenyl)methyl)amino)quinoline-3-carbonitrile | 3 | ES/MS 500.1 (M + H+) |

TABLE 1-continued

| Compd | Structure | Name | Example/Procedure | ES/MS m/z |
|---|---|---|---|---|
| 218 | 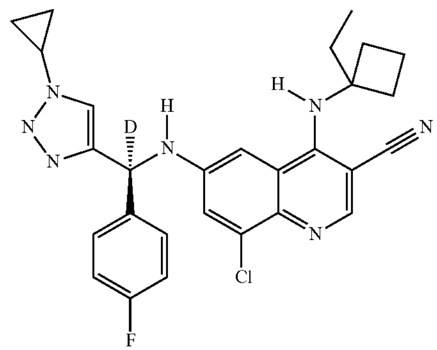 | (S)-8-chloro-6-(((1-cyclopropyl-1H-1,2,3-triazol-4-yl)(4-fluorophenyl)methyl)amino)-4-((1-ethylcyclobutyl)amino)quinoline-3-carbonitrile | 3 | ES/MS 517.2 (M + H+) |
| 219 | 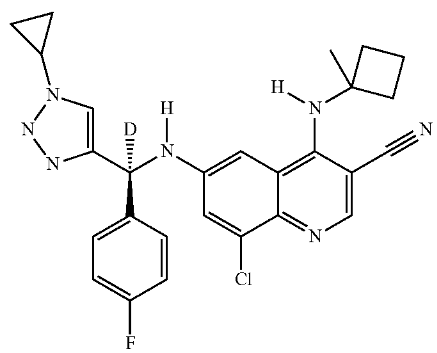 | (S)-8-chloro-6-(((1-cyclopropyl-1H-1,2,3-triazol-4-yl)(4-fluorophenyl)methyl)amino)-4-(((1-methylcyclobutyl)amino)quinoline-3-carbonitrile | 3 | ES/MS 503.1 (M + H+) |
| 220 | 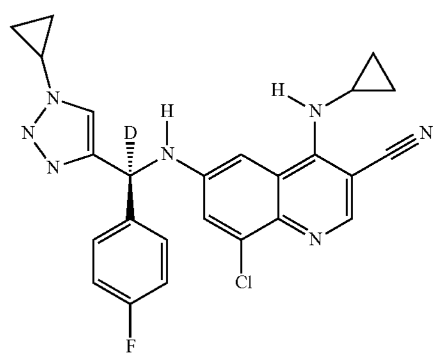 | (S)-8-chloro-6-(((1-cyclopropyl-1H-1,2,3-triazol-4-yl)(4-fluorophenyl)methyl)amino)-4-(cyclopropylamino)quinoline-3-carbonitrile | 3 | ES/MS 475.1 (M + H+) |

TABLE 1-continued
| Compd | Structure | Name | Example/Procedure | ES/MS m/z |
|---|---|---|---|---|
| 221 | 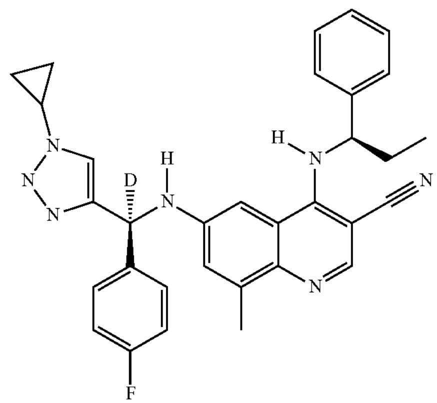 | 6-(((S)-(1-cyclopropyl-1H-1,2,3-triazol-4-yl)(4-fluorophenyl)methyl)amino)-8-methyl-4-(((R)-1-phenylpropyl)amino)quinoline-3-carbonitrile | 12 | ES/MS 533.2 (M + H+) |
| 222 | 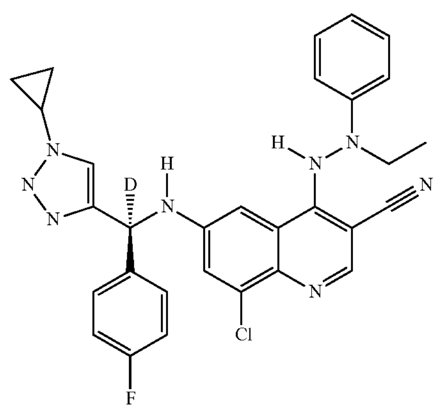 | (S)-8-chloro-6-(((1-cyclopropyl-1H-1,2,3-triazol-4-yl)(4-fluorophenyl)methyl)amino)-4-(2-ethyl-2-phenylhydrazinyl)quinoline-3-carbonitrile | 1 | ES/MS 554.1 (M + H+) |

TABLE 1-continued

| Compd | Structure | Name | Example/Procedure | ES/MS m/z |
|---|---|---|---|---|
| 223 | 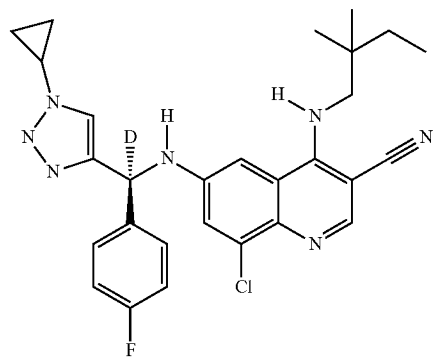 | (S)-8-chloro-6-(((1-cyclopropyl-1H-1,2,3-triazol-4-yl)(4-fluorophenyl)methyl-d)amino)-4-((2,2-dimethylbutyl)amino)quinoline-3-carbonitrile | 1 | ES/MS 519.3 (M + H+) |
| 224 | 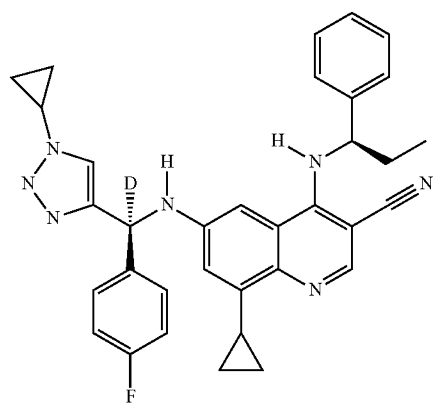 | 8-cyclopropyl-6-(((S)-(1-cyclopropyl-1H-1,2,3-triazol-4-yl)(4-fluorophenyl)methyl-d)amino)-4-(((R)-1-phenylpropyl)amino)quinoline-3-carbonitrile | 12 | ES/MS 559.3 (M + H+) |

TABLE 1-continued

| Compd | Structure | Name | Example/Procedure | ES/MS m/z |
|---|---|---|---|---|
| 225 | 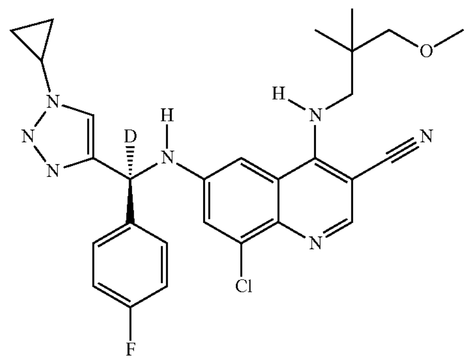 | (S)-8-chloro-6-(((1-cyclopropyl-1H-1,2,3-triazol-4-yl)(4-fluorophenyl)methyl-d)amino)-4-((3-methoxy-2,2-dimethylpropyl)amino)quinoline-3-carbonitrile | 1 | ES/MS 535.4 (M + H+) |
| 226 | 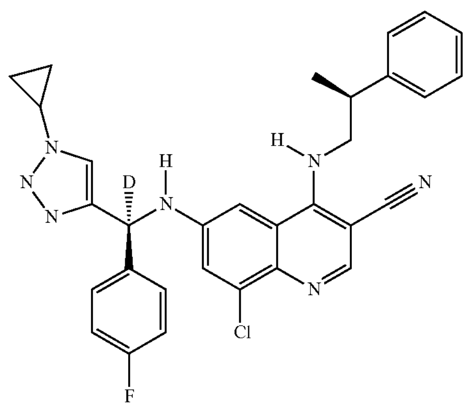 | 8-chloro-6-(((S)-(1-cyclopropyl-1H-1,2,3-triazol-4-yl)(4-fluorophenyl)methyl-d)amino)-4-(((S)-2-phenylpropyl)amino)quinoline-3-carbonitrile | 1 | ES/MS 553.0 (M + H+) |

TABLE 1-continued
| Compd | Structure | Name | Example/Procedure | ES/MS m/z |
|---|---|---|---|---|
| 227 | 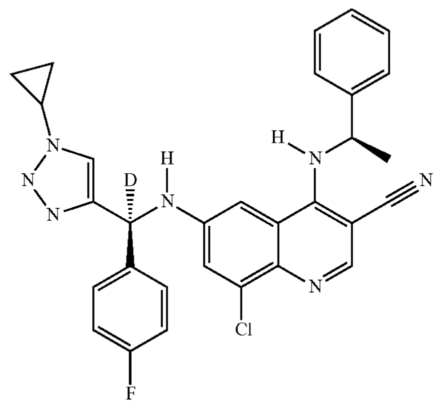 | 8-chloro-6-(((S)-(1-cyclopropyl-1H-1,2,3-triazol-4-yl)(4-fluorophenyl)methyl-d)amino)-4-(((R)-1-phenylethyl)amino)quinoline-3-carbonitrile | 1 | ES/MS 539.2 (M + H+) |
| 228 | 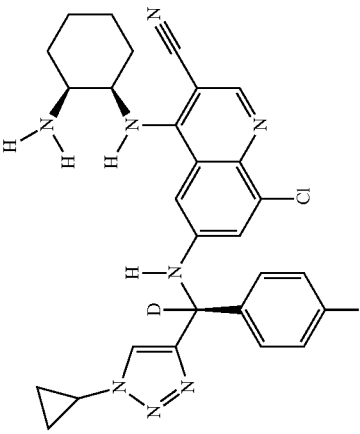 | 4-(((1R,2S)-2-aminocyclohexyl)amino)-8-chloro-6-(((S)-(1-cyclopropyl-1H-1,2,3-triazol-4-yl)(4-fluorophenyl)methyl-d)amino)quinoline-3-carbonitrile | 1 | ES/MS 532.2 (M + H+) |

TABLE 1-continued
| Compd | Structure | Name | Example/Procedure | ES/MS m/z |
|---|---|---|---|---|
| 229 | 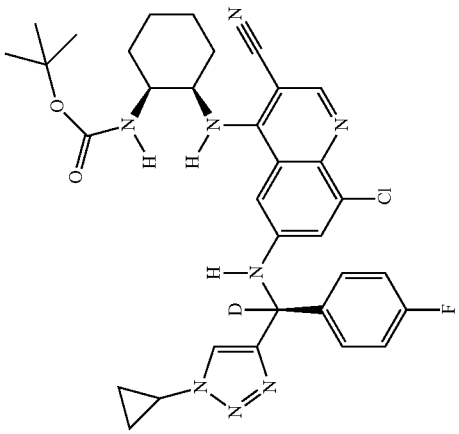 | tert-butyl ((1S,2R)-2-((8-chloro-3-cyano-6-(((S)-(1-cyclopropyl-1H-1,2,3-triazol-4-yl)(4-fluorophenyl)methyl-d)amino)quinolin-4-yl)amino)cyclohexyl)carbamate | 1 | ES/MS 632.3 (M + H+) |
| 230 | 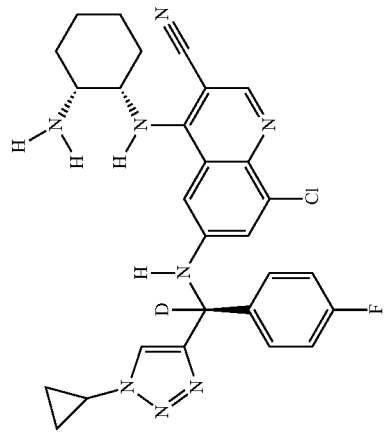 | 4-(((1S,2R)-2-aminocyclohexyl)amino)-8-chloro-6-(((S)-(1-cyclopropyl-1H-1,2,3-triazol-4-yl)(4-fluorophenyl)methyl-d)amino)quinoline-3-carbonitrile | 1 | ES/MS 532.2 (M + H+) |

TABLE 1-continued
| Compd | Structure | Name | Example/Procedure | ES/MS m/z |
|---|---|---|---|---|
| 231 | 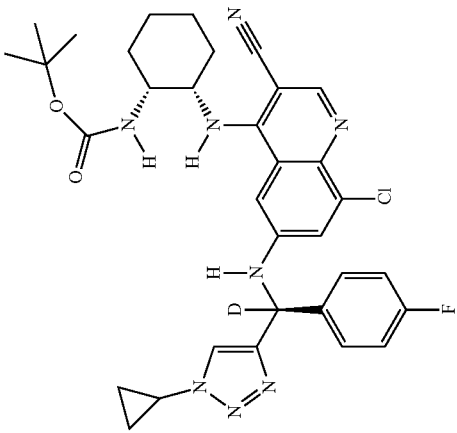 | tert-butyl ((1R,2S)-2-((8-chloro-3-cyano-6-(((S)-(1-cyclopropyl-1H-1,2,3-triazol-4-yl)(4-fluorophenyl)methyl-d)amino)quinolin-4-yl)amino)cyclohexyl)carbamate | 1 | ES/MS 632.3 (M + H+) |
| 232 | 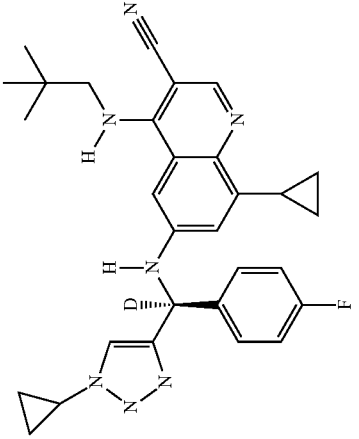 | (S)-8-cyclopropyl-6-(((1-cyclopropyl-1H-1,2,3-triazol-4-yl)(4-fluorophenyl)methyl-d)amino)-4-(neopentylamino)quinoline-3-carbonitrile | 12 | ES/MS 511.3 (M + H+) |

TABLE 1-continued

| Compd | Structure | Name | Example/Procedure | ES/MS m/z |
|---|---|---|---|---|
| 233 | 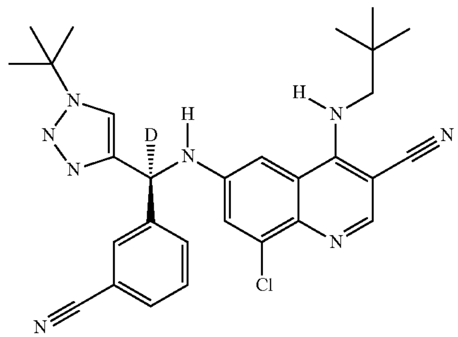 | (S)-6-((((1-(tert-butyl)-1H-1,2,3-triazol-4-yl)(3-cyanophenyl)methyl-d)amino)-8-chloro-4-(neopentylamino)quinoline-3-carbonitrile | 1 | ES/MS 528.2 (M + H+) |
| 234 | 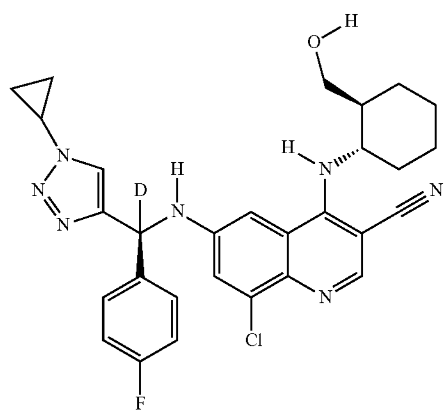 [SMILES: [2H][C@@](Nc1cc(Cl)c2ncc(C#N)c(N[C@H]3CCCC[C@@H]3CO)c2c1)(c1ccc(F)cc1)c1cn(C2CC2)nn1] | 8-chloro-6-(((S)-(1-cyclopropyl-1H-1,2,3-triazol-4-yl)(4-fluorophenyl)methyl-d)amino)-4-(((1S,2S)-2-(hydroxymethyl)cyclohexyl)amino)quinoline-3-carbonitrile | 1 | ES/MS 547.3 (M + H+) |

TABLE 1-continued

| Compd | Structure | Name | Example/Procedure | ES/MS m/z |
|---|---|---|---|---|
| 235 | 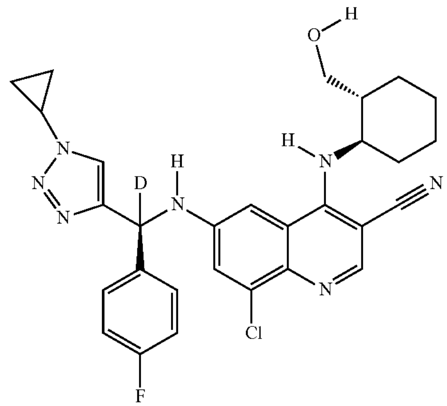 [SMILES: [2H][C@@](Nc1cc(Cl)c2ncc(C#N)c(N[C@@H]3CCCC[C@H]3CO)c2c1)(c1ccc(F)cc1)c1cn(C2CC2)nn1] | 8-chloro-6-(((S)-(1-cyclopropyl-1H-1,2,3-triazol-4-yl)(4-fluorophenyl)methyl-d)amino)-4-(((1R,2R)-2-(hydroxymethyl)cyclohexyl)amino)quinoline-3-carbonitrile | 1 | ES/MS 547.3 (M + H+) |
| 236 | 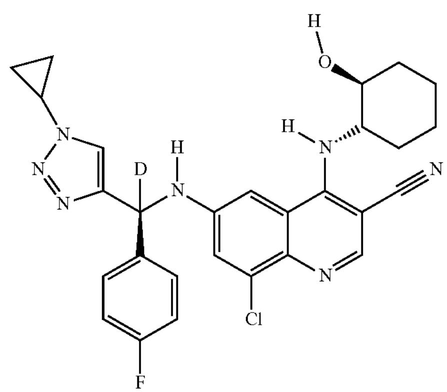 | 8-chloro-6-(((S)-(1-cyclopropyl-1H-1,2,3-triazol-4-yl)(4-fluorophenyl)methyl-d)amino)-4-(((1S,2S)-2-hydroxycyclohexyl)amino)quinoline-3-carbonitrile | 1 | ES/MS 533.3 (M + H+) |

TABLE 1-continued

| Compd | Structure | Name | Example/Procedure | ES/MS m/z |
|---|---|---|---|---|
| 237 | 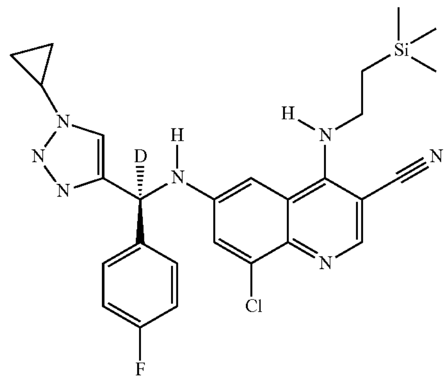 | (S)-8-chloro-6-(((1-cyclopropyl-1H-1,2,3-triazol-4-yl)(4-fluorophenyl)methyl-d)amino)-4-((2-(trimethylsilyl)ethyl)amino)quinoline-3-carbonitrile | 3 | ES/MS 535.2 (M + H+) |
| 238 | 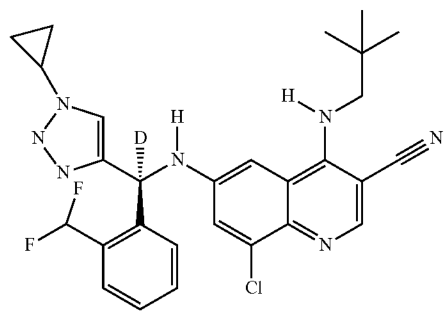 | (S)-8-chloro-6-(((1-cyclopropyl-1H-1,2,3-triazol-4-yl)(2-(difluoromethyl)phenyl)methyl-d)amino)-4-(neopentylamino)quinoline-3-carbonitrile | 3 | ES/MS 537.4 (M + H+) |
| 239 | 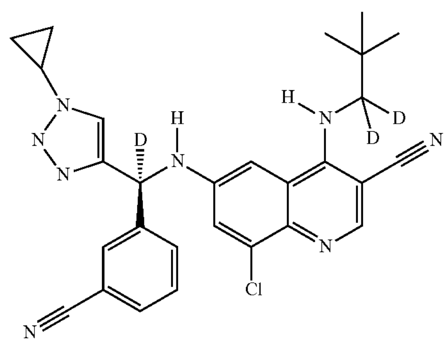 | (S)-8-chloro-6-(((3-cyanophenyl)(1-cyclopropyl-1H-1,2,3-triazol-4-yl)methyl-d)amino)-4-((2,2-dimethylpropyl-1,1-d2)amino)quinoline-3-carbonitrile | 3 | ES/MS 514.4 (M + H+) |

TABLE 1-continued

| Compd | Structure | Name | Example/Procedure | ES/MS m/z |
|---|---|---|---|---|
| 240 | 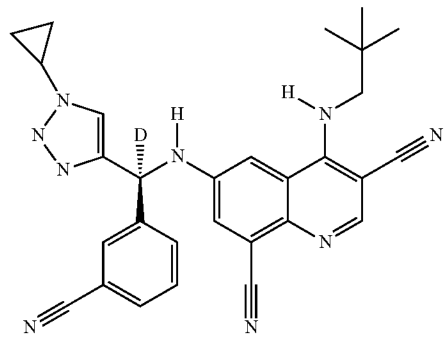 | (S)-6-(((3-cyanophenyl)(1-cyclopropyl-1H-1,2,3-triazol-4-yl)methyl-d)amino)-4-(neopentylamino)quinoline-3,8-dicarbonitrile | 1 | ES/MS 503.2 (M + H+) |
| 241 | 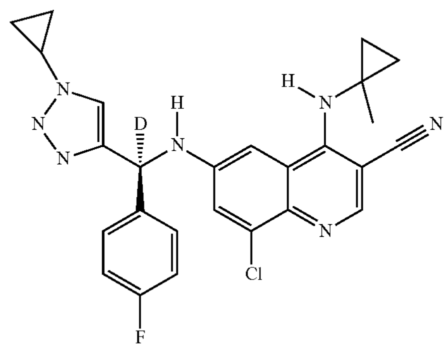 | (S)-8-chloro-6-(((1-cyclopropyl-1H-1,2,3-triazol-4-yl)(4-fluorophenyl)methyl-d)amino)-4-((1-methylcyclopropyl)amino)quinoline-3-carbonitrile | 3 | ES/MS 489.3 (M + H+) |
| 242 | 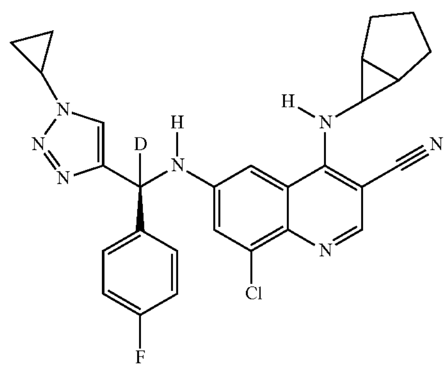 [SMILES: [2H][C@@](Nc1cc(Cl)c2ncc(C#N)c(NC3C4CCCC43)c2c1)(c1ccc(F)cc1)c1cn(C2CC2)nn1] | 4-(bicyclo[3.1.0]hexan-6-ylamino)-8-chloro-6-(((S)-(1-cyclopropyl-1H-1,2,3-triazol-4-yl)(4-fluorophenyl)methyl-d)amino)quinoline-3-carbonitrile | 1 | ES/MS 515.2 (M + H+) |

TABLE 1-continued

| Compd | Structure | Name | Example/Procedure | ES/MS m/z |
|---|---|---|---|---|
| 243 | 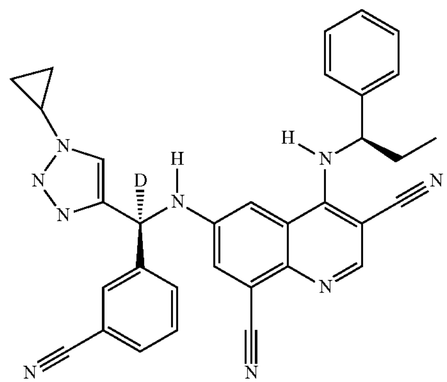 | 6-(((S)-(3-cyanophenyl)(1-cyclopropyl-1H-1,2,3-triazol-4-yl)methyl)amino)-4-(((R)-1-phenylpropyl)amino)quinoline-3,8-dicarbonitrile | 1 | ES/MS 551.2 (M + H+) |
| 244 | 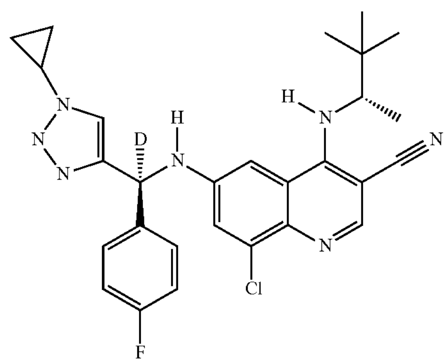 | 8-chloro-6-(((S)-(1-cyclopropyl-1H-1,2,3-triazol-4-yl)(4-fluorophenyl)methyl)amino)-4-(((S)-3,3-dimethylbutan-2-yl)amino)quinoline-3-carbonitrile | 1 | ES/MS 519.3 (M + H+) |

TABLE 1-continued

| Compd | Structure | Name | Example/Procedure | ES/MS m/z |
|---|---|---|---|---|
| 245 | 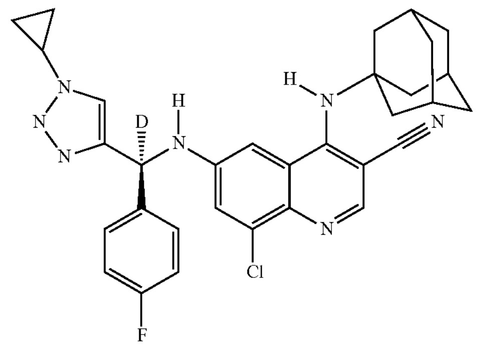 | 4-(((3R,5R,7R)-adamantan-1-yl)amino)-8-chloro-6-((((S)-(1-cyclopropyl-1H-1,2,3-triazol-4-yl)(4-fluorophenyl)methyl-d)amino)quinoline-3-carbonitrile | 1 | ES/MS 569.4 (M + H+) |
| 246 | 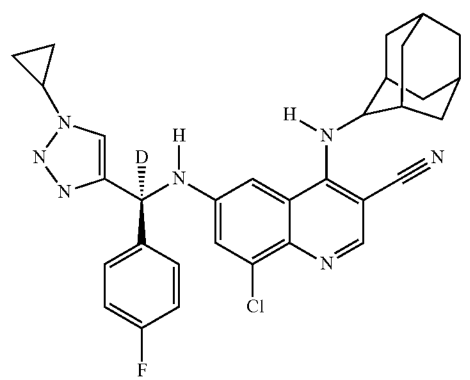 | 4-(((1S,3S,5S,7S)-adamantan-2-yl)amino)-8-chloro-6-((((S)-(1-cyclopropyl-1H-1,2,3-triazol-4-yl)(4-fluorophenyl)methyl-d)amino)quinoline-3-carbonitrile | 1 | ES/MS 569.2 (M + H+) |

TABLE 1-continued

| Compd | Structure | Name | Example/Procedure | ES/MS m/z |
|---|---|---|---|---|
| 247 | 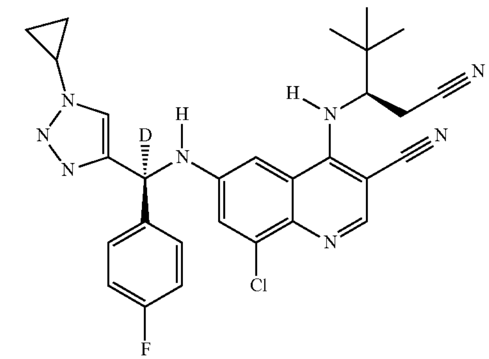 | 8-chloro-4-(((R)-1-cyano-3,3-dimethylbutan-2-yl)amino)-6-(((S)-(1-cyclopropyl-1H-1,2,3-triazol-4-yl)(4-fluorophenyl)methyl-d)amino)quinoline-3-carbonitrile | 1 | ES/MS 544.3 (M + H+) |
| 248 | 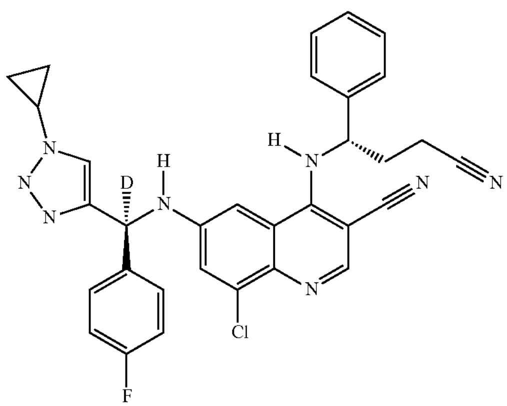 | 8-chloro-4-(((S)-3-cyano-1-phenylpropyl)amino)-6-(((S)-(1-cyclopropyl-1H-1,2,3-triazol-4-yl)(4-fluorophenyl)methyl-d)amino)quinoline-3-carbonitrile | 1 | ES/MS 578.3 (M + H+) |

TABLE 1-continued
| Compd | Structure | Name | Example/Procedure | ES/MS m/z |
|---|---|---|---|---|
| 249 | 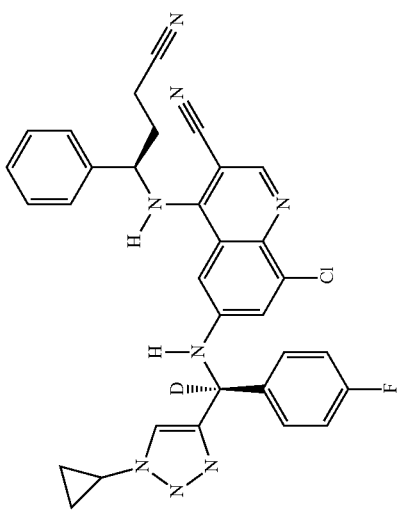 | 8-chloro-4-(((R)-3-cyano-1-phenylpropyl)amino)-6-(((S)-(1-cyclopropyl-1H-1,2,3-triazol-4-yl)(4-fluorophenyl)methyl-d)amino)quinoline-3-carbonitrile | 1 | ES/MS 578.2 (M + H+) |
| 250 | 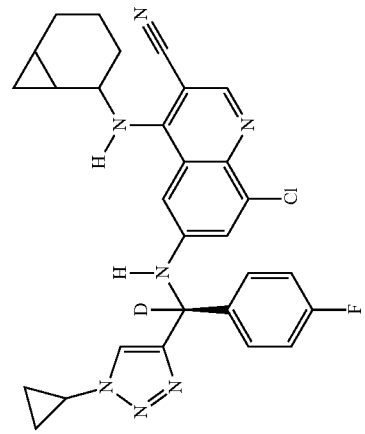 | 4-(bicyclo[4.1.0]heptan-2-ylamino)-8-chloro-6-(((S)-(1-cyclopropyl-1H-1,2,3-triazol-4-yl)(4-fluorophenyl)methyl-d)amino)quinoline-3-carbonitrile | 1 | ES/MS 529.3 (M + H+) |

TABLE 1-continued
| Compd | Structure | Name | Example/Procedure | ES/MS m/z |
|---|---|---|---|---|
| 251 | 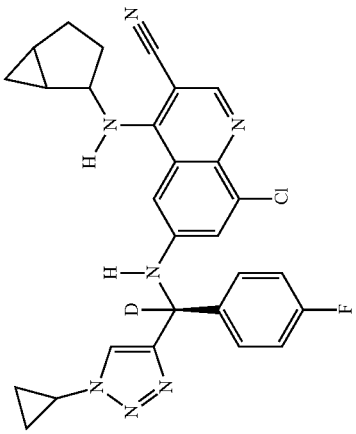 | 4-(bicyclo[3.1.0]hexan-2-ylamino)-8-chloro-6-(((S)-(1-cyclopropyl-1H-1,2,3-triazol-4-yl)(4-fluorophenyl)methyl-d)amino)quinoline-3-carbonitrile | 1 | ES/MS 515.3 (M + H+) |
| 252 | 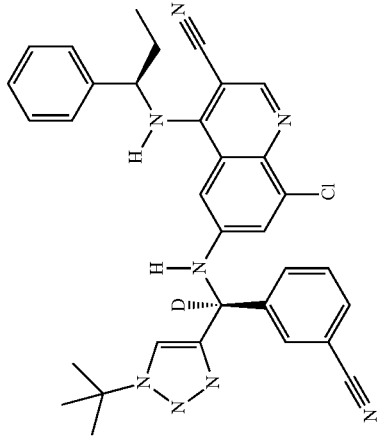 | 6-(((S)-(1-(tert-butyl)-1H-1,2,3-triazol-4-yl)(3-cyanophenyl)methyl-d)amino)-8-chloro-4-(((R)-1-phenylpropyl)amino)quinoline-3-carbonitrile | 2 | ES/MS 576.2 (M + H+) |

TABLE 1-continued

| Compd | Structure | Name | Example/Procedure | ES/MS m/z |
|---|---|---|---|---|
| 253 | 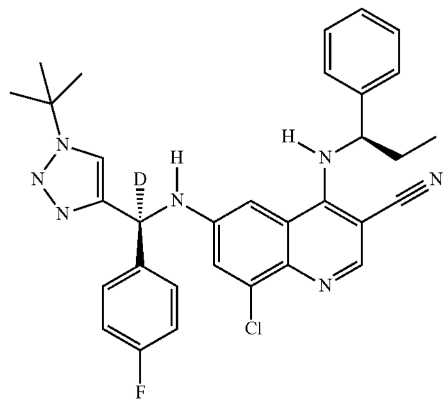 | 6-(((S)-(1-(tert-butyl)-1H-1,2,3-triazol-4-yl)(4-fluorophenyl)methyl-d)amino)-8-chloro-4-(((R)-1-phenylpropyl)amino)quinoline-3-carbonitrile | 2 | ES/MS 569.2 (M + H+) |
| 254 | 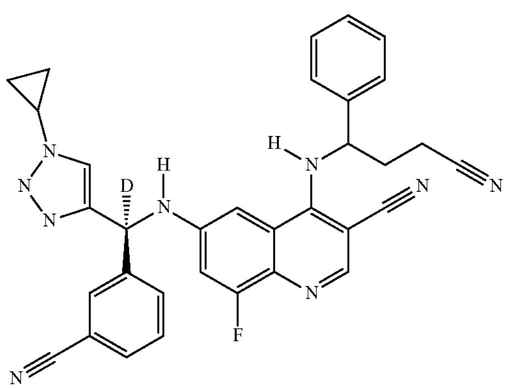 | 4-((3-cyano-1-phenylpropyl)amino)-6-(((S)-(3-cyanophenyl)(1-cyclopropyl-1H-1,2,3-triazol-4-yl)methyl-d)amino)-8-fluoroquinoline-3-carbonitrile | 1 | ES/MS 569.2 (M + H+) |

TABLE 1-continued
| Compd | Name | Structure | Example/Procedure | ES/MS m/z |
|---|---|---|---|---|
| 255 | 4-((3-cyano-1-phenylpropyl)amino)-6-(((S)-(1-cyclopropyl-1H-1,2,3-triazol-4-yl)(4-fluorophenyl)methyl-d)amino)-8-fluoroquinoline-3-carbonitrile | 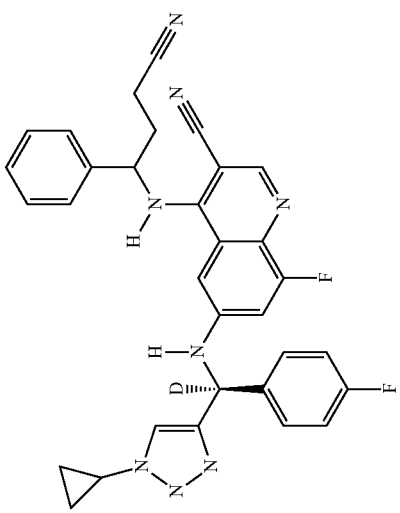 | 1 | ES/MS 562.2 (M + H+) |
| 256 | (S)-6-(((3-cyanophenyl)(1-cyclopropyl-1H-1,2,3-triazol-4-yl)methyl-d)amino)-8-fluoro-4-(neopentylamino)quinoline-3-carbonitrile | 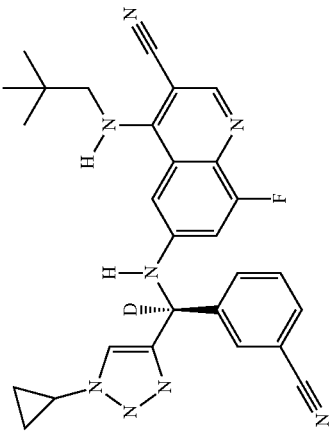 | 1 | ES/MS 496.2 (M + H+) |

TABLE 1-continued

| Compd | Structure | Name | Example/Procedure | ES/MS m/z |
|---|---|---|---|---|
| 257 | 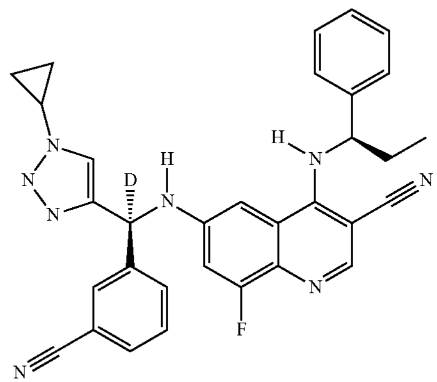 | 6-(((S)-(3-cyanophenyl)(1-cyclopropyl-1H-1,2,3-triazol-4-yl)methyl-d)amino)-8-fluoro-4-(((R)-1-phenylpropyl)amino)quinoline-3-carbonitrile | 1 | ES/MS 544.3 (M + H+) |
| 258 | 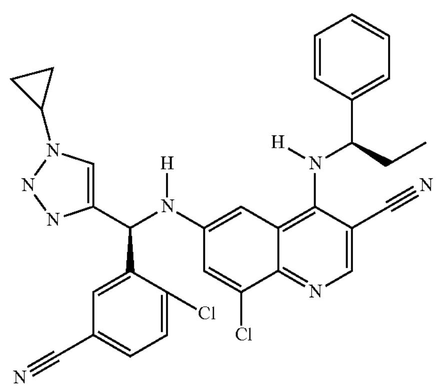 [SMILES: CC[C@@H](Nc1c(C#N)cnc2c(Cl)cc(N[C@H](C3=CN(C4CC4)NN3)c3cc(C#N)ccc3Cl)cc12)c1ccccc1] | 8-chloro-6-(((S)-(2-chloro-5-cyanophenyl)(1-cyclopropyl-1H-1,2,3-triazol-4-yl)methyl)amino)-4-(((R)-1-phenylpropyl)amino)quinoline-3-carbonitrile | 3 | ES/MS 593.3 (M + H+) |

TABLE 1-continued

| Compd | Structure | Name | Example/Procedure | ES/MS m/z |
|---|---|---|---|---|
| 259 | 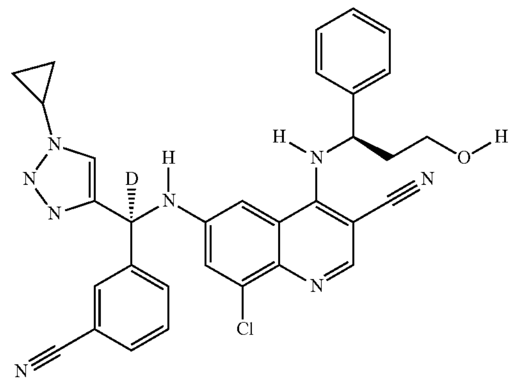 [SMILES: [2H][C@@](Nc1cc(Cl)c2ncc(C#N)c(N[C@H](CCO)c3ccccc3)c2c1)(C1=CN(C2CC2)NN1)c1cccc(C#N)c1] | 8-chloro-6-(((3-cyanophenyl)(1-cyclopropyl-1H-1,2,3-triazol-4-yl)methyl-d)amino)-4-(((R)-3-hydroxy-1-phenylpropyl)amino)quinoline-3-carbonitrile | 2 | ES/MS 576.1 (M + H+) |
| 260 | 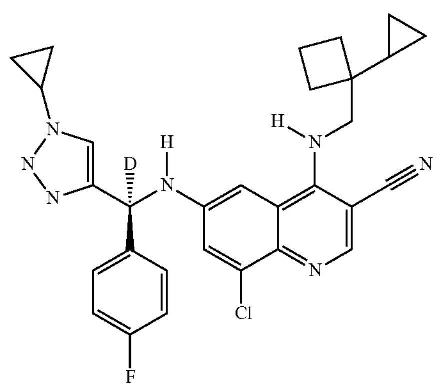 | (S)-8-chloro-6-(((1-cyclopropyl-1H-1,2,3-triazol-4-yl)(4-fluorophenyl)methyl-d)amino)-4-(((1-cyclopropylcyclobutyl)methyl)amino)-quinoline-3-carbonitrile | 3 | ES/MS 543.3 (M + H+) |

TABLE 1-continued
| Compd | Structure | Name | Example/Procedure | ES/MS m/z |
|---|---|---|---|---|
| 261 | 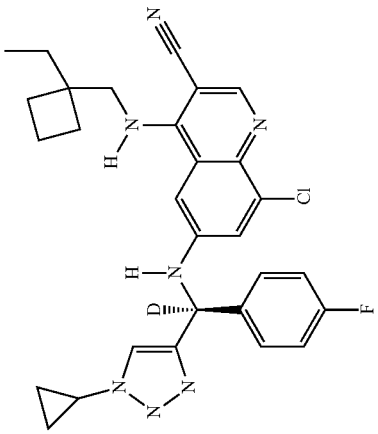 | (S)-8-chloro-6-((((1-cyclopropyl-1H-1,2,3-triazol-4-yl)(4-fluorophenyl)methyl-d)amino)-4-(((1-ethylcyclobutyl)methyl)amino)-quinoline-3-carbonitrile | 3 | ES/MS 531.4 (M + H+) |
| 262 | 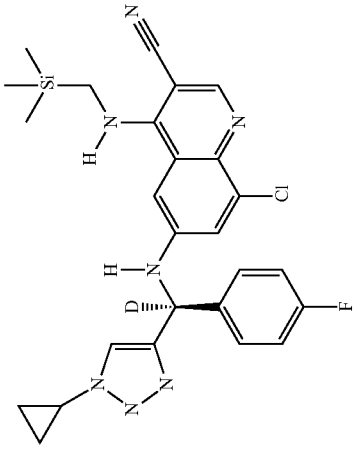 | (S)-8-chloro-6-((((1-cyclopropyl-1H-1,2,3-triazol-4-yl)(4-fluorophenyl)methyl-d)amino)-4-(((trimethylsilyl)methyl)amino)-quinoline-3-carbonitrile | 3 | ES/MS 521.3 (M + H+) |

TABLE 1-continued
| Compd | Structure | Name | Example/Procedure | ES/MS m/z |
|---|---|---|---|---|
| 263 | 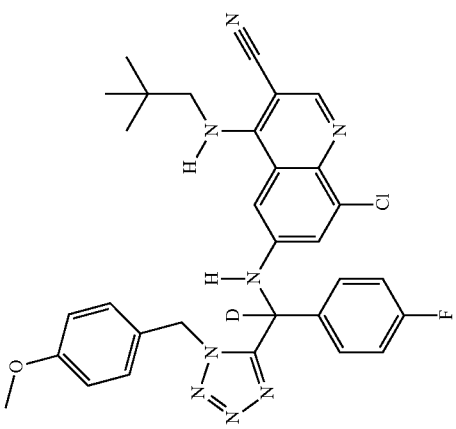 | 8-chloro-6-(((4-fluorophenyl)(1-(4-methoxybenzyl)-1H-tetrazol-5-yl)methyl-d)amino)-4-(neopentylamino)quinoline-3-carbonitrile | 7 | ES/MS 586.2 (M + H+) |
| 264 | 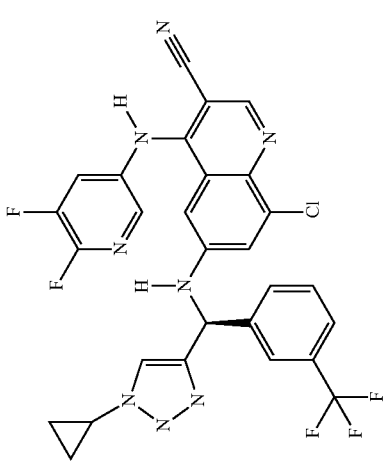 | (S)-8-chloro-6-((((1-cyclopropyl-1H-1,2,3-triazol-4-yl)(3-(trifluoromethyl)phenyl)methyl)amino)-4-((5,6-difluoropyridin-3-yl)amino)quinoline-3-carbonitrile | 1 | ES/MS 597.1 (M + H+) |

TABLE 1-continued

| Compd | Structure | Name | Example/Procedure | ES/MS m/z |
|---|---|---|---|---|
| 265 | 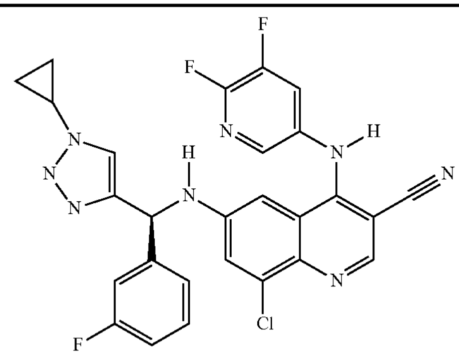 | (S)-8-chloro-6-(((1-cyclopropyl-1H-1,2,3-triazol-4-yl)(3-fluorophenyl)methyl)amino)-4-(((5,6-difluoropyridin-3-yl)amino)quinoline-3-carbonitrile | 1 | ES/MS 547.1 (M + H+) |
| 266 | 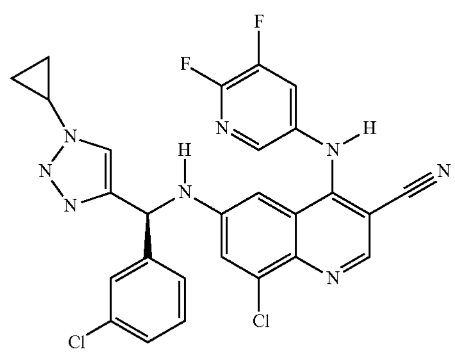 [SMILES: N#Cc1cnc2c(Cl)cc(N[C@H](C3=CN(C4CC4)NN3)c3cccc(F)c3)cc2c1Nc1cnc(F)c(F)c1] | (S)-8-chloro-6-(((3-chlorophenyl)(1-cyclopropyl-1H-1,2,3-triazol-4-yl)methyl)amino)-4-(((5,6-difluoropyridin-3-yl)amino)quinoline-3-carbonitrile | 1 | ES/MS 563.1 (M + H+) |

TABLE 1-continued

| Compd | Structure | Name | Example/Procedure | ES/MS m/z |
|---|---|---|---|---|
| 267 | 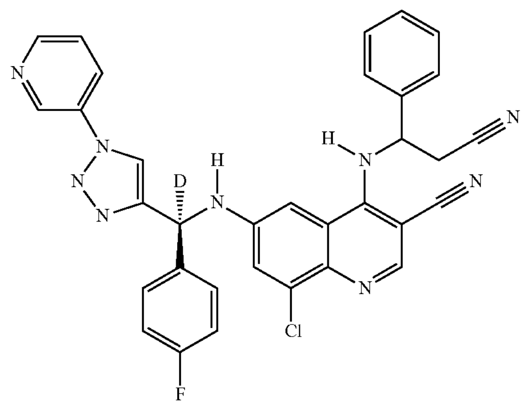 | 8-chloro-4-((2-cyano-1-phenylethyl)amino)-6-(((S)-(4-fluorophenyl)(1-(pyridin-3-yl)-1H-1,2,3-triazol-4-yl)methyl-d)amino)quinoline-3-carbonitrile | 1 | ES/MS 600.9 (M + H+) |
| 268 | 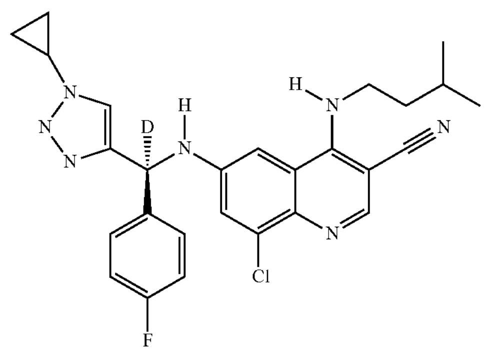 | (S)-8-chloro-6-(((1-cyclopropyl-1H-1,2,3-triazol-4-yl)(4-fluorophenyl)methyl-d)amino)-4-(isopentylamino)quinoline-3-carbonitrile | 1 | ES/MS 505.2 (M + H+) |

TABLE 1-continued

| Compd | Structure | Name | Example/Procedure | ES/MS m/z |
|---|---|---|---|---|
| 269 | 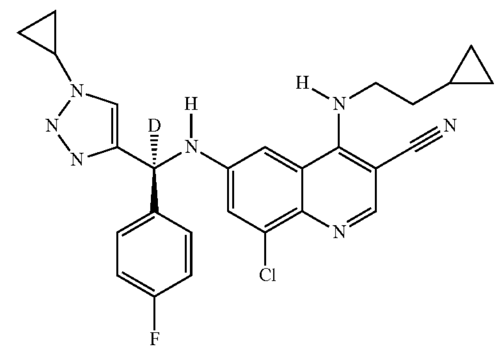 | (S)-8-chloro-6-((((1-cyclopropyl-1H-1,2,3-triazol-4-yl)(4-fluorophenyl)methyl-d)amino)-4-((2-cyclopropylethyl)amino)quinoline-3-carbonitrile | 1 | ES/MS 503.4 (M + H+) |
| 270 | 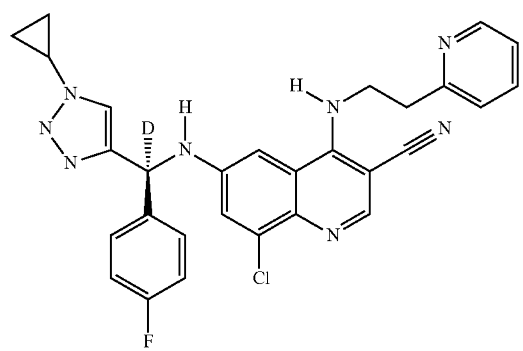 | (S)-8-chloro-6-((((1-cyclopropyl-1H-1,2,3-triazol-4-yl)(4-fluorophenyl)methyl-d)amino)-4-((2-(pyridin-2-yl)ethyl)amino)quinoline-3-carbonitrile | 1 | ES/MS 540.3 (M + H+) |
| 271 | 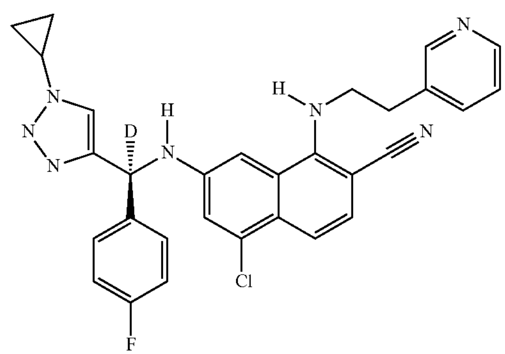 | (S)-8-chloro-6-((((1-cyclopropyl-1H-1,2,3-triazol-4-yl)(4-fluorophenyl)methyl-d)amino)-4-((2-(pyridin-3-yl)ethyl)amino)quinoline-3-carbonitrile | 1 | ES/MS 540.3 (M + H+) |

TABLE 1-continued

| Compd | Structure | Name | Example/Procedure | ES/MS m/z |
|---|---|---|---|---|
| 272 | 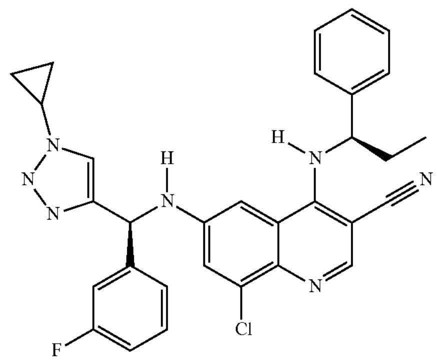 [SMILES: CC[C@@H](Nc1c(C#N)cnc2c(Cl)cc(N[C@H](C3=CN(C4CC4)NN3)c3cccc(F)c3)cc12)c1ccccc1] | 8-chloro-6-(((S)-(1-cyclopropyl-1H-1,2,3-triazol-4-yl)3-fluorophenyl)methyl)amino)-4-(((R)-1-phenylpropyl)amino)quinoline-3-carbonitrile | 1 | ES/MS 552.2 (M + H+) |
| 273 | 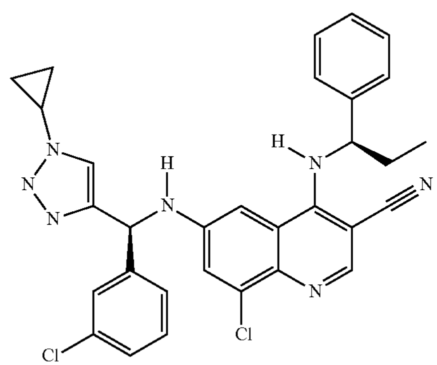 [SMILES: CC[C@@H](Nc1c(C#N)cnc2c(Cl)cc(N[C@H](C3=CN(C4CC4)NN3)c3cccc(Cl)c3)cc12)c1ccccc1] | 8-chloro-6-(((S)-(3-chlorophenyl)(1-cyclopropyl-1H-1,2,3-triazol-4-yl)methyl)amino)-4-(((R)-1-phenylpropyl)amino)quinoline-3-carbonitrile | 1 | ES/MS 568.2 (M + H+) |

TABLE 1-continued

| Compd | Structure | Name | Example/Procedure | ES/MS m/z |
|---|---|---|---|---|
| 274 | 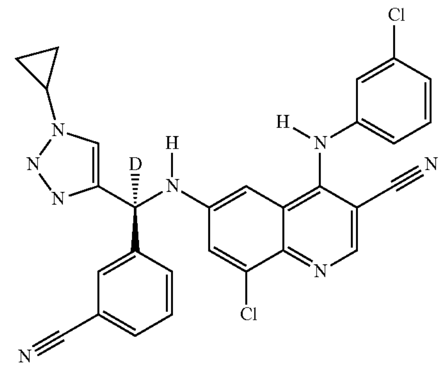 | (S)-8-chloro-4-((3-chlorophenyl)amino)-6-(((3-cyanophenyl)(1-cyclopropyl-1H-1,2,3-triazol-4-yl)methyl-d)amino)quinoline-3-carbonitrile | 3 | ES/MS 552.2 (M + H+) |
| 275 | 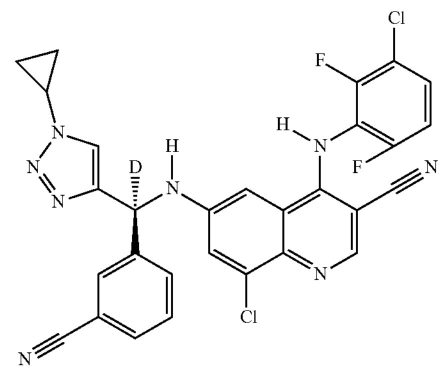 | (S)-8-chloro-4-((3-chloro-2,6-difluorophenyl)amino)-6-(((3-cyanophenyl)(1-cyclopropyl-1H-1,2,3-triazol-4-yl)methyl-d)amino)quinoline-3-carbonitrile | 3 | ES/MS 588.2 (M + H+) |
| 276 | 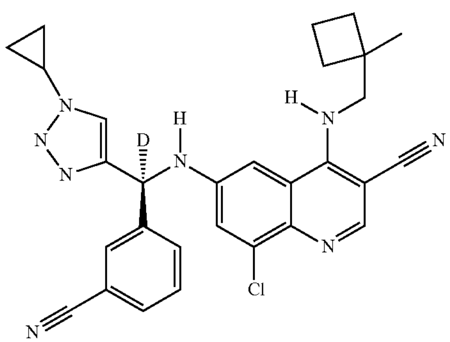 | (S)-8-chloro-6-(((3-cyanophenyl)(1-cyclopropyl-1H-1,2,3-triazol-4-yl)methyl-d)amino)-4-(((1-methylcyclobutyl)methyl)amino)quinoline-3-carbonitrile | 3 | ES/MS 524.3 (M + H+) |

TABLE 1-continued
| Compd | Structure | Name | Example/Procedure | ES/MS m/z |
|---|---|---|---|---|
| 277 | 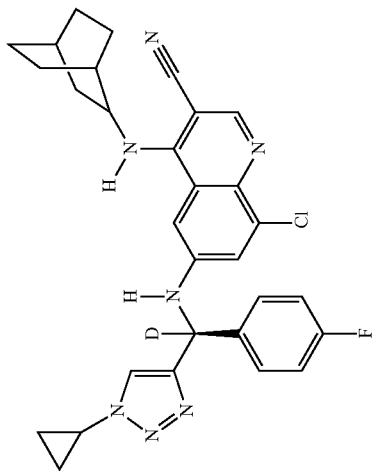 | 4-(((1s,4s)-bicyclo[2.2.2]octan-2-yl)amino)-8-chloro-6-((((S)-(1-cyclopropyl-1H-1,2,3-triazol-4-yl)(4-fluorophenyl)methyl-d)amino)quinoline-3-carbonitrile | 1 | ES/MS 543.2 (M + H+) |
| 278 | 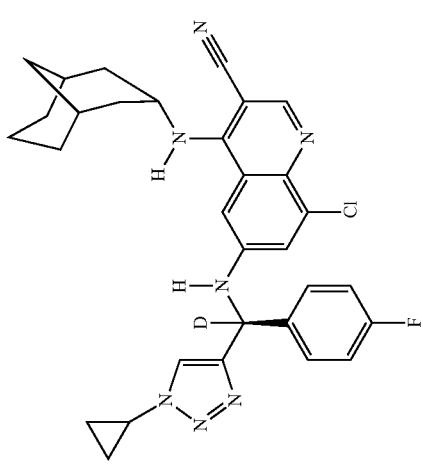 | 4-(((1R,5S)-bicyclo[3.3.1]nonan-3-yl)amino)-8-chloro-6-((((S)-(1-cyclopropyl-1H-1,2,3-triazol-4-yl)(4-fluorophenyl)methyl-d)amino)quinoline-3-carbonitrile | 1 | ES/MS 557.3 (M + H+) |

TABLE 1-continued
| Compd | Structure | Name | Example/Procedure | ES/MS m/z |
|---|---|---|---|---|
| 279 | 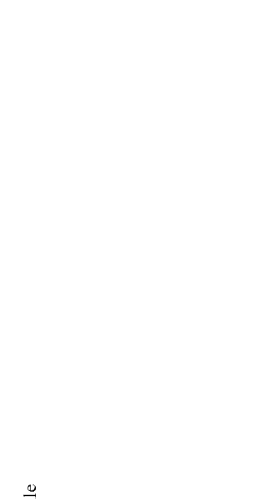 | 4-amino-8-chloro-6-(((S)-(1-cyclopropyl-1H-1,2,3-triazol-4-yl)(4-fluorophenyl)methyl-d)amino)quinoline-3-carbonitrile | 1 | ES/MS 435.0 (M + H+) |
| 280 | 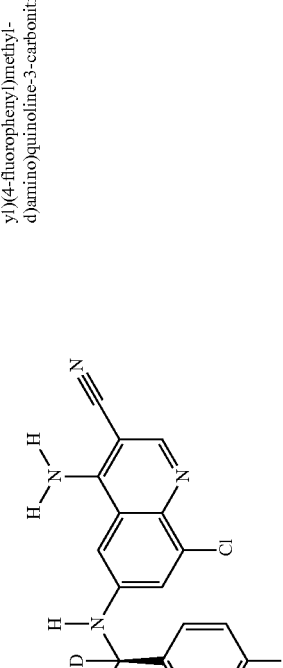 | (S)-4-(tert-butoxyamino)-8-chloro-6-(((1-cyclopropyl-1H-1,2,3-triazol-4-yl)(4-fluorophenyl)methyl-d)amino)quinoline-3-carbonitrile | 1 | ES/MS 507.2 (M + H+) |

TABLE 1-continued

| Compd | Structure | Name | Example/Procedure | ES/MS m/z |
|---|---|---|---|---|
| 281 | 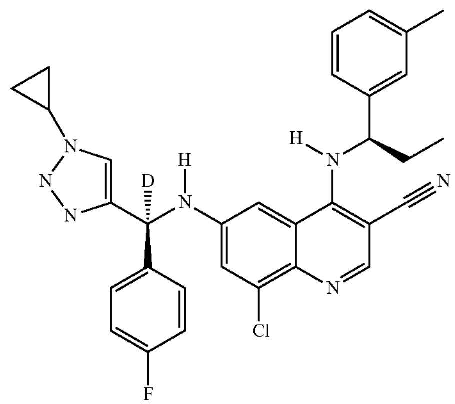 | 8-chloro-6-(((S)-(1-cyclopropyl-1H-1,2,3-triazol-4-yl)(4-fluorophenyl)methyl-d)amino)-4-(((R)-1-(m-tolyl)propyl)amino)quinoline-3-carbonitrile | 1 | ES/MS 567.2 (M + H+) |
| 282 | 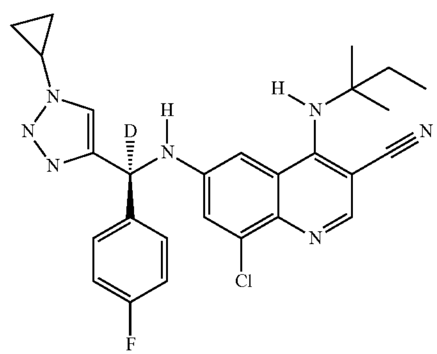 | (S)-8-chloro-6-(((1-cyclopropyl-1H-1,2,3-triazol-4-yl)(4-fluorophenyl)methyl-d)amino)-4-(tert-pentylamino)quinoline-3-carbonitrile | 1 | ES/MS 505.2 (M + H+) |

TABLE 1-continued

| Compd | Structure | Name | Example/Procedure | ES/MS m/z |
|---|---|---|---|---|
| 283 | 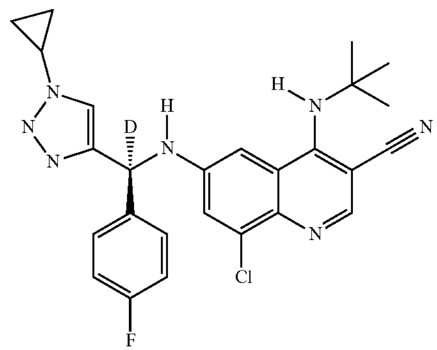 | (S)-4-(tert-butylamino)-8-chloro-6-(((1-cyclopropyl-1H-1,2,3-triazol-4-yl)(4-fluorophenyl)methyl-d)amino)quinoline-3-carbonitrile | 1 | ES/MS 491.2 (M + H+) |
| 284 | 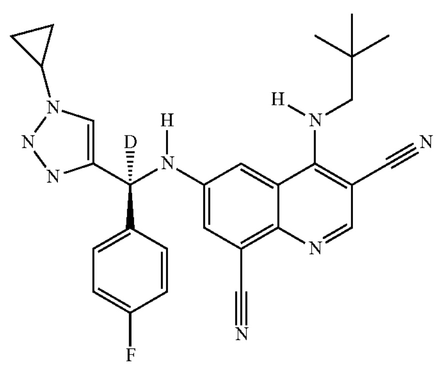 | (S)-6-(((1-cyclopropyl-1H-1,2,3-triazol-4-yl)(4-fluorophenyl)methyl-d)amino)-4-(neopentylamino)quinoline-3,8-dicarbonitrile | 9 | ES/MS 496.2 (M + H+) |

TABLE 1-continued

| Compd | Structure | Name | Example/Procedure | ES/MS m/z |
|---|---|---|---|---|
| 285 | 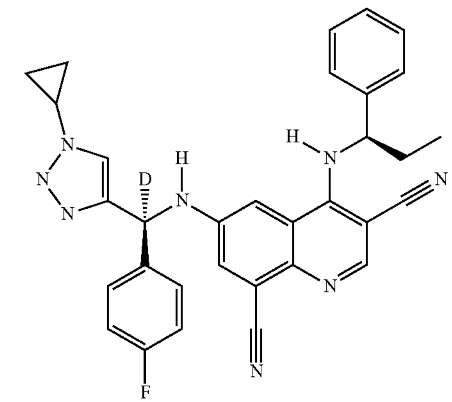 | 6-(((S)-(1-cyclopropyl-1H-1,2,3-triazol-4-yl)(4-fluorophenyl)methyl-d)amino)-4-(((R)-1-phenylpropyl)amino)quinoline-3,8-dicarbonitrile | 9 | ES/MS 544.3 (M + H+) |
| 286 | 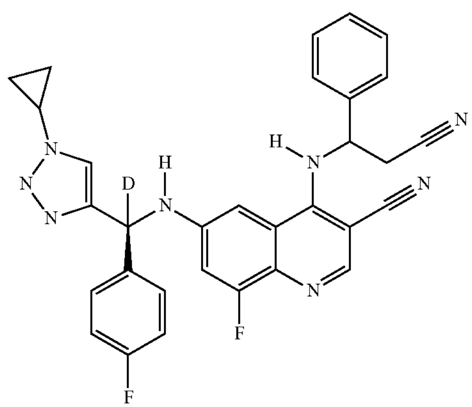 [SMILES: [2H][C@](Nc1cc(F)c2ncc(C#N)c(NC(CC#N)c3ccccc3)c2c1)(C1=CN(C2CC2)NN1)c1ccc(F)cc1] | 4-((2-cyano-1-phenylethyl)amino)-6-(((1-cyclopropyl-1H-1,2,3-triazol-4-yl)(4-fluorophenyl)methyl-d)amino)-8-fluoroquinoline-3-carbonitrile | 1 | ES/MS 548.2 (M + H+) |

TABLE 1-continued

| Compd | Structure | Name | Example/Procedure | ES/MS m/z |
|---|---|---|---|---|
| 287 | 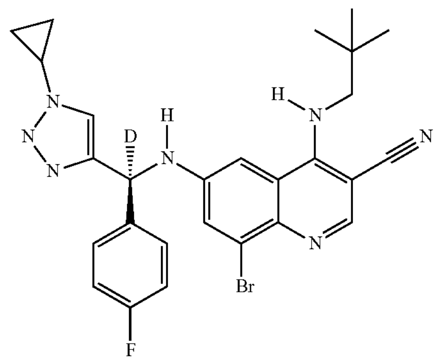 | (S)-8-bromo-6-(((1-cyclopropyl-1H-1,2,3-triazol-4-yl)(4-fluorophenyl)methyl-d)amino)-4-(neopentylamino)quinoline-3-carbonitrile | 1 | ES/MS 549.2 (M + H+) |
| 288 | 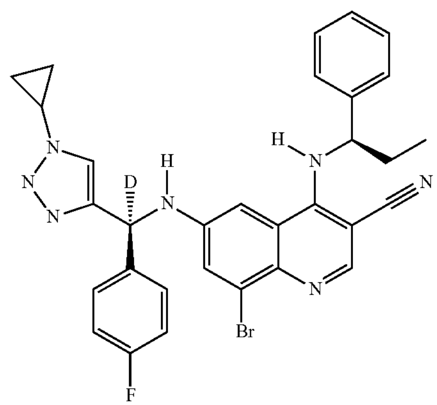 | 8-bromo-6-(((S)-(1-cyclopropyl-1H-1,2,3-triazol-4-yl)(4-fluorophenyl)methyl-d)amino)-4-(((R)-1-phenylpropyl)amino)quinoline-3-carbonitrile | 1 | ES/MS 597.1 (M + H+) |

TABLE 1-continued

| Compd | Structure | Name | Example/Procedure | ES/MS m/z |
|---|---|---|---|---|
| 289 | 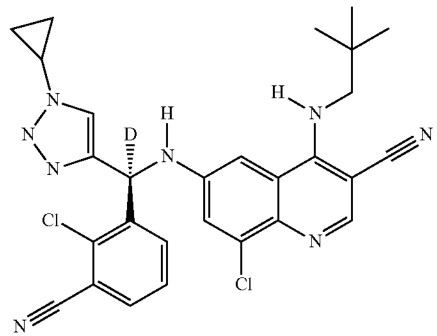 | (S)-8-chloro-6-(((2-chloro-3-cyanophenyl)(1-cyclopropyl-1H-1,2,3-triazol-4-yl)methyl-d)amino)-4-(neopentylamino)quinoline-3-carbonitrile | 5 | ES/MS 546.2 (M + H+) |
| 290 | 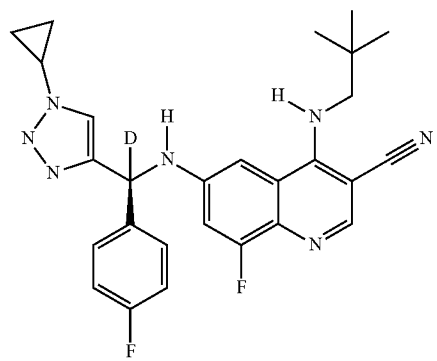 | 6-(((1-cyclopropyl-1H-1,2,3-triazol-4-yl)(4-fluorophenyl)methyl)amino)-8-fluoro-4-(neopentylamino)quinoline-3-carbonitrile | 1 | ES/MS 489.2 (M + H+) |

TABLE 1-continued

| Compd | Structure | Name | Example/Procedure | ES/MS m/z |
|---|---|---|---|---|
| 291 | 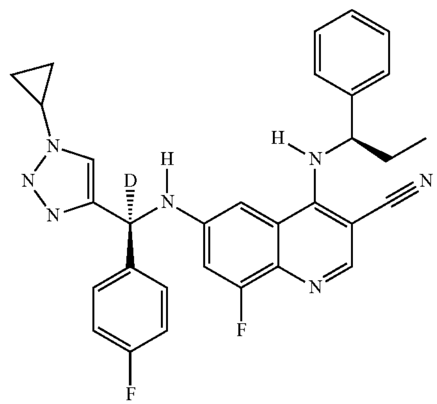 | 6-(((S)-(1-cyclopropyl-1H-1,2,3-triazol-4-yl)(4-fluorophenyl)methyl-d)amino)-8-fluoro-4-(((R)-1-phenylpropyl)amino)quinoline-3-carbonitrile | 1 | ES/MS 537.2 (M + H+) |
| 292 | 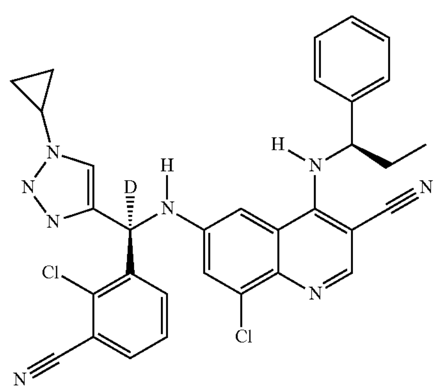 | 8-chloro-6-(((S)-(2-chloro-3-cyanophenyl)(1-cyclopropyl-1H-1,2,3-triazol-4-yl)methyl-d)amino)-4-(((R)-1-phenylpropyl)amino)quinoline-3-carbonitrile | 5 | ES/MS 594.1 (M + H+) |

TABLE 1-continued

| Compd | Structure | Name | Example/Procedure | ES/MS m/z |
|---|---|---|---|---|
| 293 | 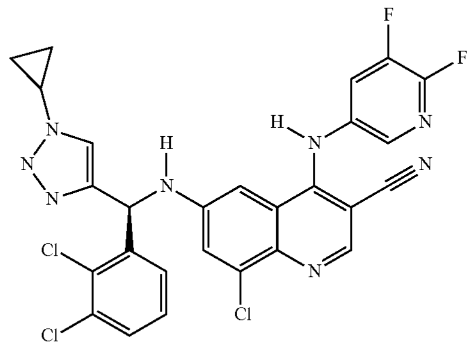 [SMILES: N#Cc1cnc2c(Cl)cc(N[C@H](C3=CN(C4CC4)NN3)c3cccc(Cl)c3Cl)cc2c1Nc1cnc(F)c(F)c1] | (S)-8-chloro-6-(((1-cyclopropyl-1H-1,2,3-triazol-4-yl)(2,3-dichlorophenyl)methyl)amino)-4-((5,6-difluoropyridin-3-yl)amino)quinoline-3-carbonitrile | 1 | ES/MS 597.1 (M + H+) |
| 294 | 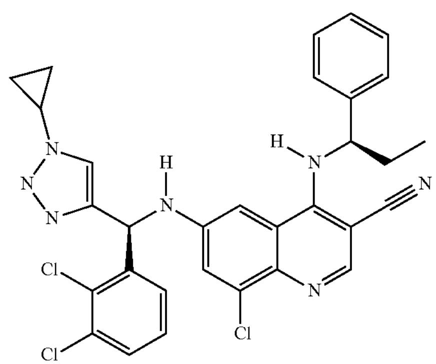 [SMILES: CC[C@@H](Nc1c(C#N)cnc2c(Cl)cc(N[C@H](C3=CN(C4CC4)NN3)c3cccc(Cl)c3Cl)cc12)c1ccccc1] | 8-chloro-6-(((S)-(1-cyclopropyl-1H-1,2,3-triazol-4-yl)(2,3-dichlorophenyl)methyl)amino)-4-(((R)-1-phenylpropyl)amino)quinoline-3-carbonitrile | 1 | ES/MS 602.1 (M + H+) |

TABLE 1-continued

| Compd | Structure | Name | Example/Procedure | ES/MS m/z |
|---|---|---|---|---|
| 295 | 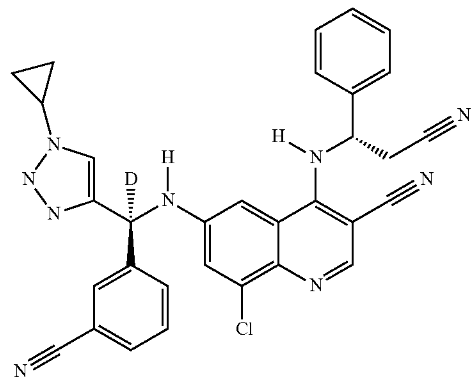 | 8-chloro-4-(((S)-2-cyano-1-phenylethyl)amino)-6-(((S)-(3-cyanophenyl)(1-cyclopropyl-1H-1,2,3-triazol-4-yl)methyl-d)amino)quinoline-3-carbonitrile | 3 | ES/MS 571.3 (M + H+) |
| 296 | 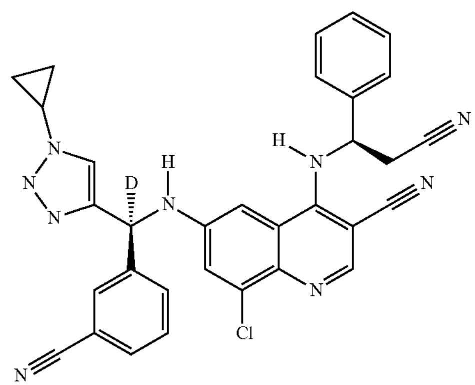 | 8-chloro-4-(((R)-2-cyano-1-phenylethyl)amino)-6-(((S)-(3-cyanophenyl)(1-cyclopropyl-1H-1,2,3-triazol-4-yl)methyl-d)amino)quinoline-3-carbonitrile | 3 | ES/MS 571.4 (M + H+) |

TABLE 1-continued

| Compd | Structure | Name | Example/Procedure | ES/MS m/z |
|---|---|---|---|---|
| 297 | 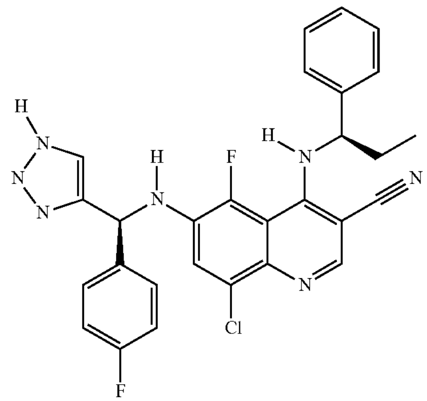 [SMILES: CC[C@@H](Nc1c(C#N)cnc2c(Cl)cc(N[C@H](C3=CNNN3)c3ccc(F)cc3)c(F)c12)c1ccccc1] | 8-chloro-5-fluoro-6-(((S)-(4-fluorophenyl)(1H-1,2,3-triazol-4-yl)methyl)amino)-4-(((R)-1-phenylpropyl)amino)quinoline-3-carbonitrile | 15 | ES/MS 530.0 (M + H+) |
| 298 | 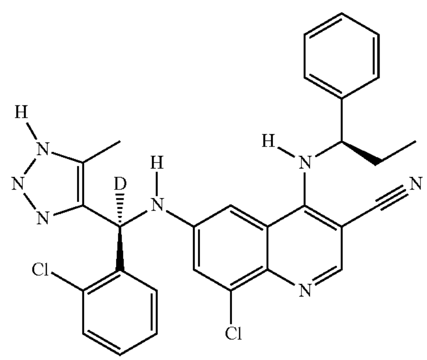 | 8-chloro-6-(((S)-(2-chlorophenyl)(5-methyl-1H-1,2,3-triazol-4-yl)methyl-d)amino)-4-(((R)-1-phenylpropyl)amino)quinoline-3-carbonitrile | 7 | |

TABLE 1-continued
| Compd | Structure | Name | Example/Procedure | ES/MS m/z |
|---|---|---|---|---|
| 299 | 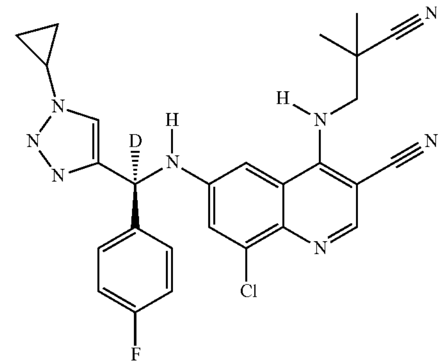 | (S)-8-chloro-4-((2-cyano-2-methylpropyl)amino)-6-(((1-cyclopropyl-1H-1,2,3-triazol-4-yl)(4-fluorophenyl)methyl-d)amino)quinoline-3-carbonitrile | 1 | ES/MS 516.2 (M + H+) |
| 300 | 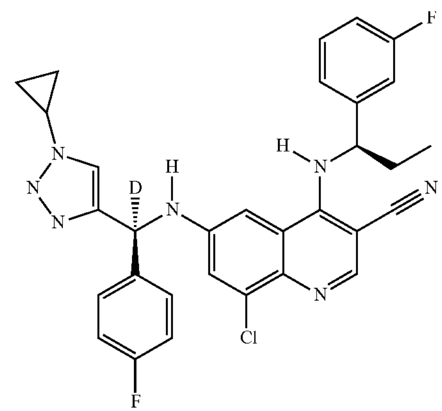 | 8-chloro-6-(((S)-(1-cyclopropyl-1H-1,2,3-triazol-4-yl)(4-fluorophenyl)methyl-d)amino)-4-(((R)-1-(3-fluorophenyl)propyl)amino)quinoline-3-carbonitrile | 1 | ES/MS 571.2 (M + H+) |

TABLE 1-continued

| Compd | Name | Structure | Example/Procedure | ES/MS m/z |
|---|---|---|---|---|
| 301 | (S)-8-chloro-4-(2-cyclohexylhydrazinyl)-6-(((1-cyclopropyl-1H-1,2,3-triazol-4-yl)(4-fluorophenyl)methyl-d)amino)quinoline-3-carbonitrile | 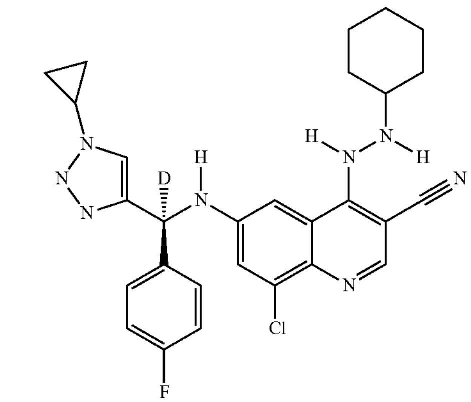 | 1 | ES/MS 532.2 (M + H+) |
| 302 | 8-chloro-4-((3-cyano-1-phenylpropyl)amino)-6-(((S)-(1-cyclopropyl-1H-1,2,3-triazol-4-yl)(4-fluorophenyl)methyl-d)amino)quinoline-3-carbonitrile | 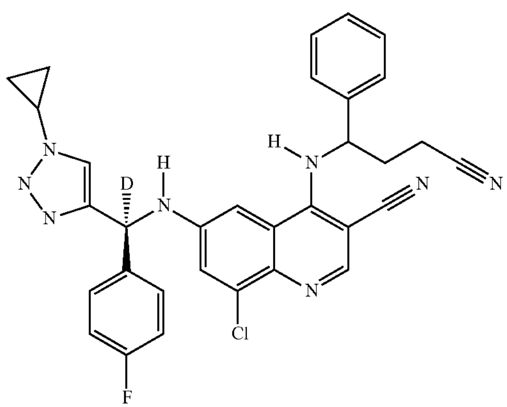 | 1 | ES/MS 578.2 (M + H+) |

TABLE 1-continued

| Compd | Structure | Name | Example/Procedure | ES/MS m/z |
|---|---|---|---|---|
| 303 | 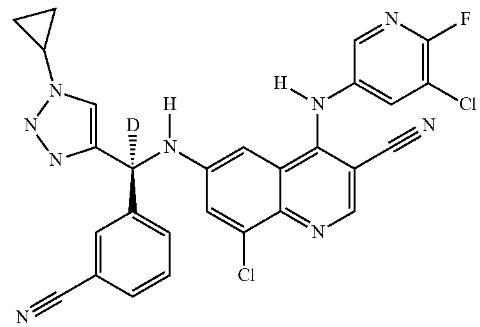 | (S)-8-chloro-4-((5-chloro-6-fluoropyridin-3-yl)amino)-6-(((3-cyanophenyl)(1-cyclopropyl-1H-1,2,3-triazol-4-yl)methyl-d)amino)quinoline-3-carbonitrile | 3 | ES/MS 571.1 (M + H+) |
| 304 | 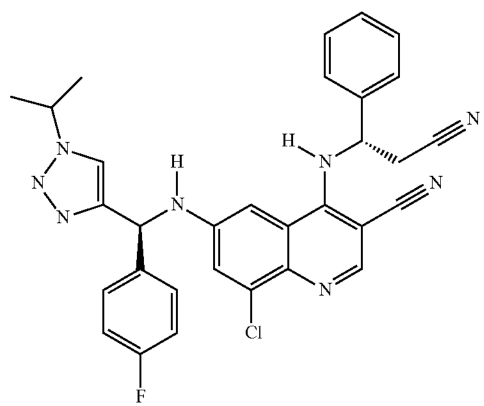 [SMILES: CC(C)N1C=C([C@@H](Nc2cc(Cl)c3ncc(C#N)c(N[C@@H](CC#N)c4ccccc4)c3c2)c2ccc(F)cc2)NN1] | 8-chloro-4-(((S)-2-cyano-1-phenylethyl)amino)-6-(((S)-(4-fluorophenyl)(1-isopropyl-1H-1,2,3-triazol-4-yl)methyl)amino)quinoline-3-carbonitrile | 1 | ES/MS 565.2 (M + H+) |

TABLE 1-continued
| Compd | Structure | Name | Example/Procedure | ES/MS m/z |
|---|---|---|---|---|
| 305 | 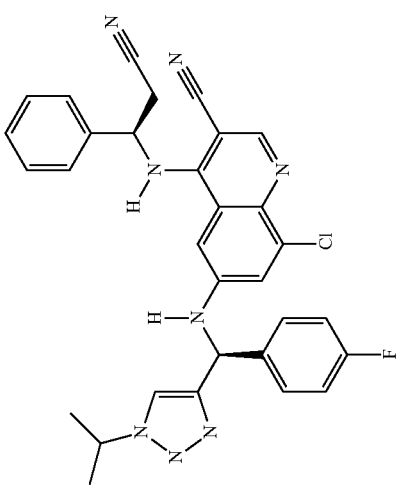 | 8-chloro-4-(((R)-2-cyano-1-phenylethyl)amino)-6-(((S)-(4-fluorophenyl)(1-isopropyl-1H-1,2,3-triazol-4-yl)methyl)amino)quinoline-3-carbonitrile | 1 | ES/MS 565.2 (M + H+) |
| 306 | 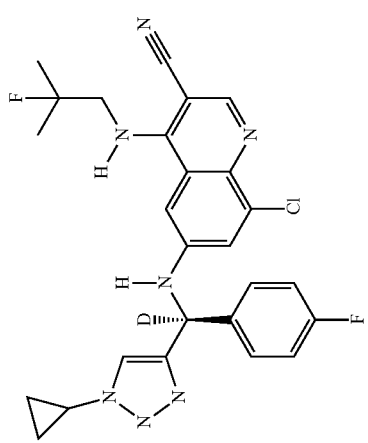 | (S)-8-chloro-6-((((1-cyclopropyl-1H-1,2,3-triazol-4-yl)(4-fluorophenyl)methyl-d)amino)-4-((2-fluoro-2-methylpropyl)amino)quinoline-3-carbonitrile | 1 | ES/MS 509.2 (M + H+) |

TABLE 1-continued

| Compd | Structure | Name | Example/Procedure | ES/MS m/z |
|---|---|---|---|---|
| 307 | 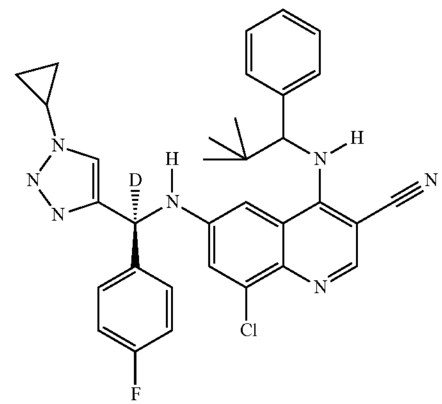 | 8-chloro-6-(((S)-(1-cyclopropyl-1H-1,2,3-triazol-4-yl)(4-fluorophenyl)methyl-d)amino)-4-((2,2-dimethyl-1-phenylpropyl)amino)quinoline-3-carbonitrile | 1 | ES/MS 581.2 (M + H+) |
| 308 | 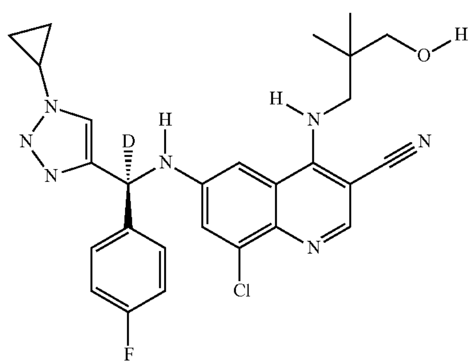 | (S)-8-chloro-6-(((1-cyclopropyl-1H-1,2,3-triazol-4-yl)(4-fluorophenyl)methyl-d)amino)-4-((3-hydroxy-2,2-dimethylpropyl)amino)quinoline-3-carbonitrile | 1 | ES/MS 521.2 (M + H+) |

TABLE 1-continued
| Compd | Structure | Name | Example/Procedure | ES/MS m/z |
|---|---|---|---|---|
| 309 | 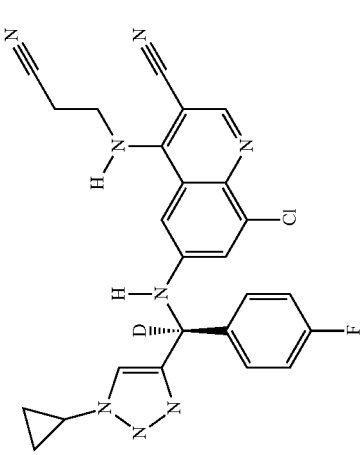 | (S)-8-chloro-4-((2-cyanoethyl)amino)-6-(((1-cyclopropyl-1H-1,2,3-triazol-4-yl)(4-fluorophenyl)methyl-d)amino)quinoline-3-carbonitrile | 1 | ES/MS 488.2 (M + H+) |
| 310 | 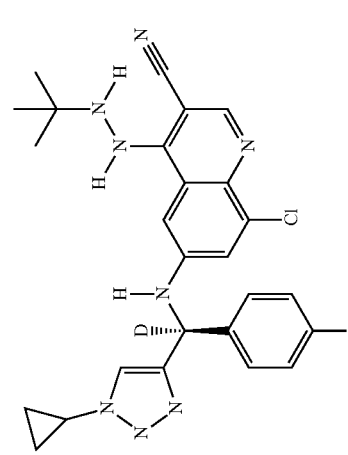 | (S)-4-(2-(tert-butyl)hydrazinyl)-8-chloro-6-(((1-cyclopropyl-1H-1,2,3-triazol-4-yl)(4-fluorophenyl)methyl-d)amino)quinoline-3-carbonitrile | 1 | ES/MS 506.2 (M + H+) |

TABLE 1-continued
| Compd | Structure | Name | Example/Procedure | ES/MS m/z |
|---|---|---|---|---|
| 311 | 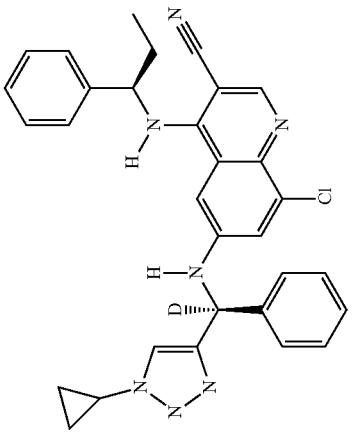 | 8-chloro-6-(((S)-(1-cyclopropyl-1H-1,2,3-triazol-4-yl)(phenyl)methyl-d)amino)-4-(((R)-1-phenylpropyl)amino)quinoline-3-carbonitrile | 3 | ES/MS 535.1 (M + H+) |
| 312 | 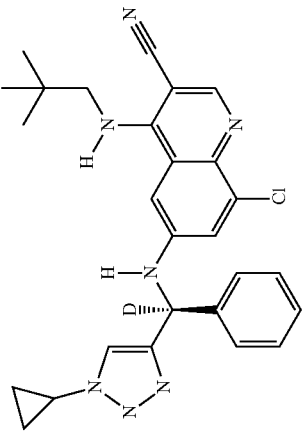 | (S)-8-chloro-6-(((1-cyclopropyl-1H-1,2,3-triazol-4-yl)(phenyl)methyl-d)amino)-4-(neopentylamino)quinoline-3-carbonitrile | 3 | ES/MS 487.2 (M + H+) |

TABLE 1-continued
| Compd | Structure | Name | Example/Procedure | ES/MS m/z |
|---|---|---|---|---|
| 313 | 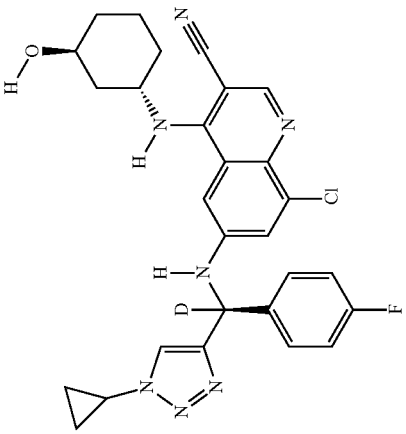 | 8-chloro-6-(((S)-(1-cyclopropyl-1H-1,2,3-triazol-4-yl)(4-fluorophenyl)methyl-d)amino)-4-(((1S,3S)-3-hydroxycyclohexyl)amino)quinoline-3-carbonitrile | 1 | ES/MS 533.2 (M + H+) |
| 314 | 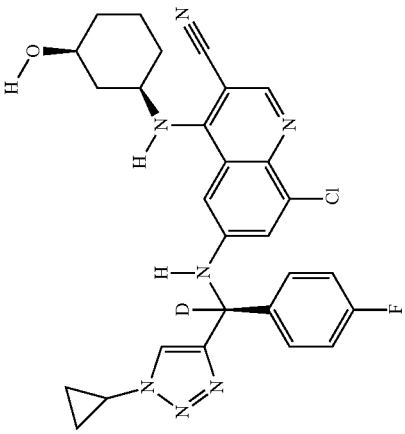 | 8-chloro-6-(((S)-(1-cyclopropyl-1H-1,2,3-triazol-4-yl)(4-fluorophenyl)methyl-d)amino)-4-(((1R,3S)-3-hydroxycyclohexyl)amino)quinoline-3-carbonitrile | 1 | ES/MS 533.2 (M + H+) |

TABLE 1-continued
| Compd | Structure | Name | Example/Procedure | ES/MS m/z |
|---|---|---|---|---|
| 315 | 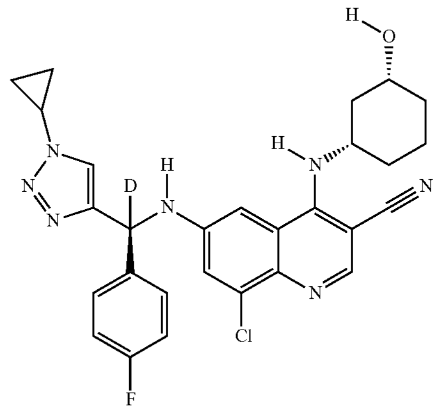 [SMILES: [2H][C@@](Nc1cc(Cl)c2ncc(C#N)c(N[C@H]3CCC[C@@H](O)C3)c2c1)(c1ccc(F)cc1)c1cn(C2CC2)nn1] | 8-chloro-6-(((S)-(1-cyclopropyl-1H-1,2,3-triazol-4-yl)(4-fluorophenyl)methyl-d)amino)-4-(((1S,3R)-3-hydroxycyclohexyl)amino)quinoline-3-carbonitrile | 1 | ES/MS 533.2 (M + H+) |
| 316 | 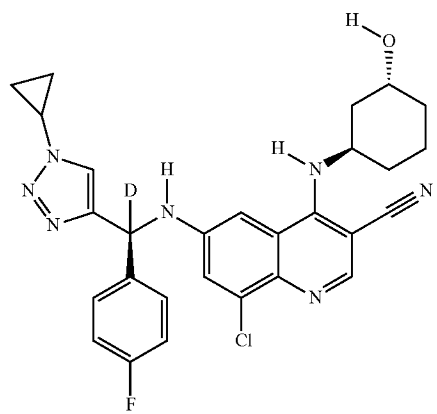 [SMILES: [2H][C@@](Nc1cc(Cl)c2ncc(C#N)c(N[C@@H]3CCC[C@@H](O)C3)c2c1)(c1ccc(F)cc1)c1cn(C2CC2)nn1] | 8-chloro-6-(((S)-(1-cyclopropyl-1H-1,2,3-triazol-4-yl)(4-fluorophenyl)methyl-d)amino)-4-(((1R,3R)-3-hydroxycyclohexyl)amino)quinoline-3-carbonitrile | 1 | ES/MS 533.2 (M + H+) |

| Compd | Structure | Name | Example/Procedure | ES/MS m/z |
|---|---|---|---|---|
| 317 | 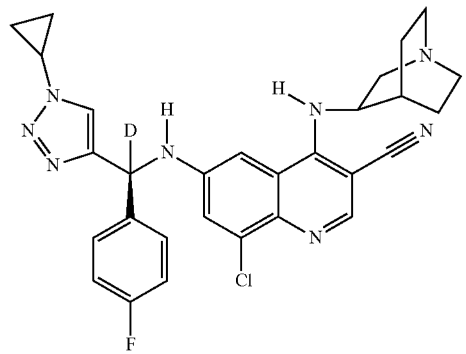 [SMILES: [2H][C@@](Nc1cc(Cl)c2ncc(C#N)c(NC3CN4CCC3CC4)c2c1)(c1ccc(F)cc1)c1cn(C2CC2)nn1] | 8-chloro-6-(((S)-(1-cyclopropyl-1H-1,2,3-triazol-4-yl)(4-fluorophenyl)methyl-d)amino)-4-(quinuclidin-3-ylamino)quinoline-3-carbonitrile | 1 | ES/MS 544.2 (M + H+) |
| 318 | 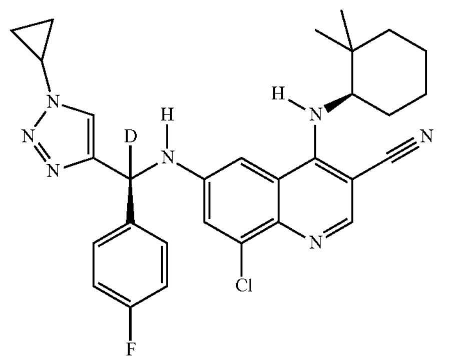 [SMILES: [2H][C@@](Nc1cc(Cl)c2ncc(C#N)c(N[C@@H]3CCCCC3(C)C)c2c1)(c1ccc(F)cc1)c1cn(C2CC2)nn1] | 8-chloro-6-(((S)-(1-cyclopropyl-1H-1,2,3-triazol-4-yl)(4-fluorophenyl)methyl-d)amino)-4-(((R)-2,2-dimethylcyclohexyl)amino)quinoline-3-carbonitrile | 1 | ES/MS 545.3 (M + H+) |
| 319 | 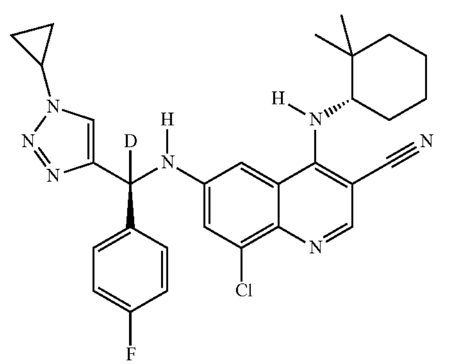 [SMILES: [2H][C@@](Nc1cc(Cl)c2ncc(C#N)c(N[C@H]3CCCCC3(C)C)c2c1)(c1ccc(F)cc1)c1cn(C2CC2)nn1] | 8-chloro-6-(((S)-(1-cyclopropyl-1H-1,2,3-triazol-4-yl)(4-fluorophenyl)methyl-d)amino)-4-(((S)-2,2-dimethylcyclohexyl)amino)quinoline-3-carbonitrile | 1 | ES/MS 545.3 (M + H+) |

TABLE 1-continued

| Compd | Structure | Name | Example/Procedure | ES/MS m/z |
|---|---|---|---|---|
| 320 | 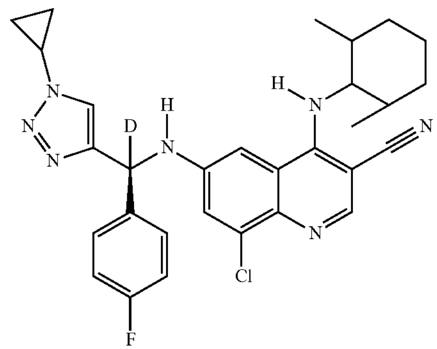 [SMILES: [2H][C@@](Nc1cc(Cl)c2ncc(C#N)c(NC3C(C)CCCC3C)c2c1)(c1ccc(F)cc1)c1cn(C2CC2)nn1] | 8-chloro-6-(((S)(1-cyclopropyl-1H-1,2,3-triazol-4-yl)(4-fluorophenyl)methyl-d)amino)-4-((2,6-dimethylcyclohexyl)amino)quinoline-3-carbonitrile | 1 | ES/MS 545.2 (M + H+) |
| 321 | 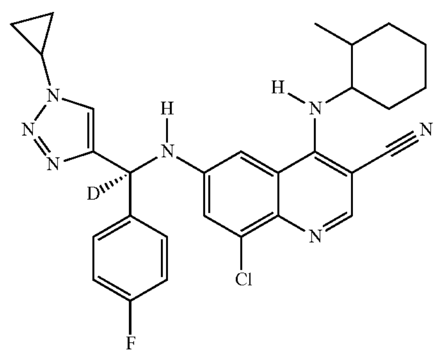 | 8-chloro-6-(((S)-(1-cyclopropyl-1H-1,2,3-triazol-4-yl)(4-fluorophenyl)methyl-d)amino)-4-((2-methylcyclohexyl)amino)quinoline-3-carbonitrile | 1 | ES/MS 531.2 (M + H+) |

TABLE 1-continued

| Compd | Structure | Name | Example/Procedure | ES/MS m/z |
|---|---|---|---|---|
| 322 | 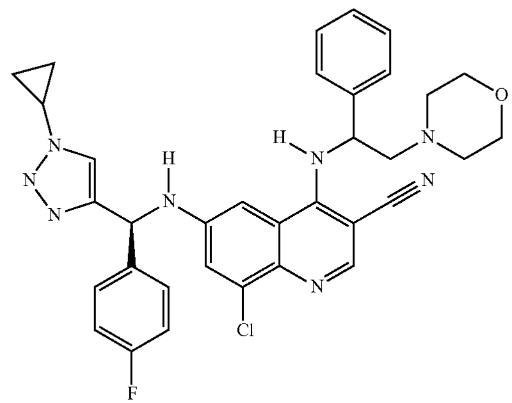 [SMILES: N#Cc1cnc2c(Cl)cc(N[C@H](C3=CN(C4CC4)NN3)c3ccc(F)cc3)cc2c1NC(CN1CCOCC1)c1ccccc1] | 8-chloro-6-(((S)-(1-cyclopropyl-1H-1,2,3-triazol-4-yl)(4-fluorophenyl)methyl)amino)-4-((2-morpholino-1-phenylethyl)amino)quinoline-3-carbonitrile | 2 | ES/MS 623.2 (M + H+) |
| 323 | 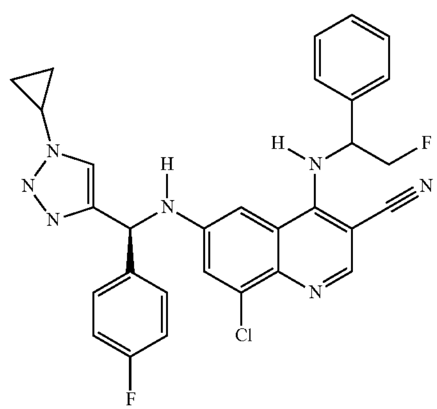 | 8-chloro-6-(((S)-(1-cyclopropyl-1H-1,2,3-triazol-4-yl)(4-fluorophenyl)methyl)amino)-4-((2-fluoro-1-phenylethyl)amino)quinoline-3-carbonitrile | 2 | ES/MS 556.0 (M + H+) |

TABLE 1-continued

| Compd | Structure | Name | Example/Procedure | ES/MS m/z |
|---|---|---|---|---|
| 324 | 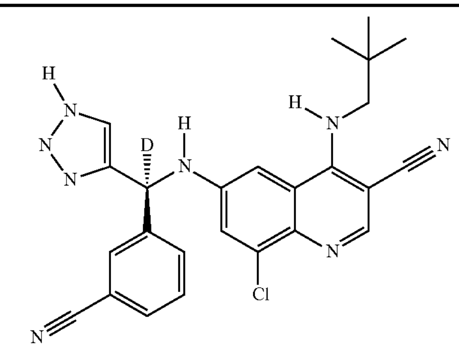 | (S)-8-chloro-6-(((3-cyanophenyl)(1H-1,2,3-triazol-4-yl)methyl)amino)-4-(neopentylamino)quinoline-3-carbonitrile | 15 | ES/MS 472.2 (M + H+) |
| 325 | 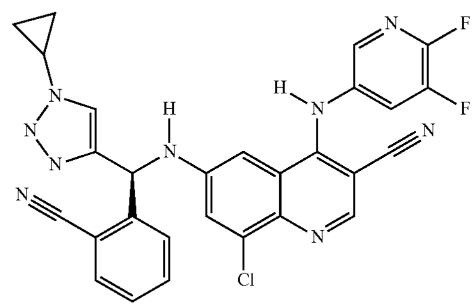 [SMILES: N#Cc1ccccc1[C@H](Nc1cc(Cl)c2ncc(C#N)c(Nc3cnc(F)c(F)c3)c2c1)C1=CN(C2CC2)NN1] | (S)-8-chloro-6-(((2-cyanophenyl)(1-cyclopropyl-1H-1,2,3-triazol-4-yl)methyl)amino)-4-(((5,6-difluoropyridin-3-yl)amino)quinoline-3-carbonitrile | 3 | ES/MS 554.0 (M + H+) |
| 326 | 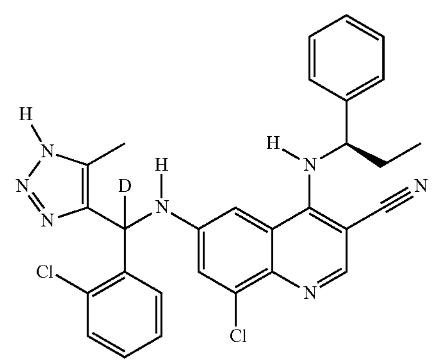 [SMILES: [2H]C(Nc1cc(Cl)c2ncc(C#N)c(N[C@H](CC)c3ccccc3)c2c1)(c1ccccc1Cl)c1nn[nH]c1C] | 8-chloro-6-(((2-chlorophenyl)(5-methyl-1H-1,2,3-triazol-4-yl)methyl)amino)-4-(((R)-1-phenylpropyl)amino)quinoline-3-carbonitrile | 7 | ES/MS 543.1 (M + H+) |

TABLE 1-continued

| Compd | Structure | Name | Example/Procedure | ES/MS m/z |
|---|---|---|---|---|
| 327 | 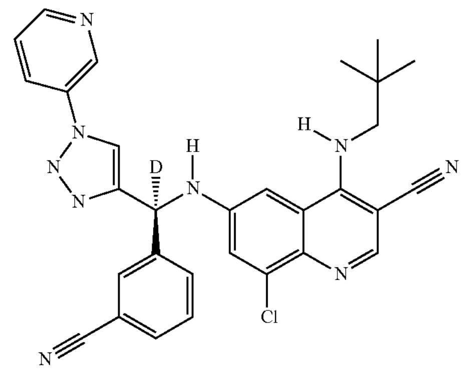 | (S)-8-chloro-6-(((3-cyanophenyl)(1-(pyridin-3-yl)-1H-1,2,3-triazol-4-yl)methyl-d)amino)-4-(neopentylamino)quinoline-3-carbonitrile | 3 | ES/MS 549.2 (M + H+) |
| 328 | 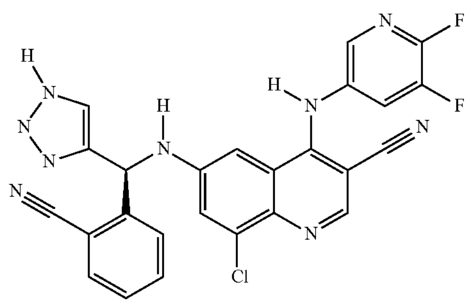 [SMILES: N#Cc1ccccc1[C@H](Nc1cc(Cl)c2ncc(C#N)c(Nc3cnc(F)c(F)c3)c2c1)C1=CNNN1] | (S)-8-chloro-6-(((2-cyanophenyl)(1H-1,2,3-triazol-4-yl)methyl)amino)-4-((5,6-difluoropyridin-3-yl)amino)quinoline-3-carbonitrile | 15 | ES/MS 514.0 (M + H+) |
| 329 | 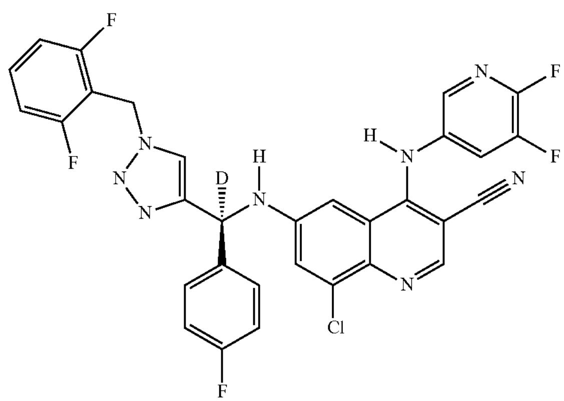 | (S)-8-chloro-6-(((1-(2,6-difluorobenzyl)-1H-1,2,3-triazol-4-yl)(4-fluorophenyl)methyl-d)amino)-4-((5,6-difluoropyridin-3-yl)amino)quinoline-3-carbonitrile | 1 | ES/MS 534.1 (M + H+) |

TABLE 1-continued

| Compd | Structure | Name | Example/Procedure | ES/MS m/z |
|---|---|---|---|---|
| 330 | 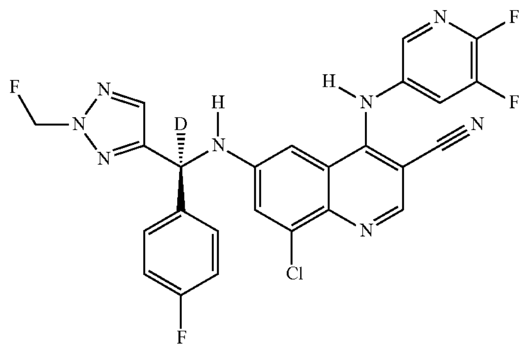 | (S)-8-chloro-4-((5,6-difluoropyridin-3-yl)amino)-6-(((2-(fluoromethyl)-2H-1,2,3-triazol-4-yl)(4-fluorophenyl)methyl)amino)quinoline-3-carbonitrile | 44 | ES/MS 540.1 (M + H+) |
| 331 | 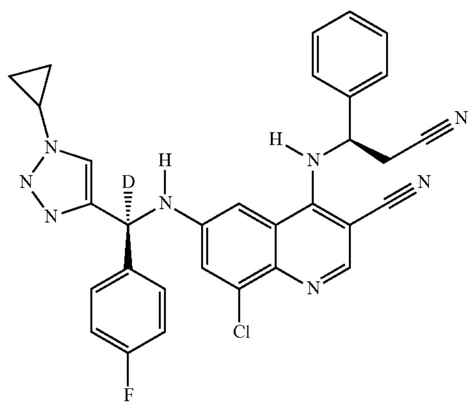 | 8-chloro-4-(((R)-2-cyano-1-phenylethyl)amino)-6-(((S)-(1-cyclopropyl-1H-1,2,3-triazol-4-yl)(4-fluorophenyl)methyl)amino)quinoline-3-carbonitrile | 1 | ES/MS 564.1 (M + H+) |

TABLE 1-continued
| Compd | Structure | Name | Example/Procedure | ES/MS m/z |
|---|---|---|---|---|
| 332 | 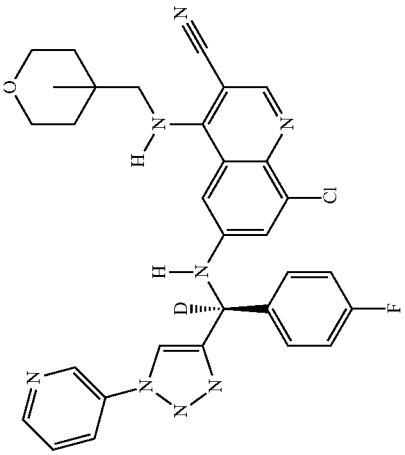 | (S)-8-chloro-6-(((4-fluorophenyl)(1-(pyridin-3-yl)-1H-1,2,3-triazol-4-yl)methyl-d)amino)-4-(((4-methyltetrahydro-2H-pyran-4-yl)methyl)amino)quinoline-3-carbonitrile | 1 | ES/MS 584.2 (M + H+) |
| 333 | 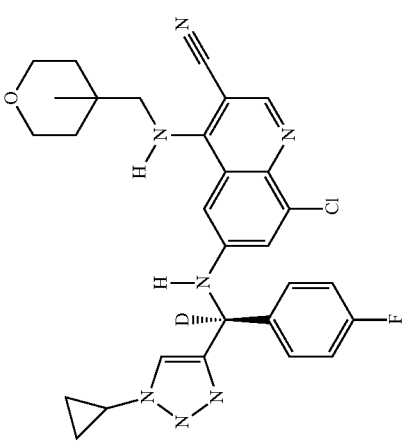 | (S)-8-chloro-6-(((1-cyclopropyl-1H-1,2,3-triazol-4-yl)(4-fluorophenyl)methyl-d)amino)-4-(((4-methyltetrahydro-2H-pyran-4-yl)methyl)amino)quinoline-3-carbonitrile | 1 | ES/MS 547.1 (M + H+) |

TABLE 1-continued

| Compd | Structure | Name | Example/Procedure | ES/MS m/z |
|---|---|---|---|---|
| 334 | 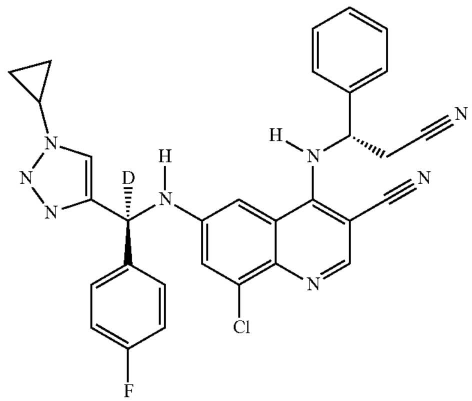 | 8-chloro-4-(((S)-2-cyano-1-phenylethyl)amino)-6-(((S)-(1-cyclopropyl-1H-1,2,3-triazol-4-yl)(4-fluorophenyl)methyl-d)amino)quinoline-3-carbonitrile | 1 | ES/MS 564.3 (M + H+) |
| 335 | 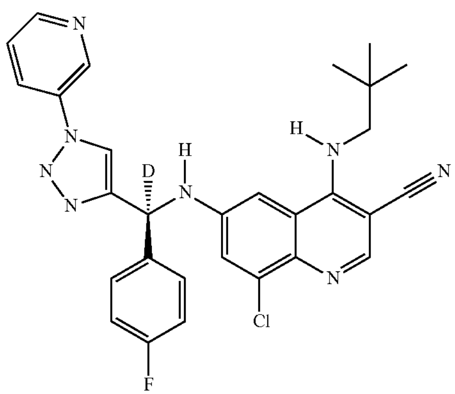 | (S)-8-chloro-6-(((4-fluorophenyl)(1-(pyridin-3-yl)-1H-1,2,3-triazol-4-yl)methyl-d)amino)-4-(neopentylamino)quinoline-3-carbonitrile | 1 | ES/MS 542.1 (M + H+) |

TABLE 1-continued

| Compd | Structure | Name | Example/Procedure | ES/MS m/z |
|---|---|---|---|---|
| 336 | 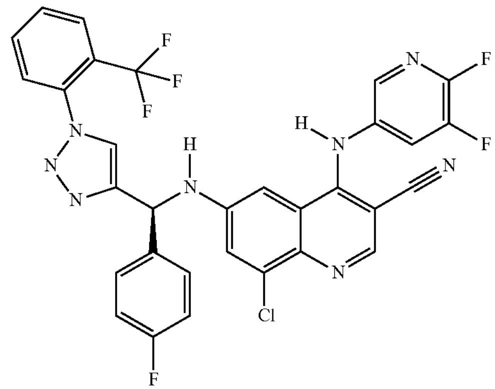 [SMILES: N#Cc1cnc2c(Cl)cc(N[C@H](C3=CN(c4ccccc4C(F)(F)F)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-(2-(trifluoromethyl)phenyl)-1H-1,2,3-triazol-4-yl)methyl)amino)quinoline-3-carbonitrile | 10 | ES/MS 651.1 (M + H+) |
| 337 | 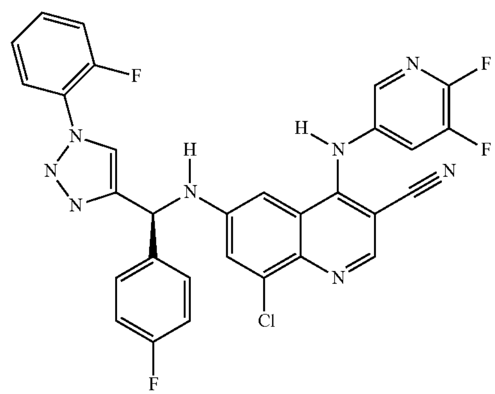 [SMILES: N#Cc1cnc2c(Cl)cc(N[C@H](C3=CN(c4ccccc4F)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-(2-fluorophenyl)-1H-1,2,3-triazol-4-yl)methyl)amino)quinoline-3-carbonitrile | 10 | ES/MS 601.1 (M + H+) |

TABLE 1-continued

| Compd | Structure | Name | Example/Procedure | ES/MS m/z |
|---|---|---|---|---|
| 338 | 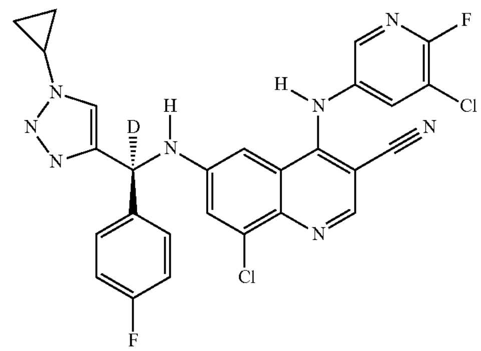 | (S)-8-chloro-4-((5-chloro-6-fluoropyridin-3-yl)amino)-6-(((1-cyclopropyl-1H-1,2,3-triazol-4-yl)(4-fluorophenyl)methyl-d)amino)quinoline-3-carbonitrile | 10 | ES/MS 564.0 (M + H+) |
| 339 | 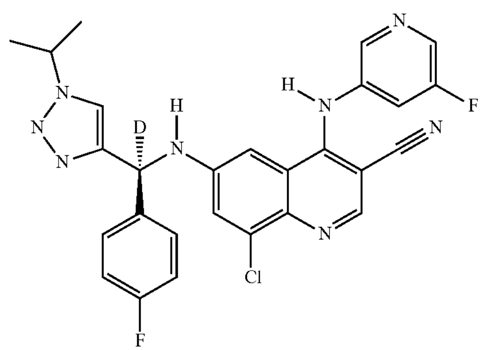 | (S)-8-chloro-6-(((4-fluorophenyl)(1-isopropyl-1H-1,2,3-triazol-4-yl)methyl-d)amino)-4-((5-fluoropyridin-3-yl)amino)quinoline-3-carbonitrile | 10 | ES/MS 532.2 (M + H+) |

TABLE 1-continued

| Compd | Structure | Name | Example/Procedure | ES/MS m/z |
|---|---|---|---|---|
| 340 | 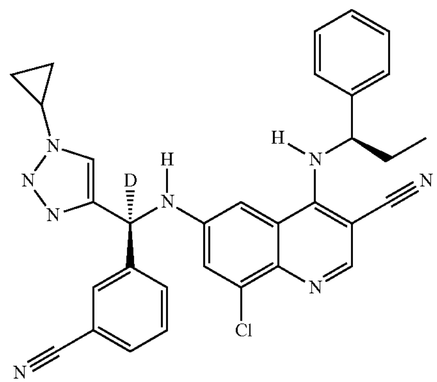 | 8-chloro-6-(((S)-(3-cyanophenyl)(1-cyclopropyl-1H-1,2,3-triazol-4-yl)methyl-d)amino)-4-(((R)-1-phenylpropyl)amino)quinoline-3-carbonitrile | 3 | ES/MS 560.1 (M + H+) |
| 341 | 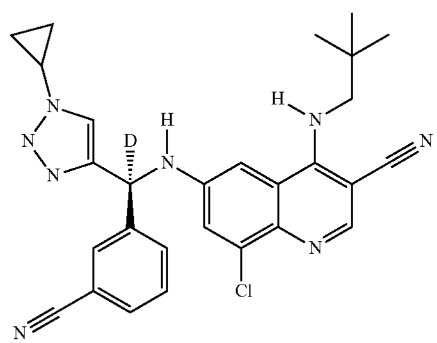 | (S)-8-chloro-6-(((3-cyanophenyl)(1-cyclopropyl-1H-1,2,3-triazol-4-yl)methyl-d)amino)-4-(neopentylamino)quinoline-3-carbonitrile | 3 | ES/MS 512.3 (M + H+) |

TABLE 1-continued

| Compd | Structure | Name | Example/Procedure | ES/MS m/z |
|---|---|---|---|---|
| 342 | 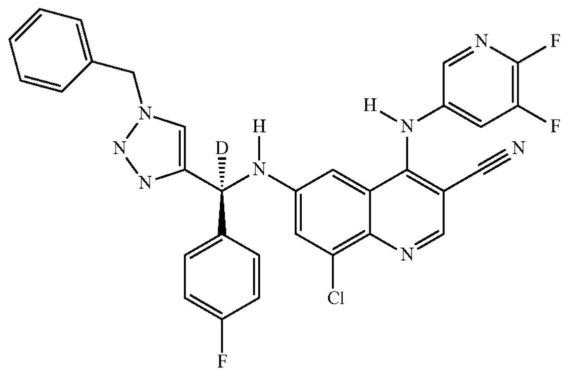 | (S)-6-(((1-benzyl-1H-1,2,3-triazol-4-yl)(4-fluorophenyl)methyl-d)amino)-8-chloro-4-((5,6-difluoropyridin-3-yl)amino)quinoline-3-carbonitrile | 1 | ES/MS 598.1 (M + H+) |
| 343 | 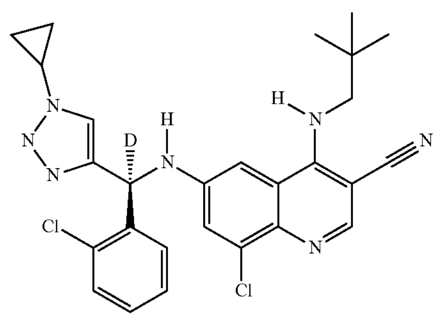 | (S)-8-chloro-6-(((2-chlorophenyl)(1-cyclopropyl-1H-1,2,3-triazol-4-yl)methyl-d)amino)-4-(neopentylamino)quinoline-3-carbonitrile | 5 | ES/MS 521.2 (M + H+) |
| 344 | 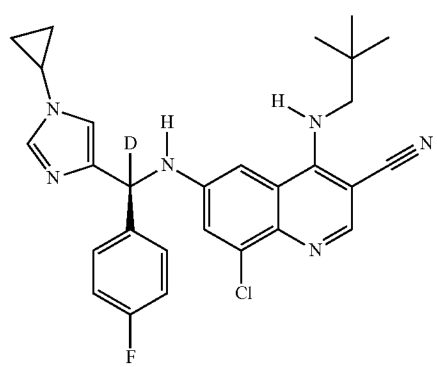 [SMILES: [2H][C@@](Nc1cc(Cl)c2ncc(C#N)c(NCC(C)(C)C)c2c1)(c1ccc(F)cc1)c1cn(C2CC2)cn1] | 8-chloro-6-(((1-cyclopropyl-1H-imidazol-4-yl)(4-fluorophenyl)methyl-d)amino)-4-(neopentylamino)quinoline-3-carbonitrile | 7 | ES/MS 504.2 (M + H+) |

TABLE 1-continued

| Compd | Structure | Name | Example/Procedure | ES/MS m/z |
|---|---|---|---|---|
| 345 | 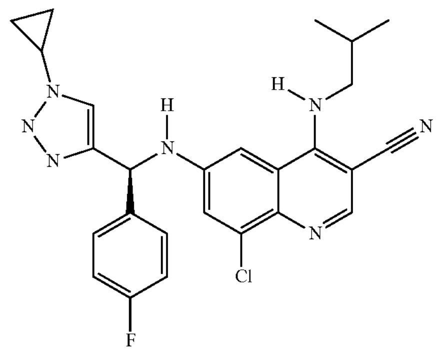 [SMILES: CC(C)CNc1c(C#N)cnc2c(Cl)cc(N[C@H](C3=CN(C4CC4)NN3)c3ccc(F)cc3)cc12] | (S)-8-chloro-6-(((1-cyclopropyl-1H-1,2,3-triazol-4-yl)(4-fluorophenyl)methyl)amino)-4-(isobutylamino)quinoline-3-carbonitrile | 1 | ES/MS 490.2 (M + H+) |
| 346 | 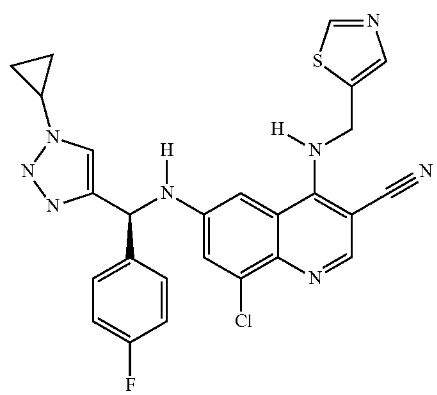 [SMILES: N#Cc1cnc2c(Cl)cc(N[C@H](C3=CN(C4CC4)NN3)c3ccc(F)cc3)cc2c1NCc1cncs1] | (S)-8-chloro-6-(((1-cyclopropyl-1H-1,2,3-triazol-4-yl)(4-fluorophenyl)methyl)amino)-4-((thiazol-5-ylmethyl)amino)quinoline-3-carbonitrile | 1 | ES/MS 531.1 (M + H+) |

TABLE 1-continued

| Compd | Structure | Name | Example/Procedure | ES/MS m/z |
|---|---|---|---|---|
| 347 | 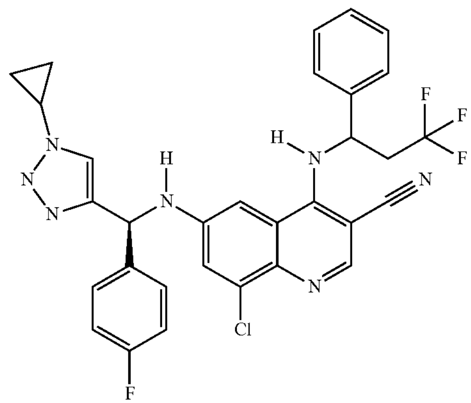 [SMILES: N#Cc1cnc2c(Cl)cc(N[C@H](C3=CN(C4CC4)NN3)c3ccc(F)cc3)cc2c1NC(CC(F)(F)F)c1ccccc1] | 8-chloro-6-(((S)-(1-cyclopropyl-1H-1,2,3-triazol-4-yl)(4-fluorophenyl)methyl)amino)-4-(((3,3,3-trifluoro-1-phenylpropyl)amino)quinoline-3-carbonitrile | 1 | ES/MS 606.2 (M + H+) |
| 348 | 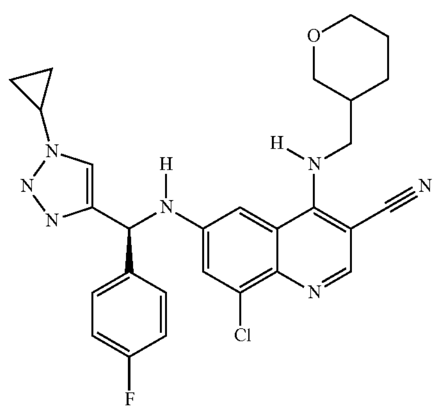 [SMILES: N#Cc1cnc2c(Cl)cc(N[C@H](C3=CN(C4CC4)NN3)c3ccc(F)cc3)cc2c1NCC1CCCOC1] | 8-chloro-6-(((S)-(1-cyclopropyl-1H-1,2,3-triazol-4-yl)(4-fluorophenyl)methyl)amino)-4-(((tetrahydro-2H-pyran-3-yl)methyl)amino)quinoline-3-carbonitrile | 1 | ES/MS 532.2 (M + H+) |

TABLE 1-continued

| Compd | Structure | Name | Example/Procedure | ES/MS m/z |
|---|---|---|---|---|
| 349 | 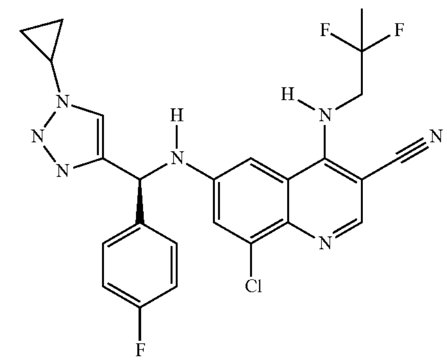 [SMILES: CC(F)(F)CNc1c(C#N)cnc2c(Cl)cc(N[C@H](C3=CN(C4CC4)NN3)c3ccc(F)cc3)cc12] | (S)-8-chloro-6-(((1-cyclopropyl-1H-1,2,3-triazol-4-yl)(4-fluorophenyl)methyl)amino)-4-((2,2-difluoropropyl)amino)quinoline-3-carbonitrile | 1 | ES/MS 512.2 (M + H+) |
| 350 | 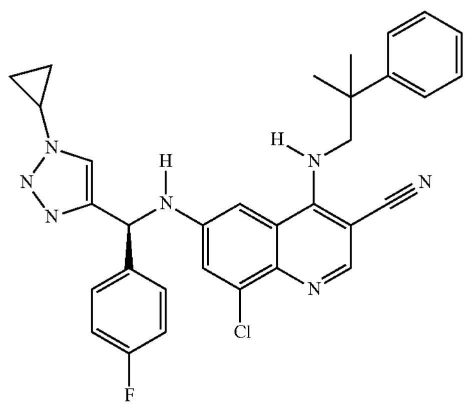 [SMILES: CC(C)(CNc1c(C#N)cnc2c(Cl)cc(N[C@H](C3=CN(C4CC4)NN3)c3ccc(F)cc3)cc12)c1ccccc1] | (S)-8-chloro-6-(((1-cyclopropyl-1H-1,2,3-triazol-4-yl)(4-fluorophenyl)methyl)amino)-4-((2-methyl-2-phenylpropyl)amino)quinoline-3-carbonitrile | 1 | ES/MS 566.2 (M + H+) |

TABLE 1-continued

| Compd | Structure | Name | Example/Procedure | ES/MS m/z |
|---|---|---|---|---|
| 351 | 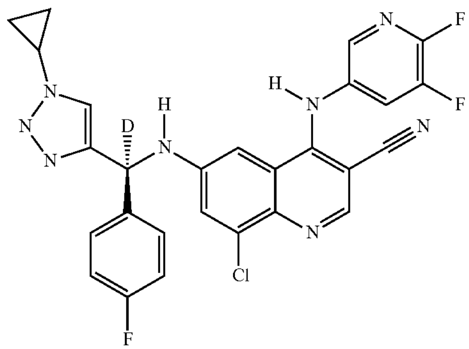 | (S)-6-(((1-cyclopropyl-1H-1,2,3-triazol-4-yl)(4-fluorophenyl)methyl-d)amino)-4-((5,6-difluoropyridin-3-yl)amino)quinoline-3,8-dicarbonitrile | 1 | ES/MS 539.2 (M + H+) |
| 352 | 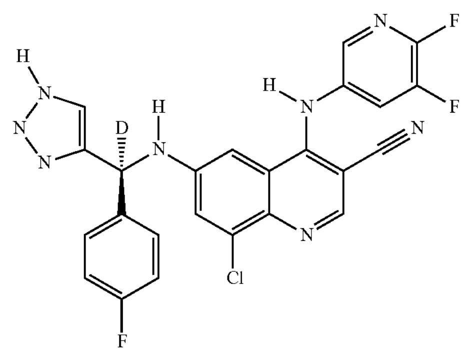 | (S)-8-chloro-4-((5,6-difluoropyridin-3-yl)amino)-6-(((4-fluorophenyl)(1H-1,2,3-triazol-4-yl)methyl-d)amino)quinoline-3-carbonitrile | 15 | ES/MS 508.0 (M + H+) |
| 353 | 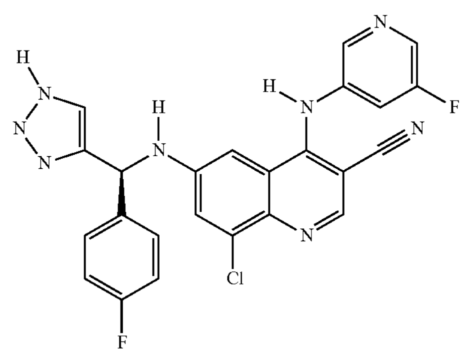 [SMILES: N#Cc1cnc2c(Cl)cc(N[C@H](C3=CNNN3)c3ccc(F)cc3)cc2c1Nc1cncc(F)c1] | (S)-8-chloro-6-(((4-fluorophenyl)(1H-1,2,3-triazol-4-yl)methyl)amino)-4-((5-fluoropyridin-3-yl)amino)quinoline-3-carbonitrile | 15 | ES/MS 489.1 (M + H+) |

TABLE 1-continued
| Compd | Structure | Name | Example/Procedure | ES/MS m/z |
|---|---|---|---|---|
| 354 | 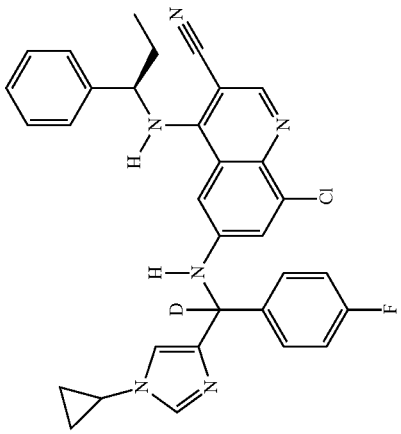 | 8-chloro-6-(((1-cyclopropyl-1H-imidazol-4-yl)(4-fluorophenyl)methyl-d)amino)-4-(((R)-1-phenylpropyl)amino)quinoline-3-carbonitrile | 7 | ES/MS 552.1 (M + H+) |
| 355 | 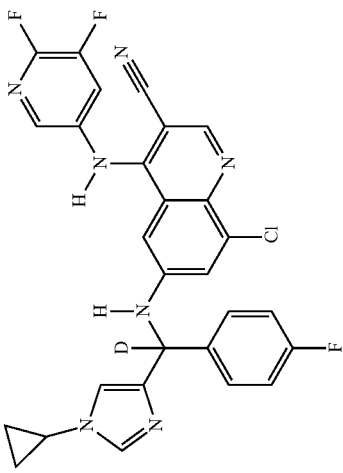 | 8-chloro-6-(((1-cyclopropyl-1H-imidazol-4-yl)(4-fluorophenyl)methyl-d)amino)-4-((5,6-difluoropyridin-3-yl)amino)quinoline-3-carbonitrile | 7 | ES/MS 546.9 (M + H+) |

TABLE 1-continued

| Compd | Structure | Name | Example/Procedure | ES/MS m/z |
|---|---|---|---|---|
| 356 | 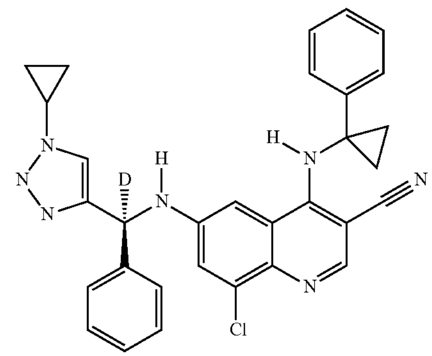 | (S)-8-chloro-6-(((2-chlorophenyl)(1-cyclopropyl-1H-1,2,3-triazol-4-yl)methyl-d)amino)-4-((1-phenylcyclopropyl)amino)quinoline-3-carbonitrile | 3 | ES/MS 567.2 (M + H+) |
| 357 | 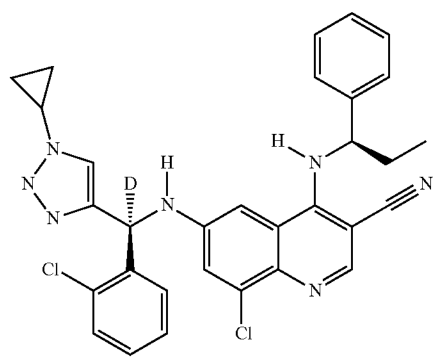 | 8-chloro-6-(((S)-(2-chlorophenyl)(1-cyclopropyl-1H-1,2,3-triazol-4-yl)methyl-d)amino)-4-(((R)-1-phenylpropyl)amino)quinoline-3-carbonitrile | 4 | ES/MS 569.1 (M + H+) |
| 358 | 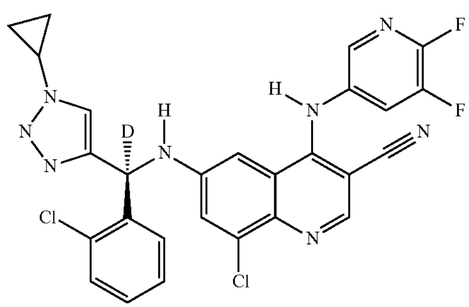 | (S)-8-chloro-6-(((2-chlorophenyl)(1-cyclopropyl-1H-1,2,3-triazol-4-yl)methyl-d)amino)-4-((5,6-difluoropyridin-3-yl)amino)quinoline-3-carbonitrile | 4 | ES/MS 564.1 (M + H+) |

TABLE 1-continued
| Compd | Structure | Name | Example/Procedure | ES/MS m/z |
|---|---|---|---|---|
| 359 | 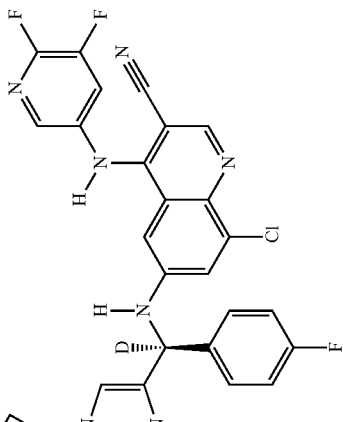 | (S)-8-chloro-4-((5,6-difluoropyridin-3-yl)amino)-6-(((1-(1,1-dioxidothietan-3-yl)-1H-1,2,3-triazol-4-yl)(4-fluorophenyl)methyl)amino)quinoline-3-carbonitrile | 4 | ES/MS 612.1 (M + H+) |
| 360 | 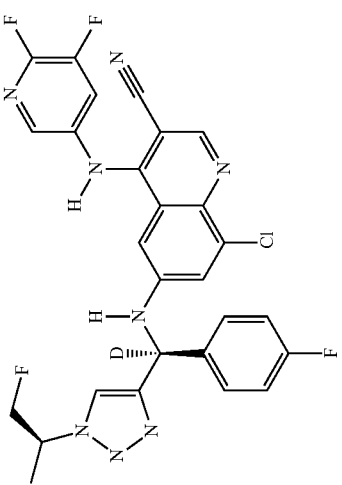 | 8-chloro-4-((5,6-difluoropyridin-3-yl)amino)-6-(((S)-(4-fluorophenyl)(1-((S)-1-fluoropropan-2-yl)-1H-1,2,3-triazol-4-yl)methyl)amino)quinoline-3-carbonitrile | 4 | ES/MS 568.1 (M + H+) |

TABLE 1-continued
| Compd | Structure | Name | Example/Procedure | ES/MS m/z |
|---|---|---|---|---|
| 361 | 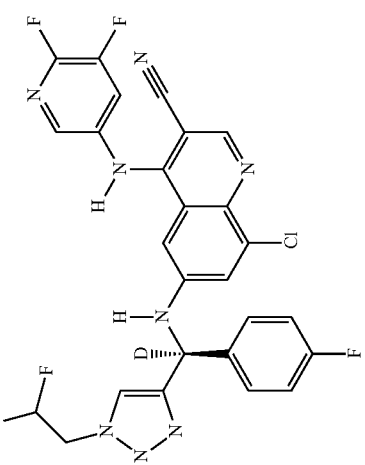 | (S)-8-chloro-6-(((1-(2,2-difluoroethyl)-1H-1,2,3-triazol-4-yl)(4-fluorophenyl)methyl-d)amino)-4-((5,6-difluoropyridin-3-yl)amino)quinoline-3-carbonitrile | 4 | ES/MS 572.1 (M + H+) |
| 362 | 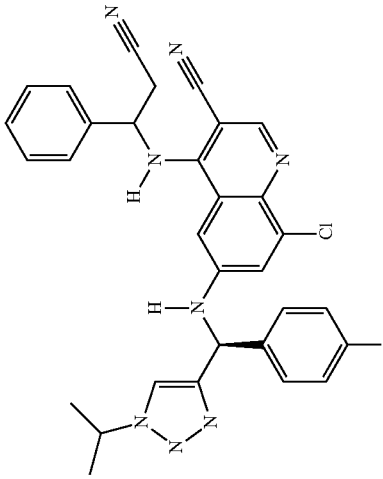 | 8-chloro-4-((2-cyano-1-phenylethyl)amino)-6-(((S)-(4-fluorophenyl)(1-isopropyl-1H-1,2,3-triazol-4-yl)methyl)amino)quinoline-3-carbonitrile | 1 | ES/MS 565.2 (M + H+) |

TABLE 1-continued
| Compd | Structure | Name | Example/Procedure | ES/MS m/z |
|---|---|---|---|---|
| 363 | 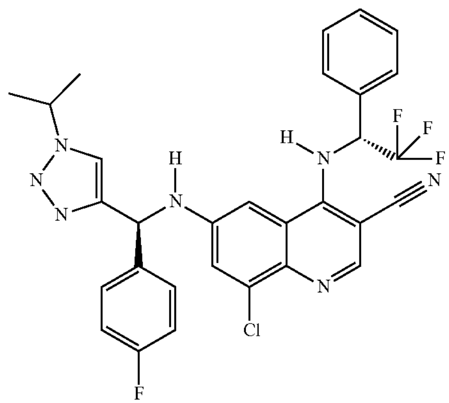 [SMILES: CC(C)N1C=C([C@@H](Nc2cc(Cl)c3ncc(C#N)c(N[C@H](c4ccccc4)C(F)(F)F)c3c2)c2ccc(F)cc2)NN1] | 8-chloro-6-(((S)-(4-fluorophenyl)(1-isopropyl-1H-1,2,3-triazol-4-yl)methyl)amino)-4-(((R)-2,2,2-trifluoro-1-phenylethyl)amino)quinoline-3-carbonitrile | 1 | ES/MS 594.2 (M + H+) |
| 364 | 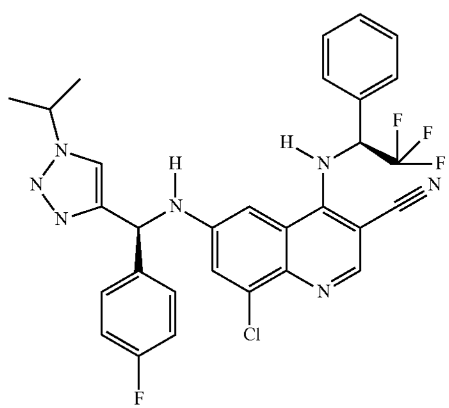 [SMILES: CC(C)N1C=C([C@@H](Nc2cc(Cl)c3ncc(C#N)c(N[C@@H](c4ccccc4)C(F)(F)F)c3c2)c2ccc(F)cc2)NN1] | 8-chloro-6-(((S)-(4-fluorophenyl)(1-isopropyl-1H-1,2,3-triazol-4-yl)methyl)amino)-4-(((S)-2,2,2-trifluoro-1-phenylethyl)amino)quinoline-3-carbonitrile | 1 | ES/MS 594.2 (M + H+) |

TABLE 1-continued

| Compd | Structure | Name | Example/Procedure | ES/MS m/z |
|---|---|---|---|---|
| 365 | 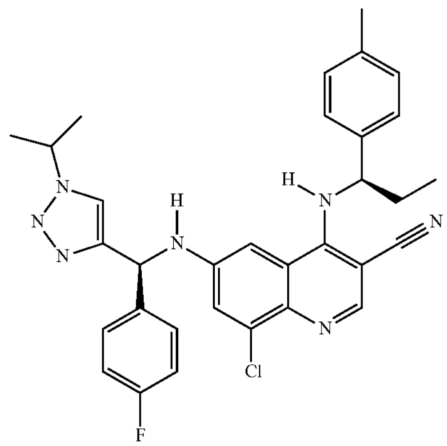 [SMILES: CC[C@@H](Nc1c(C#N)cnc2c(Cl)cc(N[C@H](C3=CN(C(C)C)NN3)c3ccc(F)cc3)cc12)c1ccc(C)cc1] | 8-chloro-6-(((S)-(4-fluorophenyl)(1-isopropyl-1H-1,2,3-triazol-4-yl)methyl)amino)-4-(((R)-1-(p-tolyl)propyl)amino)quinoline-3-carbonitrile | 1 | ES/MS 568.2 (M + H+) |
| 366 | 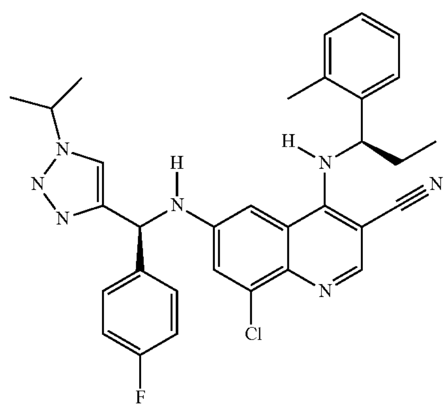 [SMILES: CC[C@@H](Nc1c(C#N)cnc2c(Cl)cc(N[C@H](C3=CN(C(C)C)NN3)c3ccc(F)cc3)cc12)c1ccccc1C] | 8-chloro-6-(((S)-(4-fluorophenyl)(1-isopropyl-1H-1,2,3-triazol-4-yl)methyl)amino)-4-(((R)-1-(o-tolyl)propyl)amino)quinoline-3-carbonitrile | 1 | ES/MS 568.2 (M + H+) |

TABLE 1-continued

| Compd | Structure | Name | Example/Procedure | ES/MS m/z |
|---|---|---|---|---|
| 367 | 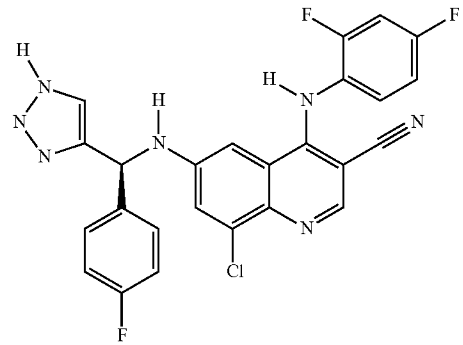 [SMILES: N#Cc1cnc2c(Cl)cc(N[C@H](C3=CNNN3)c3ccc(F)cc3)cc2c1Nc1ccc(F)cc1F] | (S)-8-chloro-4-((2,4-difluorophenyl)amino)-6-(((4-fluorophenyl)(1H-1,2,3-triazol-4-yl)methyl)amino)quinoline-3-carbonitrile | 15 | ES/MS 506.1 (M + H+) |
| 368 | 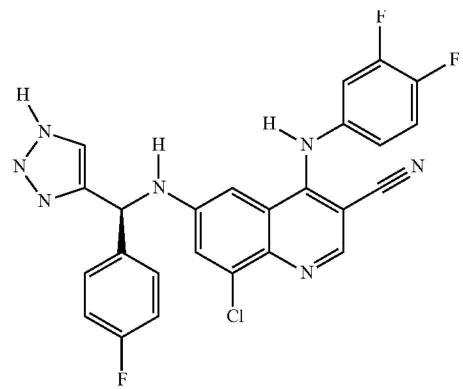 [SMILES: N#Cc1cnc2c(Cl)cc(N[C@H](C3=CNNN3)c3ccc(F)cc3)cc2c1Nc1ccc(F)c(F)c1] | (S)-8-chloro-4-((3,4-difluorophenyl)amino)-6-(((4-fluorophenyl)(1H-1,2,3-triazol-4-yl)methyl)amino)quinoline-3-carbonitrile | 15 | ES/MS 506.1 (M + H+) |
| 369 | 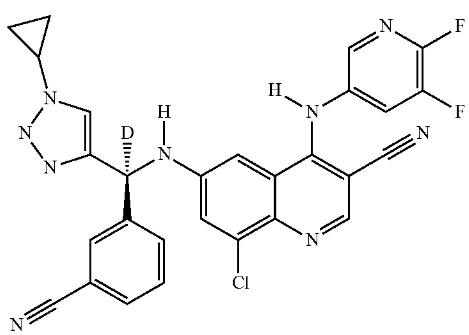 | (S)-8-chloro-6-(((3-cyanophenyl)(1-cyclopropyl)-1H-1,2,3-triazol-4-yl)methyl-d)amino)-4-((5,6-difluoropyridin-3-yl)amino)quinoline-3-carbonitrile | 3 | ES/MS 555.1 (M + H+) |

TABLE 1-continued

| Compd | Structure | Name | Example/Procedure | ES/MS m/z |
|---|---|---|---|---|
| 370 | 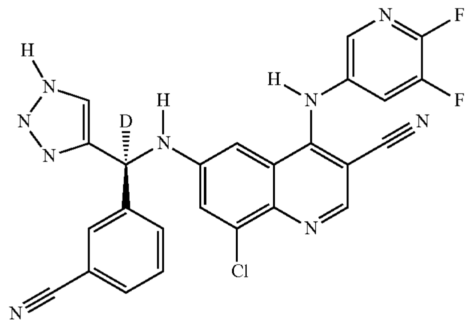 | (S)-8-chloro-6-(((3-cyanophenyl)(1H-1,2,3-triazol-4-yl)methyl)amino)-4-((5,6-difluoropyridin-3-yl)amino)quinoline-3-carbonitrile | 15 | ES/MS 515.1 (M + H+) |
| 371 | 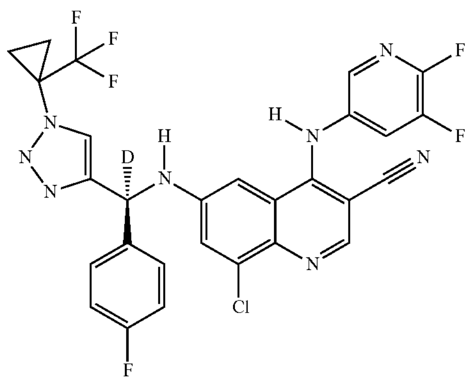 | (S)-8-chloro-4-((5,6-difluoropyridin-3-yl)amino)-6-(((4-fluorophenyl)(1-(trifluoromethyl)cyclopropyl)-1H-1,2,3-triazol-4-yl)methyl-d)amino)quinoline-3-carbonitrile | 4 | ES/MS 616.1 (M + H+) |
| 372 | 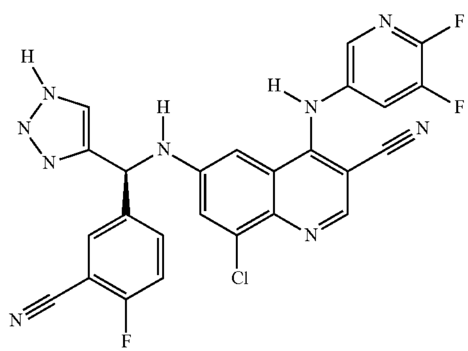 [SMILES: N#Cc1cc([C@H](Nc2cc(Cl)c3ncc(C#N)c(Nc4cnc(F)c(F)c4)c3c2)C2=CNNN2)ccc1F] | (S)-8-chloro-6-(((3-cyano-4-fluorophenyl)(1H-1,2,3-triazol-4-yl)methyl)amino)-4-((5,6-difluoropyridin-3-yl)amino)quinoline-3-carbonitrile | 15 | ES/MS 532.1 (M + H+) |

TABLE 1-continued

| Compd | Structure | Name | Example/Procedure | ES/MS m/z |
|---|---|---|---|---|
| 373 | 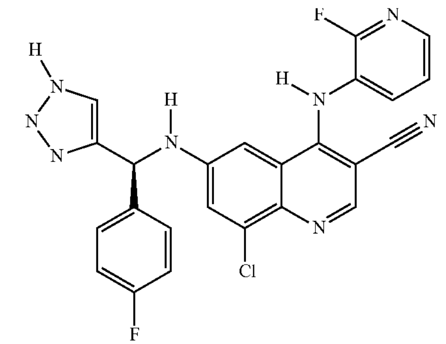 [SMILES: N#Cc1cnc2c(Cl)cc(N[C@H](C3=CNNN3)c3ccc(F)cc3)cc2c1Nc1cccnc1F] | (S)-8-chloro-6-(((4-fluorophenyl)(1H-1,2,3-triazol-4-yl)methyl)amino)-4-((2-fluoropyridin-3-yl)amino)quinoline-3-carbonitrile | 15 | ES/MS 489.1 (M + H+) |
| 374 | 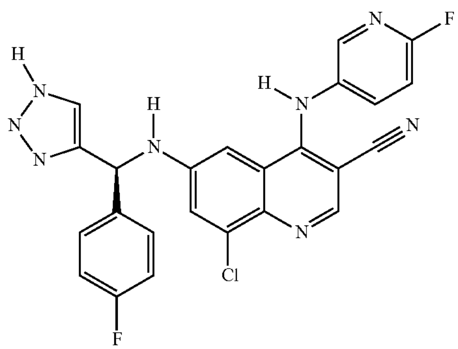 [SMILES: N#Cc1cnc2c(Cl)cc(N[C@H](C3=CNNN3)c3ccc(F)cc3)cc2c1Nc1ccc(F)nc1] | (S)-8-chloro-6-(((4-fluorophenyl)(1H-1,2,3-triazol-4-yl)methyl)amino)-4-((6-fluoropyridin-3-yl)amino)quinoline-3-carbonitrile | 15 | ES/MS 490.1 (M + H+) |
| 375 | 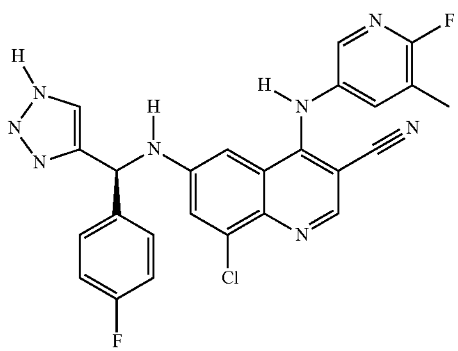 | (S)-8-chloro-4-((6-fluoro-5-methylpyridin-3-yl)amino)-6-(((4-fluorophenyl)(1H-1,2,3-triazol-4-yl)methyl)amino)quinoline-3-carbonitrile | 15 | ES/MS 503.1 (M + H+) |

TABLE 1-continued

| Compd | Structure | Name | Example/Procedure | ES/MS m/z |
|---|---|---|---|---|
| 376 | 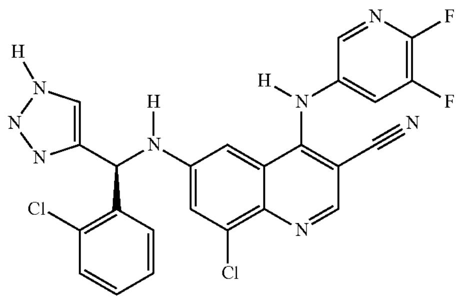 | (S)-8-chloro-6-(((2-chlorophenyl)(1H-1,2,3-triazol-4-yl)methyl)amino)-4-((5,6-difluoropyridin-3-yl)amino)quinoline-3-carbonitrile | 15 | ES/MS 523.1 (M + H+) |
| 377 | 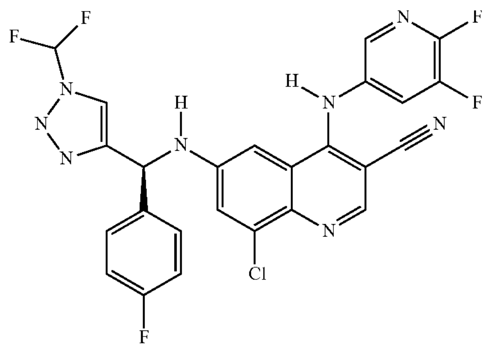 [SMILES: N#Cc1cnc2c(Cl)cc(N[C@H](C3=CN(C(F)F)NN3)c3ccc(F)cc3)cc2c1Nc1cnc(F)c(F)c1] | (S)-8-chloro-6-(((1-(difluoromethyl)-1H-1,2,3-triazol-4-yl)(4-fluorophenyl)methyl)amino)-4-((5,6-difluoropyridin-3-yl)amino)quinoline-3-carbonitrile | 44 | ES/MS 557.1 (M + H+) |
| 378 | 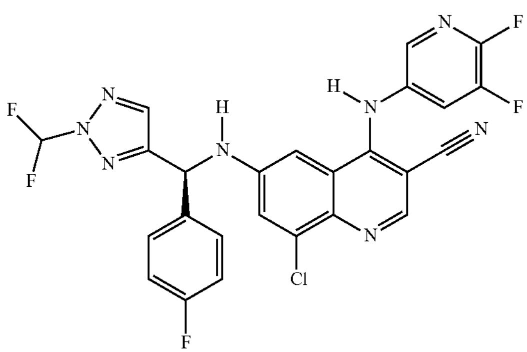 [SMILES: N#Cc1cnc2c(Cl)cc(N[C@@H](c3ccc(F)cc3)c3cnn(C(F)F)n3)cc2c1Nc1cnc(F)c(F)c1] | (S)-8-chloro-6-(((2-(difluoromethyl)-2H-1,2,3-triazol-4-yl)(4-fluorophenyl)methyl)amino)-4-((5,6-difluoropyridin-3-yl)amino)quinoline-3-carbonitrile | 44 | ES/MS 557.1 (M + H+) |

TABLE 1-continued

| Compd | Structure | Name | Example/Procedure | ES/MS m/z |
|---|---|---|---|---|
| 379 | 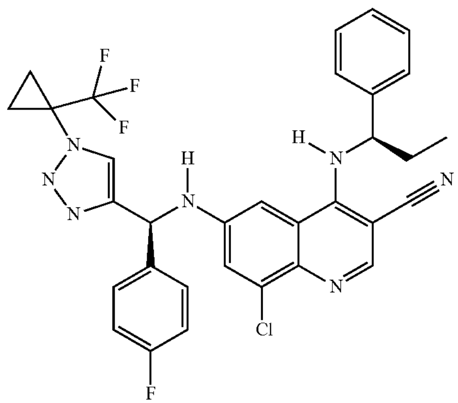 [SMILES: CC[C@@H](Nc1c(C#N)cnc2c(Cl)cc(N[C@H](C3=CN(C4(C(F)(F)F)CC4)NN3)c3ccc(F)cc3)cc12)c1ccccc1] | 8-chloro-6-(((S)-(4-fluorophenyl)(1-(1-(trifluoromethyl)cyclopropyl)-1H-1,2,3-triazol-4-yl)methyl)amino)-4-(((R)-1-phenylpropyl)amino)quinoline-3-carbonitrile | 1 | ES/MS 620.2 (M + H+) |
| 380 | 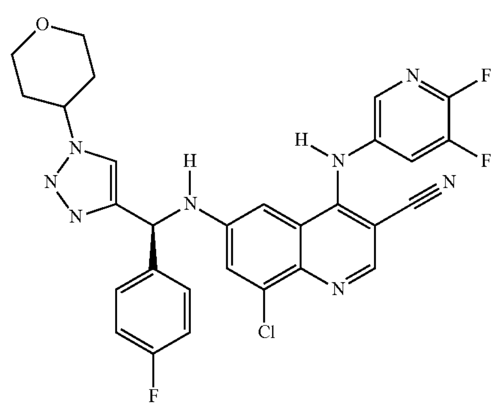 [SMILES: N#Cc1cnc2c(Cl)cc(N[C@H](C3=CN(C4CCOCC4)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-(tetrahydro-2H-pyran-4-yl)-1H-1,2,3-triazol-4-yl)methyl)amino)quinoline-3-carbonitrile | 3 | ES/MS 591.1 (M + H+) |

TABLE 1-continued

| Compd | Structure | Name | Example/Procedure | ES/MS m/z |
|---|---|---|---|---|
| 381 | 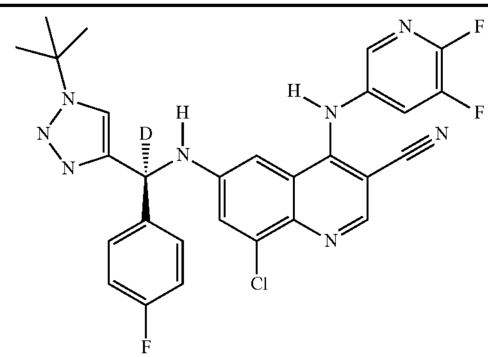 | (S)-6-((((1-(tert-butyl)-1H-1,2,3-triazol-4-yl)(4-fluorophenyl)methyl-d)amino)-8-chloro-4-((5,6-difluoropyridin-3-yl)amino)quinoline-3-carbonitrile | 3 | ES/MS 564.0 (M + H+) |
| 382 | 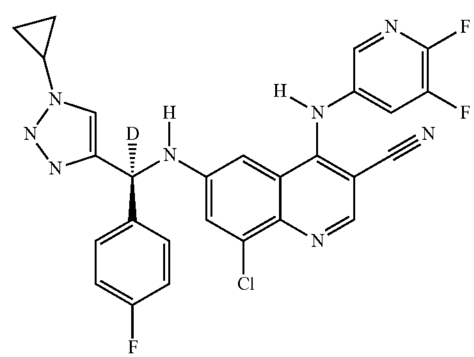 | (S)-8-chloro-6-(((1-cyclopropyl-1H-1,2,3-triazol-4-yl)(4-fluorophenyl)methyl-d)amino)-4-(((5,6-difluoropyridin-3-yl)amino)quinoline-3-carbonitrile | 4 | ES/MS 548.0 (M + H+) |

TABLE 1-continued

| Compd | Structure | Name | Example/Procedure | ES/MS m/z |
|---|---|---|---|---|
| 383 | 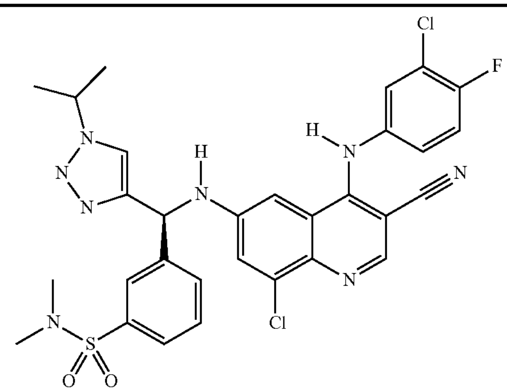 | (S)-3-(((8-chloro-4-((3-chloro-4-fluorophenyl)amino)-3-cyanoquinolin-6-yl)amino)(1-isopropyl-1H-1,2,3-triazol-4-yl)methyl)-N,N-dimethylbenzenesulfonamide | 3 | ES/MS 653.3 (M + H+) |
| 384 | 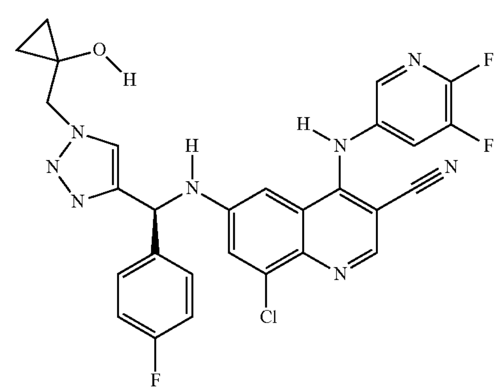 [SMILES: N#Cc1cnc2c(Cl)cc(N[C@H](C3=CN(CC4(O)CC4)NN3)c3ccc(F)cc3)cc2c1Nc1cnc(F)c(F)c1] | (S)-8-chloro-4-((5,6-difluoropyridin-3-yl)amino)-6-((((4-fluorophenyl)(1-((1-hydroxycyclopropyl)methyl)-1H-1,2,3-triazol-4-yl)methyl)amino)quinoline-3-carbonitrile | 4 | ES/MS 577.0 (M + H+) |

TABLE 1-continued

| Compd | Structure | Name | Example/Procedure | ES/MS m/z |
|---|---|---|---|---|
| 385 | 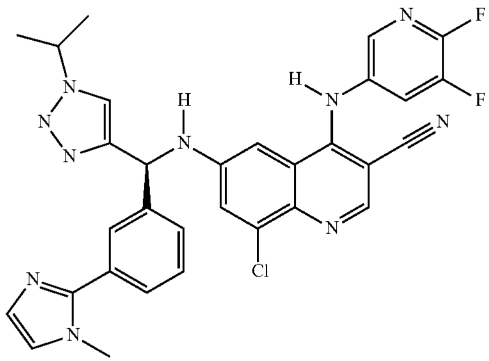 [SMILES: CC(C)N1C=C([C@@H](Nc2cc(Cl)c3ncc(C#N)c(Nc4cnc(F)c(F)c4)c3c2)c2cccc(-c3nccn3C)c2)NN1] | (S)-8-chloro-4-((5,6-difluoropyridin-3-yl)amino)-6-(((1-isopropyl-1H-1,2,3-triazol-4-yl)(3-(1-methyl-1H-imidazol-2-yl)phenyl)methyl)amino)quinoline-3-carbonitrile | 3 | ES/MS 611.0 (M + H+) |
| 386 | 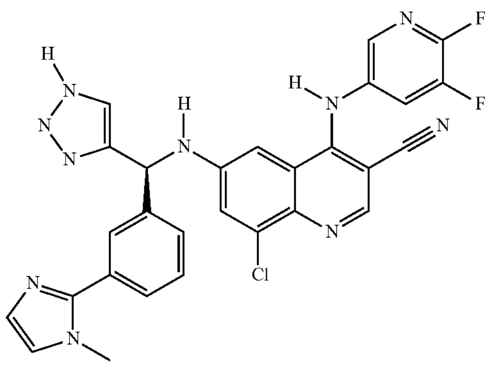 [SMILES: Cn1ccnc1-c1cccc([C@H](Nc2cc(Cl)c3ncc(C#N)c(Nc4cnc(F)c(F)c4)c3c2)C2=CNNN2)c1] | (S)-8-chloro-4-((5,6-difluoropyridin-3-yl)amino)-6-(((3-(1-methyl-1H-imidazol-2-yl)phenyl)(1H-1,2,3-triazol-4-yl)methyl)amino)quinoline-3-carbonitrile | 15 | ES/MS 569.0 (M + H+) |
| 387 | 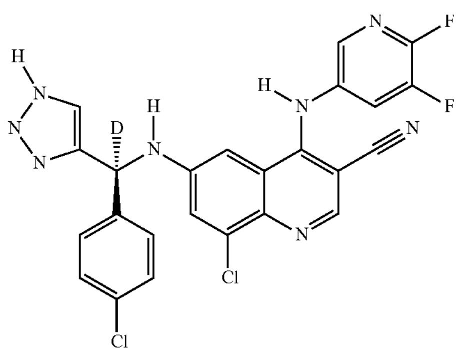 | (S)-8-chloro-6-(((4-chlorophenyl)(1H-1,2,3-triazol-4-yl)methyl-d)amino)-4-((5,6-difluoropyridin-3-yl)amino)quinoline-3-carbonitrile | 15 | ES/MS 524.0 (M + H+) |

TABLE 1-continued

| Compd | Structure | Name | Example/Procedure | ES/MS m/z |
|---|---|---|---|---|
| 388 | 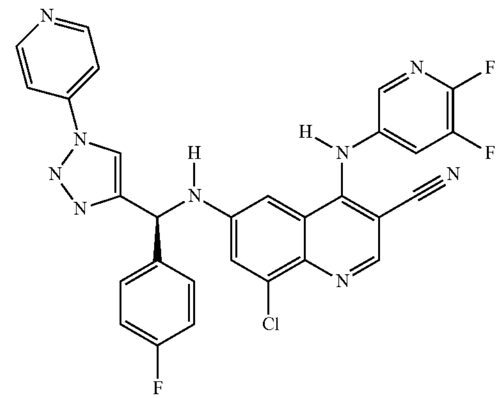 [SMILES: N#Cc1cnc2c(Cl)cc(N[C@H](C3=CN(c4ccncc4)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-(pyridin-4-yl)-1H-1,2,3-triazol-4-yl)methyl)amino)quinoline-3-carbonitrile | 10 | ES/MS 584.1 (M + H+) |
| 389 | 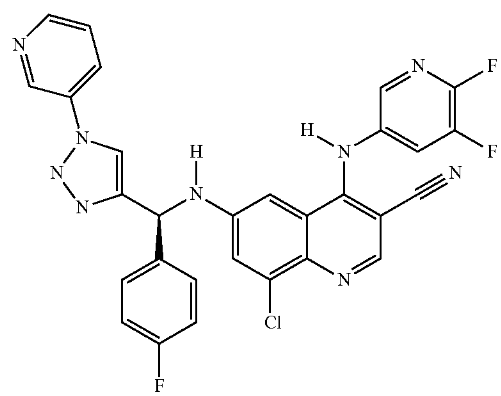 [SMILES: N#Cc1cnc2c(Cl)cc(N[C@H](C3=CN(c4cccnc4)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-(pyridin-3-yl)-1H-1,2,3-triazol-4-yl)methyl)amino)quinoline-3-carbonitrile | 10 | ES/MS 584.1 (M + H+) |

TABLE 1-continued
| Compd | Structure | Name | Example/Procedure | ES/MS m/z |
|---|---|---|---|---|
| 390 | 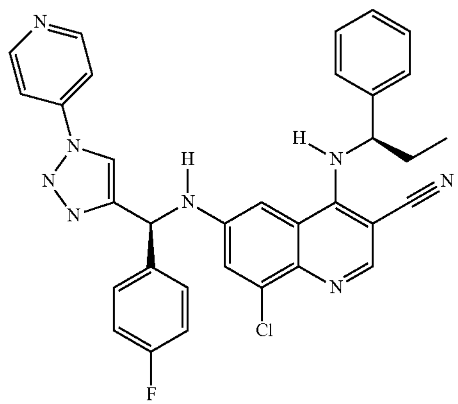 [SMILES: CC[C@@H](Nc1c(C#N)cnc2c(Cl)cc(N[C@H](C3=CN(c4ccncc4)NN3)c3ccc(F)cc3)cc12)c1ccccc1] | 8-chloro-6-(((S)-(4-fluorophenyl)(1-(pyridin-4-yl)-1H-1,2,3-triazol-4-yl)methyl)amino)-4-(((R)-1-phenylpropyl)amino)quinoline-3-carbonitrile | 1 | ES/MS 589.2 (M + H+) |
| 391 | 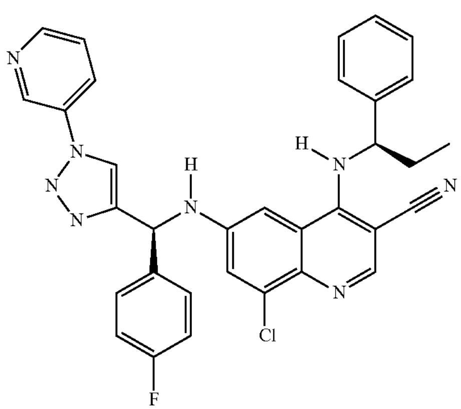 [SMILES: CC[C@@H](Nc1c(C#N)cnc2c(Cl)cc(N[C@H](C3=CN(c4cccnc4)NN3)c3ccc(F)cc3)cc12)c1ccccc1] | 8-chloro-6-(((S)-(4-fluorophenyl)(1-(pyridin-3-yl)-1H-1,2,3-triazol-4-yl)methyl)amino)-4-(((R)-1-phenylpropyl)amino)quinoline-3-carbonitrile | 1 | ES/MS 589.2 (M + H+) |

TABLE 1-continued

| Compd | Structure | Name | Example/Procedure | ES/MS m/z |
|---|---|---|---|---|
| 392 | 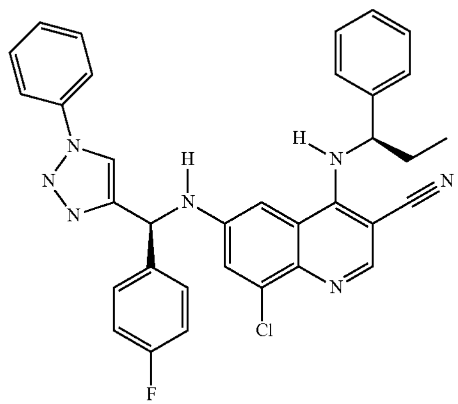 [SMILES: CC[C@@H](Nc1c(C#N)cnc2c(Cl)cc(N[C@H](C3=CN(c4ccccc4)NN3)c3ccc(F)cc3)cc12)c1ccccc1] | 8-chloro-6-(((S)-(4-fluorophenyl)(1-phenyl-1H-1,2,3-triazol-4-yl)methyl)amino)-4-(((R)-1-phenylpropyl)amino)quinoline-3-carbonitrile | 1 | ES/MS 588.2 (M + H+) |
| 393 | 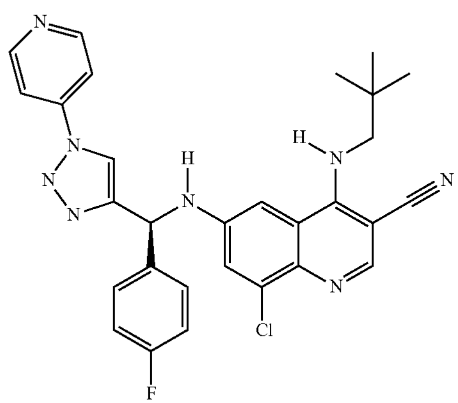 [SMILES: CC(C)(C)CNc1c(C#N)cnc2c(Cl)cc(N[C@H](C3=CN(c4ccncc4)NN3)c3ccc(F)cc3)cc12] | (S)-8-chloro-6-(((4-fluorophenyl)(1-(pyridin-4-yl)-1H-1,2,3-triazol-4-yl)methyl)amino)-4-(neopentylamino)quinoline-3-carbonitrile | 1 | ES/MS 541.2 (M + H+) |

TABLE 1-continued

| Compd | Structure | Name | Example/Procedure | ES/MS m/z |
|---|---|---|---|---|
| 394 | 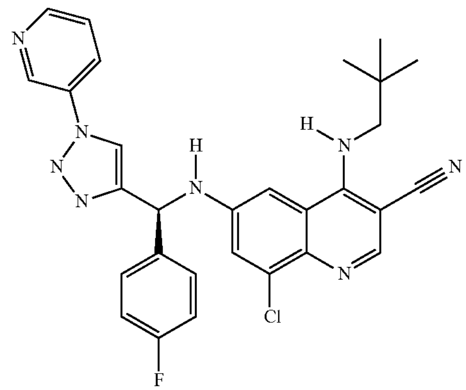 [SMILES: CC(C)(C)CNc1c(C#N)cnc2c(Cl)cc(N[C@H](C3=CN(c4cccnc4)NN3)c3ccc(F)cc3)cc12] | (S)-8-chloro-6-(((4-fluorophenyl)(1-(pyridin-3-yl)-1H-1,2,3-triazol-4-yl)methyl)amino)-4-(neopentylamino)quinoline-3-carbonitrile | 1 | ES/MS 541.2 (M + H+) |
| 395 | 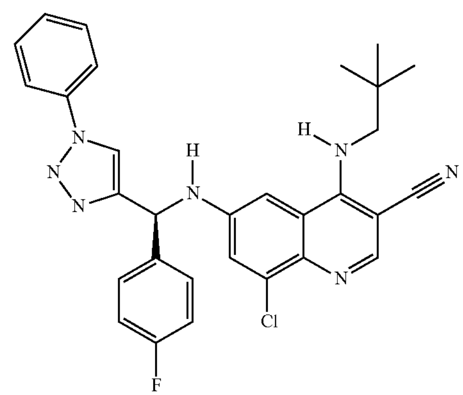 [SMILES: CC(C)(C)CNc1c(C#N)cnc2c(Cl)cc(N[C@H](C3=CN(c4ccccc4)NN3)c3ccc(F)cc3)cc12] | (S)-8-chloro-6-(((4-fluorophenyl)(1-phenyl-1H-1,2,3-triazol-4-yl)methyl)amino)-4-(neopentylamino)quinoline-3-carbonitrile | 1 | ES/MS 540.2 (M + H+) |

TABLE 1-continued

| Compd | Structure | Name | Example/Procedure | ES/MS m/z |
|---|---|---|---|---|
| 396 | 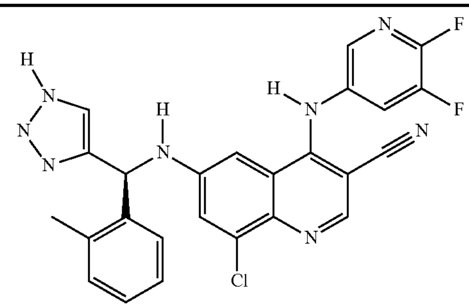 | (S)-8-chloro-4-((5,6-difluoropyridin-3-yl)amino)-6-((o-tolyl(1H-1,2,3-triazol-4-yl)methyl)amino)quinoline-3-carbonitrile | 15 | ES/MS 503.0 (M + H+) |
| 397 | 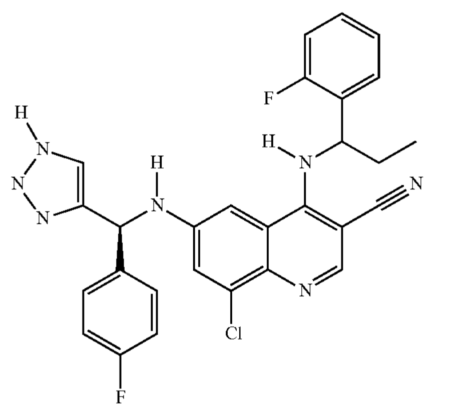 [SMILES: CCC(Nc1c(C#N)cnc2c(Cl)cc(N[C@H](C3=CNNN3)c3ccc(F)cc3)cc12)c1ccccc1F] | 8-chloro-6-(((S)-(4-fluorophenyl)(1H-1,2,3-triazol-4-yl)methyl)amino)-4-((1-(2-fluorophenyl)propyl)amino)-quinoline-3-carbonitrile | 15 | ES/MS 530.1 (M + H+) |

TABLE 1-continued
| Compd | Structure | Name | Example/Procedure | ES/MS m/z |
|---|---|---|---|---|
| 398 | 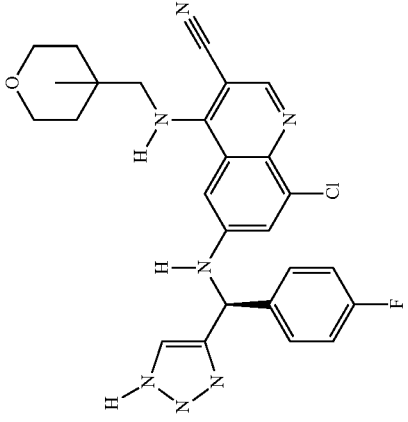 | (S)-8-chloro-6-(((4-fluorophenyl)(1H-1,2,3-triazol-4-yl)methyl)amino)-4-(((4-methyltetrahydro-2H-pyran-4-yl)methyl)amino)quinoline-3-carbonitrile | 15 | ES/MS 506.2 (M + H+) |
| 399 | 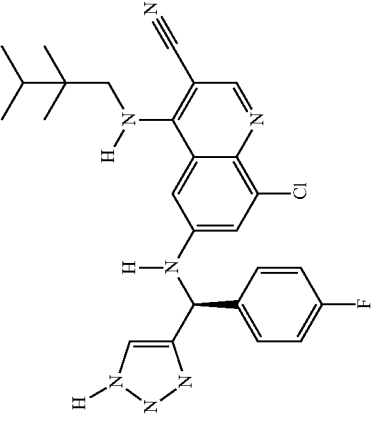 | (S)-8-chloro-6-(((4-fluorophenyl)(1H-1,2,3-triazol-4-yl)methyl)amino)-4-((2,2,3-trimethylbutyl)amino)quinoline-3-carbonitrile | 15 | ES/MS 492.2 (M + H+) |

TABLE 1-continued

| Compd | Structure | Name | Example/Procedure | ES/MS m/z |
|---|---|---|---|---|
| 400 | 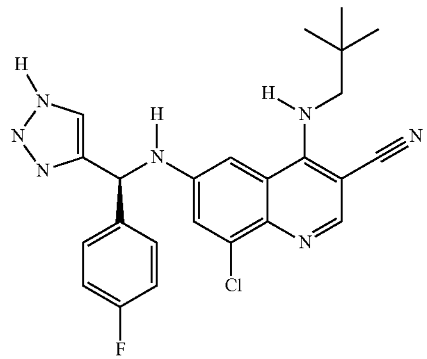 [SMILES: CC(C)(C)CNc1c(C#N)cnc2c(Cl)cc(N[C@H](C3=CNNN3)c3ccc(F)cc3)cc12] | (S)-8-chloro-6-(((4-fluorophenyl)(1H-1,2,3-triazol-4-yl)methyl)amino)-4-(neopentylamino)quinoline-3-carbonitrile | 15 | ES/MS 464.2 (M + H+) |
| 401 | 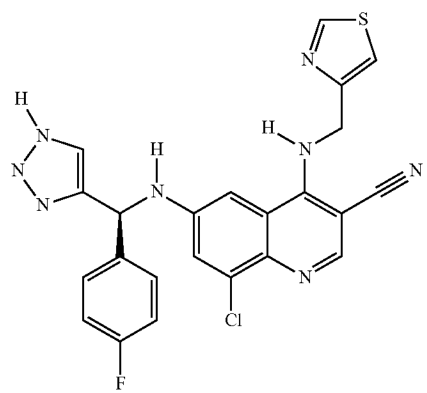 [SMILES: N#Cc1cnc2c(Cl)cc(N[C@H](C3=CNNN3)c3ccc(F)cc3)cc2c1NCc1cscn1] | (S)-8-chloro-6-(((4-fluorophenyl)(1H-1,2,3-triazol-4-yl)methyl)amino)-4-((thiazol-4-ylmethyl)amino)quinoline-3-carbonitrile | 15 | ES/MS 491.1 (M + H+) |

TABLE 1-continued

| Compd | Structure | Name | Example/Procedure | ES/MS m/z |
|---|---|---|---|---|
| 402 | 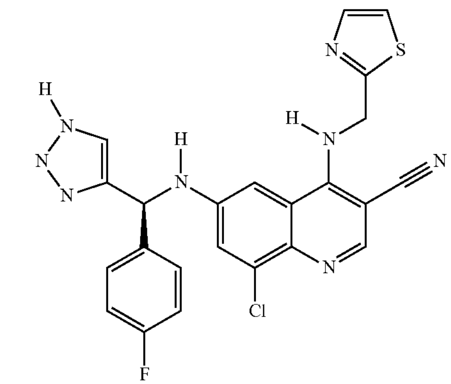 [SMILES: N#Cc1cnc2c(Cl)cc(N[C@H](C3=CNNN3)c3ccc(F)cc3)cc2c1NCc1nccs1] | (S)-8-chloro-6-(((4-fluorophenyl)(1H-1,2,3-triazol-4-yl)methyl)amino)-4-((thiazol-2-yl)methyl)amino)quinoline-3-carbonitrile | 15 | ES/MS 491.1 (M + H+) |
| 403 | 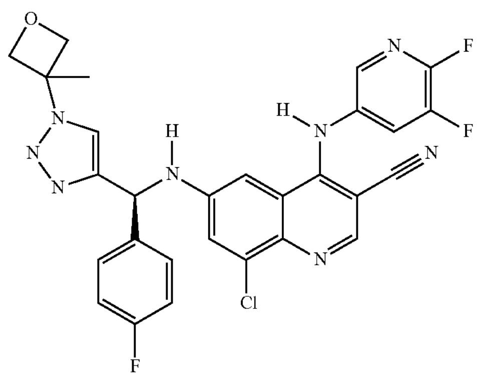 [SMILES: CC1(N2C=C([C@@H](Nc3cc(Cl)c4ncc(C#N)c(Nc5cnc(F)c(F)c5)c4c3)c3ccc(F)cc3)NN2)COC1] | (S)-8-chloro-4-((5,6-difluoropyridin-3-yl)amino)-6-(((4-fluorophenyl)(1-(3-methyloxetan-3-yl)-1H-1,2,3-triazol-4-yl)methyl)amino)quinoline-3-carbonitrile | 4 | ES/MS 577.1 (M + H+) |
| 404 | 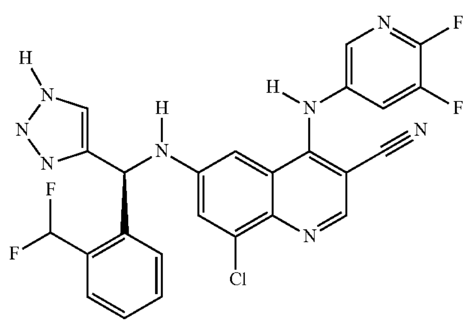 [SMILES: N#Cc1cnc2c(Cl)cc(N[C@H](C3=CNNN3)c3ccccc3C(F)F)cc2c1Nc1cnc(F)c(F)c1] | (S)-8-chloro-6-(((2-(difluoromethyl)phenyl)(1H-1,2,3-triazol-4-yl)methyl)amino)-4-((5,6-difluoropyridin-3-yl)amino)quinoline-3-carbonitrile | 15 | ES/MS 539.0 (M + H+) |

TABLE 1-continued

| Compd | Structure | Name | Example/Procedure | ES/MS m/z |
|---|---|---|---|---|
| 405 | 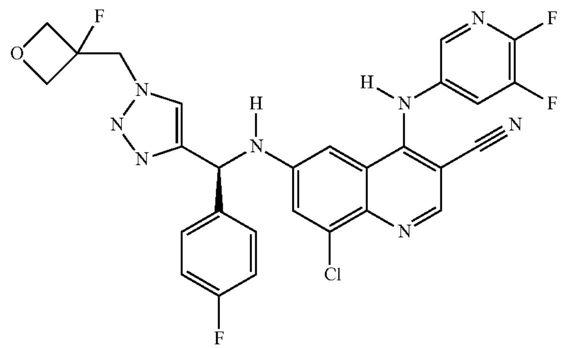 [SMILES: N#Cc1cnc2c(Cl)cc(N[C@H](C3=CN(CC4(F)COC4)NN3)c3ccc(F)cc3)cc2c1Nc1cnc(F)c(F)c1] | (S)-8-chloro-4-((5,6-difluoropyridin-3-yl)amino)-6-(((1-((3-fluorooxetan-3-yl)methyl)-1H-1,2,3-triazol-4-yl)(4-fluorophenyl)methyl)amino)-quinoline-3-carbonitrile | 4 | ES/MS 595.1 (M + H+) |
| 406 | 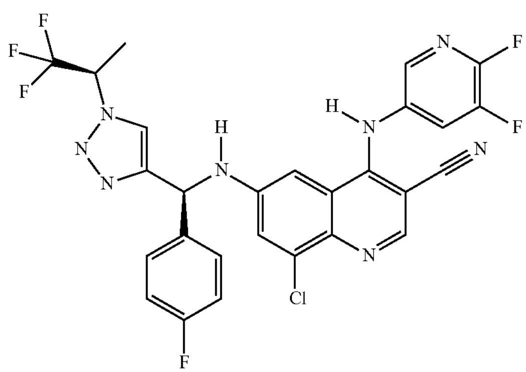 [SMILES: C[C@@H](N1C=C([C@@H](Nc2cc(Cl)c3ncc(C#N)c(Nc4cnc(F)c(F)c4)c3c2)c2ccc(F)cc2)NN1)C(F)(F)F] | 8-chloro-4-((5,6-difluoropyridin-3-yl)amino)-6-(((S)-(4-fluorophenyl)(1-((R)-1,1,1-trifluoropropan-2-yl)-1H-1,2,3-triazol-4-yl)methyl)amino)quinoline-3-carbonitrile | 4 | ES/MS 603.1 (M + H+) |

TABLE 1-continued

| Compd | Structure | Name | Example/Procedure | ES/MS m/z |
|---|---|---|---|---|
| 407 | 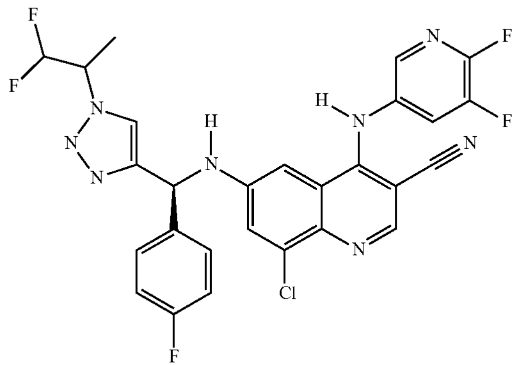 [SMILES: CC(C(F)F)N1C=C([C@@H](Nc2cc(Cl)c3ncc(C#N)c(Nc4cnc(F)c(F)c4)c3c2)c2ccc(F)cc2)NN1] | 8-chloro-6-(((1S)-(1-(1,1-difluoropropan-2-yl)-1H-1,2,3-triazol-4-yl)(4-fluorophenyl)methyl)amino)-4-(((5,6-difluoropyridin-3-yl)amino)quinoline-3-carbonitrile | 4 | ES/MS 585.1 (M + H+) |
| 408 | 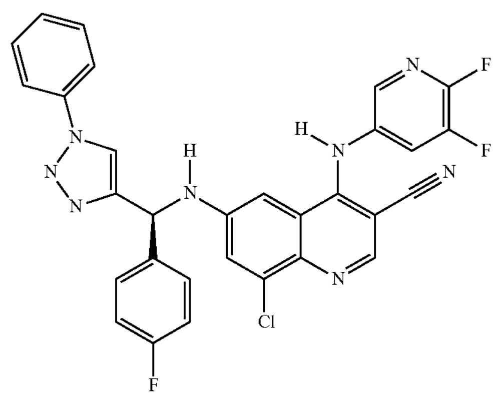 [SMILES: N#Cc1cnc2c(Cl)cc(N[C@H](C3=CN(c4ccccc4)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-phenyl-1H-1,2,3-triazol-4-yl)methyl)amino)quinoline-3-carbonitrile | 3 | ES/MS 583.0 (M + H+) |

TABLE 1-continued

| Compd | Structure | Name | Example/Procedure | ES/MS m/z |
|---|---|---|---|---|
| 409 | 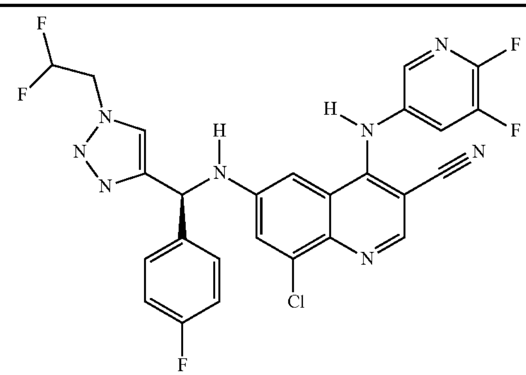 | (S)-8-chloro-6-(((1-(2,2-difluoroethyl)-1H-1,2,3-triazol-4-yl)(4-fluorophenyl)methyl)amino)-4-((5,6-difluoropyridin-3-yl)amino)quinoline-3-carbonitrile | 4 | ES/MS 571.1 (M + H+) |
| 410 | 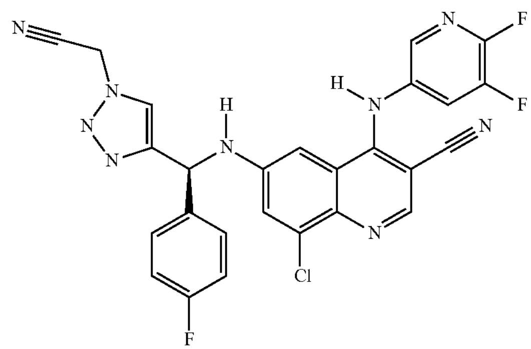 [SMILES: N#CCN1C=C([C@@H](Nc2cc(Cl)c3ncc(C#N)c(Nc4cnc(F)c(F)c4)c3c2)c2ccc(F)cc2)NN1] | (S)-8-chloro-6-(((1-(cyanomethyl)-1H-1,2,3-triazol-4-yl)(4-fluorophenyl)methyl)amino)-4-((5,6-difluoropyridin-3-yl)amino)quinoline-3-carbonitrile | 3 | ES/MS 546.1 (M + H+) |

TABLE 1-continued

| Compd | Structure | Name | Example/Procedure | ES/MS m/z |
|---|---|---|---|---|
| 411 | 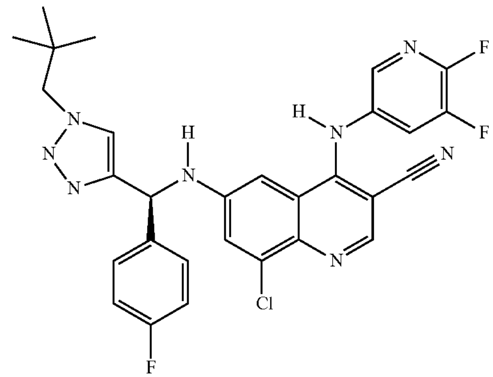 [SMILES: CC(C)(C)CN1C=C([C@@H](Nc2cc(Cl)c3ncc(C#N)c(Nc4cnc(F)c(F)c4)c3c2)c2ccc(F)cc2)NN1] | (S)-8-chloro-4-((5,6-difluoropyridin-3-yl)amino)-6-(((4-fluorophenyl)(1-neopentyl-1H-1,2,3-triazol-4-yl)methyl)amino)quinoline-3-carbonitrile | 10 | ES/MS 577.2 (M + H+) |
| 412 | 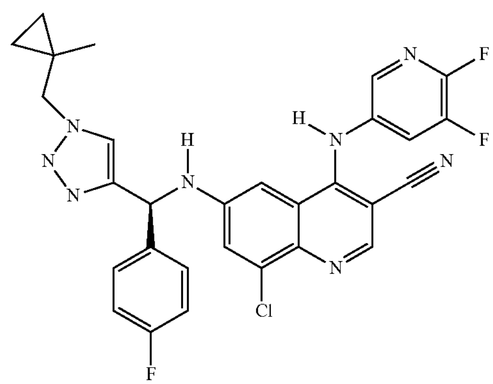 [SMILES: CC1(CN2C=C([C@@H](Nc3cc(Cl)c4ncc(C#N)c(Nc5cnc(F)c(F)c5)c4c3)c3ccc(F)cc3)NN2)CC1] | (S)-8-chloro-4-((5,6-difluoropyridin-3-yl)amino)-6-(((4-fluorophenyl)(1-((1-methylcyclopropyl)methyl)-1H-1,2,3-triazol-4-yl)methyl)amino)quinoline-3-carbonitrile | 10 | ES/MS 575.2 (M + H+) |

TABLE 1-continued

| Compd | Structure | Name | Example/Procedure | ES/MS m/z |
|---|---|---|---|---|
| 413 | 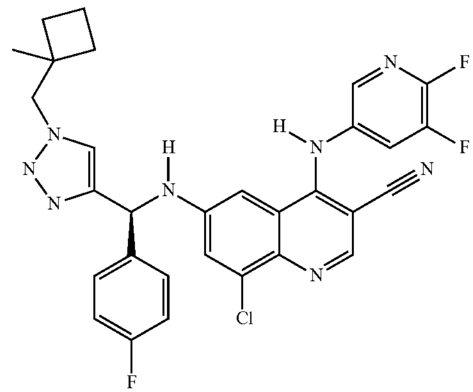 [SMILES: CC1(CN2C=C([C@@H](Nc3cc(Cl)c4ncc(C#N)c(Nc5cnc(F)c(F)c5)c4c3)c3ccc(F)cc3)NN2)CCC1] | (S)-8-chloro-4-((5,6-difluoropyridin-3-yl)amino)-6-(((4-fluorophenyl)(1-((1-methylcyclobutyl)methyl)-1H-1,2,3-triazol-4-yl)methyl)amino)quinoline-3-carbonitrile | 10 | ES/MS 589.2 (M + H+) |
| 414 | 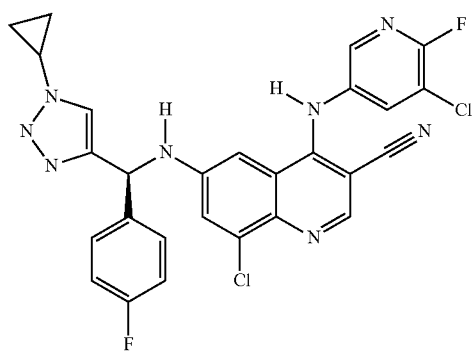 [SMILES: N#Cc1cnc2c(Cl)cc(N[C@H](C3=CN(C4CC4)NN3)c3ccc(F)cc3)cc2c1Nc1cnc(F)c(Cl)c1] | (S)-8-chloro-4-((5-chloro-6-fluoropyridin-3-yl)amino)-6-(((1-cyclopropyl-1H-1,2,3-triazol-4-yl)(4-fluorophenyl)methyl)amino)quinoline-3-carbonitrile | 10 | ES/MS 563.1 (M + H+) |

TABLE 1-continued
| Compd | Structure | Name | Example/Procedure | ES/MS m/z |
|---|---|---|---|---|
| 415 | 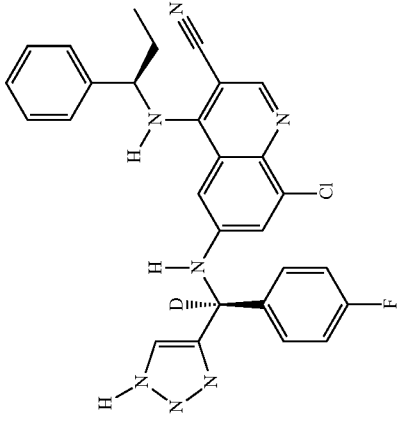 | 8-chloro-6-(((S)-(4-fluorophenyl)(1H-1,2,3-triazol-4-yl)methyl-d)amino)-4-(((R)-1-phenylpropyl)amino)quinoline-3-carbonitrile | 15 | ES/MS 513.2 (M + H+) |
| 416 | 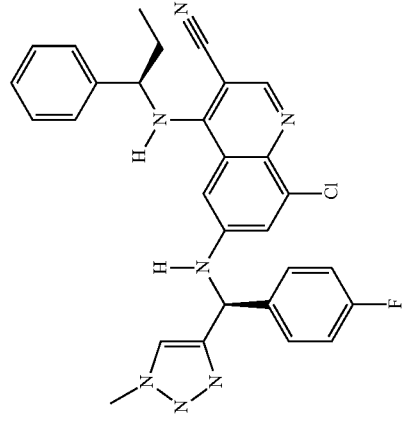 | 8-chloro-6-(((S)-(4-fluorophenyl)(1-methyl-1H-1,2,3-triazol-4-yl)methyl)amino)-4-(((R)-1-phenylpropyl)amino)quinoline-3-carbonitrile | 45 | ES/MS 526.2 (M + H+) |

TABLE 1-continued

| Compd | Structure | Name | Example/Procedure | ES/MS m/z |
|---|---|---|---|---|
| 417 | 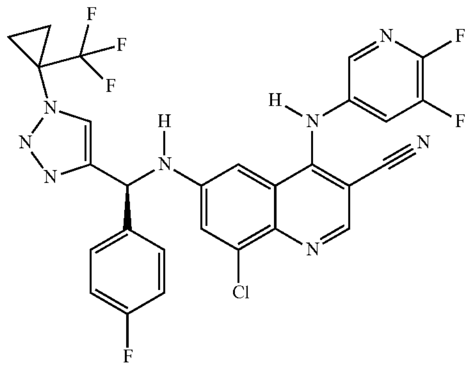 [SMILES: N#Cc1cnc2c(Cl)cc(N[C@H](C3=CN(C4(C(F)(F)F)CC4)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-(1-(trifluoromethyl)cyclopropyl)-1H-1,2,3-triazol-4-yl)methyl)amino)quinoline-3-carbonitrile | 1 | ES/MS 615.1 (M + H+) |
| 418 | 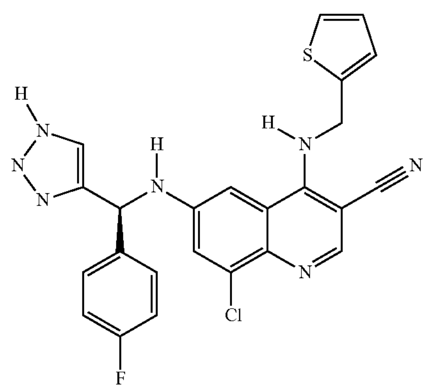 [SMILES: N#Cc1cnc2c(Cl)cc(N[C@H](C3=CNNN3)c3ccc(F)cc3)cc2c1NCc1cccs1] | (S)-8-chloro-6-(((4-fluorophenyl)(1H-1,2,3-triazol-4-yl)methyl)amino)-4-((thiophen-2-ylmethyl)amino)quinoline-3-carbonitrile | 15 | ES/MS 490.1 (M + H+) |

TABLE 1-continued

| Compd | Structure | Name | Example/Procedure | ES/MS m/z |
|---|---|---|---|---|
| 419 | 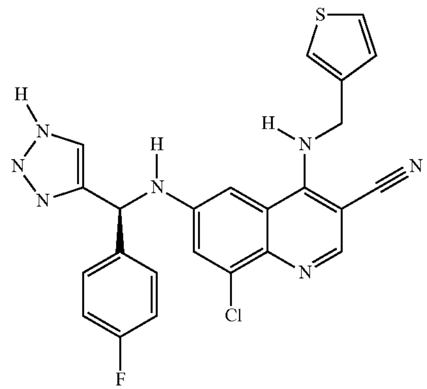 [SMILES: N#Cc1cnc2c(Cl)cc(N[C@H](C3=CNNN3)c3ccc(F)cc3)cc2c1NCc1ccsc1] | (S)-8-chloro-6-(((4-fluorophenyl)(1H-1,2,3-triazol-4-yl)methyl)amino)-4-((thiophen-3-yl)methyl)amino)quinoline-3-carbonitrile | 15 | ES/MS 490.1 (M + H+) |
| 420 | 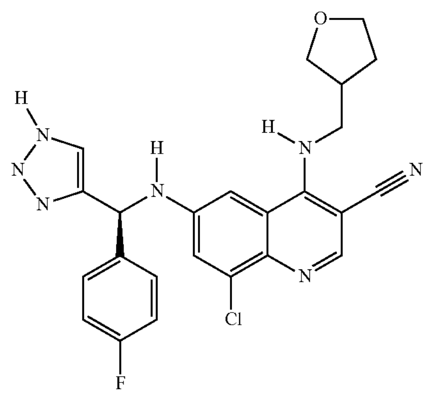 [SMILES: N#Cc1cnc2c(Cl)cc(N[C@H](C3=CNNN3)c3ccc(F)cc3)cc2c1NCC1CCOC1] | 8-chloro-6-(((S)-(4-fluorophenyl)(1H-1,2,3-triazol-4-yl)methyl)amino)-4-(((tetrahydrofuran-3-yl)methyl)amino)quinoline-3-carbonitrile | 15 | ES/MS 478.1 (M + H+) |

TABLE 1-continued
| Compd | Structure | Name | Example/Procedure | ES/MS m/z |
|---|---|---|---|---|
| 421 | 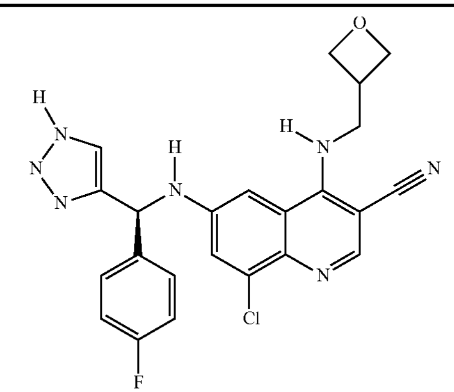 | (S)-8-chloro-6-(((4-fluorophenyl)(1H-1,2,3-triazol-4-yl)methyl)amino)-4-((oxetan-3-yl)methyl)amino)quinoline-3-carbonitrile | 15 | ES/MS 464.1 (M + H+) |
| 422 | 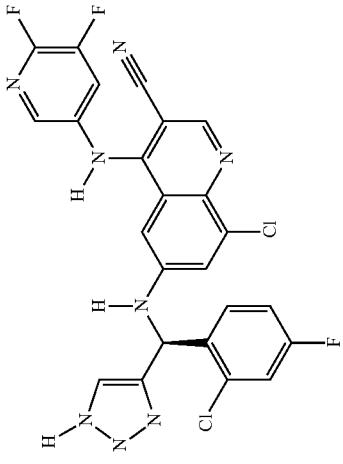 | (S)-8-chloro-6-(((2-chloro-4-fluorophenyl)(1H-1,2,3-triazol-4-yl)methyl)amino)-4-((5,6-difluoropyridin-3-yl)amino)quinoline-3-carbonitrile | 15 | ES/MS 541.1 (M + H+) |

TABLE 1-continued

| Compd | Structure | Name | Example/Procedure | ES/MS m/z |
|---|---|---|---|---|
| 423 | 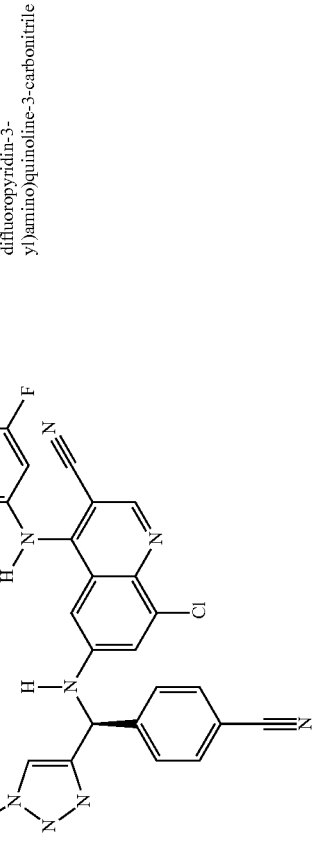 | (S)-8-chloro-6-(((4-cyanophenyl)(1H-1,2,3-triazol-4-yl)methyl)amino)-4-((5,6-difluoropyridin-3-yl)amino)quinoline-3-carbonitrile | 15 | ES/MS 514.1 (M + H+) |
| 424 | 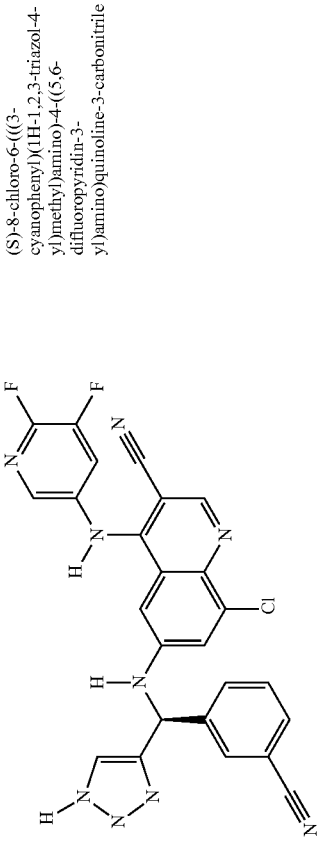 | (S)-8-chloro-6-(((3-cyanophenyl)(1H-1,2,3-triazol-4-yl)methyl)amino)-4-((5,6-difluoropyridin-3-yl)amino)quinoline-3-carbonitrile | 15 | ES/MS 514.1 (M + H+) |
| 425 | 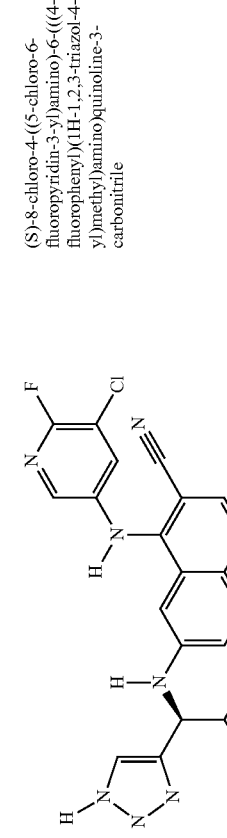 | (S)-8-chloro-4-((5-chloro-6-fluoropyridin-3-yl)amino)-6-(((4-fluorophenyl)(1H-1,2,3-triazol-4-yl)methyl)amino)quinoline-3-carbonitrile | 15 | ES/MS 523.0 (M + H+) |

TABLE 1-continued
| Compd | Structure | Name | Example/Procedure | ES/MS m/z |
|---|---|---|---|---|
| 426 | 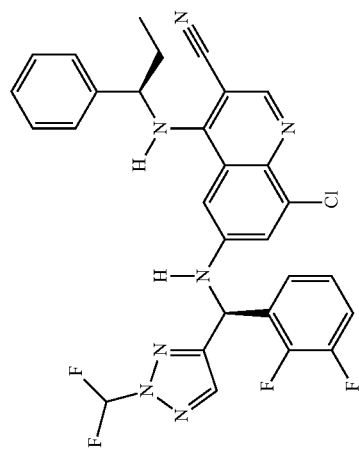 | 8-chloro-6-(((S)-(2-(difluoromethyl)-2H-1,2,3-triazol-4-yl)(2,3-difluorophenyl)methyl)amino)-4-(((R)-1-phenylpropyl)amino)quinoline-3-carbonitrile | 44 | ES/MS 580.1 (M + H+) |
| 427 | 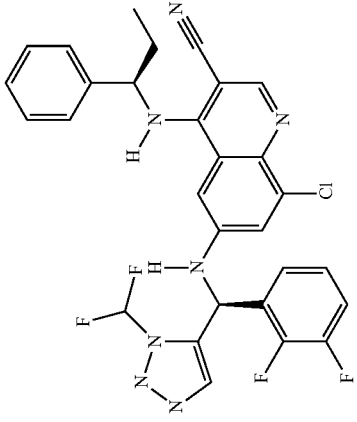 | 8-chloro-6-(((S)-(1-(difluoromethyl)-1H-1,2,3-triazol-5-yl)(2,3-difluorophenyl)methyl)amino)-4-(((R)-1-phenylpropyl)amino)quinoline-3-carbonitrile | 44 | ES/MS 580.1 (M + H+) |

TABLE 1-continued

| Compd | Structure | Name | Example/Procedure | ES/MS m/z |
|---|---|---|---|---|
| 428 | 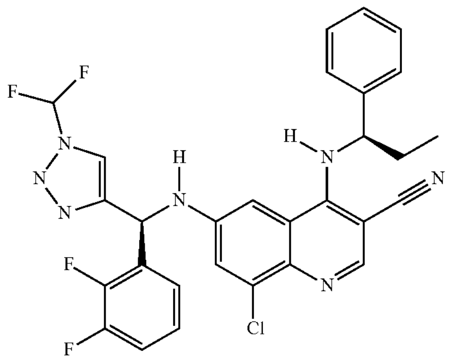 [SMILES: CC[C@@H](Nc1c(C#N)cnc2c(Cl)cc(N[C@H](C3=CN(C(F)F)NN3)c3cccc(F)c3F)cc12)c1ccccc1] | 8-chloro-6-(((S)-(1-(difluoromethyl)-1H-1,2,3-triazol-4-yl)(2,3-difluorophenyl)methyl)amino)-4-(((R)-1-phenylpropyl)amino)quinoline-3-carbonitrile | 44 | ES/MS 580.1 (M + H+) |
| 429 | 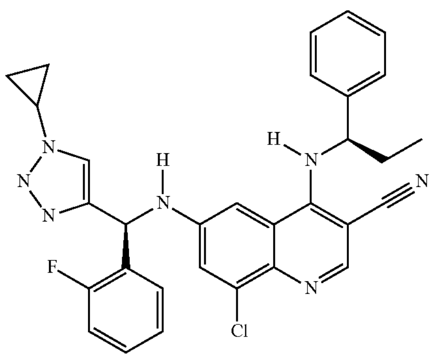 [SMILES: CC[C@@H](Nc1c(C#N)cnc2c(Cl)cc(N[C@H](C3=CN(C4CC4)NN3)c3ccccc3F)cc12)c1ccccc1] | 8-chloro-6-(((S)-(1-cyclopropyl-1H-1,2,3-triazol-4-yl)(2-fluorophenyl)methyl)amino)-4-(((R)-1-phenylpropyl)amino)quinoline-3-carbonitrile | 1 | ES/MS 552.1 (M + H+) |
| 430 | 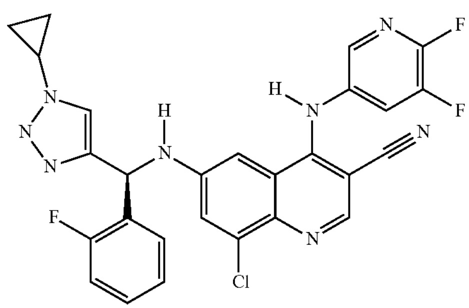 [SMILES: N#Cc1cnc2c(Cl)cc(N[C@H](C3=CN(C4CC4)NN3)c3ccccc3F)cc2c1Nc1cnc(F)c(F)c1] | (S)-8-chloro-6-(((1-cyclopropyl-1H-1,2,3-triazol-4-yl)(2-fluorophenyl)methyl)amino)-4-((5,6-difluoropyridin-3-yl)amino)quinoline-3-carbonitrile | 1 | ES/MS 547.2 (M + H+) |

TABLE 1-continued
| Compd | Structure | Name | Example/Procedure | ES/MS m/z |
|---|---|---|---|---|
| 431 | 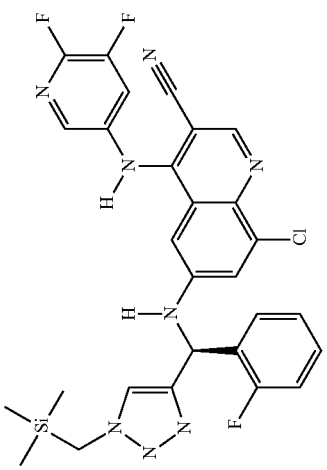 | (S)-8-chloro-4-((5,6-difluoropyridin-3-yl)amino)-6-(((2-fluorophenyl)(1-((trimethylsilyl)methyl)-1H-1,2,3-triazol-4-yl)methyl)amino)quinoline-3-carbonitrile | 1 | ES/MS 593.1 (M + H+) |
| 432 | 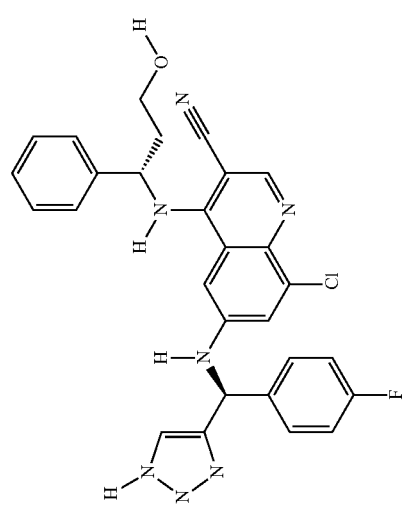 | 8-chloro-6-(((S)-(4-fluorophenyl)(1H-1,2,3-triazol-4-yl)methyl)amino)-4-(((S)-3-hydroxy-1-phenylpropyl)amino)quinoline-3-carbonitrile | 15 | ES/MS 528.1 (M + H+) |

TABLE 1-continued
| Compd | Structure | Name | Example/Procedure | ES/MS m/z |
|---|---|---|---|---|
| 433 | 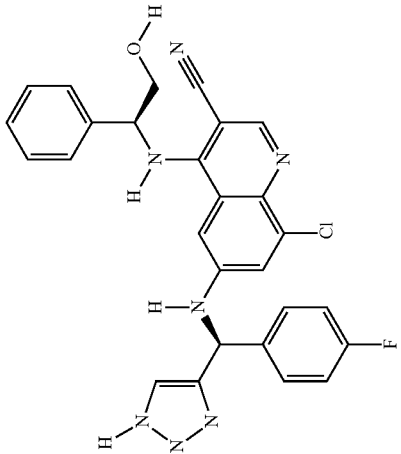 | 8-chloro-6-(((S)-(4-fluorophenyl)(1H-1,2,3-triazol-4-yl)methyl)amino)-4-(((S)-2-hydroxy-1-phenylethyl)amino)quinoline-3-carbonitrile | 15 | ES/MS 514.0 (M + H+) |
| 434 | 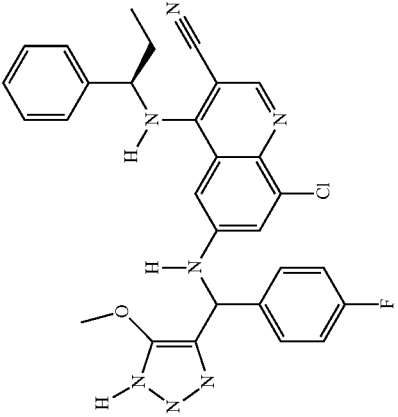 | 8-chloro-6-(((4-fluorophenyl)(5-methoxy-1H-1,2,3-triazol-4-yl)methyl)amino)-4-(((R)-1-phenylpropyl)amino)quinoline-3-carbonitrile | 7 | ES/MS 542.1 (M + H+) |

TABLE 1-continued

| Compd | Structure | Name | Example/Procedure | ES/MS m/z |
|---|---|---|---|---|
| 435 | 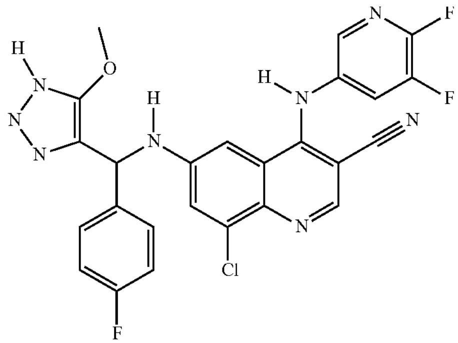 [SMILES: COC1=C(C(Nc2cc(Cl)c3ncc(C#N)c(Nc4cnc(F)c(F)c4)c3c2)c2ccc(F)cc2)NNN1] | 8-chloro-4-((5,6-difluoropyridin-3-yl)amino)-6-(((4-fluorophenyl)(5-methoxy-1H-1,2,3-triazol-4-yl)methyl)amino)quinoline-3-carbonitrile | 7 | ES/MS 537.1 (M + H+) |
| 436 | 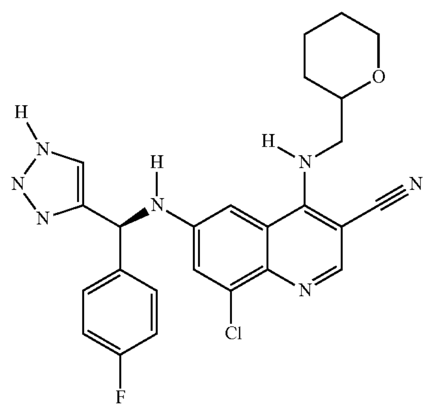 [SMILES: N#Cc1cnc2c(Cl)cc(N[C@H](C3=CNNN3)c3ccc(F)cc3)cc2c1NCC1CCCCO1] | 8-chloro-6-(((S)-(4-fluorophenyl)(1H-1,2,3-triazol-4-yl)methyl)amino)-4-(((tetrahydro-2H-pyran-2-yl)methyl)amino)quinoline-3-carbonitrile | 15 | ES/MS 492.2 (M + H+) |

TABLE 1-continued

| Compd | Structure | Name | Example/Procedure | ES/MS m/z |
|---|---|---|---|---|
| 437 | 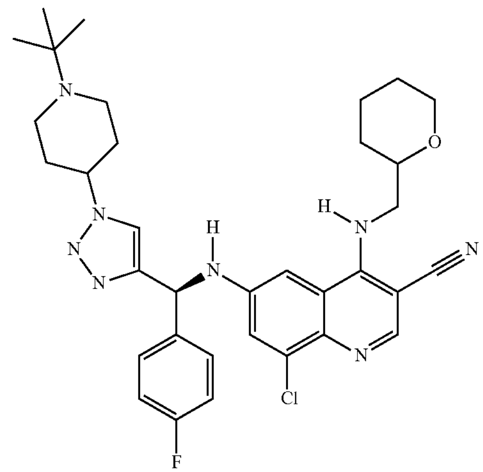 [SMILES: CC(C)(C)N1CCC(N2C=C([C@@H](Nc3cc(Cl)c4ncc(C#N)c(NCC5CCCCO5)c4c3)c3ccc(F)cc3)NN2)CC1] | 6-(((S)-(1-(1-(tert-butyl)piperidin-4-yl)-1H-1,2,3-triazol-4-yl)(4-fluorophenyl)methyl)amino)-8-chloro-4-(((tetrahydro-2H-pyran-2-yl)methyl)amino)quinoline-3-carbonitrile | 1 | ES/MS 631.3 (M + H+) |
| 438 | 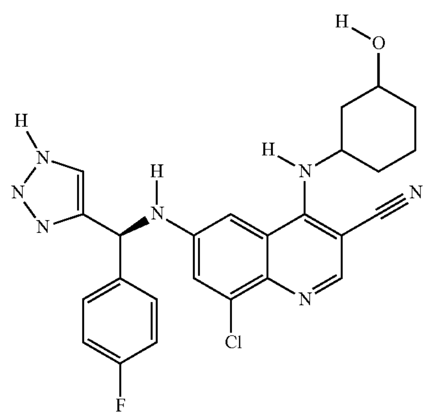 [SMILES: N#Cc1cnc2c(Cl)cc(N[C@H](C3=CNNN3)c3ccc(F)cc3)cc2c1NC1CCCC(O)C1] | 8-chloro-6-(((S)-(4-fluorophenyl)(1H-1,2,3-triazol-4-yl)methyl)amino)-4-(((3-hydroxycyclohexyl)amino)quinoline-3-carbonitrile | 15 | ES/MS 492.1 (M + H+) |

TABLE 1-continued

| Compd | Name | Structure | Example/Procedure | ES/MS m/z |
|---|---|---|---|---|
| 439 | 8-chloro-6-(((S)-(4-fluorophenyl)(1H-1,2,3-triazol-4-yl)methyl)amino)-4-((3-hydroxycyclohexyl)amino)quinoline-3-carbonitrile | 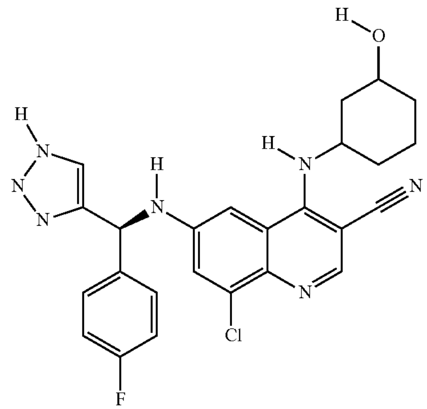 [SMILES: N#Cc1cnc2c(Cl)cc(N[C@H](C3=CNNN3)c3ccc(F)cc3)cc2c1NC1CCCC(O)C1] | 15 | ES/MS 492.1 (M + H+) |
| 440 | 6-(((S)-(1-(1-(tert-butyl)piperidin-4-yl)-1H-1,2,3-triazol-4-yl)(4-fluorophenyl)methyl)amino)-8-chloro-4-((3-hydroxycyclohexyl)amino)quinoline-3-carbonitrile | 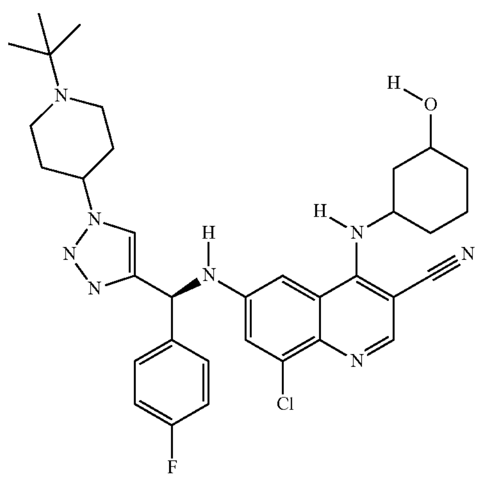 [SMILES: CC(C)(C)N1CCC(N2C=C([C@@H](Nc3cc(Cl)c4ncc(C#N)c(NC5CCCC(O)C5)c4c3)c3ccc(F)cc3)NN2)CC1] | 1 | ES/MS 631.3 (M + H+) |

TABLE 1-continued
| Compd | Structure | Name | Example/Procedure | ES/MS m/z |
|---|---|---|---|---|
| 441 | 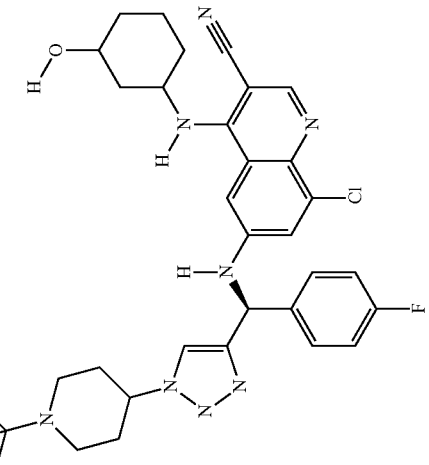 | 6-(((S)-(1-(1-(tert-butyl)piperidin-4-yl)-1H-1,2,3-triazol-4-yl)(4-fluorophenyl)methyl)amino)-8-chloro-4-((3-hydroxycyclohexyl)amino)quinoline-3-carbonitrile | 1 | ES/MS 631.3 (M + H+) |
| 442 | 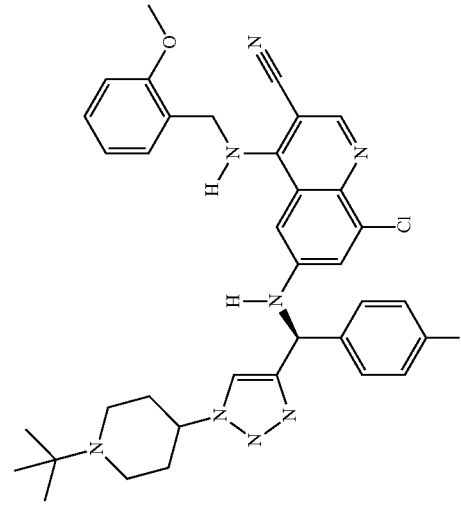 | (S)-6-((((1-(1-(tert-butyl)piperidin-4-yl)-1H-1,2,3-triazol-4-yl)(4-fluorophenyl)methyl)amino)-8-chloro-4-((2-methoxybenzyl)amino)quinoline-3-carbonitrile | 1 | ES/MS 653.3 (M + H+) |

TABLE 1-continued
| Compd | Structure | Name | Example/Procedure | ES/MS m/z |
|---|---|---|---|---|
| 443 | 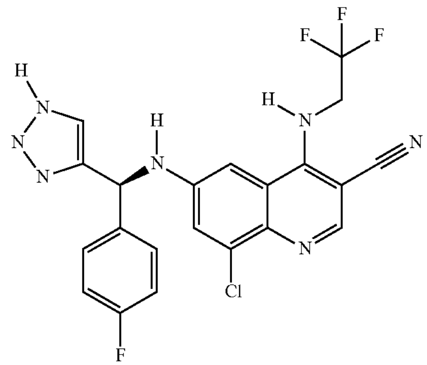 [SMILES: N#Cc1cnc2c(Cl)cc(N[C@H](C3=CNNN3)c3ccc(F)cc3)cc2c1NCC(F)(F)F] | (S)-8-chloro-6-(((4-fluorophenyl)(1H-1,2,3-triazol-4-yl)methyl)amino)-4-((2,2,2-trifluoroethyl)amino)quinoline-3-carbonitrile | 15 | ES/MS 476.1 (M + H+) |
| 444 | 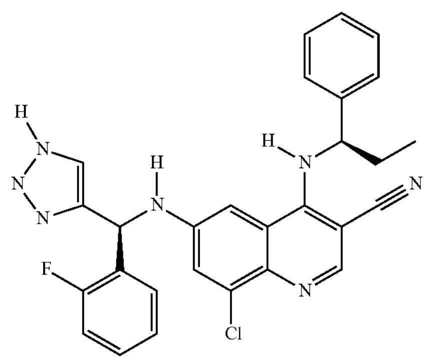 [SMILES: CC[C@@H](Nc1c(C#N)cnc2c(Cl)cc(N[C@H](C3=CNNN3)c3ccccc3F)cc12)c1ccccc1] | 8-chloro-6-(((S)-(2-fluorophenyl)(1H-1,2,3-triazol-4-yl)methyl)amino)-4-(((R)-1-phenylpropyl)amino)quinoline-3-carbonitrile | 15 | ES/MS 512.2 (M + H+) |

TABLE 1-continued

| Compd | Structure | Name | Example/Procedure | ES/MS m/z |
|---|---|---|---|---|
| 445 | 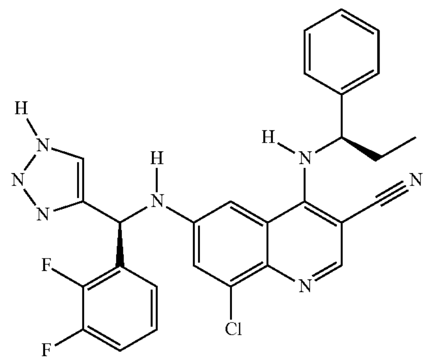 [SMILES: CC[C@@H](Nc1c(C#N)cnc2c(Cl)cc(N[C@H](C3=CNNN3)c3cccc(F)c3F)cc12)c1ccccc1] | 8-chloro-6-(((S)-(2,3-difluorophenyl)(1H-1,2,3-triazol-4-yl)methyl)amino)-4-(((R)-1-phenylpropyl)amino)quinoline-3-carbonitrile | 15 | ES/MS 530.1 (M + H+) |
| 446 | 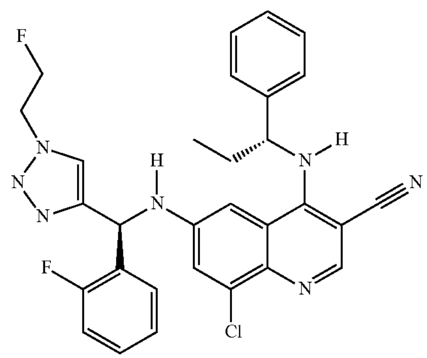 [SMILES: CC[C@@H](Nc1c(C#N)cnc2c(Cl)cc(N[C@H](C3=CN(CCF)NN3)c3ccccc3F)cc12)c1ccccc1] | 8-chloro-6-(((S)-(1-(2-fluoroethyl)-1H-1,2,3-triazol-4-yl)(2-fluorophenyl)methyl)amino)-4-(((R)-1-phenylpropyl)amino)quinoline-3-carbonitrile | 1 | ES/MS 558.2 (M + H+) |
| 447 | 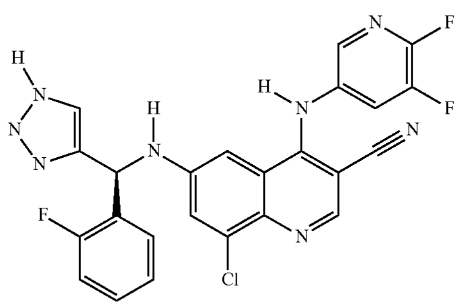 [SMILES: N#Cc1cnc2c(Cl)cc(N[C@H](C3=CNNN3)c3ccccc3F)cc2c1Nc1cnc(F)c(F)c1] | (S)-8-chloro-4-((5,6-difluoropyridin-3-yl)amino)-6-(((2-fluorophenyl)(1H-1,2,3-triazol-4-yl)methyl)amino)quinoline-3-carbonitrile | 15 | ES/MS 507.1 (M + H+) |

TABLE 1-continued

| Compd | Structure | Name | Example/Procedure | ES/MS m/z |
|---|---|---|---|---|
| 448 | 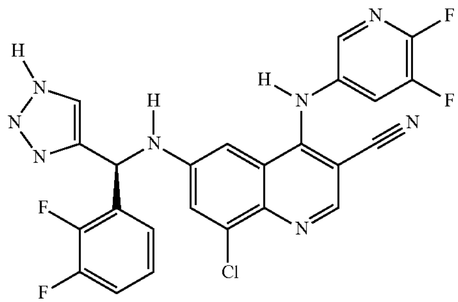 [SMILES: N#Cc1cnc2c(Cl)cc(N[C@H](C3=CNNN3)c3cccc(F)c3F)cc2c1Nc1cnc(F)c(F)c1] | (S)-8-chloro-6-(((2,3-difluorophenyl)(1H-1,2,3-triazol-4-yl)methyl)amino)-4-((5,6-difluoropyridin-3-yl)amino)quinoline-3-carbonitrile | 15 | ES/MS 525.1 (M + H+) |
| 449 | 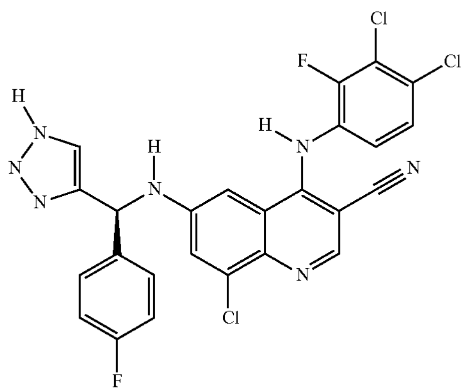 [SMILES: N#Cc1cnc2c(Cl)cc(N[C@H](C3=CNNN3)c3ccc(F)cc3)cc2c1Nc1ccc(Cl)c(Cl)c1F] | (S)-8-chloro-4-((3,4-dichloro-2-fluorophenyl)amino)-6-(((4-fluorophenyl)(1H-1,2,3-triazol-4-yl)methyl)amino)quinoline-3-carbonitrile | 15 | ES/MS 556.0 (M + H+) |
| 450 | 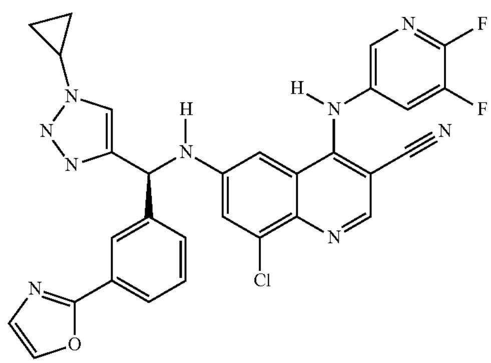 [SMILES: N#Cc1cnc2c(Cl)cc(N[C@H](C3=CN(C4CC4)NN3)c3cccc(-c4ncco4)c3)cc2c1Nc1cnc(F)c(F)c1] | (S)-8-chloro-6-(((1-cyclopropyl-1H-1,2,3-triazol-4-yl)(3-(oxazol-2-yl)phenyl)methyl)amino)-4-((5,6-difluoropyridin-3-yl)amino)quinoline-3-carbonitrile | 3 | ES/MS 595.9 (M + H+) |

TABLE 1-continued

| Compd | Structure | Name | Example/Procedure | ES/MS m/z |
|---|---|---|---|---|
| 451 | 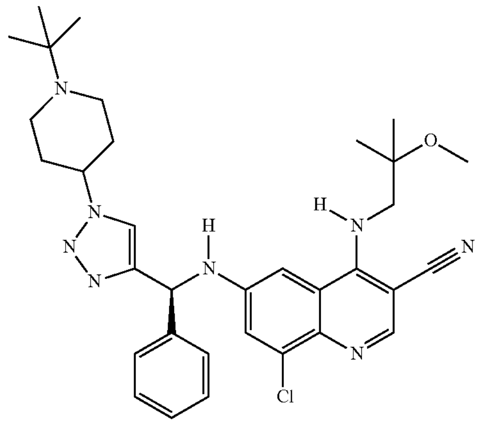 [SMILES: COC(C)(C)CNc1c(C#N)cnc2c(Cl)cc(N[C@H](C3=CN(C4CCN(C(C)(C)C)CC4)NN3)c3ccccc3)cc12] | (S)-6-(((1-(1-(tert-butyl)piperidin-4-yl)-1H-1,2,3-triazol-4-yl)(phenyl)methyl)amino)-8-chloro-4-((2-methoxy-2-methylpropyl)amino)quinoline-3-carbonitrile | 1 | ES/MS 601.3 (M + H+) |
| 452 | 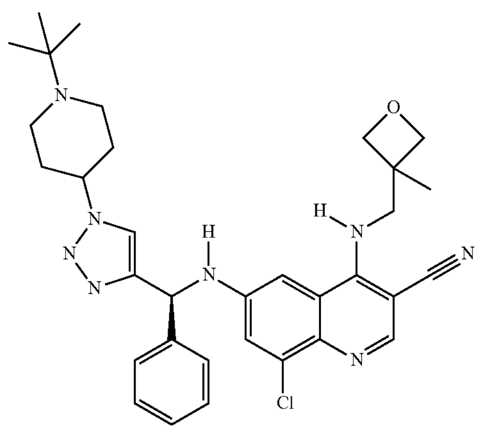 [SMILES: CC1(CNc2c(C#N)cnc3c(Cl)cc(N[C@H](C4=CN(C5CCN(C(C)(C)C)CC5)NN4)c4ccccc4)cc23)COC1] | (S)-6-(((1-(1-(tert-butyl)piperidin-4-yl)-1H-1,2,3-triazol-4-yl)(phenyl)methyl)amino)-8-chloro-4-(((3-methyloxetan-3-yl)methyl)amino)quinoline-3-carbonitrile | 1 | ES/MS 599.3 (M + H+) |

TABLE 1-continued
| Compd | Structure | Name | Example/Procedure | ES/MS m/z |
|---|---|---|---|---|
| 453 | 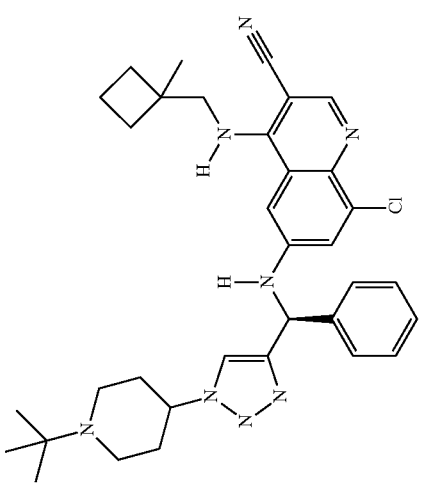 | (S)-6-(((1-(1-(tert-butyl)piperidin-4-yl)-1H-1,2,3-triazol-4-yl)(phenyl)methyl)amino)-8-chloro-4-(((1-methylcyclobutyl)methyl)amino)-quinoline-3-carbonitrile | 1 | ES/MS 597.3 (M + H+) |
| 454 | 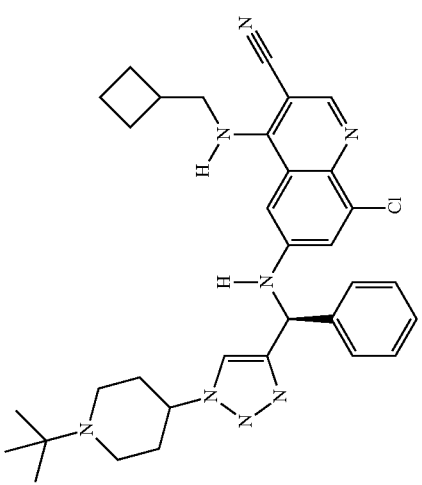 | (S)-6-(((1-(1-(tert-butyl)piperidin-4-yl)-1H-1,2,3-triazol-4-yl)(phenyl)methyl)amino)-8-chloro-4-(((cyclobutylmethyl)amino)quinoline-3-carbonitrile | 1 | ES/MS 538.3 (M + H+) |

TABLE 1-continued

| Compd | Structure | Name | Example/Procedure | ES/MS m/z |
|---|---|---|---|---|
| 455 | 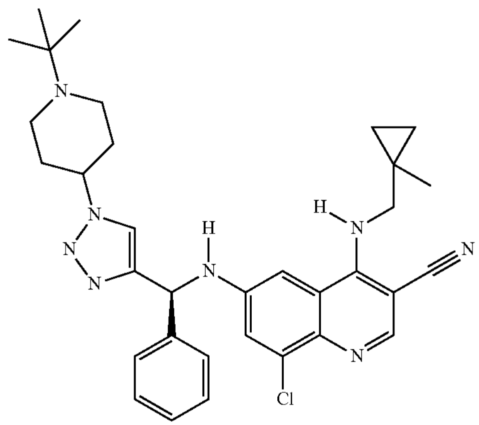 [SMILES: CC1(CNc2c(C#N)cnc3c(Cl)cc(N[C@H](C4=CN(C5CCN(C(C)(C)C)CC5)NN4)c4ccccc4)cc23)CC1] | (S)-6-((((1-(tert-butyl)piperidin-4-yl)-1H-1,2,3-triazol-4-yl)(phenyl)methyl)amino)-8-chloro-4-(((1-methylcyclopropyl)methyl)amino)quinoline-3-carbonitrile | 1 | ES/MS 583.3 (M + H+) |
| 456 | 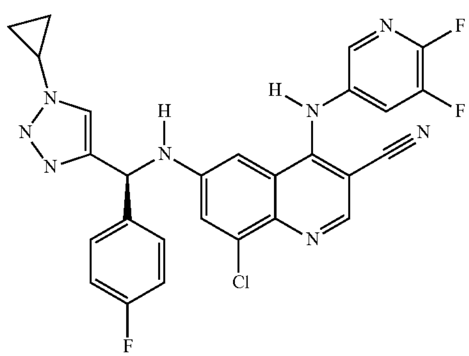 [SMILES: N#Cc1cnc2c(Cl)cc(N[C@H](C3=CN(C4CC4)NN3)c3ccc(F)cc3)cc2c1Nc1cnc(F)c(F)c1] | (S)-8-chloro-6-(((1-cyclopropyl-1H-1,2,3-triazol-4-yl)(4-fluorophenyl)methyl)amino)-4-(((5,6-difluoropyridin-3-yl)amino)quinoline-3-carbonitrile | 10 | ES/MS 547.1 (M + H+) |

TABLE 1-continued

| Compd | Structure | Name | Example/Procedure | ES/MS m/z |
|---|---|---|---|---|
| 457 | 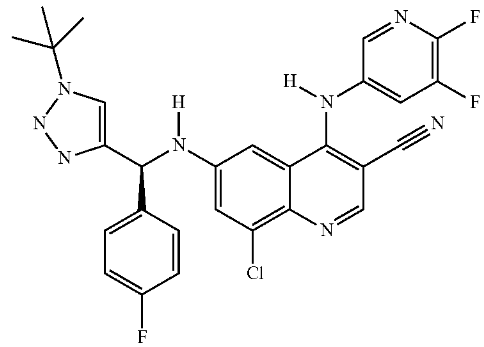 [SMILES: CC(C)(C)N1C=C([C@@H](Nc2cc(Cl)c3ncc(C#N)c(Nc4cnc(F)c(F)c4)c3c2)c2ccc(F)cc2)NN1] | (S)-6-((((1-(tert-butyl)-1H-1,2,3-triazol-4-yl)(4-fluorophenyl)methyl)amino)-8-chloro-4-((5,6-difluoropyridin-3-yl)amino)quinoline-3-carbonitrile | 10 | ES/MS 563.1 (M + H+) |
| 458 | 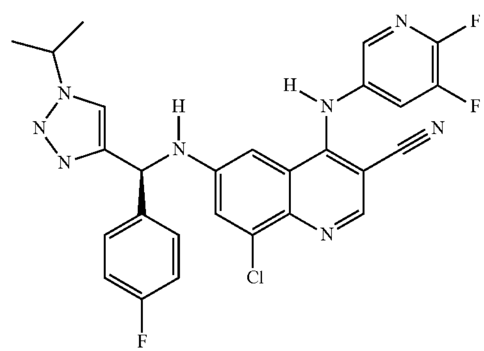 [SMILES: CC(C)N1C=C([C@@H](Nc2cc(Cl)c3ncc(C#N)c(Nc4cnc(F)c(F)c4)c3c2)c2ccc(F)cc2)NN1] | (S)-8-chloro-4-((5,6-difluoropyridin-3-yl)amino)-6-((((4-fluorophenyl)(1-isopropyl-1H-1,2,3-triazol-4-yl)methyl)amino)quinoline-3-carbonitrile | 10 | ES/MS 549.1 (M + H+) |

TABLE 1-continued

| Compd | Structure | Name | Example/Procedure | ES/MS m/z |
|---|---|---|---|---|
| 459 | 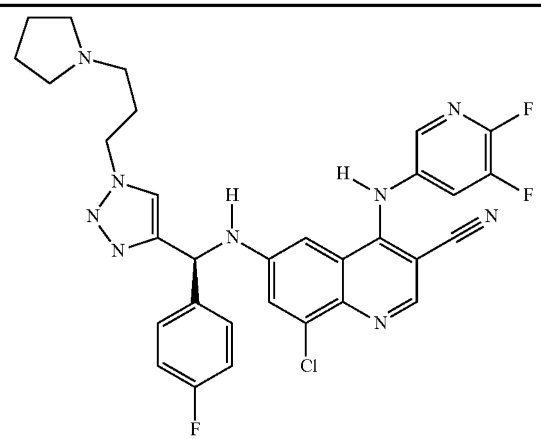 | (S)-8-chloro-4-((5,6-difluoropyridin-3-yl)amino)-6-(((4-fluorophenyl)(1-(3-(pyrrolidin-1-yl)propyl)-1H-1,2,3-triazol-4-yl)methyl)amino)quinoline-3-carbonitrile | 10 | ES/MS 618.2 (M + H+) |
| 460 | 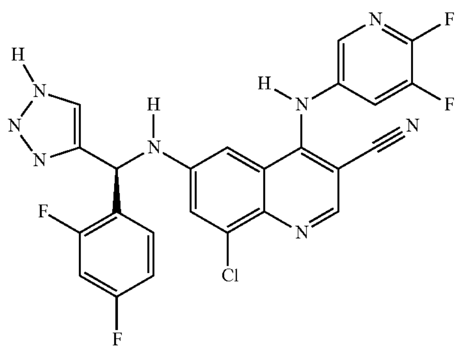 [SMILES: N#Cc1cnc2c(Cl)cc(N[C@H](C3=CNNN3)c3ccc(F)cc3F)cc2c1Nc1cnc(F)c(F)c1] | (S)-8-chloro-6-(((2,4-difluorophenyl)(1H-1,2,3-triazol-4-yl)methyl)amino)-4-((5,6-difluoropyridin-3-yl)amino)quinoline-3-carbonitrile | 15 | ES/MS 525.1 (M + H+) |
| 461 | 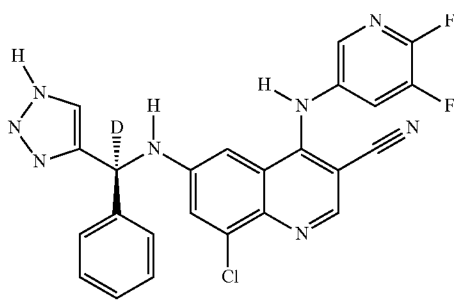 | (S)-8-chloro-4-((5,6-difluoropyridin-3-yl)amino)-6-(((phenyl)(1H-1,2,3-triazol-4-yl)methyl-d)amino)quinoline-3-carbonitrile | 15 | ES/MS 490.0 (M + H+) |

TABLE 1-continued

| Compd | Structure | Name | Example/Procedure | ES/MS m/z |
|---|---|---|---|---|
| 462 | 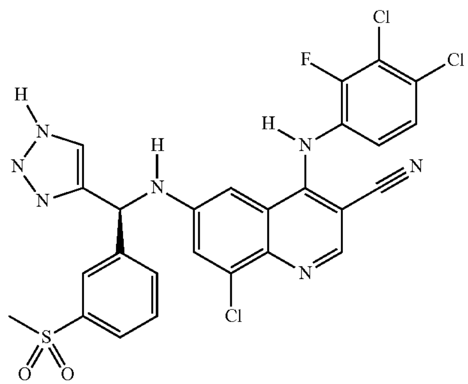 [SMILES: CS(=O)(=O)c1cccc([C@H](Nc2cc(Cl)c3ncc(C#N)c(Nc4ccc(Cl)c(Cl)c4F)c3c2)C2=CNNN2)c1] | (S)-8-chloro-4-((3,4-dichloro-2-fluorophenyl)amino)-6-(((3-(methylsulfonyl)phenyl)(1H-1,2,3-triazol-4-yl)methyl)amino)quinoline-3-carbonitrile | 15 | ES/MS 615.9 (M + H+) |
| 463 | 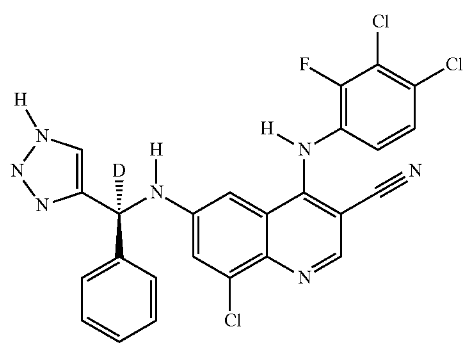 | (S)-8-chloro-4-((3,4-dichloro-2-fluorophenyl)amino)-6-(((phenyl(1H-1,2,3-triazol-4-yl)methyl-d)amino)quinoline-3-carbonitrile | 15 | ES/MS 539.0 (M + H+) |

TABLE 1-continued

| Compd | Structure | Name | Example/Procedure | ES/MS m/z |
|---|---|---|---|---|
| 464 | 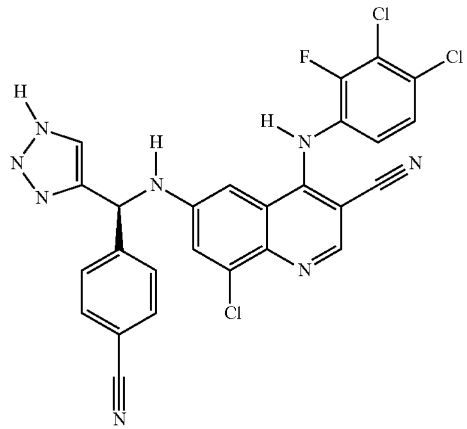 [SMILES: N#Cc1ccc([C@H](Nc2cc(Cl)c3ncc(C#N)c(Nc4ccc(Cl)c(Cl)c4F)c3c2)C2=CNNN2)cc1] | (S)-8-chloro-6-(((4-cyanophenyl)(1H-1,2,3-triazol-4-yl)methyl)amino)-4-((3,4-dichloro-2-fluorophenyl)amino)quinoline-3-carbonitrile | 15 | ES/MS 562.9 (M + H+) |
| 465 | 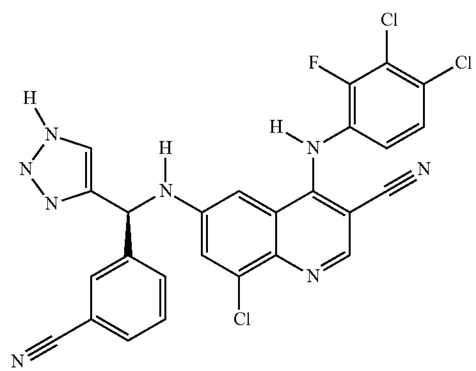 [SMILES: N#Cc1cccc([C@H](Nc2cc(Cl)c3ncc(C#N)c(Nc4ccc(Cl)c(Cl)c4F)c3c2)C2=CNNN2)c1] | (S)-8-chloro-6-(((3-cyanophenyl)(1H-1,2,3-triazol-4-yl)methyl)amino)-4-((3,4-dichloro-2-fluorophenyl)amino)quinoline-3-carbonitrile | 15 | ES/MS 562.9 (M + H+) |

TABLE 1-continued

| Compd | Structure | Name | Example/Procedure | ES/MS m/z |
|---|---|---|---|---|
| 466 | 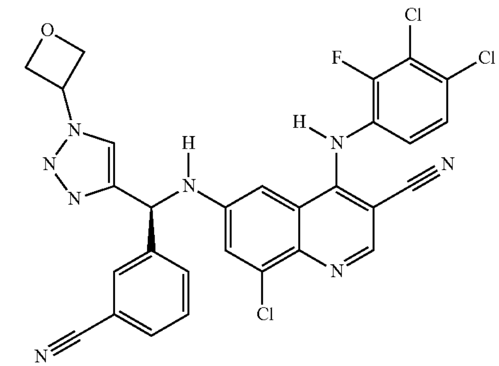 [SMILES: N#Cc1cccc([C@H](Nc2cc(Cl)c3ncc(C#N)c(Nc4ccc(Cl)c(Cl)c4F)c3c2)C2=CN(C3COC3)NN2)c1] | (S)-8-chloro-6-(((3-cyanophenyl)(1-(oxetan-3-yl)-1H-1,2,3-triazol-4-yl)methyl)amino)-4-((3,4-dichloro-2-fluorophenyl)amino)quinoline-3-carbonitrile | 3 | ES/MS 619.0 (M + H+) |
| 467 | 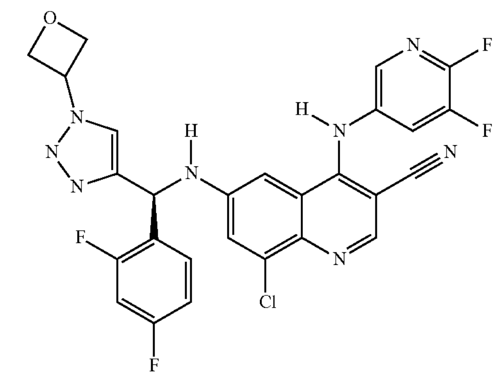 [SMILES: N#Cc1cnc2c(Cl)cc(N[C@H](C3=CN(C4COC4)NN3)c3ccc(F)cc3F)cc2c1Nc1cnc(F)c(F)c1] | (S)-8-chloro-6-(((2,4-difluorophenyl)(1-(oxetan-3-yl)-1H-1,2,3-triazol-4-yl)methyl)amino)-4-((5,6-difluoropyridin-3-yl)amino)quinoline-3-carbonitrile | 3 | ES/MS 581.0 (M + H+) |
| 468 | 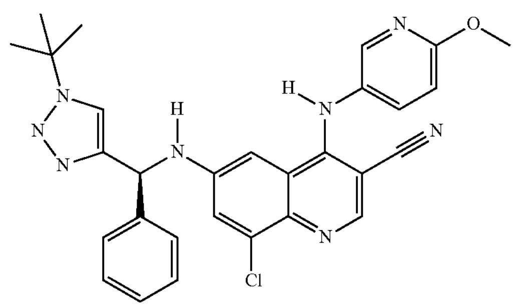 [SMILES: COc1ccc(Nc2c(C#N)cnc3c(Cl)cc(N[C@H](C4=CN(C(C)(C)C)NN4)c4ccccc4)cc23)cn1] | (S)-6-(((1-(tert-butyl)-1H-1,2,3-triazol-4-yl)(phenyl)methyl)amino)-8-chloro-4-((6-methoxypyridin-3-yl)amino)quinoline-3-carbonitrile | 3 | ES/MS 539.1 (M + H+) |

TABLE 1-continued

| Compd | Structure | Name | Example/Procedure | ES/MS m/z |
|---|---|---|---|---|
| 469 | 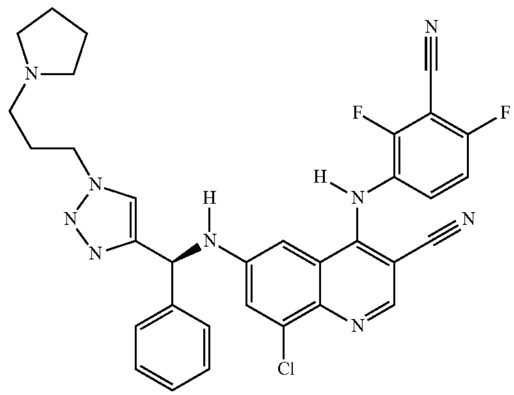 [SMILES: N#Cc1cnc2c(Cl)cc(N[C@H](C3=CN(CCCN4CCCC4)NN3)c3ccccc3)cc2c1Nc1ccc(F)c(C#N)c1F] | (S)-8-chloro-4-((3-cyano-2,4-difluorophenyl)amino)-6-((phenyl(1-(3-(pyrrolidin-1-yl)propyl)-1H-1,2,3-triazol-4-yl)methyl)amino)quinoline-3-carbonitrile | 10 | ES/MS 624.2 (M + H+) |
| 470 | 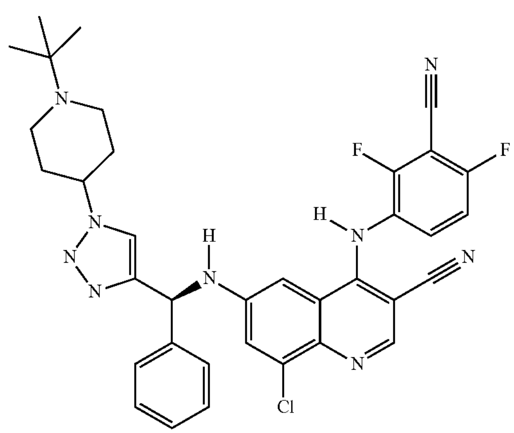 [SMILES: CC(C)(C)N1CCC(N2C=C([C@@H](Nc3cc(Cl)c4ncc(C#N)c(Nc5ccc(F)c(C#N)c5F)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((3-cyano-2,4-difluorophenyl)amino)quinoline-3-carbonitrile | 10 | ES/MS 652.2 (M + H+) |

TABLE 1-continued

| Compd | Structure | Name | Example/Procedure | ES/MS m/z |
|---|---|---|---|---|
| 471 | 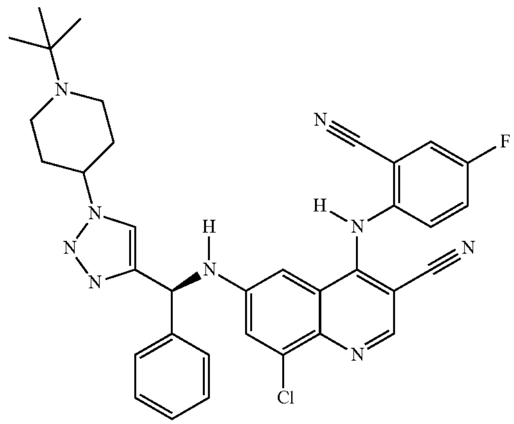 [SMILES: CC(C)(C)N1CCC(N2C=C([C@@H](Nc3cc(Cl)c4ncc(C#N)c(Nc5ccc(F)cc5C#N)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((2-cyano-4-fluorophenyl)amino)quinoline-3-carbonitrile | 10 | ES/MS 634.2 (M + H+) |
| 472 | 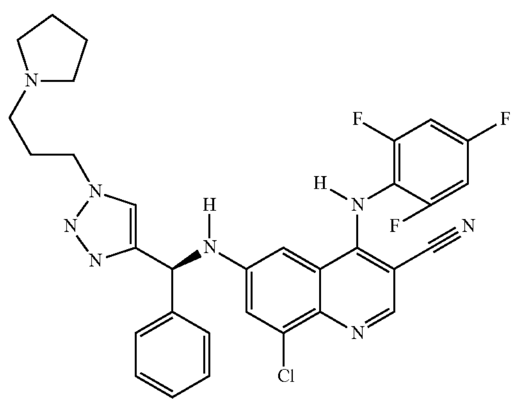 [SMILES: N#Cc1cnc2c(Cl)cc(N[C@H](C3=CN(CCCN4CCCC4)NN3)c3ccccc3)cc2c1Nc1c(F)cc(F)cc1F] | (S)-8-chloro-6-((phenyl(1-(3-(pyrrolidin-1-yl)propyl)-1H-1,2,3-triazol-4-yl)methyl)amino)-4-((2,4,6-trifluorophenyl)amino)quinoline-3-carbonitrile | 10 | ES/MS 617.2 (M + H+) |

TABLE 1-continued

| Compd | Structure | Name | Example/Procedure | ES/MS m/z |
|---|---|---|---|---|
| 473 | 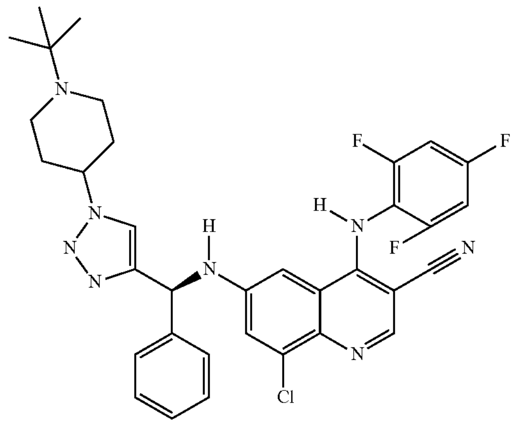 [SMILES: CC(C)(C)N1CCC(N2C=C([C@@H](Nc3cc(Cl)c4ncc(C#N)c(Nc5c(F)cc(F)cc5F)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((2,4,6-trifluorophenyl)amino)quinoline-3-carbonitrile | 10 | ES/MS 645.2 (M + H+) |
| 474 | 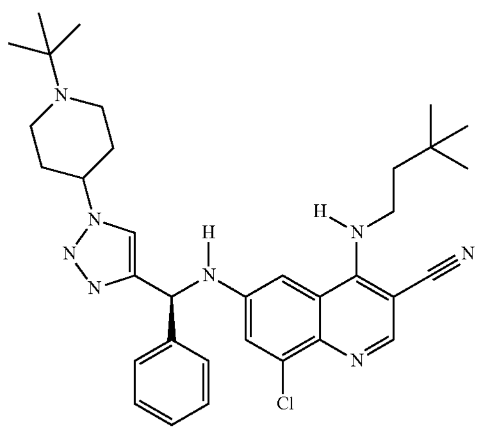 [SMILES: CC(C)(C)CCNc1c(C#N)cnc2c(Cl)cc(N[C@H](C3=CN(C4CCN(C(C)(C)C)CC4)NN3)c3ccccc3)cc12] | (S)-6-(((1-(1-(tert-butyl)piperidin-4-yl)-1H-1,2,3-triazol-4-yl)(phenyl)methyl)amino)-8-chloro-4-((3,3-dimethylbutyl)amino)quinoline-3-carbonitrile | 1 | ES/MS 599.3 (M + H+) |

TABLE 1-continued

| Compd | Structure | Name | Example/Procedure | ES/MS m/z |
|---|---|---|---|---|
| 475 | 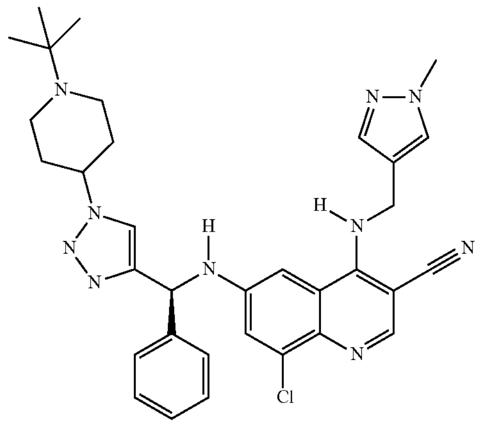 [SMILES: Cn1cc(CNc2c(C#N)cnc3c(Cl)cc(N[C@H](C4=CN(C5CCN(C(C)(C)C)CC5)NN4)c4ccccc4)cc23)cn1] | (S)-6-(((1-(1-(tert-butyl)piperidin-4-yl)-1H-1,2,3-triazol-4-yl)(phenyl)methyl)amino)-8-chloro-4-(((1-methyl-1H-pyrazol-4-yl)methyl)amino)quinoline-3-carbonitrile | 1 | ES/MS 609.3 (M + H+) |
| 476 | 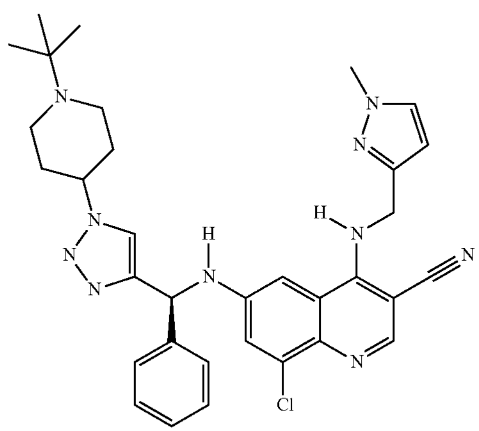 [SMILES: Cn1ccc(CNc2c(C#N)cnc3c(Cl)cc(N[C@H](C4=CN(C5CCN(C(C)(C)C)CC5)NN4)c4ccccc4)cc23)n1] | (S)-6-(((1-(1-(tert-butyl)piperidin-4-yl)-1H-1,2,3-triazol-4-yl)(phenyl)methyl)amino)-8-chloro-4-(((1-methyl-1H-pyrazol-3-yl)methyl)amino)quinoline-3-carbonitrile | 1 | ES/MS 609.3 (M + H+) |

TABLE 1-continued
| Compd | Structure | Name | Example/Procedure | ES/MS m/z |
|---|---|---|---|---|
| 477 | 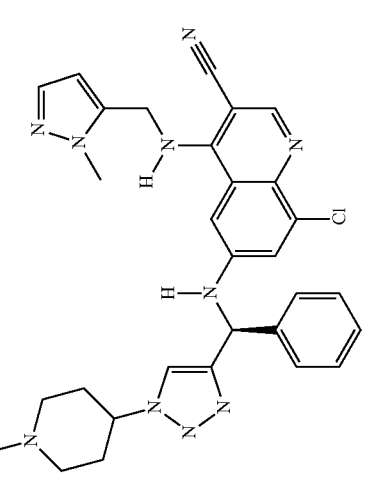 | (S)-6-((((1-(1-(tert-butyl)piperidin-4-yl)-1H-1,2,3-triazol-4-yl)(phenyl)methyl)amino)-8-chloro-4-(((1-methyl-1H-pyrazol-5-yl)methyl)amino)quinoline-3-carbonitrile | 1 | ES/MS 609.3 (M + H+) |
| 478 | 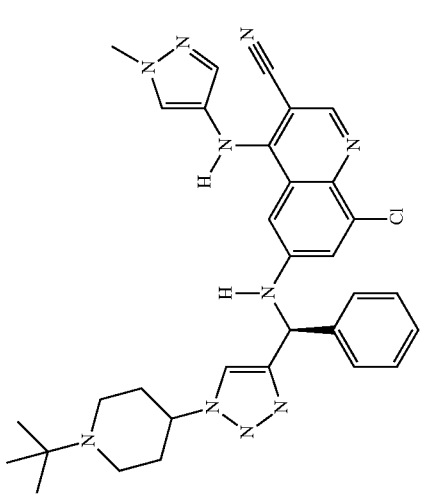 | (S)-6-((((1-(1-(tert-butyl)piperidin-4-yl)-1H-1,2,3-triazol-4-yl)(phenyl)methyl)amino)-8-chloro-4-((1-methyl-1H-pyrazol-4-yl)amino)quinoline-3-carbonitrile | 10 | ES/MS 595.3 (M + H+) |

TABLE 1-continued

| Compd | Structure | Name | Example/Procedure | ES/MS m/z |
|---|---|---|---|---|
| 479 | 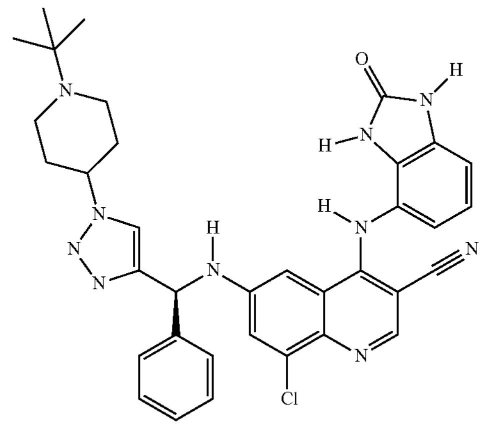 [SMILES: CC(C)(C)N1CCC(N2C=C([C@@H](Nc3cc(Cl)c4ncc(C#N)c(Nc5cccc6[nH]c(=O)[nH]c56)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((2-oxo-2,3-dihydro-1H-benzo[d]imidazol-4-yl)amino)quinoline-3-carbonitrile | 10 | ES/MS 647.3 (M + H+) |
| 480 | 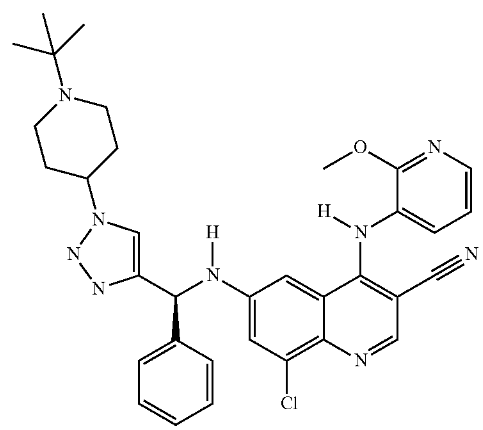 [SMILES: COc1ncccc1Nc1c(C#N)cnc2c(Cl)cc(N[C@H](C3=CN(C4CCN(C(C)(C)C)CC4)NN3)c3ccccc3)cc12] | (S)-6-(((1-(1-(tert-butyl)piperidin-4-yl)-1H-1,2,3-triazol-4-yl)(phenyl)methyl)amino)-8-chloro-4-((2-methoxypyridin-3-yl)amino)quinoline-3-carbonitrile | 10 | ES/MS 622.3 (M + H+) |

TABLE 1-continued

| Compd | Structure | Name | Example/Procedure | ES/MS m/z |
|---|---|---|---|---|
| 481 | 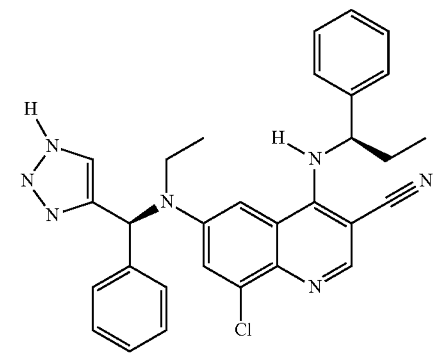 [SMILES: CC[C@@H](Nc1c(C#N)cnc2c(Cl)cc(N(CC)[C@H](C3=CNNN3)c3ccccc3)cc12)c1ccccc1] | 8-chloro-6-(ethyl((S)-phenyl(1H-1,2,3-triazol-4-yl)methyl)amino)-4-(((R)-1-phenylpropyl)amino)quinoline-3-carbonitrile | 15 | ES/MS 522.2 (M + H+) |
| 482 | 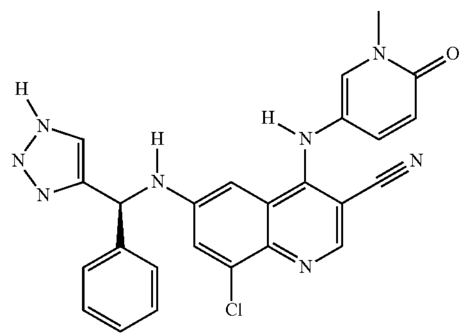 [SMILES: Cn1cc(Nc2c(C#N)cnc3c(Cl)cc(N[C@H](C4=CNNN4)c4ccccc4)cc23)ccc1=O] | (S)-8-chloro-4-((1-methyl-6-oxo-1,6-dihydropyridin-3-yl)amino)-6-((phenyl(1H-1,2,3-triazol-4-yl)methyl)amino)quinoline-3-carbonitrile | 15 | ES/MS 483.1 (M + H+) |
| 483 | 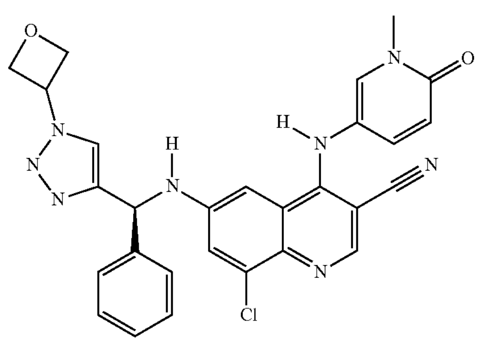 | (S)-8-chloro-4-((1-methyl-6-oxo-1,6-dihydropyridin-3-yl)amino)-6-(((1-(oxetan-3-yl)-1H-1,2,3-triazol-4-yl)(phenyl)methyl)amino)quinoline-3-carbonitrile | 3 | ES/MS 539.0 (M + H+) |

TABLE 1-continued

| Compd | Structure | Name | Example/Procedure | ES/MS m/z |
|---|---|---|---|---|
| 484 | 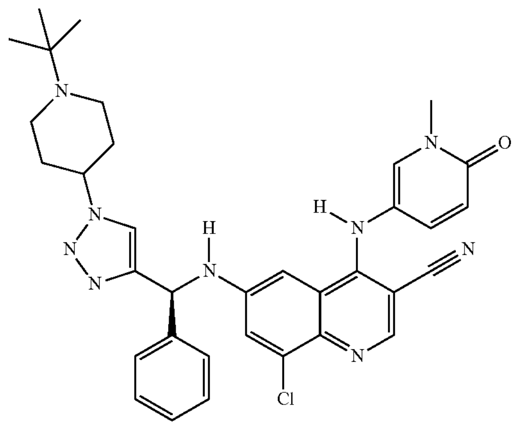 [SMILES: Cn1cc(Nc2c(C#N)cnc3c(Cl)cc(N[C@H](C4=CN(C5CCN(C(C)(C)C)CC5)NN4)c4ccccc4)cc23)ccc1=O] | (S)-6-((((1-(1-(tert-butyl)piperidin-4-yl)-1H-1,2,3-triazol-4-yl)(phenyl)methyl)amino)-8-chloro-4-((1-methyl-6-oxo-1,6-dihydropyridin-3-yl)amino)quinoline-3-carbonitrile | 3 | ES/MS 622.0 (M + H+) |
| 485 | 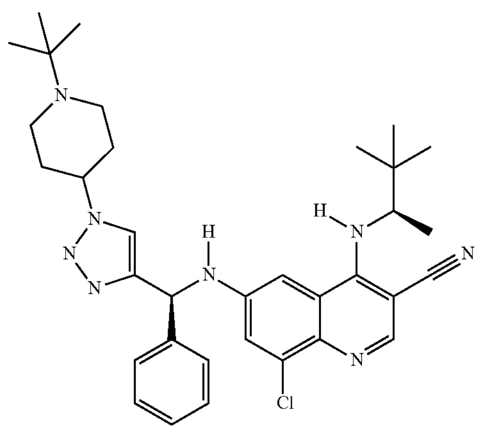 [SMILES: C[C@@H](Nc1c(C#N)cnc2c(Cl)cc(N[C@H](C3=CN(C4CCN(C(C)(C)C)CC4)NN3)c3ccccc3)cc12)C(C)(C)C] | 6-(((S)-(1-(1-(tert-butyl)piperidin-4-yl)-1H-1,2,3-triazol-4-yl)(phenyl)methyl)amino)-8-chloro-4-(((R)-3,3-dimethylbutan-2-yl)amino)quinoline-3-carbonitrile | 1 | ES/MS 599.3 (M + H+) |

TABLE 1-continued

| Compd | Structure | Name | Example/Procedure | ES/MS m/z |
|---|---|---|---|---|
| 486 | 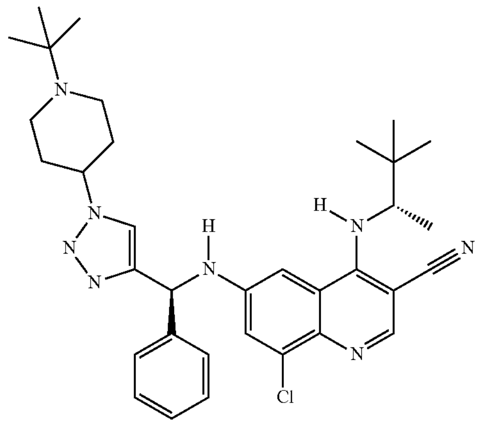 [SMILES: C[C@H](Nc1c(C#N)cnc2c(Cl)cc(N[C@H](C3=CN(C4CCN(C(C)(C)C)CC4)NN3)c3ccccc3)cc12)C(C)(C)C] | 6-(((S)-(1-(1-(tert-butyl)piperidin-4-yl)-1H-1,2,3-triazol-4-yl)(phenyl)methyl)amino)-8-chloro-4-(((S)-3,3-dimethylbutan-2-yl)amino)quinoline-3-carbonitrile | 1 | ES/MS 599.3 (M + H+) |
| 487 | 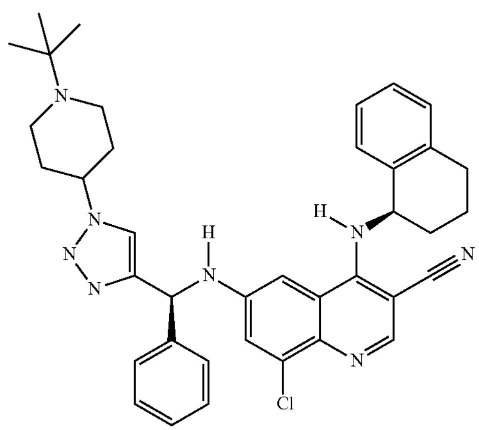 [SMILES: CC(C)(C)N1CCC(N2C=C([C@@H](Nc3cc(Cl)c4ncc(C#N)c(N[C@@H]5CCCc6ccccc65)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((R)-1,2,3,4-tetrahydronaphthalen-1-yl)amino)quinoline-3-carbonitrile | 1 | ES/MS 645.3 (M + H+) |

TABLE 1-continued

| Compd | Structure | Name | Example/Procedure | ES/MS m/z |
|---|---|---|---|---|
| 488 | 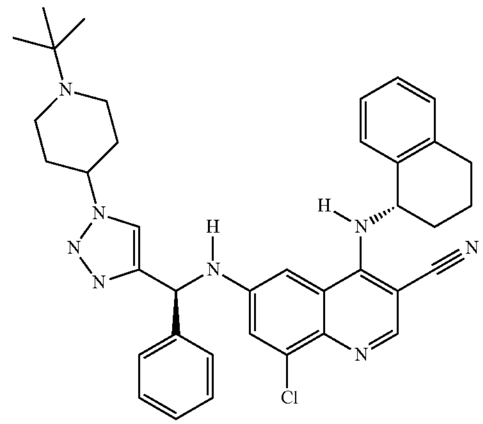 [SMILES: CC(C)(C)N1CCC(N2C=C([C@@H](Nc3cc(Cl)c4ncc(C#N)c(N[C@H]5CCCc6ccccc65)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((S)-1,2,3,4-tetrahydronaphthalen-1-yl)amino)quinoline-3-carbonitrile | 1 | ES/MS 645.3 (M + H+) |
| 489 | 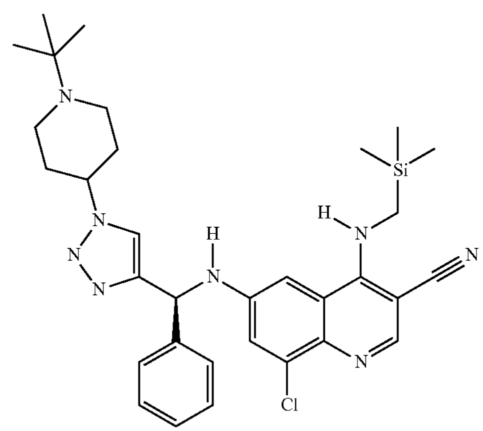 [SMILES: CC(C)(C)N1CCC(N2C=C([C@@H](Nc3cc(Cl)c4ncc(C#N)c(NC[Si](C)(C)C)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-(((trimethylsilyl)methyl)amino)-quinoline-3-carbonitrile | 1 | ES/MS 601.3 (M + H+) |

TABLE 1-continued

| Compd | Structure | Name | Example/Procedure | ES/MS m/z |
|---|---|---|---|---|
| 490 | 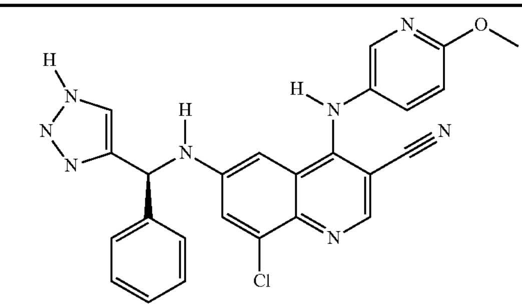 | (S)-8-chloro-4-(((6-methoxypyridin-3-yl)amino)-6-((phenyl(1H-1,2,3-triazol-4-yl)methyl)amino)quinoline-3-carbonitrile | 15 | ES/MS 483.0 (M + H+) |
| 491 | 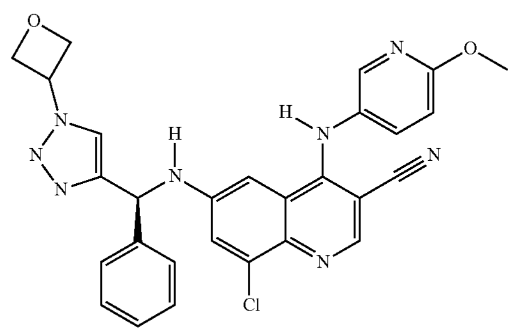 [SMILES: COc1ccc(Nc2c(C#N)cnc3c(Cl)cc(N[C@H](C4=CN(C5COC5)NN4)c4ccccc4)cc23)cn1] | (S)-8-chloro-4-(((6-methoxypyridin-3-yl)amino)-6-(((1-(oxetan-3-yl)-1H-1,2,3-triazol-4-yl)(phenyl)methyl)amino)quinoline-3-carbonitrile | 3 | ES/MS 539.0 (M + H+) |
| 492 | 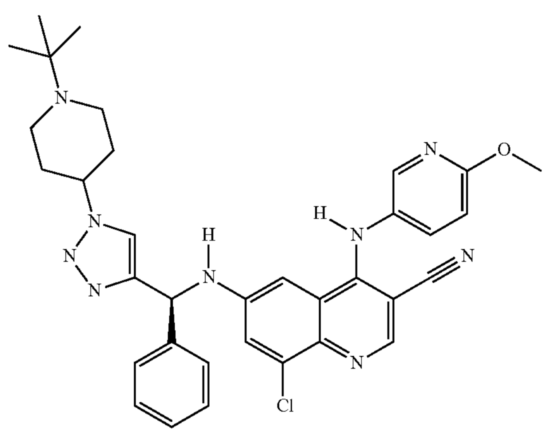 [SMILES: COc1ccc(Nc2c(C#N)cnc3c(Cl)cc(N[C@H](C4=CN(C5CCN(C(C)(C)C)CC5)NN4)c4ccccc4)cc23)cn1] | (S)-6-((((1-(1-(tert-butyl)piperidin-4-yl)-1H-1,2,3-triazol-4-yl)(phenyl)methyl)amino)-8-chloro-4-((6-methoxypyridin-3-yl)amino)quinoline-3-carbonitrile | 3 | ES/MS 622.0 (M + H+) |

TABLE 1-continued

| Compd | Structure | Name | Example/Procedure | ES/MS m/z |
|---|---|---|---|---|
| 493 | 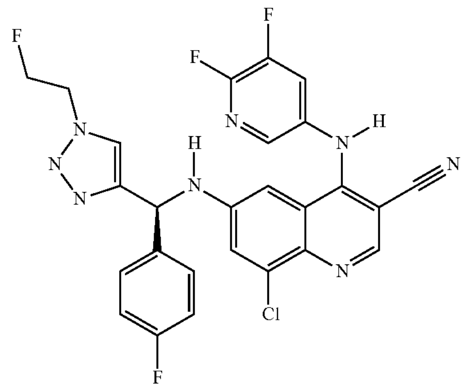 [SMILES: N#Cc1cnc2c(Cl)cc(N[C@H](C3=CN(CCF)NN3)c3ccc(F)cc3)cc2c1Nc1cnc(F)c(F)c1] | (S)-8-chloro-4-((5,6-difluoropyridin-3-yl)amino)-6-(((1-(2-fluoroethyl)-1H-1,2,3-triazol-4-yl)(4-fluorophenyl)methyl)amino)quinoline-3-carbonitrile | 1 | ES/MS 553.1 (M + H+) |
| 494 | 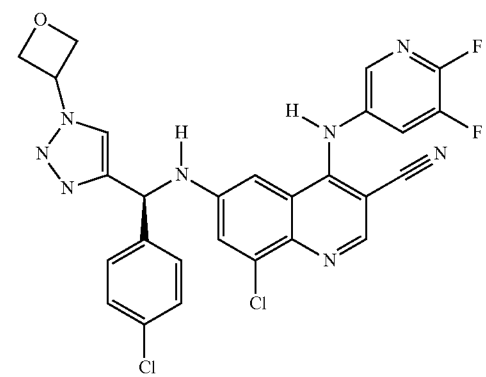 | (S)-8-chloro-6-(((4-chlorophenyl)(1-(oxetan-3-yl)-1H-1,2,3-triazol-4-yl)methyl)amino)-4-((5,6-difluoropyridin-3-yl)amino)quinoline-3-carbonitrile | 3 | ES/MS 578.9 (M + H+) |

TABLE 1-continued

| Compd | Structure | Name | Example/Procedure | ES/MS m/z |
|---|---|---|---|---|
| 495 | 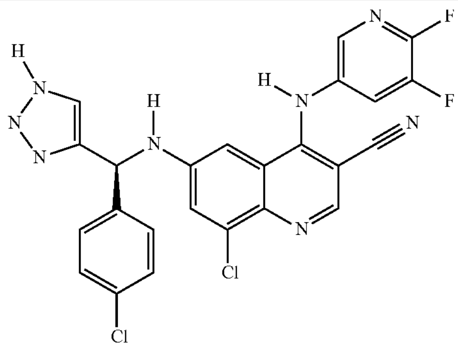 [SMILES: N#Cc1cnc2c(Cl)cc(N[C@H](C3=CNNN3)c3ccc(Cl)cc3)cc2c1Nc1cnc(F)c(F)c1] | (S)-8-chloro-6-(((4-chlorophenyl)(1H-1,2,3-triazol-4-yl)methyl)amino)-4-((5,6-difluoropyridin-3-yl)amino)quinoline-3-carbonitrile | 15 | ES/MS 523.1 (M + H+) |
| 496 | 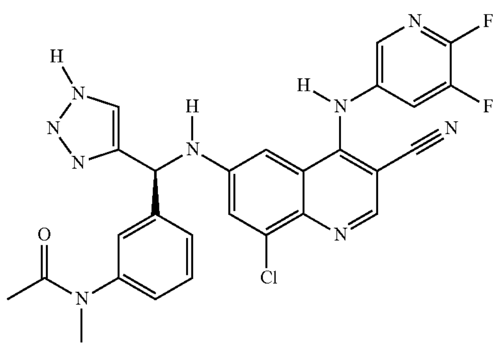 [SMILES: CC(=O)N(C)c1cccc([C@H](Nc2cc(Cl)c3ncc(C#N)c(Nc4cnc(F)c(F)c4)c3c2)C2=CNNN2)c1] | (S)-N-(3-(((8-chloro-3-cyano-4-((5,6-difluoropyridin-3-yl)amino)quinolin-6-yl)amino)(1H-1,2,3-triazol-4-yl)methyl)phenyl)-N-methylacetamide | 15 | ES/MS 559.9 (M + H+) |

TABLE 1-continued

| Compd | Structure | Name | Example/Procedure | ES/MS m/z |
|---|---|---|---|---|
| 497 | 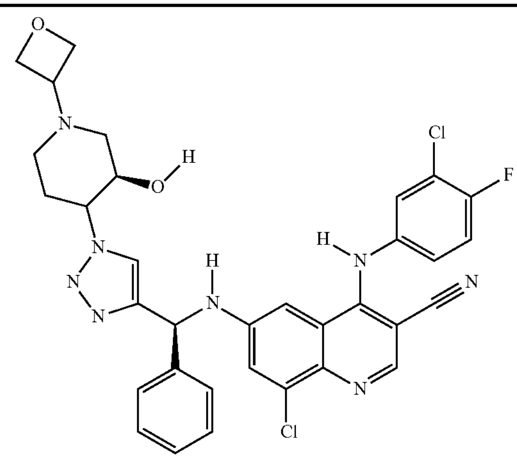 | 8-chloro-4-((3-chloro-4-fluorophenyl)amino)-6-(((S)-(1-((3R,4R)-3-hydroxy-1-(oxetan-3-yl)piperidin-4-yl)-1H-1,2,3-triazol-4-yl)(phenyl)methyl)amino)quinoline-3-carbonitrile | 5 | ES/MS 659.0 (M + H+) |
| 498 | 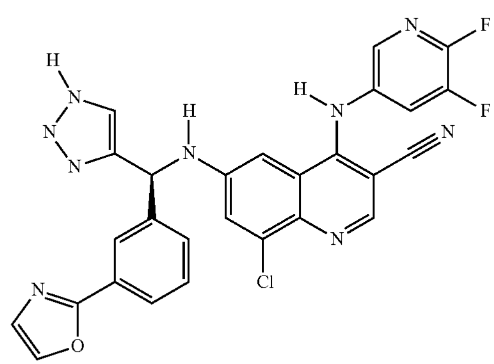 [SMILES: N#Cc1cnc2c(Cl)cc(N[C@H](C3=CNNN3)c3cccc(-c4ncco4)c3)cc2c1Nc1cnc(F)c(F)c1] | (S)-8-chloro-4-((5,6-difluoropyridin-3-yl)amino)-6-(((3-(oxazol-2-yl)phenyl)(1H-1,2,3-triazol-4-yl)methyl)amino)quinoline-3-carbonitrile | 15 | ES/MS 555.9 (M + H+) |

TABLE 1-continued

| Compd | Structure | Name | Example/Procedure | ES/MS m/z |
|---|---|---|---|---|
| 499 | 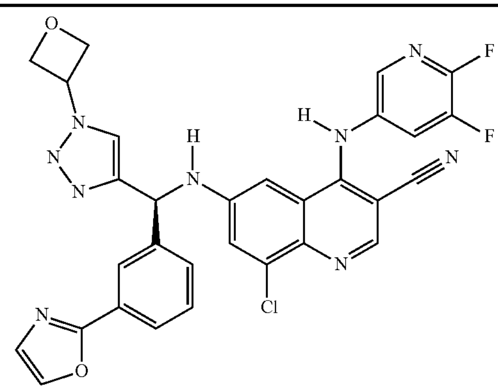 | (S)-8-chloro-4-((5,6-difluoropyridin-3-yl)amino)-6-(((3-(oxazol-2-yl)phenyl)(1-(oxetan-3-yl)-1H-1,2,3-triazol-4-yl)methyl)amino)quinoline-3-carbonitrile | 3 | ES/MS 611.9 (M + H+) |
| 500 | 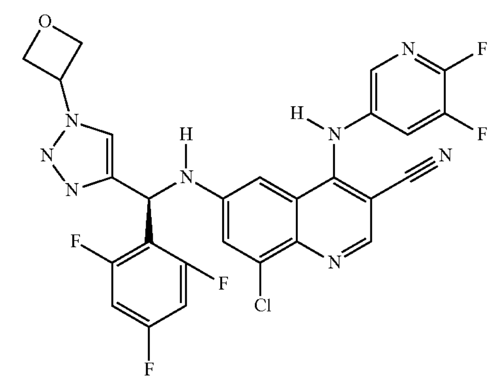 [SMILES: N#Cc1cnc2c(Cl)cc(N[C@H](C3=CN(C4COC4)NN3)c3c(F)cc(F)cc3F)cc2c1Nc1cnc(F)c(F)c1] | (S)-8-chloro-4-((5,6-difluoropyridin-3-yl)amino)-6-((((1-(oxetan-3-yl)-1H-1,2,3-triazol-4-yl)(2,4,6-trifluorophenyl)methyl)amino)quinoline-3-carbonitrile | 3 | ES/MS 599.0 (M + H+) |

TABLE 1-continued

| Compd | Structure | Name | Example/Procedure | ES/MS m/z |
|---|---|---|---|---|
| 501 | 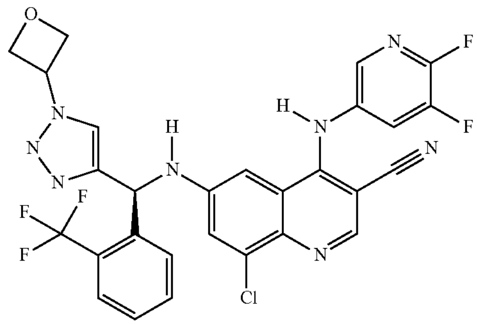 [SMILES: N#Cc1cnc2c(Cl)cc(N[C@H](C3=CN(C4COC4)NN3)c3ccccc3C(F)(F)F)cc2c1Nc1cnc(F)c(F)c1] | (S)-8-chloro-4-((5,6-difluoropyridin-3-yl)amino)-6-(((1-(oxetan-3-yl)-1H-1,2,3-triazol-4-yl)(2-(trifluoromethyl)phenyl)methyl)amino)quinoline-3-carbonitrile | 3 | ES/MS 613.0 (M + H+) |
| 502 | 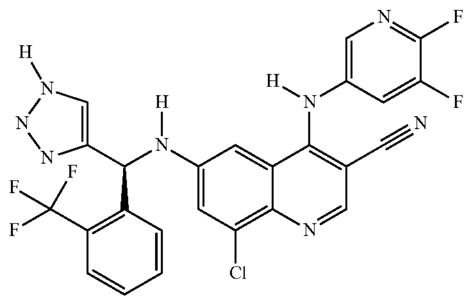 [SMILES: N#Cc1cnc2c(Cl)cc(N[C@H](C3=CNNN3)c3ccccc3C(F)(F)F)cc2c1Nc1cnc(F)c(F)c1] | (S)-6-(((1H-1,2,3-triazol-4-yl)(2-(trifluoromethyl)phenyl)methyl)amino)-8-chloro-4-((5,6-difluoropyridin-3-yl)amino)quinoline-3-carbonitrile | 15 | ES/MS 557.0 (M + H+) |
| 503 | 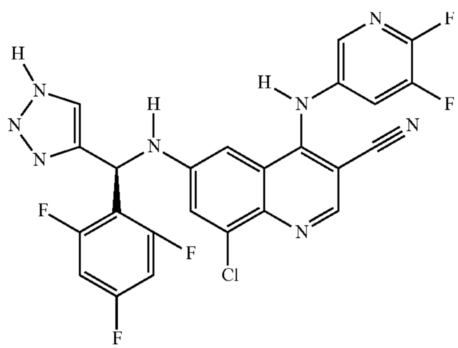 [SMILES: N#Cc1cnc2c(Cl)cc(N[C@H](C3=CNNN3)c3c(F)cc(F)cc3F)cc2c1Nc1cnc(F)c(F)c1] | (S)-6-(((1H-1,2,3-triazol-4-yl)(2,4,6-trifluorophenyl)methyl)amino)-8-chloro-4-((5,6-difluoropyridin-3-yl)amino)quinoline-3-carbonitrile | 15 | ES/MS 543.0 (M + H+) |

TABLE 1-continued
| Compd | Structure | Name | Example/Procedure | ES/MS m/z |
|---|---|---|---|---|
| 504 | 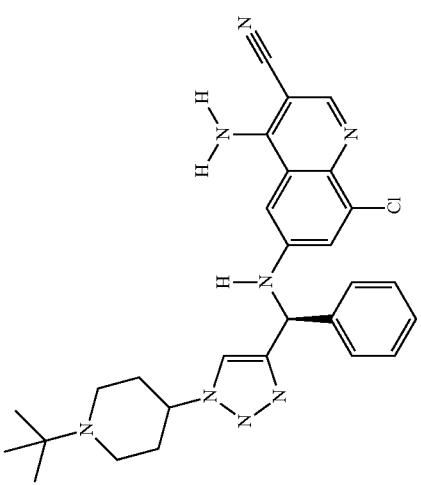 | (S)-4-amino-6-(((1-(1-(tert-butyl)piperidin-4-yl)-1H-1,2,3-triazol-4-yl)(phenyl)methyl)amino)-8-chloroquinoline-3-carbonitrile | 1 | ES/MS 515.2 (M + H+) |
| 505 | 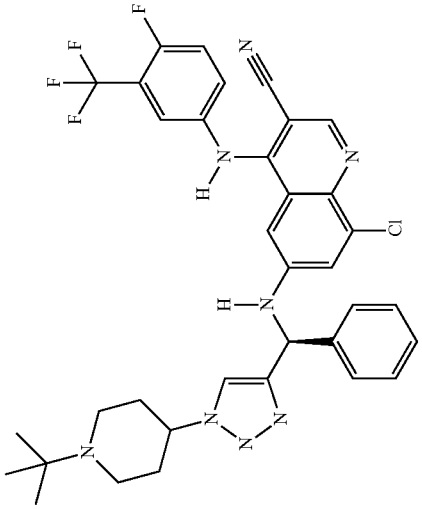 | (S)-6-(((1-(1-(tert-butyl)piperidin-4-yl)-1H-1,2,3-triazol-4-yl)(phenyl)methyl)amino)-8-chloro-4-((4-fluoro-3-(trifluoromethyl)phenyl)amino)-quinoline-3-carbonitrile | 10 | ES/MS 677.2 (M + H+) |

TABLE 1-continued

| Compd | Structure | Name | Example/Procedure | ES/MS m/z |
|---|---|---|---|---|
| 506 | 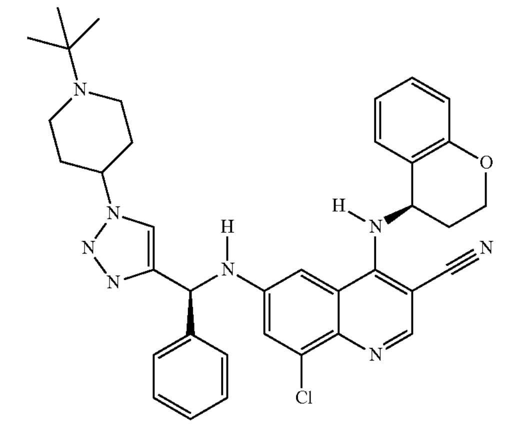 [SMILES: CC(C)(C)N1CCC(N2C=C([C@@H](Nc3cc(Cl)c4ncc(C#N)c(N[C@@H]5CCOc6ccccc65)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((R)-chroman-4-yl)amino)quinoline-3-carbonitrile | 1 | ES/MS 647.3 (M + H+) |
| 507 | 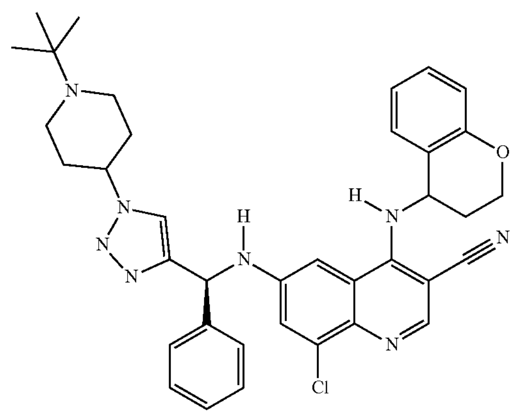 [SMILES: CC(C)(C)N1CCC(N2C=C([C@@H](Nc3cc(Cl)c4ncc(C#N)c(NC5CCOc6ccccc65)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((S)-chroman-4-yl)amino)quinoline-3-carbonitrile | 1 | ES/MS 647.3 (M + H+) |

TABLE 1-continued

| Compd | Structure | Name | Example/Procedure | ES/MS m/z |
|---|---|---|---|---|
| 508 | 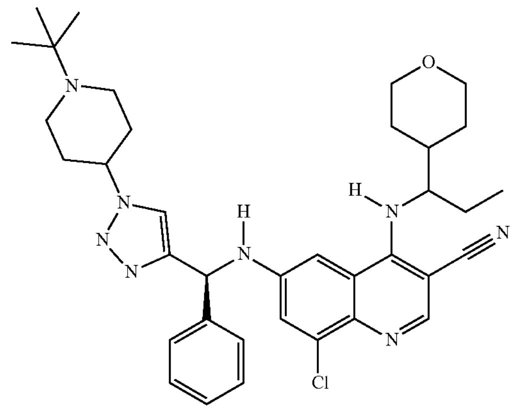 [SMILES: CCC(Nc1c(C#N)cnc2c(Cl)cc(N[C@H](C3=CN(C4CCN(C(C)(C)C)CC4)NN3)c3ccccc3)cc12)C1CCOCC1] | 6-(((S)-(1-(1-(tert-butyl)piperidin-4-yl)-1H-1,2,3-triazol-4-yl)(phenyl)methyl)amino)-8-chloro-4-((1-(tetrahydro-2H-pyran-4-yl)propyl)amino)quinoline-3-carbonitrile | 1 | ES/MS 641.3 (M + H+) |
| 509 | 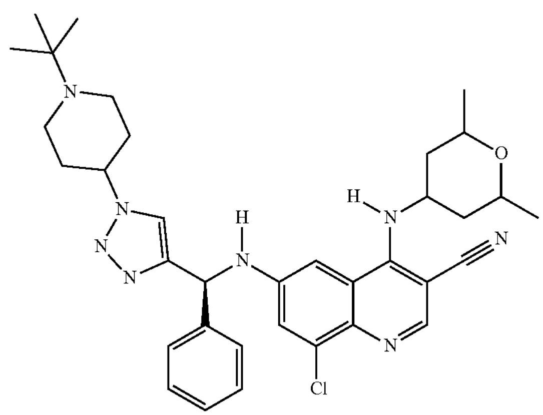 [SMILES: CC1CC(Nc2c(C#N)cnc3c(Cl)cc(N[C@H](C4=CN(C5CCN(C(C)(C)C)CC5)NN4)c4ccccc4)cc23)CC(C)O1] | 6-(((S)-(1-(1-(tert-butyl)piperidin-4-yl)-1H-1,2,3-triazol-4-yl)(phenyl)methyl)amino)-8-chloro-4-((2,6-dimethyltetrahydro-2H-pyran-4-yl)amino)quinoline-3-carbonitrile | 1 | ES/MS 627.3 (M + H+) |

TABLE 1-continued

| Compd | Structure | Name | Example/Procedure | ES/MS m/z |
|---|---|---|---|---|
| 510 | 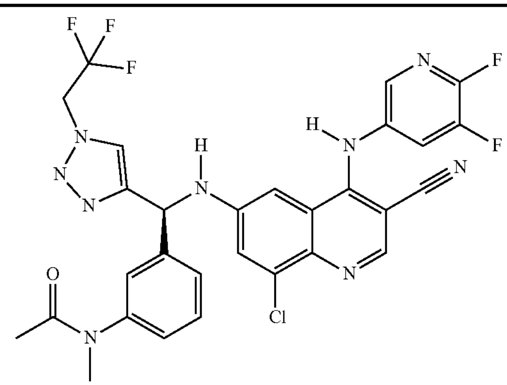 | (S)-N-(3-(((8-chloro-3-cyano-4-((5,6-difluoropyridin-3-yl)amino)quinolin-6-yl)amino)(1-(2,2,2-trifluoroethyl)-1H-1,2,3-triazol-4-yl)methyl)phenyl)-N-methylacetamide | 3 | ES/MS 641.9 (M + H+) |
| 511 | 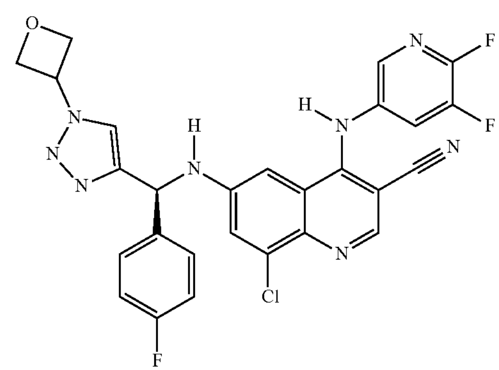 [SMILES: N#Cc1cnc2c(Cl)cc(N[C@H](C3=CN(C4COC4)NN3)c3ccc(F)cc3)cc2c1Nc1cnc(F)c(F)c1] | (S)-8-chloro-4-((5,6-difluoropyridin-3-yl)amino)-6-(((4-fluorophenyl)(1-(oxetan-3-yl)-1H-1,2,3-triazol-4-yl)methyl)amino)quinoline-3-carbonitrile | 3 | ES/MS 562.9 (M + H+) |

TABLE 1-continued
| Compd | Structure | Name | Example/Procedure | ES/MS m/z |
|---|---|---|---|---|
| 512 | 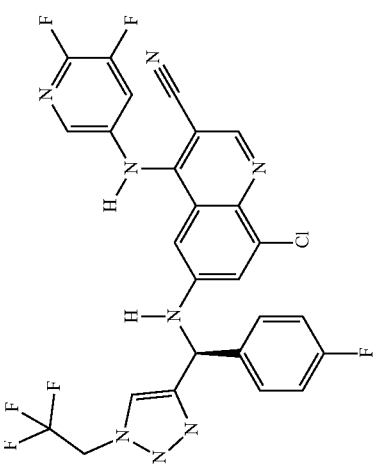 | (S)-8-chloro-4-((5,6-difluoropyridin-3-yl)amino)-6-(((4-fluorophenyl)(1-(2,2,2-trifluoroethyl)-1H-1,2,3-triazol-4-yl)methyl)amino)quinoline-3-carbonitrile | 3 | ES/MS 588.9 (M + H+) |
| 513 | 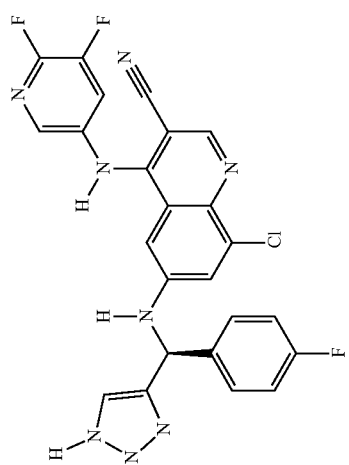 | (S)-8-chloro-4-((5,6-difluoropyridin-3-yl)amino)-6-(((4-fluorophenyl)(1H-1,2,3-triazol-4-yl)methyl)amino)quinoline-3-carbonitrile | 15 | ES/MS 507.0 (M + H+) |

TABLE 1-continued

| Compd | Structure | Name | Example/Procedure | ES/MS m/z |
|---|---|---|---|---|
| 514 | 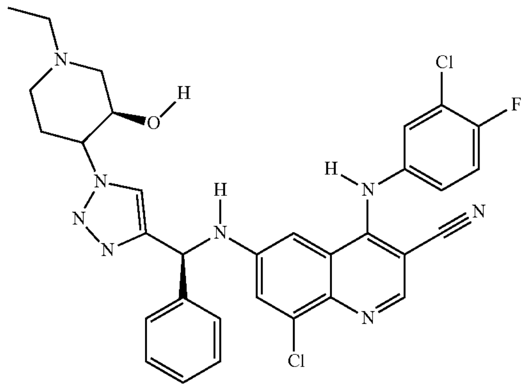 [SMILES: CCN1CCC(N2C=C([C@@H](Nc3cc(Cl)c4ncc(C#N)c(Nc5ccc(F)c(Cl)c5)c4c3)c3ccccc3)NN2)[C@H](O)C1] | 8-chloro-4-((3-chloro-4-fluorophenyl)amino)-6-(((S)-(1-((3R,4R)-1-ethyl-3-hydroxypiperidin-4-yl)-1H-1,2,3-triazol-4-yl)(phenyl)methyl)amino)quinoline-3-carbonitrile | 5 | ES/MS 631.0 (M + H+) |
| 515 | 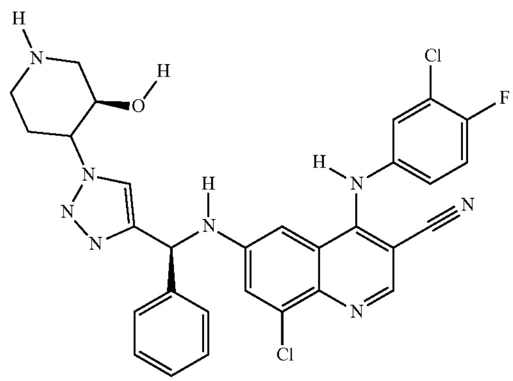 [SMILES: N#Cc1cnc2c(Cl)cc(N[C@H](C3=CN(C4CCNC[C@H]4O)NN3)c3ccccc3)cc2c1Nc1ccc(F)c(Cl)c1] | 8-chloro-4-((3-chloro-4-fluorophenyl)amino)-6-(((S)-(1-((3R,4R)-3-hydroxypiperidin-4-yl)-1H-1,2,3-triazol-4-yl)(phenyl)methyl)amino)quinoline-3-carbonitrile | 5 | ES/MS 603.1 (M + H+) |

TABLE 1-continued

| Compd | Structure | Name | Example/Procedure | ES/MS m/z |
|---|---|---|---|---|
| 516 | 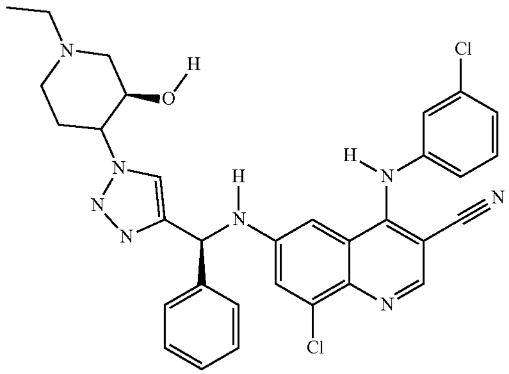 [SMILES: CCN1CCC(N2C=C([C@@H](Nc3cc(Cl)c4ncc(C#N)c(Nc5cccc(Cl)c5)c4c3)c3ccccc3)NN2)[C@H](O)C1] | 8-chloro-4-((3-chlorophenyl)amino)-6-(((S)-(1-((3R,4R)-1-ethyl-3-hydroxypiperidin-4-yl)-1H-1,2,3-triazol-4-yl)(phenyl)methyl)amino)quinoline-3-carbonitrile | 5 | ES/MS 613.1 (M + H+) |
| 517 | 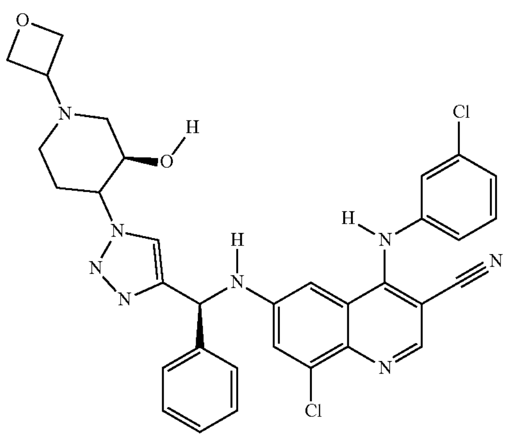 [SMILES: N#Cc1cnc2c(Cl)cc(N[C@H](C3=CN(C4CCN(C5COC5)C[C@H]4O)NN3)c3ccccc3)cc2c1Nc1cccc(Cl)c1] | 8-chloro-4-((3-chlorophenyl)amino)-6-(((S)-(1-((3R,4R)-3-hydroxy-1-(oxetan-3-yl)piperidin-4-yl)-1H-1,2,3-triazol-4-yl)(phenyl)methyl)amino)quinoline-3-carbonitrile | 5 | ES/MS 641.2 (M + H+) |

TABLE 1-continued

| Compd | Structure | Name | Example/Procedure | ES/MS m/z |
|---|---|---|---|---|
| 518 | 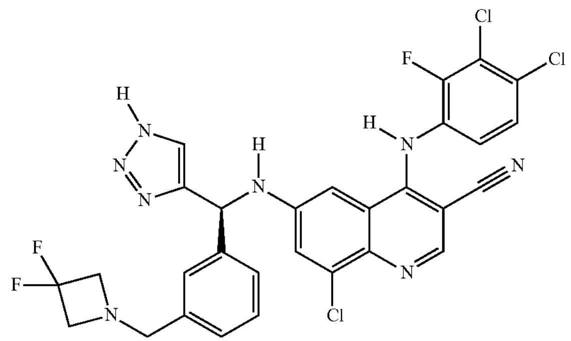 [SMILES: N#Cc1cnc2c(Cl)cc(N[C@@H](c3cccc(CN4CC(F)(F)C4)c3)c3c[nH]nn3)cc2c1Nc1ccc(Cl)c(Cl)c1F] | (S)-8-chloro-4-((3,4-dichloro-2-fluorophenyl)amino)-6-(((3-((3,3-difluoroazetidin-1-yl)methyl)phenyl)(1H-1,2,3-triazol-4-yl)methyl)amino)quinoline-3-carbonitrile | 18 | ES/MS 643.1 (M + H+) |
| 519 | 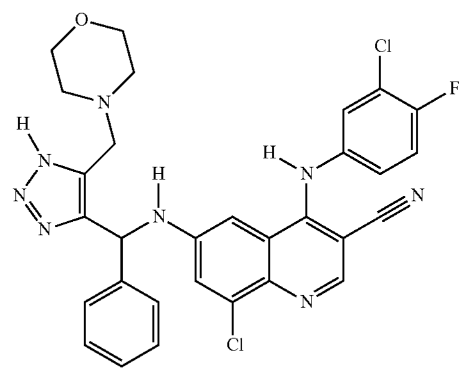 [SMILES: N#Cc1cnc2c(Cl)cc(NC(c3ccccc3)c3nn[nH]c3CN3CCOCC3)cc2c1Nc1ccc(F)c(Cl)c1] | 8-chloro-4-((3-chloro-4-fluorophenyl)amino)-6-(((5-(morpholinomethyl)-1H-1,2,3-triazol-4-yl)phenyl)methyl)amino)quinoline-3-carbonitrile | 7 | ES/MS 603.0 (M + H+) |

TABLE 1-continued

| Compd | Structure | Name | Example/Procedure | ES/MS m/z |
|---|---|---|---|---|
| 520 | 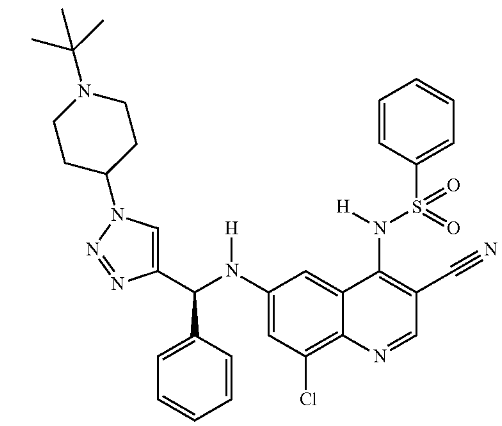 [SMILES: CC(C)(C)N1CCC(n2cc([C@@H](Nc3cc(Cl)c4ncc(C#N)c(NS(=O)(=O)c5ccccc5)c4c3)c3ccccc3)nn2)CC1] | (S)-N-(6-(((1-(1-(tert-butyl)piperidin-4-yl)-1H-1,2,3-triazol-4-yl)(phenyl)methyl)amino)-8-chloro-3-cyanoquiolin-4-yl)benzenesulfonamide | 16 | ES/MS 655.2 (M + H+) |
| 521 | 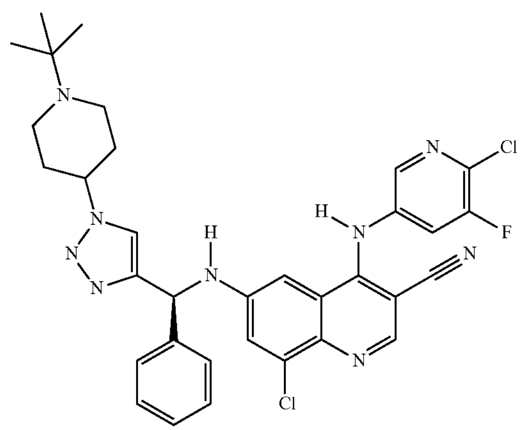 [SMILES: CC(C)(C)N1CCC(N2C=C([C@@H](Nc3cc(Cl)c4ncc(C#N)c(Nc5cnc(Cl)c(F)c5)c4c3)c3ccccc3)NN2)CC1] | (S)-6-(((1-(1-tert-butyl)piperidin-4-yl)-1H-1,2,3-triazol-4-yl)(phenyl)methyl)amino)-8-chloro-4-((6-chloro-5-fluoropyridin-3-yl)amino)quinoline-3-carbonitrile | 10 | ES/MS 644.2 (M + H+) |

TABLE 1-continued

| Compd | Structure | Name | Example/Procedure | ES/MS m/z |
|---|---|---|---|---|
| 522 | 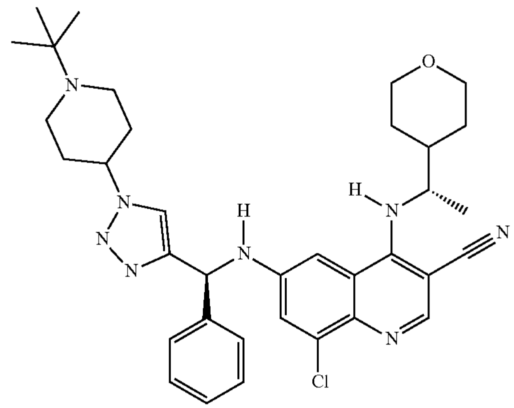 [SMILES: C[C@H](Nc1c(C#N)cnc2c(Cl)cc(N[C@H](C3=CN(C4CCN(C(C)(C)C)CC4)NN3)c3ccccc3)cc12)C1CCOCC1] | 6-(((S)-(1-(1-(tert-butyl)piperidin-4-yl)-1H-1,2,3-triazol-4-yl)(phenyl)methyl)amino)-8-chloro-4-(((S)-1-(tetrahydro-2H-pyran-4-yl)ethyl)amino)quinoline-3-carbonitrile | 1 | ES/MS 627.3 (M + H+) |
| 523 | 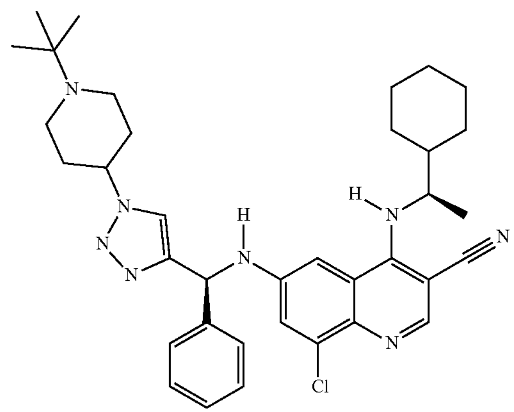 [SMILES: C[C@@H](Nc1c(C#N)cnc2c(Cl)cc(N[C@H](C3=CN(C4CCN(C(C)(C)C)CC4)NN3)c3ccccc3)cc12)C1CCCCC1] | 6-(((S)-(1-(1-(tert-butyl)piperidin-4-yl)-1H-1,2,3-triazol-4-yl)(phenyl)methyl)amino)-8-chloro-4-(((R)-1-cyclohexylethyl)amino)quinoline-3-carbonitrile | 1 | ES/MS 625.3 (M + H+) |

TABLE 1-continued

| Compd | Structure | Name | Example/Procedure | ES/MS m/z |
|---|---|---|---|---|
| 524 | 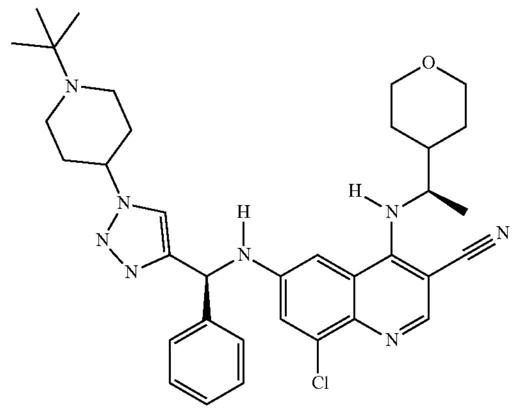 [SMILES: C[C@@H](Nc1c(C#N)cnc2c(Cl)cc(N[C@H](C3=CN(C4CCN(C(C)(C)C)CC4)NN3)c3ccccc3)cc12)C1CCOCC1] | 6-(((S)-(1-(1-(tert-butyl)piperidin-4-yl)-1H-1,2,3-triazol-4-yl)(phenyl)methyl)amino)-8-chloro-4-(((R)-1-(tetrahydro-2H-pyran-4-yl)ethyl)amino)quinoline-3-carbonitrile | 1 | ES/MS 627.3 (M + H+) |
| 525 | 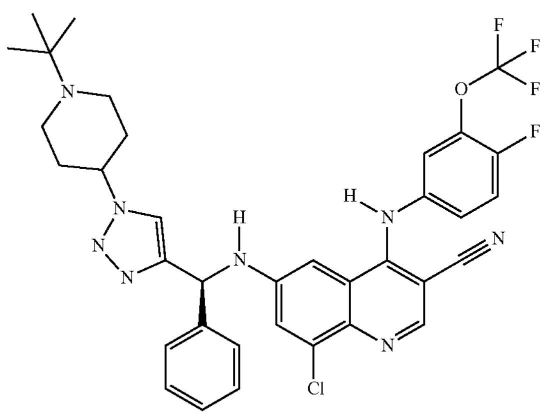 [SMILES: CC(C)(C)N1CCC(N2C=C([C@@H](Nc3cc(Cl)c4ncc(C#N)c(Nc5ccc(F)c(OC(F)(F)F)c5)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((4-fluoro-3-(trifluoromethoxy)phenyl)amino)quinoline-3-carbonitrile | 15 | ES/MS 693.2 (M + H+) |

TABLE 1-continued

| Compd | Structure | Name | Example/Procedure | ES/MS m/z |
|---|---|---|---|---|
| 526 | 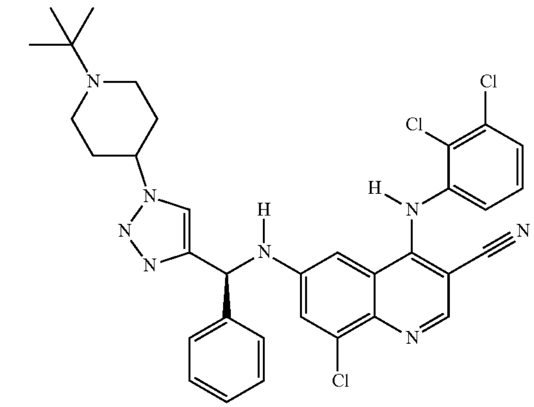 [SMILES: CC(C)(C)N1CCC(N2C=C([C@@H](Nc3cc(Cl)c4ncc(C#N)c(Nc5cccc(Cl)c5Cl)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((2,3-dichlorophenyl)amino)quinoline-3-carbonitrile | 10 | ES/MS 659.2 (M + H+) |
| 527 | 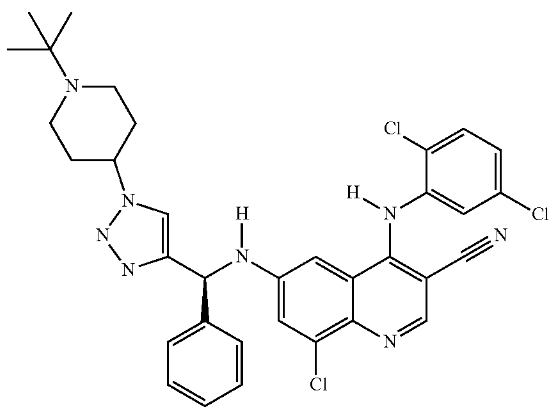 [SMILES: CC(C)(C)N1CCC(N2C=C([C@@H](Nc3cc(Cl)c4ncc(C#N)c(Nc5cc(Cl)ccc5Cl)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((2,5-dichlorophenyl)amino)quinoline-3-carbonitrile | 10 | ES/MS 661.2 (M + H+) |

TABLE 1-continued
| Compd | Structure | Name | Example/Procedure | ES/MS m/z |
|---|---|---|---|---|
| 528 | 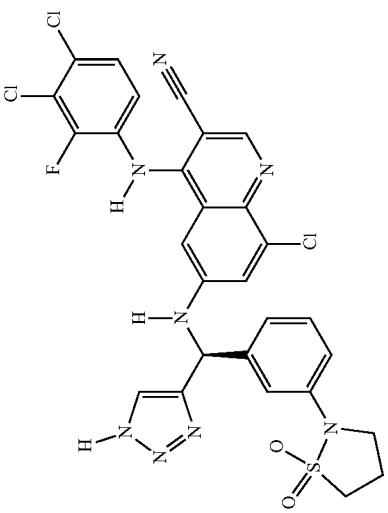 | (S)-8-chloro-4-((3,4-dichloro-2-fluorophenyl)amino)-6-(((3-(1,1-dioxidoisothiazolidin-2-yl)phenyl)(1H-1,2,3-triazol-4-yl)methyl)amino)quinoline-3-carbonitrile | 15 | ES/MS 657.0 (M + H+) |
| 529 | 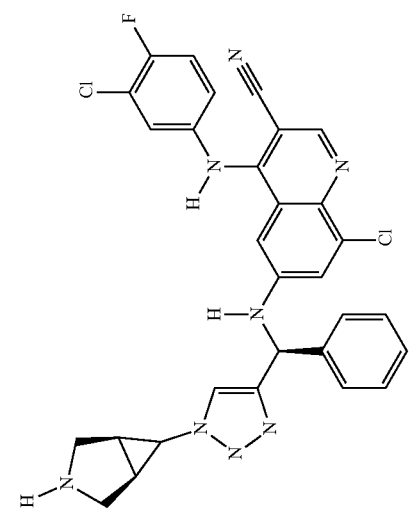 | 6-(((S)-(1-((1R,5S,6s)-3-azabicyclo[3.1.0]hexan-6-yl)-1H-1,2,3-triazol-4-yl)(phenyl)methyl)amino)-8-chloro-4-((3-chloro-4-fluorophenyl)amino)quinoline-3-carbonitrile | 4 | ES/MS 585.1 (M + H+) |

TABLE 1-continued
| Compd | Structure | Name | Example/Procedure | ES/MS m/z |
|---|---|---|---|---|
| 530 | 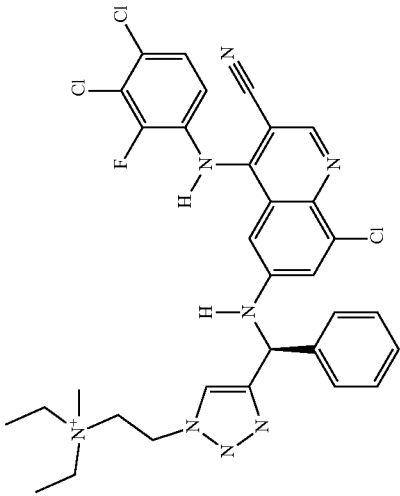 | (S)-2-(4-(((8-chloro-3-cyano-4-((3,4-dichloro-2-fluorophenyl)amino)quinolin-6-yl)amino)(phenyl)methyl)-1H-1,2,3-triazol-1-yl)-N,N-diethyl-N-methylethan-1-aminium | 1 | |
| 531 | 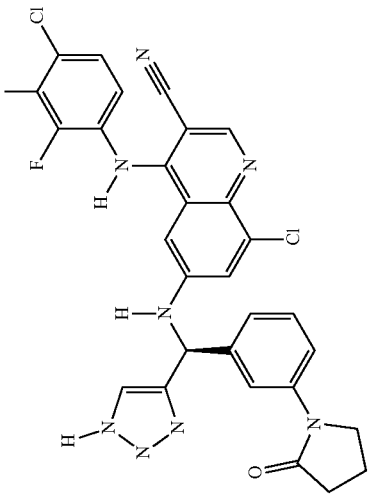 | (S)-8-chloro-4-((3,4-dichloro-2-fluorophenyl)amino)-6-(((3-(2-oxopyrrolidin-1-yl)phenyl)(1H-1,2,3-triazol-4-yl)methyl)amino)quinoline-3-carbonitrile | 15 | ES/MS 620.9 (M + H+) |

TABLE 1-continued

| Compd | Structure | Name | Example/Procedure | ES/MS m/z |
|---|---|---|---|---|
| 532 | 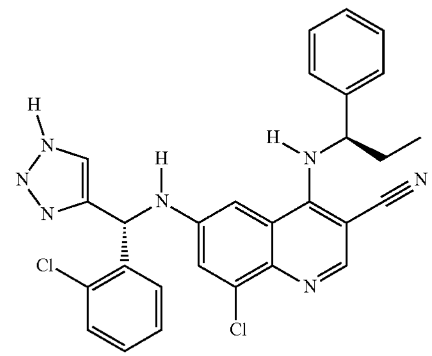 [SMILES: CC[C@@H](Nc1c(C#N)cnc2c(Cl)cc(N[C@@H](C3=CNNN3)c3ccccc3Cl)cc12)c1ccccc1] | 8-chloro-6-(((R)-(2-chlorophenyl)(1H-1,2,3-triazol-4-yl)methyl)amino)-4-(((R)-1-phenylpropyl)amino)quinoline-3-carbonitrile | 15 | ES/MS 528.2 (M + H+) |
| 533 | 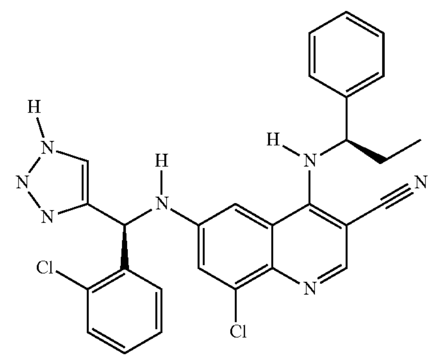 [SMILES: CC[C@@H](Nc1c(C#N)cnc2c(Cl)cc(N[C@H](C3=CNNN3)c3ccccc3Cl)cc12)c1ccccc1] | 8-chloro-6-(((S)-(2-chlorophenyl)(1H-1,2,3-triazol-4-yl)methyl)amino)-4-(((R)-1-phenylpropyl)amino)quinoline-3-carbonitrile | 15 | ES/MS 528.1 (M + H+) |
| 534 | 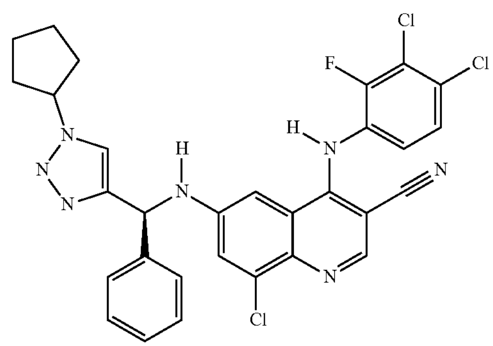 [SMILES: N#Cc1cnc2c(Cl)cc(N[C@H](C3=CN(C4CCCC4)NN3)c3ccccc3)cc2c1Nc1ccc(Cl)c(Cl)c1F] | (S)-8-chloro-6-((((1-cyclopentyl-1H-1,2,3-triazol-4-yl)(phenyl)methyl)amino)-4-((3,4-dichloro-2-fluorophenyl)amino)quinoline-3-carbonitrile | 1 | ES/MS 606.1 (M + H+) |

TABLE 1-continued
| Compd | Structure | Name | Example/Procedure | ES/MS m/z |
|---|---|---|---|---|
| 535 | 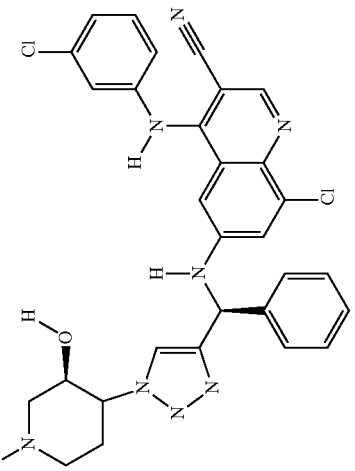 | 8-chloro-4-(3-chlorophenyl)amino)-6-(((S)-(1-((3R,4R)-3-hydroxypiperidin-4-yl)-1H-1,2,3-triazol-4-yl)(phenyl)methyl)amino)quinoline-3-carbonitrile | 5 | ES/MS 585.1 (M + H+) |
| 536 | 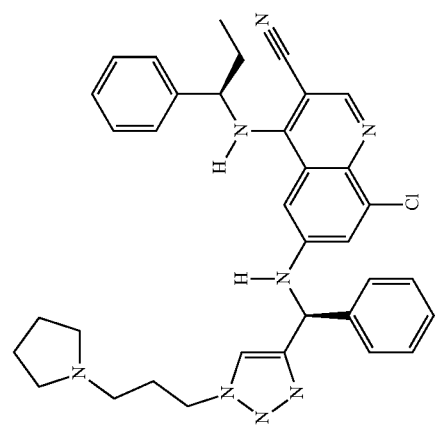 | 8-chloro-6-(((S)-phenyl(1-(3-(pyrrolidin-1-yl)propyl)-1H-1,2,3-triazol-4-yl)methyl)amino)-4-(((R)-1-phenylpropyl)amino)quinoline-3-carbonitrile | 2 | ES/MS 605.2 (M + H+) |

TABLE 1-continued

| Compd | Structure | Name | Example/Procedure | ES/MS m/z |
|---|---|---|---|---|
| 537 | 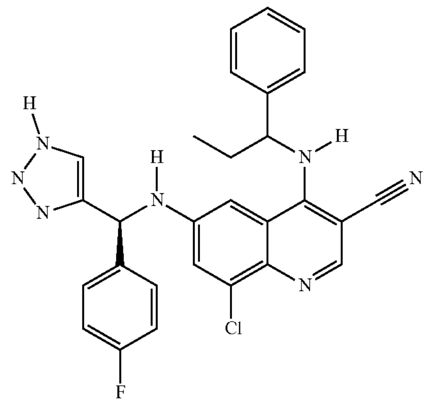 [SMILES: CCC(Nc1c(C#N)cnc2c(Cl)cc(N[C@H](C3=CNNN3)c3ccc(F)cc3)cc12)c1ccccc1] | 8-chloro-6-(((S)-(4-fluorophenyl)(1H-1,2,3-triazol-4-yl)methyl)amino)-4-(((R)-1-phenylpropyl)amino)quinoline-3-carbonitrile | 15 | ES/MS 512.2 (M + H+) |
| 538 | 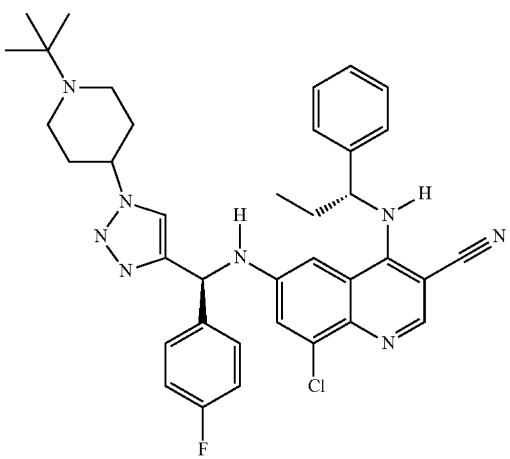 [SMILES: CC[C@@H](Nc1c(C#N)cnc2c(Cl)cc(N[C@H](C3=CN(C4CCN(C(C)(C)C)CC4)NN3)c3ccc(F)cc3)cc12)c1ccccc1] | 6-(((S)-(1-(1-(tert-butyl)piperidin-4-yl)-1H-1,2,3-triazol-4-yl)(4-fluorophenyl)methyl)amino)-8-chloro-4-(((R)-1-phenylpropyl)amino)quinoline-3-carbonitrile | 1 | ES/MS 651.3 (M + H+) |

TABLE 1-continued

| Compd | Structure | Name | Example/Procedure | ES/MS m/z |
|---|---|---|---|---|
| 539 | 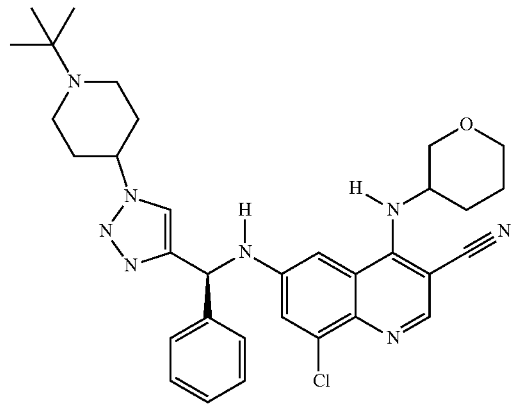 [SMILES: CC(C)(C)N1CCC(N2C=C([C@@H](Nc3cc(Cl)c4ncc(C#N)c(NC5CCCOC5)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((S)-tetrahydro-2H-pyran-3-yl)amino)quinoline-3-carbonitrile | 1 | ES/MS 599.3 (M + H+) |
| 540 | 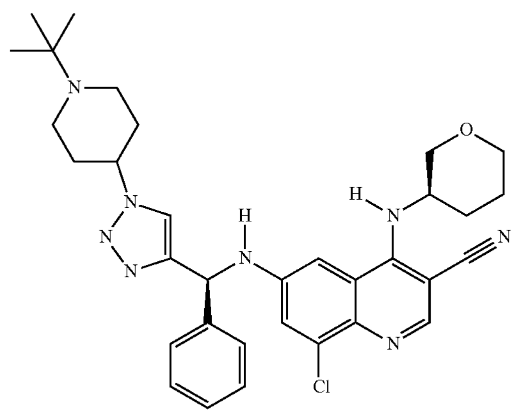 [SMILES: CC(C)(C)N1CCC(N2C=C([C@@H](Nc3cc(Cl)c4ncc(C#N)c(N[C@@H]5CCCOC5)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((R)-tetrahydro-2H-pyran-3-yl)amino)quinoline-3-carbonitrile | 1 | ES/MS 599.3 (M + H+) |

TABLE 1-continued

| Compd | Structure | Name | Example/Procedure | ES/MS m/z |
|---|---|---|---|---|
| 541 | 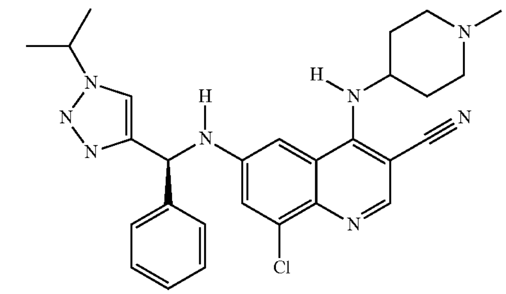 [SMILES: CC(C)N1C=C([C@@H](Nc2cc(Cl)c3ncc(C#N)c(NC4CCN(C)CC4)c3c2)c2ccccc2)NN1] | (S)-8-chloro-6-(((1-isopropyl-1H-1,2,3-triazol-4-yl)(phenyl)methyl)amino)-4-((1-methylpiperidin-4-yl)amino)quinoline-3-carbonitrile | 1 | ES/MS 515.2 (M + H+) |
| 542 | 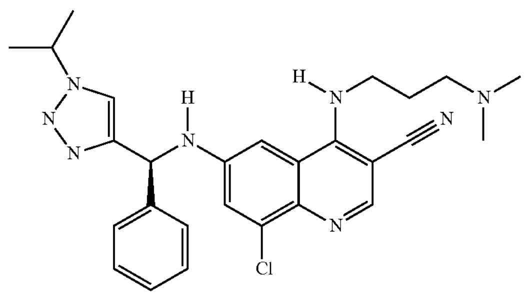 [SMILES: CC(C)N1C=C([C@@H](Nc2cc(Cl)c3ncc(C#N)c(NCCCN(C)C)c3c2)c2ccccc2)NN1] | (S)-8-chloro-4-((3-(dimethylamino)propyl)amino)-6-(((1-isopropyl-1H-1,2,3-triazol-4-yl)(phenyl)methyl)amino)quinoline-3-carbonitrile | 1 | ES/MS 503.2 (M + H+) |
| 543 | 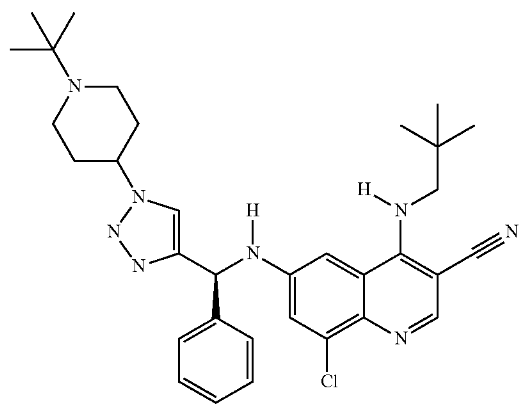 [SMILES: CC(C)(C)CNc1c(C#N)cnc2c(Cl)cc(N[C@H](C3=CN(C4CCN(C(C)(C)C)CC4)NN3)c3ccccc3)cc12] | (S)-6-((((1-(1-(tert-butyl)piperidin-4-yl)-1H-1,2,3-triazol-4-yl)(phenyl)methyl)amino)-8-chloro-4-(neopentylamino)quinoline-3-carbonitrile | 1 | ES/MS 585.3 (M + H+) |

TABLE 1-continued

| Compd | Structure | Name | Example/Procedure | ES/MS m/z |
|---|---|---|---|---|
| 544 | 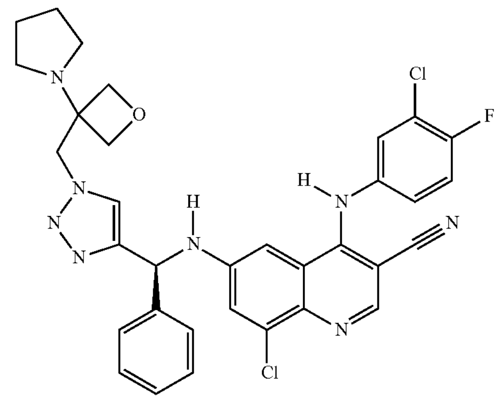 [SMILES: N#Cc1cnc2c(Cl)cc(N[C@H](C3=CN(CC4(N5CCCC5)COC4)NN3)c3ccccc3)cc2c1Nc1ccc(F)c(Cl)c1] | (S)-8-chloro-4-((3-chloro-4-fluorophenyl)amino)-6-((phenyl(1-((3-(pyrrolidin-1-yl)oxetan-3-yl)methyl)-1H-1,2,3-triazol-4-yl)methyl)amino)quinoline-3-carbonitrile | 4 | ES/MS 643.1 (M + H+) |
| 545 | 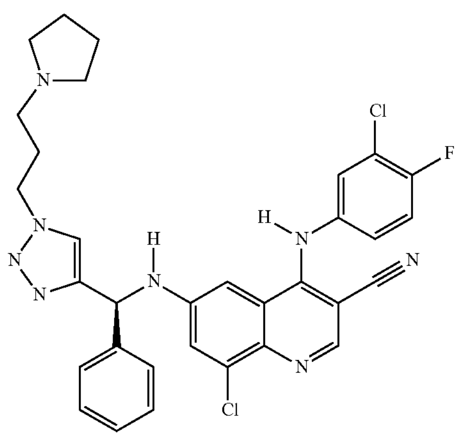 [SMILES: N#Cc1cnc2c(Cl)cc(N[C@H](C3=CN(CCCN4CCCC4)NN3)c3ccccc3)cc2c1Nc1ccc(F)c(Cl)c1] | (S)-8-chloro-4-((3-chloro-4-fluorophenyl)amino)-6-((phenyl(1-(3-(pyrrolidin-1-yl)propyl)-1H-1,2,3-triazol-4-yl)methyl)amino)quinoline-3-carbonitrile | 4 | ES/MS 615.1 (M + H+) |

TABLE 1-continued

| Compd | Structure | Name | Example/Procedure | ES/MS m/z |
|---|---|---|---|---|
| 546 | 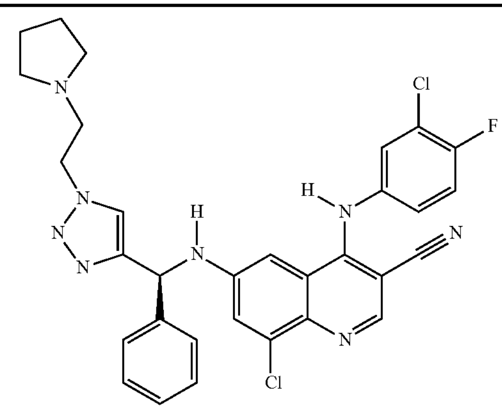 | (S)-8-chloro-4-((3-chloro-4-fluorophenyl)amino)-6-((phenyl(1-(2-(pyrrolidin-1-yl)ethyl)-1H-1,2,3-triazol-4-yl)methyl)amino)quinoline-3-carbonitrile | 4 | ES/MS 601.1 (M + H+) |
| 547 | 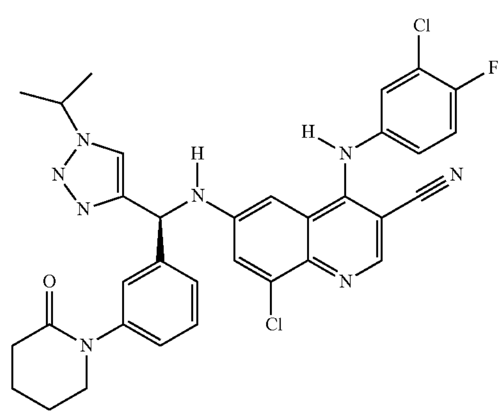 [SMILES: CC(C)N1C=C([C@@H](Nc2cc(Cl)c3ncc(C#N)c(Nc4ccc(F)c(Cl)c4)c3c2)c2cccc(N3CCCCC3=O)c2)NN1] | (S)-8-chloro-4-((3-chloro-4-fluorophenyl)amino)-6-(((1-isopropyl-1H-1,2,3-triazol-4-yl)(3-(2-oxopiperidin-1-yl)phenyl)methyl)amino)quinoline-3-carbonitrile | 3 | ES/MS 642.9 (M + H+) |

TABLE 1-continued

| Compd | Structure | Name | Example/Procedure | ES/MS m/z |
|---|---|---|---|---|
| 548 | 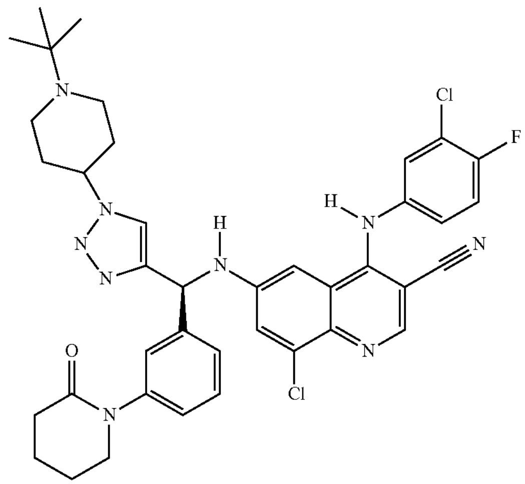 [SMILES: CC(C)(C)N1CCC(N2C=C([C@@H](Nc3cc(Cl)c4ncc(C#N)c(Nc5ccc(F)c(Cl)c5)c4c3)c3cccc(N4CCCCC4=O)c3)NN2)CC1] | (S)-6-(((1-(1-(tert-butyl)piperidin-4-yl)-1H-1,2,3-triazol-4-yl)(3-(2-oxopiperidin-1-yl)phenyl)methyl)amino)-8-chloro-4-((3-chloro-4-fluorophenyl)amino)quinoline-3-carbonitrile | 3 | ES/MS 740.0 (M + H+) |
| 549 | 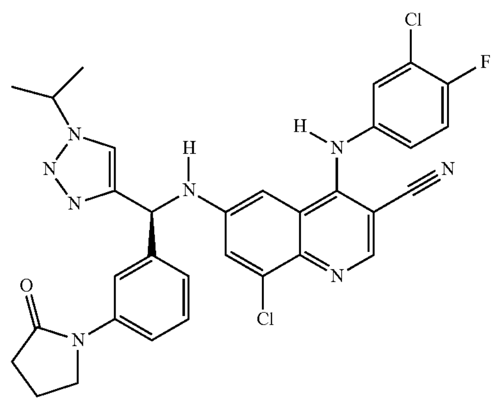 [SMILES: CC(C)N1C=C([C@@H](Nc2cc(Cl)c3ncc(C#N)c(Nc4ccc(F)c(Cl)c4)c3c2)c2cccc(N3CCCC3=O)c2)NN1] | (S)-8-chloro-4-((3-chloro-4-fluorophenyl)amino)-6-(((1-isopropyl-1H-1,2,3-triazol-4-yl)(3-(2-oxopyrrolidin-1-yl)phenyl)methyl)amino)quinoline-3-carbonitrile | 3 | ES/MS 629.0 (M + H+) |

TABLE 1-continued

| Compd | Structure | Name | Example/Procedure | ES/MS m/z |
|---|---|---|---|---|
| 550 | 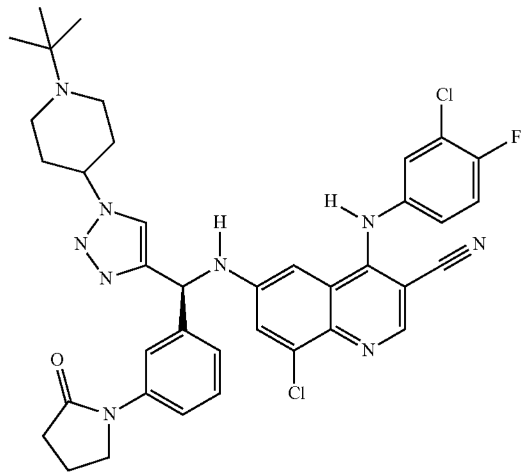 [SMILES: CC(C)(C)N1CCC(N2C=C([C@@H](Nc3cc(Cl)c4ncc(C#N)c(Nc5ccc(F)c(Cl)c5)c4c3)c3cccc(N4CCCC4=O)c3)NN2)CC1] | (S)-6-((((1-(1-(tert-butyl)piperidin-4-yl)-1H-1,2,3-triazol-4-yl)(3-(2-oxopyrrolidin-1-yl)phenyl)methyl)amino)-8-chloro-4-((3-chloro-4-fluorophenyl)amino)quinoline-3-carbonitrile | 3 | ES/MS 726.0 (M + H+) |
| 551 | 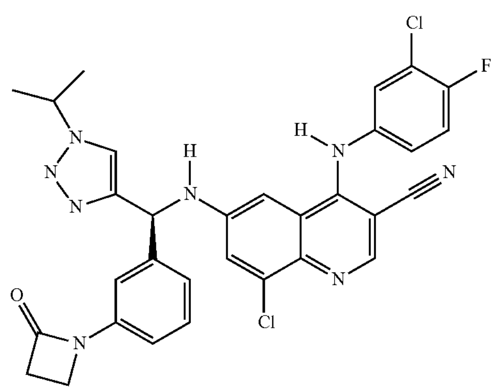 [SMILES: CC(C)N1C=C([C@@H](Nc2cc(Cl)c3ncc(C#N)c(Nc4ccc(F)c(Cl)c4)c3c2)c2cccc(N3CCC3=O)c2)NN1] | (S)-8-chloro-4-((3-chloro-4-fluorophenyl)amino)-6-(((1-isopropyl-1H-1,2,3-triazol-4-yl)(3-(2-oxoazetidin-1-yl)phenyl)methyl)amino)quinoline-3-carbonitrile | 3 | ES/MS 615.0 (M + H+) |

TABLE 1-continued

| Compd | Structure | Name | Example/Procedure | ES/MS m/z |
|---|---|---|---|---|
| 552 | 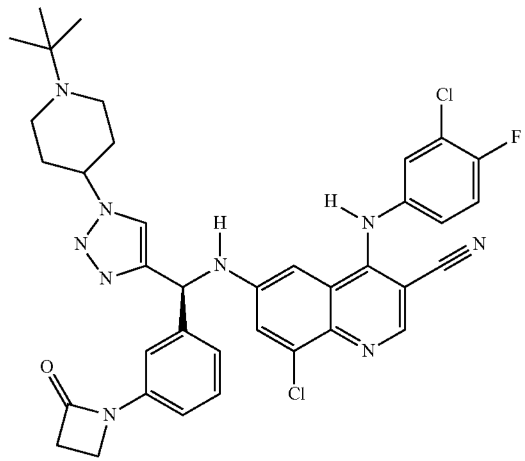 [SMILES: CC(C)(C)N1CCC(N2C=C([C@@H](Nc3cc(Cl)c4ncc(C#N)c(Nc5ccc(F)c(Cl)c5)c4c3)c3cccc(N4CCC4=O)c3)NN2)CC1] | (S)-6-((((1-(1-(tert-butyl)piperidin-4-yl)-1H-1,2,3-triazol-4-yl)(3-(2-oxoazetidin-1-yl)phenyl)methyl)amino)-8-chloro-4-((3-chloro-4-fluorophenyl)amino)quinoline-3-carbonitrile | 3 | ES/MS 712.0 (M + H+) |
| 553 | 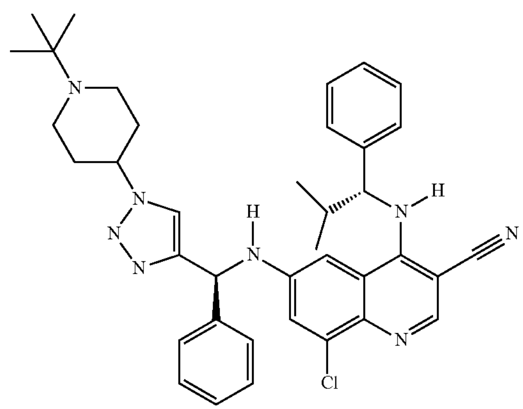 [SMILES: CC(C)[C@@H](Nc1c(C#N)cnc2c(Cl)cc(N[C@H](C3=CN(C4CCN(C(C)(C)C)CC4)NN3)c3ccccc3)cc12)c1ccccc1] | 6-(((S)-(1-(1-(tert-butyl)piperidin-4-yl)-1H-1,2,3-triazol-4-yl)(phenyl)methyl)amino)-8-chloro-4-(((R)-2-methyl-1-phenylpropyl)amino)quinoline-3-carbonitrile | 1 | ES/MS 647.3 (M + H+) |

TABLE 1-continued

| Compd | Structure | Name | Example/Procedure | ES/MS m/z |
|---|---|---|---|---|
| 554 | 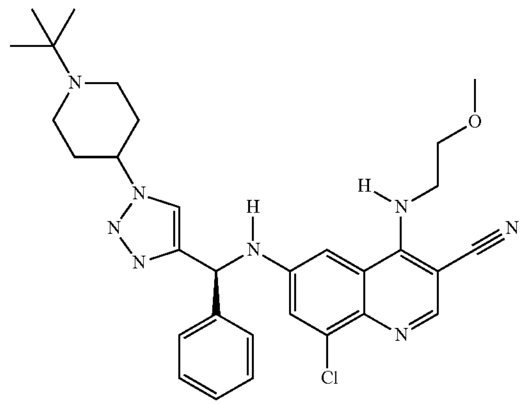 [SMILES: COCCNc1c(C#N)cnc2c(Cl)cc(N[C@H](C3=CN(C4CCN(C(C)(C)C)CC4)NN3)c3ccccc3)cc12] | (S)-6-((((1-(1-(tert-butyl)piperidin-4-yl)-1H-1,2,3-triazol-4-yl)(phenyl)methyl)amino)-8-chloro-4-((2-methoxyethyl)amino)quinoline-3-carbonitrile | 1 | ES/MS 573.3 (M + H+) |
| 555 | 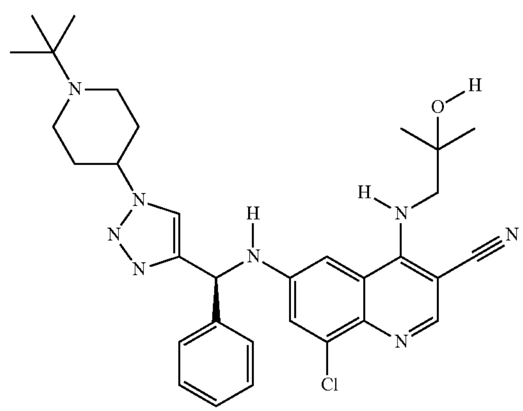 | (S)-6-((((1-(1-(tert-butyl)piperidin-4-yl)-1H-1,2,3-triazol-4-yl)(phenyl)methyl)amino)-8-chloro-4-((2-hydroxy-2-methylpropyl)amino)quinoline-3-carbonitrile | 1 | ES/MS 587.3 (M + H+) |

TABLE 1-continued

| Compd | Structure | Name | Example/Procedure | ES/MS m/z |
|---|---|---|---|---|
| 556 | 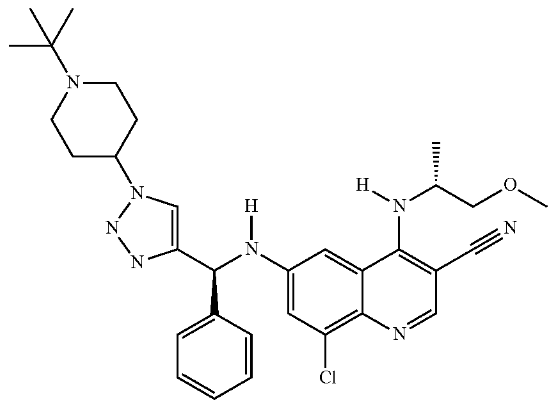 [SMILES: COC[C@@H](C)Nc1c(C#N)cnc2c(Cl)cc(N[C@H](C3=CN(C4CCN(C(C)(C)C)CC4)NN3)c3ccccc3)cc12] | 6-(((S)-(1-(1-(tert-butyl)piperidin-4-yl)-1H-1,2,3-triazol-4-yl)(phenyl)methyl)amino)-8-chloro-4-(((R)-1-methoxypropan-2-yl)amino)quinoline-3-carbonitrile | 1 | ES/MS 587.3 (M + H+) |
| 557 | 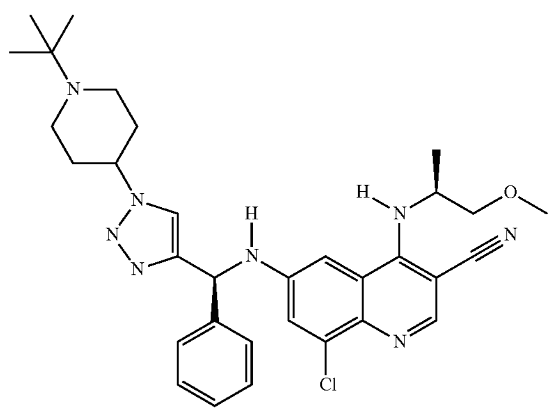 [SMILES: COC[C@H](C)Nc1c(C#N)cnc2c(Cl)cc(N[C@H](C3=CN(C4CCN(C(C)(C)C)CC4)NN3)c3ccccc3)cc12] | 6-(((S)-(1-(1-(tert-butyl)piperidin-4-yl)-1H-1,2,3-triazol-4-yl)(phenyl)methyl)amino)-8-chloro-4-(((S)-1-methoxypropan-2-yl)amino)quinoline-3-carbonitrile | 1 | ES/MS 587.3 (M + H+) |

TABLE 1-continued

| Compd | Structure | Name | Example/Procedure | ES/MS m/z |
|---|---|---|---|---|
| 558 | 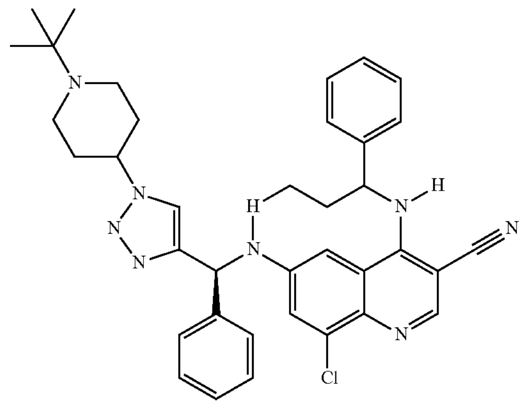 | 6-(((S)-(1-(tert-butyl)piperidin-4-yl)-1H-1,2,3-triazol-4-yl)(phenyl)methyl)amino)-8-chloro-4-(((R)-1-phenylbutyl)amino)quinoline-3-carbonitrile | 1 | ES/MS 647.3 (M + H+) |
| 559 | 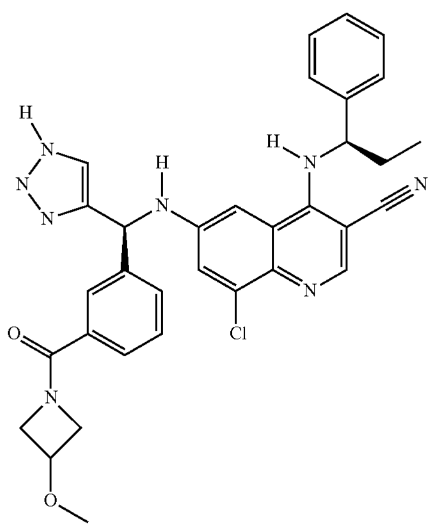 [SMILES: CC[C@@H](Nc1c(C#N)cnc2c(Cl)cc(N[C@H](C3=CNNN3)c3cccc(C(=O)N4CC(OC)C4)c3)cc12)c1ccccc1] | 8-chloro-6-(((S)-(3-(3-methoxyazetidine-1-carbonyl)phenyl)(1H-1,2,3-triazol-4-yl)methyl)amino)-4-(((R)-1-phenylpropyl)amino)quinoline-3-carbonitrile | 20 | ES/MS 607.0 (M + H+) |

TABLE 1-continued

| Compd | Structure | Name | Example/Procedure | ES/MS m/z |
|---|---|---|---|---|
| 560 | 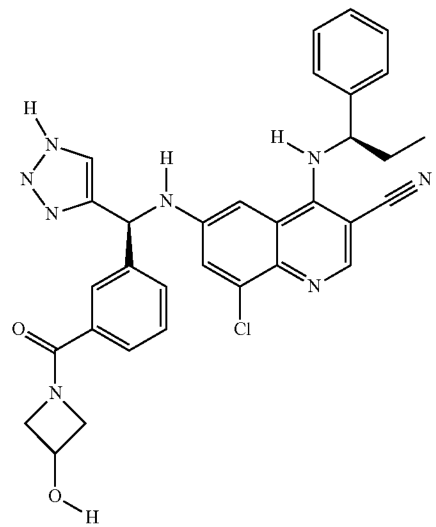 [SMILES: CC[C@@H](Nc1c(C#N)cnc2c(Cl)cc(N[C@H](C3=CNNN3)c3cccc(C(=O)N4CC(O)C4)c3)cc12)c1ccccc1] | 8-chloro-6-(((S)-(3-(3-hydroxyazetidine-1-carbonyl)phenyl)(1H-1,2,3-triazol-4-yl)methyl)amino)-4-(((R)-1-phenylpropyl)amino)quinoline-3-carbonitrile | 20 | ES/MS 593.0 (M + H+) |
| 561 | 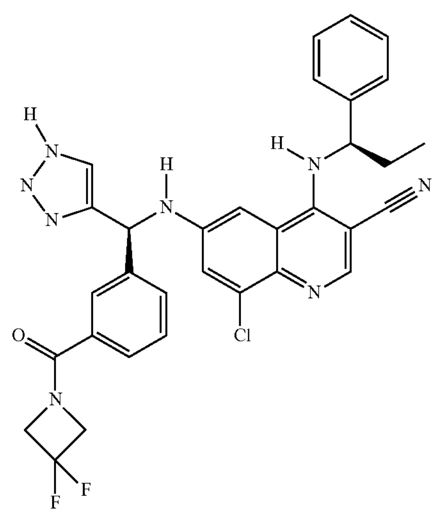 [SMILES: CC[C@@H](Nc1c(C#N)cnc2c(Cl)cc(N[C@H](C3=CNNN3)c3cccc(C(=O)N4CC(F)(F)C4)c3)cc12)c1ccccc1] | 8-chloro-6-(((S)-(3-(3,3-difluoroazetidine-1-carbonyl)phenyl)(1H-1,2,3-triazol-4-yl)methyl)amino)-4-(((R)-1-phenylpropyl)amino)quinoline-3-carbonitrile | 20 | ES/MS 613.0 (M + H+) |

TABLE 1-continued
| Compd | Structure | Name | Example/Procedure | ES/MS m/z |
|---|---|---|---|---|
| 562 | 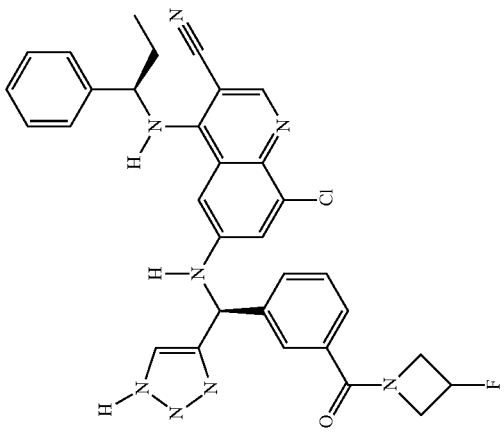 | 8-chloro-6-(((S)-(3-(3-fluoroazetidine-1-carbonyl)phenyl)(1H-1,2,3-triazol-4-yl)methyl)amino)-4-(((R)-1-phenylpropyl)amino)quinoline-3-carbonitrile | 20 | ES/MS 595.0 (M + H+) |
| 563 | 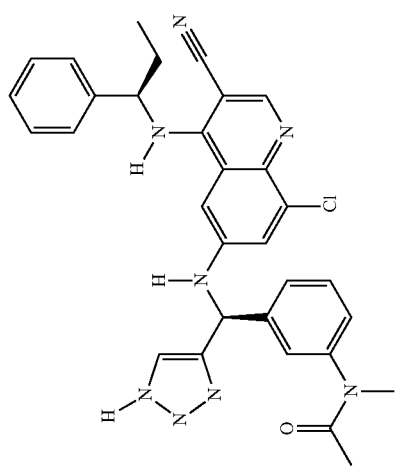 | N-(3-(((S)-((8-chloro-3-cyano-4-(((R)-1-phenylpropyl)amino)quinolin-6-yl)amino)(1H-1,2,3-triazol-4-yl)methyl)phenyl)-N-methylacetamide | 15 | ES/MS 565.1 (M + H+) |

TABLE 1-continued
| Compd | Structure | Name | Example/Procedure | ES/MS m/z |
|---|---|---|---|---|
| 564 | 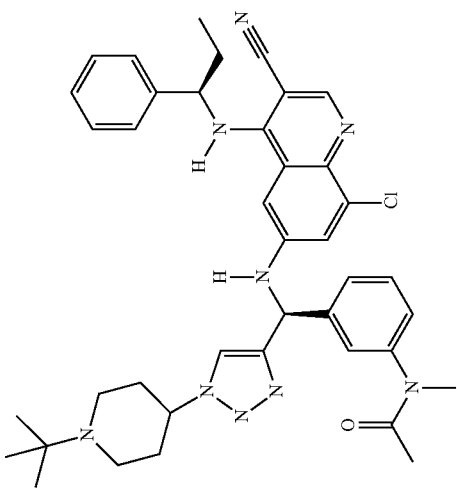 | N-(3-((S)-(1-(1-(tert-butyl)piperidin-4-yl)-1H-1,2,3-triazol-4-yl)((8-chloro-3-cyano-4-(((R)-1-phenylpropyl)amino)quinolin-6-yl)amino)methyl)phenyl)-N-methylacetamide | 3 | ES/MS 704.2 (M + H+) |
| 565 | 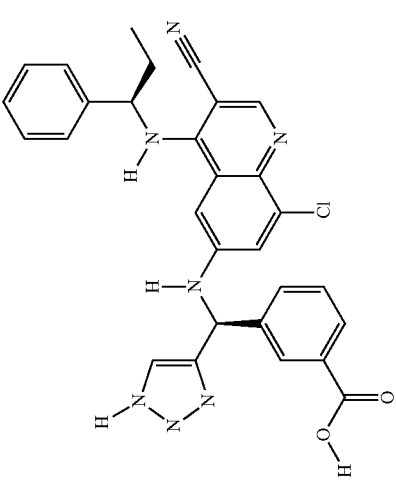 | 3-((S)-((8-chloro-3-cyano-4-(((R)-1-phenylpropyl)amino)quinolin-6-yl)amino)(1H-1,2,3-triazol-4-yl)methyl)benzoic acid | 19 | ES/MS 538.0 (M + H+) |

TABLE 1-continued

| Compd | Structure | Name | Example/Procedure | ES/MS m/z |
|---|---|---|---|---|
| 566 | 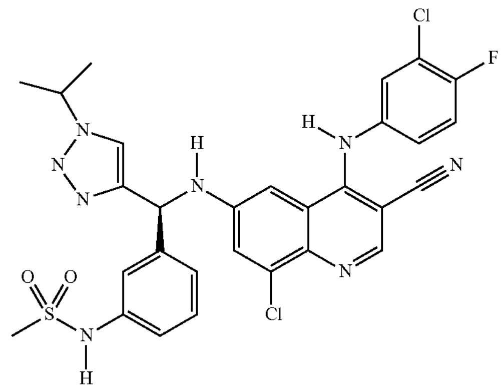 [SMILES: CC(C)N1C=C([C@@H](Nc2cc(Cl)c3ncc(C#N)c(Nc4ccc(F)c(Cl)c4)c3c2)c2cccc(NS(C)(=O)=O)c2)NN1] | (S)-N-(3-(((8-chloro-4-((3-chloro-4-fluorophenyl)amino)-3-cyanoquinolin-6-yl)amino)(1-isopropyl-1H-1,2,3-triazol-4-yl)methyl)phenyl)methanesulfonamide | 25 | ES/MS 639.0 (M + H+) |
| 567 | 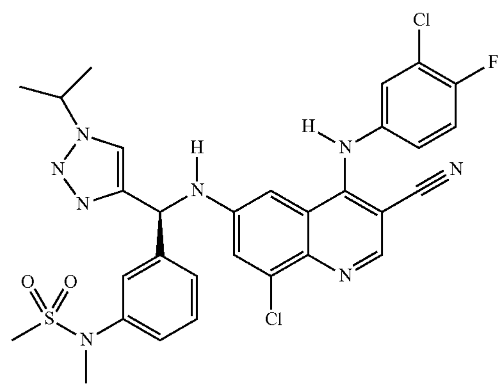 [SMILES: CC(C)N1C=C([C@@H](Nc2cc(Cl)c3ncc(C#N)c(Nc4ccc(F)c(Cl)c4)c3c2)c2cccc(N(C)S(C)(=O)=O)c2)NN1] | (S)-N-(3-(((8-chloro-4-((3-chloro-4-fluorophenyl)amino)-3-cyanoquinolin-6-yl)amino)(1-isopropyl-1H-1,2,3-triazol-4-yl)methyl)phenyl)-N-methylmethanesulfonamide | 3 | ES/MS 653.0 (M + H+) |

TABLE 1-continued
| Compd | Structure | Name | Example/Procedure | ES/MS m/z |
|---|---|---|---|---|
| 568 | 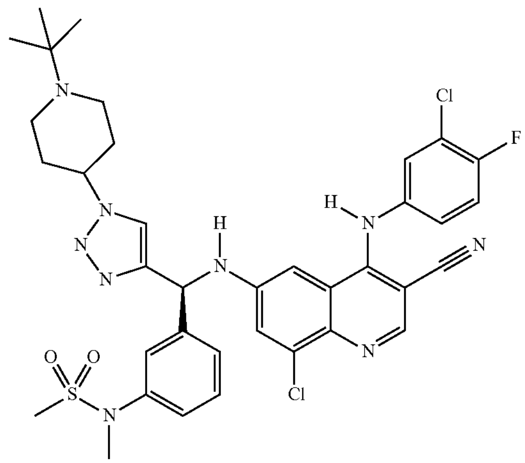 [SMILES: CN(c1cccc([C@H](Nc2cc(Cl)c3ncc(C#N)c(Nc4ccc(F)c(Cl)c4)c3c2)C2=CN(C3CCN(C(C)(C)C)CC3)NN2)c1)S(C)(=O)=O] | (S)-N-(3-(((1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)phenyl)-N-methylmethanesulfonamide | 3 | ES/MS 750.1 (M + H+) |
| 569 | 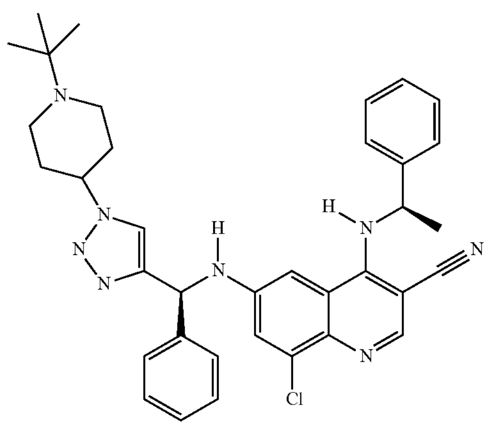 [SMILES: C[C@@H](Nc1c(C#N)cnc2c(Cl)cc(N[C@H](C3=CN(C4CCN(C(C)(C)C)CC4)NN3)c3ccccc3)cc12)c1ccccc1] | 6-(((S)-(1-(1-(tert-butyl)piperidin-4-yl)-1H-1,2,3-triazol-4-yl)(phenyl)methyl)amino)-8-chloro-4-(((R)-1-phenylethyl)amino)quinoline-3-carbonitrile | 1 | ES/MS 619.3 (M + H+) |

TABLE 1-continued

| Compd | Structure | Name | Example/Procedure | ES/MS m/z |
|---|---|---|---|---|
| 570 | 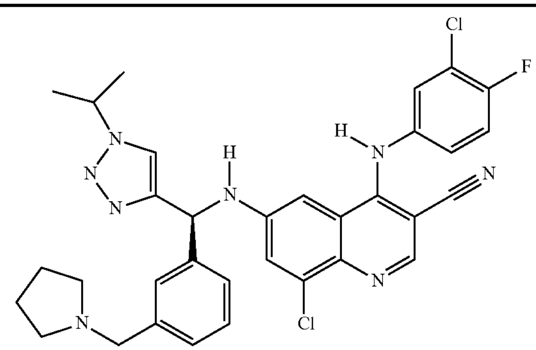 | (S)-8-chloro-4-(((3-chloro-4-fluorophenyl)amino)-6-(((1-isopropyl-1H-1,2,3-triazol-4-yl)(3-(pyrrolidin-1-ylmethyl)phenyl)methyl)amino)-quinoline-3-carbonitrile | 3 | ES/MS 629.0 (M + H+) |
| 571 | 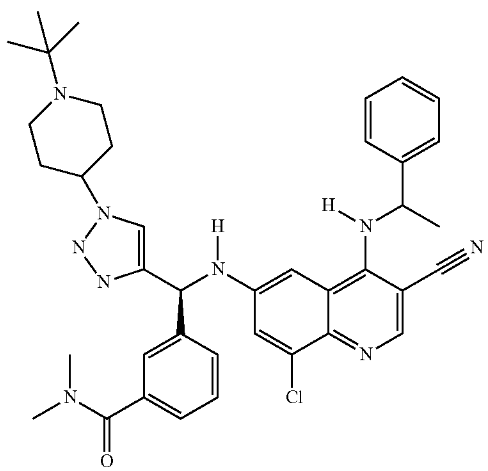 [SMILES: CC(Nc1c(C#N)cnc2c(Cl)cc(N[C@H](C3=CN(C4CCN(C(C)(C)C)CC4)NN3)c3cccc(C(=O)N(C)C)c3)cc12)c1ccccc1] | 3-((S)-(1-(1-(tert-butyl)piperidin-4-yl)-1H-1,2,3-triazol-4-yl)(8-chloro-3-cyano-4-(((R)-1-phenylethyl)amino)quinolin-6-yl)amino)methyl)-N,N-dimethylbenzamide | 3 | ES/MS 690.1 (M + H+) |

TABLE 1-continued

| Compd | Structure | Name | Example/Procedure | ES/MS m/z |
|---|---|---|---|---|
| 572 | 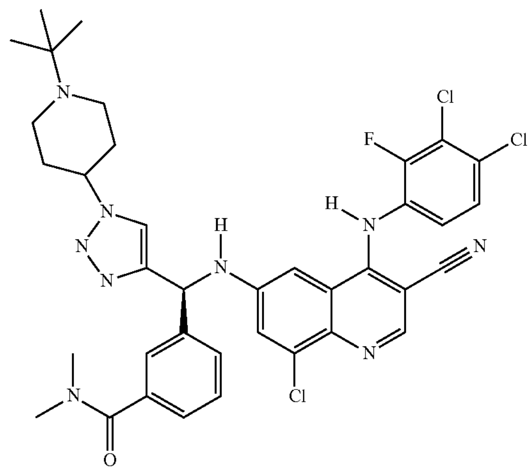 [SMILES: CN(C)C(=O)c1cccc([C@H](Nc2cc(Cl)c3ncc(C#N)c(Nc4ccc(Cl)c(Cl)c4F)c3c2)C2=CN(C3CCN(C(C)(C)C)CC3)NN2)c1] | (S)-3-((1-(1-(tert-butyl)piperidin-4-yl)-1H-1,2,3-triazol-4-yl)(8-chloro-3-cyano-4-((3,4-dichloro-2-fluorophenyl)amino)quinolin-6-yl)amino)methyl)-N,N-dimethylbenzamide | 3 | ES/MS 748.1 (M + H+) |
| 573 | 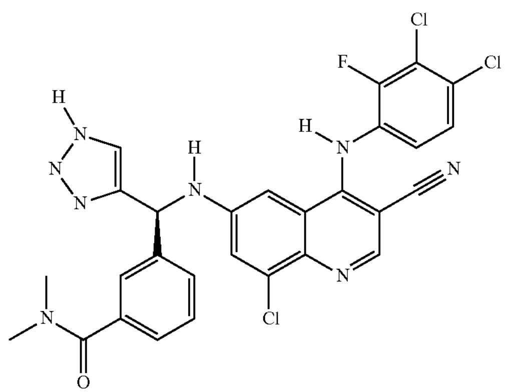 [SMILES: CN(C)C(=O)c1cccc([C@H](Nc2cc(Cl)c3ncc(C#N)c(Nc4ccc(Cl)c(Cl)c4F)c3c2)C2=CNNN2)c1] | (S)-3-(((8-chloro-3-cyano-4-((3,4-dichloro-2-fluorophenyl)amino)quinolin-6-yl)amino)(1H-1,2,3-triazol-4-yl)methyl)-N,N-dimethylbenzamide | 15 | ES/MS 609.1 (M + H+) |

TABLE 1-continued
| Compd | Structure | Name | Example/Procedure | ES/MS m/z |
|---|---|---|---|---|
| 574 | 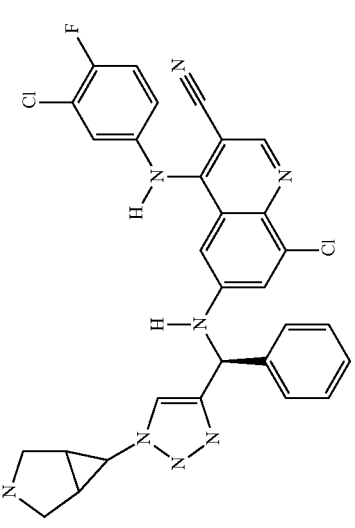 | 8-chloro-4-((3-chloro-4-fluorophenyl)amino)-6-(((1S)-(1-(3-(oxetan-3-yl)-3-azabicyclo[3.1.0]hexan-6-yl)-1H-1,2,3-triazol-4-yl)(phenyl)methyl)amino)quinoline-3-carbonitrile | 4 | ES/MS 641.1 (M + H+) |
| 575 | 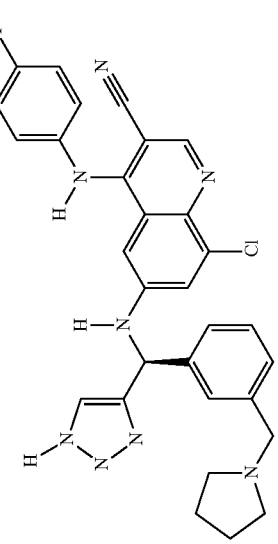 | (S)-8-chloro-4-((3-chloro-4-fluorophenyl)amino)-6-(((3-(pyrrolidin-1-ylmethyl)phenyl)(1H-1,2,3-triazol-4-yl)methyl)amino)quinoline-3-carbonitrile | 15 | ES/MS 587.2 (M + H+) |

TABLE 1-continued

| Compd | Structure | Name | Example/Procedure | ES/MS m/z |
|---|---|---|---|---|
| 576 | 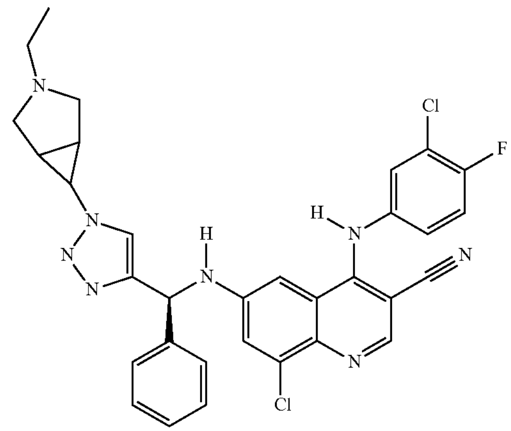 [SMILES: CCN1CC2C(C1)C2N1C=C([C@@H](Nc2cc(Cl)c3ncc(C#N)c(Nc4ccc(F)c(Cl)c4)c3c2)c2ccccc2)NN1] | 8-chloro-4-((3-chloro-4-fluorophenyl)amino)-6-(((1S)-(1-(3-ethyl-3-azabicyclo[3.1.0]hexan-6-yl)-1H-1,2,3-triazol-4-yl)(phenyl)methyl)amino)quinoline-3-carbonitrile | 4 | ES/MS 613.1 (M + H+) |
| 577 | 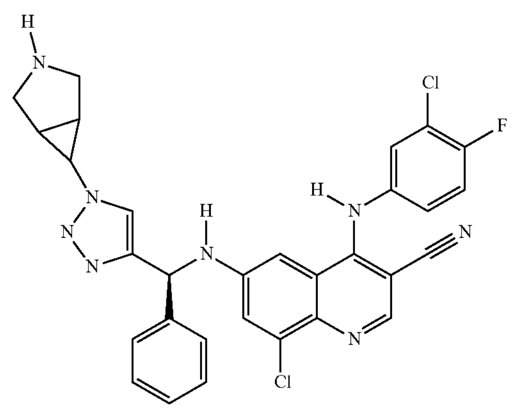 [SMILES: N#Cc1cnc2c(Cl)cc(N[C@H](C3=CN(C4C5CNCC54)NN3)c3ccccc3)cc2c1Nc1ccc(F)c(Cl)c1] | 6-(((1S)-(1-(3-azabicyclo[3.1.0]hexan-6-yl)-1H-1,2,3-triazol-4-yl)(phenyl)methyl)amino)-8-chloro-4-((3-chloro-4-fluorophenyl)amino)quinoline-3-carbonitrile | 4 | ES/MS 585.1 (M + H+) |

TABLE 1-continued
| Compd | Structure | Name | Example/Procedure | ES/MS m/z |
|---|---|---|---|---|
| 578 | 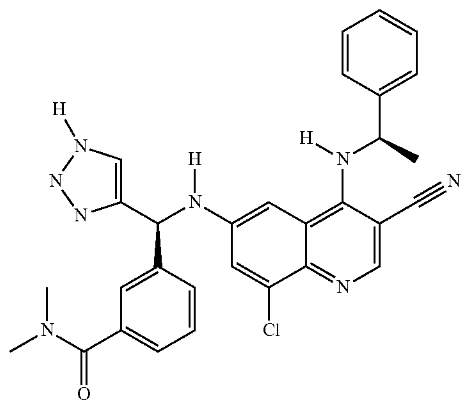 [SMILES: C[C@@H](Nc1c(C#N)cnc2c(Cl)cc(N[C@H](C3=CNNN3)c3cccc(C(=O)N(C)C)c3)cc12)c1ccccc1] | 3-((S)-((8-chloro-3-cyano-4-(((R)-1-phenylethyl)amino)quinolin-6-yl)amino)(1H-1,2,3-triazol-4-yl)methyl)-N,N-dimethylbenzamide | 15 | ES/MS 551.0 (M + H+) |
| 579 | 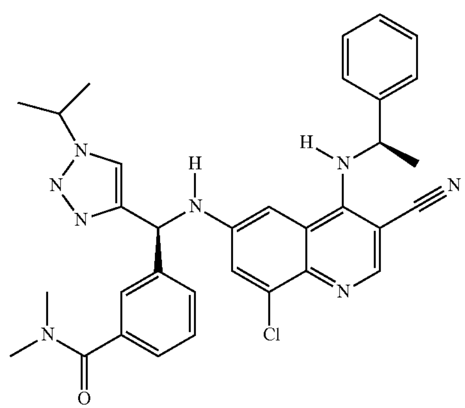 [SMILES: CC(C)N1C=C([C@@H](Nc2cc(Cl)c3ncc(C#N)c(N[C@H](C)c4ccccc4)c3c2)c2cccc(C(=O)N(C)C)c2)NN1] | 3-((S)-((8-chloro-3-cyano-4-(((R)-1-phenylethyl)amino)quinolin-6-yl)amino)(1-isopropyl-1H-1,2,3-triazol-4-yl)methyl)-N,N-dimethylbenzamide | 3 | ES/MS 593.1 (M + H+) |

TABLE 1-continued

| Compd | Structure | Name | Example/Procedure | ES/MS m/z |
|---|---|---|---|---|
| 580 | 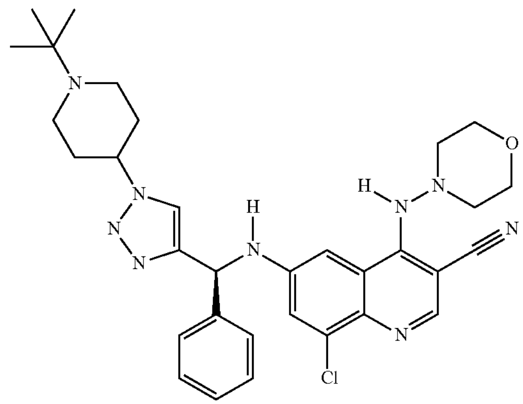 [SMILES: CC(C)(C)N1CCC(N2C=C([C@@H](Nc3cc(Cl)c4ncc(C#N)c(NN5CCOCC5)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-(morpholinoamino)quinoline-3-carbonitrile | 1 | ES/MS 600.3 (M + H+) |
| 581 | 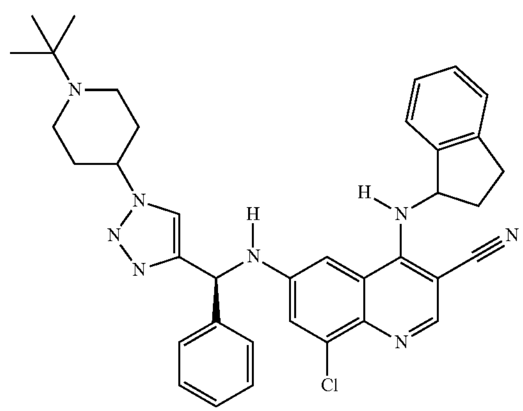 [SMILES: CC(C)(C)N1CCC(N2C=C([C@@H](Nc3cc(Cl)c4ncc(C#N)c(NC5CCc6ccccc65)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((S)-2,3-dihydro-1H-nden-1-yl)amino)quinoline-3-carbonitrile | 1 | ES/MS 631.3 (M + H+) |

TABLE 1-continued

| Compd | Structure | Name | Example/Procedure | ES/MS m/z |
|---|---|---|---|---|
| 582 | 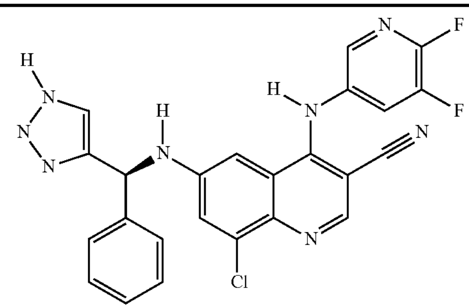 | (S)-8-chloro-4-((5,6-difluoropyridin-3-yl)amino)-6-(((phenyl(1H-1,2,3-triazol-4-yl)methyl)amino)quinoline-3-carbonitrile | 15 | ES/MS 489.1 (M + H+) |
| 583 | 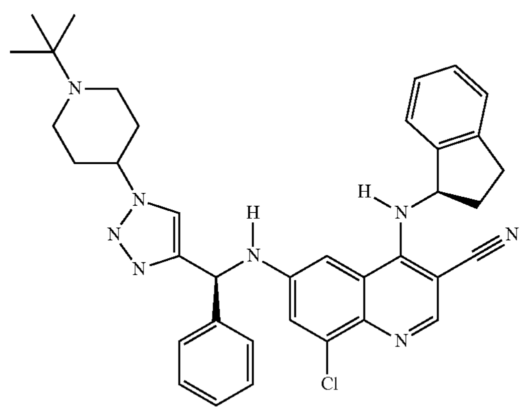 [SMILES: CC(C)(C)N1CCC(N2C=C([C@@H](Nc3cc(Cl)c4ncc(C#N)c(N[C@@H]5CCc6ccccc65)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((R)-2,3-dihydro-1H-inden-1-yl)amino)quinoline-3-carbonitrile | 1 | ES/MS 631.3 (M + H+) |

TABLE 1-continued

| Compd | Structure | Name | Example/Procedure | ES/MS m/z |
|---|---|---|---|---|
| 584 | 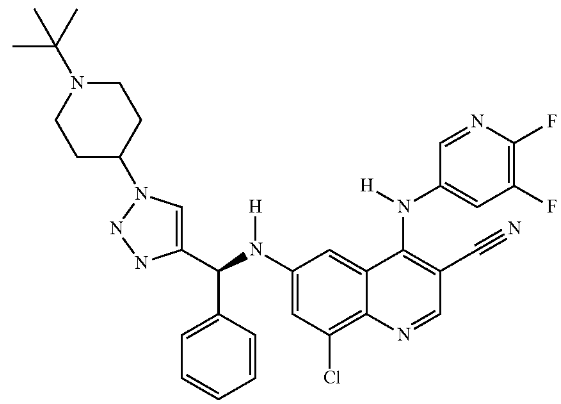 [SMILES: CC(C)(C)N1CCC(N2C=C([C@@H](Nc3cc(Cl)c4ncc(C#N)c(Nc5cnc(F)c(F)c5)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((5,6-difluoropyridin-3-yl)amino)quinoline-3-carbonitrile | 10 | ES/MS 628.2 (M + H+) |
| 585 | 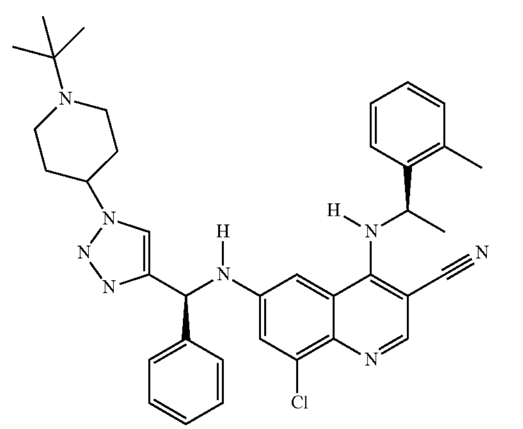 [SMILES: Cc1ccccc1[C@@H](C)Nc1c(C#N)cnc2c(Cl)cc(N[C@H](C3=CN(C4CCN(C(C)(C)C)CC4)NN3)c3ccccc3)cc12] | 6-(((S)-(1-(1-(tert-butyl)piperidin-4-yl)-1H-1,2,3-triazol-4-yl)(phenyl)methyl)amino)-8-chloro-4-(((R)-1-(o-tolyl)ethyl)amino)quinoline-3-carbonitrile | 1 | ES/MS 633.3 (M + H+) |

TABLE 1-continued

| Compd | Structure | Name | Example/Procedure | ES/MS m/z |
|---|---|---|---|---|
| 586 | 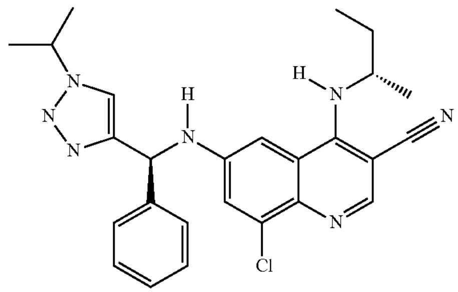 [SMILES: CC[C@H](C)Nc1c(C#N)cnc2c(Cl)cc(N[C@H](C3=CN(C(C)C)NN3)c3ccccc3)cc12] | 4-(((S)-sec-butyl)amino)-8-chloro-6-(((S)-(1-isopropyl-1H-1,2,3-triazol-4-yl)(phenyl)methyl)amino)quinoline-3-carbonitrile | 1 | ES/MS 474.1 (M + H+) |
| 587 | 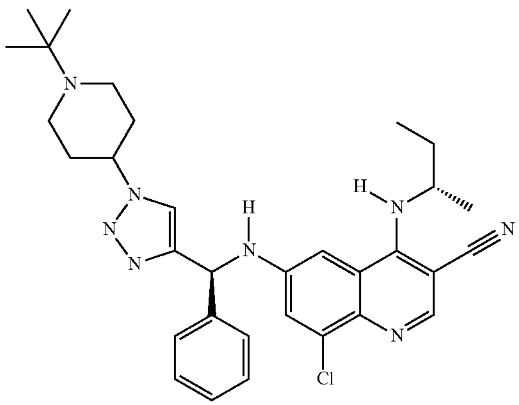 [SMILES: CC[C@H](C)Nc1c(C#N)cnc2c(Cl)cc(N[C@H](C3=CN(C4CCN(C(C)(C)C)CC4)NN3)c3ccccc3)cc12] | 4-(((S)-sec-butyl)amino)-6-(((S)-(1-(1-(tert-butyl)piperidin-4-yl)-1H-1,2,3-triazol-4-yl)(phenyl)methyl)amino)-8-chloroquinoline-3-carbonitrile | 1 | ES/MS 571.3 (M + H+) |
| 588 | 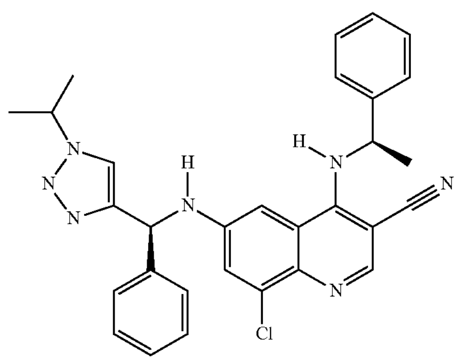 [SMILES: CC(C)N1C=C([C@@H](Nc2cc(Cl)c3ncc(C#N)c(N[C@H](C)c4ccccc4)c3c2)c2ccccc2)NN1] | 8-chloro-6-(((S)-(1-isopropyl-1H-1,2,3-triazol-4-yl)(phenyl)methyl)amino)-4-(((R)-1-phenylethyl)amino)quinoline-3-carbonitrile | 1 | ES/MS 522.2 (M + H+) |

TABLE 1-continued

| Compd | Structure | Name | Example/Procedure | ES/MS m/z |
|---|---|---|---|---|
| 589 | 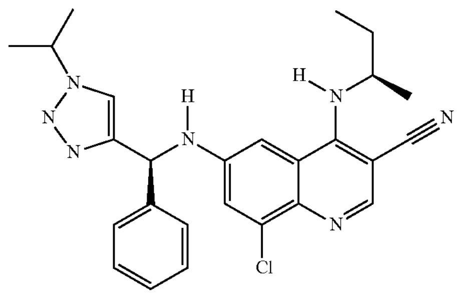 [SMILES: CC[C@@H](C)Nc1c(C#N)cnc2c(Cl)cc(N[C@H](C3=CN(C(C)C)NN3)c3ccccc3)cc12] | 4-(((R)-sec-butyl)amino)-8-chloro-6-(((S)-(1-isopropyl-1H-1,2,3-triazol-4-yl)(phenyl)methyl)amino)quinoline-3-carbonitrile | 1 | ES/MS 474.2 (M + H+) |
| 590 | 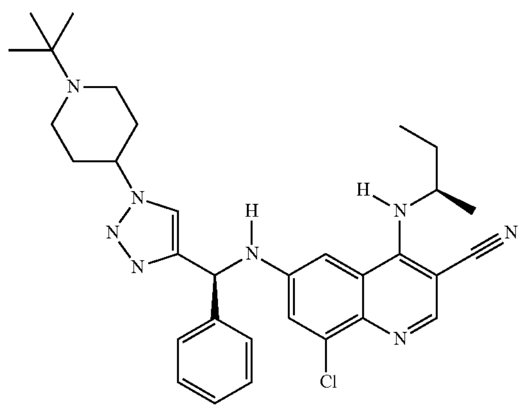 [SMILES: CC[C@@H](C)Nc1c(C#N)cnc2c(Cl)cc(N[C@H](C3=CN(C4CCN(C(C)(C)C)CC4)NN3)c3ccccc3)cc12] | 4-(((R)-sec-butyl)amino)-6-(((S)-(1-(1-(tert-butyl)piperidin-4-yl)-1H-12,3-triazol-4-yl)(phenyl)methyl)amino)-8-chloroquinoline-3-carbonitrile | 1 | ES/MS 571.3 (M + H+) |
| 591 | 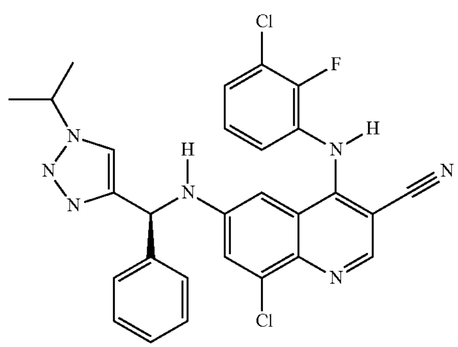 [SMILES: CC(C)N1C=C([C@@H](Nc2cc(Cl)c3ncc(C#N)c(Nc4cccc(Cl)c4F)c3c2)c2ccccc2)NN1] | (S)-8-chloro-4-((3-chloro-2-fluorophenyl)amino)-6-(((1-isopropyl-1H-1,2,3-triazol-4-yl)(phenyl)methyl)amino)quinoline-3-carbonitrile | 1 | ES/MS 546.1 (M + H+) |

TABLE 1-continued

| Compd | Structure | Name | Example/Procedure | ES/MS m/z |
|---|---|---|---|---|
| 592 | 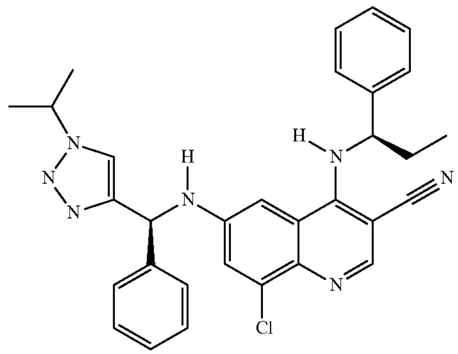 [SMILES: CC[C@@H](Nc1c(C#N)cnc2c(Cl)cc(N[C@H](C3=CN(C(C)C)NN3)c3ccccc3)cc12)c1ccccc1] | 8-chloro-6-(((S)-(1-isopropyl-1H-1,2,3-triazol-4-yl)(phenyl)methyl)amino)-4-(((R)-1-phenylpropyl)amino)quinoline-3-carbonitrile | 1 | ES/MS 536.2 (M + H+) |
| 593 | 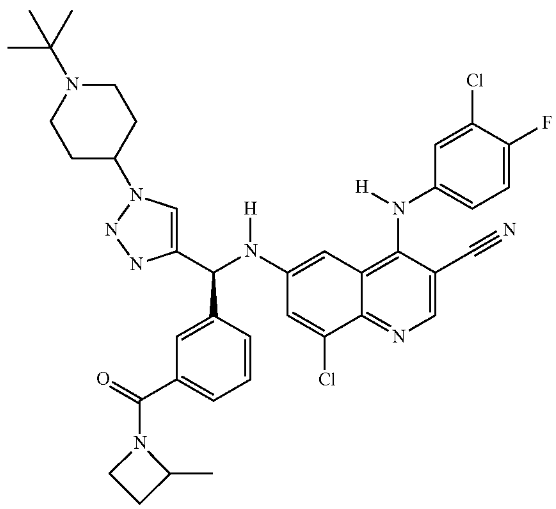 [SMILES: CC1CCN1C(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | 6-(((1S)-1-(1-(1-(tert-butyl)piperidin-4-yl)-1H-1,2,3-triazol-4-yl)(3-(2-methylazetidine-1-carbonyl)phenyl)methyl)amino)-8-chloro-4-((3-chloro-4-fluorophenyl)amino)quinoline-3-carbonitrile | 20 | ES/MS 740.5 (M + H+) |

TABLE 1-continued

| Compd | Structure | Name | Example/Procedure | ES/MS m/z |
|---|---|---|---|---|
| 594 | 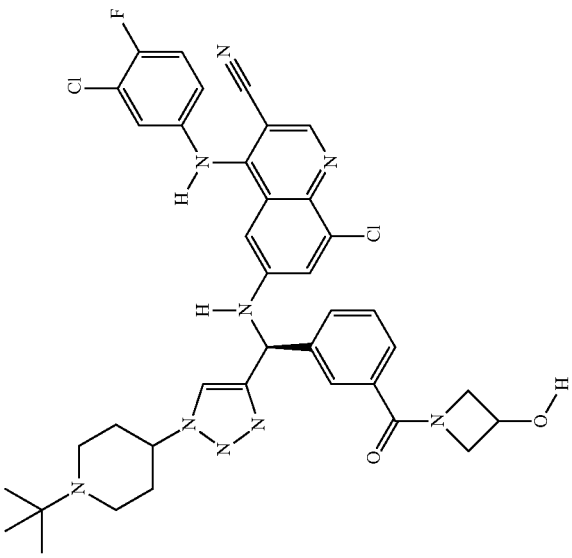 | (S)-6-(((1-(1-(tert-butyl)piperidin-4-yl)-1H-1,2,3-triazol-4-yl)(3-(3-hydroxyazetidine-1-carbonyl)phenyl)methyl)amino)-8-chloro-4-((3-chloro-4-fluorophenyl)amino)quinoline-3-carbonitrile | 20 | ES/MS 742.2 (M + H+) |
| 595 | 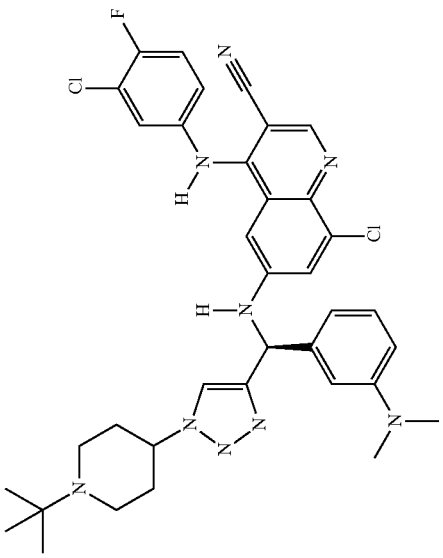 | (S)-6-(((1-(1-(tert-butyl)piperidin-4-yl)-1H-1,2,3-triazol-4-yl)(3-(dimethylamino)phenyl)methyl)amino)-8-chloro-4-((3-chloro-4-fluorophenyl)amino)quinoline-3-carbonitrile | 3 | ES/MS 686.1 (M + H+) |

TABLE 1-continued

| Compd | Structure | Name | Example/Procedure | ES/MS m/z |
|---|---|---|---|---|
| 596 | 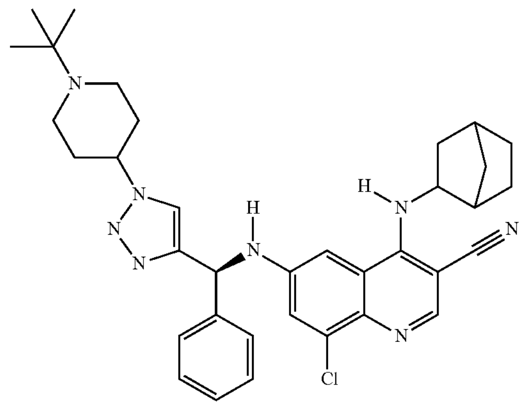 [SMILES: CC(C)(C)N1CCC(N2C=C([C@@H](Nc3cc(Cl)c4ncc(C#N)c(NC5CC6CCC5C6)c4c3)c3ccccc3)NN2)CC1] | 4-(bicyclo[2.2.1]heptan-2-ylamino)-6-(((S)-(1-(tert-butyl)piperidin-4-yl)-1H-1,2,3-triazol-4-yl)(phenyl)methyl)amino)-8-chloroquinoline-3-carbonitrile | 1 | ES/MS 609.3 (M + H+) |
| 597 | 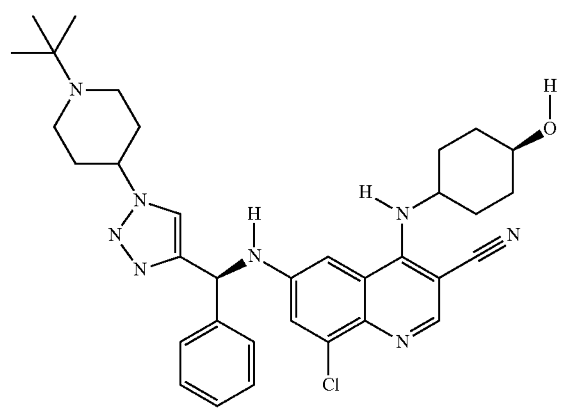 | 6-(((S)-(1-(1-(tert-butyl)piperidin-4-yl)-1H-1,2,3-triazol-4-yl)(phenyl)methyl)amino)-8-chloro-4-(((1r,4S)-4-hydroxycyclohexyl)amino)quinoline-3-carbonitrile | 1 | ES/MS 613.3 (M + H+) |

TABLE 1-continued
| Compd | Structure | Name | Example/Procedure | ES/MS m/z |
|---|---|---|---|---|
| 598 | 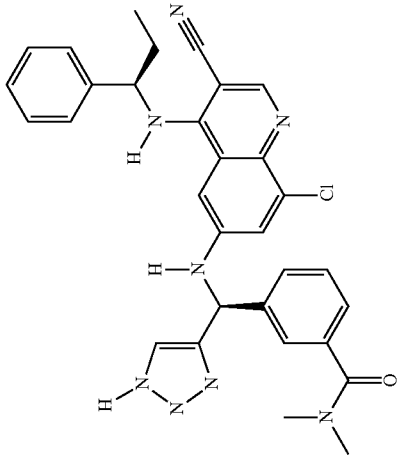 | 3-((S)-((8-chloro-3-cyano-4-(((R)-1-phenylpropyl)amino)quinolin-6-yl)amino)(1H-1,2,3-triazol-4-yl)methyl)-N,N-dimethylbenzamide | 15 | ES/MS 565.5.0 (M + H+) |
| 599 | 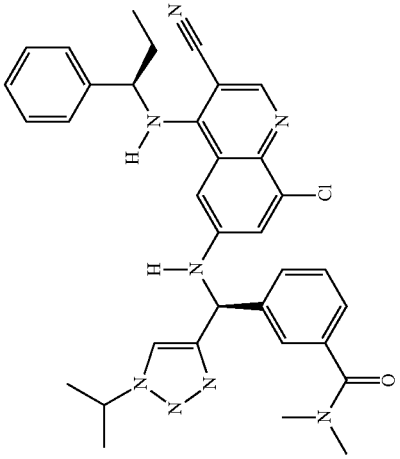 | 3-((S)-((8-chloro-3-cyano-4-(((R)-1-phenylpropyl)amino)quinolin-6-yl)amino)(1-isopropyl-1H-1,2,3-triazol-4-yl)methyl)-N,N-dimethylbenzamide | 3 | ES/MS 607.5 (M + H+) |

TABLE 1-continued

| Compd | Structure | Name | Example/Procedure | ES/MS m/z |
|---|---|---|---|---|
| 600 | 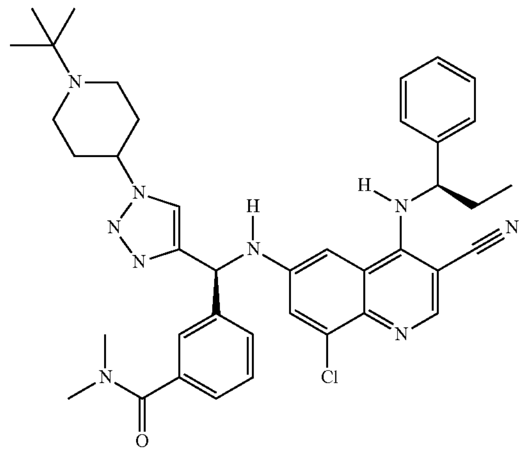 [SMILES: CC[C@@H](Nc1c(C#N)cnc2c(Cl)cc(N[C@H](C3=CN(C4CCN(C(C)(C)C)CC4)NN3)c3cccc(C(=O)N(C)C)c3)cc12)c1ccccc1] | 3-((S)-(1-(1-(tert-butyl)piperidin-4-yl)-1H-1,2,3-triazol-4-yl)(8-chloro-3-cyano-4-(((R)-1-phenylpropyl)amino)quinolin-6-yl)amino)methyl)-N,N-dimethylbenzamide | 3 | ES/MS 704.5 (M + H+) |
| 601 | 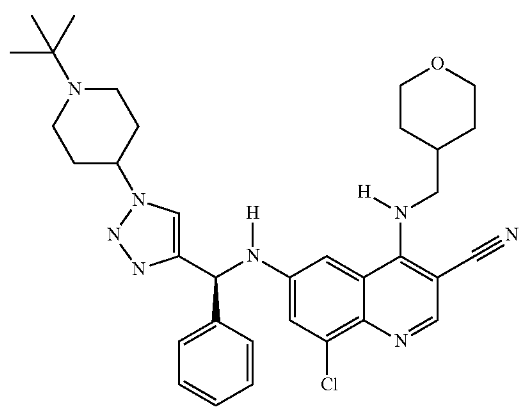 [SMILES: CC(C)(C)N1CCC(N2C=C([C@@H](Nc3cc(Cl)c4ncc(C#N)c(NCC5CCOCC5)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-(((tetrahydro-2H-pyran-4-yl)methyl)amino)quinoline-3-carbonitrile | 1 | ES/MS 613.3 (M + H+) |

TABLE 1-continued

| Compd | Structure | Name | Example/Procedure | ES/MS m/z |
|---|---|---|---|---|
| 602 | 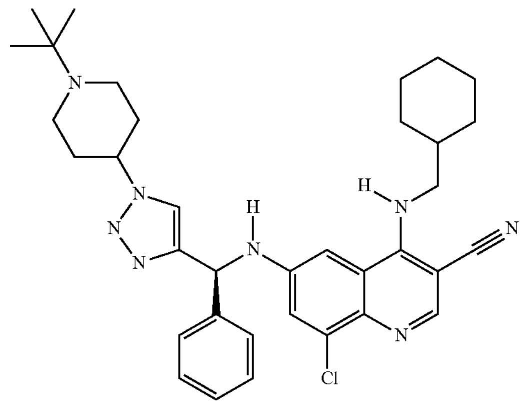 [SMILES: CC(C)(C)N1CCC(N2C=C([C@@H](Nc3cc(Cl)c4ncc(C#N)c(NCC5CCCCC5)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((cyclohexylmethyl)amino)quinoline-3-carbonitrile | 1 | ES/MS 611.3 (M + H+) |
| 603 | 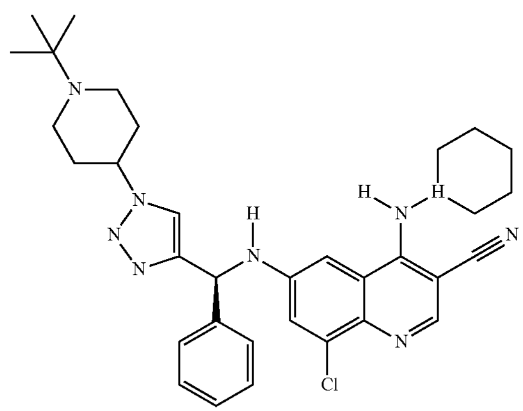 | (S)-6-((((1-(1-(tert-butyl)piperidin-4-yl)-1H-1,2,3-triazol-4-yl)(phenyl)methyl)amino)-8-chloro-4-(piperidin-1-yl)amino)quinoline-3-carbonitrile | 1 | ES/MS 598.3 (M + H+) |

TABLE 1-continued

| Compd | Structure | Name | Example/Procedure | ES/MS m/z |
|---|---|---|---|---|
| 604 | 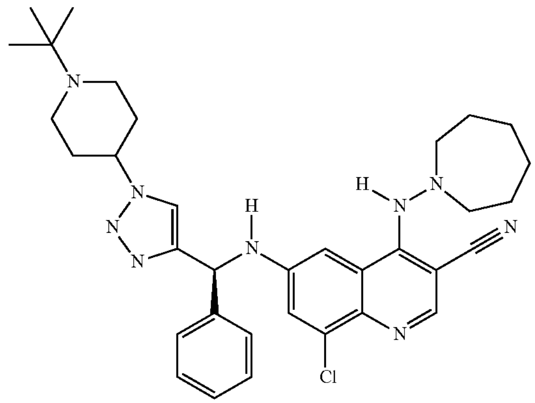 [SMILES: CC(C)(C)N1CCC(N2C=C([C@@H](Nc3cc(Cl)c4ncc(C#N)c(NN5CCCCCC5)c4c3)c3ccccc3)NN2)CC1] | (S)-4-(azepan-1-ylamino)-6-(((1-(1-(tert-butyl)piperidin-4-yl)-1H-1,2,3-triazol-4-yl)(phenyl)methyl)amino)-8-chloroquinoline-3-carbonitrile | 1 | ES/MS 612.3 (M + H+) |
| 605 | 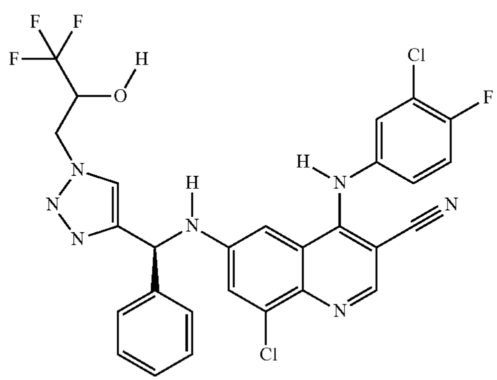 [SMILES: N#Cc1cnc2c(Cl)cc(N[C@H](C3=CN(CC(O)C(F)(F)F)NN3)c3ccccc3)cc2c1Nc1ccc(F)c(Cl)c1] | 8-chloro-4-((3-chloro-4-fluorophenyl)amino)-6-(((1S)-phenyl(1-(3,3,3-trifluoro-2-hydroxypropyl)-1H-1,2,3-triazol-4-yl)methyl)amino)quinoline-3-carbonitrile | 4 | ES/MS 616.2 (M + H+) |

TABLE 1-continued

| Compd | Structure | Name | Example/Procedure | ES/MS m/z |
|---|---|---|---|---|
| 606 | 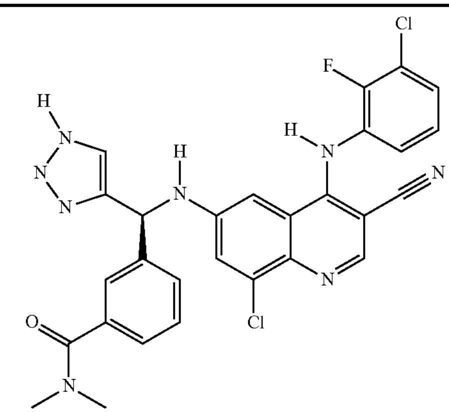 | (S)-3-(((8-chloro-4-((3-chloro-2-fluorophenyl)amino)-3-cyanoquinolin-6-yl)amino)(1H-1,2,3-triazol-4-yl)methyl)-N,N-dimethylbenzamide | 15 | ES/MS 575.3 (M + H+) |
| 607 | 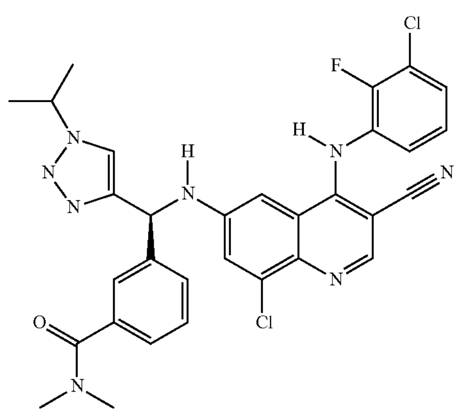 [SMILES: CC(C)N1C=C([C@@H](Nc2cc(Cl)c3ncc(C#N)c(Nc4cccc(Cl)c4F)c3c2)c2cccc(C(=O)N(C)C)c2)NN1] | (S)-3-(((8-chloro-4-((3-chloro-2-fluorophenyl)amino)-3-cyanoquinolin-6-yl)amino)(1-isopropyl-1H-1,2,3-triazol-4-yl)methyl)-N,N-dimethylbenzamide | 3 | ES/MS 617.9 (M + H+) |

TABLE 1-continued

| Compd | Structure | Name | Example/Procedure | ES/MS m/z |
|---|---|---|---|---|
| 608 | 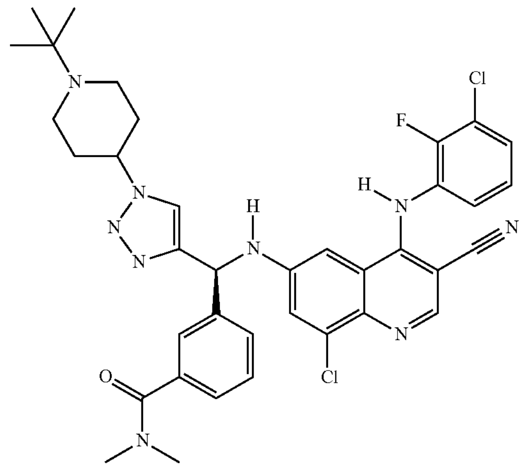 [SMILES: CN(C)C(=O)c1cccc([C@H](Nc2cc(Cl)c3ncc(C#N)c(Nc4cccc(Cl)c4F)c3c2)C2=CN(C3CCN(C(C)(C)C)CC3)NN2)c1] | (S)-3-((1-(1-(tert-butyl)piperidin-4-yl)-1H-1,2,3-triazol-4-yl)((8-chloro-4-((3-chloro-2-fluorophenyl)amino)-3-cyanoquinolin-6-yl)amino)methyl)-N,N-dimethylbenzamide | 3 | ES/MS 714.3 (M + H+) |
| 609 | 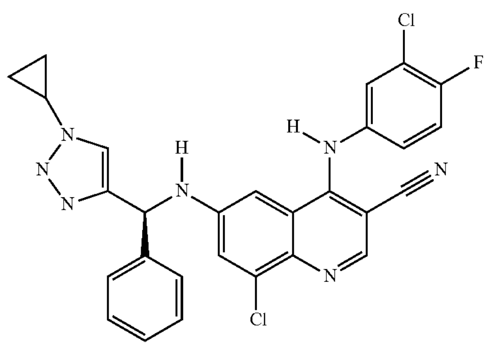 [SMILES: N#Cc1cnc2c(Cl)cc(N[C@H](C3=CN(C4CC4)NN3)c3ccccc3)cc2c1Nc1ccc(F)c(Cl)c1] | (S)-8-chloro-4-((3-chloro-4-fluorophenyl)amino)-6-(((1-cyclopropyl-1H-1,2,3-triazol-4-yl)(phenyl)methyl)amino)quinoline-3-carbonitrile | 4 | ES/MS 544.0 (M + H+) |

TABLE 1-continued

| Compd | Structure | Name | Example/Procedure | ES/MS m/z |
|---|---|---|---|---|
| 610 | 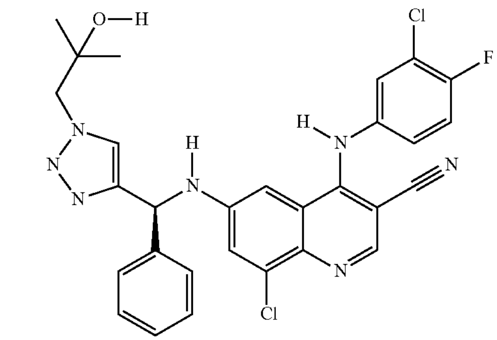 [SMILES: CC(C)(O)CN1C=C([C@@H](Nc2cc(Cl)c3ncc(C#N)c(Nc4ccc(F)c(Cl)c4)c3c2)c2ccccc2)NN1] | (S)-8-chloro-4-((3-chloro-4-fluorophenyl)amino)-6-(((1-(2-hydroxy-2-methylpropyl)-1H-1,2,3-triazol-4-yl)(phenyl)methyl)amino)quinoline-3-carbonitrile | 4 | ES/MS 576.1 (M + H+) |
| 611 | 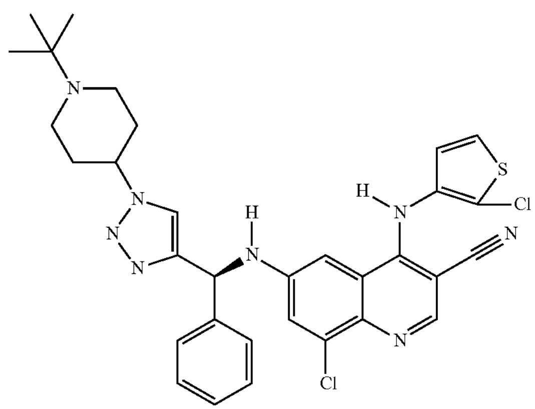 [SMILES: CC(C)(C)N1CCC(N2C=C([C@@H](Nc3cc(Cl)c4ncc(C#N)c(Nc5ccsc5Cl)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((2-chlorothiophen-3-yl)amino)quinoline-3-carbonitrile | 10 | ES/MS 631.2 (M + H+) |

TABLE 1-continued

| Compd | Structure | Name | Example/Procedure | ES/MS m/z |
|---|---|---|---|---|
| 612 | 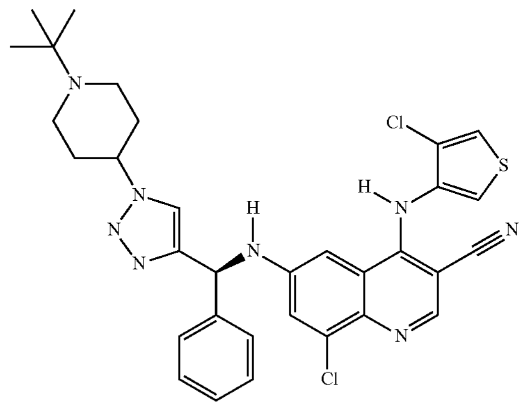 [SMILES: CC(C)(C)N1CCC(N2C=C([C@@H](Nc3cc(Cl)c4ncc(C#N)c(Nc5cscc5Cl)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((4-chlorothiophen-3-yl)amino)quinoline-3-carbonitrile | 10 | ES/MS 631.2 (M + H+) |
| 613 | 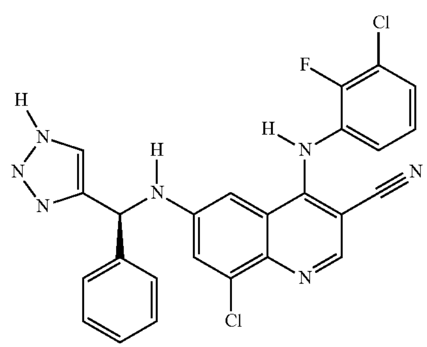 [SMILES: N#Cc1cnc2c(Cl)cc(N[C@H](C3=CNNN3)c3ccccc3)cc2c1Nc1cccc(Cl)c1F] | (S)-8-chloro-4-((3-chloro-2-fluorophenyl)amino)-6-(((phenyl(1H-1,2,3-triazol-4-yl)methyl)amino)quinoline-3-carbonitrile | 15 | ES/MS 504.1 (M + H+) |

TABLE 1-continued

| Compd | Structure | Name | Example/Procedure | ES/MS m/z |
|---|---|---|---|---|
| 614 | 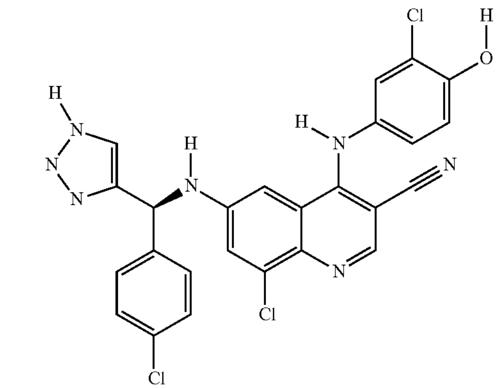 [SMILES: N#Cc1cnc2c(Cl)cc(N[C@H](C3=CNNN3)c3ccc(Cl)cc3)cc2c1Nc1ccc(O)c(Cl)c1] | (S)-8-chloro-4-((3-chloro-4-hydroxyphenyl)amino)-6-(((4-chlorophenyl)(1H-1,2,3-triazol-4-yl)methyl)amino)quinoline-3-carbonitrile | 15 | ES/MS 536.0 (M + H+) |
| 615 | 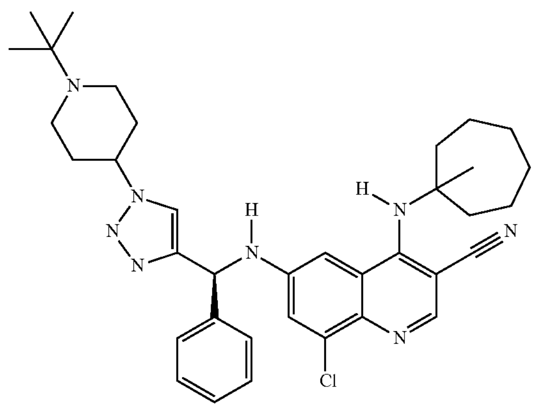 | (S)-6-((((1-(1-(tert-butyl)piperidin-4-yl)-1H-1,2,3-triazol-4-yl)(phenyl)methyl)amino)-8-chloro-4-((1-methylcycloheptyl)amino)quinoline-3-carbonitrile | 1 | ES/MS 625.3 (M + H+) |

TABLE 1-continued

| Compd | Structure | Name | Example/Procedure | ES/MS m/z |
|---|---|---|---|---|
| 616 | 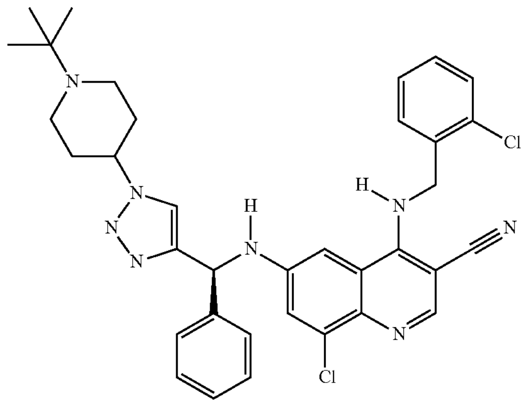 [SMILES: CC(C)(C)N1CCC(N2C=C([C@@H](Nc3cc(Cl)c4ncc(C#N)c(NCc5ccccc5Cl)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((2-chlorobenzyl)amino)quinoline-3-carbonitrile | 1 | ES/MS 639.2 (M + H+) |
| 617 | 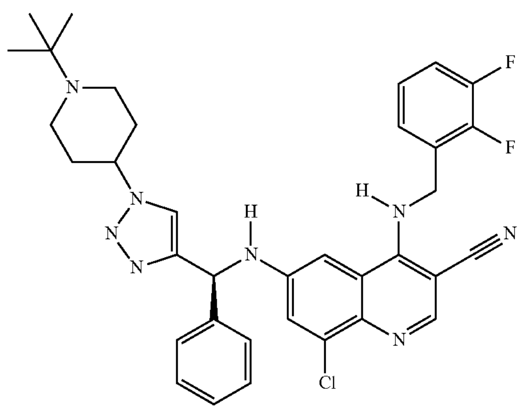 [SMILES: CC(C)(C)N1CCC(N2C=C([C@@H](Nc3cc(Cl)c4ncc(C#N)c(NCc5cccc(F)c5F)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((2,3-difluorobenzyl)amino)quinoline-3-carbonitrile | 1 | ES/MS 641.3 (M + H+) |

TABLE 1-continued

| Compd | Structure | Name | Example/Procedure | ES/MS m/z |
|---|---|---|---|---|
| 618 | 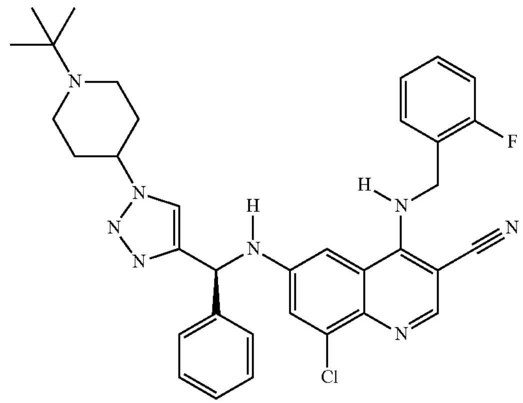 [SMILES: CC(C)(C)N1CCC(N2C=C([C@@H](Nc3cc(Cl)c4ncc(C#N)c(NCc5ccccc5F)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((2-fluorobenzyl)amino)quinoline-3-carbonitrile | 1 | ES/MS 623.3 (M + H+) |
| 619 | 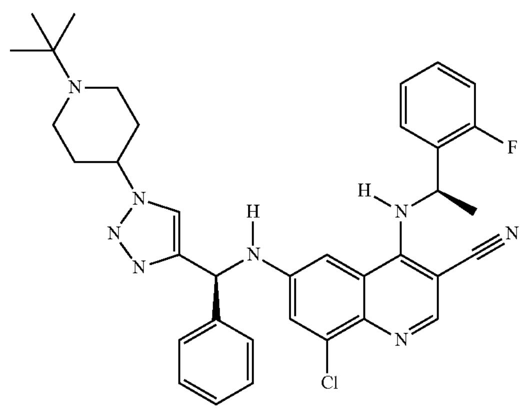 [SMILES: C[C@@H](Nc1c(C#N)cnc2c(Cl)cc(N[C@H](C3=CN(C4CCN(C(C)(C)C)CC4)NN3)c3ccccc3)cc12)c1ccccc1F] | 6-(((S)-(1-(1-(tert-butyl)piperidin-4-yl)-1H-1,2,3-triazol-4-yl)(phenyl)methyl)amino)-8-chloro-4-(((R)-1-(2-fluorophenyl)ethyl)amino)quinoline-3-carbonitrile | 1 | ES/MS 637.3 (M + H+) |

TABLE 1-continued

| Compd | Structure | Name | Example/Procedure | ES/MS m/z |
|---|---|---|---|---|
| 620 | 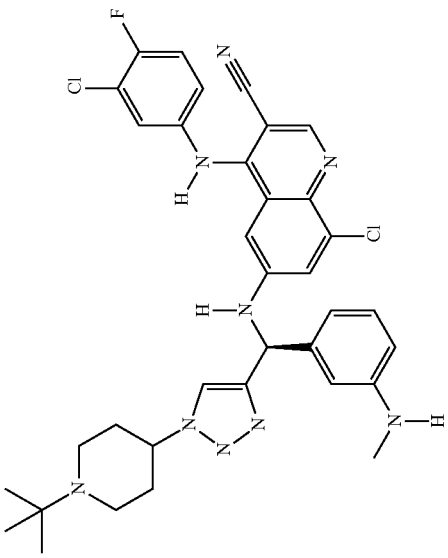 | (S)-6-(((1-(1-(tert-butyl)piperidin-4-yl)-1H-1,2,3-triazol-4-yl)(3-(methylamino)phenyl)methyl)amino)-8-chloro-4-((3-chloro-4-fluorophenyl)amino)quinoline-3-carbonitrile | 24 | ES/MS 672.0 (M + H+) |
| 621 | 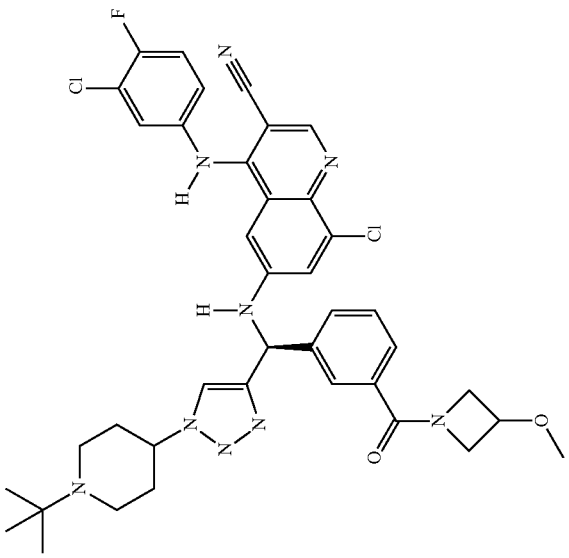 | (S)-6-(((1-(1-(tert-butyl)piperidin-4-yl)-1H-1,2,3-triazol-4-yl)(3-(3-methoxyazetidine-1-carbonyl)phenyl)methyl)amino)-8-chloro-4-((3-chloro-4-fluorophenyl)amino)quinoline-3-carbonitrile | 20 | ES/MS 756.2 (M + H+) |

TABLE 1-continued

| Compd | Structure | Name | Example/Procedure | ES/MS m/z |
|---|---|---|---|---|
| 622 | 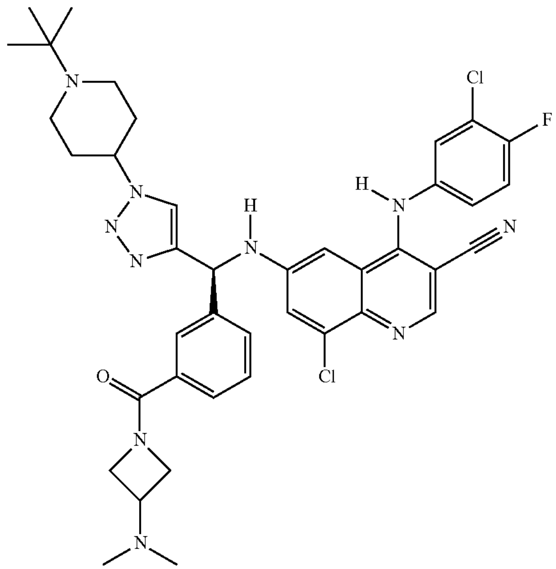 [SMILES: CN(C)C1CN(C(=O)c2cccc([C@H](Nc3cc(Cl)c4ncc(C#N)c(Nc5ccc(F)c(Cl)c5)c4c3)C3=CN(C4CCN(C(C)(C)C)CC4)NN3)c2)C1] | (S)-6-((((1-(1-(tert-butyl)piperidin-4-yl)-1H-1,2,3-triazol-4-yl)(3-(3-(dimethylamino)azetidine-1-carbonyl)phenyl)methyl)amino)-8-chloro-4-((3-chloro-4-fluorophenyl)amino)quinoline-3-carbonitrile | 20 | ES/MS 769.2 (M + H+) |
| 623 | 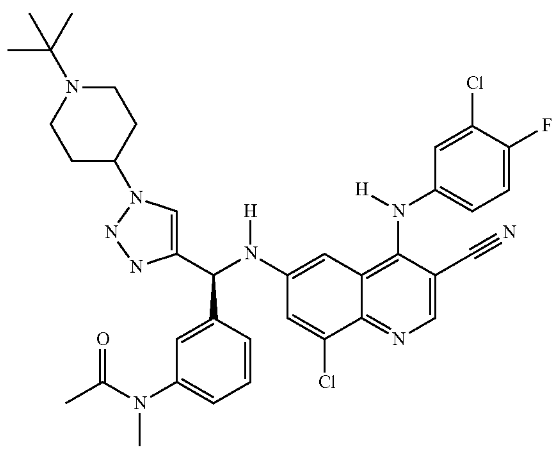 [SMILES: CC(=O)N(C)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-N-(3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)phenyl)-N-methylacetamide | 3 | ES/MS 714.3 (M + H+) |

TABLE 1-continued

| Compd | Structure | Name | Example/Procedure | ES/MS m/z |
|---|---|---|---|---|
| 624 | 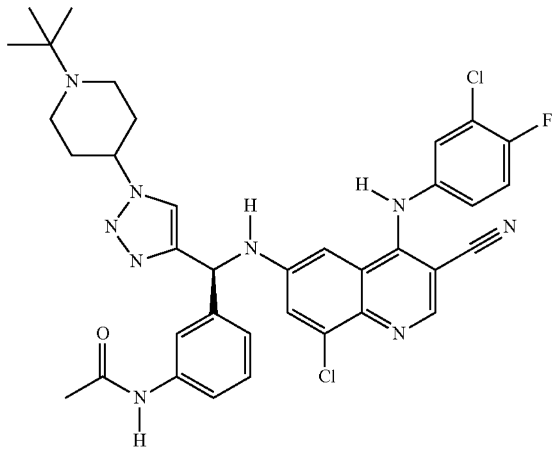 | (S)-N-(3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)phenyl)acetamide | 3 | ES/MS 799.2 (M + H+) |
| 625 | 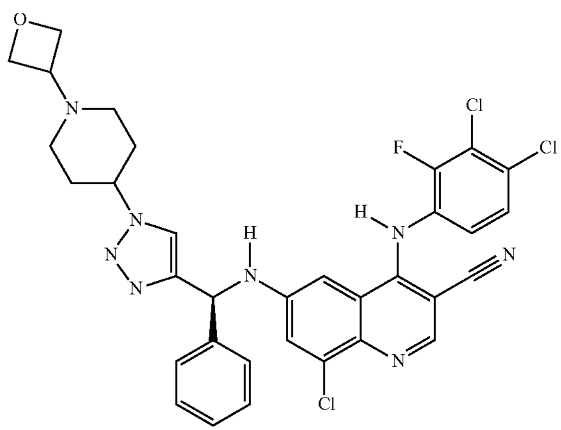 [SMILES: N#Cc1cnc2c(Cl)cc(N[C@H](C3=CN(C4CCN(C5COC5)CC4)NN3)c3ccccc3)cc2c1Nc1ccc(Cl)c(Cl)c1F] | (S)-8-chloro-4-((3,4-dichloro-2-fluorophenyl)amino)-6-(((1-(1-(oxetan-3-yl)piperidin-4-yl)-1H-1,2,3-triazol-4-yl)(phenyl)methyl)amino)quinoline-3-carbonitrile | 31 | ES/MS 677.1 (M + H+) |

TABLE 1-continued
| Compd | Structure | Name | Example/Procedure | ES/MS m/z |
|---|---|---|---|---|
| 626 | 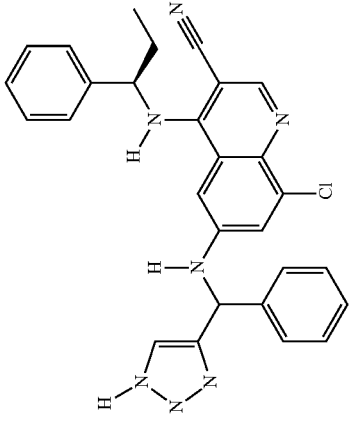 | 8-chloro-6-(((R)-phenyl(1H-1,2,3-triazol-4-yl)methyl)amino)-4-(((R)-1-phenylpropyl)amino)quinoline-3-carbonitrile | 15 | ES/MS 494.1 (M + H+) |
| 627 | 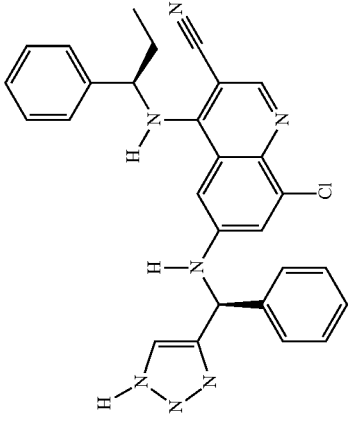 | 8-chloro-6-(((S)-phenyl(1H-1,2,3-triazol-4-yl)methyl)amino)-4-(((R)-1-phenylpropyl)amino)quinoline-3-carbonitrile | 15 | ES/MS 494.1 (M + H+) |

TABLE 1-continued

| Compd | Structure | Name | Example/Procedure | ES/MS m/z |
|---|---|---|---|---|
| 628 | 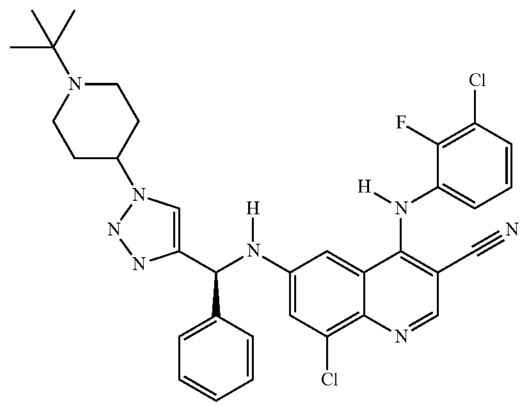 [SMILES: CC(C)(C)N1CCC(N2C=C([C@@H](Nc3cc(Cl)c4ncc(C#N)c(Nc5cccc(Cl)c5F)c4c3)c3ccccc3)NN2)CC1] | (S)-6-((((1-(tert-butyl)piperidin-4-yl)-1H-1,2,3-triazol-4-yl)(phenyl)methyl)amino)-8-chloro-4-((3-chloro-2-fluorophenyl)amino)quinoline-3-carbonitrile | 1 | ES/MS 643.2 (M + H+) |
| 629 | 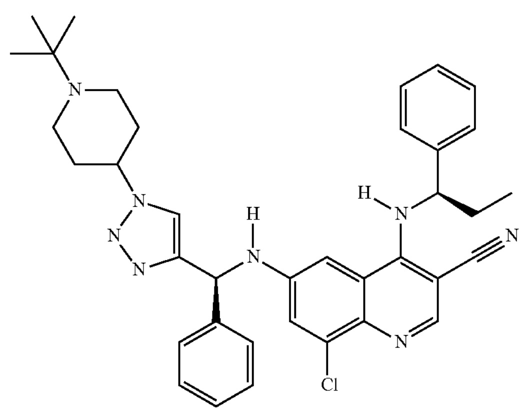 [SMILES: CC[C@@H](Nc1c(C#N)cnc2c(Cl)cc(N[C@H](C3=CN(C4CCN(C(C)(C)C)CC4)NN3)c3ccccc3)cc12)c1ccccc1] | 6-(((S)-(1-(1-(tert-butyl)piperidin-4-yl)-1H-1,2,3-triazol-4-yl)(phenyl)methyl)amino)-8-chloro-4-(((R)-1-phenylpropyl)amino)quinoline-3-carbonitrile | 1 | ES/MS 633.3 (M + H+) |

TABLE 1-continued

| Compd | Structure | Name | Example/Procedure | ES/MS m/z |
|---|---|---|---|---|
| 630 | 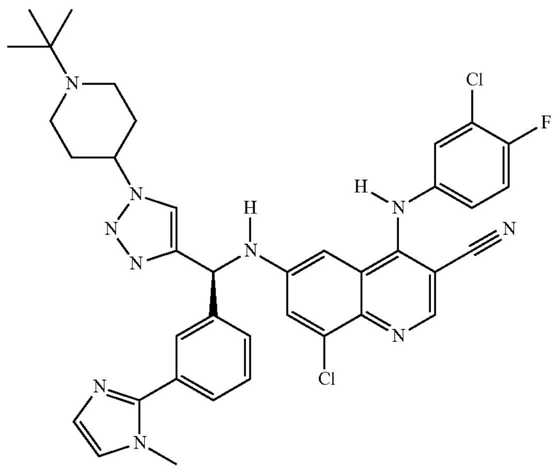 [SMILES: Cn1ccnc1-c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-6-(((1-(1-(tert-butyl)piperidin-4-yl)-1H-1,2,3-triazol-4-yl)(3-(1-methyl-1H-imidazol-2-yl)phenyl)methyl)amino)-8-chloro-4-((3-chloro-4-fluorophenyl)amino)quinoline-3-carbonitrile | 23 | ES/MS 723.2 (M + H+) |
| 631 | 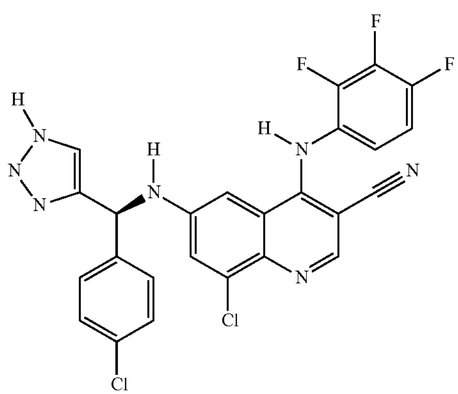 [SMILES: N#Cc1cnc2c(Cl)cc(N[C@H](C3=CNNN3)c3ccc(Cl)cc3)cc2c1Nc1ccc(F)c(F)c1F] | (S)-8-chloro-6-(((4-chlorophenyl)(1H-1,2,3-triazol-4-yl)methyl)amino)-4-((2,3,4-trifluorophenyl)amino)quinoline-3-carbonitrile | 15 | ES/MS 540.0 (M + H+) |

TABLE 1-continued

| Compd | Structure | Name | Example/Procedure | ES/MS m/z |
|---|---|---|---|---|
| 632 | 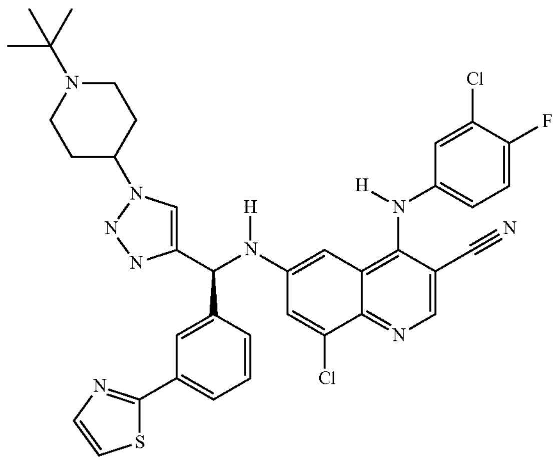 [SMILES: CC(C)(C)N1CCC(N2C=C([C@@H](Nc3cc(Cl)c4ncc(C#N)c(Nc5ccc(F)c(Cl)c5)c4c3)c3cccc(-c4nccs4)c3)NN2)CC1] | (S)-6-((((1-(1-(tert-butyl)piperidin-4-yl)-1H-1,2,3-triazol-4-yl)(3-(thiazol-2-yl)phenyl)methyl)amino)-8-chloro-4-((3-chloro-4-fluorophenyl)amino)quinoline-3-carbonitrile | 23 | ES/MS 726.0 (M + H+) |
| 633 | 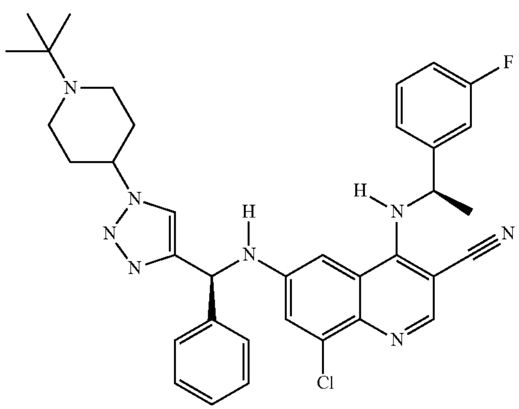 [SMILES: C[C@@H](Nc1c(C#N)cnc2c(Cl)cc(N[C@H](C3=CN(C4CCN(C(C)(C)C)CC4)NN3)c3ccccc3)cc12)c1cccc(F)c1] | 6-(((S)-(1-(1-(tert-butyl)piperidin-4-yl)-1H-1,2,3-triazol-4-yl)(phenyl)methyl)amino)-8-chloro-4-(((R)-1-(3-fluorophenyl)ethyl)amino)quinoline-3-carbonitrile | 1 | ES/MS 637.3 (M + H+) |

TABLE 1-continued
| Compd | Structure | Name | Example/Procedure | ES/MS m/z |
|---|---|---|---|---|
| 634 | 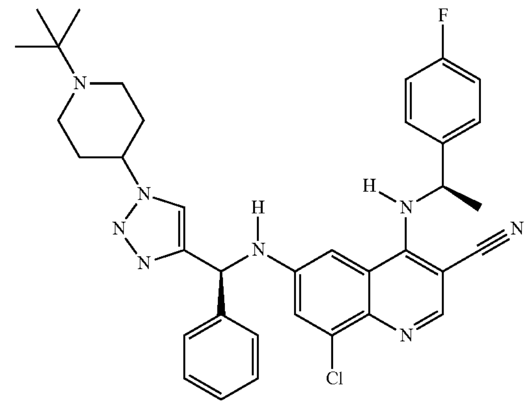 [SMILES: C[C@@H](Nc1c(C#N)cnc2c(Cl)cc(N[C@H](C3=CN(C4CCN(C(C)(C)C)CC4)NN3)c3ccccc3)cc12)c1ccc(F)cc1] | 6-(((S)-(1-(tert-butyl)piperidin-4-yl)-1H-1,2,3-triazol-4-yl)(phenyl)methyl)amino)-8-chloro-4-(((R)-1-(4-fluorophenyl)ethyl)amino)quinoline-3-carbonitrile | 1 | ES/MS 637.3 (M + H+) |
| 635 | 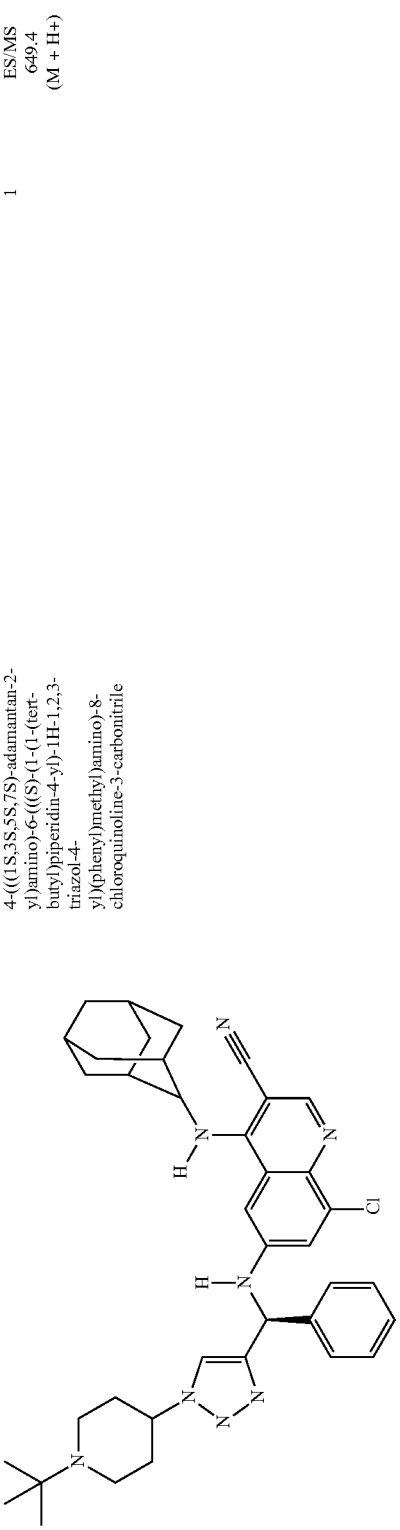 | 4-(((1S,3S,5S,7S)-adamantan-2-yl)amino)-6-(((S)-(1-(tert-butyl)piperidin-4-yl)-1H-1,2,3-triazol-4-yl)(phenyl)methyl)amino)-8-chloroquinoline-3-carbonitrile | 1 | ES/MS 649.4 (M + H+) |

TABLE 1-continued

| Compd | Structure | Name | Example/Procedure | ES/MS m/z |
|---|---|---|---|---|
| 636 | 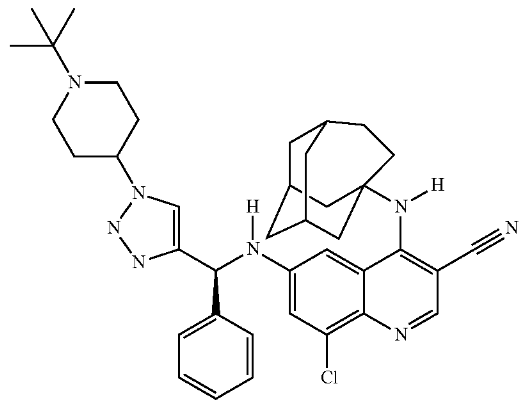 [SMILES: CC(C)(C)N1CCC(N2C=C([C@@H](Nc3cc(Cl)c4ncc(C#N)c(NC56CCC7CC(CC(C7)C5)C6)c4c3)c3ccccc3)NN2)CC1] | 6-(((S)-(1-(1-(tert-butyl)piperidin-4-yl)-1H-1,2,3-triazol-4-yl)(phenyl)methyl)amino)-8-chloro-4-(((1R,3r,6S,8S)-tricyclo[4.3.1.1³,⁸]undecan-3-yl)amino)quinoline-3-carbonitrile | 1 | ES/MS 663.4 (M + H+) |
| 637 | 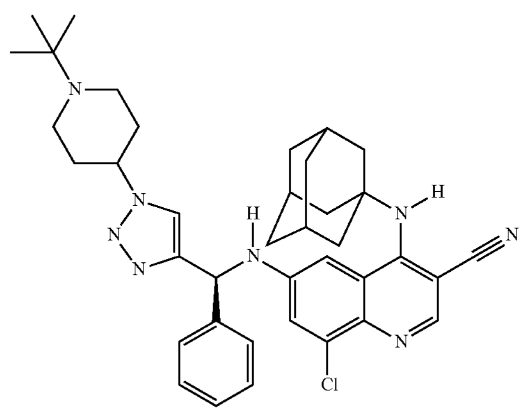 [SMILES: CC(C)(C)N1CCC(N2C=C([C@@H](Nc3cc(Cl)c4ncc(C#N)c(NC56CC7CC(CC(C7)C5)C6)c4c3)c3ccccc3)NN2)CC1] | 4-(((3R,5R,7R)-adamantan-1-yl)amino)-6-(((S)-(1-(tert-butyl)piperidin-4-yl)-1H-1,2,3-triazol-4-yl)(phenyl)methyl)amino)-8-chloroquinoline-3-carbonitrile | 1 | ES/MS 649.3 (M + H+) |

TABLE 1-continued
| Compd | Structure | Name | Example/Procedure | ES/MS m/z |
|---|---|---|---|---|
| 638 | 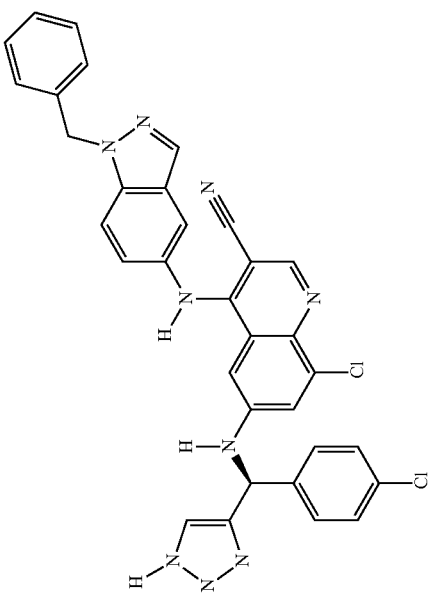 | (S)-4-((1-benzyl-1H-indazol-5-yl)amino)-8-chloro-6-(((4-chlorophenyl)(1H-1,2,3-triazol-4-yl)methyl)amino)quinoline-3-carbonitrile | 15 | ES/MS 616.2 (M + H+) |
| 639 | 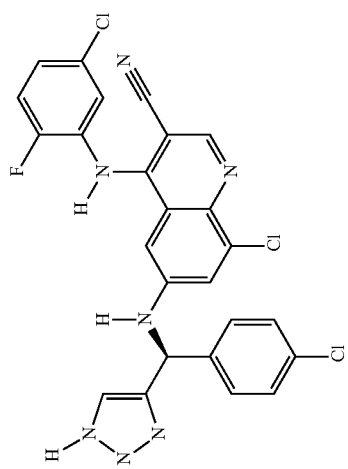 | (S)-8-chloro-4-((5-chloro-2-fluorophenyl)amino)-6-(((4-chlorophenyl)(1H-1,2,3-triazol-4-yl)methyl)amino)quinoline-3-carbonitrile | 15 | ES/MS 538.0 (M + H+) |

TABLE 1-continued

| Compd | Structure | Name | Example/Procedure | ES/MS m/z |
|---|---|---|---|---|
| 640 | 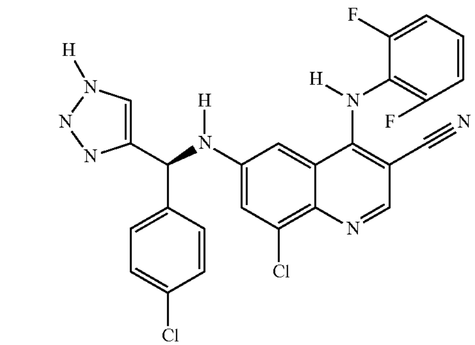 [SMILES: N#Cc1cnc2c(Cl)cc(N[C@H](C3=CNNN3)c3ccc(Cl)cc3)cc2c1Nc1c(F)cccc1F] | (S)-8-chloro-6-(((4-chlorophenyl)(1H-1,2,3-triazol-4-yl)methyl)amino)-4-((2,6-difluorophenyl)amino)quinoline-3-carbonitrile | 15 | ES/MS 522.1 (M + H+) |
| 641 | 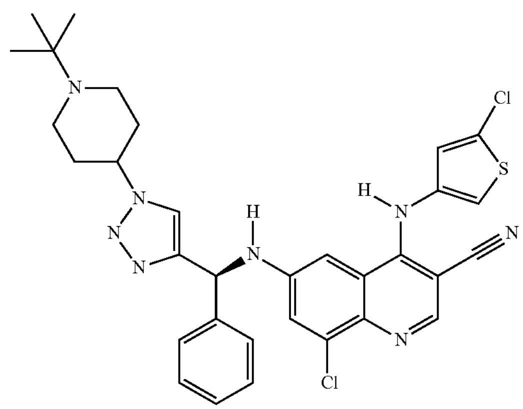 [SMILES: CC(C)(C)N1CCC(N2C=C([C@@H](Nc3cc(Cl)c4ncc(C#N)c(Nc5csc(Cl)c5)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((5-chlorothiophen-3-yl)amino)quinoline-3-carbonitrile | 3 | ES/MS 631.2 (M + H+) |

TABLE 1-continued

| Compd | Structure | Name | Example/Procedure | ES/MS m/z |
|---|---|---|---|---|
| 642 | 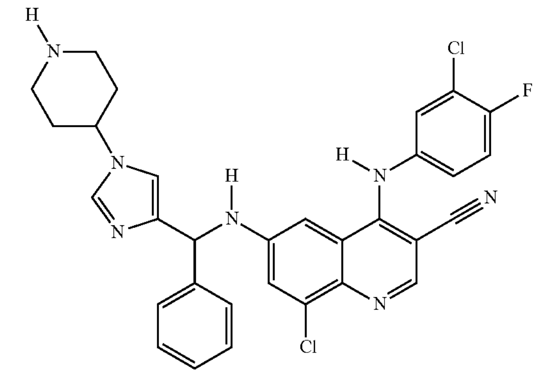 [SMILES: N#Cc1cnc2c(Cl)cc(NC(c3ccccc3)c3cn(C4CCNCC4)cn3)cc2c1Nc1ccc(F)c(Cl)c1] | 8-chloro-4-((3-chloro-4-fluorophenyl)amino)-6-((phenyl(1-(piperidin-4-yl)-1H-imidazol-4-yl)methyl)amino)quinoline-3-carbonitrile | 27 | ES/MS 585.9 (M + H+) |
| 643 | 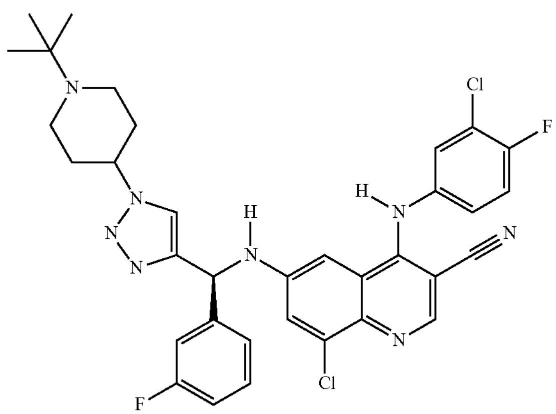 | (S)-6-((((1-(1-(tert-butyl)piperidin-4-yl)-1H-1,2,3-triazol-4-yl)(3-iodophenyl)methyl)amino)-8-chloro-4-((3-chloro-4-fluorophenyl)amino)quinoline-3-carbonitrile | 3 | ES/MS 769.0 (M + H+) |

TABLE 1-continued

| Compd | Structure | Name | Example/Procedure | ES/MS m/z |
|---|---|---|---|---|
| 644 | 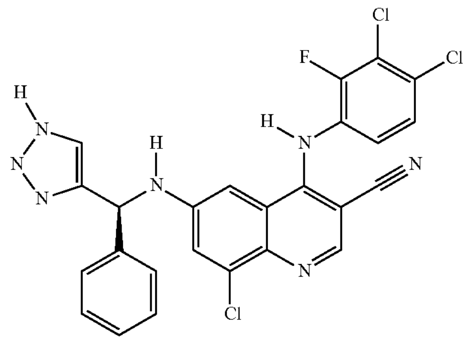 [SMILES: N#Cc1cnc2c(Cl)cc(N[C@H](C3=CNNN3)c3ccccc3)cc2c1Nc1ccc(Cl)c(Cl)c1F] | (S)-8-chloro-4-((3,4-dichloro-2-fluorophenyl)amino)-6-((phenyl(1H-1,2,3-triazol-4-yl)methyl)amino)quinoline-3-carbonitrile | 15 | |
| 645 | 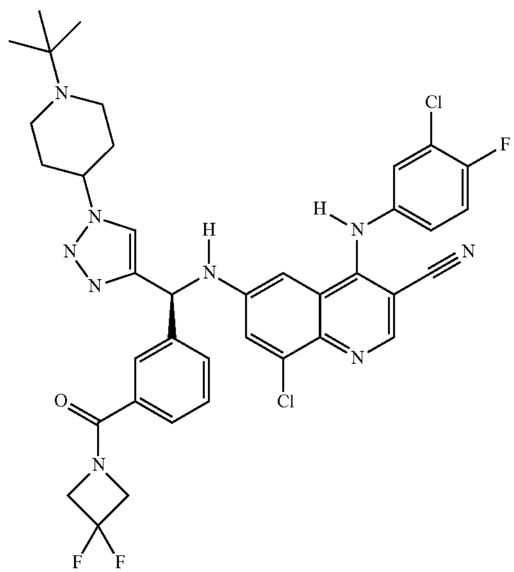 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)N4CC(F)(F)C4)c3)NN2)CC1] | (S)-6-((((1-(1-(tert-butyl)piperidin-4-yl)-1H-1,2,3-triazol-4-yl)(3-(3,3-difluoroazetidine-1-carbonyl)phenyl)methyl)amino)-8-chloro-4-((3-chloro-4-fluorophenyl)amino)quinoline-3-carbonitrile | 20 | ES/MS 762.3 (M + H+) |

TABLE 1-continued

| Compd | Structure | Name | Example/Procedure | ES/MS m/z |
|---|---|---|---|---|
| 646 | 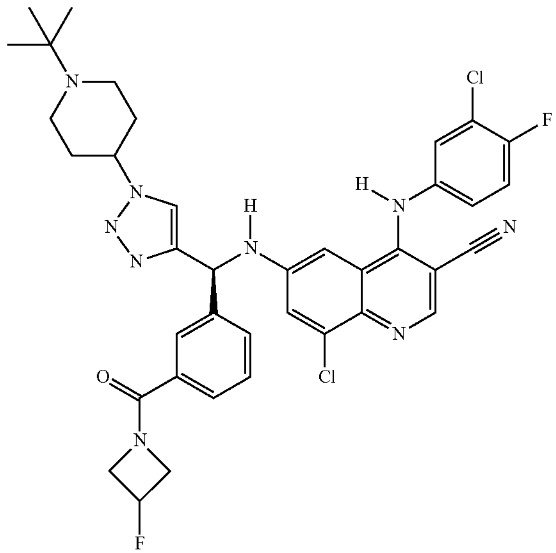 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)N4CC(F)C4)c3)NN2)CC1] | (S)-6-((((1-(1-(tert-butyl)piperidin-4-yl)-1H-1,2,3-triazol-4-yl)(3-(3-fluoroazetidine-1-carbonyl)phenyl)methyl)amino)-8-chloro-4-((3-chloro-4-fluorophenyl)amino)quinoline-3-carbonitrile | 20 | ES/MS 744.0 (M + H+) |
| 647 | 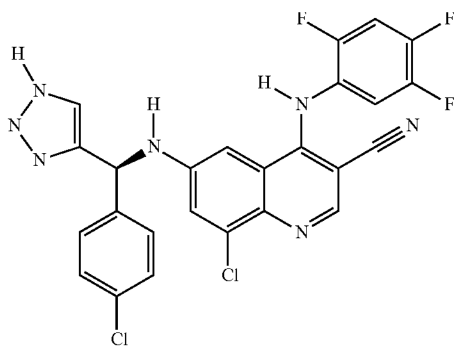 [SMILES: N#Cc1cnc2c(Cl)cc(N[C@H](C3=CNNN3)c3ccc(Cl)cc3)cc2c1Nc1cc(F)c(F)cc1F] | (S)-8-chloro-6-(((4-chlorophenyl)(1H-1,2,3-triazol-4-yl)methyl)amino)-4-((2,4,5-trifluorophenyl)amino)quinoline-3-carbonitrile | 15 | ES/MS 540.0 (M + H+) |

TABLE 1-continued

| Compd | Structure | Name | Example/Procedure | ES/MS m/z |
|---|---|---|---|---|
| 648 | 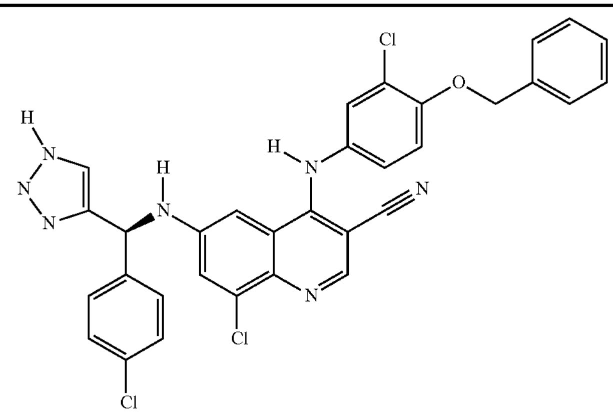 | (S)-4-((4-(benzyloxy)-3-chlorophenyl)amino)-8-chloro-6-(((4-chlorophenyl)(1H-1,2,3-triazol-4-yl)methyl)amino)quinoline-3-carbonitrile | 15 | ES/MS 626.1 (M + H+) |
| 649 | 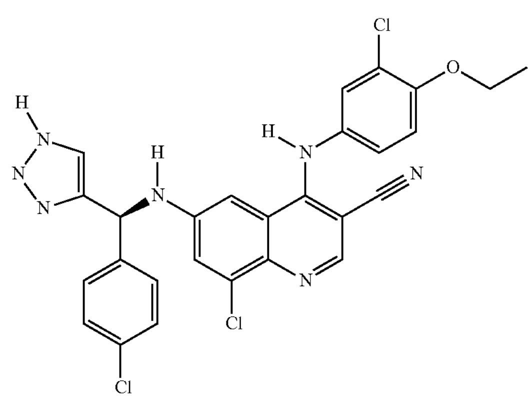 [SMILES: CCOc1ccc(Nc2c(C#N)cnc3c(Cl)cc(N[C@H](C4=CNNN4)c4ccc(Cl)cc4)cc23)cc1Cl] | (S)-8-chloro-4-((3-chloro-4-ethoxyphenyl)amino)-6-(((4-chlorophenyl)(1H-1,2,3-triazol-4-yl)methyl)amino)quinoline-3-carbonitrile | 15 | ES/MS 564.1 (M + H+) |

TABLE 1-continued
| Compd | Structure | Name | Example/Procedure | ES/MS m/z |
|---|---|---|---|---|
| 650 | 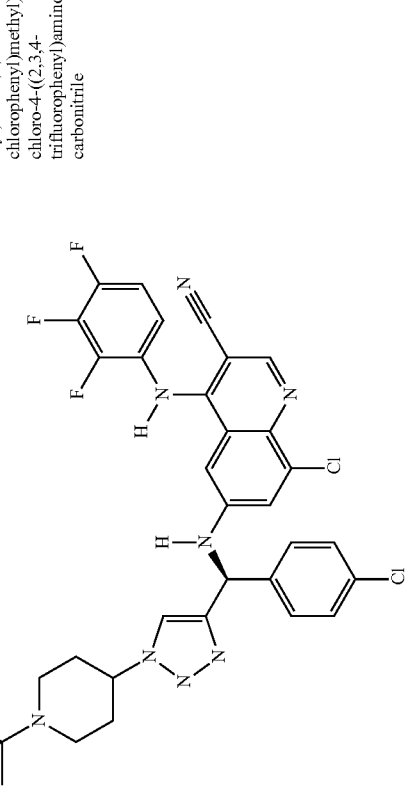 | (S)-6-((((1-(1-(tert-butyl)piperidin-4-yl)-1H-1,2,3-triazol-4-yl)(4-chlorophenyl)methyl)amino)-8-chloro-4-((2,3,4-trifluorophenyl)amino)quinoline-3-carbonitrile | 10 | ES/MS 679.3 (M + H+) |
| 651 | 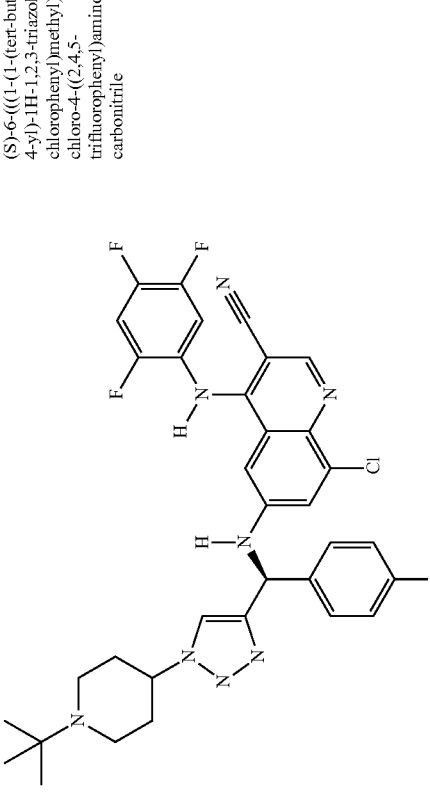 | (S)-6-((((1-(1-(tert-butyl)piperidin-4-yl)-1H-1,2,3-triazol-4-yl)(4-chlorophenyl)methyl)amino)-8-chloro-4-((2,4,5-trifluorophenyl)amino)quinoline-3-carbonitrile | 10 | ES/MS 679.2 (M + H+) |

TABLE 1-continued

| Compd | Name | Structure | Example/Procedure | ES/MS m/z |
|---|---|---|---|---|
| 652 | (S)-6-((((1-(1-(tert-butyl)piperidin-4-yl)-1H-1,2,3-triazol-4-yl)(4-chlorophenyl)methyl)amino)-8-chloro-4-((5-chloro-2-fluorophenyl)amino)quinoline-3-carbonitrile | 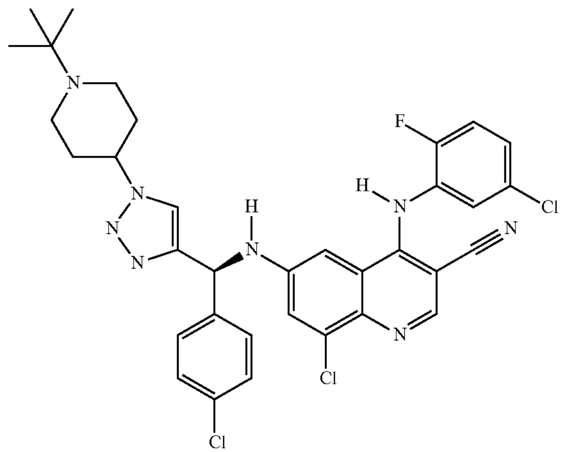 [SMILES: CC(C)(C)N1CCC(N2C=C([C@@H](Nc3cc(Cl)c4ncc(C#N)c(Nc5cc(Cl)ccc5F)c4c3)c3ccc(Cl)cc3)NN2)CC1] | 10 | ES/MS 677.3 (M + H+) |
| 653 | (S)-6-((((1-(1-(tert-butyl)piperidin-4-yl)-1H-1,2,3-triazol-4-yl)(4-chlorophenyl)methyl)amino)-8-chloro-4-((2,6-difluorophenyl)amino)quinoline-3-carbonitrile | 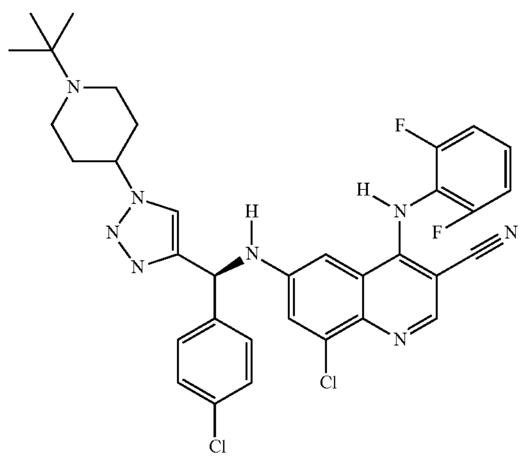 [SMILES: CC(C)(C)N1CCC(N2C=C([C@@H](Nc3cc(Cl)c4ncc(C#N)c(Nc5c(F)cccc5F)c4c3)c3ccc(Cl)cc3)NN2)CC1] | 10 | ES/MS 661.2 (M + H+) |

TABLE 1-continued

| Compd | Name | Structure | Example/Procedure | ES/MS m/z |
|---|---|---|---|---|
| 654 | (S)-4-((4-(benzyloxy)-3-chlorophenyl)amino)-6-(((1-(tert-butyl)piperidin-4-yl)(4-chlorophenyl)methyl)amino)-8-chloroquinoline-3-carbonitrile | 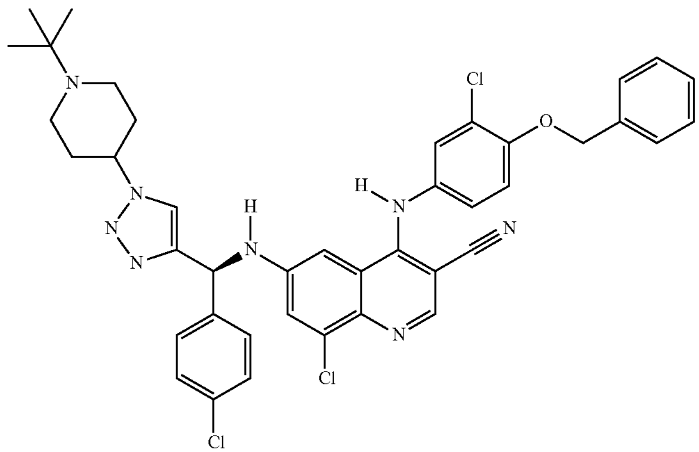 [SMILES: CC(C)(C)N1CCC(N2C=C([C@@H](Nc3cc(Cl)c4ncc(C#N)c(Nc5ccc(OCc6ccccc6)c(Cl)c5)c4c3)c3ccc(Cl)cc3)NN2)CC1] | 10 | ES/MS 765.3 (M + H+) |
| 655 | (S)-6-(((1-(1-(tert-butyl)piperidin-4-yl)-1H-1,2,3-triazol-4-yl)(4-chlorophenyl)methyl)amino)-8-chloro-4-((3-chloro-4-ethoxyphenyl)amino)quinoline-3-carbonitrile | 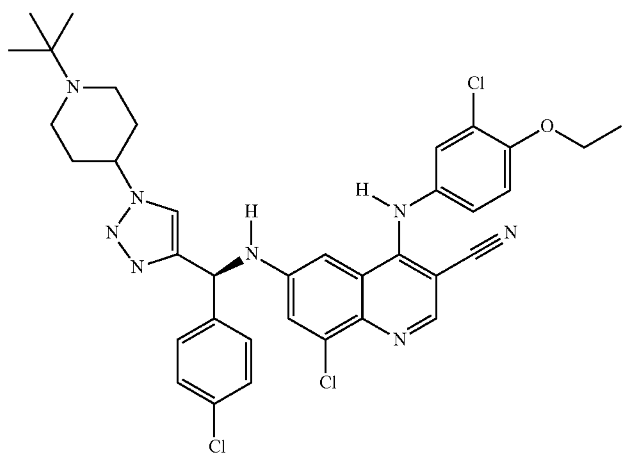 [SMILES: CCOc1ccc(Nc2c(C#N)cnc3c(Cl)cc(N[C@H](C4=CN(C5CCN(C(C)(C)C)CC5)NN4)c4ccc(Cl)cc4)cc23)cc1Cl] | 10 | ES/MS 703.2 (M + H+) |

TABLE 1-continued
| Compd | Structure | Name | Example/Procedure | ES/MS m/z |
|---|---|---|---|---|
| 656 | 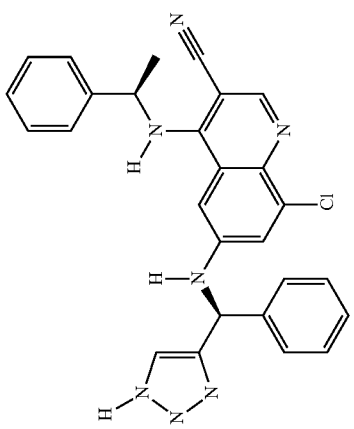 | 8-chloro-6-(((S)-phenyl(1H-1,2,3-triazol-4-yl)methyl)amino)-4-(((R)-1-phenylethyl)amino)quinoline-3-carbonitrile | 15 | ES/MS 480.2 (M + H+) |
| 657 | 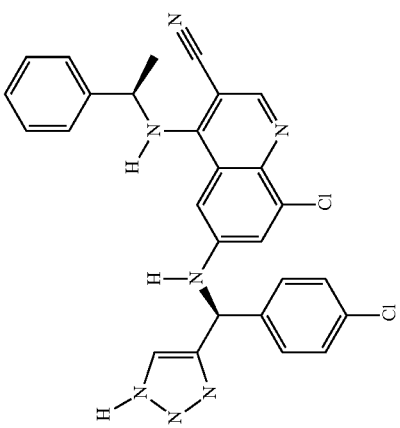 | 8-chloro-6-(((S)-(4-chlorophenyl)(1H-1,2,3-triazol-4-yl)methyl)amino)-4-(((R)-1-phenylethyl)amino)quinoline-3-carbonitrile | 15 | ES/MS 514.1 (M + H+) |

TABLE 1-continued
| Compd | Structure | Name | Example/Procedure | ES/MS m/z |
|---|---|---|---|---|
| 658 | 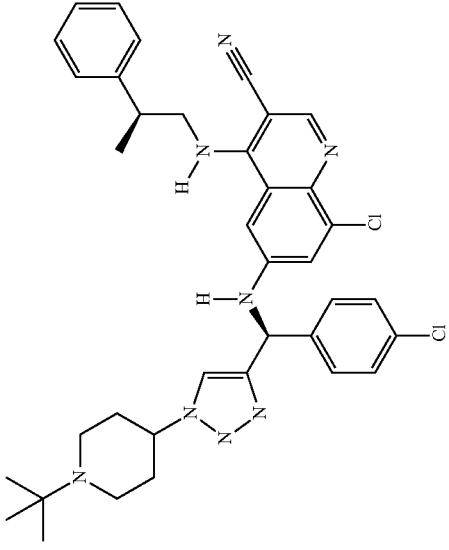 | 6-(((S)-(1-(1-(tert-butyl)piperidin-4-yl)-1H-1,2,3-triazol-4-yl)(4-chlorophenyl)methyl)amino)-8-chloro-4-(((S)-2-phenylpropyl)amino)quinoline-3-carbonitrile | 1 | ES/MS 667.3 (M + H+) |
| 659 | 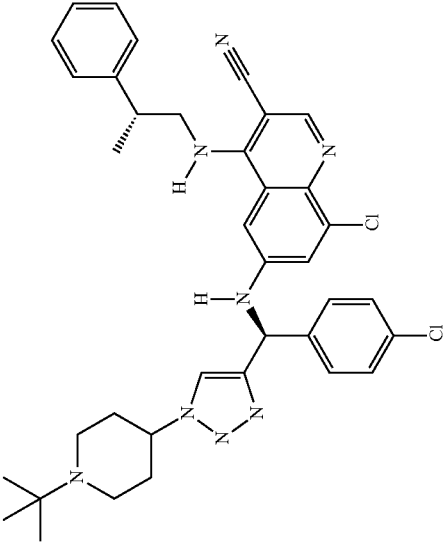 | 6-(((S)-(1-(1-(tert-butyl)piperidin-4-yl)-1H-1,2,3-triazol-4-yl)(4-chlorophenyl)methyl)amino)-8-chloro-4-(((R)-2-phenylpropyl)amino)quinoline-3-carbonitrile | 1 | ES/MS 667.3 (M + H+) |

TABLE 1-continued

| Compd | Structure | Name | Example/Procedure | ES/MS m/z |
|---|---|---|---|---|
| 660 | 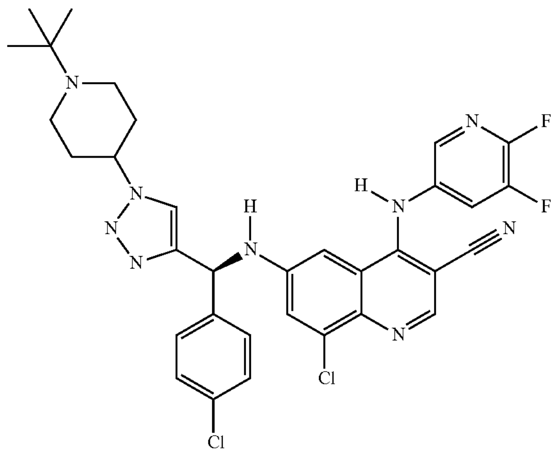 [SMILES: CC(C)(C)N1CCC(N2C=C([C@@H](Nc3cc(Cl)c4ncc(C#N)c(Nc5cnc(F)c(F)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((5,6-difluoropyridin-3-yl)amino)quinoline-3-carbonitrile | 10 | ES/MS 662.2 (M + H+) |
| 661 | 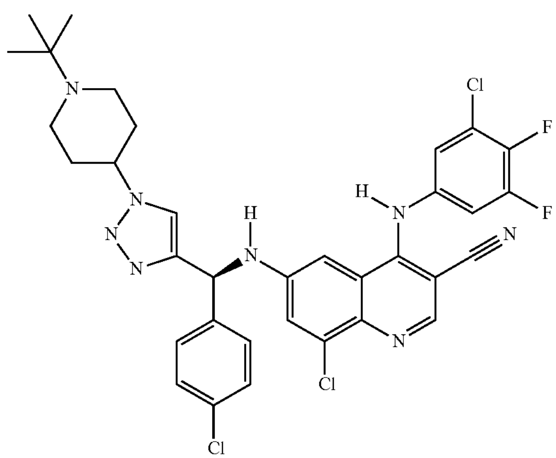 [SMILES: CC(C)(C)N1CCC(N2C=C([C@@H](Nc3cc(Cl)c4ncc(C#N)c(Nc5cc(F)c(F)c(Cl)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-chloro-4,5-difluorophenyl)amino)quinoline-3-carbonitrile | 10 | ES/MS 695.2 (M + H+) |

TABLE 1-continued

| Compd | Structure | Name | Example/Procedure | ES/MS m/z |
|---|---|---|---|---|
| 662 | 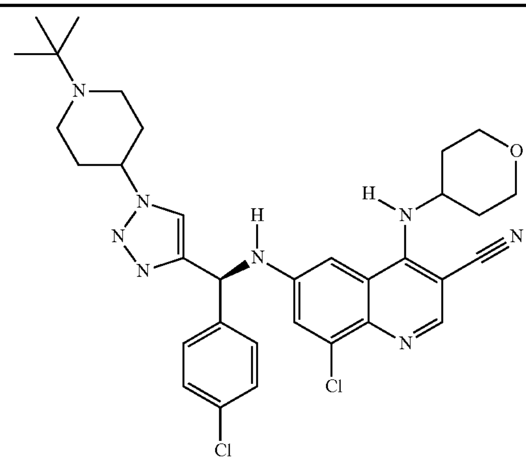 | (S)-6-((((1-(1-(tert-butyl)piperidin-4-yl)-1H-1,2,3-triazol-4-yl)(4-chlorophenyl)methyl)amino)-8-chloro-4-((tetrahydro-2H-pyran-4-yl)amino)quinoline-3-carbonitrile | 1 | ES/MS 633.2 (M + H+) |
| 663 | 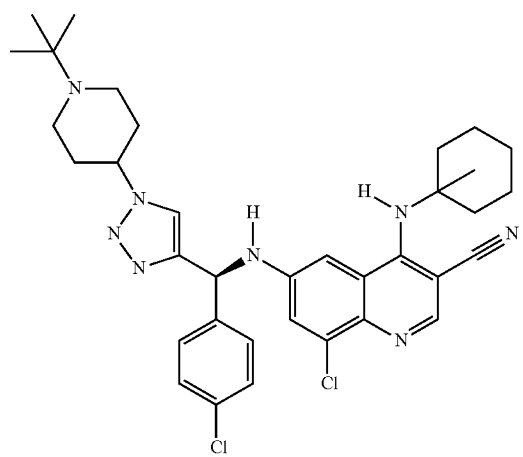 | (S)-6-((((1-(1-(tert-butyl)piperidin-4-yl)-1H-1,2,3-triazol-4-yl)(4-chlorophenyl)methyl)amino)-8-chloro-4-((1-methylcyclohexyl)amino)quinoline-3-carbonitrile | 1 | ES/MS 645.3 (M + H+) |

TABLE 1-continued

| Compd | Structure | Name | Example/Procedure | ES/MS m/z |
|---|---|---|---|---|
| 664 | 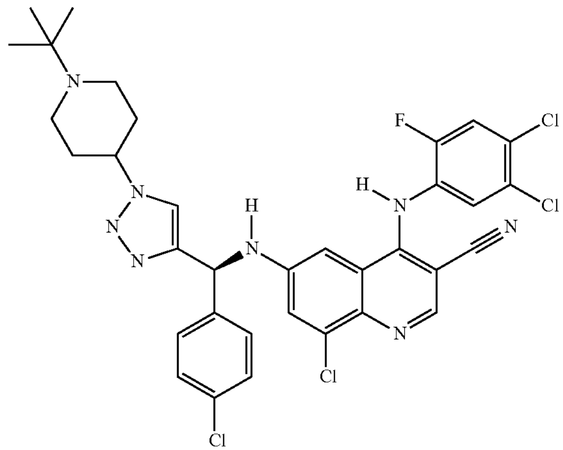 [SMILES: CC(C)(C)N1CCC(N2C=C([C@@H](Nc3cc(Cl)c4ncc(C#N)c(Nc5cc(Cl)c(Cl)cc5F)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((4,5-dichloro-2-fluorophenyl)amino)quinoline-3-carbonitrile | 10 | ES/MS 711.2 (M + H+) |
| 665 | 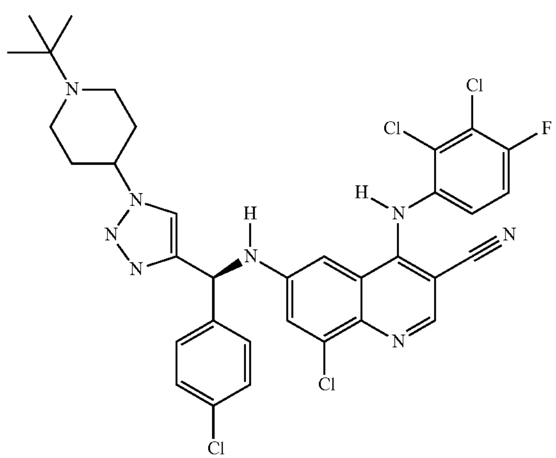 [SMILES: CC(C)(C)N1CCC(N2C=C([C@@H](Nc3cc(Cl)c4ncc(C#N)c(Nc5ccc(F)c(Cl)c5Cl)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((2,3-dichloro-4-fluorophenyl)amino)quinoline-3-carbonitrile | 10 | ES/MS 711.1 (M + H+) |

TABLE 1-continued

| Compd | Structure | Name | Example/Procedure | ES/MS m/z |
|---|---|---|---|---|
| 666 | 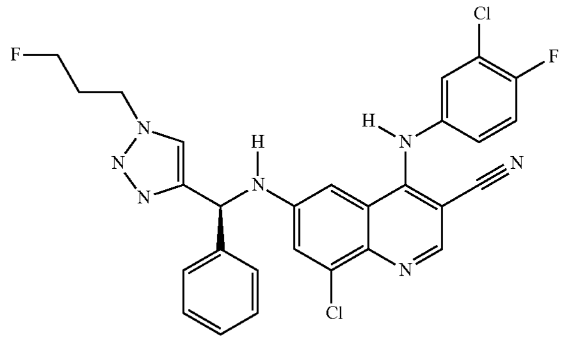 [SMILES: N#Cc1cnc2c(Cl)cc(N[C@H](C3=CN(CCCF)NN3)c3ccccc3)cc2c1Nc1ccc(F)c(Cl)c1] | (S)-8-chloro-4-((3-chloro-4-fluorophenyl)amino)-6-(((1-(3-fluoropropyl)-1H-1,2,3-triazol-4-yl)(phenyl)methyl)amino)quinoline-3-carbonitrile | 2 | ES/MS 564.1 (M + H+) |
| 667 | 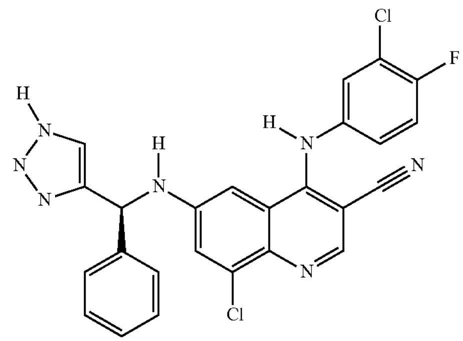 [SMILES: N#Cc1cnc2c(Cl)cc(N[C@H](C3=CNNN3)c3ccccc3)cc2c1Nc1ccc(F)c(Cl)c1] | (S)-8-chloro-4-((3-chloro-4-fluorophenyl)amino)-6-(((phenyl(1H-1,2,3-triazol-4-yl)methyl)amino)quinoline-3-carbonitrile | 15 | ES/MS 504.1 (M + H+) |
| 668 | 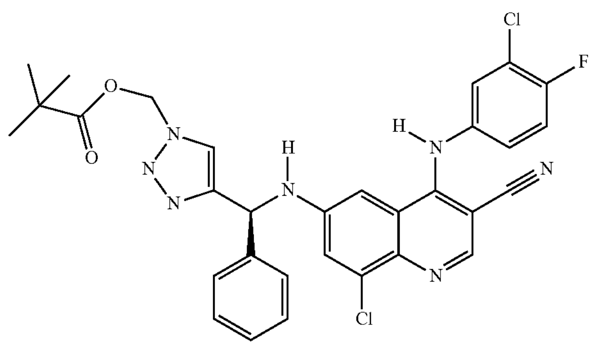 [SMILES: CC(C)(C)C(=O)OCN1C=C([C@@H](Nc2cc(Cl)c3ncc(C#N)c(Nc4ccc(F)c(Cl)c4)c3c2)c2ccccc2)NN1] | (S)-(4-(((8-chloro-4-((3-chloro-4-fluorophenyl)amino)-3-cyanoquinolin-6-yl)amino)(phenyl)methyl)-1H-1,2,3-triazol-1-yl)methyl pivalate | 15 | ES/MS 618.9 (M + H+) |

TABLE 1-continued

| Compd | Structure | Name | Example/Procedure | ES/MS m/z |
|---|---|---|---|---|
| 669 | 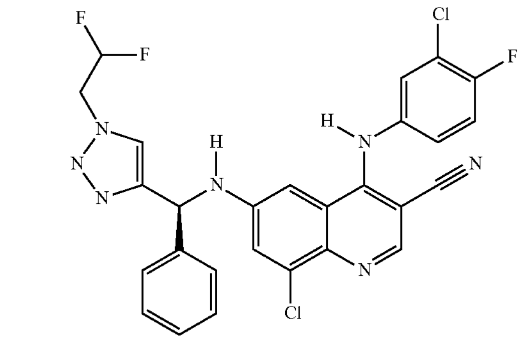 [SMILES: N#Cc1cnc2c(Cl)cc(N[C@H](C3=CN(CC(F)F)NN3)c3ccccc3)cc2c1Nc1ccc(F)c(Cl)c1] | (S)-8-chloro-4-((3-chloro-4-fluorophenyl)amino)-6-(((1-(2,2-difluoroethyl)-1H-1,2,3-triazol-4-yl)(phenyl)methyl)amino)quinoline-3-carbonitrile | 3 | ES/MS 568.1 (M + H+) |
| 670 | 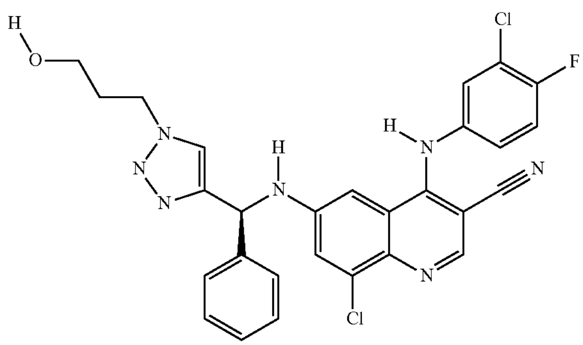 [SMILES: N#Cc1cnc2c(Cl)cc(N[C@H](C3=CN(CCCO)NN3)c3ccccc3)cc2c1Nc1ccc(F)c(Cl)c1] | (S)-8-chloro-4-((3-chloro-4-fluorophenyl)amino)-6-(((1-(3-hydroxypropyl)-1H-1,2,3-triazol-4-yl)(phenyl)methyl)amino)quinoline-3-carbonitrile | 3 | ES/MS 562.1 (M + H+) |

TABLE 1-continued

| Compd | Structure | Name | Example/Procedure | ES/MS m/z |
|---|---|---|---|---|
| 671 | 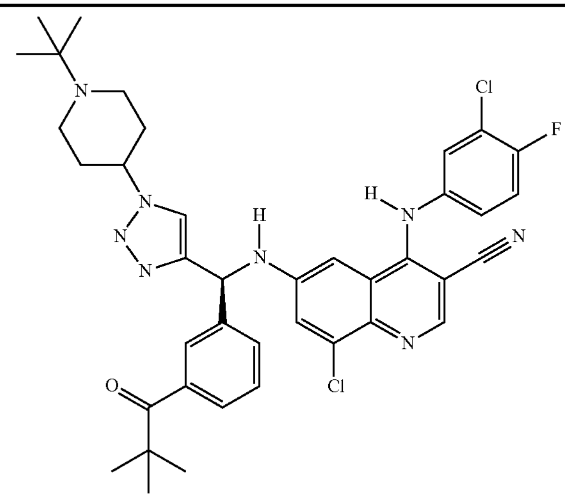 | (S)-6-((((1-(1-(tert-butyl)piperidin-4-yl)-1H-1,2,3-triazol-4-yl)(3-pivaloylphenyl)methyl)amino)-8-chloro-4-((3-chloro-4-fluorophenyl)amino)quinoline-3-carbonitrile | 21 | ES/MS 727.1 (M + H+) |
| 672 | 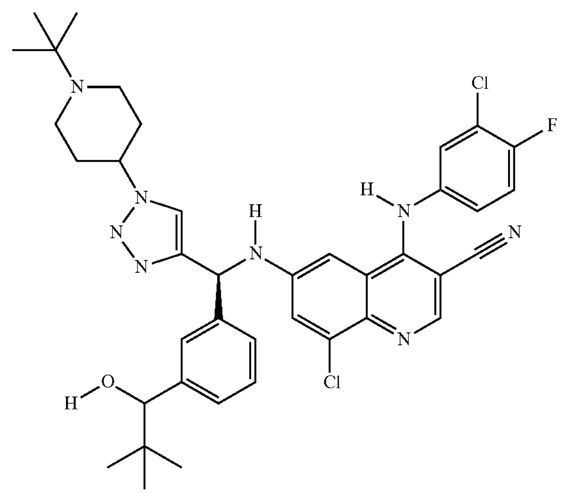 [SMILES: CC(C)(C)C(O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | 6-(((1S)-(1-(1-(tert-butyl)piperidin-4-yl)-1H-1,2,3-triazol-4-yl)(3-(1-hydroxy-2,2-dimethylpropyl)phenyl)methyl)amino)-8-chloro-4-((3-chloro-4-fluorophenyl)amino)quinoline-3-carbonitrile | 22 | ES/MS 729.3 (M + H+) |

TABLE 1-continued

| Compd | Name | Structure | Example/Procedure | ES/MS m/z |
|---|---|---|---|---|
| 673 | (S)-3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)amino)methyl)benzamide | 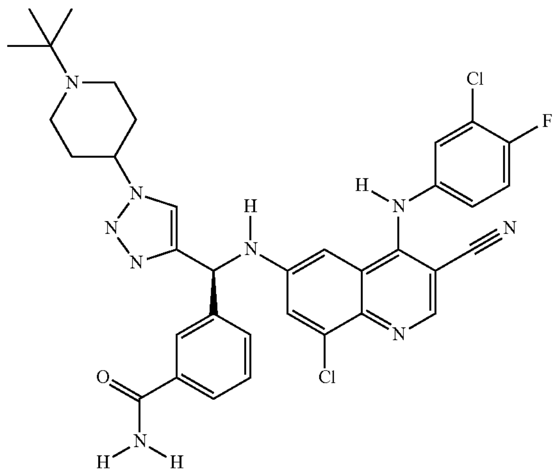 | 20 | ES/MS 686.1 (M + H+) |
| 674 | (S)-3-((1-(1-(tert-butyl)piperidin-4-yl)-1H-1,2,3-triazol-4-yl)((8-chloro-4-((3-chloro-4-fluorophenyl)amino)-3-cyanoquinolin-6-yl)amino)methyl)-N-ethyl-N-methylbenzamide | 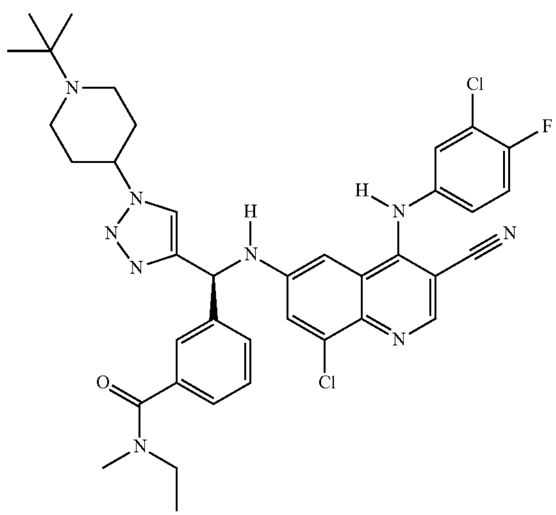 [SMILES: CCN(C)C(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | 20 | ES/MS 728.1 (M + H+) |

TABLE 1-continued

| Compd | Structure | Name | Example/Procedure | ES/MS m/z |
|---|---|---|---|---|
| 675 | 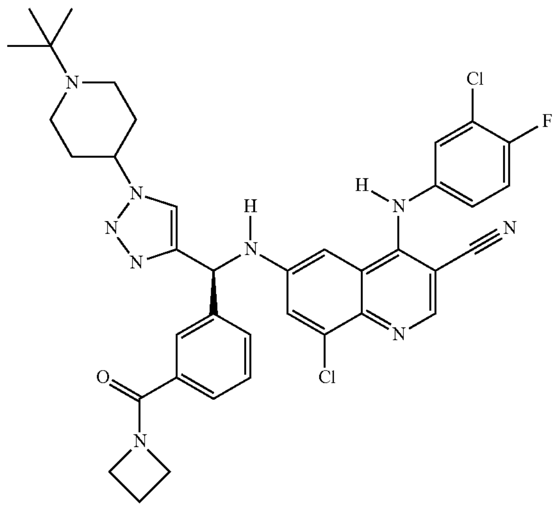 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)N4CCC4)c3)NN2)CC1] | (S)-6-(((3-(azetidine-1-carbonyl)phenyl)(1-(1-(tert-butyl)piperidin-4-yl)-1H-1,2,3-triazol-4-yl)methyl)amino)-8-chloro-4-((3-chloro-4-fluorophenyl)amino)quinoline-3-carbonitrile | 20 | ES/MS 726.0 (M + H+) |
| 676 | 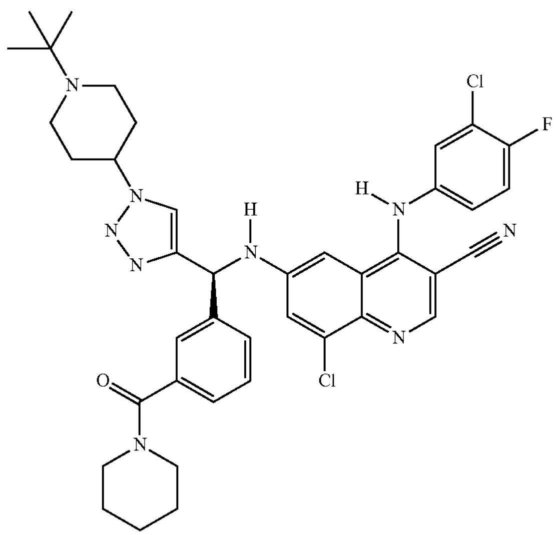 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)N4CCCCC4)c3)NN2)CC1] | (S)-6-(((1-(1-(tert-butyl)piperidin-4-yl)-1H-1,2,3-triazol-4-yl)(3-(piperidine-1-carbonyl)phenyl)methyl)amino)-8-chloro-4-((3-chloro-4-fluorophenyl)amino)quinoline-3-carbonitrile | 20 | ES/MS 754.1 (M + H+) |

TABLE 1-continued

| Compd | Structure | Name | Example/Procedure | ES/MS m/z |
|---|---|---|---|---|
| 677 | 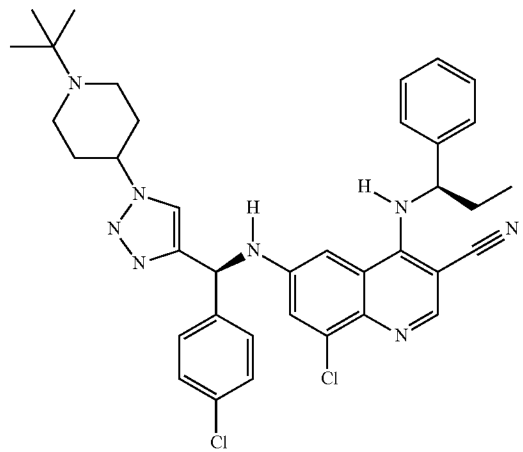 [SMILES: CC[C@@H](Nc1c(C#N)cnc2c(Cl)cc(N[C@H](C3=CN(C4CCN(C(C)(C)C)CC4)NN3)c3ccc(Cl)cc3)cc12)c1ccccc1] | 6-(((S)-(1-(tert-butyl)piperidin-4-yl)-1H-1,2,3-triazol-4-yl)(4-chlorophenyl)methyl)amino)-8-chloro-4-(((R)-1-phenylpropyl)amino)quinoline-3-carbonitrile | 1 | ES/MS 667.3 (M + H+) |
| 678 | 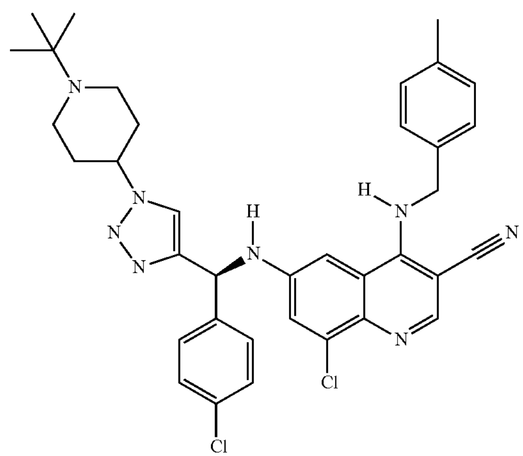 [SMILES: Cc1ccc(CNc2c(C#N)cnc3c(Cl)cc(N[C@H](C4=CN(C5CCN(C(C)(C)C)CC5)NN4)c4ccc(Cl)cc4)cc23)cc1] | (S)-6-(((1-(1-(tert-butyl)piperidin-4-yl)-1H-1,2,3-triazol-4-yl)(4-chlorophenyl)methyl)amino)-8-chloro-4-((4-methylbenzyl)amino)quinoline-3-carbonitrile | 1 | ES/MS 653.3 (M + H+) |

TABLE 1-continued

| Compd | Structure | Name | Example/Procedure | ES/MS m/z |
|---|---|---|---|---|
| 679 | 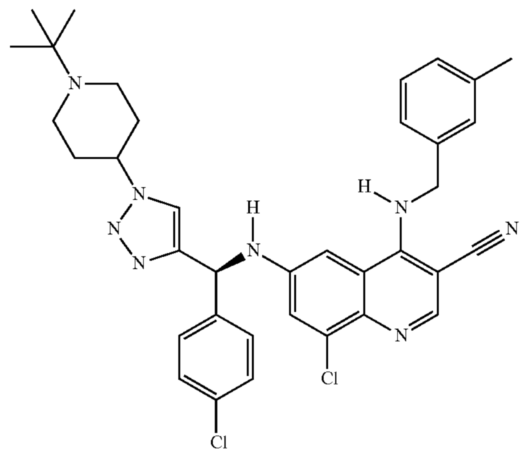 [SMILES: Cc1cccc(CNc2c(C#N)cnc3c(Cl)cc(N[C@H](C4=CN(C5CCN(C(C)(C)C)CC5)NN4)c4ccc(Cl)cc4)cc23)c1] | (S)-6-(((1-(1-(tert-butyl)piperidin-4-yl)-1H-1,2,3-triazol-4-yl)(4-chlorophenyl)methyl)amino)-8-chloro-4-((3-methylbenzyl)amino)quinoline-3-carbonitrile | 1 | ES/MS 653.3 (M + H+) |
| 680 | 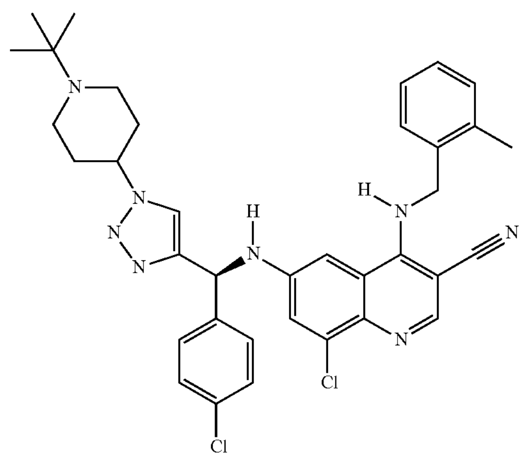 [SMILES: Cc1ccccc1CNc1c(C#N)cnc2c(Cl)cc(N[C@H](C3=CN(C4CCN(C(C)(C)C)CC4)NN3)c3ccc(Cl)cc3)cc12] | (S)-6-(((1-(1-(tert-butyl)piperidin-4-yl)-1H-1,2,3-triazol-4-yl)(4-chlorophenyl)methyl)amino)-8-chloro-4-((2-methylbenzyl)amino)quinoline-3-carbonitrile | 1 | ES/MS 653.3 (M + H+) |

TABLE 1-continued

| Compd | Structure | Name | Example/Procedure | ES/MS m/z |
|---|---|---|---|---|
| 681 | 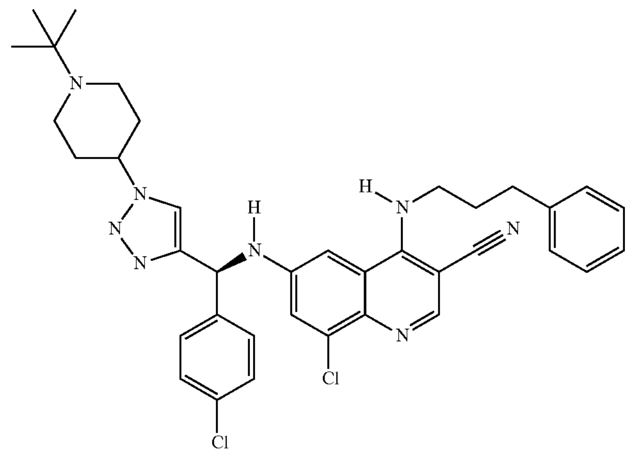 [SMILES: CC(C)(C)N1CCC(N2C=C([C@@H](Nc3cc(Cl)c4ncc(C#N)c(NCCCc5ccccc5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-phenylpropyl)amino)quinoline-3-carbonitrile | 1 | ES/MS 667.3 (M + H+) |
| 682 | 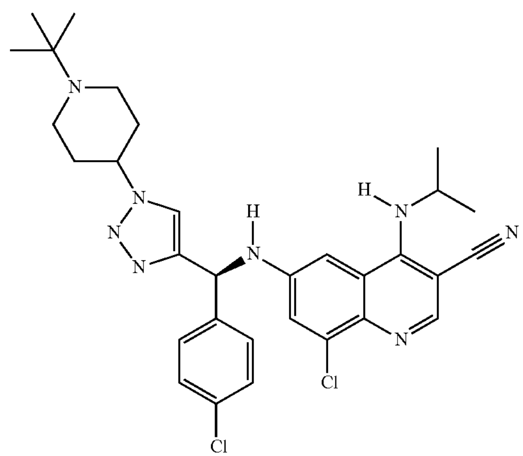 [SMILES: CC(C)Nc1c(C#N)cnc2c(Cl)cc(N[C@H](C3=CN(C4CCN(C(C)(C)C)CC4)NN3)c3ccc(Cl)cc3)cc12] | (S)-6-(((1-(1-(tert-butyl)piperidin-4-yl)-1H-1,2,3-triazol-4-yl)(4-chlorophenyl)methyl)amino)-8-chloro-4-(isopropylamino)quinoline-3-carbonitrile | 1 | ES/MS 591.2 (M + H+) |

TABLE 1-continued

| Compd | Structure | Name | Example/Procedure | ES/MS m/z |
|---|---|---|---|---|
| 683 | 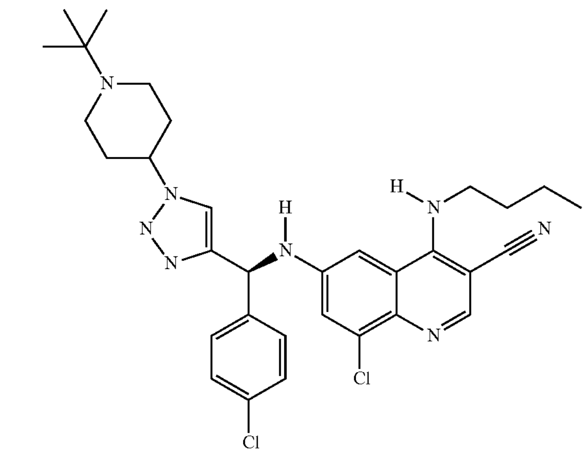 [SMILES: CCCCNc1c(C#N)cnc2c(Cl)cc(N[C@H](C3=CN(C4CCN(C(C)(C)C)CC4)NN3)c3ccc(Cl)cc3)cc12] | (S)-6-(((1-(1-(tert-butyl)piperidin-4-yl)-1H-1,2,3-triazol-4-yl)(4-chlorophenyl)methyl)amino)-4-(butylamino)-8-chloroquinoline-3-carbonitrile | 1 | ES/MS 605.3 (M + H+) |
| 684 | 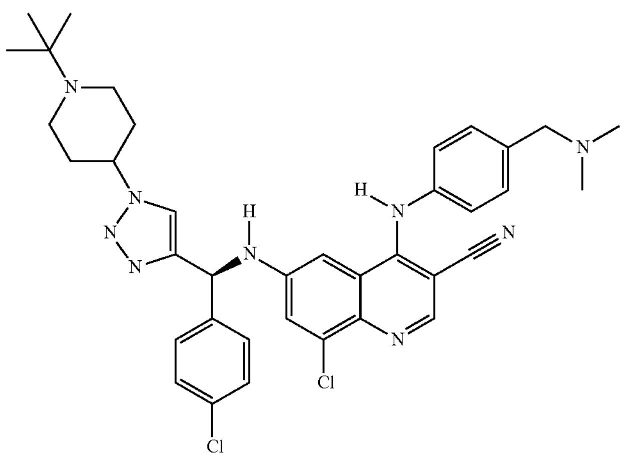 [SMILES: CN(C)Cc1ccc(Nc2c(C#N)cnc3c(Cl)cc(N[C@H](C4=CN(C5CCN(C(C)(C)C)CC5)NN4)c4ccc(Cl)cc4)cc23)cc1] | (S)-6-(((1-(1-(tert-butyl)piperidin-4-yl)-1H-1,2,3-triazol-4-yl)(4-chlorophenyl)methyl)amino)-8-chloro-4-((4-((dimethylamino)methyl)phenyl)amino)quinoline-3-carbonitrile | 10 | ES/MS 682.3 (M + H+) |

TABLE 1-continued

| Compd | Structure | Name | Example/Procedure | ES/MS m/z |
|---|---|---|---|---|
| 685 | 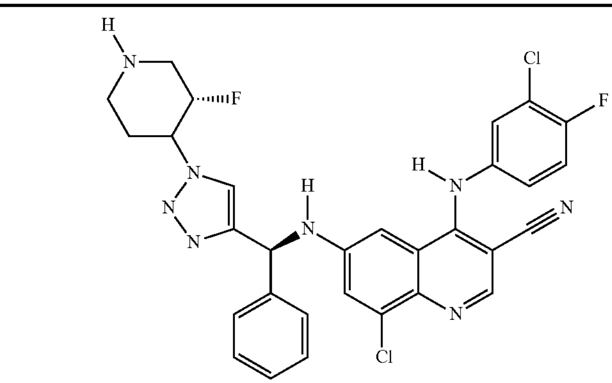 | 8-chloro-4-((3-chloro-4-fluorophenyl)amino)-6-(((S)-(((3S,4R)-3-fluoropiperidin-4-yl)-1H-1,2,3-triazol-4-yl)(phenyl)methyl)amino)quinoline-3-carbonitrile | 5 | ES/MS 605.1 (M + H+) |
| 686 | 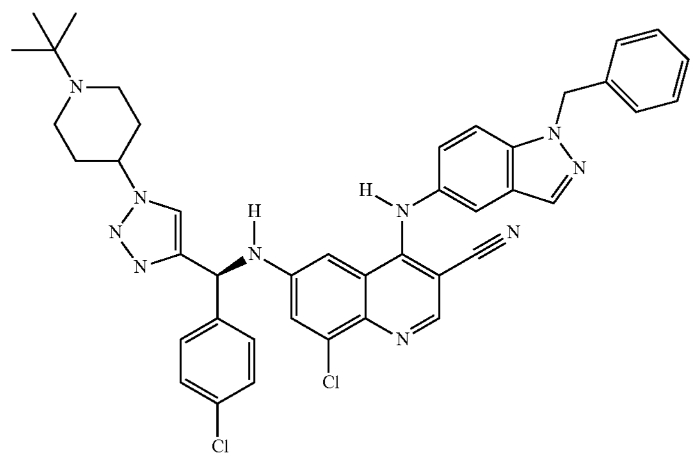 [SMILES: CC(C)(C)N1CCC(N2C=C([C@@H](Nc3cc(Cl)c4ncc(C#N)c(Nc5ccc6c(cnn6Cc6ccccc6)c5)c4c3)c3ccc(Cl)cc3)NN2)CC1] | (S)-4-((1-benzyl-1H-indazol-5-yl)amino)-6-(((1-(1-(tert-butyl)piperidin-4-yl)-1H-1,2,3-triazol-4-yl)(4-chlorophenyl)methyl)amino)-8-chloroquinoline-3-carbonitrile | 10 | ES/MS 755.4 (M + H+) |

TABLE 1-continued

| Compd | Structure | Name | Example/Procedure | ES/MS m/z |
|---|---|---|---|---|
| 687 | 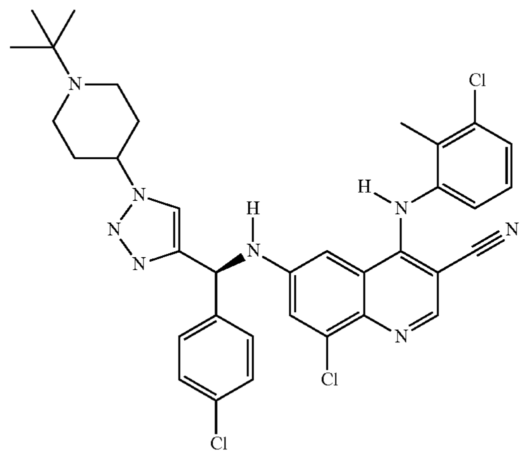 [SMILES: Cc1c(Cl)cccc1Nc1c(C#N)cnc2c(Cl)cc(N[C@H](C3=CN(C4CCN(C(C)(C)C)CC4)NN3)c3ccc(Cl)cc3)cc12] | (S)-6-((((1-(1-(tert-butyl)piperidin-4-yl)-1H-1,2,3-triazol-4-yl)(4-chlorophenyl)methyl)amino)-8-chloro-4-((3-chloro-2-methylphenyl)amino)quinoline-3-carbonitrile | 10 | ES/MS 673.2 (M + H+) |
| 688 | 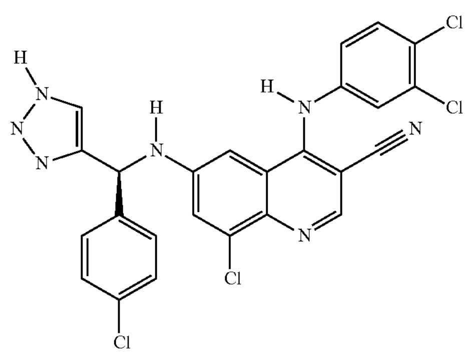 [SMILES: N#Cc1cnc2c(Cl)cc(N[C@H](C3=CNNN3)c3ccc(Cl)cc3)cc2c1Nc1ccc(Cl)c(Cl)c1] | (S)-8-chloro-6-(((4-chlorophenyl)(1H-1,2,3-triazol-4-yl)methyl)amino)-4-((3,4-dichlorophenyl)amino)quinoline-3-carbonitrile | 15 | ES/MS 554.0 (M + H+) |

TABLE 1-continued

| Compd | Structure | Name | Example/Procedure | ES/MS m/z |
|---|---|---|---|---|
| 689 | 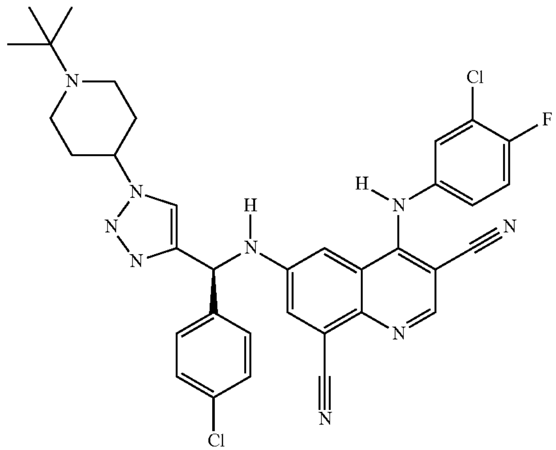 [SMILES: CC(C)(C)N1CCC(N2C=C([C@@H](Nc3cc(C#N)c4ncc(C#N)c(Nc5ccc(F)c(Cl)c5)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-4-((3-chloro-4-fluorophenyl)amino)quinoline-3,8-dicarbonitrile | 9 | ES/MS 669.2 (M + H+) |
| 690 | 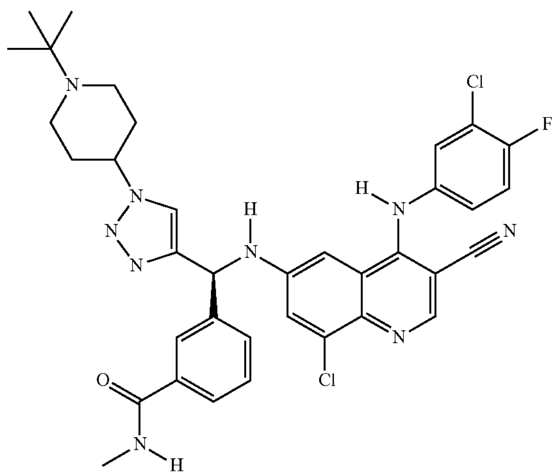 [SMILES: CNC(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-3-((1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)-N-methylbenzamide | 20 | ES/MS 700.0 (M + H+) |

TABLE 1-continued

| Compd | Structure | Name | Example/Procedure | ES/MS m/z |
|---|---|---|---|---|
| 691 | 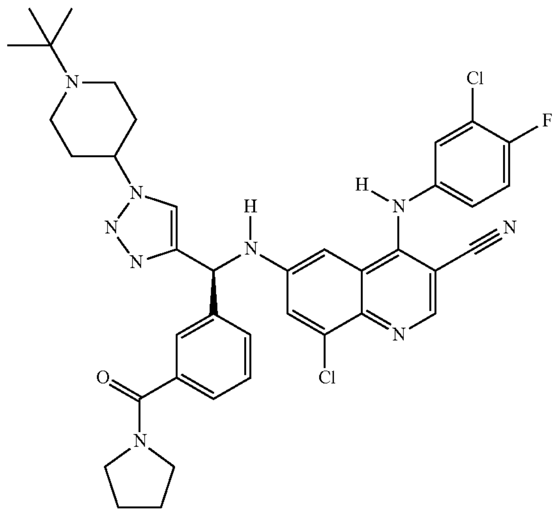 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)N4CCCC4)c3)NN2)CC1] | (S)-6-(((1-(1-(tert-butyl)piperidin-4-yl)-1H-1,2,3-triazol-4-yl)(3-(pyrrolidine-1-carbonyl)phenyl)methyl)amino)-8-chloro-4-((3-chloro-4-fluorophenyl)amino)quinoline-3-carbonitrile | 20 | ES/MS 740.0 (M + H+) |
| 692 | 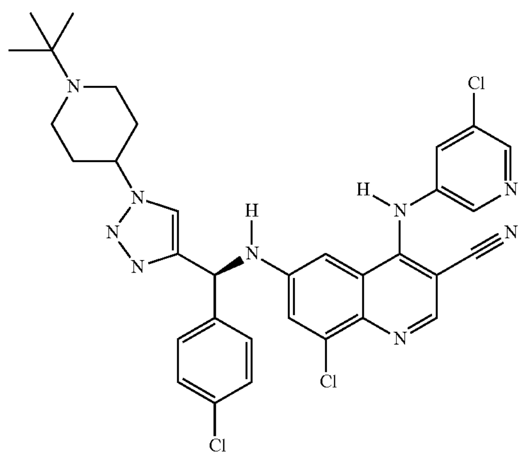 [SMILES: CC(C)(C)N1CCC(N2C=C([C@@H](Nc3cc(Cl)c4ncc(C#N)c(Nc5cncc(Cl)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((5-chloropyridin-3-yl)amino)quinoline-3-carbonitrile | 10 | ES/MS 660.2 (M + H+) |

TABLE 1-continued

| Compd | Structure | Name | Example/Procedure | ES/MS m/z |
|---|---|---|---|---|
| 693 | 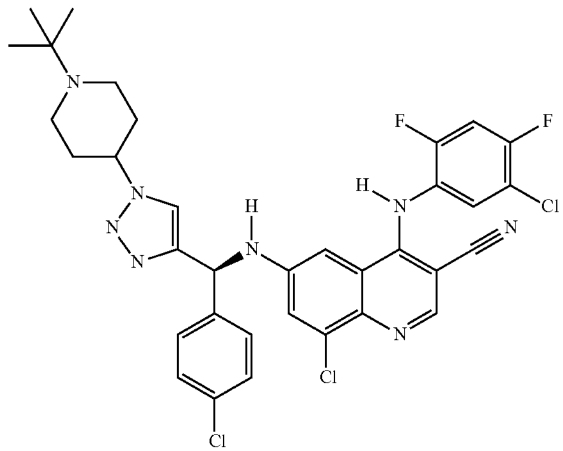 [SMILES: CC(C)(C)N1CCC(N2C=C([C@@H](Nc3cc(Cl)c4ncc(C#N)c(Nc5cc(Cl)c(F)cc5F)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-8-chloro-4-((5-chloro-2,4-difluorophenyl)amino)quinoline-3-carbonitrile | 10 | ES/MS 695.2 (M + H+) |
| 694 | 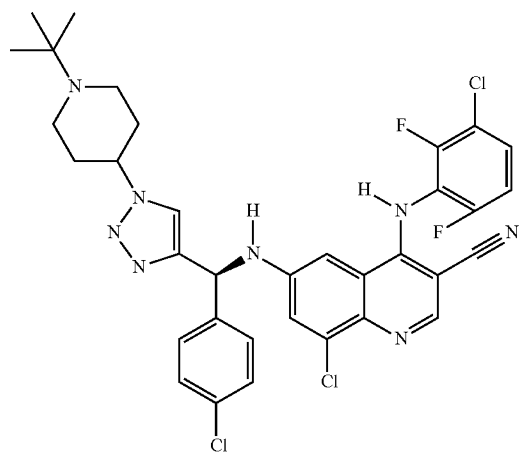 [SMILES: CC(C)(C)N1CCC(N2C=C([C@@H](Nc3cc(Cl)c4ncc(C#N)c(Nc5c(F)ccc(Cl)c5F)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-8-chloro-4-((3-chloro-2,6-difluorophenyl)amino)quinoline-3-carbonitrile | 10 | ES/MS 695.2 (M + H+) |

TABLE 1-continued

| Compd | Structure | Name | Example/Procedure | ES/MS m/z |
|---|---|---|---|---|
| 695 | 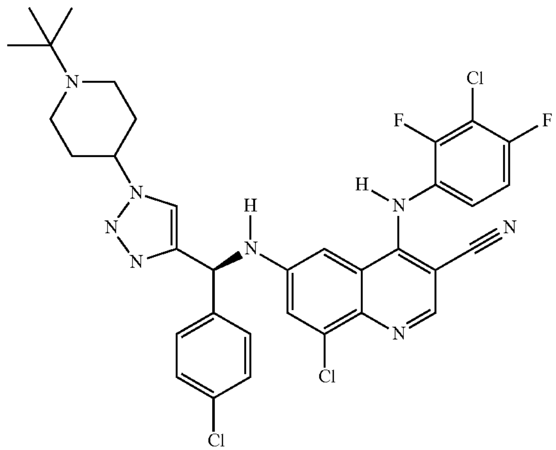 | (S)-6-((((1-(1-(tert-butyl)piperidin-4-yl)-1H-1,2,3-triazol-4-yl)(4-chlorophenyl)methyl)amino)-8-chloro-4-((3-chloro-2,4-difluorophenyl)amino)quinoline-3-carbonitrile | 10 | ES/MS 695.2 (M + H+) |
| 696 | 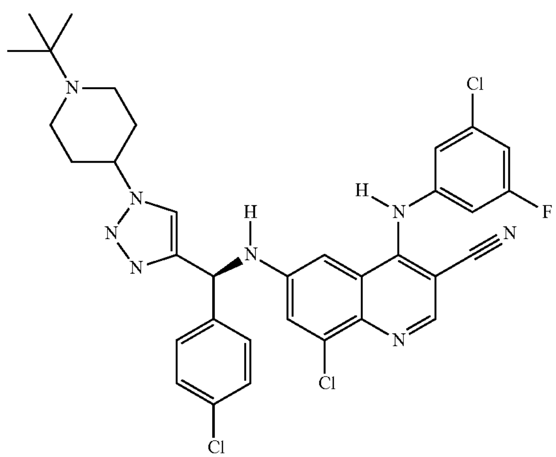 | (S)-6-((((1-(1-(tert-butyl)piperidin-4-yl)-1H-1,2,3-triazol-4-yl)(4-chlorophenyl)methyl)amino)-8-chloro-4-((3-chloro-5-fluorophenyl)amino)quinoline-3-carbonitrile | 10 | ES/MS 677.2 (M + H+) |

TABLE 1-continued

| Compd | Structure | Name | Example/Procedure | ES/MS m/z |
|---|---|---|---|---|
| 697 | 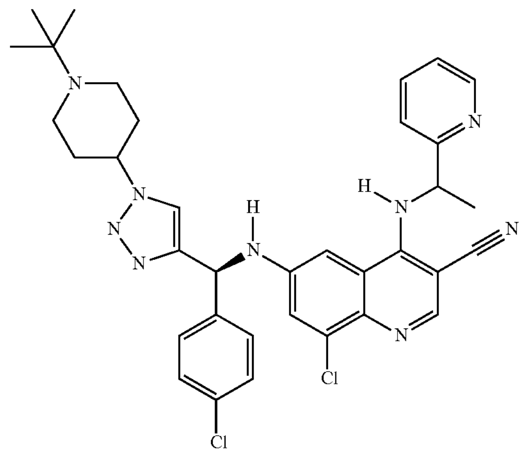 [SMILES: CC(Nc1c(C#N)cnc2c(Cl)cc(N[C@H](C3=CN(C4CCN(C(C)(C)C)CC4)NN3)c3ccc(Cl)cc3)cc12)c1ccccn1] | 6-(((S)-(1-(1-(tert-butyl)piperidin-4-yl)-1H-1,2,3-triazol-4-yl)(4-chlorophenyl)methyl)amino)-8-chloro-4-((1-(pyridin-2-yl)ethyl)amino)quinoline-3-carbonitrile | 1 | ES/MS 655.2 (M + H+) |
| 698 | 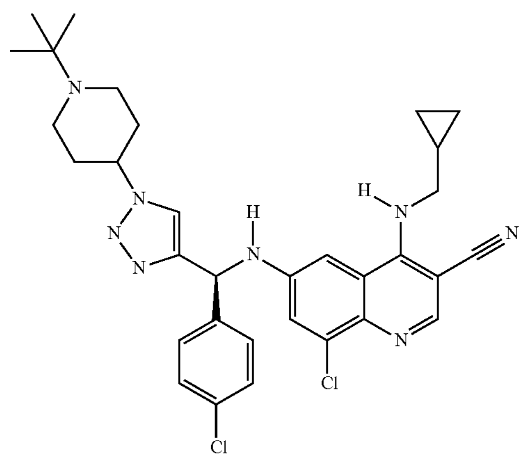 [SMILES: CC(C)(C)N1CCC(N2C=C([C@@H](Nc3cc(Cl)c4ncc(C#N)c(NCC5CC5)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-8-chloro-4-((cyclopropylmethyl)amino)quinoline-3-carbonitrile | 1 | ES/MS 603.2 (M + H+) |

TABLE 1-continued

| Compd | Name | Structure | Example/Procedure | ES/MS m/z |
|---|---|---|---|---|
| 699 | 6-(((S)-(1-(1-(tert-butyl)piperidin-4-yl)-1H-1,2,3-triazol-4-yl)(4-chlorophenyl)methyl)amino)-8-chloro-4-((1-(pyridin-3-yl)ethyl)amino)quinoline-3-carbonitrile | 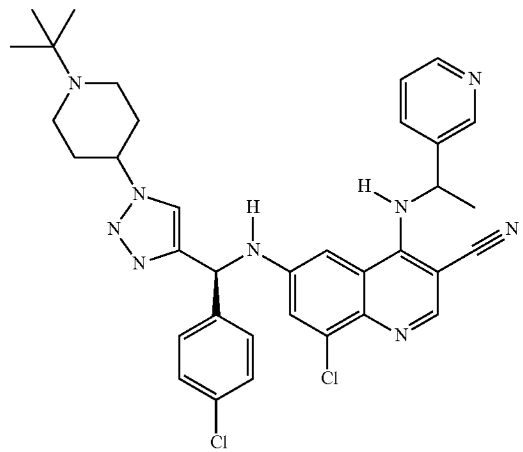 [SMILES: CC(Nc1c(C#N)cnc2c(Cl)cc(N[C@H](C3=CN(C4CCN(C(C)(C)C)CC4)NN3)c3ccc(Cl)cc3)cc12)c1cccnc1] | 1 | ES/MS 654.2 (M + H+) |
| 700 | (S)-8-chloro-4-((3-chloro-4-hydroxyphenyl)amino)-6-(((4-chlorophenyl)(1-(1-(oxetan-3-yl)piperidin-4-yl)-1H-1,2,3-triazol-4-yl)methyl)amino)quinoline-3-carbonitrile | 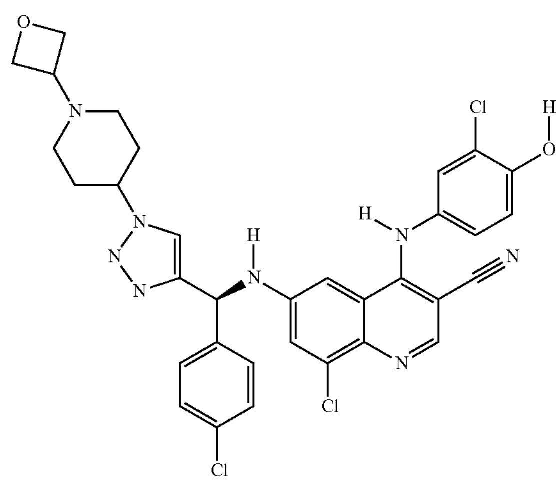 [SMILES: N#Cc1cnc2c(Cl)cc(N[C@H](C3=CN(C4CCN(C5COC5)CC4)NN3)c3ccc(Cl)cc3)cc2c1Nc1ccc(O)c(Cl)c1] | 10 | ES/MS 675.1 (M + H+) |

TABLE 1-continued

| Compd | Structure | Name | Example/Procedure | ES/MS m/z |
|---|---|---|---|---|
| 701 | 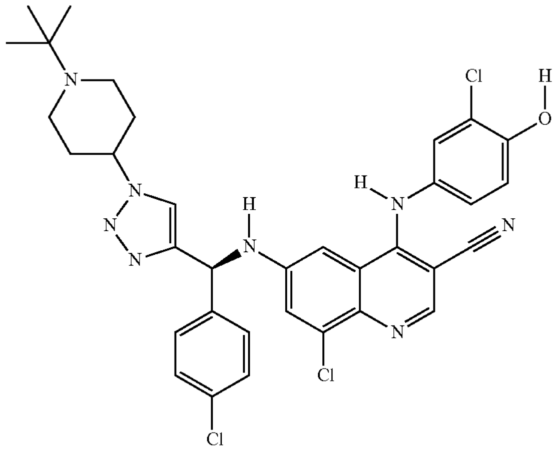 [SMILES: CC(C)(C)N1CCC(N2C=C([C@@H](Nc3cc(Cl)c4ncc(C#N)c(Nc5ccc(O)c(Cl)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-chloro-4-hydroxyphenyl)amino)quinoline-3-carbonitrile | 10 | ES/MS 675.2 (M + H+) |
| 702 | 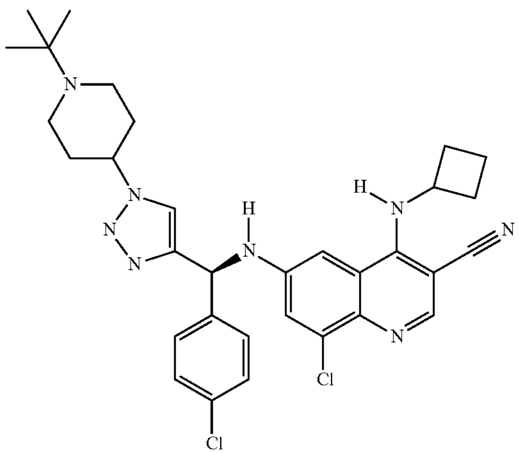 [SMILES: CC(C)(C)N1CCC(N2C=C([C@@H](Nc3cc(Cl)c4ncc(C#N)c(NC5CCC5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-(cyclobutylamino)quinoline-3-carbonitrile | 1 | ES/MS 603.2 (M + H+) |

TABLE 1-continued

| Compd | Structure | Name | Example/Procedure | ES/MS m/z |
|---|---|---|---|---|
| 703 | 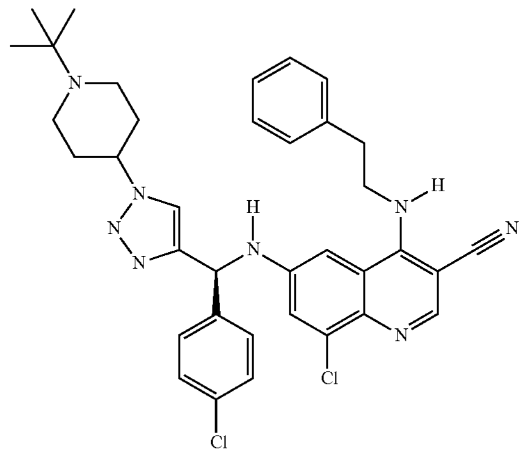 [SMILES: CC(C)(C)N1CCC(N2C=C([C@@H](Nc3cc(Cl)c4ncc(C#N)c(NCCc5ccccc5)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-8-chloro-4-(phenethylamino)quinoline-3-carbonitrile | 1 | ES/MS 653.3 (M + H+) |
| 704 | 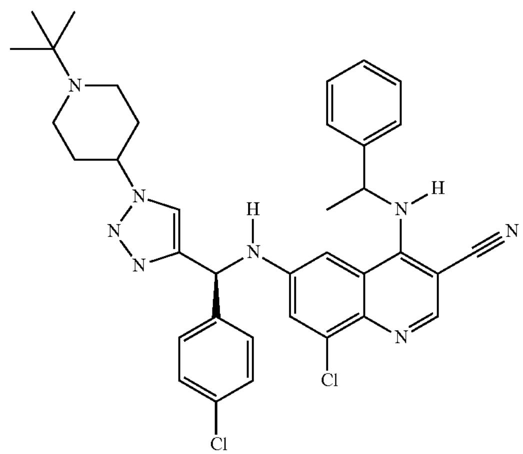 [SMILES: CC(Nc1c(C#N)cnc2c(Cl)cc(N[C@H](C3=CN(C4CCN(C(C)(C)C)CC4)NN3)c3ccc(Cl)cc3)cc12)c1ccccc1] | 6-(((S)-(1-(1-(tert-butyl)piperidin-4-yl)-1H-1,2,3-triazol-4-yl)(4-chlorophenyl)methyl)amino)-8-chloro-4-(((R)-1-phenylethyl)amino)quinoline-3-carbonitrile | 1 | ES/MS 653.3 (M + H+) |

TABLE 1-continued

| Compd | Structure | Name | Example/Procedure | ES/MS m/z |
|---|---|---|---|---|
| 705 | 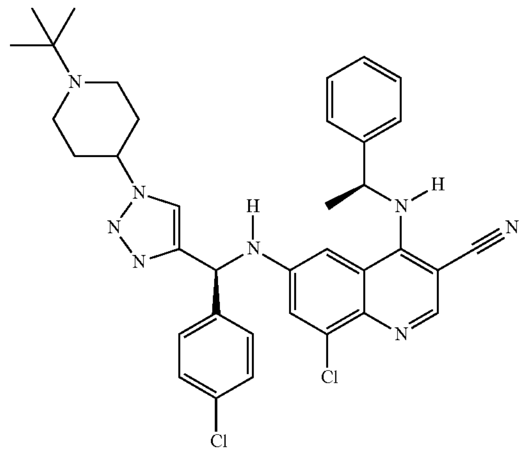 [SMILES: C[C@H](Nc1c(C#N)cnc2c(Cl)cc(N[C@H](C3=CN(C4CCN(C(C)(C)C)CC4)NN3)c3ccc(Cl)cc3)cc12)c1ccccc1] | 6-(((S)-(1-(1-(tert-butyl)piperidin-4-yl)-1H-1,2,3-triazol-4-yl)(4-chlorophenyl)methyl)amino)-8-chloro-4-(((S)-1-phenylethyl)amino)quinoline-3-carbonitrile | 1 | ES/MS 653.3 (M + H+) |
| 706 | 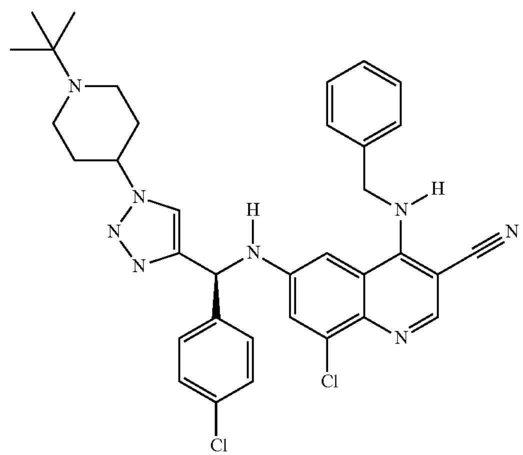 [SMILES: CC(C)(C)N1CCC(N2C=C([C@@H](Nc3cc(Cl)c4ncc(C#N)c(NCc5ccccc5)c4c3)c3ccc(Cl)cc3)NN2)CC1] | (S)-4-(benzylamino)-6-(((1-(1-(tert-butyl)piperidin-4-yl)-1H-1,2,3-triazol-4-yl)(4-chlorophenyl)methyl)amino)-8-chloroquinoline-3-carbonitrile | 1 | ES/MS 639.3 (M + H+) |

TABLE 1-continued

| Compd | Structure | Name | Example/Procedure | ES/MS m/z |
|---|---|---|---|---|
| 707 | 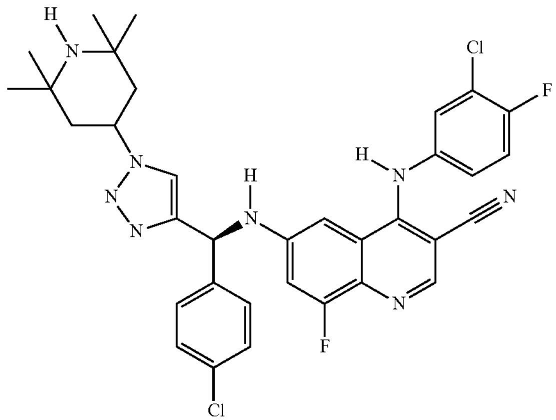 [SMILES: CC1(C)CC(N2C=C([C@@H](Nc3cc(F)c4ncc(C#N)c(Nc5ccc(F)c(Cl)c5)c4c3)c3ccc(Cl)cc3)NN2)CC(C)(C)N1] | (S)-4-((3-chloro-4-fluorophenyl)amino)-6-(((4-chlorophenyl)(1-(2,2,6,6-tetramethylpiperidin-4-yl)-1H-1,2,3-triazol-4-yl)methyl)amino)-8-fluoroquinoline-3-carbonitrile | 10 | ES/MS 661.2 (M + H+) |
| 708 | 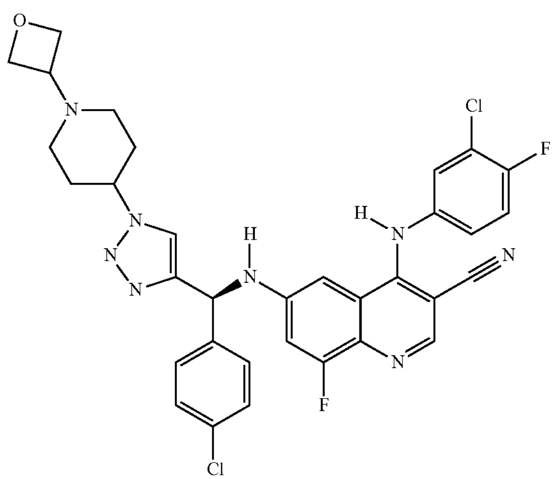 [SMILES: N#Cc1cnc2c(F)cc(N[C@H](C3=CN(C4CCN(C5COC5)CC4)NN3)c3ccc(Cl)cc3)cc2c1Nc1ccc(F)c(Cl)c1] | (S)-4-((3-chloro-4-fluorophenyl)amino)-6-(((4-chlorophenyl)(1-(1-(oxetan-3-yl)piperidin-4-yl)-1H-1,2,3-triazol-4-yl)methyl)amino)-8-fluoroquinoline-3-carbonitrile | 10 | ES/MS 661.1 (M + H+) |

TABLE 1-continued

| Compd | Structure | Name | Example/Procedure | ES/MS m/z |
|---|---|---|---|---|
| 709 | 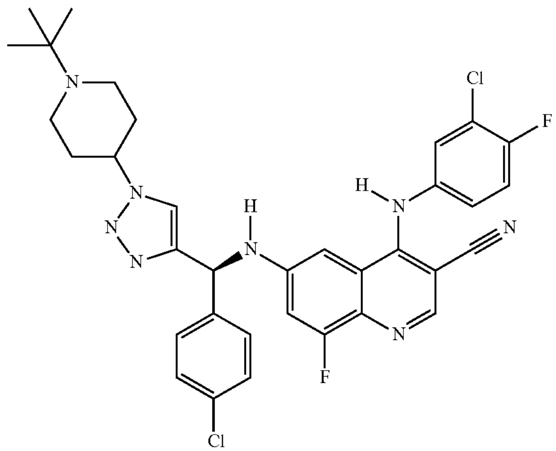 [SMILES: CC(C)(C)N1CCC(N2C=C([C@@H](Nc3cc(F)c4ncc(C#N)c(Nc5ccc(F)c(Cl)c5)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-4-((3-chloro-4-fluorophenyl)amino)-8-fluoroquinoline-3-carbonitrile | 10 | ES/MS 661.1 (M + H+) |
| 710 | 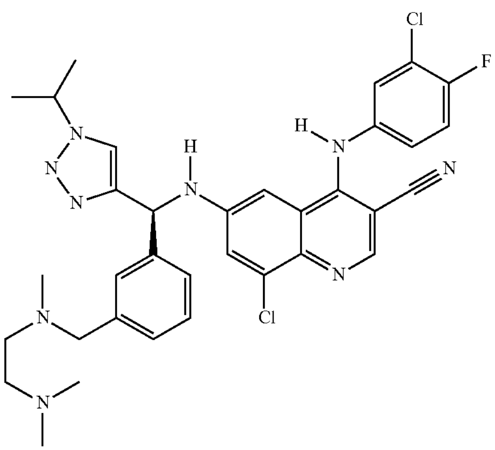 | (S)-8-chloro-4-((3-chloro-4-fluorophenyl)amino)-6-(((3-(((2-(dimethylamino)ethyl)(methyl)amino)methyl)phenyl)(1-isopropyl-1H-1,2,3-triazol-4-yl)methyl)amino)quinoline-3-carbonitrile | 18 | ES/MS 660.0 (M + H+) |

TABLE 1-continued

| Compd | Structure | Name | Example/Procedure | ES/MS m/z |
|---|---|---|---|---|
| 711 | 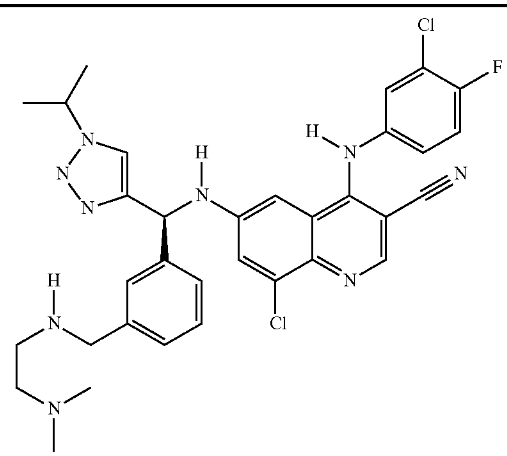 | (S)-8-chloro-4-((3-chloro-4-fluorophenyl)amino)-6-(((3-(((2-(dimethylamino)ethyl)amino)methyl)-phenyl)(1-isopropyl-1H-1,2,3-triazol-4-yl)methyl)amino)quinoline-3-carbonitrile | 18 | ES/MS 646.0 (M + H+) |
| 712 | 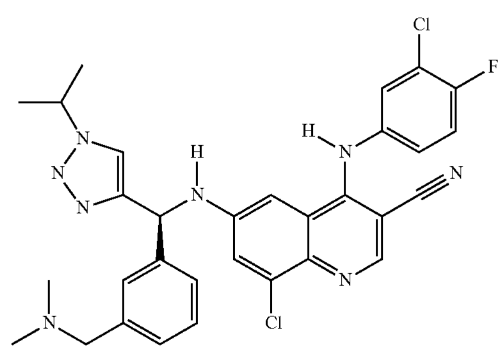 [SMILES: CC(C)N1C=C([C@@H](Nc2cc(Cl)c3ncc(C#N)c(Nc4ccc(F)c(Cl)c4)c3c2)c2cccc(CN(C)C)c2)NN1] | (S)-8-chloro-4-((3-chloro-4-fluorophenyl)amino)-6-(((3-(((dimethylamino)methyl)phenyl)(1-isopropyl-1H-1,2,3-triazol-4-yl)methyl)amino)quinoline-3-carbonitrile | 18 | ES/MS 602.8 (M + H+) |

TABLE 1-continued

| Compd | Structure | Name | Example/Procedure | ES/MS m/z |
|---|---|---|---|---|
| 713 | 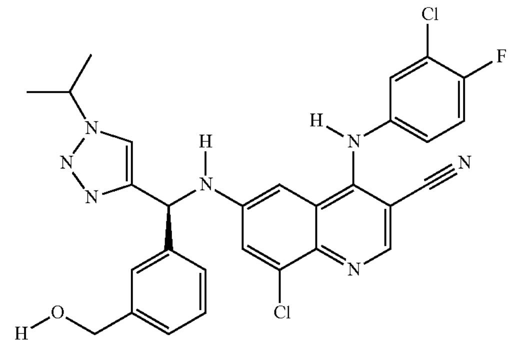 [SMILES: CC(C)N1C=C([C@@H](Nc2cc(Cl)c3ncc(C#N)c(Nc4ccc(F)c(Cl)c4)c3c2)c2cccc(CO)c2)NN1] | (S)-8-chloro-4-((3-chloro-4-fluorophenyl)amino)-6-(((3-(hydroxymethyl)phenyl)(1-isopropyl-1H-1,2,3-triazol-4-yl)methyl)amino)quinoline-3-carbonitrile | 17 | ES/MS 576.2 (M + H+) |
| 714 | 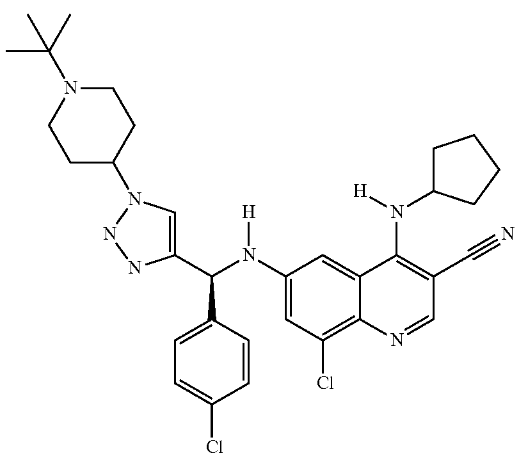 [SMILES: CC(C)(C)N1CCC(N2C=C([C@@H](Nc3cc(Cl)c4ncc(C#N)c(NC5CCCC5)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-8-chloro-4-(cyclopentylamino)quinoline-3-carbonitrile | 1 | ES/MS 617.3 (M + H+) |

TABLE 1-continued

| Compd | Structure | Name | Example/Procedure | ES/MS m/z |
|---|---|---|---|---|
| 715 | 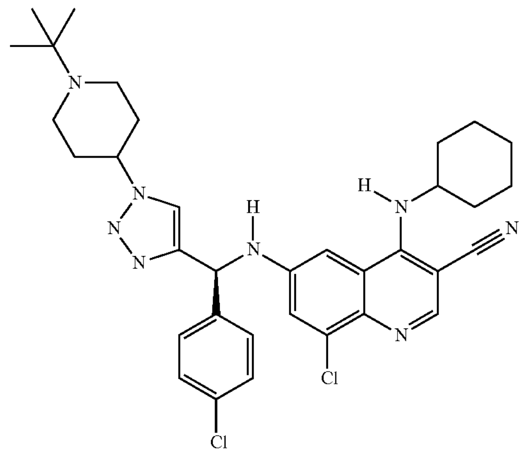 [SMILES: CC(C)(C)N1CCC(N2C=C([C@@H](Nc3cc(Cl)c4ncc(C#N)c(NC5CCCCC5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-(cyclohexylamino)quinoline-3-carbonitrile | 1 | ES/MS 631.3 (M + H+) |
| 716 | 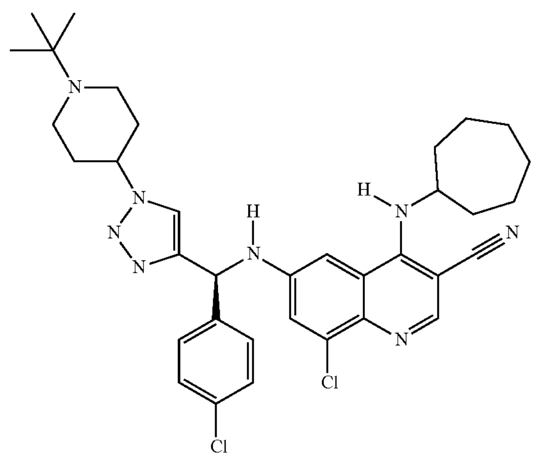 [SMILES: CC(C)(C)N1CCC(N2C=C([C@@H](Nc3cc(Cl)c4ncc(C#N)c(NC5CCCCCC5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-(cycloheptylamino)quinoline-3-carbonitrile | 1 | ES/MS 645.3 (M + H+) |

TABLE 1-continued
| Compd | Structure | Name | Example/Procedure | ES/MS m/z |
|---|---|---|---|---|
| 717 | 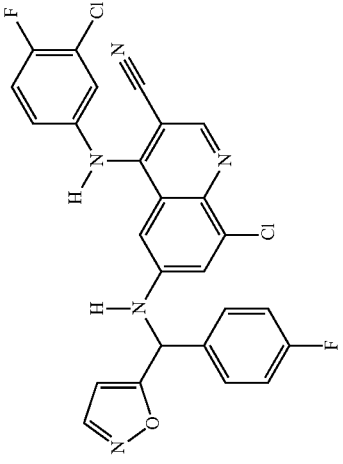 | 8-chloro-4-((3-chloro-4-fluorophenyl)amino)-6-(((4-fluorophenyl)(isoxazol-5-yl)methyl)amino)quinoline-3-carbonitrile | 7 | ES/MS 522.1 (M + H+) |
| 718 | 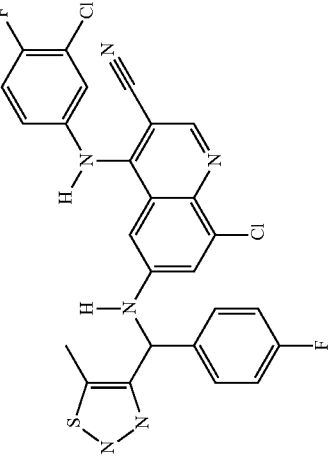 | 8-chloro-4-((3-chloro-4-fluorophenyl)amino)-6-(((4-fluorophenyl)(5-methyl-1,2,3-thiadiazol-4-yl)methyl)amino)quinoline-3-carbonitrile | 7 | ES/MS 553.0 (M + H+) |

TABLE 1-continued

| Compd | Structure | Name | Example/Procedure | ES/MS m/z |
|---|---|---|---|---|
| 719 | 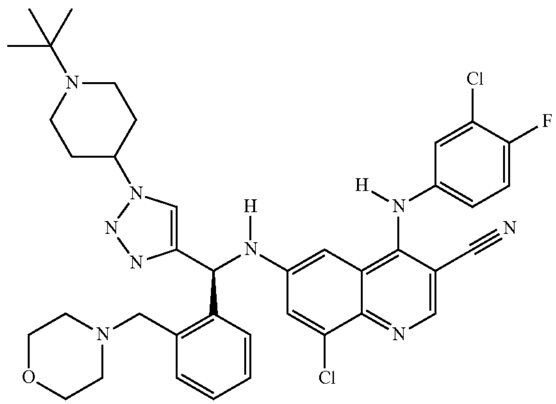 [SMILES: CC(C)(C)N1CCC(N2C=C([C@@H](Nc3cc(Cl)c4ncc(C#N)c(Nc5ccc(F)c(Cl)c5)c4c3)c3ccccc3CN3CCOCC3)NN2)CC1] | (S)-6-(((1-(1-(tert-butyl)piperidin-4-yl)-1H-1,2,3-triazol-4-yl)(2-(morpholinomethyl)phenyl)methyl)amino)-8-chloro-4-((3-chloro-4-fluorophenyl)amino)quinoline-3-carbonitrile | 18 | ES/MS 742.2 (M + H+) |
| 720 | 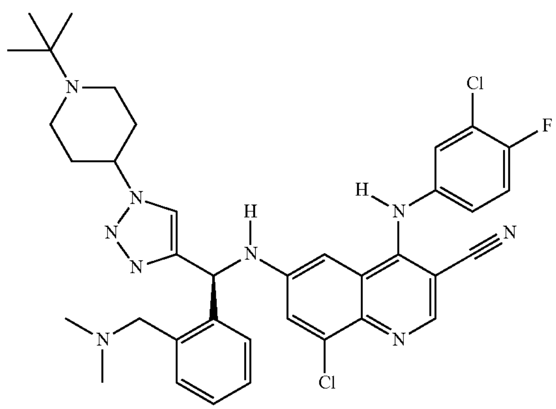 [SMILES: CN(C)Cc1ccccc1[C@H](Nc1cc(Cl)c2ncc(C#N)c(Nc3ccc(F)c(Cl)c3)c2c1)C1=CN(C2CCN(C(C)(C)C)CC2)NN1] | (S)-6-(((1-(1-(tert-butyl)piperidin-4-yl)-1H-1,2,3-triazol-4-yl)(2-((dimethylamino)methyl)phenyl)methyl)amino)-8-chloro-4-((3-chloro-4-fluorophenyl)amino)quinoline-3-carbonitrile | 18 | ES/MS 700.3 (M + H+) |

TABLE 1-continued

| Compd | Structure | Name | Example/Procedure | ES/MS m/z |
|---|---|---|---|---|
| 721 | 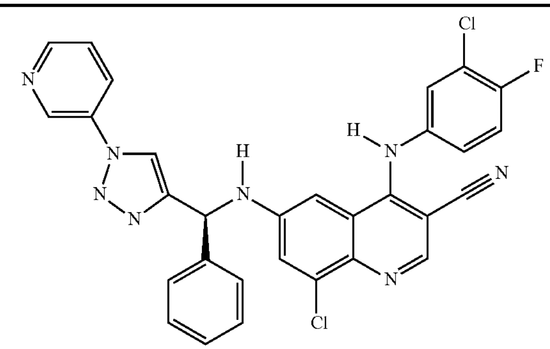 | (S)-8-chloro-4-((3-chloro-4-fluorophenyl)amino)-6-((phenyl(1-(pyridin-3-yl)-1H-1,2,3-triazol-4-yl)methyl)amino)quinoline-3-carbonitrile | 3 | ES/MS 581.0 (M + H+) |
| 722 | 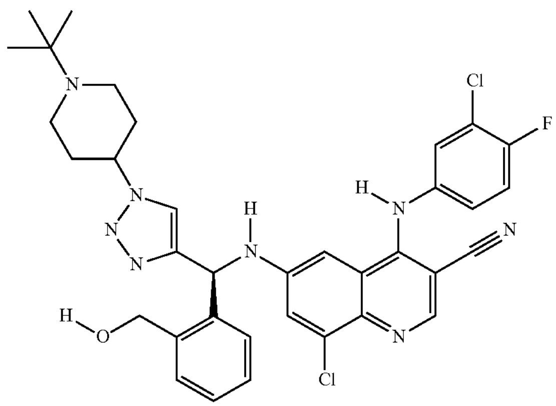 [SMILES: CC(C)(C)N1CCC(N2C=C([C@@H](Nc3cc(Cl)c4ncc(C#N)c(Nc5ccc(F)c(Cl)c5)c4c3)c3ccccc3CO)NN2)CC1] | (S)-6-(((1-(1-(tert-butyl)piperidin-4-yl)-1H-1,2,3-triazol-4-yl)(2-(hydroxymethyl)phenyl)methyl)amino)-8-chloro-4-((3-chloro-4-fluorophenyl)amino)quinoline-3-carbonitrile | 17 | ES/MS 673.1 (M + H+) |

TABLE 1-continued
| Compd | Structure | Name | Example/Procedure | ES/MS m/z |
|---|---|---|---|---|
| 723 | 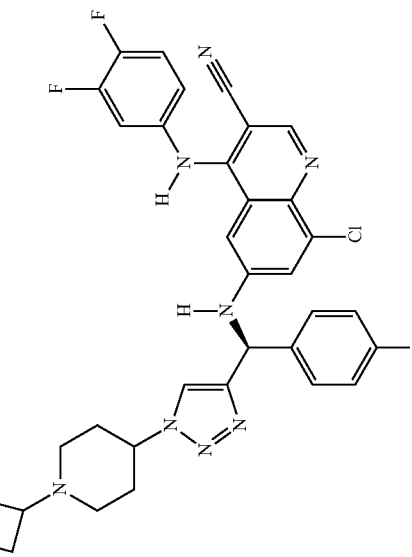 | (S)-8-chloro-6-(((4-chlorophenyl)(1-(1-(oxetan-3-yl)piperidin-4-yl)-1H-1,2,3-triazol-4-yl)methyl)amino)-4-((3,4-difluorophenyl)amino)quinoline-3-carbonitrile | 10 | ES/MS 661.2 (M + H+) |
| 724 | 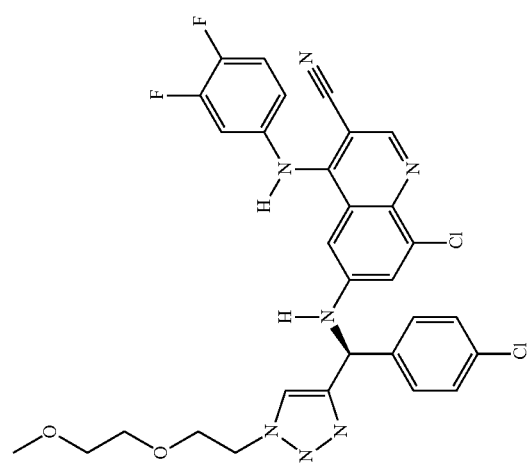 | (S)-8-chloro-6-(((4-chlorophenyl)(1-(2-(2-methoxyethoxy)ethyl)-1H-1,2,3-triazol-4-yl)methyl)amino)-4-((3,4-difluorophenyl)amino)quinoline-3-carbonitrile | 10 | ES/MS 624.1 (M + H+) |

TABLE 1-continued

| Compd | Structure | Name | Example/Procedure | ES/MS m/z |
|---|---|---|---|---|
| 725 | 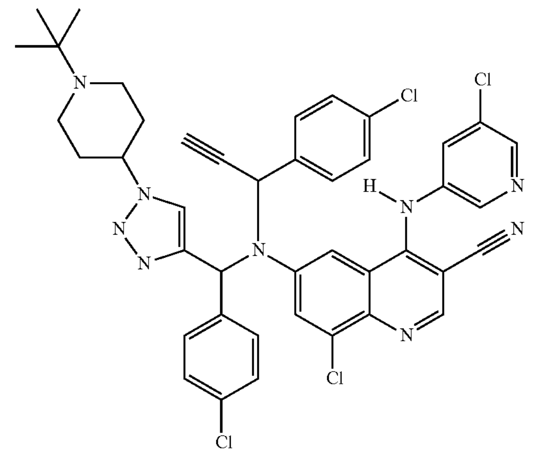 [SMILES: C#CC(c1ccc(Cl)cc1)N(c1cc(Cl)c2ncc(C#N)c(Nc3cncc(Cl)c3)c2c1)C(C1=CN(C2CCN(C(C)(C)C)CC2)NN1)c1ccc(Cl)cc1] | 6-(((1-(1-(tert-butyl)piperidin-4-yl)-1H-1,2,3-triazol-4-yl)(4-chlorophenyl)methyl)(1-(4-chlorophenyl)prop-2-yn-1-yl)amino)-8-chloro-4-((5-chloropyridin-3-yl)amino)quinoline-3-carbonitrile | 10 | ES/MS 808.2 (M + H+) |
| 726 | 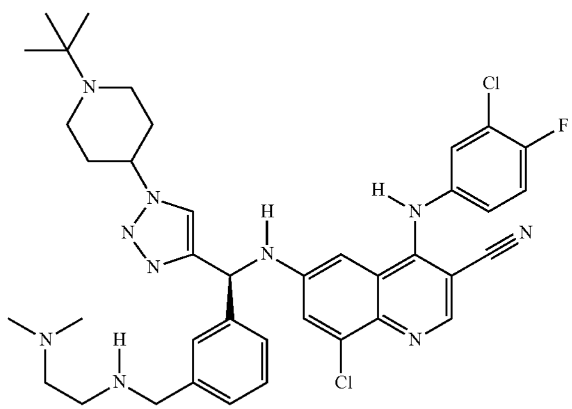 [SMILES: CN(C)CCNCc1cccc([C@H](Nc2cc(Cl)c3ncc(C#N)c(Nc4ccc(F)c(Cl)c4)c3c2)C2=CN(C3CCN(C(C)(C)C)CC3)NN2)c1] | (S)-6-((((1-(1-(tert-butyl)piperidin-4-yl)-1H-1,2,3-triazol-4-yl)(3-(((2-(dimethylamino)ethyl)amino)methyl)phenyl)methyl)amino)-8-chloro-4-((3-chloro-4-fluorophenyl)amino)quinoline-3-carbonitrile | 18 | ES/MS 743.2 (M + H+) |

TABLE 1-continued
| Compd | Structure | Name | Example/Procedure | ES/MS m/z |
|---|---|---|---|---|
| 727 | 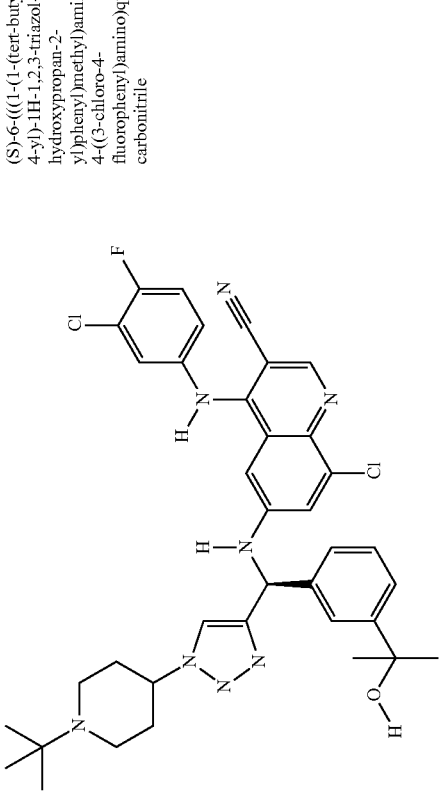 | (S)-6-((((1-(1-(tert-butyl)piperidin-4-yl)-1H-1,2,3-triazol-4-yl)(3-(2-hydroxypropan-2-yl)phenyl)methyl)amino)-8-chloro-4-((3-chloro-4-fluorophenyl)amino)quinoline-3-carbonitrile | 22 | ES/MS 701.1 (M + H+) |
| 728 | 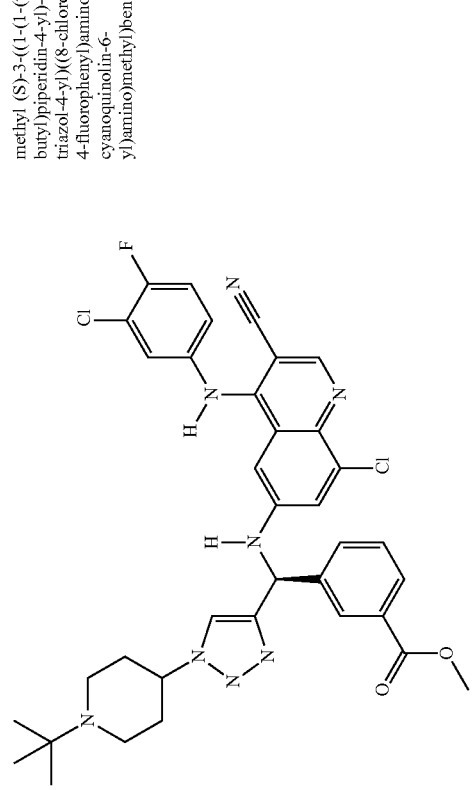 | methyl (S)-3-(1-(1-(tert-butyl)piperidin-4-yl)-1H-1,2,3-triazol-4-yl)(8-chloro-4-((3-chloro-4-fluorophenyl)amino)-3-cyanoquinolin-6-yl)amino)methyl)benzoate | 3 | ES/MS 701.2 (M + H+) |

TABLE 1-continued

| Compd | Structure | Name | Example/Procedure | ES/MS m/z |
|---|---|---|---|---|
| 729 | 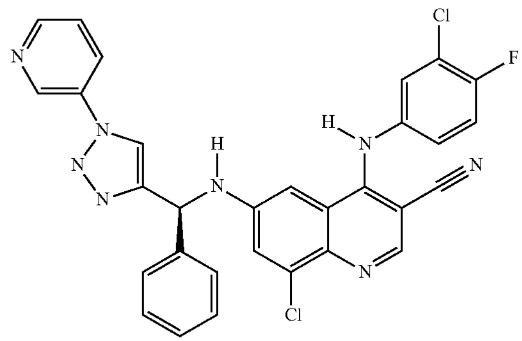 [SMILES: N#Cc1cnc2c(Cl)cc(N[C@H](C3=CN(c4cccnc4)NN3)c3ccccc3)cc2c1Nc1ccc(F)c(Cl)c1] | (S)-8-chloro-4-((3-chloro-4-fluorophenyl)amino)-6-((phenyl(1-(pyridin-2-yl)methyl)-1H-1,2,3-triazol-4-yl)methyl)amino)quinoline-3-carbonitrile | 3 | ES/MS 595.0 (M + H+) |
| 730 | 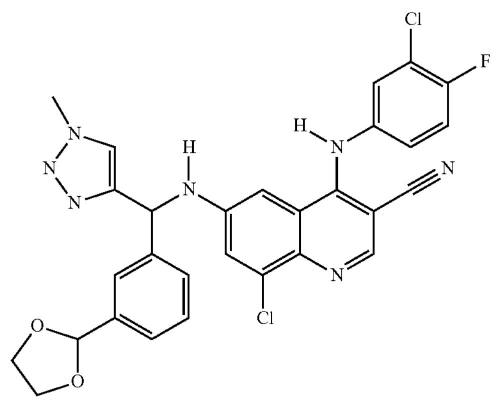 [SMILES: CN1C=C(C(Nc2cc(Cl)c3ncc(C#N)c(Nc4ccc(F)c(Cl)c4)c3c2)c2cccc(C3OCCO3)c2)NN1] | 6-(((3-(1,3-dioxolan-2-yl)phenyl)(1-methyl-1H-1,2,3-triazol-4-yl)methyl)amino)-8-chloro-4-((3-chloro-4-fluorophenyl)amino)quinoline-3-carbonitrile | 6 | ES/MS 590.1 (M + H+) |

TABLE 1-continued

| Compd | Structure | Name | Example/Procedure | ES/MS m/z |
|---|---|---|---|---|
| 731 | 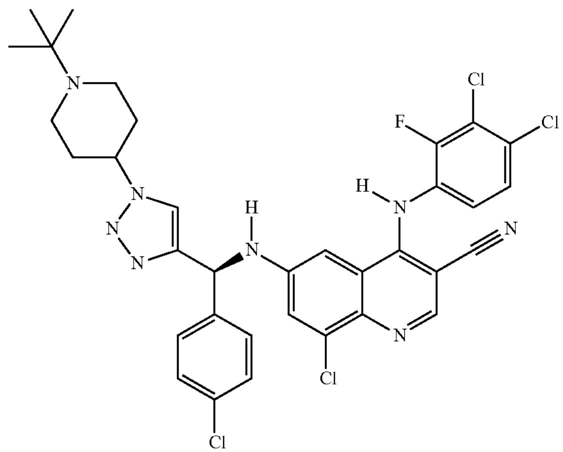 [SMILES: CC(C)(C)N1CCC(N2C=C([C@@H](Nc3cc(Cl)c4ncc(C#N)c(Nc5ccc(Cl)c(Cl)c5F)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3,4-dichloro-2-fluorophenyl)amino)quinoline-3-carbonitrile | 10 | ES/MS 711.1 (M + H+) |
| 732 | 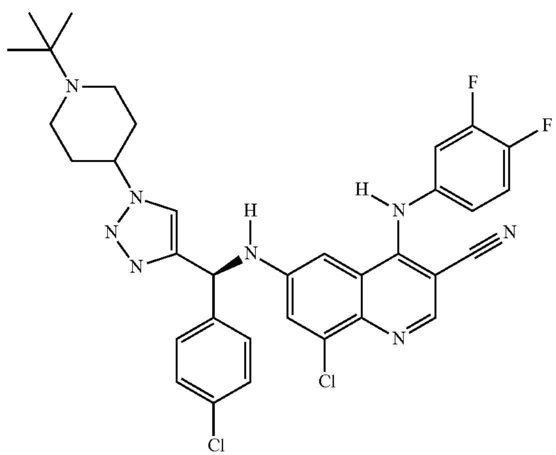 [SMILES: CC(C)(C)N1CCC(N2C=C([C@@H](Nc3cc(Cl)c4ncc(C#N)c(Nc5ccc(F)c(F)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3,4-difluorophenyl)amino)quinoline-3-carbonitrile | 10 | ES/MS 661.2 (M + H+) |

TABLE 1-continued
| Compd | Name | Structure | Example/Procedure | ES/MS m/z |
|---|---|---|---|---|
| 733 | (S)-6-((((1-(1-(tert-butyl)piperidin-4-yl)-1H-1,2,3-triazol-4-yl)(3-(morpholinomethyl)phenyl)methyl)amino)-8-chloro-4-((3-chloro-4-fluorophenyl)amino)quinoline-3-carbonitrile | 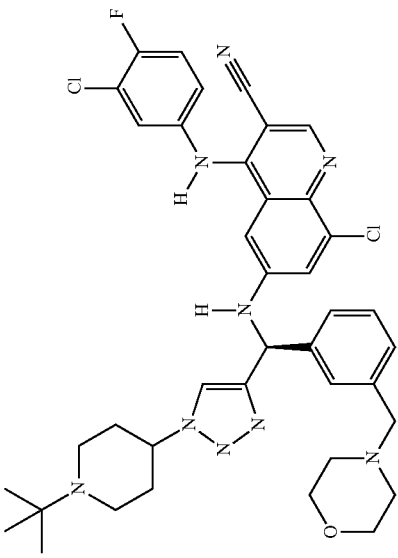 | 18 | ES/MS 744.0 (M + H+) |
| 734 | 8-chloro-4-((3-chloro-4-fluorophenyl)amino)-6-(((4-fluorophenyl)(5-methyl-1,3,4-oxadiazol-2-yl)methyl)amino)quinoline-3-carbonitrile | 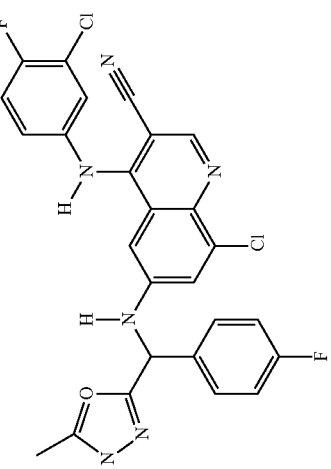 | 7 | ES/MS 537.0 (M + H+) |

TABLE 1-continued

| Compd | Structure | Name | Example/Procedure | ES/MS m/z |
|---|---|---|---|---|
| 735 | 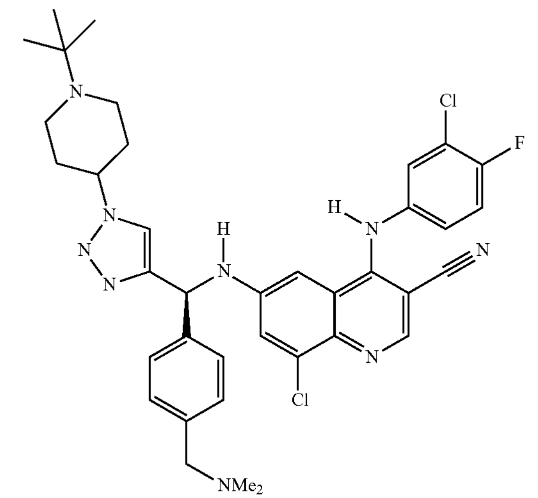 [SMILES: CN(C)Cc1ccc([C@H](Nc2cc(Cl)c3ncc(C#N)c(Nc4ccc(F)c(Cl)c4)c3c2)C2=CN(C3CCN(C(C)(C)C)CC3)NN2)cc1] | (S)-6-((((1-(1-(tert-butyl)piperidin-4-yl)-1H-1,2,3-triazol-4-yl)(4-(((dimethylamino)methyl)phenyl)-methyl)amino)-8-chloro-4-((3-chloro-4-fluorophenyl)amino)quinoline-3-carbonitrile | 3 | ES/MS 700.1 (M + H+) |
| 736 | 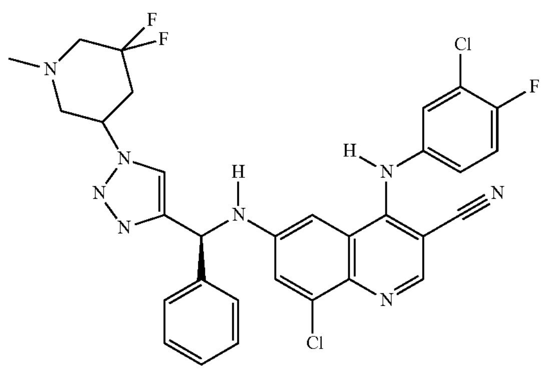 [SMILES: CN1CC(N2C=C([C@@H](Nc3cc(Cl)c4ncc(C#N)c(Nc5ccc(F)c(Cl)c5)c4c3)c3ccccc3)NN2)CC(F)(F)C1] | 8-chloro-4-((3-chloro-4-fluorophenyl)amino)-6-(((1S)-(1-(5,5-difluoro-1-methylpiperidin-3-yl))-1H-1,2,3-triazol-4-yl)(phenyl)methyl)amino)quinoline-3-carbonitrile | 5 | ES/MS 637.1 (M + H+) |

TABLE 1-continued

| Compd | Structure | Name | Example/Procedure | ES/MS m/z |
|---|---|---|---|---|
| 737 | 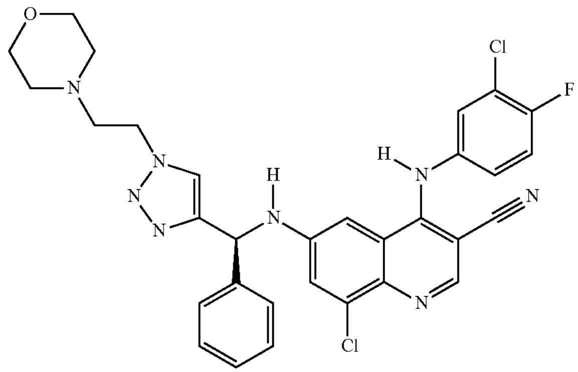 [SMILES: N#Cc1cnc2c(Cl)cc(N[C@H](C3=CN(CCN4CCOCC4)NN3)c3ccccc3)cc2c1Nc1ccc(F)c(Cl)c1] | (S)-8-chloro-4-((3-chloro-4-fluorophenyl)amino)-6-(((1-(2-morpholinoethyl)-1H-1,2,3-triazol-4-yl)(phenyl)methyl)amino)quinoline-3-carbonitrile | 3 | ES/MS 617.0 (M + H+) |
| 738 | 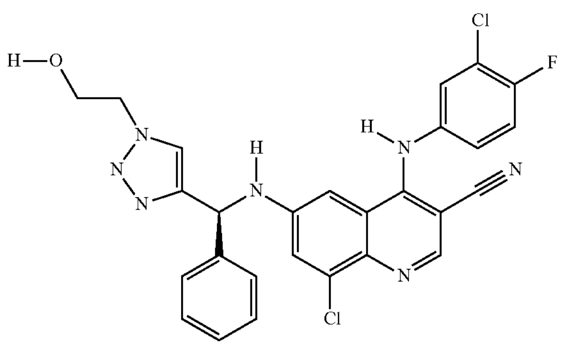 | (S)-8-chloro-4-((3-chloro-4-fluorophenyl)amino)-6-(((1-(2-hydroxyethyl)-1H-1,2,3-triazol-4-yl)(phenyl)methyl)amino)quinoline-3-carbonitrile | 3 | ES/MS 548.1 (M + H+) |

TABLE 1-continued

| Compd | Structure | Name | Example/Procedure | ES/MS m/z |
|---|---|---|---|---|
| 739 | 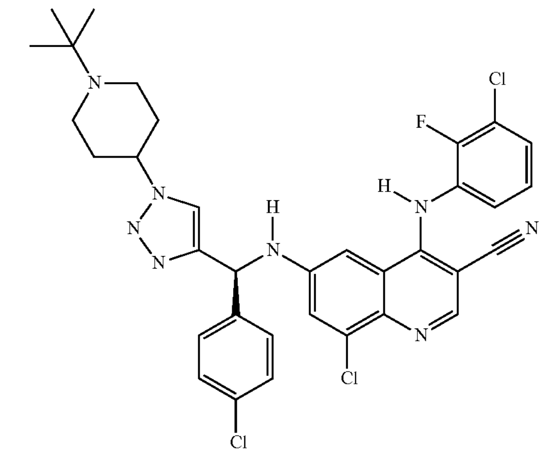 [SMILES: CC(C)(C)N1CCC(N2C=C([C@@H](Nc3cc(Cl)c4ncc(C#N)c(Nc5cccc(Cl)c5F)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-chloro-2-fluorophenyl)amino)quinoline-3-carbonitrile | 10 | ES/MS 677.1 (M + H+) |
| 740 | 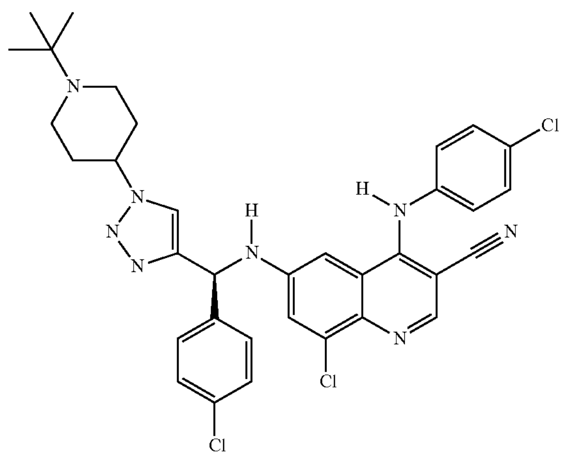 [SMILES: CC(C)(C)N1CCC(N2C=C([C@@H](Nc3cc(Cl)c4ncc(C#N)c(Nc5ccc(Cl)cc5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((4-chlorophenyl)amino)quinoline-3-carbonitrile | 10 | ES/MS 661.2 (M + H+) |

TABLE 1-continued

| Compd | Structure | Name | Example/Procedure | ES/MS m/z |
|---|---|---|---|---|
| 741 | 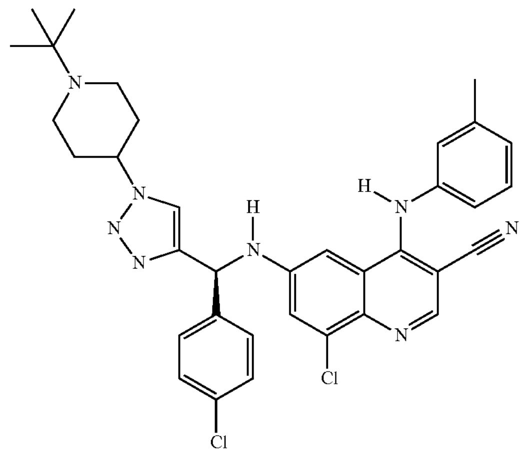 [SMILES: Cc1cccc(Nc2c(C#N)cnc3c(Cl)cc(N[C@H](C4=CN(C5CCN(C(C)(C)C)CC5)NN4)c4ccc(Cl)cc4)cc23)c1] | (S)-6-(((1-(1-(tert-butyl)piperidin-4-yl)-1H-1,2,3-triazol-4-yl)(4-chlorophenyl)methyl)amino)-8-chloro-4-(m-tolylamino)quinoline-3-carbonitrile | 10 | ES/MS 639.2 (M + H+) |
| 742 | 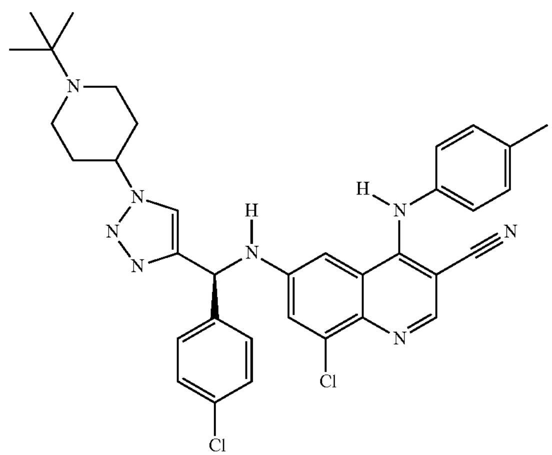 [SMILES: Cc1ccc(Nc2c(C#N)cnc3c(Cl)cc(N[C@H](C4=CN(C5CCN(C(C)(C)C)CC5)NN4)c4ccc(Cl)cc4)cc23)cc1] | (S)-6-(((1-(1-(tert-butyl)piperidin-4-yl)-1H-1,2,3-triazol-4-yl)(4-chlorophenyl)methyl)amino)-8-chloro-4-(p-tolylamino)quinoline-3-carbonitrile | 10 | ES/MS 639.2 (M + H+) |

TABLE 1-continued

| Compd | Structure | Name | Example/Procedure | ES/MS m/z |
|---|---|---|---|---|
| 743 | 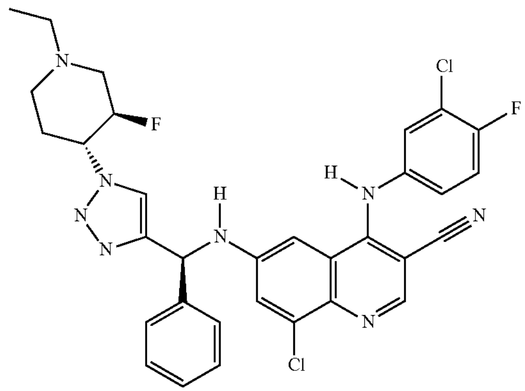 [SMILES: CCN1CC[C@@H](N2C=C([C@@H](Nc3cc(Cl)c4ncc(C#N)c(Nc5ccc(F)c(Cl)c5)c4c3)c3ccccc3)NN2)[C@H](F)C1] | 8-chloro-4-((3-chloro-4-fluorophenyl)amino)-6-(((S)-(1-((3R,4R)-1-ethyl-3-fluoropiperidin-4-yl)-1H-1,2,3-triazol-4-yl)(phenyl)methyl)amino)quinoline-3-carbonitrile | 5 | ES/MS 633.1 (M + H+) |
| 744 | 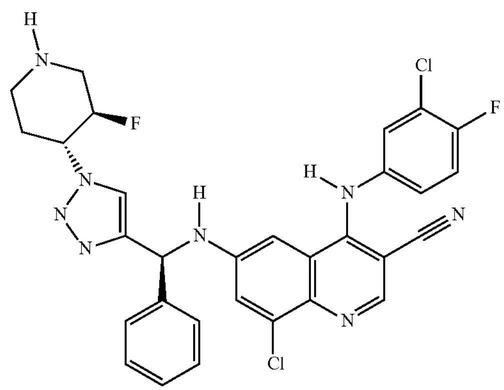 [SMILES: N#Cc1cnc2c(Cl)cc(N[C@H](C3=CN([C@@H]4CCNC[C@H]4F)NN3)c3ccccc3)cc2c1Nc1ccc(F)c(Cl)c1] | 8-chloro-4-((3-chloro-4-fluorophenyl)amino)-6-(((S)-(1-((3R,4R)-3-fluoropiperidin-4-yl)-1H-1,2,3-triazol-4-yl)(phenyl)methyl)amino)quinoline-3-carbonitrile | 5 | ES/MS 605.0 (M + H+) |

TABLE 1-continued

| Compd | Structure | Name | Example/Procedure | ES/MS m/z |
|---|---|---|---|---|
| 745 | 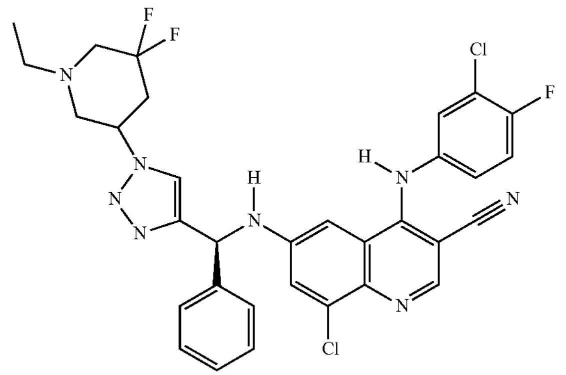 [SMILES: CCN1CC(N2C=C([C@@H](Nc3cc(Cl)c4ncc(C#N)c(Nc5ccc(F)c(Cl)c5)c4c3)c3ccccc3)NN2)CC(F)(F)C1] | 8-chloro-4-((3-chloro-4-fluorophenyl)amino)-6-(((1S)-(1-(1-ethyl-5,5-difluoropiperidin-3-yl)-1H-1,2,3-triazol-4-yl)(phenyl)methyl)amino)quinoline-3-carbonitrile | 5 | ES/MS 651.0 (M + H+) |
| 746 | 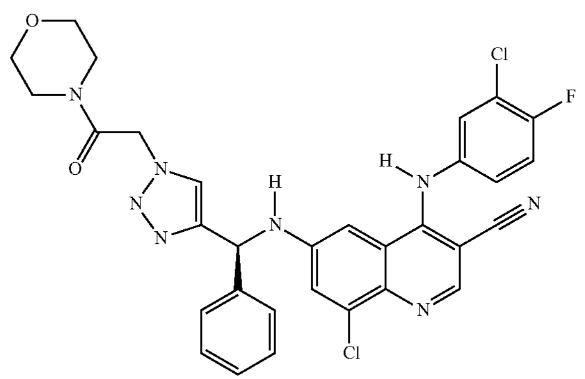 [SMILES: N#Cc1cnc2c(Cl)cc(N[C@H](C3=CN(CC(=O)N4CCOCC4)NN3)c3ccccc3)cc2c1Nc1ccc(F)c(Cl)c1] | (S)-8-chloro-4-((3-chloro-4-fluorophenyl)amino)-6-(((1-(2-morpholino-2-oxoethyl)-1H-1,2,3-triazol-4-yl)(phenyl)methyl)amino)quinoline-3-carbonitrile | 3 | ES/MS 631.1 (M + H+) |

TABLE 1-continued

| Compd | Structure | Name | Example/Procedure | ES/MS m/z |
|---|---|---|---|---|
| 747 | 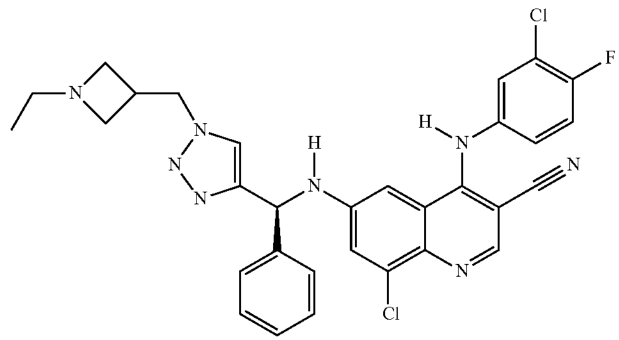 [SMILES: CCN1CC(CN2C=C([C@@H](Nc3cc(Cl)c4ncc(C#N)c(Nc5ccc(F)c(Cl)c5)c4c3)c3ccccc3)NN2)C1] | (S)-8-chloro-4-((3-chloro-4-fluorophenyl)amino)-6-(((1-((1-ethylazetidin-3-yl)methyl)-1H-1,2,3-triazol-4-yl)(phenyl)methyl)amino)quinoline-3-carbonitrile | 5 | ES/MS 601.1 (M + H+) |
| 748 | 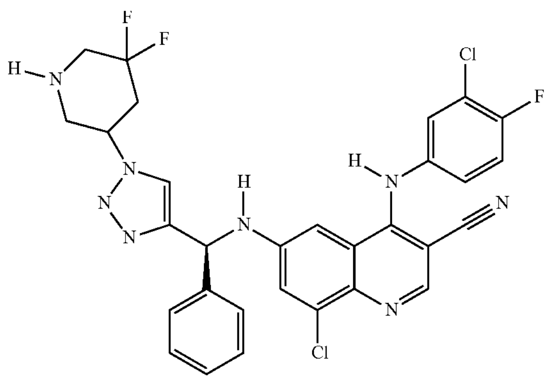 [SMILES: N#Cc1cnc2c(Cl)cc(N[C@H](C3=CN(C4CNCC(F)(F)C4)NN3)c3ccccc3)cc2c1Nc1ccc(F)c(Cl)c1] | 8-chloro-4-((3-chloro-4-fluorophenyl)amino)-6-(((1S)-(1-(5,5-difluoropiperidin-3-yl)-1H-1,2,3-triazol-4-yl)(phenyl)methyl)amino)quinoline-3-carbonitrile | 5 | |

TABLE 1-continued

| Compd | Structure | Name | Example/Procedure | ES/MS m/z |
|---|---|---|---|---|
| 749 | 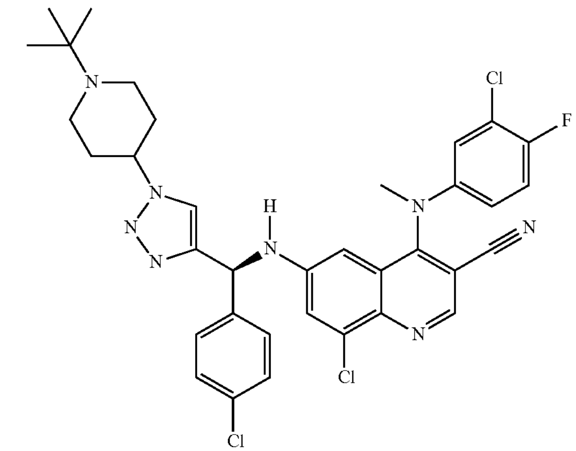 [SMILES: CN(c1ccc(F)c(Cl)c1)c1c(C#N)cnc2c(Cl)cc(N[C@H](C3=CN(C4CCN(C(C)(C)C)CC4)NN3)c3ccc(Cl)cc3)cc12] | (S)-6-(((1-(1-(tert-butyl)piperidin-4-yl)-1H-1,2,3-triazol-4-yl)(4-chlorophenyl)methyl)amino)-8-chloro-4-((3-chloro-4-fluorophenyl)(methyl)amino)quinoline-3-carbonitrile | 10 | ES/MS 691.2 (M + H+) |
| 750 | 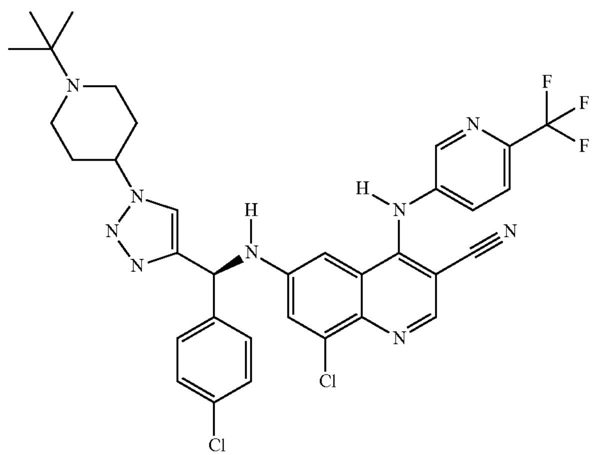 [SMILES: CC(C)(C)N1CCC(N2C=C([C@@H](Nc3cc(Cl)c4ncc(C#N)c(Nc5ccc(C(F)(F)F)nc5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((6-(trifluoromethyl)pyridin-3-yl)amino)quinoline-3-carbonitrile | 10 | ES/MS 694.2 (M + H+) |

TABLE 1-continued

| Compd | Structure | Name | Example/Procedure | ES/MS m/z |
|---|---|---|---|---|
| 751 | 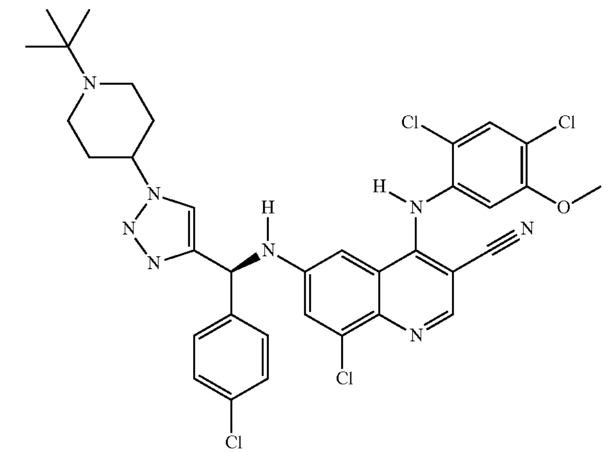 [SMILES: COc1cc(Nc2c(C#N)cnc3c(Cl)cc(N[C@H](C4=CN(C5CCN(C(C)(C)C)CC5)NN4)c4ccc(Cl)cc4)cc23)c(Cl)cc1Cl] | (S)-6-((((1-(1-(tert-butyl)piperidin-4-yl)-1H-1,2,3-triazol-4-yl)(4-chlorophenyl)methyl)amino)-8-chloro-4-((2,4-dichloro-5-methoxyphenyl)amino)quinoline-3-carbonitrile | 10 | ES/MS 723.2 (M + H+) |
| 752 | 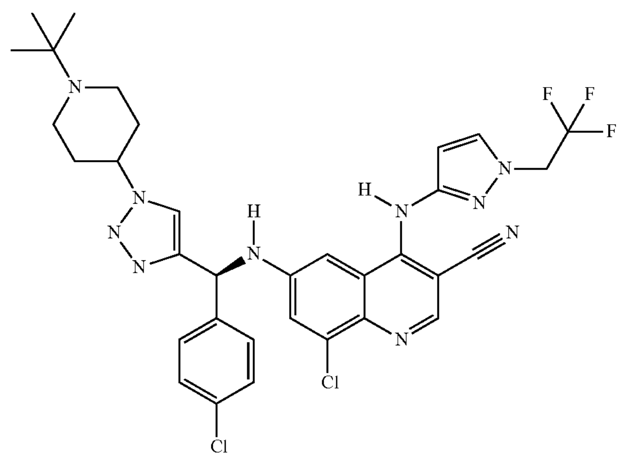 [SMILES: CC(C)(C)N1CCC(N2C=C([C@@H](Nc3cc(Cl)c4ncc(C#N)c(Nc5ccn(CC(F)(F)F)n5)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-8-chloro-4-((1-(2,2,2-trifluoroethyl)-1H-pyrazol-3-yl)amino)quinoline-3-carbonitrile | 10 | ES/MS 697.2 (M + H+) |

TABLE 1-continued

| Compd | Structure | Name | Example/Procedure | ES/MS m/z |
|---|---|---|---|---|
| 753 | 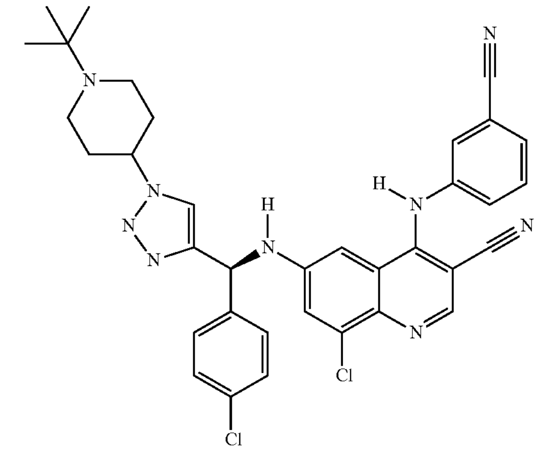 [SMILES: CC(C)(C)N1CCC(N2C=C([C@@H](Nc3cc(Cl)c4ncc(C#N)c(Nc5cccc(C#N)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-cyanophenyl)amino)quinoline-3-carbonitrile | 10 | ES/MS 650.2 (M + H+) |
| 754 | 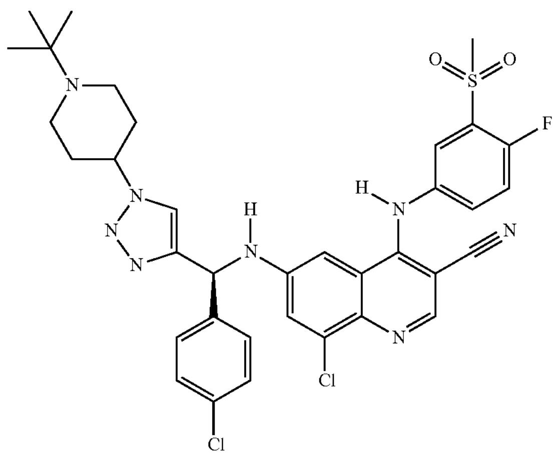 [SMILES: CC(C)(C)N1CCC(N2C=C([C@@H](Nc3cc(Cl)c4ncc(C#N)c(Nc5ccc(F)c(S(C)(=O)=O)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((4-fluoro-3-(methylsulfonyl)phenyl)amino)quinoline-3-carbonitrile | 10 | ES/MS 721.2 (M + H+) |

TABLE 1-continued

| Compd | Structure | Name | Example/Procedure | ES/MS m/z |
|---|---|---|---|---|
| 755 | 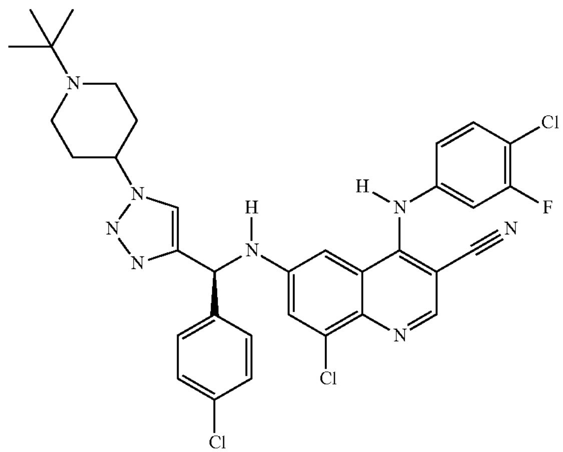 [SMILES: CC(C)(C)N1CCC(N2C=C([C@@H](Nc3cc(Cl)c4ncc(C#N)c(Nc5ccc(Cl)c(F)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((4-chloro-3-fluorophenyl)amino)quinoline-3-carbonitrile | 10 | ES/MS 677.1 (M + H+) |
| 756 | 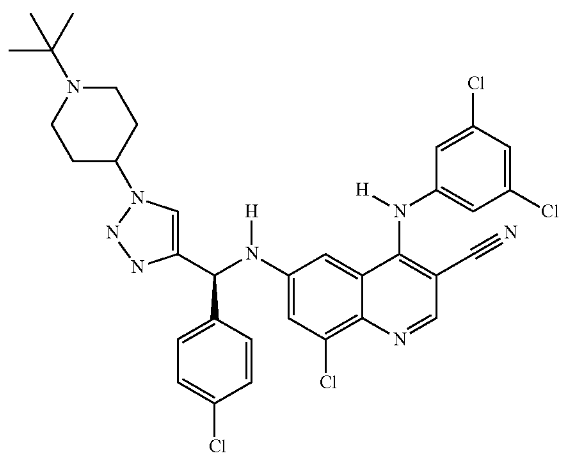 [SMILES: CC(C)(C)N1CCC(N2C=C([C@@H](Nc3cc(Cl)c4ncc(C#N)c(Nc5cc(Cl)cc(Cl)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3,5-dichlorophenyl)amino)quinoline-3-carbonitrile | 10 | ES/MS 695.1 (M + H+) |

TABLE 1-continued

| Compd | Structure | Name | Example/Procedure | ES/MS m/z |
|---|---|---|---|---|
| 757 | 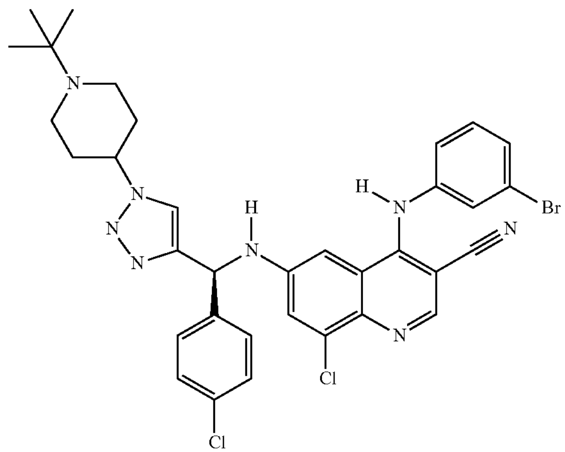 [SMILES: CC(C)(C)N1CCC(N2C=C([C@@H](Nc3cc(Cl)c4ncc(C#N)c(Nc5cccc(Br)c5)c4c3)c3ccc(Cl)cc3)NN2)CC1] | (S)-4-((3-bromophenyl)amino)-6-(((1-(1-(tert-butyl)piperidin-4-yl)-1H-1,2,3-triazol-4-yl)(4-chlorophenyl)methyl)amino)-8-chloroquinoline-3-carbonitrile | 10 | ES/MS 705.1 (M + H+) |
| 758 | 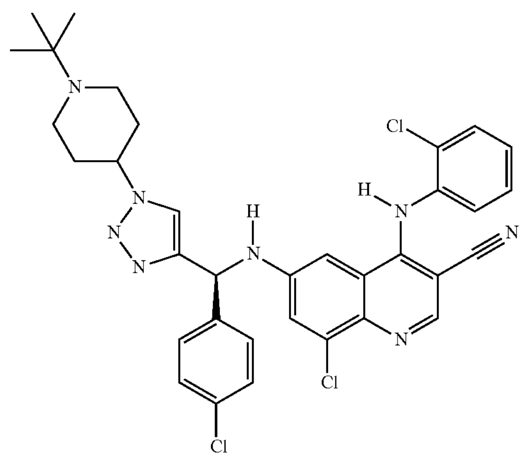 [SMILES: CC(C)(C)N1CCC(N2C=C([C@@H](Nc3cc(Cl)c4ncc(C#N)c(Nc5ccccc5Cl)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((2-chlorophenyl)amino)quinoline-3-carbonitrile | 10 | ES/MS 661.2 (M + H+) |

TABLE 1-continued
| Compd | Name | Structure | Example/Procedure | ES/MS m/z |
|---|---|---|---|---|
| 759 | (S)-6-(((1-(1-(tert-butyl)piperidin-4-yl)-1H-1,2,3-triazol-4-yl)(4-chlorophenyl)methyl)amino)-8-chloro-4-((4-(trifluoromethoxy)phenyl)amino)quinoline-3-carbonitrile | 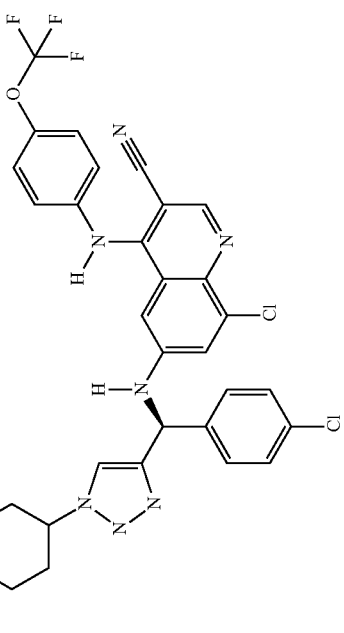 | 10 | ES/MS 709.2 (M + H+) |
| 760 | (S)-2-amino-6-(((1-(1-(tert-butyl)piperidin-4-yl)-1H-1,2,3-triazol-4-yl)(4-chlorophenyl)methyl)amino)-4-((3-chloro-4-fluorophenyl)amino)quinoline-3-carbonitrile | 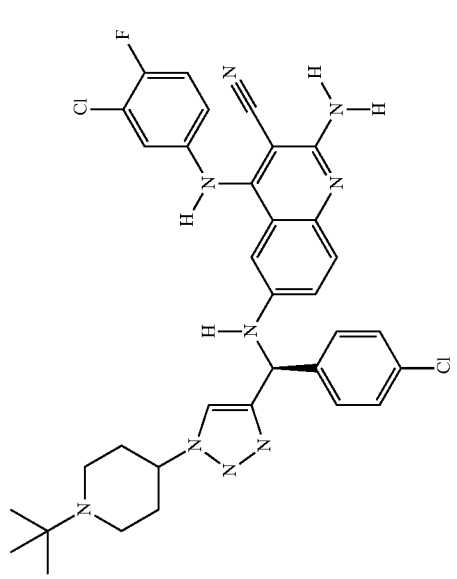 | 1 | ES/MS 658.2 (M + H+) |

TABLE 1-continued
| Compd | Structure | Name | Example/Procedure | ES/MS m/z |
|---|---|---|---|---|
| 761 | 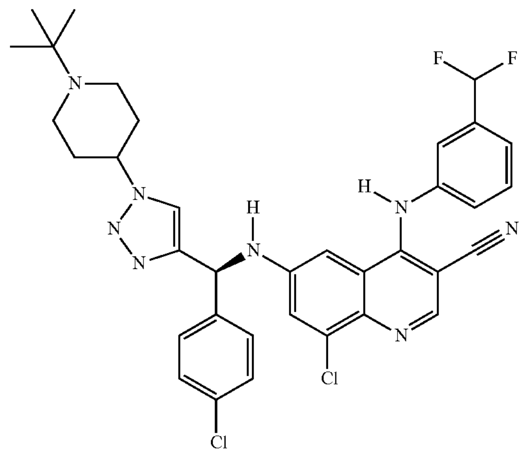 [SMILES: CC(C)(C)N1CCC(N2C=C([C@@H](Nc3cc(Cl)c4ncc(C#N)c(Nc5cccc(C(F)F)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-(difluoromethyl)phenyl)amino)-quinoline-3-carbonitrile | 10 | ES/MS 675.2 (M + H+) |
| 762 | 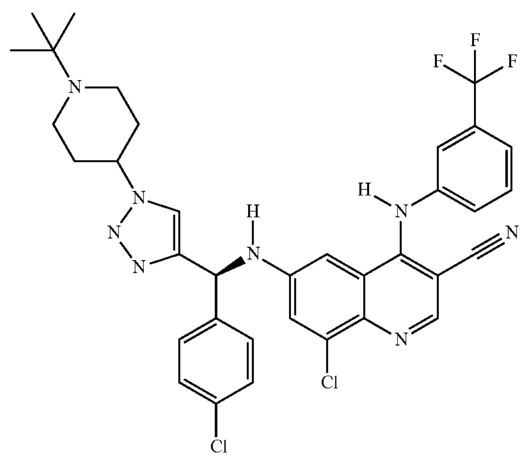 [SMILES: CC(C)(C)N1CCC(N2C=C([C@@H](Nc3cc(Cl)c4ncc(C#N)c(Nc5cccc(C(F)(F)F)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-(trifluoromethyl)phenyl)amino)-quinoline-3-carbonitrile | 10 | ES/MS 693.2 (M + H+) |

TABLE 1-continued

| Compd | Structure | Name | Example/Procedure | ES/MS m/z |
|---|---|---|---|---|
| 763 | 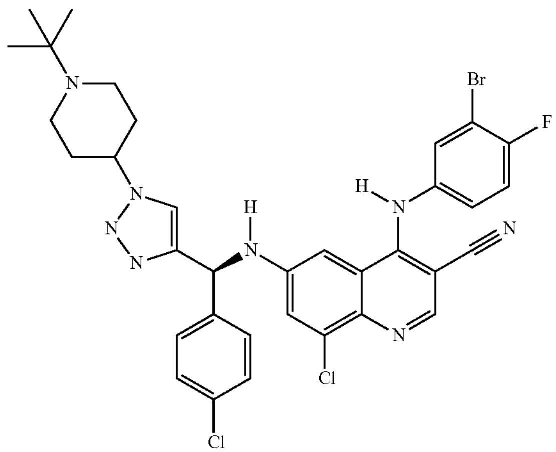 [SMILES: CC(C)(C)N1CCC(N2C=C([C@@H](Nc3cc(Cl)c4ncc(C#N)c(Nc5ccc(F)c(Br)c5)c4c3)c3ccc(Cl)cc3)NN2)CC1] | (S)-4-((3-bromo-4-fluorophenyl)amino)-6-(((1-(1-(tert-butyl)piperidin-4-yl)-1H-1,2,3-triazol-4-yl)(4-chlorophenyl)methyl)amino)-8-chloroquinoline-3-carbonitrile | 10 | ES/MS 721.1 (M + H+) |
| 764 | 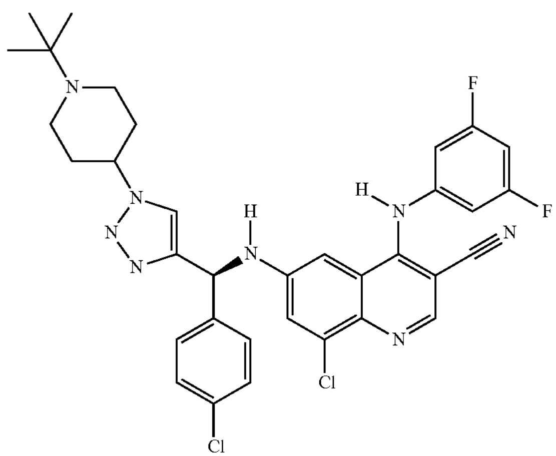 [SMILES: CC(C)(C)N1CCC(N2C=C([C@@H](Nc3cc(Cl)c4ncc(C#N)c(Nc5cc(F)cc(F)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3,5-difluorophenyl)amino)quinoline-3-carbonitrile | 10 | ES/MS 661.2 (M + H+) |

TABLE 1-continued

| Compd | Structure | Name | Example/Procedure | ES/MS m/z |
|---|---|---|---|---|
| 765 | 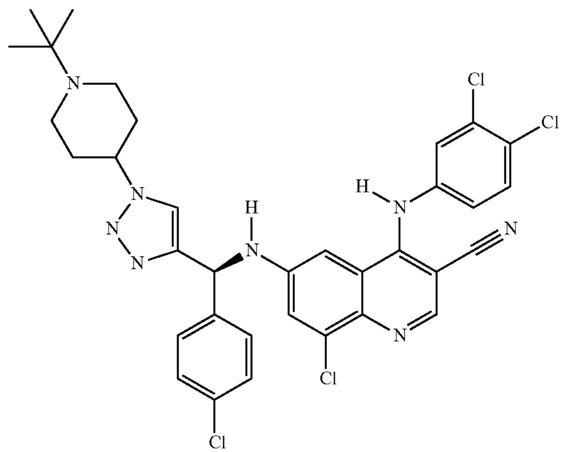 [SMILES: CC(C)(C)N1CCC(N2C=C([C@@H](Nc3cc(Cl)c4ncc(C#N)c(Nc5ccc(Cl)c(Cl)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3,4-dichlorophenyl)amino)quinoline-3-carbonitrile | 10 | ES/MS 695.1 (M + H+) |
| 766 | 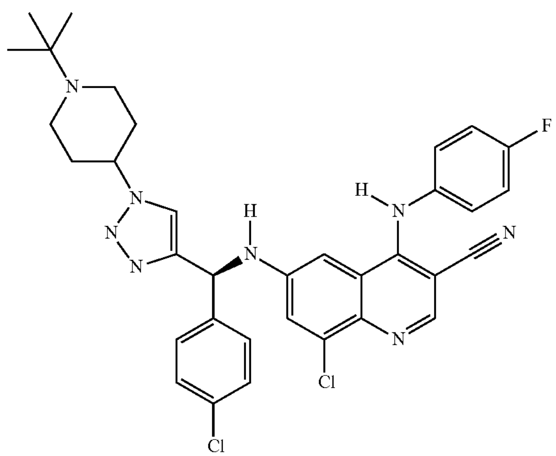 [SMILES: CC(C)(C)N1CCC(N2C=C([C@@H](Nc3cc(Cl)c4ncc(C#N)c(Nc5ccc(F)cc5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((4-fluorophenyl)amino)quinoline-3-carbonitrile | 10 | ES/MS 643.2 (M + H+) |

TABLE 1-continued

| Compd | Structure | Name | Example/Procedure | ES/MS m/z |
|---|---|---|---|---|
| 767 | 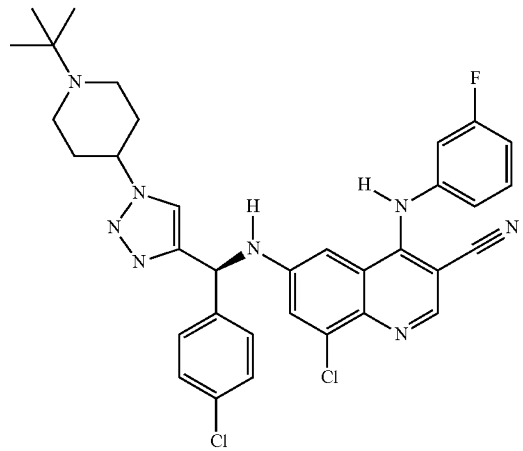 [SMILES: CC(C)(C)N1CCC(N2C=C([C@@H](Nc3cc(Cl)c4ncc(C#N)c(Nc5cccc(F)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-fluorophenyl)amino)quinoline-3-carbonitrile | 10 | ES/MS 643.2 (M + H+) |
| 768 | 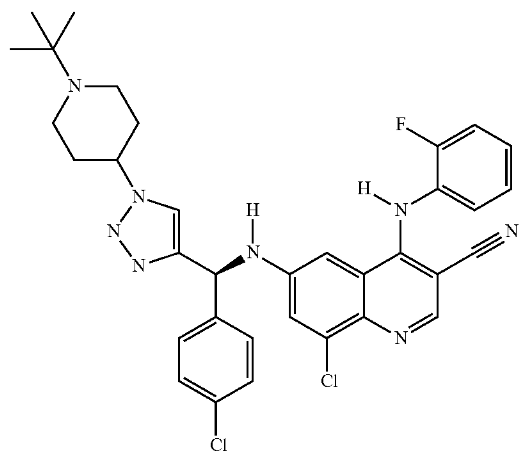 [SMILES: CC(C)(C)N1CCC(N2C=C([C@@H](Nc3cc(Cl)c4ncc(C#N)c(Nc5ccccc5F)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((2-fluorophenyl)amino)quinoline-3-carbonitrile | 10 | ES/MS 643.2 (M + H+) |

TABLE 1-continued

| Compd | Structure | Name | Example/Procedure | ES/MS m/z |
|---|---|---|---|---|
| 769 | 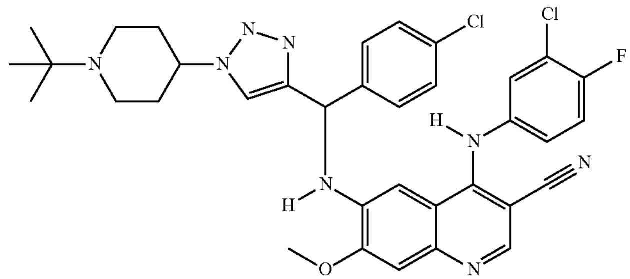 [SMILES: COc1cc2ncc(C#N)c(Nc3ccc(F)c(Cl)c3)c2cc1NC(C1=CN(C2CCN(C(C)(C)C)CC2)NN1)c1ccc(Cl)cc1] | (S)-6-(((1-(1-(tert-butyl)piperidin-4-yl)-1H-1,2,3-triazol-4-yl)(4-chlorophenyl)methyl)amino)-4-((3-chloro-4-fluorophenyl)amino)-7-methoxyquinoline-3-carbonitrile | 8 | ES/MS 673.2 (M + H+) |
| 770 | 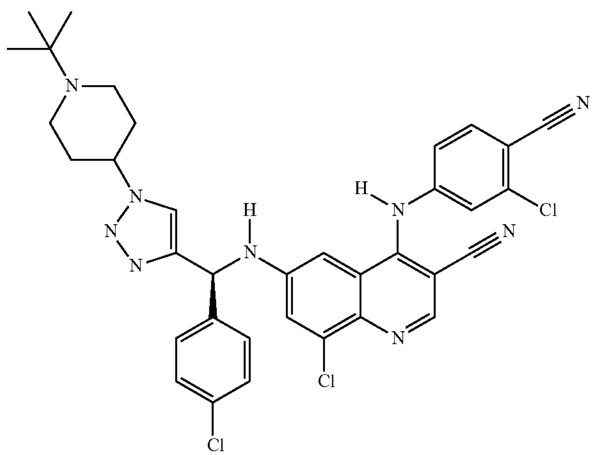 [SMILES: CC(C)(C)N1CCC(N2C=C([C@@H](Nc3cc(Cl)c4ncc(C#N)c(Nc5ccc(C#N)c(Cl)c5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-((3-chloro-4-cyanophenyl)amino)quinoline-3-carbonitrile | 10 | ES/MS 684.1 (M + H+) |

TABLE 1-continued

| Compd | Structure | Name | Example/Procedure | ES/MS m/z |
|---|---|---|---|---|
| 771 | 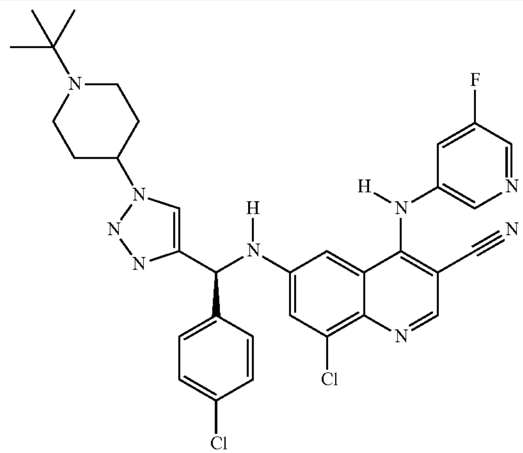 | (S)-6-(((1-(1-(tert-butyl)piperidin-4-yl)-1H-1,2,3-triazol-4-yl)(4-chlorophenyl)methyl)amino)-8-chloro-4-((5-fluoropyridin-3-yl)amino)quinoline-3-carbonitrile | 10 | ES/MS 644.2 (M + H+) |
| 772 | 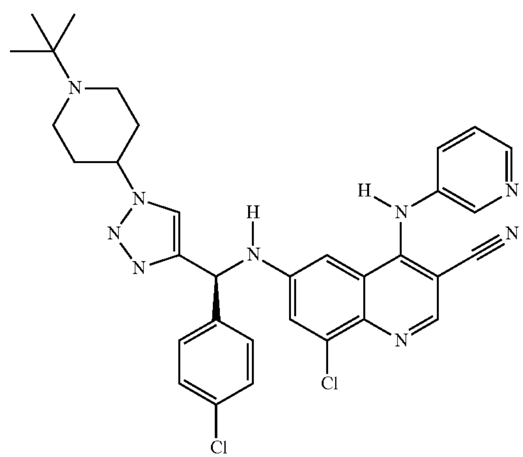 [SMILES: CC(C)(C)N1CCC(N2C=C([C@@H](Nc3cc(Cl)c4ncc(C#N)c(Nc5cccnc5)c4c3)c3ccc(Cl)cc3)NN2)CC1] | (S)-6-(((1-(1-(tert-butyl)piperidin-4-yl)-1H-1,2,3-triazol-4-yl)(4-chlorophenyl)methyl)amino)-8-chloro-4-(pyridin-3-ylamino)quinoline-3-carbonitrile | 10 | ES/MS 626.3 (M + H+) |

TABLE 1-continued

| Compd | Structure | Name | Example/Procedure | ES/MS m/z |
|---|---|---|---|---|
| 773 | 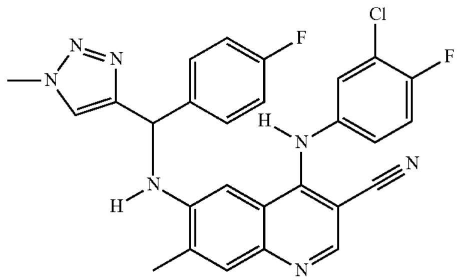 [SMILES: Cc1cc2ncc(C#N)c(Nc3ccc(F)c(Cl)c3)c2cc1NC(c1ccc(F)cc1)c1cn(C)nn1] | 4-((3-chloro-4-fluorophenyl)amino)-6-(((4-fluorophenyl)(1-methyl-1H-1,2,3-triazol-4-yl)methyl)amino)-7-methylquinoline-3-carbonitrile | 8 | ES/MS 516.1 (M + H+) |
| 774 | 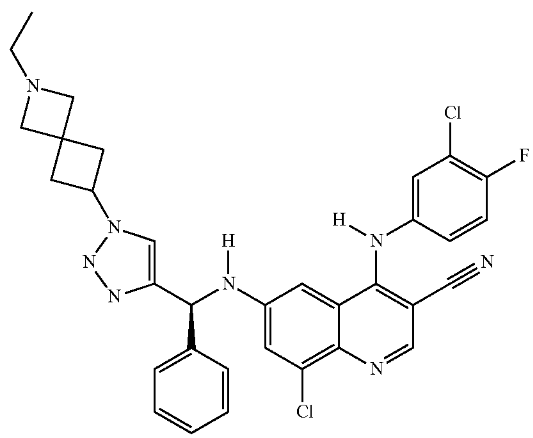 [SMILES: CCN1CC2(CC(N3C=C([C@@H](Nc4cc(Cl)c5ncc(C#N)c(Nc6ccc(F)c(Cl)c6)c5c4)c4ccccc4)NN3)C2)C1] | (S)-8-chloro-4-((3-chloro-4-fluorophenyl)amino)-6-(((1-(2-ethyl-2-azaspiro[3.3]heptan-6-yl)-1H-1,2,3-triazol-4-yl)(phenyl)methyl)amino)quinoline-3-carbonitrile | 5 | ES/MS 627.1 (M + H+) |

TABLE 1-continued

| Compd | Structure | Name | Example/Procedure | ES/MS m/z |
|---|---|---|---|---|
| 775 | 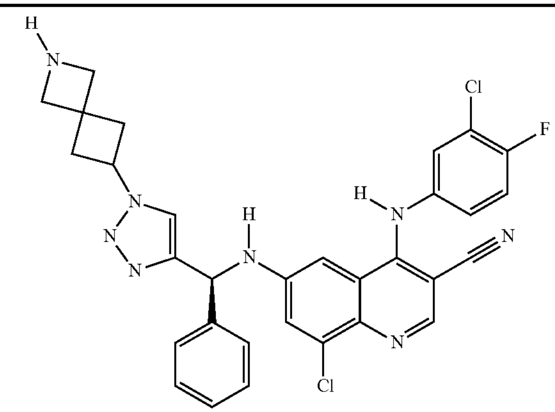 | (S)-6-((((1-(2-azaspiro[3.3]heptan-6-yl)-1H-1,2,3-triazol-4-yl)(phenyl)methyl)amino)-8-chloro-4-((3-chloro-4-fluorophenyl)amino)quinoline-3-carbonitrile | 5 | ES/MS 599.1 (M + H+) |
| 776 | 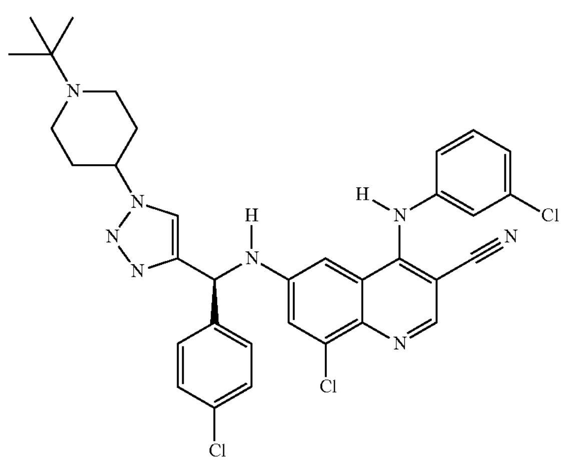 [SMILES: CC(C)(C)N1CCC(N2C=C([C@@H](Nc3cc(Cl)c4ncc(C#N)c(Nc5cccc(Cl)c5)c4c3)c3ccc(Cl)cc3)NN2)CC1] | (S)-6-((((1-(1-(tert-butyl)piperidin-4-yl)-1H-1,2,3-triazol-4-yl)(4-chlorophenyl)methyl)amino)-8-chloro-4-((3-chlorophenyl)amino)quinoline-3-carbonitrile | 10 | ES/MS 659.2 (M + H+) |

TABLE 1-continued
| Compd | Structure | Name | Example/Procedure | ES/MS m/z |
|---|---|---|---|---|
| 777 | 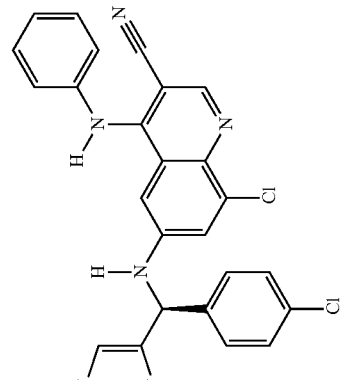 | (S)-6-(((1-(1-(tert-butyl)piperidin-4-yl)-1H-1,2,3-triazol-4-yl)(4-chlorophenyl)methyl)amino)-8-chloro-4-(phenylamino)quinoline-3-carbonitrile | 10 | ES/MS 625.3 (M + H+) |
| 778 | 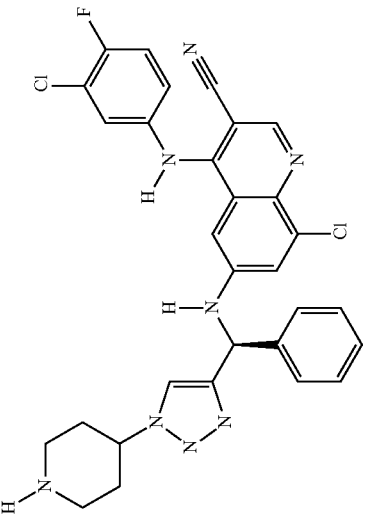 | (S)-8-chloro-4-((3-chloro-4-fluorophenyl)amino)-6-((phenyl(1-(piperidin-4-yl)-1H-1,2,3-triazol-4-yl)methyl)amino)quinoline-3-carbonitrile | 5 | ES/MS 587.15 (M + H+) |

TABLE 1-continued

| Compd | Structure | Name | Example/Procedure | ES/MS m/z |
|---|---|---|---|---|
| 779 | 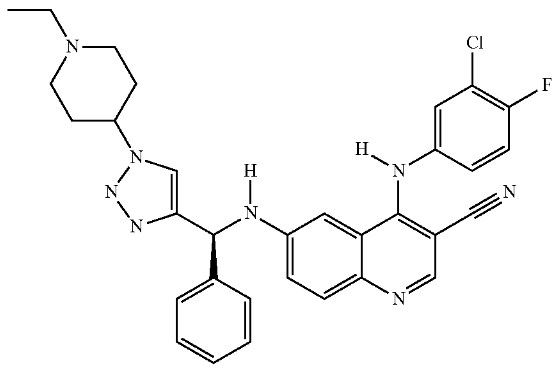 [SMILES: CCN1CCC(N2C=C([C@@H](Nc3ccc4ncc(C#N)c(Nc5ccc(F)c(Cl)c5)c4c3)c3ccccc3)NN2)CC1] | (S)-4-((3-chloro-4-fluorophenyl)amino)-6-(((1-(1-ethylpiperidin-4-yl)-1H-1,2,3-triazol-4-yl)(phenyl)methyl)amino)quinoline-3-carbonitrile | 5 | ES/MS 581.2 (M + H+) |
| 780 | 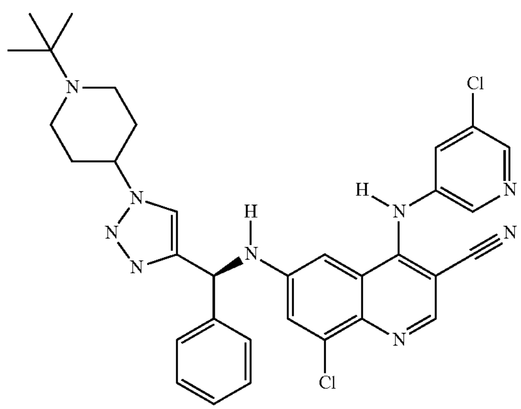 [SMILES: CC(C)(C)N1CCC(N2C=C([C@@H](Nc3cc(Cl)c4ncc(C#N)c(Nc5cncc(Cl)c5)c4c3)c3ccccc3)NN2)CC1] | (S)-6-(((1-(1-(tert-butyl)piperidin-4-yl)-1H-1,2,3-triazol-4-yl)(phenyl)methyl)amino)-8-chloro-4-((5-chloropyridin-3-yl)amino)quinoline-3-carbonitrile | 10 | ES/MS 626.2 (M + H+) |

TABLE 1-continued
| Compd | Structure | Name | Example/Procedure | ES/MS m/z |
|---|---|---|---|---|
| 781 | 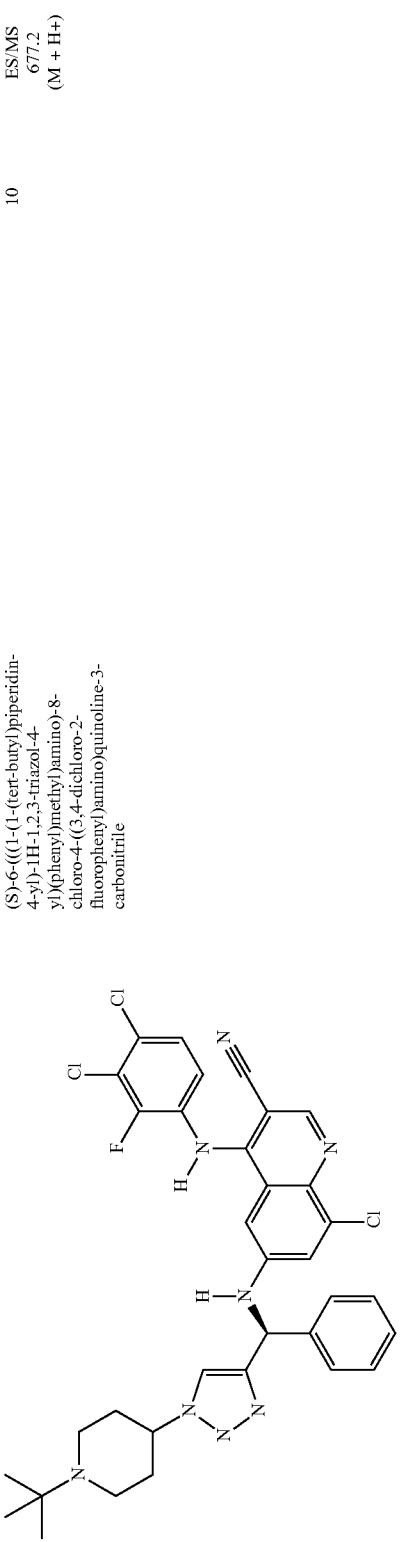 | (S)-6-((((1-(1-(tert-butyl)piperidin-4-yl)-1H-1,2,3-triazol-4-yl)(phenyl)methyl)amino)-8-chloro-4-((3,4-dichloro-2-fluorophenyl)amino)quinoline-3-carbonitrile | 10 | ES/MS 677.2 (M + H+) |
| 782 | 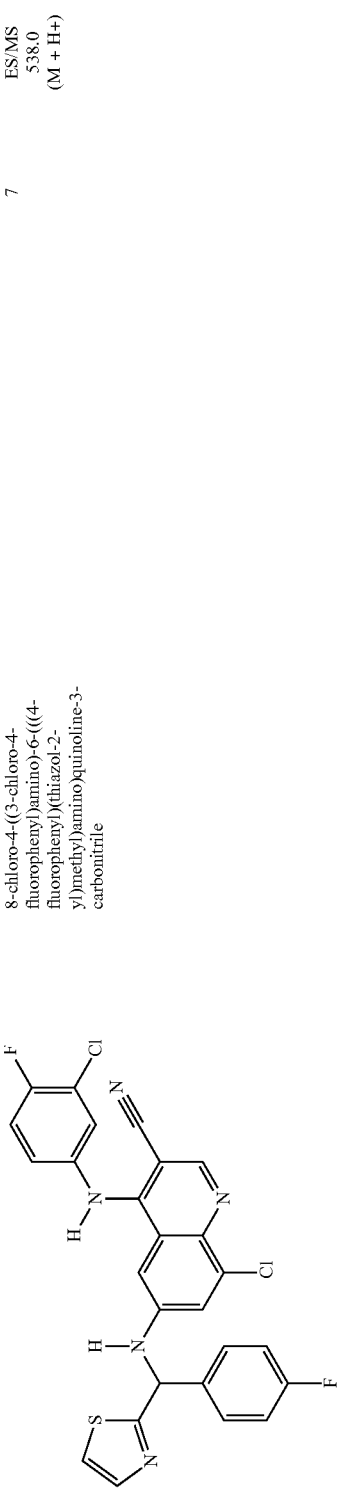 | 8-chloro-4-((3-chloro-4-fluorophenyl)amino)-6-(((4-fluorophenyl)(thiazol-2-yl)methyl)amino)quinoline-3-carbonitrile | 7 | ES/MS 538.0 (M + H+) |

TABLE 1-continued

| Compd | Structure | Name | Example/Procedure | ES/MS m/z |
|---|---|---|---|---|
| 783 | 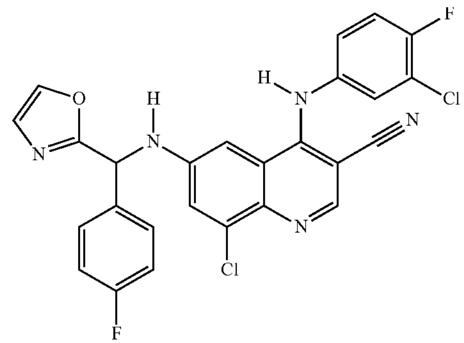 [SMILES: N#Cc1cnc2c(Cl)cc(NC(c3ccc(F)cc3)c3ncco3)cc2c1Nc1ccc(F)c(Cl)c1] | 8-chloro-4-((3-chloro-4-fluorophenyl)amino)-6-(((4-fluorophenyl)(oxazol-2-yl)methyl)amino)quinoline-3-carbonitrile | 7 | ES/MS 522.1 (M + H+) |
| 784 | 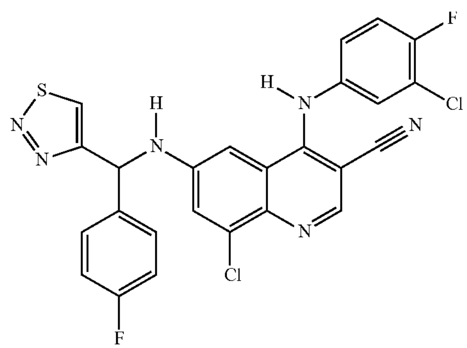 [SMILES: N#Cc1cnc2c(Cl)cc(NC(c3ccc(F)cc3)c3csnn3)cc2c1Nc1ccc(F)c(Cl)c1] | 8-chloro-4-((3-chloro-4-fluorophenyl)amino)-6-(((4-fluorophenyl)(1,2,3-thiadiazol-4-yl)methyl)amino)quinoline-3-carbonitrile | 7 | ES/MS 539.0 (M + H+) |

TABLE 1-continued

| Compd | Structure | Name | Example/Procedure | ES/MS m/z |
|---|---|---|---|---|
| 785 | 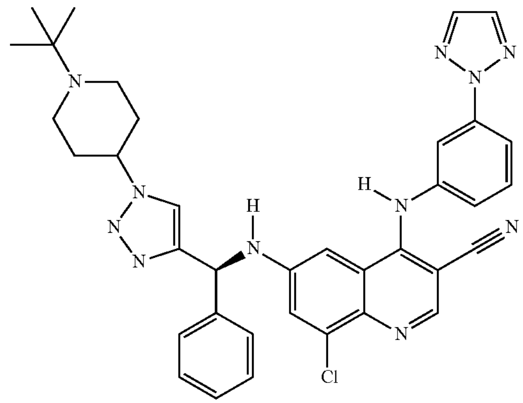 [SMILES: CC(C)(C)N1CCC(N2C=C([C@@H](Nc3cc(Cl)c4ncc(C#N)c(Nc5cccc(-n6nccn6)c5)c4c3)c3ccccc3)NN2)CC1] | (S)-4-((3-(2H-1,2,3-triazol-2-yl)phenyl)amino)-6-(((1-(tert-butyl)piperidin-4-yl)-1H-1,2,3-triazol-4-yl)(phenyl)methyl)amino)-8-chloroquinoline-3-carbonitrile | 10 | ES/MS 658.3 (M + H+) |
| 786 | 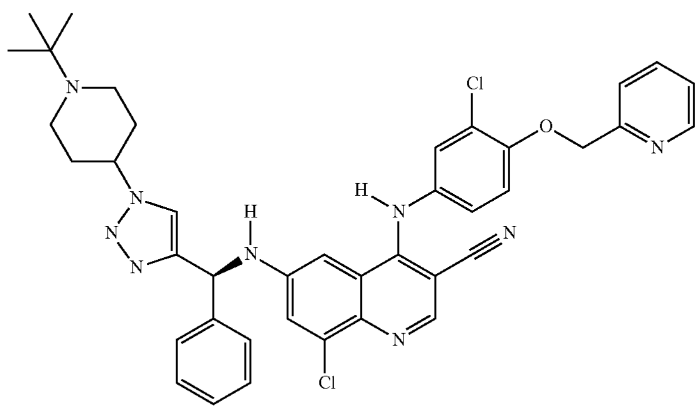 [SMILES: CC(C)(C)N1CCC(N2C=C([C@@H](Nc3cc(Cl)c4ncc(C#N)c(Nc5ccc(OCc6ccccn6)c(Cl)c5)c4c3)c3ccccc3)NN2)CC1] | (S)-6-((((1-(tert-butyl)piperidin-4-yl)-1H-1,2,3-triazol-4-yl)(phenyl)methyl)amino)-8-chloro-4-((3-chloro-4-(pyridin-2-ylmethoxy)phenyl)amino)quinoline-3-carbonitrile | 10 | ES/MS 732.3 (M + H+) |

TABLE 1-continued

| Compd | Structure | Name | Example/Procedure | ES/MS m/z |
|---|---|---|---|---|
| 787 | 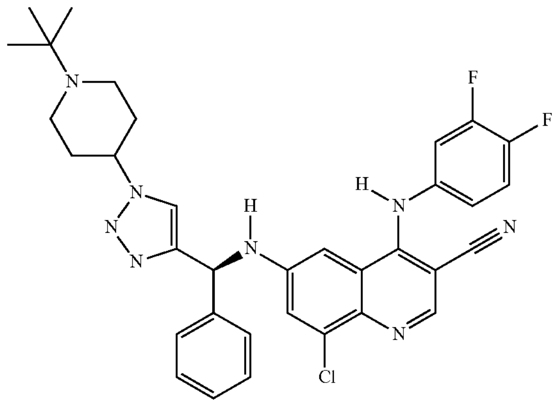 [SMILES: CC(C)(C)N1CCC(N2C=C([C@@H](Nc3cc(Cl)c4ncc(C#N)c(Nc5ccc(F)c(F)c5)c4c3)c3ccccc3)NN2)CC1] | (S)-6-((((1-(1-(tert-butyl)piperidin-4-yl)-1H-1,2,3-triazol-4-yl)(phenyl)methyl)amino)-8-chloro-4-((3,4-difluorophenyl)amino)quinoline-3-carbonitrile | 10 | ES/MS 627.3 (M + H+) |
| 788 | 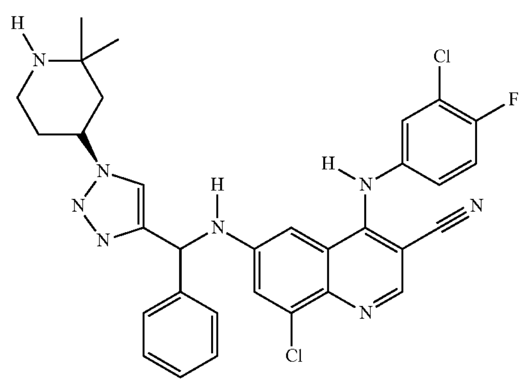 | 8-chloro-4-((3-chloro-4-fluorophenyl)amino)-6-(((R)-(1-((R)-2,2-dimethylpiperidin-4-yl)-1H-1,2,3-triazol-4-yl)(phenyl)methyl)amino)quinoline-3-carbonitrile | 6 | ES/MS 615.1 (M + H+) |

TABLE 1-continued
| Compd | Structure | Name | Example/Procedure | ES/MS m/z |
|---|---|---|---|---|
| 789 | 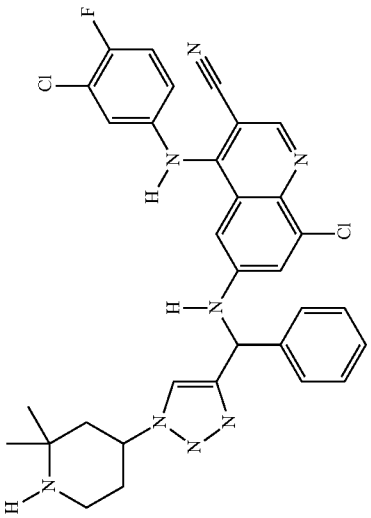 | 8-chloro-4-((3-chloro-4-fluorophenyl)amino)-6-(((R)-(1-((R)-2,2-dimethylpiperidin-4-yl)-1H-1,2,3-triazol-4-yl)(phenyl)methyl)amino)quinoline-3-carbonitrile | 6 | |
| 790 | 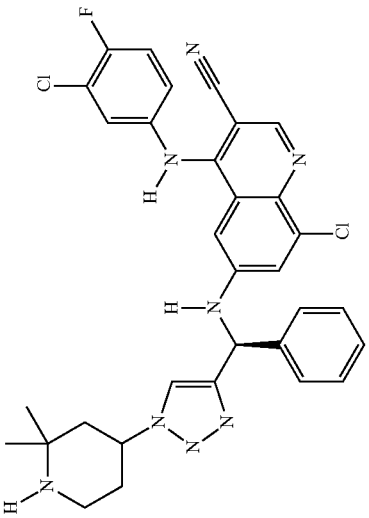 | 8-chloro-4-((3-chloro-4-fluorophenyl)amino)-6-(((1S)-(1-(2,2-dimethylpiperidin-4-yl)-1H-1,2,3-triazol-4-yl)(phenyl)methyl)amino)quinoline-3-carbonitrile | 6 | |

TABLE 1-continued

| Compd | Structure | Name | Example/Procedure | ES/MS m/z |
|---|---|---|---|---|
| 791 | 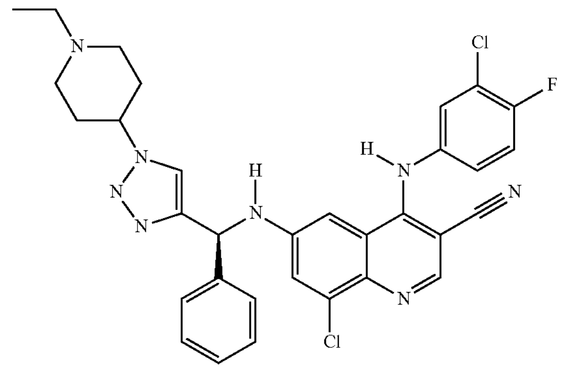 | (S)-4-((3-chloro-4-fluorophenyl)amino)-6-(((1-(1-ethylpiperidin-4-yl)-1H-1,2,3-triazol-4-yl)(phenyl)methyl)amino)-8-fluoroquinoline-3-carbonitrile | 5 | ES/MS 599.0 (M + H+) |
| 792 | 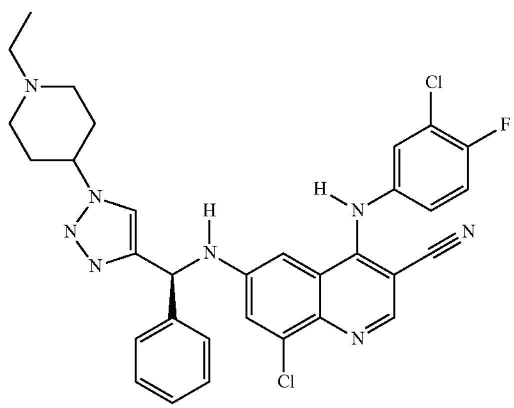 | (S)-8-chloro-4-((3-chloro-4-fluorophenyl)amino)-6-(ethyl((1-(1-ethylpiperidin-4-yl)-1H-1,2,3-triazol-4-yl)(phenyl)methyl)amino)quinoline-3-carbonitrile | 5 | ES/MS 643.2 (M + H+) |

TABLE 1-continued

| Compd | Structure | Name | Example/Procedure | ES/MS m/z |
|---|---|---|---|---|
| 793 | 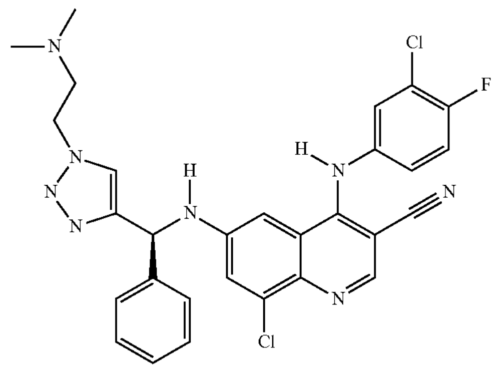 [SMILES: CN(C)CCN1C=C([C@@H](Nc2cc(Cl)c3ncc(C#N)c(Nc4ccc(F)c(Cl)c4)c3c2)c2ccccc2)NN1] | (S)-8-chloro-4-((3-chloro-4-fluorophenyl)amino)-6-(((1-(2-(dimethylamino)ethyl)-1H-1,2,3-triazol-4-yl)(phenyl)methyl)amino)quinoline-3-carbonitrile | 3 | ES/MS 575.1 (M + H+) |
| 794 | 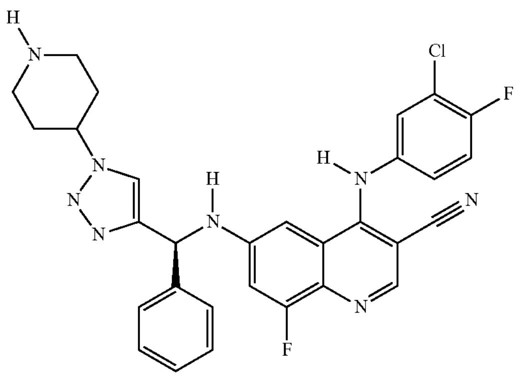 [SMILES: N#Cc1cnc2c(F)cc(N[C@H](C3=CN(C4CCNCC4)NN3)c3ccccc3)cc2c1Nc1ccc(F)c(Cl)c1] | (S)-4-((3-chloro-4-fluorophenyl)amino)-8-fluoro-6-(((phenyl(1-(piperidin-4-yl)-1H-1,2,3-triazol-4-yl)methyl)amino)quinoline-3-carbonitrile | 5 | |

TABLE 1-continued

| Compd | Structure | Name | Example/Procedure | ES/MS m/z |
|---|---|---|---|---|
| 795 | 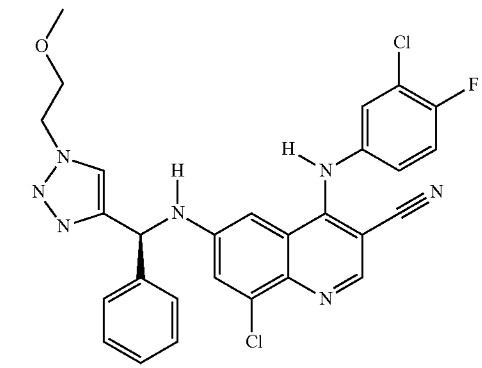 | (S)-8-chloro-4-((3-chloro-4-fluorophenyl)amino)-6-(((1-(2-methoxyethyl)-1H-1,2,3-triazol-4-yl)(phenyl)methyl)amino)quinoline-3-carbonitrile | 3 | ES/MS 562.0 (M + H+) |
| 796 | 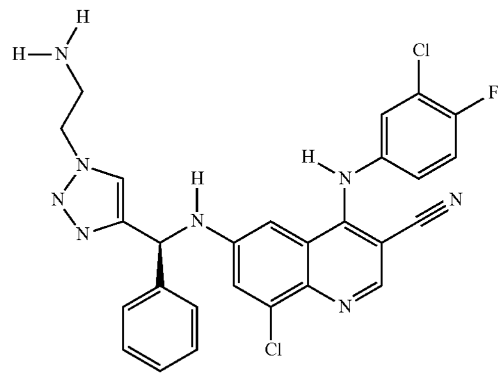 [SMILES: N#Cc1cnc2c(Cl)cc(N[C@H](C3=CN(CCN)NN3)c3ccccc3)cc2c1Nc1ccc(F)c(Cl)c1] | (S)-6-(((1-(2-aminoethyl)-1H-1,2,3-triazol-4-yl)(phenyl)methyl)amino)-8-chloro-4-((3-chloro-4-fluorophenyl)amino)quinoline-3-carbonitrile | 3 | ES/MS 547.0 (M + H+) |

TABLE 1-continued

| Compd | Structure | Name | Example/Procedure | ES/MS m/z |
|---|---|---|---|---|
| 797 | 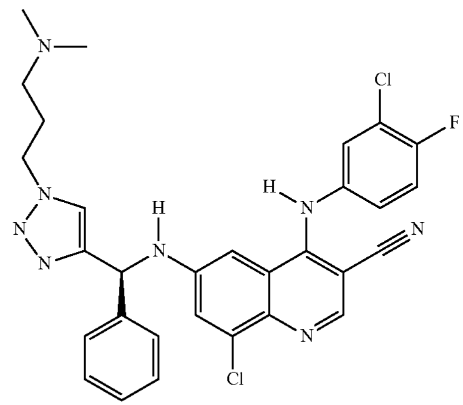 [SMILES: CN(C)CCCN1C=C([C@@H](Nc2cc(Cl)c3ncc(C#N)c(Nc4ccc(F)c(Cl)c4)c3c2)c2ccccc2)NN1] | (S)-8-chloro-4-((3-chloro-4-fluorophenyl)amino)-6-(((1-(3-(dimethylamino)propyl)-1H-1,2,3-triazol-4-yl)(phenyl)methyl)amino)quinoline-3-carbonitrile | 3 | ES/MS 589.0 (M + H+) |
| 798 | 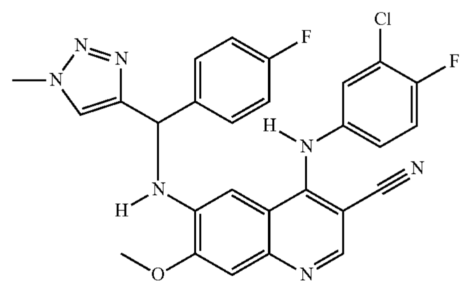 [SMILES: COc1cc2ncc(C#N)c(Nc3ccc(F)c(Cl)c3)c2cc1NC(c1ccc(F)cc1)c1cn(C)nn1] | 4-((3-chloro-4-fluorophenyl)amino)-6-(((4-fluorophenyl)(1-methyl-1H-1,2,3-triazol-4-yl)methyl)amino)-7-methoxyquinoline-3-carbonitrile | 8 | ES/MS 532.1 (M + H+) |
| 799 | 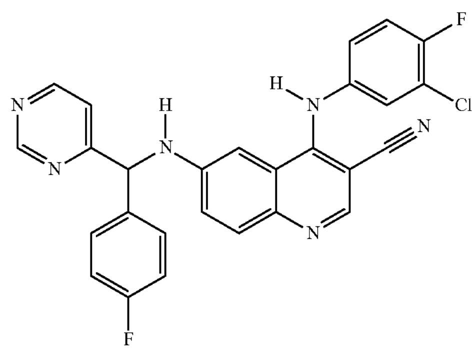 [SMILES: N#Cc1cnc2ccc(NC(c3ccc(F)cc3)c3ccncn3)cc2c1Nc1ccc(F)c(Cl)c1] | 4-((3-chloro-4-fluorophenyl)amino)-6-(((4-fluorophenyl)(pyrimidin-4-yl)methyl)amino)quinoline-3-carbonitrile | 7 | ES/MS 533.1 (M + H+) |

TABLE 1-continued

| Compd | Structure | Name | Example/Procedure | ES/MS m/z |
|---|---|---|---|---|
| 800 | 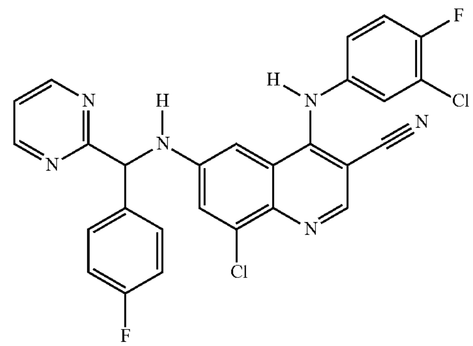 [SMILES: N#Cc1cnc2c(Cl)cc(NC(c3ccc(F)cc3)c3ncccn3)cc2c1Nc1ccc(F)c(Cl)c1] | 8-chloro-4-((3-chloro-4-fluorophenyl)amino)-6-(((4-fluorophenyl)(pyrimidin-2-yl)methyl)amino)quinoline-3-carbonitrile | 7 | ES/MS 533.0 (M + H+) |
| 801 | 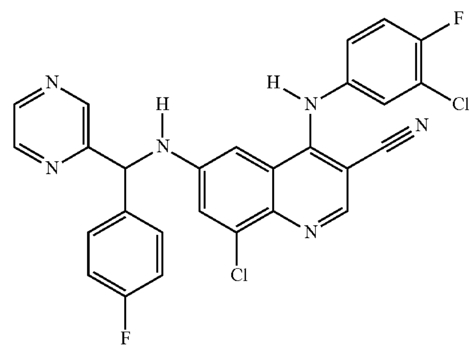 [SMILES: N#Cc1cnc2c(Cl)cc(NC(c3ccc(F)cc3)c3cnccn3)cc2c1Nc1ccc(F)c(Cl)c1] | 8-chloro-4-((3-chloro-4-fluorophenyl)amino)-6-(((4-fluorophenyl)(pyrazin-2-yl)methyl)amino)quinoline-3-carbonitrile | 7 | ES/MS 533.1 (M + H+) |

TABLE 1-continued
| Compd | Structure | Name | Example/Procedure | ES/MS m/z |
|---|---|---|---|---|
| 802 | 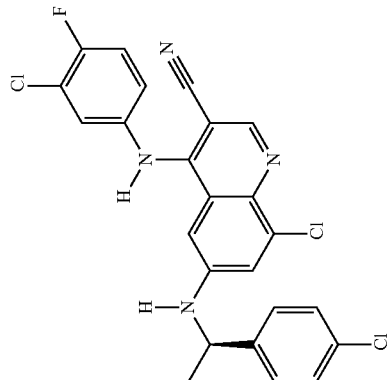 | (S)-8-chloro-4-((3-chloro-4-fluorophenyl)amino)-6-(((4-chlorophenyl)(1-(1-(oxetan-3-yl)piperidin-4-yl)-1H-1,2,3-triazol-4-yl)methyl)amino)quinoline-3-carbonitrile | 5 | ES/MS 678.9 (M + H+) |
| 803 | 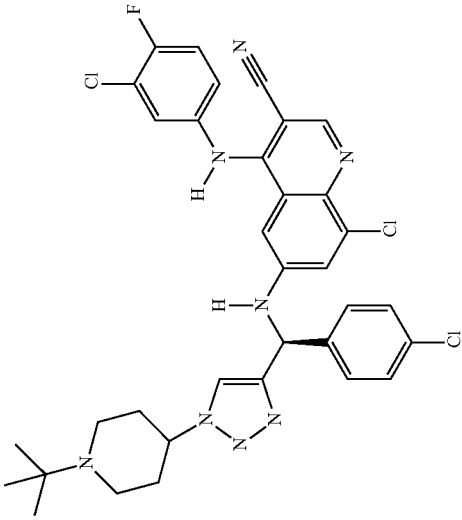 | (S)-6-(((1-(1-(tert-butyl)piperidin-4-yl)-1H-1,2,3-triazol-4-yl)(4-chlorophenyl)methyl)amino)-8-chloro-4-((3-chloro-4-fluorophenyl)amino)quinoline-3-carbonitrile | 3 | ES/MS 679.2 (M + H+) |

TABLE 1-continued
| Compd | Structure | Name | Example/Procedure | ES/MS m/z |
|---|---|---|---|---|
| 804 | 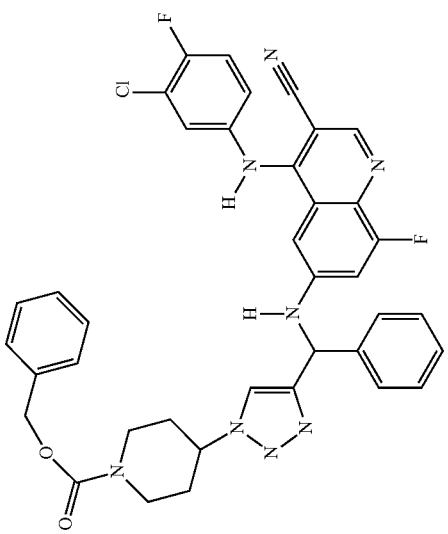 | benzyl 4-(4-(((4-((3-chloro-4-fluorophenyl)amino)-3-cyano-8-fluoroquinolin-6-yl)amino)(phenyl)methyl)-1H-1,2,3-triazol-1-yl)piperidine-1-carboxylate | 6 | |
| 805 | 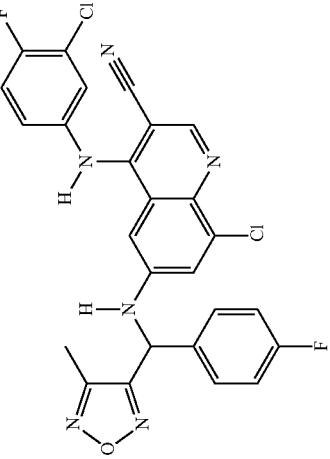 | 8-chloro-4-((3-chloro-4-fluorophenyl)amino)-6-(((4-fluorophenyl)(4-methyl-1,2,5-oxadiazol-3-yl)methyl)amino)quinoline-3-carbonitrile | 7 | ES/MS 537.1 (M + H+) |

TABLE 1-continued

| Compd | Structure | Name | Example/Procedure | ES/MS m/z |
|---|---|---|---|---|
| 806 | 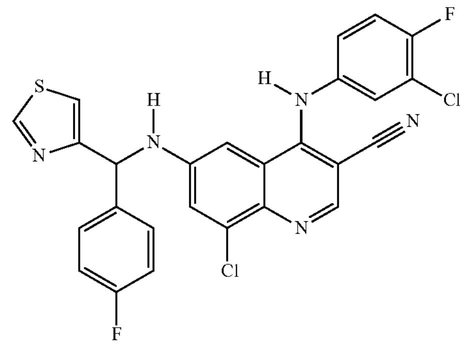 | 8-chloro-4-((3-chloro-4-fluorophenyl)amino)-6-(((4-fluorophenyl)(thiazol-4-yl)methyl)amino)quinoline-3-carbonitrile | 7 | ES/MS 538.0 (M + H+) |
| 807 | 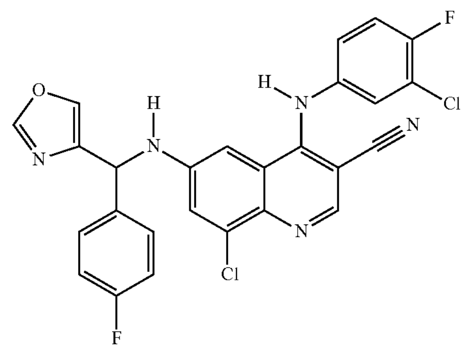 | 8-chloro-4-((3-chloro-4-fluorophenyl)amino)-6-(((4-fluorophenyl)(oxazol-4-yl)methyl)amino)quinoline-3-carbonitrile | 7 | ES/MS 522.0 (M + H+) |

TABLE 1-continued
| Compd | Structure | Name | Example/Procedure | ES/MS m/z |
|---|---|---|---|---|
| 808 | 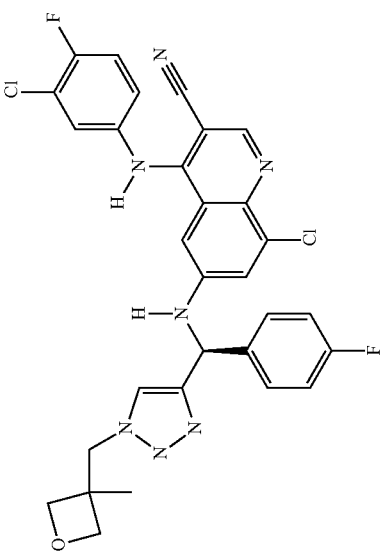 | (S)-8-chloro-4-((3-chloro-4-fluorophenyl)amino)-6-(((4-fluorophenyl)(1-((3-methyloxetan-3-yl)methyl)-1H-1,2,3-triazol-4-yl)methyl)amino)quinoline-3-carbonitrile | 3 | ES/MS 606.1 (M + H+) |
| 809 | 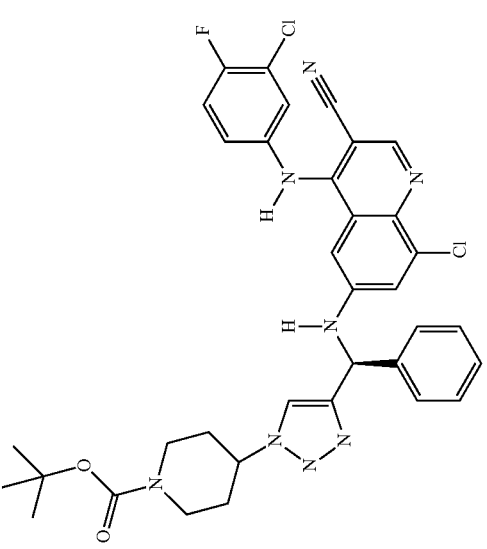 | tert-butyl (S)-4-(4-(((8-chloro-4-((3-chloro-4-fluorophenyl)amino)-3-cyanoquinolin-6-yl)amino)(phenyl)methyl)-1H-1,2,3-triazol-1-yl)piperidine-1-carboxylate | 3 | ES/MS 687.2 (M + H+) |

TABLE 1-continued

| Compd | Structure | Name | Example/Procedure | ES/MS m/z |
|---|---|---|---|---|
| 810 | 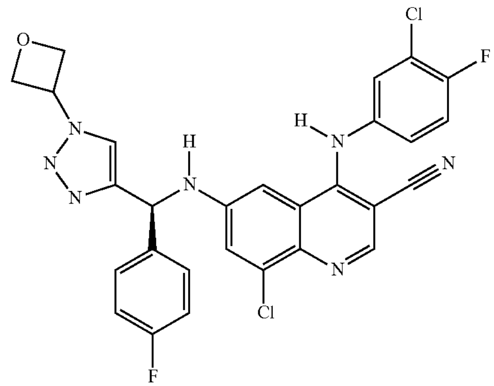 [SMILES: N#Cc1cnc2c(Cl)cc(N[C@H](C3=CN(C4COC4)NN3)c3ccc(F)cc3)cc2c1Nc1ccc(F)c(Cl)c1] | (S)-8-chloro-4-((3-chloro-4-fluorophenyl)amino)-6-(((4-fluorophenyl)(1-(oxetan-3-yl)-1H-1,2,3-triazol-4-yl)methyl)amino)quinoline-3-carbonitrile | 3 | ES/MS 578.0 (M + H+) |
| 811 | 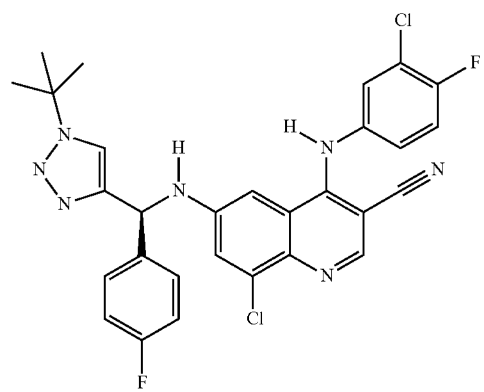 [SMILES: CC(C)(C)N1C=C([C@@H](Nc2cc(Cl)c3ncc(C#N)c(Nc4ccc(F)c(Cl)c4)c3c2)c2ccc(F)cc2)NN1] | (S)-6-((((1-(tert-butyl)-1H-1,2,3-triazol-4-yl)(4-fluorophenyl)methyl)amino)-8-chloro-4-((3-chloro-4-fluorophenyl)amino)quinoline-3-carbonitrile | 3 | ES/MS 578.1 (M + H+) |

TABLE 1-continued

| Compd | Structure | Name | Example/Procedure | ES/MS m/z |
|---|---|---|---|---|
| 812 | 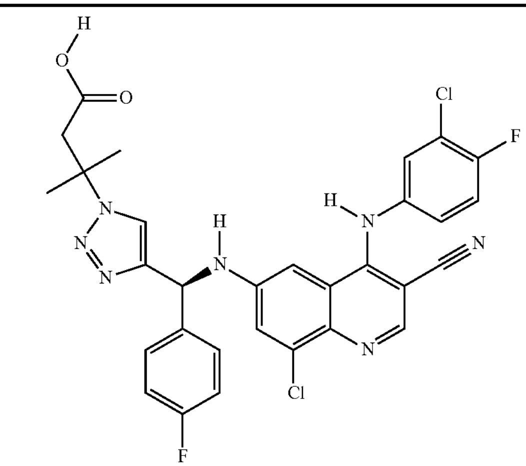 | (S)-3-(4-(((8-chloro-4-((3-chloro-4-fluorophenyl)amino)-3-cyanoquinolin-6-yl)amino)(4-fluorophenyl)methyl)-1H-1,2,3-triazol-1-yl)-3-methylbutanoic acid | 3 | ES/MS 622.1 (M + H+) |
| 813 | 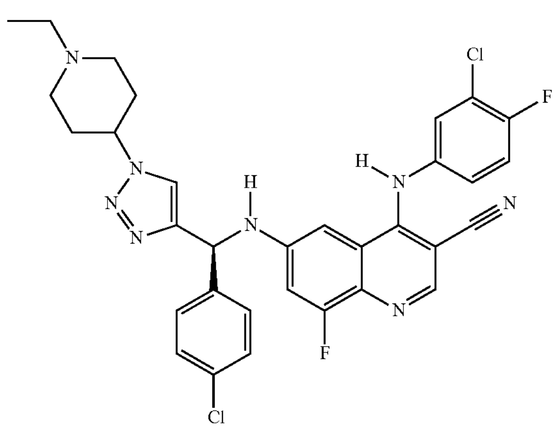 [SMILES: CCN1CCC(n2cc([C@@H](Nc3cc(F)c4ncc(C#N)c(Nc5ccc(F)c(Cl)c5)c4c3)c3ccc(Cl)cc3)nn2)CC1] | (S)-4-((3-chloro-4-fluorophenyl)amino)-6-(((4-chlorophenyl)(1-(1-ethylpiperidin-4-yl)-1H-1,2,3-triazol-4-yl)methyl)amino)-8-fluoroquinoline-3-carbonitrile | 5 | ES/MS 633.9 (M + H+) |

TABLE 1-continued
| Compd | Structure | Name | Example/Procedure | ES/MS m/z |
|---|---|---|---|---|
| 814 | 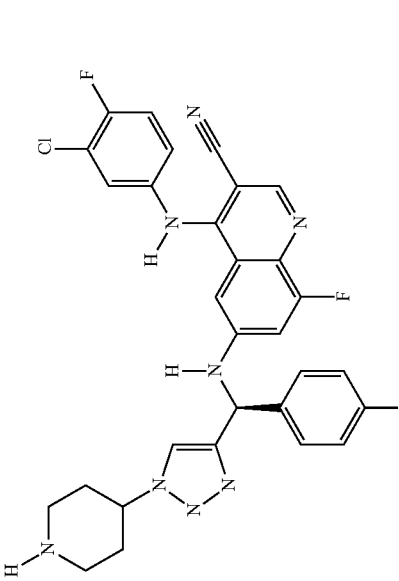 | (S)-4-((3-chloro-4-fluorophenyl)amino)-6-(((4-chlorophenyl)(1-(piperidin-4-yl)-1H-1,2,3-triazol-4-yl)methyl)amino)-8-fluoroquinoline-3-carbonitrile | 5 | |
| 815 | 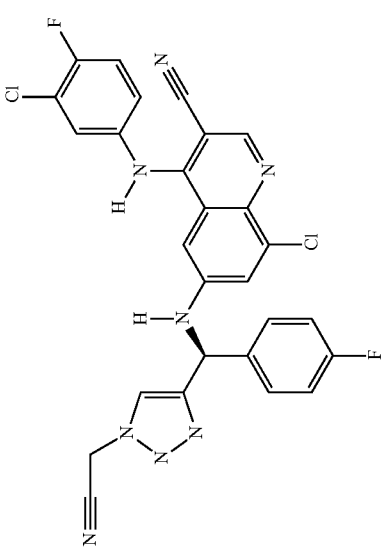 | (S)-8-chloro-4-((3-chloro-4-fluorophenyl)amino)-6-(((1-(cyanomethyl)-1H-1,2,3-triazol-4-yl)(4-fluorophenyl)methyl)amino)quinoline-3-carbonitrile | 3 | ES/MS 560.9 (M + H+) |

TABLE 1-continued

| Compd | Structure | Name | Example/Procedure | ES/MS m/z |
|---|---|---|---|---|
| 816 | 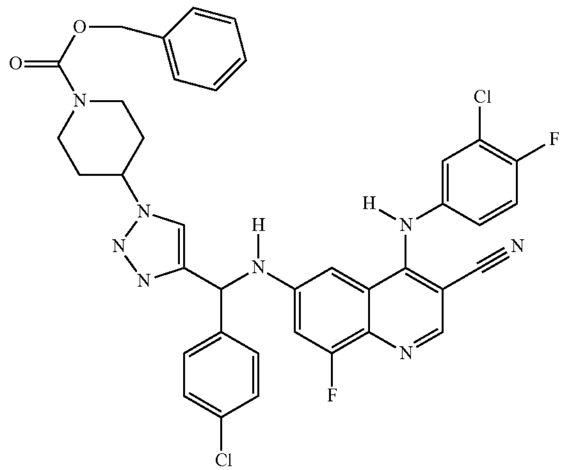 [SMILES: N#Cc1cnc2c(F)cc(NC(C3=CN(C4CCN(C(=O)OCc5ccccc5)CC4)NN3)c3ccc(Cl)cc3)cc2c1Nc1ccc(F)c(Cl)c1] | benzyl 4-(4-(((4-((3-chloro-4-fluorophenyl)amino)-3-cyano-8-fluoroquinolin-6-yl)amino)(4-chlorophenyl)methyl)-1H-1,2,3-triazol-1-yl)piperidine-1-carboxylate | 6 | |
| 817 | 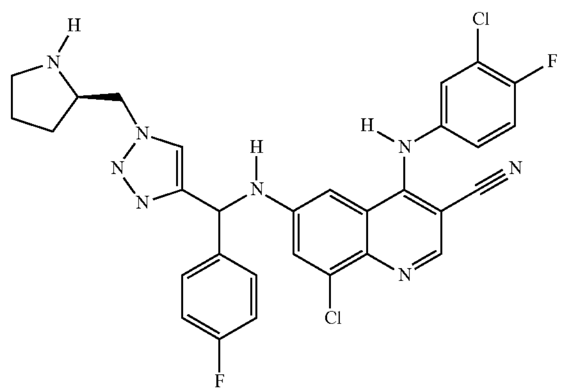 [SMILES: N#Cc1cnc2c(Cl)cc(NC(C3=CN(C[C@H]4CCCN4)NN3)c3ccc(F)cc3)cc2c1Nc1ccc(F)c(Cl)c1] | 8-chloro-4-((3-chloro-4-fluorophenyl)amino)-6-(((4-fluorophenyl)(1-(((R)-pyrrolidin-2-yl)methyl)-1H-1,2,3-triazol-4-yl)methyl)amino)quinoline-3-carbonitrile | 6 | ES/MS 605.1 (M + H+) |

TABLE 1-continued

| Compd | Structure | Name | Example/Procedure | ES/MS m/z |
|---|---|---|---|---|
| 818 | 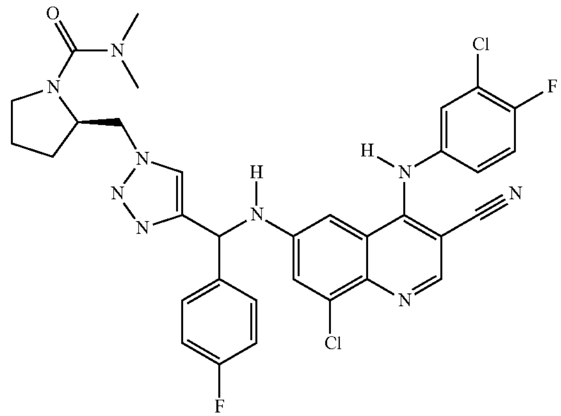 [SMILES: CN(C)C(=O)N1CCC[C@@H]1CN1C=C(C(Nc2cc(Cl)c3ncc(C#N)c(Nc4ccc(F)c(Cl)c4)c3c2)c2ccc(F)cc2)NN1] | (2R)-2-((4-(((8-chloro-4-((3-chloro-4-fluorophenyl)amino)-3-cyanoquinolin-6-yl)amino)(4-fluorophenyl)methyl)-1H-1,2,3-triazol-1-yl)methyl)-N,N-dimethylpyrrolidine-1-carboxamide | 6 | |
| 819 | 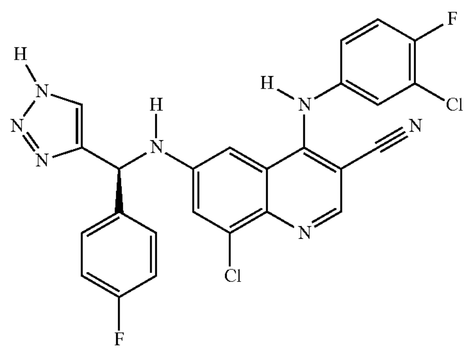 [SMILES: N#Cc1cnc2c(Cl)cc(N[C@@H](c3ccc(F)cc3)c3c[nH]nn3)cc2c1Nc1ccc(F)c(Cl)c1] | (S)-8-chloro-4-((3-chloro-4-fluorophenyl)amino)-6-(((4-fluorophenyl)(1H-1,2,3-triazol-4-yl)methyl)amino)quinoline-3-carbonitrile | 15 | ES/MS 522.1 (M + H+) |

TABLE 1-continued

| Compd | Structure | Name | Example/Procedure | ES/MS m/z |
|---|---|---|---|---|
| 820 | 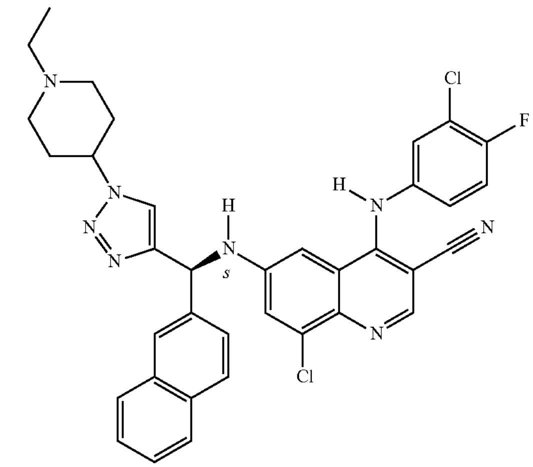 [SMILES: CCN1CCC(n2cc([C@@H](Nc3cc(Cl)c4ncc(C#N)c(Nc5ccc(F)c(Cl)c5)c4c3)c3ccc4ccccc4c3)nn2)CC1] | (S)-8-chloro-4-((3-chloro-4-fluorophenyl)amino)-6-(((1-(1-ethylpiperidin-4-yl)-1H-1,2,3-triazol-4-yl)(naphthalen-2-yl)methyl)amino)quinoline-3-carbonitrile | 5 | ES/MS 665.5 (M + H+) |
| 821 | 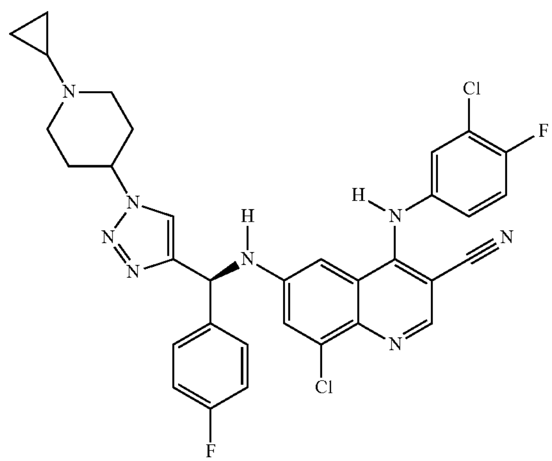 [SMILES: N#Cc1cnc2c(Cl)cc(N[C@@H](c3ccc(F)cc3)c3cn(C4CCN(C5CC5)CC4)nn3)cc2c1Nc1ccc(F)c(Cl)c1] | (S)-8-chloro-4-((3-chloro-4-fluorophenyl)amino)-6-(((1-(1-cyclopropylpiperidin-4-yl)-1H-1,2,3-triazol-4-yl)(4-fluorophenyl)methyl)amino)quinoline-3-carbonitrile | 1 | ES/MS 645.1 (M + H+) |

TABLE 1-continued

| Compd | Structure | Name | Example/Procedure | ES/MS m/z |
|---|---|---|---|---|
| 822 | 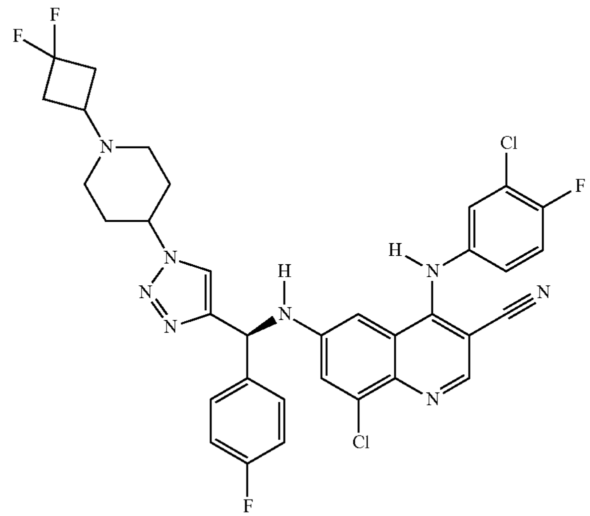 [SMILES: N#Cc1cnc2c(Cl)cc(N[C@@H](c3ccc(F)cc3)c3cn(C4CCN(C5CC(F)(F)C5)CC4)nn3)cc2c1Nc1ccc(F)c(Cl)c1] | (S)-8-chloro-4-((3-chloro-4-fluorophenyl)amino)-6-(((1-(3,3-difluorocyclobutyl)piperidin-4-yl)-1H-1,2,3-triazol-4-yl)(4-fluorophenyl)methyl)amino)-quinoline-3-carbonitrile | 31 | ES/MS 695.1 (M + H+) |
| 823 | 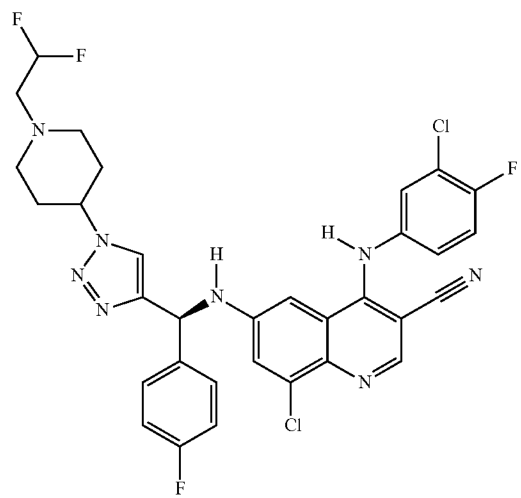 | (S)-8-chloro-4-((3-chloro-4-fluorophenyl)amino)-6-(((1-(2,2-difluoroethyl)piperidin-4-yl)-1H-1,2,3-triazol-4-yl)(4-fluorophenyl)methyl)amino)-quinoline-3-carbonitrile | 35 | ES/MS 669.0 (M + H+) |

TABLE 1-continued
| Compd | Structure | Name | Example/Procedure | ES/MS m/z |
|---|---|---|---|---|
| 824 | 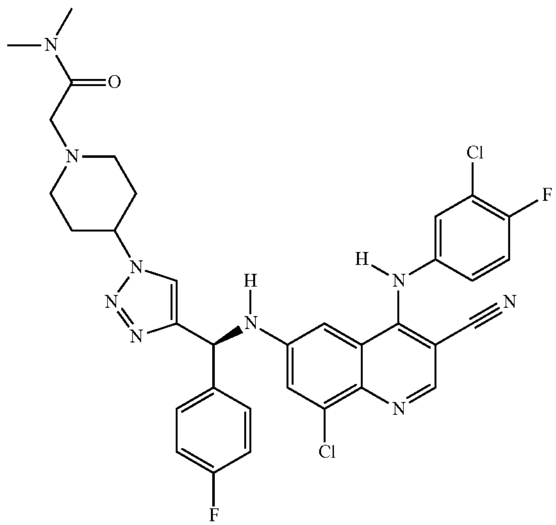 [SMILES: CN(C)C(=O)CN1CCC(n2cc([C@@H](Nc3cc(Cl)c4ncc(C#N)c(Nc5ccc(F)c(Cl)c5)c4c3)c3ccc(F)cc3)nn2)CC1] | (S)-2-(4-(4-(((8-chloro-4-((3-chloro-4-fluorophenyl)amino)-3-cyanoquinolin-6-yl)amino)(4-fluorophenyl)methyl)-1H-1,2,3-triazol-1-yl)piperidin-1-yl)-N,N-dimethylacetamide | 35 | ES/MS 690.3 (M + H+) |
| 825 | 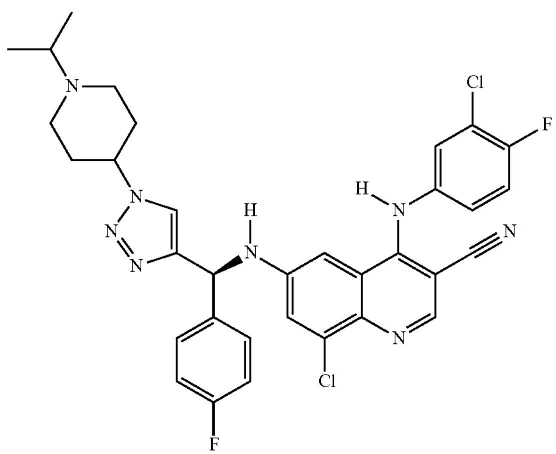 [SMILES: CC(C)N1CCC(n2cc([C@@H](Nc3cc(Cl)c4ncc(C#N)c(Nc5ccc(F)c(Cl)c5)c4c3)c3ccc(F)cc3)nn2)CC1] | (S)-8-chloro-4-((3-chloro-4-fluorophenyl)amino)-6-(((4-fluorophenyl)(1-(1-isopropylpiperidin-4-yl)-1H-1,2,3-triazol-4-yl)methyl)amino)quinoline-3-carbonitrile | 1 | 647.6 |

TABLE 1-continued
| Compd | Structure | Name | Example/Procedure | ES/MS m/z |
|---|---|---|---|---|
| 826 | 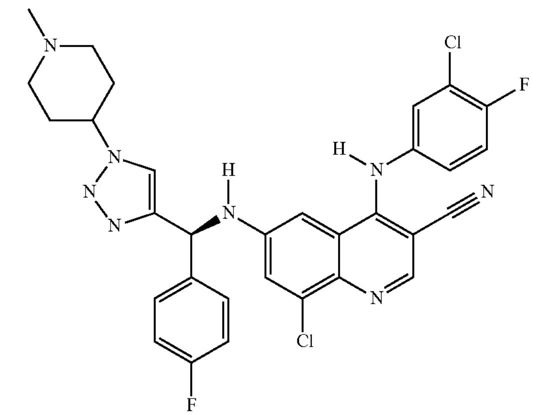 [SMILES: CN1CCC(N2C=C([C@@H](Nc3cc(Cl)c4ncc(C#N)c(Nc5ccc(F)c(Cl)c5)c4c3)c3ccc(F)cc3)NN2)CC1] | (S)-8-chloro-4-((3-chloro-4-fluorophenyl)amino)-6-(((1-(1-methylpiperidin-4-yl)(4-fluorophenyl)(1H-1,2,3-triazol-4-yl)methyl)amino)quinoline-3-carbonitrile | 31 | ES/MS 619.2 (M + H+) |
| 827 | 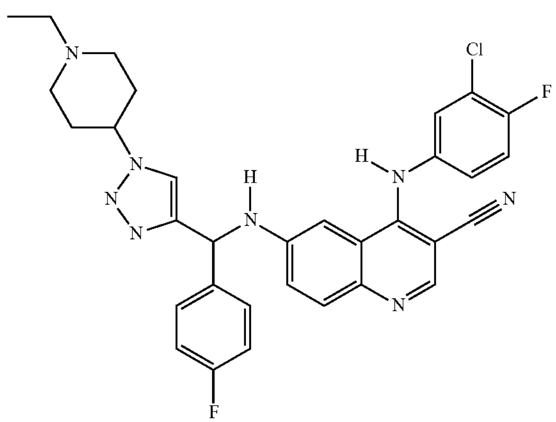 | 4-(3-chloro-4-fluorophenyl)amino)-6-(((1-(1-ethylpiperidin-4-yl)-1H-1,2,3-triazol-4-yl)(4-fluorophenyl)methyl)amino)-quinoline-3-carbonitrile | 5 | |

TABLE 1-continued
| Compd | Structure | Name | Example/Procedure | ES/MS m/z |
|---|---|---|---|---|
| 828 | 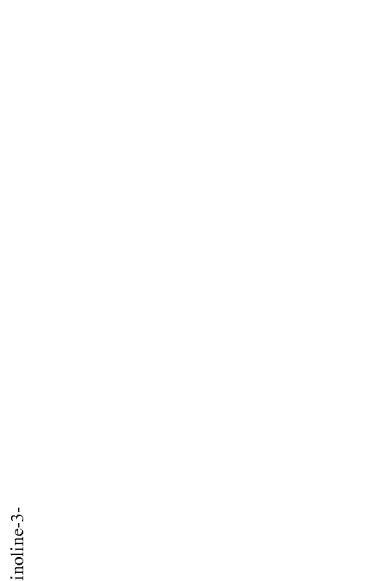 | (S)-8-chloro-4-((3-chloro-4-fluorophenyl)amino)-6-(((4-fluorophenyl)(1-(2,2,2-trifluoroethyl)piperidin-4-yl)-1H-1,2,3-triazol-4-yl)methyl)amino)quinoline-3-carbonitrile | 35 | ES/MS 688.1 (M + H+) |
| 829 | 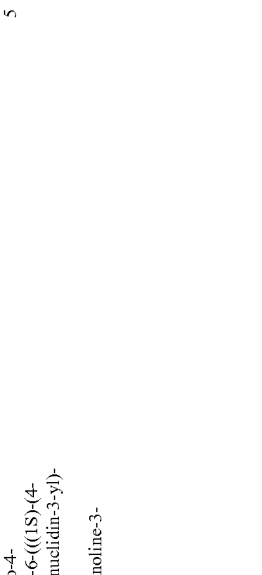 | 8-chloro-4-((3-chloro-4-fluorophenyl)amino)-6-(((1S)-(4-fluorophenyl)(1-(quinuclidin-3-yl)-1H-1,2,3-triazol-4-yl)methyl)amino)quinoline-3-carbonitrile | 5 | ES/MS 631.2 (M + H+) |

TABLE 1-continued

| Compd | Structure | Name | Example/Procedure | ES/MS m/z |
|---|---|---|---|---|
| 830 | 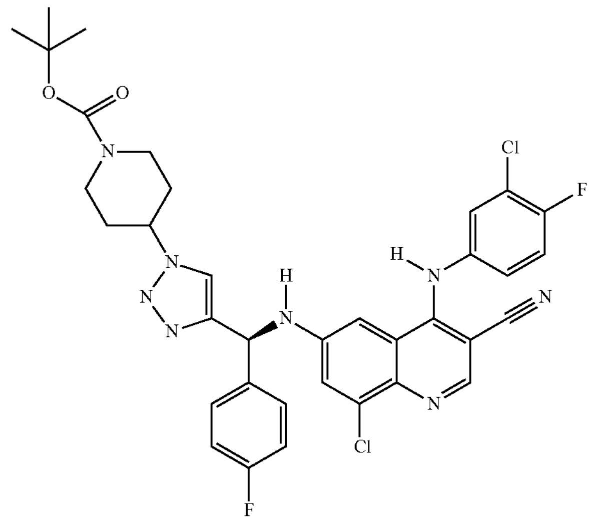 [SMILES: CC(C)(C)OC(=O)N1CCC(N2C=C([C@@H](Nc3cc(Cl)c4ncc(C#N)c(Nc5ccc(F)c(Cl)c5)c4c3)c3ccc(F)cc3)NN2)CC1] | tert-butyl (S)-4-(4-(((8-chloro-4-((3-chloro-4-fluorophenyl)amino)-cyanoquinolin-6-yl)amino)(4-fluorophenyl)methyl)-1H-1,2,3-triazol-1-yl)piperidine-1-carboxylate | 31 | ES/MS 705.6 (M + H+) |
| 831 | 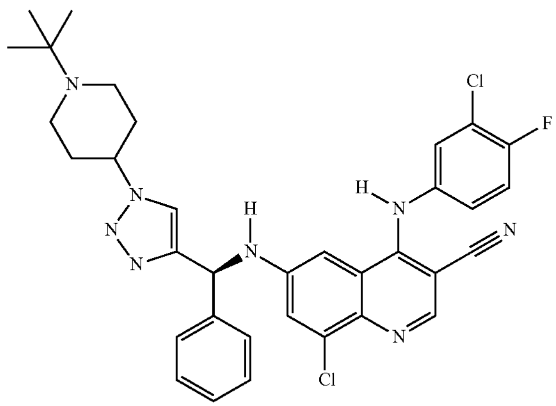 | (S)-6-(((1-(1-(tert-butyl)piperidin-4-yl)-1H-1,2,3-triazol-4-yl)(phenyl)methyl)amino)-8-chloro-4-((3-chloro-4-fluorophenyl)amino)quinoline-3-carbonitrile | 1 | ES/MS 643.2 (M + H+) |

TABLE 1-continued
| Compd | Structure | Name | Example/Procedure | ES/MS m/z |
|---|---|---|---|---|
| 832 | 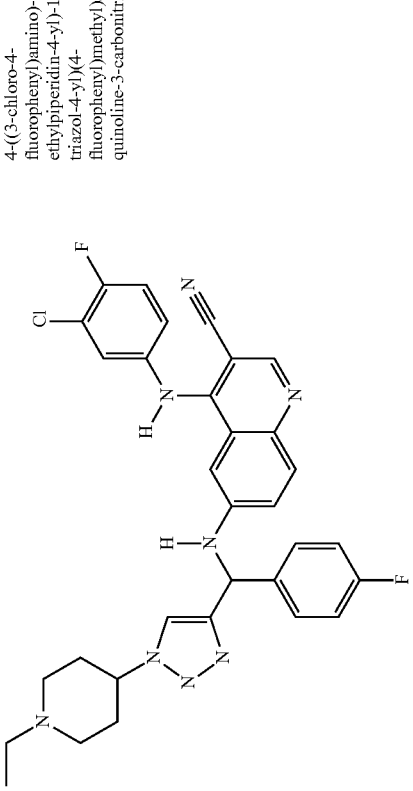 | 4-((3-chloro-4-fluorophenyl)amino)-6-(((1-(1-ethylpiperidin-4-yl)-1H-1,2,3-triazol-4-yl)(4-fluorophenyl)methyl)amino)quinoline-3-carbonitrile | 6 | |
| 833 | 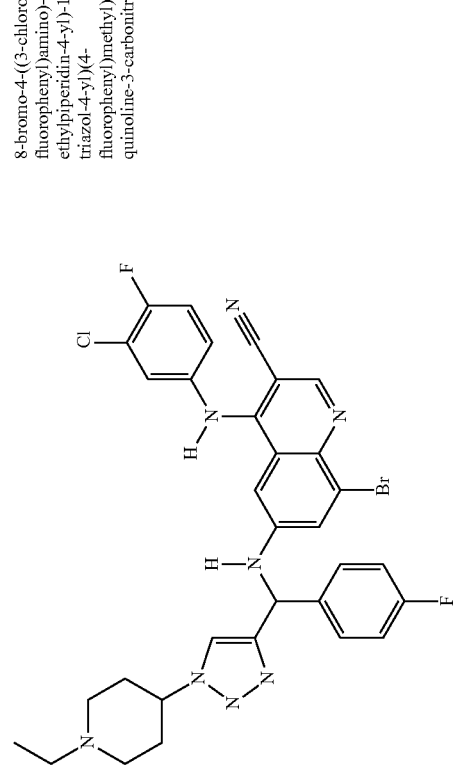 | 8-bromo-4-((3-chloro-4-fluorophenyl)amino)-6-(((1-(1-ethylpiperidin-4-yl)-1H-1,2,3-triazol-4-yl)(4-fluorophenyl)methyl)amino)quinoline-3-carbonitrile | 6 | ES/MS 677.2 (M + H+) |

TABLE 1-continued
| Compd | Structure | Name | Example/Procedure | ES/MS m/z |
|---|---|---|---|---|
| 834 | 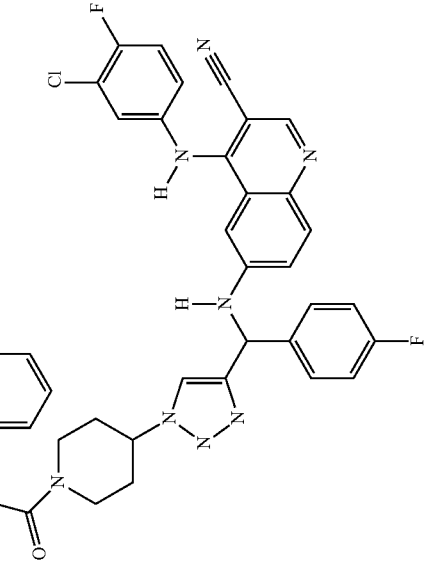 | benzyl 4-(4-(((4-((3-chloro-4-fluorophenyl)amino)-3-cyanoquinolin-6-yl)amino)(4-fluorophenyl)methyl)-1H-1,2,3-triazol-1-yl)piperidine-1-carboxylate | 6 | ES/MS 705.9 (M + H+) |
| 835 | 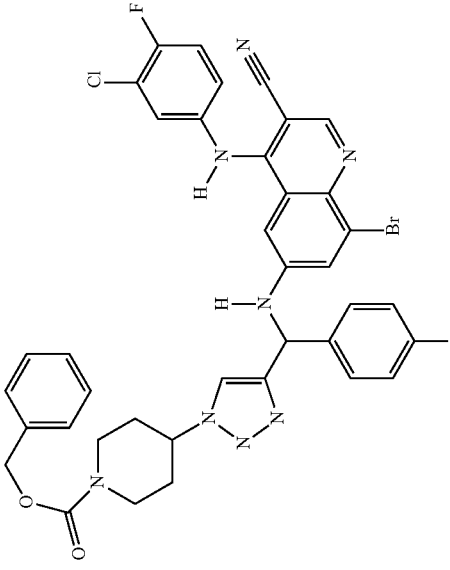 | benzyl 4-(4-(((8-bromo-4-((3-chloro-4-fluorophenyl)amino)-3-cyanoquinolin-6-yl)amino)(4-fluorophenyl)methyl)-1H-1,2,3-triazol-1-yl)piperidine-1-carboxylate | 6 | |

TABLE 1-continued

| Compd | Structure | Name | Example/Procedure | ES/MS m/z |
|---|---|---|---|---|
| 836 | 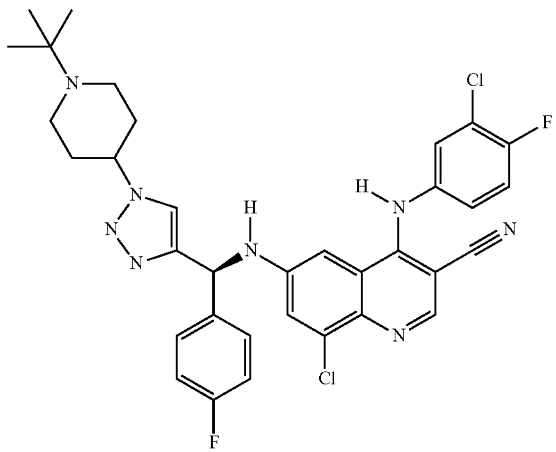 [SMILES: CC(C)(C)N1CCC(N2C=C([C@@H](Nc3cc(Cl)c4ncc(C#N)c(Nc5ccc(F)c(Cl)c5)c4c3)c3ccc(F)cc3)NN2)CC1] | (S)-6-((((1-(1-(tert-butyl)piperidin-4-yl)-1H-1,2,3-triazol-4-yl)(4-fluorophenyl)methyl)amino)-8-fluorophenyl)amino)quinoline-3-carbonitrile | 1 | ES/MS 662.1 (M + H+) |
| 837 | 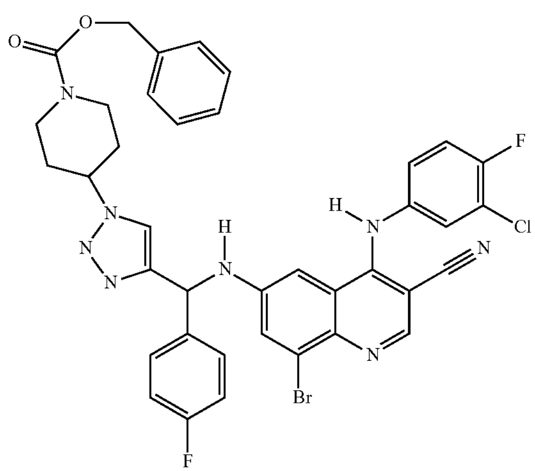 [SMILES: N#Cc1cnc2c(Br)cc(NC(C3=CN(C4CCN(C(=O)OCc5ccccc5)CC4)NN3)c3ccc(F)cc3)cc2c1Nc1ccc(F)c(Cl)c1] | benzyl 4-(4-(((8-bromo-4-((3-chloro-4-fluorophenyl)amino)-3-cyanoquinolin-6-yl)amino)(4-fluorophenyl)methyl)-1H-1,2,3-triazol-1-yl)piperidine-1-carboxylate | 6 | |

TABLE 1-continued

| Compd | Structure | Name | Example/Procedure | ES/MS m/z |
|---|---|---|---|---|
| 838 | 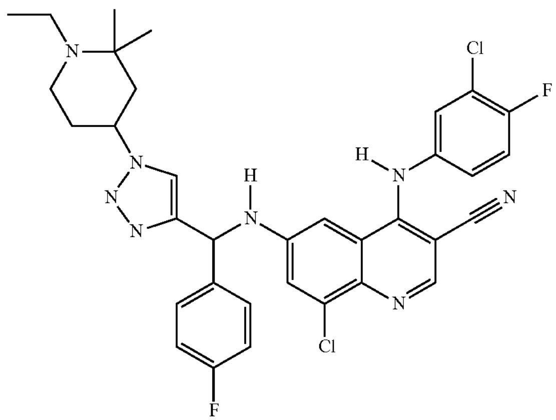 [SMILES: CCN1CCC(N2C=C(C(Nc3cc(Cl)c4ncc(C#N)c(Nc5ccc(F)c(Cl)c5)c4c3)c3ccc(F)cc3)NN2)CC1(C)C] | 8-chloro-4-((3-chloro-4-fluorophenyl)amino)-6-(((1-(1-ethyl-2,2-dimethylpiperidin-4-yl)-1H-1,2,3-triazol-4-yl)(4-fluorophenyl)methyl)amino)quinoline-3-carbonitrile | 6 | |
| 839 | 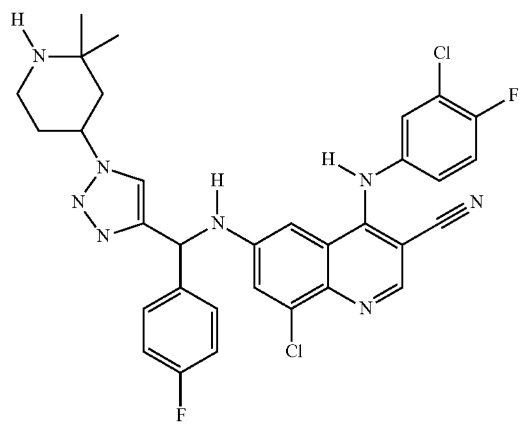 [SMILES: CC1(C)CC(N2C=C(C(Nc3cc(Cl)c4ncc(C#N)c(Nc5ccc(F)c(Cl)c5)c4c3)c3ccc(F)cc3)NN2)CCN1] | 8-chloro-4-((3-chloro-4-fluorophenyl)amino)-6-(((1-(2,2-dimethylpiperidin-4-yl)-1H-1,2,3-triazol-4-yl)(4-fluorophenyl)methyl)amino)quinoline-3-carbonitrile | 6 | |

TABLE 1-continued

| Compd | Structure | Name | Example/Procedure | ES/MS m/z |
|---|---|---|---|---|
| 840 | 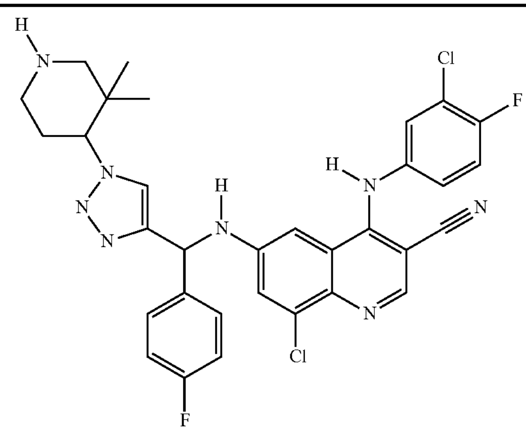 | 8-chloro-4-((3-chloro-4-fluorophenyl)amino)-6-(((1-(3,3-dimethylpiperidin-4-yl)-1H-1,2,3-triazol-4-yl)(4-fluorophenyl)methyl)amino)-quinoline-3-carbonitrile | 6 | ES/MS 633.0 (M + H+) |
| 841 | 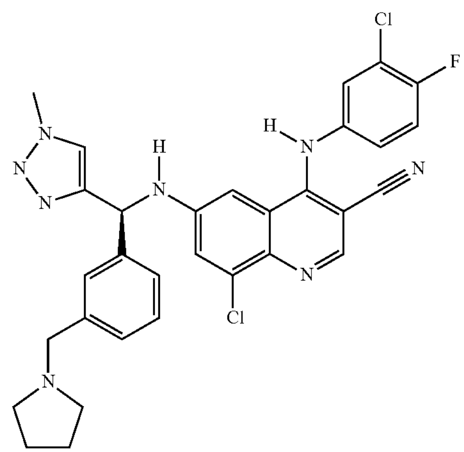 | (S)-8-chloro-4-((3-chloro-4-fluorophenyl)amino)-6-(((1-methyl-1H-1,2,3-triazol-4-yl)(3-(pyrrolidin-1-ylmethyl)phenyl)methyl)amino)-quinoline-3-carbonitrile | 6 | ES/MS 610.0 (M + H+) |

TABLE 1-continued

| Compd | Structure | Name | Example/Procedure | ES/MS m/z |
|---|---|---|---|---|
| 842 | 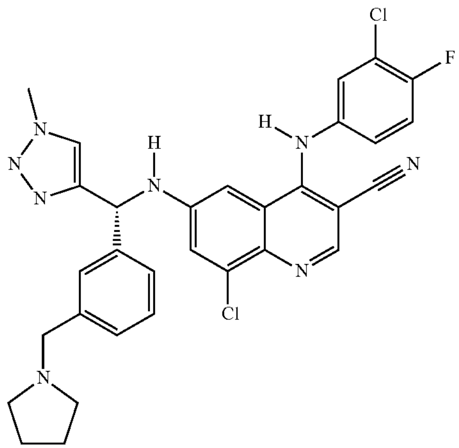 | (R)-8-chloro-4-((3-chloro-4-fluorophenyl)amino)-6-(((1-methyl-1H-1,2,3-triazol-4-yl)(3-(pyrrolidin-1-ylmethyl)phenyl)methyl)amino)quinoline-3-carbonitrile | 6 | ES/MS 601.0 (M + H+) |
| 843 | 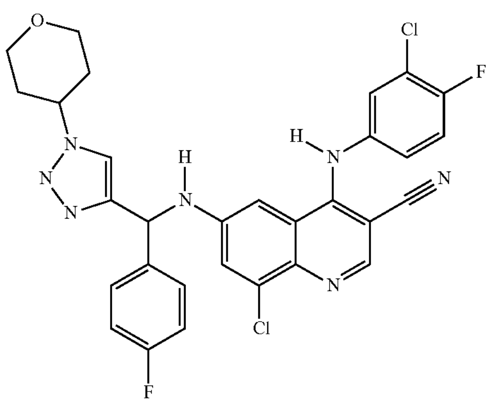 [SMILES: N#Cc1cnc2c(Cl)cc(NC(C3=CN(C4CCOCC4)NN3)c3ccc(F)cc3)cc2c1Nc1ccc(F)c(Cl)c1] | 8-chloro-4-((3-chloro-4-fluorophenyl)amino)-6-(((4-fluorophenyl)(1-(tetrahydro-2H-pyran-4-yl)-1H-1,2,3-triazol-4-yl)methyl)amino)quinoline-3-carbonitrile | 6 | |

TABLE 1-continued

| Compd | Structure | Name | Example/Procedure | ES/MS m/z |
|---|---|---|---|---|
| 844 | 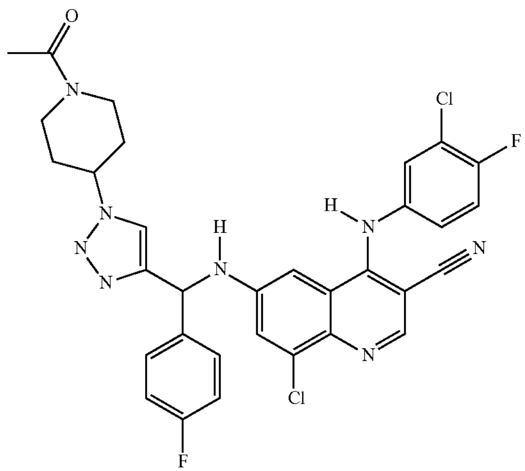 [SMILES: CC(=O)N1CCC(N2C=C(C(Nc3cc(Cl)c4ncc(C#N)c(Nc5ccc(F)c(Cl)c5)c4c3)c3ccc(F)cc3)NN2)CC1] | 6-(((1-(1-acetylpiperidin-4-yl)-1H-1,2,3-triazol-4-yl)(4-fluorophenyl)methyl)amino)-8-chloro-4-((3-chloro-4-fluorophenyl)amino)quinoline-3-carbonitrile | 6 | ES/MS 647.1 (M + H+) |
| 845 | 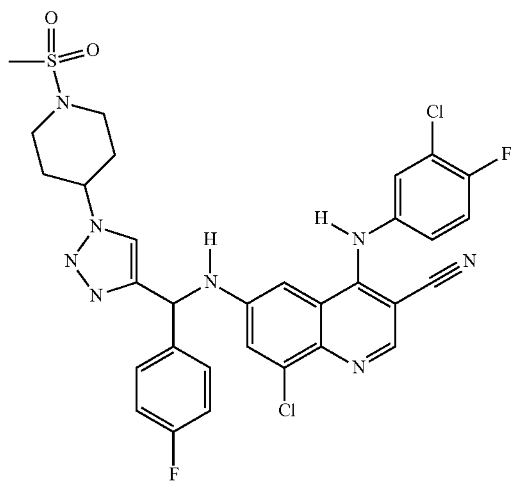 [SMILES: CS(=O)(=O)N1CCC(N2C=C(C(Nc3cc(Cl)c4ncc(C#N)c(Nc5ccc(F)c(Cl)c5)c4c3)c3ccc(F)cc3)NN2)CC1] | 8-chloro-4-((3-chloro-4-fluorophenyl)amino)-6-(((4-fluorophenyl)(1-(1-(methylsulfonyl)piperidin-4-yl)-1H-1,2,3-triazol-4-yl)methyl)amino)quinoline-3-carbonitrile | 6 | ES/MS 683.1 (M + H+) |

TABLE 1-continued

| Compd | Structure | Name | Example/Procedure | ES/MS m/z |
|---|---|---|---|---|
| 846 | 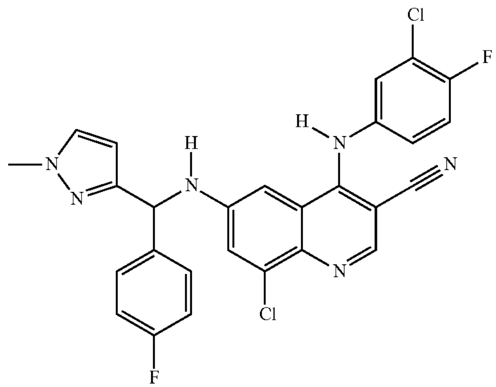 [SMILES: Cn1ccc(C(Nc2cc(Cl)c3ncc(C#N)c(Nc4ccc(F)c(Cl)c4)c3c2)c2ccc(F)cc2)n1] | 8-chloro-4-((3-chloro-4-fluorophenyl)amino)-6-(((4-fluorophenyl)(1-methyl-1H-pyrazol-3-yl)methyl)amino)quinoline-3-carbonitrile | 6 | ES/MS 535.0 (M + H+) |
| 847 | 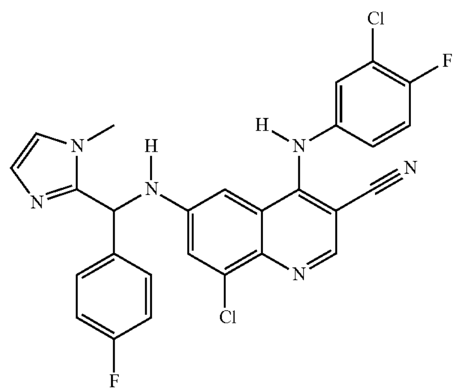 | 8-chloro-4-((3-chloro-4-fluorophenyl)amino)-6-(((4-fluorophenyl)(1-methyl-1H-imidazol-2-yl)methyl)amino)quinoline-3-carbonitrile | 6 | ES/MS 534.9 (M + H+) |

TABLE 1-continued

| Compd | Name | Structure | Example/Procedure | ES/MS m/z |
|---|---|---|---|---|
| 848 | benzyl 4-(4-(((8-chloro-4-((3-chloro-4-fluorophenyl)amino)-3-cyanoquinolin-6-yl)amino)(phenyl)methyl)-1H-1,2,3-triazol-1-yl)piperidine-1-carboxylate | 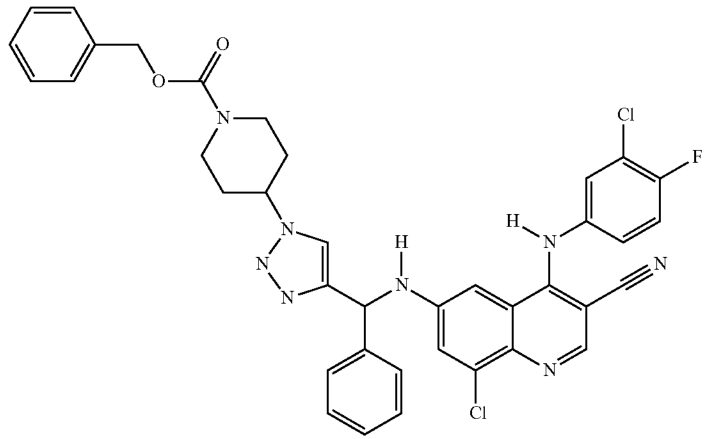 [SMILES: N#Cc1cnc2c(Cl)cc(NC(C3=CN(C4CCN(C(=O)OCc5ccccc5)CC4)NN3)c3ccccc3)cc2c1Nc1ccc(F)c(Cl)c1] | 6 | |
| 849 | (R)-8-chloro-4-((3-chloro-4-fluorophenyl)amino)-6-(((1-(1-ethylpiperidin-4-yl)-1H-1,2,3-triazol-4-yl)(4-fluorophenyl)methyl)amino)quinoline-3-carbonitrile | 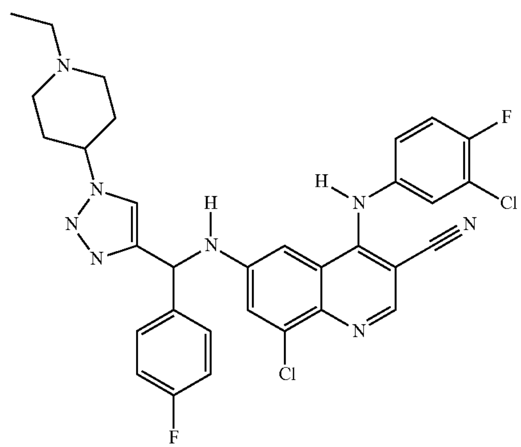 [SMILES: CCN1CCC(N2C=C(C(Nc3cc(Cl)c4ncc(C#N)c(Nc5ccc(F)c(Cl)c5)c4c3)c3ccc(F)cc3)NN2)CC1] | 6 | ES/MS 633.1 (M + H+) |

TABLE 1-continued

| Compd | Structure | Name | Example/Procedure | ES/MS m/z |
|---|---|---|---|---|
| 850 | 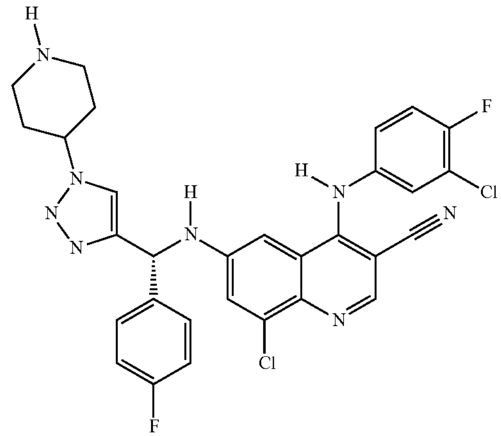 | (R)-8-chloro-4-((3-chloro-4-fluorophenyl)amino)-6-(((4-fluorophenyl)(1-(piperidin-4-yl)-1H-1,2,3-triazol-4-yl)methyl)amino)quinoline-3-carbonitrile | 6 | ES/MS 605.1 (M + H+) |
| 851 | 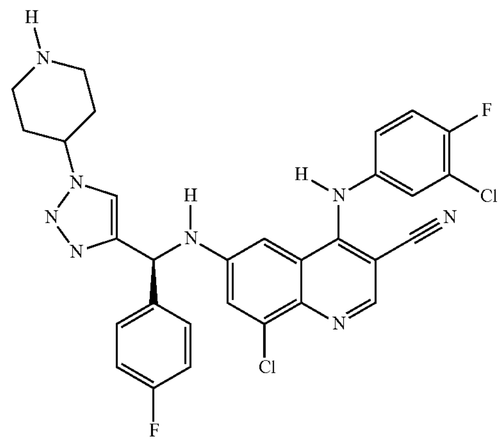 | (S)-8-chloro-4-((3-chloro-4-fluorophenyl)amino)-6-(((4-fluorophenyl)(1-(piperidin-4-yl)-1H-1,2,3-triazol-4-yl)methyl)amino)quinoline-3-carbonitrile | 6 | ES/MS 605.1 (M + H+) |

TABLE 1-continued
| Compd | Structure | Name | Example/Procedure | ES/MS m/z |
|---|---|---|---|---|
| 852 | 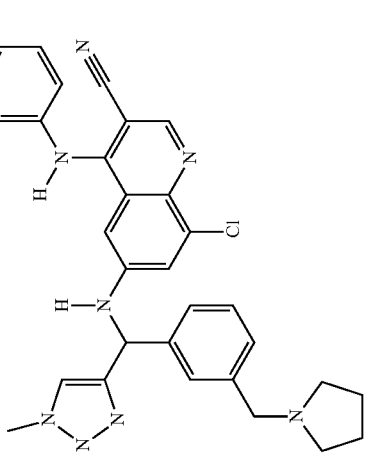 | 8-chloro-4-((3-chloro-4-fluorophenyl)amino)-6-(((1-methyl-1H-1,2,3-triazol-4-yl)(3-(pyrrolidin-1-ylmethyl)phenyl)methyl)amino)quinoline-3-carbonitrile | | |
| 853 | 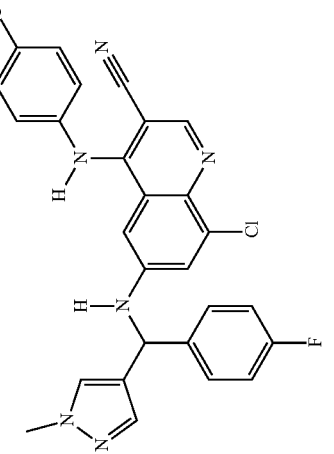 | 8-chloro-4-((3-chloro-4-fluorophenyl)amino)-6-(((4-fluorophenyl)(1-methyl-1H-pyrazol-4-yl)methyl)amino)quinoline-3-carbonitrile | 6 | ES/MS 535.1 (M + H+) |

TABLE 1-continued

| Compd | Structure | Name | Example/Procedure | ES/MS m/z |
|---|---|---|---|---|
| 854 | 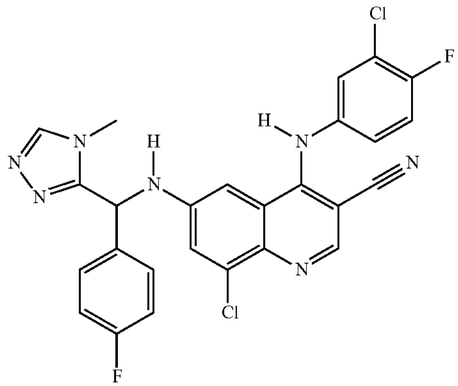 [SMILES: Cn1cnnc1C(Nc1cc(Cl)c2ncc(C#N)c(Nc3ccc(F)c(Cl)c3)c2c1)c1ccc(F)cc1] | 8-chloro-4-((3-chloro-4-fluorophenyl)amino)-6-(((4-fluorophenyl)(4-methyl-4H-1,2,4-triazol-3-yl)methyl)amino)quinoline-3-carbonitrile | 6 | ES/MS 536.1 (M + H+) |
| 855 | 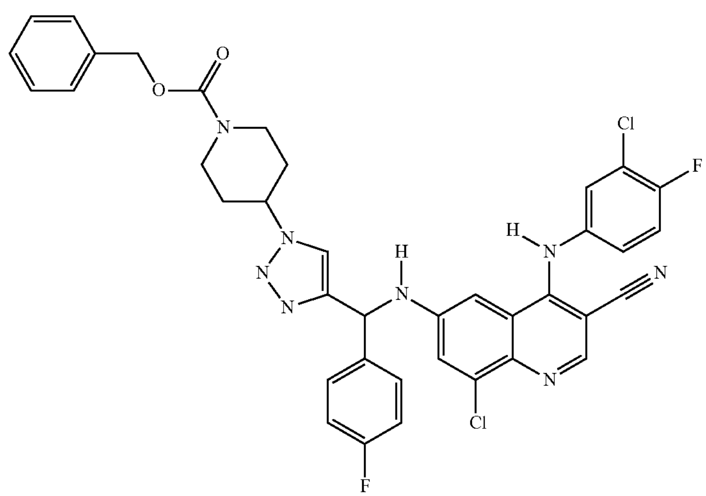 [SMILES: N#Cc1cnc2c(Cl)cc(NC(C3=CN(C4CCN(C(=O)OCc5ccccc5)CC4)NN3)c3ccc(F)cc3)cc2c1Nc1ccc(F)c(Cl)c1] | benzyl 4-(4-(((8-chloro-4-((3-chloro-4-fluorophenyl)amino)-3-cyanoquinolin-6-yl)amino)(4-fluorophenyl)methyl)-1H-1,2,3-triazol-1-yl)piperidine-1-carboxylate | 6 | ES/MS 738.8 (M + H+) |

TABLE 1-continued

| Compd | Structure | Name | Example/Procedure | ES/MS m/z |
|---|---|---|---|---|
| 856 | 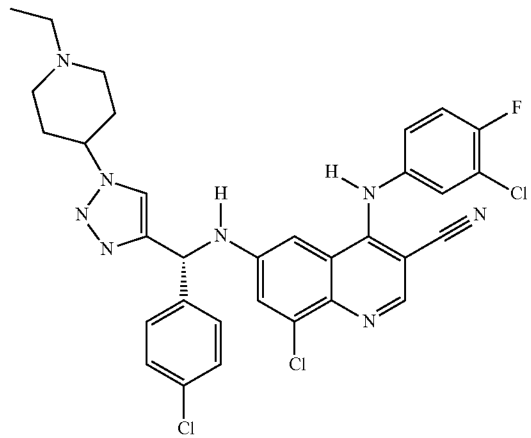 [SMILES: CCN1CCC(N2C=C([C@H](Nc3cc(Cl)c4ncc(C#N)c(Nc5ccc(F)c(Cl)c5)c4c3)c3ccc(Cl)cc3)NN2)CC1] | (R)-8-chloro-4-((3-chloro-4-fluorophenyl)amino)-6-(((4-chlorophenyl)(1-(1-ethylpiperidin-4-yl)-1H-1,2,3-triazol-4-yl)methyl)amino)quinoline-3-carbonitrile | 6 | ES/MS 649.0 (M + H+) |
| 857 | 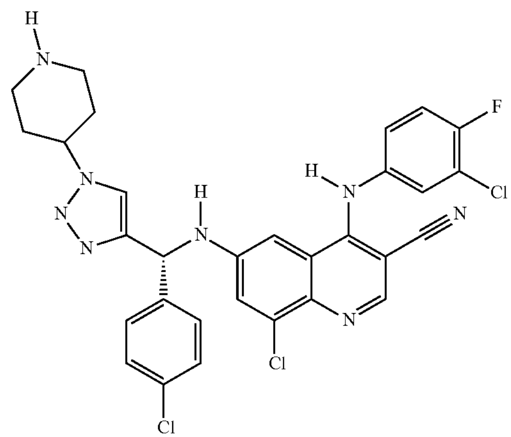 [SMILES: N#Cc1cnc2c(Cl)cc(N[C@@H](C3=CN(C4CCNCC4)NN3)c3ccc(Cl)cc3)cc2c1Nc1ccc(F)c(Cl)c1] | (R)-8-chloro-4-((3-chloro-4-fluorophenyl)amino)-6-(((4-chlorophenyl)(1-(piperidin-4-yl)-1H-1,2,3-triazol-4-yl)methyl)amino)quinoline-3-carbonitrile | 6 | ES/MS 620.4 (M + H+) |

TABLE 1-continued

| Compd | Structure | Name | Example/Procedure | ES/MS m/z |
|---|---|---|---|---|
| 858 | 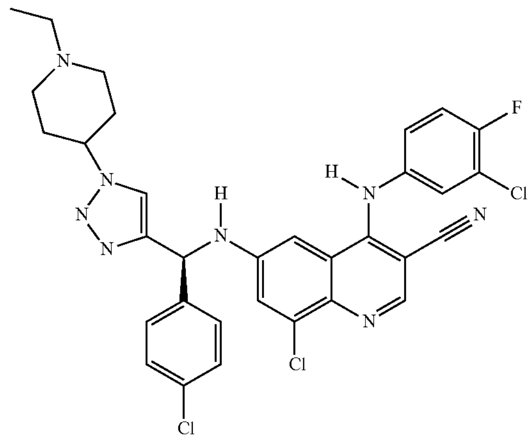 [SMILES: CCN1CCC(N2C=C([C@@H](Nc3cc(Cl)c4ncc(C#N)c(Nc5ccc(F)c(Cl)c5)c4c3)c3ccc(Cl)cc3)NN2)CC1] | (S)-8-chloro-4-((3-chloro-4-fluorophenyl)amino)-6-(((4-chlorophenyl)(1-(1-ethylpiperidin-4-yl)-1H-1,2,3-triazol-4-yl)methyl)amino)quinoline-3-carbonitrile | 6 | ES/MS 651.1 (M + H+) |
| 859 | 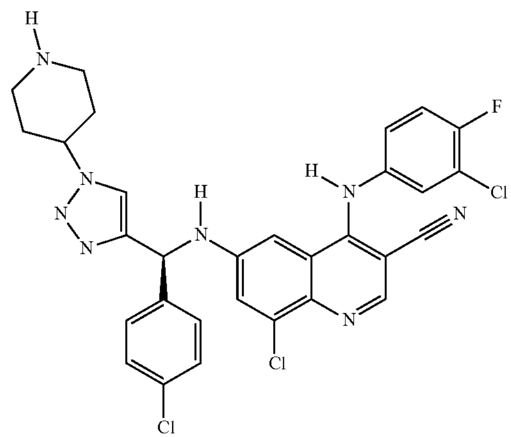 [SMILES: N#Cc1cnc2c(Cl)cc(N[C@H](C3=CN(C4CCNCC4)NN3)c3ccc(Cl)cc3)cc2c1Nc1ccc(F)c(Cl)c1] | (S)-8-chloro-4-((3-chloro-4-fluorophenyl)amino)-6-(((4-chlorophenyl)(1-(piperidin-4-yl)-1H-1,2,3-triazol-4-yl)methyl)amino)quinoline-3-carbonitrile | 6 | ES/MS 621.2 (M + H+) |

TABLE 1-continued
| Compd | Structure | Name | Example/Procedure | ES/MS m/z |
|---|---|---|---|---|
| 860 | 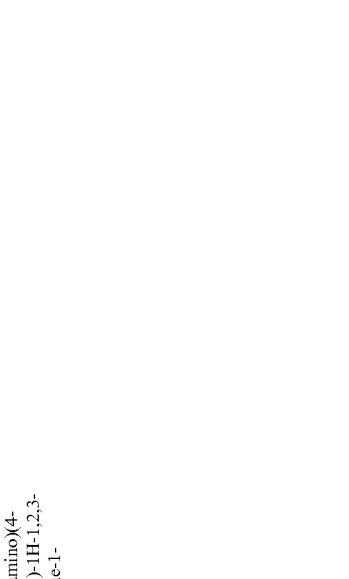 | benzyl (R)-4-(4-(((8-chloro-4-((3-chloro-4-fluorophenyl)amino)-3-cyanoquinolin-6-yl)amino)(4-chlorophenyl)methyl)-1H-1,2,3-triazol-1-yl)piperidine-1-carboxylate | 6 | ES/MS 755.0 (M + H+) |
| 861 | 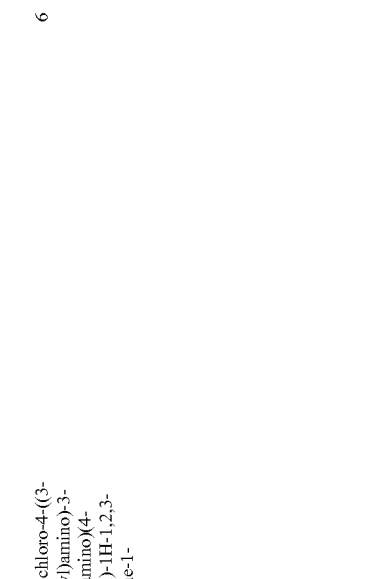 | benzyl (S)-4-(4-(((8-chloro-4-((3-chloro-4-fluorophenyl)amino)-3-cyanoquinolin-6-yl)amino)(4-chlorophenyl)methyl)-1H-1,2,3-triazol-1-yl)piperidine-1-carboxylate | 6 | ES/MS 756.4 (M + H+) |

TABLE 1-continued

| Compd | Structure | Name | Example/Procedure | ES/MS m/z |
|---|---|---|---|---|
| 862 | 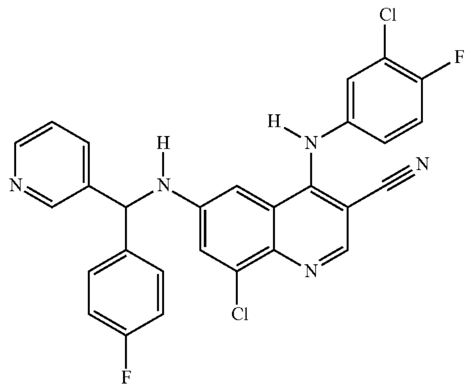 [SMILES: N#Cc1cnc2c(Cl)cc(NC(c3ccc(F)cc3)c3cccnc3)cc2c1Nc1ccc(F)c(Cl)c1] | 8-chloro-4-((3-chloro-4-fluorophenyl)amino)-6-(((4-fluorophenyl)(pyridin-3-yl)methyl)amino)quinoline-3-carbonitrile | 6 | ES/MS 531.5 (M + H+) |
| 863 | 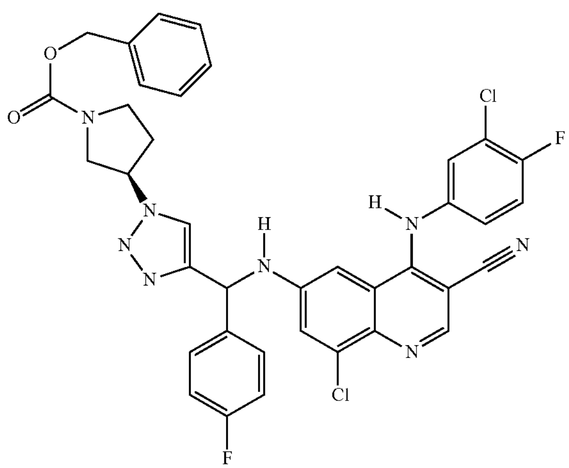 [SMILES: N#Cc1cnc2c(Cl)cc(NC(C3=CN([C@@H]4CCN(C(=O)OCc5ccccc5)C4)NN3)c3ccc(F)cc3)cc2c1Nc1ccc(F)c(Cl)c1] | benzyl (3R)-3-(4-(((8-chloro-4-((3-chloro-4-fluorophenyl)amino)-3-cyanoquinolin-6-yl)amino)(4-fluorophenyl)methyl)-1H-1,2,3-triazol-1-yl)pyrrolidine-1-carboxylate | 6 | ES/MS 725.6 (M + H+) |

TABLE 1-continued
| Compd | Structure | Name | Example/Procedure | ES/MS m/z |
|---|---|---|---|---|
| 864 | 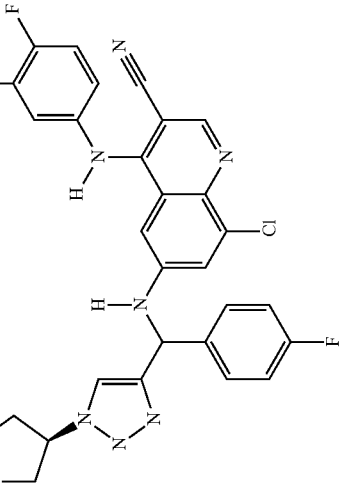 | 8-chloro-4-((3-chloro-4-fluorophenyl)amino)-6-(((4-fluorophenyl)(1-((R)-pyrrolidin-3-yl)-1H-1,2,3-triazol-4-yl)methyl)amino)quinoline-3-carbonitrile | 6 | |
| 865 | 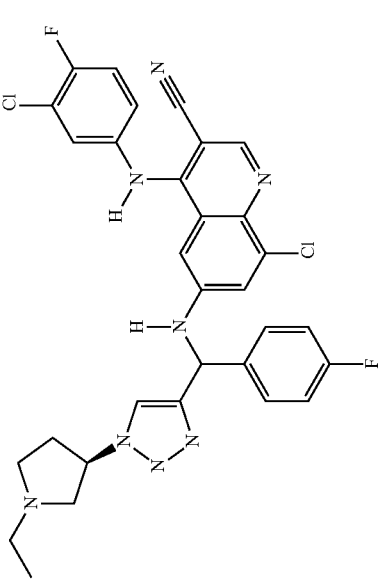 | 8-chloro-4-((3-chloro-4-fluorophenyl)amino)-6-(((1-((R)-1-ethylpyrrolidin-3-yl)-1H-1,2,3-triazol-4-yl)(4-fluorophenyl)methyl)amino)quinoline-3-carbonitrile | 6 | |

TABLE 1-continued

| Compd | Structure | Name | Example/Procedure | ES/MS m/z |
|---|---|---|---|---|
| 866 | 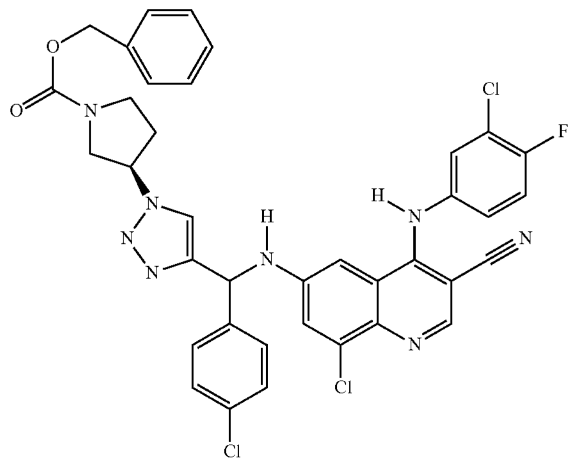 [SMILES: N#Cc1cnc2c(Cl)cc(NC(C3=CN([C@@H]4CCN(C(=O)OCc5ccccc5)C4)NN3)c3ccc(Cl)cc3)cc2c1Nc1ccc(F)c(Cl)c1] | benzyl (3R)-3-(4-(((8-chloro-4-((3-chloro-4-fluorophenyl)amino)-3-cyanoquinolin-6-yl)amino)(4-chlorophenyl)methyl)-1H-1,2,3-triazol-1-yl)pyrrolidine-1-carboxylate | 6 | ES/MS 741.2 (M + H+) |
| 867 | 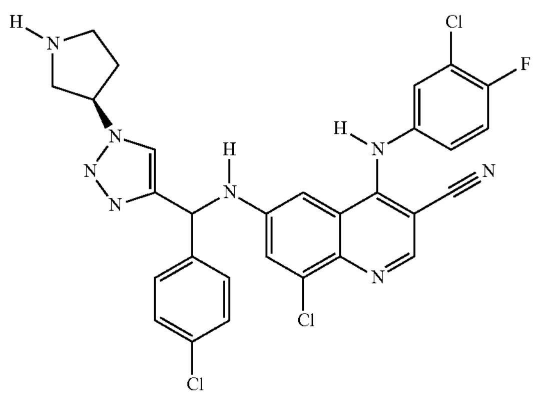 [SMILES: N#Cc1cnc2c(Cl)cc(NC(C3=CN([C@@H]4CCNC4)NN3)c3ccc(Cl)cc3)cc2c1Nc1ccc(F)c(Cl)c1] | 8-chloro-4-((3-chloro-4-fluorophenyl)amino)-6-(((4-chlorophenyl)(1-((R)-pyrrolidin-3-yl)-1H-1,2,3-triazol-4-yl)methyl)amino)quinoline-3-carbonitrile | 6 | ES/MS 607.2 (M + H+) |

TABLE 1-continued

| Compd | Structure | Name | Example/Procedure | ES/MS m/z |
|---|---|---|---|---|
| 868 | 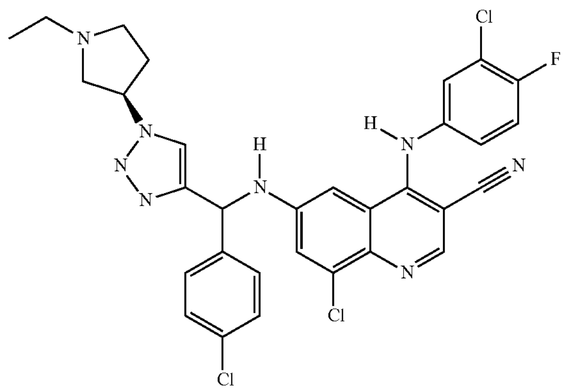 [SMILES: CCN1CC[C@@H](N2C=C(C(Nc3cc(Cl)c4ncc(C#N)c(Nc5ccc(F)c(Cl)c5)c4c3)c3ccc(Cl)cc3)NN2)C1] | 8-chloro-4-((3-chloro-4-fluorophenyl)amino)-6-(((4-chlorophenyl)(1-((R)-1-ethylpyrrolidin-3-yl)-1H-1,2,3-triazol-4-yl)methyl)amino)quinoline-3-carbonitrile | 6 | ES/MS 634.5 (M + H+) |
| 869 | 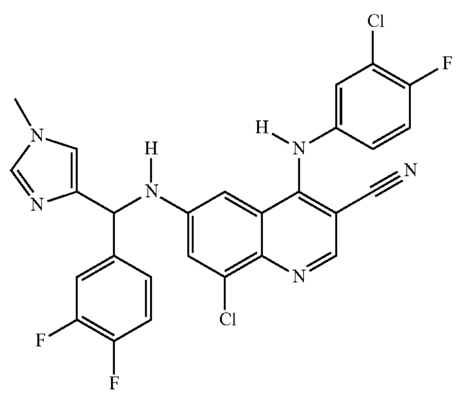 [SMILES: Cn1cnc(C(Nc2cc(Cl)c3ncc(C#N)c(Nc4ccc(F)c(Cl)c4)c3c2)c2ccc(F)c(F)c2)c1] | 8-chloro-4-((3-chloro-4-fluorophenyl)amino)-6-(((3,4-difluorophenyl)(1-methyl-1H-imidazol-4-yl)methyl)amino)quinoline-3-carbonitrile | 6 | ES/MS 553.2 (M + H+) |

TABLE 1-continued

| Compd | Structure | Name | Example/Procedure | ES/MS m/z |
|---|---|---|---|---|
| 870 | 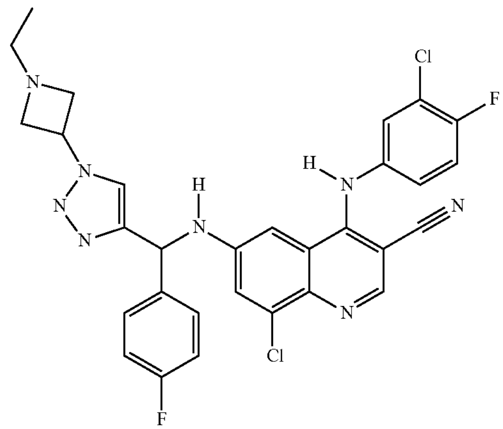 [SMILES: CCN1CC(N2C=C(C(Nc3cc(Cl)c4ncc(C#N)c(Nc5ccc(F)c(Cl)c5)c4c3)c3ccc(F)cc3)NN2)C1] | 8-chloro-4-((3-chloro-4-fluorophenyl)amino)-6-(((1-(1-ethylazetidin-3-yl)-1H-1,2,3-triazol-4-yl)(4-fluorophenyl)methyl)amino)quinoline-3-carbonitrile | 6 | ES/MS 605.0 (M + H+) |
| 871 | 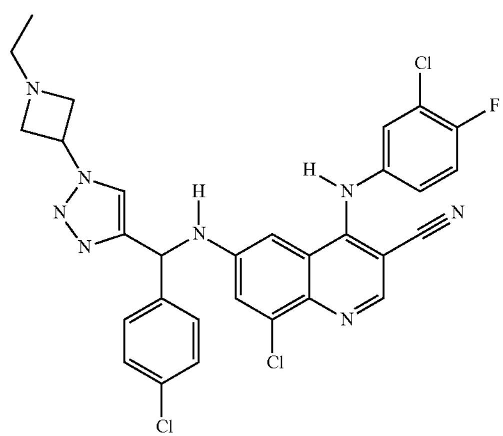 | 8-chloro-4-((3-chloro-4-fluorophenyl)amino)-6-(((4-chlorophenyl)(1-(1-ethylazetidin-3-yl)-1H-1,2,3-triazol-4-yl)methyl)amino)quinoline-3-carbonitrile | 6 | ES/MS 620.8 (M + H+) |

TABLE 1-continued

| Compd | Structure | Name | Example/Procedure | ES/MS m/z |
|---|---|---|---|---|
| 872 | 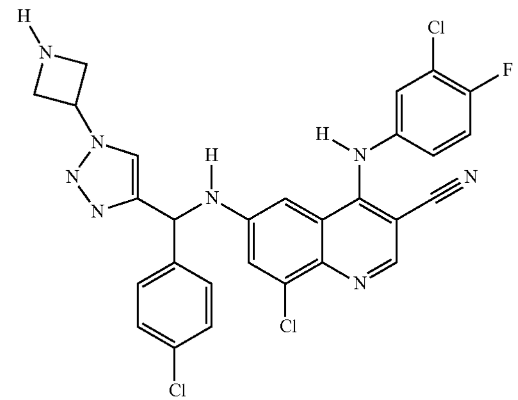 [SMILES: N#Cc1cnc2c(Cl)cc(NC(C3=CN(C4CNC4)NN3)c3ccc(Cl)cc3)cc2c1Nc1ccc(F)c(Cl)c1] | 6-(((1-(azetidin-3-yl)-1H-1,2,3-triazol-4-yl)(4-chlorophenyl)methyl)amino)-8-chloro-4-((3-chloro-4-fluorophenyl)amino)quinoline-3-carbonitrile | 6 | ES/MS 594.0 (M + H+) |
| 873 | 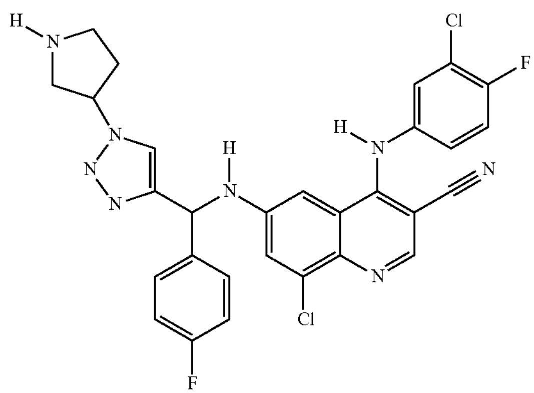 [SMILES: N#Cc1cnc2c(Cl)cc(NC(C3=CN(C4CCNC4)NN3)c3ccc(F)cc3)cc2c1Nc1ccc(F)c(Cl)c1] | 8-chloro-4-((3-chloro-4-fluorophenyl)amino)-6-(((4-fluorophenyl)(1-((S)-pyrrolidin-3-yl)-1H-1,2,3-triazol-4-yl)methyl)amino)quinoline-3-carbonitrile | 6 | ES/MS 591.0 (M + H+) |

TABLE 1-continued
| Compd | Structure | Name | Example/Procedure | ES/MS m/z |
|---|---|---|---|---|
| 874 | 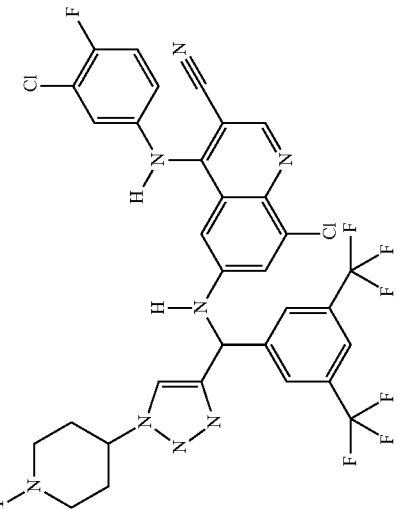 | 6-(((3,5-bis(trifluoromethyl)phenyl)(1-(piperidin-4-yl)-1H-1,2,3-triazol-4-yl)methyl)amino)-8-chloro-4-((3-chloro-4-fluorophenyl)amino)quinoline-3-carbonitrile | 6 | |
| 875 | 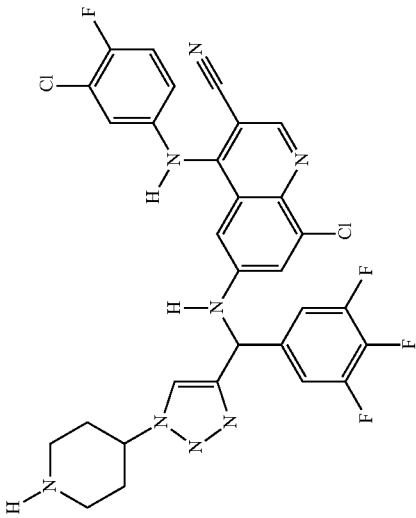 | 8-chloro-4-((3-chloro-4-fluorophenyl)amino)-6-(((1-(piperidin-4-yl)-1H-1,2,3-triazol-4-yl)(3,4,5-trifluorophenyl)methyl)amino)quinoline-3-carbonitrile | 6 | |

TABLE 1-continued

| Compd | Structure | Name | Example/Procedure | ES/MS m/z |
|---|---|---|---|---|
| 876 | 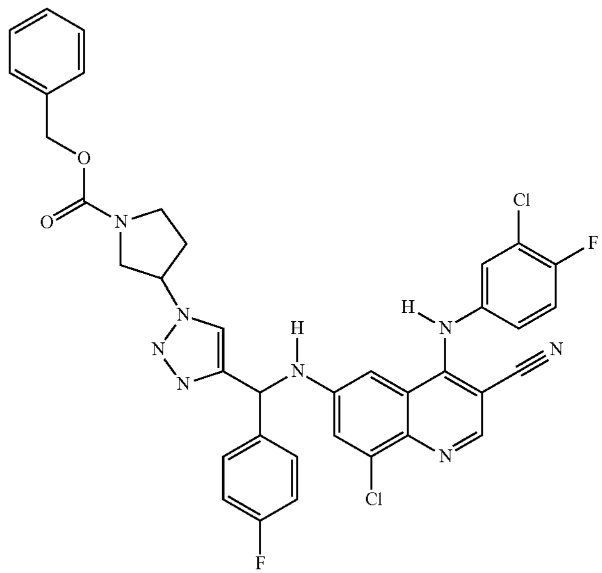 [SMILES: N#Cc1cnc2c(Cl)cc(NC(C3=CN(C4CCN(C(=O)OCc5ccccc5)C4)NN3)c3ccc(F)cc3)cc2c1Nc1ccc(F)c(Cl)c1] | benzyl (3S)-3-(4-(((8-chloro-4-((3-chloro-4-fluorophenyl)amino)-3-cyanoquinolin-6-yl)amino)(4-fluorophenyl)methyl)-1H-1,2,3-triazol-1-yl)pyrrolidine-1-carboxylate | 6 | ES/MS 724.7 (M + H+) |
| 877 | 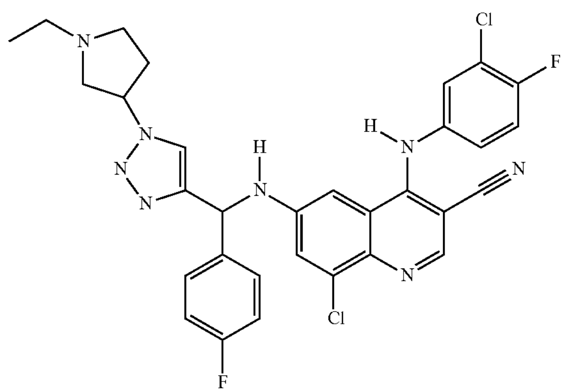 [SMILES: CCN1CCC(N2C=C(C(Nc3cc(Cl)c4ncc(C#N)c(Nc5ccc(F)c(Cl)c5)c4c3)c3ccc(F)cc3)NN2)C1] | 8-chloro-4-((3-chloro-4-fluorophenyl)amino)-6-(((1-((S)-1-ethylpyrrolidin-3-yl)-1H-1,2,3-triazol-4-yl)(4-fluorophenyl)methyl)amino)-quinoline-3-carbonitrile | 6 | ES/MS 619.0 (M + H+) |

TABLE 1-continued

| Compd | Structure | Name | Example/Procedure | ES/MS m/z |
|---|---|---|---|---|
| 878 | 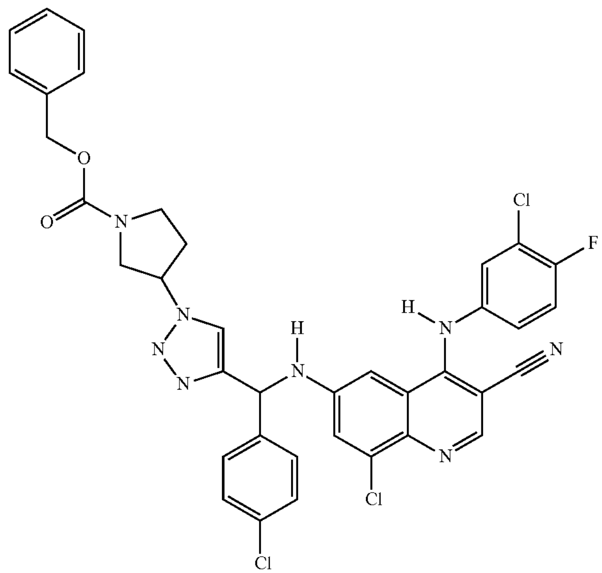 [SMILES: N#Cc1cnc2c(Cl)cc(NC(C3=CN(C4CCN(C(=O)OCc5ccccc5)C4)NN3)c3ccc(Cl)cc3)cc2c1Nc1ccc(F)c(Cl)c1] | benzyl (3S)-3-(4-(((8-chloro-4-((3-chloro-4-fluorophenyl)amino)-3-cyanoquinolin-6-yl)amino)(4-chlorophenyl)methyl)-1H-1,2,3-triazol-1-yl)pyrrolidine-1-carboxylate | 6 | ES/MS 742.8 (M + H+) |
| 879 | 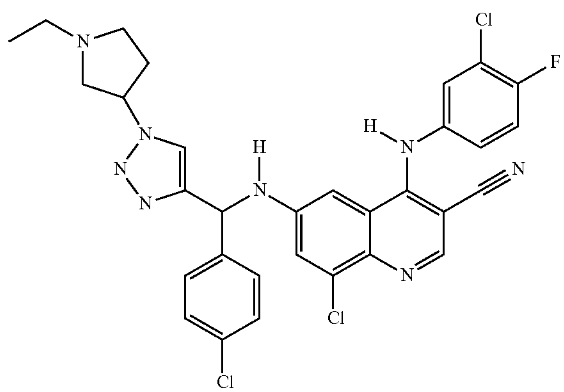 [SMILES: CCN1CCC(N2C=C(C(Nc3cc(Cl)c4ncc(C#N)c(Nc5ccc(F)c(Cl)c5)c4c3)c3ccc(Cl)cc3)NN2)C1] | 8-chloro-4-((3-chloro-4-fluorophenyl)amino)-6-(((4-chlorophenyl)(1-((S)-1-ethylpyrrolidin-3-yl)-1H-1,2,3-triazol-4-yl)methyl)amino)quinoline-3-carbonitrile | 6 | ES/MS 635.0 (M + H+) |

TABLE 1-continued

| Compd | Structure | Name | Example/Procedure | ES/MS m/z |
|---|---|---|---|---|
| 880 | 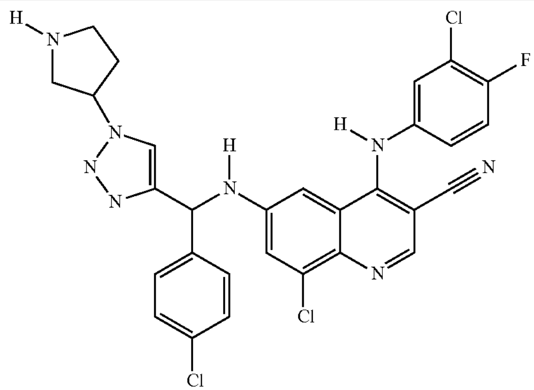 [SMILES: N#Cc1cnc2c(Cl)cc(NC(C3=CN(C4CCNC4)NN3)c3ccc(Cl)cc3)cc2c1Nc1ccc(F)c(Cl)c1] | 8-chloro-4-((3-chloro-4-fluorophenyl)amino)-6-(((4-chlorophenyl)(1-((S)-pyrrolidin-3-yl)-1H-1,2,3-triazol-4-yl)methyl)amino)quinoline-3-carbonitrile | 6 | ES/MS 606.7 (M + H+) |
| 881 | 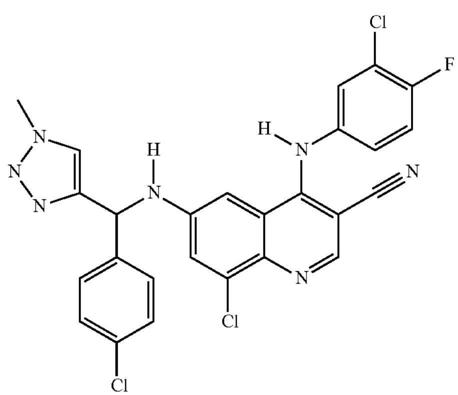 [SMILES: CN1C=C(C(Nc2cc(Cl)c3ncc(C#N)c(Nc4ccc(F)c(Cl)c4)c3c2)c2ccc(Cl)cc2)NN1] | 8-chloro-4-((3-chloro-4-fluorophenyl)amino)-6-(((4-chlorophenyl)(1-methyl-1H-1,2,3-triazol-4-yl)methyl)amino)quinoline-3-carbonitrile | 6 | ES/MS 553.6 (M + H+) |

TABLE 1-continued
| Compd | Structure | Name | Example/Procedure | ES/MS m/z |
|---|---|---|---|---|
| 882 | 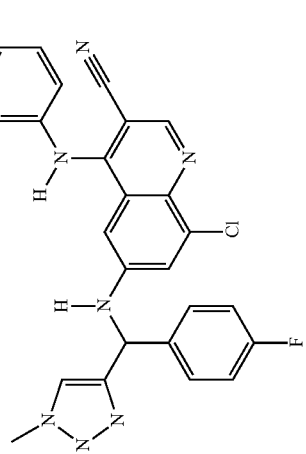 | 8-chloro-4-((3-chloro-4-fluorophenyl)amino)-6-(((4-fluorophenyl)(1-methyl-1H-1,2,3-triazol-4-yl)methyl)amino)quinoline-3-carbonitrile | 6 | ES/MS 536.0 (M + H+) |
| 883 | 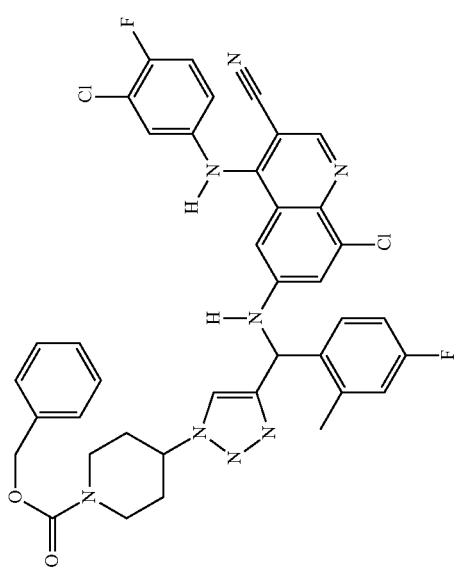 | benzyl 4-(4-(((8-chloro-4-((3-chloro-4-fluorophenyl)amino)-3-cyanoquinolin-6-yl)amino)(4-fluoro-2-methylphenyl)methyl)-1H-1,2,3-triazol-1-yl)piperidine-1-carboxylate | 6 | |

TABLE 1-continued

| Compd | Structure | Name | Example/Procedure | ES/MS m/z |
|---|---|---|---|---|
| 884 | 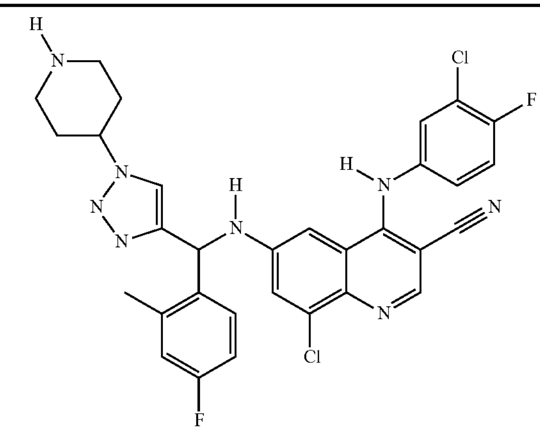 | 8-chloro-4-((3-chloro-4-fluorophenyl)amino)-6-(((4-fluoro-2-methylphenyl)(1-(piperidin-4-yl)-1H-1,2,3-triazol-4-yl)methyl)amino)quinoline-3-carbonitrile | 6 | ES/MS 619.1 (M + H+) |
| 885 | 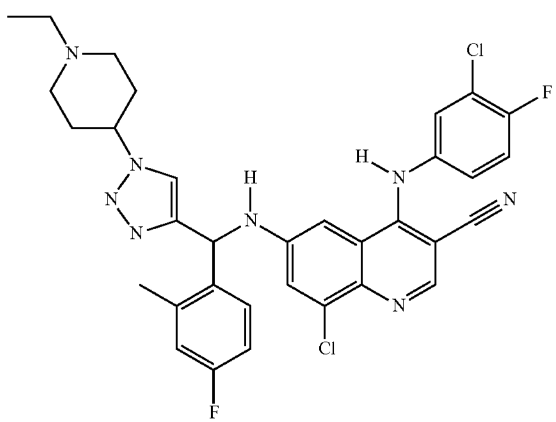 [SMILES: CCN1CCC(N2C=C(C(Nc3cc(Cl)c4ncc(C#N)c(Nc5ccc(F)c(Cl)c5)c4c3)c3ccc(F)cc3C)NN2)CC1] | 8-chloro-4-((3-chloro-4-fluorophenyl)amino)-6-(((1-(1-ethylpiperidin-4-yl)-1H-1,2,3-triazol-4-yl)(4-fluoro-2-methylphenyl)methyl)amino)quinoline-3-carbonitrile | 6 | |

TABLE 1-continued
| Compd | Structure | Name | Example/Procedure | ES/MS m/z |
|---|---|---|---|---|
| 886 | 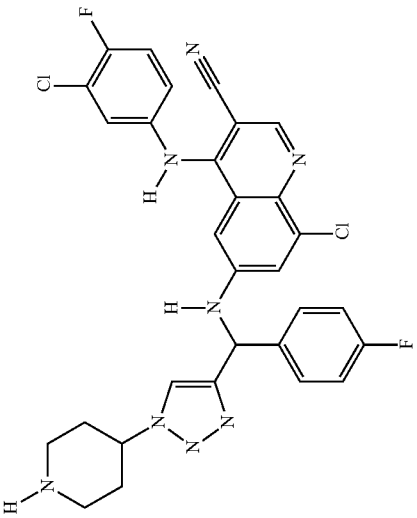 | 8-chloro-4-((3-chloro-4-fluorophenyl)amino)-6-(((4-fluorophenyl)(1-(piperidin-4-yl)-1H-1,2,3-triazol-4-yl)methyl)amino)quinoline-3-carbonitrile | 6 | ES/MS 607.3 (M + H+), 602.9 (M − H−) |
| 887 | 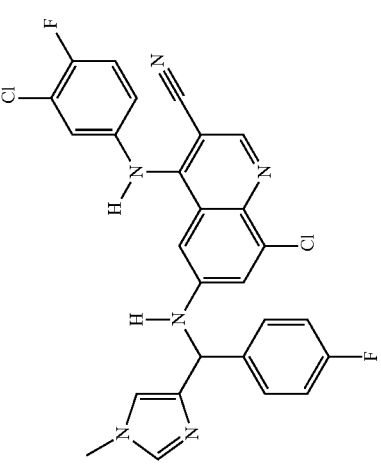 | 8-chloro-4-((3-chloro-4-fluorophenyl)amino)-6-(((4-fluorophenyl)(1-methyl-1H-imidazol-4-yl)methyl)amino)quinoline-3-carbonitrile | 6 | ES/MS 535.4 (M + H+) |

TABLE 1-continued
| Compd | Structure | Name | Example/Procedure | ES/MS m/z |
|---|---|---|---|---|
| 888 | 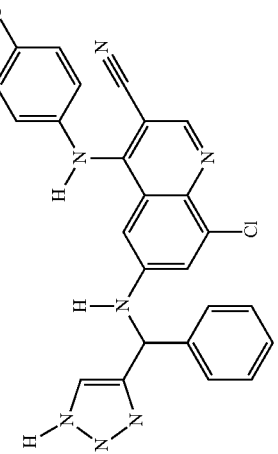 | 8-chloro-4-((3-chloro-4-fluorophenyl)amino)-6-((phenyl(1H-1,2,3-triazol-4-yl)methyl)amino)quinoline-3-carbonitrile | 6 | ES/MS 504.0 (M + H+) |
| 889 | 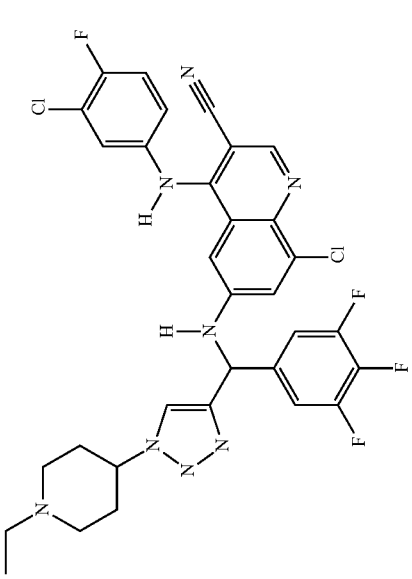 | 8-chloro-4-((3-chloro-4-fluorophenyl)amino)-6-(((1-(1-ethylpiperidin-4-yl)-1H-1,2,3-triazol-4-yl)(3,4,5-trifluorophenyl)methyl)amino)-quinoline-3-carbonitrile | 6 | |

TABLE 1-continued

| Compd | Structure | Name | Example/Procedure | ES/MS m/z |
|---|---|---|---|---|
| 890 | 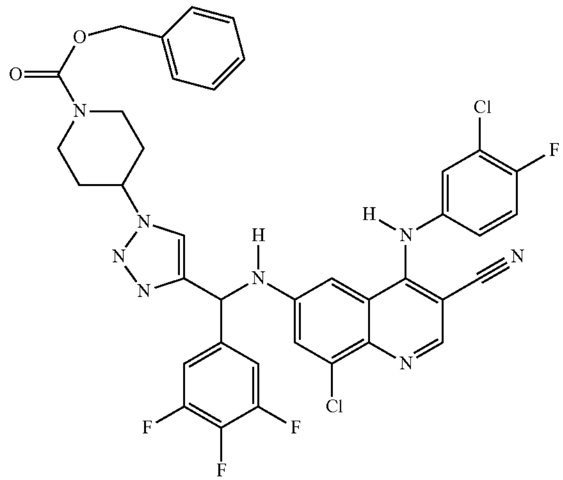 [SMILES: N#Cc1cnc2c(Cl)cc(NC(C3=CN(C4CCN(C(=O)OCc5ccccc5)CC4)NN3)c3cc(F)c(F)c(F)c3)cc2c1Nc1ccc(F)c(Cl)c1] | benzyl 4-(4-(((8-chloro-4-((3-chloro-4-fluorophenyl)amino)-3-cyanoquinolin-6-yl)amino)(3,4,5-trifluorophenyl)methyl)-1H-1,2,3-triazol-1-yl)piperidine-1-carboxylate | 6 | |
| 891 | 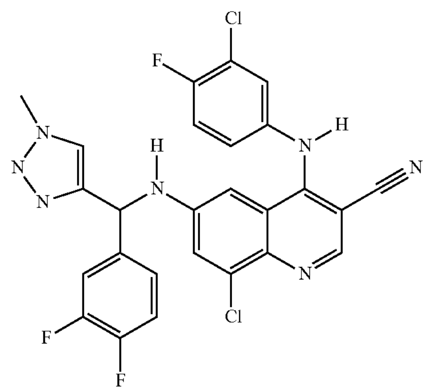 [SMILES: CN1C=C(C(Nc2cc(Cl)c3ncc(C#N)c(Nc4ccc(F)c(Cl)c4)c3c2)c2ccc(F)c(F)c2)NN1] | 8-chloro-4-(3-chloro-4-fluorophenyl)amino)-6-(((3,4-difluorophenyl)(1-methyl-1H-1,2,3-triazol-4-yl)methyl)amino)quinoline-3-carbonitrile | 6 | ES/MS 554.1 (M + H+) |

TABLE 1-continued

| Compd | Structure | Name | Example/Procedure | ES/MS m/z |
|---|---|---|---|---|
| 892 | 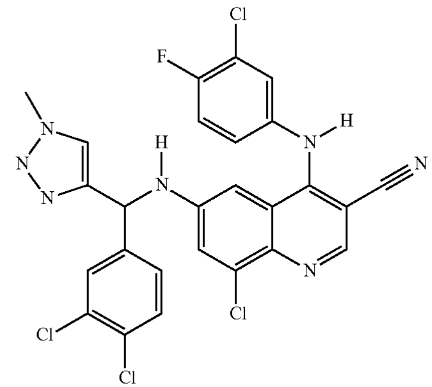 [SMILES: CN1C=C(C(Nc2cc(Cl)c3ncc(C#N)c(Nc4ccc(F)c(Cl)c4)c3c2)c2ccc(Cl)c(Cl)c2)NN1] | 8-chloro-4-((3-chloro-4-fluorophenyl)amino)-6-(((3,4-dichlorophenyl)(1-methyl-1H-1,2,3-triazol-4-yl)methyl)amino)quinoline-3-carbonitrile | 6 | ES/MS 588.1 (M + H+) |
| 893 | 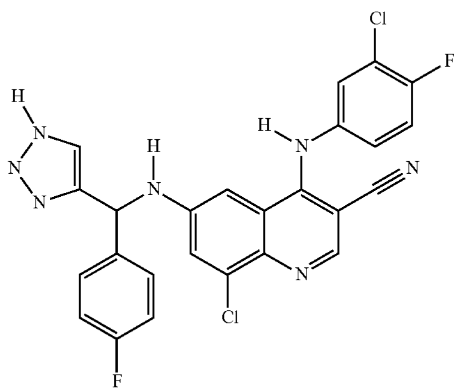 [SMILES: N#Cc1cnc2c(Cl)cc(NC(C3=CNNN3)c3ccc(F)cc3)cc2c1Nc1ccc(F)c(Cl)c1] | 8-chloro-4-((3-chloro-4-fluorophenyl)amino)-6-(((4-fluorophenyl)(1H-1,2,3-triazol-4-yl)methyl)amino)quinoline-3-carbonitrile | 15 | ES/MS 522.0 (M + H+) |

TABLE 1-continued

| Compd | Structure | Name | Example/Procedure | ES/MS m/z |
|---|---|---|---|---|
| 894 | 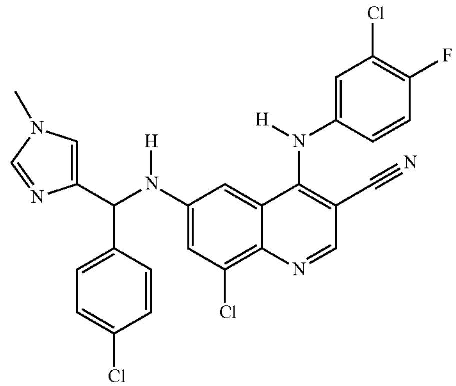 [SMILES: Cn1cnc(C(Nc2cc(Cl)c3ncc(C#N)c(Nc4ccc(F)c(Cl)c4)c3c2)c2ccc(Cl)cc2)c1] | 8-chloro-4-((3-chloro-4-fluorophenyl)amino)-6-(((4-chlorophenyl)(1-methyl-1H-imidazol-4-yl)methyl)amino)quinoline-3-carbonitrile | 6 | ES/MS 551.1 (M + H+) |
| 895 | 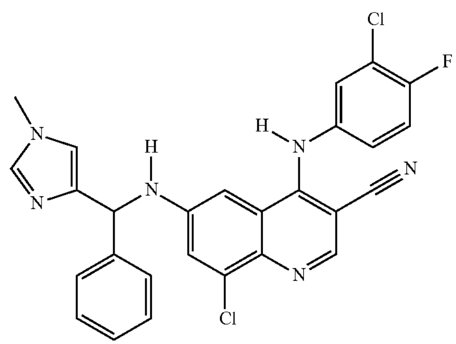 [SMILES: Cn1cnc(C(Nc2cc(Cl)c3ncc(C#N)c(Nc4ccc(F)c(Cl)c4)c3c2)c2ccccc2)c1] | 8-chloro-4-((3-chloro-4-fluorophenyl)amino)-6-(((1-methyl-1H-imidazol-4-yl)(phenyl)methyl)amino)-quinoline-3-carbonitrile | 6 | ES/MS 516.9 (M + H+) |

TABLE 1-continued

| Compd | Structure | Name | Example/Procedure | ES/MS m/z |
|---|---|---|---|---|
| 896 | 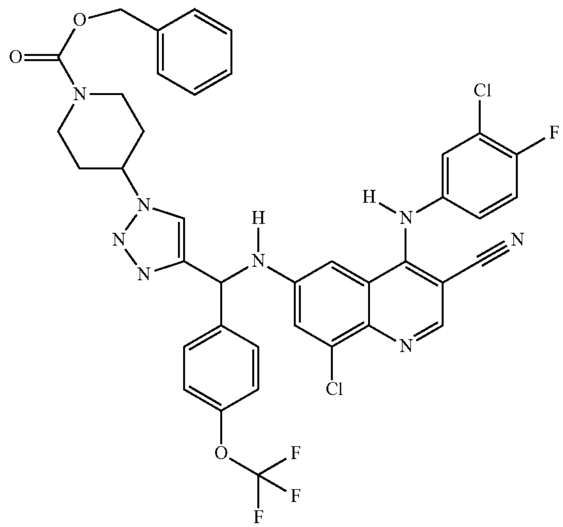 [SMILES: N#Cc1cnc2c(Cl)cc(NC(C3=CN(C4CCN(C(=O)OCc5ccccc5)CC4)NN3)c3ccc(OC(F)(F)F)cc3)cc2c1Nc1ccc(F)c(Cl)c1] | benzyl 4-(4-(((8-chloro-4-(((3-chloro-4-fluorophenyl)amino)-3-cyanoquinolin-6-yl)amino)(4-(trifluoromethoxy)phenyl)methyl)-1H-1,2,3-triazol-1-yl)piperidine-1-carboxylate | 6 | |
| 897 | 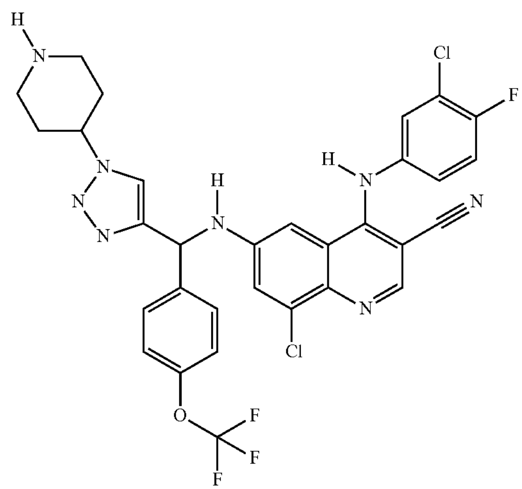 [SMILES: N#Cc1cnc2c(Cl)cc(NC(C3=CN(C4CCNCC4)NN3)c3ccc(OC(F)(F)F)cc3)cc2c1Nc1ccc(F)c(Cl)c1] | 8-chloro-4-((3-chloro-4-fluorophenyl)amino)-6-(((1-(piperidin-4-yl)-1H-1,2,3-triazol-4-yl)(4-(trifluoromethoxy)phenyl)methyl)amino)quinoline-3-carbonitrile | 6 | |

TABLE 1-continued
| Compd | Structure | Name | Example/Procedure | ES/MS m/z |
|---|---|---|---|---|
| 898 | 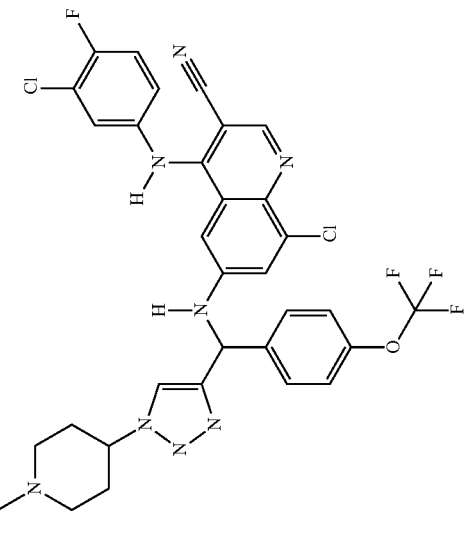 | 8-chloro-4-((3-chloro-4-fluorophenyl)amino)-6-(((1-(1-ethylpiperidin-4-yl)-1H-1,2,3-triazol-4-yl)(4-(trifluoromethoxy)phenyl)methyl)amino)quinoline-3-carbonitrile | 6 | ES/MS 698.9 (M + H+) |
| 899 | 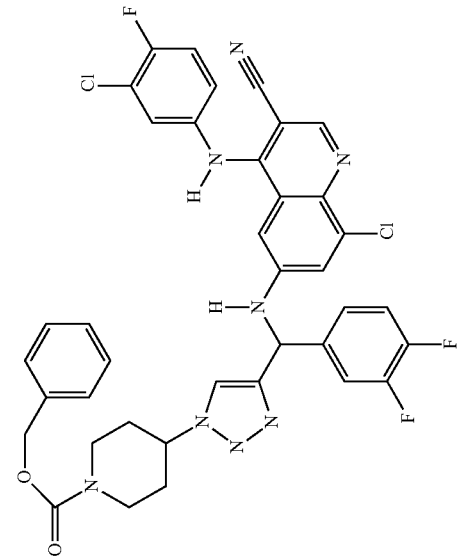 | benzyl 4-(4-(((8-chloro-4-((3-chloro-4-fluorophenyl)amino)-3-cyanoquinolin-6-yl)amino)(3,4-difluorophenyl)methyl)-1H-1,2,3-triazol-1-yl)piperidine-1-carboxylate | 6 | |

TABLE 1-continued
| Compd | Structure | Name | Example/Procedure | ES/MS m/z |
|---|---|---|---|---|
| 900 | 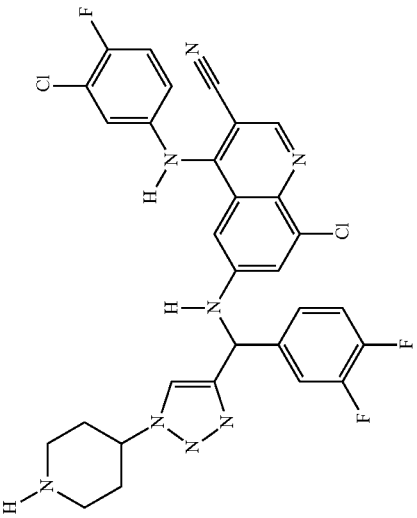 | 8-chloro-4-((3-chloro-4-fluorophenyl)amino)-6-(((3,4-difluorophenyl)(1-(piperidin-4-yl)-1H-1,2,3-triazol-4-yl)methyl)amino)quinoline-3-carbonitrile | 6 | ES/MS 620.9 (M + H+) |
| 901 | 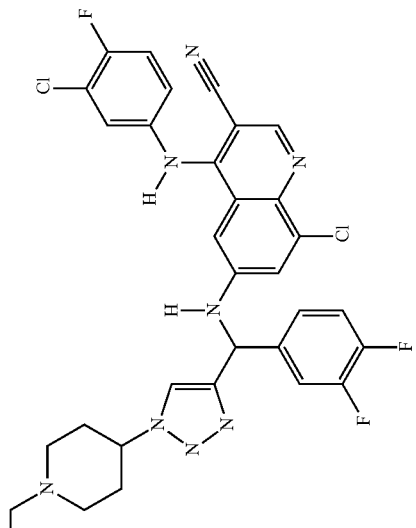 | 8-chloro-4-((3-chloro-4-fluorophenyl)amino)-6-(((3,4-difluorophenyl)(1-(1-ethylpiperdin-4-yl)-1H-1,2,3-triazol-4-yl)methyl)amino)quinoline-3-carbonitrile | 6 | |

TABLE 1-continued
| Compd | Structure | Name | Example/Procedure | ES/MS m/z |
|---|---|---|---|---|
| 902 | 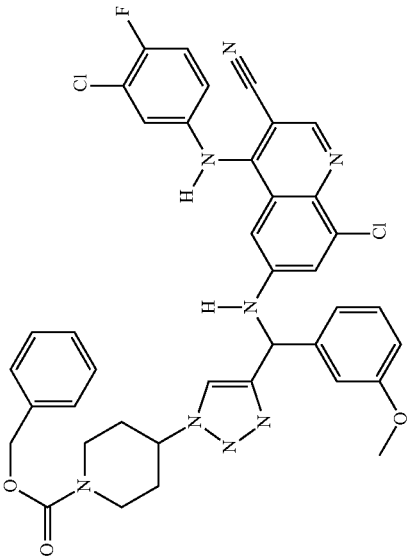 | benzyl 4-(4-(((8-chloro-4-((3-chloro-4-fluorophenyl)amino)-3-cyanoquinolin-6-yl)amino)(3-methoxyphenyl)methyl)-1H-1,2,3-triazol-1-yl)piperidine-1-carboxylate | 6 | |
| 903 | 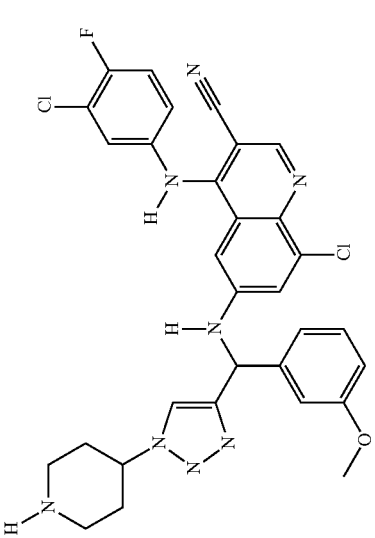 | 8-chloro-4-((3-chloro-4-fluorophenyl)amino)-6-(((3-methoxyphenyl)(1-(piperidin-4-yl)-1H-1,2,3-triazol-4-yl)methyl)amino)quinoline-3-carbonitrile | 6 | |

TABLE 1-continued

| Compd | Structure | Name | Example/Procedure | ES/MS m/z |
|---|---|---|---|---|
| 904 | 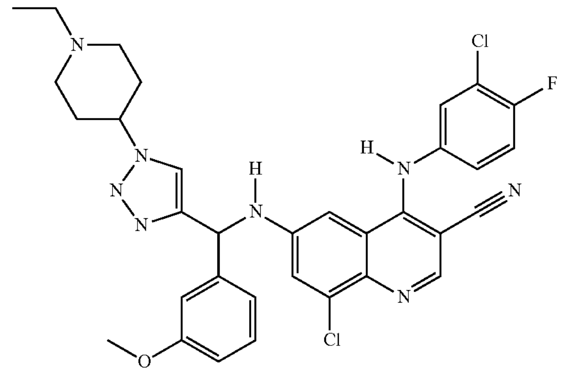 [SMILES: CCN1CCC(N2C=C(C(Nc3cc(Cl)c4ncc(C#N)c(Nc5ccc(F)c(Cl)c5)c4c3)c3cccc(OC)c3)NN2)CC1] | 8-chloro-4-((3-chloro-4-fluorophenyl)amino)-6-(((1-(1-ethylpiperidin-4-yl)-1H-1,2,3-triazol-4-yl)(3-methoxyphenyl)methyl)amino)quinoline-3-carbonitrile | 6 | |
| 905 | 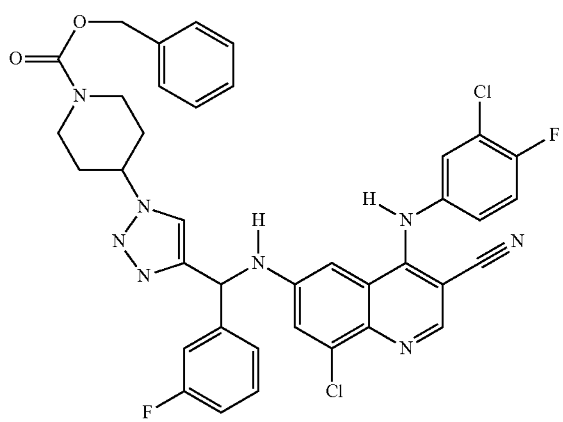 [SMILES: N#Cc1cnc2c(Cl)cc(NC(C3=CN(C4CCN(C(=O)OCc5ccccc5)CC4)NN3)c3cccc(F)c3)cc2c1Nc1ccc(F)c(Cl)c1] | benzyl 4-(4-(((8-chloro-4-((3-chloro-4-fluorophenyl)amino)-3-cyanoquinolin-6-yl)amino)(3-fluorophenyl)methyl)-1H-1,2,3-triazol-1-yl)piperidine-1-carboxylate | 6 | ES/MS 738.9 (M + H+) |

TABLE 1-continued
| Compd | Structure | Name | Example/Procedure | ES/MS m/z |
|---|---|---|---|---|
| 906 | 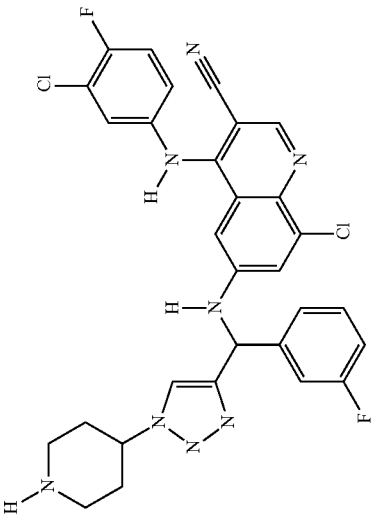 | 8-chloro-4-((3-chloro-4-fluorophenyl)amino)-6-(((3-fluorophenyl)(1-(piperidin-4-yl)-1H-1,2,3-triazol-4-yl)methyl)amino)quinoline-3-carbonitrile | 6 | |
| 907 | 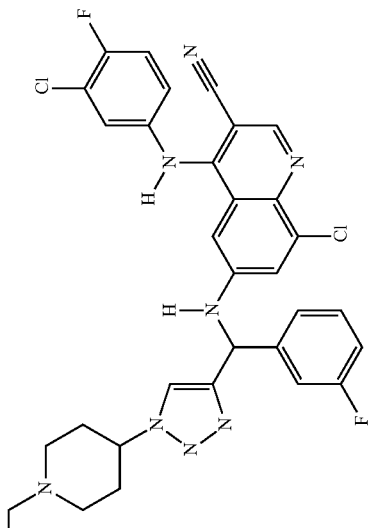 | 8-chloro-4-((3-chloro-4-fluorophenyl)amino)-6-(((1-(1-ethylpiperidin-4-yl)-1H-1,2,3-triazol-4-yl)(3-fluorophenyl)methyl)amino)quinoline-3-carbonitrile | 6 | |

TABLE 1-continued

| Compd | Structure | Name | Example/Procedure | ES/MS m/z |
|---|---|---|---|---|
| 908 | 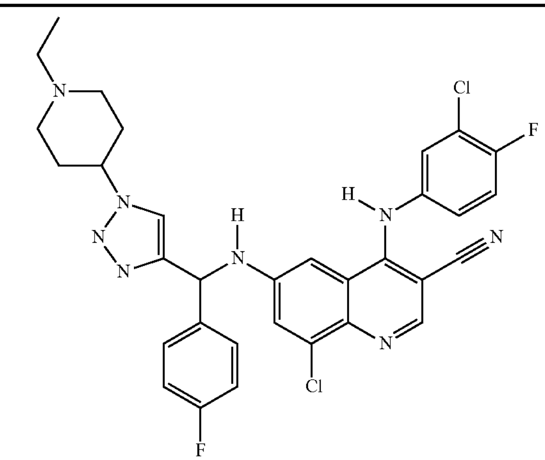 | 8-chloro-4-((3-chloro-4-fluorophenyl)amino)-6-(((1-(1-ethylpiperidin-4-yl)-1H-1,2,3-triazol-4-yl)(4-fluorophenyl)methyl)amino)quinoline-3-carbonitrile | 6 | ES/MS 635.2 (M + H+), 631.0 (M − H−) |
| 909 | 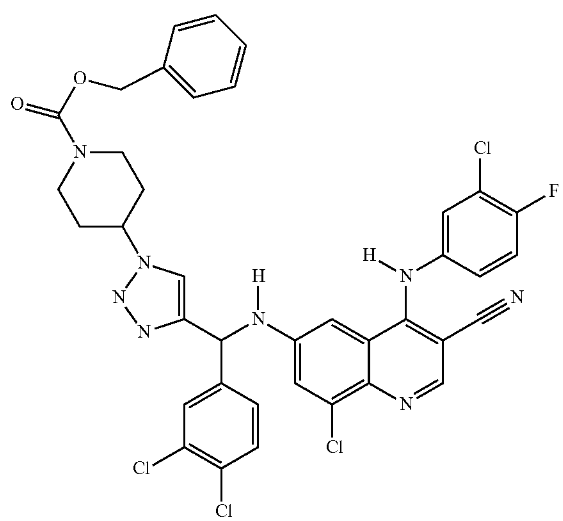 [SMILES: N#Cc1cnc2c(Cl)cc(NC(C3=CN(C4CCN(C(=O)OCc5ccccc5)CC4)NN3)c3ccc(Cl)c(Cl)c3)cc2c1Nc1ccc(F)c(Cl)c1] | benzyl 4-(4-(((8-chloro-4-((3-chloro-4-fluorophenyl)amino)-3-cyanoquinolin-6-yl)amino)(3,4-dichlorophenyl)methyl)-1H-1,2,3-triazol-1-yl)piperidine-1-carboxylate | 6 | |

TABLE 1-continued

| Compd | Structure | Name | Example/Procedure | ES/MS m/z |
|---|---|---|---|---|
| 910 | 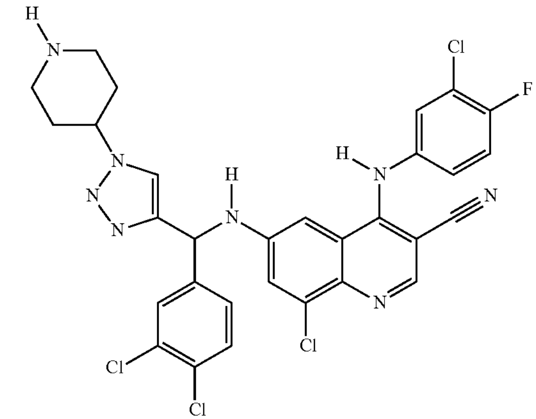 [SMILES: N#Cc1cnc2c(Cl)cc(NC(C3=CN(C4CCNCC4)NN3)c3ccc(Cl)c(Cl)c3)cc2c1Nc1ccc(F)c(Cl)c1] | 8-chloro-4-((3-chloro-4-fluorophenyl)amino)-6-(((3,4-dichlorophenyl)(1-(piperidin-4-yl)-1H-1,2,3-triazol-4-yl)methyl)amino)quinoline-3-carbonitrile | 6 | ES/MS 654.7 (M + H+) |
| 911 | 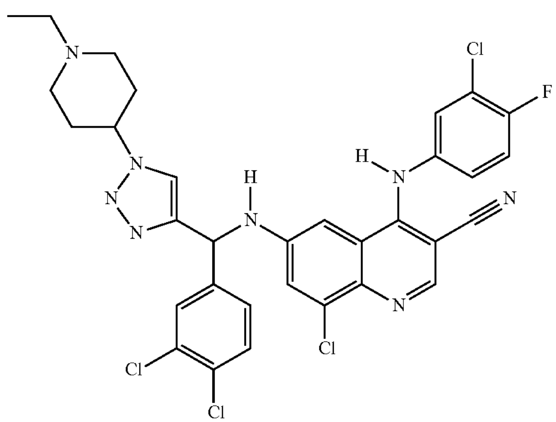 [SMILES: CCN1CCC(N2C=C(C(Nc3cc(Cl)c4ncc(C#N)c(Nc5ccc(F)c(Cl)c5)c4c3)c3ccc(Cl)c(Cl)c3)NN2)CC1] | 8-chloro-4-((3-chloro-4-fluorophenyl)amino)-6-(((3,4-dichlorophenyl)(1-(1-ethylpiperidin-4-yl)-1H-1,2,3-triazol-4-yl)methyl)amino)quinoline-3-carbonitrile | 6 | ES/MS 683.0 (M + H+) |

TABLE 1-continued

| Compd | Structure | Name | Example/Procedure | ES/MS m/z |
|---|---|---|---|---|
| 912 | 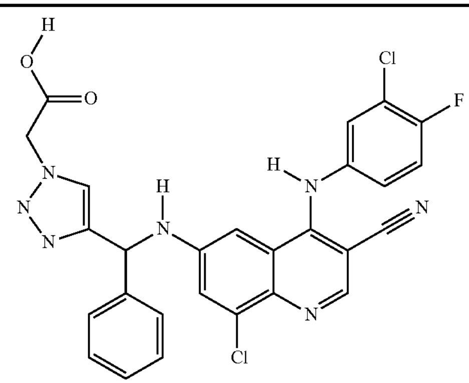 | 2-(4-(((8-chloro-4-((3-chloro-4-fluorophenyl)amino)-3-cyanoquinolin-6-yl)amino)(phenyl)methyl)-1H-1,2,3-triazol-1-yl)acetic acid | 6 | ES/MS 561.4 (M + H+) |
| 913 | 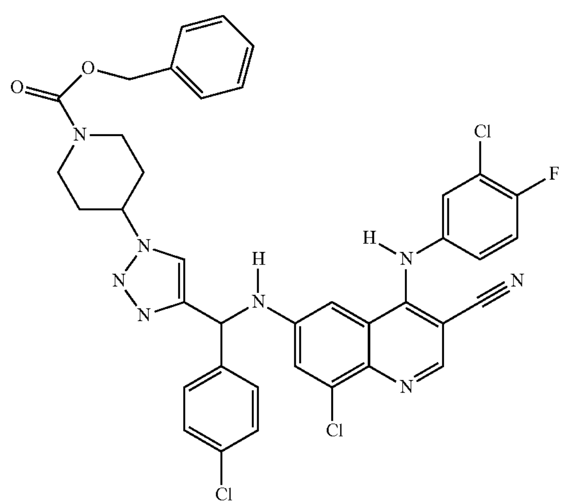 [SMILES: N#Cc1cnc2c(Cl)cc(NC(C3=CN(C4CCN(C(=O)OCc5ccccc5)CC4)NN3)c3ccc(Cl)cc3)cc2c1Nc1ccc(F)c(Cl)c1] | benzyl 4-(4-(((8-chloro-4-((3-chloro-4-fluorophenyl)amino)-3-cyanoquinolin-6-yl)amino)(4-chlorophenyl)methyl)-1H-1,2,3-triazol-1-yl)piperidine-1-carboxylate | 6 | |

TABLE 1-continued
| Compd | Structure | Name | Example/Procedure | ES/MS m/z |
|---|---|---|---|---|
| 914 | 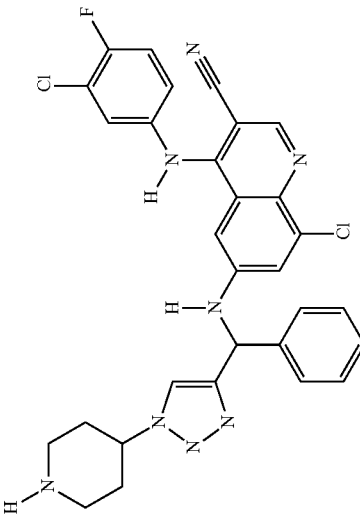 | 8-chloro-4-((3-chloro-4-fluorophenyl)amino)-6-(((4-chlorophenyl)(1-(piperidin-4-yl)-1H-1,2,3-triazol-4-yl)methyl)amino)quinoline-3-carbonitrile | 6 | |
| 915 | 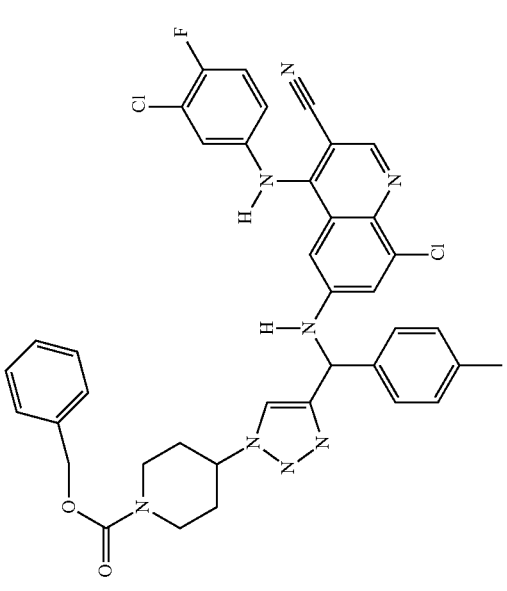 | benzyl 4-(4-(((8-chloro-4-((3-chloro-4-fluorophenyl)amino)-3-cyanoquinolin-6-yl)amino)(p-tolyl)methyl)-1H-1,2,3-triazol-1-yl)piperidine-1-carboxylate | 6 | |

TABLE 1-continued

| Compd | Structure | Name | Example/Procedure | ES/MS m/z |
|---|---|---|---|---|
| 916 | 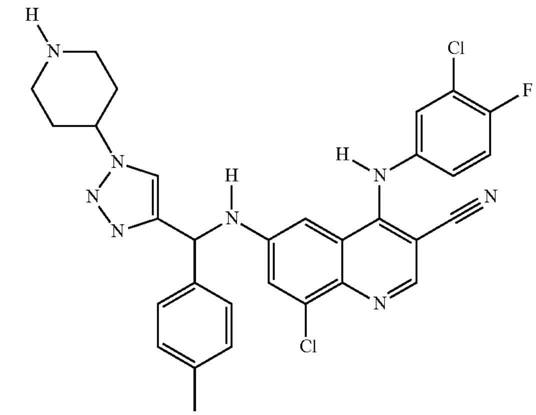 [SMILES: Cc1ccc(C(Nc2cc(Cl)c3ncc(C#N)c(Nc4ccc(F)c(Cl)c4)c3c2)C2=CN(C3CCNCC3)NN2)cc1] | 8-chloro-4-((3-chloro-4-fluorophenyl)amino)-6-(((1-(piperidin-4-yl)-1H-1,2,3-triazol-4-yl)(p-tolyl)methyl)amino)quinoline-3-carbonitrile | 6 | ES/MS 601.0 (M + H+) |
| 917 | 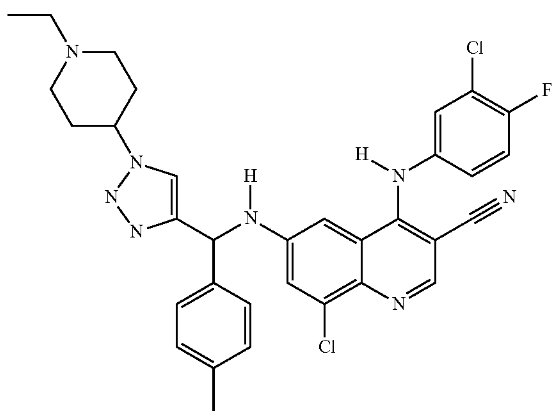 [SMILES: CCN1CCC(N2C=C(C(Nc3cc(Cl)c4ncc(C#N)c(Nc5ccc(F)c(Cl)c5)c4c3)c3ccc(C)cc3)NN2)CC1] | 8-chloro-4-((3-chloro-4-fluorophenyl)amino)-6-(((1-(1-ethylpiperidin-4-yl)-1H-1,2,3-triazol-4-yl)(p-tolyl)methyl)amino)quinoline-3-carbonitrile | 6 | |

TABLE 1-continued

| Compd | Structure | Name | Example/Procedure | ES/MS m/z |
|---|---|---|---|---|
| 918 | 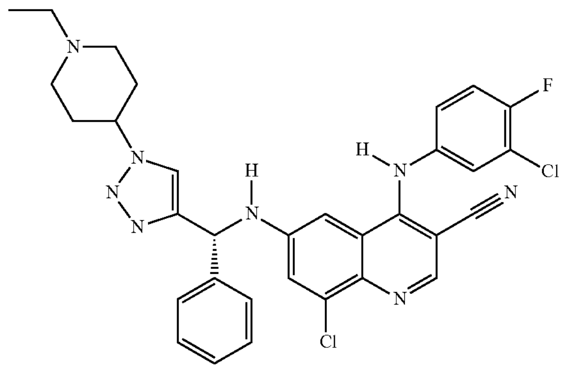 [SMILES: CCN1CCC(N2C=C([C@H](Nc3cc(Cl)c4ncc(C#N)c(Nc5ccc(F)c(Cl)c5)c4c3)c3ccccc3)NN2)CC1] | (R)-8-chloro-4-((3-chloro-4-fluorophenyl)amino)-6-(((1-(1-ethylpiperidin-4-yl)-1H-1,2,3-triazol-4-yl)(phenyl)methyl)amino)quinoline-3-carbonitrile | 6 | ES/MS 615.2 (M + H+) |
| 919 | 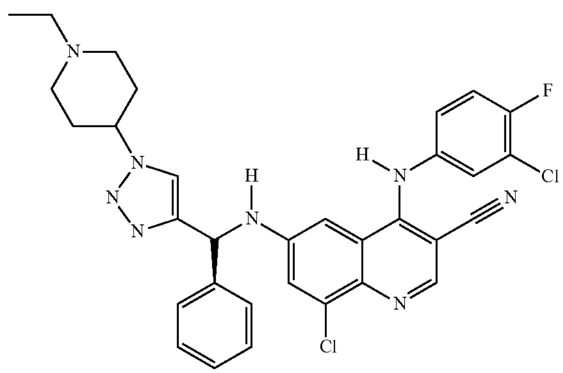 | (S)-8-chloro-4-((3-chloro-4-fluorophenyl)amino)-6-(((1-(1-ethylpiperidin-4-yl)-1H-1,2,3-triazol-4-yl)(phenyl)methyl)amino)quinoline-3-carbonitrile | 6 | ES/MS 614.7 (M + H+) |

TABLE 1-continued

| Compd | Structure | Name | Example/Procedure | ES/MS m/z |
|---|---|---|---|---|
| 920 | 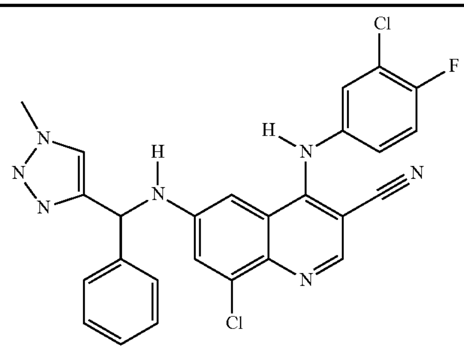 | 8-chloro-4-((3-chloro-4-fluorophenyl)amino)-6-(((1-methyl-1H-1,2,3-triazol-4-yl)(phenyl)methyl)amino)quinoline-3-carbonitrile | 6 | ES/MS 518.1 (M + H+) |
| 921 | 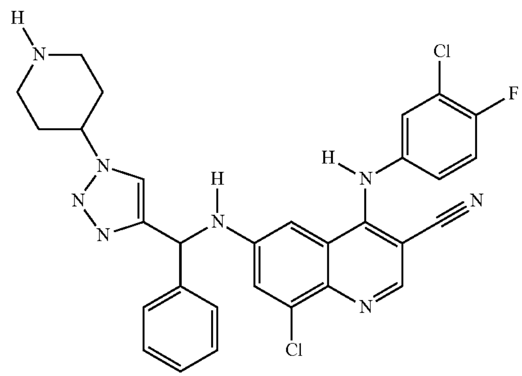 [SMILES: N#Cc1cnc2c(Cl)cc(NC(C3=CN(C4CCNCC4)NN3)c3ccccc3)cc2c1Nc1ccc(F)c(Cl)c1] | 8-chloro-4-((3-chloro-4-fluoropenyl)amino)-6-((penyl(1-(piperidin-4-yl)-1H-1,2,3-triazol-4-yl)methyl)amino)quinoline-3-carbonitrile | 6 | ES/MS 584.7 (M − H−) |

TABLE 1-continued

| Compd | Structure | Name | Example/Procedure | ES/MS m/z |
|---|---|---|---|---|
| 922 | 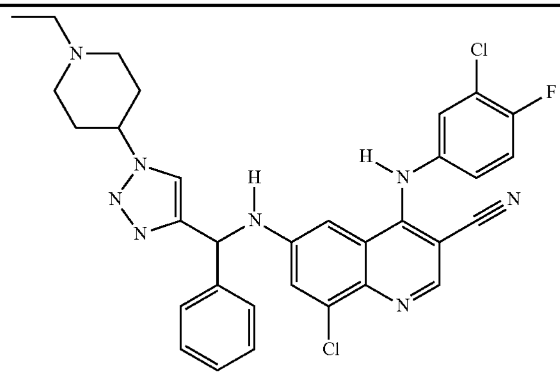 | 8-chloro-4-((3-chloro-4-fluorophenyl)amino)-6-(((1-(1-ethylpiperidin-4-yl)-1H-1,2,3-triazol-4-yl)(phenyl)methyl)amino)quinoline-3-carbonitrile | 6 | ES/MS 615.4 (M + H+) |
| 923 | 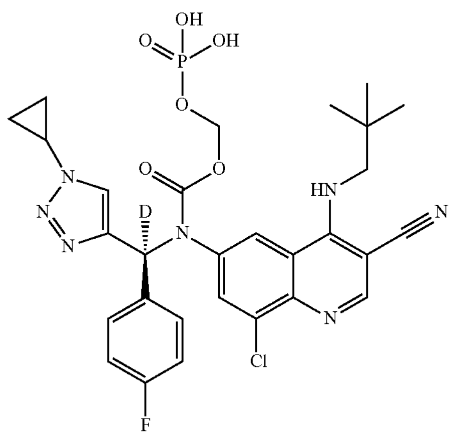 | (phosphonooxy)methyl (S)-(8-chloro-3-cyano-4-(neopentylamino)quinolin-6-yl)((1-cyclopropyl-1H-1,2,3-triazol-4-yl)(4-fluorophenyl)methyl-d)carbamate | | ES/MS 659.0 (M + H+) |

TABLE 1-continued
| Compd | Structure | Name | Example/Procedure | ES/MS m/z |
|---|---|---|---|---|
| 924 | 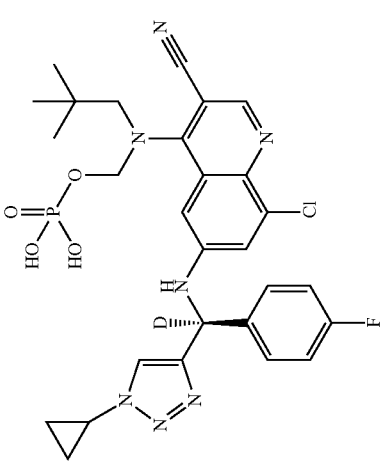 | (phosphonooxy)methyl (S)-(benzo[d]thiazol-7-yl(1-(1-(trifluoromethyl)cyclopropyl)-1H-1,2,3-triazol-4-yl)methyl)(3,8-dicyano-4-(neopentylamino)quinolin-6-yl)carbamate | | |
| 925 | 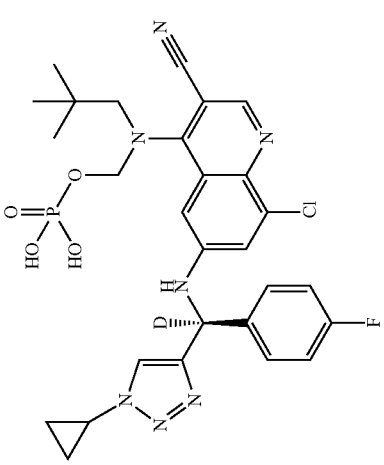 | 8-chloro-6-(((1-cyclopropyl-1H-1,2,3-triazol-4-yl)(4-fluorophenyl)methyl-d)amino)-4-(((R)-3-methoxy-1-phenylpropyl)amino)quinoline-3-carbonitrile | 1 | 583.37 |

TABLE 1-continued

| Compd | Structure | Name | Example/Procedure | ES/MS m/z |
|---|---|---|---|---|
| 926 | 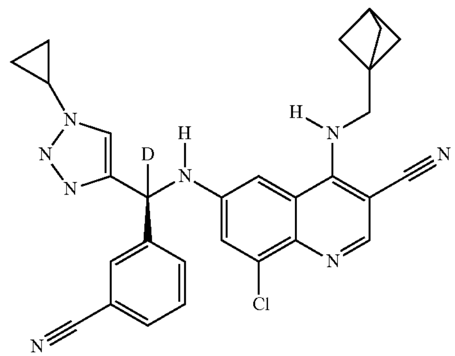 [SMILES: [2H][C@](Nc1cc(Cl)c2ncc(C#N)c(NCC34CC(C3)C4)c2c1)(C1=CN(C2CC2)NN1)c1cccc(C#N)c1] | 4-((bicyclo[1.1.1]pentan-1-ylmethyl)amino)-8-chloro-6-(((3-cyanophenyl)(1-cyclopropyl-1H-1,2,3-triazol-4-yl)methyl-d)amino)quinoline-3-carbonitrile | 10 | 522.30 |
| 927 | 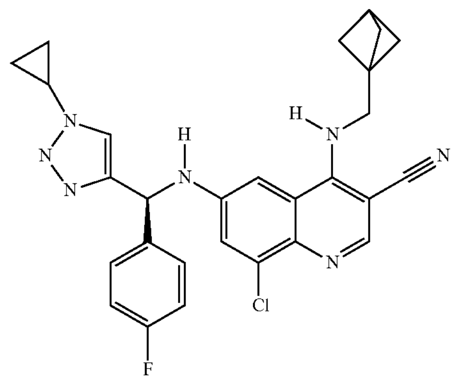 [SMILES: N#Cc1cnc2c(Cl)cc(N[C@H](C3=CN(C4CC4)NN3)c3ccc(F)cc3)cc2c1NCC12CC(C1)C2] | (S)-4-((bicyclo[1.1.1]pentan-1-ylmethyl)amino)-8-chloro-6-(((1-cyclopropyl-1H-1,2,3-triazol-4-yl)(4-fluorophenyl)methyl)amino)quinoline-3-carbonitrile | 10 | 514.40 |
| 928 | 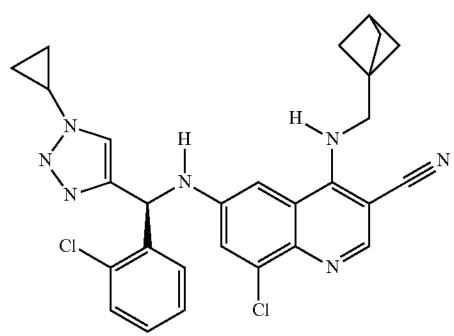 [SMILES: N#Cc1cnc2c(Cl)cc(N[C@H](C3=CN(C4CC4)NN3)c3ccccc3Cl)cc2c1NCC12CC(C1)C2] | (S)-4-((bicyclo[1.1.1]pentan-1-ylmethyl)amino)-8-chloro-6-(((2-chlorophenyl)(1-cyclopropyl-1H-1,2,3-triazol-4-yl)methyl)amino)quinoline-3-carbonitrile | 10 | 530.50 |

TABLE 1-continued

| Compd | Structure | Name | Example/Procedure | ES/MS m/z |
|---|---|---|---|---|
| 929 | 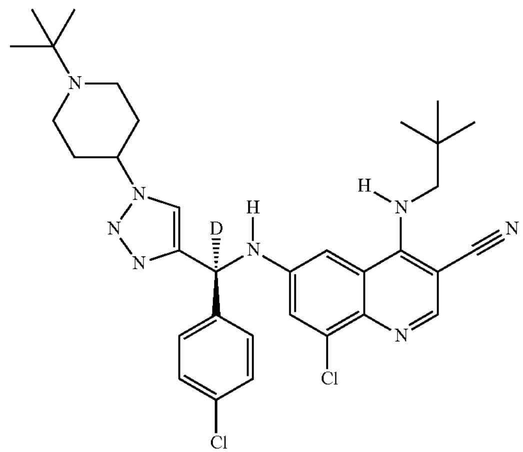 | (S)-6-(((1-(1-(tert-butyl)piperidin-4-yl)-1H-1,2,3-triazol-4-yl)(4-chlorophenyl)methyl-d)amino)-8-chloro-4-(neopentylamino)quinoline-3-carbonitrile | 3 | 620.20 |
| 930 | 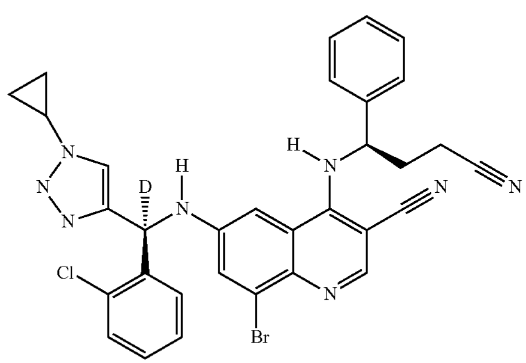 | 8-bromo-6-(((S)-(2-chlorophenyl)(1-cyclopropyl-1H-1,2,3-triazol-4-yl)methyl-d)amino)-4-(((R)-3-cyano-1-phenylpropyl)amino)quinoline-3-carbonitrile | 2 | 640.35 |

TABLE 1-continued

| Compd | Structure | Name | Example/Procedure | ES/MS m/z |
|---|---|---|---|---|
| 931 | 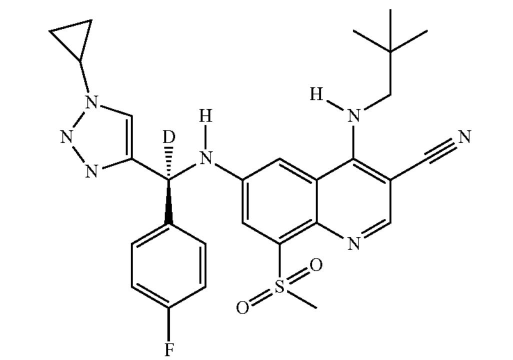 | (S)-6-(((1-cyclopropyl-1H-1,2,3-triazol-4-yl)(4-fluorophenyl)methyl-d)amino)-8-(methylsulfonyl)-4-(neopentylamino)quinoline-3-carbonitrile | 58 | 549.43 |
| 932 | 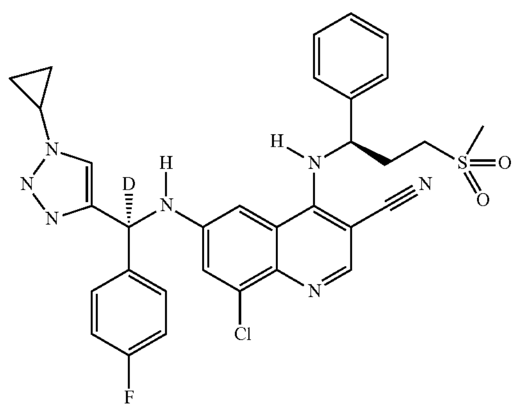 [SMILES: [2H][C@@](Nc1cc(Cl)c2ncc(C#N)c(N[C@H](CCS(C)(=O)=O)c3ccccc3)c2c1)(C1=CN(C2CC2)NN1)c1ccc(F)cc1] | 8-chloro-6-(((1-cyclopropyl-1H-1,2,3-triazol-4-yl)(4-fluorophenyl)methyl-d)amino)-4-(((R)-3-(methylsulfonyl)-1-phenylpropyl)amino)quinoline-3-carbonitrile | 1 | 631.10 |

TABLE 1-continued

| Compd | Structure | Name | Example/Procedure | ES/MS m/z |
|---|---|---|---|---|
| 933 | 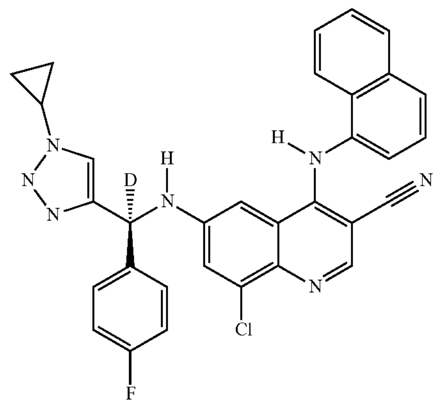 | (S)-8-chloro-6-((((1-cyclopropyl-1H-1,2,3-triazol-4-yl)(4-fluorophenyl)methyl-d)amino)(naphthalen-1-ylamino)quinoline-3-carbonitrile | 3 | 561.30 |
| 934 | 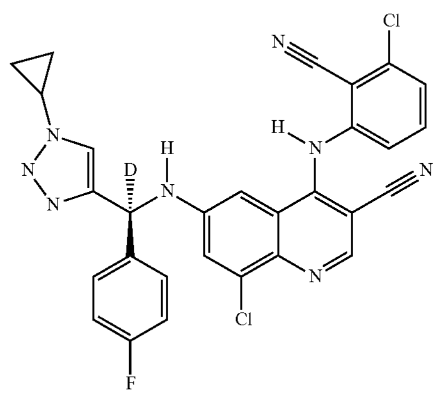 | (S)-8-chloro-4-((3-chloro-2-cyanophenyl)amino)-6-(((1-cyclopropyl-1H-1,2,3-triazol-4-yl)(4-fluorophenyl)methyl-d)amino)quinoline-3-carbonitrile | 3 | 570 |

TABLE 1-continued
| Compd | Structure | Name | Example/Procedure | ES/MS m/z |
|---|---|---|---|---|
| 935 | 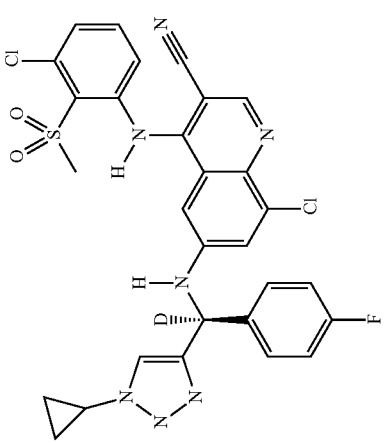 | (S)-8-chloro-4-((3-chloro-2-(methylsulfonyl)phenyl)amino)-6-(((1-cyclopropyl-1H-1,2,3-triazol-4-yl)(4-fluorophenyl)methyl-d)amino)quinoline-3-carbonitrile | 3 | 623 |
| 936 | 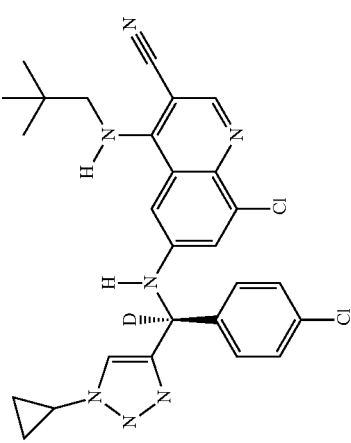 | (S)-8-chloro-6-(((4-chlorophenyl)(1-cyclopropyl-1H-1,2,3-triazol-4-yl)methyl-d)amino)-4-(neopentylamino)quinoline-3-carbonitrile | 3 | 521.20 |

TABLE 1-continued
| Compd | Structure | Name | Example/Procedure | ES/MS m/z |
|---|---|---|---|---|
| 937 | 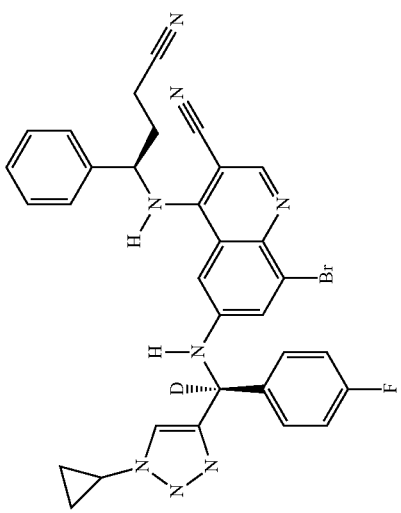 | 8-bromo-4-(((R)-3-cyano-1-phenylpropyl)amino)-6-(((S)-(1-cyclopropyl-1H-1,2,3-triazol-4-yl)(4-fluorophenyl)methyl-d)amino)quinoline-3-carbonitrile | 2 | 622.09 |
| 938 | 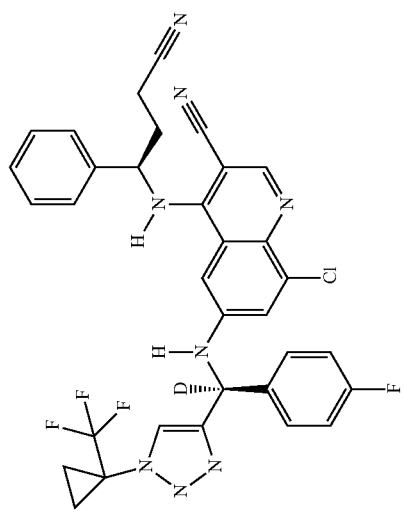 | 8-chloro-4-(((R)-3-cyano-1-phenylpropyl)amino)-6-(((S)-(4-fluorophenyl)(1-(1-(trifluoromethyl)cyclopropyl)-1H-1,2,3-triazol-4-yl)methyl-d)amino)quinoline-3-carbonitrile | 2 | 646.20 |

TABLE 1-continued

| Compd | Structure | Name | Example/Procedure | ES/MS m/z |
|---|---|---|---|---|
| 939 | 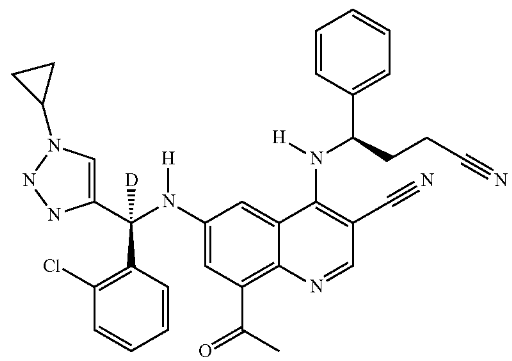 | 8-acetyl-6-(((S)-(2-chlorophenyl)(1-cyclopropyl-1H-1,2,3-triazol-4-yl)methyl-d)amino)-4-(((R)-3-cyano-1-phenylpropyl)amino)quinoline-3-carbonitrile | 14 | 602.33 |
| 940 | 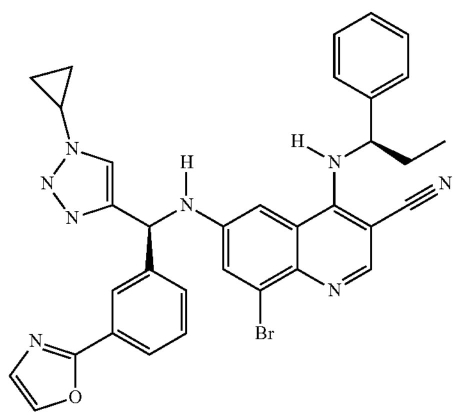 [SMILES: CC[C@@H](Nc1c(C#N)cnc2c(Br)cc(N[C@H](C3=CN(C4CC4)NN3)c3cccc(-c4ncco4)c3)cc12)c1ccccc1] | 8-bromo-6-(((S)-(1-cyclopropyl-1H-1,2,3-triazol-4-yl)(3-(oxazol-2-yl)phenyl)methyl)amino)-4-(((R)-1-phenylpropyl)amino)quinoline-3-carbonitrile | 3 | 647.10 |

TABLE 1-continued

| Compd | Structure | Name | Example/Procedure | ES/MS m/z |
|---|---|---|---|---|
| 941 | 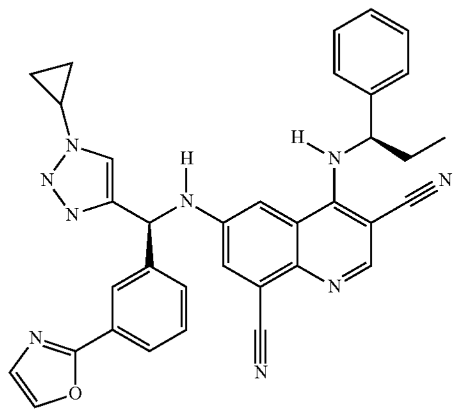 [SMILES: CC[C@@H](Nc1c(C#N)cnc2c(C#N)cc(N[C@H](C3=CN(C4CC4)NN3)c3cccc(-c4ncco4)c3)cc12)c1ccccc1] | 6-(((S)-(1-cyclopropyl-1H-1,2,3-triazol-4-yl)(3-(oxazol-2-yl)phenyl)methyl)amino)-4-(((R)-1-phenylpropyl)amino)quinoline-3,8-dicarbonitrile | 9 | 592.10 |
| 942 | 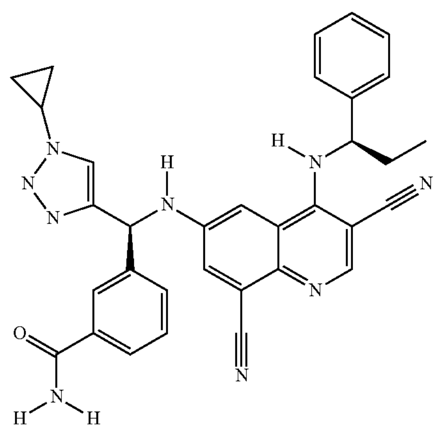 [SMILES: CC[C@@H](Nc1c(C#N)cnc2c(C#N)cc(N[C@H](C3=CN(C4CC4)NN3)c3cccc(C(N)=O)c3)cc12)c1ccccc1] | 3-((S)-(1-cyclopropyl-1H-1,2,3-triazol-4-yl)(3,8-dicyano-4-(((R)-1-phenylpropyl)amino)quinolin-6-yl)amino)methyl)benzamide | 20 | 568.10 |

TABLE 1-continued

| Compd | Structure | Name | Example/Procedure | ES/MS m/z |
|---|---|---|---|---|
| 943 | 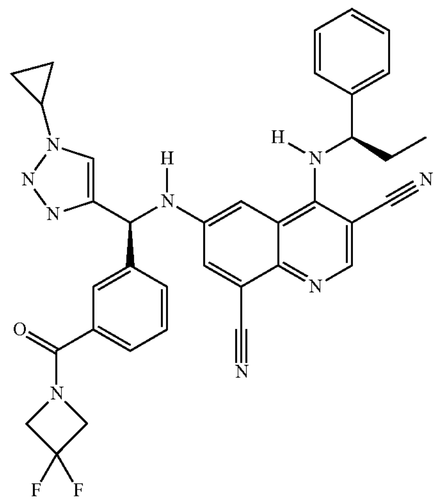 [SMILES: CC[C@@H](Nc1c(C#N)cnc2c(C#N)cc(N[C@H](C3=CN(C4CC4)NN3)c3cccc(C(=O)N4CC(F)(F)C4)c3)cc12)c1ccccc1] | 6-(((S)-(1-cyclopropyl-1H-1,2,3-triazol-4-yl)(3-(3,3-difluoroazetidine-1-carbonyl)phenyl)methyl)amino)-4-(((R)-1-phenylpropyl)amino)quinoline-3,8-dicarbonitrile | 20 | 644.10 |
| 944 | 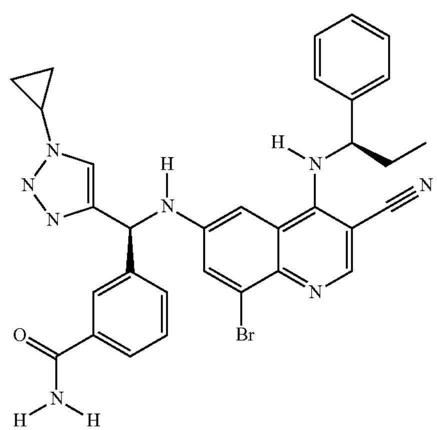 | 3-((S)-((8-bromo-3-cyano-4-(((R)-1-phenylpropyl)amino)quinolin-6-yl)amino)(1-cyclopropyl-1H-1,2,3-triazol-4-yl)methyl)benzamide | 20 | 621.20 |

TABLE 1-continued

| Compd | Structure | Name | Example/Procedure | ES/MS m/z |
|---|---|---|---|---|
| 945 | 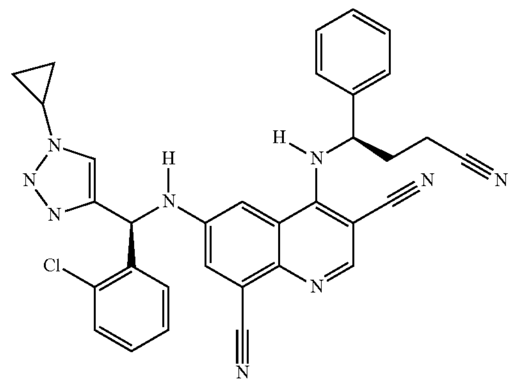 [SMILES: N#CCC[C@@H](Nc1c(C#N)cnc2c(C#N)cc(N[C@H](C3=CN(C4CC4)NN3)c3ccccc3Cl)cc12)c1ccccc1] | 6-(((S)-(2-chlorophenyl)(1-cyclopropyl-1H-1,2,3-triazol-4-yl)methyl)amino)-4-(((R)-3-cyano-1-phenylpropyl)amino)quinoline-3,8-dicarbonitrile | 9 | 584.10 |
| 946 | 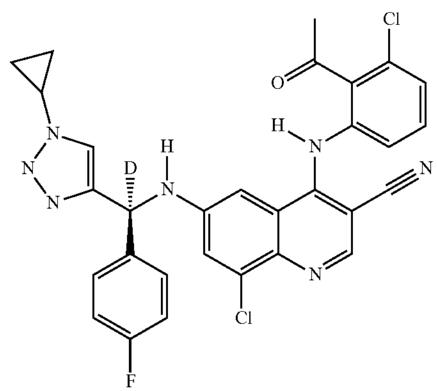 | (S)-4-((2-acetyl-3-chlorophenyl)amino)-8-chloro-6-(((1-cyclopropyl-1H-1,2,3-triazol-4-yl)(4-fluorophenyl)methyl-d)amino)quinoline-3-carbonitrile | 56 | 587.40 |

TABLE 1-continued
| Compd | Structure | Name | Example/Procedure | ES/MS m/z |
|---|---|---|---|---|
| 947 | 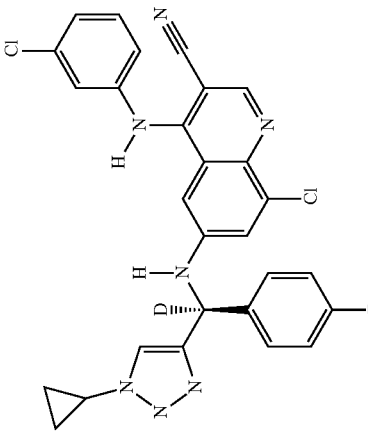 | (S)-8-chloro-4-((3-chlorophenyl)amino)-6-(((1-cyclopropyl-1H-1,2,3-triazol-4-yl)(4-fluorophenyl)methyl-d)amino)quinoline-3-carbonitrile | 56 | 545.20 |
| 948 | 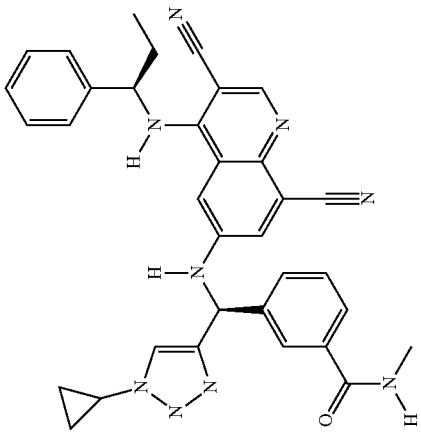 | 3-((S)-(1-cyclopropyl-1H-1,2,3-triazol-4-yl)((3,8-dicyano-4-(((R)-1-phenylpropyl)amino)quinolin-6-yl)amino)methyl)-N-methylbenzamide | 20 | 582.10 |

TABLE 1-continued
| Compd | Structure | Name | Example/Procedure | ES/MS m/z |
|---|---|---|---|---|
| 949 | 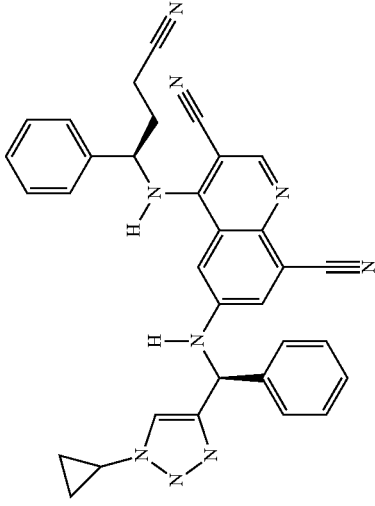 | 4-(((R)-3-cyano-1-phenylpropyl)amino)-6-(((S)-(1-cyclopropyl-1H-1,2,3-triazol-4-yl)(phenyl)methyl)amino)quinoline-3,8-dicarbonitrile | 9 | 550.2 |
| 950 | 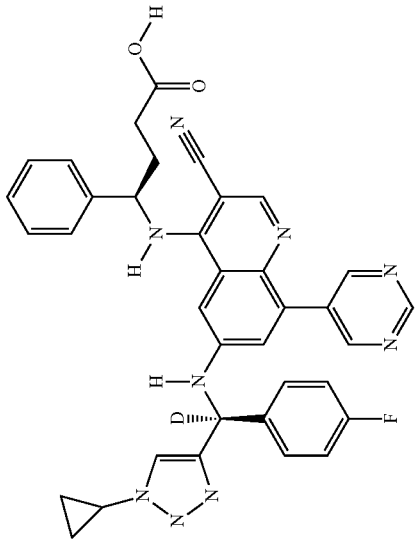 | (R)-4-((3-cyano-6-(((S)-(1-cyclopropyl-1H-1,2,3-triazol-4-yl)(4-fluorophenyl)methyl-d)amino)-8-(pyrimidin-5-yl)quinolin-4-yl)amino)-4-phenylbutanoic acid | 12 | 641.16 |

TABLE 1-continued
| Compd | Structure | Name | Example/Procedure | ES/MS m/z |
|---|---|---|---|---|
| 951 | 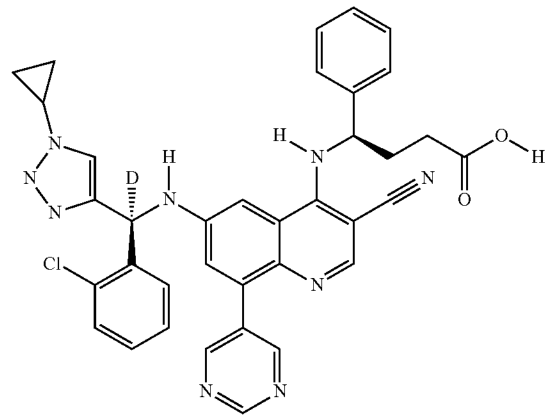 | (R)-4-((6-(((S)-(2-chlorophenyl)(1-cyclopropyl-1H-1,2,3-triazol-4-yl)methyl-d)amino)-3-cyano-8-(pyrimidin-5-yl)quinolin-4-yl)amino)-4-phenylbutanoic acid | 12 | 657.09 |
| 952 | 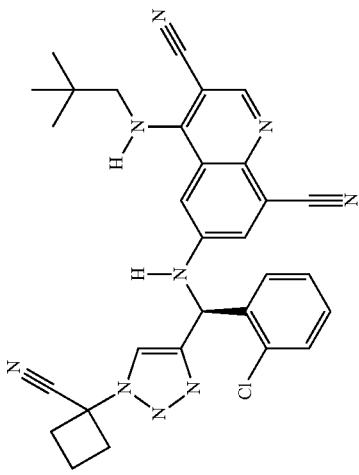 | (S)-6-(((2-chlorophenyl)(1-(1-cyanocyclobutyl)-1H-1,2,3-triazol-4-yl)methyl)amino)-4-(neopentylamino)quinoline-3,8-dicarbonitrile | 9 | 550.20 |

TABLE 1-continued
| Compd | Structure | Name | Example/Procedure | ES/MS m/z |
|---|---|---|---|---|
| 953 | 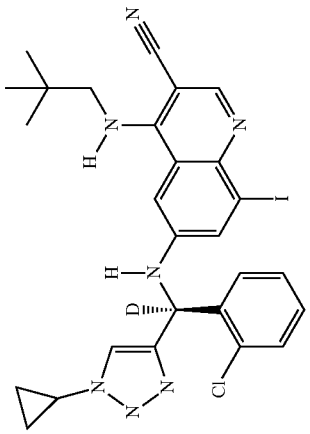 | (S)-6-(((2-chlorophenyl)(1-cyclopropyl-1H-1,2,3-triazol-4-yl)methyl)amino)-8-iodo-4-(neopentylamino)quinoline-3-carbonitrile | 1 | 613.07 |
| 954 | 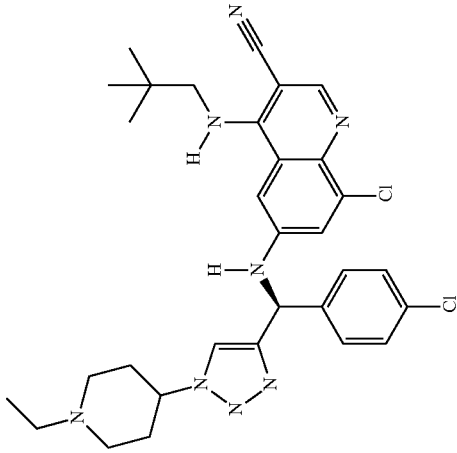 | (S)-8-chloro-6-(((4-chlorophenyl)(1-(1-ethylpiperidin-4-yl)-1H-1,2,3-triazol-4-yl)methyl)amino)-4-(neopentylamino)quinoline-3-carbonitrile | 20 | 591.21 |

TABLE 1-continued

| Compd | Structure | Name | Example/Procedure | ES/MS m/z |
|---|---|---|---|---|
| 955 | 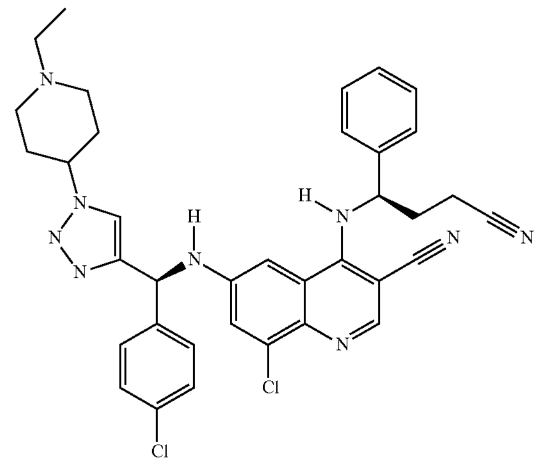 [SMILES: CCN1CCC(N2C=C([C@@H](Nc3cc(Cl)c4ncc(C#N)c(N[C@H](CCC#N)c5ccccc5)c4c3)c3ccc(Cl)cc3)NN2)CC1] | 8-chloro-6-(((S)-(4-chlorophenyl)(1-(1-ethylpiperidin-4-yl)-1H-1,2,3-triazol-4-yl)methyl)amino)-4-(((R)-3-cyano-1-phenylpropyl)amino)quinoline-3-carbonitrile | 20 | 664.04 |
| 956 | 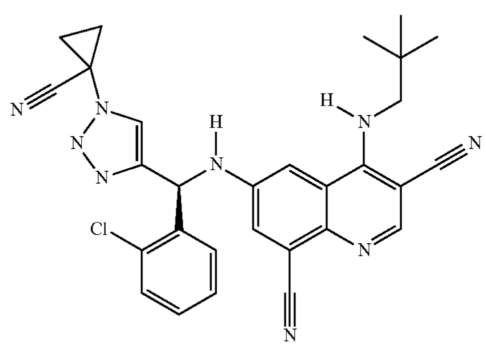 [SMILES: CC(C)(C)CNc1c(C#N)cnc2c(C#N)cc(N[C@H](C3=CN(C4(C#N)CC4)NN3)c3ccccc3Cl)cc12] | (S)-6-(((2-chlorophenyl)(1-(1-cyanocyclopropyl)-1H-1,2,3-triazol-4-yl)methyl)amino)-4-(neopentylamino)quinoline-3,8-dicarbonitrile | 9 | 536.30 |

TABLE 1-continued

| Compd | Structure | Name | Example/Procedure | ES/MS m/z |
|---|---|---|---|---|
| 957 | 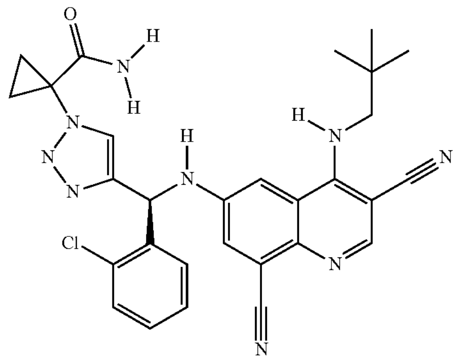 [SMILES: CC(C)(C)CNc1c(C#N)cnc2c(C#N)cc(N[C@H](C3=CN(C4(C(N)=O)CC4)NN3)c3ccccc3Cl)cc12] | (S)-1-(4-((2-chlorophenyl)((3,8-dicyano-4-(neopentylamino)quinolin-6-yl)amino)methyl)-1H-1,2,3-triazol-1-yl)cyclopropane-1-carboxamide | 9 | 554.40 |
| 958 | 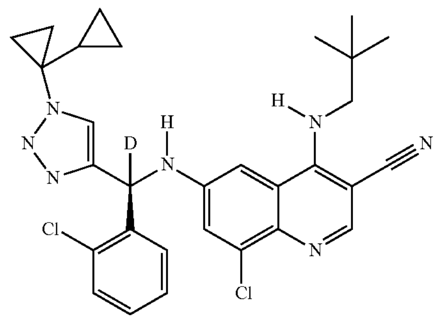 [SMILES: [2H][C@](Nc1cc(Cl)c2ncc(C#N)c(NCC(C)(C)C)c2c1)(C1=CN(C2(C3CC3)CC2)NN1)c1ccccc1Cl] | 6-(((1-([1,1'-bi(cyclopropan)]-1-yl)-1H-1,2,3-triazol-4-yl)(2-chlorophenyl)methyl)amino)-8-chloro-4-(neopentylamino)quinoline-3-carbonitrile | 4 | 561.40 |
| 959 | 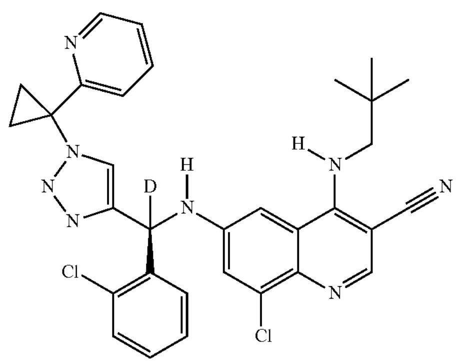 [SMILES: [2H][C@](Nc1cc(Cl)c2ncc(C#N)c(NCC(C)(C)C)c2c1)(C1=CN(C2(c3ccccn3)CC2)NN1)c1ccccc1Cl] | 8-chloro-6-(((2-chlorophenyl)(1-(1-(pyridin-2-yl)cyclopropyl)-1H-1,2,3-triazol-4-yl)methyl)amino)-4-(neopentylamino)quinoline-3-carbonitrile | 4 | 598.40 |

TABLE 1-continued
| Compd | Structure | Name | Example/Procedure | ES/MS m/z |
|---|---|---|---|---|
| 960 | 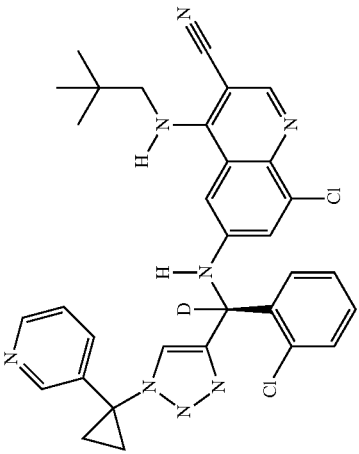 | 8-chloro-6-(((2-chlorophenyl)(1-(pyridin-3-yl)cyclopropyl)-1H-1,2,3-triazol-4-yl)methyl-d)amino)-4-(neopentylamino)quinoline-3-carbonitrile | 4 | 598.50 |
| 961 | 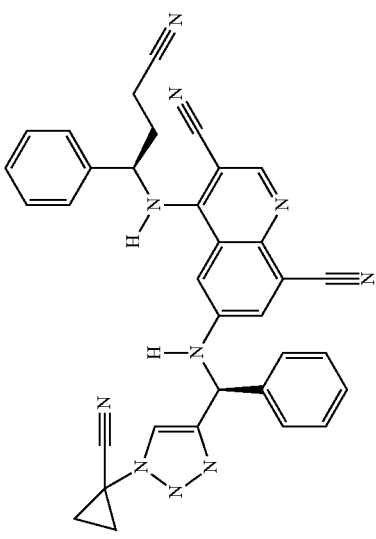 | 4-(((R)-3-cyano-1-phenylpropyl)amino)-6-(((S)-(1-cyanocyclopropyl)-1H-1,2,3-triazol-4-yl)(phenyl)methyl)amino)quinoline-3,8-dicarbonitrile | 9 | 575.2 |

TABLE 1-continued

| Compd | Structure | Name | Example/Procedure | ES/MS m/z |
|---|---|---|---|---|
| 962 | 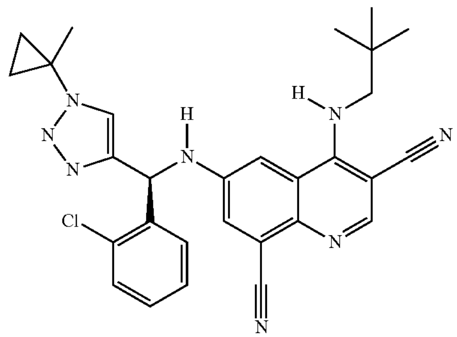 [SMILES: CC(C)(C)CNc1c(C#N)cnc2c(C#N)cc(N[C@H](C3=CN(C4(C)CC4)NN3)c3ccccc3Cl)cc12] | (S)-6-(((2-chlorophenyl)(1-(1-methylcyclopropyl)-1H-1,2,3-triazol-4-yl)methyl)amino)-4-(neopentylamino)quinoline-3,8-dicarbonitrile | 9 | 525.30 |
| 963 | 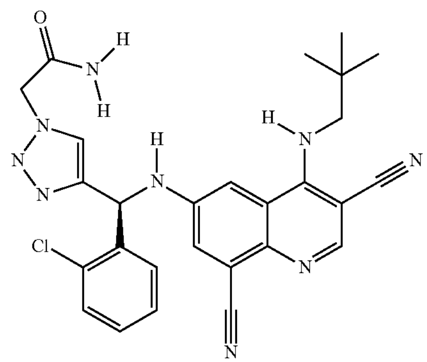 [SMILES: CC(C)(C)CNc1c(C#N)cnc2c(C#N)cc(N[C@H](C3=CN(CC(N)=O)NN3)c3ccccc3Cl)cc12] | (S)-2-(4-((2-chlorophenyl)((3,8-dicyano-4-(neopentylamino)quinolin-6-yl)amino)methyl)-1H-1,2,3-triazol-1-yl)acetamide | 9 | 528.20 |
| 964 | 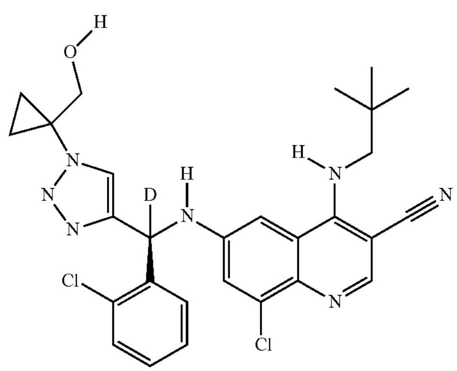 [SMILES: [2H][C@](Nc1cc(Cl)c2ncc(C#N)c(NCC(C)(C)C)c2c1)(C1=CN(C2(CO)CC2)NN1)c1ccccc1Cl] | 8-chloro-6-(((2-chlorophenyl)(1-(1-(hydroxymethyl)cyclopropyl)-1H-1,2,3-triazol-4-yl)methyl-d)amino)-4-(neopentylamino)quinoline-3-carbonitrile | 4 | 551.20 |

TABLE 1-continued
| Compd | Name | Structure | Example/Procedure | ES/MS m/z |
|---|---|---|---|---|
| 965 | 8-chloro-6-(((2-chlorophenyl)(1-(3-(hydroxymethyl)oxetan-3-yl)-1H-1,2,3-triazol-4-yl)methyl-d)amino)-4-(neopentylamino)quinoline-3-carbonitrile | 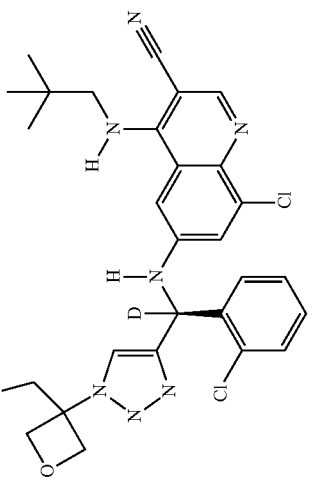 | 4 | 567.20 |
| 966 | (S)-8-chloro-4-((3-chloro-2-(trifluoromethoxy)phenyl)amino)-6-(((1-cyclopropyl-1H-1,2,3-triazol-4-yl)(4-fluorophenyl)methyl-d)amino)quinoline-3-carbonitrile | 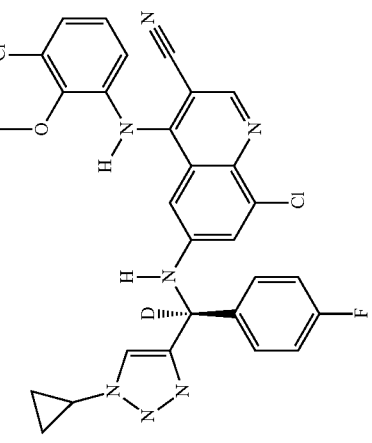 | 3 | 629.30 |

TABLE 1-continued

| Compd | Structure | Name | Example/Procedure | ES/MS m/z |
|---|---|---|---|---|
| 967 | 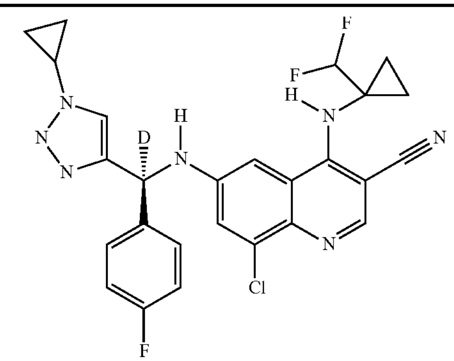 | (S)-8-chloro-6-((((1-cyclopropyl-1H-1,2,3-triazol-4-yl)(4-fluorophenyl)methyl-d)amino)-(((1-(difluoromethyl)cyclopropyl)amino)-quinoline-3-carbonitrile | 3 | 525.30 |
| 968 | 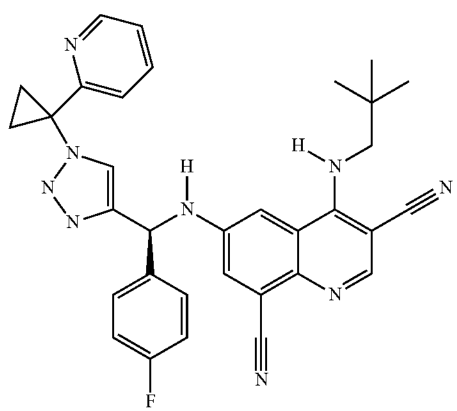 [SMILES: CC(C)(C)CNc1c(C#N)cnc2c(C#N)cc(N[C@H](C3=CN(C4(c5ccccn5)CC4)NN3)c3ccc(F)cc3)cc12] | (S)-6-(((4-fluorophenyl)(1-(1-(pyridin-2-yl)cyclopropyl)-1H-1,2,3-triazol-4-yl)methyl)amino)-4-(neopentylamino)quinoline-3,8-dicarbonitrile | 9 | 572.20 |

TABLE 1-continued

| Compd | Structure | Name | Example/Procedure | ES/MS m/z |
|---|---|---|---|---|
| 969 | 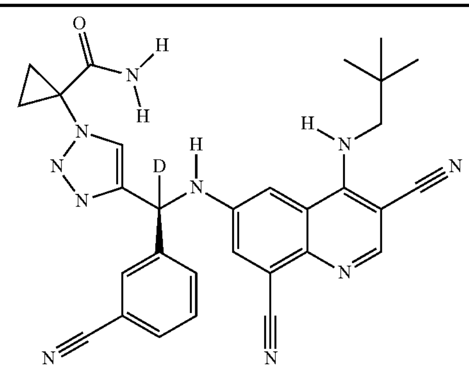 | 1-(4-((3-cyanophenyl)((3,8-dicyano-4-(neopentylamino)quinolin-6-yl)amino)methyl-d)-1H-1,2,3-triazol-1-yl)cyclopropane-1-carboxamide | 9 | 546.30 |
| 970 | 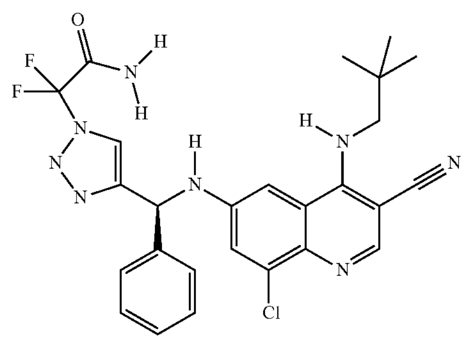 [SMILES: CC(C)(C)CNc1c(C#N)cnc2c(Cl)cc(N[C@H](C3=CN(C(F)(F)C(N)=O)NN3)c3ccccc3)cc12] | (S)-2-(4-(((8-chloro-3-cyano-4-(neopentylamino)quinolin-6-yl)amino)(phenyl)methyl)-1H-1,2,3-triazol-1-yl)-2,2-difluoroacetamide | 1 | 539.10 |
| 971 | 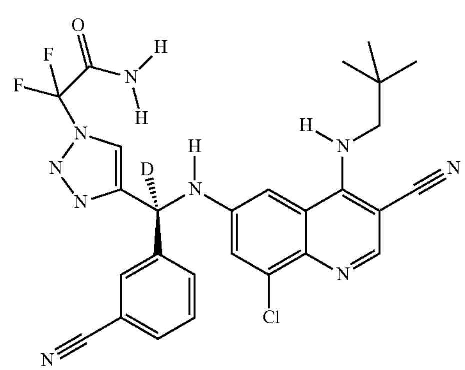 [SMILES: [2H][C@](Nc1cc(Cl)c2ncc(C#N)c(NCC(C)(C)C)c2c1)(C1=CN(C(F)(F)C(N)=O)NN1)c1cccc(C#N)c1] | (S)-2-(4-(((8-chloro-3-cyano-4-(neopentylamino)quinolin-6-yl)amino)(3-cyanophenyl)methyl-d)-1H-1,2,3-triazol-1-yl)-2,2-difluoroacetamide | 3 | 565.10 |

TABLE 1-continued

| Compd | Structure | Name | Example/Procedure | ES/MS m/z |
|---|---|---|---|---|
| 972 | 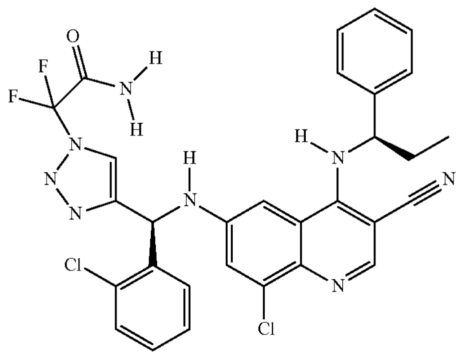 [SMILES: CC[C@@H](Nc1c(C#N)cnc2c(Cl)cc(N[C@H](C3=CN(C(F)(F)C(N)=O)NN3)c3ccccc3Cl)cc12)c1ccccc1] | 2-(4-((S)-((8-chloro-3-cyano-4-(((R)-1-phenylpropyl)amino)quinolin-6-yl)amino)(2-chlorophenyl)methyl)-1H-1,2,3-triazol-1-yl)-2,2-difluoroacetamide | 3 | 621.10 |
| 973 | 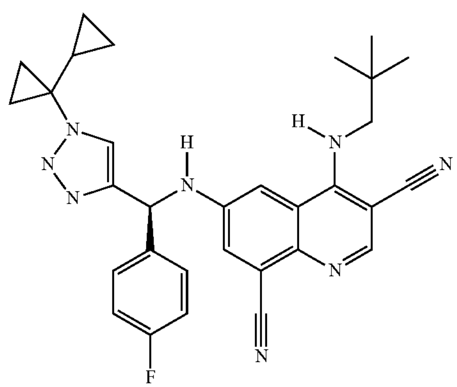 [SMILES: CC(C)(C)CNc1c(C#N)cnc2c(C#N)cc(N[C@H](C3=CN(C4(C5CC5)CC4)NN3)c3ccc(F)cc3)cc12] | (S)-6-(((1-([1,1'-bi(cyclopropan)]-1-yl)-1H-1,2,3-triazol-4-yl)(4-fluorophenyl)methyl)amino)-4-(neopentylamino)quinoline-3,8-dicarbonitrile | 9 | 535.20 |

TABLE 1-continued

| Compd | Structure | Name | Example/Procedure | ES/MS m/z |
|---|---|---|---|---|
| 974 | 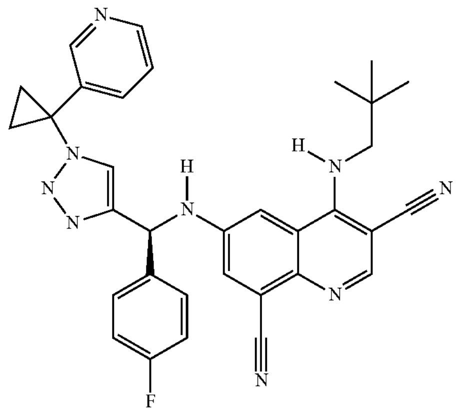 [SMILES: CC(C)(C)CNc1c(C#N)cnc2c(C#N)cc(N[C@H](C3=CN(C4(c5cccnc5)CC4)NN3)c3ccc(F)cc3)cc12] | (S)-6-(((4-fluorophenyl)(1-(1-(pyridin-3-yl)cyclopropyl)-1H-1,2,3-triazol-4-yl)methyl)amino)-4-(neopentylamino)quinoline-3,8-dicarbonitrile | 9 | 572.20 |
| 975 | 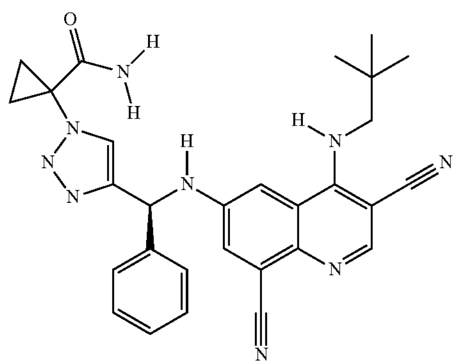 | (S)-1-(4-(((3,8-dicyano-4-(neopentylamino)quinolin-6-yl)amino)(phenyl)methyl)-1H-1,2,3-triazol-1-yl)cyclopropane-1-carboxamide | 9 | 520.20 |

TABLE 1-continued
| Compd | Structure | Name | Example/Procedure | ES/MS m/z |
|---|---|---|---|---|
| 976 | 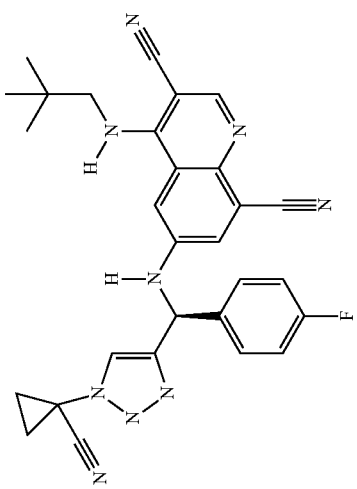 | (S)-6-((((1-(1-cyanocyclopropyl)-1H-1,2,3-triazol-4-yl)(4-fluorophenyl)methyl)amino)-4-(neopentylamino)quinoline-3,8-dicarbonitrile | 9 | 520.20 |
| 977 | 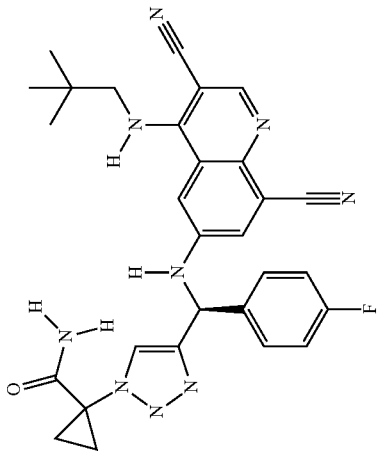 | (S)-1-(4-(((3,8-dicyano-4-(neopentylamino)quinolin-6-yl)amino)(4-fluorophenyl)methyl)-1H-1,2,3-triazol-1-yl)cyclopropane-1-carboxamide | 9 | 538.20 |

TABLE 1-continued
| Compd | Structure | Name | Example/Procedure | ES/MS m/z |
|---|---|---|---|---|
| 978 | 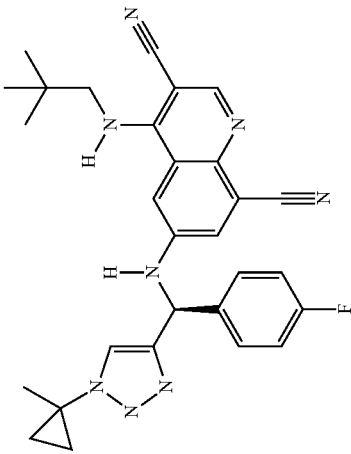 | (S)-6-(((4-fluorophenyl)(1-(1-methylcyclopropyl)-1H-1,2,3-triazol-4-yl)methyl)amino)-4-(neopentylamino)quinoline-3,8-dicarbonitrile | 9 | 509.30 |
| 979 | 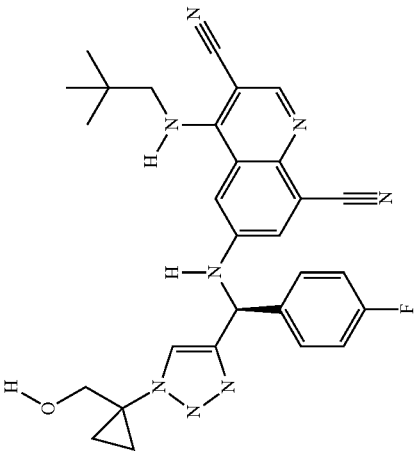 | (S)-6-(((4-fluorophenyl)(1-(1-(hydroxymethyl)cyclopropyl)-1H-1,2,3-triazol-4-yl)methyl)amino)-4-(neopentylamino)quinoline-3,8-dicarbonitrile | 9 | 525.20 |

TABLE 1-continued
| Compd | Structure | Name | Example/Procedure | ES/MS m/z |
|---|---|---|---|---|
| 980 | 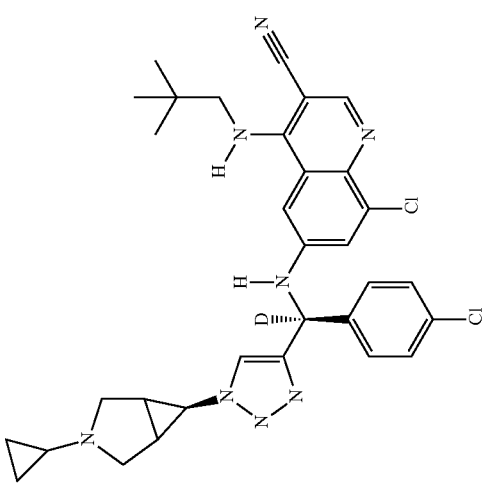 | 8-chloro-6-(((S)-(4-chlorophenyl)((1R,5S,6s)-3-cyclopropyl-3-azabicyclo[3.1.0]hexan-6-yl)-1H-1,2,3-triazol-4-yl)methyl)amino)-4-(neopentylamino)quinoline-3-carbonitrile | 55 | 602.30 |
| 981 | 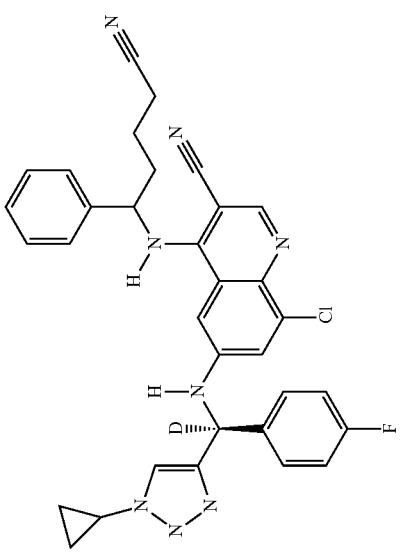 | 8-chloro-4-((4-cyano-1-phenylbutyl)amino)-6-(((1-cyclopropyl-1H-1,2,3-triazol-4-yl)(4-fluorophenyl)methyl-d)amino)quinoline-3-carbonitrile | 1 | 593.22 |

TABLE 1-continued
| Compd | Structure | Name | Example/Procedure | ES/MS m/z |
|---|---|---|---|---|
| 982 | 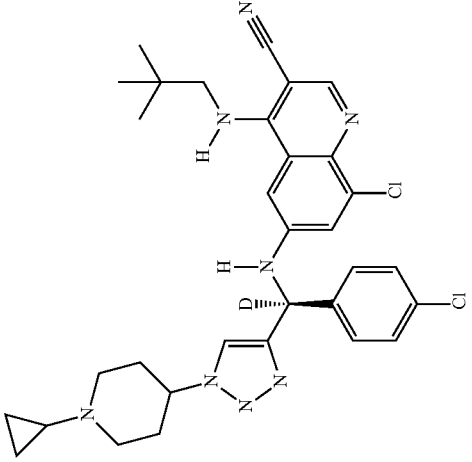 | (S)-8-chloro-6-((((4-chlorophenyl)(1-(1-cyclopropylpiperidin-4-yl)-1H-1,2,3-triazol-4-yl)methyl-d)amino)-4-(neopentylamino)quinoline-3-carbonitrile | 4 | 604.30 |
| 983 | 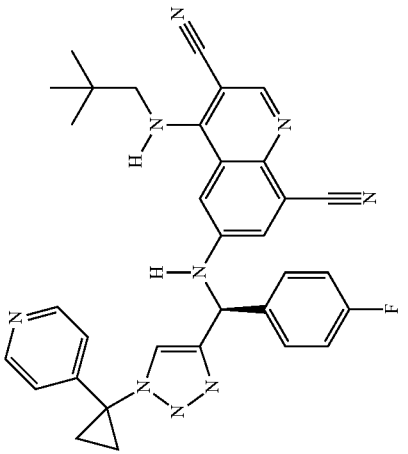 | (S)-6-((((4-fluorophenyl)(1-(1-(pyridin-4-yl)cyclopropyl)-1H-1,2,3-triazol-4-yl)methyl)amino)-4-(neopentylamino)quinoline-3,8-dicarbonitrile | 57 | 572.3 |

TABLE 1-continued

| Compd | Structure | Name | Example/Procedure | ES/MS m/z |
|---|---|---|---|---|
| 984 | 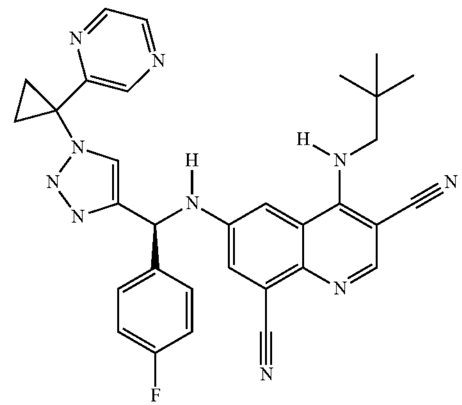 [SMILES: CC(C)(C)CNc1c(C#N)cnc2c(C#N)cc(N[C@H](C3=CN(C4(c5cnccn5)CC4)NN3)c3ccc(F)cc3)cc12] | (S)-6-((((4-fluorophenyl)(1-(1-(pyrazin-2-yl)cyclopropyl)-1H-1,2,3-triazol-4-yl)methyl)amino)-4-(neopentylamino)quinoline-3,8-dicarbonitrile | 57 | 573.2 |
| 985 | 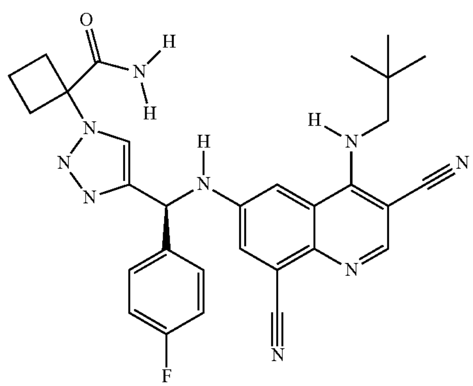 [SMILES: CC(C)(C)CNc1c(C#N)cnc2c(C#N)cc(N[C@H](C3=CN(C4(C(N)=O)CCC4)NN3)c3ccc(F)cc3)cc12] | (S)-1-(4-(((3,8-dicyano-4-(neopentylamino)quinolin-6-yl)amino)(4-fluorophenyl)methyl)-1H-1,2,3-triazol-1-yl)cyclobutane-1-carboxamide | 57 | 552.3 |

TABLE 1-continued
| Compd | Structure | Name | Example/Procedure | ES/MS m/z |
|---|---|---|---|---|
| 986 | 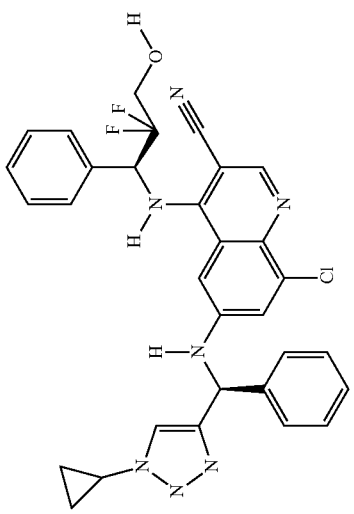 | 8-chloro-6-(((S)-(1-cyclopropyl-1H-1,2,3-triazol-4-yl)(phenyl)methyl)amino)-4-(((S)-2,2-difluoro-3-hydroxy-1-phenylpropyl)amino)quinoline-3-carbonitrile | 2 | 586.2 |
| 987 | 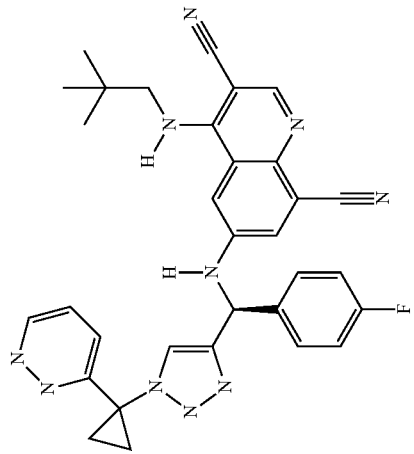 | (S)-6-(((4-fluorophenyl)(1-(1-(pyridazin-3-yl)cyclopropyl)-1H-1,2,3-triazol-4-yl)methyl)amino)-4-(neopentylamino)quinoline-3,8-dicarbonitrile | 57 | 573.2 |

TABLE 1-continued
| Compd | Structure | Name | Example/Procedure | ES/MS m/z |
|---|---|---|---|---|
| 988 | 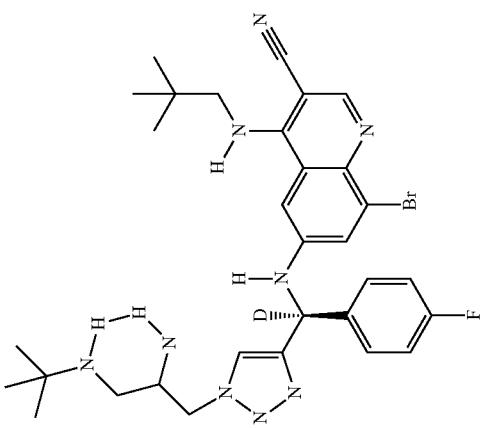 | 8-bromo-6-(((1S)-(1-(3-(tert-butylamino)-2-hydroxypropyl)-1H-1,2,3-triazol-4-yl)(4-fluorophenyl)methyl-d)amino)-4-(neopentylamino)quinoline-3-carbonitrile | 46 | 637.90 |
| 989 | 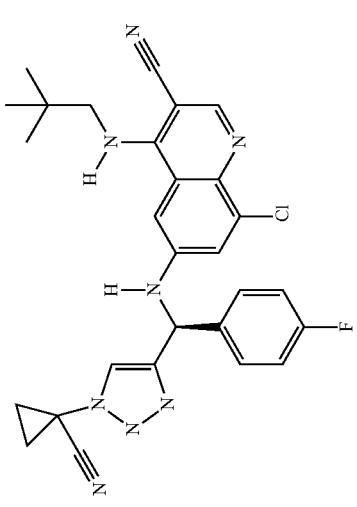 | (S)-8-chloro-6-(((1-(1-cyanocyclopropyl)-1H-1,2,3-triazol-4-yl)(4-fluorophenyl)methyl)amino)-4-(neopentylamino)quinoline-3-carbonitrile | 4 | 529.20 |

TABLE 1-continued

| Compd | Structure | Name | Example/Procedure | ES/MS m/z |
|---|---|---|---|---|
| 990 | 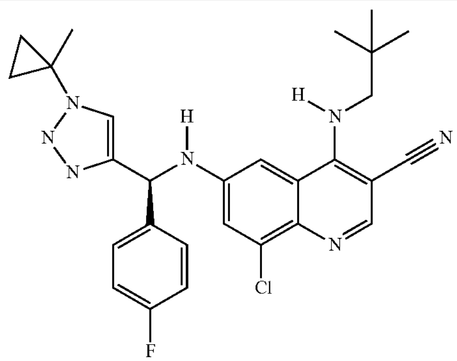 [SMILES: CC(C)(C)CNc1c(C#N)cnc2c(Cl)cc(N[C@H](C3=CN(C4(C)CC4)NN3)c3ccc(F)cc3)cc12] | (S)-8-chloro-6-(((4-fluorophenyl)(1-(1-methylcyclopropyl)-1H-1,2,3-triazol-4-yl)methyl)amino)-4-(neopentylamino)quinoline-3-carbonitrile | 4 | 518.3 |
| 991 | 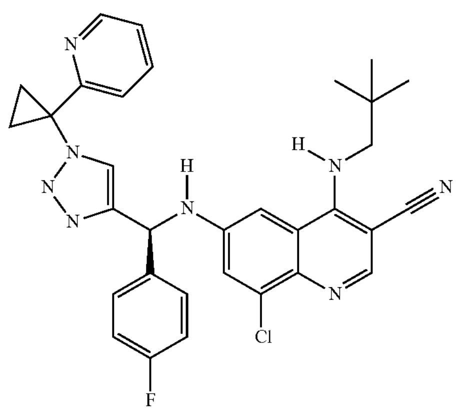 [SMILES: CC(C)(C)CNc1c(C#N)cnc2c(Cl)cc(N[C@H](C3=CN(C4(c5ccccn5)CC4)NN3)c3ccc(F)cc3)cc12] | (S)-8-chloro-6-(((4-fluorophenyl)(1-(1-(pyridin-2-yl)cyclopropyl)-1H-1,2,3-triazol-4-yl)methyl)amino)-4-(neopentylamino)quinoline-3-carbonitrile | 4 | 581.2 |

TABLE 1-continued

| Compd | Structure | Name | Example/Procedure | ES/MS m/z |
|---|---|---|---|---|
| 992 | 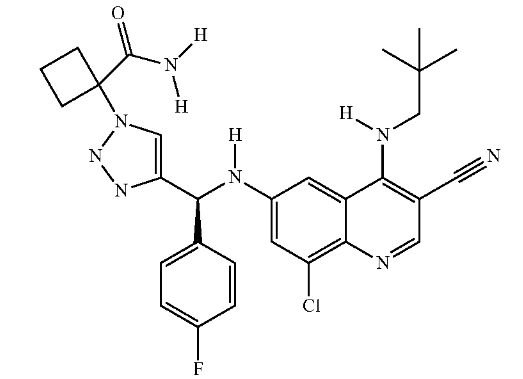 [SMILES: CC(C)(C)CNc1c(C#N)cnc2c(Cl)cc(N[C@H](C3=CN(C4(C(N)=O)CCC4)NN3)c3ccc(F)cc3)cc12] | (S)-1-(4-(((8-chloro-3-cyano-4-(neopentylamino)quinolin-6-yl)amino)(4-fluorophenyl)methyl)-1H-1,2,3-triazol-1-yl)cyclobutane-1-carboxamide | 4 | 561.30 |
| 993 | 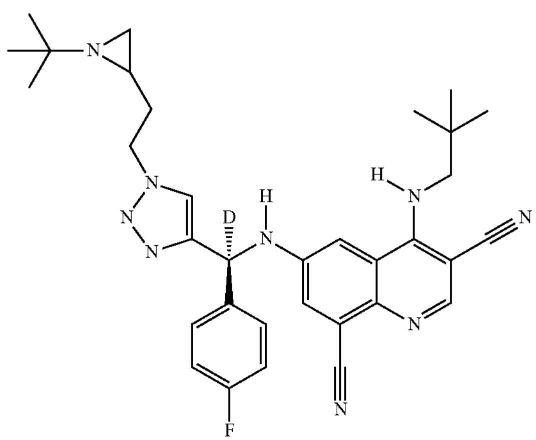 | 6-(((1S)-(1-(2-(1-(tert-butyl)aziridin-2-yl)ethyl)-1H-1,2,3-triazol-4-yl)(4-fluorophenyl)methyl-d)amino)-4-(neopentylamino)quinoline-3,8-dicarbonitrile | 9 | 581.40 |

TABLE 1-continued

| Compd | Structure | Name | Example/Procedure | ES/MS m/z |
|---|---|---|---|---|
| 994 | 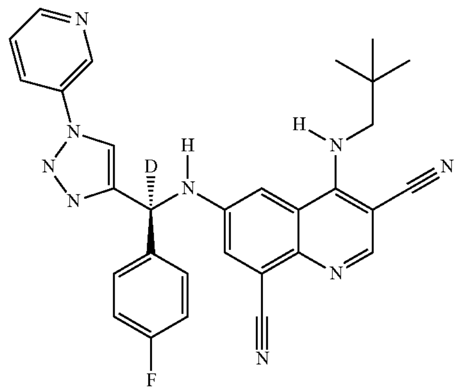 | (S)-6-(((4-fluorophenyl)(1-(pyridin-3-yl)-1H-1,2,3-triazol-4-yl)methyl)amino)-4-(neopentylamino)quinoline-3,8-dicarbonitrile | 9 | 533.40 |
| 995 | 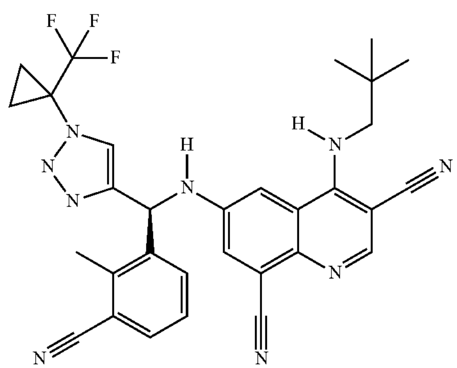 [SMILES: Cc1c(C#N)cccc1[C@H](Nc1cc(C#N)c2ncc(C#N)c(NCC(C)(C)C)c2c1)C1=CN(C2(C(F)(F)F)CC2)NN1] | (S)-6-(((3-cyano-2-methylphenyl)(1-(1-(trifluoromethyl)cyclopropyl)-1H-1,2,3-triazol-4-yl)methyl)amino)-4-(neopentylamino)quinoline-3,8-dicarbonitrile | 9 | 584.30 |

TABLE 1-continued
| Compd | Structure | Name | Example/Procedure | ES/MS m/z |
|---|---|---|---|---|
| 996 | 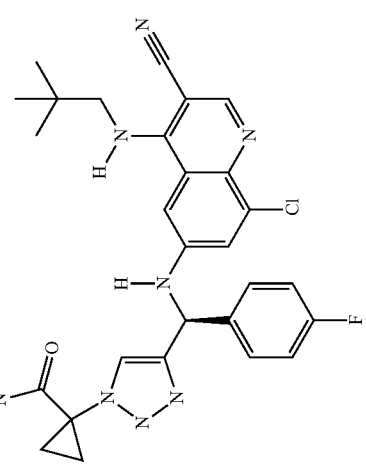 | (S)-1-(4-(((8-chloro-3-cyano-4-(neopentylamino)quinolin-6-yl)amino)(4-fluorophenyl)methyl)-1H-1,2,3-triazol-1-yl)cyclopropane-1-carboxamide | 4 | 547.3 |
| 997 | 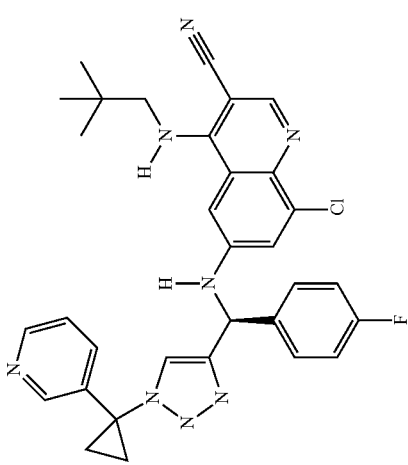 | (S)-8-chloro-6-(((4-fluorophenyl)(1-(1-(pyridin-3-yl)cyclopropyl)-1H-1,2,3-triazol-4-yl)methyl)amino)-4-(neopentylamino)quinoline-3-carbonitrile | 4 | 581.2 |

TABLE 1-continued

| Compd | Structure | Name | Example/Procedure | ES/MS m/z |
|---|---|---|---|---|
| 998 | 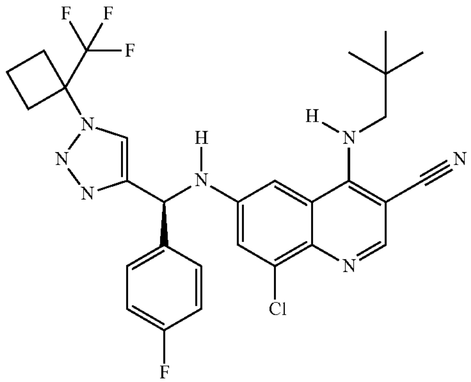 [SMILES: CC(C)(C)CNc1c(C#N)cnc2c(Cl)cc(N[C@H](C3=CN(C4(C(F)(F)F)CCC4)NN3)c3ccc(F)cc3)cc12] | (S)-8-chloro-6-((((4-fluorophenyl)(1-(1-(trifluoromethyl)cyclobutyl)-1H-1,2,3-triazol-4-yl)methyl)amino)-4-(neopentylamino)quinoline-3-carbonitrile | 4 | 586.2 |
| 999 | 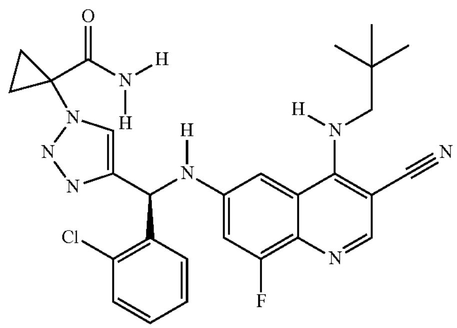 [SMILES: CC(C)(C)CNc1c(C#N)cnc2c(F)cc(N[C@H](C3=CN(C4(C(N)=O)CC4)NN3)c3ccccc3Cl)cc12] | (S)-1-(4-((2-chlorophenyl)(3-cyano-8-fluoro-4-(neopentylamino)quinolin-6-yl)amino)methyl)-1H-1,2,3-triazol-1-yl)cyclopropane-1-carboxamide | 4 | 547.2 |
| 1000 | 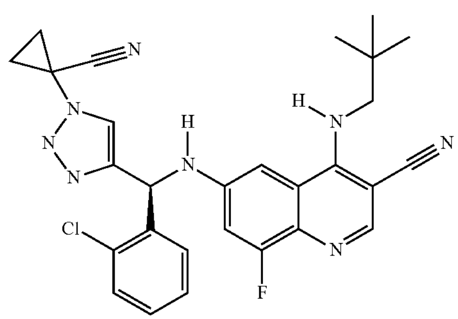 [SMILES: CC(C)(C)CNc1c(C#N)cnc2c(F)cc(N[C@H](C3=CN(C4(C#N)CC4)NN3)c3ccccc3Cl)cc12] | (S)-6-((((2-chlorophenyl)(1-(1-cyanocyclopropyl)-1H-1,2,3-triazol-4-yl)methyl)amino)-8-fluoro-4-(neopentylamino)quinoline-3-carbonitrile | 4 | 529.2 |

TABLE 1-continued

| Compd | Structure | Name | Example/Procedure | ES/MS m/z |
|---|---|---|---|---|
| 1001 | 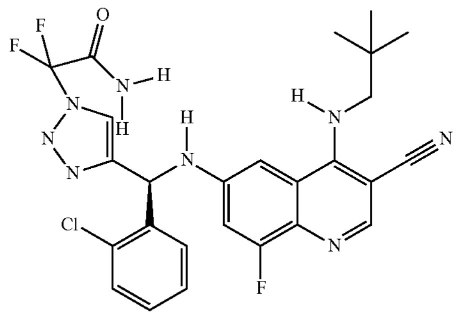 [SMILES: CC(C)(C)CNc1c(C#N)cnc2c(F)cc(N[C@H](C3=CN(C(F)(F)C(N)=O)NN3)c3ccccc3Cl)cc12] | (S)-2-(4-((2-chlorophenyl)((3-cyano-8-fluoro-4-(neopentylamino)quinolin-6-yl)amino)methyl)-1H-1,2,3-triazol-1-yl)-2,2-difluoroacetamide | 1 | 557.1 |
| 1002 | 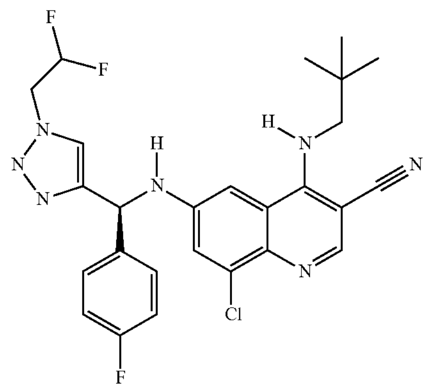 [SMILES: CC(C)(C)CNc1c(C#N)cnc2c(Cl)cc(N[C@H](C3=CN(CC(F)F)NN3)c3ccc(F)cc3)cc12] | (S)-8-chloro-6-(((1-(2,2-difluoroethyl)-1H-1,2,3-triazol-4-yl)(4-fluorophenyl)methyl)amino)-4-(neopentylamino)quinoline-3-carbonitrile | 4 | 528.2 |
| 1003 | 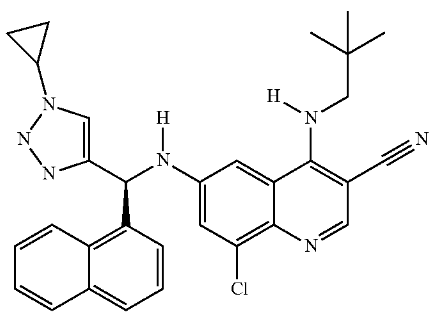 [SMILES: CC(C)(C)CNc1c(C#N)cnc2c(Cl)cc(N[C@H](C3=CN(C4CC4)NN3)c3cccc4ccccc34)cc12] | (S)-8-chloro-6-(((1-cyclopropyl-1H-1,2,3-triazol-4-yl)(naphthalen-1-yl)methyl)amino)-4-(neopentylamino)quinoline-3-carbonitrile | 3 | 536.4 |

TABLE 1-continued

| Compd | Structure | Name | Example/Procedure | ES/MS m/z |
|---|---|---|---|---|
| 1004 | 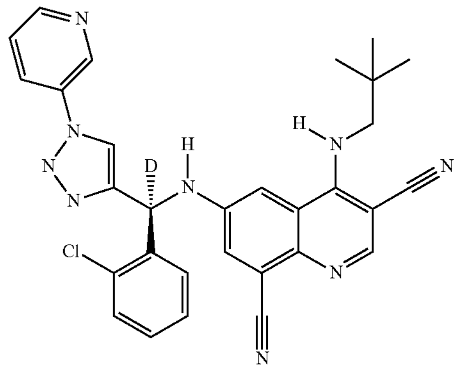 | (S)-6-(((2-chlorophenyl)(1-(pyridin-3-yl)-1H-1,2,3-triazol-4-yl)methyl-d)amino)-4-(neopentylamino)quinoline-3,8-dicarbonitrile | 9 | 549.3 |
| 1005 | 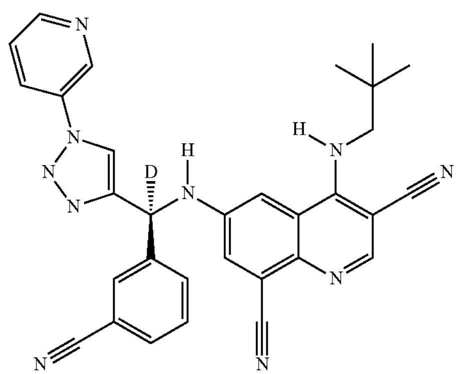 | (S)-6-(((3-cyanophenyl)(1-(pyridin-3-yl)-1H-1,2,3-triazol-4-yl)methyl-d)amino)-4-(neopentylamino)quinoline-3,8-dicarbonitrile | 9 | 540.3 |

TABLE 1-continued

| Compd | Structure | Name | Example/Procedure | ES/MS m/z |
|---|---|---|---|---|
| 1006 | 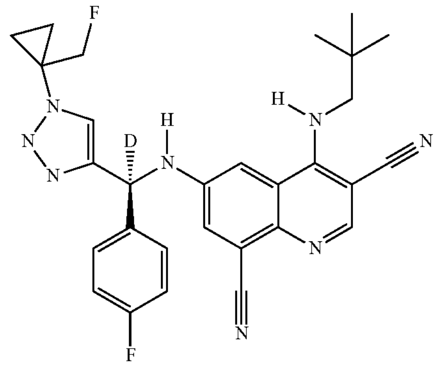 | (S)-6-(((1-(fluoromethyl)cyclopropyl)-1H-1,2,3-triazol-4-yl)(4-fluorophenyl)methyl-d)amino)-4-(neopentylamino)quinoline-3,8-dicarbonitrile | 9 | 528.3 |
| 1007 | 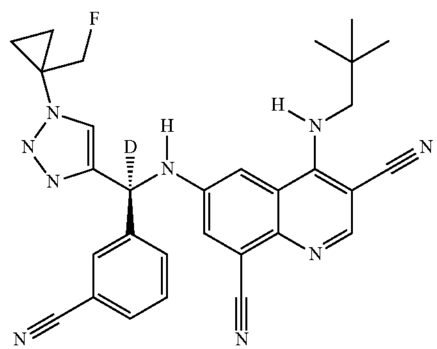 | (S)-6-(((3-cyanophenyl)(1-(1-(fluoromethyl)cyclopropyl)-1H-1,2,3-triazol-4-yl)methyl-d)amino)-4-(neopentylamino)quinoline-3,8-dicarbonitrile | 9 | 535.3 |

TABLE 1-continued
| Compd | Structure | Name | Example/Procedure | ES/MS m/z |
|---|---|---|---|---|
| 1008 | 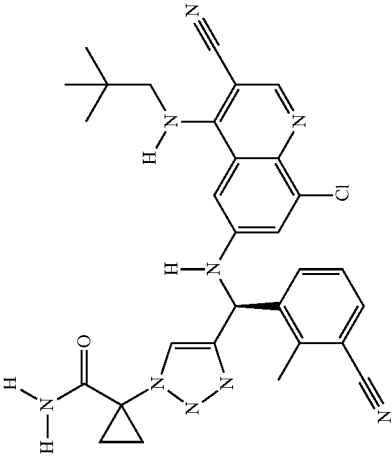 | (S)-1-(4-(((8-chloro-3-cyano-4-(neopentylamino)quinolin-6-yl)amino)(3-cyano-2-methylphenyl)methyl)-1H-1,2,3-triazol-1-yl)cyclopropane-1-carboxamide | 4 | 568.3 |
| 1009 | 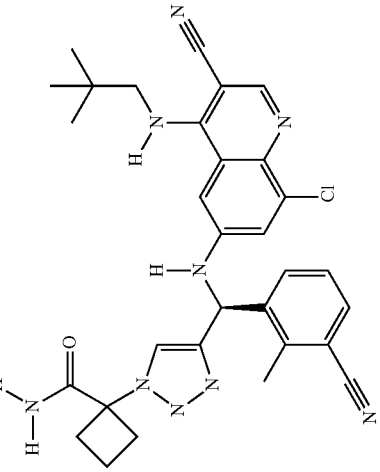 | (S)-1-(4-(((8-chloro-3-cyano-4-(neopentylamino)quinolin-6-yl)amino)(3-cyano-2-methylphenyl)methyl)-1H-1,2,3-triazol-1-yl)cyclobutane-1-carboxamide | 4 | 582.3 |

TABLE 1-continued

| Compd | Structure | Name | Example/Procedure | ES/MS m/z |
|---|---|---|---|---|
| 1010 | 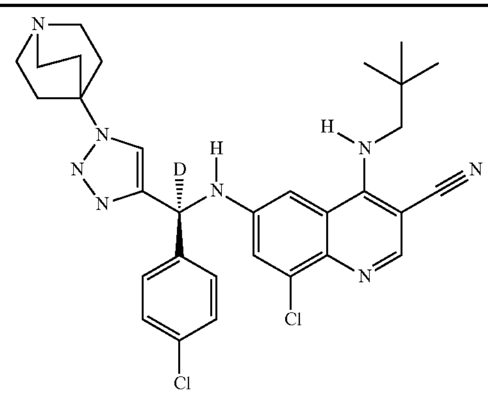 | (S)-8-chloro-6-(((4-chlorophenyl)(1-(quinuclidin-4-yl)-1H-1,2,3-triazol-4-yl)methyl-d)amino)-4-(neopentylamino)quinoline-3-carbonitrile | 4 | 590.3 |
| 1011 | 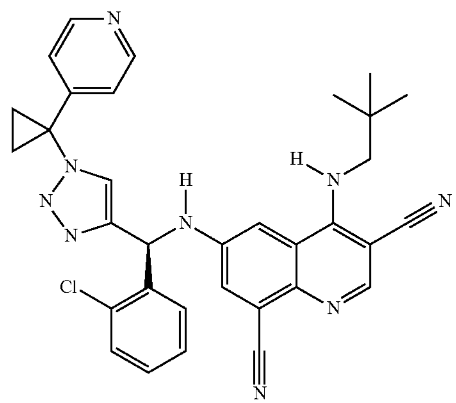 [SMILES: CC(C)(C)CNc1c(C#N)cnc2c(C#N)cc(N[C@H](C3=CN(C4(c5ccncc5)CC4)NN3)c3ccccc3Cl)cc12] | (S)-6-(((2-chlorophenyl)(1-(1-(pyridin-4-yl)cyclopropyl)-1H-1,2,3-triazol-4-yl)methyl)amino)-4-(neopentylamino)quinoline-3,8-dicarbonitrile | 57 | 588.3 |

TABLE 1-continued
| Compd | Structure | Name | Example/Procedure | ES/MS m/z |
|---|---|---|---|---|
| 1012 | 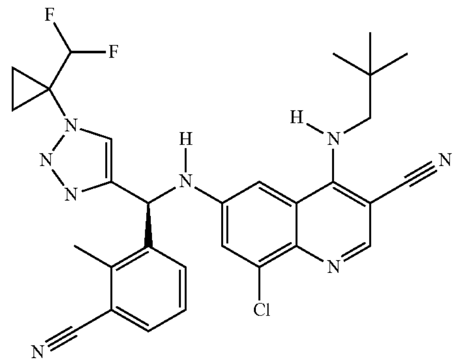 [SMILES: Cc1c(C#N)cccc1[C@H](Nc1cc(Cl)c2ncc(C#N)c(NCC(C)(C)C)c2c1)C1=CN(C2(C(F)F)CC2)NN1] | (S)-8-chloro-6-(((3-cyano-2-methylphenyl)(1-(1-(difluoromethyl)cyclopropyl)-1H-1,2,3-triazol-4-yl)methyl)amino)-4-(neopentylamino)quinoline-3-carbonitrile | 4 | 575.3 |
| 1013 | 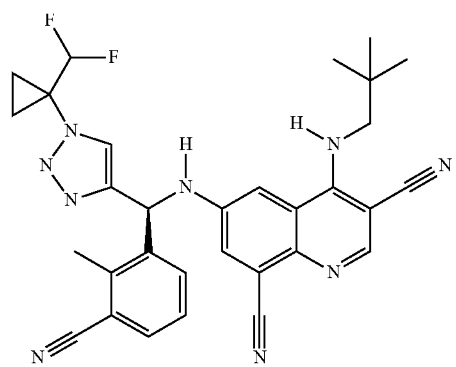 [SMILES: Cc1c(C#N)cccc1[C@H](Nc1cc(C#N)c2ncc(C#N)c(NCC(C)(C)C)c2c1)C1=CN(C2(C(F)F)CC2)NN1] | (S)-6-(((3-cyano-2-methylphenyl)(1-(1-(difluoromethyl)cyclopropyl)-1H-1,2,3-triazol-4-yl)methyl)amino)-4-(neopentylamino)quinoline-3,8-dicarbonitrile | 57 | 566.3 |

TABLE 1-continued
| Compd | Structure | Name | Example/Procedure | ES/MS m/z |
|---|---|---|---|---|
| 1014 | 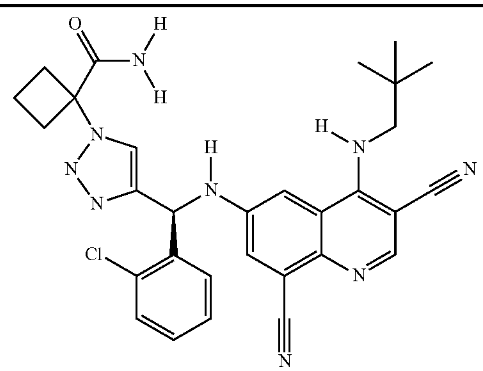 | (S)-1-(4-((2-chlorophenyl)((3,8-dicyano-4-(neopentylamino)quinolin-6-yl)amino)methyl)-1H-1,2,3-triazol-1-yl)cyclobutane-1-carboxamide | 57 | 568.3 |
| 1015 | 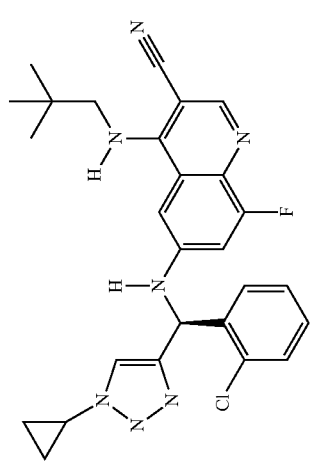 | (S)-6-(((2-chlorophenyl)(1-cyclopropyl-1H-1,2,3-triazol-4-yl)methyl)amino)-8-fluoro-4-(neopentylamino)quinoline-3-carbonitrile | 1 | 504.30 |

TABLE 1-continued
| Compd | Structure | Name | Example/Procedure | ES/MS m/z |
|---|---|---|---|---|
| 1016 | 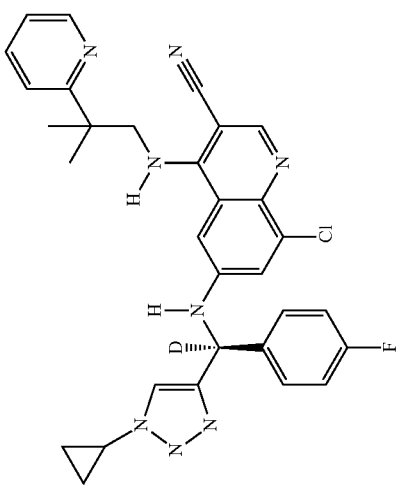 | (S)-8-chloro-6-((((1-cyclopropyl-1H-1,2,3-triazol-4-yl)(4-fluorophenyl)methyl-d)amino)-4-((2-methyl-2-(pyridin-2-yl)propyl)amino)quinoline-3-carbonitrile | 1 | 568.39 |
| 1017 | 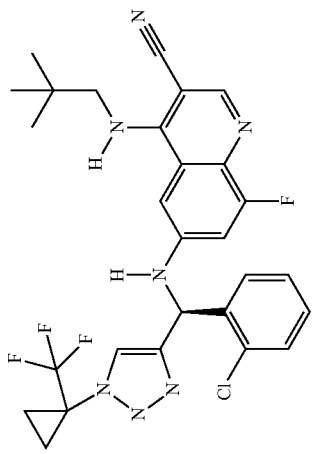 | (S)-6-(((2-chlorophenyl)(1-(1-(trifluoromethyl)cyclopropyl)-1H-1,2,3-triazol-4-yl)methyl)amino)-8-fluoro-4-(neopentylamino)quinoline-3-carbonitrile | 4 | 572.2 |

TABLE 1-continued

| Compd | Structure | Name | Example/Procedure | ES/MS m/z |
|---|---|---|---|---|
| 1018 | 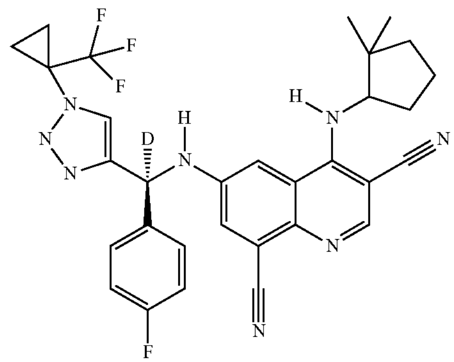 | 4-((2,2-dimethylcyclopentyl)amino)-6-(((S)-(4-fluorophenyl)(1-(1-(trifluoromethyl)cyclopropyl)-1H-1,2,3-triazol-4-yl)methyl)amino)quinoline-3,8-dicarbonitrile | 9 | 590.37 |
| 1019 | 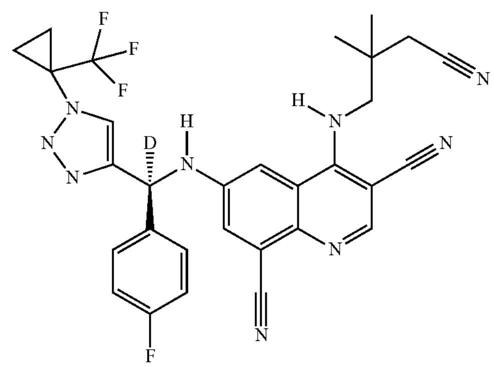 | (S)-4-((3-cyano-2,2-dimethylpropyl)amino)-6-(((4-fluorophenyl)(1-(1-(trifluoromethyl)cyclopropyl)-1H-1,2,3-triazol-4-yl)methyl)amino)quinoline-3,8-dicarbonitrile | 57 | 589.30 |

TABLE 1-continued
| Compd | Structure | Name | Example/Procedure | ES/MS m/z |
|---|---|---|---|---|
| 1020 | 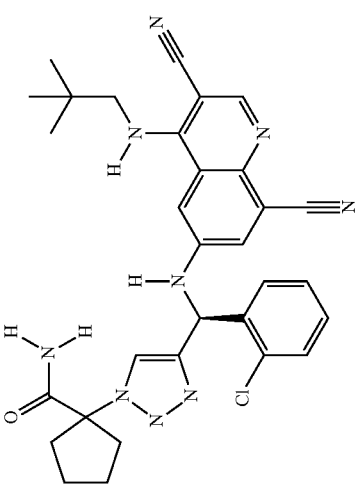 | (S)-1-(4-((2-chlorophenyl)((3,8-dicyano-4-(neopentylamino)quinolin-6-yl)amino)methyl)-1H-1,2,3-triazol-1-yl)cyclopentane-1-carboxamide | 57 | 582.3 |
| 1021 | 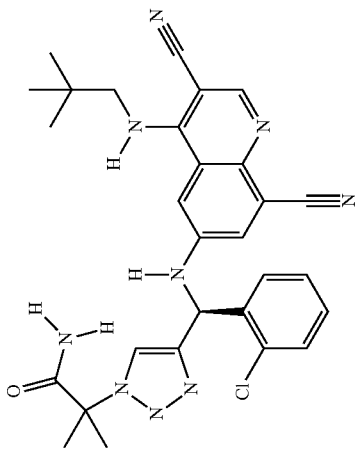 | (S)-2-(4-((2-chlorophenyl)((3,8-dicyano-4-(neopentylamino)quinolin-6-yl)amino)methyl)-1H-1,2,3-triazol-1-yl)-2-methylpropanamide | 57 | 556.3 |

TABLE 1-continued

| Compd | Structure | Name | Example/Procedure | ES/MS m/z |
|---|---|---|---|---|
| 1022 | 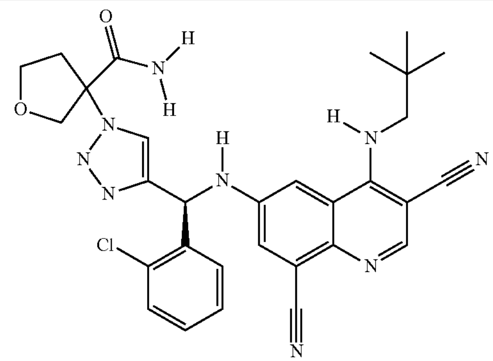 [SMILES: CC(C)(C)CNc1c(C#N)cnc2c(C#N)cc(N[C@H](C3=CN(C4(C(N)=O)CCOC4)NN3)c3ccccc3Cl)cc12] | 3-(4-((S)-(2-chlorophenyl)((3,8-dicyano-4-(neopentylamino)quinolin-6-yl)amino)methyl)-1H-1,2,3-triazol-1-yl)tetrahydrofuran-3-carboxamide | 57 | 584.3 |
| 1023 | 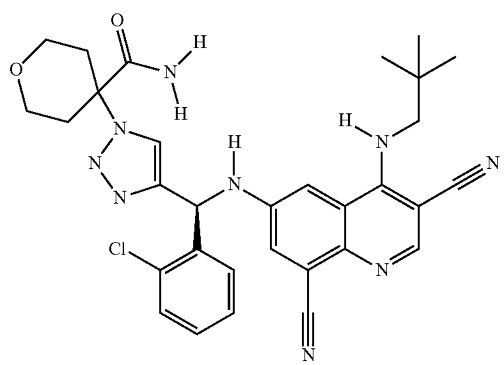 [SMILES: CC(C)(C)CNc1c(C#N)cnc2c(C#N)cc(N[C@H](C3=CN(C4(C(N)=O)CCOCC4)NN3)c3ccccc3Cl)cc12] | (S)-4-(4-((2-chlorophenyl)((3,8-dicyano-4-(neopentylamino)quinolin-6-yl)amino)methyl)-1H-1,2,3-triazol-1-yl)tetrahydro-2H-pyran-4-carboxamide | 57 | 598.3 |

TABLE 1-continued

| Compd | Structure | Name | Example/Procedure | ES/MS m/z |
|---|---|---|---|---|
| 1024 | 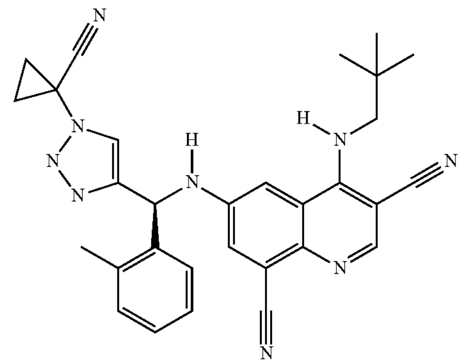 [SMILES: Cc1ccccc1[C@H](Nc1cc(C#N)c2ncc(C#N)c(NCC(C)(C)C)c2c1)C1=CN(C2(C#N)CC2)NN1] | (S)-6-(((1-(1-cyanocyclopropyl)-1H-1,2,3-triazol-4-yl)(o-tolyl)methyl)amino)-4-(neopentylamino)quinoline-3,8-dicarbonitrile | 57 | 516.3 |
| 1025 | 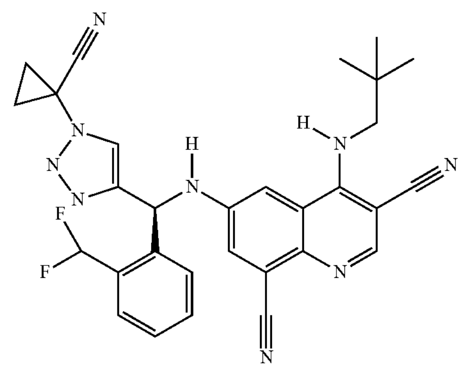 [SMILES: CC(C)(C)CNc1c(C#N)cnc2c(C#N)cc(N[C@H](C3=CN(C4(C#N)CC4)NN3)c3ccccc3C(F)F)cc12] | (S)-6-(((1-(1-cyanocyclopropyl)-1H-1,2,3-triazol-4-yl)(2-(difluoromethyl)phenyl)methyl)amino)-4-(neopentylamino)quinoline-3,8-dicarbonitrile | 57 | 552.2 |

TABLE 1-continued
| Compd | Structure | Name | Example/Procedure | ES/MS m/z |
|---|---|---|---|---|
| 1026 | 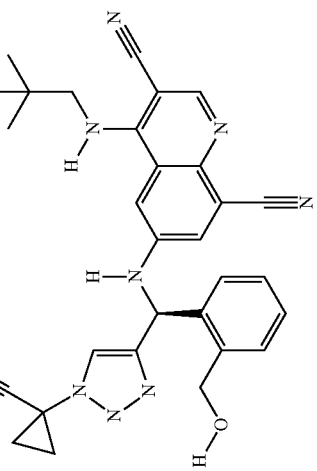 | (S)-6-((((1-(1-cyanocyclopropyl)-1H-1,2,3-triazol-4-yl)(2-(hydroxymethyl)phenyl)methyl)amino)-4-(neopentylamino)quinoline-3,8-dicarbonitrile | 17 | 532.2 |
| 1027 | 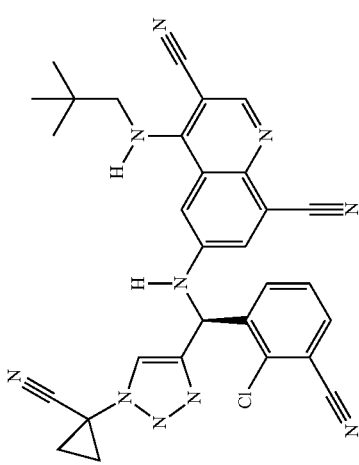 | (S)-6-(((2-chloro-3-cyanophenyl)(1-(1-cyanocyclopropyl)-1H-1,2,3-triazol-4-yl)methyl)amino)-4-(neopentylamino)quinoline-3,8-dicarbonitrile | 57 | 562.2 |

TABLE 1-continued
| Compd | Structure | Name | Example/Procedure | ES/MS m/z |
|---|---|---|---|---|
| 1028 | 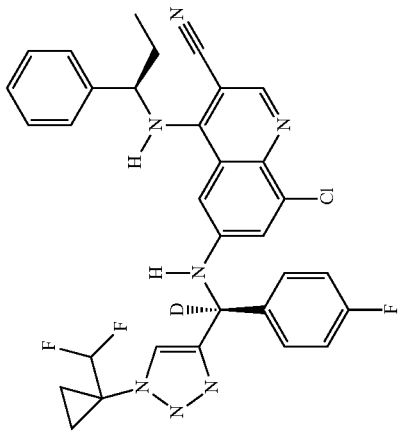 | 8-chloro-6-(((S)-(1-(difluoromethyl)cyclopropyl)-1H-1,2,3-triazol-4-yl)(4-fluorophenyl)methyl)amino)-4-(((R)-1-phenylpropyl)amino)quinoline-3-carbonitrile | 2 | 603.30 |
| 1029 | 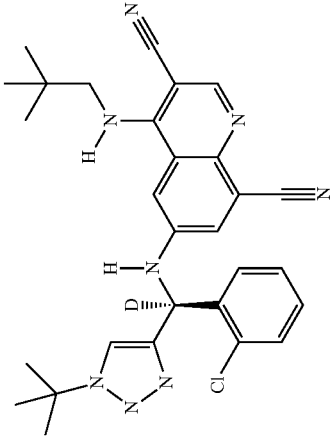 | (S)-6-(((1-(tert-butyl)-1H-1,2,3-triazol-4-yl)(2-chlorophenyl)methyl)amino)-4-(neopentylamino)quinoline-3,8-dicarbonitrile | 9 | 528.3 |

TABLE 1-continued

| Compd | Structure | Name | Example/Procedure | ES/MS m/z |
|---|---|---|---|---|
| 1030 | 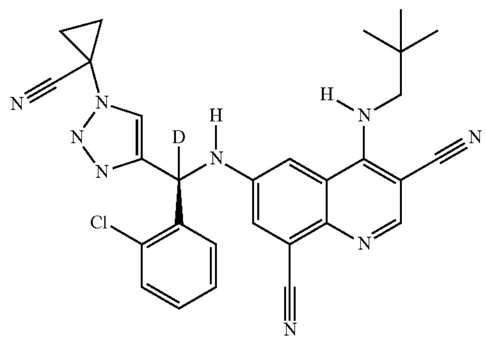 [SMILES: [2H][C@](Nc1cc(C#N)c2ncc(C#N)c(NCC(C)(C)C)c2c1)(C1=CN(C2(C#N)CC2)NN1)c1ccccc1Cl] | 6-(((2-chlorophenyl)(1-(1-cyanocyclopropyl)-1H-1,2,3-triazol-4-yl)methyl-d)amino)-4-(neopentylamino)quinoline-3,8-dicarbonitrile | 57 | 537.1 |
| 1031 | 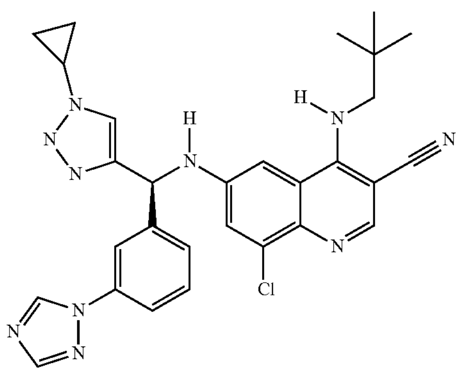 [SMILES: CC(C)(C)CNc1c(C#N)cnc2c(Cl)cc(N[C@H](C3=CN(C4CC4)NN3)c3cccc(-n4cncn4)c3)cc12] | (S)-6-(((3-(1H-1,2,4-triazol-1-yl)phenyl)(1-cyclopropyl-1H-1,2,3-triazol-4-yl)methyl)amino)-8-chloro-4-(neopentylamino)quinoline-3-carbonitrile | 3 | 553.3 |

TABLE 1-continued

| Compd | Structure | Name | Example/Procedure | ES/MS m/z |
|---|---|---|---|---|
| 1032 | 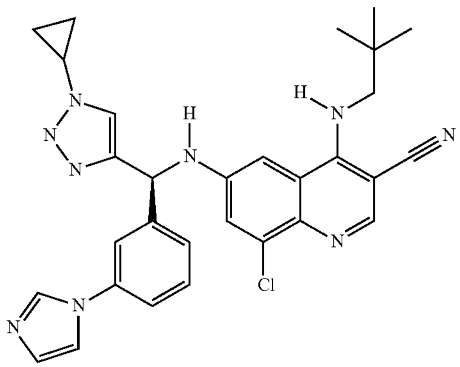 | (S)-6-(((3-(1H-imidazol-1-yl)phenyl)(1-cyclopropyl-1H-1,2,3-triazol-4-yl)methyl)amino)-8-chloro-4-(neopentylamino)quinoline-3-carbonitrile | 3 | 552.1 |
| 1033 | 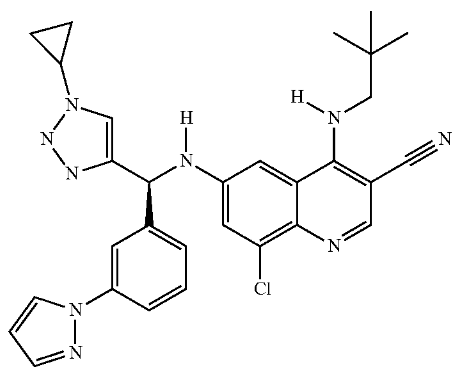 [SMILES: CC(C)(C)CNc1c(C#N)cnc2c(Cl)cc(N[C@H](C3=CN(C4CC4)NN3)c3cccc(-n4cccn4)c3)cc12] | (S)-6-(((3-(1H-pyrazol-1-yl)phenyl)(1-cyclopropyl-1H-1,2,3-triazol-4-yl)methyl)amino)-8-chloro-4-(neopentylamino)quinoline-3-carbonitrile | 3 | 552.1 |

TABLE 1-continued

| Compd | Structure | Name | Example/Procedure | ES/MS m/z |
|---|---|---|---|---|
| 1034 | 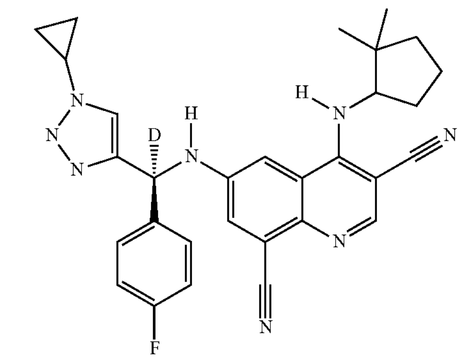 | 6-(((S)-(1-cyclopropyl-1H-1,2,3-triazol-4-yl)(4-fluorophenyl)methyl-d)amino)-4-((2,2-dimethylcyclopentyl)amino)quinoline-3,8-dicarbonitrile | 48 | 522.32 |
| 1035 | 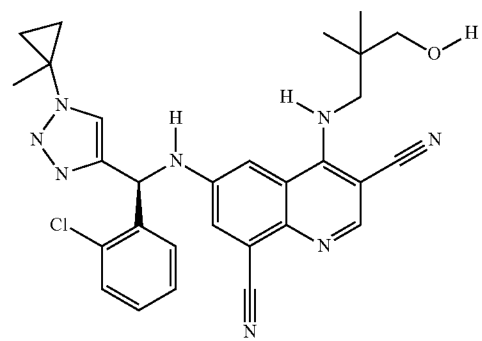 [SMILES: CC(C)(CO)CNc1c(C#N)cnc2c(C#N)cc(N[C@H](C3=CN(C4(C)CC4)NN3)c3ccccc3Cl)cc12] | (S)-6-(((2-chlorophenyl)(1-(1-methylcyclopropyl)-1H-1,2,3-triazol-4-yl)methyl)amino)-4-((3-hydroxy-2,2-dimethylpropyl)amino)quinoline-3,8-dicarbonitrile | 57 | 541.1 |
| 1036 | 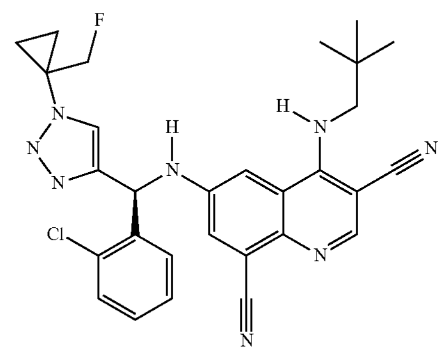 [SMILES: CC(C)(C)CNc1c(C#N)cnc2c(C#N)cc(N[C@H](C3=CN(C4(CF)CC4)NN3)c3ccccc3Cl)cc12] | (S)-6-(((2-chlorophenyl)(1-(1-(fluoromethyl)cyclopropyl)-1H-1,2,3-triazol-4-yl)methyl)amino)-4-(neopentylamino)quinoline-3,8-dicarbonitrile | 9 | 543.3 |

TABLE 1-continued

| Compd | Structure | Name | Example/Procedure | ES/MS m/z |
|---|---|---|---|---|
| 1037 | 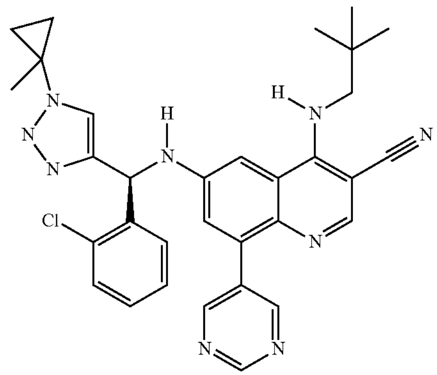 [SMILES: CC(C)(C)CNc1c(C#N)cnc2c(-c3cncnc3)cc(N[C@H](C3=CN(C4(C)CC4)NN3)c3ccccc3Cl)cc12] | (S)-6-(((2-chlorophenyl)(1-(1-methylcyclopropyl)-1H-1,2,3-triazol-4-yl)methyl)amino)-4-(neopentylamino)-8-(pyrimidin-5-yl)quinoline-3-carbonitrile | 12 | 578.19 |
| 1038 | 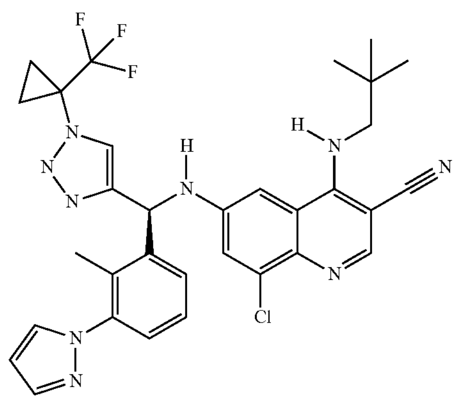 [SMILES: Cc1c([C@H](Nc2cc(Cl)c3ncc(C#N)c(NCC(C)(C)C)c3c2)C2=CN(C3(C(F)(F)F)CC3)NN2)cccc1-n1cccn1] | (S)-8-chloro-6-(((2-methyl-3-(1H-pyrazol-1-yl)phenyl)(1-(1-(trifluoromethyl)cyclopropyl)-1H-1,2,3-triazol-4-yl)methyl)amino)-4-(neopentylamino)quinoline-3-carbonitrile | 4 | 634.4 |

TABLE 1-continued

| Compd | Structure | Name | Example/Procedure | ES/MS m/z |
|---|---|---|---|---|
| 1039 | 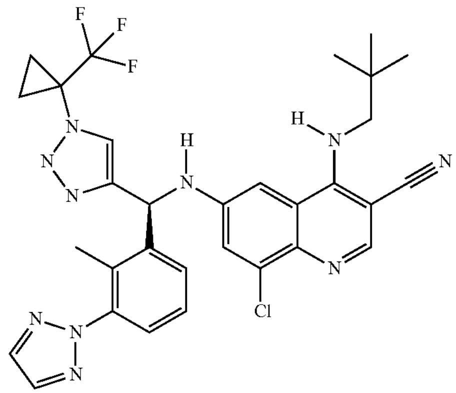 [SMILES: Cc1c([C@H](Nc2cc(Cl)c3ncc(C#N)c(NCC(C)(C)C)c3c2)C2=CN(C3(C(F)(F)F)CC3)NN2)cccc1-n1nccn1] | (S)-8-chloro-6-(((2-methyl-3-(2H-1,2,3-triazol-2-yl)phenyl)(1-(1-(trifluoromethyl)cyclopropyl)-1H-1,2,3-triazol-4-yl)methyl)amino)-4-(neopentylamino)quinoline-3-carbonitrile | 4 | 635.3 |
| 1040 | 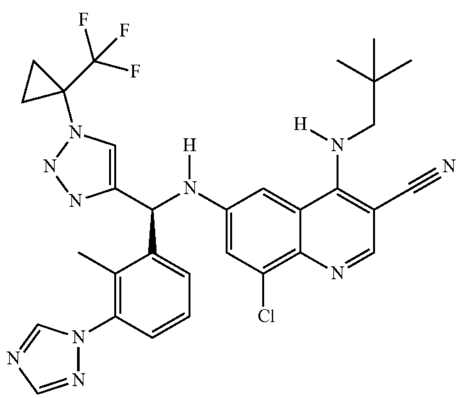 [SMILES: Cc1c([C@H](Nc2cc(Cl)c3ncc(C#N)c(NCC(C)(C)C)c3c2)C2=CN(C3(C(F)(F)F)CC3)NN2)cccc1-n1cncn1] | (S)-8-chloro-6-(((2-methyl-3-(1H-1,2,4-triazol-1-yl)phenyl)(1-(1-(trifluoromethyl)cyclopropyl)-1H-1,2,3-triazol-4-yl)methyl)amino)-4-(neopentylamino)quinoline-3-carbonitrile | 4 | 635.4 |

TABLE 1-continued
| Compd | Structure | Name | Example/Procedure | ES/MS m/z |
|---|---|---|---|---|
| 1041 | 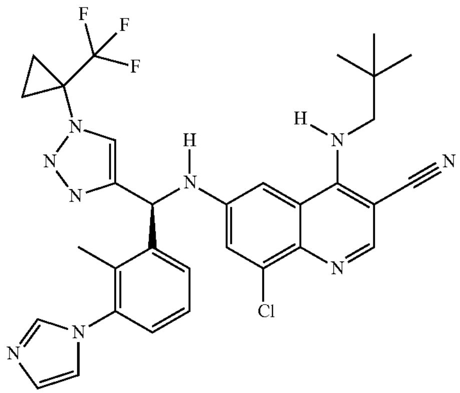 [SMILES: Cc1c([C@H](Nc2cc(Cl)c3ncc(C#N)c(NCC(C)(C)C)c3c2)C2=CN(C3(C(F)(F)F)CC3)NN2)cccc1-n1ccnc1] | (S)-6-(((3-(1H-imidazol-1-yl)-2-methylphenyl)(1-(1-(trifluoromethyl)cyclopropyl)-1H-1,2,3-triazol-4-yl)methyl)amino)-8-chloro-4-(neopentylamino)quinoline-3-carbonitrile | 4 | 634.2 |
| 1042 | 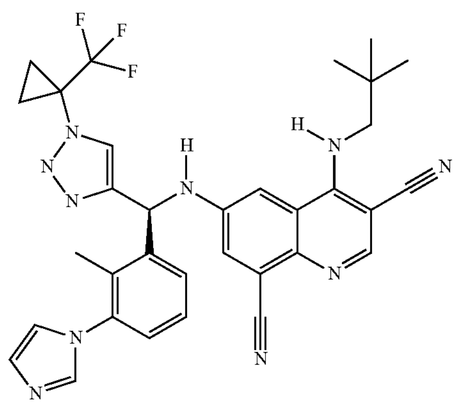 [SMILES: Cc1c([C@H](Nc2cc(C#N)c3ncc(C#N)c(NCC(C)(C)C)c3c2)C2=CN(C3(C(F)(F)F)CC3)NN2)cccc1-n1ccnc1] | (S)-6-(((3-(1H-imidazol-1-yl)-2-methylphenyl)(1-(1-(trifluoromethyl)cyclopropyl)-1H-1,2,3-triazol-4-yl)methyl)amino)-4-(neopentylamino)quinoline-3,8-dicarbonitrile | 48 | 625.2 |

TABLE 1-continued

| Compd | Structure | Name | Example/Procedure | ES/MS m/z |
|---|---|---|---|---|
| 1043 | 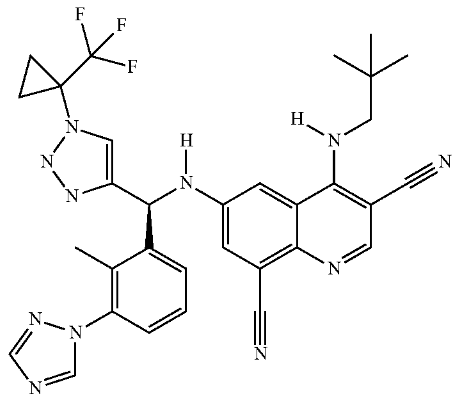 | (S)-6-(((2-methyl-3-(1H-1,2,4-triazol-1-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 626.2 |
| 1044 | 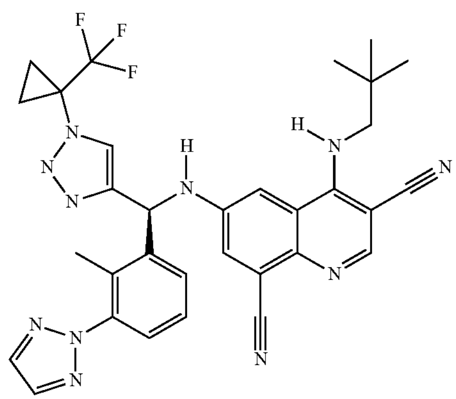 [SMILES: Cc1c([C@H](Nc2cc(C#N)c3ncc(C#N)c(NCC(C)(C)C)c3c2)C2=CN(C3(C(F)(F)F)CC3)NN2)cccc1-n1nccn1] | (S)-6-(((2-methyl-3-(2H-1,2,3-triazol-2-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 626.2 |

TABLE 1-continued

| Compd | Structure | Name | Example/Procedure | ES/MS m/z |
|---|---|---|---|---|
| 1045 | 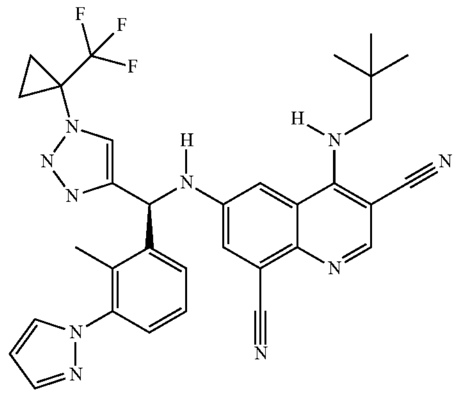 [SMILES: Cc1c([C@H](Nc2cc(C#N)c3ncc(C#N)c(NCC(C)(C)C)c3c2)C2=CN(C3(C(F)(F)F)CC3)NN2)cccc1-n1cccn1] | (S)-6-(((2-methyl-3-(1H-pyrazol-1-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 625.1 |
| 1046 | 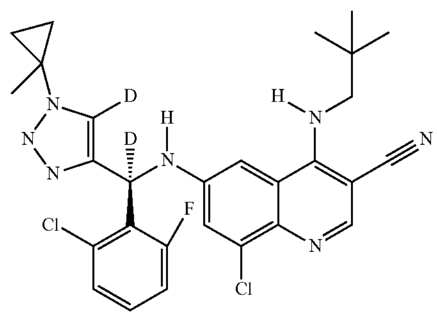 | (S)-8-chloro-6-(((2-chloro-6-fluorophenyl)(1-(1-methylcyclopropyl)-1H-1,2,3-triazol-4-yl-5-d)methyl-d)amino)-4-(neopentylamino)quinoline-3-carbonitrile | 59 | 554.32 |
| 1047 | 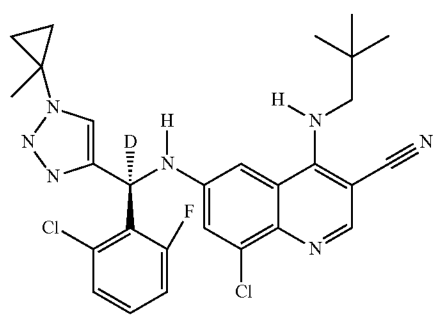 | (S)-8-chloro-6-(((2-chloro-6-fluorophenyl)(1-(1-methylcyclopropyl)-1H-1,2,3-triazol-4-yl)methyl-d)amino)-4-(neopentylamino)quinoline-3-carbonitrile | 1 | 553.31 |

TABLE 1-continued
| Compd | Structure | Name | Example/Procedure | ES/MS m/z |
|---|---|---|---|---|
| 1048 | 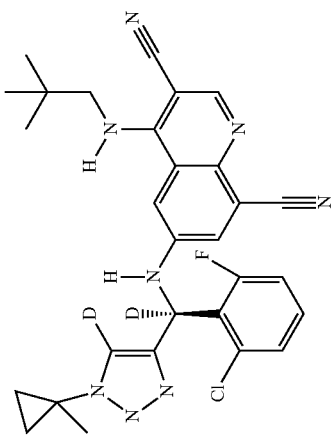 | (S)-6-(((2-chloro-6-fluorophenyl)(1-(1-methylcyclopropyl)-1H-1,2,3-triazol-4-yl-5-d)methyl-d)amino)-4-(neopentylamino)quinoline-3,8-dicarbonitrile | 48 | 545.33 |
| 1049 | 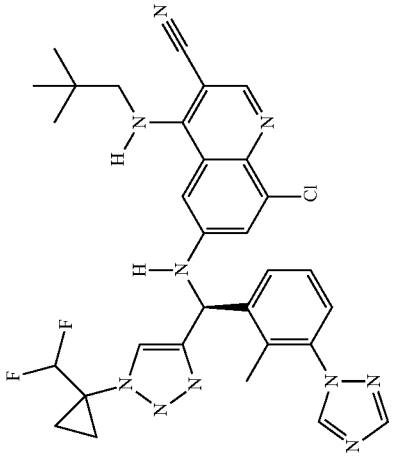 | (S)-8-chloro-6-(((1-(1-(difluoromethyl)cyclopropyl)-1H-1,2,3-triazol-4-yl)(2-methyl-3-(1H-1,2,4-triazol-1-yl)phenyl)methyl)amino)-4-(neopentylamino)quinoline-3-carbonitrile | 4 | 617.3 |

TABLE 1-continued

| Compd | Structure | Name | Example/Procedure | ES/MS m/z |
|---|---|---|---|---|
| 1050 | 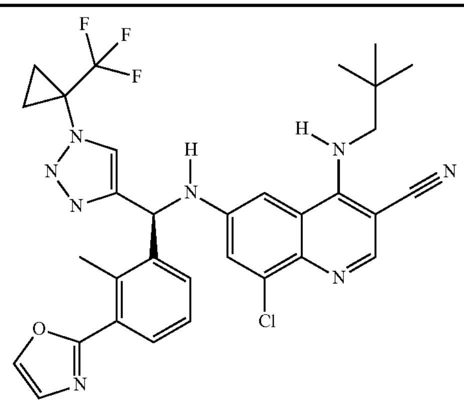 | (S)-8-chloro-6-(((2-methyl-3-(oxazol-2-yl)phenyl)(1-(1-(trifluoromethyl)cyclopropyl)-1H-1,2,3-triazol-4-yl)methyl)amino)-4-(neopentylamino)quinoline-3-carbonitrile | 4 | 635.4 |
| 1051 | 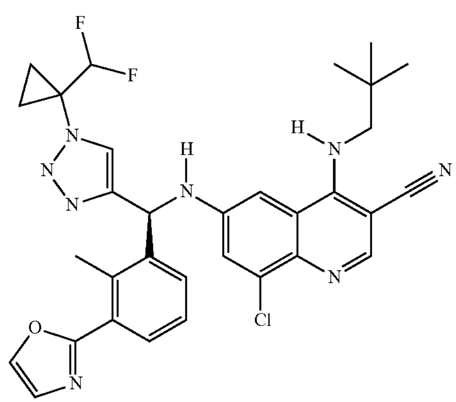 | (S)-8-chloro-6-(((1-(1-(difluoromethyl)cyclopropyl)-1H-1,2,3-triazol-4-yl)(2-methyl-3-(oxazol-2-yl)phenyl)methyl)amino)-4-(neopentylamino)quinoline-3-carbonitrile | 4 | 617.2 |

TABLE 1-continued

| Compd | Structure | Name | Example/Procedure | ES/MS m/z |
|---|---|---|---|---|
| 1052 | 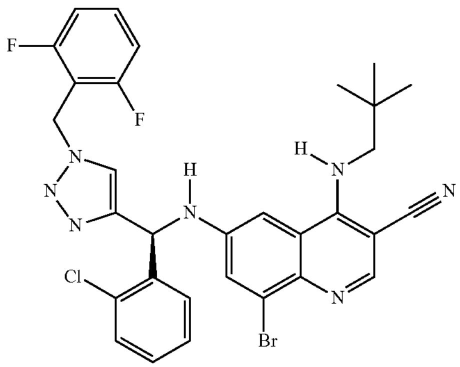 [SMILES: CC(C)(C)CNc1c(C#N)cnc2c(Br)cc(N[C@H](C3=CN(Cc4c(F)cccc4F)NN3)c3ccccc3Cl)cc12] | (S)-8-bromo-6-(((2-chlorophenyl)(1-(2,6-difluorobenzyl)-1H-1,2,3-triazol-4-yl)methyl)amino)-4-(neopentylamino)quinoline-3-carbonitrile | 1 | 650.20 |
| 1053 | 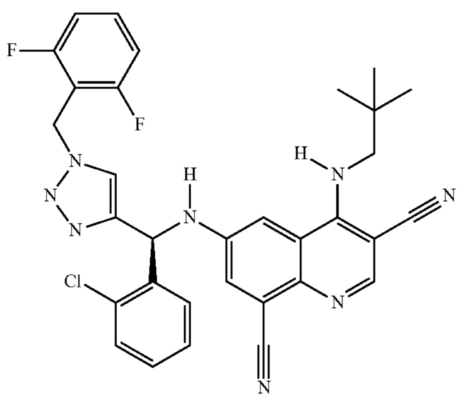 [SMILES: CC(C)(C)CNc1c(C#N)cnc2c(C#N)cc(N[C@H](C3=CN(Cc4c(F)cccc4F)NN3)c3ccccc3Cl)cc12] | (S)-6-(((2-chlorophenyl)(1-(2,6-difluorobenzyl)-1H-1,2,3-triazol-4-yl)methyl)amino)-4-(neopentylamino)quinoline-3,8-dicarbonitrile | 9 | 597.30 |

TABLE 1-continued
| Compd | Structure | Name | Example/Procedure | ES/MS m/z |
|---|---|---|---|---|
| 1054 | 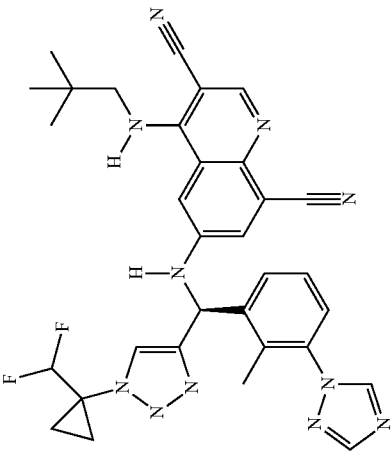 | (S)-6-(((1-(difluoromethyl)cyclopropyl)-1H-1,2,3-triazol-4-yl)(2-methyl-3-(1H-1,2,4-triazol-1-yl)phenyl)methyl)amino)-4-(neopentylamino)quinoline-3,8-dicarbonitrile | 48 | 608.1 |
| 1055 | 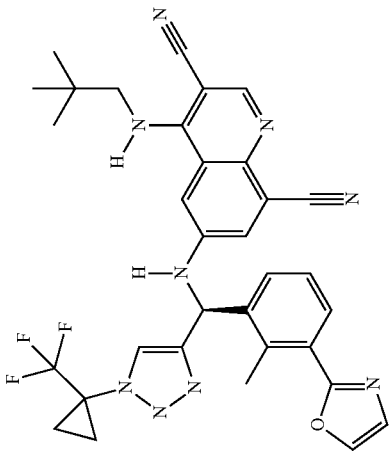 | (S)-6-(((2-methyl-3-(oxazol-2-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 626.2 |

TABLE 1-continued
| Compd | Structure | Name | Example/Procedure | ES/MS m/z |
|---|---|---|---|---|
| 1056 | 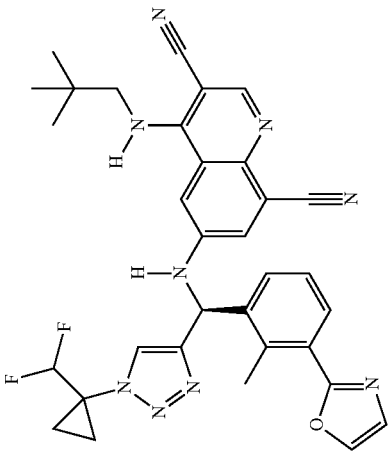 | (S)-6-(((1-(difluoromethyl)cyclopropyl)-1H-1,2,3-triazol-4-yl)(2-methyl-3-(oxazol-2-yl)phenyl)methyl)amino)-4-(neopentylamino)quinoline-3,8-dicarbonitrile | 48 | 608.2 |
| 1057 | 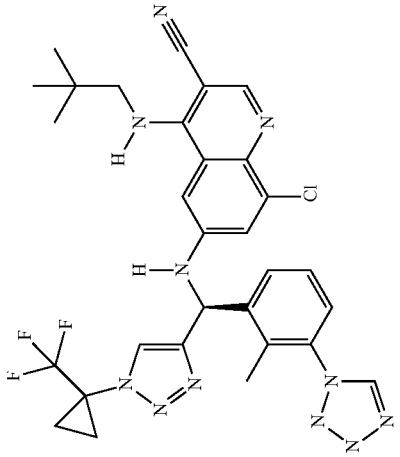 | (S)-8-chloro-6-(((2-methyl-3-(1H-tetrazol-1-yl)phenyl)(1-(1-(trifluoromethyl)cyclopropyl)-1H-1,2,3-triazol-4-yl)methyl)amino)-4-(neopentylamino)quinoline-3-carbonitrile | 4 | 636.2 |

TABLE 1-continued

| Compd | Structure | Name | Example/Procedure | ES/MS m/z |
|---|---|---|---|---|
| 1058 | 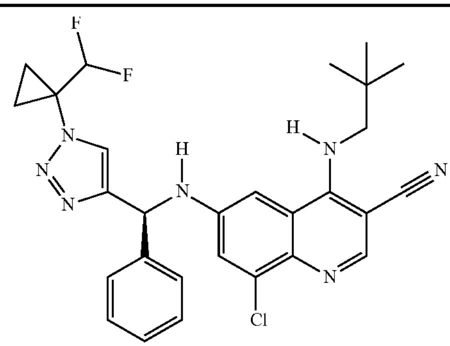 | (S)-8-chloro-6-(((1-(difluoromethyl)cyclopropyl)-1H-1,2,3-triazol-4-yl)(phenyl)methyl)amino)-4-(neopentylamino)quinoline-3-carbonitrile | 4 | 536.3 |
| 1059 | 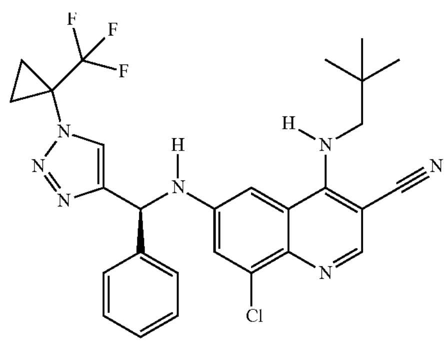 [SMILES: CC(C)(C)CNc1c(C#N)cnc2c(Cl)cc(N[C@@H](c3ccccc3)c3cn(C4(C(F)(F)F)CC4)nn3)cc12] | (S)-8-chloro-4-(neopentylamino)-6-(((phenyl(1-(1-(trifluoromethyl)cyclopropyl)-1H-1,2,3-triazol-4-yl)methyl)amino)quinoline-3-carbonitrile | 4 | 554.4 |
| 1060 | 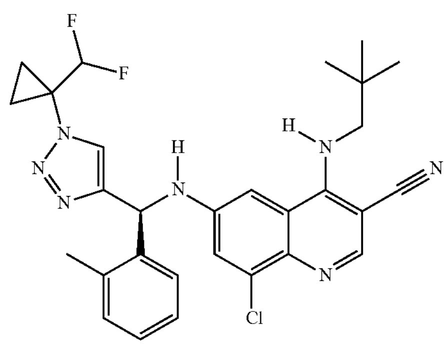 [SMILES: Cc1ccccc1[C@H](Nc1cc(Cl)c2ncc(C#N)c(NCC(C)(C)C)c2c1)c1cn(C2(C(F)F)CC2)nn1] | (S)-8-chloro-6-(((1-(difluoromethyl)cyclopropyl)-1H-1,2,3-triazol-4-yl)(o-tolyl)methyl)amino)-4-(neopentylamino)quinoline-3-carbonitrile | 4 | 550.3 |

TABLE 1-continued

| Compd | Structure | Name | Example/Procedure | ES/MS m/z |
|---|---|---|---|---|
| 1061 | 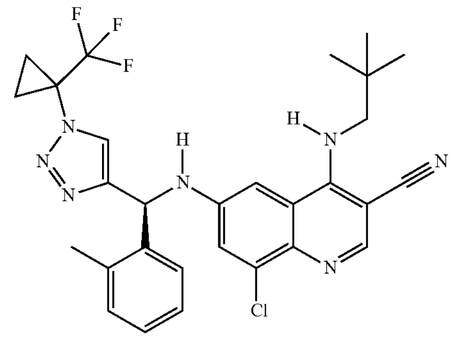 [SMILES: Cc1ccccc1[C@H](Nc1cc(Cl)c2ncc(C#N)c(NCC(C)(C)C)c2c1)c1cn(C2(C(F)(F)F)CC2)nn1] | (S)-8-chloro-4-(neopentylamino)-6-((o-tolyl(1-(1-(trifluoromethyl)cyclopropyl)-1H-1,2,3-triazol-4-yl)methyl)amino)quinoline-3-carbonitrile | 4 | 568.3 |
| 1062 | 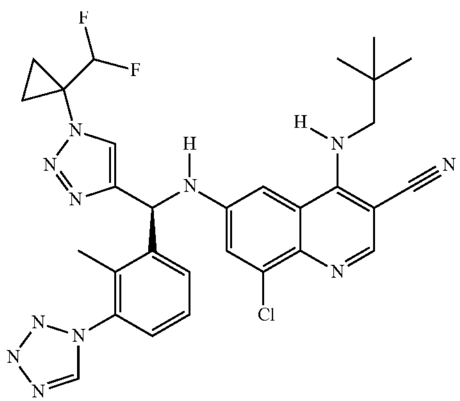 [SMILES: Cc1c([C@H](Nc2cc(Cl)c3ncc(C#N)c(NCC(C)(C)C)c3c2)c2cn(C3(C(F)F)CC3)nn2)cccc1N1C=NNN1] | (S)-8-chloro-6-(((1-(1-(difluoromethyl)cyclopropyl)-1H-1,2,3-triazol-4-yl)(2-methyl-3-(1H-tetrazol-1-yl)phenyl)methyl)amino)-4-(neopentylamino)quinoline-3-carbonitrile | 4 | 618.6 |

TABLE 1-continued
| Compd | Structure | Name | Example/Procedure | ES/MS m/z |
|---|---|---|---|---|
| 1063 | 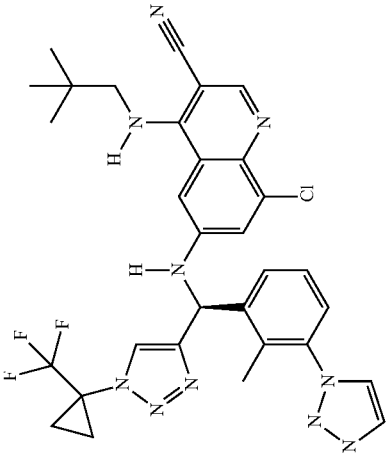 | (S)-8-chloro-6-(((2-methyl-3-(1H-1,2,3-triazol-1-yl)phenyl)(1-(1-(trifluoromethyl)cyclopropyl)-1H-1,2,3-triazol-4-yl)methyl)amino)-4-(neopentylamino)quinoline-3-carbonitrile | 4 | 635.4 |
| 1064 | 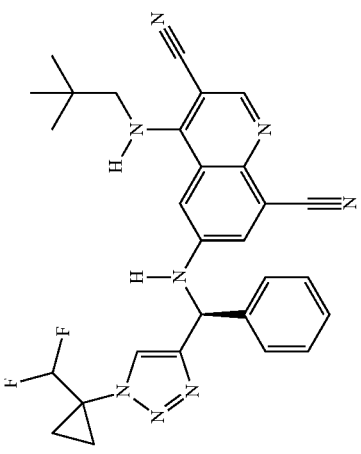 | (S)-6-(((1-(1-(difluoromethyl)cyclopropyl)-1H-1,2,3-triazol-4-yl)(phenyl)methyl)amino)-4-(neopentylamino)quinoline-3,8-dicarbonitrile | 48 | 527.3 |

TABLE 1-continued

| Compd | Structure | Name | Example/Procedure | ES/MS m/z |
|---|---|---|---|---|
| 1065 | 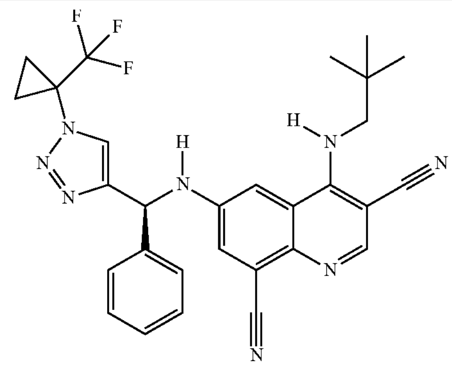 [SMILES: CC(C)(C)CNc1c(C#N)cnc2c(C#N)cc(N[C@@H](c3ccccc3)c3cn(C4(C(F)(F)F)CC4)nn3)cc12] | (S)-4-(neopentylamino)-6-((phenyl(1-(1-(trifluoromethyl)cyclopropyl)-1H-1,2,3-triazol-4-yl)methyl)amino)quinoline-3,8-dicarbonitrile | 48 | 545.3 |
| 1066 | 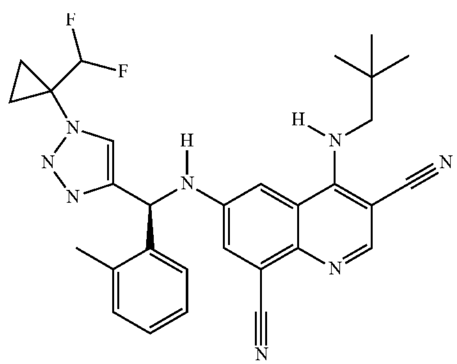 [SMILES: Cc1ccccc1[C@H](Nc1cc(C#N)c2ncc(C#N)c(NCC(C)(C)C)c2c1)C1=CN(C2(C(F)F)CC2)NN1] | (S)-6-(((1-(difluoromethyl)cyclopropyl)-1H-1,2,3-triazol-4-yl)(o-tolyl)methyl)(neopentylamino)quinoline-3,8-dicarbonitrile | 48 | 541.3 |

TABLE 1-continued
| Compd | Structure | Name | Example/Procedure | ES/MS m/z |
|---|---|---|---|---|
| 1067 | 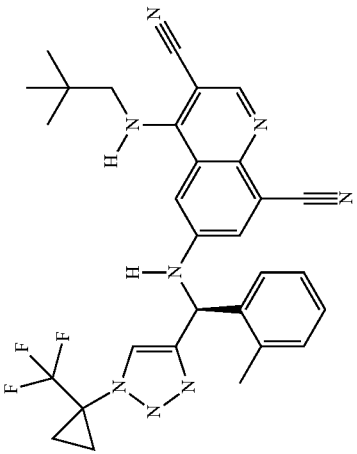 | (S)-4-(neopentylamino)-6-((o-tolyl((1-(1-(trifluoromethyl)cyclopropyl)-1H-1,2,3-triazol-4-yl)methyl)amino)quinoline-3,8-dicarbonitrile | 48 | 559.3 |
| 1068 | 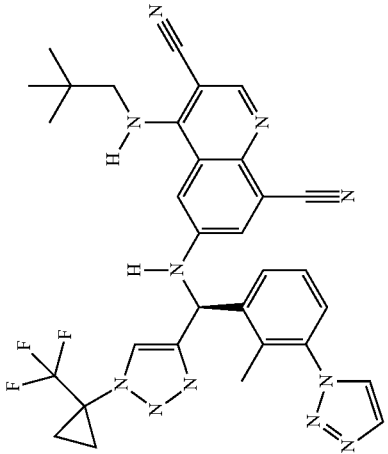 | (S)-6-(((2-methyl-3-(1H-1,2,3-triazol-1-yl)phenyl)((1-(1-(trifluoromethyl)cyclopropyl)-1H-1,2,3-triazol-4-yl)methyl)amino)-4-(neopentylamino)quinoline-3,8-dicarbonitrile | 48 | 626.5 |

TABLE 1-continued
| Compd | Structure | Name | Example/Procedure | ES/MS m/z |
|---|---|---|---|---|
| 1069 | 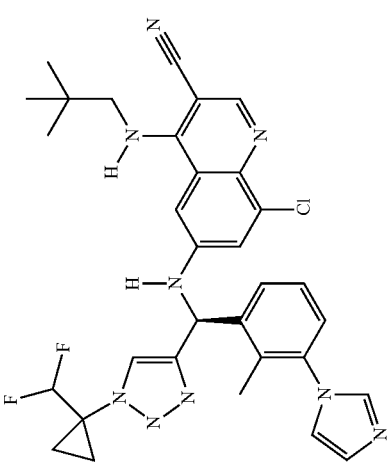 | (S)-6-(((3-(1H-imidazol-1-yl)-2-methylphenyl)(1-(1-(difluoromethyl)cyclopropyl)-1H-1,2,3-triazol-4-yl)methyl)amino)-8-chloro-4-(neopentylamino)quinoline-3-carbonitrile | 4 | 616.4 |
| 1070 | 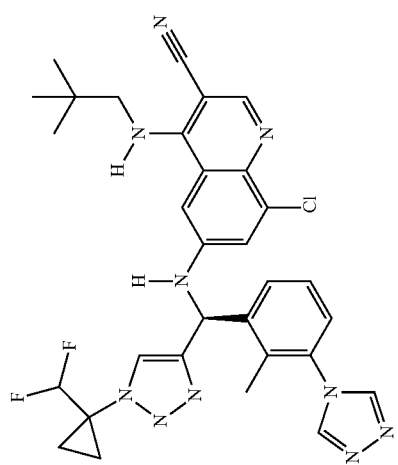 | (S)-8-chloro-6-(((1-(1-(difluoromethyl)cyclopropyl)-1H-1,2,3-triazol-4-yl)(2-methyl-3-(4H-1,2,4-triazol-4-yl)phenyl)methyl)amino)-4-(neopentylamino)quinoline-3-carbonitrile | 4 | 617.3 |

TABLE 1-continued
| Compd | Structure | Name | Example/Procedure | ES/MS m/z |
|---|---|---|---|---|
| 1071 | 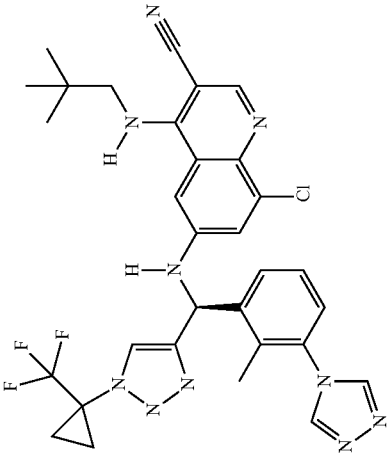 | (S)-8-chloro-6-(((2-methyl-3-(4H-1,2,4-triazol-4-yl)phenyl)(1-(1-(trifluoromethyl)cyclopropyl)-1H-1,2,3-triazol-4-yl)methyl)amino)-4-(neopentylamino)quinoline-3-carbonitrile | 4 | 635.7 |
| 1072 | 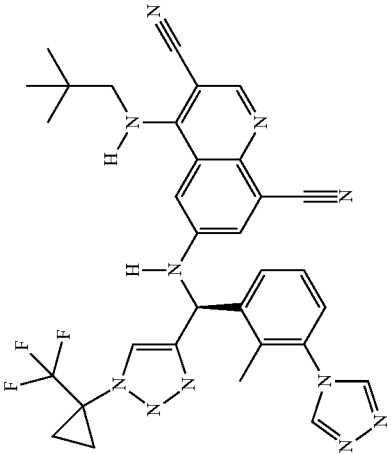 | (S)-6-(((2-methyl-3-(4H-1,2,4-triazol-4-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 626.5 |

TABLE 1-continued
| Compd | Structure | Name | Example/Procedure | ES/MS m/z |
|---|---|---|---|---|
| 1073 | 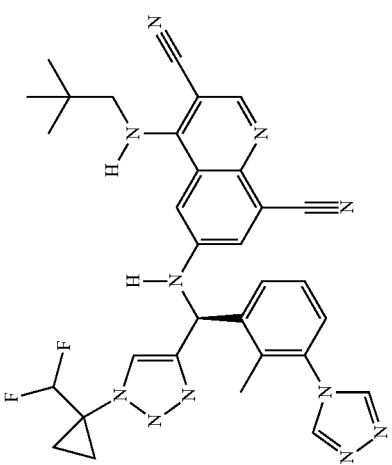 | (S)-6-(((1-(difluoromethyl)cyclopropyl)-1H-1,2,3-triazol-4-yl)(2-methyl-3-(4H-1,2,4-triazol-4-yl)phenyl)methyl)amino)-4-(neopentylamino)quinoline-3,8-dicarbonitrile | 48 | 608.3 |
| 1074 | 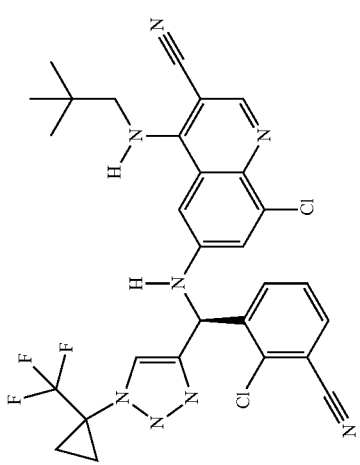 | (S)-8-chloro-6-(((2-chloro-3-cyanophenyl)(1-(1-(trifluoromethyl)cyclopropyl)-1H-1,2,3-triazol-4-yl)methyl)amino)-4-(neopentylamino)quinoline-3-carbonitrile | 4 | 614.2 |

TABLE 1-continued

| Compd | Structure | Name | Example/Procedure | ES/MS m/z |
|---|---|---|---|---|
| 1075 | 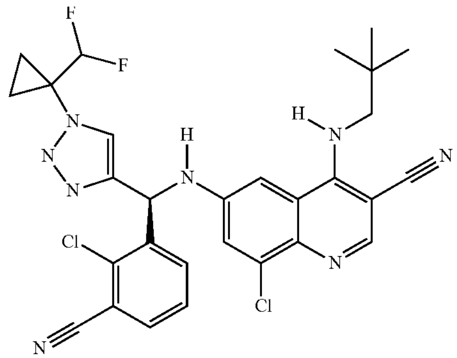 [SMILES: CC(C)(C)CNc1c(C#N)cnc2c(Cl)cc(N[C@H](C3=CN(C4(C(F)F)CC4)NN3)c3cccc(C#N)c3Cl)cc12] | (S)-8-chloro-6-(((2-chloro-3-cyanophenyl)(1-(1-(difluoromethyl)cyclopropyl)-1H-1,2,3-triazol-4-yl)methyl)amino)-4-(neopentylamino)quinoline-3-carbonitrile | 4 | 596.6 |
| 1076 | 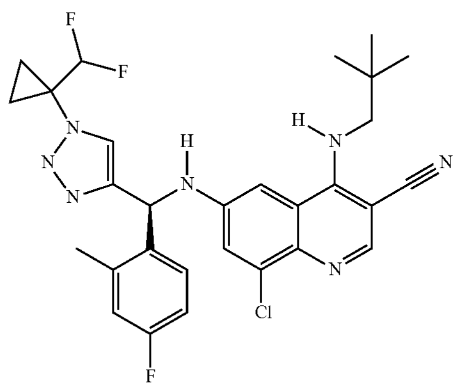 [SMILES: Cc1cc(F)ccc1[C@H](Nc1cc(Cl)c2ncc(C#N)c(NCC(C)(C)C)c2c1)C1=CN(C2(C(F)F)CC2)NN1] | (S)-8-chloro-6-(((1-(1-(difluoromethyl)cyclopropyl)-1H-1,2,3-triazol-4-yl)(4-fluoro-2-methylphenyl)methyl)amino)-4-(neopentylamino)quinoline-3-carbonitrile | 4 | 568.7 |

TABLE 1-continued
| Compd | Structure | Name | Example/Procedure | ES/MS m/z |
|---|---|---|---|---|
| 1077 | 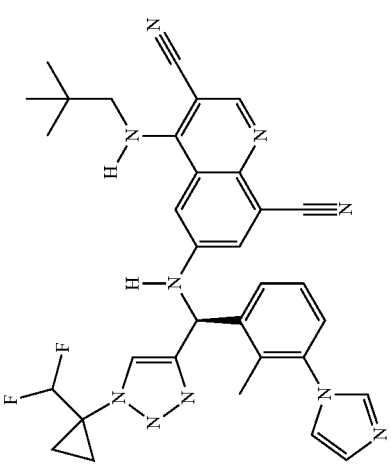 | (S)-6-(((3-(1H-imidazol-1-yl)-2-methylphenyl)(1-(1-(difluoromethyl)cyclopropyl)-1H-1,2,3-triazol-4-yl)methyl)amino)-4-(neopentylamino)quinoline-3,8-dicarbonitrile | 48 | 607.3 |
| 1078 | 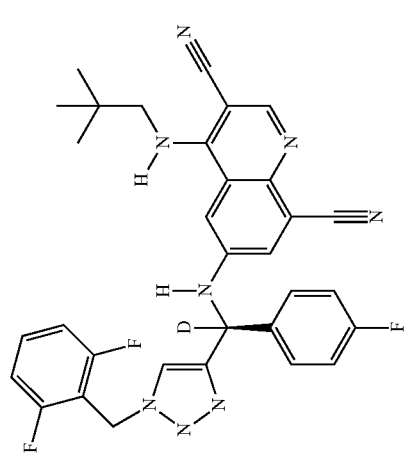 | (S)-6-(((1-(2,6-difluorobenzyl)-1H-1,2,3-triazol-4-yl)(4-fluorophenyl)methyl-d)amino)-4-(neopentylamino)quinoline-3,8-dicarbonitrile | 9 | 582.3 |

TABLE 1-continued

| Compd | Structure | Name | Example/Procedure | ES/MS m/z |
|---|---|---|---|---|
| 1079 | 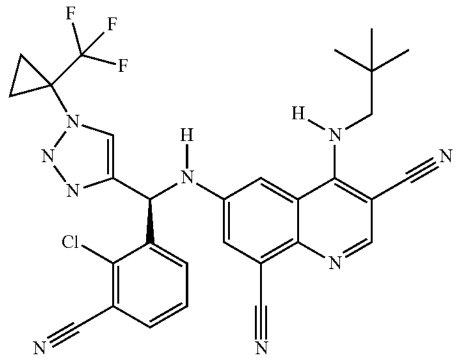 [SMILES: CC(C)(C)CNc1c(C#N)cnc2c(C#N)cc(N[C@H](C3=CN(C4(C(F)(F)F)CC4)NN3)c3cccc(C#N)c3Cl)cc12] | (S)-6-(((2-chloro-3-cyanophenyl)(1-(1-(trifluoromethyl)cyclopropyl)-1H-1,2,3-triazol-4-yl)methyl)amino)-4-(neopentylamino)quinoline-3,8-dicarbonitrile | 48 | 605.2 |
| 1080 | 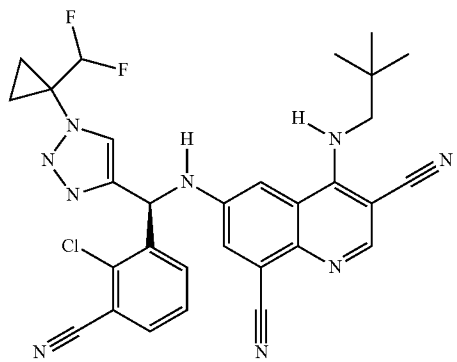 [SMILES: CC(C)(C)CNc1c(C#N)cnc2c(C#N)cc(N[C@H](C3=CN(C4(C(F)F)CC4)NN3)c3cccc(C#N)c3Cl)cc12] | (S)-6-(((2-chloro-3-cyanophenyl)(1-(1-(difluoromethyl)cyclopropyl)-1H-1,2,3-triazol-4-yl)methyl)amino)-4-(neopentylamino)quinoline-3,8-dicarbonitrile | 48 | 587.2 |

TABLE 1-continued
| Compd | Structure | Name | Example/Procedure | ES/MS m/z |
|---|---|---|---|---|
| 1081 | 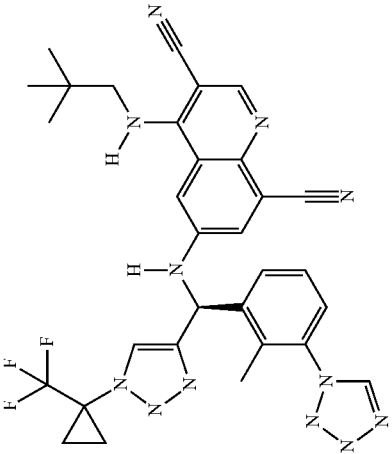 | (S)-6-(((2-methyl-3-(1H-tetrazol-1-yl)phenyl)(1-(1-(trifluoromethyl)cyclopropyl)-1H-1,2,3-triazol-4-yl)methyl)amino)-4-(neopentylamino)quinoline-3,8-dicarbonitrile | 57 | 627.1 |
| 1082 | 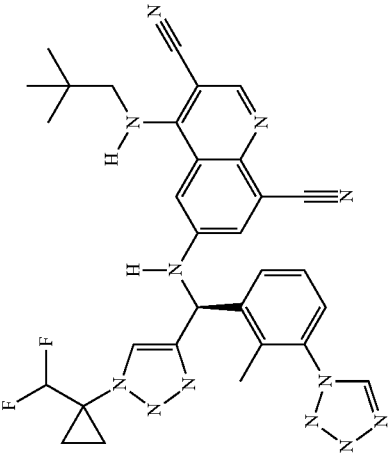 | (S)-6-(((1-(difluoromethyl)cyclopropyl)-1H-1,2,3-triazol-4-yl)(2-methyl-3-(1H-tetrazol-1-yl)phenyl)methyl)amino)-4-(neopentylamino)quinoline-3,8-dicarbonitrile | 57 | 609.3 |

| Compd | Structure | Name | Example/Procedure | ES/MS m/z |
|---|---|---|---|---|
| 1083 | 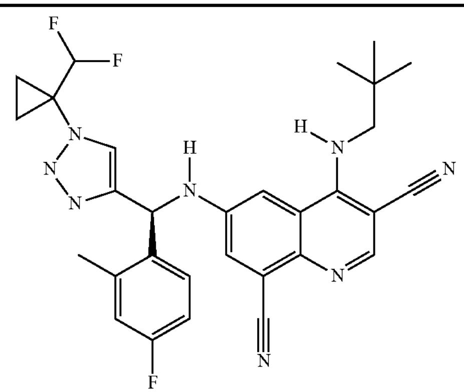 | (S)-6-(((1-(difluoromethyl)cyclopropyl)-1H-1,2,3-triazol-4-yl)(4-fluoro-2-methylphenyl)methyl)amino)-4-(neopentylamino)quinoline-3,8-dicarbonitrile | 48 | 559.3 |
| 1084 | 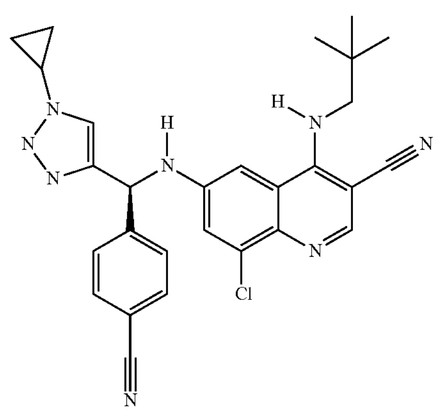 [SMILES: CC(C)(C)CNc1c(C#N)cnc2c(Cl)cc(N[C@H](C3=CN(C4CC4)NN3)c3ccc(C#N)cc3)cc12] | (S)-8-chloro-6-(((4-cyanophenyl)(1-cyclopropyl-1H-1,2,3-triazol-4-yl)methyl)amino)-4-(neopentylamino)quinoline-3-carbonitrile | 3 | 511.3 |

TABLE 1-continued

| Compd | Structure | Name | Example/Procedure | ES/MS m/z |
|---|---|---|---|---|
| 1085 | 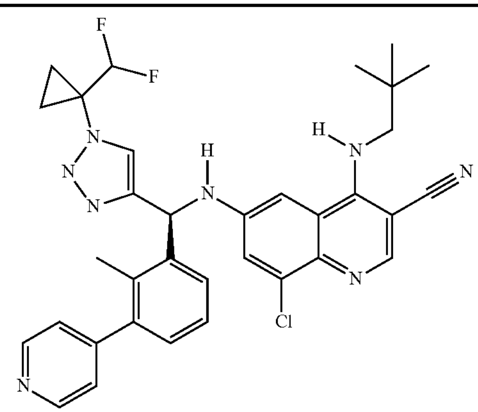 | (S)-8-chloro-6-(((1-(difluoromethyl)cyclopropyl)-1H-1,2,3-triazol-4-yl)(2-methyl-3-(pyridin-4-yl)phenyl)methyl)amino)-4-(neopentylamino)quinoline-3-carbonitrile | 3 | 626 |
| 1086 | 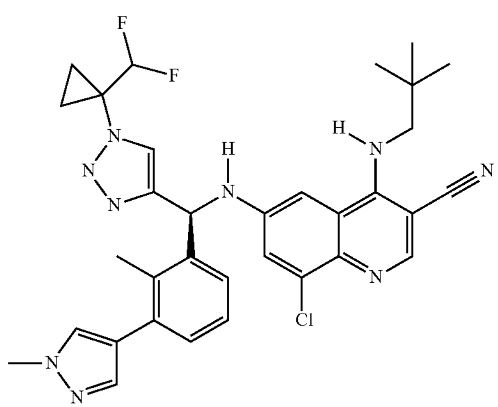 [SMILES: Cc1c(-c2cnn(C)c2)cccc1[C@H](Nc1cc(Cl)c2ncc(C#N)c(NCC(C)(C)C)c2c1)C1=CN(C2(C(F)F)CC2)NN1] | (S)-8-chloro-6-(((1-(difluoromethyl)cyclopropyl)-1H-1,2,3-triazol-4-yl)(2-methyl-3-(1-methyl-1H-pyrazol-4-yl)phenyl)methyl)amino)-4-(neopentylamino)quinoline-3-carbonitrile | 3 | 629.10 |

TABLE 1-continued
| Compd | Structure | Name | Example/Procedure | ES/MS m/z |
|---|---|---|---|---|
| 1087 | 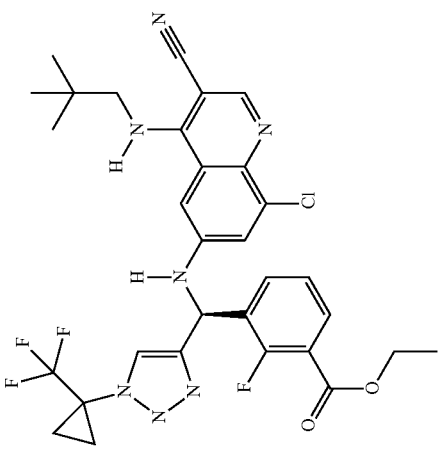 | ethyl (S)-3-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluorobenzoate | 3 | 644.13 |
| 1088 | 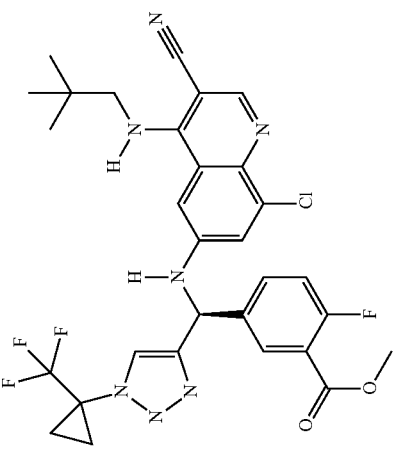 | methyl (S)-5-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluorobenzoate | 3 | 630.05 |

TABLE 1-continued
| Compd | Structure | Name | Example/Procedure | ES/MS m/z |
|---|---|---|---|---|
| 1089 | 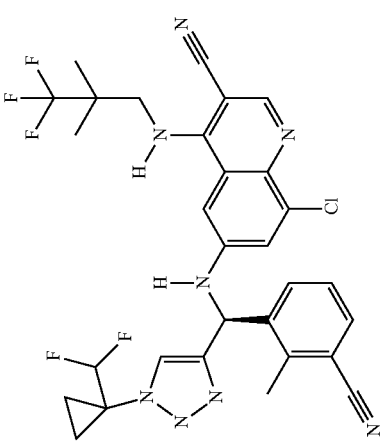 | (S)-8-chloro-6-(((3-cyano-2-methylphenyl)(1-(1-(difluoromethyl)cyclopropyl)-1H-1,2,3-triazol-4-yl)methyl)amino)-4-((3,3,3-trifluoro-2,2-dimethylpropyl)amino)quinoline-3-carbonitrile | 4 | 629.4 (M + H⁺) |
| 1090 | 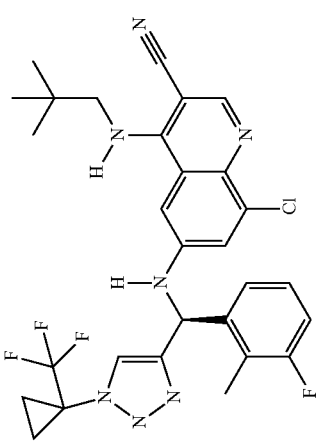 | (S)-8-chloro-6-(((3-fluoro-2-methylphenyl)(1-(1-(trifluoromethyl)cyclopropyl)-1H-1,2,3-triazol-4-yl)methyl)amino)-4-(neopentylamino)quinoline-3-carbonitrile | 4 | 535.4 (M + H⁺) |

TABLE 1-continued

| Compd | Structure | Name | Example/Procedure | ES/MS m/z |
|---|---|---|---|---|
| 1091 | 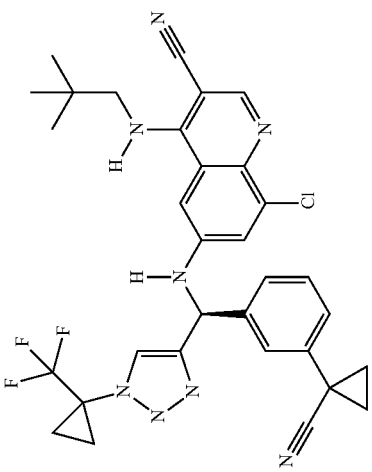 | (S)-8-chloro-6-(((3-(1-cyanocyclopropyl)phenyl)(1-(1-(trifluoromethyl)cyclopropyl)-1H-1,2,3-triazol-4-yl)methyl)amino)-4-(neopentylamino)quinoline-3-carbonitrile | 4 | 619.40 |
| 1092 | 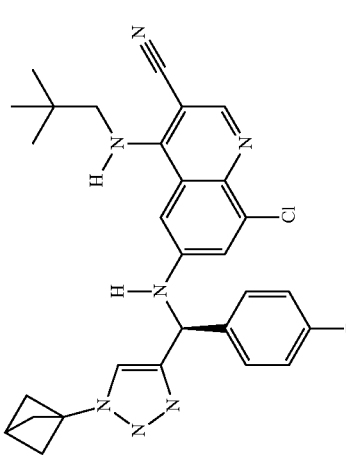 | (S)-6-((((1-(bicyclo[1.1.1]pentan-1-yl)-1H-1,2,3-triazol-4-yl)(4-fluorophenyl)methyl)amino)-8-(neopentylamino)quinoline-3-carbonitrile | 4 | 530.20 |
| 1093 | 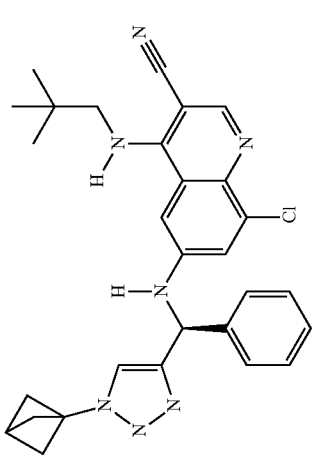 | (S)-6-((((1-(bicyclo[1.1.1]pentan-1-yl)-1H-1,2,3-triazol-4-yl)(phenyl)methyl)amino)-8-chloro-4-(neopentylamino)quinoline-3-carbonitrile | 4 | 512.30 |

TABLE 1-continued

| Compd | Structure | Name | Example/Procedure | ES/MS m/z |
|---|---|---|---|---|
| 1094 | 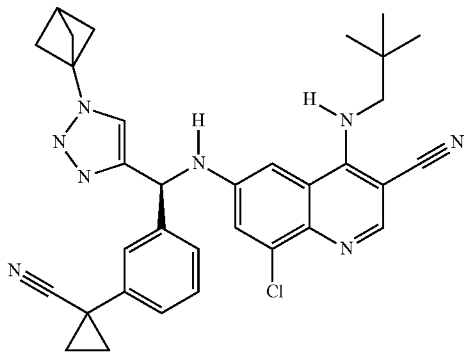 [SMILES: CC(C)(C)CNc1c(C#N)cnc2c(Cl)cc(N[C@H](C3=CN(C45CC(C4)C5)NN3)c3cccc(C4(C#N)CC4)c3)cc12] | (S)-6-(((1-(bicyclo[1.1.1]pentan-1-yl)-1H-1,2,3-triazol-4-yl)(3-(1-cyanocyclopropyl)phenyl)methyl)amino)-8-chloro-4-(neopentylamino)quinoline-3-carbonitrile | 4 | 577.30 |
| 1095 | 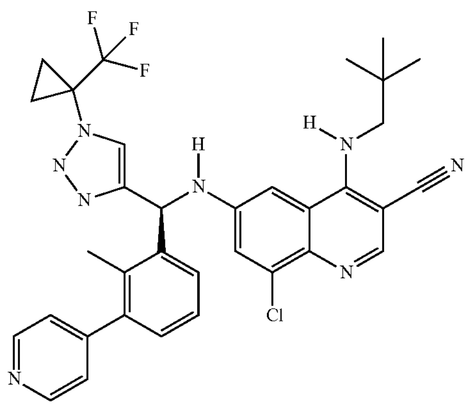 [SMILES: Cc1c(-c2ccncc2)cccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-methyl-3-(pyridin-4-yl)phenyl)(1-(1-(trifluoromethyl)cyclopropyl)-1H-1,2,3-triazol-4-yl)methyl)amino)-4-(neopentylamino)quinoline-3-carbonitrile | 4 | 645.20 |

TABLE 1-continued

| Compd | Structure | Name | Example/Procedure | ES/MS m/z |
|---|---|---|---|---|
| 1096 | 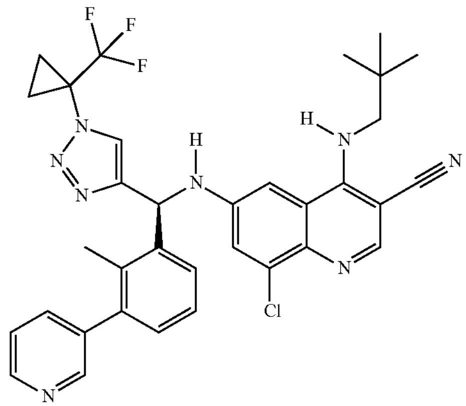 [SMILES: Cc1c(-c2cccnc2)cccc1[C@H](Nc1cc(Cl)c2ncc(C#N)c(NCC(C)(C)C)c2c1)c1cn(C2(C(F)(F)F)CC2)nn1] | (S)-8-chloro-6-(((2-methyl-3-(pyridin-3-yl)phenyl)(1-(1-(trifluoromethyl)cyclopropyl)-1H-1,2,3-triazol-4-yl)methyl)amino)-4-(neopentylamino)quinoline-3-carbonitrile | 4 | 645.20 |
| 1097 | 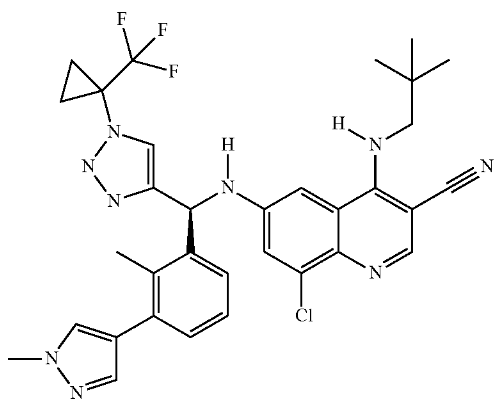 [SMILES: Cc1c(-c2cnn(C)c2)cccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-methyl-3-(1-methyl-1H-pyrazol-4-yl)phenyl)(1-(1-(trifluoromethyl)cyclopropyl)-1H-1,2,3-triazol-4-yl)methyl)amino)-4-(neopentylamino)quinoline-3-carbonitrile | 4 | 648.30 |

TABLE 1-continued
| Compd | Structure | Name | Example/Procedure | ES/MS m/z |
|---|---|---|---|---|
| 1098 | 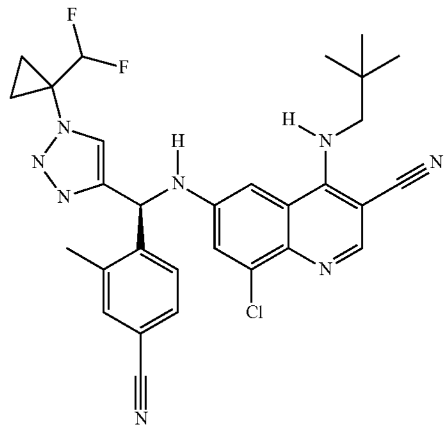 [SMILES: Cc1cc(C#N)ccc1[C@H](Nc1cc(Cl)c2ncc(C#N)c(NCC(C)(C)C)c2c1)C1=CN(C2(C(F)F)CC2)NN1] | (S)-8-chloro-6-(((4-cyano-2-methylphenyl)(1-(1-(difluoromethyl)cyclopropyl)-1H-1,2,3-triazol-4-yl)methyl)amino)-4-(neopentylamino)quinoline-3-carbonitrile | 4 | 575.40 |
| 1099 | 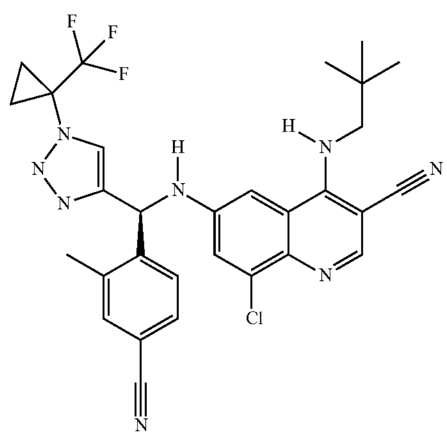 [SMILES: Cc1cc(C#N)ccc1[C@H](Nc1cc(Cl)c2ncc(C#N)c(NCC(C)(C)C)c2c1)C1=CN(C2(C(F)(F)F)CC2)NN1] | (S)-8-chloro-6-(((4-cyano-2-methylphenyl)(1-(1-(trifluoromethyl)cyclopropyl)-1H-1,2,3-triazol-4-yl)methyl)amino)-4-(neopentylamino)quinoline-3-carbonitrile | 4 | 593.30 |

TABLE 1-continued

| Compd | Structure | Name | Example/Procedure | ES/MS m/z |
|---|---|---|---|---|
| 1100 | 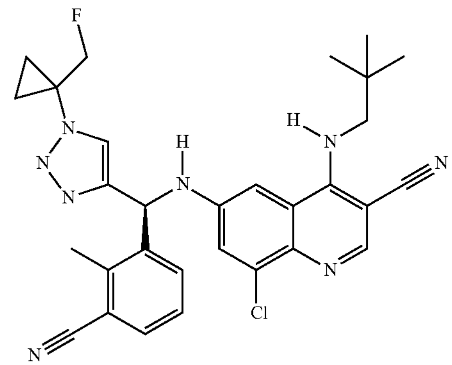 [SMILES: Cc1c(C#N)cccc1[C@H](Nc1cc(Cl)c2ncc(C#N)c(NCC(C)(C)C)c2c1)C1=CN(C2(CF)CC2)NN1] | (S)-8-chloro-6-(((3-cyano-2-methylphenyl)(1-(1-(fluoromethyl)cyclopropyl)-1H-1,2,3-triazol-4-yl)methyl)amino)-4-(neopentylamino)quinoline-3-carbonitrile | 4 | 557.30 |
| 1101 | 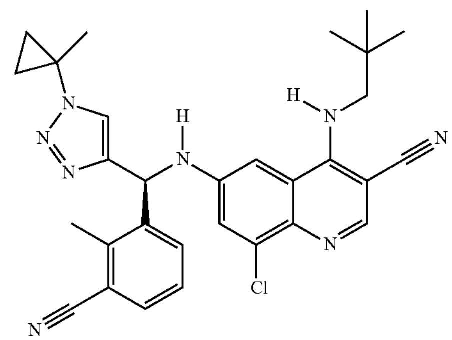 [SMILES: Cc1c(C#N)cccc1[C@H](Nc1cc(Cl)c2ncc(C#N)c(NCC(C)(C)C)c2c1)c1cn(C2(C)CC2)nn1] | (S)-8-chloro-6-(((3-cyano-2-methylphenyl)(1-(1-methylcyclopropyl)-1H-1,2,3-triazol-4-yl)methyl)amino)-4-(neopentylamino)quinoline-3-carbonitrile | 4 | 539.30 |
| 1102 | 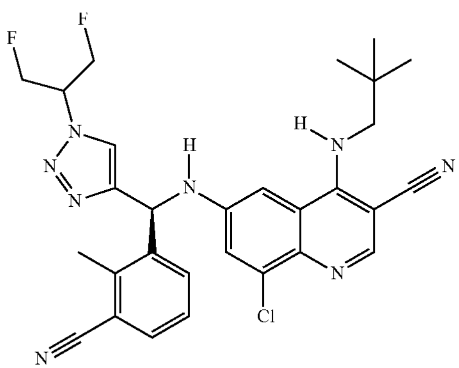 [SMILES: Cc1c(C#N)cccc1[C@H](Nc1cc(Cl)c2ncc(C#N)c(NCC(C)(C)C)c2c1)c1cn(C(CF)CF)nn1] | (S)-8-chloro-6-(((3-cyano-2-methylphenyl)(1-(1,3-difluoropropan-2-yl)-1H-1,2,3-triazol-4-yl)methyl)amino)-4-(neopentylamino)quinoline-3-carbonitrile | 4 | 563.20 |

TABLE 1-continued

| Compd | Structure | Name | Example/Procedure | ES/MS m/z |
|---|---|---|---|---|
| 1103 | 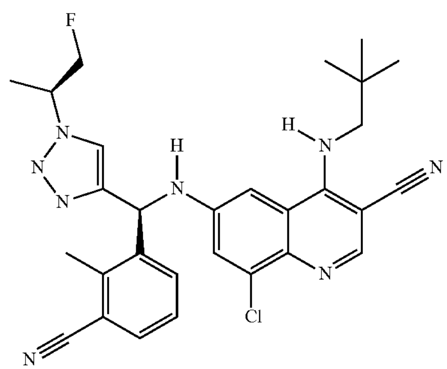 [SMILES: Cc1c(C#N)cccc1[C@H](Nc1cc(Cl)c2ncc(C#N)c(NCC(C)(C)C)c2c1)C1=CN([C@@H](C)CF)NN1] | 8-chloro-6-(((S)-(3-cyano-2-methylphenyl)(1-((S)-1-fluoropropan-2-yl)-1H-1,2,3-triazol-4-yl)methyl)amino)-4-(neopentylamino)quinoline-3-carbonitrile | 4 | 545.30 |
| 1104 | 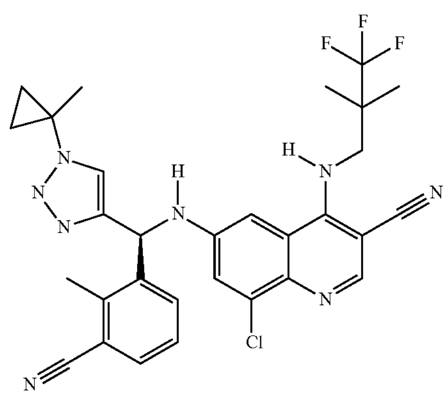 [SMILES: Cc1c(C#N)cccc1[C@H](Nc1cc(Cl)c2ncc(C#N)c(NCC(C)(C)C(F)(F)F)c2c1)C1=CN(C2(C)CC2)NN1] | (S)-8-chloro-6-(((3-cyano-2-methylphenyl)(1-(1-methylcyclopropyl)-1H-1,2,3-triazol-4-yl)methyl)amino)-4-((3,3,3-trifluoro-2,2-dimethylpropyl)amino)quinoline-3-carbonitrile | 4 | 593.30 |

TABLE 1-continued
| Compd | Structure | Name | Example/Procedure | ES/MS m/z |
|---|---|---|---|---|
| 1105 | 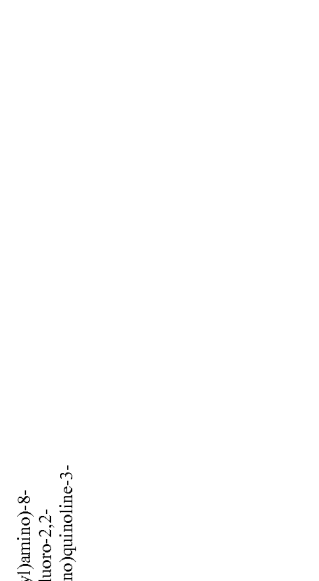 | (S)-6-(((1-(([1,1'-bi(cyclopropan)]-1-yl)-1H-1,2,3-triazol-4-yl)(3-cyano-2-methylphenyl)methyl)amino)-8-chloro-4-((3,3,3-trifluoro-2,2-dimethylpropyl)amino)quinoline-3-carbonitrile | 4 | 619.40 |
| 1106 | 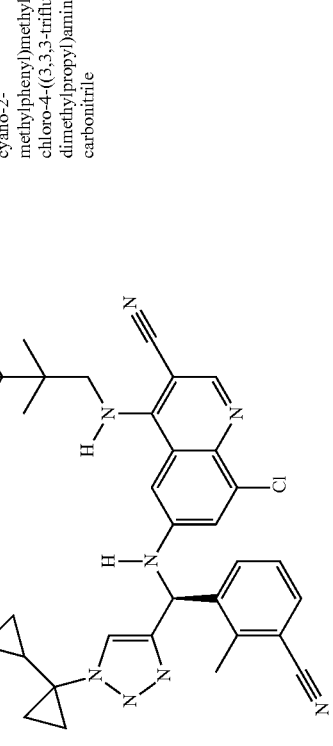 | 8-chloro-6-(((S)-(3-cyano-2-methylphenyl)(1-((S)-1-fluoropropan-2-yl)-1H-1,2,3-triazol-4-yl)methyl)amino)-4-((3,3,3-trifluoro-2,2-dimethylpropyl)amino)quinoline-3-carbonitrile | 4 | 599.30 |

TABLE 1-continued
| Compd | Structure | Name | Example/Procedure | ES/MS m/z |
|---|---|---|---|---|
| 1107 | 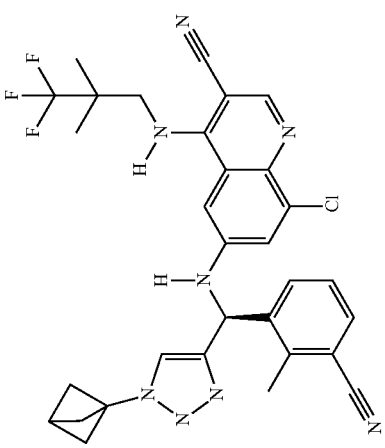 | (S)-6-((((1-(bicyclo[1.1.1]pentan-1-yl)-1H-1,2,3-triazol-4-yl)(3-cyano-2-methylphenyl)methyl)amino)-8-chloro-4-((3,3,3-trifluoro-2,2-dimethylpropyl)amino)quinoline-3-carbonitrile | 4 | 605.30 |
| 1108 | 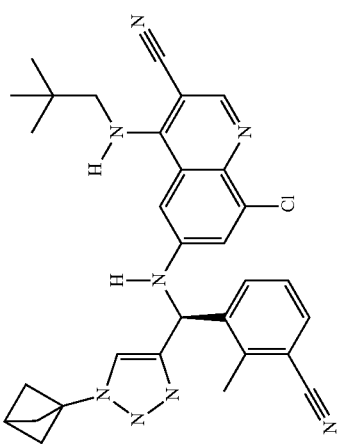 | (S)-6-((((1-(bicyclo[1.1.1]pentan-1-yl)-1H-1,2,3-triazol-4-yl)(3-cyano-2-methylphenyl)methyl)amino)-8-chloro-4-(neopentylamino)quinoline-3-carbonitrile | 4 | 551.40 |

TABLE 1-continued

| Compd | Structure | Name | Example/Procedure | ES/MS m/z |
|---|---|---|---|---|
| 1109 | 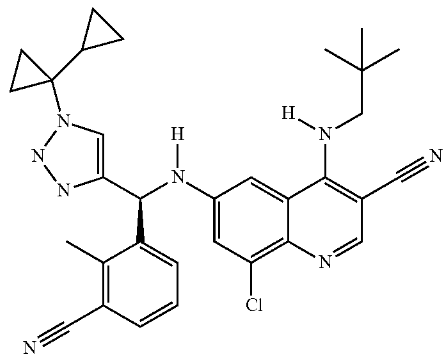 [SMILES: Cc1c(C#N)cccc1[C@H](Nc1cc(Cl)c2ncc(C#N)c(NCC(C)(C)C)c2c1)C1=CN(C2(C3CC3)CC2)NN1] | (S)-6-(((1-([1,1'-bi(cyclopropan)]-cyano-2-methylphenyl)methyl)amino)-8-chloro-4-(neopentylamino)quinoline-3-carbonitrile | 4 | 565.40 |
| 1110 | 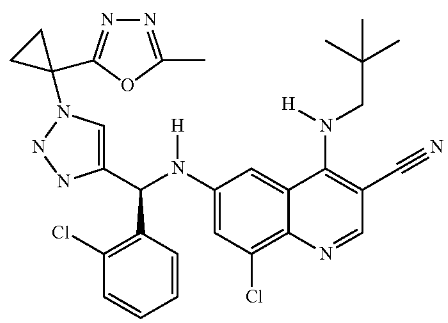 [SMILES: Cc1nnc(C2(N3C=C([C@@H](Nc4cc(Cl)c5ncc(C#N)c(NCC(C)(C)C)c5c4)c4ccccc4Cl)NN3)CC2)o1] | (S)-8-chloro-6-(((2-chlorophenyl)(1-(1-(5-methyl-1,3,4-oxadiazol-2-yl)cyclopropyl)-1H-1,2,3-triazol-4-yl)methyl)amino)-4-(neopentylamino)quinoline-3-carbonitrile | 4 | 602.3 (M + H) |
| 1111 | 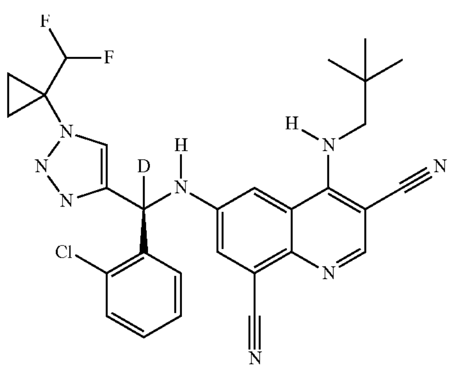 [SMILES: [2H][C@](Nc1cc(C#N)c2ncc(C#N)c(NCC(C)(C)C)c2c1)(C1=CN(C2(C(F)F)CC2)NN1)c1ccccc1Cl] | 6-(((2-chlorophenyl)(1-(1-(difluoromethyl)cyclopropyl)-1H-1,2,3-triazol-4-yl)methyl-d)amino)-4-(neopentylamino)quinoline-3,8-dicarbonitrile | 9 | 562.30 |

TABLE 1-continued

| Compd | Structure | Name | Example/Procedure | ES/MS m/z |
|---|---|---|---|---|
| 1112 | 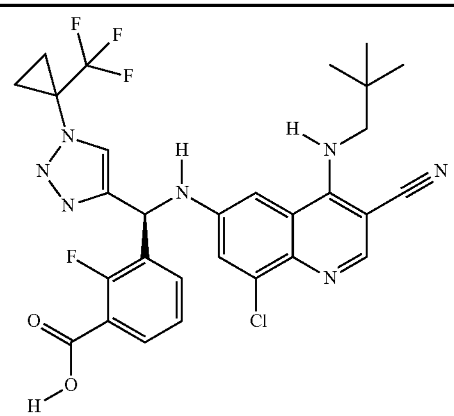 | (S)-3-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluorobenzoic acid | 19 | 616.16 |
| 1113 | 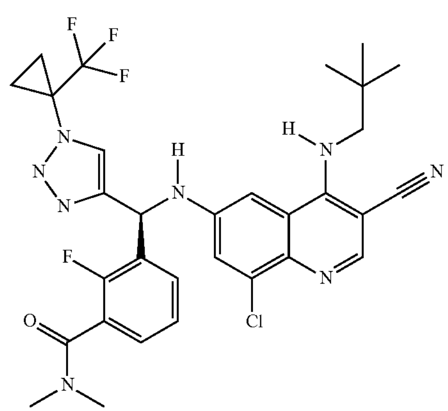 [SMILES: CN(C)C(=O)c1cccc([C@H](Nc2cc(Cl)c3ncc(C#N)c(NCC(C)(C)C)c3c2)C2=CN(C3(C(F)(F)F)CC3)NN2)c1F] | (S)-3-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluoro-N,N-dimethylbenzamide | 20 | 643.23 |

TABLE 1-continued

| Compd | Structure | Name | Example/Procedure | ES/MS m/z |
|---|---|---|---|---|
| 1114 | 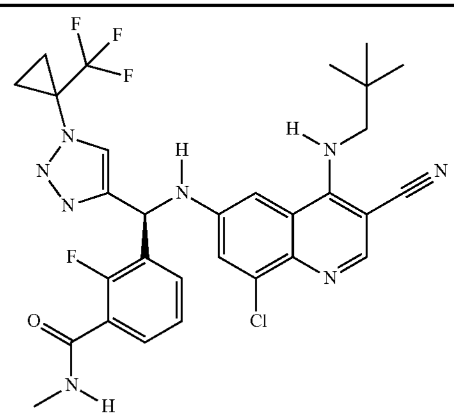 | (S)-3-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluoro-N-methylbenzamide | 20 | 629.26 |
| 1115 | 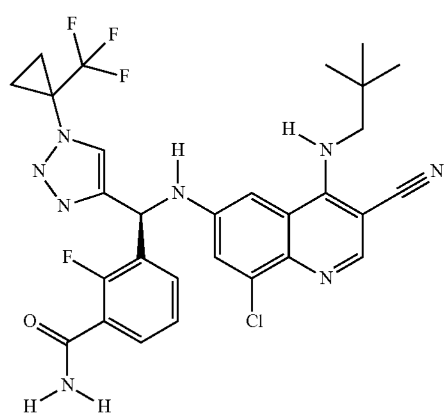 [SMILES: CC(C)(C)CNc1c(C#N)cnc2c(Cl)cc(N[C@H](C3=CN(C4(C(F)(F)F)CC4)NN3)c3cccc(C(N)=O)c3F)cc12] | (S)-3-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluorobenzamide | 20 | 615.34 |

TABLE 1-continued

| Compd | Structure | Name | Example/Procedure | ES/MS m/z |
|---|---|---|---|---|
| 1116 | 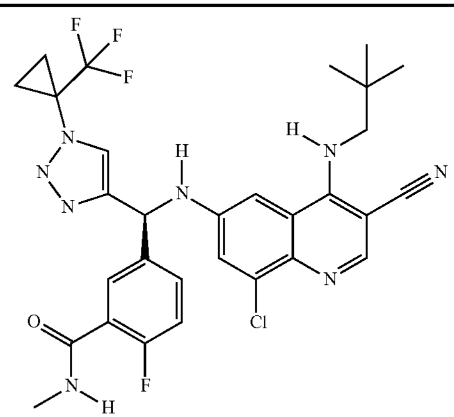 | (S)-5-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluoro-N-methylbenzamide | 20 | 629.19 |
| 1117 | 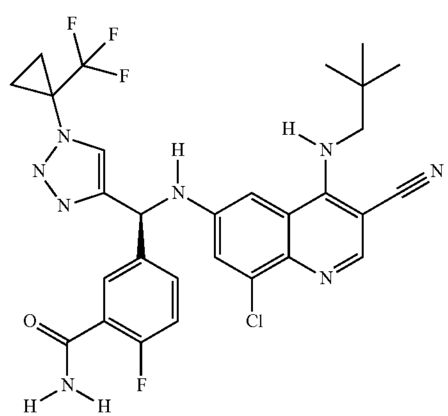 [SMILES: CC(C)(C)CNc1c(C#N)cnc2c(Cl)cc(N[C@H](C3=CN(C4(C(F)(F)F)CC4)NN3)c3ccc(F)c(C(N)=O)c3)cc12] | (S)-5-(((8-chloro-3-cyano-4-(neopentylamino)quinolin-6-yl)amino)(1-(1-(trifluoromethyl)cyclopropyl)-1H-1,2,3-triazol-4-yl)methyl)-2-fluorobenzamide | 20 | 615.22 |

TABLE 1-continued

| Compd | Structure | Name | Example/Procedure | ES/MS m/z |
|---|---|---|---|---|
| 1118 | 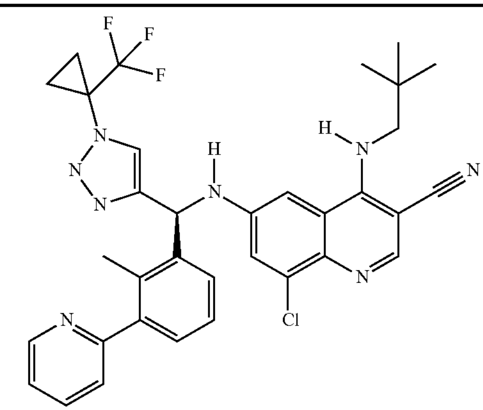 | (S)-8-chloro-6-(((2-methyl-3-(pyridin-2-yl)phenyl)(1-(1-(trifluoromethyl)cyclopropyl)-1H-1,2,3-triazol-4-yl)methyl)amino)-4-(neopentylamino)quinoline-3-carbonitrile | 23 | 645.10 |
| 1119 | 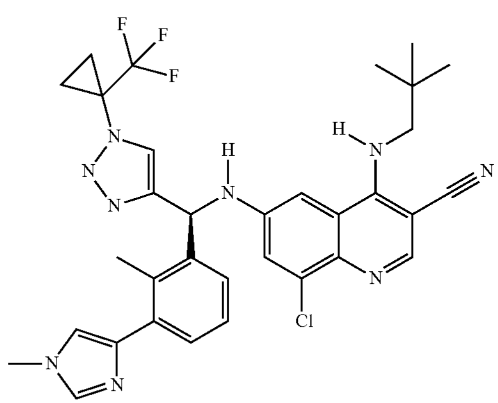 [SMILES: Cc1c(-c2cn(C)cn2)cccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-methyl-3-(1-methyl-1H-imidazol-4-yl)phenyl)(1-(1-(trifluoromethyl)cyclopropyl)-1H-1,2,3-triazol-4-yl)methyl)amino)-4-(neopentylamino)quinoline-3-carbonitrile | 23 | 647.90 |

TABLE 1-continued

| Compd | Structure | Name | Example/Procedure | ES/MS m/z |
|---|---|---|---|---|
| 1120 | 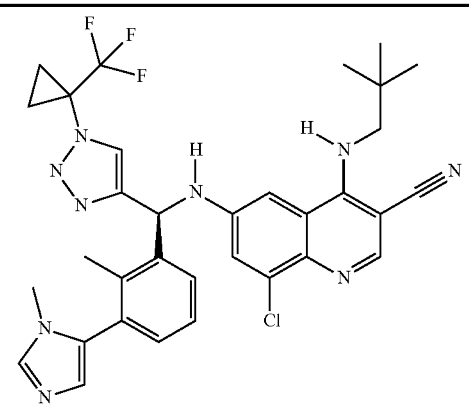 | (S)-8-chloro-6-(((2-methyl-3-(1-methyl-1H-imidazol-5-yl)phenyl)(1-(1-(trifluoromethyl)cyclopropyl)-1H-1,2,3-triazol-4-yl)methyl)amino)-4-(neopentylamino)quinoline-3-carbonitrile | 23 | 648.30 |
| 1121 | 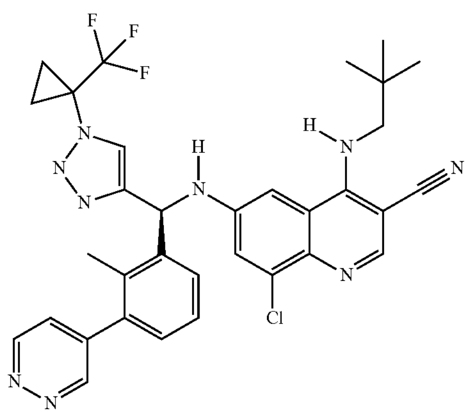 [SMILES: Cc1c(-c2ccnnc2)cccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-methyl-3-(pyridazin-4-yl)phenyl)(1-(1-(trifluoromethyl)cyclopropyl)-1H-1,2,3-triazol-4-yl)methyl)amino)-4-(neopentylamino)quinoline-3-carbonitrile | 23 | 646.30 |

TABLE 1-continued
| Compd | Structure | Name | Example/Procedure | ES/MS m/z |
|---|---|---|---|---|
| 1122 | 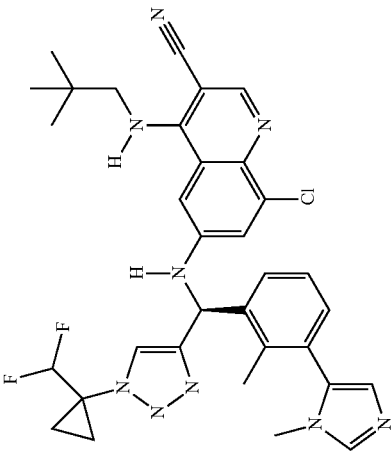 | (S)-8-chloro-6-(((1-(1-(difluoromethyl)cyclopropyl)-1H-1,2,3-triazol-4-yl)(2-methyl-3-(1-methyl-1H-imidazol-5-yl)phenyl)methyl)amino)-4-(neopentylamino)quinoline-3-carbonitrile | 23 | 630.30 |
| 1123 | 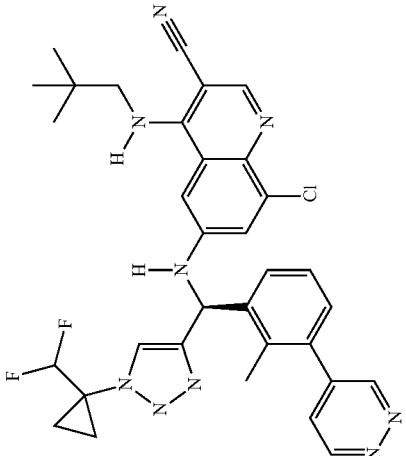 | (S)-8-chloro-6-(((1-(1-(difluoromethyl)cyclopropyl)-1H-1,2,3-triazol-4-yl)(2-methyl-3-(pyridazin-4-yl)phenyl)methyl)amino)-4-(neopentylamino)quinoline-3-carbonitrile | 23 | 628.30 |

TABLE 1-continued

| Compd | Structure | Name | Example/Procedure | ES/MS m/z |
|---|---|---|---|---|
| 1124 | 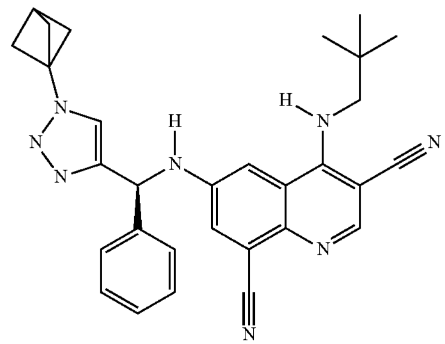 [SMILES: CC(C)(C)CNc1c(C#N)cnc2c(C#N)cc(N[C@H](C3=CN(C45CC(C4)C5)NN3)c3ccccc3)cc12] | (S)-6-((((1-(bicyclo[1.1.1]pentan-1-yl)-1H-1,2,3-triazol-4-yl)(phenyl)methyl)amino)-4-(neopentylamino)quinoline-3,8-dicarbonitrile | 24 | 503.40 |
| 1125 | 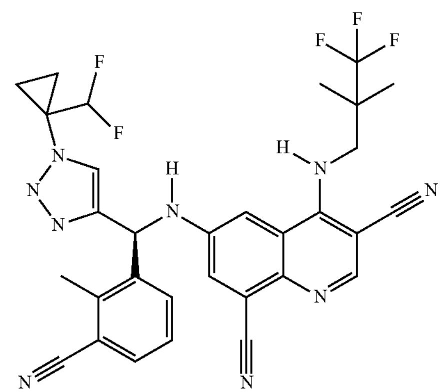 [SMILES: Cc1c(C#N)cccc1[C@H](Nc1cc(C#N)c2ncc(C#N)c(NCC(C)(C)C(F)(F)F)c2c1)C1=CN(C2(C(F)F)CC2)NN1] | (S)-6-(((3-cyano-2-methylphenyl)(1-(1-(difluoromethyl)cyclopropyl)-1H-1,2,3-triazol-4-yl)methyl)amino)-4-((3,3,3-trifluoro-2,2-dimethylpropyl)amino)quinoline-3,8-dicarbonitrile | 48 | 620.2 (M + H⁺) |

TABLE 1-continued
| Compd | Structure | Name | Example/Procedure | ES/MS m/z |
|---|---|---|---|---|
| 1126 | 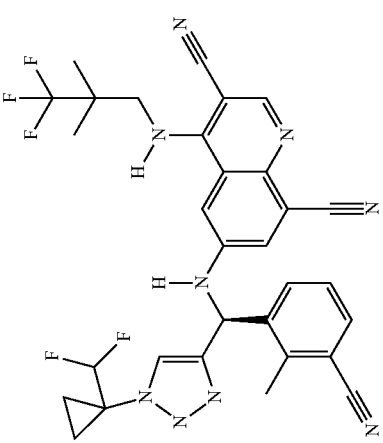 | (S)-6-(((3-cyano-2-methylphenyl)(1-(1-(difluoromethyl)cyclopropyl)-1H-1,2,3-triazol-4-yl)methyl)amino)-4-((3,3,3-trifluoro-2,2-dimethylpropyl)amino)quinoline-3,8-dicarbonitrile | 48 | 620.15 (M + H⁺) |
| 1127 | 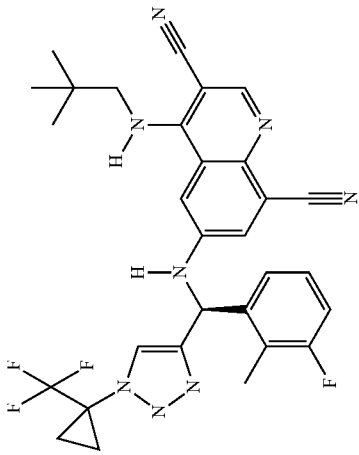 | (S)-6-(((3-fluoro-2-methylphenyl)(1-(1-(trifluoromethyl)cyclopropyl)-1H-1,2,3-triazol-4-yl)methyl)amino)-4-(neopentylamino)quinoline-3,8-dicarbonitrile | 48 | 576.49 (M + H⁺) |

TABLE 1-continued
| Compd | Structure | Name | Example/Procedure | ES/MS m/z |
|---|---|---|---|---|
| 1128 | 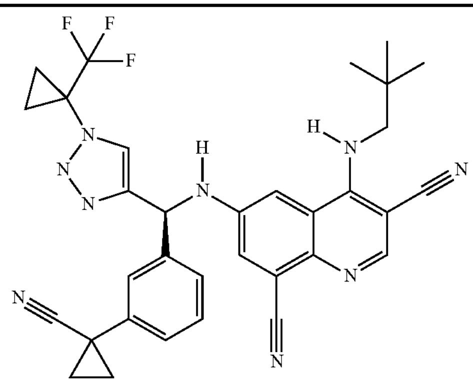 | (S)-6-(((3-(1-cyanocyclopropyl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 610.30 |
| 1129 | 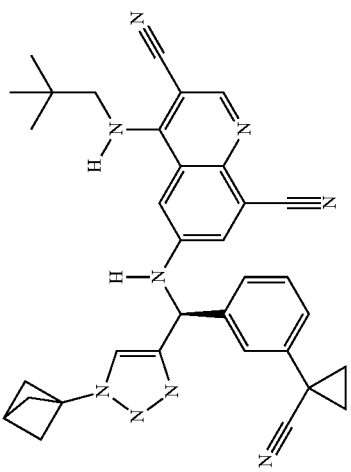 | (S)-6-((((1-(bicyclo[1.1.1]pentan-1-yl)-1H-1,2,3-triazol-4-yl)(3-(1-cyanocyclopropyl)phenyl)methyl)amino)-4-(neopentylamino)quinoline-3,8-dicarbonitrile | 48 | 568.40 |

TABLE 1-continued

| Compd | Structure | Name | Example/Procedure | ES/MS m/z |
|---|---|---|---|---|
| 1130 | 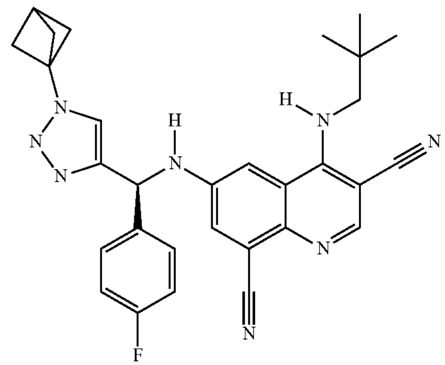 [SMILES: CC(C)(C)CNc1c(C#N)cnc2c(C#N)cc(N[C@H](C3=CN(C45CC(C4)C5)NN3)c3ccc(F)cc3)cc12] | (S)-6-((((1-(bicyclo[1.1.1]pentan-1-yl)-1H-1,2,3-triazol-4-yl)(4-fluorophenyl)methyl)amino)-4-(neopentylamino)quinoline-3,8-dicarbonitrile | 48 | 521.40 |
| 1131 | 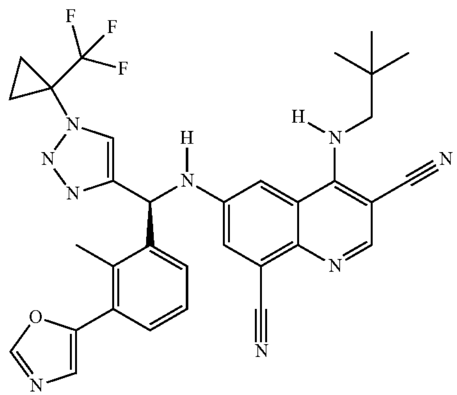 [SMILES: Cc1c(-c2cncn2C)cccc1[C@H](Nc1cc(C#N)c2ncc(C#N)c(NCC(C)(C)C)c2c1)C1=CN(C2(C(F)(F)F)CC2)NN1] | (S)-6-(((2-methyl-3-(oxazol-5-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 626.30 |

TABLE 1-continued
| Compd | Structure | Name | Example/Procedure | ES/MS m/z |
|---|---|---|---|---|
| 1132 | 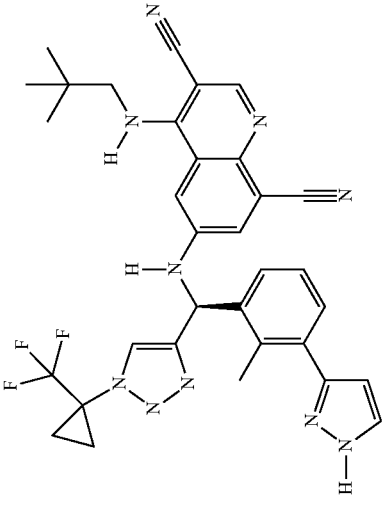 | (S)-6-(((2-methyl-3-(1H-pyrazol-3-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 625.30 |
| 1133 | 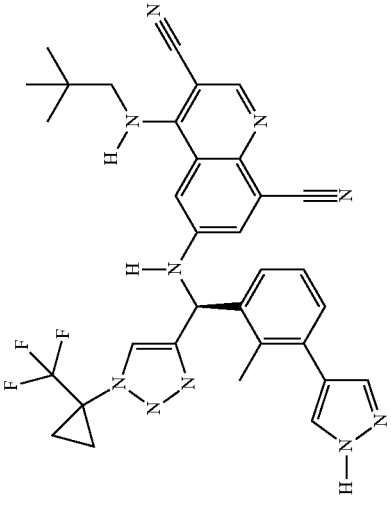 | (S)-6-(((2-methyl-3-(1H-pyrazol-4-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 625.30 |

TABLE 1-continued
| Compd | Structure | Name | Example/Procedure | ES/MS m/z |
|---|---|---|---|---|
| 1134 | 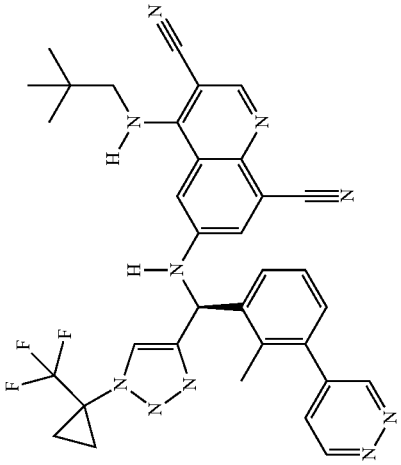 | (S)-6-(((2-methyl-3-(pyridazin-4-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 637.30 |
| 1135 | 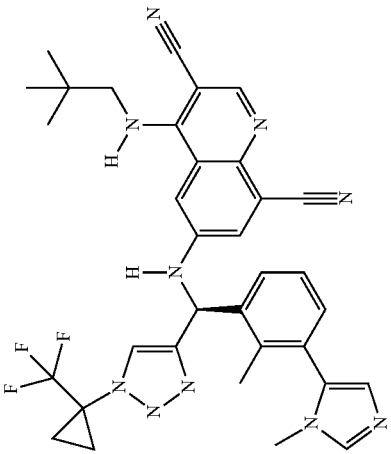 | (S)-6-(((2-methyl-3-(1-methyl-1H-imidazol-5-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 639.30 |

TABLE 1-continued

| Compd | Structure | Name | Example/Procedure | ES/MS m/z |
|---|---|---|---|---|
| 1136 | 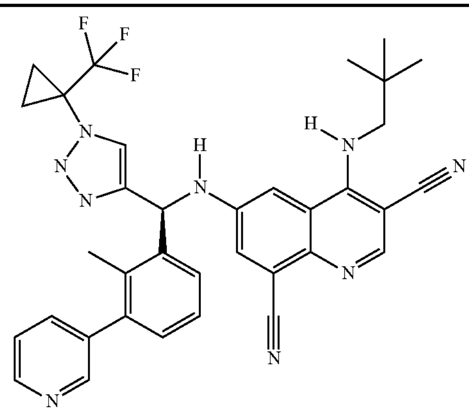 | (S)-6-(((2-methyl-3-(pyridin-3-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 635.10 |
| 1137 | 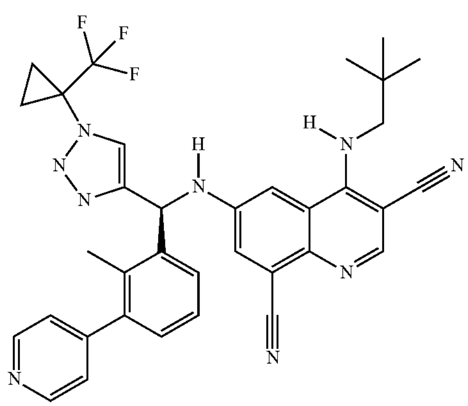 [SMILES: Cc1c(-c2ccncc2)cccc1[C@H](Nc1cc(C#N)c2ncc(C#N)c(NCC(C)(C)C)c2c1)C1=CN(C2(C(F)(F)F)CC2)NN1] | (S)-6-(((2-methyl-3-(pyridin-4-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 635.10 |

TABLE 1-continued
| Compd | Structure | Name | Example/Procedure | ES/MS m/z |
|---|---|---|---|---|
| 1138 | 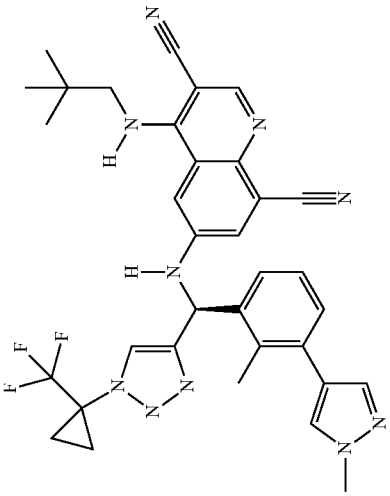 | (S)-6-(((2-methyl-3-(1-methyl-1H-pyrazol-4-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 638 |
| 1139 | 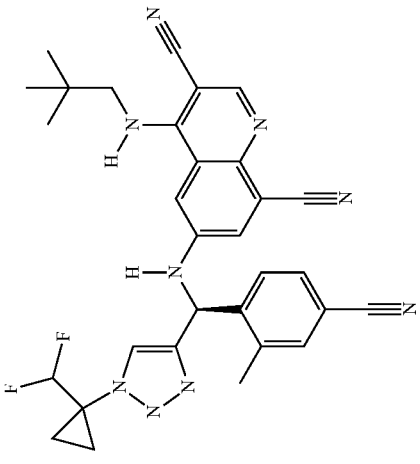 | (S)-6-(((4-cyano-2-methylphenyl)(1-(1-(difluoromethyl)cyclopropyl)-1H-1,2,3-triazol-4-yl)methyl)amino)-4-(neopentylamino)quinoline-3,8-dicarbonitrile | 48 | 566.30 |

TABLE 1-continued
| Compd | Structure | Name | Example/Procedure | ES/MS m/z |
|---|---|---|---|---|
| 1140 | 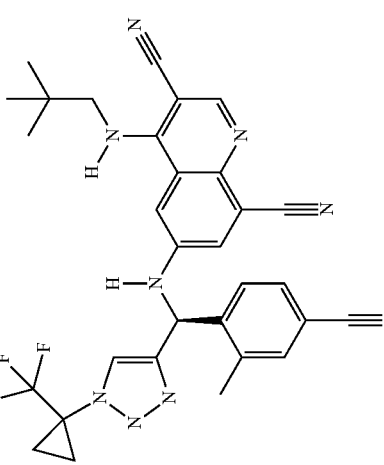 | (S)-6-(((4-cyano-2-methylphenyl)(1-(1-(trifluoromethyl)cyclopropyl)-1H-1,2,3-triazol-4-yl)methyl)amino)-4-(neopentylamino)quinoline-3,8-dicarbonitrile | 48 | 584.30 |
| 1141 | 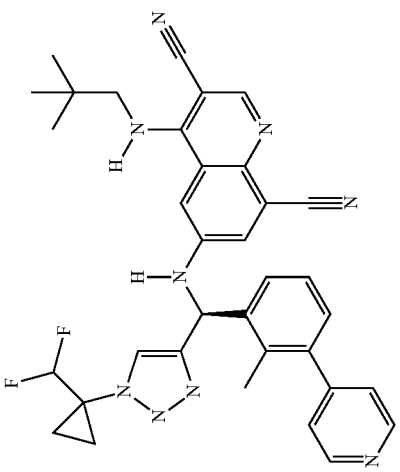 | (S)-6-(((1-(difluoromethyl)cyclopropyl)-1H-1,2,3-triazol-4-yl)(2-methyl-3-(pyridin-4-yl)phenyl)methyl)amino)-4-(neopentylamino)quinoline-3,8-dicarbonitrile | 48 | 617 |

TABLE 1-continued
| Compd | Structure | Name | Example/Procedure | ES/MS m/z |
|---|---|---|---|---|
| 1142 | 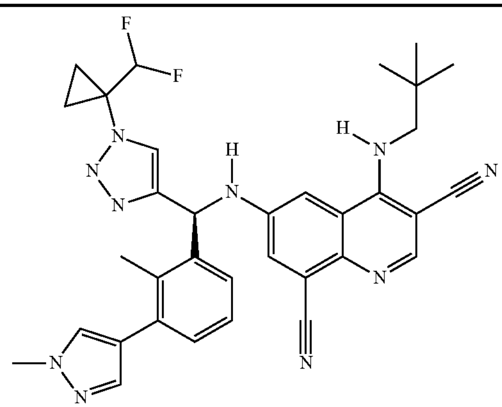 | (S)-6-(((1-(1-(difluoromethyl)cyclopropyl)-1H-1,2,3-triazol-4-yl)(2-methyl-3-(1-methyl-1H-pyrazol-4-yl)phenyl)methyl)amino)-4-(neopentylamino)quinoline-3,8-dicarbonitrile | 48 | 620 |
| 1143 | 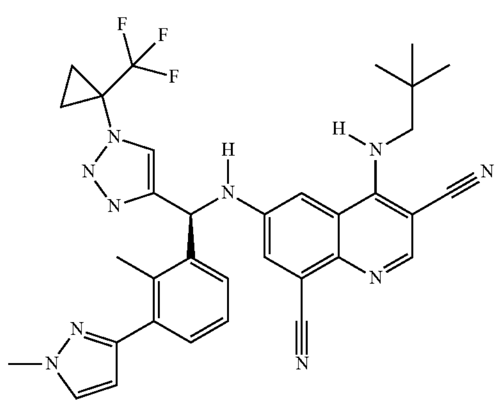 [SMILES: Cc1c(-c2ccn(C)n2)cccc1[C@H](Nc1cc(C#N)c2ncc(C#N)c(NCC(C)(C)C)c2c1)C1=CN(C2(C(F)(F)F)CC2)NN1] | (S)-6-(((2-methyl-3-(1-methyl-H-pyrazol-3-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 639.10 |

TABLE 1-continued
| Compd | Structure | Name | Example/Procedure | ES/MS m/z |
|---|---|---|---|---|
| 1144 | 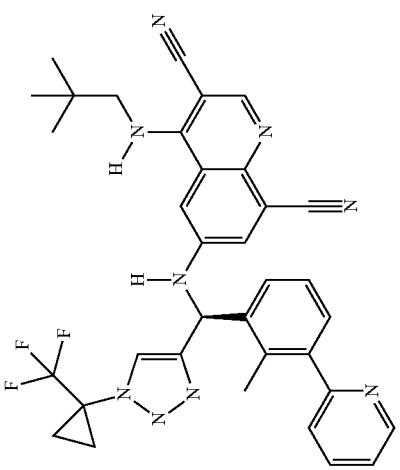 | (S)-6-(((2-methyl-3-(pyridin-2-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 636 |
| 1145 | 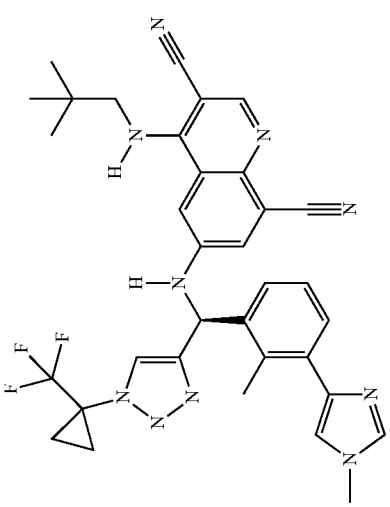 | (S)-6-(((2-methyl-3-(1-methyl-H-imidazol-4-yl)phenyl)(1-(1-(trifluoromethyl)cyclopropyl)-1H-1,2,3-triazol-4-yl)methyl)amino)-4-(neopentylamino)quinoline-3,8-dicarbonitrile | 48 | 639 |

TABLE 1-continued
| Compd | Structure | Name | Example/Procedure | ES/MS m/z |
|---|---|---|---|---|
| 1146 | 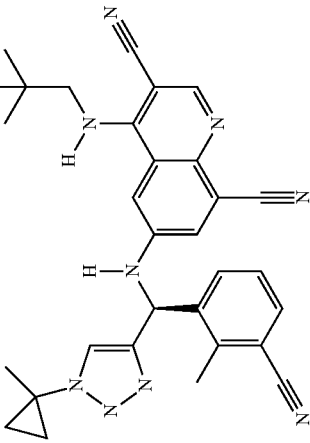 | (S)-6-(((3-cyano-2-methylphenyl)(1-(1-methylcyclopropyl)-1H-1,2,3-triazol-4-yl)methyl)amino)-4-((3,3,3-trifluoro-2,2-dimethylpropyl)amino)quinoline-3,8-dicarbonitrile | 48 | 584.20 |
| 1147 | 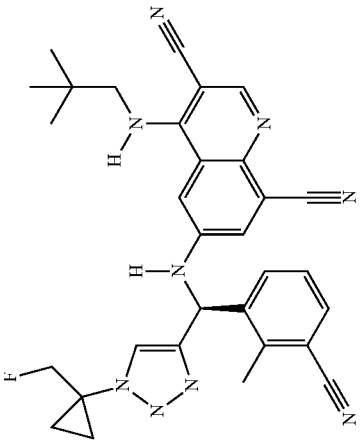 | (S)-6-(((3-cyano-2-methylphenyl)(1-(1-(fluoromethyl)cyclopropyl)-1H-1,2,3-triazol-4-yl)methyl)amino)-4-(neopentylamino)quinoline-3,8-dicarbonitrile | 48 | 548.20 |

TABLE 1-continued

| Compd | Structure | Name | Example/Procedure | ES/MS m/z |
|---|---|---|---|---|
| 1148 | 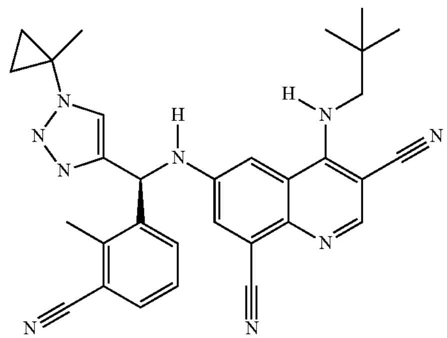 | (S)-6-(((3-cyano-2-methylphenyl)(1-(1-methylcyclopropyl)-1H-1,2,3-triazol-4-yl)methyl)amino)-4-(neopentylamino)quinoline-3,8-dicarbonitrile | 48 | 530.20 |
| 1149 | 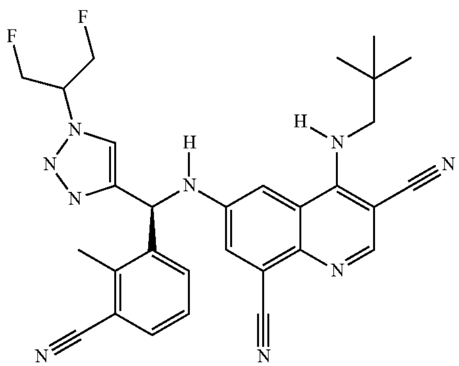 [SMILES: Cc1c(C#N)cccc1[C@H](Nc1cc(C#N)c2ncc(C#N)c(NCC(C)(C)C)c2c1)C1=CN(C(CF)CF)NN1] | (S)-6-(((3-cyano-2-methylphenyl)(1-(1,3-difluoropropan-2-yl)-1H-1,2,3-triazol-4-yl)methyl)amino)-4-(neopentylamino)quinoline-3,8-dicarbonitrile | 48 | 554.30 |
| 1150 | 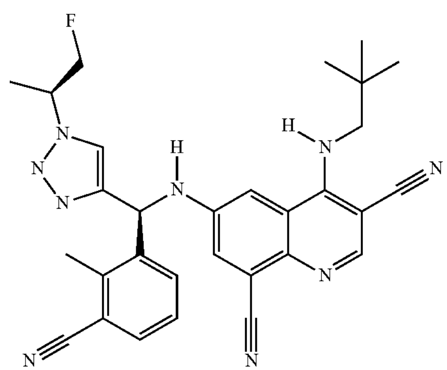 [SMILES: Cc1c(C#N)cccc1[C@H](Nc1cc(C#N)c2ncc(C#N)c(NCC(C)(C)C)c2c1)C1=CN([C@@H](C)CF)NN1] | 6-(((S)-(3-cyano-2-methylphenyl)(1-((S)-1-fluoropropan-2-yl)-1H-1,2,3-triazol-4-yl)methyl)amino)-4-neopentylamino)quinoline-3,8-dicarbonitrile | 48 | 536.30 |

TABLE 1-continued

| Compd | Structure | Name | Example/Procedure | ES/MS m/z |
|---|---|---|---|---|
| 1151 | 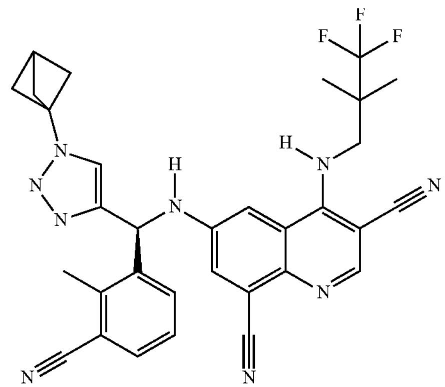 | (S)-6-(((1-(bicyclo[1.1.1]pentan-1-yl)-1H-1,2,3-triazol-4-yl)(3-cyano-2-methylphenyl)methyl)amino)-4-((3,3,3-trifluoro-2,2-dimethylpropyl)amino)quinoline-3,8-dicarbonitrile | 48 | 596.20 |
| 1152 | 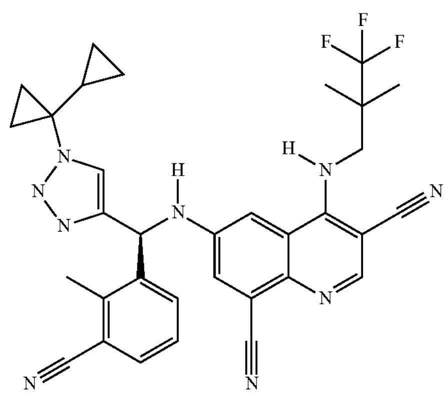 | (S)-6-(((1-([1,1'-bi(cyclopropan)]-1-yl)-1H-1,2,3-triazol-4-yl)(3-cyano-2-methylphenyl)methyl)amino)-4-((3,3,3-trifluoro-2,2-dimethylpropyl)amino)quinoline-3,8-dicarbonitrile | 48 | 610.30 |

TABLE 1-continued

| Compd | Structure | Name | Example/Procedure | ES/MS m/z |
|---|---|---|---|---|
| 1153 | 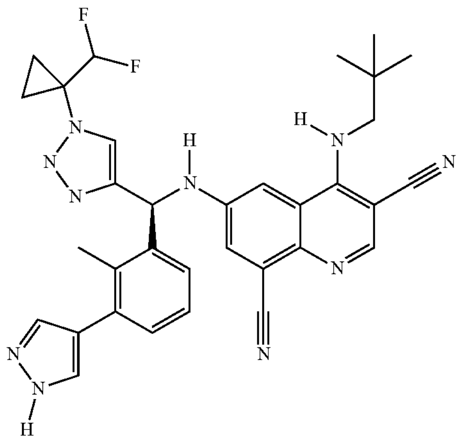 [SMILES: Cc1c(-c2cn[nH]c2)cccc1[C@H](Nc1cc(C#N)c2ncc(C#N)c(NCC(C)(C)C)c2c1)C1=CN(C2(C(F)F)CC2)NN1] | (S)-6-(((1-(difluoromethyl)cyclopropyl)-1H-1,2,3-triazol-4-yl)(2-methyl-3-(1H-pyrazol-4-yl)phenyl)methyl)amino)-4-(neopentylamino)quinoline-3,8-dicarbonitrile | 48 | 607.20 |
| 1154 | 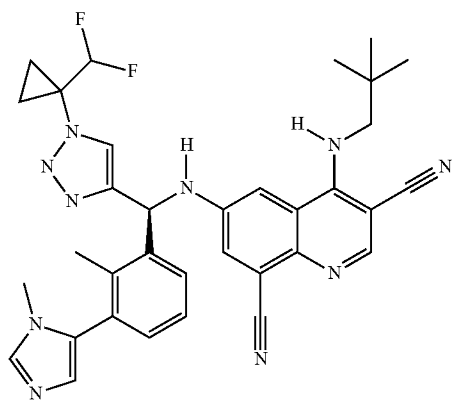 [SMILES: Cc1c(-c2cncn2C)cccc1[C@H](Nc1cc(C#N)c2ncc(C#N)c(NCC(C)(C)C)c2c1)C1=CN(C2(C(F)F)CC2)NN1] | (S)-6-(((1-(difluoromethyl)cyclopropyl)-1H-1,2,3-triazol-4-yl)(2-methyl-3-(1-methyl-1H-imidazol-5-yl)phenyl)methyl)amino)-4-(neopentylamino)quinoline-3,8-dicarbonitrile | 48 | 621.20 |

TABLE 1-continued
| Compd | Structure | Name | Example/Procedure | ES/MS m/z |
|---|---|---|---|---|
| 1155 | 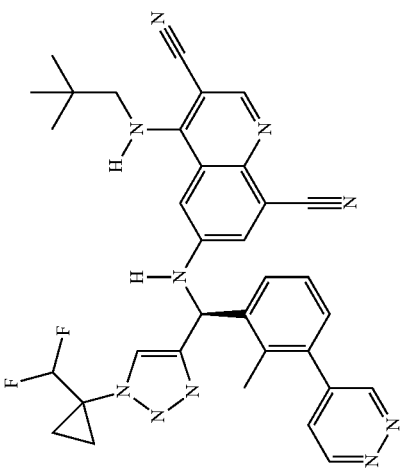 | (S)-6-(((1-(1-(difluoromethyl)cyclopropyl)-1H-1,2,3-triazol-4-yl)(2-methyl-3-(pyridazin-4-yl)phenyl)methyl)amino)-4-(neopentylamino)quinoline-3,8-dicarbonitrile | 48 | 619.20 |
| 1156 | 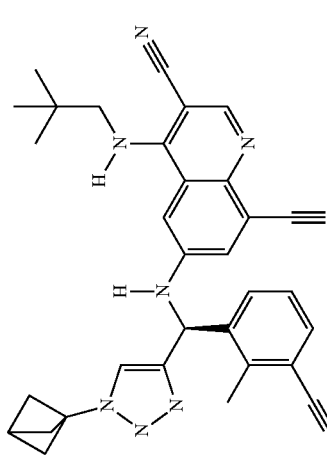 | (S)-6-(((1-(bicyclo[1.1.1]pentan-1-yl)-1H-1,2,3-triazol-4-yl)(3-cyano-2-methylphenyl)methyl)amino)-4-(neopentylamino)quinoline-3,8-dicarbonitrile | 48 | 542.20 |

TABLE 1-continued

| Compd | Structure | Name | Example/Procedure | ES/MS m/z |
|---|---|---|---|---|
| 1157 | 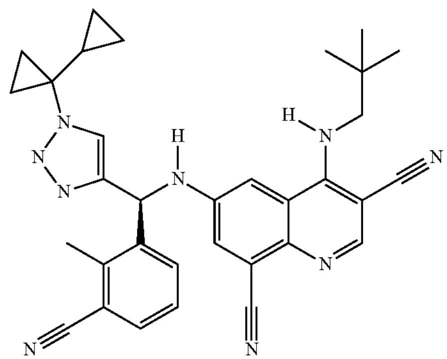 [SMILES: Cc1c(C#N)cccc1[C@H](Nc1cc(C#N)c2ncc(C#N)c(NCC(C)(C)C)c2c1)C1=CN(C2(C3CC3)CC2)NN1] | (S)-6-((((1-([1,1'-bi(cyclopropan)]-1-yl)-1H-1,2,3-triazol-4-yl)(3-cyano-2-methylphenyl)methyl)amino)-4-(neopentylamino)quinoline-3,8-dicarbonitrile | 48 | 556.30 |
| 1158 | 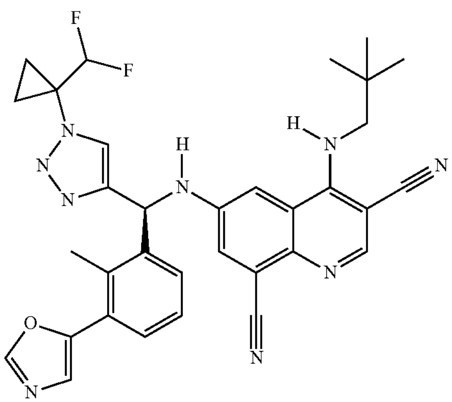 [SMILES: Cc1c(-c2cnco2)cccc1[C@H](Nc1cc(C#N)c2ncc(C#N)c(NCC(C)(C)C)c2c1)C1=CN(C2(C(F)F)CC2)NN1] | (S)-6-((((1-(1-(difluoromethyl)cyclopropyl)-1H-1,2,3-triazol-4-yl)(2-methyl-3-(oxazol-5-yl)phenyl)methyl)amino)-4-(neopentylamino)quinoline-3,8-dicarbonitrile | 48 | 608.30 |

TABLE 1-continued

| Compd | Structure | Name | Example/Procedure | ES/MS m/z |
|---|---|---|---|---|
| 1159 | 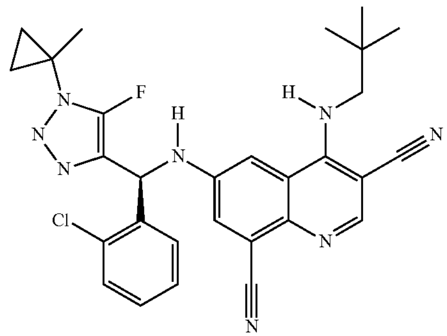 [SMILES: CC(C)(C)CNc1c(C#N)cnc2c(C#N)cc(N[C@H](C3=C(F)N(C4(C)CC4)NN3)c3ccccc3Cl)cc12] | (S)-6-(((2-chlorophenyl)(5-fluoro-1-(1-methylcyclopropyl)-1H-1,2,3-triazol-4-yl)methyl)amino)-4-(neopentylamino)quinoline-3,8-dicarbonitrile | 48 | 543.10 |
| 1160 | 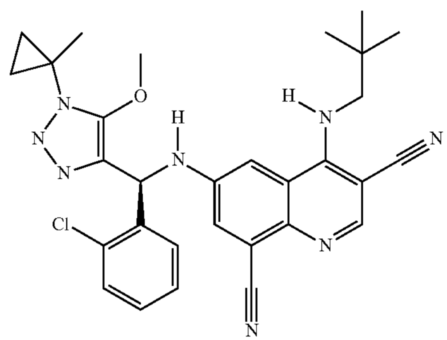 [SMILES: COC1=C([C@@H](Nc2cc(C#N)c3ncc(C#N)c(NCC(C)(C)C)c3c2)c2ccccc2Cl)NNN1C1(C)CC1] | (S)-6-(((2-chlorophenyl)(5-methoxy-1-(1-methylcyclopropyl)-1H-1,2,3-triazol-4-yl)methyl)amino)-4-(neopentylamino)quinoline-3,8-dicarbonitrile | 48 | 555.20 |
| 1161 | 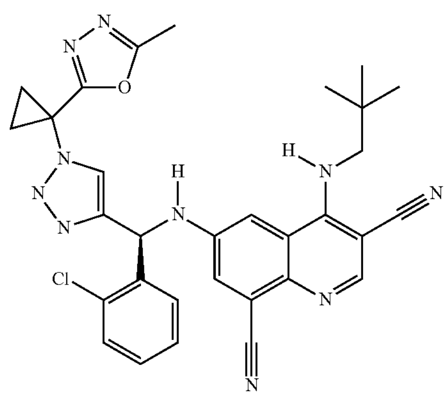 [SMILES: Cc1nnc(C2(N3C=C([C@@H](Nc4cc(C#N)c5ncc(C#N)c(NCC(C)(C)C)c5c4)c4ccccc4Cl)NN3)CC2)o1] | (S)-6-(((2-chlorophenyl)(1-(1-(5-methyl-1,3,4-oxadiazol-2-yl)cyclopropyl)-1H-1,2,3-triazol-4-yl)methyl)amino)-4-(neopentylamino)quinoline-3,8-dicarbonitrile | 48 | 593.30 |

TABLE 1-continued

| Compd | Structure | Name | Example/Procedure | ES/MS m/z |
|---|---|---|---|---|
| 1162 | 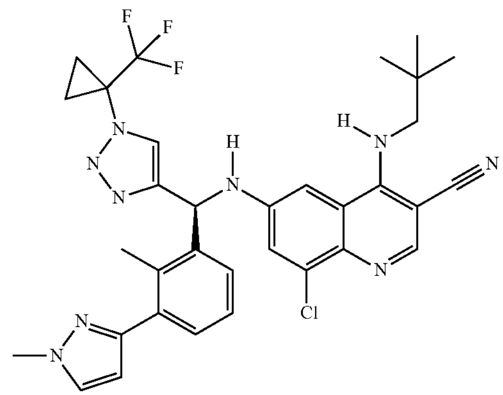 [SMILES: Cc1c(-c2ccn(C)n2)cccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-methyl-3-(1-methyl-1H-pyrazol-3-yl)phenyl)(1-(1-(trifluoromethyl)cyclopropyl)-1H-1,2,3-triazol-4-yl)methyl)amino)-4-(neopentylamino)quinoline-3-carbonitrile | 62 | 648.20 |
| 1163 | 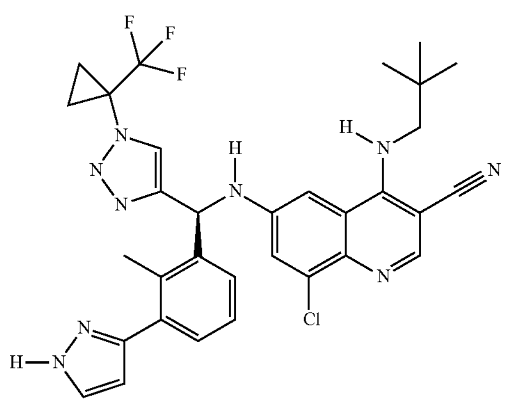 [SMILES: Cc1c(-c2cc[nH]n2)cccc1[C@H](Nc1cc(Cl)c2ncc(C#N)c(NCC(C)(C)C)c2c1)C1=CN(C2(C(F)(F)F)CC2)NN1] | (S)-8-chloro-6-(((2-methyl-3-(1H-pyrazol-3-yl)phenyl)(1-(1-(trifluoromethyl)cyclopropyl)-1H-1,2,3-triazol-4-yl)methyl)amino)-4-(neopentylamino)quinoline-3-carbonitrile | 62 | 634.40 |

TABLE 1-continued
| Compd | Structure | Name | Example/Procedure | ES/MS m/z |
|---|---|---|---|---|
| 1164 | 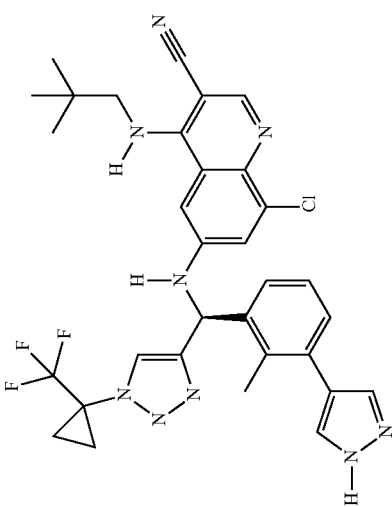 | (S)-8-chloro-6-(((2-methyl-3-(1H-pyrazol-4-yl)phenyl)(1-(trifluoromethyl)cyclopropyl)-1H-1,2,3-triazol-4-yl)methyl)amino)-4-(neopentylamino)quinoline-3-carbonitrile | 62 | 634.30 |
| 1165 | 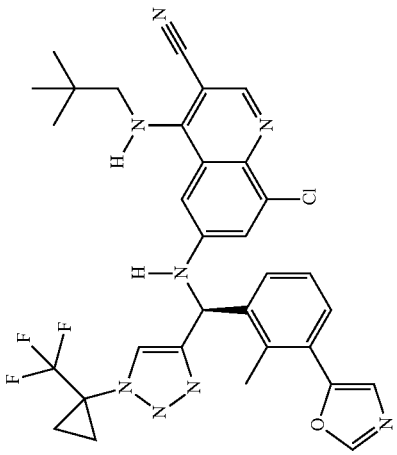 | (S)-8-chloro-6-(((2-methyl-3-(oxazol-5-yl)phenyl)(1-(trifluoromethyl)cyclopropyl)-1H-1,2,3-triazol-4-yl)methyl)amino)-4-(neopentylamino)quinoline-3-carbonitrile | 62 | 635.30 |

TABLE 1-continued

| Compd | Structure | Name | Example/Procedure | ES/MS m/z |
|---|---|---|---|---|
| 1166 | 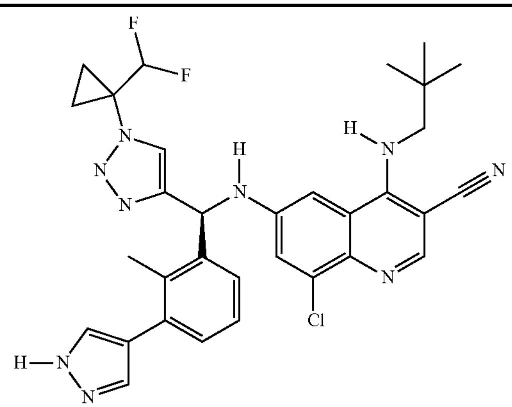 | (S)-8-chloro-6-(((1-(1-(difluoromethyl)cyclopropyl)-1H-1,2,3-triazol-4-yl)(2-methyl-3-(1H-pyrazol-4-yl)phenyl)methyl)amino)-4-(neopentylamino)quinoline-3-carbonitrile | 62 | 616.30 |
| 1167 | 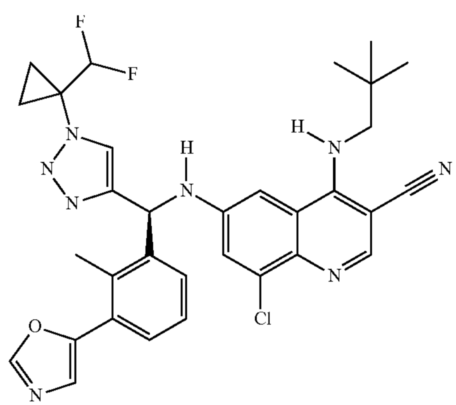 [SMILES: Cc1c(-c2cnco2)cccc1[C@H](Nc1cc(Cl)c2ncc(C#N)c(NCC(C)(C)C)c2c1)C1=CN(C2(C(F)F)CC2)NN1] | (S)-8-chloro-6-(((1-(1-(difluoromethyl)cyclopropyl)-1H-1,2,3-triazol-4-yl)(2-methyl-3-(oxazol-5-yl)phenyl)methyl)amino)-4-(neopentylamino)quinoline-3-carbonitrile | 62 | 617.30 |

TABLE 1-continued

| Compd | Structure | Name | Example/Procedure | ES/MS m/z |
|---|---|---|---|---|
| 1168 | 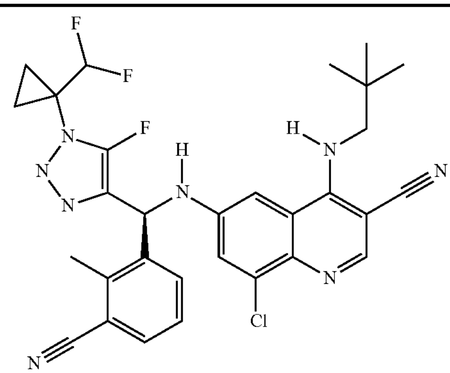 | (S)-8-chloro-6-(((3-cyano-2-methylphenyl)(1-(difluoromethyl)cyclopropyl)-5-fluoro-1H-1,2,3-triazol-4-yl)methyl)amino)-4-(neopentylamino)quinoline-3-carbonitrile | 60 | 593.10 |
| 1169 | 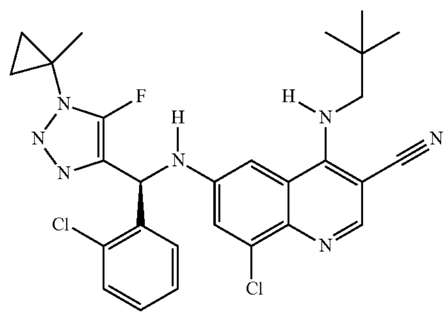 [SMILES: CC(C)(C)CNc1c(C#N)cnc2c(Cl)cc(N[C@H](C3=C(F)N(C4(C)CC4)NN3)c3ccccc3Cl)cc12] | (S)-8-chloro-6-(((2-chlorophenyl)(5-fluoro-1-(1-methylcyclopropyl)-1H-1,2,3-triazol-4-yl)methyl)amino)-4-(neopentylamino)quinoline-3-carbonitrile | 60 | 552.20 |
| 1170 | 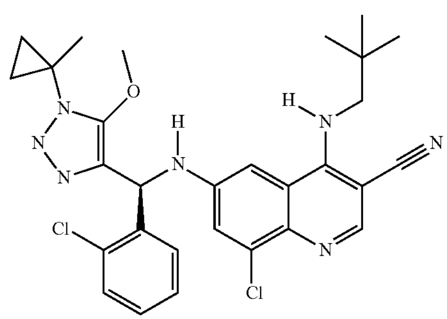 [SMILES: COC1=C([C@@H](Nc2cc(Cl)c3ncc(C#N)c(NCC(C)(C)C)c3c2)c2ccccc2Cl)NNN1C1(C)CC1] | (S)-8-chloro-6-(((2-chlorophenyl)(5-methoxy-1-(1-methylcyclopropyl)-1H-1,2,3-triazol-4-yl)methyl)amino)-4-(neopentylamino)quinoline-3-carbonitrile | 61 | 564.20 |

Proton NMR data for select compounds is shown below in Table 2.

TABLE 2

| Cmpd | 1H-NMR |
|---|---|
| 1 | 1H NMR (400 MHz, DMSO-d6) δ 8.34 (d, J = 1.2 Hz, 1H), 8.01 (s, 1H), 7.72 (s, 1H), 7.59 (d, J = 2.2 Hz, 1H), 7.57-7.47 (m, 2H), 7.40 (s, 1H), 7.21-7.04 (m, 3H), 4.07-3.86 (m, 2H), 3.46 (dd, J = 13.9, 5.5 Hz, 1H), 1.23-1.00 (m, 4H), 0.88 (s, 9H). |
| 2 | 1H NMR (400 MHz, DMSO-d6) δ 8.26 (s, 1H), 8.03 (s, 1H), 7.62-7.51 (m, 3H), 7.45-7.29 (m, 3H), 7.29-7.20 (m, 4H), 7.20-7.12 (m, 2H), 5.52-5.36 (m, 1H), 4.00-3.94 (m, 1H), 2.19-2.09 (m, 1H), 1.98-1.89 (m, 1H), 1.19-1.12 (m, 2H), 1.13-1.06 (m, 2H), 0.99-0.88 (m, 3H). |
| 4 | 1H NMR (400 MHz, Methanol-d4) δ 8.52 (s, 1H), 7.83 (s, 1H), 7.63 (t, J = 1.5 Hz, 1H), 7.50 (d, J = 7.3 Hz, 2H), 7.40-7.30 (m, 2H), 7.02 (d, J = 2.3 Hz, 1H), 5.25-5.12 (m, 2H), 4.11 (d, J = 13.8 Hz, 1H), 3.84 (d, J = 13.8 Hz, 1H), 1.00 (s, 9H). |
| 5 | 1H NMR (400 MHz, DMSO-d6) δ 9.39 (s, 1H), 8.40 (s, 1H), 7.99 (s, 1H), 7.66 (d, J = 2.2 Hz, 1H), 7.49-7.43 (m, 4H), 7.41 (t, J = 9.0 Hz, 2H), 7.36 (s, 1H), 7.25-7.18 (m, 3H), 7.18-7.11 (m, 2H), 6.06 (d, J = 7.4 Hz, 1H), 4.72 (ddd, J = 11.8, 7.7, 4.1 Hz, 1H), 3.60 (d, J = 12.3 Hz, 2H), 3.29-2.97 (m, 5H), 2.41-2.30 (m, 3H), 2.26-2.09 (m, 2H), 1.22 (t, J = 7.3 Hz, 3H). |
| 6 | 1H NMR (400 MHz, DMSO-d6) δ 9.40 (m, 2H), 8.40 (s, 1H), 8.06 (s, 1H) 7.66 (m, 1H), 7.44-7.14 (m, 6H), 7.22 (m, 2H), 6.07 (m, 1H), 4.73 (m, 1H), 3.61 (m 2H), 3.21-3.05 (m, 4H), 2.32 (m, 2H), 2.17 (m, 2H), 1.21 (m, 3H). |
| 7 | 1H NMR (400 MHz, DMSO-d6) δ 9.44 (s, 1H), 8.89 (dd, J = 1.7, 0.5 Hz, 1H), 8.42 (s, 1H), 7.69 (d, J = 2.3 Hz, 1H), 7.58-7.41 (m, 5H), 7.34 (d, J = 2.4 Hz, 1H), 7.27 (ddd, J = 8.9, 4.2, 2.7 Hz, 1H), 7.25-7.17 (m, 2H), 6.62 (d, J = 1.7 Hz, 1H), 6.21 (d, J = 9.4 Hz, 1H). |
| 8 | 1H NMR (400 MHz, DMSO-d6) δ 9.85 (s, 1H), 9.42 (s, 1H), 8.38 (s, 1H), 7.88-7.81 (m, 2H), 7.57-7.31 (m, 5H), 7.28-7.06 (m, 3H), 6.05 (s, 1H), 3.97 (s, 3H) |
| 10 | 1H NMR (400 MHz, DMSO-d6) δ 9.61 (s, 1H), 9.22 (s, 1H), 8.46 (s, 1H), 8.18-8.09 (m, 2H), 7.99 (s, 1H), 7.72 (d, J = 2.2 Hz, 1H), 7.53-7.42 (m, 3H), 7.38-7.19 (m, 4H), 6.12-6.04 (m, 1H), 4.87-4.73 (m, 1H), 3.65 (d, J = 11.7 Hz, 2H), 3.12 (dt, J = 13.1, 10.2 Hz, 2H), 2.43-2.17 (m, 4H), 1.36 (s, 9H) |
| 13 | 1H NMR (400 MHz, DMSO-d6) δ 8.33 (s, 1H), 7.88 (d, J = 2.1 Hz, 1H), 7.73 (s, 1H), 7.58-7.50 (m, 2H), 7.39 (s, 1H), 7.15-7.07 (m, 3H), 4.03 (dd, J = 13.9, 8.1 Hz, 1H), 3.98-3.88 (m, 1H), 3.41 (dd, J = 13.9, 5.3 Hz, 1H), 2.26 (d, J = 0.5 Hz, 3H), 1.28-1.14 (m, 4H), 0.85 (s, 9H). |
| 17 | 1H NMR (400 MHz, Methanol-d4) δ 8.44 (s, 1H), 7.78 (s, 1H), 7.65 (d, J = 2.4 Hz, 1H), 7.47 (d, J = 4.8 Hz, 2H), 7.38-7.23 (m, 5H), 7.18 (d, J = 2.4 Hz, 1H), 6.02 (s, 1H), 4.89-4.71 (m, 1H), 4.58 (s, 2H), 3.79 (d, J = 12.8 Hz, 2H), 3.21 (t, J = 13.0 Hz, 2H), 2.42 (d, J = 25.2 Hz, 4H), 1.46 (s, 9H) |
| 18 | 1H NMR (400 MHz, Methanol-d4) δ 8.45 (s, 1H), 8.00 (s, 1H), 7.67 (d, J = 2.4 Hz, 1H), 7.65 (s, 1H), 7.56 (d, J = 7.8 Hz, 1H), 7.53-7.40 (m, 3H), 7.36-7.23 (m, 2H), 7.21 (d, J = 2.3 Hz, 1H), 6.09 (s, 1H), 4.80 (d, J = 5.1 Hz, 1H), 4.35-4.21 (m, 2H), 3.79 (d, J = 12.7 Hz, 2H), 3.28-3.16 (m, 2H), 2.80 (s, 6H), 2.45 (m, 4H), 1.46 (s, 9H) |
| 20 | 1H NMR (400 MHz, Methanol-d4) δ 8.43 (s, 1H), 7.84 (s, 1H), 7.65 (d, J = 2.3 Hz, 1H), 7.56 (d, J = 7.8 Hz, 1H), 7.51 (s, 1H), 7.46 (t, J = 7.7 Hz, 2H), 7.37 (d, J = 7.6 Hz, 1H), 7.32 (t, J = 8.8 Hz, 1H), 7.25 (d, J = 2.9 Hz, 1H), 7.15 (d, J = 2.4 Hz, 1H), 6.07 (s, 1H), 4.82-4.72 (m, 1H), 3.81 (d, J = 13.0 Hz, 2H), 3.21 (d, J = 12.3 Hz, 2H), 3.06 (s, 3H), 2.88 (s, 3H), 2.54-2.32 (m, 4H), 1.46 (s, 9H) |
| 22 | 1H NMR (400 MHz, Methanol-d4) δ 8.47 (s, 1H), 7.81 (d, J = 3.4 Hz, 1H), 7.68 (d, J = 2.3 Hz, 1H), 7.53 (dd, J = 11.1, 4.7 Hz, 2H), 7.41-7.24 (m, 6H), 6.06 (s, 1H), 4.80 (m, 2H), 3.79 (d, J = 12.6 Hz, 2H), 3.23 (d, J = 12.6 Hz, 2H), 2.43 (m, 4H), 1.46 (s, 9H), 1.37 (d, J = 6.4 Hz, 3H) |
| 26 | 1H NMR D2O exchange (400 MHz, DMSO-d6) δ 8.55 (s, 1H), 8.40 (s, 1H), 7.64 (s, 1H), 7.52 (t, J = 7.9 Hz, 2H), 7.39 (d, J = 5.7 Hz, 2H), 7.11 (s, 1H), 4.36 (dd, J = 13.0, 10.4 Hz, 2H), 3.81 (d, J = 13.9 Hz, 1H), 3.66 (d, J = 13.8 Hz, 1H), 0.90 (s, 9H). |
| 27 | 1H NMR D2O exchange (400 MHz, DMSO-d6) δ 8.97 (s, 1H), 8.42 (s, 1H), 7.64 (d, J = 2.4 Hz, 1H), 7.47-7.42 (m, 4H), 7.42-7.36 (m, 4H), 7.36-7.30 (m, 2H), 7.19 (qd, J = 4.1, 2.8 Hz, 3H), 5.96 (s, 1H), 4.51-4.38 (m, 1H), 3.58 (d, J = 13.0 Hz, 4H), 3.25 (d, J = 12.2 Hz, 1H), 3.12 (q, J = 7.3 Hz, 2H), 3.06-2.93 (m, 2H), 2.35-2.25 (m, 3H), 2.05-1.91 (m, 2H), 1.20 (t, J = 7.3 Hz, 3H). |
| 32 | 1H NMR (400 MHz, Methanol-d4) δ 8.41 (s, 1H), 7.83 (m, 1H), 7.65 (m, 1H), 7.54-7.18 (m, 8H), 7.16-7.03 (m, 2H), 6.17-6.05 (m, 2H), 4.93-4.76 (m, 2H), 4.67-4.58 (m, 1H), 4.51 (m, 1H), 3.93-3.82 (m, 1H), 1.26-1.09 (m, 4H). |
| 33 | 1H NMR (400 MHz, Methanol-d4) δ 9.11 (s, 1H), 7.84 (s, 1H), 7.70 (m, 2H), 7.56 (m, 2H), 7.10 (m, 2H), 4.96-4.86 (m, 1H), 3.93-3.82 (m, 1H), 1.46 (s, 9H), 1.25-1.09 (m, 4H). |
| 37 | 1H NMR (400 MHz, DMSO-d6) δ 8.25 (d, J = 5.6 Hz, 1H), 8.00 (d, J = 1.7 Hz, 1H), 7.86 (t, J = 7.3 Hz, 2H), 7.64 (t, J = 7.8 Hz, 1H), 7.56 (d, J = 2.2 Hz, 1H), 7.46 (s, 1H), 7.33 (d, J = 4.4 Hz, 1H), 7.30 (s, 1H), 7.27 (t, J = 4.3 Hz, 1H), 7.21 (d, J = 6.8 Hz, 4H), 7.10 (dd, J = 7.3, 2.1 Hz, 2H), 5.41 (q, J = 7.3 Hz, 1H), 3.78 (tt, J = 7.3, 3.8 Hz, 1H), 2.10 (dt, J = 14.1, 7.2 Hz, 1H), 1.91 (ddt, J = 20.8, 13.9, 7.1 Hz, 1H), 1.38-1.29 (m, 1H), 1.19-1.11 (m, 1H), 1.11-0.99 (m, 2H), 0.89 (t, J = 7.3 Hz, 3H), 0.81 (t, J = 7.2 Hz, 1H). |
| 38 | 1H NMR (400 MHz, Methanol-d4) δ 8.43 (s, 1H), 7.78 (s, 1H), 7.65 (d, J = 2.4 Hz, 1H), 7.45 (s, 2H), 7.40-7.20 (m, 5H), 7.16 (d, J = 1.7 Hz, 1H), 6.02 (s, 1H), 4.77 (s, 1H), 4.42 (s, 2H), 3.79 (d, J = 12.3 Hz, 2H), 3.32 (s, 3H), 3.23 (d, J = 12.3 Hz, 2H), 2.57-2.29 (m, 4H), 1.46 (s, 9H) |

TABLE 2-continued

| Cmpd | 1H-NMR |
|---|---|
| 40 | 1H NMR (400 MHz, Methanol-d4) δ 8.43 (s, 1H), 7.84 (s, 1H), 7.63 (d, J = 2.4 Hz, 1H), 7.47 (s, 1H), 7.44 (dd, J = 6.4, 2.6 Hz, 1H), 7.42-7.28 (m, 5H), 7.27-7.21 (m, 1H), 7.15 (d, J = 2.4 Hz, 1H), 6.00 (d, J = 0.9 Hz, 1H), 4.80 (m, 1H), 4.58 (s, 2H), 3.74-3.67 (m, 2H), 3.33-3.28 (m, 2H), 2.84 (s, 6H), 1.53 (d, J = 6.7 Hz, 6H) |
| 41 | 1H NMR (400 MHz, Methanol-d4) δ 8.43 (s, 1H), 7.85 (s, 1H), 7.64 (d, J = 2.3 Hz, 1H), 7.56 (d, J = 8.0 Hz, 1H), 7.51 (s, 1H), 7.48-7.43 (m, 2H), 7.36 (d, J = 7.7 Hz, 1H), 7.32 (t, J = 8.8 Hz, 1H), 7.26-7.22 (m, 1H), 7.15 (d, J = 2.5 Hz, 1H), 6.07 (s, 1H), 4.86-4.75 (m, 1H), 3.75 (d, J = 13.6 Hz, 2H), 3.24 (q, J = 7.2 Hz, 2H), 3.20-3.10 (m, 2H), 3.05 (s, 3H), 2.88 (s, 3H), 2.46 (d, J = 14.2 Hz, 2H), 2.36 (t, J = 13.0 Hz, 2H), 1.37 (t, J = 7.4 Hz, 3H) |
| 43 | 1H NMR (400 MHz, DMSO-d6) δ 8.35 (s, 1H), 7.97 (s, 1H), 7.49 (dd, J = 8.6, 5.6 Hz, 2H), 7.10 (t, J = 8.8 Hz, 2H), 6.91 (s, 1H), 6.70 (s, 1H), 6.05 (d, J = 7.6 Hz, 1H), 4.08 (s, 1H), 4.00-3.86 (m, 1H), 3.51 (s, 1H), 1.16-1.00 (m, 4H), 0.89 (s, 9H). |
| 45 | 1H NMR (400 MHz, DMSO-d6) δ 9.70 (s, 1H), 8.49 (s, 1H), 8.05-7.89 (m, 3H), 7.73 (d, J = 2.2 Hz, 1H), 7.46 (td, J = 7.9, 1.9 Hz, 1H), 7.41-7.28 (m, 2H), 7.24-7.11 (m, 3H), 6.25 (s, 1H), 4.00 (s, 3H) |
| 46 | 1H NMR (400 MHz, DMSO-d6) δ 8.30-8.18 (m, 2H), 8.00-7.94 (m, 1H), 7.63-7.53 (m, 3H), 7.44-7.12 (m, 10H), 5.52-5.31 (m, 1H), 4.84 (brs), 4.57-4.40 (m, 2H), 3.81-3.66 (m, 1H), 2.96 (t, J = 11.0 Hz, 1H), 2.74 (d, J = 11.4 Hz, 1H), 2.19-2.00 (m, 2H), 1.98-1.85 (m, 2H), 1.24 (s, 9H), 0.99-0.86 (m, 3H). |
| 47 | 1H NMR (400 MHz, Methanol-d4) δ 8.45 (s, 1H), 8.21 (s, 1H), 7.89 (d, J = 1.7 Hz, 1H), 7.82 (d, J = 7.9 Hz, 1H), 7.73 (dd, J = 7.7, 1.4 Hz, 1H), 7.67 (d, J = 2.3 Hz, 1H), 7.58 (t, J = 7.8 Hz, 1H), 7.42 (dd, J = 9.4, 2.4 Hz, 1H), 7.35 (td, J = 4.9, 4.1, 2.4 Hz, 3H), 7.33-7.27 (m, 2H), 5.98 (dd, J = 8.6, 5.9 Hz, 1H), 2.66 (t, J = 7.1 Hz, 2H), 2.54 (dt, J = 22.5, 7.5 Hz, 1H), 2.40 (tt, J = 13.5, 7.1 Hz, 1H), 2.05-1.96 (m, 2H), 1.95 (d, J = 3.7 Hz, 2H). |
| 48 | 1H NMR (400 MHz, DMSO-d6) δ 8.38 (d, J = 14.5 Hz, 1H), 8.23 (s, 1H), 7.66-7.43 (m, 3H), 7.42-7.13 (m, 9H), 6.37 (d, J = 6.4 Hz, 1H), 5.77-5.58 (m, 1H), 2.69-2.55 (m, 2H), 2.46-2.35 (m, 1H), 2.27-2.03 (m, 1H). |
| 49 | 1H NMR (400 MHz, Methanol-d4) δ 8.44 (s, 1H), 8.17 (s, 1H), 7.63 (d, J = 2.3 Hz, 1H), 7.48 (ddd, J = 9.6, 7.1, 2.3 Hz, 2H), 7.42-7.25 (m, 8H), 7.18 (d, J = 2.3 Hz, 1H), 6.56 (s, 1H), 5.75 (t, J = 7.2 Hz, 1H), 2.20 (dt, J = 14.4, 7.3 Hz, 1H), 2.09 (dt, J = 14.1, 7.3 Hz, 1H), 2.04-1.97 (m, 2H), 1.97-1.91 (m, 2H), 1.01 (t, J = 7.3 Hz, 3H). |
| 50 | 1H NMR (400 MHz, Methanol-d4) δ 8.52 (s, 1H), 8.19 (s, 1H), 7.86 (d, J = 1.7 Hz, 1H), 7.80 (dt, J = 7.9, 1.3 Hz, 1H), 7.73-7.67 (m, 2H), 7.56 (t, J = 7.8 Hz, 1H), 7.08 (d, J = 2.4 Hz, 1H), 4.24 (d, J = 14.0 Hz, 1H), 3.72 (d, J = 14.0 Hz, 1H), 2.05-1.96 (m, 2H), 1.96-1.90 (m, 2H), 0.97 (s, 9H). |
| 65 | 1H NMR (400 MHz, Methanol-d4) δ 8.47 (s, 1H), 8.02 (s, 1H), 7.63 (d, J = 2.3 Hz, 1H), 7.56-7.44 (m, 2H), 7.43-7.26 (m, 6H), 6.57 (s, 1H), 5.99 (dd, J = 8.2, 6.0 Hz, 1H), 5.79 (tt, J = 7.8, 6.0 Hz, 1H), 5.15-5.04 (m, 2H), 5.01 (t, J = 6.5 Hz, 2H), 2.63 (t, J = 7.0 Hz, 2H), 2.55 (dt, J = 14.8, 6.4 Hz, 1H), 2.40 (dq, J = 13.8, 6.8 Hz, 1H). |
| 66 | 1H NMR (400 MHz, Methanol-d4) δ 8.46 (s, 1H), 7.97 (d, J = 3.3 Hz, 1H), 7.63 (d, J = 2.5 Hz, 1H), 7.55-7.46 (m, 2H), 7.46-7.30 (m, 6H), 7.28 (d, J = 2.3 Hz, 1H), 6.58 (s, 1H), 5.98 (dd, J = 8.2, 6.0 Hz, 1H), 5.62 (s, 2H), 2.62 (t, J = 7.1 Hz, 2H), 2.59-2.47 (m, 1H), 2.40 (dq, J = 13.7, 6.9 Hz, 1H). |
| 70 | 1H NMR (400 MHz, DMSO-d6) δ 8.32 (s, 1H), 8.08 (s, 1H), 7.55-7.49 (m, 2H), 7.45-7.37 (m, 1H), 7.28 (dd, J = 5.9, 3.5 Hz, 2H), 7.00 (d, J = 2.4 Hz, 1H), 3.82 (d, J = 13.8 Hz, 1H), 3.50 (d, J = 14.3 Hz, 1H), 1.67 (q, J = 5.1 Hz, 2H), 1.46 (q, J = 5.2 Hz, 2H), 0.85 (s, 9H). |
| 71 | 1H NMR (400 MHz, DMSO-d6) δ 8.20 (s, 1H), 7.89 (s, 1H), 7.69 (s, 1H), 7.60 (d, J = 2.1 Hz, 1H), 7.55 (dd, J = 5.9, 3.6 Hz, 1H), 7.52-7.42 (m, 2H), 7.39-7.28 (m, 5H), 7.23 (s, 4H), 6.55 (d, J = 8.1 Hz, 1H), 5.62 (d, J = 5.9 Hz, 1H), 5.05 (s, 2H), 2.69-2.54 (m, 2H), 2.36 (s, 1H), 2.21-2.11 (m, 1H). |
| 72 | 1H NMR (400 MHz, DMSO-d6) δ 8.22 (s, 1H), 8.06 (s, 1H), 7.57 (d, J = 2.1 Hz, 1H), 7.53 (dt, J = 7.4, 3.6 Hz, 1H), 7.46 (td, J = 8.0, 6.9, 3.9 Hz, 1H), 7.33 (td, J = 6.3, 3.0 Hz, 3H), 7.23 (dd, J = 10.2, 2.7 Hz, 5H), 6.50 (d, J = 6.7 Hz, 1H), 5.63 (q, J = 7.7 Hz, 1H), 2.71-2.53 (m, 2H), 2.32 (ddt, J = 20.3, 13.7, 7.6 Hz, 1H), 2.17 (dq, J = 13.6, 7.1 Hz, 1H), 1.61 (d, J = 2.9 Hz, 3H), 1.26 (t, J = 3.5 Hz, 2H), 1.06-0.98 (m, 2H). |
| 73 | 1H NMR (400 MHz, DMSO-d6) δ 8.39 (s, 1H), 8.22 (s, 1H), 7.57 (d, J = 2.1 Hz, 1H), 7.55-7.43 (m, 2H), 7.43-7.30 (m, 3H), 7.24 (dd, J = 12.3, 2.6 Hz, 5H), 6.54 (d, J = 7.8 Hz, 1H), 5.63 (q, J = 7.9 Hz, 1H), 2.69-2.56 (m, 1H), 2.38-2.24 (m, 1H), 2.17 (q, J = 6.5 Hz, 1H), 2.10-1.99 (m, 2H), 1.99-1.86 (m, 2H). |
| 74 | 1H NMR (400 MHz, Methanol-d4) δ 8.42 (s, 1H), 7.81 (s, 1H), 7.64 (d, J = 2.3 Hz, 1H), 7.51-7.43 (m, 2H), 7.44-7.26 (m, 7H), 7.25 (d, J = 2.3 Hz, 1H), 5.96 (dd, J = 8.2, 6.1 Hz, 1H), 3.88 (m, 1H), 2.64 (m, 2H), 2.58-2.44 (m, 1H), 2.38 (m, 1H), 1.26-1.09 (m, 4H) |
| 84 | 1H NMR (400 MHz, Methanol-d4) δ 8.35 (s, 1H), 7.79 (d, J = 2.5 Hz, 1H), 7.75 (s, 1H), 7.51-7.43 (m, 2H), 7.41-7.32 (m, 2H), 7.34-7.25 (m, 1H), 7.23 (d, J = 2.5 Hz, 1H), 3.97 (d, J = 13.9 Hz, 1H), 3.86 (m, 1H), 3.66 (d, J = 13.9 Hz, 1H), 1.24-1.08 (m, 4H), 0.94 (s, 9H) |
| 90 | 1H NMR (400 MHz, Methanol-d4) δ 8.44 (d, J = 1.5 Hz, 1H), 7.85 (s, 1H), 7.61 (d, J = 2.4 Hz, 1H), 7.47 (dt, J = 6.1, 2.8 Hz, 2H), 7.33 (dt, J = 7.8, 5.6 Hz, 2H), 6.97 (d, J = 2.4 Hz, 1H), 5.13 (s, 1H), 4.68 (dd, J = 14.6, 5.7 Hz, 1H), 4.62-4.45 (m, 2H), 4.19 (dt, J = 9.4, 6.1 Hz, 1H), 4.01 (d, J = 13.9 Hz, 1H), 3.81 (d, J = 13.8 Hz, 1H), 2.71 (m, 1H), 2.43-2.25 (m, 1H), 0.97 (d, J = 2.2 Hz, 9H). |

TABLE 2-continued

| Cmpd | 1H-NMR |
|---|---|
| 91 | 1H NMR (400 MHz, Methanol-d4) δ 8.45 (d, J = 0.9 Hz, 1H), 8.16 (d, J = 0.9 Hz, 1H), 7.60 (dd, J = 2.4, 0.9 Hz, 1H), 7.47 (td, J = 8.4, 8.0, 2.0 Hz, 2H), 7.39-7.27 (m, 2H), 6.95 (d, J = 2.3 Hz, 1H), 4.01 (d, J = 13.7 Hz, 1H), 3.79 (d, J = 13.9 Hz, 1H), 2.02-1.96 (m, 2H), 1.96-1.88 (m, 2H), 1.02-0.93 (m, 9H). |
| 92 | 1H NMR (400 MHz, Methanol-d4) δ 8.52 (s, 1H), 7.89 (d, J = 5.5 Hz, 1H), 7.66 (s, 1H), 7.50 (d, J = 8.0 Hz, 2H), 7.35 (p, J = 7.3 Hz, 2H), 7.04 (d, J = 2.3 Hz, 1H), 4.76 (dd, J = 14.0, 3.2 Hz, 1H), 4.64-4.52 (m, 1H), 4.47 (s, 1H), 4.11 (dd, J = 13.8, 8.3 Hz, 1H), 3.84 (dd, J = 13.9, 9.4 Hz, 1H), 1.02 (s, 9H). |
| 93 | 1H NMR (400 MHz, Methanol-d4) δ 8.53 (s, 1H), 7.96 (s, 1H), 7.66 (d, J = 2.2 Hz, 1H), 7.54-7.49 (m, 1H), 7.49-7.44 (m, 1H), 7.37 (td, J = 8.2, 6.1 Hz, 2H), 7.04 (d, J = 2.3 Hz, 1H), 5.39-5.25 (m, 2H), 4.11 (d, J = 13.9 Hz, 1H), 3.83 (d, J = 13.8 Hz, 1H), 1.00 (s, 9H). |
| 98 | 1H NMR (400 MHz, Methanol-d4) δ 8.51 (s, 1H), 7.98 (s, 1H), 7.64 (d, J = 2.3 Hz, 1H), 7.49 (t, J = 8.1 Hz, 2H), 7.41-7.30 (m, 2H), 6.99 (d, J = 2.2 Hz, 1H), 4.41 (dd, J = 8.5, 4.3 Hz, 1H), 4.07 (d, J = 13.8 Hz, 1H), 3.84 (d, J = 13.8 Hz, 1H), 2.72 (d, J = 8.1 Hz, 1H), 1.86 (d, J = 14.6 Hz, 1H), 1.68 (q, J = 7.3 Hz, 1H), 1.00 (s, 9H). |
| 99 | 1H NMR (400 MHz, Methanol-d4) δ 8.52 (s, 1H), 7.99 (s, 1H), 7.65 (d, J = 2.2 Hz, 1H), 7.51 (d, J = 7.6 Hz, 1H), 7.46 (m, J = 7.1 Hz, 1H), 7.40-7.30 (m, 2H), 7.02 (t, J = 2.4 Hz, 1H), 4.64 (d, J = 8.7 Hz, 1H), 4.07 (dd, J = 13.7, 2.7 Hz, 1H), 3.89-3.81 (m, 1H), 2.53 (ddd, J = 15.1, 9.8, 5.3 Hz, 1H), 2.39 (t, J = 10.3 Hz, 1H), 1.00 (s, 9H). |
| 100 | 1H NMR (400 MHz, Methanol-d4) δ 8.52 (s, 1H), 7.93 (s, 1H), 7.64 (d, J = 2.3 Hz, 1H), 7.53-7.45 (m, 2H), 7.43-7.29 (m, 2H), 7.00 (d, J = 2.3 Hz, 1H), 4.87 (d, J = 7.3 Hz, 1H), 4.68 (dd, J = 7.9, 5.2 Hz, 2H), 4.34 (s, 1H), 4.17 (d, J = 2.9 Hz, 1H), 4.10 (d, J = 13.8 Hz, 1H), 3.82 (d, J = 13.8 Hz, 1H), 3.71 (s, 2H), 3.50-3.37 (m, 2H), 2.70 (s, 2H), 1.00 (s, 9H). |
| 103 | 1H NMR (400 MHz, DMSO-d6) δ 8.33 (s, 1H), 7.96 (s, 1H), 7.58 (d, J = 2.2 Hz, 1H), 7.47-7.39 (m, 2H), 7.36 (s, 1H), 7.33-7.26 (m, 2H), 7.04 (d, J = 2.3 Hz, 1H), 4.99 (dd, J = 21.6, 1.8 Hz, 2H), 4.77 (dd, J = 8.2, 4.4 Hz, 1H), 4.74-4.69 (m, 1H), 4.60 (dd, J = 20.4, 8.3 Hz, 2H), 3.82 (dd, J = 13.7, 7.3 Hz, 1H), 3.50 (dd, J = 13.8, 5.2 Hz, 1H), 0.86 (s, 9H). |
| 104 | 1H NMR (400 MHz, DMSO-d6) δ 8.33 (s, 1H), 7.85 (s, 1H), 7.59 (d, J = 2.2 Hz, 1H), 7.51-7.45 (m, 1H), 7.45-7.39 (m, 1H), 7.37 (s, 1H), 7.33-7.26 (m, 2H), 7.05 (d, J = 2.3 Hz, 1H), 4.72-4.59 (m, 2H), 4.48 (dd, J = 6.5, 5.1 Hz, 2H), 4.39 (t, J = 7.0 Hz, 2H), 3.84 (dd, J = 13.6, 7.4 Hz, 1H), 3.50 (dd, J = 13.7, 5.4 Hz, 1H), 0.87 (s, 9H). |
| 105 | 1H NMR (400 MHz, DMSO-d6) δ 8.31 (s, 1H), 8.02 (s, 1H), 7.58 (d, J = 2.2 Hz, 1H), 7.51 (s, 1H), 7.44 (ddd, J = 9.4, 4.5, 2.8 Hz, 2H), 7.35 (s, 1H), 7.33-7.26 (m, 2H), 7.03 (d, J = 2.4 Hz, 1H), 5.02 (dq, J = 18.1, 6.2 Hz, 1H), 4.76 (d, J = 5.6 Hz, 1H), 4.64 (d, J = 5.6 Hz, 1H), 3.80 (dd, J = 13.7, 7.3 Hz, 1H), 3.51 (dd, J = 13.7, 5.4 Hz, 1H), 1.45 (dd, J = 7.0, 1.4 Hz, 3H), 0.86 (s, 9H). |
| 106 | 1H NMR (400 MHz, DMSO-d6) δ 8.31 (d, J = 1.1 Hz, 2H), 7.57 (d, J = 2.2 Hz, 1H), 7.55-7.47 (m, 1H), 7.44 (ddd, J = 6.0, 3.5, 1.6 Hz, 2H), 7.34-7.26 (m, 3H), 7.03 (d, J = 2.4 Hz, 1H), 3.75 (dd, J = 13.7, 7.3 Hz, 1H), 3.56 (dd, J = 13.7, 5.8 Hz, 1H), 1.77-1.69 (m, 2H), 1.66 (d, J = 6.0 Hz, 2H), 0.85 (s, 9H). |
| 107 | 1H NMR (400 MHz, DMSO-d6) δ 8.29 (s, 1H), 8.03 (s, 1H), 7.55 (d, J = 2.2 Hz, 1H), 7.49-7.38 (m, 2H), 7.32-7.24 (m, 2H), 6.97 (d, J = 2.4 Hz, 1H), 3.75 (dd, J = 13.7, 7.3 Hz, 1H), 3.54 (dd, J = 13.7, 5.7 Hz, 1H), 1.59 (s, 3H), 1.23 (t, J = 3.6 Hz, 2H), 1.01 (dd, J = 4.1, 2.9 Hz, 2H), 0.85 (s, 9H). |
| 109 | 1H NMR (400 MHz, DMSO-d6) δ 8.28 (s, 1H), 8.01 (s, 1H), 7.58-7.54 (m, 1H), 7.52-7.45 (m, 1H), 7.45-7.37 (m, 1H), 7.35-7.23 (m, 3H), 6.98 (d, J = 2.3 Hz, 1H), 3.76 (dd, J = 13.9, 7.3 Hz, 1H), 3.52 (dd, J = 13.8, 5.6 Hz, 1H), 1.56 (s, 8H), 0.86 (s, 9H). |
| 115 | 1H NMR (400 MHz, DMSO-d6) δ 8.23 (s, 1H), 7.92 (d, J = 4.5 Hz, 1H), 7.67-7.51 (m, 3H), 7.49-7.09 (m, 8H), 6.35 (s, 1H), 5.48 (d, J = 7.6 Hz, 1H), 5.24 (s, 2H), 2.13 (dt, J = 14.2, 7.2 Hz, 1H), 1.91 (dt, J = 14.0, 7.1 Hz, 1H), 0.94 (t, J = 7.3 Hz, 3H). |
| 116 | 1H NMR (400 MHz, DMSO-d6) δ 9.55 (s, 1H), 8.44 (s, 1H), 7.95 (d, J = 31.1 Hz, 3H), 7.70 (d, J = 2.2 Hz, 1H), 7.47 (dd, J = 8.5, 5.4 Hz, 3H), 7.23 (s, 1H), 7.14 (t, J = 8.7 Hz, 2H), 6.11 (s, 1H), 5.22 (s, 2H). |
| 117 | 1H NMR (400 MHz, DMSO-d6) δ 8.72 (s, 1H), 8.36 (d, J = 1.5 Hz, 1H), 8.00 (d, J = 11.2 Hz, 4H), 7.56-7.47 (m, 3H), 7.46-7.37 (m, 3H), 7.35-7.21 (m, 1H), 7.21-7.09 (m, 7H), 3.99-3.86 (m, 3H), 2.80 (s, 1H), 2.17-2.02 (m, 2H), 1.77-1.47 (m, 5H), 1.18-1.00 (m, 13H) |
| 118 | 1H NMR (400 MHz, DMSO-d6) δ 8.29 (s, 1H), 8.14 (s, 1H), 7.56 (d, J = 2.2 Hz, 1H), 7.44 (ddd, J = 9.5, 6.4, 4.0 Hz, 2H), 7.30 (dd, J = 5.9, 3.4 Hz, 3H), 6.99 (d, J = 2.4 Hz, 1H), 5.80 (p, J = 6.8 Hz, 1H), 4.96 (td, J = 7.3, 2.6 Hz, 2H), 4.87 (q, J = 6.5 Hz, 2H), 3.74 (dd, J = 13.7, 7.3 Hz, 1H), 3.58-3.49 (m, 1H), 0.84 (s, 9H). |
| 119 | 1H NMR (400 MHz, DMSO-d6) δ 8.28 (s, 1H), 8.08 (s, 1H), 7.56 (d, J = 2.2 Hz, 1H), 7.44 (td, J = 6.3, 3.4 Hz, 2H), 7.34-7.28 (m, 3H), 7.01 (s, 1H), 5.74 (d, J = 1.3 Hz, 2H), 3.75 (m, 1H), 3.51 (dd, J = 13.6, 5.7 Hz, 1H), 0.84 (s, 9H). |
| 120 | 1H NMR (400 MHz, DMSO-d6) δ 8.39 (s, 1H), 7.99 (s, 1H), 7.58 (d, J = 2.3 Hz, 1H), 7.52-7.40 (m, 2H), 7.36 (s, 1H), 7.33-7.22 (m, 2H), 6.75 (s, 1H), 5.92 (s, 1H), 3.95 (tt, J = 7.9, 4.3 Hz, 1H), 2.40-2.32 (m, 1H), 1.23 (s, 3H), 1.19 (s, 3H), 1.12 (q, J = 3.3 Hz, 2H), 1.07 (dd, J = 7.7, 5.2 Hz, 2H), 0.84 (d, J = 6.7 Hz, 3H), 0.76 (d, J = 6.7 Hz, 3H). |
| 121 | 1H NMR (400 MHz, DMSO-d6) δ 8.30 (s, 1H), 8.00 (s, 1H), 7.68 (s, 1H), 7.55 (d, J = 2.2 Hz, 1H), 7.47-7.40 (m, 2H), 7.32-7.25 (m, 2H), 7.03 (d, J = 2.4 Hz, 1H), 3.94 (tt, J = 7.5, 4.0 Hz, 1H), 3.84 (dd, J = 14.1, 7.0 Hz, 1H), 3.65 (dd, J = 14.1, 5.7 Hz, 1H), 1.97-1.86 (m, 2H), 1.82 (dt, J = 11.4, 8.6 Hz, 1H), 1.68-1.52 (m, 3H), 1.12 (dq, J = 4.1, 2.4 Hz, 2H), 1.10-1.03 (m, 5H). |

TABLE 2-continued

| Cmpd | 1H-NMR |
|---|---|
| 123 | 1H NMR (400 MHz, DMSO-d6) δ 8.56 (s, 1H), 8.40 (s, 1H), 8.01 (s, 1H), 7.52 (d, J = 2.2 Hz, 1H), 7.48-7.43 (m, 1H), 7.43-7.39 (m, 1H), 7.35-7.28 (m, 2H), 7.19 (d, J = 2.4 Hz, 2H), 3.95 (tt, J = 7.5, 4.0 Hz, 1H), 1.55 (s, 3H), 1.17-1.10 (m, 2H), 1.10-1.04 (m, 2H), 1.01 (dd, J = 7.0, 2.9 Hz, 2H), 0.89 (t, J = 2.9 Hz, 2H). |
| 124 | 1H NMR (400 MHz, DMSO-d6) δ 8.38 (s, 1H), 8.20 (s, 1H), 8.00 (s, 1H), 7.52 (d, J = 2.2 Hz, 1H), 7.49-7.41 (m, 2H), 7.34-7.26 (m, 2H), 7.17 (d, J = 2.5 Hz, 2H), 3.95 (tt, J = 7.5, 3.7 Hz, 1H), 2.80 (s, 1H), 2.08 (ddd, J = 12.9, 7.9, 5.3 Hz, 2H), 1.81-1.63 (m, 2H), 1.63-1.49 (m, 3H), 1.15-1.09 (m, 2H), 1.09-0.99 (m, 2H). |
| 125 | 1H NMR (400 MHz, Methanol-d4) δ 8.47 (s, 1H), 7.92-7.84 (m, 2H), 7.82-7.77 (m, 1H), 7.72 (dt, J = 7.8, 1.4 Hz, 1H), 7.68 (d, J = 2.3 Hz, 1H), 7.57 (t, J = 7.8 Hz, 1H), 7.42-7.28 (m, 5H), 6.00 (dd, J = 8.5, 5.9 Hz, 1H), 3.89 (m, 1H), 2.66 (t, J = 7.1 Hz, 2H), 2.54 (m, 1H), 2.40 (m, 1H), 1.35-1.10 (m, 4H). |
| 128 | 1H NMR (400 MHz, DMSO-d6) δ 8.36 (d, J = 10.8 Hz, 2H), 7.99 (d, J = 7.6 Hz, 2H), 7.88-7.82 (m, 1H), 7.75 (d, J = 2.4 Hz, 1H), 7.56-7.19 (m, 11H), 7.11 (d, J = 2.5 Hz, 1H), 6.83 (d, J = 10.2 Hz, 1H), 6.62 (d, J = 10.1 Hz, 1H), 4.34-3.87 (m, 8H), 3.47-3.30 (m, 4H), 3.05 (dd, J = 14.8, 11.5 Hz, 2H), 1.93-1.75 (m, 3H), 1.19-1.01 (m, 7H), 0.91 (d, J = 6.0 Hz, 6H), 0.62 (s, 3H), 0.41 (s, 3H) |
| 129 | 1H NMR (400 MHz, DMSO-d6) δ 8.33 (d, J = 7.4 Hz, 2H), 7.81 (d, J = 2.4 Hz, 1H), 7.54-7.38 (m, 4H), 7.37-7.27 (m, 3H), 3.73 (dd, J = 13.8, 7.3 Hz, 1H), 3.57 (dd, J = 13.8, 5.9 Hz, 1H), 1.79-1.62 (m, 4H), 0.85 (s, 9H) |
| 130 | 1H NMR (400 MHz, DMSO-d6) δ 8.32 (d, J = 4.2 Hz, 2H), 7.83 (d, J = 2.3 Hz, 1H), 7.59-7.46 (m, 4H), 7.41 (d, J = 2.5 Hz, 1H), 7.20-7.09 (m, 2H), 3.91 (dd, J = 14.0, 7.8 Hz, 1H), 3.51-3.43 (m, 1H), 1.79-1.63 (m, 4H), 0.88 (s, 9H) |
| 131 | 1H NMR (400 MHz, DMSO-d6) δ 8.36 (d, J = 3.4 Hz, 1H), 8.26 (d, J = 8.8 Hz, 1H), 7.84 (d, J = 2.4 Hz, 1H), 7.65-7.42 (m, 5H), 7.41-7.17 (m, 7H), 5.50-5.27 (m, 1H), 2.15-1.81 (m, 2H), 1.81-1.64 (m, 4H), 0.91 (td, J = 7.3, 1.6 Hz, 3H) |
| 132 | 1H NMR (400 MHz, DMSO-d6) δ 8.38-8.23 (m, 2H), 7.84 (d, J = 2.4 Hz, 1H), 7.68-7.47 (m, 5H), 7.43-7.12 (m, 7H), 5.53-5.33 (m, 1H), 2.12 (dt, J = 13.5, 7.3 Hz, 1H), 2.04-1.85 (m, 1H), 1.81-1.64 (m, 4H), 1.05-0.86 (m, 3H) |
| 134 | 1H NMR (400 MHz, DMSO-d6) δ 8.36 (s, 1H), 7.99 (s, 1H), 7.69 (d, J = 8.0 Hz, 1H), 7.60 (d, J = 2.1 Hz, 1H), 7.54-7.47 (m, 2H), 7.40 (s, 1H), 7.21-7.08 (m, 2H), 7.06 (d, J = 2.4 Hz, 1H), 4.03 (dd, J = 14.2, 7.8 Hz, 1H), 3.98-3.89 (m, 1H), 3.59 (dd, J = 14.2, 5.3 Hz, 1H), 1.18-1.03 (m, 4H), 0.98 (s, 3H), 0.93 (s, 3H) |
| 136 | 1H NMR (400 MHz, Methanol-d4) δ 8.45 (s, 1H), 7.85 (s, 1H), 7.69-7.64 (m, 1H), 7.60 (m, 2H), 7.44-7.31 (m, 6H), 7.15 (d, J = 2.3 Hz, 1H), 5.94 (m, 1H), 3.95-3.80 (m, 1H), 2.62 (m, 2H), 2.60 (s, 3H), 2.56-2.35 (m, 2H), 1.27-1.05 (m, 4H) |
| 141 | 1H NMR (400 MHz, DMSO-d6) δ 8.34 (d, J = 10.8 Hz, 1H), 7.98 (d, J = 11.2 Hz, 1H), 7.65-7.16 (m, 5H), 6.86 (dd, J = 34.5, 2.4 Hz, 1H), 4.24 (dtd, J = 33.9, 10.5, 4.5 Hz, 1H), 3.95 (ddq, J = 14.6, 11.3, 3.8 Hz, 1H), 3.58-2.78 (m, 3H), 2.09-1.47 (m, 2H), 1.36-0.21 (m, 9H) |
| 142 | 1H NMR (400 MHz, DMSO-d6) δ 8.35 (s, 1H), 8.08 (s, 1H), 7.99 (s, 1H), 7.59-7.41 (m, 3H), 7.41-7.22 (m, 1H), 7.22-7.00 (m, 3H), 4.11 (dd, J = 14.0, 8.5 Hz, 2H), 4.02-3.86 (m, 1H), 3.68 (ddd, J = 14.5, 8.4, 2.9 Hz, 2H), 2.89-2.75 (m, 1H), 2.12-1.88 (m, 2H), 1.21-1.00 (m, 4H) |
| 145 | 1H NMR (400 MHz, DMSO-d6) δ 8.36 (s, 1H), 7.97 (d, J = 0.5 Hz, 1H), 7.62 (dd, J = 2.3, 0.6 Hz, 1H), 7.52-7.44 (m, 2H), 7.41 (s, 1H), 7.10 (ddd, J = 9.0, 7.7, 1.3 Hz, 2H), 6.95 (d, J = 2.4 Hz, 1H), 6.83 (d, J = 10.1 Hz, 1H), 4.32 (td, J = 11.0, 4.4 Hz, 1H), 4.07-3.89 (m, 2H), 3.50-3.28 (m, 2H), 3.05 (d, J = 11.5 Hz, 1H), 1.98 (qd, J = 12.1, 4.7 Hz, 1H), 1.87-1.71 (m, 1H), 1.24-1.01 (m, 4H), 0.91 (s, 3H), 0.45 (s, 3H) |
| 151 | 1H NMR (400 MHz, DMSO-d6) δ 8.00 (s, 1H), 7.65-7.48 (m, 3H), 7.45-7.30 (m, 2H), 7.15-7.06 (m, 3H), 4.03-3.89 (m, 2H), 3.44 (dd, J = 13.9, 5.4 Hz, 1H), 1.18-1.02 (m, 4H), 0.89 (s, 10H) |
| 152 | 1H NMR (400 MHz, DMSO-d6) δ 8.32 (s, 1H), 8.01 (s, 1H), 7.80 (d, J = 2.3 Hz, 1H), 7.50-7.35 (m, 4H), 7.35-7.26 (m, 3H), 4.01-3.90 (m, 1H), 3.73 (dd, J = 13.7, 7.3 Hz, 1H), 3.54 (dd, J = 13.7, 5.8 Hz, 1H), 1.19-1.03 (m, 4H), 0.85 (s, 9H) |
| 158 | 1H NMR (400 MHz, Methanol-d4) δ 8.15 (s, 1H), 7.90 (s, 1H), 7.59-7.46 (m, 3H), 7.39-7.26 (m, 5H), 7.12 m, 2H), 7.03 (s, 1H), 6.36 (m, 1H), 3.98 (m, 1H), 3.92-3.74 (m, 2H), 2.87 (s, 3H), 1.40-1.06 (m, 4H). |
| 164 | 1H NMR (400 MHz, DMSO-d6) δ 8.17-8.11 (m, 2H), 8.01 (td, J = 1.7, 0.8 Hz, 1H), 7.95-7.87 (m, 1H), 7.80 (ddt, J = 7.6, 1.6, 0.8 Hz, 1H), 7.60 (t, J = 7.8 Hz, 1H), 7.42 (s, 1H), 7.35-7.12 (m, 8H), 5.72-5.61 (m, 1H), 4.03-3.93 (m, 1H), 2.72-2.58 (m, 2H), 2.53-2.36 (m, 1H), 2.26-2.15 (m, 1H), 1.22-1.05 (m, 4H) |
| 165 | 1H NMR (400 MHz, DMSO-d6) δ 8.14 (d, J = 7.0 Hz, 2H), 7.96 (t, J = 1.7 Hz, 1H), 7.93-7.82 (m, 1H), 7.75 (dt, J = 7.7, 1.4 Hz, 1H), 7.58 (t, J = 7.7 Hz, 1H), 7.46-7.18 (m, 7H), 7.14 (d, J = 2.3 Hz, 1H), 5.63-5.52 (m, 1H), 4.03-3.93 (m, 1H), 2.57-2.51 (m, 2H), 2.38-2.24 (m, 2H), 1.26-1.00 (m, 5H) |
| 172 | 1H NMR (400 MHz, DMSO-d6) δ 8.59 (s, 1H), 8.47 (s, 1H), 8.01 (s, 1H), 7.64-7.44 (m, 3H), 7.17-7.04 (m, 3H), 6.80 (d, J = 2.0 Hz, 1H), 4.13 (dd, J = 14.0, 8.0 Hz, 1H), 4.00-3.87 (m, 4H), 3.56 (dd, J = 14.0, 5.8 Hz, 1H), 1.22-0.99 (m, 4H), 0.89 (s, 9H) |
| 179 | 1H NMR (400 MHz, DMSO-d6) δ 9.27 (s, 1H), 8.36 (s, 1H), 8.04 (s, 1H), 7.70-7.45 (m, 3H), 7.35 (s, 1H), 7.32-6.97 (m, 3H), 4.07-3.85 (m, 1H), 3.03 (m, 4H), 1.89 (s, 4H), 1.35-0.94 (m, 4H) |
| 182 | 1H NMR (400 MHz, DMSO-d6) δ 9.65 (s, 1H), 8.51 (s, 1H), 8.01 (s, 1H), 7.90 (d, J = 2.5 Hz, 1H), 7.52-7.28 (m, 8H), 7.22-7.13 (m, 1H), 4.00-3.90 (m, 1H), 1.17-1.01 (m, 4H) |
| 183 | 1H NMR (400 MHz, DMSO-d6) δ 9.51 (s, 1H), 8.53 (s, 1H), 8.01 (s, 1H), 7.67 (s, 1H), 7.49-7.25 (m, 6H), 7.12 (t, J = 8.6 Hz, 1H), 6.99 (s, 1H), 4.00-3.90 (m, 1H), 1.17-1.01 (m, 4H) |

TABLE 2-continued

| Cmpd | 1H-NMR |
|---|---|
| 184 | 1H NMR (400 MHz, DMSO-d6) δ 8.32 (s, 1H), 7.59 (d, J = 2.2 Hz, 1H), 7.57 (s, 1H), 7.55-7.48 (m, 2H), 7.35 (s, 1H), 7.20 (t, J = 8.8 Hz, 2H), 7.11 (d, J = 2.4 Hz, 1H), 4.03 (s, 3H), 3.82 (dd, J = 13.9, 7.3 Hz, 1H), 3.59-3.49 (m, 1H), 0.85 (s, 9H). |
| 192 | 1H NMR (400 MHz, DMSO-d6) δ 8.36 (s, 1H), 8.01 (s, 1H), 7.63-7.58 (m, 1H), 7.56-7.47 (m, 2H), 7.41 (s, 1H), 7.18-7.10 (m, 2H), 7.06 (d, J = 2.4 Hz, 1H), 4.09 (dd, J = 14.0, 8.0 Hz, 1H), 4.00-3.91 (m, 1H), 3.62 (dd, J = 14.1, 5.1 Hz, 1H), 3.55 (d, J = 11.0 Hz, 1H), 3.48 (d, J = 11.0 Hz, 1H), 1.23-1.03 (m, 4H), 0.94 (s, 3H), 0.92 (s, 3H) |
| 197 | 1H NMR (400 MHz, Methanol-d4) δ 8.48 (s, 1H), 7.83 (s, 1H), 7.66 (dd, J = 7.8, 1.3 Hz, 1H), 7.63 (d, J = 2.2 Hz, 1H), 7.62-7.58 (m, 1H), 7.34 (t, J = 7.9 Hz, 1H), 6.80 (d, J = 2.3 Hz, 1H), 4.09 (d, J = 13.9 Hz, 1H), 3.89 (m, 1H), 3.73 (d, J = 13.9 Hz, 1H), 2.57 (s, 3H), 1.26-1.09 (m, 4H), 0.92 (s, 9H) |
| 202 | 1H NMR (400 MHz, DMSO-d6) δ 8.33 (d, J = 4.8 Hz, 1H), 8.06 (d, J = 6.2 Hz, 1H), 7.90-7.82 (m, 2H), 7.68-7.53 (m, 4H), 7.49-7.23 (m, 5H), 7.22-7.10 (m, 2H), 6.03-5.88 (m, 1H), 4.02-3.91 (m, 1H), 3.42-3.22 (m, 2H), 1.22-1.03 (m, 4H). 555.3 (M + H+). |
| 208 | 1H NMR (400 MHz, DMSO-d6) δ 8.29-8.22 (m, 1H), 7.94-7.89 (m, 1H), 7.84 (d, J = 2.3 Hz, 1H), 7.62-7.49 (m, 4H), 7.41-7.30 (m, 1H), 7.31-7.12 (m, 5H), 5.47 (q, J = 7.6 Hz, 1H), 4.02 (s, 3H), 2.18-2.04 (m, 1H), 2.06-1.83 (m, 2H), 0.98-0.85 (m, 4H) |
| 209 | 1H NMR (400 MHz, DMSO-d6) δ 8.30 (s, 1H), 7.90 (s, 1H), 7.82 (d, J = 2.3 Hz, 1H), 7.57-7.47 (m, 2H), 7.39 (d, J = 2.5 Hz, 1H), 7.19-7.09 (m, 1H), 4.00 (s, 3H), 3.94 (dd, J = 14.0, 7.9 Hz, 1H), 3.42 (dd, J = 13.9, 5.5 Hz, 1H), 3.20-3.11 (m, 1H), 1.56 (t, J = 8.5 Hz, 1H), 1.30 (q, J = 7.4 Hz, 1H), 0.93 (t, J = 7.3 Hz, 1H), 0.87 (s, 9H) |
| 210 | 1H NMR (400 MHz, DMSO-d6) δ 8.30-8.23 (m, 1H), 8.03 (s, 1H), 7.83 (d, J = 2.3 Hz, 1H), 7.65-7.40 (m, 5H), 7.39-7.16 (m, 6H), 6.54 (s, 2H), 5.43 (td, J = 7.8, 6.2 Hz, 1H), 3.98 (tt, J = 7.5, 4.0 Hz, 1H), 2.14-1.81 (m, 2H), 1.22-1.02 (m, 4H), 0.95-0.83 (m, 3H) |
| 211 | 1H NMR (400 MHz, DMSO-d6) δ 8.32 (s, 1H), 8.02 (s, 1H), 7.80 (d, J = 2.3 Hz, 1H), 7.51-7.37 (m, 4H), 7.35-7.25 (m, 3H), 6.37 (d, J = 5.6 Hz, 1H), 4.01-3.90 (m, 1H), 3.73 (dd, J = 13.7, 7.3 Hz, 1H), 3.53 (dd, J = 13.7, 5.8 Hz, 1H), 1.18-1.02 (m, 4H), 0.84 (s, 9H) |
| 223 | 1H NMR (400 MHz, DMSO-d6) δ 8.35 (d, J = 1.0 Hz, 1H), 8.01 (s, 1H), 7.61 (d, J = 2.2 Hz, 1H), 7.56-7.48 (m, 2H), 7.43 (s, 1H), 7.20-7.10 (m, 2H), 7.07 (d, J = 2.4 Hz, 1H), 4.07-3.88 (m, 2H), 3.52-3.41 (m, 1H), 1.23 (q, J = 7.4 Hz, 2H), 1.19-1.03 (m, 4H), 0.90-0.70 (m, 9H) |
| 239 | 1H NMR (400 MHz, Methanol-d4) δ 8.47 (s, 1H), 7.86 (s, 1H), 7.84-7.82 (m, 1H), 7.78 (ddd, J = 7.9, 1.8, 1.2 Hz, 1H), 7.68 (dt, J = 7.7, 1.4 Hz, 1H), 7.66 (d, J = 2.3 Hz, 1H), 7.55 (td, J = 7.8, 0.6 Hz, 1H), 7.02 (d, J = 2.3 Hz, 1H), 3.94-3.83 (m, 1H), 1.25-1.10 (m, 4H), 0.96 (s, 9H) |
| 240 | 1H NMR (400 MHz, DMSO-d6) δ 8.32 (s, 1H), 8.11 (s, 1H), 7.91 (t, J = 1.7 Hz, 1H), 7.87-7.78 (m, 2H), 7.73 (dt, J = 7.7, 1.4 Hz, 1H), 7.54 (q, J = 8.4, 7.8 Hz, 2H), 7.33 (d, J = 2.5 Hz, 1H), 5.61 (s, 1H), 4.08-3.90 (m, 2H), 3.34 (dd, J = 14.0, 5.1 Hz, 1H), 1.20-1.04 (m, 4H), 0.84 (s, 9H) |
| 243 | 1H NMR (400 MHz, DMSO-d6) δ 8.27 (d, J = 5.4 Hz, 1H), 8.14 (d, J = 2.3 Hz, 1H), 8.03-7.95 (m, 1H), 7.93-7.71 (m, 3H), 7.63-7.47 (m, 4H), 7.43-7.32 (m, 1H), 7.31-7.08 (m, 4H), 5.47 (q, J = 7.4 Hz, 1H), 4.03-3.92 (m, 1H), 2.19-2.05 (m, 1H), 2.03-1.83 (m, 1H), 1.25-1.05 (m, 4H), 0.98-0.82 (m, 3H) |
| 249 | 1H NMR (400 MHz, DMSO-d6) δ 8.26 (s, 1H), 8.01 (s, 1H), 7.69-7.48 (m, 4H), 7.37 (d, J = 5.4 Hz, 0H), 7.32-7.04 (m, 8H), 5.68 (td, J = 8.7, 5.5 Hz, 1H), 4.13-3.86 (m, 1H), 2.79-2.54 (m, 2H), 2.41 (dtd, J = 14.2, 8.2, 5.9 Hz, 1H), 2.31-2.07 (m, 1H), 1.29-0.92 (m, 4H). |
| 252 | 1H NMR (400 MHz, DMSO-d6) δ 8.27 (s, 1H), 8.19 (s, 1H), 8.02 (dd, J = 2.0, 1.4 Hz, 1H), 7.91 (ddd, J = 7.9, 1.8, 1.2 Hz, 1H), 7.79 (dt, J = 7.7, 1.4 Hz, 1H), 7.62 (d, J = 2.2 Hz, 1H), 7.61-7.55 (m, 1H), 7.52 (d, J = 9.9 Hz, 2H), 7.28 (d, J = 2.3 Hz, 1H), 7.22 (qd, J = 3.7, 2.0 Hz, 3H), 7.14 (dd, J = 7.4, 2.1 Hz, 2H), 5.51 (d, J = 7.6 Hz, 1H), 2.14 (s, 1H), 1.93 (d, J = 7.0 Hz, 1H), 1.60 (d, J = 1.4 Hz, 9H), 0.95 (t, J = 7.3 Hz, 3H) |
| 254 | 1H NMR (400 MHz, DMSO-d6) δ 8.31 (d, J = 5.4 Hz, 1H), 8.15 (d, J = 5.6 Hz, 1H), 8.03-7.69 (m, 3H), 7.59 (q, J = 7.7 Hz, 2H), 7.45-7.16 (m, 8H), 5.69 (dtd, J = 31.7, 8.7, 5.5 Hz, 1H), 4.03-3.91 (m, 1H), 2.74-2.17 (m, 4H), 1.25-1.02 (m, 4H) |
| 255 | 1H NMR (400 MHz, DMSO-d6) δ 8.29 (d, J = 1.7 Hz, 1H), 8.04 (d, J = 4.8 Hz, 1H), 7.88 (d, J = 8.8 Hz, 1H), 7.63-7.51 (m, 3H), 7.44-7.13 (m, 9H), 5.78-5.57 (m, 1H), 4.03-3.93 (m, 1H), 2.72-2.51 (m, 2H), 2.49-2.31 (m, 2H), 1.21-1.04 (m, 4H) |
| 256 | 1H NMR (400 MHz, DMSO-d6) δ 8.43 (s, 1H), 8.11 (s, 1H), 8.01 (s, 1H), 7.92 (dd, J = 1.9, 1.4 Hz, 1H), 7.83 (ddd, J = 7.9, 1.8, 1.2 Hz, 1H), 7.73 (dt, J = 7.7, 1.4 Hz, 1H), 7.65 (s, 1H), 7.57-7.48 (m, 1H), 7.31 (dd, J = 12.6, 2.0 Hz, 1H), 6.96 (d, J = 2.1 Hz, 1H), 4.13 (dd, J = 14.0, 8.4 Hz, 1H), 4.01-3.90 (m, 1H), 3.40 (dd, J = 14.0, 5.2 Hz, 1H), 1.20-1.04 (m, 4H), 0.87 (s, 9H) |
| 257 | 1H NMR (400 MHz, DMSO-d6) δ 8.37 (s, 1H), 8.13 (s, 1H), 7.99 (t, J = 1.7 Hz, 1H), 7.93-7.69 (m, 3H), 7.65-7.52 (m, 2H), 7.45-7.17 (m, 7H), 5.57 (q, J = 7.6 Hz, 1H), 4.02-3.92 (m, 1H), 2.25-1.89 (m, 2H), 1.22-1.05 (m, 4H), 1.00-0.84 (m, 3H) |
| 259 | 1H NMR (400 MHz, Methanol-d4) δ 8.24 (s, 1H), 7.87-7.71 (m, 3H), 7.68-7.45 (m, 3H), 7.33-7.16 (m, 4H), 7.13-7.06 (m, 2H), 6.92 (m, 1H), 6.05 (m, 1H), 4.83-4.66 (m, 3H), 3.86-3.70 (m, 2H), 1.18-1.02 (m, 4H). |
| 263 | 1H NMR (400 MHz, DMSO-d6) δ 8.33 (s, 1H), 7.53 (s, 1H), 7.49 (d, J = 2.2 Hz, 1H), 7.46 (ddd, J = 9.0, 5.4, 1.9 Hz, 2H), 7.35 (s, 1H), 7.18-7.07 (m, 3H), 7.03-6.95 (m, 2H), 6.76-6.69 (m, 2H), 5.74-5.55 (m, 2H), 3.84 (dd, J = 13.9, 7.4 Hz, 1H), 3.65 (s, 3H), 3.56 (dd, J = 13.9, 5.9 Hz, 1H), 2.06 (s, 2H), 0.87 (s, 9H). |

TABLE 2-continued

| Cmpd | 1H-NMR |
|---|---|
| 264 | 1H NMR (400 MHz, DMSO-d6) δ 9.65 (s, 1H), 8.49 (s, 1H), 8.10 (s, 1H), 8.06-7.95 (m, 2H), 7.88 (t, J = 1.8 Hz, 1H), 7.85-7.65 (m, 2H), 7.65-7.52 (m, 3H), 7.22 (d, J = 2.4 Hz, 1H), 6.15 (s, 1H), 4.02-3.91 (m, 1H), 1.20-1.03 (m, 4H) |
| 265 | 1H NMR (400 MHz, DMSO-d6) δ 9.60 (s, 1H), 8.48 (s, 1H), 8.08-7.95 (m, 3H), 7.70 (d, J = 2.3 Hz, 1H), 7.46 (d, J = 8.2 Hz, 1H), 7.42-7.17 (m, 5H), 7.07 (tdd, J = 8.1, 2.7, 1.0 Hz, 1H), 6.06 (s, 1H), 4.00-3.90 (m, 1H), 1.19-1.02 (m, 4H) |
| 266 | 1H NMR (400 MHz, DMSO-d6) δ 9.61 (s, 1H), 8.48 (s, 1H), 8.10-7.96 (m, 3H), 7.70 (d, J = 2.2 Hz, 1H), 7.52 (t, J = 1.8 Hz, 1H), 7.48-7.26 (m, 3H), 7.20 (d, J = 2.4 Hz, 1H), 6.06 (s, 1H), 4.01-3.90 (m, 1H), 1.20-1.02 (m, 5H) |
| 268 | 1H NMR (400 MHz, DMSO-d6) δ 8.37 (d, J = 4.8 Hz, 1H), 8.11 (s, 1H), 8.02 (d, J = 0.7 Hz, 1H), 7.58 (t, J = 2.2 Hz, 1H), 7.55-7.46 (m, 2H), 7.38 (s, 1H), 7.22-7.09 (m, 3H), 4.02-3.92 (m, 1H), 3.92-3.71 (m, 2H), 1.77-1.44 (m, 3H), 1.22-1.03 (m, 5H), 0.94 (d, J = 6.3 Hz, 3H), 0.90 (d, J = 6.3 Hz, 3H) |
| 272 | 1H NMR (400 MHz, DMSO-d6) δ 8.26 (s, 1H), 8.08 (s, 1H), 7.64-7.51 (m, 2H), 7.44-7.07 (m, 11H), 6.34 (s, 1H), 5.50 (q, J = 7.4 Hz, 1H), 4.03-3.92 (m, 1H), 2.22-2.05 (m, 1H), 1.98-1.84 (m, 1H), 1.21-1.04 (m, 4H), 0.95 (t, J = 7.3 Hz, 3H) |
| 273 | 1H NMR (400 MHz, DMSO-d6) δ 30.78 (s, 1H), 30.59 (s, 1H), 30.15-29.93 (m, 5H), 29.93-29.63 (m, 8H), 28.83 (s, 1H), 28.00 (q, J = 7.5 Hz, 1H), 26.53-26.43 (m, 1H), 24.73-24.57 (m, 1H), 24.54-24.35 (m, 1H), 23.72-23.54 (m, 4H), 23.45 (t, J = 7.2 Hz, 3H) |
| 284 | 1H NMR (400 MHz, DMSO-d6) δ 8.31 (s, 1H), 8.02 (s, 1H), 7.81 (d, J = 2.3 Hz, 1H), 7.59-7.44 (m, 4H), 7.37 (d, J = 2.5 Hz, 1H), 7.19-7.08 (m, 2H), 4.00-3.88 (m, 2H), 3.43 (dd, J = 13.9, 5.5 Hz, 1H), 1.18-1.03 (m, 4H), 0.86 (s, 9H) |
| 285 | 1H NMR (400 MHz, DMSO-d6) δ 8.27 (s, 1H), 8.03 (s, 1H), 7.83 (d, J = 2.3 Hz, 1H), 7.61-7.46 (m, 5H), 7.30-7.11 (m, 7H), 5.47 (q, J = 7.6 Hz, 1H), 4.02-3.92 (m, 1H), 2.18-2.04 (m, 1H), 1.99-1.85 (m, 1H), 1.20-1.04 (m, 4H), 0.94 (t, J = 7.3 Hz, 3H) |
| 286 | 1H NMR (400 MHz, DMSO-d6) δ 8.75 (s, 1H), 8.38-8.11 (m, 2H), 8.05 (d, J = 7.9 Hz, 1H), 7.77-7.52 (m, 4H), 7.52-7.02 (m, 7H), 6.04-5.81 (m, 1H), 3.97 (dq, J = 11.4, 3.8 Hz, 1H), 3.39-3.22 (m, 2H), 1.33-0.93 (m, 4H) |
| 287 | 1H NMR (400 MHz, DMSO-d6) δ 8.31 (s, 1H), 8.01 (s, 1H), 7.78 (d, J = 2.2 Hz, 1H), 7.71 (s, 1H), 7.57-7.46 (m, 2H), 7.38 (s, 1H), 7.18-7.07 (m, 3H), 4.04-3.89 (m, 2H), 3.46 (dd, J = 13.9, 5.5 Hz, 1H), 1.19-1.03 (m, 4H), 0.87 (s, 9H) |
| 288 | 1H NMR (400 MHz, DMSO-d6) δ 8.24 (s, 1H), 8.02 (s, 1H), 7.78 (d, J = 2.2 Hz, 1H), 7.63-7.51 (m, 2H), 7.48 (d, J = 9.0 Hz, 1H), 7.41-7.31 (m, 1H), 7.31-7.10 (m, 8H), 5.54-5.43 (m, 1H), 4.02-3.92 (m, 1H), 2.21-2.05 (m, 1H), 2.02-1.84 (m, 1H), 1.20-1.04 (m, 4H), 0.95 (t, J = 7.3 Hz, 3H).) |
| 289 | 1H NMR (400 MHz, DMSO-d6) δ 8.31 (s, 1H), 8.09 (s, 1H), 7.90 (dd, J = 7.7, 1.6 Hz, 1H), 7.74 (dd, J = 8.0, 1.6 Hz, 1H), 7.58 (d, J = 2.2 Hz, 1H), 7.50 (t, J = 7.8 Hz, 1H), 7.43 (s, 1H), 6.82 (d, J = 2.4 Hz, 1H), 3.99-3.92 (m, 1H), 3.85 (dd, J = 13.7, 8.1 Hz, 1H), 3.36 (dd, J = 13.7, 4.9 Hz, 1H), 1.18-1.11 (m, 2H), 1.11-1.06 (m, 2H), 0.78 (s, 9H). |
| 290 | 1H NMR (400 MHz, DMSO-d6) δ 8.88 (d, J = 6.4 Hz, 1H), 8.47 (s, 1H), 8.27-8.19 (m, 1H), 8.03 (s, 1H), 7.61 (s, 1H), 7.58-7.49 (m, 2H), 7.44-7.26 (m, 1H), 7.21-7.08 (m, 1H), 7.08-7.02 (m, 1H), 4.06 (dd, J = 14.0, 7.9 Hz, 1H), 4.00-3.89 (m, 1H), 3.58-3.48 (m, 1H), 1.18-1.03 (m, 4H), 0.90 (s, 9H) |
| 291 | 1H NMR (400 MHz, DMSO-d6) δ 8.36 (s, 1H), 8.03 (s, 1H), 7.88 (d, J = 8.7 Hz, 1H), 7.55 (ddt, J = 7.3, 5.4, 2.6 Hz, 2H), 7.43-7.10 (m, 10H), 5.56 (q, J = 7.7 Hz, 1H), 4.01-3.91 (m, 1H), 2.23-2.07 (m, 1H), 2.07-1.89 (m, 1H), 1.20-1.04 (m, 4H), 0.99-0.86 (m, 3H) |
| 293 | 1H NMR (400 MHz, DMSO-d6) δ 9.64 (s, 1H), 8.55 (s, 1H), 8.05 (s, 1H), 7.87-7.73 (m, 2H), 7.68 (d, J = 2.3 Hz, 1H), 7.62-7.48 (m, 2H), 7.44 (dd, J = 7.9, 1.6 Hz, 1H), 7.35 (t, J = 7.9 Hz, 1H), 6.88 (d, J = 2.4 Hz, 1H), 6.17 (d, J = 6.8 Hz, 1H), 4.00-3.90 (m, 1H), 1.20-1.02 (m, 4H) |
| 294 | 1H NMR (400 MHz, DMSO-d6) δ 8.26 (d, J = 2.6 Hz, 1H), 8.07 (d, J = 2.4 Hz, 1H), 7.65-7.44 (m, 5H), 7.42-7.14 (m, 7H), 6.60-6.49 (m, 1H), 5.44 (q, J = 7.4 Hz, 1H), 4.04-3.93 (m, 1H), 2.16-2.00 (m, 1H), 2.01-1.80 (m, 1H), 1.23-1.04 (m, 4H), 0.94-0.82 (m, 3H).) |
| 296 | 1H NMR (400 MHz, Methanol-d4) δ 8.20 (s, 1H), 7.90 (s, 1H), 7.87 (t, J = 1.7 Hz, 1H), 7.82 (dt, J = 7.9, 1.4 Hz, 1H), 7.72-7.61 (m, 1H), 7.58-7.49 (m, 2H), 7.37-7.23 (m, 5H), 7.12 (d, J = 2.4 Hz, 1H), 6.04 (t, J = 6.9 Hz, 1H), 3.88 (m, 1H), 3.22 (d, J = 6.9 Hz, 2H), 1.24-1.11 (m, 4H) |
| 300 | 1H NMR (400 MHz, DMSO-d6) δ 8.26 (s, 1H), 8.03 (s, 1H), 7.63-7.42 (m, 4H), 7.42-7.22 (m, 3H), 7.22-7.01 (m, 5H), 5.48 (q, J = 7.6 Hz, 1H), 4.07-3.87 (m, 1H), 2.12 (dt, J = 14.4, 7.4 Hz, 1H), 1.95 (dt, J = 13.8, 6.8 Hz, 1H), 1.24-1.01 (m, 4H), 0.94 (t, J = 7.2 Hz, 3H) |
| 305 | 1H NMR (400 MHz, DMSO-d6) δ 8.27 (s, 1H), 8.02 (s, 1H), 7.73-7.56 (m, 4H), 7.45 (d, J = 8.3 Hz, 1H), 7.34-7.22 (m, 6H), 7.17 (t, J = 8.9 Hz, 1H), 6.25 (d, J = 8.2 Hz, 1H), 6.02-5.92 (m, 1H), 4.81 (p, J = 6.7 Hz, 1H), 3.34 (m, 2H), 1.49 (d, J = 2.3 Hz, 3H), 1.47 (d, J = 2.3 Hz, 3H) |
| 329 | 1H NMR (400 MHz, DMSO-d6) δ 9.68 (s, 1H), 8.48 (s, 1H), 8.08-7.97 (m, 3H), 7.68 (d, J = 2.3 Hz, 1H), 7.59-7.42 (m, 4H), 7.27-7.09 (m, 5H), 5.64 (d, J = 1.2 Hz, 2H) |
| 330 | 1H NMR (400 MHz, DMSO-d6) δ 9.63 (s, 1H), 8.49 (s, 1H), 8.08-7.97 (m, 3H), 7.71 (d, J = 2.3 Hz, 1H), 7.60-7.45 (m, 3H), 7.28 (d, J = 2.4 Hz, 1H), 7.26-7.13 (m, 2H), 6.43 (s, 1H), 6.30 (s, 1H) |
| 331 | 1H NMR (400 MHz, DMSO-d6) δ 8.28 (s, 1H), 8.04 (s, 1H), 7.71 (d, J = 8.6 Hz, 1H), 7.66-7.53 (m, 3H), 7.53-7.38 (m, 2H), 7.38-7.23 (m, 6H), 7.23-7.07 (m, 3H), 5.98 (td, J = 8.3, 5.8 Hz, 1H), 4.09-3.82 (m, 1H), 3.50-3.25 (m, 2H), 1.29-1.01 (m, 6H) |

TABLE 2-continued

| Cmpd | 1H-NMR |
|---|---|
| 333 | 1H NMR (400 MHz, DMSO-d6) δ 8.35 (s, 1H), 8.01 (s, 1H), 7.73 (s, 1H), 7.60 (d, J = 2.2 Hz, 1H), 7.57-7.47 (m, 2H), 7.42 (s, 1H), 7.26-7.00 (m, 3H), 4.08 (dd, J = 14.1, 8.0 Hz, 1H), 4.01-3.90 (m, 1H), 3.74-3.57 (m, 2H), 3.57-3.41 (m, 3H), 1.45 (ddd, J = 16.3, 10.4, 5.1 Hz, 2H), 1.27-1.02 (m, 6H), 0.94 (s, 3H) |
| 340 | 1H NMR (400 MHz, Methanol-d4) δ 8.29 (s, 1H), 7.78 (s, 1H), 7.76 (d, J = 2.1 Hz, 1H), 7.71-7.66 (m, 1H), 7.60 (dt, J = 7.8, 1.3 Hz, 1H), 7.55 (d, J = 2.3 Hz, 1H), 7.45 (t, J = 7.6 Hz, 1H), 7.32-7.16 (m, 3H), 7.19-7.08 (m, 3H), 5.62 (t, J = 7.1 Hz, 1H), 3.80 (m, 1H), 2.10 (m, 1H), 2.04-1.89 (m, 1H), 1.17-1.01 (m, 4H), 0.92 (t, J = 7.3 Hz, 3H) |
| 341 | 1H NMR (400 MHz, Methanol-d4) δ 8.48 (s, 1H), 7.88-7.80 (m, 2H), 7.78 (dt, J = 8.0, 1.3 Hz, 1H), 7.72-7.64 (m, 2H), 7.55 (t, J = 7.7 Hz, 1H), 7.02 (d, J = 2.3 Hz, 1H), 4.20 (d, J = 14.0 Hz, 1H), 3.88 (m, 1H), 3.71 (d, J = 14.0 Hz, 1H), 1.24-1.10 (m, 4H), 0.96 (s, 9H) |
| 342 | 1H NMR (400 MHz, DMSO-d6) δ 9.61 (s, 1H), 8.47 (s, 1H), 8.05-7.95 (m, 3H), 7.67 (d, J = 2.3 Hz, 1H), 7.53-7.41 (m, 3H), 7.39-7.09 (m, 9H), 5.56 (s, 2H) |
| 343 | 1H NMR (400 MHz, DMSO-d6) δ 8.33 (s, 1H), 7.99 (s, 1H), 7.61 (s, 1H), 7.57 (d, J = 2.2 Hz, 1H), 7.43 (dt, J = 5.9, 3.6 Hz, 2H), 7.29 (dp, J = 7.3, 4.2 Hz, 3H), 6.99 (d, J = 2.4 Hz, 1H), 3.99-3.89 (m, 1H), 3.77 (dd, J = 13.7, 7.3 Hz, 1H), 3.56 (dd, J = 13.7, 5.8 Hz, 1H), 1.15-1.09 (m, 2H), 1.09-1.04 (m, 2H), 0.85 (s, 9H). |
| 344 | 1H NMR (400 MHz, DMSO-d6) δ 9.03 (s, 1H), 8.29 (s, 1H), 7.56-7.47 (m, 3H), 7.40 (s, 2H), 7.26 (s, 1H), 7.24-7.16 (m, 2H), 7.07 (d, J = 2.4 Hz, 1H), 3.80 (dd, J = 14.0, 7.3 Hz, 1H), 3.67 (tt, J = 7.4, 4.2 Hz, 1H), 3.57 (dd, J = 14.0, 6.1 Hz, 1H), 1.12-1.04 (m, 2H), 1.04-0.96 (m, 2H), 0.85 (s, 9H). |
| 351 | 1H NMR (400 MHz, DMSO-d6) δ 9.73 (s, 1H), 8.70 (s, 1H), 8.54-8.31 (m, 1H), 8.11-7.86 (m, 3H), 7.64-7.02 (m, 6H), 3.92 (s, 1H), 1.14-0.96 (m, 4H) |
| 355 | 1H NMR (400 MHz, DMSO-d6) δ 9.55 (d, J = 8.0 Hz, 1H), 8.95 (s, 1H), 8.50 (s, 1H), 7.93 (d, J = 7.4 Hz, 2H), 7.65 (d, J = 2.3 Hz, 1H), 7.53-7.43 (m, 2H), 7.43-7.32 (m, 2H), 7.25-7.15 (m, 2H), 7.12 (d, J = 2.4 Hz, 1H), 1.09-0.95 (m, 4H). |
| 357 | 1H NMR (400 MHz, DMSO-d6) δ 8.22 (s, 1H), 8.00 (s, 1H), 7.57 (d, J = 2.2 Hz, 1H), 7.54-7.49 (m, 1H), 7.48-7.43 (m, 2H), 7.41 (s, 3H), 7.34-7.28 (m, 4H), 7.26-7.20 (m, 5H), 7.19 (d, J = 2.3 Hz, 2H), 5.42 (q, J = 7.5 Hz, 1H), 3.96 (tt, J = 7.4, 3.7 Hz, 1H), 2.05 (dq, J = 14.5, 7.2 Hz, 1H), 1.89 (dq, J = 13.7, 7.3, 6.8 Hz, 1H), 1.20-1.12 (m, 2H), 1.12-1.03 (m, 2H), 0.90 (t, J = 7.3 Hz, 3H). |
| 358 | 1H NMR (400 MHz, DMSO-d6) δ 9.60 (s, 1H), 8.53 (s, 1H), 7.97 (s, 1H), 7.82 (t, J = 2.1 Hz, 1H), 7.73 (ddd, J = 10.9, 8.4, 2.4 Hz, 1H), 7.66 (d, J = 2.4 Hz, 1H), 7.47-7.43 (m, 1H), 7.42 (d, J = 5.3 Hz, 1H), 7.38-7.35 (m, 1H), 7.33-7.25 (m, 2H), 6.88 (d, J = 2.2 Hz, 1H), 3.97-3.89 (m, 1H), 1.16-1.07 (m, 2H), 1.07-1.00 (m, 2H). |
| 359 | 1H NMR (400 MHz, DMSO-d6) δ 9.53 (s, 1H), 8.45 (s, 1H), 8.15 (s, 1H), 7.98 (s, 1H), 7.68 (d, J = 2.3 Hz, 1H), 7.52-7.45 (m, 2H), 7.45 (s, 1H), 7.20 (s, 1H), 7.18-7.11 (m, 2H), 5.56 (tt, J = 9.3, 4.8 Hz, 1H), 4.93-4.81 (m, 2H), 4.71 (m, 2H). |
| 360 | 1H NMR (400 MHz, DMSO-d6) δ 9.53 (s, 1H), 8.45 (s, 1H), 8.01 (s, 1H), 7.96 (d, J = 12.8 Hz, 2H), 7.68 (d, J = 2.3 Hz, 1H), 7.47 (ddd, J = 11.6, 5.9, 3.1 Hz, 3H), 7.19 (d, J = 2.4 Hz, 1H), 7.17-7.09 (m, 2H), 5.00 (dtt, J = 18.1, 7.0, 3.7 Hz, 1H), 4.78-4.71 (m, 1H), 4.67-4.57 (m, 1H), 1.48-1.40 (m, 3H). |
| 361 | 1H NMR (400 MHz, DMSO-d6) δ 9.53 (s, 1H), 8.45 (s, 1H), 7.99 (d, J = 8.9 Hz, 2H), 7.96 (s, 1H), 7.72-7.66 (m, 1H), 7.46 (ddd, J = 8.6, 5.5, 2.6 Hz, 3H), 7.22 (s, 1H), 7.18-7.11 (m, 2H), 6.59-6.25 (m, 1H), 4.90 (td, J = 15.7, 3.3 Hz, 2H). |
| 371 | 1H NMR (400 MHz, DMSO-d6) δ 9.54 (s, 1H), 8.46 (s, 1H), 8.28 (s, 1H), 8.02-7.90 (m, 2H), 7.68 (d, J = 2.3 Hz, 1H), 7.47 (ddd, J = 10.5, 6.3, 3.6 Hz, 3H), 7.19 (d, J = 2.4 Hz, 1H), 7.17-7.07 (m, 2H), 1.79-1.61 (m, 4H). |
| 376 | 1H NMR (400 MHz, DMSO-d6) δ 9.63 (s, 1H), 8.54 (s, 1H), 7.86 (d, J = 2.4 Hz, 1H), 7.83-7.64 (m, 3H), 7.55-7.36 (m, 4H), 7.37-7.27 (m, 2H), 6.93 (s, 1H), 6.22 (d, J = 7.1 Hz, 1H) |
| 377 | 1H NMR (400 MHz, DMSO-d6) δ 9.15 (d, J = 32.1 Hz, 1H), 9.01 (d, J = 3.3 Hz, 1H), 8.57-8.41 (m, 1H), 8.41-7.91 (m, 2H), 7.93-7.79 (m, 2H), 7.76-6.88 (m, 4H), 6.58-6.11 (m, 2H), 5.84 (d, J = 6.0 Hz, 1H) |
| 378 | 1H NMR (400 MHz, DMSO-d6) δ 9.17 (d, J = 24.8 Hz, 1H), 9.02 (s, 1H), 8.33-7.77 (m, 4H), 7.77-6.88 (m, 6H), 6.51-6.33 (m, 1H), 5.92 (d, J = 6.5 Hz, 1H) |
| 379 | 1H NMR (400 MHz, DMSO-d6) δ 8.34 (d, J = 7.0 Hz, 1H), 8.22 (d, J = 5.1 Hz, 1H), 7.62-7.55 (m, 3H), 7.43-7.31 (m, 3H), 7.30-7.11 (m, 5H), 6.39-6.31 (m, 1H), 5.48 (q, J = 7.5 Hz, 1H), 2.22-2.07 (m, 1H), 2.02-1.86 (m, 1H), 1.81-1.63 (m, 4H), 1.30-1.18 (m, 3H), 0.98-0.84 (m, 3H) |
| 381 | 1H NMR (400 MHz, DMSO-d6) δ 9.53 (s, 1H), 8.45 (s, 1H), 8.02 (s, 1H), 7.97 (s, 2H), 7.68 (d, J = 2.3 Hz, 1H), 7.51-7.44 (m, 2H), 7.40 (s, 1H), 7.15 (d, J = 5.2 Hz, 1H), 7.14-7.08 (m, 2H), 1.54 (s, 9H). |
| 382 | 1H NMR (400 MHz, DMSO-d6) δ 9.54 (s, 1H), 8.45 (s, 1H), 7.97 (s, 2H), 7.67 (d, J = 2.3 Hz, 1H), 7.51-7.42 (m, 2H), 7.38 (s, 1H), 7.16 (d, J = 2.4 Hz, 1H), 3.97-3.87 (m, 1H), 1.10 (m, 2H), 1.08-1.02 (m, 2H). |
| 393 | 1H NMR (400 MHz, DMSO-d6) δ 8.88 (s, 1H), 8.85-8.71 (m, 2H), 8.35 (d, J = 2.1 Hz, 1H), 8.08-7.98 (m, 2H), 7.73 (d, J = 9.7 Hz, 1H), 7.66-7.43 (m, 4H), 7.24-7.07 (m, 3H), 6.25 (s, 1H), 3.90 (dd, J = 13.8, 7.6 Hz, 1H), 3.53 (dd, J = 13.9, 5.8 Hz, 1H), 0.83 (s, 9H) |
| 403 | 1H NMR (400 MHz, Methanol-d4) δ 8.52 (s, 1H), 8.01 (t, J = 2.1 Hz, 1H), 7.95 (d, J = 0.6 Hz, 1H), 7.85 (ddd, J = 9.8, 8.2, 2.4 Hz, 1H), 7.69 (d, J = 2.4 Hz, 1H), 7.51-7.45 (m, 2H), 7.17 (dd, J = 2.4, 0.6 Hz, 1H), 7.15-7.04 (m, 2H), 6.06 (s, 1H), 5.09 (d, J = 6.8 Hz, 2H), 4.78-4.71 (m, 2H), 1.92 (s, 3H). |

TABLE 2-continued

| Cmpd | 1H-NMR |
|---|---|
| 405 | 1H NMR D2O exchange (400 MHz, DMSO-d6) δ 8.50 (d, J = 2.1 Hz, 1H), 8.07-7.93 (m, 3H), 7.73 (t, J = 2.2 Hz, 1H), 7.51 (dd, J = 8.1, 5.0 Hz, 2H), 7.27-7.12 (m, 3H), 6.10 (d, J = 3.5 Hz, 1H), 5.00 (dd, J = 21.8, 3.2 Hz, 2H), 4.82-4.70 (m, 2H), 4.63 (dd, J = 20.3, 8.5 Hz, 2H). |
| 406 | 1H NMR (400 MHz, DMSO-d6) δ 9.58 (d, J = 2.9 Hz, 1H), 8.51 (s, 1H), 8.24-8.16 (m, 1H), 8.00 (d, J = 12.9 Hz, 2H), 7.74 (s, 1H), 7.58-7.46 (m, 3H), 7.21 (qd, J = 9.4, 8.8, 2.2 Hz, 3H), 6.20-6.13 (m, 1H), 5.83 (p, J = 7.1 Hz, 1H), 1.77 (dd, J = 6.6, 1.8 Hz, 3H). |
| 407 | 1H NMR (400 MHz, DMSO-d6) δ 9.61 (s, 1H), 8.51 (d, J = 2.1 Hz, 1H), 8.09 (d, J = 2.3 Hz, 1H), 8.06-7.97 (m, 2H), 7.74 (d, J = 2.3 Hz, 1H), 7.61-7.45 (m, 3H), 7.26 (t, J = 2.4 Hz, 1H), 7.20 (tt, J = 8.9, 2.5 Hz, 2H), 6.38 (td, J = 54.7, 3.4 Hz, 1H), 6.15 (s, 1H), 5.41-5.12 (m, 1H), 1.61 (dd, J = 7.3, 4.4 Hz, 3H). |
| 408 | 1H NMR (400 MHz, DMSO-d6) δ 9.60 (s, 1H), 8.69 (d, J = 1.8 Hz, 1H), 8.55-8.46 (m, 1H), 8.01 (d, J = 14.9 Hz, 2H), 7.77 (s, 1H), 7.65-7.47 (m, 6H), 7.32-7.13 (m, 3H), 6.20 (d, J = 7.3 Hz, 1H). |
| 409 | 1H NMR (400 MHz, DMSO-d6) δ 9.56 (s, 1H), 8.45 (s, 1H), 8.05-7.91 (m, 3H), 7.69 (d, J = 2.2 Hz, 1H), 7.47 (ddd, J = 8.7, 5.5, 2.8 Hz, 3H), 7.22 (d, J = 2.4 Hz, 1H), 7.21-7.08 (m, 2H), 6.42 (tt, J = 54.3, 3.3 Hz, 1H), 6.11 (s, 1H), 4.90 (td, J = 15.7, 3.3 Hz, 2H). |
| 410 | 1H NMR (400 MHz, DMSO-d6) δ 9.54 (s, 1H), 8.45 (s, 1H), 8.07 (s, 1H), 7.96 (d, J = 12.1 Hz, 2H), 7.68 (d, J = 2.2 Hz, 1H), 7.51-7.42 (m, 3H), 7.21 (d, J = 2.4 Hz, 1H), 7.19-7.10 (m, 2H), 6.11 (d, J = 7.3 Hz, 1H), 5.74 (s, 2H). |
| 416 | 1H NMR (400 MHz, DMSO-d6) δ 8.28 (s, 1H), 7.88 (s, 1H), 7.66-7.47 (m, 4H), 7.44-7.05 (m, 12H), 6.31 (s, 1H), 5.58-5.39 (m, 1H), 2.23-2.06 (m, 1H), 2.06-1.89 (m, 1H), 1.03-0.87 (m, 3H) |
| 417 | 1H NMR (400 MHz, DMSO-d6) δ 9.45 (s, 1H), 8.47 (s, 1H), 8.25 (s, 1H), 7.97-7.85 (m, 2H), 7.71 (d, J = 2.3 Hz, 1H), 7.53-7.45 (m, 2H), 7.36 (d, J = 9.4 Hz, 1H), 7.22-7.08 (m, 3H), 6.08 (s, 1H), 1.82-1.62 (m, 4H) |
| 420 | 1H NMR (400 MHz, DMSO-d6) δ 8.38 (s, 1H), 8.18 (s, 1H), 7.79 (s, 1H), 7.69-7.35 (m, 3H), 7.31-7.04 (m, 3H), 6.21 (s, 1H), 4.03-3.39 (m, 6H), 2.68 (d, J = 9.0 Hz, 1H), 2.09-1.85 (m, 1H), 1.59 (tq, J = 12.5, 6.8 Hz, 1H) |
| 426 | 1H NMR (400 MHz, DMSO-d6) δ 8.70 (dd, J = 4.1, 0.6 Hz, 1H), 8.23-8.22 (m, 1H), 8.23 (t, J = 56 Hz, 1H), 7.61 (t, J = 2.1 Hz, 1H), 7.50-7.16 (m, 11H), 6.71-6.64 (m, 1H), 5.53-5.25 (m, 1H), 2.15-1.81 (m, 2H), 0.95-0.84 (m, 3H) |
| 427 | 1H NMR (400 MHz, DMSO-d6) δ 8.27 (t, J = 57 Hz, 1H), 8.23 (s, 1H), 7.66 (dd, J = 5.2, 0.7 Hz, 1H), 7.55-7.38 (m, 3H), 7.35-7.08 (m, 9H), 6.67 (dd, J = 8.4, 4.2 Hz, 1H), 5.42-5.25 (m, 1H), 2.09-1.77 (m, 2H), 0.92-0.75 (m, 3H) |
| 428 | 1H NMR (400 MHz, DMSO-d6) δ 8.30 (d, J = 5.6 Hz, 1H), 8.23 (d, J = 7.7 Hz, 1H), 8.15 (d, t = 56 Hz, 1H), 7.61 (t, J = 2.4 Hz, 1H), 7.51-7.17 (m, 11H), 6.70 (t, J = 8.8 Hz, 1H), 5.51-5.28 (m, 1H), 2.15-1.81 (m, 2H), 0.96-0.80 (m, 3H) |
| 430 | 1H NMR (400 MHz, DMSO-d6) δ 9.67 (s, 1H), 8.49 (s, 1H), 8.04 (s, 1H), 8.01-7.90 (m, 2H), 7.71 (d, J = 2.3 Hz, 1H), 7.47 (td, J = 7.9, 1.9 Hz, 1H), 7.42-7.26 (m, 2H), 7.22-7.08 (m, 3H), 6.21 (s, 1H), 4.01-3.89 (m, 1H), 1.18-0.96 (m, 4H) |
| 431 | 1H NMR (400 MHz, DMSO-d6) δ 9.68 (s, 1H), 8.48 (s, 1H), 8.04-7.92 (m, 2H), 7.77 (s, 1H), 7.73 (d, J = 2.3 Hz, 1H), 7.44 (td, J = 7.7, 1.8 Hz, 1H), 7.40-7.28 (m, 2H), 7.25-7.12 (m, 3H), 6.23 (s, 1H), 3.96 (s, 2H), −0.01 (s, 9H) |
| 435 | 1H NMR (400 MHz, DMSO-d6) δ 9.58 (s, 1H), 8.45 (s, 1H), 8.03-7.89 (m, 2H), 7.73 (d, J = 2.2 Hz, 1H), 7.50-7.39 (m, 2H), 7.32 (s, 1H), 7.14-7.04 (m, 4H), 5.88 (s, 1H), 3.84 (s, 3H). |
| 444 | 1H NMR (400 MHz, DMSO-d6) δ 8.31 (s, 1H), 7.89 (d, J = 8.6 Hz, 1H), 7.80 (d, J = 3.5 Hz, 1H), 7.68-7.61 (m, 1H), 7.53-7.42 (m, 1H), 7.41-7.09 (m, 11H), 6.54 (s, 1H), 5.54-5.34 (m, 1H), 2.16-2.00 (m, 1H), 2.04-1.84 (m, 1H), 0.94-0.83 (m, 3H) |
| 445 | 1H NMR (400 MHz, DMSO-d6) δ 8.29 (s, 1H), 7.92-7.83 (m, 1H), 7.79 (d, J = 8.5 Hz, 1H), 7.68-7.60 (m, 1H), 7.49-7.09 (m, 11H), 6.63-6.55 (m, 1H), 5.58-5.44 (m, 1H), 2.16-1.82 (m, 2H), 0.95-0.81 (m, 3H) |
| 446 | 1H NMR (400 MHz, DMSO-d6) δ 8.25 (d, J = 2.9 Hz, 1H), 8.03 (d, J = 2.1 Hz, 1H), 7.70 (d, J = 8.6 Hz, 1H), 7.66-7.59 (m, 1H), 7.56-7.46 (m, 1H), 7.44-7.10 (m, 11H), 6.57-6.46 (m, 1H), 5.47 (td, J = 7.9, 6.3 Hz, 1H), 4.89-4.81 (m, 1H), 4.77-4.62 (m, 3H), 2.16-1.81 (m, 2H), 0.94-0.83 (m, 3H) |
| 447 | 1H NMR (400 MHz, DMSO-d6) δ 9.64 (s, 1H), 8.45 (s, 1H), 7.99-7.90 (m, 2H), 7.77-7.65 (m, 2H), 7.52-7.25 (m, 3H), 7.23-7.05 (m, 3H), 6.26 (d, J = 6.0 Hz, 1H), 4.85 (s, 2H) |
| 448 | 1H NMR (400 MHz, DMSO-d6) δ 9.60 (s, 1H), 8.46 (s, 1H), 8.01-7.89 (m, 2H), 7.80 (s, 1H), 7.70 (d, J = 2.2 Hz, 1H), 7.42 (d, J = 8.5 Hz, 1H), 7.38-7.27 (m, 1H), 7.25 (dd, J = 7.8, 6.1 Hz, 1H), 7.21-7.09 (m, 2H), 6.29 (d, J = 8.1 Hz, 1H), 3.91 (s, 2H) |
| 469 | 1H NMR (400 MHz, DMSO-d6) δ 9.59-9.51 (m, 2H), 8.79 (s, 1H), 8.53-8.32 (m, 1H), 7.99 (s, 1H), 7.94-7.83 (m, 1H), 7.71 (s, 1H), 7.61-7.42 (m, 3H), 7.42-7.23 (m, 5H), 7.18 (dd, J = 6.7, 2.9 Hz, 1H), 6.53 (d, J = 4.1 Hz, 1H), 6.12 (d, J = 7.6 Hz, 1H), 4.95 (s, 1H), 4.42 (t, J = 7.1 Hz, 2H), 3.69-3.41 (m, 2H), 3.23-3.06 (m, 2H), 2.96 (q, J = 10.7, 9.0 Hz, 2H), 2.30-2.09 (m, 2H), 2.07-1.90 (m, 2H), 1.90-1.74 (m, 1H). |
| 470 | 1H NMR (400 MHz, DMSO-d6) δ 9.53 (s, 1H), 9.03 (s, 1H), 8.78 (s, 1H), 8.53-8.33 (m, 1H), 7.99 (s, 1H), 7.89 (s, 1H), 7.71 (s, 1H), 7.64-7.41 (m, 4H), 7.41-7.22 (m, 5H), 7.18 (dd, J = 6.5, 2.9 Hz, 1H), 6.52 (d, J = 4.1 Hz, 1H), 6.10 (d, J = 7.5 Hz, 1H), 4.80 (ddt, J = 11.8, 8.6, 4.4 Hz, 1H), 3.66 (d, J = 12.0 Hz, 2H), 3.12 (q, J = 11.7 Hz, 2H), 2.44-2.30 (m, 1H), 2.30-2.12 (m, 2H), 1.35 (s, 9H). |

TABLE 2-continued

| Cmpd | 1H-NMR |
|---|---|
| 471 | 1H NMR (400 MHz, DMSO-d6) δ 9.65 (s, 1H), 9.01 (s, 2H), 8.78 (s, 1H), 8.50-8.32 (m, 1H), 8.01 (s, 1H), 7.67 (s, 2H), 7.58 (s, 1H), 7.55-7.45 (m, 2H), 7.45-7.22 (m, 5H), 7.18 (dd, J = 6.8, 3.0 Hz, 1H), 6.52 (d, J = 4.1 Hz, 0H), 6.10 (d, J = 7.9 Hz, 1H), 5.06-4.67 (m, 1H), 3.62 (dd, J = 27.7, 13.0 Hz, 3H), 3.21-3.05 (m, 1H), 2.45-2.30 (m, 1H), 2.25 (d, J = 23.7 Hz, 1H), 1.35 (s, 9H). |
| 472 | 1H NMR (400 MHz, DMSO-d6) δ 9.53 (s, 1H), 9.21 (s, 1H), 8.44-8.30 (m, 1H), 8.01 (s, 1H), 7.70 (s, 1H), 7.58-7.43 (m, 3H), 7.43-7.23 (m, 6H), 7.18 (dd, J = 6.7, 3.0 Hz, 1H), 6.52 (d, J = 4.2 Hz, 1H), 6.17 (d, J = 8.6 Hz, 1H), 4.58-4.28 (m, 2H), 3.63-3.41 (m, 1H), 3.13 (dt, J = 10.3, 5.8 Hz, 2H), 2.95 (q, J = 11.7, 9.5 Hz, 3H), 2.26-2.08 (m, 2H), 1.99 (d, J = 6.8 Hz, 2H), 1.83 (dd, J = 7.5, 4.9 Hz, 1H). |
| 473 | 1H NMR (400 MHz, DMSO-d6) δ 9.20 (s, 1H), 8.99 (d, J = 10.4 Hz, 1H), 8.77 (d, J = 5.4 Hz, 1H), 8.44-8.28 (m, 1H), 8.01 (s, 1H), 7.71 (s, 1H), 7.59-7.41 (m, 4H), 7.40-7.21 (m, 5H), 7.18 (dd, J = 6.7, 2.9 Hz, 1H), 6.52 (d, J = 4.1 Hz, 1H), 6.15 (d, J = 8.2 Hz, 1H), 5.02-4.69 (m, 1H), 3.66 (d, J = 12.1 Hz, 2H), 3.12 (d, J = 11.7 Hz, 2H), 2.43-2.31 (m, 2H), 2.23 (d, J = 12.7 Hz, 1H), 1.35 (s, 9H). |
| 489 | 1H NMR (400 MHz, DMSO-d6) δ 9.27 (d, J = 10.7 Hz, 1H), 8.49 (s, 1H), 8.34 (s, 1H), 8.00 (s, 1H), 7.71-7.40 (m, 4H), 7.40-7.13 (m, 4H), 6.17 (d, J = 5.8 Hz, 1H), 4.96-4.71 (m, 1H), 3.85-3.56 (m, 3H), 3.42 (dd, J = 15.5, 6.2 Hz, 1H), 3.13 (dt, J = 12.9, 10.2 Hz, 2H), 2.45-2.14 (m, 4H), 1.36 (s, 9H), 0.09 (s, 9H). |
| 493 | 1H NMR (400 MHz, DMSO-d6) δ 9.63 (s, 1H), 8.47 (s, 1H), 8.07-7.94 (m, 3H), 7.71 (d, J = 2.2 Hz, 1H), 7.57-7.41 (m, 3H), 7.26-7.10 (m, 3H), 6.11 (s, 1H), 4.85 (dd, J = 5.2, 4.1 Hz, 1H), 4.78-4.61 (m, 3H) |
| 514 | 1H NMR (400 MHz, DMSO-d6) δ 9.45 (m, 2H), 8.39 (s, 1H), 7.92 (d, J = 8.0 Hz, 1H), 7.68 (t, J = 1.8 Hz, 1H), 7.53-7.14 (m, 11H), 6.17-5.99 (m, 1H), 5.88 (m, 1H), 4.49 (m, 1H), 4.06 (m, 1H), 3.19 (m, 2H), 3.04 (m, 1H), 2.87 (m, 1H), 2.36-2.17 (m, 2H), 1.23 (t, J = 7.3 Hz, 3H). |
| 515 | 1H NMR (400 MHz, DMSO-d6) δ 9.43 (s, 1H), 8.91 (d, J = 11.2 Hz, 1H), 8.67 (s, 1H), 8.39 (s, 1H), 7.90 (d, J = 7.9 Hz, 1H), 7.68 (dd, J = 2.3, 1.2 Hz, 1H), 7.54-7.15 (m, 10H), 6.08 (s, 1H), 4.66-4.41 (m, 1H), 3.93 (m, 1H) 3.36 (d, J = 12.7 Hz, 2H), 3.01 (d, J = 11.7 Hz, 1H), 2.91-2.70 (m, 1H), 2.35-2.09 (m, 2H). |
| 516 | 1H NMR (400 MHz, DMSO-d6) δ 9.59 (brs, 1H), 9.40 (s, 1H), 8.45 (s, 1H), 7.90 (d, J = 9.0 Hz, 1H), 7.77-7.62 (m, 1H), 7.49-7.14 (m, 10H), 7.09 (ddt, J = 8.2, 2.2, 1.1 Hz, 1H), 5.94 (m, 1H), 4.57-4.38 (m, 1H), 4.05 (m, 1H), 3.60-3.48 (m, 3H), 3.18 (m, 2H), 3.04 (m, 1H), 2.87 (m, 1H), 2.40-2.15 (m, 2H), 1.22 (t, J = 7.3 Hz, 3H). |
| 530 | 1H NMR (400 MHz, DMSO-d6) δ 9.53 (s, 1H), 8.44 (s, 1H), 8.09 (d, J = 0.5 Hz, 1H), 7.71 (s, 1H), 7.56 (dd, J = 8.9, 1.7 Hz, 1H), 7.48-7.19 (m, 8H), 6.12 (d, J = 7.8 Hz, 1H), 5.07 (s, 0H), 4.87 (t, J = 6.9 Hz, 2H), 4.6 (brs, 1H), 3.75 (d, J = 13.9 Hz, 1H), 3.37-3.26 (m, 4H), 2.95 (s, 3H), 1.12 (td, J = 7.2, 2.7 Hz, 6H) |
| 532 | 1H NMR (400 MHz, DMSO-d6) δ 8.47-6.25 (m, 14H), 5.34 (d, J = 7.5 Hz, 1H), 4.04 (s, 3H), 2.11-1.68 (m, 2H), 0.90 (d, J = 9.7 Hz, 3H) |
| 533 | 1H NMR (400 MHz, DMSO-d6) δ 8.26 (d, J = 3.8 Hz, 1H), 7.78 (s, 1H), 7.61 (d, J = 2.2 Hz, 2H), 7.56-7.38 (m, 4H), 7.38-7.16 (m, 8H), 6.57 (d, J = 7.0 Hz, 1H), 5.52-5.29 (m, 1H), 2.17-1.82 (m, 2H), 0.91 (td, J = 7.3, 2.3 Hz, 3H) |
| 534 | 1H NMR (400 MHz, DMSO-d6) δ 9.70-9.44 (m, 1H), 8.44 (s, 1H), 7.98 (s, 1H), 7.70 (d, J = 2.2 Hz, 1H), 7.55 (dd, J = 8.9, 1.7 Hz, 1H), 7.50-7.43 (m, 2H), 7.43-7.19 (m, 5H), 6.06 (s, 1H), 5.58-4.51 (m, 2H), 2.20-2.04 (m, 2H), 1.95-1.80 (m, 2H), 1.80-1.54 (m, 4H) |
| 536 | 1H NMR (400 MHz, DMSO-d6) δ 8.14 (s, 1H), 7.91 (s, 1H), 7.59-7.50 (m, 3H), 7.35-7.25 (m, 5H), 7.25-7.14 (m, 5H), 6.31 (d, J = 8.2 Hz, 1H), 5.41 (q, J = 7.6 Hz, 1H), 4.36 (t, J = 7.0 Hz, 2H), 3.39 (t, J = 6.7 Hz, 2H), 2.15-1.94 (m, 5H), 1.92-1.82 (m, 2H), 1.74 (d, J = 29.8 Hz, 6H), 0.91 (t, J = 7.3 Hz, 3H) |
| 538 | 1H NMR (400 MHz, DMSO-d6) δ 9.03 (s, 1H), 8.22 (s, 1H), 8.00 (s, 1H), 7.69-7.52 (m, 3H), 7.36 (dd, J = 12.1, 6.5 Hz, 3H), 7.30-7.08 (m, 7H), 6.34 (d, J = 7.4 Hz, 1H), 5.46 (q, J = 7.5 Hz, 1H), 4.90-4.72 (m, 1H), 3.68 (d, J = 12.1 Hz, 2H), 3.13 (q, J = 11.7 Hz, 2H), 2.46-2.20 (m, 4H), 2.12 (dd, J = 14.1, 7.0 Hz, 1H), 2.03-1.83 (m, 1H), 1.36 (s, 9H), 0.94 (t, J = 7.3 Hz, 3H) |
| 543 | 1H NMR (400 MHz, DMSO-d6) δ 9.13 (s, 1H), 8.30 (s, 1H), 7.98 (s, 1H), 7.61 (d, J = 2.2 Hz, 2H), 7.57-7.48 (m, 2H), 7.39 (s, 1H), 7.36-7.27 (m, 2H), 7.27-7.19 (m, 1H), 7.16 (d, J = 2.4 Hz, 1H), 6.17 (d, J = 5.0 Hz, 1H), 4.80 (tt, J = 11.6, 4.5 Hz, 1H), 3.95 (dd, J = 13.9, 7.8 Hz, 1H), 3.67 (d, J = 12.0 Hz, 2H), 3.48 (dd, J = 13.9, 5.6 Hz, 1H), 3.12 (q, J = 11.4 Hz, 2H), 2.46-2.17 (m, 4H), 1.36 (s, 9H), 0.89 (s, 9H) |
| 544 | 1H NMR (400 MHz, DMSO-d6) δ 9.45 (s, 1H), 8.39 (s, 1H), 8.16 (s, 1H), 7.69 (d, J = 2.2 Hz, 1H), 7.48-7.42 (m, H), 7.38-7.31 (m, 3H), 7.27 (dd, J = 6.6, 1.9 Hz, 2H), 7.25-7.19 (m, 1H), 6.16-6.06 (m, 1H), 4.97 (s, 2H), 4.70 (dd, J = 14.1, 8.7 Hz, 2H), 4.61 (d, J = 8.7 Hz, 1H), 4.54 (d, J = 8.7 Hz, 1H), 3.49-3.27 (m, 4H), 1.91 (s, 4H). |
| 545 | 1H NMR (400 MHz, DMSO-d6) δ 9.55 (s, 1H), 9.42 (s, 1H), 8.40 (d, J = 2.2 Hz, 1H), 7.95 (d, J = 2.2 Hz, 1H), 7.68 (t, J = 2.3 Hz, 1H), 7.51-7.38 (m, 4H), 7.32 (ddd, J = 8.7, 7.2, 2.1 Hz, 2H), 7.28-7.18 (m, 3H), 6.06 (d, J = 6.9 Hz, 1H), 4.45-4.36 (m, 2H), 3.52 (d, J = 11.2 Hz, 2H), 3.12 (q, J = 7.1 Hz, 2H), 2.94 (p, J = 7.6 Hz, 2H), 2.16 (qd, J = 8.1, 5.7 Hz, 1H), 1.96 (d, J = 7.6 Hz, 3H), 1.89-1.75 (m, 3H). |
| 546 | 1H NMR (400 MHz, DMSO-d6) δ 9.75 (s, 1H), 9.43 (s, 1H), 8.40 (d, J = 2.3 Hz, 1H), 8.00 (d, J = 2.2 Hz, 1H), 7.68 (t, J = 2.4 Hz, 1H), 7.49-7.39 (m, 4H), 7.34 (qd, J = 7.4, 3.8 Hz, 2H), 7.24 (tdd, J = 9.0, 6.7, 2.4 Hz, 3H), 6.18-6.00 (m, 1H), 4.71 (ddd, J = 7.8, 4.5, 1.9 Hz, 2H), 3.66 (dd, J = 7.9, 3.9 Hz, 2H), 3.45 (s, 2H), 2.98 (d, J = 10.4 Hz, 2H), 1.93 (d, J = 7.8 Hz, 2H), 1.81 (dd, J = 15.4, 8.6 Hz, 2H). |

TABLE 2-continued

| Cmpd | 1H-NMR |
|---|---|
| 548 | 1H NMR (400 MHz, Methanol-d4) δ 8.46 (s, 1H), 7.83 (s, 1H), 7.67 (d, J = 2.4 Hz, 1H), 7.59-7.51 (m, 1H), 7.48-7.28 (m, 5H), 7.27-7.18 (m, 2H), 6.03 (s, 1H), 4.81-4.73 (m, 1H), 3.80 (d, J = 12.6 Hz, 2H), 3.61 (m, 2H), 3.28-3.17 (m, 2H), 2.48 (m, 4H), 2.37 (m, 2H), 1.92 (m, 4H), 1.46 (s, 9H) |
| 555 | 1H NMR (400 MHz, DMSO-d6) δ 9.08 (s, 1H), 8.31 (s, 1H), 8.00 (s, 1H), 7.59 (d, J = 2.1 Hz, 1H), 7.57-7.51 (m, 2H), 7.41 (s, 1H), 7.38-7.21 (m, 3H), 7.14 (d, J = 2.4 Hz, 1H), 6.13 (d, J = 6.0 Hz, 1H), 4.80 (td, J = 11.7, 5.9 Hz, 1H), 3.90 (dd, J = 13.3, 6.6 Hz, 1H), 3.76-3.60 (m, 3H), 3.12 (q, J = 11.7, 11.1 Hz, 2H), 2.29 (dt, J = 36.9, 12.2 Hz, 4H), 1.36 (s, 10H), 1.15 (d, J = 3.8 Hz, 6H) |
| 564 | 1H NMR (400 MHz, Methanol-d4) δ 8.40 (s, 1H), 7.95 (s, 1H), 7.64 (d, J = 2.2 Hz, 1H), 7.55-7.46 (m, 1H), 7.40 (m, 2H), 7.31 (m, 7H), 6.28 (s, 1H), 5.74 (t, J = 7.2 Hz, 1H), 4.87-4.76 (m, 1H), 3.81 (d, J = 12.7 Hz, 2H), 3.23 (t, J = 11.6 Hz, 2H), 3.17 (s, 3H), 2.55-2.35 (m, 4H), 2.20 (m, 1H), 2.07 (m, 1H), 1.62 (s, 3H), 1.46 (s, 9H), 1.01 (t, J = 7.3 Hz, 3H) |
| 567 | 1H NMR (400 MHz, Methanol-d4) δ 8.48 (s, 1H), 7.78 (s, 1H), 7.68 (d, J = 2.3 Hz, 1H), 7.59-7.56 (m, 2H), 7.47-7.33 (m, 4H), 7.26 (d, J = 2.4 Hz, 1H), 6.06 (s, 1H), 4.84-4.76 (m, 1H), 3.27 (s, 3H), 2.82 (s, 3H), 1.53 (dd, J = 6.7, 1.6 Hz, 6H) |
| 569 | 1H NMR (400 MHz, DMSO-d6) δ 9.23 (s, 1H), 8.23 (d, J = 4.9 Hz, 1H), 8.01 (d, J = 2.8 Hz, 1H), 7.68-7.52 (m, 4H), 7.45-7.14 (m, 11H), 6.32 (d, J = 3.4 Hz, 1H), 5.80-5.68 (m, 1H), 4.83 (tt, J = 11.7, 4.4 Hz, 1H), 3.13 (dt, J = 14.6, 10.7 Hz, 2H), 2.43-2.21 (m, 4H), 1.67 (d, J = 6.7, 3.7 Hz, 3H), 1.36 (s, 9H) |
| 570 | 1H NMR (400 MHz, DMSO-d6) δ 9.69 (s, 1H), 9.39 (s, 1H), 8.40 (s, 1H), 7.99 (s, 1H), 7.68 (d, J = 2.2 Hz, 1H), 7.56 (t, J = 1.8 Hz, 1H), 7.48 (dt, J = 7.7, 1.6 Hz, 1H), 7.46-7.40 (m, 2H), 7.40 (m, 2H), 7.22-7.15 (m, 2H), 6.11-6.04 (m, 1H), 4.77 (p, J = 6.7 Hz, 1H), 4.29 (d, J = 5.6 Hz, 2H), 3.34-3.16 (m, 2H), 2.99 (ddt, J = 21.0, 15.3, 7.9 Hz, 2H), 1.90 (q, J = 5.0, 4.3 Hz, 2H), 1.72 (p, J = 8.5 Hz, 2H), 1.45 (d, J = 2.1 Hz, 3H), 1.43 (d, J = 2.1 Hz, 3H). |
| 572 | 1H NMR (400 MHz, DMSO-d6) δ 9.47 (brs, 1H), 8.99 (brs, 1H), 8.39 (d, J = 27.5 Hz, 1H), 8.01 (s, 1H), 7.75-7.65 (m, 1H), 7.64-7.17 (m, 7H), 6.12 (d, J = 7.8 Hz, 1H), 4.79 (ddt, J = 11.5, 8.2, 4.3 Hz, 1H), 3.71-3.56 (m, 2H), 3.10 (q, J = 11.5 Hz, 2H), 2.90 (s, 3H), 2.73 (s, 3H), 2.42-2.30 (m, 2H), 2.23 (t, J = 12.9 Hz, 2H), 1.34 (s, 9H). |
| 574 | 1H NMR (400 MHz, DMSO-d6) δ 9.43 (s, 1H), 8.40 (s, 1H), 8.02 (s, 1H), 7.67 (d, J = 2.2 Hz, 1H), 7.47 (dd, J = 6.6, 2.7 Hz, 1H), 7.45-7.38 (m, 4H), 7.36-7.28 (m, 3H), 7.27-7.19 (m, 4H), 6.04 (d, J = 5.7 Hz, 1H), 4.73 (t, J = 7.5 Hz, 3H), 4.58 (dd, J = 8.0, 5.0 Hz, 3H), 4.38 (s, 1H), 4.11 (s, 1H), 3.80 (s, 1H), 3.28 (s, 2H), 2.63 (d, J = 15.7 Hz, 3H). |
| 575 | 1H NMR (400 MHz, DMSO-d6) δ 9.74 (s, 1H), 9.43 (s, 1H), 8.40 (s, 1H), 7.75 (d, J = 3.0 Hz, 1H), 7.68 (d, J = 2.2 Hz, 1H), 7.54 (t, J = 1.7 Hz, 1H), 7.50-7.35 (m, 6H), 7.21 (qd, J = 5.1, 4.7, 2.7 Hz, 3H), 6.13 (d, J = 6.8 Hz, 1H), 4.29 (d, J = 5.7 Hz, 2H), 3.40-3.17 (m, 2H), 3.10-2.94 (m, 2H), 1.91 (tdd, J = 12.7, 9.0, 4.6 Hz, 2H), 1.84-1.65 (m, 2H). |
| 577 | 1H NMR (400 MHz, DMSO-d6) δ 9.40 (s, 1H), 9.19 (s, 1H), 8.66 (s, 1H), 8.39 (s, 1H), 8.01 (s, 1H), 7.66 (d, J = 2.2 Hz, 1H), 7.46 (dd, J = 6.6, 2.7 Hz, 1H), 7.45-7.38 (m, 3H), 7.34-7.29 (m, 3H), 7.27-7.18 (m, 3H), 6.03 (d, J = 7.3 Hz, 1H), 3.90 (t, J = 2.5 Hz, 1H), 3.59-3.49 (m, 2H), 3.44 (q, J = 9.5, 8.5 Hz, 2H), 2.56 (q, J = 2.2 Hz, 2H). |
| 582 | 1H NMR (400 MHz, DMSO-d6) δ 9.61 (s, 1H), 8.46 (s, 1H), 8.06-7.97 (m, 2H), 7.72 (d, J = 2.3 Hz, 2H), 7.50-7.40 (m, 4H), 7.32 (tt, J = 6.7, 0.8 Hz, 3H), 7.29-7.19 (m, 3H), 6.12 (s, 1H). |
| 586 | 1H NMR (400 MHz, DMSO-d6) δ 8.83 (s, 1H), 8.45-8.34 (m, 1H), 8.00 (s, 1H), 7.68-7.48 (m, 4H), 7.44-7.13 (m, 5H), 6.22 (s, 1H), 4.86-4.70 (m, 1H), 4.50-4.38 (m, 1H), 1.91-1.29 (m, 10H), 0.93 (t, J = 7.4 Hz, 3H) |
| 587 | 1H NMR (400 MHz, DMSO-d6) δ 9.15 (s, 1H), 8.33 (s, 1H), 7.99 (s, 1H), 7.61-7.49 (m, 3H), 7.39-7.17 (m, 6H), 6.23 (s, 1H), 4.87-4.73 (m, 1H), 4.44-4.31 (m, 1H), 3.12 (q, J = 11.1 Hz, 2H), 2.39-2.17 (m, 5H), 1.89-1.73 (m, 1H), 1.71-1.55 (m, 1H), 1.40-1.28 (m, 13H), 0.91 (t, J = 7.4 Hz, 3H) |
| 588 | 1H NMR (400 MHz, DMSO-d6) δ 8.27 (s, 1H), 8.01 (s, 1H), 7.77 (d, J = 8.6 Hz, 1H), 7.67-7.52 (m, 3H), 7.44 (s, 1H), 7.43-7.14 (m, 10H), 6.29 (s, 1H), 5.77 (p, J = 6.9 Hz, 1H), 4.81 (p, J = 6.7 Hz, 1H), 1.69 (d, J = 6.7 Hz, 3H), 1.59-1.39 (m, 6H) |
| 589 | 1H NMR (400 MHz, DMSO-d6) δ 8.38 (s, 1H), 8.02 (d, J = 16.9 Hz, 1H), 7.66-7.46 (m, 3H), 7.44-7.14 (m, 7H), 4.78 (dhept, J = 15.7, 6.7 Hz, 1H), 4.37 (qd, J = 8.0, 5.7 Hz, 1H), 3.24 (s, 1H), 1.85-1.59 (m, 2H), 1.59-1.29 (m, 11H) |
| 590 | 1H NMR (400 MHz, DMSO-d6) δ 9.08-9.03 (m, 1H), 8.31 (s, 1H), 7.99 (s, 1H), 7.60-7.47 (m, 3H), 7.42-7.15 (m, 6H), 6.22 (d, J = 6.5 Hz, 1H), 4.88-4.74 (m, 1H), 4.32 (p, J = 7.2 Hz, 1H), 3.19-3.05 (m, 2H), 2.42-2.33 (m, 2H), 2.31-2.20 (m, 2H), 1.81-1.58 (m, 2H), 1.40-1.27 (m, 13H), 0.77 (t, J = 7.3 Hz, 3H) |
| 591 | 1H NMR (400 MHz, DMSO-d6) δ 9.48 (s, 1H), 8.39 (d, J = 11.8 Hz, 1H), 7.98 (s, 1H), 7.70 (d, J = 2.2 Hz, 1H), 7.56-7.43 (m, 3H), 7.42-7.14 (m, 7H), 6.11-6.06 (m, 1H), 4.78 (hept, J = 6.7 Hz, 1H), 1.44 (dd, J = 6.7, 1.0 Hz, 6H).) |
| 592 | 1H NMR (400 MHz, DMSO-d6) δ 8.27 (s, 1H), 7.99 (s, 1H), 7.68-7.52 (m, 4H), 7.48-7.14 (m, 11H), 6.32 (s, 1H), 5.51 (q, J = 7.6 Hz, 1H), 4.88-4.73 (m, 1H), 2.23-2.07 (m, 2H), 2.04-1.86 (m, 1H), 1.47 (dd, J = 6.6, 1.5 Hz, 6H), 0.99-0.87 (m, 3H) |
| 596 | 1H NMR (400 MHz, DMSO-d6) δ 9.03 (d, J = 11.0 Hz, 1H), 8.29 (d, J = 4.4 Hz, 1H), 7.97 (d, J = 4.4 Hz, 1H), 7.62-7.43 (m, 2H), 7.41-7.12 (m, 5H), 6.97 (d, J = 6.5 Hz, 1H), 6.27 (dd, J = 13.8, 6.6 Hz, 1H), 4.88-4.64 (m, 1H), 4.52 (d, J = 8.5 Hz, 1H), 3.67 (d, J = 11.9 Hz, 2H), 3.13 (s, 2H), 2.43-2.05 (m, 5H), 1.61-1.42 (m, 1H), 1.41-1.29 (m, 9H), 1.25-1.12 (m, 2H) |

TABLE 2-continued

| Cmpd | 1H-NMR |
|---|---|
| 597 | 1H NMR (400 MHz, DMSO-d6) δ 9.02 (d, J = 14.1 Hz, 1H), 8.34-8.23 (m, 1H), 7.99 (s, 1H), 7.98-7.91 (m, 1H), 7.67-7.46 (m, 2H), 7.42-7.30 (m, 1H), 7.30-7.17 (m, 2H), 6.23 (d, J = 7.2 Hz, 1H), 4.89-4.71 (m, 1H), 4.21 (d, J = 10.3 Hz, 1H), 3.88 (s, 1H), 3.67 (d, J = 12.2 Hz, 2H), 3.13 (q, J = 11.8 Hz, 2H), 2.46-2.16 (m, 3H), 2.07-1.86 (m, 1H), 1.86-1.70 (m, 2H), 1.70-1.45 (m, 2H), 1.36 (s, 9H) |
| 600 | 1H NMR (400 MHz, Methanol-d4) δ 8.40 (d, J = 1.3 Hz, 1H), 7.90 (s, 1H), 7.68-7.59 (m, 2H), 7.53 (s, 1H), 7.46 (t, J = 7.4 Hz, 1H), 7.42-7.37 (m, 2H), 7.38-7.26 (m, 5H), 6.28 (s, 1H), 5.74 (t, J = 7.2 Hz, 1H), 4.85-4.78 (m, 1H), 3.81 (d, J = 12.5 Hz, 2H), 3.23 (t, J = 12.5 Hz, 2H), 3.04 (s, 3H), 2.82 (s, 3H), 2.57-2.32 (m, 4H), 2.27-2.01 (m, 2H), 1.46 (s, 9H), 1.01 (t, J = 7.4 Hz, 3H) |
| 608 | 1H NMR (400 MHz, Methanol-d4) δ 8.45 (s, 1H), 7.86 (s, 1H), 7.67 (d, J = 2.4 Hz, 1H), 7.57 (d, J = 7.6 Hz, 1H), 7.53-7.43 (m, 3H), 7.37 (d, J = 7.7 Hz, 1H), 7.34-7.28 (m, 1H), 7.24 (t, J = 8.0 Hz, 1H), 7.19 (d, J = 2.4 Hz, 1H), 6.09 (s, 1H), 4.83-4.72 (m, 1H), 3.80 (d, J = 12.5 Hz, 2H), 3.22 (t, J = 12.4 Hz, 2H), 3.05 (s, 3H), 2.87 (s, 3H), 2.52-2.31 (m, 4H), 1.46 (s, 9H) |
| 609 | 1H NMR D2O exchange (400 MHz, DMSO-d6) δ 8.40 (s, 1H), 7.93 (s, 1H), 7.65 (d, J = 2.3 Hz, 1H), 7.49 (dd, J = 6.6, 2.7 Hz, 1H), 7.47-7.38 (m, 4H), 7.33-7.27 (m, 3H), 7.27-7.18 (m, 4H), 6.02 (s, 1H), 3.94-3.84 (m, 1H), 1.06 (m, 4H). |
| 610 | 1H NMR (400 MHz, DMSO-d6) δ 9.54 (s, 1H), 8.41 (s, 1H), 7.80 (s, 1H), 7.69 (d, J = 2.2 Hz, 1H), 7.50 (dd, J = 6.6, 2.6 Hz, 1H), 7.47-7.40 (m, 3H), 7.35-7.29 (m, 2H), 7.29 (d, J = 2.3 Hz, 1H), 7.27-7.21 (m, 2H), 6.09 (s, 1H), 4.22 (s, 2H), 1.01 (d, J = 1.6 Hz, 6H). |
| 613 | 1H NMR (400 MHz, DMSO-d6) δ 9.55-9.47 (m, 1H), 8.42 (s, 1H), 7.78-7.68 (m, 2H), 7.57-7.20 (m, 11H), 6.15 (s, 1H) |
| 614 | 1H NMR (400 MHz, DMSO-d6) δ 10.38 (s, 1H), 9.49 (s, 1H), 8.33 (s, 1H), 7.79 (s, 1H), 7.66 (d, J = 2.3 Hz, 1H), 7.56-7.29 (m, 5H), 7.13 (dd, J = 8.7, 2.6 Hz, 1H), 7.00 (d, J = 8.6 Hz, 1H), 6.20 (d, J = 6.9 Hz, 1H) |
| 623 | 1H NMR (400 MHz, Methanol-d4) δ 8.44 (s, 1H), 7.92 (s, 1H), 7.65 (d, J = 2.3 Hz, 1H), 7.50-7.42 (m, 3H), 7.39 (s, 1H), 7.32 (t, J = 8.8 Hz, 1H), 7.25 (d, J = 6.3 Hz, 2H), 7.18 (d, J = 2.4 Hz, 1H), 6.07 (s, 1H), 4.85-4.75 (m, 1H), 3.80 (d, J = 12.6 Hz, 2H), 3.22 (t, J = 12.4 Hz, 1H), 3.18 (s, 3H), 2.49-2.36 (m, 4H), 1.71 (s, 3H), 1.46 (s, 9H) |
| 626 | 1H NMR (400 MHz, DMSO-d6) δ 8.26 (s, 1H), 7.59 (d, J = 2.0 Hz, 1H), 7.53-7.14 (m, 14H), 6.57 (s, 1H), 5.40-5.29 (m, 2H), 1.97-1.87 (m, 1H), 1.78 (s, 1H), 0.83-0.75 (m, 3H) |
| 627 | 1H NMR (400 MHz, DMSO-d6) δ 8.30 (s, 1H), 7.76 (q, J = 8.3, 7.3 Hz, 2H), 7.64 (d, J = 2.1 Hz, 1H), 7.60-7.44 (m, 3H), 7.44-7.19 (m, 10H), 6.36 (s, 1H), 5.60-5.46 (m, 1H), 2.13 (tq, J = 14.0, 7.0 Hz, 1H), 1.95 (dp, J = 14.1, 7.6 Hz, 1H), 0.95 (t, J = 7.3 Hz, 3H) |
| 628 | 1H NMR (400 MHz, DMSO-d6) δ 9.49 (s, 1H), 9.23-9.13 (m, 1H), 8.41 (d, J = 1.1 Hz, 1H), 7.99 (s, 1H), 7.73-7.68 (m, 1H), 7.56-7.21 (m, 8H), 6.11 (d, J = 4.0 Hz, 1H), 4.87-4.74 (m, 1H), 3.69-3.61 (m, 2H), 3.19-3.05 (m, 2H), 2.57-2.47 (m, 1H), 2.39-2.16 (m, 4H), 1.35 (s, 9H) |
| 629 | 1H NMR (400 MHz, DMSO-d6) δ 9.22 (t, J = 9.9 Hz, 1H), 8.23 (s, 1H), 8.00 (s, 1H), 7.64-7.54 (m, 3H), 7.50-7.14 (m, 10H), 6.34 (d, J = 4.0 Hz, 1H), 5.48 (q, J = 7.4 Hz, 1H), 4.82 (tt, J = 11.9, 4.4 Hz, 1H), 3.67 (d, J = 12.0 Hz, 2H), 3.13 (dt, J = 14.5, 10.6 Hz, 2H), 2.42-2.20 (m, 4H), 2.21-2.06 (m, 1H), 2.02-1.84 (m, 1H), 1.36 (s, 9H), 1.02-0.87 (m, 3H) |
| 631 | 1H NMR (400 MHz, DMSO-d6) δ 9.48 (s, 1H), 8.39 (d, J = 6.2 Hz, 1H), 7.80 (s, 1H), 7.69 (d, J = 2.1 Hz, 1H), 7.59-7.37 (m, 4H), 7.33 (q, J = 6.9 Hz, 2H), 6.18 (d, J = 7.4 Hz, 1H) |
| 638 | 1H NMR (400 MHz, DMSO-d6) δ 9.68 (s, 1H), 8.32 (s, 1H), 8.15 (d, J = 0.9 Hz, 1H), 7.82-7.70 (m, 3H), 7.67 (d, J = 2.3 Hz, 1H), 7.49-7.38 (m, 5H), 7.35 (dd, J = 8.9, 2.0 Hz, 1H), 7.33-7.22 (m, 3H), 7.22-7.16 (m, 2H), 6.18 (d, J = 7.5 Hz, 1H), 5.72 (s, 3H) |
| 639 | 1H NMR (400 MHz, DMSO-d6) δ 9.40 (s, 1H), 8.41 (d, J = 19.9 Hz, 1H), 7.79 (s, 1H), 7.69 (d, J = 2.2 Hz, 1H), 7.57-7.43 (m, 4H), 7.43-7.35 (m, 4H), 7.29 (d, J = 2.4 Hz, 1H), 6.15 (d, J = 7.3 Hz, 1H) |
| 640 | 1H NMR (400 MHz, DMSO-d6) δ 9.23 (s, 1H), 8.74 (s, 1H), 8.37 (d, J = 5.8 Hz, 1H), 7.81 (s, 1H), 7.69 (s, 1H), 7.55-7.44 (m, 2H), 7.45-7.34 (m, 3H), 7.34-7.22 (m, 2H), 7.21-7.14 (m, 1H), 6.20 (d, J = 8.0 Hz, 1H) |
| 644 | 1H NMR (400 MHz, DMSO-d6) δ 8.42 (s, 1H), 7.78-7.63 (m, 2H), 7.53 (dd, J = 8.8, 1.7 Hz, 1H), 7.48-7.17 (m, 9H), 6.11 (s, 1H). |
| 645 | 1H NMR (400 MHz, Methanol-d4) δ 8.44 (s, 1H), 7.87 (s, 1H), 7.78 (s, 1H), 7.69-7.58 (m, 3H), 7.50 (d, J = 7.8 Hz, 1H), 7.48-7.41 (m, 1H), 7.37-7.21 (m, 1H), 7.17 (d, J = 2.4 Hz, 1H), 6.11 (s, 1H), 4.83-4.75 (m, 1H), 4.52 (br s, 4H), 3.80 (d, J = 12.2 Hz, 2H), 3.22 (t, J = 11.8 Hz, 2H), 2.55-2.30 (m, 4H), 1.46 (s, 9H) |
| 646 | 1H NMR (400 MHz, Methanol-d4) δ 8.43 (s, 1H), 7.85 (s, 1H), 7.74 (s, 1H), 7.66 (d, J = 2.4 Hz, 1H), 7.63 (d, J = 7.8 Hz, 1H), 7.58 (d, J = 7.7 Hz, 1H), 7.52-7.41 (m, 2H), 7.31 (t, J = 8.8 Hz, 1H), 7.27-7.20 (m, 1H), 7.16 (d, J = 2.4 Hz, 1H), 6.10 (s, 1H), 5.31 (d, J = 57.3 Hz, 1H), 4.83-4.71 (m, 1H), 4.50-4.10 (m, 4H), 3.80 (d, J = 12.5 Hz, 2H), 3.21 (t, J = 12.9 Hz, 2H), 2.58-2.28 (m, 4H), 1.46 (s, 9H) |
| 647 | 1H NMR (400 MHz, DMSO-d6) δ 9.38 (s, 1H), 8.39 (d, J = 4.8 Hz, 1H), 7.85-7.71 (m, 3H), 7.69 (d, J = 2.1 Hz, 1H), 7.52-7.43 (m, 2H), 7.43-7.37 (m, 2H), 7.33 (d, J = 4.2 Hz, 1H), 7.19 (d, J = 5.5 Hz, 1H), 6.19 (d, J = 7.7 Hz, 1H), 5.25 (s, 1H), 1.32-1.09 (m, 2H) |

TABLE 2-continued

| Cmpd | 1H-NMR |
|---|---|
| 648 | 1H NMR (400 MHz, DMSO-d6) δ 9.42 (s, 1H), 8.73 (s, 1H), 8.35 (s, 1H), 7.78 (s, 1H), 7.66 (d, J = 2.2 Hz, 1H), 7.53-7.46 (m, 3H), 7.46-7.38 (m, 7H), 7.38-7.30 (m, 2H), 7.30-7.22 (m, 2H), 6.17 (d, J = 7.9 Hz, 1H), 5.24 (s, 2H) |
| 649 | 1H NMR (400 MHz, DMSO-d6) δ 9.43 (s, 1H), 8.34 (s, 1H), 7.78 (s, 1H), 7.66 (d, J = 2.2 Hz, 1H), 7.51-7.44 (m, 2H), 7.44-7.36 (m, 3H), 7.33 (s, 1H), 7.28-7.13 (m, 2H), 6.18 (d, J = 7.9 Hz, 1H), 4.15 (t, J = 7.0 Hz, 2H), 1.38 (t, J = 7.0 Hz, 3H) |
| 650 | 1H NMR (400 MHz, DMSO-d6) δ 9.47 (s, 1H), 9.09 (s, 2H), 8.79 (d, J = 4.5 Hz, 1H), 8.43-8.35 (m, 1H), 8.03 (s, 1H), 7.69 (d, J = 1.9 Hz, 1H), 7.51 (d, J = 8.5 Hz, 2H), 7.47-7.37 (m, 2H), 7.37-7.27 (m, 1H), 7.22-7.14 (m, 1H), 6.53 (d, J = 4.1 Hz, 1H), 6.15 (d, J = 8.3 Hz, 1H), 4.95 (s, 1H), 4.80 (ddt, J = 11.7, 8.6, 4.3 Hz, 1H), 3.66 (d, J = 12.1 Hz, 2H), 3.19-3.06 (m, 2H), 2.36 (d, J = 13.5 Hz, 2H), 2.24 (q, J = 13.0 Hz, 2H), 1.36 (s, 9H), 1.31 (d, J = 11.0 Hz, 2H) |
| 651 | 1H NMR (400 MHz, DMSO-d6) δ 9.36 (s, 1H), 8.99 (s, 1H), 8.39 (d, J = 7.7 Hz, 1H), 8.02 (s, 1H), 7.84-7.66 (m, 3H), 7.62 (d, J = 7.6 Hz, 1H), 7.55-7.38 (m, 4H), 7.38-7.28 (m, 1H), 7.18 (d, J = 4.3 Hz, 1H), 6.15 (d, J = 8.5 Hz, 1H), 4.95 (s, 1H), 4.86-4.75 (m, 1H), 3.66 (d, J = 12.2 Hz, 2H), 3.12 (q, J = 11.6 Hz, 2H), 2.36 (d, J = 13.8 Hz, 2H), 2.23 (q, J = 13.0 Hz, 2H), 1.35 (s, 9H) |
| 652 | 1H NMR (400 MHz, DMSO-d6) δ 9.37 (s, 1H), 8.97 (s, 1H), 8.44 (s, 1H), 8.38 (d, J = 2.6 Hz, 0H), 8.15 (s, 1H), 8.01 (s, 1H), 7.69 (s, 1H), 7.58-7.44 (m, 3H), 7.45-7.33 (m, 4H), 7.33-7.22 (m, 1H), 7.18 (d, J = 4.1 Hz, 1H), 6.52 (d, J = 4.2 Hz, 1H), 6.11 (d, J = 8.3 Hz, 1H), 4.85-4.74 (m, 1H), 3.66 (d, J = 12.1 Hz, 2H), 3.12 (q, J = 11.4 Hz, 2H), 2.36 (d, J = 12.5 Hz, 2H), 2.23 (q, J = 12.8 Hz, 2H), 1.35 (s, 9H) |
| 653 | 1H NMR (400 MHz, DMSO-d6) δ 9.22 (s, 1H), 9.01 (s, 1H), 8.38 (d, J = 4.7 Hz, 1H), 8.04 (s, 1H), 7.69 (s, 1H), 7.61-7.47 (m, 2H), 7.47-7.40 (m, 2H), 7.37 (d, J = 9.2 Hz, 1H), 7.34-7.22 (m, 2H), 6.16 (d, J = 8.5 Hz, 1H), 4.89-4.73 (m, 1H), 3.66 (d, J = 12.2 Hz, 2H), 3.13 (dd, J = 21.9, 10.6 Hz, 2H), 2.36 (d, J = 14.1 Hz, 2H), 2.24 (d, J = 13.0 Hz, 1H), 1.35 (s, 9H) |
| 654 | 1H NMR (400 MHz, DMSO-d6) δ 9.33 (s, 1H), 8.96 (s, 1H), 8.35 (s, 1H), 8.01 (s, 1H), 7.65 (d, J = 2.2 Hz, 1H), 7.52-7.46 (m, 4H), 7.46-7.39 (m, 5H), 7.39-7.34 (m, 1H), 7.30-7.25 (m, 2H), 7.22 (dd, J = 8.8, 2.5 Hz, 1H), 6.12 (d, J = 8.6 Hz, 1H), 5.24 (s, 2H), 4.88-4.66 (m, 1H), 3.66 (d, J = 12.0 Hz, 2H), 3.12 (q, J = 11.4 Hz, 2H), 2.43-2.29 (m, 2H), 2.24 (t, J = 12.8 Hz, 2H), 1.35 (s, 9H) |
| 655 | 1H NMR (400 MHz, DMSO-d6) δ 9.33 (s, 1H), 8.96 (s, 1H), 8.36 (d, J = 19.4 Hz, 1H), 8.01 (s, 1H), 7.65 (d, J = 2.2 Hz, 1H), 7.54-7.46 (m, 1H), 7.46-7.32 (m, 3H), 7.30 (d, J = 2.5 Hz, 1H), 7.26-7.13 (m, 1H), 6.14 (d, J = 8.6 Hz, 1H), 4.86-4.70 (m, 1H), 4.14 (q, J = 6.9 Hz, 1H), 3.66 (d, J = 12.0 Hz, 1H), 3.16-3.05 (m, 1H), 2.36 (d, J = 13.1 Hz, 1H), 2.30-2.19 (m, 1H), 1.42-1.22 (m, 9H) |
| 664 | 1H NMR (400 MHz, DMSO-d6) δ 9.42 (s, 1H), 8.99 (s, 1H), 8.77 (s, 1H), 8.47 (s, 1H), 8.41-8.35 (m, 0H), 8.02 (s, 1H), 7.88 (d, J = 10.4 Hz, 1H), 7.71 (d, J = 12.5 Hz, 2H), 7.66-7.52 (m, 1H), 7.52-7.45 (m, 3H), 7.45-7.39 (m, 2H), 7.37-7.29 (m, 1H), 7.25 (s, 1H), 7.22-7.15 (1, 0H), 6.52 (d, J = 4.0 Hz, 1H), 6.11 (d, J = 8.2 Hz, 1H), 4.85-4.74 (m, 1H), 3.65 (d, J = 12.0 Hz, 2H), 3.12 (q, J = 11.3 Hz, 2H), 2.35 (d, J = 12.7 Hz, 2H), 2.24 (t, J = 13.1 Hz, 2H), 1.35 (s, 9H) |
| 665 | 1H NMR (400 MHz, DMSO-d6) δ 9.55 (s, 1H), 8.96 (s, 1H), 8.37 (d, J = 12.8 Hz, 1H), 8.03 (s, 1H), 7.68 (s, 1H), 7.54-7.47 (m, 2H), 7.48-7.37 (m, 2H), 7.33 (d, J = 4.0 Hz, 1H), 6.14 (d, J = 8.4 Hz, 1H), 4.89-4.71 (m, 1H), 3.67 (d, J = 12.2 Hz, 2H), 3.12 (q, J = 10.4, 9.5 Hz, 2H), 2.35 (t, J = 10.4 Hz, 2H), 2.25 (t, J = 12.8 Hz, 1H), 1.35 (s, 9H) |
| 666 | 1H NMR (400 MHz, DMSO-d6) δ 9.47 (s, 1H), 8.40 (s, 1H), 7.94 (s, 1H), 7.67 (d, J = 2.3 Hz, 1H), 7.48 (dd, J = 6.6, 2.6 Hz, 1H), 7.45-7.39 (m, 3H), 7.35-7.29 (m, 2H), 7.28-7.20 (m, 3H), 6.06 (s, 1H), 4.46 (t, J = 5.9 Hz, 1H), 4.42 (t, J = 7.1 Hz, 2H), 4.34 (t, J = 5.7 Hz, 1H), 2.23-2.15 (m, 1H), 2.15-2.08 (m, 1H). |
| 669 | 1H NMR (400 MHz, DMSO-d6) δ 9.47 (s, 1H), 8.40 (s, 1H), 7.95 (s, 1H), 7.68 (d, J = 2.2 Hz, 1H), 7.49 (dd, J = 6.6, 2.6 Hz, 1H), 7.47-7.38 (m, 4H), 7.37-7.30 (m, 3H), 7.28 (d, J = 2.4 Hz, 1H), 7.28-7.20 (m, 3H), 6.42 (tt, J = 54.4, 3.3 Hz, 1H), 6.11 (s, 1H), 4.91 (td, J = 15.7, 3.3 Hz, 2H). |
| 670 | 1H NMR (400 MHz, DMSO-d6) δ 9.37 (s, 1H), 8.37 (s, 1H), 7.89 (s, 1H), 7.66 (d, J = 2.2 Hz, 1H), 7.49-7.37 (m, 4H), 7.32 (td, J = 8.1, 6.8 Hz, 3H), 7.26-7.18 (m, 3H), 6.04 (d, J = 8.6 Hz, 1H), 4.60 (t, J = 5.1 Hz, 1H), 4.35 (dd, J = 7.5, 6.7 Hz, 2H), 3.34 (td, J = 6.1, 5.0 Hz, 2H), 1.94-1.83 (m, 2H). |
| 677 | 1H NMR (400 MHz, DMSO-d6) δ 9.11 (s, 1H), 8.23 (d, J = 3.2 Hz, 1H), 8.03 (d, J = 6.1 Hz, 1H), 7.68-7.53 (m, 3H), 7.48-7.34 (m, 4H), 7.34-7.12 (m, 5H), 6.35 (d, J = 7.2 Hz, 1H), 5.47 (q, J = 7.5 Hz, 1H), 4.93-4.75 (m, 1H), 3.68 (d, J = 11.9 Hz, 2H), 3.14 (q, J = 11.1, 10.6 Hz, 2H), 2.47-2.20 (m, 4H), 2.14 (dt, J = 14.2, 7.3 Hz, 1H), 2.05-1.79 (m, 1H), 1.37 (s, 9H), 1.03-0.77 (m, 3H) |
| 683 | 1H NMR (400 MHz, DMSO-d6) δ 9.10 (s, 1H), 8.32 (s, 1H), 8.03 (s, 1H), 7.67-7.48 (m, 3H), 7.48-7.30 (m, 2H), 7.18 (s, 1H), 6.20 (d, J = 7.7 Hz, 1H), 4.97-4.75 (m, 1H), 3.98-3.59 (m, 4H), 3.13 (q, J = 11.6 Hz, 2H), 2.44-2.16 (m, 4H), 1.66 (qd, J = 7.4, 2.6 Hz, 2H), 1.52-1.21 (m, 10H), 0.92 (t, J = 7.4 Hz, 3H) |
| 684 | 1H NMR (400 MHz, DMSO-d6) δ 9.76 (s, 1H), 9.52 (s, 1H), 9.20 (s, 1H), 8.41 (s, 1H), 8.01 (s, 1H), 7.68 (d, J = 2.2 Hz, 1H), 7.53-7.43 (m, 4H), 7.43-7.36 (m, 2H), 7.34-7.26 (m, 2H), 7.13 (d, J = 8.5 Hz, 1H), 6.71 (d, J = 8.5 Hz, 1H), 6.11 (d, J = 8.3 Hz, 1H), 4.80 (dq, J = 11.6, 5.8, 4.6 Hz, 1H), 4.31 (d, J = 5.1 Hz, 2H), 3.66 (d, J = 11.9 Hz, 2H), 3.12 (q, J = 11.3 Hz, 2H), 2.76-2.70 (m, 5H), 2.65 (d, J = 4.9 Hz, 1H), 2.36 (d, J = 13.7 Hz, 2H), 2.25 (d, J = 12.7 Hz, 1H), 1.36 (s, 9H) |

TABLE 2-continued

| Cmpd | 1H-NMR |
|---|---|
| 686 | 1H NMR (400 MHz, DMSO-d6) δ 9.56 (s, 1H), 9.04 (s, 1H), 8.31 (s, 1H), 8.15 (d, J = 0.9 Hz, 1H), 8.00 (s, 1H), 7.78 (dt, J = 9.0, 0.9 Hz, 1H), 7.68 (dd, J = 18.9, 2.1 Hz, 2H), 7.48 (d, J = 8.6 Hz, 2H), 7.44-7.39 (m, 2H), 7.36 (dd, J = 11.5, 2.2 Hz, 2H), 7.33-7.25 (m, 3H), 7.22-7.17 (m, 2H), 6.52 (d, J = 4.1 Hz, 0H), 6.13 (d, J = 8.1 Hz, 1H), 5.72 (s, 2H), 4.85-4.74 (m, 1H), 3.52 (s, 1H), 3.11 (q, J = 11.3 Hz, 2H), 2.36 (d, J = 13.4 Hz, 2H), 2.24 (q, J = 12.9 Hz, 2H), 1.35 (s, 9H). |
| 687 | 1H NMR (400 MHz, DMSO-d6) δ 9.37 (s, 1H), 8.97 (s, 1H), 8.30 (s, 1H), 8.03 (s, 1H), 7.66 (d, J = 2.2 Hz, 1H), 7.57-7.46 (m, 2H), 7.46-7.36 (m, 3H), 7.35-7.20 (m, 3H), 6.12 (d, J = 8.2 Hz, 1H), 4.87-4.72 (m, 1H), 3.67 (d, J = 12.0 Hz, 2H), 3.12 (d, J = 11.7 Hz, 1H), 2.36 (d, J = 13.6 Hz, 2H), 2.24 (d, J = 12.9 Hz, 1H), 2.16 (s, 3H), 1.36 (s, 9H) |
| 689 | 1H NMR (400 MHz, DMSO-d6) δ 9.61 (s, 1H), 9.06 (s, 1H), 8.47 (s, 1H), 8.01 (s, 1H), 7.94 (d, J = 2.3 Hz, 1H), 7.66-7.37 (m, 6H), 7.34-7.25 (m, 1H), 6.13 (d, J = 8.3 Hz, 1H), 4.86-4.73 (m, 1H), 3.65 (d, J = 12.1 Hz, 2H), 3.11 (q, J = 11.4, 10.9 Hz, 2H), 2.39-2.16 (m, 4H), 1.35 (s, 9H) |
| 692 | 1H NMR (400 MHz, DMSO-d6) δ 9.54 (s, 1H), 9.02 (s, 1H), 8.78 (s, 1H), 8.55 (s, 1H), 8.38 (dd, J = 10.6, 7.6 Hz, 2H), 7.99 (s, 1H), 7.72 (d, J = 2.3 Hz, 1H), 7.65 (t, J = 2.1 Hz, 1H), 7.52 (d, J = 8.2 Hz, 1H), 7.48-7.43 (m, 2H), 7.42-7.33 (m, 3H), 7.33-7.28 (m, 1H), 7.18 (dd, J = 6.8, 3.0 Hz, 1H), 7.10 (s, 1H), 6.52 (d, J = 4.1 Hz, 1H), 6.02 (d, J = 7.9 Hz, 1H), 4.95 (s, 1H), 4.84-4.73 (m, 1H), 3.65 (d, J = 11.8 Hz, 2H), 3.11 (q, J = 11.1, 10.6 Hz, 2H), 2.34 (d, J = 13.6 Hz, 2H), 2.22 (q, J = 13.2 Hz, 2H), 1.35 (s, 9H) |
| 693 | 1H NMR (400 MHz, DMSO-d6) δ 9.37 (s, 1H), 9.00 (s, 1H), 8.39 (d, J = 7.4 Hz, 1H), 8.16 (s, 1H), 8.03 (s, 1H), 7.87-7.72 (m, 2H), 7.69 (s, 1H), 7.55-7.47 (m, 2H), 7.46-7.38 (m, 2H), 7.30 (s, 1H), 6.14 (d, J = 8.5 Hz, 1H), 4.86-4.75 (m, 1H), 3.66 (d, J = 12.2 Hz, 2H), 3.12 (q, J = 11.4 Hz, 2H), 2.36 (d, J = 13.8 Hz, 3H), 2.23 (q, J = 13.0 Hz, 2H), 1.35 (s, 9H), 1.30 (s, 1H) |
| 694 | 1H NMR (400 MHz, DMSO-d6) δ 9.36 (s, 1H), 8.99 (s, 1H), 8.44-8.35 (m, 1H), 8.04 (s, 1H), 7.71 (s, 2H), 7.56-7.47 (m, 2H), 7.47-7.37 (m, 2H), 7.35 (s, 2H), 7.25-7.08 (m, 1H), 7.00-6.90 (m, 1H), 6.67 (ddd, J = 9.0, 7.9, 5.3 Hz, 1H), 6.52 (d, J = 4.1 Hz, 1H), 6.14 (d, J = 8.3 Hz, 1H), 4.95 (s, 1H), 4.86-4.75 (m, 1H), 3.66 (d, J = 12.1 Hz, 2H), 3.12 (q, J = 11.6 Hz, 2H), 2.36 (d, J = 13.4 Hz, 2H), 2.24 (q, J = 12.9, 12.4 Hz, 2H), 1.35 (s, 9H) |
| 695 | 1H NMR (400 MHz, DMSO-d6) δ 9.45 (s, 1H), 9.02 (s, 1H), 8.39 (d, J = 4.6 Hz, 1H), 8.03 (s, 1H), 7.69 (s, 1H), 7.55-7.47 (m, 1H), 7.47-7.38 (m, 1H), 7.32 (d, J = 2.6 Hz, 1H), 6.14 (d, J = 8.5 Hz, 1H), 4.88-4.73 (m, 1H), 3.66 (d, J = 12.2 Hz, 2H), 3.12 (q, J = 11.5 Hz, 2H), 2.36 (d, J = 13.6 Hz, 2H), 2.25 (t, J = 12.8 Hz, 2H), 1.35 (s, 9H) |
| 696 | 1H NMR (400 MHz, DMSO-d6) δ 9.49 (s, 1H), 8.96 (s, 1H), 8.59 (s, 1H), 7.98 (s, 1H), 7.73 (d, J = 2.3 Hz, 1H), 7.51 (d, J = 7.9 Hz, 1H), 7.47-7.28 (m, 4H), 7.08 (dt, J = 8.7, 2.1 Hz, 1H), 7.04-6.93 (m, 2H), 6.85 (dt, J = 10.5, 2.1 Hz, 1H), 5.97 (d, J = 7.6 Hz, 1H), 4.83-4.72 (m, 1H), 3.65 (d, J = 12.1 Hz, 2H), 3.15-3.04 (m, 2H), 2.35 (s, 1H), 2.23 (t, J = 13.0 Hz, 2H), 1.35 (s, 9H) |
| 700 | 1H NMR (400 MHz, DMSO-d6) δ 10.36 (s, 1H), 9.30 (s, 1H), 8.30 (s, 1H), 8.04 (s, 1H), 7.64 (d, J = 2.2 Hz, 1H), 7.53-7.39 (m, 4H), 7.39-7.29 (m, 3H), 7.10 (dd, J = 8.7, 2.6 Hz, 1H), 6.99 (d, J = 8.6 Hz, 1H), 6.16 (d, J = 8.6 Hz, 1H), 4.74 (s, 6H), 3.54 (s, 2H), 3.00 (s, 2H), 2.36 (s, 2H), 2.19 (s, 2H) |
| 701 | 1H NMR (400 MHz, DMSO-d6) δ 10.36 (s, 1H), 9.29 (s, 1H), 8.95 (s, 1H), 8.30 (s, 1H), 8.01 (s, 1H), 7.73-7.61 (m, 1H), 7.54-7.47 (m, 2H), 7.46-7.39 (m, 2H), 7.36 (d, J = 8.6 Hz, 1H), 7.31 (d, J = 2.7 Hz, 1H), 7.19 (s, 1H), 7.10 (dd, J = 8.6, 2.6 Hz, 1H), 7.00 (d, J = 8.6 Hz, 1H), 6.16 (d, J = 8.8 Hz, 1H), 4.83-4.74 (m, 1H), 3.97 (s, 1H), 3.66 (d, J = 12.1 Hz, 2H), 3.12 (d, J = 11.9 Hz, 1H), 2.36 (d, J = 13.5 Hz, 2H), 2.24 (t, J = 12.9 Hz, 2H), 1.35 (s, 9H) |
| 707 | 1H NMR (400 MHz, DMSO-d6) δ 9.46 (s, 1H), 8.90 (d, J = 12.3 Hz, 1H), 8.36 (s, 1H), 7.97 (s, 2H), 7.80-7.55 (m, 1H), 7.58-7.35 (m, 7H), 7.35-7.14 (m, 2H), 7.10 (d, J = 2.2 Hz, 1H), 6.10 (d, J = 8.0 Hz, 1H), 5.34-5.13 (m, 1H), 2.19 (t, J = 9.9 Hz, 2H), 2.03 (t, J = 12.9 Hz, 2H), 1.46 (s, 6H), 1.40 (s, 6H) |
| 708 | 1H NMR (400 MHz, DMSO-d6) δ 10.65 (s, 1H), 9.48 (s, 1H), 8.37 (s, 1H), 8.03 (s, 1H), 7.55-7.34 (m, 6H), 7.36-7.22 (m, 2H), 7.10 (d, J = 2.2 Hz, 1H), 6.10 (d, J = 7.7 Hz, 1H), 4.75 (d, J = 6.8 Hz, 5H), 4.40 (s, 1H), 3.53 (s, 1H), 3.00 (s, 2H), 2.36 (s, 2H), 2.19 (d, J = 13.6 Hz, 2H) |
| 709 | 1H NMR (400 MHz, DMSO-d6) δ 9.44 (s, 1H), 9.02 (d, J = 14.7 Hz, 1H), 8.36 (s, 1H), 8.00 (s, 1H), 7.54-7.37 (m, 6H), 7.35-7.21 (m, 2H), 7.09 (s, 1H), 6.09 (d, J = 8.1 Hz, 1H), 4.95-4.70 (m, 1H), 3.66 (d, J = 12.0 Hz, 2H), 3.12 (q, J = 11.7 Hz, 2H), 2.35 (d, J = 12.8 Hz, 2H), 2.23 (q, J = 13.0 Hz, 2H), 1.35 (s, 9H) |
| 711 | 1H NMR (400 MHz, Methanol-d4) δ 8.42 (s, 1H), 8.02 (s, 1H), 7.72 (s, 1H), 7.66-7.59 (m, 2H), 7.55 (t, J = 7.5 Hz, 1H), 7.51 (d, J = 7.7 Hz, 1H), 7.36 (dd, J = 6.4, 2.6 Hz, 1H), 7.27 (t, J = 8.8 Hz, 1H), 7.18 (m, 1H), 7.12 (d, J = 2.3 Hz, 1H), 6.07 (s, 1H), 4.85-4.77 (m, 1H), 4.61 (s, 2H), 3.65 (dd, J = 10.7, 5.4 Hz, 2H), 3.54 (dd, J = 10.2, 5.4 Hz, 2H), 3.10 (d, J = 6.5 Hz, 6H), 1.54 (d, J = 6.7 Hz, 6H) |
| 712 | 1H NMR (400 MHz, Methanol-d4) δ 8.44 (s, 1H), 7.94 (s, 1H), 7.65 (d, J = 2.3 Hz, 1H), 7.63 (s, 1H), 7.56 (d, J = 7.7 Hz, 1H), 7.50 (t, J = 7.6 Hz, 1H), 7.43 (m, 2H), 7.30 (t, J = 8.8 Hz, 1H), 7.23 (m, 1H), 7.16 (d, J = 2.4 Hz, 1H), 6.07 (s, 1H), 4.86-4.76 (m, 1H), 4.30 (d, J = 12.9 Hz, 1H), 4.26 (d, J = 12.9 Hz, 1H), 2.80 (s, 6H), 1.54 (d, J = 6.7 Hz, 6H) |
| 713 | 1H NMR (400 MHz, Methanol-d4) δ 8.47 (s, 1H), 7.72 (s, 1H), 7.68 (d, J = 2.3 Hz, 1H), 7.59-7.52 (m, 1H), 7.48 (s, 1H), 7.41-7.30 (m, 4H), 7.29 (d, J = 4.6 Hz, 1H), 7.24 (d, J = 2.3 Hz, 1H), 6.04 (s, 1H), 4.79 (p, J = 6.6 Hz, 1H), 4.58 (s, 2H), 1.52 (dd, J = 6.7, 1.7 Hz, 6H) |

TABLE 2-continued

| Cmpd | 1H-NMR |
|---|---|
| 719 | 1H NMR (400 MHz, Methanol-d4) δ 8.47 (s, 1H), 8.29 (s, 1H), 7.68 (d, J = 2.6 Hz, 1H), 7.57-7.39 (m, 4H), 7.35 (dd, J = 6.4, 2.7 Hz, 1H), 7.27 (t, J = 8.8 Hz, 1H), 7.20 (d, J = 2.4 Hz, 1H), 7.19-7.12 (m, 1H), 6.38 (s, 1H), 4.90 (m, 1H), 4.79 (d, J = 13.5 Hz, 1H), 4.57 (d, J = 13.5 Hz, 1H), 3.94 (br s, 4H), 3.81 (d, J = 12.7 Hz, 2H), 3.22 (m, 2H), 2.46 (m, 4H), 1.47 (s, 9H) |
| 720 | 1H NMR (400 MHz, Methanol-d4) δ 8.46 (s, 1H), 8.19 (s, 1H), 7.66 (d, J = 2.5 Hz, 1H), 7.55 (d, J = 7.3 Hz, 1H), 7.52-7.42 (m, 3H), 7.37 (dd, J = 6.4, 2.6 Hz, 1H), 7.28 (t, J = 8.8 Hz, 1H), 7.22 (d, J = 2.4 Hz, 1H), 7.18 (m, 1H), 6.33 (s, 1H), 4.84-4.75 (m, 1H), 4.69 (d, J = 13.5 Hz, 1H), 4.55 (d, J = 13.6 Hz, 1H), 3.79 (d, J = 12.6 Hz, 2H), 3.22 (t, J = 12.7 Hz, 2H), 2.93 (s, 6H), 2.53-2.34 (m, 4H), 1.46 (s, 9H) |
| 721 | 1H NMR (400 MHz, DMSO-d6) δ 9.59 (s, 1H), 9.17 (d, J = 2.5 Hz, 1H), 8.81 (d, J = 1.3 Hz, 1H), 8.72 (dt, J = 4.8, 1.3 Hz, 1H), 8.47 (d, J = 1.2 Hz, 1H), 8.36 (ddt, J = 8.4, 2.7, 1.4 Hz, 1H), 7.79-7.75 (m, 1H), 7.67 (dd, J = 8.3, 4.7 Hz, 1H), 7.60-7.51 (m, 3H), 7.47 (td, J = 9.0, 1.3 Hz, 1H), 7.43-7.37 (m, 2H), 7.32 (ddd, J = 12.6, 7.5, 3.9 Hz, 3H), 6.24 (d, J = 4.1 Hz, 1H). |
| 722 | 1H NMR (400 MHz, Methanol-d4) δ 8.42 (s, 1H), 7.77 (s, 1H), 7.67 (d, J = 2.3 Hz, 1H), 7.57-7.47 (m, 2H), 7.43-7.26 (m, 6H), 6.40 (s, 1H), 4.94 (d, J = 11.7 Hz, 1H), 4.85-4.72 (m, 1H), 4.59 (d, J = 11.8 Hz, 1H), 3.80 (d, J = 12.7 Hz, 2H), 3.22 (m, 2H), 2.43 (m, 4H), 1.46 (s, 9H) |
| 723 | 1H NMR (400 MHz, DMSO-d6) δ 9.44 (s, 1H), 8.80 (s, 1H), 8.45-8.35 (m, 1H), 8.04 (s, 1H), 7.68 (d, J = 2.3 Hz, 1H), 7.53-7.26 (m, 7H), 7.27-7.03 (m, 2H), 6.53 (d, J = 4.1 Hz, 1H), 6.10 (d, J = 8.1 Hz, 1H), 4.95 (s, 1H), 4.75 (d, J = 6.7 Hz, 5H), 3.54 (s, 1H), 3.00 (s, 1H), 2.59-2.49 (m, 1H), 2.34 (d, J = 7.6 Hz, 2H), 2.20 (s, 2H) |
| 724 | 1H NMR (400 MHz, DMSO-d6) δ 9.49 (s, 1H), 8.42 (s, 1H), 7.91 (d, J = 0.4 Hz, 1H), 7.69 (d, J = 2.2 Hz, 1H), 7.54-7.43 (m, 3H), 7.43-7.35 (m, 3H), 7.27 (d, J = 2.3 Hz, 1H), 7.15-7.06 (m, 1H), 6.11 (d, J = 5.6 Hz, 1H), 4.53-4.46 (m, 2H), 3.77 (dd, J = 5.7, 4.8 Hz, 2H), 3.49-3.42 (m, 2H), 3.35-3.28 (m, 2H), 3.24-3.01 (m, 4H) |
| 726 | 1H NMR (400 MHz, Methanol-d4) δ 8.41 (s, 1H), 8.07 (s, 1H), 7.75 (s, 1H), 7.66-7.49 (m, 4H), 7.37 (dd, J = 6.4, 2.7 Hz, 1H), 7.28 (t, J = 8.8 Hz, 1H), 7.22-7.14 (m, 2H), 6.12 (s, 1H), 4.82 (m, 1H), 4.63 (s, 2H), 3.80 (d, J = 12.6 Hz, 2H), 3.68 (dd, J = 10.4, 5.4 Hz, 2H), 3.56 (dd, J = 10.1, 5.5 Hz, 2H), 3.23 (t, J = 12.2 Hz, 2H), 3.10 (d, J = 7.3 Hz, 6H), 2.56-2.28 (m, 4H), 1.47 (s, 9H) |
| 727 | 1H NMR (400 MHz, Methanol-d4) δ 8.39 (s, 1H), 7.79 (s, 1H), 7.67-7.59 (m, 2H), 7.41 (m, 2H), 7.37-7.18 (m, 4H), 7.14 (d, J = 2.4 Hz, 1H), 6.01 (s, 1H), 4.97-4.70 (m, 1H), 3.80 (d, J = 12.4 Hz, 2H), 3.29-3.16 (m, 2H), 2.56-2.26 (m, 4H), 1.46 (s, 6H), 1.46 (s, 9H) |
| 728 | 1H NMR (400 MHz, Methanol-d4) δ 8.41 (s, 1H), 8.12 (s, 1H), 7.96 (d, J = 7.9 Hz, 1H), 7.83 (s, 1H), 7.69 (d, J = 7.7 Hz, 1H), 7.64 (d, J = 2.4 Hz, 1H), 7.49 (t, J = 7.8 Hz, 1H), 7.39 (dd, J = 6.4, 2.6 Hz, 1H), 7.28 (t, J = 8.8 Hz, 1H), 7.24-7.13 (m, 1H), 7.11 (d, J = 2.4 Hz, 1H), 6.08 (s, 1H), 4.79-4.71 (m, 1H), 3.86 (s, 3H), 3.80 (d, J = 12.9 Hz, 2H), 3.20 (m, 2H), 2.60-2.27 (m, 4H), 1.46 (s, 9H) |
| 729 | 1H NMR (400 MHz, DMSO-d6) δ 9.53 (s, 1H), 8.55 (ddd, J = 4.9, 1.8, 0.9 Hz, 1H), 8.45 (s, 1H), 8.06 (s, 1H), 7.83 (td, J = 7.7, 1.8 Hz, 1H), 7.72 (d, J = 2.2 Hz, 1H), 7.54 (dd, J = 6.6, 2.6 Hz, 1H), 7.52-7.45 (m, 3H), 7.41-7.34 (m, 3H), 7.33 (d, J = 2.3 Hz, 1H), 7.32-7.25 (m, 3H), 6.15 (s, 1H), 5.72 (s, 2H). |
| 731 | 1H NMR (400 MHz, DMSO-d6) δ 9.49 (s, 1H), 9.02 (s, 1H), 8.78 (s, 1H), 8.46 (s, 1H), 8.02 (s, 1H), 7.70 (s, 1H), 7.66-7.59 (m, 1H), 7.59-7.52 (m, 1H), 7.52-7.45 (m, 3H), 7.44-7.37 (m, 3H), 7.35 (d, J = 1.8 Hz, 1H), 7.33-7.29 (m, 1H), 7.27 (s, 1H), 7.18 (dd, J = 6.7, 2.9 Hz, 1H), 6.52 (d, J = 4.1 Hz, 1H), 6.11 (d, J = 8.1 Hz, 1H), 4.95 (s, 1H), 4.85-4.74 (m, 1H), 3.65 (d, J = 11.9 Hz, 2H), 3.12 (q, J = 11.3 Hz, 2H), 2.39-2.30 (m, 2H), 2.24 (t, J = 13.2 Hz, 2H), 1.35 (s, 9H), 1.29 (s, 1H) |
| 732 | 1H NMR (400 MHz, DMSO-d6) δ 9.42 (s, 1H), 8.99 (s, 1H), 8.40 (d, J = 17.2 Hz, 1H), 8.00 (s, 1H), 7.68 (d, J = 2.2 Hz, 1H), 7.52-7.28 (m, 7H), 7.25-7.15 (m, 1H), 7.07 (d, J = 8.8 Hz, 1H), 6.52 (d, J = 4.1 Hz, 1H), 6.09 (d, J = 8.2 Hz, 1H), 4.91 (s, 1H), 4.85-4.74 (m, 1H), 3.65 (d, J = 12.2 Hz, 2H), 3.12 (q, J = 11.4 Hz, 2H), 2.39-2.30 (m, 2H), 2.24 (t, J = 13.2 Hz, 2H), 1.35 (s, 9H) |
| 733 | 1H NMR (400 MHz, Methanol-d4) δ 8.45 (s, 1H), 7.98 (s, 1H), 7.67 (d, J = 2.4 Hz, 1H), 7.66 (s, 1H), 7.56 (d, J = 7.7 Hz, 1H), 7.49 (t, J = 7.6 Hz, 1H), 7.44 (dd, J = 6.6, 2.4 Hz, 2H), 7.32 (t, J = 8.8 Hz, 1H), 7.28-7.21 (m, 1H), 7.19 (d, J = 2.4 Hz, 1H), 6.08 (s, 1H), 4.83-4.76 (m, 1H), 4.33 (q, J = 12.9 Hz, 2H), 3.93 (br s, 2H), 3.80 (d, J = 12.6 Hz, 2H), 3.64 (br s, 2H), 3.28-3.17 (m, 6H), 2.46 (m, 4H), 1.46 (s, 9H) |
| 735 | 1H NMR (400 MHz, Methanol-d4) δ 8.42 (s, 1H), 7.97 (s, 1H), 7.64 (d, J = 2.3 Hz, 1H), 7.59 (d, J = 8.0 Hz, 2H), 7.49 (d, J = 8.1 Hz, 2H), 7.42 (dd, J = 6.5, 2.6 Hz, 1H), 7.30 (t, J = 8.8 Hz, 1H), 7.23 (m, 1H), 7.17 (d, J = 2.4 Hz, 1H), 6.09 (s, 1H), 4.80 (m, 1H), 4.29 (s, 2H), 3.79 (d, J = 12.3 Hz, 2H), 3.27-3.16 (m, 2H), 2.82 (s, 6H), 2.45 (m, 4H), 1.46 (s, 9H) |
| 737 | 1H NMR (400 MHz, DMSO-d6) δ 9.40 (s, 1H), 8.37 (s, 1H), 7.88 (s, 1H), 7.67 (s, 1H), 7.45 (d, J = 9.2 Hz, 1H), 7.44-7.39 (m, 2H), 7.36 (d, J = 8.8 Hz, 1H), 7.31 (t, J = 7.6 Hz, 2H), 7.27-7.19 (m, 3H), 6.06 (d, J = 8.7 Hz, 1H), 4.42 (t, J = 6.3 Hz, 2H), 3.42 (t, J = 4.6 Hz, 4H), 2.72-2.60 (m, 2H), 2.31 (dd, J = 6.1, 3.3 Hz, 4H). |
| 738 | 1H NMR (400 MHz, DMSO-d6) δ 9.39 (s, 1H), 8.37 (s, 1H), 7.88 (s, 1H), 7.67 (s, 1H), 7.50-7.35 (m, 4H), 7.34-7.27 (m, 2H), 7.27-7.18 (m, 3H), 6.07 (d, J = 8.9 Hz, 1H), 4.99 (t, J = 5.2 Hz, 1H), 4.35 (t, J = 5.4 Hz, 2H), 3.72 (q, J = 5.3 Hz, 2H). |
| 746 | 1H NMR (400 MHz, DMSO-d6) δ 9.54 (s, 1H), 8.40 (s, 1H), 7.80 (s, 1H), 7.70 (d, J = 2.2 Hz, 1H), 7.52 (dd, J = 6.6, 2.6 Hz, 1H), 7.48-7.40 (m, 3H), 7.37-7.29 (m, 3H), 7.29-7.20 (m, 2H), 6.11 (s, 1H), 5.41 (d, J = 1.6 Hz, 2H), 3.57 (dt, J = 21.9, 4.6 Hz, 4H), 3.43 (dt, J = 22.7, 4.8 Hz, 4H). |

TABLE 2-continued

| Cmpd | 1H-NMR |
|---|---|
| 748 | 1H NMR (400 MHz, DMSO-d6) δ 9.44 (s, 1H), 8.39 (s, 1H), 8.14 (m, 1H), 7.67 (m, 1H), 7.51-7.08 (m, 10H), 6.09 (m, 1H), 5.01 (m, 1H), 3.76 (m, 1H), 3.64 (m, 1H), 3.50 (m, 2H), 2.73 (m, 2H). |
| 749 | 1H NMR (400 MHz, DMSO-d6) δ 8.98 (s, 1H), 8.86 (s, 1H), 7.95 (s, 1H), 7.80 (d, J = 2.4 Hz, 1H), 7.66 (d, J = 6.5 Hz, 1H), 7.39-7.26 (m, 4H), 7.14 (t, J = 9.0 Hz, 1H), 6.82 (dd, J = 6.1, 3.0 Hz, 1H), 6.44 (dt, J = 9.1, 3.4 Hz, 1H), 6.38 (d, J = 6.1, 1H), 5.79 (d, J = 6.3 Hz, 1H), 4.87 (s, 1H), 4.82-4.71 (m, 1H), 3.65 (d, J = 12.1 Hz, 2H), 3.40 (s, 1H), 3.24 (s, 3H), 3.11 (q, J = 11.5 Hz, 2H), 2.33 (d, J = 13.1 Hz, 2H), 2.21 (q, J = 12.5 Hz, 2H), 1.35 (s, 9H) |
| 750 | 1H NMR (400 MHz, DMSO-d6) δ 9.74 (s, 1H), 8.98 (s, 1H), 8.63 (d, J = 19.1 Hz, 1H), 8.55 (d, J = 2.6 Hz, 1H), 8.39 (d, J = 2.7 Hz, 1H), 7.98 (s, 1H), 7.82-7.72 (m, 2H), 7.61-7.49 (m, 2H), 7.48-7.38 (m, 2H), 7.38-7.28 (m, 2H), 7.05 (s, 1H), 6.52 (d, J = 3.9 Hz, 1H), 6.30 (d, J = 8.1 Hz, 1H), 5.97 (d, J = 7.5 Hz, 1H), 4.83-4.72 (m, 1H), 3.64 (d, J = 11.7 Hz, 2H), 3.10 (d, J = 11.8 Hz, 2H), 2.31 (s, 3H), 2.21 (d, J = 12.8 Hz, 1H), 1.35 (s, 9H), 1.30 (s, 1H) |
| 751 | 1H NMR (400 MHz, DMSO-d6) δ 9.47 (s, 1H), 9.00 (s, 1H), 8.77 (s, 1H), 8.41-8.33 (m, 1H), 8.03 (s, 1H), 7.76 (s, 1H), 7.67 (s, 1H), 7.55-7.47 (m, 2H), 7.47-7.28 (m, 8H), 7.18 (dd, J = 6.7, 2.9 Hz, 1H), 6.52 (d, J = 4.1 Hz, 1H), 6.17 (d, J = 8.7 Hz, 1H), 4.95 (s, 1H), 4.86-4.75 (m, 1H), 3.85 (s, 3H), 3.66 (d, J = 12.1 Hz, 2H), 3.12 (d, J = 11.8 Hz, 2H), 2.36 (d, J = 13.3 Hz, 3H), 2.26 (t, J = 12.2 Hz, 2H), 1.35 (s, 9H), 1.30 (s, 1H) |
| 752 | 1H NMR (400 MHz, DMSO-d6) δ 9.44 (s, 1H), 9.03 (d, J = 7.7 Hz, 1H), 8.34 (s, 1H), 8.02 (s, 1H), 7.92 (d, J = 2.4 Hz, 1H), 7.67 (d, J = 2.2 Hz, 1H), 7.61-7.55 (m, 2H), 7.54-7.48 (m, 2H), 7.46-7.39 (m, 2H), 7.40-7.33 (m, 2H), 7.32 (d, J = 2.7 Hz, 1H), 7.18 (d, J = 6.0 Hz, 1H), 6.37 (d, J = 2.4 Hz, 1H), 6.19 (d, J = 8.5 Hz, 1H), 5.12 (q, J = 9.0 Hz, 2H), 4.86-4.75 (m, 1H), 3.66 (d, J = 12.2 Hz, 2H), 3.12 (q, J = 11.2 Hz, 2H), 2.37 (d, J = 14.1 Hz, 3H), 2.24 (q, J = 12.7 Hz, 2H), 1.35 (s, 9H), 1.28 (s, 1H) |
| 753 | 1H NMR (400 MHz, DMSO-d6) δ 9.50 (s, 1H), 9.00 (s, 1H), 8.53 (s, 1H), 8.41-8.35 (m, 0H), 7.98 (s, 1H), 7.71 (d, J = 2.3 Hz, 1H), 7.59-7.51 (m, 2H), 7.47 (s, 1H), 7.47-7.41 (m, 3H), 7.40-7.34 (m, 2H), 7.33-7.29 (m, 1H), 7.24-7.15 (1, 0H), 7.10 (d, J = 2.4 Hz, 1H), 6.52 (d, J = 4.0 Hz, 1H), 6.00 (d, J = 7.8 Hz, 1H), 4.95 (s, 1H), 4.90 (s, 1H), 4.83-4.73 (m, 1H), 3.65 (d, J = 11.8 Hz, 2H), 3.11 (q, J = 11.4 Hz, 2H), 2.33 (d, J = 12.6 Hz, 2H), 2.23 (t, J = 12.6 Hz, 2H), 1.35 (s, 9H) |
| 759 | 1H NMR (400 MHz, DMSO-d6) δ 9.41 (s, 1H), 8.96 (s, 1H), 8.44 (s, 1H), 7.99 (s, 1H), 7.68 (d, J = 2.2 Hz, 1H), 7.50-7.42 (m, 3H), 7.42-7.33 (m, 4H), 7.33-7.25 (m, 2H), 7.19 (d, J = 2.4 Hz, 1H), 6.03 (d, J = 8.1 Hz, 1H), 4.84-4.73 (m, 1H), 3.65 (d, J = 12.1 Hz, 2H), 3.11 (q, J = 11.4 Hz, 2H), 2.38-2.30 (m, 2H), 2.24 (t, J = 12.8 Hz, 2H), 1.35 (s, 9H) |
| 760 | 1H NMR (400 MHz, DMSO-d6) δ 8.98 (s, 1H), 7.99 (s, 1H), 7.45-7.17 (m, 9H), 7.01 (dt, J = 7.9, 3.4 Hz, 1H), 6.92-6.87 (m, 1H), 6.64 (s, 8.1 Hz, 1H), 6.12-6.06 (m, 1H), 5.80 (d, J = 8.0 Hz, 1H), 4.37 (m, 1H), 3.10-2.99 (m, 2H), 2.88-2.78 (m, 1H), 2.18 (m, 2H), 2.04-1.91 (m, 2H), 1.85 (m, 2H), 1.02 (s, 9H) |
| 761 | 1H NMR (400 MHz, DMSO-d6) δ 9.48 (s, 1H), 9.11 (s, 1H), 8.48 (s, 1H), 7.99 (s, 1H), 7.69 (d, J = 2.3 Hz, 1H), 7.55-7.27 (m, 9H), 7.18 (d, J = 2.6 Hz, 1H), 7.05 (s, 1H), 6.91 (s, 1H), 6.53 (d, J = 4.0 Hz, 1H), 6.01 (d, J = 7.3 Hz, 1H), 4.87-4.64 (m, 1H), 3.65 (d, J = 12.1 Hz, 2H), 3.11 (d, J = 11.9 Hz, 1H), 2.40-2.13 (m, 3H), 1.35 (s, 9H) |
| 762 | 1H NMR (400 MHz, DMSO-d6) δ 9.53 (s, 1H), 9.00 (s, 1H), 8.51 (s, 1H), 7.99 (s, 1H), 7.71 (d, J = 2.2 Hz, 1H), 7.57 (td, J = 8.1, 0.8 Hz, 1H), 7.51-7.29 (m, 7H), 7.15 (d, J = 2.4 Hz, 1H), 6.01 (d, J = 7.8 Hz, 1H), 4.84-4.73 (m, 1H), 3.65 (d, J = 11.9 Hz, 2H), 3.11 (q, J = 11.3 Hz, 2H), 2.34 (d, J = 12.4 Hz, 2H), 2.22 (q, J = 12.9 Hz, 2H), 1.35 (s, 9H) |
| 766 | 1H NMR (400 MHz, DMSO-d6) δ 9.41 (s, 1H), 9.10 (s, 1H), 8.37 (d, J = 13.0 Hz, 1H), 8.02 (s, 1H), 7.66 (d, J = 2.2 Hz, 1H), 7.54-7.45 (m, 2H), 7.45-7.36 (m, 2H), 7.36-7.20 (m, 4H), 6.13 (d, J = 8.1 Hz, 1H), 4.88-4.71 (m, 1H), 3.66 (d, J = 12.2 Hz, 2H), 3.13 (t, J = 11.5 Hz, 2H), 2.43-2.30 (m, 2H), 2.26 (t, J = 12.8 Hz, 2H), 1.36 (s, 9H) |
| 767 | 1H NMR (400 MHz, DMSO-d6) δ 9.43 (s, 1H), 8.77 (d, J = 7.8 Hz, 1H), 8.48 (s, 1H), 8.38 (d, J = 0.9 Hz, 1H), 7.99 (s, 1H), 7.69 (d, J = 2.3 Hz, 1H), 7.49-7.27 (m, 6H), 7.22-7.12 (m, 1H), 7.05-6.90 (m, 2H), 6.52 (d, J = 4.1 Hz, 1H), 6.03 (d, J = 7.8 Hz, 1H), 4.95 (s, 1H), 4.87-4.70 (m, 1H), 3.65 (d, J = 12.2 Hz, 2H), 3.11 (q, J = 11.2 Hz, 2H), 2.34 (q, J = 11.0 Hz, 2H), 2.24 (t, J = 12.9 Hz, 1H), 1.41-1.27 (m, 9H) |
| 768 | 1H NMR (400 MHz, DMSO-d6) δ 9.33 (s, 1H), 9.05 (d, J = 8.2 Hz, 1H), 8.79 (s, 1H), 8.43-8.34 (m, 1H), 8.02 (s, 1H), 7.67 (d, J = 2.2 Hz, 1H), 7.56-7.46 (m, 1H), 7.46-7.23 (m, 11H), 7.22-7.14 (m, 1H), 6.53 (d, J = 4.1 Hz, 0H), 6.15 (d, J = 8.5 Hz, 1H), 4.95 (s, 1H), 4.86-4.75 (m, 1H), 3.67 (s, 1H), 3.19-3.04 (m, 2H), 2.36 (d, J = 13.8 Hz, 2H), 2.24 (q, J = 12.2, 11.6 Hz, 1H), 1.35 (s, 9H) |
| 769 | 1H NMR (400 MHz, DMSO-d6) δ 9.15 (s, 1H), 8.42 (s, 1H), 8.10 (s, 1H), 7.47-7.25 (m, 7H), 7.14-7.04 (m, 2H), 6.26 (d, J = 8.0 Hz, 1H), 5.99 (d, J = 7.9 Hz, 1H), 4.50-4.40 (m, 1H), 4.04 (s, 3H), 2.06 (m, 3H), 1.96-1.89 (m, 5H), 1.09 (s, 9H) |
| 773 | 1H NMR (400 MHz, DMSO-d6) δ 10.72 (s, 1H), 8.87 (s, 1H), 7.93 (s, 1H), 7.82 (dd, J = 6.6, 2.5 Hz, 1H), 7.69 (s, 1H), 7.64-7.44 (m, 5H), 7.24-7.10 (m, 2H), 6.60 (d, J = 8.7 Hz, 1H), 6.33 (d, J = 8.2 Hz, 1H), 4.02 (s, 3H), 2.50 (s, 3H) |
| 774 | 1H NMR D2O exchange (400 MHz, DMSO-d6) δ 8.38 (d, J = 0.7 Hz, 1H), 7.97 (s, 1H), 7.64 (d, J = 2.3 Hz, 1H), 7.47-7.36 (m, 5H), 7.30 (t, J = 7.6 Hz, 3H), 7.26-7.17 (m, 4H), 6.02 (s, 1H), 5.01 (p, J = 8.2 Hz, 1H), 4.27-4.19 (m, 1H), 4.18-3.94 (m, 5H), 3.09 (q, J = 7.2 Hz, 3H), 2.85 (dt, J = 12.3, 6.1 Hz, 1H), 2.81-2.71 (m, 2H), 2.65 (ddt, J = 12.5, 8.2, 4.6 Hz, 2H), 1.01 (t, J = 7.2 Hz, 3H) |

TABLE 2-continued

| Cmpd | 1H-NMR |
|---|---|
| 775 | 1H NMR (400 MHz, DMSO-d6) δ 9.40 (s, 1H), 8.57 (s, 2H), 8.39 (s, 1H), 7.99 (s, 1H), 7.66 (d, J = 2.2 Hz, 1H), 7.45 (dd, J = 6.6, 2.6 Hz, 1H), 7.44-7.37 (m, 3H), 7.31 (dd, J = 8.3, 6.8 Hz, 3H), 7.26-7.18 (m, 3H), 6.04 (d, J = 6.8 Hz, 1H), 5.00 (p, J = 8.2 Hz, 1H), 4.05 (t, J = 6.2 Hz, 2H), 3.95 (t, J = 6.2 Hz, 2H), 2.85-2.74 (m, 2H), 2.67 (tq, J = 8.4, 5.0, 4.0 Hz, 2H). |
| 776 | 1H NMR (400 MHz, DMSO-d6) δ 9.40 (s, 1H), 8.95 (s, 1H), 8.49 (s, 1H), 7.98 (s, 1H), 7.69 (d, J = 2.3 Hz, 1H), 7.49-7.32 (m, 7H), 7.24-7.16 (m, 2H), 7.14 (d, J = 2.4 Hz, 1H), 7.11-7.06 (m, 1H), 6.01 (d, J = 7.9 Hz, 1H), 4.76 (d, J = 11.8 Hz, 1H), 3.65 (d, J = 12.2 Hz, 2H), 3.11 (q, J = 11.4 Hz, 2H), 2.34 (d, J = 12.4 Hz, 2H), 2.22 (d, J = 13.0 Hz, 2H), 1.35 (s, 9H) |
| 778 | 1H NMR (400 MHz, DMSO-d6) δ 9.43 (s, 1H), 8.65 (s, 1H), 8.41 (s, 2H), 7.98 (s, 1H), 7.68 (d, J = 2.2 Hz, 1H), 7.54-7.13 (m, 9H), 6.07 (d, J = 7.9 Hz, 1H), 4.84-4.69 (m, 1H), 3.39 (d, J = 13.0 Hz, 2H), 3.06 (d, J = 11.7 Hz, 2H), 2.31-2.00 (m, 4H) |
| 780 | 1H NMR (400 MHz, DMSO-d6) δ 9.55 (s, 1H), 8.98 (s, 1H), 8.77 (s, 1H), 8.53 (s, 1H), 8.43-8.35 (m, 2H), 7.96 (s, 1H), 7.76-7.65 (m, 2H), 7.51-7.10 (m, 7H), 5.99 (d, J = 7.7 Hz, 1H), 4.78 (t, J = 11.9 Hz, 1H), 3.64 (d, J = 11.7 Hz, 2H), 3.08 (dd, J = 23.6, 12.4 Hz, 2H), 2.33 (d, J = 13.2 Hz, 2H), 2.21 (d, J = 13.0 Hz, 3H), 1.35 (s, 9H) |
| 781 | 1H NMR (400 MHz, DMSO-d6) δ 9.50 (s, 2H), 8.44 (s, 1H), 8.04 (s, 1H), 7.72 (d, J = 2.3 Hz, 2H), 7.55 (d, J = 8.4 Hz, 1H), 7.51-7.44 (m, 4H), 7.44-7.21 (m, 9H), 6.15-6.00 (m, 1H), 4.79 (s, 1H), 4.38 (s, 1H), 3.41-3.27 (m, 19H), 3.31-3.24 (m, 1H), 3.03 (s, 3H), 2.15 (s, 2H), 1.97 (s, 2H), 1.91 (s, 1H), 1.02 (s, 9H) |
| 785 | 1H NMR (400 MHz, DMSO-d6) δ 9.57 (s, 1H), 8.97 (s, 1H), 8.78 (s, 1H), 8.51 (s, 1H), 8.42-8.35 (m, 1H), 8.21-8.02 (m, 2H), 7.95 (s, 1H), 7.85-7.77 (m, 2H), 7.72 (d, J = 2.3 Hz, 1H), 7.58-7.48 (m, 1H), 7.46-7.12 (m, 8H), 6.72 (s, 1H), 6.52 (d, J = 4.1 Hz, 1H), 5.98 (d, J = 7.4 Hz, 1H), 5.89 (s, 1H), 4.95 (s, 1H), 4.82-4.71 (m, 1H), 3.61 (d, J = 12.1 Hz, 2H), 3.08 (q, J = 12.0 Hz, 2H), 2.31 (d, J = 14.4 Hz, 2H), 2.21 (t, J = 13.2 Hz, 2H), 1.34 (s, 9H) |
| 786 | 1H NMR (400 MHz, DMSO-d6) δ 9.41 (s, 1H), 9.04 (s, 1H), 8.62 (d, J = 4.7 Hz, 1H), 8.35 (s, 1H), 7.98 (s, 1H), 7.90 (td, J = 7.7, 1.8 Hz, 1H), 7.72-7.57 (m, 2H), 7.55-7.18 (m, 8H), 6.12 (d, J = 7.0 Hz, 1H), 5.32 (s, 2H), 4.85-4.74 (m, 1H), 3.65 (d, J = 11.9 Hz, 2H), 3.11 (q, J = 10.0, 8.8 Hz, 2H), 2.54 (s, 1H), 2.39-2.30 (m, 2H), 2.23 (q, J = 12.0, 11.1 Hz, 2H), 1.40-1.27 (m, 9H) |
| 787 | 1H NMR (400 MHz, DMSO-d6) δ 9.45 (s, 1H), 8.99 (s, 1H), 8.42 (s, 1H), 7.97 (s, 1H), 7.69 (d, J = 2.2 Hz, 1H), 7.52-7.21 (m, 9H), 7.07 (d, J = 9.0 Hz, 1H), 6.08 (d, J = 7.8 Hz, 1H), 4.85-4.74 (m, 1H), 3.65 (d, J = 12.0 Hz, 2H), 3.52 (s, 1H), 3.11 (q, J = 11.7 Hz, 2H), 2.57-2.47 (m, 10H), 2.35 (d, J = 12.8 Hz, 2H), 2.22 (q, J = 13.4 Hz, 2H), 1.35 (s, 9H) |
| 789 | 1H NMR (400 MHz, DMSO-d6) δ 9.39 (s, 1H), 8.77 (m, 1H), 8.48 (m, 1H), 8.39 (s, 1H), 7.93 (s, 1H), 7.66 (m, 1H) 7.49-7.15 (m, 9H), 6.04 (m, 1H), 4.92 (m, 1H), 3.24 (m, 2H), 2.17 (m, 2H), 2.01 (m, 2H), 1.34 (s, 3H), 1.32 (s, 3H). |
| 790 | 1H NMR (400 MHz, DMSO-d6) δ 9.40 (s, 1H), 8.88 (m, 1H), 8.49 (m, 1H), 8.39 (s, 1H), 7.93 (s, 1H), 7.67 (s, 1H) 7.49-7.15 (m, 11H), 6.04 (m, 1H), 4.91 (m, 1H), 3.27 (m, 2H), 2.17 (m, 2H), 2.01 (m, 2H), 1.34 (s, 3H), 1.32 (s, 3H). |
| 791 | 1H NMR (400 MHz, DMSO-d6) δ 9.48 (s, 1H), 9.42 (brs, 1H), 8.34 (s, 1H), 8.05 (s, 1H), 7.44-7.30 (m, 5H), 7.25-7.15 (m, 6H), 7.10 (s, 1H) 6.06 (s, 1H), 4.73 (m, 1H), 3.60 (d, J = 12.0 Hz, 2H), 3.24-3.04 (m, 4H), 2.32 (m, 2H), 2.17 (m, 2H), 1.20 (m, 3H). |
| 792 | 1H NMR (400 MHz, DMSO-d6) δ 9.43-9.32 (m, 1H), 8.39 (s, 1H), 8.01 (s, 1H), 7.68 (d, J = 2.3 Hz, 1H), 7.50-7.16 (m, 8H), 6.03 (d, J = 8.5 Hz, 1H), 4.49-4.33 (m, 2H), 2.96-2.81 (m, 2H), 2.31-2.23 (m, 2H), 2.06-1.83 (m, 5H), 1.46-1.21 (m, 5H), 0.87 (t, J = 7.3 Hz, 3H) |
| 793 | 1H NMR (400 MHz, DMSO-d6) δ 9.58 (s, 1H), 9.43 (s, 1H), 8.39 (s, 1H), 8.00 (s, 1H), 7.68 (d, J = 2.2 Hz, 1H), 7.48 (dd, J = 6.6, 2.6 Hz, 1H), 7.46-7.39 (m, 3H), 7.37 (d, J = 8.7 Hz, 1H), 7.33 (dd, J = 8.3, 6.8 Hz, 2H), 7.28-7.20 (m, 3H), 6.09 (d, J = 7.8 Hz, 1H), 4.74 (t, J = 6.5 Hz, 2H), 3.58 (q, J = 5.4 Hz, 2H), 2.78 (d, J = 3.7 Hz, 6H). |
| 794 | 1H NMR (400 MHz, DMSO-d6) δ 9.42 (s, 1H), 8.64 (brs, 1H), 8.42 (brs, 1H), 8.32 (s, 1H), 7.97 (s, 1H), 7.49-7.15 (m, 11H), 7.08 (s, 1H) 6.05 (s, 1H), 4.75 (m, 1H), 3.38 (d, J = 12.0 Hz, 2H), 3.04 (m, 2H), 2.22 (m, 2H), 2.08 (m, 2H). |
| 795 | 1H NMR (400 MHz, DMSO-d6) δ 9.50 (s, 1H), 8.40 (s, 1H), 7.87 (s, 1H), 7.68 (d, J = 2.2 Hz, 1H), 7.50 (dd, J = 6.6, 2.6 Hz, 1H), 7.46-7.39 (m, 4H), 7.31 (t, J = 7.6 Hz, 2H), 7.28-7.20 (m, 3H), 6.08 (s, 1H), 4.48 (t, J = 5.2 Hz, 2H), 3.67 (dd, J = 5.6, 4.7 Hz, 2H), 3.17 (s, 3H). |
| 796 | 1H NMR (400 MHz, DMSO-d6) δ 8.39 (s, 1H), 7.99 (s, 1H), 7.67 (d, J = 2.4 Hz, 1H), 7.48 (dd, J = 6.6, 2.7 Hz, 1H), 7.46-7.39 (m, 3H), 7.31 (dd, J = 8.4, 6.8 Hz, 2H), 7.23 (ddt, J = 8.5, 4.5, 2.3 Hz, 3H), 6.08 (s, 1H), 4.54 (t, J = 6.2 Hz, 2H), 3.29 (t, J = 6.3 Hz, 2H). |
| 797 | 1H NMR (400 MHz, DMSO-d6) δ 9.42 (s, 1H), 8.39 (s, 1H), 7.95 (s, 1H), 7.67 (d, J = 2.2 Hz, 1H), 7.47 (dd, J = 6.6, 2.6 Hz, 1H), 7.45-7.39 (m, 3H), 7.38-7.29 (m, 3H), 7.27-7.19 (m, 3H), 6.06 (d, J = 7.2 Hz, 1H), 4.38 (t, J = 7.1 Hz, 2H), 3.10-3.00 (m, 2H), 2.74 (s, 3H), 2.73 (s, 3H), 2.21-2.10 (m, 2H). |
| 798 | 1H NMR (400 MHz, DMSO-d6) δ 10.40 (s, 1H), 8.82 (s, 1H), 7.92 (s, 1H), 7.72 (dd, J = 6.6, 2.5 Hz, 1H), 7.57-7.34 (m, 5H), 7.29 (s, 1H), 7.21-7.08 (m, 2H), 6.73 (d, J = 9.0 Hz, 1H), 6.18 (d, J = 8.6 Hz, 1H), 4.05 (s, 3H), 3.98 (s, 3H) |
| 803 | 1H NMR (400 MHz, DMSO-d6) δ 9.37 (s, 1H), 8.92 (s, 1H), 8.41 (s, 1H), 7.97 (s, 1H), 7.66 (d, J = 2.2 Hz, 1H), 7.48-7.42 (m, 3H), 7.39 (td, J = 5.9, 2.7 Hz, 4H), 7.24-7.20 (m, 1H), 7.19 (d, J = 2.5 Hz, 2H), 6.06 (d, J = 8.2 Hz, 1H), 4.77 (ddt, J = 11.7, 8.4, 4.6 Hz, 1H), 3.63 (d, J = 12.3 Hz, 3H), 3.10 (q, J = 11.6 Hz, 2H), 2.38-2.28 (m, 3H), 2.21 (d, J = 13.1 Hz, 2H), 1.33 (s, 9H). |

TABLE 2-continued

| Cmpd | 1H-NMR |
|---|---|
| 804 | 1H NMR (400 MHz, DMSO-d6) δ 9.34 (s, 1H), 8.30 (s, 1H), 8.00 (s, 1H), 7.49-7.17 (m, 16 H), 7.05 (s, 1H), 6.02 (m, 1H), 5.07 (s, 2H), 4.69 (m, 1H), 4.06 (m 2H), 2.99 (m, 2H), 2.01 (m, 2H), 1.83 (m, 2H) |
| 808 | 1H NMR (400 MHz, DMSO-d6) δ 9.41 (s, 1H), 8.39 (s, 1H), 7.93 (s, 1H), 7.66 (d, J = 2.2 Hz, 1H), 7.52-7.39 (m, 5H), 7.34 (d, J = 9.8 Hz, 1H), 7.22 (tt, J = 6.3, 3.4 Hz, 2H), 7.19-7.12 (m, 2H), 6.06 (d, J = 4.0 Hz, 1H), 4.55 (s, 2H), 4.48 (dd, J = 6.0, 2.1 Hz, 2H), 4.17 (dd, J = 6.0, 2.1 Hz, 2H), 1.07 (s, 3H). |
| 810 | 1H NMR (400 MHz, DMSO-d6) δ 9.36 (s, 1H), 8.38 (s, 1H), 8.14 (s, 1H), 7.65 (s, 1H), 7.47 (ddd, J = 9.1, 5.7, 2.9 Hz, 3H), 7.39 (q, J = 9.0 Hz, 2H), 7.21 (s, 2H), 7.18-7.10 (m, 2H), 6.09 (d, J = 8.6 Hz, 1H), 5.78 (tt, J = 7.5, 6.0 Hz, 1H), 5.00-4.92 (m, 2H), 4.84 (dt, J = 8.8, 6.6 Hz, 2H). |
| 812 | 1H NMR (400 MHz, DMSO-d6) δ 9.45 (s, 1H), 8.40 (s, 1H), 8.04 (s, 1H), 7.67 (d, J = 2.2 Hz, 1H), 7.51-7.39 (m, 4H), 7.36 (s, 1H), 7.24 (ddt, J = 8.9, 4.2, 2.1 Hz, 2H), 7.17-7.05 (m, 2H), 6.07 (s, 1H), 2.91 (s, 2H), 1.64 (d, J = 3.0 Hz, 6H). |
| 814 | 1H NMR (400 MHz, DMSO-d6) δ 9.37 (s, 1H), 8.63 (brs, 1H), 8.35 (brs, 1H), 8.33 (s, 1H), 7.98 (s, 1H), 7.42 (m, 7H), 7.25 (m, 2H), 7.06 (m, 1H), 6.06 (m, 1H), 4.74 (m, 1H), 3.38 (m, 2H), 3.05 (m, 2H), 2.23 (m, 2H), 2.09 (m, 2H). |
| 815 | 1H NMR (400 MHz, DMSO-d6) δ 9.47 (s, 1H), 8.41 (s, 1H), 8.08 (s, 1H), 7.66 (d, J = 2.2 Hz, 1H), 7.51-7.45 (m, 4H), 7.42 (t, J = 9.0 Hz, 2H), 7.27 (d, J = 2.6 Hz, 1H), 7.26-7.22 (m, 1H), 7.20-7.12 (m, 2H), 6.13 (s, 1H), 5.74 (s, 2H). |
| 816 | 1H NMR (400 MHz, DMSO-d6) δ 9.31 (s, 1H), 8.31 (s, 1H), 7.97 (s, 1H), 7.49-7.17 (m, 15 H), 7.03 (s, 1H), 6.03 (m, 1H), 5.07 (s, 2H), 4.69 (m, 1H), 4.06 (m 2H), 3.00 (m, 2H), 1.98 (m, 2H), 1.84 (m, 2H) |
| 818 | 1H NMR (400 MHz, DMSO-d6) δ 9.41 (s, 1H), 8.39 (s, 1H), 7.66 (m, 2H), 7.45 (m, 5H), 7.19 (m, 4H), 6.07 (m, 1H), 4.30 (m, 3H), 3.09 (m, 1H), 2.92 (m, 1H), 2.60 (s, 6H), 1.80 (m, 1H), 1.53 (m, 2H), 1.38 (m, 1H). |
| 827 | 1H NMR (400 MHz, DMSO-d6) δ 9.33 (brs, 1H), 8.59 (s, 1H), 8.05 (s, 1H), 7.74 (m, 1H), 7.50 (m, 5H), 7.31 (m, 2H), 7.15 (t, J = 8.0 Hz, 2H), 6.09 (s, 1H), 4.73 (m, 1H), 3.61 (m 2H), 3.15-3.02 (m, 4H), 2.33 (m, 2H), 2.15 (m, 2H), 1.20 (m, 3H). |
| 829 | 1H NMR (400 MHz, DMSO-d6) δ 9.77 (s, 1H), 9.43-9.33 (m, 1H), 8.40 (s, 1H), 8.14 (s, 1H), 8.09 (s, 1H), 7.66 (t, J = 2.2 Hz, 1H), 7.50-7.44 (m, 3H), 7.41 (t, J = 9.0 Hz, 2H), 7.36 (d, J = 8.2 Hz, 2H), 7.23-7.19 (m, 3H), 7.16 (t, J = 8.9 Hz, 2H), 6.08 (d, J = 7.5 Hz, 1H), 5.11 (dd, J = 9.6, 4.6 Hz, 1H), 4.01 (dd, J = 13.5, 5.1 Hz, 1H), 3.84 (t, J = 12.1 Hz, 1H), 3.38 (s, 2H), 3.33-3.19 (m, 4H), 2.41-2.27 (m, 1H), 2.02-1.89 (m, 3H), 1.68 (s, 1H), 1.50 (s, 1H). |
| 832 | 1H NMR (400 MHz, DMSO-d6) δ 8.68 (s, 1H), 7.95 (s, 1H), 7.74 (m, 1H), 7.66 (m, 1H), 7.52 (m, 4H), 7.39 (m, 2H), 7.14 (t, J = 8.0 Hz, 2H) 6.10 (s, 1H), 4.73 (m, 1H), 3.60 (m 2H), 3.18-3.04 (m, 4H), 2.32 (m, 2H), 2.14 (m, 2H), 1.20 (m, 3H). |
| 835 | 1H NMR (400 MHz, DMSO-d6) δ 9.37 (s, 1H), 8.39 (s, 1H), 8.01 (s, 1H), 7.85 (m, 1H), 7.49-7.17 (m, 11 H), 7.17 (m, 4H), 6.03 (m, 1H), 5.07 (s, 2H), 4.69 (m, 1H), 4.07 (m 2H), 2.99 (m, 2H), 2.00 (m, 2H), 1.82 (m, 2H) |
| 838 | 1H NMR (400 MHz, DMSO-d6) δ 9.39 (s, 1H), 9.02 (brs, 1H), 8.40 (s, 1H), 7.93 (m, 1H), 7.66 (m, 1H), 7.44 (m, 6H), 7.25-7.15 (m, 5H), 6.06 (m, 1H), 4.95 (m, 1H), 3.65 (m, 1H), 3.43 (m, 1H), 3.14 (m, 1H), 2.78 (m, 1H), 2.20 (m, 4H), 1.35 (s, 3H), 1.33 (s, 3H), 1.25 (t, J = 8 Hz, 3H). |
| 839 | 1H NMR (400 MHz, DMSO-d6) δ 9.40 (s, 1H), 8.86 (m, 1H), 8.55 (m, 1H), 8.40 (s, 1H), 7.95 (s, 1H), 7.66 (m, 1H) 7.49-7.15 (m, 9H), 6.06 (m, 1H), 4.91 (m, 1H), 3.27 (m, 2H), 2.12 (m, 2H), 2.01 (m, 2H), 1.35 (s, 3H), 1.33 (s, 3H). |
| 840 | 1H NMR D2O exchange (400 MHz, DMSO-d6) δ 8.39 (d, J = 1.2 Hz, 1H), 7.94 (d, J = 7.2 Hz, 1H), 7.65 (d, J = 2.4 Hz, 1H), 7.50-7.37 (m, 4H), 7.23-7.12 (m, 4H), 6.04 (s, 1H), 4.64 (ddd, J = 11.8, 8.2, 3.8 Hz, 1H), 3.39-3.32 (m, 1H), 3.19-3.09 (m, 1H), 3.02 (td, J = 12.6, 3.7 Hz, 1H), 2.92 (dd, J = 12.9, 5.0 Hz, 1H), 2.44-2.35 (m, 1H), 2.05-1.94 (m, 1H), 0.76 (dd, J = 16.5, 11.0 Hz, 6H). |
| 843 | 1H NMR (400 MHz, DMSO-d6) δ 9.45 (s, 1H), 8.41 (s, 1H), 8.01 (s, 1H), 7.66 (m, 1H), 7.44 (m, 5H), 7.25-7.15 (m, 3H), 6.05 (m, 1H), 4.69 (m, 1H), 3.91 (m, 2H), 3.43 (m, 2H), 1.94 (m, 4H). |
| 846 | 1H NMR (400 MHz, DMSO-d6) δ 9.51 (s, 1H), 8.40 (s, 1H), 7.69 (d, J = 2.2 Hz, 1H), 7.59 (d, J = 2.2 Hz, 1H), 7.48 (dd, J = 6.6, 2.6 Hz, 1H), 7.42 (ddd, J = 9.1, 7.4, 1.9 Hz, 3H), 7.26-7.22 (m, 1H), 7.20 (d, J = 2.4 Hz, 1H), 7.10 (t, J = 8.9 Hz, 2H), 6.14 (d, J = 2.2 Hz, 1H), 5.91 (s, 1H), 3.76 (s, 3H). |
| 847 | 1H NMR (400 MHz, DMSO-d6) δ 9.43 (s, 1H), 8.51 (s, 1H), 7.72 (d, J = 1.9 Hz, 1H), 7.65 (d, J = 2.3 Hz, 1H), 7.59 (d, J = 1.9 Hz, 1H), 7.49 (d, J = 7.2 Hz, 1H), 7.42 (dd, J = 8.7, 5.4 Hz, 2H), 7.39-7.35 (m, 2H), 7.30 (t, J = 8.8 Hz, 2H), 7.16 (ddd, J = 8.9, 4.1, 2.7 Hz, 1H), 7.07 (d, J = 2.4 Hz, 1H), 6.38 (d, J = 6.9 Hz, 1H), 3.67 (s, 3H). |
| 848 | 1H NMR (400 MHz, DMSO-d6) δ 9.35 (s, 1H), 8.38 (s, 1H), 8.00 (s, 1H), 7.66 (d, J = 2.2 Hz, 1H), 7.47-7.40 (m, 3H), 7.39-7.27 (m, 10H), 7.25-7.16 (m, 4H), 6.02 (d, J = 8.4 Hz, 1H), 5.14-5.04 (m, 3H), 4.68 (ddt, J = 11.4, 7.9, 4.1 Hz, 1H), 4.48 (td, J = 6.5, 4.5 Hz, 1H), 4.32 (t, J = 5.2 Hz, 1H), 4.08 (s, 1H), 4.04 (d, J = 4.1 Hz, 2H), 3.35 (td, J = 6.5, 5.2 Hz, 1H), 2.00 (d, J = 12.1 Hz, 2H), 1.83 (ddt, J = 12.2, 7.4, 3.7 Hz, 2H), 1.59 (ddd, J = 8.2, 6.3, 2.0 Hz, 1H), 1.46 (ddd, J = 13.3, 7.7, 6.3 Hz, 1H), 1.35 (ddt, J = 12.9, 8.7, 6.4 Hz, 1H). |
| 849 | 1H NMR (400 MHz, DMSO-d6) δ 9.39 (s, 1H), 9.33 (s, 1H), 8.40 (s, 1H), 7.99 (s, 1H), 7.66 (d, J = 2.3 Hz, 1H), 7.51-7.44 (m, 4H), 7.41 (t, J = 9.0 Hz, 1H), 7.36 (s, 1H), 7.21 (qd, J = 4.5, 2.7 Hz, 3H), 7.18-7.11 (m, 2H), 6.06 (d, J = 7.3 Hz, 1H), 4.72 (tt, J = 11.9, 4.2 Hz, 1H), 3.60 (d, J = 12.3 Hz, 2H), 3.30-2.97 (m, 5H), 2.39-2.28 (m, 3H), 2.16 (ddd, J = 14.8, 8.6, 3.6 Hz, 2H), 1.22 (t, J = 7.3 Hz, 4H). |

TABLE 2-continued

| Cmpd | 1H-NMR |
|---|---|
| 850 | 1H NMR (400 MHz, DMSO-d6) δ 9.37 (s, 1H), 8.62 (s, 1H), 8.40 (s, 1H), 7.97 (s, 1H), 7.65 (d, J = 2.2 Hz, 1H), 7.49-7.43 (m, 3H), 7.41 (t, J = 9.0 Hz, 1H), 7.36 (d, J = 8.6 Hz, 1H), 7.20 (dq, J = 6.7, 2.6 Hz, 2H), 7.14 (t, J = 8.9 Hz, 2H), 6.06 (d, J = 8.2 Hz, 1H), 4.74 (ddt, J = 10.9, 7.9, 4.1 Hz, 1H), 3.38 (d, J = 13.2 Hz, 3H), 3.06 (dd, J = 13.3, 10.3 Hz, 2H), 2.29-2.17 (m, 2H), 2.16-2.00 (m, 2H). |
| 851 | 1H NMR (400 MHz, DMSO-d6) δ 9.38 (s, 1H), 8.64 (s, 1H), 8.40 (s, 1H), 7.97 (s, 1H), 7.65 (d, J = 2.2 Hz, 1H), 7.50-7.43 (m, 3H), 7.41 (t, J = 9.0 Hz, 1H), 7.38-7.34 (m, 1H), 7.25-7.18 (m, 2H), 7.14 (t, J = 8.8 Hz, 2H), 6.06 (d, J = 7.9 Hz, 1H), 4.75 (tt, J = 11.0, 4.1 Hz, 1H), 3.38 (d, J = 12.8 Hz, 2H), 3.05 (q, J = 11.9 Hz, 2H), 2.30-2.18 (m, 2H), 2.16-1.98 (m, 2H). |
| 852 | 1H NMR (400 MHz, DMSO-d6) δ 9.80 (s, 1H), 9.43 (s, 1H), 8.39 (s, 1H), 7.89 (s, 1H), 7.68 (d, J = 2.2 Hz, 1H), 7.55 (t, J = 1.7 Hz, 1H), 7.41 (ddt, J = 14.4, 11.9, 5.1 Hz, 6H), 7.24-7.19 (m, 2H), 6.09 (d, J = 5.2 Hz, 1H), 4.29 (d, J = 5.7 Hz, 2H), 3.99 (s, 3H), 3.35-3.19 (m, 2H), 3.12-2.92 (m, 2H), 1.91 (dt, J = 6.9, 3.8 Hz, 2H), 1.73 (p, J = 7.6, 7.1 Hz, 2H). |
| 853 | 1H NMR (400 MHz, DMSO-d6) δ 9.32 (s, 1H), 8.38 (s, 1H), 7.60 (d, J = 2.2 Hz, 1H), 7.45-7.36 (m, 7H), 7.27 (d, J = 0.8 Hz, 1H), 7.24-7.15 (m, 3H), 7.12 (t, J = 8.9 Hz, 2H), 7.08 (d, J = 2.4 Hz, 2H), 5.81-5.74 (m, 1H), 3.75 (s, 3H). |
| 854 | 1H NMR (400 MHz, DMSO-d6) δ 9.43 (s, 1H), 8.45 (s, 1H), 7.87 (s, 1H), 7.73 (d, J = 2.3 Hz, 1H), 7.50-7.43 (m, 4H), 7.40 (t, J = 9.0 Hz, 1H), 7.24 (d, J = 2.6 Hz, 2H), 7.23-7.20 (m, 1H), 7.17 (t, J = 8.9 Hz, 2H), 6.24-6.18 (m, 1H), 3.81 (s, 3H). |
| 856 | 1H NMR (400 MHz, DMSO-d6) δ 9.36 (s, 1H), 9.21 (s, 1H), 8.40 (s, 1H), 8.00 (s, 1H), 7.66 (d, J = 2.2 Hz, 1H), 7.48-7.43 (m, 4H), 7.39 (td, J = 6.6, 3.1 Hz, 5H), 7.24-7.21 (m, 1H), 7.20 (d, J = 2.6 Hz, 2H), 6.06 (d, J = 8.2 Hz, 1H), 4.72 (ddt, J = 11.9, 7.9, 4.2 Hz, 1H), 3.60 (d, J = 12.6 Hz, 3H), 3.25-2.92 (m, 5H), 2.39-2.27 (m, 3H), 2.25-2.07 (m, 3H), 1.22 (t, J = 7.3 Hz, 3H). |
| 857 | 1H NMR (400 MHz, DMSO-d6) δ 9.39 (s, 1H), 8.65 (s, 1H), 8.40 (s, 1H), 7.99 (s, 1H), 7.65 (d, J = 2.2 Hz, 1H), 7.48-7.42 (m, 3H), 7.42-7.35 (m, 4H), 7.24-7.21 (m, 1H), 6.07 (d, J = 7.8 Hz, 1H), 4.75 (tt, J = 11.0, 4.1 Hz, 1H), 3.45-3.33 (m, 2H), 3.05 (q, J = 11.7 Hz, 2H), 2.30-2.17 (m, 2H), 2.15-2.01 (m, 2H). |
| 858 | 1H NMR (400 MHz, DMSO-d6) δ 9.37 (s, 1H), 9.25 (d, J = 9.6 Hz, 1H), 8.40 (s, 1H), 8.00 (s, 1H), 7.66 (d, J = 2.2 Hz, 1H), 7.49-7.42 (m, 5H), 7.42-7.36 (m, 5H), 7.26-7.21 (m, 1H), 6.07 (d, J = 8.1 Hz, 2H), 4.72 (tt, J = 12.0, 4.1 Hz, 1H), 3.27-2.97 (m, 6H), 2.39-2.28 (m, 3H), 2.14 (q, J = 12.7 Hz, 2H), 1.22 (t, J = 7.3 Hz, 3H). |
| 859 | 1H NMR (400 MHz, DMSO-d6) δ 9.38 (s, 1H), 8.65 (s, 1H), 8.40 (s, 1H), 7.99 (s, 1H), 7.65 (d, J = 2.2 Hz, 1H), 7.49-7.42 (m, 3H), 7.42-7.35 (m, 4H), 7.24-7.21 (m, 1H), 7.20 (d, J = 2.6 Hz, 1H), 6.07 (d, J = 8.0 Hz, 1H), 4.75 (tt, J = 11.1, 4.1 Hz, 1H), 3.38 (d, J = 13.4 Hz, 3H), 3.05 (q, J = 11.7 Hz, 2H), 2.28-2.18 (m, 2H), 2.15-2.00 (m, 2H). |
| 862 | 1H NMR D2O exchange (400 MHz, DMSO-d6) δ 8.67 (d, J = 7.1 Hz, 2H), 8.20 (d, J = 2.4 Hz, 1H), 8.16-8.09 (m, 2H), 7.55 (dd, J = 6.6, 2.6 Hz, 1H), 7.45 (t, J = 9.0 Hz, 1H), 7.42-7.36 (m, 2H), 7.31 (ddd, J = 8.8, 4.2, 2.6 Hz, 1H), 7.21-7.13 (m, 2H), 6.44 (d, J = 7.7 Hz, 1H), 5.67 (dd, J = 7.7, 5.5 Hz, 1H), 4.96 (d, J = 5.5 Hz, 1H). |
| 864 | 1H NMR (400 MHz, DMSO-d6) δ 9.40 (s, 1H), 9.11 (brs, 1H), 8.40 (s, 1H), 8.09 (d, J = 8 Hz, 1H), 7.66 (m, 1H), 7.43 (m, 5H), 7.19 (m, 4H), 6.09 (m, 1H), 5.38 (m, 1H), 3, 67 (m, 2H), 3.36 (m, 2H), 2.48 (m, 1H), 2.27 (m, 1H). |
| 865 | 1H NMR (400 MHz, DMSO-d6) δ 10.1 (m, 1H), 9.41 (s, 1H), 8.40 (s, 1H), 8.10 (d, J = 8 Hz, 1H), 7.66 (m, 1H), 7.45 (m, 5H), 7.19 (m, 4H), 6.11 (m, 1H), 5.43 (m, 1H), 4.01 (m, 1H), 3.63 (m, 2H), 3.23 (m, 3H), 2.68 (m, 1H), 2.33 (m, 1H), 121 (t, J = 8 Hz, 3H). |
| 870 | 1H NMR D2O exchange (400 MHz, DMSO-d6) δ 8.39 (s, 1H), 8.08 (d, J = 8.9 Hz, 1H), 7.65 (d, J = 2.3 Hz, 1H), 7.51-7.43 (m, 3H), 7.41 (t, J = 9.1 Hz, 1H), 7.25-7.18 (m, 2H), 7.15 (t, J = 8.8 Hz, 2H), 6.10 (d, J = 4.9 Hz, 2H), 5.53 (t, J = 9.2 Hz, 1H), 4.64 (d, J = 11.5 Hz, 1H), 4.50 (d, J = 6.6 Hz, 2H), 4.43 (d, J = 10.5 Hz, 2H), 3.30 (dt, J = 20.9, 7.3 Hz, 2H), 1.09 (q, J = 6.9 Hz, 3H). |
| 871 | 1H NMR D2O exchange (400 MHz, DMSO-d6) δ 8.39 (d, J = 0.8 Hz, 1H), 8.10 (d, J = 1.3 Hz, 1H), 8.09-8.05 (m, 1H), 7.65 (d, J = 2.3 Hz, 1H), 7.44 (dt, J = 7.3, 2.5 Hz, 4H), 7.39 (dd, J = 8.7, 6.7 Hz, 4H), 7.25-7.19 (m, 3H), 6.17-6.06 (m, 1H), 5.62-5.47 (m, 1H), 4.63 (s, 2H), 4.50 (d, J = 6.6 Hz, 2H), 4.42 (s, 2H), 3.37-3.19 (m, 2H), 1.09 (q, J = 6.8 Hz, 3H). |
| 872 | 1H NMR D2O exchange (400 MHz, DMSO-d6) δ 8.40 (d, J = 0.7 Hz, 1H), 8.07 (s, 1H), 7.65 (d, J = 2.3 Hz, 1H), 7.49-7.42 (m, 3H), 7.39 (t, J = 8.5 Hz, 3H), 7.22 (qd, J = 4.2, 2.7 Hz, 2H), 6.11 (s, 1H), 5.64-5.47 (m, 1H), 4.43 (dd, J = 11.5, 8.7 Hz, 2H), 4.35 (ddd, J = 11.5, 6.7, 3.4 Hz, 2H). |
| 873 | 1H NMR D2O exchange (400 MHz, DMSO-d6) δ 8.37 (s, 1H), 8.01 (d, J = 2.8 Hz, 1H), 7.63 (d, J = 2.3 Hz, 1H), 7.50-7.30 (m, 6H), 7.18 (dq, J = 5.4, 3.0, 2.5 Hz, 2H), 7.12 (t, J = 8.8 Hz, 2H), 7.08-7.00 (m, 1H), 6.04 (d, J = 4.7 Hz, 1H), 6.02-5.95 (m, 1H), 5.20 (tt, J = 7.7, 4.1 Hz, 1H), 3.42 (ddd, J = 12.4, 7.1, 3.4 Hz, 1H), 3.28-3.20 (m, 1H), 3.20-3.05 (m, 2H), 2.76 (dd, J = 13.9, 8.7 Hz, 1H), 2.34 (dq, J = 13.5, 7.9 Hz, 2H), 2.15-2.03 (m, 1H). |
| 874 | 1H NMR (400 MHz, DMSO-d6) δ 9.34 (s, 1H), 8.42 (s, 1H), 8.23 (s, 1H), 8.18 (s, 1H), 8.02 (s, 1H), 7.64 (m, 2H), 7.42 (m, 3H), 7.21 (m, 2H), 6.29 (m, 1H), 4.77 (m, 1H), 3.39 (m, 2H), 3.07 (m, 2H), 2.27 (m, 2H), 2.09 (m, 2H). |
| 875 | 1H NMR (400 MHz, DMSO-d6) δ 9.39 (s, 1H), 8.75 (brs, 1H), 8.45 (s, 1H), 8.07 (s, 1H), 7.66 (m, 1H), 7.37 (m, 5H), 7.16 (m, 2H), 6.06 (m, 1H), 4.75 (m, 1H), 3.39 (m, 2H), 3.06 (m, 2H), 2.24 (m, 2H), 2.10 (m, 2H). |

TABLE 2-continued

| Cmpd | 1H-NMR |
|---|---|
| 876 | 1H NMR D2O exchange (400 MHz, DMSO-d6) δ 8.40 (s, 1H), 8.00 (s, 1H), 7.64 (d, J = 2.3 Hz, 1H), 7.45 (dd, J = 8.5, 5.7 Hz, 4H), 7.40 (t, J = 9.0 Hz, 2H), 7.30 (dd, J = 11.1, 5.9 Hz, 6H), 7.25-7.22 (m, 1H), 7.20 (t, J = 2.4 Hz, 2H), 7.12 (t, J = 8.8 Hz, 3H), 6.04 (d, J = 1.6 Hz, 1H), 5.20 (s, 1H), 5.12-4.94 (m, 3H), 3.83 (dt, J = 12.3, 6.1 Hz, 1H), 3.80-3.72 (m, 1H), 3.64 (d, J = 11.9 Hz, 1H), 2.40 (s, 2H), 2.29 (d, J = 14.8 Hz, 2H). |
| 878 | 1H NMR D2O exchange (400 MHz, DMSO-d6) δ 8.39 (s, 1H), 8.00 (d, J = 2.2 Hz, 1H), 7.63 (d, J = 2.3 Hz, 1H), 7.49-7.25 (m, 12H), 7.25-7.20 (m, 1H), 7.19 (d, J = 2.4 Hz, 1H), 6.04 (s, 1H), 5.20 (s, 1H), 5.13-4.94 (m, 2H), 3.84 (dd, J = 11.6, 6.5 Hz, 1H), 3.79-3.73 (m, 1H), 3.66 (s, 1H), 3.46 (d, J = 9.5 Hz, 1H), 2.40 (s, 2H), 2.31 (s, 2H). |
| 880 | 1H NMR D2O exchange (400 MHz, DMSO-d6) δ 8.40 (s, 1H), 8.07 (d, J = 8.0 Hz, 1H), 7.65 (dd, J = 2.4, 1.5 Hz, 1H), 7.45 (dt, J = 8.5, 3.0 Hz, 4H), 7.38 (t, J = 8.7 Hz, 4H), 7.21 (dq, J = 8.4, 2.9 Hz, 3H), 6.08 (s, 1H), 5.37 (qt, J = 6.5, 2.7 Hz, 2H), 3.74-3.64 (m, 1H), 3.59 (dd, J = 12.8, 3.8 Hz, 1H), 3.36 (ddd, J = 8.2, 6.4, 1.7 Hz, 3H), 2.47-2.38 (m, 1H), 2.26 (tdd, J = 10.0, 7.9, 5.2 Hz, 2H). |
| 881 | 1H NMR (400 MHz, DMSO-d6) δ 9.36 (s, 1H), 8.38 (s, 1H), 7.87 (s, 1H), 7.65 (d, J = 2.2 Hz, 1H), 7.47 (dd, J = 6.7, 2.6 Hz, 1H), 7.43 (d, J = 8.6 Hz, 2H), 7.41-7.35 (m, 4H), 7.22 (dd, J = 7.3, 2.1 Hz, 2H), 6.07 (d, J = 8.7 Hz, 1H), 3.98 (s, 3H). |
| 882 | 1H NMR (400 MHz, DMSO-d6) δ 9.51 (s, 1H), 8.41 (s, 1H), 7.86 (s, 1H), 7.66 (d, J = 2.2 Hz, 1H), 7.49 (dd, J = 6.6, 2.6 Hz, 1H), 7.48-7.39 (m, 4H), 7.29-7.20 (m, 3H), 7.19-7.10 (m, 3H), 6.07 (s, 1H), 3.98 (s, 3H). |
| 883 | 1H NMR (400 MHz, DMSO-d6) δ 9.40 (s, 1H), 8.44 (s, 1H), 7.94 (s, 1H) 7.65 (m, 1H), 7.44-7.21 (m, 8H), 7.10 (m, 1H), 6.98 (m, 3H), 6.00 (m, 1H), 5.06 (s, 2H), 4.67 (m, 1H), 4.06 (m 2H), 2.98 (m, 2H), 2.25 (s, 3H), 1.98 (m, 2H), 1.82 (m, 2H). |
| 885 | 1H NMR (400 MHz, DMSO-d6) δ 9.38 (m, 2H), 9.26 (brs, 1H), 8.45 (s, 1H), 7.97 (s, 1H) 7.65 (m, 1H), 7.34 (m, 2H), 7.24 (m, 2H), 7.09 (m, 1H), 6.99 (m, 3H), 6.03 (m, 1H), 4.70 (m, 1H), 3.59 (m 2H), 3.24-3.04 (m, 4H), 2.27 (m, 5H), 2.15 (m, 2H), 1.20 (m, 3H). |
| 886 | 1H NMR D2O exchange (400 MHz, DMSO-d6) 7.50-7.43 (m, 3H), 7.40 (t, J = 9.0 Hz, 1H), 7.23-7.20 (m, 1H), 7.19 (d, J = 2.5 Hz, 2H), 7.13 (t, J = 8.8 Hz, 2H), 6.05 (s, 1H), 4.74 (tt, J = 11.1, 4.1 Hz, 1H), 3.37 (dt, J = 13.1, 3.6 Hz, 2H), 3.04 (td, J = 12.9, 3.1 Hz, 2H), 2.29-2.15 (m, 2H), 2.08 (qd, J = 12.9, 12.5, 4.0 Hz, 2H). |
| 887 | 1H NMR (400 MHz, DMSO-d6) δ 9.42 (s, 1H), 9.00 (s, 1H), 8.44 (s, 1H), 7.62 (d, J = 2.3 Hz, 1H), 7.51-7.37 (m, 6H), 7.31-7.28 (m, 1H), 7.26-7.18 (m, 5H), 6.02 (d, J = 7.8 Hz, 1H), 3.76 (s, 3H). |
| 888 | 1H NMR (400 MHz, DMSO-d6) δ 9.44 (s, 1H), 8.39 (s, 1H), 7.71 (s, 1H), 7.68 (d, J = 2.2 Hz, 1H), 7.48 (dd, J = 6.6, 2.6 Hz, 1H), 7.45-7.37 (m, 4H), 7.34-7.28 (m, 3H), 7.28-7.20 (m, 4H), 6.10 (s, 1H). |
| 889 | 1H NMR (400 MHz, DMSO-d6) δ 9.28 (m, 2H), 8.46 (s, 1H), 8.12 (s, 1H), 7.66 (m, 1H), 7.37 (m, 5H), 7.16 (m, 2H), 6.04 (m, 1H), 4.71 (m, 1H), 3.61 (m 2H), 3.21-3.05 (m, 4H), 2.33 (m, 2H), 2.14 (m, 2H), 1.20 (m, 3H). |
| 890 | 1H NMR (400 MHz, DMSO-d6) δ 9.36 (s, 1H), 8.45 (s, 1H), 8.07 (s, 1H) 7.65 (m, 1H), 7.44-7.21 (m, 8H), 7.18 (m, 1H), 7.11 (m, 1H), 6.98 (m, 3H), 6.01 (m, 1H), 5.06 (s, 2H), 4.69 (m, 1H), 4.08 (m 2H), 3.00 (m, 2H), 2.02 (m, 2H), 1.83 (m, 2H). |
| 893 | 1H NMR (400 MHz, DMSO-d6) δ 9.46 (s, 1H), 8.40 (s, 1H), 7.73 (s, 1H), 7.66 (d, J = 2.2 Hz, 1H), 7.49 (dd, J = 6.6, 2.7 Hz, 1H), 7.47-7.38 (m, 4H), 7.28-7.19 (m, 3H), 7.19-7.09 (m, 3H), 6.11 (d, J = 4.8 Hz, 1H). |
| 894 | 1H NMR D2O exchange (400 MHz, DMSO-d6) δ 9.00 (d, J = 2.1 Hz, 1H), 8.44 (s, 1H), 7.60 (d, J = 2.3 Hz, 1H), 7.45 (s, 5H), 7.44 (d, J = 2.8 Hz, 1H), 7.40 (t, J = 9.0 Hz, 1H), 7.29-7.27 (m, 1H), 7.23-7.18 (m, 2H), 6.01 (s, 1H), 3.76 (s, 3H). |
| 896 | 1H NMR (400 MHz, DMSO-d6) δ 9.45 (s, 1H), 8.41 (s, 1H), 8.07 (s, 1H), 7.66 (m, 1H), 7.55 (m, 2H), 7.44-7.17 (m, 10 H), 6.10 (m, 1H), 5.07 (s, 2H), 4.70 (m, 1H), 4.07 (m 2H), 3.00 (m, 2H), 2.01 (m, 2H), 1.84 (m, 2H). |
| 897 | 1H NMR (400 MHz, DMSO-d6) δ 9.38 (s, 1H), 8.40 (s, 1H), 8.03 (s, 1H), 7.66 (m, 1H), 7.56 (m, 2H), 7.43 (m, 3H), 7.32 (m, 2H), 7.21 (m, 2H), 6.11 (m, 1H), 4.75 (m, 1H), 3.38 (m, 2H), 3.05 (m, 2H), 2.23 (m, 2H), 2.10 (m, 2H). |
| 899 | 1H NMR (400 MHz, DMSO-d6) δ 9.38 (s, 1H), 8.41 (s, 1H), 8.05 (s, 1H) 7.65 (m, 1H), 7.44-7.21 (m, 13H), 7.20 (m, 3H), 6.03 (m, 1H), 5.07 (s, 2H), 4.70 (m, 1H), 4.07 (m 2H), 3.00 (m, 2H), 2.01 (m, 2H), 1.82 (m, 2H). |
| 901 | 1H NMR (400 MHz, DMSO-d6) δ 9.33 (m, 1H), 9.25 (brs, 1H), 8.42 (s, 1H), 8.03 (s, 1H) 7.66 (m, 1H), 7.44-7.14 (m, 6H), 7.20 (m, 2H) 6.06 (m, 1H), 4.71 (m, 1H), 3.61 (m 2H), 3.22-3.05 (m, 4H), 2.33 (m, 2H), 2.15 (m, 2H), 1.20 (m, 3H). |
| 902 | 1H NMR (400 MHz, DMSO-d6) δ 9.46 (s, 1H), 8.40 (s, 1H), 8.01 (s, 1H) 7.66 (m, 1H), 7.44-7.21 (m, 11H), 7.04 (m, 2H), 6.78 (m, 1H) 5.99 (m, 1H), 4.69 (m, 1H), 4.07 (m 2H), 3.66 (s, 3H), 2.99 (m, 2H), 2.01 (m, 2H), 1.84 (m, 2H). |
| 903 | 1H NMR (400 MHz, DMSO-d6) δ 9.43 (s, 1H), 8.69 (brs, 1H), 8.40 (s, 1H), 7.98 (s, 1H) 7.66 (m, 1H), 7.44 (m, 3H), 7.23 (m, 3H), 7.04 (m, 2H), 6.79 (m, 1H) 6.01 (m, 1H), 4.75 (m, 1H), 3.66 (s, 3H), 3.38 (m 2H), 3.05 (m, 2H), 2.23 (m, 2H), 2.10 (m, 2H). |
| 904 | 1H NMR (400 MHz, DMSO-d6) δ 9.38 (s, 1H), 9.30 (brs, 1H), 8.40 (s, 1H), 8.12 (s, 1H), 7.98 (s, 1H) 7.66 (m, 1H), 7.44 (m, 2H), 7.23 (m, 3H), 7.04 (m, 2H), 6.80 (m, 1H) 6.01 (m, 1H), 4.73 (m, 1H), 3.67 (s, 3H), 3.60 (m 2H), 3.24-3.04 (m, 4H), 2.33 (m, 2H), 2.15 (m, 2H), 1.21 (m, 3H). |
| 906 | 1H NMR (400 MHz, DMSO-d6) δ 9.41 (m, 2H), 8.69 (brs, 1H), 8.41 (s, 1H), 8.02 (s, 1H) 7.67 (m, 1H), 7.44-7.04 (m, 9H), 7.07 (m, 1H), 6.09 (m, 1H), 4.76 (m, 1H), 3.38 (m, 2H), 3.04 (m, 2H), 2.18 (m, 2H), 2.05 (m, 2H). |

TABLE 2-continued

| Cmpd | 1H-NMR |
|---|---|
| 907 | 1H NMR (400 MHz, DMSO-d6) δ 9.40 (m, 2H), 8.41 (s, 1H), 8.16 (s, 1H), 8.03 (s, 1H) 7.67 (m, 1H), 7.44-7.04 (m, 9H), 7.07 (m, 1H) 6.09 (m, 1H), 4.73 (m, 1H), 3.61 (m 2H), 3.24-3.04 (m, 4H), 2.33 (m, 2H), 2.17 (m, 2H), 1.20 (m, 3H). |
| 908 | 1H NMR (400 MHz, DMSO-d6) δ 9.36 (s, 1H), 9.14 (s, 1H), 8.40 (s, 1H), 7.98 (s, 1H), 7.66 (s, 1H), 7.49-7.34 (m, 7H), 6.05 (d, J = 8.3 Hz, 1H), 4.72 (s, 1H), 3.60 (d, J = 12.3 Hz, 2H), 3.26-2.99 (m, 3H), 2.34-2.26 (m, 2H), 2.23-2.06 (m, 1H), 1.22 (t, J = 7.4 Hz, 3H). |
| 909 | 1H NMR (400 MHz, DMSO-d6) δ 9.42 (s, 1H), 8.42 (s, 1H), 8.09 (s, 1H) 7.67 (m, 2H), 7.58 (m, 1H), 7.44-7.21 (m, 11H), 7.20 (m, 3H), 6.05 (m, 1H), 5.07 (s, 2H), 4.70 (m, 1H), 4.08 (m 2H), 3.00 (m, 2H), 2.02 (m, 2H), 1.85 (m, 2H). |
| 912 | 1H NMR (400 MHz, DMSO-d6) δ 9.44 (s, 1H), 8.38 (s, 1H), 7.89 (s, 1H), 7.69 (d, J = 2.2 Hz, 1H), 7.49 (dd, J = 6.6, 2.6 Hz, 1H), 7.46-7.38 (m, 4H), 7.35-7.27 (m, 3H), 7.26-7.21 (m, 2H), 6.11 (d, J = 6.3 Hz, 1H), 5.22 (s, 2H). |
| 913 | 1H NMR (400 MHz, DMSO-d6) δ 9.43 (s, 1H), 8.40 (s, 1H), 8.02 (s, 1H) 7.65 (m, 1H), 7.44-7.21 (m, 16H), 6.04 (m, 1H), 5.07 (s, 2H), 4.69 (m, 1H), 4.06 (m 2H), 3.00 (m, 2H), 2.01 (m, 2H), 1.84 (m, 2H). |
| 914 | 1H NMR (400 MHz, DMSO-d6) δ 9.42 (s, 1H), 8.72 (brs, 1H), 8.40 (m, 2H), 8.00 (s, 1H), 7.66 (m, 1H), 7.43 (m, 7H), 7.22 (m, 2H), 6.07 (m, 1H), 4.76 (m, 1H), 3.38 (m, 2H), 3.07 (m, 2H), 2.24 (m, 2H), 2.10 (m, 2H). |
| 915 | 1H NMR (400 MHz, DMSO-d6) δ 9.44 (s, 1H), 8.40 (s, 1H), 7.96 (s, 1H) 7.66 (m, 1H), 7.44-7.21 (m, 9H), 7.20 (m, 2H), 7.10 (m, 2H), 5.97 (m, 1H), 5.07 (s, 2H), 4.68 (m, 1H), 4.06 (m 2H), 2.97 (m, 2H), 2.22 (s, 3H), 1.99 (m, 2H), 1.83 (m, 2H). |
| 917 | 1H NMR (400 MHz, DMSO-d6) δ 9.39 (m, 1H), 9.27 (brs, 1H), 8.39 (s, 1H), 8.00 (s, 1H), 7.66 (m, 1H), 7.42 (m, 2H) 7.31 (m, 3H), 7.17 (m, 4H), 5.99 (m, 1H), 4.71 (m, 1H), 3.60 (m 2H), 3.21-3.05 (m, 4H), 2.31 (m, 2H), 2.23 (s, 3H), 2.14 (m, 2H), 1.21 (m, 3H). |
| 920 | 1H NMR (400 MHz, DMSO-d6) δ 9.49 (s, 1H), 8.39 (s, 1H), 7.85 (s, 1H), 7.67 (d, J = 2.2 Hz, 1H), 7.49 (dd, J = 6.6, 2.6 Hz, 1H), 7.45-7.39 (m, 4H), 7.34-7.28 (m, 2H), 7.27-7.20 (m, 4H), 6.06 (s, 1H), 3.98 (s, 3H). |
| 925 | 1H NMR (400 MHz, Methanol-d4) δ 8.43 (s, 1H), 7.84 (m, 2H), 7.66 (m, 1H), 7.50 (m, 2H), 7.45-7.02 (m, 7H), 6.11 (m, 1H), 3.87 (m, 2H), 3.48 (m, 2H), 3.36-3.27 (m, 3H), 2.39-2.25 (m, 1H), 1.24-1.08 (m, 4H). |
| 926 | 1H NMR (400 MHz, Methanol-d4) δ 8.48 (s, 1H), 7.88 (s, 1H), 7.83 (s, 1H), 7.78 (m, 1H), 7.69 (m, 1H), 7.65 (m, 1H), 7.56 (t, J = 7.8 Hz, 1H), 7.13 (d, J = 2.4 Hz, 1H), 4.22 (d, J = 15.0 Hz, 1H), 4.06 (d, J = 15.0 Hz, 1H), 3.89 (m, 1H), 2.52 (s, 1H), 1.82 (s, 6H), 1.26-1.18 (m, 2H), 1.18-1.10 (m, 2H).0 |
| 927 | 1H NMR (400 MHz, Methanol-d4) δ 8.46 (s, 1H), 7.80 (s, 1H), 7.62 (m, 1H), 7.52-7.42 (m, 2H), 7.16-7.04 (m, 3H), 6.06 (s, 1H), 4.19 (d, J = 15.1 Hz, 1H), 4.08 (d, J = 15.0 Hz, 1H), 3.87 (m, 1H), 2.52 (s, 1H), 1.82 (s, 6H), 1.18 (m, 2H), 1.17-1.11 (m, 2H). |
| 928 | 1H NMR (400 MHz, Methanol-d4) δ 8.46 (s, 1H), 7.85 (s, 1H), 7.57 (m, 1H), 7.48 (m, 1H), 7.42 (m, 1H), 7.37-7.28 (m, 2H), 7.09 (d, J = 2.3 Hz, 1H), 6.40 (s, 1H), 4.19-4.04 (m, 2H), 3.89 (m, 1H), 2.52 (s, 1H), 1.82 (s, 6H), 1.20 (m, 2H), 1.16-1.14 (m, 2H). |
| 929 | 1H NMR (400 MHz, Methanol-d4) δ 8.48 (s, 1H), 7.84 (s, 1H), 7.65 (d, J = 2.3 Hz, 1H), 7.50-7.44 (m, 2H), 7.39-7.33 (m, 2H), 7.04 (d, J = 2.3 Hz, 1H), 4.83-4.75 (m, 1H), 4.21 (d, J = 13.9 Hz, 1H), 3.80 (d, J = 12.5 Hz, 2H), 3.69 (d, J = 14.0 Hz, 1H), 3.27-3.16 (m, 2H), 2.56-2.34 (m, 4H), 1.46 (s, 9H), 0.96 (s, 9H). |
| 930 | 1H NMR (400 MHz, DMSO-d6) δ 8.23 (d, J = 6.8 Hz, 1H), 8.03 (d, J = 1.1 Hz, 1H), 7.79 (d, J = 2.2 Hz, 1H), 7.61-7.45 (m, 3H), 7.39-7.19 (m, 9H), 5.65 (td, J = 8.4, 5.1 Hz, 1H), 3.98 (dd, J = 7.5, 4.1 Hz, 1H), 2.71-2.53 (m, 2H), 2.42-2.12 (m, 2H), 1.23-1.07 (m, 4H). |
| 931 | 1H NMR (400 MHz, DMSO-d6) δ 8.33 (s, 1H), 8.11 (d, J = 2.4 Hz, 1H), 8.04 (s, 1H), 7.65 (s, 1H), 7.58-7.50 (m, 3H), 7.35 (d, J = 2.6 Hz, 1H), 7.17-7.09 (m, 2H), 4.04-3.92 (m, 2H), 3.49 (s, 3H), 3.42 (dd, J = 13.9, 5.4 Hz, 1H), 1.19-1.04 (m, 4H), 0.88 (s, 9H). |
| 932 | 1H NMR (400 MHz, Chloroform-d) δ 8.28 (s, 1H), 7.55 (m, 2H), 7.49-7.37 (m, 2H), 7.41-7.30 (m, 2H), 7.34-7.25 (m, 4H), 7.18 (m, 1H), 7.04 m, 3H), 5.93 (m, 1H), 3.73 (m, 2H), 3.01 (s, 3H), 1.68-1.57 (m, 1H), 1.28-1.19 (m, 4H), 1.23-1.10 (m, 2H). |
| 933 | 1H NMR (400 MHz, Methanol-d4) δ 8.36 (s, 1H), 8.10-8.00 (m, 2H), 7.78 (s, 2H), 7.70 (d, J = 2.3 Hz, 1H), 7.66-7.52 (m, 4H), 7.50-7.30 (m, 3H), 7.08 (t, J = 8.7 Hz, 2H), 3.87 (tt, J = 7.5, 4.0 Hz, 1H), 1.24-1.09 (m, 4H). |
| 934 | 1H NMR (400 MHz, Methanol-d4) δ 8.39 (s, 1H), 7.68 (s, 1H), 7.54 (d, J = 2.5 Hz, 1H), 7.49 (t, J = 8.2 Hz, 1H), 7.37 (dd, J = 8.2, 1.0 Hz, 1H), 7.35-7.28 (m, 2H), 7.09-7.02 (m, 1H), 7.02-6.92 (m, 3H), 3.81-3.71 (m, 1H), 1.14-0.98 (m, 4H). |
| 935 | 1H NMR (400 MHz, Methanol-d4) δ 8.45 (s, 1H), 7.70 (s, 1H), 7.57 (d, J = 2.4 Hz, 1H), 7.34 (ddd, J = 8.7, 5.7, 3.0 Hz, 4H), 6.95 (t, J = 8.5 Hz, 3H), 6.82 (s, 1H), 3.76 (tt, J = 7.4, 4.0 Hz, 1H), 3.32 (s, 3H), 1.11-1.00 (m, 4H). |
| 936 | 1H NMR (400 MHz, Methanol-d4) δ 8.46 (s, 1H), 7.79 (s, 1H), 7.64 (d, J = 2.0 Hz, 1H), 7.44 (d, J = 8.5 Hz, 2H), 7.36 (d, J = 8.5 Hz, 2H), 7.00 (d, J = 2.1 Hz, 1H), 4.16 (d, J = 13.9 Hz, 1H), 3.87 (tt, J = 7.3, 3.6 Hz, 1H), 3.72 (d, J = 13.9 Hz, 1H), 1.22-1.09 (m, 4H), 0.96 (s, 9H). |
| 937 | 1H NMR (400 MHz, DMSO-d6) δ 8.22 (d, J = 5.5 Hz, 1H), 8.04 (d, J = 5.1 Hz, 1H), 7.80 (d, J = 2.2 Hz, 1H), 7.58 (ddd, J = 8.3, 5.3, 2.5 Hz, 2H), 7.43 (d, J = 8.6 Hz, 1H), 7.38 (d, J = 4.4 Hz, 1H), 7.31 (d, J = 2.3 Hz, 1H), 7.24 (q, J = 2.8 Hz, 2H), 7.19 (ddt, J = 8.2, 6.0, 3.7 Hz, 4H), 5.74-5.54 (m, 1H), 3.98 (tt, J = 7.5, 4.0 Hz, 1H), 2.73-2.53 (m, 2H), 2.48-2.15 (m, 2H), 1.23-1.05 (m, 4H). |

TABLE 2-continued

| Cmpd | 1H-NMR |
|---|---|
| 938 | 1H NMR (400 MHz, DMSO-d6) δ 8.35 (d, J = 7.9 Hz, 1H), 8.24 (d, J = 5.0 Hz, 1H), 7.64-7.55 (m, 3H), 7.48-7.32 (m, 3H), 7.36-7.29 (m, 1H), 7.31-7.14 (m, 6H), 5.73-5.63 (m, 1H), 2.73-2.52 (m, 2H), 2.47-2.32 (m, 1H), 2.28-2.15 (m, 1H), 1.81-1.66 (m, 4H). |
| 939 | 1H NMR (400 MHz, DMSO-d6) δ 8.28 (s, 1H), 8.03 (s, 1H), 7.61-7.41 (m, 4H), 7.39-7.31 (m, 4H), 7.28 (s, 4H), 5.71 (s, 1H), 4.05-3.93 (m, 1H), 2.66 (d, J = 5.3 Hz, 3H), 2.33 (s, 3H), 1.23-1.05 (m, 5H). |
| 940 | 1H NMR (400 MHz, Methanol-d4) δ 8.25 (s, 1H), 8.08 (s, 1H), 8.01-7.97 (m, 1H), 7.92 (s, 1H), 7.85 (s, 1H), 7.75 (d, J = 2.4 Hz, 1H), 7.69 (d, J = 7.8 Hz, 1H), 7.54 (t, J = 7.8 Hz, 1H), 7.30 (d, J = 4.3 Hz, 1H), 7.25 (d, J = 0.9 Hz, 1H), 7.15-7.03 (m, 4H), 7.04-6.97 (m, 2H), 6.25 (s, 1H), 5.42 (t, J = 7.1 Hz, 1H), 3.89 (tt, J = 7.6, 4.0 Hz, 1H), 2.05 (dt, J = 14.1, 7.2 Hz, 1H), 1.80 (dq, J = 14.6, 7.3 Hz, 1H), 1.22-1.09 (m, 4H), 0.91 (t, J = 7.4 Hz, 3H). |
| 941 | 1H NMR (400 MHz, Methanol-d4) δ 8.23 (d, J = 3.2 Hz, 2H), 8.00 (d, J = 7.9 Hz, 1H), 7.94 (d, J = 0.8 Hz, 1H), 7.86 (s, 1H), 7.82 (d, J = 2.4 Hz, 1H), 7.67 (d, J = 7.8 Hz, 1H), 7.54 (t, J = 7.8 Hz, 1H), 7.42 (d, J = 2.5 Hz, 1H), 7.36-7.28 (m, 1H), 7.26 (d, J = 0.9 Hz, 1H), 7.16-7.02 (m, 4H), 6.28 (s, 1H), 5.52 (t, J = 7.1 Hz, 1H), 3.94-3.83 (m, 1H), 2.10 (dt, J = 13.9, 7.2 Hz, 1H), 1.88 (dt, J = 14.4, 7.2 Hz, 1H), 1.24-1.12 (m, 4H), 0.94 (t, J = 7.3 Hz, 3H). |
| 942 | 1H NMR (400 MHz, Methanol-d4) δ 8.26 (s, 1H), 8.06 (s, 1H), 7.84 (s, 1H), 7.82 (s, 1H), 7.80 (d, J = 2.5 Hz, 1H), 7.70 (d, J = 7.8 Hz, 1H), 7.47 (t, J = 7.8 Hz, 1H), 7.41 (d, J = 2.6 Hz, 1H), 7.34 (d, J = 4.3 Hz, 1H), 7.30-7.18 (m, 2H), 7.17-7.08 (m, 2H), 6.24 (s, 1H), 5.55 (t, J = 7.2 Hz, 1H), 3.93-3.82 (m, 1H), 2.12 (dt, J = 14.4, 7.2 Hz, 1H), 1.95 (dt, J = 14.0, 7.1 Hz, 1H), 1.26-1.09 (m, 4H), 0.98 (t, J = 7.3 Hz, 3H). |
| 943 | 1H NMR (400 MHz, Methanol-d4) δ 8.27 (s, 1H), 7.87 (s, 1H), 7.83 (s, 1H), 7.80 (d, J = 2.5 Hz, 1H), 7.71 (d, J = 7.6 Hz, 1H), 7.64 (d, J = 7.6 Hz, 1H), 7.56-7.46 (m, 1H), 7.43 (d, J = 2.5 Hz, 1H), 7.34 (d, J = 4.4 Hz, 1H), 7.27-7.20 (m, 2H), 7.19-7.12 (m, 2H), 6.26 (s, 1H), 5.57 (t, J = 7.1 Hz, 1H), 4.47 (t, J = 11.7 Hz, 3H), 3.89 (tt, J = 7.3, 3.9 Hz, 1H), 2.12 (dq, J = 15.1, 7.5 Hz, 1H), 1.96 (dt, J = 13.8, 7.1 Hz, 1H), 1.26-1.10 (m, 4H), 0.99 (t, J = 7.3 Hz, 3H). |
| 944 | 1H NMR (400 MHz, Methanol-d4) δ 8.37 (s, 1H), 8.03 (s, 1H), 7.87-7.80 (m, 2H), 7.66 (d, J = 7.7 Hz, 1H), 7.46 (t, J = 7.7 Hz, 1H), 7.38 (d, J = 4.2 Hz, 1H), 7.35-7.23 (m, 4H), 7.25-7.18 (m, 2H), 6.24 (s, 1H), 5.72 (t, J = 7.1 Hz, 1H), 3.94-3.81 (m, 1H), 2.19 (dt, J = 14.4, 7.3 Hz, 1H), 2.05 (dq, J = 14.0, 7.3 Hz, 1H), 1.26-1.11 (m, 4H), 1.00 (t, J = 7.3 Hz, 3H). |
| 945 | 1H NMR (400 MHz, Methanol-d4) δ 8.26 (s, 1H), 7.86 (s, 1H), 7.74 (d, J = 2.5 Hz, 1H), 7.53 (m, 1H), 7.51-7.46 (m, 1H), 7.38-7.32 (m, 3H), 7.29 (m, 3H), 7.26-7.21 (m, 2H), 6.52 (s, 1H), 5.75 (m, 1H), 3.92-3.88 (m, 1H), 2.60 (m, 2H), 2.44 (m, 1H), 2.31 (m, 1H), 1.29-1.15 (m, 4H). |
| 946 | 1H NMR (400 MHz, Methanol-d4) δ 8.41 (s, 1H), 7.80 (s, 1H), 7.64 (d, J = 2.4 Hz, 1H), 7.55 (dd, J = 8.1, 1.2 Hz, 1H), 7.52-7.41 (m, 3H), 7.34 (d, J = 7.5 Hz, 1H), 7.15-7.07 (m, 2H), 7.06 (d, J = 2.4 Hz, 1H), 3.88 (tt, J = 7.5, 3.9 Hz, 1H), 2.39 (s, 3H), 1.23-1.09 (m, 4H). |
| 947 | 1H NMR (400 MHz, Methanol-d4) δ 8.47 (s, 1H), 7.75 (s, 1H), 7.64 (d, J = 2.4 Hz, 1H), 7.46-7.37 (m, 3H), 7.33 (dd, J = 8.0, 1.4 Hz, 2H), 7.22-7.15 (m, 1H), 7.13-7.03 (m, 3H), 3.86 (tt, J = 7.6, 4.1 Hz, 1H), 1.19-1.11 (m, 4H). |
| 948 | 1H NMR (400 MHz, Methanol-d4) δ 8.12 (s, 1H), 7.93 (s, 1H), 7.75 (s, 1H), 7.68 (d, J = 2.5 Hz, 1H), 7.60 (d, J = 7.9 Hz, 1H), 7.38 (t, J = 7.7 Hz, 1H), 7.29 (d, J = 2.5 Hz, 1H), 7.24 (d, J = 4.3 Hz, 1H), 7.21-7.07 (m, 3H), 7.02 (dd, J = 7.4, 2.3 Hz, 2H), 6.14 (s, 1H), 5.42 (t, J = 7.2 Hz, 1H), 3.79 (tt, J = 7.5, 4.0 Hz, 1H), 2.77 (s, 3H), 2.02 (dt, J = 14.4, 7.3 Hz, 1H), 1.83 (dt, J = 14.0, 7.1 Hz, 1H), 1.12-1.01 (m, 4H), 0.88 (t, J = 7.3 Hz, 3H). |
| 949 | 1H NMR (400 MHz, DMSO-d6) δ 8.25 (s, 1H), 8.00 (s, 1H), 7.84 (d, J = 2.3 Hz, 1H), 7.64-7.48 (m, 4H), 7.42-7.13 (m, 8H), 6.27 (s, 1H), 5.74-5.57 (m, 1H), 3.96 (dq, J = 7.7, 3.7 Hz, 1H), 2.61 (m, 2H), 2.44-2.32 (m, 1H), 2.25-2.15 (m, 1H), 1.23-1.00 (m, 4H). |
| 950 | 1H NMR (400 MHz, DMSO-d6) δ 8.49 (s, 1H), 8.07 (s, 2H), 7.87-7.80 (m, 2H), 7.72-7.65 (m, 2H), 7.36-7.28 (m, 3H), 7.04 (t, J = 7.4 Hz, 1H), 6.93 (t, J = 7.6 Hz, 2H), 6.71 (d, J = 7.7 Hz, 2H), 6.56 (d, J = 2.4 Hz, 1H), 5.08 (dd, J = 9.3, 6.2 Hz, 1H), 3.95 (tt, J = 7.5, 3.8 Hz, 1H), 2.81-2.55 (m, 3H), 1.97 (t, J = 9.6 Hz, 1H), 1.24-1.02 (m, 5H). |
| 951 | 1H NMR (400 MHz, DMSO-d6) δ 8.46 (s, 1H), 8.13 (s, 1H), 8.05 (s, 1H), 7.84 (d, J = 2.4 Hz, 1H), 7.82-7.78 (m, 2H), 7.59-7.51 (m, 4H), 7.35 (td, J = 7.6, 1.6 Hz, 2H), 6.95 (t, J = 7.4 Hz, 1H), 6.77 (t, J = 7.6 Hz, 3H), 6.53 (d, J = 7.8 Hz, 3H), 6.47 (d, J = 2.4 Hz, 1H), 5.06 (dd, J = 9.9, 5.9 Hz, 1H), 3.96 (tt, J = 7.5, 4.0 Hz, 1H), 2.58 (dd, J = 19.0, 10.0 Hz, 1H), 1.24-1.03 (m, 6H). |
| 952 | 1H NMR (400 MHz, Methanol-d4) δ 8.36 (s, 1H), 8.15 (s, 1H), 7.77 (m, 1H), 7.53-7.44 (m, 2H), 7.36-7.28 (m, 2H), 7.14 (d, J = 2.5 Hz, 1H), 6.46 (s, 1H), 3.88 (d, J = 13.7 Hz, 1H), 3.70 (d, J = 13.7 Hz, 1H), 3.10-2.96 (m, 4H), 2.41-2.26 (m, 1H), 2.24-2.11 (m, 1H), 0.94 (s, 9H). |
| 953 | 1H NMR (400 MHz, DMSO-d6) δ 8.22 (d, J = 0.6 Hz, 1H), 8.02 (d, J = 2.2 Hz, 1H), 8.01 (d, J = 0.6 Hz, 1H), 7.50-7.42 (m, 2H), 7.33-7.28 (m, 2H), 7.16 (s, 1H), 7.12 (t, J = 6.6 Hz, 1H), 7.00 (d, J = 2.4 Hz, 1H), 3.99-3.91 (m, 1H), 3.72 (dd, J = 13.7, 7.3 Hz, 1H), 3.51 (dd, J = 13.6, 5.7 Hz, 1H), 1.21-1.05 (m, 5H), 0.85 (s, 9H). |

TABLE 2-continued

| Cmpd | 1H-NMR |
|---|---|
| 954 | 1H NMR (400 MHz, Methanol-d4) δ 8.46 (s, 1H), 7.85 (s, 1H), 7.65 (d, J = 2.2 Hz, 1H), 7.47 (d, J = 8.4 Hz, 2H), 7.37 (d, J = 8.5 Hz, 2H), 7.02 (d, J = 2.4 Hz, 1H), 6.08 (s, 1H), 4.94-4.87 (m, 6H), 4.20 (d, J = 14.0 Hz, 1H), 3.71 (dd, J = 32.8, 13.3 Hz, 3H), 3.55 (s, 2H), 3.29-3.14 (m, 3H), 2.43 (s, 4H), 2.37 (d, J = 12.9 Hz, 1H), 1.37 (t, J = 7.3 Hz, 3H), 1.06 (d, J = 7.3 Hz, 2H), 0.95 (s, 9H). |
| 955 | 1H NMR (400 MHz, Methanol-d4) δ 8.28 (s, 1H), 7.87 (s, 1H), 7.59 (d, J = 2.4 Hz, 1H), 7.52 (d, J = 8.3 Hz, 2H), 7.41 (t, J = 7.8 Hz, 3H), 7.35-7.17 (m, 5H), 6.21 (s, 1H), 5.87-5.78 (m, 1H), 4.93 (d, J = 16.4 Hz, 6H), 4.80 (s, 1H), 3.76 (d, J = 13.0 Hz, 2H), 3.30-3.13 (m, 4H), 2.63 (t, J = 7.3 Hz, 2H), 2.48 (d, J = 8.8 Hz, 1H), 2.36 (d, J = 14.3 Hz, 3H), 1.38 (t, J = 7.3 Hz, 4H). |
| 956 | 1H NMR (400 MHz, Methanol-d4) δ 8.35 (s, 1H), 8.16 (s, 1H), 7.75 (d, J = 2.6 Hz, 1H), 7.48 (m, 2H), 7.32 (m, 2H), 7.12 (d, J = 2.5 Hz, 1H), 6.43 (s, 1H), 3.88 (d, J = 13.7 Hz, 1H), 3.67 (d, J = 13.6 Hz, 1H), 1.99 (m, 2H), 1.95 (m, 1H), 0.94 (s, 9H). |
| 957 | 1H NMR (400 MHz, Methanol-d4) δ 8.34 (s, 1H), 8.01 (s, 1H), 7.73 (d, J = 2.3 Hz, 1H), 7.59-7.51 (m, 1H), 7.49-7.42 (m, 1H), 7.35-7.26 (m, 2H), 7.09 (d, J = 2.5 Hz, 1H), 6.40 (s, 1H), 3.93 (d, J = 13.6 Hz, 1H), 3.61 (d, J = 13.6 Hz, 1H), 1.82 (m, 2H), 1.61 (m, 2H), 0.94 (s, 9H). |
| 958 | 1H NMR (400 MHz, Methanol-d4) δ 8.49 (s, 1H), 7.92 (s, 1H), 7.62 (d, J = 2.3, 1H), 7.46 (m, 2H), 7.36-7.29 (m, 2H), 6.98 (m, 1H), 4.07 (d, J = 13.8 Hz, 1H), 3.82 (d, J = 13.8 Hz, 1H), 1.54 (m, 1H), 1.22 (m, 2H), 1.02 (m, 2H), 0.98 (s, 9H), 0.57-0.48 (m, 2H), 0.33 (m, 2H). |
| 959 | 1H NMR (400 MHz, Methanol-d4) δ 8.50 (s, 1H), 8.46 (m, 1H), 8.03 (s, 1H), 7.68-7.59 (m, 2H), 7.56-7.50 (m, 1H), 7.50-7.45 (m, 1H), 7.38-7.29 (m, 2H), 7.26-7.18 (m, 1H), 7.02 (d, J = 2.4 Hz, 1H), 6.55 (d, J = 8.0, 1H), 4.10 (d, J = 13.8 Hz, 1H), 3.79 (d, J = 13.8 Hz, 1H), 1.94 (m, 2H), 1.77 (m, 2H), 0.97 (s, 9H). |
| 960 | 1H NMR (400 MHz, Methanol-d4) δ 8.52 (d, J = 5.3 Hz, 1H), 8.49 (s, 1H), 8.30 (s, 1H), 8.08 (s, 1H), 7.82-7.75 (m, 1H), 7.61 (d, J = 2.3 Hz, 1H), 7.53 (dd, J = 8.1, 5.0 Hz, 1H), 7.50-7.44 (m, 2H), 7.37-7.26 (m, 2H), 6.98 (m, 1H), 4.09 (d, J = 13.8 Hz, 1H), 3.77 (d, J = 13.8 Hz, 1H), 1.87 (m, 2H), 1.76 (m, 2H), 0.95 (s, 9H). |
| 961 | 1H NMR (400 MHz, Methanol-d4) δ 8.23 (d, J = 0.6 Hz, 1H), 8.09 (s, 1H), 7.78 (d, J = 2.4 Hz, 1H), 7.61-7.49 (m, 2H), 7.47-7.31 (m, 4H), 7.31-7.22 (m, 3H), 7.22-7.12 (m, 2H), 6.22 (s, 1H), 5.74 (dd, J = 8.4, 5.9 Hz, 1H), 2.61 (t, J = 7.3 Hz, 2H), 2.41 (dd, J = 14.4, 7.3 Hz, 1H), 2.26 (dt, J = 13.9, 6.8 Hz, 1H), 2.07-1.81 (m, 4H). |
| 962 | 1H NMR (400 MHz, Methanol-d4) δ 8.37 (2, 1H), 7.88 (s, 1H), 7.76 (m, 1H), 7.46 (m, 2H), 7.36-7.27 (m, 2H), 7.12 (d, J = 2.5 Hz, 1H), 6.38 (s, 1H), 3.90 (d, J = 13.7 Hz, 1H), 3.72 (m, 1H), 1.65 (s, 3H), 1.34-1.28 (m, 2H), 1.09-1.03 (m, 2H), 0.94 (s, 9H). |
| 963 | 1H NMR (400 MHz, Methanol-d4) δ 8.37 (s, 1H), 7.81 (s, 1H), 7.76 (m, 1H), 7.50-7.46 (m, 2H), 7.35-7.29 (m, 2H), 7.14 (d, J = 2.5 Hz, 1H), 6.41 (s, 1H), 5.15 (m, 2H), 3.92 (d, J = 13.7 Hz, 1H), 3.68 (d, J = 13.7 Hz, 1H), 0.95 (s, 9H). |
| 964 | 1H NMR (400 MHz, Methanol-d4) δ 8.46 (s, 1H), 7.86 (s, 1H), 7.60 (d, J = 2.4 Hz, 1H), 7.46 (m, 1H), 7.46 (m, 1H), 7.35-7.28 (m, 2H), 6.96 (d, J = 2.4 Hz, 1H), 4.05 (d, J = 13.8 Hz, 1H), 3.81-3.77 (m, 3H), 1.32 (m, 2H), 1.20 (m, 2H), 0.98 (s, 9H). |
| 965 | 1H NMR (400 MHz, Methanol-d4) δ 8.48 (s, 1H), 7.94 (s, 1H), 7.61 (d, J = 2.4 Hz, 1H), 7.50 (m, 1H), 7.47 (m, 1H), 7.36-7.29 (m, 2H), 6.99 (d, J = 2.3 Hz, 1H), 5.06 (dd, J = 9.6, 7.0 Hz, 2H), 4.83 (m, 2H), 4.13 (s, 2H), 4.05 (d, J = 13.8 Hz, 1H), 3.82 (d, J = 13.8 Hz, 1H), 0.98 (s, 9H). |
| 966 | 1H NMR (400 MHz, Methanol-d4) δ 8.49 (s, 1H), 7.78 (s, 1H), 7.69 (d, J = 2.4 Hz, 1H), 7.62 (dd, J = 7.0, 2.7 Hz, 1H), 7.51-7.37 (m, 4H), 7.13 (d, J = 2.3 Hz, 1H), 7.07 (t, J = 8.7 Hz, 2H), 3.86 (tt, J = 7.5, 4.0 Hz, 1H), 1.24-1.08 (m, 4H). |
| 967 | 1H NMR (400 MHz, Methanol-d4) δ 8.54 (s, 1H), 7.79 (s, 1H), 7.62 (d, J = 2.3 Hz, 1H), 7.51-7.42 (m, 2H), 7.24 (d, J = 2.3 Hz, 1H), 7.15-7.04 (m, 2H), 6.28 (t, J = 56.3 Hz, 1H), 3.92-3.82 (m, 1H), 1.56-1.47 (m, 2H), 1.47-1.33 (m, 2H), 1.24-1.09 (m, 4H). |
| 968 | 1H NMR (400 MHz, Methanol-d4) δ 8.45 (m, 1H), 8.39 (m, 1H), 8.01 (s, 1H), 7.82 (d, J = 2.6, 1H), 7.60 (m, 1H), 7.54 (dd, J = 8.6, 5.3 Hz, 2H), 7.28 (d, J = 2.5 Hz, 1H), 7.22 (m, 1H), 7.11 (t, J = 8.7 Hz, 2H), 6.52 (d, J = 8.0 Hz, 1H), 6.13 (s, 1H), 4.03 (d, J = 13.9 Hz, 1H), 3.66 (d, J = 13.9 Hz, 1H), 1.92 (m, 2H), 1.77 (m, 2H), 0.94 (s, 9H). |
| 969 | 1H NMR (400 MHz, Methanol-d4) δ 8.35 (m, 1H), 8.02 (d, J = 0.8 Hz, 1H), 7.89 (s, 1H), 7.84 (d, J = 8.0 Hz, 1H), 7.79 (d, J = 2.5 Hz, 1H), 7.68 (m, 1H), 7.55 (m, 1H), 7.18 (m, 1H), 4.10 (d, J = 13.9 Hz, 1H), 3.51 (d, J = 13.9 Hz, 1H), 1.83 (m, 2H), 1.61 (m, 2H), 0.92 (s, J = 0.9 Hz, 9H). |
| 970 | 1H NMR (400 MHz, DMSO-d6) δ 8.87 (s, 1H), 8.58 (d, J = 12.6 Hz, 2H), 8.30 (s, 1H), 7.68-7.48 (m, 3H), 7.43 (brs, 1H), 7.39-7.11 (m, 4H), 6.24 (d, J = 6.3 Hz, 1H), 3.89 (dd, J = 13.9, 7.2 Hz, 1H), 3.52 (dd, J = 13.9, 5.7 Hz, 1H), 0.87 (s, 9H). |
| 971 | 1H NMR (400 MHz, DMSO-d6) δ 8.87 (s, 1H), 8.72 (s, 1H), 8.62 (s, 1H), 8.32 (s, 1H), 7.95 (d, J = 2.2 Hz, 1H), 7.84 (d, J = 7.9 Hz, 1H), 7.74 (d, J = 7.7 Hz, 1H), 7.66-7.47 (m, 3H), 7.10 (d, J = 2.4 Hz, 1H), 4.01 (dd, J = 14.1, 8.0 Hz, 1H), 3.40 (dd, J = 14.0, 5.2 Hz, 1H), 0.85 (s, 9H). |
| 972 | 1H NMR (400 MHz, DMSO-d6) δ 8.89 (s, 1H), 8.61 (d, J = 7.8 Hz, 2H), 8.22 (d, J = 6.8 Hz, 1H), 7.63-7.27 (m, 7H), 7.28-7.11 (m, 5H), 6.62 (d, J = 7.9 Hz, 1H), 2.04 (dd, J = 14.2, 6.9 Hz, 1H), 1.88 (dt, J = 13.8, 7.0 Hz, 1H), 0.89 (t, J = 7.3 Hz, 3H). |
| 973 | 1H NMR (400 MHz, Methanol-d4) δ 8.36 (s, 1H), 7.89 (s, 1H), 7.79 (d, J = 2.5 Hz, 1H), 7.49 (dd, J = 8.7, 5.2 Hz, 2H), 7.22 (d, J = 2.5 Hz, 1H), 7.09 (t, J = 8.5 Hz, 2H), 6.05 (s, 1H), 4.01 (d, J = 14.0 Hz, 1H), 3.64 (d, J = 13.9 Hz, 1H), 1.53 (m, 1H), 1.21 (m 2H), 1.01 (m, 2H), 0.94 (s, 9H), 0.52 (m, 2H), 0.33 (m, 2H). |

TABLE 2-continued

| Cmpd | 1H-NMR |
|---|---|
| 974 | 1H NMR (400 MHz, Methanol-d4) δ 8.59 (d, J = 5.1 Hz, 1H), 8.43 (s, 1H), 8.33 (s, 1H), 8.05 (s, 1H), 7.94 (m, 1H), 7.75 (dd, J = 2.4, 0.7 Hz, 1H), 7.66 (d, J = 8.2 Hz, 1H), 7.50 (dd, J = 8.6, 5.3 Hz, 2H), 7.21 (d, J = 2.5 Hz, 1H), 7.09 (t, J = 8.6 Hz, 2H), 6.08 (s, 1H), 3.99 (d, J = 13.8 Hz, 1H), 3.58 (d, J = 13.8 Hz, 1H), 1.89 (m, 2H), 1.79 (m, 2H), 0.92 (s, 9H). |
| 975 | 1H NMR (400 MHz, Methanol-d4) δ 8.31 (d, J = 0.7 Hz, 1H), 7.89 (s, 1H), 7.76 (d, J = 2.4 Hz, 1H), 7.53 (s, 1H), 7.51 (s, 1H), 7.36 (m, 2H), 7.29 (m, 1H), 7.21 (d, J = 2.5 Hz, 1H), 6.06 (s, 1H), 4.03 (d, J = 13.8 Hz, 1H), 3.54 (d, J = 13.8 Hz, 1H), 1.81 (m, 2H), 1.60 (m, 2H), 0.93 (s, 9H). |
| 976 | 1H 1.NMR (400 MHz, Methanol-d4) δ 8.28 (d, J = 0.7 Hz, 1H), 8.10 (d, J = 0.8 Hz, 1H), 7.75 (dd, J = 2.5, 0.7 Hz, 1H), 7.50 (dd, J = 8.7, 5.2 Hz, 2H), 7.18 (d, J = 2.5 Hz, 1H), 7.10 (t, J = 8.7 Hz, 2H), 6.08 (s, 1H), 3.93 (d, J = 13.8 Hz, 1H), 3.58 (d, J = 13.8 Hz, 1H), 2.02-1.95 (m, 2H), 1.95-1.88 (m, 2H), 0.96-0.86 (m, 9H). |
| 977 | 1H NMR (400 MHz, Methanol-d4) δ 8.36 (s, 1H), 7.93 (s, 1H), 7.78 (d, J = 2.3 Hz, 1H), 7.53 (dd, J = 8.7, 5.3 Hz, 2H), 7.21 (d, J = 2.5 Hz, 1H), 7.09 (t, J = 8.7 Hz, 2H), 6.07 (s, 1H), 4.08 (d, J = 13.9 Hz, 1H), 3.56 (d, J = 13.9 Hz, 1H), 1.85-1.76 (m, 2H), 1.60 (m, 2H), 0.94 (s, 9H). |
| 978 | 1H NMR (400 MHz, Methanol-d4) δ 8.33 (d, J = 0.7 Hz, 1H), 7.84 (s, 1H), 7.77 (dd, J = 2.4, 0.7 Hz, 1H), 7.48 (dd, J = 8.6, 5.3 Hz, 2H), 7.19 (d, J = 2.5 Hz, 1H), 7.09 (t, J = 8.6 Hz, 2H), 6.03 (s, 1H), 3.97 (d, J = 13.9 Hz, 1H), 3.63 (d, J = 13.9 Hz, 1H), 1.70-1.60 (s, 3H), 1.34-1.26 (m, 2H), 1.10-0.98 (m, 2H), 0.93 (s, 9H). |
| 979 | 1H NMR (400 MHz, Methanol-d4) δ 8.33 (s, 1H), 7.83 (s, 1H), 7.77 (d, J = 2.5 Hz, 1H), 7.50 (dd, J = 8.4, 5.4 Hz, 2H), 7.20 (d, J = 2.6 Hz, 1H), 7.09 (t, J = 8.6 Hz, 2H), 6.05 (s, 1H), 4.01 (d, J = 13.9 Hz, 1H), 3.76 (d, J = 2.0 Hz, 2H), 3.59 (s, 1H), 1.30 (m, 2H), 1.20 (m, 2H), 0.94 (d, 9H). |
| 980 | 1H NMR (400 MHz, Methanol-d4) δ 8.44 (s, 1H), 7.85 (s, 1H), 7.62 (d, J = 2.3 Hz, 1H), 7.45 (d, J = 8.5 Hz, 2H), 7.36 (d, J = 8.5 Hz, 2H), 6.99 (d, J = 2.3 Hz, 1H), 4.15 (d, J = 13.9 Hz, 1H), 4.07 (s, 1H), 3.73 (s, 2H), 3.67 (d, J = 13.9 Hz, 1H), 2.82 (s, 1H), 2.72 (s, 2H), 0.95 (s, 13H). |
| 981 | 1H NMR (400 MHz, Methanol-d4) δ 8.37 (d, J = 2.5 Hz, 1H), 8.31-8.21 (m, 1H), 7.99-7.88 (m, 1H), 7.85 (d, J = 7.2 Hz, 1H), 7.56 (m, 1H), 7.47-7.19 (m, 7H), 7.00 (m, 1H), 5.80 (m, 1H), 3.87-3.73 (m, 1H), 2.47 (m, 3H), 2.28-2.06 (m, 1H), 1.82-1.54 (m, 2H), 1.26-1.00 (m, 4H). |
| 982 | 1H NMR (400 MHz, Methanol-d4) δ 8.45 (s, 1H), 7.86 (s, 1H), 7.63 (d, J = 2.3 Hz, 1H), 7.47 (d, J = 8.5 Hz, 2H), 7.36 (d, J = 8.4 Hz, 2H), 7.01 (d, J = 2.3 Hz, 1H), 4.87-4.83 (m, 1H), 4.19 (d, J = 13.9 Hz, 1H), 3.78 (s, 2H), 3.66 (d, J = 13.9 Hz, 1H), 3.42 (s, 2H), 2.87 (s, 1H), 2.41 (s, 4H), 1.05-0.96 (m, 4H), 0.95 (s, 9H). |
| 983 | 1H NMR (400 MHz, Methanol-d4) δ 8.64 (m, 2H), 8.31 (s, 1H), 8.09 (s, 1H), 7.77 (m, 1H), 7.55 (m, 2H), 7.25 (m, 1H), 7.17 (m, 2H), 7.11 (t, J = 8.6 Hz, 2H), 6.14 (s, 1H), 3.98 (d, J = 13.8 Hz, 1H), 3.58 (d, J = 13.8 Hz, 1H), 2.16 (m, 2H), 2.03 (m, 2H), 0.93 (s, 9H). |
| 984 | 1H NMR (400 MHz, Methanol-d4) δ 8.52 (m, 1H), 8.42 (d, J = 2.6 Hz, 1H), 8.38 (s, 1H), 8.08 (s, 1H), 7.84-7.79 (m, 1H), 7.63 (s, 1H), 7.55 (dd, J = 8.5, 5.3 Hz, 2H), 7.27 (d, J = 2.5 Hz, 1H), 7.11 (t, J = 8.6 Hz, 2H), 6.15 (s, 1H), 4.02 (d, J = 13.9 Hz, 1H), 3.65 (d, J = 13.8 Hz, 1H), 1.98 (m, 1H), 1.86 (m, 1H), 0.97-0.89 (s, 9H). |
| 985 | 1H NMR (400 MHz, Methanol-d4) δ 8.38 (s, 1H), 7.83 (s, 1H), 7.80 (d, J = 2.4 Hz, 1H), 7.51 (dd, J = 8.5, 5.3 Hz, 2H), 7.23 (d, J = 2.5 Hz, 1H), 7.09 (t, J = 8.6 Hz, 2H), 6.09 (s, 1H), 4.05 (d, J = 13.9 Hz, 1H), 3.63 (d, J = 13.9 Hz, 1H), 2.98-2.88 (m, 2H), 2.88-2.76 (m, 2H), 2.18-1.97 (m, 2H), 0.99-0.88 (s, 9H). |
| 986 | 1H NMR (400 MHz, DMSO-d6) δ 8.27 (s, 1H), 7.96 (s, 1H), 7.64 (d, J = 2.1 Hz, 1H), 7.53 (d, J = 7.2 Hz, 2H), 7.47-7.20 (m, 10H), 7.08 (d, J = 2.4 Hz, 1H), 6.26-6.00 (m, 2H), 3.94 (tt, J = 7.5, 3.9 Hz, 1H), 3.85-3.57 (m, 2H), 1.22-0.99 (m, 4H). |
| 987 | 1H NMR (400 MHz, Methanol-d4) δ 9.05 (d, J = 5.0 Hz, 1H), 8.36 (d, J = 0.7 Hz, 1H), 8.07 (s, 1H), 7.83-7.75 (m, 1H), 7.56 (m, 3H), 7.25 (d, J = 2.5 Hz, 1H), 7.11 (t, J = 8.5 Hz, 2H), 6.97-6.89 (m, 1H), 6.13 (s, 1H), 4.03 (d, J = 13.9 Hz, 1H), 3.61 (d, J = 13.8 Hz, 1H), 2.13-2.03 (m, 2H), 1.94 (m, 2H), 0.99-0.88 (s, 9H). |
| 988 | 1H NMR (400 MHz, DMSO-d6) δ 8.32 (s, 1H), 8.26 (s, 1H), 7.93 (s, 1H), 7.81-7.77 (m, 1H), 7.54 (dd, J = 8.5, 5.5 Hz, 2H), 7.36 (s, 1H), 7.29 (d, J = 19.4 Hz, 1H), 7.19-7.10 (m, 3H), 5.92 (s, 1H), 4.57-4.46 (m, 1H), 4.39 (dd, J = 14.0, 7.1 Hz, 1H), 4.13 (s, 1H), 4.01-3.90 (m, 1H), 3.42 (dd, J = 14.0, 5.3 Hz, 1H), 3.10-3.05 (m, 1H), 2.74-2.69 (m, 1H), 1.24 (s, 9H), 0.88 (s, 9H). |
| 989 | 1H NMR (400 MHz, Methanol-d4) δ 8.49 (s, 1H), 8.09 (s, 1H), 7.66 (m, 1H), 7.49 (dd, J = 8.6, 5.2 Hz, 2H), 7.11 (t, J = 8.7 Hz, 2H), 7.05 (d, J = 2.3 Hz, 1H), 6.09 (s, 1H), 4.17 (d, J = 14.0 Hz, 1H), 3.76 (d, J = 13.9 Hz, 1H), 2.04-1.86 (m, 4H), 0.98 (s, 9H). |
| 990 | 1H NMR (400 MHz, Methanol-d4) δ 8.47 (s, 1H), 7.82 (s, 1H), 7.64 (d, J = 2.2 Hz, 1H), 7.47 (dd, J = 8.5, 5.3 Hz, 2H), 7.09 (t, J = 8.6 Hz, 2H), 7.01 (d, J = 2.3 Hz, 1H), 6.04 (s, 1H), 4.15 (d, J = 13.9 Hz, 1H), 3.75 (d, J = 14.0 Hz, 1H), 1.64 (s, 3H), 1.29 (m, 2H), 1.08-1.03 (m, 2H), 0.97 (s, 9H). |
| 991 | 1H NMR (400 MHz, Methanol-d4) δ 8.50 (s, 1H), 8.48-8.43 (m, 1H), 7.98 (s, 1H), 7.67 (d, J = 2.3 Hz, 1H), 7.62 (m, 1H), 7.52 (dd, J = 8.5, 5.2 Hz, 2H), 7.25-7.19 (m, 1H), 7.16-7.06 (m, 3H), 6.55 (d, J = 8.0 Hz, 1H), 6.13 (s, 1H), 4.19 (d, J = 14.0 Hz, 1H), 3.75 (d, J = 14.0 Hz, 1H), 1.92 (m, 2H), 1.76 (m, 2H), 0.97 (s, 9H). |
| 992 | 1H NMR (400 MHz, Methanol-d4) δ 8.47 (s, 1H), 7.81 (s, 1H), 7.66-7.62 (m, 1H), 7.50 (dd, J = 8.5, 5.2 Hz, 2H), 7.10 (t, J = 8.6 Hz, 2H), 7.03 (d, J = 2.3 Hz, 1H), 6.09 (s, 1H), 4.18 (d, J = 13.9 Hz, 1H), 3.72 (d, J = 14.0 Hz, 1H), 2.99-2.88 (m, 2H), 2.83 (m, 2H), 2.17-1.97 (m, 2H), 0.97 (s, 9H). |

TABLE 2-continued

| Cmpd | 1H-NMR |
|---|---|
| 994 | 1H NMR (400 MHz, DMSO-d6) δ 9.17-9.11 (m, 1H), 8.78 (d, J = 0.9 Hz, 1H), 8.73-8.66 (m, 1H), 8.37-8.29 (m, 2H), 7.85 (dd, J = 2.5, 0.9 Hz, 1H), 7.69-7.55 (m, 3H), 7.59-7.51 (m, 2H), 7.41 (d, J = 2.3 Hz, 1H), 7.23-7.14 (m, 2H), 3.86 (dd, J = 14.0, 7.5 Hz, 1H), 3.50 (dd, J = 14.0, 5.8 Hz, 1H), 0.82 (s, 9H). |
| 995 | 1H NMR (400 MHz, Methanol-d4) δ 8.35 (s, 1H), 8.14 (s, 1H), 7.79 (d, J = 2.5 Hz, 1H), 7.66 (dd, J = 7.8, 1.3 Hz, 1H), 7.62 (d, J = 8.0 Hz, 1H), 7.35 (t, J = 7.8 Hz, 1H), 7.01 (d, J = 2.5 Hz, 1H), 6.30 (s, 1H), 3.95 (d, J = 13.8 Hz, 1H), 3.60 (d, J = 13.8 Hz, 1H), 2.58 (s, 3H), 1.84-1.60 (m, 4H), 0.88 (s, 9H). |
| 996 | 1H NMR (400 MHz, Methanol-d4) δ 8.41 (s, 1H), 7.92 (s, 1H), 7.60 (d, J = 2.2 Hz, 1H), 7.52 (dd, J = 8.4, 5.2 Hz, 2H), 7.09 (t, J = 8.7 Hz, 2H), 6.97 (d, J = 2.3 Hz, 1H), 6.06 (s, 1H), 4.17 (d, J = 13.9 Hz, 1H), 3.63 (d, J = 13.8 Hz, 1H), 1.82 (m, 2H), 1.62-1.57 (m, 2H), 0.96 (s, 9H). |
| 997 | 1H NMR (400 MHz, Methanol-d4) δ 8.53-8.45 (m, 2H), 8.28 (s, 1H), 8.01 (s, 1H), 7.73 (d, J = 8.2 Hz, 1H), 7.67-7.61 (m, 1H), 7.47 (m, 3H), 7.09 (t, J = 8.6 Hz, 2H), 7.03 (d, J = 2.3 Hz, 1H), 6.08 (s, 1H), 4.17 (d, J = 14.0 Hz, 1H), 3.72 (d, J = 13.9 Hz, 1H), 1.84 (m, 2H), 1.74 (m, 2H), 0.95 (s, 9H). |
| 998 | 1H NMR (400 MHz, Methanol-d4) δ 8.44 (s, 1H), 7.95 (s, 1H), 7.64 (m, 1H), 7.50 (m, 2H), 7.11 (t, J = 8.6 Hz, 2H), 7.04 (m, 1H), 6.11 (s, 1H), 4.12 (d, J = 13.9 Hz, 1H), 3.75 (d, J = 13.9 Hz, 1H), 2.93 (t, J = 8.0 Hz, 4H), 2.25-2.02 (m, 2H), 0.97 (s, 9H). |
| 999 | 1H NMR (400 MHz, DMSO-d6) δ 8.37 (s, 1H), 8.10 (s, 1H), 7.73 (s, 1H), 7.53 (dd, J = 5.9, 3.6 Hz, 1H), 7.48-7.15 (m, 5H), 6.90 (s, 1H), 6.59 (s, 1H), 6.33 (d, J = 6.4 Hz, 1H), 3.83 (dd, J = 13.7, 7.4 Hz, 1H), 3.55 (dd, J = 13.7, 5.7 Hz, 1H), 1.75-1.61 (m, 2H), 1.47 (q, J = 5.1 Hz, 2H), 0.87 (s, 9H). |
| 1000 | 1H NMR (400 MHz, DMSO-d6) δ 8.37 (s, 1H), 8.32 (s, 1H), 7.50-7.15 (m, 5H), 6.87 (s, 1H), 6.37 (d, J = 7.2 Hz, 1H), 3.65 (m, 4H), 2.02 (d, J = 3.2 Hz, 2H), 1.95-1.81 (m, 2H), 0.85 (s, 9H). |
| 1001 | 1H NMR (400 MHz, DMSO-d6) δ 8.87 (s, 1H), 8.59 (s, 1H), 8.27 (s, 1H), 7.53-7.28 (m, 4H), 7.20 (d, J = 12.7 Hz, 1H), 6.90 (s, 1H), 6.45 (d, J = 7.6 Hz, 1H), 3.73 (dd, J = 13.7, 7.2 Hz, 1H), 3.58 (dd, J = 13.8, 5.9 Hz, 1H), 0.85 (s, 9H). |
| 1002 | 1H NMR (400 MHz, Methanol-d4) δ 8.48 (s, 1H), 7.78 (s, 1H), 7.69-7.64 (m, 1H), 7.49 (dd, J = 8.6, 5.3 Hz, 2H), 7.10 (t, J = 8.7 Hz, 1H), 7.07 (d, J = 2.3 Hz, 1H), 6.41-6.11 (m, 1H), 6.10 (s, 1H), 4.89-4.80 (m, 2H), 4.17 (d, J = 14.0 Hz, 1H), 3.75 (d, J = 14.0 Hz, 1H), 0.97 (s, 9H). |
| 1003 | 1H NMR (400 MHz, Methanol-d4) δ 8.48 (s, 1H), 8.11-8.04 (m, 1H), 7.99-7.90 (m, 1H), 7.87 (d, J = 8.3 Hz, 1H), 7.69 (s, 1H), 7.66 (d, J = 2.3 Hz, 1H), 7.57-7.47 (m, 3H), 7.48-7.39 (m, 1H), 6.91 (d, J = 2.3 Hz, 1H), 6.80 (s, 1H), 3.96 (d, J = 13.8 Hz, 1H), 3.88-3.78 (m, 1H), 3.68 (d, J = 13.9 Hz, 1H), 1.19-1.05 (m, 4H), 0.70 (s, 9H). |
| 1004 | 1H NMR (400 MHz, DMSO-d6) δ 9.14 (d, J = 2.5 Hz, 1H), 8.81 (d, J = 0.5 Hz, 1H), 8.68 (dd, J = 4.8, 1.4 Hz, 1H), 8.38-8.28 (m, 1H), 8.32 (s, 1H), 7.84 (d, J = 2.4 Hz, 1H), 7.68-7.60 (m, 1H), 7.55-7.43 (m, 3H), 7.41-7.31 (m, 3H), 4.67 (s, 1H), 3.69-3.55 (m, 2H), 0.76 (s, 9H) |
| 1005 | 1H NMR (400 MHz, DMSO-d6) δ 8.84 (d, J = 0.6 Hz, 1H), 8.70 (dd, J = 4.7, 1.5 Hz, 1H), 8.37-8.29 (m, 2H), 7.99 (t, J = 1.7 Hz, 1H), 7.93-7.84 (m, 2H), 7.81-7.74 (m, 1H), 7.73-7.61 (m, 2H), 7.62-7.52 (m, 2H), 7.39 (d, J = 2.5 Hz, 1H), 3.98 (dd, J = 14.0, 8.1 Hz, 1H), 3.39 (dd, J = 14.0, 5.2 Hz, 1H), 1.23 (s, 2H), 0.82 (s, 9H) |
| 1006 | 1H NMR (400 MHz, DMSO-d6) δ 8.30 (d, J = 0.9 Hz, 1H), 8.10 (d, J = 1.0 Hz, 1H), 7.82 (dd, J = 2.5, 1.0 Hz, 1H), 7.58-7.46 (m, 4H), 7.39 (d, J = 2.5 Hz, 1H), 7.13 (td, J = 8.9, 1.0 Hz, 2H), 4.74 (s, 1H), 4.61 (s, 1H), 3.95 (dd, J = 14.0, 7.9 Hz, 1H), 3.42 (dd, J = 13.9, 5.4 Hz, 1H), 1.40 (t, J = 6.8 Hz, 2H), 1.33 (s, 2H), 0.90-0.85 (m, 9H) |
| 1007 | 1H NMR (400 MHz, DMSO-d6) δ 8.32 (d, J = 0.9 Hz, 1H), 8.21 (s, 1H), 7.94 (t, J = 1.7 Hz, 1H), 7.87-7.80 (m, 2H), 7.73 (dd, J = 7.5, 1.3 Hz, 1H), 7.61 (s, 1H), 7.53 (t, J = 7.7 Hz, 2H), 7.35 (d, J = 2.5 Hz, 1H), 4.75 (s, 1H), 4.63 (s, 1H), 4.04 (dd, J = 14.0, 8.3 Hz, 1H), 3.34 (dd, J = 14.0, 5.1 Hz, 1H), 1.46-1.39 (m, 2H), 1.36-1.31 (m, 2H), 0.85 (s, 9H) |
| 1008 | 1H NMR (400 MHz, Methanol-d4) δ 8.51 (s, 1H), 7.98 (s, 1H), 7.67 (t, J = 8.2 Hz, 2H), 7.63 (d, J = 2.3 Hz, 1H), 7.34 (t, J = 7.8 Hz, 1H), 6.79 (d, J = 2.3 Hz, 1H), 6.26 (s, 1H), 4.20 (d, J = 13.9 Hz, 1H), 3.65 (d, J = 13.8 Hz, 1H), 2.59 (s, 3H), 1.87-1.77 (m, 2H), 1.68-1.58 (m, 2H), 0.92 (s, 9H). |
| 1009 | 1H NMR (400 MHz, Methanol-d4) δ 8.50 (s, 1H), 7.87 (s, 1H), 7.70-7.61 (m, 3H), 7.34 (t, J = 7.8 Hz, 1H), 6.82 (d, J = 2.3 Hz, 1H), 6.27 (s, 1H), 4.15 (d, J = 13.9 Hz, 1H), 3.70 (d, J = 13.9 Hz, 1H), 2.97-2.79 (m, 4H), 2.58 (s, 3H), 2.17-2.00 (m, 2H), 0.92 (s, 9H). |
| 1010 | 1H NMR (400 MHz, Methanol-d4) δ 8.46 (s, 1H), 7.96 (s, 1H), 7.64 (d, J = 2.3 Hz, 1H), 7.47 (d, J = 8.5 Hz, 2H), 7.36 (d, J = 8.5 Hz, 2H), 7.02 (d, J = 2.3 Hz, 1H), 4.20 (d, J = 13.9 Hz, 1H), 3.83-3.73 (m, 6H), 3.67 (d, J = 14.0 Hz, 1H), 2.72-2.58 (m, 6H), 0.96 (s, 9H). |
| 1011 | 1H NMR (400 MHz, Methanol-d4) δ 8.62 (d, J = 6.1 Hz, 2H), 8.32 (s, 1H), 8.13 (s, 1H), 7.75 (d, J = 2.5 Hz, 1H), 7.61-7.56 (m, 1H), 7.50-7.43 (m, 1H), 7.37-7.29 (m, 2H), 7.17 (d, J = 6.0 Hz, 2H), 7.11 (d, J = 2.5 Hz, 1H), 6.46 (s, 1H), 3.89 (d, J = 13.6 Hz, 1H), 3.58 (d, J = 13.5 Hz, 1H), 2.18-2.11 (m, 2H), 2.04 (m, 2H), 0.93 (s, 9H). |
| 1012 | 1H NMR (400 MHz, Methanol-d4) δ 8.47 (s, 1H), 7.97 (s, 1H), 7.67 (d, J = 7.6 Hz, 1H), 7.64 (d, J = 2.3 Hz, 1H), 7.61 (d, J = 8.0 Hz, 1H), 7.35 (t, J = 7.8 Hz, 1H), 6.82 (d, J = 2.3 Hz, 1H), 6.28 (s, 1H), 5.94 (t, J = 54.6 Hz, 1H), 4.09 (d, J = 13.9 Hz, 1H), 3.72 (d, J = 13.9 Hz, 1H), 2.57 (s, 3H), 1.53 (s, 4H), 0.92 (s, 9H). |

TABLE 2-continued

| Cmpd | 1H-NMR |
|---|---|
| 1013 | 1H NMR (400 MHz, Methanol-d4) δ 8.35 (s, 1H), 7.98 (s, 1H), 7.79 (d, J = 2.5 Hz, 1H), 7.64 (dd, J = 11.6, 7.8 Hz, 2H), 7.34 (t, J = 7.9 Hz, 1H), 6.99 (d, J = 2.6 Hz, 1H), 6.28 (s, 1H), 5.95 (t, J = 54.7 Hz, 1H), 3.94 (d, J = 13.7 Hz, 1H), 3.59 (d, J = 13.8 Hz, 1H), 2.58 (s, 3H), 1.53 (s, 4H), 0.88 (s, 9H). |
| 1014 | 1H NMR (400 MHz, Methanol-d4) δ 8.33 (s, 1H), 7.88 (s, 1H), 7.76-7.72 (m, 1H), 7.54-7.49 (m, 1H), 7.47 (d, J = 8.1 Hz, 1H), 7.32 (dd, J = 6.8, 3.3 Hz, 2H), 7.11 (s, 1H), 6.42 (s, 1H), 3.89 (d, J = 13.6 Hz, 1H), 3.64 (d, J = 13.6 Hz, 1H), 2.93 (s, 2H), 2.84 (m, 2H), 2.17-1.98 (m, 2H), 0.94 (s, 9H). |
| 1015 | 1H NMR (400 MHz, DMSO-d6) δ 8.42 (s, 1H), 7.99 (s, 1H), 7.43 (dt, J = 5.7, 2.7 Hz, 3H), 7.35-7.19 (m, 3H), 6.89 (s, 1H), 6.32 (d, J = 5.7 Hz, 1H), 3.99-3.89 (m, 1H), 3.81 (dd, J = 13.7, 7.3 Hz, 1H), 3.61 (dd, J = 13.7, 5.8 Hz, 1H), 1.21-0.99 (m, 4H), 0.86 (s, 9H). |
| 1016 | 1H NMR (400 MHz, DMSO-d6) δ 8.58 (t, J = 4.5 Hz, 1H), 8.34 (d, J = 4.6 Hz, 1H), 8.23 (s, 1H), 8.05-8.01 (m, 1H), 7.79-7.72 (m, 1H), 7.64 (q, J = 2.3 Hz, 1H), 7.48 (dq, J = 8.8, 3.3, 2.2 Hz, 2H), 7.41-7.27 (m, 2H), 7.22-7.12 (m, 2H), 6.96 (d, J = 3.1 Hz, 1H), 4.31 (d, J = 14.6 Hz, 1H), 4.02-3.88 (m, 2H), 1.35 (t, J = 5.1 Hz, 6H), 1.20-1.05 (m, 4H). |
| 1017 | 1H NMR (400 MHz, Methanol-d4) δ 8.52 (s, 1H), 8.10 (s, 1H), 7.55-7.41 (m, 2H), 7.41-7.24 (m, 3H), 6.88 (s, 1H), 6.44 (s, 1H), 4.05 (d, J = 13.8 Hz, 1H), 3.82 (d, J = 13.8 Hz, 1H), 1.71 (d, J = 33.6 Hz, 4H), 0.98 (s, 9H). |
| 1018 | 1H NMR (400 MHz, DMSO-d6) δ 8.37-8.27 (m, 2H), 7.84 (dd, J = 16.5, 2.3 Hz, 1H), 7.59-7.47 (m, 2H), 7.44 (d, J = 2.4 Hz, 1H), 7.34 (d, J = 2.6 Hz, 1H), 7.23 (t, J = 8.6 Hz, 1H), 7.14 (t, J = 8.7 Hz, 1H), 6.73 (dd, J = 47.4, 10.1 Hz, 1H), 4.59-4.47 (m, 1H), 1.83-1.55 (m, 10H), 0.93 (d, J = 24.4 Hz, 3H), 0.80 (d, J = 43.1 Hz, 3H). |
| 1020 | 1H NMR (400 MHz, Methanol-d4) δ 8.34 (s, 1H), 7.91 (s, 1H), 7.75 (d, J = 2.5 Hz, 1H), 7.54-7.48 (m, 1H), 7.48-7.44 (m, 1H), 7.35-7.28 (m, 2H), 7.11 (d, J = 2.5 Hz, 1H), 6.40 (s, 1H), 3.90 (d, J = 13.7 Hz, 1H), 3.65 (d, J = 13.7 Hz, 1H), 2.67 (m, 2H), 2.54-2.42 (m, 1H), 1.90 (m, 2H), 1.62 (m, 2H), 0.94 (s, 9H). |
| 1021 | 1H NMR (400 MHz, Methanol-d4) δ 8.35 (s, 1H), 7.94 (s, 1H), 7.75 (s, 1H), 7.50 (m, 1H), 7.48-7.43 (m, 1H), 7.35-7.27 (m, 2H), 7.12 (s, 1H), 6.41 (s, 1H), 3.91 (d, J = 13.6 Hz, 1H), 3.67 (d, J = 13.6 Hz, 1H), 1.90 (s, 6H), 0.95 (s, 9H). |
| 1022 | 1H NMR (400 MHz, Methanol-d4) δ 8.36 (s, 1H), 8.03 (s, 1H), 7.75 (s, 1H), 7.51 (m, 1H), 7.47 (m, 1H), 7.32 (m, 2H), 7.13 (s, 1H), 6.42 (s, 1H), 4.52 (dd, J = 10.0, 6.8 Hz, 1H), 4.36 (dd, J = 10.0, 3.5 Hz, 1H), 4.10 (td, J = 8.7, 4.6 Hz, 1H), 3.97-3.86 (m, 2H), 3.65 (d, J = 13.6 Hz, 1H), 3.09-2.97 (m, 1H), 2.86 (m, 1H), 0.95 (s, 9H). |
| 1023 | 1H NMR (400 MHz, Methanol-d4) δ 8.37 (s, 1H), 7.99 (s, 1H), 7.77 (s, 1H), 7.48 (m, 2H), 7.38-7.27 (m, 2H), 7.14 (s, 1H), 6.43 (s, 1H), 3.93 (d, J = 13.6 Hz, 1H), 3.81 (m, 2H), 3.67 (d, J = 13.7 Hz, 1H), 3.47 (m, 2H), 2.56 (m, 4H), 0.95 (s, 9H). |
| 1024 | 1H NMR (400 MHz, Methanol-d4) δ 8.35 (s, 1H), 8.06 (s, 1H), 7.76 (d, J = 2.5 Hz, 1H), 7.30-7.13 (m, 4H), 7.08 (d, J = 2.5 Hz, 1H), 6.22 (s, 1H), 3.82 (d, J = 13.7 Hz, 1H), 3.73 (d, J = 13.7 Hz, 1H), 2.40 (s, 3H), 2.02-1.86 (m, 4H), 0.91 (s, 9H). |
| 1025 | 1H NMR (400 MHz, Methanol-d4) δ 8.34 (s, 1H), 8.11 (s, 1H), 7.75 (d, J = 2.5 Hz, 1H), 7.68 (d, J = 7.6 Hz, 1H), 7.59 (d, J = 7.8 Hz, 1H), 7.56-7.42 (m, 2H), 7.16 (t, J = 56.0 Hz, 1H), 7.15 (s, 1H), 6.41 (s, 1H), 3.81 (d, J = 13.8 Hz, 1H), 3.76 (d, J = 13.7 Hz, 1H), 2.05-1.79 (m, 4H), 0.94 (s, 9H). |
| 1026 | 1H NMR (400 MHz, Methanol-d4) δ 8.32 (s, 1H), 8.05 (d, J = 0.6 Hz, 1H), 7.79 (d, J = 2.5 Hz, 1H), 7.60 (d, J = 8.1 Hz, 1H), 7.53 (d, J = 2.6 Hz, 1H), 7.42-7.22 (m, 3H), 6.44 (s, 1H), 5.03 (d, J = 11.5 Hz, 1H), 4.62 (d, J = 11.5 Hz, 1H), 4.14 (d, J = 14.1 Hz, 1H), 3.51 (d, J = 14.1 Hz, 1H), 2.06-1.79 (m, 4H), 0.93 (s, 9H). |
| 1027 | 1H NMR (400 MHz, Methanol-d4) δ 8.35 (s, 1H), 8.28 (s, 1H), 7.81 (d, J = 7.8 Hz, 2H), 7.78 (d, J = 2.5 Hz, 1H), 7.49 (t, J = 7.8 Hz, 1H), 7.04 (d, J = 2.6 Hz, 1H), 3.94 (d, J = 13.7 Hz, 1H), 3.57 (d, J = 13.6 Hz, 1H), 2.06-1.87 (m, 4H), 0.92 (s, 9H). |
| 1028 | 1H NMR (400 MHz, DMSO-d6) δ 8.23 (d, J = 4.3 Hz, 1H), 8.16 (d, J = 7.9 Hz, 1H), 7.63-7.54 (m, 3H), 7.46-7.31 (m, 3H), 7.31-7.11 (m, 7H), 6.13 (t, J = 54.0 Hz, 1H), 5.49 (q, J = 7.5 Hz, 1H), 2.14 (dt, J = 14.2, 7.2 Hz, 1H), 1.92 (dt, J = 13.9, 7.0 Hz, 1H), 1.51 (s, 4H), 1.00-0.86 (m, 3H). |
| 1029 | 1H NMR (400 MHz, DMSO-d6) δ 8.31 (d, J = 0.7 Hz, 1H), 8.04 (d, J = 0.8 Hz, 1H), 7.81 (d, J = 2.4 Hz, 1H), 7.51-7.38 (m, 3H), 7.35-7.26 (m, 3H), 5.34 (s, 1H), 3.75 (dd, J = 13.7, 7.4 Hz, 1H), 3.53 (dd, J = 13.7, 5.7 Hz, 1H), 1.58 (d, J = 0.7 Hz, 9H), 0.86 (s, 9H). |
| 1030 | 1H NMR (400 MHz, DMSO-d6) δ 8.37 (s, 1H), 8.30 (s, 1H), 7.78 (d, J = 2.4 Hz, 1H), 7.49-7.42 (m, 2H), 7.40 (m, 2H), 7.36-7.27 (m, 3H), 3.69 (dd, J = 13.8, 7.2 Hz, 1H), 3.56 (dd, J = 14.1, 6.2 Hz, 1H), 2.07-1.99 (m, 2H), 1.94-1.86 (m, 2H), 0.83 (s, 9H). |
| 1031 | 1H NMR (400 MHz, Methanol-d4) δ 9.08 (s, 1H), 8.47 (s, 1H), 8.15 (s, 1H), 7.96 (d, J = 1.8 Hz, 1H), 7.86 (s, 1H), 7.83-7.71 (m, 1H), 7.68 (d, J = 2.3 Hz, 1H), 7.60-7.52 (m, 2H), 7.06 (d, J = 2.3 Hz, 1H), 6.16 (s, 1H), 4.18 (d, J = 13.9 Hz, 1H), 3.93-3.83 (m, 1H), 3.68 (d, J = 13.9 Hz, 1H), 1.25-1.09 (m, 4H), 0.89 (s, 9H). |
| 1032 | 1H NMR (400 MHz, Methanol-d4) δ 9.30 (s, 1H), 8.39 (s, 1H), 8.00 (s, 1H), 7.97 (s, 1H), 7.85 (s, 1H), 7.74-7.59 (m, 5H), 7.06 (d, J = 2.3 Hz, 1H), 6.18 (s, 1H), 4.07 (d, J = 13.9 Hz, 1H), 3.94-3.84 (m, 1H), 3.69 (d, J = 13.9 Hz, 1H), 1.25-1.11 (m, 4H), 0.92 (s, 9H). |
| 1033 | 1H NMR (400 MHz, Methanol-d4) δ 8.45 (s, 1H), 8.21 (d, J = 2.5 Hz, 1H), 7.89 (s, 1H), 7.83 (s, 1H), 7.71 (d, J = 1.8 Hz, 1H), 7.67 (d, J = 2.3 Hz, 2H), 7.48 (t, J = 7.8 Hz, 1H), 7.43 (d, J = 7.7 Hz, 1H), 7.04 (d, J = 2.2 Hz, 1H), 6.52 (dd, J = 2.6, 1.8 Hz, 1H), 6.12 (s, 1H), 4.16 (d, J = 13.9 Hz, 1H), 3.92-3.83 (m, 1H), 3.65 (d, J = 13.9 Hz, 1H), 1.23-1.09 (m, 4H), 0.88 (s, 9H). |

TABLE 2-continued

| Cmpd | 1H-NMR |
|---|---|
| 1034 | 1H NMR (400 MHz, DMSO-d6) δ 8.34 (d, J = 8.2 Hz, 1H), 8.01-7.96 (m, 1H), 7.82 (dd, J = 10.5, 2.5 Hz, 1H), 7.53-7.45 (m, 2H), 7.34 (dd, J = 32.2, 5.2 Hz, 1H), 7.25-7.17 (m, 1H), 7.16-7.07 (m, 1H), 6.70 (dd, J = 59.0, 10.0 Hz, 1H), 4.58-4.43 (m, 1H), 4.02-3.88 (m, 1H), 2.20 (dd, J = 9.8, 6.4 Hz, 1H), 1.97-1.40 (m, 4H), 1.22-1.01 (m, 4H), 1.00-0.67 (m, 6H). |
| 1035 | 1H NMR (400 MHz, Methanol-d4) δ 8.40 (s, 1H), 7.91 (s, 1H), 7.75 (d, J = 2.5 Hz, 1H), 7.50-7.46 (m, 1H), 7.44 (m, 1H), 7.37-7.27 (m, 2H), 7.01 (d, J = 2.5 Hz, 1H), 6.29 (s, 1H), 3.95 (d, J = 13.2 Hz, 1H), 3.88 (d, J = 13.1 Hz, 1H), 3.53 (s, 2H), 1.66 (s, 3H), 1.36-1.29 (m, 2H), 1.09-1.03 (m, 2H), 0.99 (s, 3H), 0.98 (s, 3H) |
| 1036 | 1H NMR (400 MHz, DMSO-d6) δ 8.32 (s, 1H), 8.09 (s, 1H), 7.81 (d, J = 2.4 Hz, 1H), 7.50-7.38 (m, 4H), 7.31 (dd, J = 5.9, 3.5 Hz, 3H), 6.40 (d, J = 7.5 Hz, 1H), 4.74 (s, 1H), 4.62 (s, 1H), 3.76 (dd, J = 13.8, 7.5 Hz, 1H), 3.52 (dd, J = 13.7, 5.7 Hz, 1H), 1.45-1.29 (m, 4H), 0.86 (s, 9H). |
| 1037 | 1H NMR (400 MHz, DMSO-d6) δ 9.22 (s, 1H), 8.94 (s, 2H), 8.30 (s, 1H), 8.07 (d, J = 0.5 Hz, 1H), 7.56-7.51 (m, 1H), 7.48 (d, J = 2.3 Hz, 1H), 7.47-7.43 (m, 1H), 7.35-7.28 (m, 2H), 7.15 (d, J = 2.4 Hz, 1H), 6.42 (s, 1H), 3.83 (dd, J = 13.7, 7.3 Hz, 1H), 3.59 (dd, J = 13.7, 5.7 Hz, 1H), 1.62 (d, J = 0.6 Hz, 3H), 1.29-1.22 (m, 2H), 1.09-0.99 (m, 2H), 0.90 (s, 9H). |
| 1038 | 1H NMR (400 MHz, Methanol-d4) δ 8.51 (s, 1H), 8.12 (s, 1H), 7.80 (d, J = 2.4, 0.6 Hz, 1H), 7.74 (dd, J = 1.9, 0.6 Hz, 1H), 7.65 (d, J = 2.3 Hz, 1H), 7.44 (dd, J = 6.1, 3.1 Hz, 1H), 7.39-7.30 (m, 2H), 7.05 (d, J = 2.3 Hz, 1H), 6.54 (t, J = 2.2 Hz, 1H), 6.33 (s, 1H), 3.99 (d, J = 14.0 Hz, 1H), 3.93 (d, J = 13.9 Hz, 1H), 2.11 (s, 3H), 1.80-1.66 (m, 4H), 0.96 (s, 9H). |
| 1039 | 1H NMR (400 MHz, Methanol-d4) δ 8.50 (s, 1H), 8.11 (s, 1H), 7.97 (s, 2H), 7.67 (d, J = 2.3 Hz, 1H), 7.46 (dd, J = 11.1, 8.1 Hz, 2H), 7.37 (t, J = 7.8 Hz, 1H), 6.98 (d, J = 2.3 Hz, 1H), 6.36 (s, 1H), 4.02 (d, J = 13.9 Hz, 1H), 3.83 (d, J = 13.9 Hz, 1H), 2.17 (s, 3H), 1.80-1.66 (m, 4H), 0.92 (s, 9H). |
| 1040 | 1H NMR (400 MHz, Methanol-d4) δ 8.69 (s, 1H), 8.52 (s, 1H), 8.22 (s, 1H), 8.15 (s, 1H), 7.66 (d, J = 2.3 Hz, 1H), 7.50 (q, J = 4.4 Hz, 1H), 7.39 (dd, J = 4.6, 0.7 Hz, 2H), 7.05 (d, J = 2.3 Hz, 1H), 6.36 (s, 1H), 4.01 (d, J = 14.0 Hz, 1H), 3.91 (d, J = 14.0 Hz, 1H), 2.15 (s, 3H), 1.83-1.60 (m, 4H), 0.95 (s, 9H). |
| 1041 | 1H NMR (400 MHz, Methanol-d4) δ 8.99 (s, 1H), 8.29 (s, 1H), 8.15 (s, 1H), 7.66 (s, 2H), 7.48 (dd, J = 6.8, 2.5 Hz, 1H), 7.46 (d, J = 2.3 Hz, 1H), 7.42-7.32 (m, 2H), 6.97 (d, J = 2.4 Hz, 1H), 6.29 (s, 1H), 3.85-3.71 (m, 2H), 2.14 (s, 3H), 1.82-1.42 (m, 4H), 0.86 (s, 9H). |
| 1042 | 1H NMR (400 MHz, Methanol-d4) δ 9.20 (t, J = 1.5 Hz, 1H), 8.30 (s, 1H), 8.25 (s, 1H), 7.80 (d, J = 1.4 Hz, 2H), 7.69 (d, J = 2.5 Hz, 1H), 7.61 (dd, J = 6.9, 2.5 Hz, 1H), 7.52-7.42 (m, 2H), 7.31 (d, J = 2.5 Hz, 1H), 6.39 (s, 1H), 3.76 (q, 2H), 2.25 (s, 3H), 1.82-1.59 (m, 4H), 0.94 (s, 9H). |
| 1043 | 1H NMR (400 MHz, Methanol-d4) δ 8.69 (s, 1H), 8.37 (s, 1H), 8.22 (s, 1H), 8.14 (s, 1H), 7.79 (d, J = 2.5 Hz, 1H), 7.56-7.48 (m, 1H), 7.44-7.36 (m, 2H), 7.22 (d, J = 2.5 Hz, 1H), 6.36 (s, 1H), 3.85 (d, J = 13.9 Hz, 1H), 3.78 (d, J = 13.9 Hz, 1H), 2.16 (s, 3H), 1.81-1.64 (m, 4H), 0.92 (s, 9H). |
| 1044 | 1H NMR (400 MHz, Methanol-d4) δ 8.37 (s, 1H), 8.10 (s, 1H), 7.96 (s, 2H), 7.81 (d, J = 2.5 Hz, 1H), 7.55-7.47 (m, 1H), 7.47-7.41 (m, 1H), 7.37 (t, J = 7.8 Hz, 1H), 7.16 (d, J = 2.5 Hz, 1H), 6.36 (s, 1H), 3.84 (d, J = 13.8 Hz, 1H), 3.72 (d, J = 13.8 Hz, 1H), 2.18 (s, 3H), 1.79-1.65 (m, 4H), 0.89 (s, 9H). |
| 1045 | 1H NMR (400 MHz, Methanol-d4) δ 8.37 (s, 1H), 8.12 (s, 1H), 7.84-7.76 (m, 2H), 7.74 (dd, J = 1.9, 0.7 Hz, 1H), 7.45 (dd, J = 6.8, 2.6 Hz, 1H), 7.39-7.28 (m, 2H), 7.23 (d, J = 2.6 Hz, 1H), 6.57-6.51 (m, 1H), 6.33 (s, 1H), 3.84 (d, J = 13.9 Hz, 1H), 3.79 (d, J = 13.9 Hz, 1H), 2.12 (s, 3H), 1.79-1.63 (m, 4H), 0.92 (s, 9H). |
| 1046 | 1H NMR (400 MHz, DMSO-d6) δ 8.32 (s, 1H), 7.64 (d, J = 2.3 Hz, 1H), 7.42-7.30 (m, 2H), 7.24-7.17 (m, 2H), 7.07 (s, 1H), 3.82 (dd, J = 13.7, 7.2 Hz, 1H), 3.58 (dd, J = 13.8, 6.0 Hz, 1H), 1.62 (d, J = 0.6 Hz, 3H), 1.27-1.18 (m, 2H), 1.07-0.98 (m, 2H), 0.94 (s, 9H). |
| 1047 | 1H NMR (400 MHz, DMSO-d6) δ 8.34 (s, 1H), 8.15 (s, 1H), 7.65 (d, J = 2.3 Hz, 1H), 7.43-7.31 (m, 2H), 7.25-7.17 (m, 2H), 7.11 (s, 1H), 3.83 (dd, J = 13.8, 7.3 Hz, 1H), 3.59 (dd, J = 13.8, 6.1 Hz, 1H), 1.62 (d, J = 0.6 Hz, 3H), 1.28-1.19 (m, 2H), 1.07-1.00 (m, 2H), 0.94 (s, 9H). |
| 1048 | 1H NMR (400 MHz, DMSO-d6) δ 8.33 (s, 1H), 7.87 (d, J = 2.4 Hz, 1H), 7.55-7.49 (m, 2H), 7.43-7.32 (m, 2H), 7.24-7.18 (m, 1H), 7.17 (s, 1H), 3.83-3.76 (m, 1H), 3.59 (dd, J = 13.9, 6.2 Hz, 1H), 1.61 (s, 3H), 1.23 (t, J = 3.7 Hz, 2H), 1.07-0.98 (m, 2H), 0.93 (s, 9H). |
| 1049 | 1H NMR (400 MHz, Methanol-d4) δ 8.68 (s, 1H), 8.51 (s, 1H), 8.22 (s, 1H), 8.00 (s, 1H), 7.65 (d, J = 2.3 Hz, 1H), 7.51 (q, J = 4.1 Hz, 1H), 7.44-7.36 (m, 2H), 7.04 (d, J = 2.3 Hz, 1H), 6.34 (s, 1H), 5.94 (t, J = 54.7 Hz, 1H), 4.01 (d, J = 14.0 Hz, 1H), 3.90 (d, J = 14.0 Hz, 1H), 2.15 (s, 3H), 1.54 (s, 4H), 0.96 (s, 9H). |
| 1050 | 1H NMR (400 MHz, Methanol-d4) δ 8.48 (s, 1H), 8.09-8.01 (m, 2H), 7.83-7.76 (m, 1H), 7.65 (d, J = 2.2 Hz, 1H), 7.49-7.42 (m, 1H), 7.35 (d, J = 0.9 Hz, 1H), 7.32 (t, J = 7.8 Hz, 1H), 6.91 (d, J = 2.3 Hz, 1H), 6.37 (s, 1H), 4.03 (d, J = 13.9 Hz, 1H), 3.78 (d, J = 13.9 Hz, 1H), 2.60 (s, 3H), 1.79-1.65 (m, 4H), 0.87 (s, 9H). |
| 1051 | 1H NMR (400 MHz, Methanol-d4) δ 8.49 (s, 1H), 8.04 (d, J = 0.9 Hz, 1H), 7.91 (s, 1H), 7.83-7.76 (m, 1H), 7.66 (d, J = 2.2 Hz, 1H), 7.46 (d, J = 7.8 Hz, 1H), 7.35 (d, J = 0.9 Hz, 1H), 7.32 (t, J = 7.8 Hz, 1H), 6.92 (d, J = 2.3 Hz, 1H), 6.36 (s, 1H), 5.94 (t, J = 54.8 Hz, 1H), 4.04 (d, J = 13.8 Hz, 1H), 3.78 (d, J = 13.9 Hz, 1H), 2.59 (s, 3H), 1.53 (s, 4H), 0.88 (s, 9H). |

TABLE 2-continued

| Cmpd | 1H-NMR |
|---|---|
| 1052 | 1H NMR (400 MHz, DMSO-d6) δ 8.27 (s, 1H), 7.98 (s, 1H), 7.75 (d, J = 2.2 Hz, 1H), 7.56-7.39 (m, 4H), 7.35-7.25 (m, 3H), 7.23-7.12 (m, 2H), 7.03 (d, J = 2.4 Hz, 1H), 6.37 (d, J = 7.3 Hz, 1H), 5.64 (s, 2H), 3.77 (dd, J = 13.7, 7.5 Hz, 1H), 3.48 (dd, J = 13.6, 5.6 Hz, 1H), 0.84 (s, 9H).; 1H NMR (400 MHz, DMSO-d6) δ 8.31 (s, 1H), 7.99 (s, 1H), 7.79 (d, J = 2.4 Hz, 1H), 7.57-7.38 (m, 4H), 7.37-7.26 (m, 4H), 7.22-7.12 (m, 2H), 6.41 (d, J = 7.0 Hz, 1H), 5.64 (s, 2H), 3.77 (dd, J = 13.7, 7.5 Hz, 1H), 3.49 (dd, J = 13.7, 5.6 Hz, 1H), 0.84 (s, 9H). |
| 1053 | 1H NMR (400 MHz, DMSO-d6) δ 8.27 (s, 1H), 7.98 (s, 1H), 7.75 (d, J = 2.2 Hz, 1H), 7.56-7.39 (m, 4H), 7.35-7.25 (m, 3H), 7.23-7.12 (m, 2H), 7.03 (d, J = 2.4 Hz, 1H), 6.37 (d, J = 7.3 Hz, 1H), 5.64 (s, 2H), 3.77 (dd, J = 13.7, 7.5 Hz, 1H), 3.48 (dd, J = 13.6, 5.6 Hz, 1H), 0.84 (s, 9H).; 1H NMR (400 MHz, DMSO-d6) δ 8.31 (s, 1H), 7.99 (s, 1H), 7.79 (d, J = 2.4 Hz, 1H), 7.57-7.38 (m, 4H), 7.37-7.26 (m, 4H), 7.22-7.12 (m, 2H), 6.41 (d, J = 7.0 Hz, 1H), 5.64 (s, 2H), 3.77 (dd, J = 13.7, 7.5 Hz, 1H), 3.49 (dd, J = 13.7, 5.6 Hz, 1H), 0.84 (s, 9H). |
| 1054 | 1H NMR (400 MHz, Methanol-d4) δ 8.69 (s, 1H), 8.35 (s, 1H), 8.22 (s, 1H), 8.00 (s, 1H), 7.78 (d, J = 2.5 Hz, 1H), 7.57-7.50 (m, 1H), 7.44-7.34 (m, 2H), 7.20 (d, J = 2.5 Hz, 1H), 6.34 (s, 1H), 5.95 (t, J = 54.8 Hz, 1H), 3.84 (d, J = 13.8 Hz, 1H), 3.75 (d, J = 13.8 Hz, 1H), 2.16 (s, 3H), 1.53 (s, 4H), 0.92 (s, 9H). |
| 1055 | 1H NMR (400 MHz, Methanol-d4) δ 8.35 (s, 1H), 8.06 (s, 1H), 8.03 (d, J = 0.9 Hz, 1H), 7.82-7.76 (m, 2H), 7.47 (d, J = 7.5 Hz, 1H), 7.37-7.27 (m, 2H), 7.07 (d, J = 2.5 Hz, 1H), 6.37 (s, 1H), 3.85 (d, J = 13.7 Hz, 1H), 3.64 (d, J = 13.7 Hz, 1H), 2.61 (s, 3H), 1.79-1.64 (m, 4H), 0.83 (s, 9H). |
| 1056 | 1H NMR (400 MHz, Methanol-d4) δ 8.33 (s, 1H), 8.03 (d, J = 0.9 Hz, 1H), 7.91 (s, 1H), 7.84-7.70 (m, 2H), 7.48 (d, J = 7.8 Hz, 1H), 7.34 (d, J = 0.9 Hz, 1H), 7.32 (t, J = 7.8 Hz, 1H), 7.06 (d, J = 2.5 Hz, 1H), 6.35 (s, 1H), 5.95 (t, J = 54.8 Hz, 1H), 3.85 (d, J = 13.8 Hz, 1H), 3.62 (d, J = 13.7 Hz, 1H), 2.61 (s, 3H), 1.52 (s, 4H), 0.83 (s, 9H). |
| 1057 | 1H NMR (400 MHz, Methanol-d4) δ 9.45 (s, 1H), 8.47 (s, 1H), 8.19 (s, 1H), 7.65 (d, J = 2.3 Hz, 1H), 7.61-7.56 (m, 1H), 7.48-7.41 (m, 2H), 6.99 (d, J = 2.4 Hz, 1H), 6.38 (s, 1H), 4.00 (d, J = 13.9 Hz, 1H), 3.83 (d, J = 13.9 Hz, 1H), 2.12 (s, 3H), 1.81-1.66 (m, 4H), 0.94 (s, 9H). |
| 1058 | 1H NMR (400 MHz, Methanol-d4) δ 8.45 (s, 1H), 7.84 (s, 1H), 7.65 (d, J = 2.3 Hz, 1H), 7.47 (d, J = 7.2 Hz, 2H), 7.41-7.32 (m, 2H), 7.35-7.26 (m, 1H), 7.07 (d, J = 2.3 Hz, 1H), 6.08 (s, 1H), 5.93 (t, J = 54.7 Hz, 1H), 4.15 (d, J = 13.9 Hz, 1H), 3.74 (d, J = 14.0 Hz, 1H), 1.51 (s, 4H), 0.97 (s, 9H). |
| 1059 | 1H NMR (400 MHz, Methanol-d4) δ 8.47 (s, 1H), 7.98 (s, 1H), 7.66 (d, J = 2.2 Hz, 1H), 7.51-7.44 (m, 2H), 7.42-7.33 (m, 2H), 7.36-7.27 (m, 1H), 7.09 (d, J = 2.2 Hz, 1H), 6.10 (s, 1H), 4.16 (d, J = 13.9 Hz, 1H), 3.76 (d, J = 13.9 Hz, 1H), 1.78-1.59 (m, 4H), 0.97 (s, 9H). |
| 1060 | 1H NMR (400 MHz, Methanol-d4) δ 8.46 (s, 1H), 7.82 (s, 1H), 7.61 (d, J = 2.3 Hz, 1H), 7.28-7.19 (m, 3H), 7.16 (t, J = 7.0 Hz, 1H), 6.91 (d, J = 2.3 Hz, 1H), 6.21 (s, 1H), 5.92 (t, J = 54.7 Hz, 1H), 3.99 (d, J = 13.8 Hz, 1H), 3.84 (d, J = 13.9 Hz, 1H), 2.38 (s, 3H), 1.51 (s, 4H), 0.94 (s, 9H). |
| 1061 | 1H NMR (400 MHz, Methanol-d4) δ 8.47 (s, 1H), 7.98 (s, 1H), 7.62 (d, J = 2.3 Hz, 1H), 7.28-7.19 (m, 3H), 7.19-7.13 (m, 1H), 6.93 (d, J = 2.3 Hz, 1H), 6.23 (s, 1H), 4.00 (d, J = 13.8 Hz, 1H), 3.86 (d, J = 13.9 Hz, 1H), 2.38 (s, 3H), 1.78-1.59 (m, 4H), 0.94 (s, 9H). |
| 1062 | 1H NMR (400 MHz, Methanol-d4) δ 9.45 (s, 1H), 8.50 (s, 1H), 8.04 (s, 1H), 7.66 (d, J = 2.3 Hz, 1H), 7.59 (dd, J = 5.9, 3.3 Hz, 1H), 7.45 (d, J = 2.7 Hz, 1H), 7.43 (s, 1H), 7.00 (d, J = 2.4 Hz, 1H), 6.36 (s, 1H), 5.94 (t, J = 54.6 Hz, 1H), 4.03 (d, J = 13.9 Hz, 1H), 3.84 (d, J = 14.0 Hz, 1H), 2.11 (s, 3H), 1.54 (s, 4H), 0.95 (s, 9H). |
| 1063 | 1H NMR (400 MHz, Methanol-d4) δ 8.49 (s, 1H), 8.19 (d, J = 1.1 Hz, 1H), 8.17 (s, 1H), 7.94 (d, J = 1.1 Hz, 1H), 7.66 (d, J = 2.3 Hz, 1H), 7.54 (dd, J = 7.0, 2.1 Hz, 1H), 7.46-7.35 (m, 2H), 7.01 (d, J = 2.2 Hz, 1H), 6.37 (s, 1H), 4.00 (d, J = 13.9 Hz, 1H), 3.86 (d, J = 13.9 Hz, 1H), 2.10 (s, 3H), 1.81-1.66 (m, 4H), 0.94 (s, 9H). |
| 1064 | 1H NMR (400 MHz, Methanol-d4) δ 8.35 (s, 1H), 7.86 (s, 1H), 7.80 (d, J = 2.5 Hz, 1H), 7.52-7.45 (m, 2H), 7.36 (dd, J = 8.5, 6.6 Hz, 2H), 7.33-7.27 (m, 1H), 7.26 (d, J = 2.5 Hz, 1H), 6.08 (s, 1H), 5.93 (t, J = 54.7 Hz, 1H), 4.03 (d, J = 13.8 Hz, 1H), 3.63 (d, J = 13.9 Hz, 1H), 1.51 (s, 4H), 0.94 (s, 9H). |
| 1065 | 1H NMR (400 MHz, Methanol-d4) δ 8.35 (s, 1H), 8.00 (s, 1H), 7.80 (d, J = 2.5 Hz, 1H), 7.52-7.45 (m, 2H), 7.37 (dd, J = 8.2, 6.5 Hz, 2H), 7.30 (t, J = 7.3 Hz, 1H), 7.26 (d, J = 2.5 Hz, 1H), 6.10 (s, 1H), 4.01 (d, J = 13.9 Hz, 1H), 3.64 (d, J = 13.9 Hz, 1H), 1.78-1.62 (m, 4H), 0.94 (s, 9H). |
| 1066 | 1H NMR (400 MHz, Methanol-d4) δ 8.37 (s, 1H), 7.85 (s, 1H), 7.77 (d, J = 2.5 Hz, 1H), 7.29-7.19 (m, 3H), 7.19-7.13 (m, 1H), 7.10 (d, J = 2.5 Hz, 1H), 6.22 (s, 1H), 5.93 (t, J = 54.7 Hz, 1H), 3.87 (d, J = 13.8 Hz, 1H), 3.74 (d, J = 13.8 Hz, 1H), 2.38 (s, 3H), 1.51 (s, 4H), 0.90 (s, 9H). |
| 1067 | 1H NMR (400 MHz, Methanol-d4) δ 8.36 (s, 1H), 8.00 (s, 1H), 7.77 (d, J = 2.5 Hz, 1H), 7.28-7.19 (m, 3H), 7.19-7.13 (m, 1H), 7.11 (d, J = 2.5 Hz, 1H), 6.23 (s, 1H), 3.86 (d, J = 13.8 Hz, 1H), 3.74 (d, J = 13.8 Hz, 1H), 2.39 (s, 3H), 1.78-1.62 (m, 4H), 0.90 (s, 9H). |
| 1068 | 1H NMR (400 MHz, Methanol-d4) δ 8.38 (s, 1H), 8.19 (d, J = 1.1 Hz, 1H), 8.17 (s, 1H), 7.94 (d, J = 1.1 Hz, 1H), 7.81 (d, J = 2.5 Hz, 1H), 7.54 (dd, J = 7.3, 2.0 Hz, 1H), 7.46-7.35 (m, 2H), 7.20 (d, J = 2.5 Hz, 1H), 6.37 (s, 1H), 3.86 (d, J = 13.9 Hz, 1H), 3.75 (d, J = 13.8 Hz, 1H), 2.11 (s, 3H), 1.80-1.66 (m, 4H), 0.91 (s, 9H). |
| 1069 | 1H NMR (400 MHz, Methanol-d4) δ 9.16 (s, 1H), 8.47 (s, 1H), 8.10 (s, 1H), 7.78 (s, 2H), 7.59 (dd, J = 5.2, 2.1 Hz, 2H), 7.52-7.41 (m, 2H), 7.13 (d, J = 2.4 Hz, 1H), 6.38 (s, 1H), 5.94 (t, J = 54.7 Hz, 1H), 3.97 (d, J = 13.9 Hz, 1H), 3.91 (d, J = 14.0 Hz, 1H), 2.23 (s, 3H), 1.55 (s, 4H), 0.98 (s, 9H). |

TABLE 2-continued

| Cmpd | 1H-NMR |
|---|---|
| 1070 | 1H NMR (400 MHz, Methanol-d4) δ 8.73 (s, 2H), 8.52 (s, 1H), 8.04 (s, 1H), 7.64 (d, J = 2.3 Hz, 1H), 7.55-7.48 (m, 1H), 7.46-7.36 (m, 2H), 7.08 (d, J = 2.2 Hz, 1H), 6.35 (s, 1H), 5.94 (t, J = 54.6 Hz, 1H), 4.00 (d, J = 13.9 Hz, 1H), 3.95 (d, J = 14.0 Hz, 1H), 2.16 (s, 3H), 1.54 (s, 4H), 0.97 (s, 9H). |
| 1071 | 1H NMR (400 MHz, Methanol-d4) δ 8.72 (s, 2H), 8.51 (s, 1H), 8.19 (s, 1H), 7.64 (d, J = 2.2 Hz, 1H), 7.51 (d, J = 6.5 Hz, 1H), 7.44-7.38 (m, 2H), 7.08 (d, J = 2.2 Hz, 1H), 6.36 (s, 1H), 3.97 (d, J = 1.3 Hz, 2H), 2.16 (s, 3H), 1.88-1.55 (m, 4H), 0.97 (s, 9H). |
| 1072 | 1H NMR (400 MHz, Methanol-d4) δ 8.79 (s, 2H), 8.35 (s, 1H), 8.19 (s, 1H), 7.76 (d, J = 2.5 Hz, 1H), 7.54 (dd, J = 7.2, 1.9 Hz, 1H), 7.47-7.36 (m, 2H), 7.26 (d, J = 2.5 Hz, 1H), 6.37 (s, 1H), 3.81 (d, J = 1.3 Hz, 2H), 2.18 (s, 3H), 1.89-1.55 (m, 4H), 0.93 (s, 9H). |
| 1073 | 1H NMR (400 MHz, Methanol-d4) δ 8.77 (s, 2H), 8.33 (s, 1H), 8.05 (s, 1H), 7.75 (d, J = 2.5 Hz, 1H), 7.55 (d, J = 7.2 Hz, 1H), 7.46-7.35 (m, 2H), 7.24 (d, J = 2.5 Hz, 1H), 6.35 (s, 1H), 5.95 (t, J = 54.7 Hz, 1H), 3.83 (d, J = 13.9 Hz, 1H), 3.77 (d, J = 13.8 Hz, 1H), 2.17 (s, 3H), 1.54 (s, 4H), 0.93 (s, 9H). |
| 1074 | 1H NMR (400 MHz, Methanol-d4) δ 8.52 (s, 1H), 8.27 (s, 1H), 7.82 (dd, J = 7.7, 1.6 Hz, 1H), 7.77 (dd, J = 8.0, 1.6 Hz, 1H), 7.66 (d, J = 2.3 Hz, 1H), 7.49 (t, J = 7.9 Hz, 1H), 6.92 (d, J = 2.4 Hz, 1H), 4.14 (d, J = 13.9 Hz, 1H), 3.73 (d, J = 13.9 Hz, 1H), 1.85-1.62 (m, 4H), 0.96 (s, 9H). |
| 1075 | 1H NMR (400 MHz, Methanol-d4) δ 8.51 (s, 1H), 8.11 (s, 1H), 7.82 (dd, J = 7.7, 1.6 Hz, 1H), 7.77 (dd, J = 8.0, 1.6 Hz, 1H), 7.65 (d, J = 2.3 Hz, 1H), 7.49 (t, J = 7.9 Hz, 1H), 6.92 (d, J = 2.3 Hz, 1H), 5.95 (t, J = 54.7 Hz, 1H), 4.14 (d, J = 13.9 Hz, 1H), 3.73 (d, J = 13.9 Hz, 1H), 1.54 (s, 4H), 0.96 (s, 9H). |
| 1076 | 1H NMR (400 MHz, Methanol-d4) δ 8.51 (s, 1H), 7.90 (s, 1H), 7.63 (d, J = 2.3 Hz, 1H), 7.23 (dd, J = 8.6, 5.8 Hz, 1H), 7.02 (dd, J = 9.6, 2.6 Hz, 1H), 6.95-6.84 (m, 2H), 6.19 (s, 1H), 5.92 (t, J = 54.6 Hz, 1H), 4.04 (d, J = 13.9 Hz, 1H), 3.86 (d, J = 13.9 Hz, 1H), 2.37 (s, 3H), 1.52 (s, 4H), 0.94 (s, 9H). |
| 1077 | 1H NMR (400 MHz, Methanol-d4) δ 9.22 (t, J = 1.4 Hz, 1H), 8.31 (s, 1H), 8.12 (s, 1H), 7.81 (d, J = 1.5 Hz, 2H), 7.70 (d, J = 2.5 Hz, 1H), 7.61 (dd, J = 7.0, 2.3 Hz, 1H), 7.53-7.42 (m, 2H), 7.30 (d, J = 2.5 Hz, 1H), 6.38 (s, 1H), 5.94 (t, J = 54.6 Hz, 1H), 3.86-3.73 (m, 2H), 2.24 (s, 3H), 1.57-1.50 (m, 4H), 0.94 (s, 9H). |
| 1078 | 1H NMR (400 MHz, DMSO-d6) δ 8.30 (s, 1H), 8.00 (s, 1H), 7.79 (d, J = 2.4 Hz, 1H), 7.57-7.45 (m, 4H), 7.39 (d, J = 2.5 Hz, 1H), 7.23-7.08 (m, 4H), 5.66-5.61 (m, 2H), 4.47 (s, 1H), 3.94 (dd, J = 14.0, 8.0 Hz, 1H), 3.41 (dd, J = 13.9, 5.5 Hz, 1H), 0.86 (s, 9H). |
| 1079 | 1H NMR (400 MHz, Methanol-d4) δ 8.35 (s, 1H), 8.26 (s, 1H), 7.85-7.76 (m, 3H), 7.49 (t, J = 7.8 Hz, 1H), 7.05 (d, J = 2.5 Hz, 1H), 3.95 (d, J = 13.7 Hz, 1H), 3.57 (d, J = 13.7 Hz, 1H), 1.81-1.66 (m, 4H), 0.92 (s, 9H). |
| 1080 | 1H NMR (400 MHz, Methanol-d4) δ 8.34 (s, 1H), 8.11 (s, 1H), 7.85-7.75 (m, 3H), 7.48 (t, J = 7.8 Hz, 1H), 7.03 (d, J = 2.5 Hz, 1H), 5.96 (t, J = 54.7 Hz, 1H), 3.94 (d, J = 13.7 Hz, 1H), 3.56 (d, J = 13.6 Hz, 1H), 1.54 (s, 4H), 0.92 (s, 9H). |
| 1081 | 1H NMR (400 MHz, Methanol-d4) δ 9.45 (s, 1H), 8.30 (s, 1H), 8.18 (s, 1H), 7.76 (d, J = 2.5 Hz, 1H), 7.61 (dd, J = 7.1, 2.2 Hz, 1H), 7.49-7.36 (m, 2H), 7.16 (d, J = 2.6 Hz, 1H), 6.38 (s, 1H), 3.80 (d, J = 13.8 Hz, 1H), 3.68 (d, J = 13.8 Hz, 1H), 2.13 (s, 3H), 1.80-1.65 (m, 4H), 0.90 (s, 9H). |
| 1082 | 1H NMR (400 MHz, Methanol-d4) δ 9.45 (s, 1H), 8.33 (s, 1H), 8.04 (s, 1H), 7.78 (d, J = 2.5 Hz, 1H), 7.61 (d, J = 7.0 Hz, 1H), 7.49-7.39 (m, 2H), 7.17 (d, J = 2.5 Hz, 1H), 6.37 (s, 1H), 5.95 (t, J = 54.8 Hz, 1H), 3.84 (d, J = 13.8 Hz, 1H), 3.69 (d, J = 13.9 Hz, 1H), 2.13 (s, 3H), 1.54 (s, 4H), 0.91 (s, 9H). |
| 1083 | 1H NMR (400 MHz, Methanol-d4) δ 8.33 (s, 1H), 7.90 (s, 1H), 7.75 (d, J = 2.5 Hz, 1H), 7.26 (dd, J = 8.7, 5.8 Hz, 1H), 7.06 (d, J = 2.5 Hz, 1H), 7.01 (dd, J = 9.8, 2.6 Hz, 1H), 6.93-6.85 (m, 1H), 6.18 (s, 1H), 5.94 (t, J = 54.7 Hz, 1H), 3.84 (d, J = 13.8 Hz, 1H), 3.70 (d, J = 13.8 Hz, 1H), 2.39 (s, 3H), 1.52 (s, 4H), 0.90 (s, 9H). |
| 1084 | 1H NMR (400 MHz, Methanol-d4) δ 8.49 (s, 1H), 7.86 (s, 1H), 7.73 (d, J = 8.3 Hz, 2H), 7.69-7.61 (m, 3H), 6.99 (d, J = 2.2 Hz, 1H), 6.13 (s, 1H), 4.53 (s, 8H), 4.20 (d, J = 13.9 Hz, 1H), 3.88 (ddd, J = 11.4, 7.3, 4.1 Hz, 1H), 3.69 (d, J = 14.0 Hz, 1H), 1.24-1.07 (m, 4H), 0.94 (s, 9H). |
| 1085 | 1H NMR (400 MHz, Methanol-d4) δ 8.85 (br s, 2H), 8.49 (s, 1H), 8.04 (s, 1H), 7.94 (br s, 2H), 7.63 (d, J = 1.9 Hz, 1H), 7.46 (d, J = 8.0 Hz, 1H), 7.43-7.31 (m, 2H), 7.05 (s, 1H), 6.36 (s, 1H), 5.94 (t, J = 54.6 Hz, 1H), 3.95 (d, J = 4.7 Hz, 2H), 2.35 (s, 3H), 1.54 (s, 4H), 0.95 (s, 9H). |
| 1086 | 1H NMR (400 MHz, Methanol-d4) δ 8.49 (s, 1H), 7.88 (s, 1H), 7.71 (s, 1H), 7.64 (d, J = 2.2 Hz, 1H), 7.55 (s, 1H), 7.30 (dd, J = 6.9, 2.1 Hz, 1H), 7.24-7.13 (m, 2H), 6.96 (s, 1H), 6.30 (s, 1H), 5.93 (t, J = 54.7 Hz, 1H), 4.01 (d, J = 13.9 Hz, 1H), 3.94 (s, 3H), 3.84 (d, J = 13.9 Hz, 1H), 2.38 (s, 3H), 1.53 (s, 4H), 0.91 (s, 9H). |
| 1087 | 1H NMR (400 MHz, Chloroform-d) δ 8.24 (s, 1H), 7.91-7.82 (m, 2H), 7.78 (s, 1H), 7.41 (s, 1H), 7.22-7.15 (m, 2H), 6.52-6.45 (m, 1H), 4.38 (q, 2H), 3.99-3.90 (m, 1H), 3.73-3.63 (m, 1H), 1.70-1.61 (m, 4H), 1.38 (t, 3H), 0.94 (s, 9H). |
| 1088 | 1H NMR (400 MHz, Methanol-d4) δ 8.43 (s, 1H), 8.10 (s, 1H), 8.04 (dd, 1H), 7.75-7.68 (m, 1H), 7.65 (d, 1H), 7.27-7.16 (m, 2H), 7.00 (d, 1H), 6.15 (s, 1H), 4.14 (d, 1H), 3.87 (s, 3H), 3.70-3.65 (m, 1H), 1.78-1.59 (m, 4H), 0.93 (s, 9H). |
| 1089 | 1H NMR (400 MHz, Methanol-d4) δ 8.51 (d, J = 1.3 Hz, 1H), 7.98 (s, 1H), 7.73-7.64 (m, 2H), 7.58 (d, J = 7.9 Hz, 1H), 7.34 (t, J = 7.8 Hz, 1H), 6.78 (d, J = 2.2 Hz, 1H), 6.26 (s, 1H), 5.94 (t, J = 54.6 Hz, 1H), 4.42 (d, J = 14.9 Hz, 1H), 4.09 (d, J = 14.9 Hz, 1H), 2.57 (s, 3H), 1.53 (s, 4H), 1.13 (d, J = 6.4 Hz, 6H). |

TABLE 2-continued

| Cmpd | 1H-NMR |
|---|---|
| 1090 | 1H NMR (400 MHz, Methanol-d4) δ 8.47 (s, 1H), 8.04 (s, 1H), 7.63 (d, J = 2.2 Hz, 1H), 7.25-6.98 (m, 3H), 6.89 (d, J = 2.3 Hz, 1H), 6.24 (s, 1H), 4.04 (d, J = 13.8 Hz, 1H), 3.78 (d, J = 13.9 Hz, 1H), 2.26 (d, J = 2.0 Hz, 3H), 1.83-1.60 (m, 4H), 0.93 (s, 9H). |
| 1091 | 1H NMR (400 MHz, Methanol-d4) δ 8.47 (s, 1H), 8.06 (s, 1H), 7.67 (d, J = 2.3 Hz, 1H), 7.48 (d, J = 2.0 Hz, 1H), 7.43-7.36 (m, 2H), 7.26-7.19 (m, 1H), 7.08 (d, J = 2.3 Hz, 1H), 6.14 (s, 1H), 4.13 (d, J = 14.0 Hz, 1H), 3.77 (d, J = 13.9 Hz, 1H), 1.77-1.73 (m, 2H), 1.73-1.69 (m, 2H), 1.69-1.61 (m, 2H), 1.49-1.44 (m, 1H), 1.44-1.37 (m, 1H), 0.97 (s, 9H). |
| 1092 | 1H NMR (400 MHz, Methanol-d4) δ 8.47 (s, 1H), 7.76 (s, 1H), 7.64 (d, J = 2.3 Hz, 1H), 7.47 (dd, J = 8.6, 5.2 Hz, 2H), 7.09 (t, J = 8.7 Hz, 2H), 7.02 (d, J = 2.3 Hz, 1H), 6.05 (s, 1H), 4.14 (d, J = 13.9 Hz, 1H), 3.76 (d, J = 13.9 Hz, 1H), 2.68 (s, 1H), 2.36 (s, 6H), 0.96 (s, 9H). |
| 1093 | 1H NMR (400 MHz, Methanol-d4) δ 8.44 (s, 1H), 7.71 (s, 1H), 7.64 (d, J = 2.3 Hz, 1H), 7.46 (d, J = 7.5 Hz, 2H), 7.36 (t, J = 7.5 Hz, 2H), 7.31 (d, J = 7.2 Hz, 1H), 7.03 (d, J = 2.3 Hz, 1H), 6.05 (s, 1H), 4.11 (d, J = 13.9 Hz, 1H), 3.75 (d, J = 13.9 Hz, 1H), 2.68 (s, 1H), 2.36 (s, 6H), 0.96 (s, 9H). |
| 1094 | 1H NMR (400 MHz, Methanol-d4) δ 8.49 (s, 1H), 7.78 (s, 1H), 7.67 (d, J = 2.3 Hz, 1H), 7.48 (s, 1H), 7.41-7.35 (m, 2H), 7.22 (td, J = 4.7, 2.0 Hz, 1H), 7.04 (d, J = 2.3 Hz, 1H), 6.10 (s, 1H), 4.13 (d, J = 14.0 Hz, 1H), 3.78 (d, J = 13.9 Hz, 1H), 2.68 (s, 1H), 2.37 (s, 6H), 1.75-1.64 (m, 2H), 1.53-1.36 (m, 2H), 0.96 (s, 9H). |
| 1095 | 1H NMR (400 MHz, Methanol-d4) δ 8.84 (s, 1H), 8.49 (s, 1H), 8.19 (s, 1H), 7.91 (d, J = 5.7 Hz, 2H), 7.63 (d, J = 2.3 Hz, 1H), 7.45 (d, J = 7.5 Hz, 1H), 7.40 (d, J = 7.6 Hz, 1H), 7.38-7.32 (m, 2H), 7.07 (d, J = 2.3 Hz, 1H), 6.38 (s, 1H), 3.95 (s, 2H), 2.35 (s, 3H), 1.84-1.57 (m, 4H), 0.95 (s, 9H). |
| 1096 | 1H NMR (400 MHz, Methanol-d4) δ 8.70 (d, J = 19.0 Hz, 1H), 8.49 (s, 1H), 8.19 (d, J = 8.0 Hz, 1H), 8.15 (s, 1H), 7.94-7.78 (m, 1H), 7.64 (d, J = 2.3 Hz, 1H), 7.41-7.38 (m, 1H), 7.35 (t, J = 7.6 Hz, 2H), 7.32-7.28 (m, 1H), 7.06 (d, J = 2.3 Hz, 1H), 6.37 (s, 1H), 4.05-3.83 (m, 2H), 2.29 (s, 3H), 1.85-1.61 (m, 4H), 0.95 (s, 9H). |
| 1097 | 1H NMR (400 MHz, Methanol-d4) δ 8.50 (s, 1H), 8.03 (s, 1H), 7.71 (s, 1H), 7.65 (d, J = 2.2 Hz, 1H), 7.54 (s, 1H), 7.34-7.25 (m, 1H), 7.20 (s, 1H), 7.18 (d, J = 3.6 Hz, 1H), 6.98 (d, J = 2.2 Hz, 1H), 6.33 (s, 1H), 4.02 (d, J = 13.9 Hz, 1H), 3.94 (s, 3H), 3.86 (d, J = 13.9 Hz, 1H), 2.38 (s, 3H), 1.78-1.72 (m, 2H), 1.67 (s, 2H), 0.91 (s, 9H). |
| 1098 | 1H NMR (400 MHz, Methanol-d4) δ 8.49 (s, 1H), 7.98 (s, 1H), 7.63 (d, J = 1.9 Hz, 2H), 7.54 (d, J = 8.2 Hz, 1H), 7.49 (d, J = 8.1 Hz, 1H), 6.86 (s, 1H), 6.26 (s, 1H), 5.93 (t, J = 54.7 Hz, 1H), 4.08 (d, J = 13.9 Hz, 1H), 3.75 (d, J = 13.9 Hz, 1H), 2.41 (s, 3H), 1.53 (s, 4H), 0.92 (s, 9H). |
| 1099 | 1H NMR (400 MHz, Methanol-d4) δ 8.48 (s, 1H), 8.12 (s, 1H), 7.63 (d, J = 2.3 Hz, 2H), 7.55 (d, J = 8.4 Hz, 1H), 7.48 (d, J = 8.0 Hz, 1H), 6.88-6.83 (m, 1H), 6.27 (s, 1H), 4.07 (d, J = 13.9 Hz, 1H), 3.75 (d, J = 13.9 Hz, 1H), 2.41 (s, 3H), 1.86-1.56 (m, 4H), 0.92 (s, 9H). |
| 1100 | 1H NMR (400 MHz, Methanol-d4) δ 8.48 (d, J = 1.4 Hz, 1H), 7.93 (s, 1H), 7.67 (d, J = 7.7 Hz, 1H), 7.64 (d, J = 2.1 Hz, 1H), 7.61 (d, J = 8.0 Hz, 1H), 7.34 (t, J = 7.8 Hz, 1H), 6.80 (d, J = 2.1 Hz, 1H), 6.26 (s, 1H), 4.61 (d, J = 48.4 Hz, 2H), 4.11 (d, J = 13.9 Hz, 1H), 3.71 (d, J = 13.8 Hz, 1H), 2.57 (s, 3H), 1.55-1.44 (m, 2H), 1.38-1.31 (m, 2H), 0.91 (d, J = 1.3 Hz, 9H). |
| 1101 | 1H NMR (400 MHz, Methanol-d4) δ 8.48 (s, 1H), 7.90 (s, 1H), 7.66 (d, J = 7.8 Hz, 1H), 7.63 (d, J = 2.1 Hz, 1H), 7.60 (d, J = 8.2 Hz, 1H), 7.34 (t, J = 7.8 Hz, 1H), 6.78 (d, J = 2.1 Hz, 1H), 6.23 (s, 1H), 4.10 (d, J = 13.8 Hz, 1H), 3.70 (d, J = 13.9 Hz, 1H), 2.56 (s, 3H), 1.66 (s, 3H), 1.36-1.27 (m, 2H), 1.10-1.02 (m, 2H), 0.90 (d, J = 1.3 Hz, 9H). |
| 1102 | 1H NMR (400 MHz, Methanol-d4) δ 8.52 (s, 1H), 7.95 (s, 1H), 7.74-7.65 (m, 2H), 7.61 (d, J = 7.7 Hz, 1H), 7.35 (t, J = 7.8 Hz, 1H), 6.84 (d, J = 2.2 Hz, 1H), 6.30 (s, 1H), 5.42-5.11 (m, 1H), 5.03-4.77 (m, 4H), 4.14 (d, J = 14.0 Hz, 1H), 3.73 (d, J = 13.9 Hz, 1H), 2.57 (s, 3H), 0.92 (s, 9H). |
| 1103 | 1H NMR (400 MHz, Methanol-d4) δ 8.49 (d, J = 1.3 Hz, 1H), 7.87 (s, 1H), 7.67 (d, J = 7.7 Hz, 1H), 7.65 (d, J = 2.1 Hz, 1H), 7.61 (d, J = 8.0 Hz, 1H), 7.35 (t, J = 7.8 Hz, 1H), 6.81 (d, J = 2.2 Hz, 1H), 6.27 (s, 1H), 5.06-4.94 (m, 1H), 4.70 (d, J = 46.8 Hz, 1H), 4.68 (d, J = 47.3 Hz, 1H), 4.12 (d, J = 13.8 Hz, 1H), 3.71 (d, J = 13.9 Hz, 1H), 2.56 (s, 3H), 1.56 (dd, J = 7.1, 1.3 Hz, 3H), 0.91 (s, 9H). |
| 1104 | 1H NMR (400 MHz, Methanol-d4) δ 8.48 (s, 1H), 7.88 (s, 1H), 7.69-7.63 (m, 1H), 7.62 (d, J = 2.3 Hz, 1H), 7.60-7.54 (m, 1H), 7.34 (t, J = 7.8 Hz, 1H), 6.74 (d, J = 2.4 Hz, 1H), 6.21 (s, 1H), 4.38 (d, J = 15.0 Hz, 1H), 4.09 (d, J = 15.0 Hz, 1H), 2.56 (s, 3H), 1.65 (s, 3H), 1.40-1.25 (m, 2H), 1.13 (s, 3H), 1.11 (s, 3H), 1.09-0.97 (m, 2H). |
| 1105 | 1H NMR (400 MHz, Methanol-d4) δ 9.86 (s, 1H), 9.30 (s, 1H), 9.07-8.98 (m, 2H), 8.95 (d, J = 8.0 Hz, 1H), 8.70 (t, J = 7.8 Hz, 1H), 8.12 (s, 1H), 7.59 (s, 1H), 5.79 (d, J = 14.9 Hz, 1H), 5.43 (d, J = 15.1 Hz, 1H), 3.93 (s, 3H), 2.93-2.88 (m, 1H), 2.59 (s, 2H), 2.49 (d, J = 6.7 Hz, 6H), 2.37 (s, 2H), 1.89 (d, J = 7.8 Hz, 2H), 1.69 (d, J = 5.2 Hz, 2H). |
| 1106 | 1H NMR (400 MHz, Methanol-d4) δ 9.82 (s, 1H), 9.21 (s, 1H), 9.02 (d, J = 7.8 Hz, 1H), 8.99 (s, 1H), 8.95 (d, J = 8.0 Hz, 1H), 8.70 (t, J = 8.0 Hz, 1H), 8.10 (s, 1H), 7.61 (s, 1H), 6.40-6.31 (m, 1H), 6.05 (d, J = 46.9 Hz, 1H), 6.04 (d, J = 46.9 Hz, 1H), 5.75 (d, J = 14.8 Hz, 1H), 5.41 (d, J = 15.1 Hz, 1H), 4.66 (d, J = 7.2 Hz, 5H), 3.92 (s, 3H), 2.92 (d, J = 7.1 Hz, 3H), 2.47 (d, J = 6.2 Hz, 6H). |
| 1107 | 1H NMR (400 MHz, Methanol-d4) δ 9.86 (s, 1H), 9.18 (s, 1H), 9.05-8.96 (m, 2H), 8.91 (d, J = 7.7 Hz, 1H), 8.76-8.58 (m, 1H), 8.10 (s, 1H), 7.58 (s, 1H), 5.73 (d, J = 14.8 Hz, 1H), 5.47 (d, J = 15.0 Hz, 1H), 4.04 (d, J = 1H), 3.92 (s, 3H), 3.72 (s, 6H), 2.48 (s, 3H), 2.47 (s, 3H). |

TABLE 2-continued

| Cmpd | 1H-NMR |
|---|---|
| 1108 | 1H NMR (400 MHz, Methanol-d4) δ 8.52 (s, 1H), 7.85 (s, 1H), 7.67 (dd, J = 7.8, 1.3 Hz, 1H), 7.65 (d, J = 2.2 Hz, 1H), 7.59 (dd, J = 8.0, 1.3 Hz, 1H), 7.34 (t, J = 7.8 Hz, 1H), 6.82 (d, J = 2.3 Hz, 1H), 6.26 (s, 1H), 4.12 (d, J = 13.9 Hz, 1H), 3.75 (d, J = 13.9 Hz, 1H), 2.69 (s, 1H), 2.57 (s, 3H), 2.37 (s, 6H), 0.91 (s, 9H). |
| 1109 | 1H NMR (400 MHz, Methanol-d4) δ 8.18 (s, 1H), 7.63 (s, 1H), 7.37-7.31 (m, 2H), 7.28 (dd, J = 8.0, 1.3 Hz, 1H), 7.02 (t, J = 7.8 Hz, 1H), 6.49 (d, J = 2.3 Hz, 1H), 5.92 (s, 1H), 3.82 (d, J = 13.9 Hz, 1H), 3.39 (d, J = 13.9 Hz, 1H), 2.23 (s, 3H), 1.28-1.16 (m, 1H), 0.94-0.86 (m, 2H), 0.77-0.65 (m, 2H), 0.59 (s, 9H), 0.25-0.13 (m, 2H), 0.09--0.08 (m, 2H). |
| 1110 | 1H NMR (400 MHz, Methanol-d4) δ 8.48 (s, 1H), 8.13 (s, 1H), 7.60 (d, J = 2.3 Hz, 1H), 7.54-7.43 (m, 2H), 7.33 (m, 2H), 6.99 (d, J = 2.1 Hz, 1H), 6.44 (s, 1H), 4.09 (d, J = 13.8 Hz, 1H), 3.77 (d, J = 13.8 Hz, 1H), 2.46 (s, 3H), 2.00 (m, 4H), 0.97 (s, 9H). |
| 1111 | 1H NMR (400 MHz, Methanol-d4) δ 8.36 (s, 1H), 7.96 (s, 1H), 7.76 (d, J = 2.5 Hz, 1H), 7.51-7.44 (m, 2H), 7.38-7.29 (m, 2H), 7.14 (d, J = 2.5 Hz, 1H), 5.95 (t, J = 54.8 Hz, 1H), 3.90 (d, J = 13.6 Hz, 1H), 3.68 (d, J = 13.7 Hz, 1H), 1.59-1.48 (m, 4H), 0.95 (s, 9H). |
| 1112 | 1H NMR (400 MHz, DMSO-d6) δ 8.41 (s, 1H), 8.26 (s, 1H), 7.80-7.71 (m, 1H), 7.71-7.63 (m, 1H), 7.62-7.59 (m, 1H), 7.42 (s, 1H), 7.34-7.27 (m, 1H), 7.21 (t, 1H), 7.03 (s, 1H), 6.41 (d, 1H), 3.94-3.81 (m, 1H), 3.43-3.34 (m, 1H), 1.78-1.71 (m, 2H), 1.71-1.64 (m, 2H), 0.78 (s, 9H). |
| 1113 | 1H NMR (400 MHz, Chloroform-d) δ 8.20 (s, 1H), 7.92-7.86 (m, 1H), 7.76-7.65 (m, 1H), 7.52-7.48 (m, 1H), 7.38-7.28 (m, 3H), 7.23-7.14 (m, 1H), 6.45-6.35 (m, 1H), 4.03-3.90 (m, 1H), 3.88-3.74 (m, 1H), 3.14 (s, 3H), 2.90 (s, 3H), 1.75-1.62 (m, 4H), 0.99 (s, 9H). |
| 1114 | 1H NMR (400 MHz, Chloroform-d) δ 8.00-7.89 (m, 2H), 7.77 (s, 1H), 7.67-7.58 (m, 1H), 7.44 (s, 1H), 7.24-7.14 (m, 3H), 6.92 (s, 1H), 6.98-6.86 (m, 1H), 6.43-6.32 (m, 1H), 4.06 (d, 1H), 3.55 (d, 1H), 3.03 (d, 3H), 1.76-1.62 (m, 4H), 0.85 (d, 9H). |
| 1115 | 1H NMR (400 MHz, Chloroform-d) δ 9.18-9.06 (m, 1H), 8.06-7.94 (m, 2H), 7.82 (s, 1H), 7.76-7.62 (m, 1H), 7.49-7.41 (m, 1H), 7.24-7.23 (m, 1H), 6.98-6.86 (m, 1H), 6.57-6.45 (m, 1H), 6.39 (s, 1H), 4.02 (d, 1H), 3.60 (d, 1H), 1.79-1.71 (m, 2H), 1.70-1.60 (m, 2H), 0.86 (s, 9H). |
| 1116 | 1H NMR (400 MHz, Chloroform-d) δ 8.85-8.71 (m, 1H), 8.21 (d, 1H), 8.13 (s, 1H), 7.83-7.73 (m, 1H), 7.63 (s, 1H), 7.37 (s, 1H), 7.18 (s, 1H), 7.10 (dd, 1H), 6.83-6.76 (m, 1H), 6.29-6.08 (m, 1H), 4.10 (d, 1H), 3.56 (d, 1H), 2.99 (d, 3H), 1.76-1.56 (m, 4H), 0.91 (s, 9H). |
| 1117 | 1H NMR (400 MHz, Chloroform-d) δ 8.94-8.75 (m, 1H), 8.30 (d, 1H), 8.15 (s, 1H), 7.88-7.79 (m, 1H), 7.64 (s, 1H), 7.39 (s, 1H), 7.22 (s, 1H), 7.13 (dd, 1H), 6.80-6.71 (m, 1H), 6.33-6.24 (m, 1H), 6.23-6.10 (m, 1H), 4.10 (s, 1H), 3.57 (d, 1H), 1.75-1.55 (m, 4H), 0.92 (s, 9H). |
| 1118 | 1H NMR (400 MHz, Methanol-d4) δ 8.69 (d, J = 5.1 Hz, 1H), 8.47 (s, 1H), 8.18-8.09 (m, 2H), 7.67-7.56 (m, 2H), 7.44 (dd, J = 6.5, 2.8 Hz, 1H), 7.39-7.32 (m, 2H), 7.04 (d, J = 2.3 Hz, 1H), 6.35 (s, 1H), 3.94 (s, 2H), 2.28 (s, 3H), 1.82-1.63 (m, 4H), 0.96 (s, 9H). |
| 1119 | 1H NMR (400 MHz, Methanol-d4) δ 8.95 (s, 1H), 8.40 (s, 1H), 8.17 (s, 1H), 7.66 (d, J = 1.4 Hz, 1H), 7.55 (d, J = 2.3 Hz, 1H), 7.49-7.40 (m, 2H), 7.36 (t, J = 7.6 Hz, 1H), 7.01 (d, J = 2.3 Hz, 1H), 6.37 (s, 1H), 4.00 (s, 3H), 3.90 (d, J = 13.9 Hz, 1H), 3.85 (d, J = 14.0 Hz, 1H), 2.44 (s, 3H), 1.82-1.73 (m, 2H), 1.67 (s, 2H), 0.93 (s, 9H). |
| 1120 | 1H NMR (400 MHz, Methanol-d4) δ 9.03 (s, 1H), 8.49 (s, 1H), 8.22 (s, 1H), 7.60 (d, J = 2.3 Hz, 1H), 7.57 (s, 1H), 7.48 (dd, J = 6.9, 2.2 Hz, 1H), 7.44-7.34 (m, 2H), 7.13 (d, J = 2.3 Hz, 1H), 6.38 (s, 1H), 4.02 (d, J = 14.0 Hz, 1H), 3.89 (d, J = 14.0 Hz, 1H), 3.63 (s, 3H), 2.25 (s, 3H), 1.82-1.66 (m, 4H), 0.97 (s, 9H). |
| 1121 | 1H NMR (400 MHz, Methanol-d4) δ 9.28 (d, J = 5.3 Hz, 1H), 9.22 (s, 1H), 8.51 (s, 1H), 8.16 (s, 1H), 7.75 (dd, J = 5.4, 2.3 Hz, 1H), 7.66 (d, J = 2.2 Hz, 1H), 7.43 (d, J = 7.0 Hz, 1H), 7.37 (t, J = 7.6 Hz, 1H), 7.33 (d, J = 7.2 Hz, 1H), 7.03 (d, J = 2.2 Hz, 1H), 6.36 (s, 1H), 4.01 (d, J = 13.8 Hz, 1H), 3.90 (d, J = 13.9 Hz, 1H), 2.31 (s, 3H), 1.82-1.62 (m, 4H), 0.94 (s, 9H). |
| 1122 | 1H NMR (400 MHz, Methanol-d4) δ 9.02 (d, J = 0.9 Hz, 1H), 8.47 (s, 1H), 8.04 (s, 1H), 7.59 (d, J = 2.3 Hz, 1H), 7.56 (d, J = 1.6 Hz, 1H), 7.49 (dd, J = 7.3, 2.0 Hz, 1H), 7.44-7.33 (m, 2H), 7.09 (d, J = 2.2 Hz, 1H), 6.35 (s, 1H), 5.92 (t, J = 54.6 Hz, 1H), 3.98 (d, J = 14.0 Hz, 1H), 3.89 (d, J = 13.9 Hz, 1H), 3.62 (s, 3H), 2.25 (s, 3H), 1.62-1.48 (m, 4H), 0.96 (s, 9H). |
| 1123 | 1H NMR (400 MHz, Methanol-d4) δ 9.29 (s, 1H), 9.23 (s, 1H), 8.51 (s, 1H), 8.00 (s, 1H), 7.76 (d, J = 4.8 Hz, 1H), 7.65 (d, J = 2.3 Hz, 1H), 7.44 (dd, J = 7.6, 1.6 Hz, 1H), 7.37 (t, J = 7.6 Hz, 1H), 7.32 (dd, J = 7.7, 1.7 Hz, 1H), 7.02 (d, J = 2.3 Hz, 1H), 6.35 (s, 1H), 5.94 (t, J = 54.6 Hz, 1H), 4.02 (d, J = 13.9 Hz, 1H), 3.89 (d, J = 14.0 Hz, 1H), 2.31 (s, 3H), 1.54 (s, 4H), 0.94 (s, 9H). |
| 1124 | 1H NMR (400 MHz, Methanol-d4) δ 8.32 (s, 1H), 7.77 (d, J = 2.5 Hz, 1H), 7.73 (s, 1H), 7.47 (d, J = 7.5 Hz, 2H), 7.41-7.33 (m, 2H), 7.33-7.26 (m, 1H), 7.20 (d, J = 2.5 Hz, 1H), 6.04 (s, 1H), 3.93 (d, J = 13.8 Hz, 1H), 3.64 (d, J = 13.8 Hz, 1H), 2.68 (s, 1H), 2.36 (s, 6H), 0.92 (s, 9H). |
| 1125 | 1H NMR (400 MHz, Methanol-d4) δ 8.36 (s, 1H), 7.96 (s, 1H), 7.79 (d, J = 2.5 Hz, 1H), 7.66 (dd, J = 7.8, 1.3 Hz, 1H), 7.59 (d, J = 7.8 Hz, 1H), 7.34 (t, J = 7.8 Hz, 1H), 6.96 (d, J = 2.5 Hz, 1H), 6.26 (s, 1H), 5.94 (t, J = 54.8 Hz, 1H), 4.27 (d, J = 14.9 Hz, 1H), 3.97 (d, J = 14.8 Hz, 1H), 2.57 (s, 3H), 1.52 (s, 4H), 1.08 (d, J = 5.7 Hz, 6H). |
| 1126 | 1H NMR (400 MHz, Methanol-d4) δ 8.36 (s, 1H), 7.97 (s, 1H), 7.79 (d, J = 2.5 Hz, 1H), 7.72-7.64 (m, 1H), 7.60 (dd, J = 7.9, 1.2 Hz, 1H), 7.34 (t, J = 7.8 Hz, 1H), 6.96 (d, J = 2.5 Hz, 1H), 6.26 (s, 1H), 5.95 (t, J = 54.8 Hz, 1H), 4.26 (d, J = 14.8 Hz, 1H), 3.97 (d, J = 14.9 Hz, 1H), 2.58 (s, 3H), 1.53 (s, 4H), 1.08 (d, J = 5.7 Hz, 6H). |

TABLE 2-continued

| Cmpd | 1H-NMR |
|---|---|
| 1127 | 1H NMR (400 MHz, Methanol-d4) δ 8.35 (s, 1H), 8.04 (s, 1H), 7.78 (d, J = 2.5 Hz, 1H), 7.25-6.95 (m, 4H), 6.24 (s, 1H), 3.89 (d, J = 13.7 Hz, 1H), 3.66 (d, J = 13.8 Hz, 1H), 2.27 (d, J = 1.9 Hz, 3H), 1.82-1.57 (m, 4H), 0.89 (s, 9H). |
| 1128 | 1H NMR (400 MHz, Methanol-d4) δ 8.33 (s, 1H), 8.07 (s, 1H), 7.79 (d, J = 2.4 Hz, 1H), 7.49-7.44 (m, 1H), 7.44-7.35 (m, 2H), 7.28-7.21 (m, 2H), 6.13 (s, 1H), 3.95 (d, J = 13.9 Hz, 1H), 3.64 (d, J = 13.8 Hz, 1H), 1.74 (m, 2H), 1.70 (m, 2H), 1.66 (m, 2H), 1.50-1.37 (m, 2H), 0.93 (s, 9H). |
| 1129 | 1H NMR (400 MHz, Methanol-d4) δ 8.36 (s, 1H), 7.83-7.76 (m, 2H), 7.47 (d, J = 1.9 Hz, 1H), 7.42-7.34 (m, 2H), 7.26-7.19 (m, 2H), 6.09 (s, 1H), 3.96 (d, J = 13.9 Hz, 1H), 3.67 (d, J = 13.9 Hz, 1H), 2.68 (s, 1H), 2.37 (s, 6H), 1.75-1.64 (m, 2H), 1.52-1.43 (m, 1H), 1.43-1.36 (m, 1H), 0.93 (s, 9H). |
| 1130 | 1H NMR (400 MHz, Methanol-d4) δ 8.31 (s, 1H), 7.78 (s, 1H), 7.76 (d, J = 2.5 Hz, 1H), 7.48 (dd, J = 8.6, 5.3 Hz, 2H), 7.17 (d, J = 2.5 Hz, 1H), 7.09 (t, J = 8.7 Hz, 2H), 6.04 (s, 1H), 3.93 (d, J = 13.9 Hz, 1H), 3.63 (d, J = 13.8 Hz, 1H), 2.68 (s, 1H), 2.36 (s, 6H), 0.92 (s, 9H). |
| 1131 | 1H NMR (400 MHz, Methanol-d4) δ 8.23 (s, 1H), 8.22 (s, 1H), 7.98 (s, 1H), 7.68 (d, J = 2.4 Hz, 1H), 7.52 (d, J = 7.8 Hz, 1H), 7.29 (d, J = 7.6 Hz, 1H), 7.24 (s, 1H), 7.20 (t, J = 7.8 Hz, 1H), 6.97 (d, J = 2.6 Hz, 1H), 6.27 (s, 1H), 3.74 (d, J = 13.8 Hz, 1H), 3.53 (d, J = 13.8 Hz, 1H), 2.36 (s, 3H), 1.69-1.54 (m, 4H), 0.73 (s, 9H). |
| 1132 | 1H NMR (400 MHz, Methanol-d4) δ 8.26 (s, 1H), 7.97 (s, 1H), 7.69 (d, J = 2.4 Hz, 1H), 7.63 (d, J = 2.1 Hz, 1H), 7.29 (d, J = 7.1 Hz, 1H), 7.23 (d, J = 7.3 Hz, 1H), 7.15 (t, J = 7.7 Hz, 1H), 7.07 (d, J = 2.4 Hz, 1H), 6.33 (d, J = 2.2 Hz, 1H), 6.24 (s, 1H), 3.73 (d, J = 13.8 Hz, 1H), 3.66 (d, J = 14.3 Hz, 1H), 2.30 (s, 3H), 1.70-1.55 (m, 4H), 0.79 (s, 9H). |
| 1133 | 1H NMR (400 MHz, Methanol-d4) δ 8.36 (s, 1H), 8.05 (s, 1H), 7.79 (d, J = 2.5 Hz, 1H), 7.73 (s, 2H), 7.32 (dd, J = 7.0, 2.1 Hz, 1H), 7.26-7.15 (m, 2H), 7.14 (d, J = 2.5 Hz, 1H), 6.33 (s, 1H), 3.86 (d, J = 13.8 Hz, 1H), 3.72 (d, J = 13.8 Hz, 1H), 2.39 (s, 3H), 1.80-1.60 (m, 4H), 0.87 (s, 9H). |
| 1134 | 1H NMR (400 MHz, Methanol-d4) δ 9.33 (d, J = 5.5 Hz, 1H), 9.28 (s, 1H), 8.38 (s, 1H), 8.18 (s, 1H), 7.86 (dd, J = 5.4, 2.3 Hz, 1H), 7.80 (d, J = 2.5 Hz, 1H), 7.49-7.42 (m, 1H), 7.38 (t, J = 7.6 Hz, 1H), 7.36-7.32 (m, 1H), 7.23 (d, J = 2.5 Hz, 1H), 6.37 (s, 1H), 3.86 (d, J = 14.0 Hz, 1H), 3.79 (d, J = 14.0 Hz, 1H), 2.34 (s, 3H), 1.81-1.60 (m, 4H), 0.91 (s, 9H). |
| 1135 | 1H NMR (400 MHz, Methanol-d4) δ 9.02 (d, J = 1.4 Hz, 1H), 8.29 (s, 1H), 8.22 (s, 1H), 7.68 (d, J = 2.5 Hz, 1H), 7.57 (d, J = 1.5 Hz, 1H), 7.50 (dd, J = 7.8, 1.7 Hz, 1H), 7.44-7.33 (m, 2H), 7.28 (d, J = 2.5 Hz, 1H), 6.37 (s, 1H), 3.83 (d, J = 13.9 Hz, 1H), 3.72 (d, J = 13.9 Hz, 1H), 3.63 (s, 3H), 2.27 (s, 3H), 1.82-1.60 (m, 4H), 0.93 (s, 9H). |
| 1136 | 1H NMR (400 MHz, Methanol-d4) δ 8.85-8.74 (m, 2H), 8.43 (dt, J = 8.0, 1.8 Hz, 1H), 8.31 (s, 1H), 8.19 (s, 1H), 8.02 (dd, J = 8.1, 5.6 Hz, 1H), 7.73 (d, J = 2.5 Hz, 1H), 7.49-7.41 (m, 1H), 7.37 (t, J = 7.7 Hz, 1H), 7.32 (dd, J = 7.6, 1.5 Hz, 1H), 7.23 (d, J = 2.5 Hz, 1H), 6.37 (s, 1H), 3.78 (s, 2H), 2.33 (s, 3H), 1.84-1.55 (m, 4H), 0.92 (s, 9H). |
| 1137 | 1H NMR (400 MHz, Methanol-d4) δ 8.85 (d, J = 6.0 Hz, 2H), 8.30 (s, 1H), 8.19 (s, 1H), 7.97 (d, J = 6.3 Hz, 2H), 7.72 (d, J = 2.5 Hz, 1H), 7.48 (d, J = 7.7 Hz, 1H), 7.40 (t, J = 7.6 Hz, 1H), 7.35 (d, J = 7.6 Hz, 1H), 7.21 (d, J = 2.5 Hz, 1H), 6.37 (s, 1H), 3.76 (s, 2H), 2.37 (s, 3H), 1.86-1.58 (m, 4H), 0.91 (s, 9H). |
| 1138 | 1H NMR (400 MHz, Methanol-d4) δ 8.37 (s, 1H), 8.04 (s, 1H), 7.79 (d, J = 2.5 Hz, 1H), 7.71 (s, 1H), 7.55 (s, 1H), 7.34-7.26 (m, 1H), 7.23-7.15 (m, 2H), 7.14 (d, J = 2.5 Hz, 1H), 6.32 (s, 1H), 3.94 (s, 3H), 3.84 (d, J = 13.8 Hz, 1H), 3.73 (d, J = 13.8 Hz, 1H), 2.39 (s, 3H), 1.84-1.59 (m, 4H), 0.88 (s, 9H). |
| 1139 | 1H NMR (400 MHz, Methanol-d4) δ 8.33 (s, 1H), 7.99 (s, 1H), 7.76 (d, J = 2.5 Hz, 1H), 7.62 (d, J = 1.4 Hz, 1H), 7.57-7.44 (m, 2H), 7.00 (d, J = 2.5 Hz, 1H), 6.25 (s, 1H), 5.94 (t, J = 54.7 Hz, 1H), 3.90 (d, J = 13.8 Hz, 1H), 3.58 (d, J = 13.7 Hz, 1H), 2.42 (s, 3H), 1.53 (s, 4H), 0.87 (s, 9H). |
| 1140 | 1H NMR (400 MHz, Methanol-d4) δ 8.34 (s, 1H), 8.14 (s, 1H), 7.76 (d, J = 2.5 Hz, 1H), 7.63 (d, J = 1.5 Hz, 1H), 7.58-7.52 (m, 1H), 7.50 (d, J = 8.0 Hz, 1H), 7.02 (d, J = 2.5 Hz, 1H), 6.27 (s, 1H), 3.90 (d, J = 13.8 Hz, 1H), 3.60 (d, J = 13.8 Hz, 1H), 2.42 (s, 3H), 1.81-1.61 (m, 4H), 0.87 (s, 9H). |
| 1141 | 1H NMR (400 MHz, Methanol-d4) δ 8.86 (d, J = 6.4 Hz, 2H), 8.30 (s, 1H), 8.06 (s, 1H), 7.99 (d, J = 6.5 Hz, 2H), 7.73 (d, J = 2.5 Hz, 1H), 7.49 (d, J = 8.4 Hz, 1H), 7.40 (t, J = 7.6 Hz, 1H), 7.37-7.32 (m, 1H), 7.20 (d, J = 2.5 Hz, 1H), 6.36 (s, 1H), 5.95 (t, J = 54.6 Hz, 1H), 3.83-3.69 (m, 2H), 2.37 (s, 3H), 1.54 (d, J = 6.3 Hz, 4H), 0.90 (s, 9H). |
| 1142 | 1H NMR (400 MHz, Methanol-d4) δ 8.39 (s, 1H), 7.90 (s, 1H), 7.80 (d, J = 2.4 Hz, 1H), 7.72 (s, 1H), 7.56 (s, 1H), 7.30 (dd, J = 7.1, 2.0 Hz, 1H), 7.23-7.15 (m, 2H), 7.14 (d, J = 2.5 Hz, 1H), 6.31 (s, 1H), 5.94 (t, J = 54.7 Hz, 1H), 3.95 (s, 3H), 3.89 (d, J = 13.8 Hz, 1H), 3.73 (d, J = 13.9 Hz, 1H), 3.33-3.27 (m, 7H), 2.38 (s, 3H), 1.52 (s, 4H), 0.87 (s, 9H). |
| 1143 | 1H NMR (400 MHz, Methanol-d4) δ 8.33 (s, 1H), 8.03 (s, 1H), 7.76 (d, J = 2.5 Hz, 1H), 7.65 (d, J = 2.2 Hz, 1H), 7.38 (d, J = 7.5 Hz, 1H), 7.29 (d, J = 7.4 Hz, 1H), 7.22 (t, J = 7.7 Hz, 1H), 7.15 (d, J = 2.5 Hz, 1H), 6.35 (d, J = 2.2 Hz, 1H), 6.32 (s, 1H), 3.94 (s, 3H), 3.79 (d, J = 13.8 Hz, 1H), 3.73 (d, J = 13.8 Hz, 1H), 2.40 (s, 3H), 1.82-1.58 (m, 4H), 0.88 (s, 9H). |
| 1144 | 1H NMR (400 MHz, Methanol-d4) δ 8.80-8.72 (m, 1H), 8.36 (t, J = 7.9 Hz, 1H), 8.30 (s, 1H), 8.18 (s, 1H), 7.81 (dd, J = 15.7, 7.6 Hz, 2H), 7.72 (d, J = 2.5 Hz, 1H), 7.56-7.47 (m, 1H), 7.44-7.34 (m, 2H), 7.25 (d, J = 2.5 Hz, 1H), 6.38 (s, 1H), 3.86-3.68 (m, 2H), 2.33 (s, 3H), 1.85-1.61 (m, 4H), 0.92 (s, 9H). |

TABLE 2-continued

| Cmpd | 1H-NMR |
|---|---|
| 1145 | 1H NMR (400 MHz, Methanol-d4) δ 8.98 (s, 1H), 8.28 (s, 1H), 8.19 (s, 1H), 7.68 (d, J = 2.0 Hz, 2H), 7.47 (d, J = 7.6 Hz, 1H), 7.42 (d, J = 7.0 Hz, 1H), 7.36 (t, J = 7.7 Hz, 1H), 7.22 (d, J = 2.5 Hz, 1H), 6.38 (s, 1H), 4.01 (s, 3H), 3.82-3.65 (m, 2H), 2.45 (s, 3H), 1.86-1.59 (m, 4H), 0.90 (s, 9H). |
| 1146 | 1H NMR (400 MHz, Methanol-d4) δ 8.35 (s, 1H), 7.88 (s, 1H), 7.77 (d, J = 2.5 Hz, 1H), 7.65 (d, J = 7.8 Hz, 1H), 7.59 (d, J = 7.7 Hz, 1H), 7.33 (t, J = 7.8 Hz, 1H), 6.92 (d, J = 2.5 Hz, 1H), 6.21 (s, 1H), 4.25 (d, J = 14.9 Hz, 1H), 3.97 (d, J = 14.9 Hz, 1H), 2.57 (s, 3H), 1.65 (s, 3H), 1.35-1.28 (m, 2H), 1.08 (s, 3H), 1.07 (s, 3H), 1.05-1.02 (m, 2H). |
| 1147 | 1H NMR (400 MHz, Methanol-d4) δ 8.37 (d, J = 1.1 Hz, 1H), 7.94 (s, 1H), 7.80 (d, J = 2.3 Hz, 1H), 7.66 (d, J = 7.7 Hz, 1H), 7.62 (d, J = 7.8 Hz, 1H), 7.34 (t, J = 7.9 Hz, 1H), 6.99 (d, J = 2.4 Hz, 1H), 6.27 (s, 1H), 4.61 (d, J = 48.6 Hz, 2H), 3.97 (d, J = 13.9 Hz, 1H), 3.60 (d, J = 13.8 Hz, 1H), 2.57 (s, 3H), 1.53-1.43 (m, 2H), 1.39-1.29 (m, 2H), 0.88 (s, 9H). |
| 1148 | 1H NMR (400 MHz, Methanol-d4) δ 8.35 (s, 1H), 7.91 (s, 1H), 7.78 (d, J = 2.4 Hz, 1H), 7.65 (d, J = 7.7 Hz, 1H), 7.61 (d, J = 8.0 Hz, 1H), 7.34 (t, J = 7.9 Hz, 1H), 6.96 (d, J = 2.4 Hz, 1H), 6.23 (s, 1H), 3.94 (d, J = 13.8 Hz, 1H), 3.59 (d, J = 13.8 Hz, 1H), 2.57 (s, 3H), 1.66 (s, 3H), 1.39-1.22 (m, 2H), 1.14-0.98 (m, 2H), 0.87 (s, 9H). |
| 1149 | 1H NMR (400 MHz, Methanol-d4) δ 8.38 (d, J = 1.1 Hz, 1H), 7.95 (s, 1H), 7.81 (d, J = 2.4 Hz, 1H), 7.66 (d, J = 7.9 Hz, 1H), 7.63 (d, J = 8.0 Hz, 1H), 7.35 (t, J = 7.8 Hz, 1H), 7.02 (d, J = 2.4 Hz, 1H), 6.30 (s, 1H), 5.45-5.16 (m, 1H), 5.03-4.91 (m, 2H), 4.90-4.76 (m, 2H), 3.98 (d, J = 13.9 Hz, 1H), 3.60 (d, J = 13.8 Hz, 1H), 2.57 (s, 3H), 0.88 (s, 9H). |
| 1150 | 1H NMR (400 MHz, Methanol-d4) δ 8.37 (s, 1H), 7.88 (s, 1H), 7.80 (d, J = 2.4 Hz, 1H), 7.66 (d, J = 7.7 Hz, 1H), 7.62 (d, J = 7.7 Hz, 1H), 7.34 (t, J = 7.8 Hz, 1H), 7.00 (d, J = 2.4 Hz, 1H), 6.28 (s, 1H), 5.08-4.92 (m, 1H), 4.70 (d, J = 46.9 Hz, 1H), 4.68 (d, J = 47.2 Hz, 1H), 3.97 (d, J = 13.8 Hz, 1H), 3.59 (d, J = 13.8 Hz, 1H), 2.57 (s, 3H), 1.56 (dd, J = 7.0, 1.3 Hz, 3H), 0.87 (d, J = 1.3 Hz, 9H). |
| 1151 | 1H NMR (400 MHz, Methanol-d4) δ 8.37 (s, 1H), 7.83 (s, 1H), 7.78 (d, J = 2.5 Hz, 1H), 7.69-7.62 (m, 1H), 7.57 (d, J = 7.9 Hz, 1H), 7.34 (t, J = 7.9 Hz, 1H), 6.94 (d, J = 2.4 Hz, 1H), 6.23 (s, 1H), 4.24 (d, J = 14.8 Hz, 1H), 4.01 (d, J = 14.9 Hz, 1H), 2.68 (s, 1H), 2.58 (s, 3H), 2.37 (s, 6H), 1.09 (s, 3H), 1.07 (s, 3H). |
| 1152 | 1H NMR (400 MHz, Methanol-d4) δ 8.36 (s, 1H), 7.93 (s, 1H), 7.78 (d, J = 2.5 Hz, 1H), 7.65 (d, J = 8.0 Hz, 1H), 7.60 (d, J = 7.6 Hz, 1H), 7.34 (t, J = 7.9 Hz, 1H), 6.94 (d, J = 2.5 Hz, 1H), 6.23 (s, 1H), 4.28 (d, J = 14.8 Hz, 1H), 3.96 (d, J = 14.8 Hz, 1H), 2.57 (s, 3H), 1.60-1.48 (m, 1H), 1.26-1.18 (m, 2H), 1.09 (s, 3H), 1.07 (s, 3H), 1.01 (d, J = 1.9 Hz, 2H), 0.59-0.46 (m, 2H), 0.36-0.29 (m, 2H). |
| 1153 | 1H NMR (400 MHz, Methanol-d4) δ 8.34 (s, 1H), 7.89 (s, 1H), 7.78 (d, J = 2.5 Hz, 1H), 7.72 (s, 2H), 7.31 (dd, J = 7.3, 1.5 Hz, 1H), 7.27-7.15 (m, 2H), 7.11 (d, J = 2.5 Hz, 1H), 6.30 (s, 1H), 5.94 (t, J = 54.7 Hz, 1H), 3.84 (d, J = 13.8 Hz, 1H), 3.69 (d, J = 13.8 Hz, 1H), 2.39 (s, 3H), 1.52 (s, 4H), 0.87 (s, 9H). |
| 1154 | 1H NMR (400 MHz, Methanol-d4) δ 9.04-8.99 (m, 1H), 8.29 (s, 1H), 8.05 (s, 1H), 7.67 (d, J = 2.5 Hz, 1H), 7.57 (d, J = 1.6 Hz, 1H), 7.54-7.48 (m, 1H), 7.40 (t, J = 7.6 Hz, 1H), 7.35 (dd, J = 7.7, 1.7 Hz, 1H), 7.26 (d, J = 2.5 Hz, 1H), 6.34 (s, 1H), 5.93 (t, J = 54.6 Hz, 1H), 3.80 (d, J = 13.9 Hz, 1H), 3.73 (d, J = 13.8 Hz, 1H), 3.63 (d, J = 0.6 Hz, 3H), 2.26 (s, 3H), 1.53 (q, J = 8.2, 6.7 Hz, 4H), 0.93 (s, 9H). |
| 1155 | 1H NMR (400 MHz, Methanol-d4) δ 9.30 (d, J = 5.4 Hz, 1H), 9.26 (s, 1H), 8.36 (s, 1H), 8.01 (s, 1H), 7.82 (dd, J = 5.4, 2.3 Hz, 1H), 7.78 (d, J = 2.5 Hz, 1H), 7.46 (d, J = 6.7 Hz, 1H), 7.38 (t, J = 7.7 Hz, 1H), 7.35-7.28 (m, 1H), 7.20 (d, J = 2.6 Hz, 1H), 6.35 (s, 1H), 5.95 (t, J = 54.7 Hz, 1H), 3.85 (d, J = 13.9 Hz, 1H), 3.75 (d, J = 13.9 Hz, 1H), 2.33 (s, 3H), 1.54 (s, 4H), 0.91 (s, 9H). |
| 1156 | 1H NMR (400 MHz, Methanol-d4) δ 8.33 (s, 1H), 7.85 (s, 1H), 7.76 (d, J = 2.5 Hz, 1H), 7.66 (d, J = 7.8 Hz, 1H), 7.61 (d, J = 7.8 Hz, 1H), 7.34 (t, J = 7.8 Hz, 1H), 6.95 (d, J = 2.5 Hz, 1H), 6.25 (s, 1H), 3.90 (d, J = 13.8 Hz, 1H), 3.58 (d, J = 13.8 Hz, 1H), 2.69 (s, 1H), 2.58 (s, 3H), 2.37 (d, J = 0.9 Hz, 6H), 0.86 (s, 9H). |
| 1157 | 1H NMR (400 MHz, Methanol-d4) δ 8.01 (s, 1H), 7.63 (s, 1H), 7.45 (d, J = 2.5 Hz, 1H), 7.36-7.27 (m, 2H), 7.02 (t, J = 7.8 Hz, 1H), 6.64 (d, J = 2.5 Hz, 1H), 5.92 (s, 1H), 3.62 (d, J = 13.8 Hz, 1H), 3.24 (d, J = 13.8 Hz, 1H), 2.25 (s, 3H), 1.28-1.16 (m, 1H), 0.94-0.85 (m, 2H), 0.72-0.65 (m, 2H), 0.54 (s, 9H), 0.23-0.16 (m, 2H), 0.06--0.09 (m, 2H). |
| 1158 | 1H NMR (400 MHz, Methanol-d4) δ 8.36-8.30 (m, 2H), 7.93 (s, 1H), 7.79 (d, J = 2.5 Hz, 1H), 7.61 (d, J = 7.5 Hz, 1H), 7.39 (d, J = 7.7 Hz, 1H), 7.33 (s, 1H), 7.30 (t, J = 7.8 Hz, 1H), 7.07 (d, J = 2.5 Hz, 1H), 6.35 (s, 1H), 5.94 (t, J = 54.7 Hz, 1H), 3.87 (d, J = 13.9 Hz, 1H), 3.62 (d, J = 13.8 Hz, 1H), 2.45 (s, 3H), 1.52 (s, 4H), 0.83 (s, 9H). |
| 1159 | 1H NMR (400 MHz, Methanol-d4) δ 8.32 (s, 1H), 7.74 (d, J = 2.5 Hz, 1H), 7.58-7.40 (m, 2H), 7.36-7.25 (m, 2H), 7.07 (d, J = 2.5 Hz, 1H), 6.32 (s, 1H), 3.90 (d, J = 13.6 Hz, 1H), 3.58 (d, J = 13.6 Hz, 1H), 1.60 (s, 3H), 1.32 (s, 2H), 1.10 (s, 2H), 0.91 (s, 9H). |
| 1160 | 1H NMR (400 MHz, Methanol-d4) δ 8.35 (s, 1H), 7.76 (d, J = 2.5 Hz, 1H), 7.53 (dd, J = 6.9, 2.5 Hz, 1H), 7.48-7.38 (m, 1H), 7.29 (ddd, J = 6.5, 3.9, 2.0 Hz, 2H), 7.03 (d, J = 2.5 Hz, 1H), 6.33 (s, 1H), 3.98 (m, 4H), 3.54 (d, J = 13.6 Hz, 1H), 1.59 (s, 3H), 1.30 (s, 2H), 1.12-0.98 (m, 2H), 0.90 (s, 9H). |
| 1161 | 1H NMR (400 MHz, Methanol-d4) δ 8.39 (s, 1H), 8.14 (s, 1H), 7.77 (d, J = 2.5 Hz, 1H), 7.58-7.41 (m, 2H), 7.39-7.24 (m, 2H), 7.17 (d, J = 2.5 Hz, 1H), 6.44 (s, 1H), 3.95 (d, J = 13.7 Hz, 1H), 3.68 (d, J = 13.7 Hz, 1H), 2.46 (s, 3H), 2.08-1.92 (m, 4H), 0.95 (s, 9H). |

TABLE 2-continued

| Cmpd | 1H-NMR |
|---|---|
| 1162 | 1H NMR (400 MHz, Methanol-d4) δ 8.49 (s, 1H), 8.02 (s, 1H), 7.64 (t, J = 2.4 Hz, 2H), 7.39 (d, J = 6.9 Hz, 1H), 7.28 (d, J = 7.4 Hz, 1H), 7.22 (t, J = 7.7 Hz, 1H), 6.99 (d, J = 2.3 Hz, 1H), 6.34 (d, J = 2.3 Hz, 1H), 6.32 (s, 1H), 3.99 (d, J = 13.9 Hz, 1H), 3.94 (s, 3H), 3.89 (d, J = 13.8 Hz, 1H), 2.39 (s, 3H), 1.82-1.62 (m, 4H), 0.93 (s, 9H). |
| 1163 | 1H NMR (400 MHz, Methanol-d4) δ 8.49 (s, 1H), 8.04 (s, 1H), 7.71 (s, 1H), 7.65 (s, 1H), 7.39 (d, J = 7.5 Hz, 1H), 7.30 (d, J = 7.7 Hz, 1H), 7.24 (t, J = 7.4 Hz, 1H), 6.99 (s, 1H), 6.40 (s, 1H), 6.33 (s, 1H), 3.99 (d, J = 13.9 Hz, 1H), 3.88 (d, J = 14.0 Hz, 1H), 2.38 (s, 3H), 1.71 (d, J = 29.2 Hz, 4H), 0.92 (s, 9H). |
| 1164 | 1H NMR (400 MHz, Methanol-d4) δ 8.48 (s, 1H), 8.04 (s, 1H), 7.71 (s, 2H), 7.64 (d, J = 2.3 Hz, 1H), 7.32 (dd, J = 6.4, 2.6 Hz, 1H), 7.20 (d, J = 6.7 Hz, 2H), 6.94 (d, J = 2.3 Hz, 1H), 6.32 (s, 1H), 4.01 (d, J = 13.8 Hz, 1H), 3.82 (d, J = 13.9 Hz, 1H), 2.38 (s, 3H), 1.71 (d, J = 30.2 Hz, 4H), 0.90 (s, 9H). |
| 1165 | 1H NMR (400 MHz, Methanol-d4) δ 8.50 (s, 1H), 8.33 (s, 1H), 8.08 (s, 1H), 7.66 (d, J = 2.2 Hz, 1H), 7.62 (d, J = 7.5 Hz, 1H), 7.40-7.35 (m, 1H), 7.34 (s, 1H), 7.30 (t, J = 7.8 Hz, 1H), 6.92 (d, J = 2.3 Hz, 1H), 6.37 (s, 1H), 4.06 (d, J = 13.9 Hz, 1H), 3.78 (d, J = 13.9 Hz, 1H), 2.44 (s, 3H), 1.81-1.58 (m, 4H), 0.88 (s, 9H). |
| 1166 | 1H NMR (400 MHz, Methanol-d4) δ 8.50 (s, 1H), 7.88 (s, 1H), 7.71 (s, 2H), 7.65 (d, J = 2.3 Hz, 1H), 7.32 (dd, J = 6.9, 2.1 Hz, 1H), 7.25-7.14 (m, 2H), 6.95 (d, J = 2.3 Hz, 1H), 6.31 (s, 1H), 5.94 (t, J = 54.7 Hz, 1H), 4.04 (d, J = 13.9 Hz, 1H), 3.83 (d, J = 13.9 Hz, 1H), 2.38 (s, 3H), 1.53 (s, 4H), 0.91 (s, 9H). |
| 1167 | 1H NMR (400 MHz, Methanol-d4) δ 8.49 (s, 1H), 8.33 (s, 1H), 7.92 (s, 1H), 7.65 (d, J = 2.2 Hz, 1H), 7.62 (d, J = 6.9 Hz, 1H), 7.37 (d, J = 7.7 Hz, 1H), 7.33 (s, 1H), 7.30 (t, J = 7.8 Hz, 1H), 6.91 (d, J = 2.3 Hz, 1H), 6.36 (s, 1H), 5.94 (t, J = 54.7 Hz, 1H), 4.05 (d, J = 13.9 Hz, 1H), 3.76 (d, J = 13.9 Hz, 1H), 3.30 (q, J = 1.6 Hz, 7H), 2.43 (s, 3H), 1.53 (s, 4H), 0.88 (s, 9H). |
| 1168 | 1H NMR (400 MHz, Methanol-d4) δ 8.52 (s, 1H), 7.70-7.63 (m, 3H), 7.35 (t, J = 7.8 Hz, 1H), 6.88 (d, J = 2.3 Hz, 1H), 6.27 (s, 1H), 5.89 (t, J = 54.1 Hz, 1H), 4.15 (d, J = 13.9 Hz, 1H), 3.73 (d, J = 13.9 Hz, 1H), 2.57 (s, 3H), 1.58 (s, 4H), 0.93 (s, 9H). |
| 1169 | 1H NMR (400 MHz, Methanol-d4) δ 8.46 (s, 1H), 7.61 (m, 1H), 7.48 (m, 2H), 7.38-7.23 (m, 2H), 6.92 (d, J = 2.3 Hz, 1H), 6.33 (s, 1H), 4.07 (d, J = 13.8 Hz, 1H), 3.72 (d, J = 13.8 Hz, 1H), 1.60 (s, 3H), 1.32 (s, 2H), 1.10 (s, 2H), 0.95 (s, 9H). |
| 1170 | 1H NMR (400 MHz, Methanol-d4) δ 8.44 (s, 1H), 7.60 (d, J = 2.3 Hz, 1H), 7.51 (dd, J = 7.1, 2.3 Hz, 1H), 7.44 (dd, J = 7.5, 1.8 Hz, 1H), 7.30 (m, 2H), 6.84 (d, J = 2.3 Hz, 1H), 6.32 (s, 1H), 4.09 (d, J = 13.7 Hz, 1H), 3.98 (s, 3H), 3.65 (d, J = 13.7 Hz, 1H), 1.59 (s, 3H), 1.29 (m, 2H), 1.06 (m, 2H), 0.93 (s, 9H). |

Biological Assays

The following examples, from Examples 60 to 62, describe biological assays for measuring certain test compounds' activity against TNFα, Cot (also known as Tpl2), and EGFR. As summarized in Table 3, the test compounds are effective inhibitors of Cot.

Example 60

Cot Monocyte TNFα Cell Based Assay

Cryopreserved human monocytes (Stem Cell Technologies) were thawed, diluted in RPMI with Glutamax (10 mM HEPES, 1× Pen-Strep, 55 μM β-mercaptoethanol, 1 mM Sodium pyruvate) media containing 10% FBS to 0.125× 10^6 cells/ml and recovered at 37° C. for 2 hours. The cell suspension was then plated at a density of 5,000 cells/well onto black 384 well Greiner clear bottom plates. Plates were pre-spotted with test compounds and serially diluted in DMSO where 200 nL/well were delivered using the Echo 550 acoustic liquid dispenser (Labcyte®) for a final DMSO concentration of 0.5%. Plated cells were treated with compound for 1 hour at 37° C. Cells were then stimulated with 50 pg/ml of LPS (Sigma) excluding outside columns of plate used for unstimulated cell control wells. Cells were incubated for an additional 4 hours at 37° C. Cells were then spun out of the media and 5 ul of sample were taken and analyzed for total TNFα content using the TR-FRET Human TNFα detection system (CisBio). This system utilizes two labeled antibodies (cryptate and XL665) that bind to two different epitopes of the TNFα molecule and produce FRET signal proportional to the concentration of TNFα in the sample. Detection antibodies are mixed 50:50 and 5 μL were dispensed into each well. Plates were covered with clear seals and incubated at room temp overnight. The following morning plates were read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent of control was calculated as follows:

% Control=100×(Ratio$_{Sample}$−Ratio$_{0\% \, Stimulation}$)/(Ratio$_{100\% \, Stimulation}$−Ratio$_{0\% \, Stimulation}$)

where unstimulated cells (0% stimulation) were the negative control and stimulated cells (100% stimulation) were used as the positive control.

Example 61

High Throughput Cot Biochemical Assay

Human Cot enzyme activity was measured using KinEASE (Cisbio), a time-resolved fluorescence resonance energy transfer (TR-FRET) immunoassay. In this assay, Cot-catalyzes the phosporylation of a XL665-labeled peptide substrate. Europium conjugated phospho-tyrosine specific antibody binds the resulting phosphorylated peptide. Formation of phosphorylated peptide is quantified by TR-FRET with Europium as the donor and XL665 the acceptor in a 2-step endpoint assay. Purified recombinant human Cot catalytic domain (30-397 amino acids) was purchased from Cama Biosciences. In brief, test compounds serially diluted in DMSO were delivered into Proxy white, low volume, 384 well plates using the Echo 550 acoustic liquid dispenser (Labcyte®). Cot enzyme and substrates were dispensed into assay plates using a Multi-Flo (Bio-Tek Instruments). The standard 5 µL reaction mixture contained 400 µM ATP, 1 µM STK3 peptide, 5 nM of Cot in reaction buffer (10 mM MOPS, pH 7.0, 0.02% NaN$_3$, 0.5 mg/mL BSA, 10 mM MgOAc, 1 mM DIT, 0.025% NP-40, 1.5% glycerol) and 0.1% DMSO. After 2.5 hrs of incubation at room temperature, 5 µL of Stop and Detect Solution (1:200 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for 120 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows:

% Inhibition=100×(Ratio$_{Sample}$−Ratio$_{0\% \ Inhibition}$)/(Ratio$_{100\% \ Inhibition}$−Ratio$_{0\% \ Inhibition}$)

where 0.1% DMSO (0% inhibition) was the negative control and 100 µM Comparative Example 1 (100% inhibition) was used as the positive control.

Example 62

High Throughput EGFR Biochemical Assay

EGFR activity was measured using KinEASE (Cisbio), a time-resolved fluorescence resonance energy transfer (TR-FRET) immunoassay. In this assay, EGFR-catalyzes the phosphorylation of a universal Tyrosine kinase peptide substrate labeled with XL665. Europium conjugated phosphortyrosine specific antibody binds the resulting phosphorylated peptide. Formation of phosphorylated peptide is quantified by TR-FRET with Europium as the donor and XL665 the acceptor. The assay was performed in two main steps. The first step is the kinase reaction step and the second step is the detection step with TR-FRET reagents. In brief, test compounds 1:3 serially diluted in DMSO were delivered into Corning white, low volume, non-binding 384 well plates using the Echo 550 acoustic liquid dispenser (Labcyte®). EGFR enzyme (Human EGFR, cytoplasmic domain [669-1210] from Carna Biosciences Cat. No. 08-115) and substrates TK substrate-biotin (included in Cisbio HTRF KinEASE-TK kit Cat. No. 62TK0PEJ) were dispensed into assay plates using a Multi-Flo (Bio-Tek Instruments). The standard 10 µL reaction mixture contained 6 µM ATP (1×Km) or 12 µM ATP (2×Km), 1 µM biotinylated peptide, 0.3 nM EGFR (for 1×Km ATP) or 0.1 nM EGFR (for 2×Km ATP) in reaction buffer (10 mM MOPs, pH 7.0, 1.5% Glycerol, 0.5 mg/ml BSA, 10 mM Mg-Acetate, 1 mM DTF, 0.025% NP-40). After 60 min of incubation at room temperature, 10 ILL of Stop and Detect Solution (1:400 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for over 60 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows:

% Inhibition=100×(Ratio$_{Sample}$−Ratio$_{0\% \ Inhibition}$)/(Ratio$_{100\% \ Inhibition}$−Ratio$_{0\% \ Inhibition}$)

where 0.05% DMSO (0% inhibition) was the negative control and 100 µM Staurosporine and Gefitinib (100% inhibition) was used as the positive control.

As shown in Table 3, the compounds of Formula I are inhibitors of Cot (cancer Osaka thyroid).

TABLE 3

| Compound | IC$_{50}$ HTRF (nM) | EC$_{50}$ TNF (nM) |
| --- | --- | --- |
| 1 | 6 | 143 |
| 2 | 6 | 151 |
| 3 | 7 | 246 |
| 4 | 6 | 280 |
| 5 | 2 | 153 |
| 7 | 187 | 1517 |
| 8 | 33 | 571 |
| 9 | 2 | 172 |
| 10 | 4 | 71 |
| 11 | 5 | 98 |
| 12 | 20 | 205 |
| 13 | 71 | 221 |
| 14 | 13 | 298 |
| 15 | 4 | 134 |
| 16 | 1405 | >10000 |
| 17 | 4 | 260 |
| 18 | 7 | 1219 |
| 19 | 5 | 18017 |
| 20 | 1 | 41 |
| 21 | 5 | 234 |
| 22 | 2 | 158 |
| 23 | 2 | 95 |
| 24 | 6 | 120 |
| 25 | 4 | 975 |
| 26 | 13 | 380 |
| 27 | 11 | 232 |
| 28 | 2005 | >1000 |
| 29 | 217 | >1000 |
| 30 | 7213 | >10000 |
| 32 | 5 | 78 |
| 33 | 1625 | >10000 |
| 34 | 13 | 192 |
| 35 | 15 | 229 |
| 36 | >10000 | >10000 |
| 37 | 810 | >1000 |
| 40 | 25 | 1258 |
| 41 | 1 | 74 |
| 42 | 5 | 138 |
| 43 | 1936 | >10000 |
| 44 | 53 | 902 |
| 45 | 10 | 877 |
| 49 | 26 | 330 |
| 50 | 2 | 54 |
| 51 | 1 | 57 |
| 52 | 4 | >1000 |
| 53 | 5 | 163 |
| 54 | 2 | 267 |
| 55 | 2 | 414 |
| 56 | 3 | 184 |
| 57 | 3 | >1000 |
| 58 | 3 | 269 |
| 59 | 1 | 612 |
| 60 | 17 | >1000 |
| 61 | 3 | 75 |
| 62 | 29 | 447 |
| 63 | 213 | >1000 |
| 64 | 106 | >1000 |
| 65 | 3 | 95 |
| 66 | 5 | 96 |
| 67 | 2 | 41 |
| 68 | 3 | >1000 |
| 69 | 3 | 124 |
| 70 | 9 | 124 |
| 71 | 4 | 657 |
| 72 | 2 | 66 |
| 73 | 2 | 34 |
| 74 | 3 | 30 |
| 75 | 199 | >1000 |
| 76 | 2 | 462 |
| 77 | 9 | 108 |

TABLE 3-continued

| Compound | IC$_{50}$ HTRF (nM) | EC$_{50}$ TNF (nM) |
|---|---|---|
| 78 | 5 | 436 |
| 79 | 8 | 278 |
| 80 | 31 | 395 |
| 81 | 20 | 316 |
| 82 | 1 | 183 |
| 83 | 2 | 165 |
| 84 | 2 | 47 |
| 85 | 42 | 862 |
| 86 | 22 | 244 |
| 87 | >10000 | >1000 |
| 88 | 190 | >1000 |
| 89 | 2 | 38 |
| 90 | 26 | 287 |
| 91 | 16 | 127 |
| 92 | 50 | 495 |
| 93 | 59 | 832 |
| 94 | 12 | >1000 |
| 95 | 24 | >1000 |
| 96 | 778 | >1000 |
| 97 | 985 | >1000 |
| 98 | 128 | >1000 |
| 99 | 19 | 454 |
| 100 | 16 | 337 |
| 101 | 83 | >1000 |
| 102 | 58 | >1000 |
| 103 | 50 | 522 |
| 104 | 23 | 584 |
| 105 | 19 | 345 |
| 106 | 58 | 826 |
| 107 | 14 | 272 |
| 108 | 48 | >1000 |
| 109 | 17 | 210 |
| 110 | 16 | 133 |
| 111 | 72 | 960 |
| 112 | 6 | 125 |
| 113 | 373 | 1609 |
| 114 | 6 | 190 |
| 115 | 3 | >10000 |
| 116 | 14 | >10000 |
| 117 | 16 | 377 |
| 118 | 11 | 279 |
| 119 | 26 | 166 |
| 120 | >10000 | 1568 |
| 121 | 28 | 469 |
| 122 | 19 | 201 |
| 123 | 431 | 4388 |
| 124 | 14 | 218 |
| 125 | 1 | 13 |
| 126 | 397 | >10000 |
| 127 | 4 | 86 |
| 128 | 2 | 54 |
| 129 | 20 | 344 |
| 130 | 23 | 195 |
| 131 | 26 | 435 |
| 132 | 14 | 140 |
| 133 | 21 | 313 |
| 134 | 6 | 142 |
| 135 | 962 | 7504 |
| 136 | 1 | 20 |
| 137 | 606 | 4374 |
| 138 | 139 | 1358 |
| 139 | 33 | 276 |
| 140 | 1496 | >10000 |
| 141 | 5 | 72 |
| 142 | 8 | 77 |
| 143 | 99 | 1166 |
| 144 | 3242 | >10000 |
| 145 | 2 | 43 |
| 146 | 95 | 895 |
| 147 | 254 | 3607 |
| 148 | 2139 | 8667 |
| 149 | 162 | 2111 |
| 151 | >10000 | 5870 |
| 152 | 7 | 213 |
| 153 | 196 | 892 |
| 154 | 39 | 576 |
| 155 | 36 | 348 |
| 156 | 30 | 477 |
| 157 | 3737 | >10000 |
| 158 | 20 | 360 |
| 159 | 114 | 1338 |
| 160 | 496 | 3256 |
| 161 | 941 | >10000 |
| 162 | 7887 | >10000 |
| 163 | 3 | 170 |
| 164 | 1 | 15 |
| 165 | 2087 | 6266 |
| 166 | 61 | 979 |
| 167 | 171 | >10000 |
| 168 | 2065 | 9570 |
| 169 | 543 | 2910 |
| 170 | 48 | 562 |
| 171 | 9533 | >10000 |
| 172 | 139 | 1640 |
| 173 | 140 | 1853 |
| 174 | 837 | >10000 |
| 175 | 280 | 5915 |
| 176 | 83 | 809 |
| 177 | 370 | 2455 |
| 178 | 110 | 674 |
| 179 | 193 | 2306 |
| 180 | 194 | 3590 |
| 181 | 28 | 348 |
| 182 | 4 | 136 |
| 183 | 89 | 1408 |
| 184 | 154 | 4377 |
| 185 | 11 | 199 |
| 186 | >10000 | >10000 |
| 187 | 85 | 793 |
| 188 | 16 | 203 |
| 189 | 10 | 157 |
| 190 | 3 | 55 |
| 191 | 56 | 487 |
| 192 | 3 | 107 |
| 193 | 57 | 833 |
| 194 | 286 | 2417 |
| 195 | 160 | 1192 |
| 196 | 267 | 1514 |
| 197 | 2 | 38 |
| 198 | 12 | 229 |
| 199 | 21 | 395 |
| 200 | 244 | 7584 |
| 201 | 251 | 2542 |
| 202 | 2 | 44 |
| 203 | 38 | 608 |
| 204 | 97 | 1057 |
| 205 | 38 | 873 |
| 206 | 52 | 547 |
| 207 | 17 | 305 |
| 208 | 3 | 83 |
| 209 | 3 | 83 |
| 210 | 6 | 243 |
| 211 | 6 | 173 |
| 212 | 169 | 2184 |
| 213 | 24 | 407 |
| 214 | 151 | 4216 |
| 215 | 119 | 2885 |
| 216 | 492 | 5724 |
| 217 | 327 | 3584 |
| 218 | 432 | 5388 |
| 219 | 534 | 4928 |
| 220 | 296 | 1624 |
| 221 | 244 | 2519 |
| 222 | 8200 | >10000 |
| 223 | 5 | 157 |
| 224 | 28 | 397 |
| 225 | 38 | 800 |
| 226 | 16 | 606 |
| 227 | 11 | 426 |
| 228 | 807 | >10000 |
| 229 | 2608 | >10000 |
| 230 | 337 | >10000 |
| 231 | >10000 | >10000 |
| 232 | 215 | 2435 |

TABLE 3-continued

| Compound | IC$_{50}$ HTRF (nM) | EC$_{50}$ TNF (nM) |
|---|---|---|
| 233 | 5 | 259 |
| 234 | 523 | 5629 |
| 235 | 605 | 10000 |
| 236 | 294 | 6634 |
| 237 | 231 | 5121 |
| 238 | 12 | 162 |
| 239 | 2 | 55 |
| 240 | 1 | 71 |
| 241 | 951 | 5084 |
| 242 | 8 | 270 |
| 243 | 2 | 41 |
| 244 | 576 | 5692 |
| 245 | 46 | 557 |
| 246 | 19 | 490 |
| 247 | 28 | 635 |
| 248 | 3198 | >10000 |
| 249 | 1 | 21 |
| 250 | 147 | 993 |
| 251 | 105 | 1280 |
| 252 | 5 | 80 |
| 253 | 16 | 214 |
| 254 | 3 | 42 |
| 255 | 5 | 62 |
| 256 | 3 | 121 |
| 257 | 3 | 93 |
| 258 | 44 | 651 |
| 259 | 5 | 87 |
| 260 | 33 | 584 |
| 261 | 25 | 504 |
| 262 | 10 | 259 |
| 263 | 733 | >10000 |
| 264 | 45 | 567 |
| 265 | 12 | 471 |
| 266 | 16 | 424 |
| 267 | 7 | 194 |
| 268 | 166 | 2894 |
| 269 | 253 | 4524 |
| 270 | 96 | 2282 |
| 271 | 434 | 4558 |
| 272 | 12 | 215 |
| 273 | 13 | 178 |
| 274 | 5 | 254 |
| 275 | 23 | 246 |
| 276 | 3 | 166 |
| 277 | 32 | 858 |
| 278 | 222 | >10000 |
| 279 | 3046 | 8201 |
| 280 | 228 | 1472 |
| 281 | 68 | 1044 |
| 282 | 39 | 525 |
| 283 | 90 | 764 |
| 284 | 4 | 52 |
| 285 | 3 | 45 |
| 286 | 7 | 127 |
| 287 | 10 | 140 |
| 288 | 6 | 130 |
| 289 | 4 | 116 |
| 290 | 8 | 117 |
| 291 | 8 | 173 |
| 292 | 13 | 237 |
| 293 | 24 | 469 |
| 294 | 92 | 1877 |
| 295 | 389 | >10000 |
| 296 | 2 | 44 |
| 297 | >10000 | 4250 |
| 298 | 121 | 1468 |
| 299 | 12 | 309 |
| 300 | 4 | 126 |
| 301 | >10000 | 1242 |
| 302 | 3 | 74 |
| 303 | 4 | 174 |
| 304 | 864 | >10000 |
| 305 | 4 | 78 |
| 306 | 52 | 536 |
| 307 | 116 | 950 |
| 308 | 26 | 361 |
| 309 | 476 | 4156 |
| 310 | >10000 | 2355 |
| 311 | 5 | 158 |
| 312 | 5 | 177 |
| 313 | 39 | 527 |
| 314 | 1328 | 6386 |
| 315 | 134 | 1012 |
| 316 | 1822 | 3641 |
| 317 | 1000 | 8260 |
| 318 | 34 | 451 |
| 319 | 372 | 4476 |
| 320 | 1151 | 6432 |
| 321 | 159 | 391 |
| 322 | 140 | 959 |
| 323 | 82 | 1605 |
| 324 | 4 | 450 |
| 325 | 8 | 356 |
| 326 | 199 | 1965 |
| 327 | 4 | 166 |
| 328 | 24 | 1241 |
| 329 | 32 | 808 |
| 330 | 1419 | >10000 |
| 331 | 4 | 75 |
| 332 | 25 | 426 |
| 333 | 9 | 260 |
| 334 | 258 | >10000 |
| 335 | 40 | 204 |
| 336 | 71 | 619 |
| 337 | 49 | 674 |
| 338 | 8 | 183 |
| 339 | 55 | 1167 |
| 340 | 2 | 57 |
| 341 | 1 | 71 |
| 342 | 64 | 1227 |
| 343 | 13 | 151 |
| 344 | 89 | 2225 |
| 345 | 57 | 976 |
| 346 | 338 | 6097 |
| 347 | 24 | 773 |
| 348 | 44 | 1197 |
| 349 | 131 | 687 |
| 350 | 9 | 387 |
| 351 | 6 | 206 |
| 352 | 21 | 1293 |
| 353 | 104 | 3177 |
| 354 | 86 | 689 |
| 355 | 121 | 4660 |
| 356 | 550 | 6664 |
| 357 | 20 | 522 |
| 358 | 12 | 673 |
| 359 | 53 | 2256 |
| 360 | 21 | 423 |
| 361 | 35 | 653 |
| 362 | 5 | 83 |
| 363 | 874 | >10000 |
| 364 | 48 | 631 |
| 365 | 868 | 9333 |
| 366 | 110 | 1302 |
| 367 | 297 | 3849 |
| 368 | 50 | 1128 |
| 369 | 4 | 93 |
| 370 | 5 | 417 |
| 371 | 154 | 877 |
| 372 | 11 | 771 |
| 373 | 3011 | 7515 |
| 374 | 161 | 3838 |
| 375 | 48 | 1256 |
| 376 | 47 | 1608 |
| 377 | 495 | >10000 |
| 378 | >10000 | >10000 |
| 379 | 30 | 191 |
| 380 | 78 | 1285 |
| 381 | 44 | 644 |
| 382 | 8 | 323 |
| 383 | 11 | 148 |
| 384 | 8 | 832 |
| 385 | 4 | 692 |
| 386 | 5 | 1441 |

TABLE 3-continued

| Compound | IC$_{50}$ HTRF (nM) | EC$_{50}$ TNF (nM) |
|---|---|---|
| 387 | 50 | 809 |
| 388 | 83 | 1258 |
| 389 | 37 | 817 |
| 390 | 30 | 318 |
| 391 | 17 | 214 |
| 392 | 35 | 308 |
| 393 | 179 | 333 |
| 394 | 36 | 160 |
| 395 | 47 | 273 |
| 396 | 25 | 1234 |
| 397 | 125 | 726 |
| 398 | 28 | 1050 |
| 399 | 38 | 891 |
| 400 | 47 | 1232 |
| 401 | 758 | 4794 |
| 402 | 353 | 3651 |
| 403 | 15 | 532 |
| 404 | 34 | 570 |
| 405 | 69 | 2305 |
| 406 | 212 | 4432 |
| 407 | 47 | 1529 |
| 408 | 41 | 779 |
| 409 | 23 | 776 |
| 410 | 30 | 723 |
| 411 | 111 | 3406 |
| 412 | 50 | 2225 |
| 413 | 93 | 2746 |
| 414 | 4 | 140 |
| 415 | 9 | 409 |
| 416 | 6 | 209 |
| 417 | 74 | 1929 |
| 418 | 361 | 4172 |
| 419 | 392 | 4305 |
| 420 | 191 | 5158 |
| 421 | 1492 | >10000 |
| 422 | 48 | 1346 |
| 423 | 17 | 1256 |
| 424 | 6 | 415 |
| 425 | 10 | 438 |
| 426 | 3154 | >10000 |
| 427 | 316 | 8879 |
| 428 | 87 | 1830 |
| 429 | 9 | 257 |
| 430 | 7 | 679 |
| 431 | 96 | 3279 |
| 432 | 624 | 3926 |
| 433 | 31 | 1379 |
| 434 | 2761 | 2382 |
| 435 | 7927 | >10000 |
| 436 | 1363 | 3034 |
| 437 | 448 | 3911 |
| 438 | 135 | 5130 |
| 439 | 2963 | >10000 |
| 440 | 46 | 371 |
| 441 | 804 | 5824 |
| 442 | 193 | 4898 |
| 443 | 2698 | >10000 |
| 444 | 28 | 855 |
| 445 | 46 | 1273 |
| 446 | 11 | 338 |
| 447 | 23 | 1930 |
| 448 | 26 | 1860 |
| 449 | 161 | 830 |
| 450 | 3 | 305 |
| 451 | 68 | 266 |
| 452 | 98 | 420 |
| 453 | 11 | 231 |
| 454 | 49 | 1773 |
| 455 | 48 | 171 |
| 456 | 7 | 305 |
| 457 | 43 | 616 |
| 458 | 17 | 598 |
| 459 | 9 | 454 |
| 460 | 23 | 1256 |
| 461 | 20 | 1532 |
| 462 | 17 | 787 |
| 463 | 144 | 1412 |
| 464 | 61 | 694 |
| 465 | 41 | 821 |
| 466 | 53 | 1397 |
| 467 | 13 | 978 |
| 468 | 173 | 3146 |
| 469 | 14 | 315 |
| 470 | 13 | 608 |
| 471 | 333 | 8642 |
| 472 | 96 | 2356 |
| 473 | 59 | 784 |
| 474 | 68 | 1567 |
| 475 | 459 | >10000 |
| 476 | 1738 | >10000 |
| 477 | 243 | 6652 |
| 478 | 1051 | 5530 |
| 479 | 5276 | >10000 |
| 480 | 1223 | 8513 |
| 481 | 298 | 8800 |
| 482 | 332 | >10000 |
| 483 | 387 | >10000 |
| 484 | 371 | >10000 |
| 485 | 306 | 7243 |
| 486 | 24 | 637 |
| 487 | 2253 | 6783 |
| 488 | 1305 | 9013 |
| 489 | 10 | 184 |
| 490 | 172 | 3186 |
| 491 | 123 | 3837 |
| 492 | 65 | 966 |
| 493 | 18 | 1215 |
| 494 | 47 | 585 |
| 495 | 32 | 641 |
| 496 | 4 | 1836 |
| 497 | 26 | 985 |
| 498 | 8 | 520 |
| 499 | 6 | 985 |
| 500 | 92 | 2155 |
| 501 | 94 | 2136 |
| 502 | 160 | 1952 |
| 503 | 98 | 1690 |
| 504 | 1780 | 8508 |
| 505 | 240 | 2620 |
| 506 | 1687 | 5286 |
| 507 | 741 | 8513 |
| 508 | 5347 | >10000 |
| 509 | 206 | 2990 |
| 510 | 5 | 321 |
| 511 | 17 | 701 |
| 512 | 85 | 1103 |
| 513 | 22 | 1335 |
| 514 | 2 | 62 |
| 515 | 1 | 324 |
| 516 | 4 | 92 |
| 517 | 10 | 255 |
| 518 | 52 | 570 |
| 519 | 301 | 3149 |
| 520 | >10000 | >10000 |
| 521 | 41 | 934 |
| 522 | 786 | 9719 |
| 523 | 300 | 4882 |
| 524 | 787 | >10000 |
| 525 | 726 | 4257 |
| 526 | 24 | 503 |
| 527 | 52 | 1365 |
| 528 | 54 | 830 |
| 529 | 2 | 71 |
| 530 | 198 | >10000 |
| 531 | 16 | 491 |
| 532 | >10000 | >10000 |
| 533 | 73 | 660 |
| 534 | 57 | 3147 |
| 535 | 4 | 500 |
| 536 | 3 | 84 |
| 537 | 17 | 458 |
| 538 | 3 | 58 |
| 539 | 337 | 3069 |
| 540 | 404 | 5148 |

TABLE 3-continued

| Compound | IC$_{50}$ HTRF (nM) | EC$_{50}$ TNF (nM) |
|---|---|---|
| 541 | 7306 | >10000 |
| 542 | >10000 | >10000 |
| 543 | 7 | 51 |
| 544 | 94 | 1190 |
| 545 | 3 | 88 |
| 546 | 8 | 200 |
| 547 | 2 | 508 |
| 548 | 1 | 40 |
| 549 | 3 | 650 |
| 550 | 1 | 115 |
| 551 | 5 | 475 |
| 552 | 5 | 135 |
| 553 | 10 | 423 |
| 554 | 1301 | 8250 |
| 555 | 183 | 537 |
| 556 | 725 | >10000 |
| 557 | 999 | >10000 |
| 558 | 11 | 199 |
| 559 | 14 | 6046 |
| 560 | 3 | 8831 |
| 561 | 6 | 1153 |
| 562 | 4 | 848 |
| 563 | 2 | 280 |
| 564 | 1 | 68 |
| 565 | 24 | >10000 |
| 566 | 5 | 353 |
| 567 | 3 | 76 |
| 568 | 2 | 143 |
| 569 | 7 | 721 |
| 570 | 13 | 207 |
| 571 | 6 | 382 |
| 572 | 2 | 111 |
| 573 | 10 | 462 |
| 574 | 42 | 161 |
| 575 | 10 | 429 |
| 576 | 2 | 72 |
| 577 | 3 | 38 |
| 578 | 13 | 2150 |
| 579 | 8 | 713 |
| 580 | 287 | 1593 |
| 581 | 333 | 4220 |
| 582 | 25 | 734 |
| 583 | 1001 | 4359 |
| 584 | 10 | 403 |
| 585 | 16 | 427 |
| 586 | 892 | 8557 |
| 587 | 144 | 3897 |
| 588 | 17 | 1020 |
| 589 | 480 | 8440 |
| 590 | 131 | 3515 |
| 591 | 27 | 713 |
| 592 | 7 | 352 |
| 593 | 1 | 147 |
| 594 | 1 | 1716 |
| 595 | 8 | 305 |
| 596 | 33 | 3049 |
| 597 | 189 | 3177 |
| 598 | 4 | 418 |
| 599 | 3 | 134 |
| 600 | 2 | 78 |
| 601 | 64 | 2063 |
| 602 | 77 | 3053 |
| 603 | 61 | 561 |
| 604 | 156 | 3038 |
| 605 | 41 | 375 |
| 606 | 2 | 348 |
| 607 | 2 | 198 |
| 608 | 1 | 41 |
| 609 | 7 | 384 |
| 610 | 14 | 337 |
| 611 | 51 | 369 |
| 612 | 84 | 2015 |
| 613 | 41 | 708 |
| 614 | 123 | 1113 |
| 615 | 141 | 719 |
| 616 | 40 | 2182 |
| 617 | 43 | 12252 |
| 618 | 53 | 1700 |
| 619 | 16 | 826 |
| 620 | 6 | 96 |
| 621 | 2 | 112 |
| 622 | 5 | 851 |
| 623 | 1 | 90 |
| 624 | 3 | 266 |
| 625 | 116 | 1161 |
| 626 | 784 | >50000 |
| 627 | 16 | 456 |
| 628 | 7 | 109 |
| 629 | 3 | 72 |
| 630 | 3 | 1634 |
| 631 | 166 | 1083 |
| 632 | 3 | 163 |
| 633 | 10 | 1576 |
| 634 | 30 | 3088 |
| 635 | 13 | 1084 |
| 636 | 143 | 2391 |
| 637 | 36 | 1277 |
| 638 | >10000 | 2647 |
| 639 | 664 | 1713 |
| 640 | 2335 | 2841 |
| 641 | 35 | 1531 |
| 642 | 17 | 383 |
| 643 | 7 | 151 |
| 644 | 132 | 1098 |
| 645 | 2 | 41 |
| 646 | 1 | 49 |
| 647 | 377 | 3240 |
| 648 | >10000 | 4430 |
| 649 | 1462 | 2744 |
| 650 | 32 | 661 |
| 651 | 52 | 10609 |
| 652 | 61 | 7656 |
| 653 | 160 | 9285 |
| 654 | 2040 | >50000 |
| 655 | 324 | 10497 |
| 656 | 39 | 1824 |
| 657 | 143 | 2494 |
| 658 | 27 | 12197 |
| 659 | 95 | 5354 |
| 660 | 14 | 807 |
| 661 | 25 | 1087 |
| 662 | 70 | 1270 |
| 663 | 72 | 4738 |
| 664 | 379 | 8153 |
| 665 | 25 | 1971 |
| 666 | 14 | 458 |
| 667 | 28 | 887 |
| 668 | 97 | 1610 |
| 669 | 39 | 1093 |
| 671 | 10 | 682 |
| 672 | 32 | 889 |
| 673 | 2 | 1547 |
| 674 | 3 | 318 |
| 675 | 1 | 81 |
| 676 | 6 | 434 |
| 677 | 10 | 809 |
| 678 | 1432 | 5686 |
| 679 | 355 | 12454 |
| 680 | 44 | 6752 |
| 681 | 434 | 12822 |
| 682 | 599 | 15714 |
| 683 | 165 | 7249 |
| 684 | 7351 | 6041 |
| 685 | 16 | 359 |
| 686 | 7243 | 5898 |
| 687 | 40 | 2832 |
| 688 | 621 | 1252 |
| 689 | 11 | 343 |
| 690 | 2 | 317 |
| 691 | 2 | 90 |
| 692 | 51 | 797 |
| 693 | 46 | 1543 |
| 694 | 20 | 843 |
| 695 | 19 | 434 |

TABLE 3-continued

| Compound | IC$_{50}$ HTRF (nM) | EC$_{50}$ TNF (nM) |
|---|---|---|
| 696 | 85 | 3288 |
| 697 | >10000 | 17149 |
| 698 | 317 | 16083 |
| 699 | 379 | 10554 |
| 700 | 444 | 2236 |
| 701 | 48 | 795 |
| 702 | 314 | 17597 |
| 703 | 95 | 11965 |
| 704 | 37 | 3513 |
| 705 | 2825 | 12188 |
| 706 | 95 | 12761 |
| 707 | 134 | 3012 |
| 708 | 103 | 533 |
| 709 | 18 | 307 |
| 710 | 20 | 352 |
| 711 | 46 | >10000 |
| 712 | 14 | 498 |
| 713 | 17 | 358 |
| 714 | 131 | 1696 |
| 715 | 62 | 2076 |
| 716 | 60 | 847 |
| 719 | 41 | 2585 |
| 720 | 72 | 3990 |
| 721 | 21 | 470 |
| 722 | 4 | 76 |
| 723 | 217 | 1295 |
| 724 | 87 | 1402 |
| 727 | 3 | 178 |
| 728 | 3 | 124 |
| 729 | 32 | 532 |
| 731 | 78 | 4451 |
| 733 | 6 | 884 |
| 734 | 151 | 3897 |
| 736 | 41 | 376 |
| 737 | 21 | 411 |
| 738 | 7 | 274 |
| 739 | 22 | 1097 |
| 740 | 244 | 5547 |
| 741 | 122 | 1243 |
| 742 | 315 | 1773 |
| 743 | 29 | 575 |
| 744 | 13 | 363 |
| 745 | 70 | 615 |
| 746 | 29 | 349 |
| 747 | 4 | 110 |
| 748 | 60 | 610 |
| 750 | 1894 | 4721 |
| 753 | 88 | 1677 |
| 755 | 201 | 3195 |
| 756 | 108 | 2985 |
| 757 | 41 | 738 |
| 758 | 97 | 1312 |
| 759 | 2140 | 2749 |
| 764 | 38 | 3270 |
| 765 | 70 | 1290 |
| 766 | 41 | 1769 |
| 767 | 48 | 1270 |
| 768 | 83 | 2504 |
| 774 | 3 | 127 |
| 776 | 25 | 1242 |
| 777 | 72 | 6968 |
| 778 | 2 | 305 |
| 779 | 4 | 196 |
| 780 | 20 | 865 |
| 781 | 11 | 597 |
| 784 | 249 | 1986 |
| 786 | 173 | 6626 |
| 787 | 11 | 362 |
| 790 | 4 | 305 |
| 791 | 3 | 50 |
| 792 | 5 | 91 |
| 793 | 7 | 209 |
| 794 | 4 | 441 |
| 795 | 13 | 314 |
| 796 | 2 | 200 |
| 797 | 3 | 107 |
| 802 | 78 | 963 |
| 803 | 7 | 206 |
| 805 | 588 | >1000 |
| 806 | 850 | >50000 |
| 808 | 26 | 434 |
| 813 | 6 | 116 |
| 814 | 10 | 704 |
| 815 | 25 | 311 |
| 819 | 22 | 426 |
| 824 | 58 | 450 |
| 825 | 4 | 150 |
| 828 | 297 | 1154 |
| 831 | 10 | 381 |
| 836 | 8 | 241 |
| 841 | 8 | 141 |
| 842 | 998 | 22096 |
| 847 | 366 | 7862 |
| 849 | 687 | 6276 |
| 853 | 6301 | >1000 |
| 854 | 469 | >10000 |
| 858 | 8 | 99 |
| 859 | 12 | 533 |
| 869 | 125 | 2757 |
| 872 | 41 | 1306 |
| 881 | 39 | 673 |
| 882 | 20 | 321 |
| 884 | 11 | 466 |
| 885 | 9 | 287 |
| 887 | 70 | 1894 |
| 889 | 32 | 362 |
| 894 | 168 | 1747 |
| 895 | 56 | 1003 |
| 907 | 5 | 128 |
| 918 | 194 | 8578 |
| 919 | 2 | 62 |
| 920 | 10 | 215 |
| 6 | 13 | |
| 31 | 19 | |
| 38 | 2 | |
| 39 | 1992 | |
| 717 | 1580 | |
| 718 | 3465 | |
| 725 | 338 | |
| 726 | 39 | |
| 730 | 12 | |
| 732 | 30 | |
| 735 | 105 | |
| 749 | 3212 | |
| 751 | >10000 | |
| 752 | >10000 | |
| 754 | 2534 | |
| 760 | 2337 | |
| 761 | 484 | |
| 762 | 513 | |
| 763 | 23 | |
| 769 | >10000 | |
| 770 | 60 | |
| 771 | 93 | |
| 772 | 324 | |
| 773 | 1861 | |
| 775 | 5 | |
| 782 | 444 | |
| 783 | 291 | |
| 785 | 782 | |
| 788 | 1009 | |
| 789 | 657 | |
| 798 | 7915 | |
| 799 | 1479 | |
| 800 | >10000 | |
| 801 | 1066 | |
| 807 | 437 | |
| 810 | 12 | |
| 811 | 34 | |
| 812 | 794 | |
| 817 | 7 | |
| 818 | 447 | |
| 820 | 23 | |
| 821 | 21 | |

TABLE 3-continued

| Compound | IC$_{50}$ HTRF (nM) | EC$_{50}$ TNF (nM) |
|---|---|---|
| 822 | 90 | |
| 823 | 97 | |
| 826 | 6 | |
| 827 | 34 | |
| 829 | 6 | |
| 830 | 363 | |
| 832 | 9 | |
| 833 | 7 | |
| 834 | 756 | |
| 838 | 32 | |
| 839 | 24 | |
| 840 | 84 | |
| 843 | 58 | |
| 844 | 48 | |
| 845 | 99 | |
| 846 | >10000 | |
| 850 | 926 | |
| 851 | 7 | |
| 852 | 22 | |
| 855 | 2396 | |
| 856 | 860 | |
| 857 | 1343 | |
| 862 | 3962 | |
| 863 | 364 | |
| 864 | 22 | |
| 865 | 46 | |
| 866 | 2098 | |
| 867 | 46 | |
| 868 | 119 | |
| 870 | 27 | |
| 871 | 90 | |
| 873 | 21 | |
| 874 | 97 | |
| 875 | 66 | |
| 876 | 385 | |
| 877 | 47 | |
| 878 | 7695 | |
| 879 | 101 | |
| 880 | 68 | |
| 883 | 6684 | |
| 886 | 11 | |
| 888 | 50 | |
| 890 | >10000 | |
| 891 | 30 | |
| 892 | 78 | |
| 893 | 39 | |
| 896 | >10000 | |
| 897 | 59 | |
| 898 | 40 | |
| 899 | >1000 | |
| 900 | 14 | |
| 901 | 11 | |
| 902 | >1000 | |
| 903 | 7 | |
| 904 | 5 | |
| 905 | >1000 | |
| 906 | 8 | |
| 908 | 5 | |
| 909 | >1000 | |
| 910 | 52 | |
| 911 | 36 | |
| 912 | 60 | |
| 913 | >1000 | |
| 914 | 23 | |
| 915 | >1000 | |
| 916 | 48 | |
| 917 | 23 | |
| 921 | 8 | |
| 922 | 4 | |
| 925 | 10 | 187 |
| 926 | 7 | 346 |
| 927 | 34 | 576 |
| 928 | 68 | 443 |
| 929 | 7 | 98 |
| 930 | 5 | 66 |
| 931 | 27 | 447 |
| 932 | 25 | 505 |

TABLE 3-continued

| Compound | IC$_{50}$ HTRF (nM) | EC$_{50}$ TNF (nM) |
|---|---|---|
| 933 | 314 | 1000 |
| 934 | 371 | 1000 |
| 935 | 10000 | 1000 |
| 936 | 12 | 222 |
| 937 | 3 | 35 |
| 938 | 6 | 71 |
| 939 | 4 | 92 |
| 940 | 4 | 144 |
| 941 | 1 | 52 |
| 942 | 1 | 141 |
| 943 | 4 | 93 |
| 944 | 1 | 51 |
| 945 | 2 | 29 |
| 946 | 745 | 1000 |
| 947 | 14 | 282 |
| 948 | 1 | 78 |
| 949 | 1 | 19 |
| 950 | 10000 | 1000 |
| 951 | 10000 | 1000 |
| 952 | 8 | 134 |
| 953 | 111 | 1000 |
| 954 | 5 | 130 |
| 955 | 2 | 31 |
| 956 | 5 | 61 |
| 957 | 3 | 170 |
| 958 | 31 | 460 |
| 959 | 25 | 84 |
| 960 | 12 | 86 |
| 961 | 1 | 21 |
| 962 | 7 | 116 |
| 963 | 3 | 777 |
| 964 | 12 | 254 |
| 965 | 14 | 286 |
| 966 | 86 | 1000 |
| 967 | 714 | 1000 |
| 968 | 17 | 110 |
| 969 | 1 | 1000 |
| 970 | 8 | 202 |
| 971 | 4 | 270 |
| 972 | 27 | 636 |
| 973 | 9 | 67 |
| 974 | 46 | 46 |
| 975 | 3 | 321 |
| 976 | 6 | 58 |
| 977 | 6 | 285 |
| 978 | 5 | 65 |
| 979 | 4 | 103 |
| 980 | 80 | 1000 |
| 981 | 22 | 318 |
| 982 | 23 | 540 |
| 983 | 11 | 39 |
| 984 | 125 | 93 |
| 985 | 4 | 119 |
| 986 | 13 | 222 |
| 987 | 32 | 69 |
| 988 | 14 | 334 |
| 989 | 12 | 111 |
| 990 | 12 | 76 |
| 991 | 34 | 136 |
| 992 | 5 | 76 |
| 993 | 32 | 3612 |
| 994 | 33 | 103 |
| 995 | 3 | 49 |
| 996 | 6 | 109 |
| 997 | 48 | 61 |
| 998 | 53 | 250 |
| 999 | 63 | 306 |
| 1000 | 58 | 177 |
| 1001 | 22 | 344 |
| 1002 | 14 | 202 |
| 1003 | 19 | 227 |
| 1004 | 33 | 1000 |
| 1005 | 10000 | 1000 |
| 1006 | 9 | 72 |
| 1007 | 2 | 66 |
| 1008 | 1 | 123 |
| 1009 | 1 | 67 |

TABLE 3-continued

| Compound | IC$_{50}$ HTRF (nM) | EC$_{50}$ TNF (nM) |
|---|---|---|
| 1010 | 69 | 928 |
| 1011 | 3 | 22 |
| 1012 | 3 | 36 |
| 1013 | 2 | 23 |
| 1014 | 3 | 106 |
| 1015 | 14 | 462 |
| 1016 | 28 | 1000 |
| 1017 | 85 | 1000 |
| 1018 | 22 | 326 |
| 1020 | 6 | 161 |
| 1021 | 4 | 234 |
| 1022 | 7 | 503 |
| 1023 | 21 | 1000 |
| 1024 | 5 | 54 |
| 1025 | 10 | 131 |
| 1026 | 7 | 371 |
| 1027 | 4 | 141 |
| 1028 | 17 | 259 |
| 1029 | 14 | 225 |
| 1030 | 5 | 82 |
| 1031 | 1 | 118 |
| 1032 | 1 | 161 |
| 1033 | 2 | 456 |
| 1034 | 4 | 93 |
| 1035 | 19 | 316 |
| 1036 | 9 | 195 |
| 1037 | 102 | 1000 |
| 1038 | 10 | 566 |
| 1039 | 19 | 496 |
| 1040 | 4 | 87 |
| 1041 | 4 | 86 |
| 1042 | 2 | 105 |
| 1043 | 3 | 110 |
| 1044 | 8 | 214 |
| 1045 | 5 | 268 |
| 1046 | 142 | 1000 |
| 1047 | 101 | 1000 |
| 1048 | 33 | 637 |
| 1049 | 2 | 35 |
| 1050 | 7 | 202 |
| 1051 | 4 | 163 |
| 1052 | 189 | 1000 |
| 1053 | 26 | 200 |
| 1054 | 1 | 81 |
| 1055 | 3 | 100 |
| 1056 | 2 | 63 |
| 1057 | 4 | 73 |
| 1058 | 35 | 314 |
| 1059 | 75 | 553 |
| 1060 | 33 | 311 |
| 1061 | 85 | 620 |
| 1062 | 3 | 70 |
| 1063 | 6 | 73 |
| 1064 | 12 | 103 |
| 1065 | 22 | 237 |
| 1066 | 10 | 85 |
| 1067 | 17 | 213 |
| 1068 | 3 | 58 |
| 1069 | 2 | 54 |
| 1070 | 2 | 272 |
| 1071 | 3 | 215 |
| 1072 | 3 | 1000 |
| 1073 | 1 | 1000 |
| 1074 | 48 | 435 |
| 1075 | 23 | 185 |
| 1076 | 37 | 182 |
| 1077 | 2 | 77 |
| 1078 | 12 | 175 |
| 1079 | 19 | 220 |
| 1080 | 7 | 148 |
| 1081 | 3 | 219 |
| 1082 | 2 | 262 |
| 1083 | 13 | 63 |
| 1084 | 7 | 73 |
| 1085 | 5 | 205 |
| 1086 | 4 | 76 |
| 1087 | 22 | 375 |
| 1088 | 22 | 934 |
| 1089 | 7 | 23 |
| 1090 | 75 | 614 |
| 1091 | 28 | 1000 |
| 1092 | 20 | 395 |
| 1093 | 17 | 424 |
| 1094 | 10 | 407 |
| 1095 | 12 | 226 |
| 1096 | 10 | 262 |
| 1097 | 9 | 166 |
| 1098 | 23 | 73 |
| 1099 | 35 | 188 |
| 1100 | 4 | 45 |
| 1101 | 3 | 27 |
| 1102 | 8 | 63 |
| 1103 | 5 | 26 |
| 1104 | 3 | 53 |
| 1105 | 5 | 90 |
| 1106 | 5 | 76 |
| 1107 | 3 | 65 |
| 1108 | 4 | 31 |
| 1109 | 5 | 57 |
| 1110 | 26 | 79 |
| 1111 | 13 | 98 |
| 1112 | 76 | 1000 |
| 1113 | 22 | 444 |
| 1114 | 5 | 408 |
| 1115 | 6 | 176 |
| 1116 | 38 | 1000 |
| 1117 | 29 | 561 |
| 1118 | 28 | 921 |
| 1119 | 11 | 351 |
| 1120 | 6 | 88 |
| 1121 | 2 | 59 |
| 1122 | 2 | 47 |
| 1123 | 2 | 42 |
| 1124 | 4 | 138 |
| 1125 | 4 | 51 |
| 1126 | 5 | 66 |
| 1127 | 13 | 221 |
| 1128 | 9 | 307 |
| 1129 | 5 | 148 |
| 1130 | 10 | 103 |
| 1131 | 3 | 38 |
| 1132 | 8 | 175 |
| 1133 | 4 | 27 |
| 1134 | 2 | 57 |
| 1135 | 2 | 44 |
| 1136 | 4 | 128 |
| 1137 | 5 | 70 |
| 1138 | 4 | 61 |
| 1139 | 13 | 82 |
| 1140 | 22 | 119 |
| 1141 | 2 | 69 |
| 1142 | 2 | 31 |
| 1143 | 7 | 239 |
| 1144 | 11 | 379 |
| 1145 | 5 | 99 |
| 1146 | 2 | 33 |
| 1147 | 2 | 15 |
| 1148 | 2 | 20 |
| 1149 | 4 | 45 |
| 1150 | 2 | 27 |
| 1151 | 2 | 36 |
| 1152 | 3 | 49 |
| 1153 | 2 | 42 |
| 1154 | 2 | 45 |
| 1155 | 1 | 60 |
| 1156 | 1 | 13 |
| 1157 | 3 | 15 |
| 1158 | 2 | 26 |
| 1159 | 50 | 421 |
| 1160 | 71 | 930 |

TABLE 3-continued

| Compound | IC$_{50}$ HTRF (nM) | EC$_{50}$ TNF (nM) |
|---|---|---|
| 1161 | 14 | 45 |
| 1162 | 16 | 477 |
| 1163 | 19 | 463 |
| 1164 | 13 | 66 |
| 1165 | 9 | 102 |
| 1166 | 5 | 47 |
| 1167 | 5 | 62 |
| 1168 | 4 | 75 |

TABLE 3-continued

| Compound | IC$_{50}$ HTRF (nM) | EC$_{50}$ TNF (nM) |
|---|---|---|
| 1169 | 234 | 1000 |
| 1170 | 217 | 1000 |

The data in Table 4 and Table 5 shows that the compounds disclosed herein are effective inhibitors of cancer Osaka thyroid (Cot). In addition, the claimed compounds are not significant EGFR ligands.

TABLE 4

| Compound | Compound Structure | IC$_{50}$/EC$_{50}$ [nM] | EGFR (IC$_{50}$) [nM] |
|---|---|---|---|
| Comparative Example 1 | 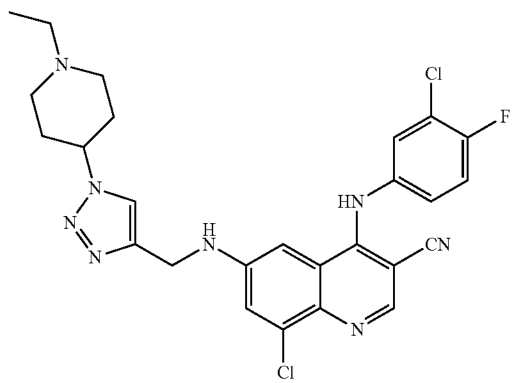 [SMILES: CCN1CCC(n2cc(CNc3cc(Cl)c4ncc(C#N)c(Nc5ccc(F)c(Cl)c5)c4c3)nn2)CC1] | 4/310 | 357 |
| Comparative Example 2 | 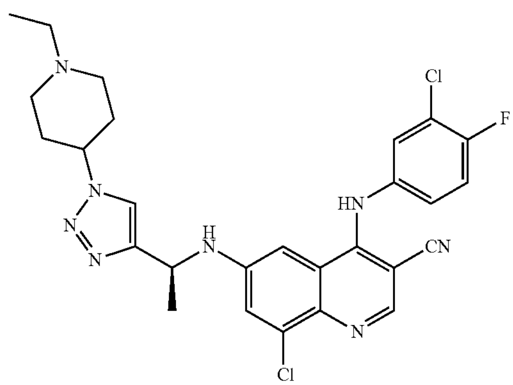 [SMILES: CCN1CCC(n2cc([C@H](C)Nc3cc(Cl)c4ncc(C#N)c(Nc5ccc(F)c(Cl)c5)c4c3)nn2)CC1] | 62/Na | Na |
| 919 | 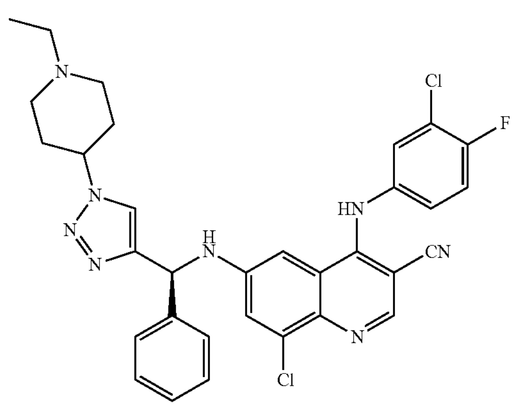 [SMILES: CCN1CCC(n2cc([C@@H](Nc3cc(Cl)c4ncc(C#N)c(Nc5ccc(F)c(Cl)c5)c4c3)c3ccccc3)nn2)CC1] | 2/62 | 2291 |

TABLE 5

| Compound | Compound Structure | IC$_{50}$/EC$_{50}$ [nM] | EGFR (IC$_{50}$) [nM] |
|---|---|---|---|
| Comparative Example 3 | 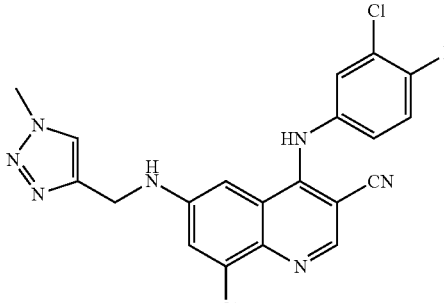 | 67/ >10000 | >10000 |
| Comparative Example 4 | 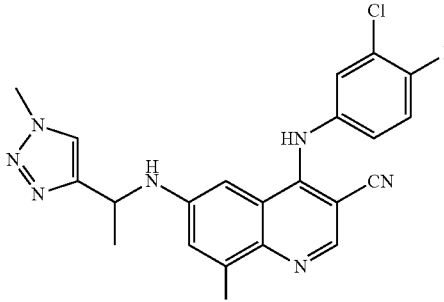 | >10000/Na | >10000 |
| 920 | 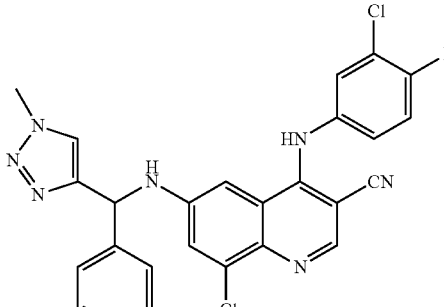 | 10/215 | >10000 |

The invention claimed is:

1. A compound of Formula I:

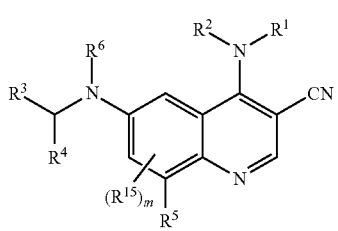

wherein
R$^1$ is hydrogen, —O—R$^7$, —N(R$^8$)(R$^9$), —C(O)—R$^7$, —S(O)$_2$—R$^7$, —C$_{1-9}$ alkyl, C$_{2-6}$ alkenyl, C$_{2-6}$ alkynyl, C$_{3-15}$ cycloalkyl, heterocyclyl, aryl, or heteroaryl;
wherein each C$_{1-9}$ alkyl, C$_{2-6}$ alkenyl, C$_{2-6}$ alkynyl, C$_{3-15}$ cycloalkyl, heterocyclyl, aryl, and heteroaryl may be optionally substituted with one to four Z$^1$;

R$^2$ is hydrogen, —C(O)—R$^7$, —C(O)O—R$^7$, —C(O)N (R$^7$)$_2$, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl may be optionally substituted with one to four Z$^2$;
or R$^1$ and R$^2$ together with the nitrogen to which they are attached to form a heterocyclyl or heteroaryl, wherein each heterocyclyl or heteroaryl is optionally substituted with one to four Z$^2$;
R$^3$ is heterocyclyl or heteroaryl, wherein each heterocyclyl or heteroaryl is optionally substituted with one to four Z$^3$;
R$^4$ is aryl, wherein said aryl is optionally substituted with one to four Z$^4$;
R$^5$ is hydrogen, halo, —CN, —NO$_2$, —O—R$^7$, —N(R$^8$) (R$^9$), —S(O)—R$^7$, —S(O)$_2$R$^7$, —S(O)$_2$N(R$^7$)$_2$, —C(O)R$^7$, —OC(O)—R$^7$, —C(O)O—R$^7$, —OC(O) O—R$^7$, —OC(O)N(R$^{10}$)(R$^{11}$), —C(O)N(R$^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;

$R^6$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;

each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

$R^8$ and $R^9$ at each occurrence are independently hydrogen, —S(O)$_2R^{10}$, —C(O)—$R^{10}$, —C(O)O—$R^{10}$, —C(O)N($R^{10}$)($R^{11}$), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;

$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl, wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^2$, $Z^3$, $Z^4$, $Z^5$, $Z^6$, $Z^7$ and $Z^8$ is independently hydrogen, oxo, halo, —NO$_2$, —N$_3$, —CN, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^2$), —OC(O)$R^{12}$, —OC(O)—N($R^{13}$)($R^{14}$), —P(O)(O$R^{12}$)$_2$, —OP(O)(O$R^{12}$)$_2$, —CH$_2$P(O)(O$R^{12}$)$_2$, —OCH$_2$P(O)(O$R^{12}$)$_2$, —C(O)OCH$_2$P(O)(O$R^{12}$)$_2$, —P(O)($R^{12}$)(O$R^{12}$), —OP(O)($R^{12}$)(O$R^{12}$), —CH$_2$P(O)($R^{12}$)(O$R^{12}$), —OCH$_2$P(O)($R^{12}$)(O$R^{12}$), —C(O)OCH$_2$P(O)($R^{12}$)(O$R^{12}$), —P(O)(N($R^{12}$))$_2$, —OP(O)(N($R^{12}$)$_2$)($R^{12}$), —CH$_2$P(O)(N($R^{12}$)$_2$)$_2$, —OCH$_2$P(O)(N($R^{12}$)$_2$)$_2$, —C(O)OCH$_2$P(O)(N($R^2$)$_2$)$_2$, —P(O)(N($R^{12}$)$_2$)(O$R^{12}$), —OP(O)(N($R^{12}$)$_2$)(O$R^{12}$), —CH$_2$P(O)(N($R^{12}$)$_2$)(O$R^{12}$), —OCH$_2$P(O)(N($R^{12}$)$_2$)(O$R^{12}$), —C(O)OCH$_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —CH$_2$P(O)($R^{12}$)(N($R^{12}$)$_2$), —OCH$_2$P(O)($R^{12}$)(N($R^{12}$)$_2$), —C(O)OCH$_2$P(O)($R^{12}$)(N($R^{12}$)$_2$), —Si($R^{12}$)$_3$, —S—$R^{12}$, —S(O)$R^{12}$, —S(O)NH$R^{12}$, —S(O)$_2R^{12}$ or —S(O)$_2$N($R^{13}$)($R^{14}$);
  wherein any alkyl, alkenyl, alkynyl, cycloalkyl, haloalkyl aryl, heteroaryl or heterocyclyl is optionally substituted with one to four $Z^{1a}$ groups;

each $Z^{1a}$ is independently oxo, halo, thioxo, —NO$_2$, —CN, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —Si($R^{12}$)$_3$, —S—$R^{12}$, —S(O)$R^{12}$, —S(O)NH$R^{12}$, —S(O)$_2R^{12}$ or —S(O)$_2$N($R^{13}$)($R^{14}$);
  wherein any alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl,
  wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

each $R^{15}$ is independently halo, —CN, —NO$_2$, —O—$R^7$, —N(R)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)(N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl; and each $Z^{1b}$ is independently oxo, thioxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)<($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)

(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)<S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)<C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)heteroaryl), —NHC(O)heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-5}$ cycloalkyl), —O(C$_{1-8}$ haloalkyl), —O(aryl), —O(heteroaryl), —O(heterocyclyl), or —O(C$_{1-9}$ alkyl);

m is 0, 1, or 2;

or a pharmaceutically acceptable salt, tautomer, stereoisomer, mixture of stereoisomers, or deuterated analog thereof.

2. The compound of claim 1, wherein R$^2$ is hydrogen, or a pharmaceutically acceptable salt thereof.

3. The compound of claim 1, wherein m is 0, or a pharmaceutically acceptable salt thereof.

4. A compound of Formula II:

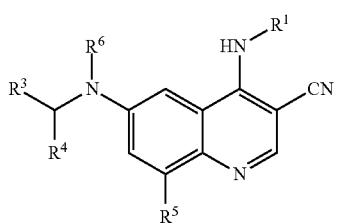

II wherein R$^1$, R$^3$, R$^4$, R$^5$ and R$^6$ are as defined in claim 1, or a pharmaceutically acceptable salt thereof.

5. A compound of Formula IIA:

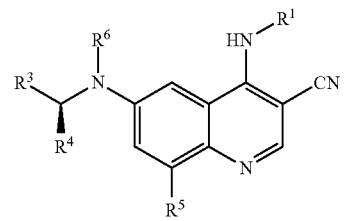

IIA wherein R$^1$, R$^3$, R$^4$, R$^5$ and R$^6$ are as defined in claim 1.

6. A compound of Formula IIIA:

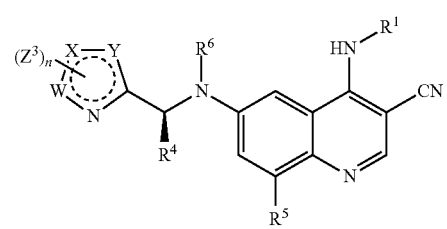

IIIA wherein R$^1$, R$^4$, R$^5$ and R$^6$ are as defined in claim 1,

W, X and Y are each independently N or C;

n is 1, 2, or 3;

each Z$^3$ is independently hydrogen, oxo, halo, —NO$_2$, —N$_3$, —CN, thioxo, C$_{1-9}$, alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$), —OCH$_2$P(O)(N(R$^2$)$_2$)$_2$, —C(O)OCH$_2$P(O)(N(R$^2$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$(R$^{13}$)(R$^{14}$);

wherein any alkyl, alkenyl, alkynyl, cycloalkyl, haloalkyl aryl, heteroaryl or heterocyclyl is optionally substituted with one to four Z$^{1a}$ groups;

each Z$^{1a}$ is independently oxo, halo, thioxo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)

$R^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups; and each $Z^{1b}$ is independently oxo, thioxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_1$ s alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$alkenyl), —NHC(O)($C_{2-6}$alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$alkenyl), —NHC(O)O($C_{2-6}$alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)((NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

or a pharmaceutically acceptable salt, tautomer, stereoisomer, mixture of stereoisomers, or deuterated analog thereof.

7. The compound according to claim 1, wherein $R^5$ is hydrogen, halo, —CN, —S(O)—R$^7$, —S(O)$_2$R$^7$, —SO$_2$N(R)(R$^9$), —C(O)R$^7$, —C(O)N(R$^8$)(R$^9$), $C_{1-9}$ alkyl, $C_{2-6}$ alkenyl, $C_{2-6}$ alkynyl, $C_{3-15}$ cycloalkyl, aryl, heterocyclyl, or heteroaryl;

wherein each $C_{1-9}$ alkyl, $C_{2-6}$ alkenyl, $C_{2-6}$ alkynyl, $C_{3-15}$ cycloalkyl, aryl, heterocyclyl, and heteroaryl may be optionally substituted with one to four $Z^5$, or a pharmaceutically acceptable salt thereof.

8. The compound according to claim 1, wherein $R^5$ is hydrogen, halo, —CN, —C(O)R$^7$, —S(O)$_2$R$^7$, or heteroaryl, or a pharmaceutically acceptable salt thereof.

9. The compound according to claim 1, wherein $R^6$ is hydrogen, or a pharmaceutically acceptable salt thereof.

10. The compound according to claim 1, wherein $R^1$ is $C_{1-9}$ alkyl, $C_{3-15}$ cycloalkyl, heterocyclyl, aryl, or heteroaryl; and said $C_{1-9}$ alkyl, $C_{3-15}$ cycloalkyl, heterocyclyl, aryl, or heteroaryl may be optionally substituted with one to four substituents independently selected the group consisting of halo, —CN, —O—R$^{12}$, —C(O)—R$^{12}$, —C(O)O—R$^{12}$, $C_{1-9}$ alkyl, and aryl, or a pharmaceutically acceptable salt thereof.

11. The compound according to claim 1, wherein $R^1$ is $C_{1-9}$ alkyl, optionally substituted with one to four substituents independently selected the group consisting of halo, —CN, —O—R$^{12}$, —C(O)O—R$^{12}$, $C_{1-9}$ alkyl, and aryl, or a pharmaceutically acceptable salt thereof.

12. The compound of claim 6, wherein W is N, X is N—Z$^3$, and Y is C—Z$^3$, or a pharmaceutically acceptable salt thereof.

13. The compound according to claim 1, wherein $R^1$ is $C_{3-15}$ cycloalkyl, heterocyclyl, or heteroaryl;

wherein said $C_{3-15}$ cycloalkyl, heterocyclyl, or heteroaryl may be optionally substituted with one to four substituents independently selected from the group consisting of —CN, halo, —O—$R^{12}$, —N($R^{13}$)($R^{14}$), —NH—C(O)O—$R^{12}$, —S(O)$_2$—$R^{12}$, —Si($R^{12}$)$_3$, $C_{1-9}$ alkyl, $C_{3-15}$ cycloalkyl, heterocyclyl, aryl, and heteroaryl; and wherein said $C_{1-9}$ alkyl, $C_{3-15}$ cycloalkyl, aryl, or heteroaryl may be optionally substituted with one to three substituents independently selected from the group consisting of —CN, halo, —O—$R^{12}$, —N($R^{13}$)($R^{14}$), $C_{1-9}$ alkyl, $C_{3-15}$ cycloalkyl, and aryl, or a pharmaceutically acceptable salt thereof.

14. The compound according to claim 1, wherein $R^1$ is $C_{3-15}$ cycloalkyl, heterocyclyl or heteroaryl, wherein said $C_{3-15}$ cycloalkyl, heterocyclyl or heteroaryl is optionally substituted with one to four substituents independently selected the group consisting of halo, —CN, —O—$R^{12}$, $C_{1-9}$ alkyl, and aryl, or a pharmaceutically acceptable salt thereof.

15. The compound according to claim 1, wherein $R^1$ is aryl;
wherein said aryl may be optionally substituted with one to four substituents independently selected from the group consisting of —CN, halo, —O—$R^{12}$, —C(O)—$R^{12}$, —N($R^{13}$)($R^{14}$), —NH—C(O)O—$R^{12}$, —S(O)$_2$—$R^{12}$, —Si($R^{12}$)$_3$, $C_{1-9}$ alkyl, $C_{3-15}$ cycloalkyl, heterocyclyl, aryl, and heteroaryl; and
wherein said $C_{1-9}$ alkyl, $C_{3-15}$ cycloalkyl, aryl, or heteroaryl may be optionally substituted with one to three substituents independently selected from the group consisting of —CN, halo, —O—$R^{12}$, —N($R^{13}$)($R^{14}$), $C_{1-9}$ alkyl, $C_{3-15}$ cycloalkyl, and aryl, or a pharmaceutically acceptable salt thereof.

16. The compound according to claim 1, wherein $R^1$ is aryl, wherein said aryl may be optionally substituted with one to four substituents independently selected the group consisting of halo, —CN, —O—$R^{12}$, —C(O)—$R^{12}$, $C_{1-9}$ alkyl, and aryl, or a pharmaceutically acceptable salt thereof.

17. The compound of claim 15, wherein $Z^3$ is hydrogen, $C_{1-9}$ alkyl, $C_{3-15}$ cycloalkyl, heterocyclyl, aryl, or heteroaryl;
wherein said $C_{1-9}$ alkyl, $C_{3-15}$ cycloalkyl, aryl, or heterocyclyl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl, or a pharmaceutically acceptable salt thereof.

18. The compound of claim 15, wherein $Z^3$ is hydrogen or $C_{1-9}$ alkyl;
wherein said $C_{1-9}$ alkyl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl, or a pharmaceutically acceptable salt thereof.

19. The compound of claim 15, wherein $Z^3$ is hydrogen or $C_{1-9}$ alkyl optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl, or a pharmaceutically acceptable salt thereof.

20. The compound of claim 15, wherein $Z^3$ is $C_{3-15}$ cycloalkyl, heterocyclyl, aryl, or heteroaryl;
wherein said $C_{1-9}$ alkyl, $C_{3-15}$ cycloalkyl, aryl, or heterocyclyl, may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl; and
wherein said $C_{1-9}$ alkyl, $C_{3-15}$ cycloalkyl, heterocyclyl, or aryl may be optionally substituted with one to three substituents independently selected from the group consisting of halo, hydroxy, —O($C_{1-9}$ alkyl), —C(O)N($C_{1-9}$ alkyl)$_2$, $C_{1-9}$ alkyl, and heterocyclyl, or a pharmaceutically acceptable salt thereof.

21. The compound of claim 15, wherein $Z^3$ is $C_{3-15}$ cycloalkyl, heterocyclyl, aryl, or heteroaryl; and said $C_{3-15}$ cycloalkyl, heterocyclyl, aryl, or heteroaryl may be optionally substituted with one to four substituents independently selected from the group consisting of —CN, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ alkyl, heterocyclyl, and heteroaryl, or a pharmaceutically acceptable salt thereof.

22. The compound of claim 1, wherein $R^1$ and $R^2$ together with the nitrogen to which they are attached to form a heterocyclyl or heteroaryl, wherein said heterocyclyl may be optionally substituted with one to three $C_{1-9}$ alkyl, or a pharmaceutically acceptable salt thereof.

23. The compound of claim 1, wherein the compound is represented by Formula VIA:

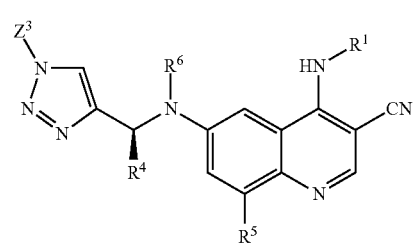

VIA wherein $Z^3$, $R^1$, $R^4$, $R^5$ and $R^6$ are as defined in claim 1, or a pharmaceutically acceptable salt thereof.

24. The compound of claim 23, wherein:
$Z^3$ is hydrogen, $C_{1-9}$ alkyl, $C_{3-15}$ cycloalkyl, heterocyclyl, aryl, or heteroaryl;
wherein said $C_{1-9}$ alkyl, $C_{3-15}$ cycloalkyl, aryl, or heterocyclyl may be optionally substituted with one to four substituents independently selected from the group consisting of —CN, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{3-15}$ cycloalkyl, aryl, heterocyclyl, and heteroaryl;
wherein said $C_{1-9}$ alkyl, $C_{3-15}$ cycloalkyl, heterocyclyl, or aryl may be optionally substituted with one to three substituents independently selected from the group consisting of halo, hydroxy, —O(C$_{1-9}$ alkyl), —C(O)—N(C$_{1-9}$ alkyl)$_2$, C$_{1-9}$ alkyl, and heterocyclyl;

R$^1$ is hydrogen, —O—R$^7$, —N(R$^8$)(R$^9$), —C(O)—R$^7$, —S(O)$_2$—R$^7$, C$_{1-9}$ alkyl, C$_{3-15}$ cycloalkyl, heterocyclyl, aryl, or heteroaryl;
wherein said C$_{1-9}$ alkyl, C$_{3-15}$ cycloalkyl, heterocyclyl, aryl, or heteroaryl may be optionally substituted with one to four substituents independently selected from the group consisting of —CN, halo, —O—R$^{12}$, —C(O)—R$^{12}$, —C(O)O—R$^{12}$, —N(R$^{13}$)(R$^{14}$), —N(R$^{12}$)C(O)O—R$^{12}$, —S(O)$_2$—R$^{12}$, —Si(R$^{12}$)$_3$, C$_{1-9}$ alkyl, C$_{3-15}$ cycloalkyl, heterocyclyl, aryl, and heteroaryl;
wherein said C$_{1-9}$ alkyl, C$_{3-15}$ cycloalkyl, aryl, or heteroaryl may be optionally substituted with one to three substituents independently selected from the group consisting of —CN, halo, —O—R$^{12}$, —N(R$^{13}$)(R$^{14}$), C$_{1-9}$ alkyl, C$_{3-15}$ cycloalkyl, and aryl;

R$^4$ is aryl;
wherein said aryl is optionally substituted with one to three substituents independently selected from the group consisting of —CN, halo, —O—R$^{12}$, —C(O)—R$^{12}$, —C(O)O—R$^{12}$, —S(O)$_2$—R$^{12}$, —N(R$^{12}$)C(O)—R$^{12}$, —N(R$^{12}$)S(O)$_2$R$^{12}$, —C(O)N(R$^{13}$)(R$^{14}$), —N(R$^{13}$)(R$^{14}$), C$_{1-9}$ alkyl, C$_{3-15}$ cycloalkyl, heterocyclyl, aryl, and heteroaryl;
wherein said C$_{1-9}$ alkyl, C$_{3-15}$ cycloalkyl, or heteroaryl may be optionally substituted with one to three substituents independently selected from the group consisting of halo, —CN, —O—R$^{12}$, —N(R$^{13}$)(R$^{14}$), C$_{1-9}$ alkyl, and heterocyclyl;

R$^5$ is —CN, halo, —O—R$^7$, —C(O)R$^7$, —N(R$^8$)C(O)(R$^7$), —C(O)N(R$^8$)(R$^9$), —S(O)$_2$R$^7$, C$_{1-9}$ alkyl, C$_{2-6}$ alkynyl, C$_{3-15}$ cycloalkyl, aryl, or heteroaryl;
wherein said C$_{1-9}$ alkyl, aryl, or heteroaryl may be optionally substituted with one to three substituents independently selected from the group consisting of halo, —O—R$^{12}$, and C$_{1-9}$ alkyl;

each R$^7$ is independently hydrogen, C$_{1-9}$ alkyl, C$_{3-15}$ cycloalkyl, heterocyclyl, or aryl;
wherein said C$_{1-9}$ alkyl, or heterocyclyl may be optionally substituted with one to three substituents independently selected from the group consisting of halo, —O—R$^{12}$, —N(R$^{13}$)(R$^{14}$), C$_{1-9}$ alkyl, aryl, and heteroaryl;

each R$^{12}$ is independently hydrogen, C$_{1-9}$ alkyl, C$_{3-15}$ cycloalkyl, heterocyclyl, or aryl;
wherein said C$_{1-9}$ alkyl, or heterocyclyl may be optionally substituted with one to three substituents independently selected from the group consisting of halo, hydroxy, —O(C$_{1-9}$ alkyl), —N(C$_{1-9}$ alkyl)$_2$, C$_{1-9}$ alkyl, aryl, and heterocyclyl; and each R$^{13}$ and R$^{14}$ are independently hydrogen, C$_{1-9}$ alkyl, C$_{3-15}$ cycloalkyl, heterocyclyl, or aryl;
wherein said C$_{1-9}$ alkyl, or heterocyclyl may be optionally substituted with one to three substituents independently selected from the group consisting of halo, hydroxy, —O(C$_{1-9}$ alkyl), —N(C$_{1-9}$ alkyl)$_2$, C$_{1-9}$ alkyl, aryl, and heterocyclyl;

or a pharmaceutically acceptable salt, tautomer, stereoisomer, mixture of stereoisomers, prodrug, or deuterated analog thereof.

25. The compound of claim 23, wherein R$^5$ is cyano or halo, or a pharmaceutically acceptable salt thereof.

26. The compound of claim 23, wherein R$^6$ is hydrogen, or a pharmaceutically acceptable salt thereof.

27. The compound according to claim 1, wherein R$^4$ is aryl optionally substituted with one to three substituents independently selected from the group consisting of —CN, halo, —O—R$^{12}$, —C(O)—R$^{12}$, C$_{1-9}$ alkyl, C$_{1-9}$ haloalkyl, and heterocyclyl, or a pharmaceutically acceptable salt thereof.

28. The compound according to claim 1, wherein R$^4$ is

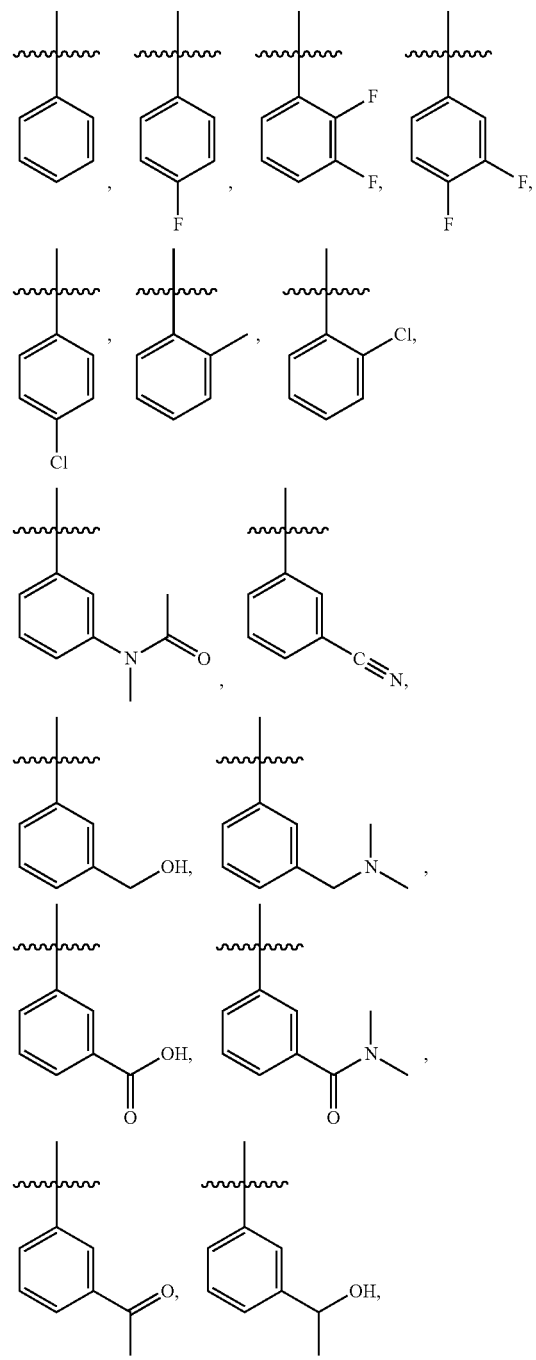

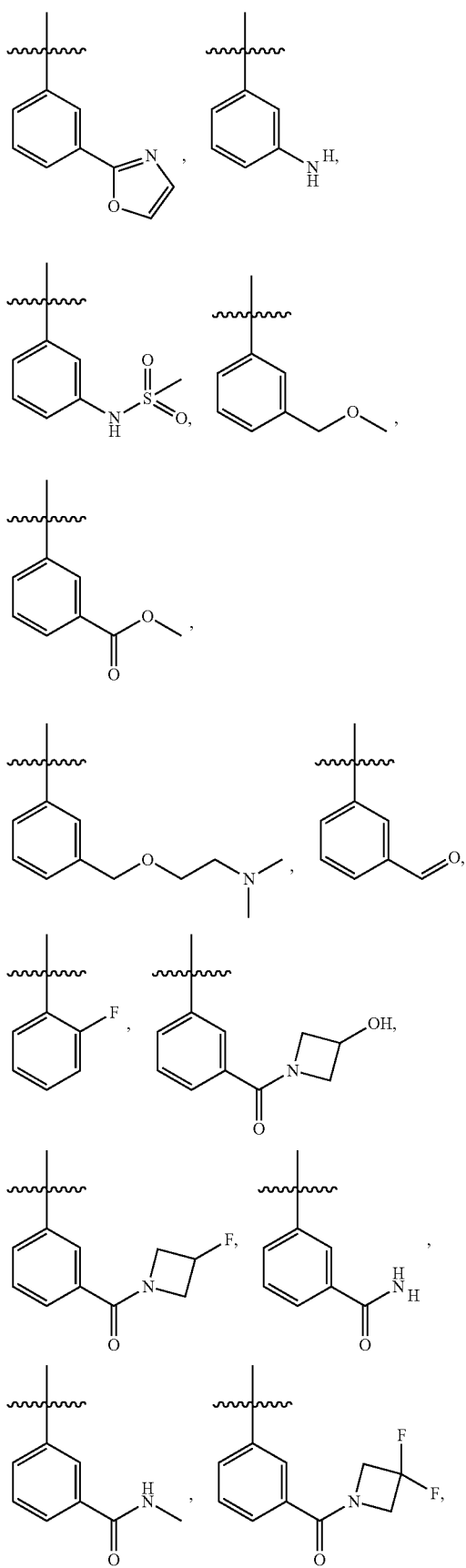
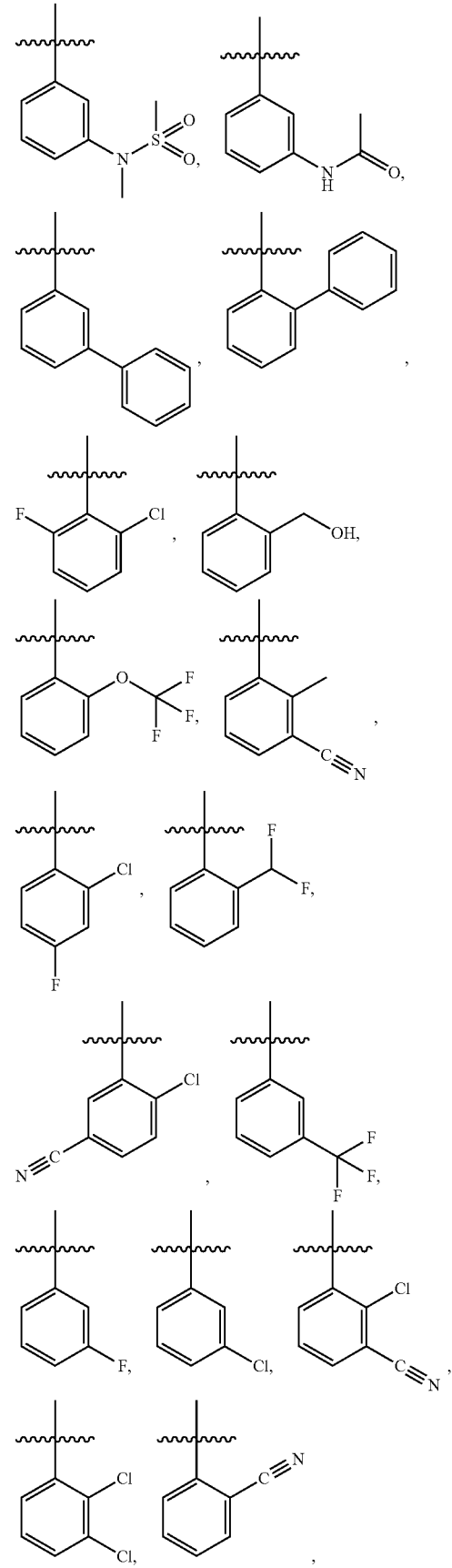

1389
-continued
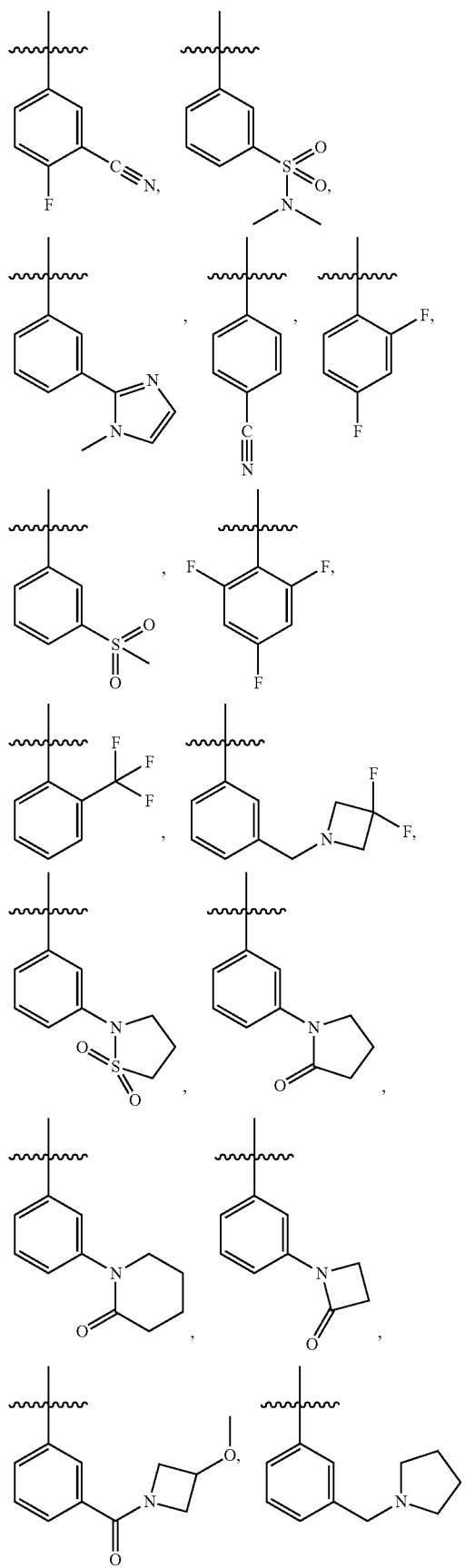
1390
-continued
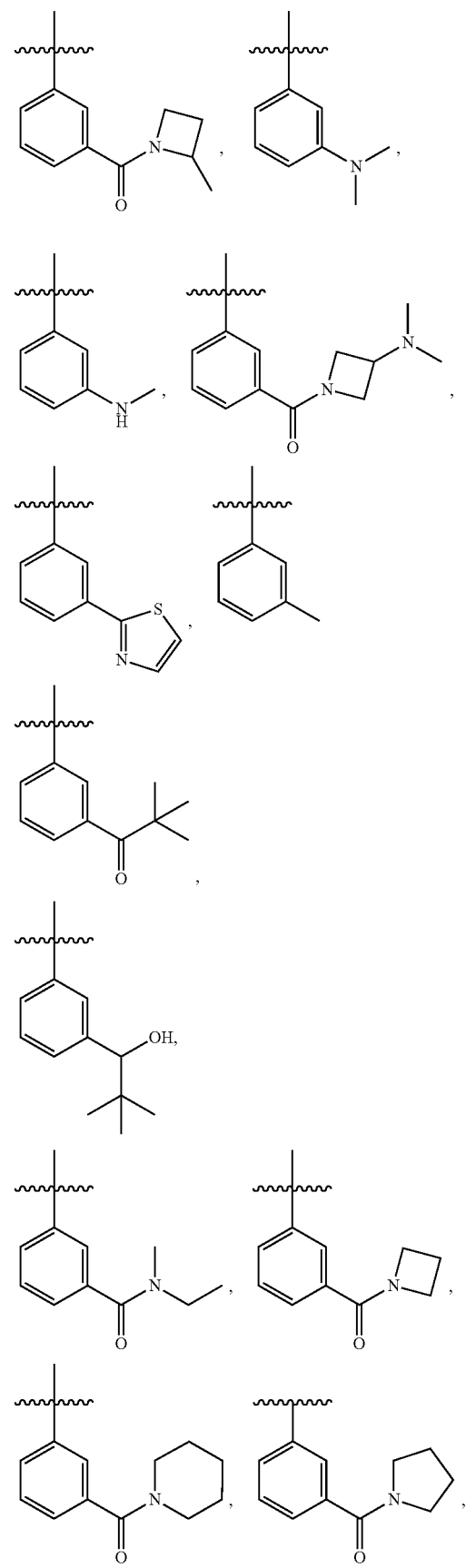

1391
-continued
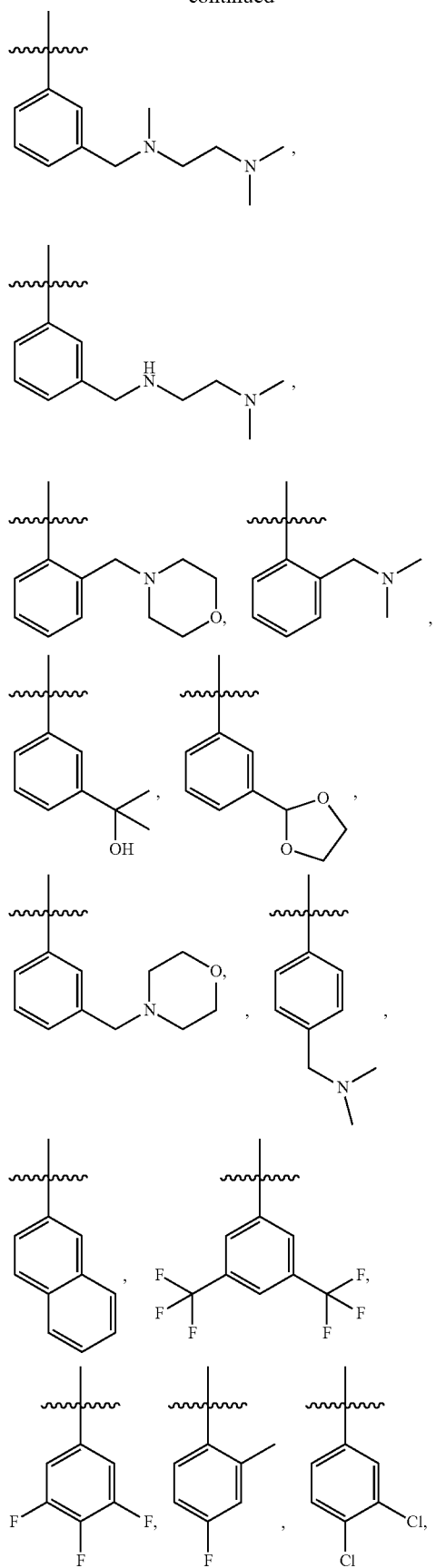
1392
-continued
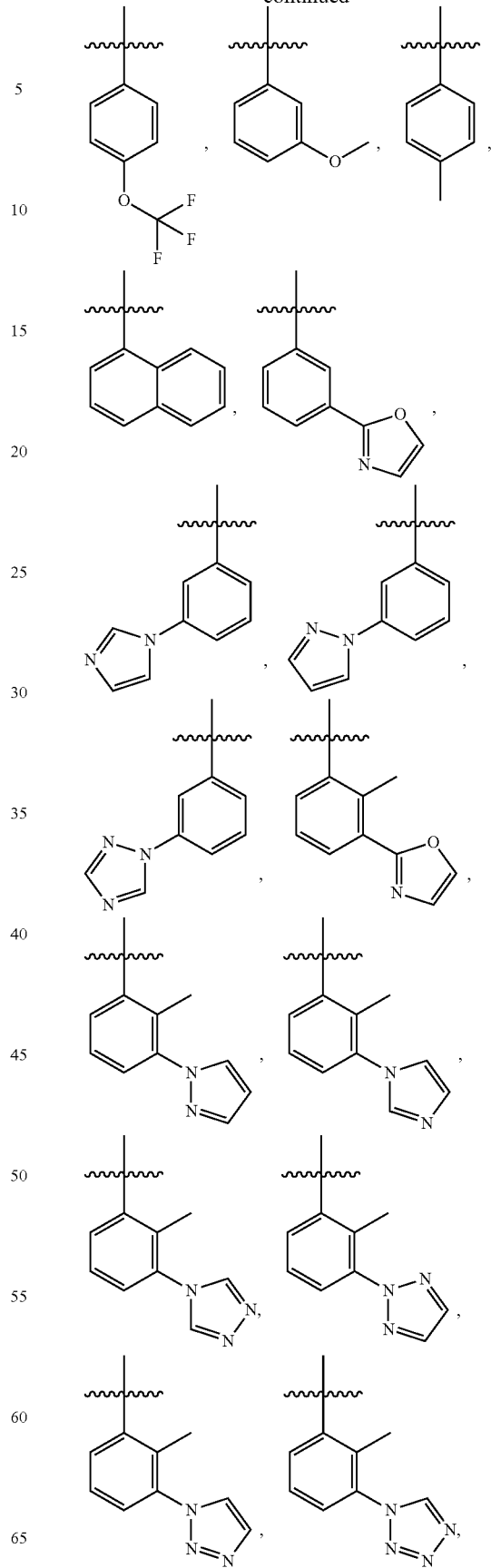

1393
-continued
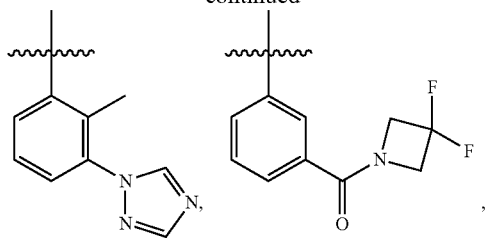
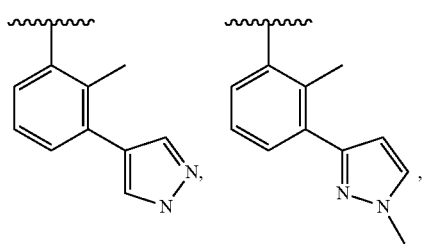
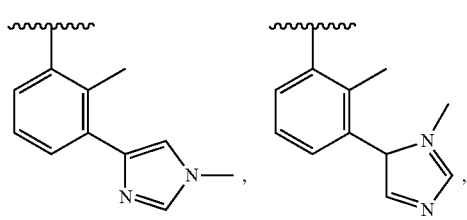
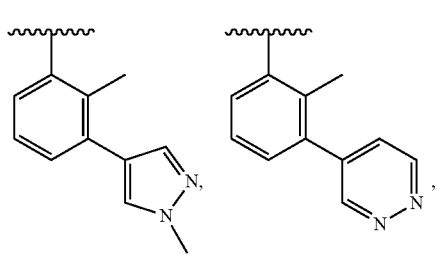
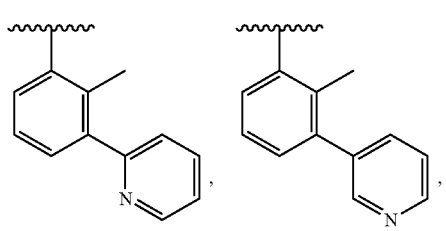
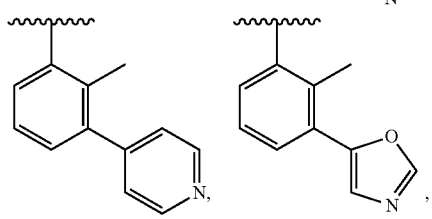
1394
-continued
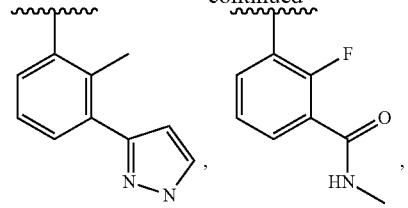
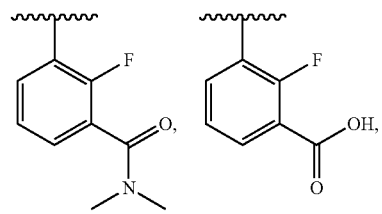
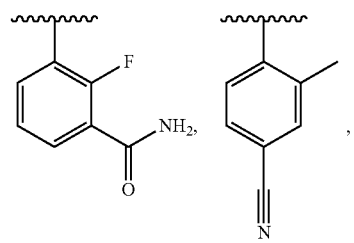
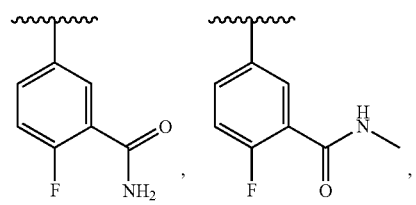
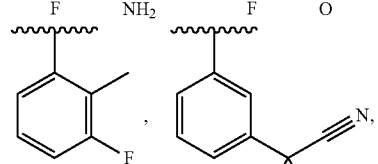
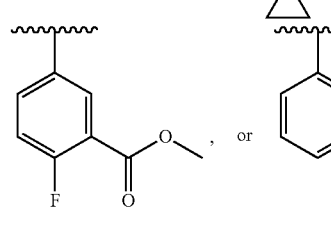
29. The compound according to claim 1, wherein $R^4$ is 2-chlorophenyl, 3-(dimethylcarbamoyl)phenyl, 3-cyanophenyl, 4-chlorophenyl, 4-fluorophenyl, or phenyl, or a pharmaceutically acceptable salt thereof.
30. A compound selected from Table 1, or a pharmaceutically acceptable salt thereof;

TABLE 1

| Compound | Structure |
|---|---|
| 1 | (structure) |
| 2 | (structure) |
| 3 | (structure) |
| 4 | (structure) |

TABLE 1-continued
| Compound | Structure |
|---|---|
| 5 | 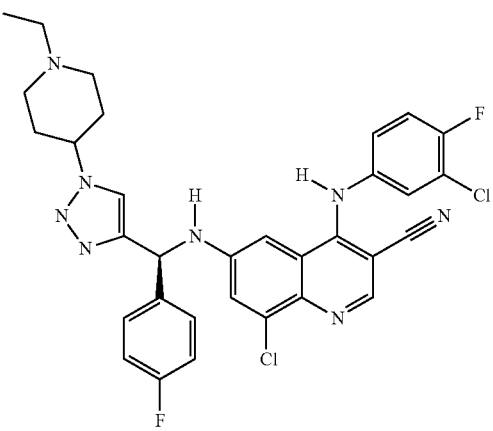 [SMILES: CCN1CCC(N2C=C([C@@H](Nc3cc(Cl)c4ncc(C#N)c(Nc5ccc(F)c(Cl)c5)c4c3)c3ccc(F)cc3)NN2)CC1] |
| 6 | 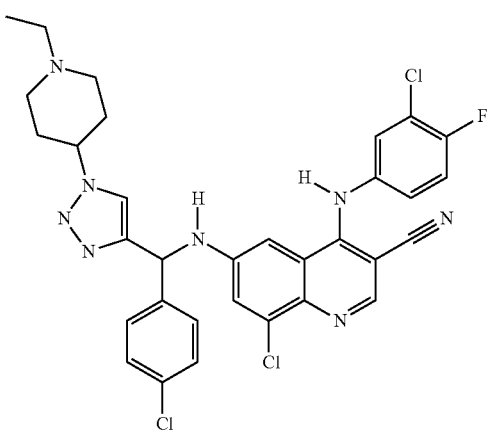 [SMILES: CCN1CCC(N2C=C(C(Nc3cc(Cl)c4ncc(C#N)c(Nc5ccc(F)c(Cl)c5)c4c3)c3ccc(Cl)cc3)NN2)CC1] |
| 7 | 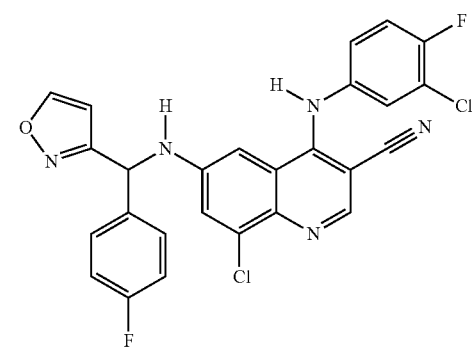 [SMILES: N#Cc1cnc2c(Cl)cc(NC(c3ccc(F)cc3)c3ccon3)cc2c1Nc1ccc(F)c(Cl)c1] |
| 8 | 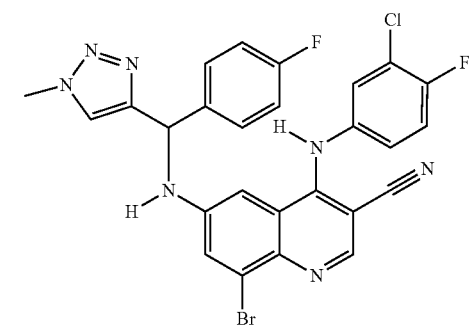 [SMILES: Cn1cc(C(Nc2cc(Br)c3ncc(C#N)c(Nc4ccc(F)c(Cl)c4)c3c2)c2ccc(F)cc2)nn1] |

TABLE 1-continued
| Compound | Structure |
|---|---|
| 9 | 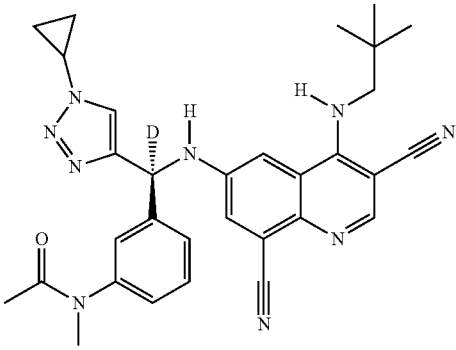 |
| 10 | 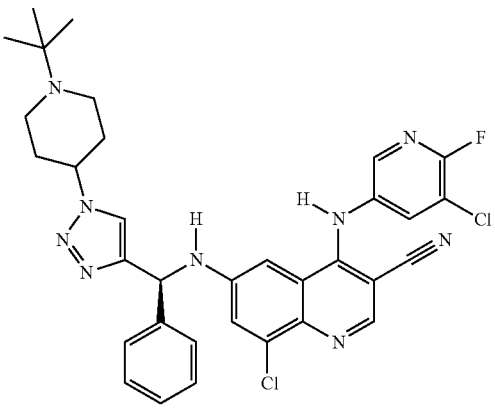 [SMILES: CC(C)(C)N1CCC(n2cc([C@@H](Nc3cc(Cl)c4ncc(C#N)c(Nc5cnc(F)c(Cl)c5)c4c3)c3ccccc3)nn2)CC1] |
| 11 | 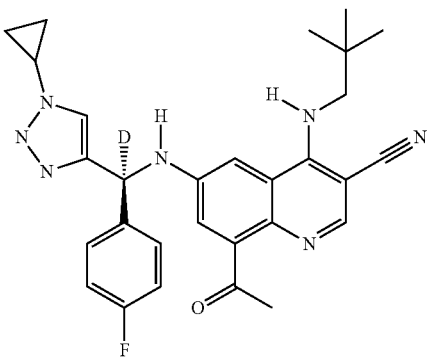 |
| 12 | 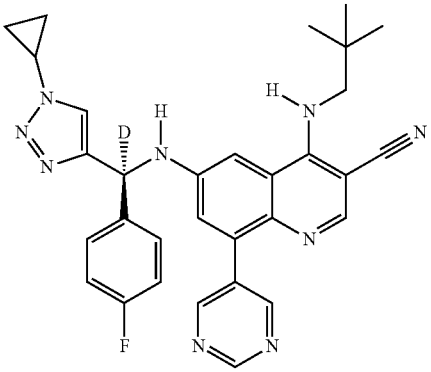 |

TABLE 1-continued
| Compound | Structure |
|---|---|
| 13 | 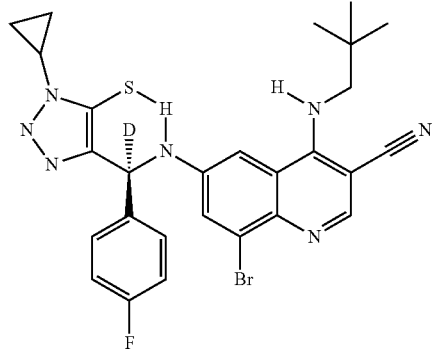 |
| 14 | 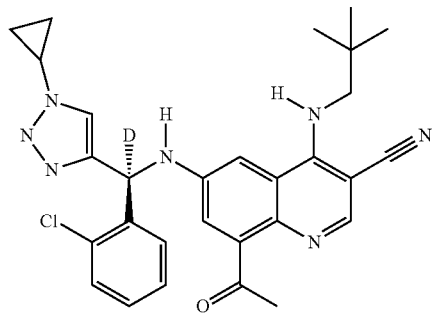 |
| 15 | 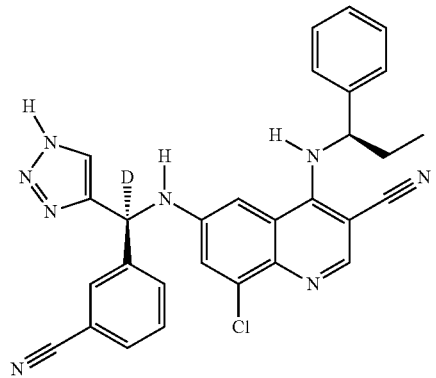 |
| 16 | 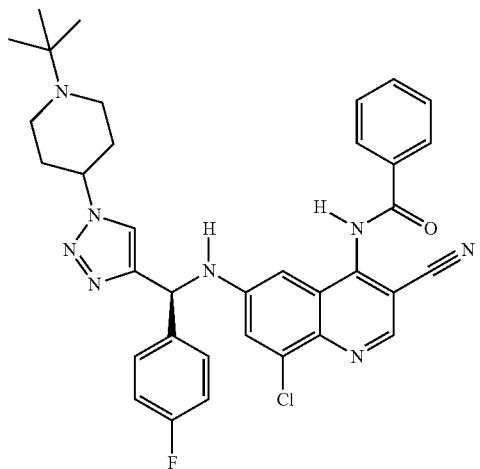 [SMILES: CC(C)(C)N1CCC(n2cc([C@@H](Nc3cc(Cl)c4ncc(C#N)c(NC(=O)c5ccccc5)c4c3)c3ccc(F)cc3)nn2)CC1] |

TABLE 1-continued
| Compound | Structure |
|---|---|
| 17 | 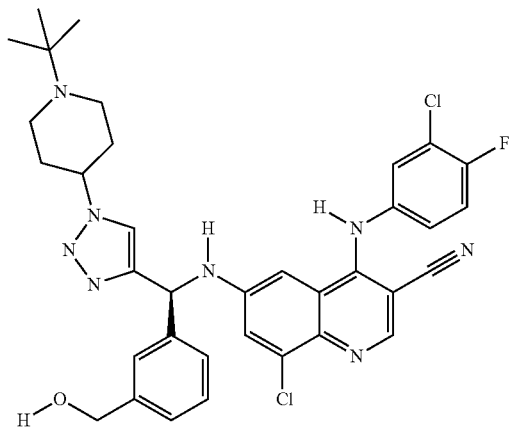 [SMILES: CC(C)(C)N1CCC(N2C=C([C@@H](Nc3cc(Cl)c4ncc(C#N)c(Nc5ccc(F)c(Cl)c5)c4c3)c3cccc(CO)c3)NN2)CC1] |
| 18 | 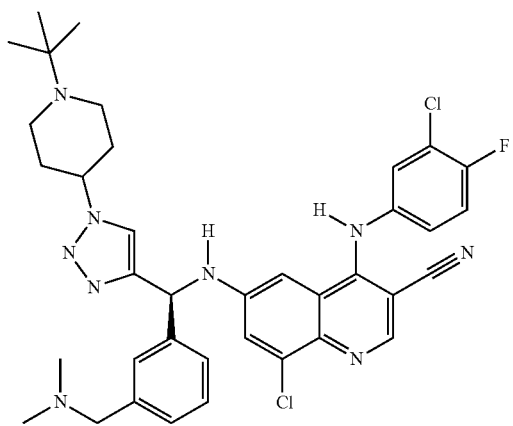 [SMILES: CN(C)Cc1cccc([C@H](Nc2cc(Cl)c3ncc(C#N)c(Nc4ccc(F)c(Cl)c4)c3c2)C2=CN(C3CCN(C(C)(C)C)CC3)NN2)c1] |
| 19 | 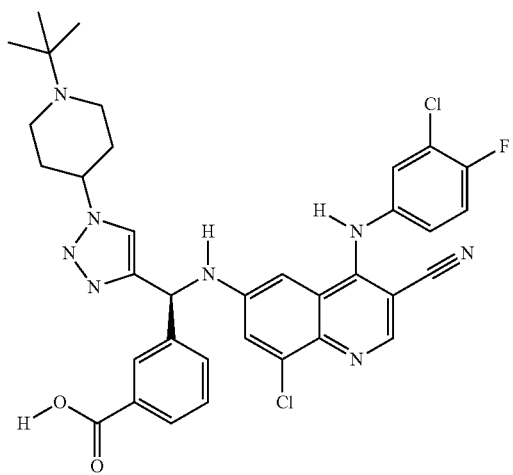 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)O)c3)NN2)CC1] |

TABLE 1-continued
| Compound | Structure |
|---|---|
| 20 | 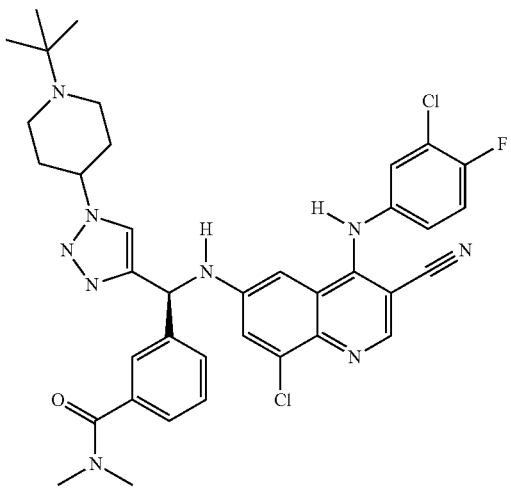 [SMILES: CN(C)C(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] |
| 21 | 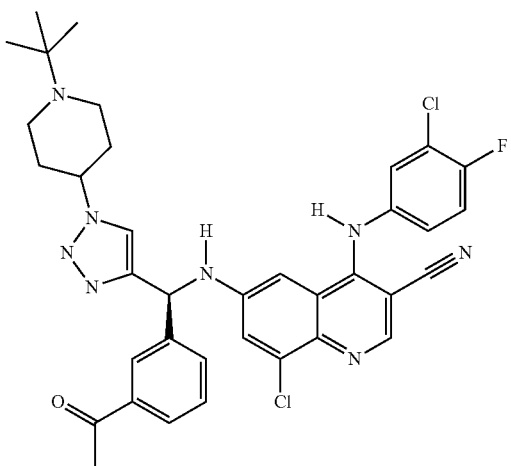 [SMILES: CC(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] |
| 22 | 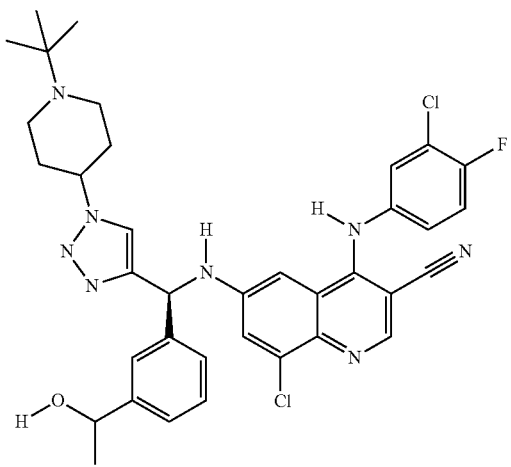 [SMILES: CC(O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] |

TABLE 1-continued
| Compound | Structure |
|---|---|
| 23 | 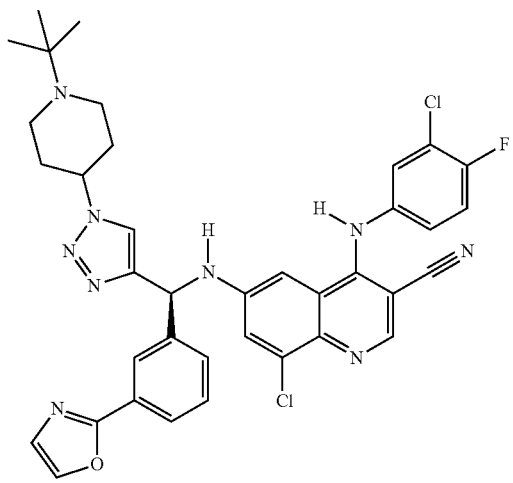 [SMILES: CC(C)(C)N1CCC(n2cc([C@@H](Nc3cc(Cl)c4ncc(C#N)c(Nc5ccc(F)c(Cl)c5)c4c3)c3cccc(-c4ncco4)c3)nn2)CC1] |
| 24 | 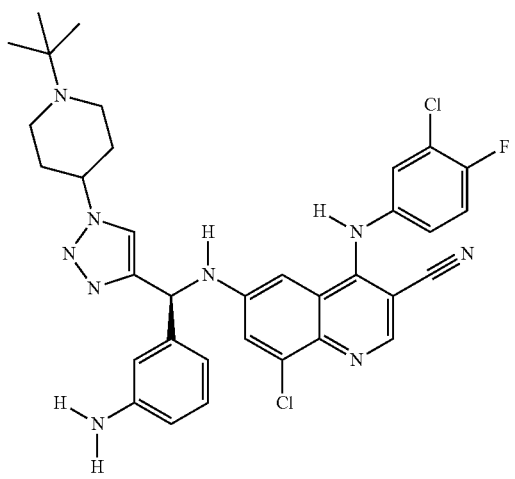 [SMILES: CC(C)(C)N1CCC(N2C=C([C@@H](Nc3cc(Cl)c4ncc(C#N)c(Nc5ccc(F)c(Cl)c5)c4c3)c3cccc(N)c3)NN2)CC1] |
| 25 | 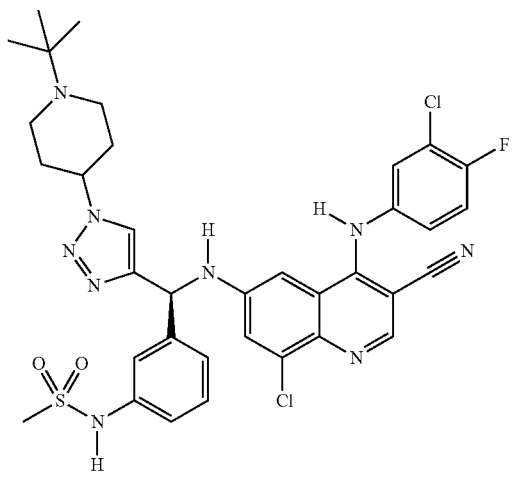 [SMILES: CC(C)(C)N1CCC(n2cc([C@@H](Nc3cc(Cl)c4ncc(C#N)c(Nc5ccc(F)c(Cl)c5)c4c3)c3cccc(NS(C)(=O)=O)c3)nn2)CC1] |

TABLE 1-continued
| Compound | Structure |
|---|---|
| 26 | 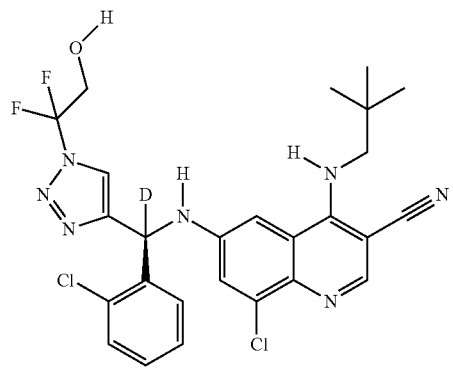 |
| 27 | 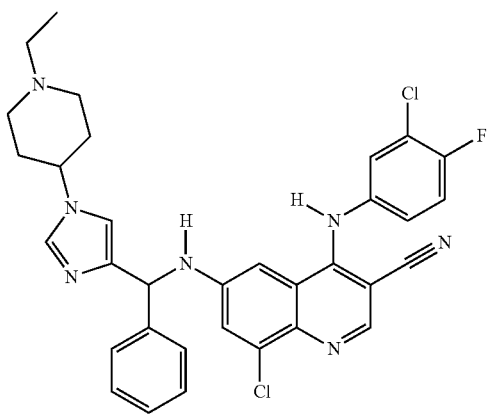 [SMILES: CCN1CCC(n2cnc(C(Nc3cc(Cl)c4ncc(C#N)c(Nc5ccc(F)c(Cl)c5)c4c3)c3ccccc3)c2)CC1] |
| 28 | 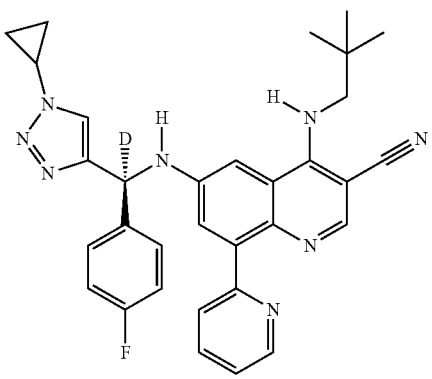 |
| 29 | 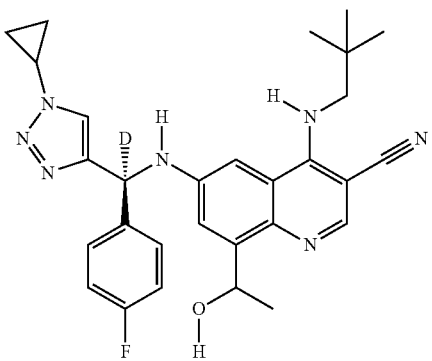 |

TABLE 1-continued
| Compound | Structure |
|---|---|
| 30 | 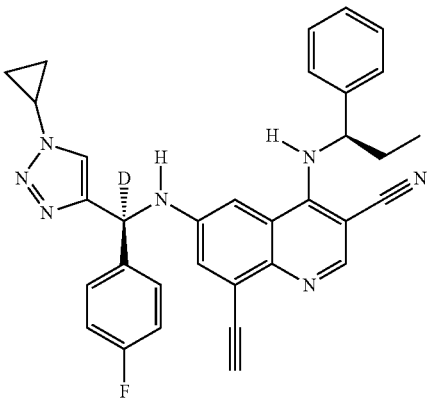 |
| 31 | 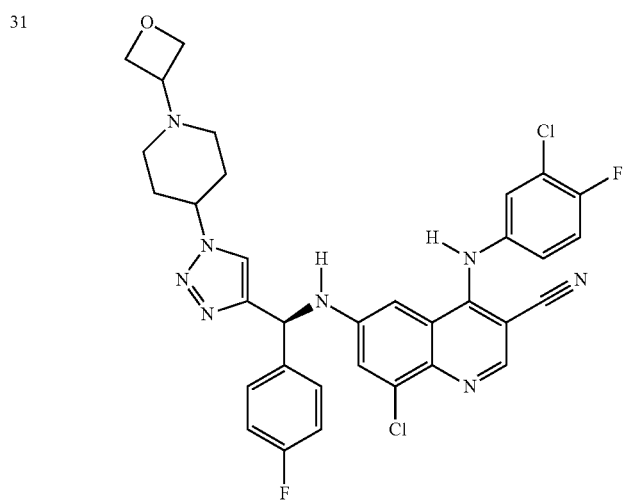 |
| 32 | 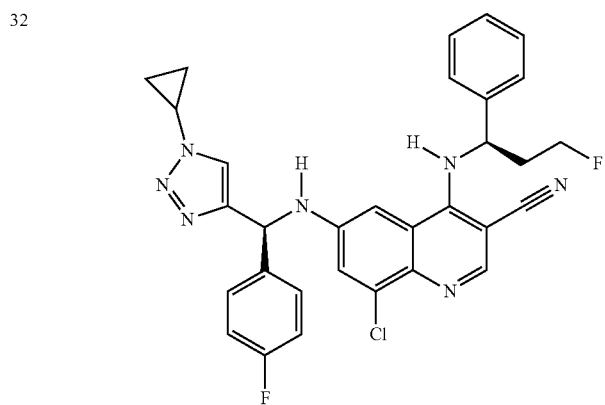 |

TABLE 1-continued
| Compound | Structure |
|---|---|
| 33 | 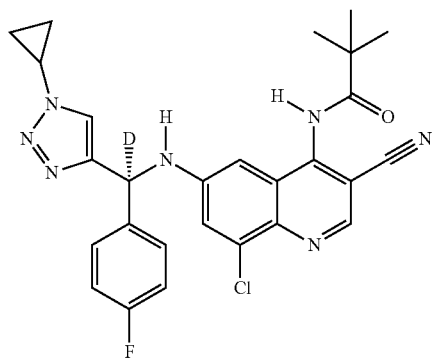 [SMILES: [2H][C@](Nc1cc(Cl)c2ncc(C#N)c(NC(=O)C(C)(C)C)c2c1)(c1ccc(F)cc1)c1cn(C2CC2)nn1] |
| 34 | 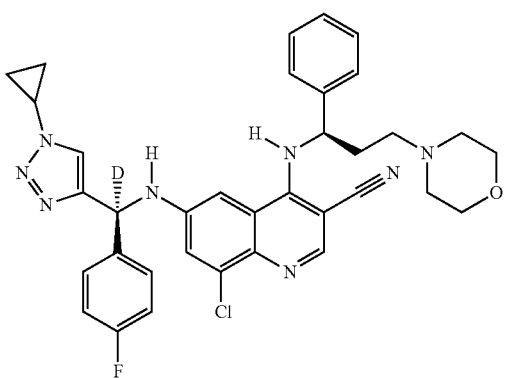 |
| 35 | 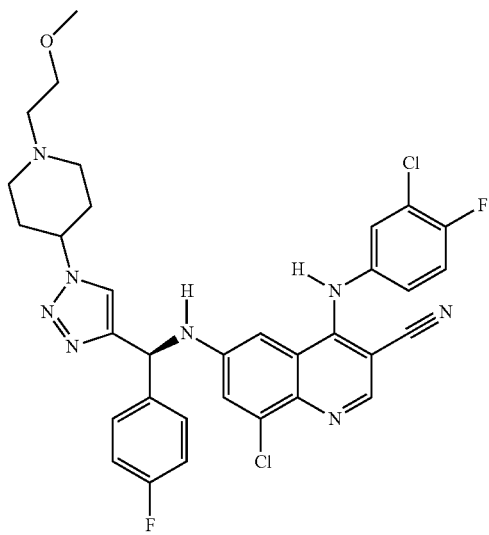 [SMILES: COCCN1CCC(n2cc([C@@H](Nc3cc(Cl)c4ncc(C#N)c(Nc5ccc(F)c(Cl)c5)c4c3)c3ccc(F)cc3)nn2)CC1] |

TABLE 1-continued
| Compound | Structure |
|---|---|
| 36 | 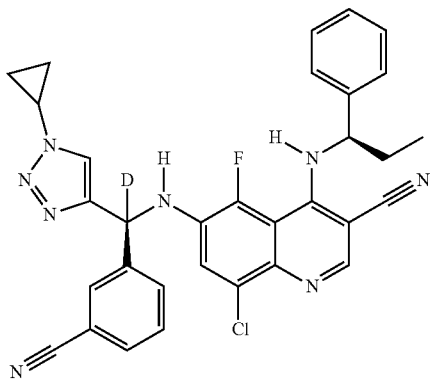 [SMILES: [2H][C@@](Nc1cc(Cl)c2ncc(C#N)c(N[C@H](CC)c3ccccc3)c2c1F)(c1cccc(C#N)c1)c1cn(C2CC2)nn1] |
| 37 | 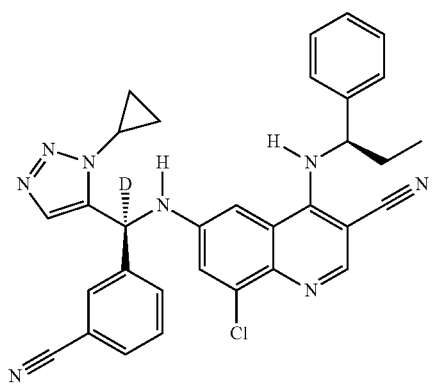 |
| 38 | 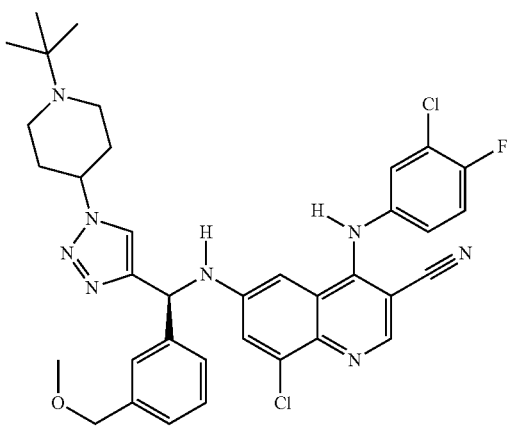 [SMILES: COCc1cccc([C@H](Nc2cc(Cl)c3ncc(C#N)c(Nc4ccc(F)c(Cl)c4)c3c2)c2cn(C3CCN(C(C)(C)C)CC3)nn2)c1] |

TABLE 1-continued
| Compound | Structure |
|---|---|
| 39 | 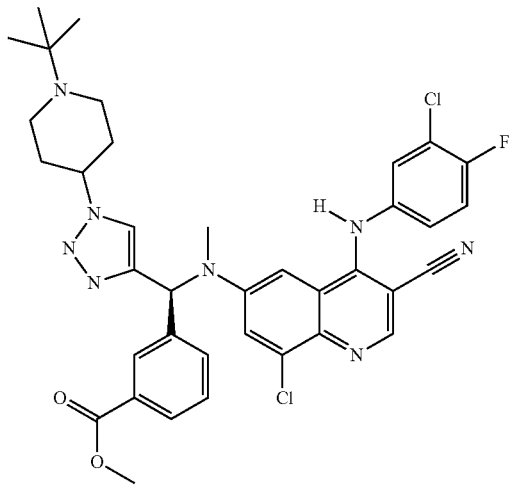 [SMILES: COC(=O)c1cccc([C@@H](C2=CN(C3CCN(C(C)(C)C)CC3)NN2)N(C)c2cc(Cl)c3ncc(C#N)c(Nc4ccc(F)c(Cl)c4)c3c2)c1] |
| 40 | 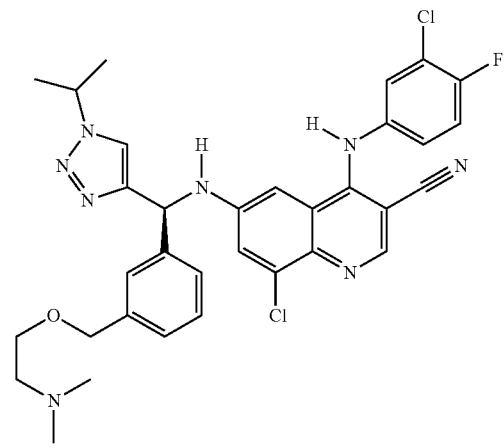 [SMILES: CC(C)n1cc([C@@H](Nc2cc(Cl)c3ncc(C#N)c(Nc4ccc(F)c(Cl)c4)c3c2)c2cccc(COCCN(C)C)c2)nn1] |
| 41 | 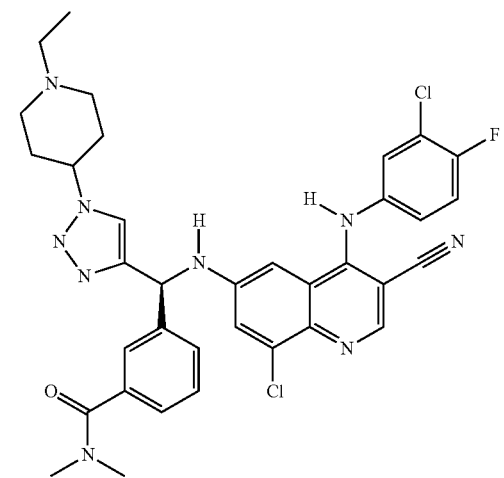 [SMILES: CCN1CCC(N2C=C([C@@H](Nc3cc(Cl)c4ncc(C#N)c(Nc5ccc(F)c(Cl)c5)c4c3)c3cccc(C(=O)N(C)C)c3)NN2)CC1] |

TABLE 1-continued
| Compound | Structure |
|---|---|
| 42 | 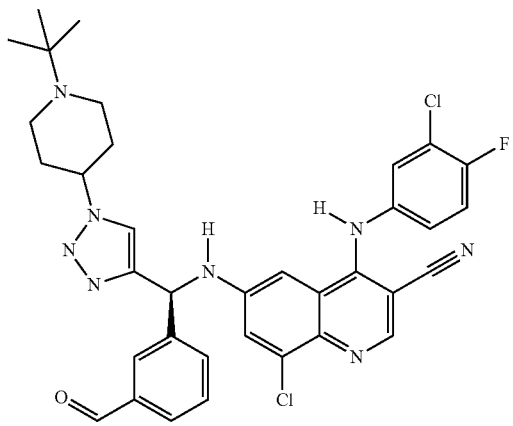 [SMILES: CC(C)(C)N1CCC(N2C=C([C@@H](Nc3cc(Cl)c4ncc(C#N)c(Nc5ccc(F)c(Cl)c5)c4c3)c3cccc(C=O)c3)NN2)CC1] |
| 43 | 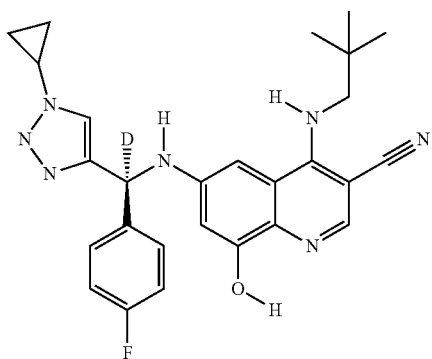 |
| 44 | 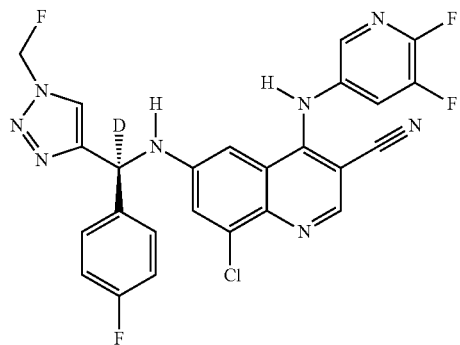 |
| 45 | 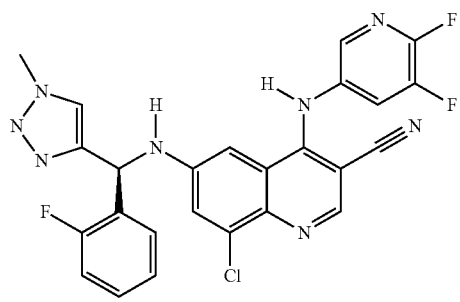 |

TABLE 1-continued
| Compound | Structure |
|---|---|
| 46 | 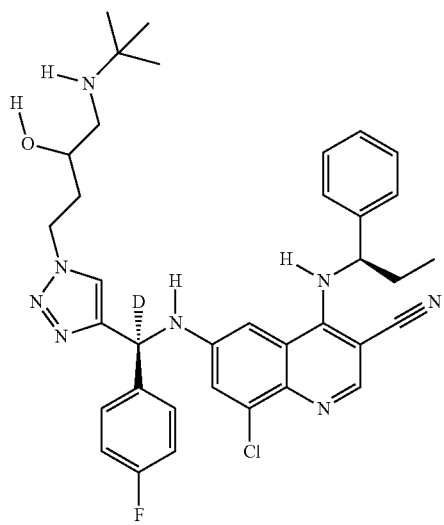 |
| 47 | 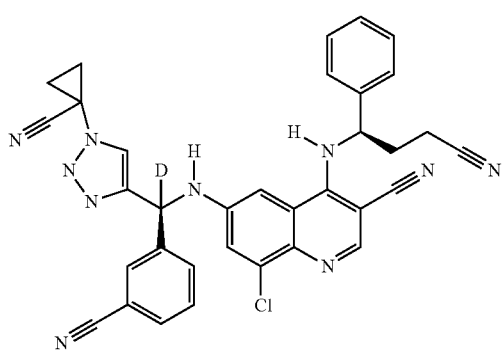 [SMILES: [2H][C@](Nc1cc(Cl)c2ncc(C#N)c(N[C@H](CCC#N)c3ccccc3)c2c1)(C1=CN(C2(C#N)CC2)NN1)c1cccc(C#N)c1] |
| 48 | 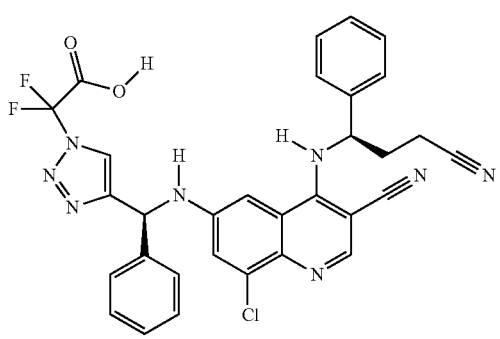 [SMILES: N#CCC[C@@H](Nc1c(C#N)cnc2c(Cl)cc(N[C@@H](c3ccccc3)c3cn(C(F)(F)C(=O)O)nn3)cc12)c1ccccc1] |
| 49 | 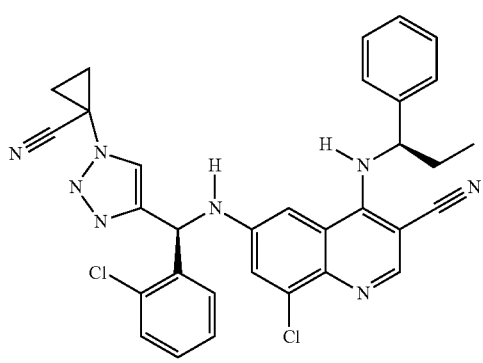 [SMILES: CC[C@@H](Nc1c(C#N)cnc2c(Cl)cc(N[C@H](C3=CN(C4(C#N)CC4)NN3)c3ccccc3Cl)cc12)c1ccccc1] |

TABLE 1-continued
| Compound | Structure |
|---|---|
| 50 | 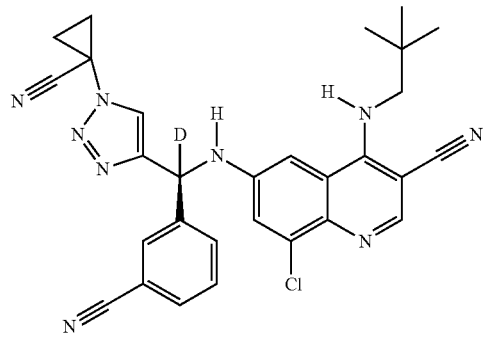 [SMILES: [2H][C@@](Nc1cc(Cl)c2ncc(C#N)c(NCC(C)(C)C)c2c1)(c1cccc(C#N)c1)c1cn(C2(C#N)CC2)nn1] |
| 51 | 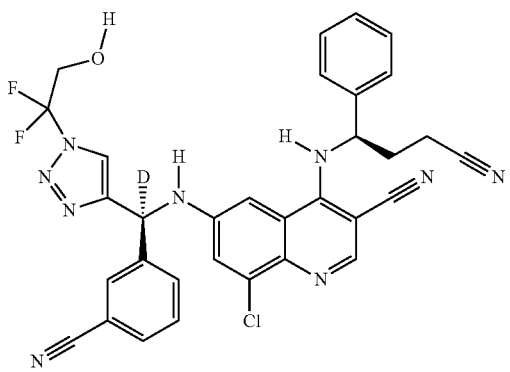 |
| 52 | 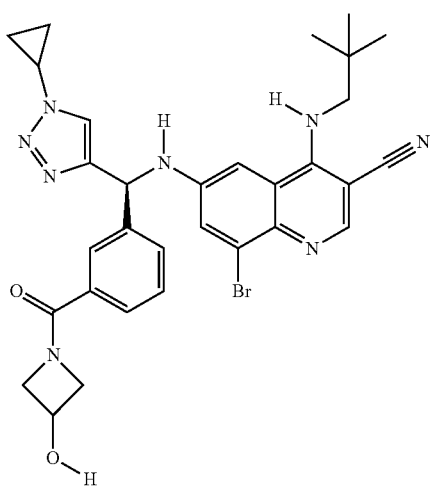 |

TABLE 1-continued
| Compound | Stucture |
|---|---|
| 53 | 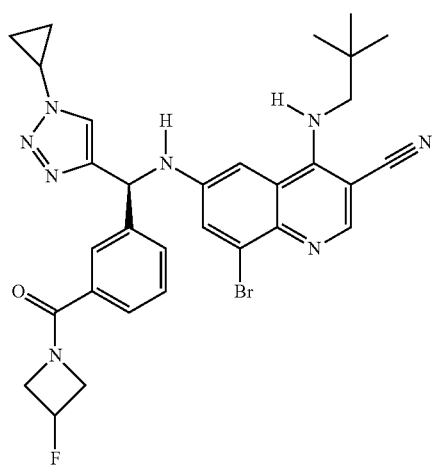 |
| 54 | 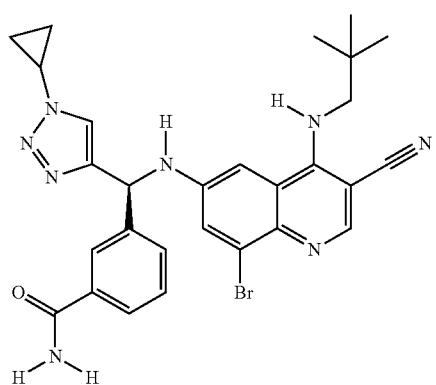 |
| 55 | 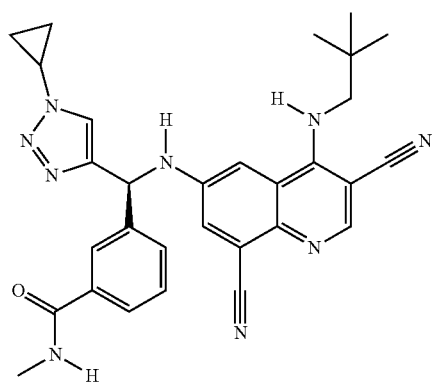 |

TABLE 1-continued

| Compound | Structure |
|---|---|
| 56 | |
| 57 | |
| 58 | |

TABLE 1-continued
| Compound | Structure |
|---|---|
| 59 | 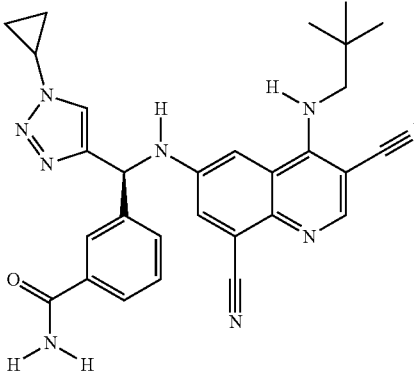 |
| 60 | 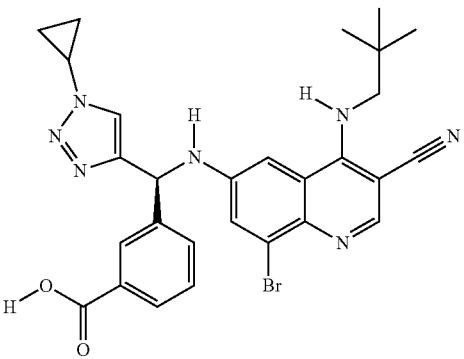 [SMILES: CC(C)(C)CNc1c(C#N)cnc2c(Br)cc(N[C@@H](c3cccc(C(=O)O)c3)c3cn(C4CC4)nn3)cc12] |
| 61 | 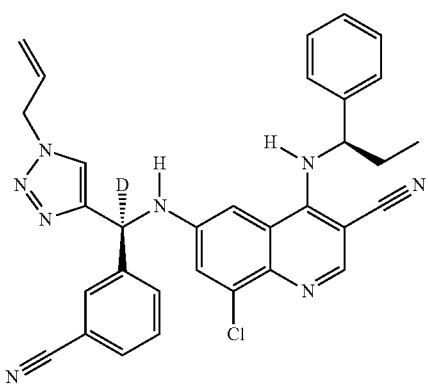 |
| 62 | 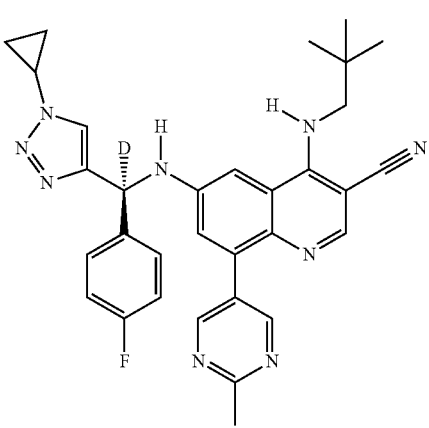 |

TABLE 1-continued

| Compound | Structure |
|---|---|
| 63 | |
| 64 | |
| 65 | |
| 66 | |

TABLE 1-continued
| Compound | Structure |
|---|---|
| 67 | 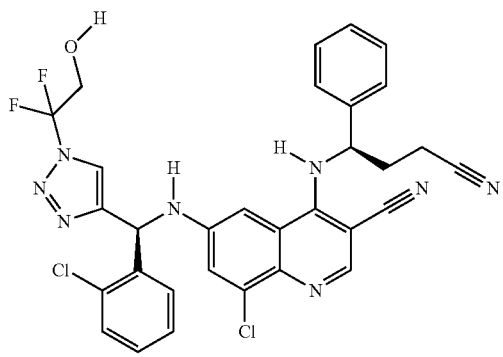 [SMILES: N#CCC[C@@H](Nc1c(C#N)cnc2c(Cl)cc(N[C@H](c3cn(C(F)(F)CO)nn3)c3ccccc3Cl)cc12)c1ccccc1] |
| 68 | 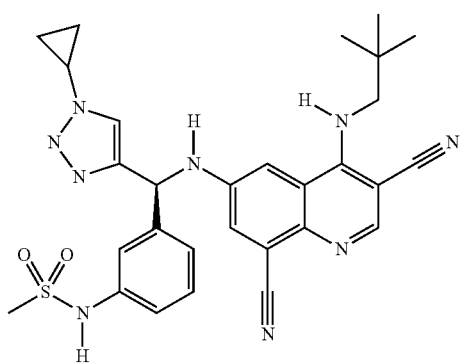 [SMILES: CC(C)(C)CNc1c(C#N)cnc2c(C#N)cc(N[C@H](C3=CN(C4CC4)NN3)c3cccc(NS(C)(=O)=O)c3)cc12] |
| 69 | 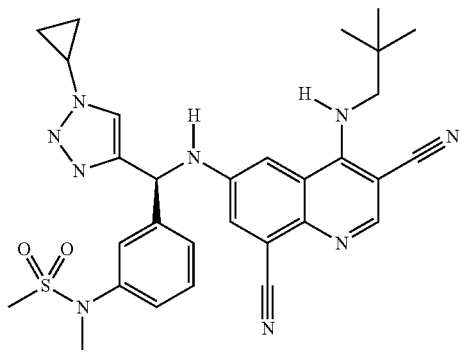 [SMILES: CN(c1cccc([C@H](Nc2cc(C#N)c3ncc(C#N)c(NCC(C)(C)C)c3c2)C2=CN(C3CC3)NN2)c1)S(C)(=O)=O] |
| 70 | 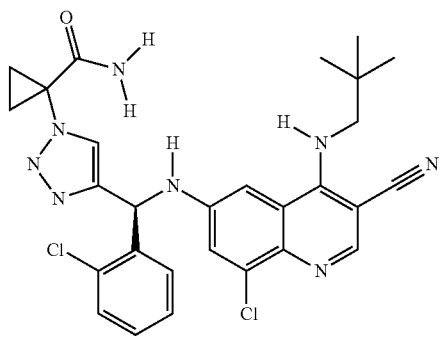 [SMILES: CC(C)(C)CNc1c(C#N)cnc2c(Cl)cc(N[C@H](C3=CN(C4(C(N)=O)CC4)NN3)c3ccccc3Cl)cc12] |

TABLE 1-continued

| Compound | Structure |
|---|---|
| 71 | |
| 72 | |
| 73 | |
| 74 | |

TABLE 1-continued
| Compound | Structure |
|---|---|
| 75 | 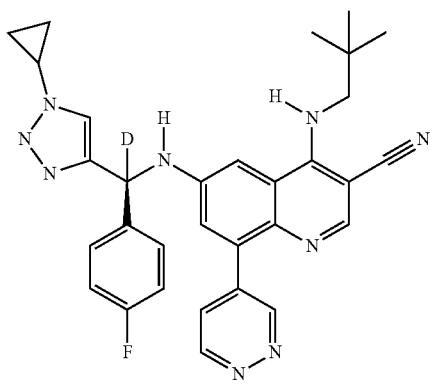 [SMILES: [2H][C@](Nc1cc(-c2ccnnc2)c2ncc(C#N)c(NCC(C)(C)C)c2c1)(C1=CN(C2CC2)NN1)c1ccc(F)cc1] |
| 76 | 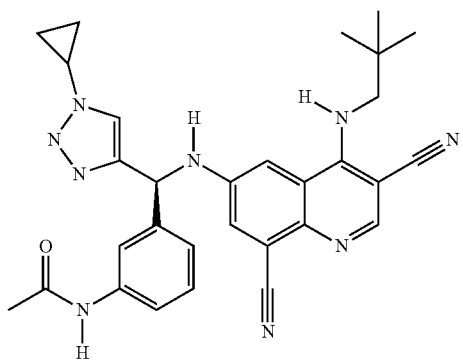 [SMILES: CC(=O)Nc1cccc([C@H](Nc2cc(C#N)c3ncc(C#N)c(NCC(C)(C)C)c3c2)C2=CN(C3CC3)NN2)c1] |
| 77 | 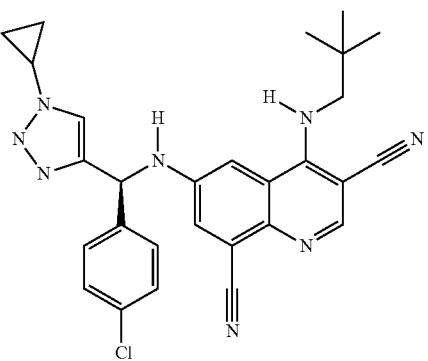 [SMILES: CC(C)(C)CNc1c(C#N)cnc2c(C#N)cc(N[C@H](C3=CN(C4CC4)NN3)c3ccc(Cl)cc3)cc12] |
| 78 | 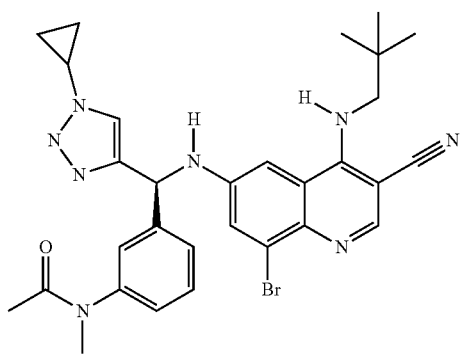 [SMILES: CC(=O)N(C)c1cccc([C@H](Nc2cc(Br)c3ncc(C#N)c(NCC(C)(C)C)c3c2)C2=CN(C3CC3)NN2)c1] |

TABLE 1-continued

| Compound | Structure |
|---|---|
| 79 | |
| 80 | |
| 81 | |
| 82 | |

TABLE 1-continued
| Compound | Structure |
|---|---|
| 83 | 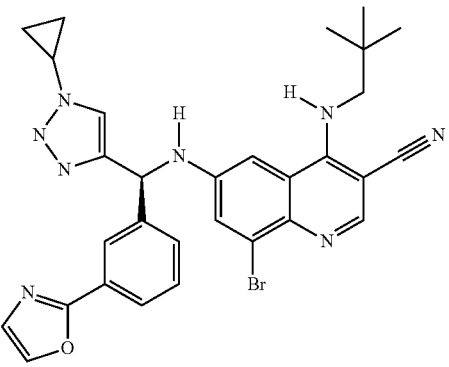 [SMILES: CC(C)(C)CNc1c(C#N)cnc2c(Br)cc(N[C@H](C3=CN(C4CC4)NN3)c3cccc(-c4ncco4)c3)cc12] |
| 84 | 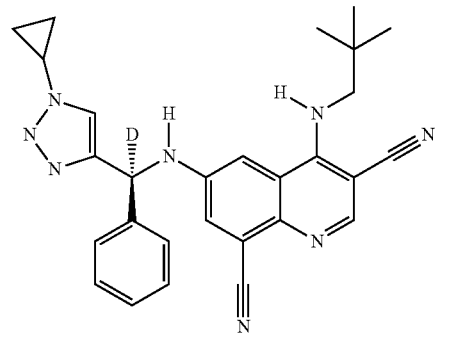 |
| 85 | 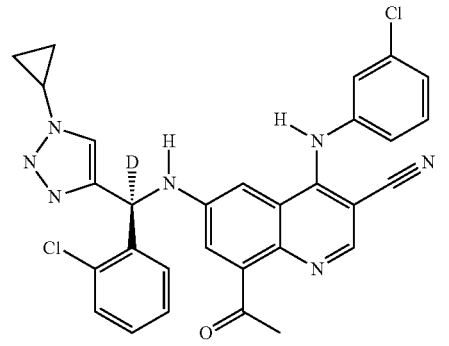 |
| 86 | 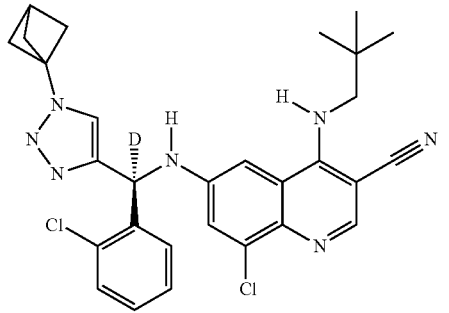 |

TABLE 1-continued
| Compound | Structure |
|---|---|
| 87 | 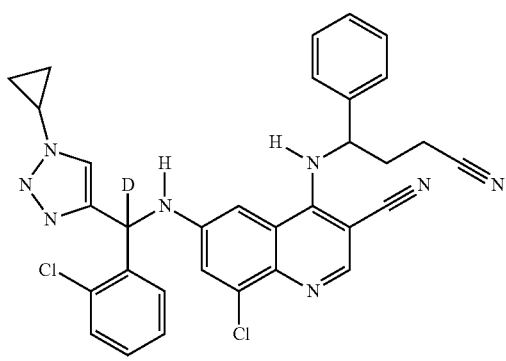 [SMILES: [2H]C(Nc1cc(Cl)c2ncc(C#N)c(NC(CCC#N)c3ccccc3)c2c1)(C1=CN(C2CC2)NN1)c1ccccc1Cl] |
| 88 | 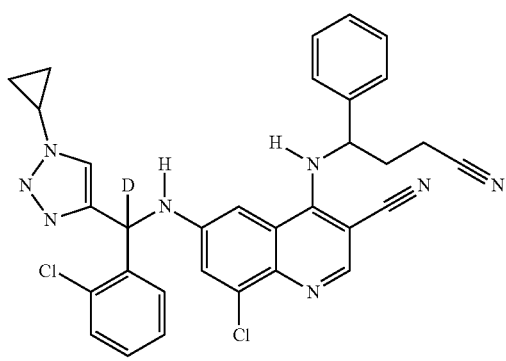 [SMILES: [2H]C(Nc1cc(Cl)c2ncc(C#N)c(NC(CCC#N)c3ccccc3)c2c1)(C1=CN(C2CC2)NN1)c1ccccc1Cl] |
| 89 | 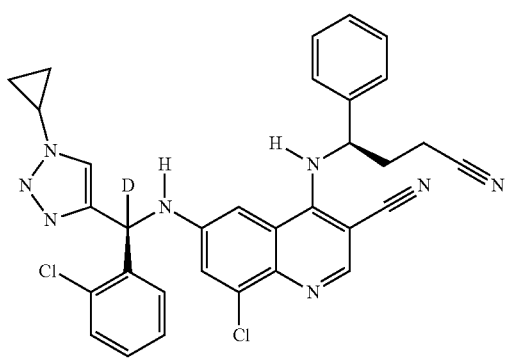 [SMILES: [2H][C@](Nc1cc(Cl)c2ncc(C#N)c(N[C@H](CCC#N)c3ccccc3)c2c1)(C1=CN(C2CC2)NN1)c1ccccc1Cl] |
| 90 | 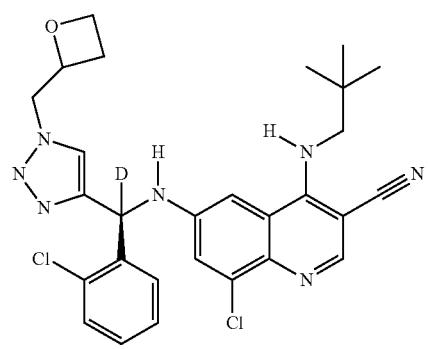 [SMILES: [2H][C@](Nc1cc(Cl)c2ncc(C#N)c(NCC(C)(C)C)c2c1)(C1=CN(CC2CCO2)NN1)c1ccccc1Cl] |

TABLE 1-continued

| Compound | Structure |
|---|---|
| 91 | |
| 92 | |
| 93 | |
| 94 | |

TABLE 1-continued
| Compound | Structure |
|---|---|
| 95 | 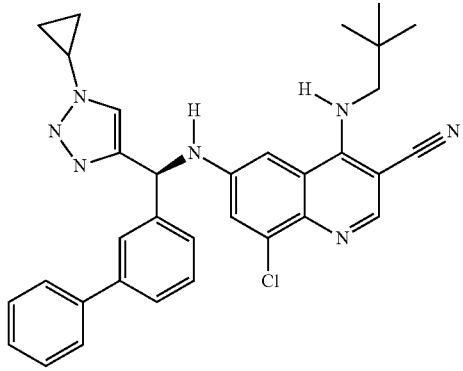 [SMILES: CC(C)(C)CNc1c(C#N)cnc2c(Cl)cc(N[C@H](C3=CN(C4CC4)NN3)c3cccc(-c4ccccc4)c3)cc12] |
| 96 | 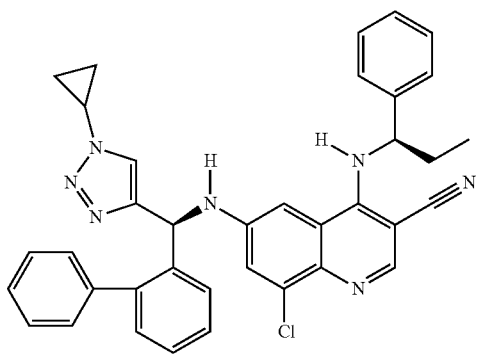 [SMILES: CC[C@@H](Nc1c(C#N)cnc2c(Cl)cc(N[C@H](c3cn(C4CC4)nn3)c3ccccc3-c3ccccc3)cc12)c1ccccc1] |
| 97 | 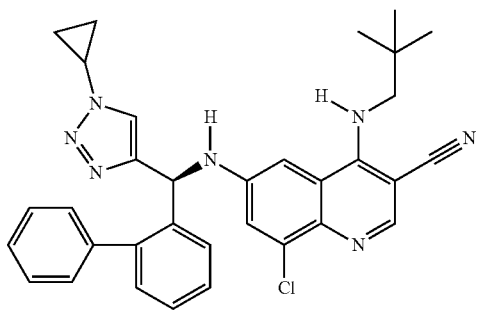 [SMILES: CC(C)(C)CNc1c(C#N)cnc2c(Cl)cc(N[C@H](c3cn(C4CC4)nn3)c3ccccc3-c3ccccc3)cc12] |
| 98 | 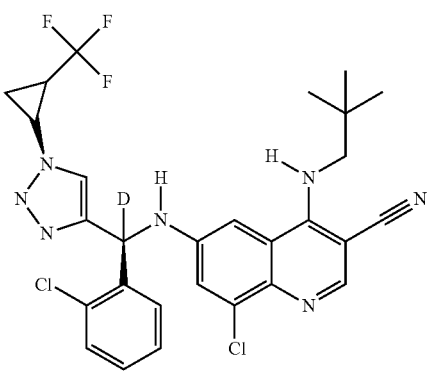 |

TABLE 1-continued

| Compound | Structure |
|---|---|
| 99 | |
| 100 | |
| 101 | |
| 102 | |

TABLE 1-continued

| Compound | Structure |
|---|---|
| 103 | |
| 104 | |
| 105 | |
| 106 | |

TABLE 1-continued

| Compound | Structure |
|---|---|
| 107 | |
| 108 | |
| 109 | |
| 110 | |

TABLE 1-continued

| Compound | Structure |
|---|---|
| 111 | |
| 116 | |
| 113 | |
| 114 | |

TABLE 1-continued
| Compound | Structure |
|---|---|
| 115 | 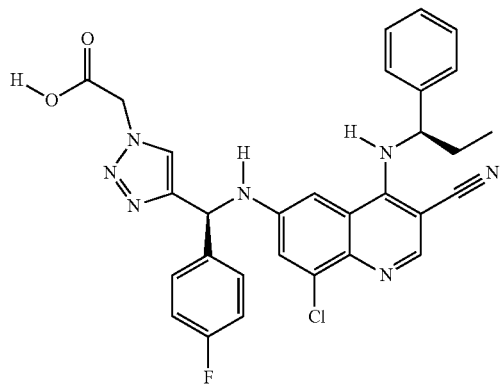 |
| 116 | 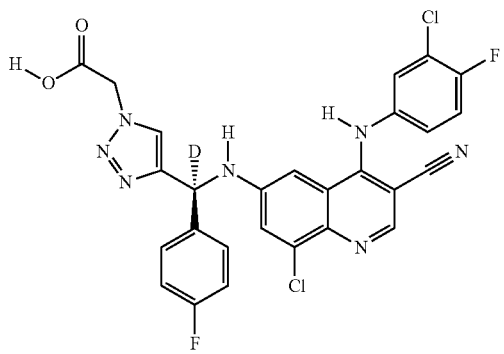 |
| 117 | 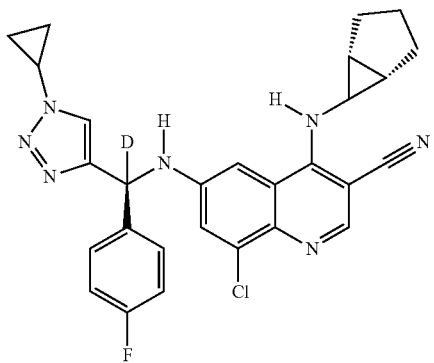 [SMILES: [2H][C@@](Nc1cc(Cl)c2ncc(C#N)c(NC3[C@H]4CCC[C@@H]34)c2c1)(c1ccc(F)cc1)c1cn(C2CC2)nn1] |
| 118 | 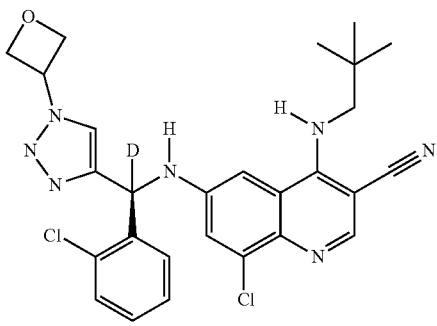 [SMILES: [2H][C@](Nc1cc(Cl)c2ncc(C#N)c(NCC(C)(C)C)c2c1)(C1=CN(C2COC2)NN1)c1ccccc1Cl] |

TABLE 1-continued

| Compound | Structure |
|---|---|
| 119 | |
| 120 | |
| 121 | |
| 122 | |
| 123 | |

TABLE 1-continued
| Compound | Structure |
|---|---|
| 124 | 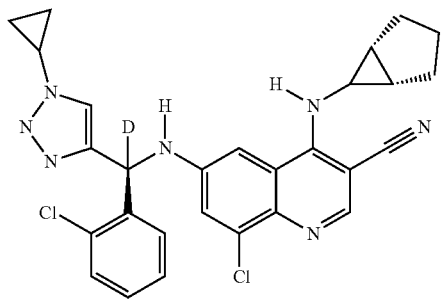 [SMILES: [2H][C@](Nc1cc(Cl)c2ncc(C#N)c(NC3[C@H]4CCC[C@@H]34)c2c1)(C1=CN(C2CC2)NN1)c1ccccc1Cl] |
| 125 | 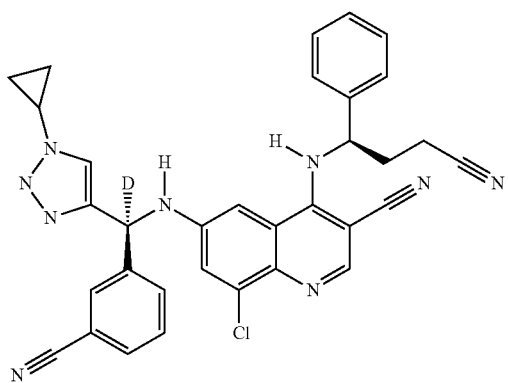 |
| 126 | 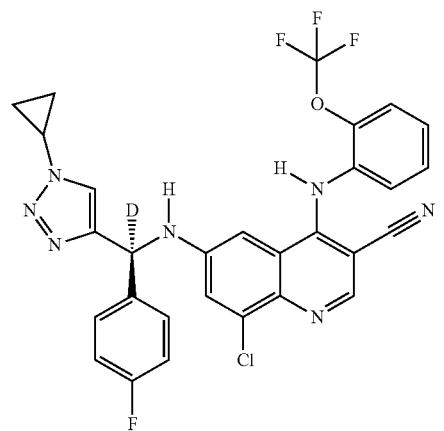 |
| 127 | 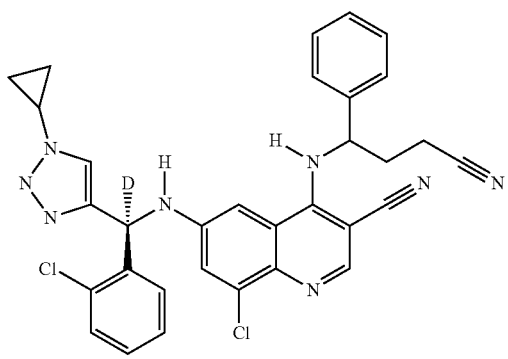 |

TABLE 1-continued
| Compound | Structure |
|---|---|
| 128 | 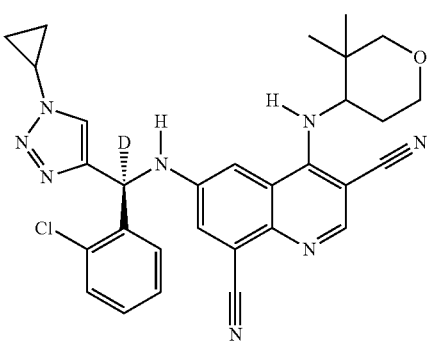 |
| 129 | 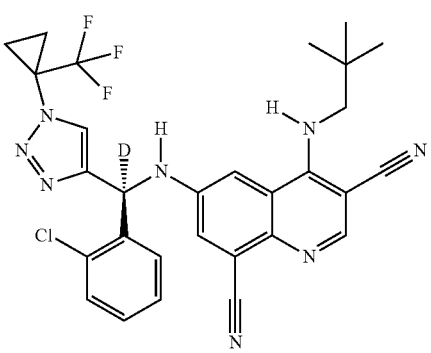 |
| 130 | 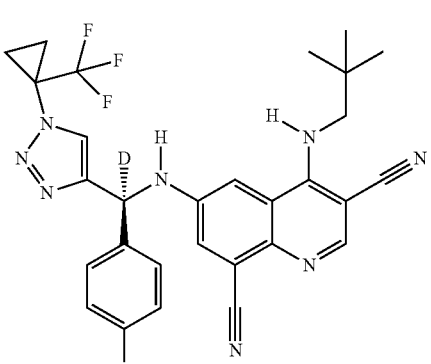 |
| 131 | 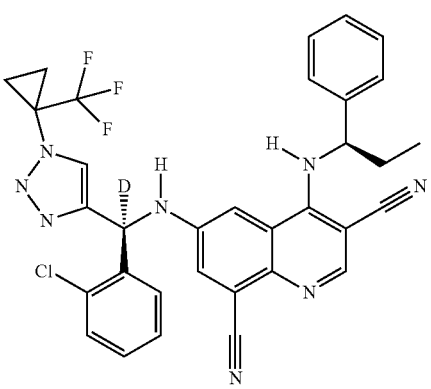 |

TABLE 1-continued

| Compound | Structure |
|---|---|
| 132 | |
| 133 | |
| 134 | |
| 135 | |

TABLE 1-continued

| Compound | Structure |
|---|---|
| 136 | |
| 137 | |
| 138 | |
| 139 | |

TABLE 1-continued

| Compound | Structure |
|---|---|
| 140 | |
| 141 | |
| 142 | |
| 143 | |

TABLE 1-continued

| Compound | Structure |
|---|---|
| 144 | |
| 145 | |
| 146 | |
| 147 | |

TABLE 1-continued

| Compound | Structure |
|---|---|
| 148 | |
| 149 | |
| 150 | |
| 151 | |

TABLE 1-continued

| Compound | Structure |
|---|---|
| 152 | |
| 153 | |
| 154 | |
| 155 | |

TABLE 1-continued

| Compound | Structure |
|---|---|
| 156 | |
| 157 | |
| 158 | |
| 159 | |

TABLE 1-continued

| Compound | Structure |
|---|---|
| 160 | |
| 161 | |
| 162 | |
| 163 | |

TABLE 1-continued

| Compound | Structure |
|---|---|
| 164 | |
| 165 | |
| 166 | |
| 167 | |

TABLE 1-continued
| Compound | Structure |
|---|---|
| 168 | 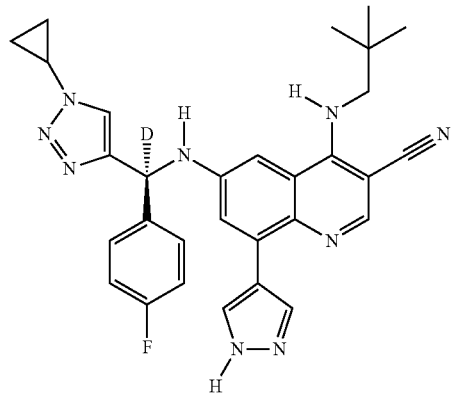 |
| 169 | 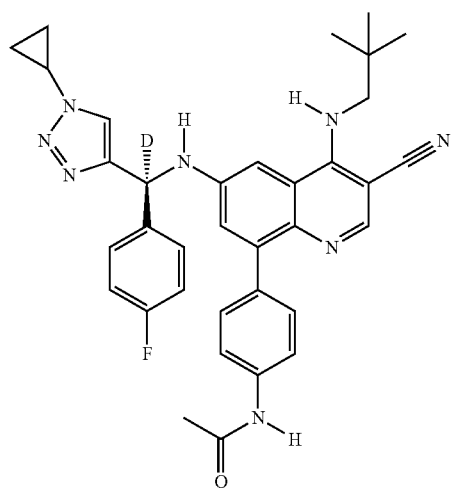 |
| 170 | 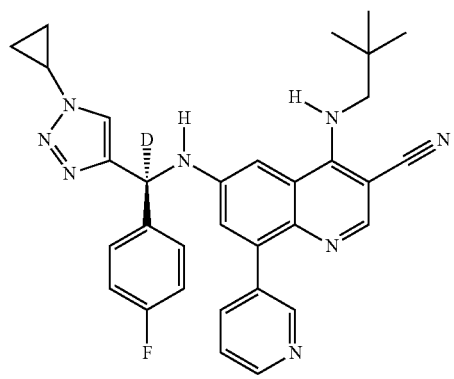 |

TABLE 1-continued

| Compound | Structure |
|---|---|
| 171 | *(chemical structure)* |
| 172 | *(chemical structure)* |
| 173 | *(chemical structure)* |
| 174 | *(chemical structure)* |

TABLE 1-continued

| Compound | Structure |
|---|---|
| 175 | |
| 176 | |
| 177 | |
| 178 | |

TABLE 1-continued

| Compound | Structure |
|---|---|
| 179 | |
| 180 | |
| 181 | |
| 182 | |

TABLE 1-continued

| Compound | Structure |
|---|---|
| 183 | |
| 184 | |
| 185 | |
| 186 | |

TABLE 1-continued

| Compound | Structure |
|---|---|
| 187 | |
| 188 | |
| 189 | |
| 190 | |

TABLE 1-continued

| Compound | Structure |
|---|---|
| 191 | |
| 192 | |
| 193 | |
| 194 | |

TABLE 1-continued

| Compound | Structure |
|---|---|
| 195 | |
| 196 | |
| 197 | |
| 198 | |

TABLE 1-continued

| Compound | Structure |
|---|---|
| 199 | |
| 200 | |
| 201 | |
| 202 | |

TABLE 1-continued

| Compound | Structure |
|---|---|
| 203 | |
| 204 | |
| 205 | |
| 206 | |

TABLE 1-continued

| Compound | Structure |
|---|---|
| 207 | |
| 208 | |
| 209 | |
| 210 | |

TABLE 1-continued

| Compound | Structure |
|---|---|
| 211 | |
| 212 | |
| 213 | |
| 214 | |

TABLE 1-continued
| Compound | Structure |
|---|---|
| 215 | 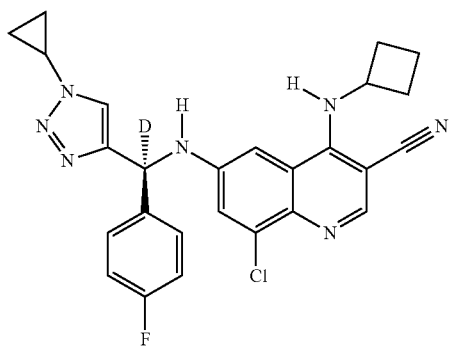 |
| 216 | 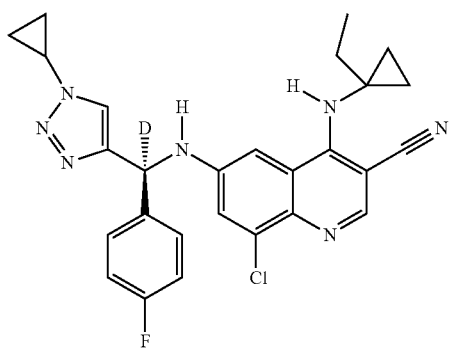 |
| 217 | 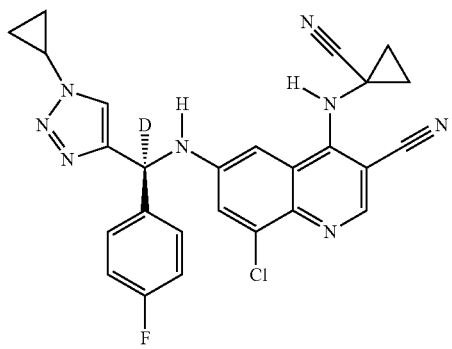 |
| 218 | 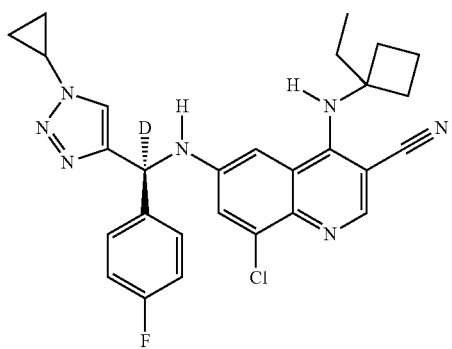 |

TABLE 1-continued

| Compound | Structure |
|---|---|
| 219 | |
| 220 | |
| 221 | |
| 222 | |

TABLE 1-continued

| Compound | Structure |
|---|---|
| 223 | |
| 224 | |
| 225 | |
| 226 | |

TABLE 1-continued
| Compound | Structure |
|---|---|
| 227 | 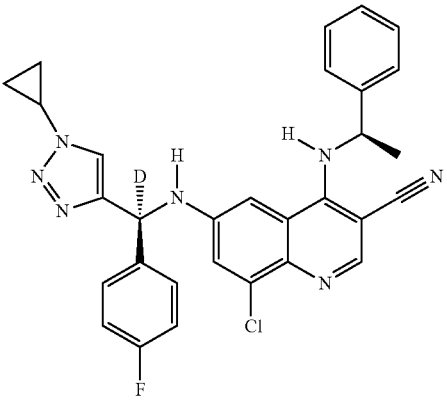 |
| 228 | 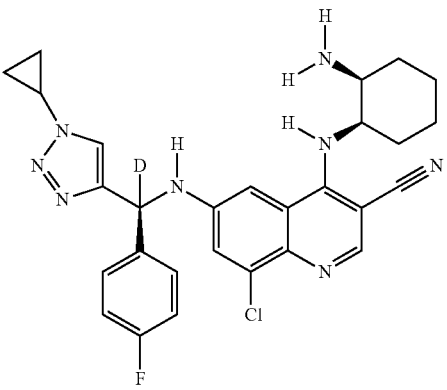 [SMILES: [2H][C@@](Nc1cc(Cl)c2ncc(C#N)c(N[C@@H]3CCCC[C@@H]3N)c2c1)(c1ccc(F)cc1)c1cn(C2CC2)nn1] |
| 229 | 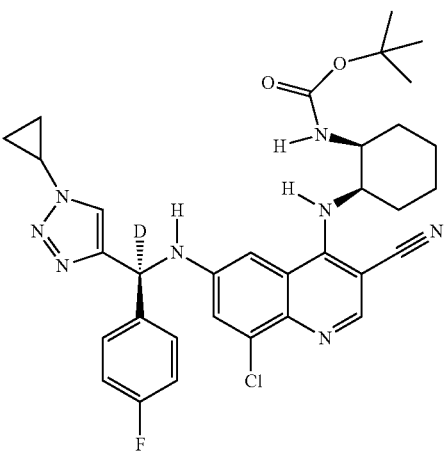 |

TABLE 1-continued

| Compound | Structure |
|---|---|
| 230 | |
| 231 | |
| 232 | |
| 233 | |

TABLE 1-continued
| Compound | Structure |
|---|---|
| 234 | 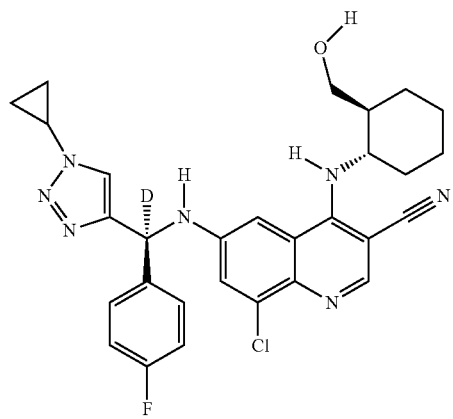 |
| 235 | 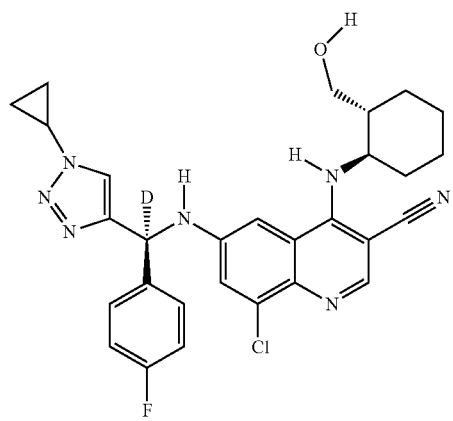 |
| 236 | 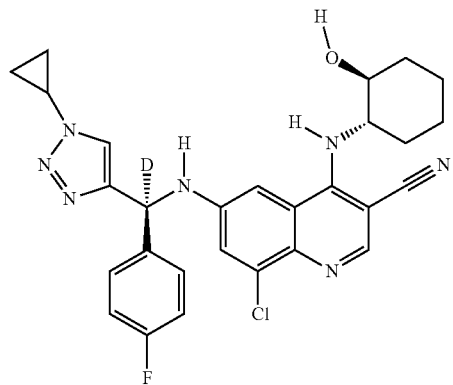 |
| 237 | 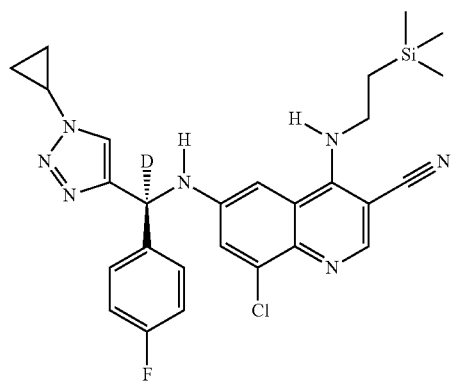 |

TABLE 1-continued
| Compound | Structure |
|---|---|
| 238 | 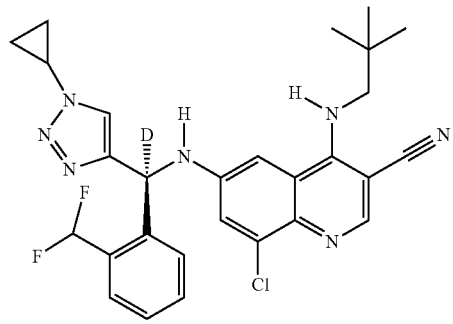 |
| 239 | 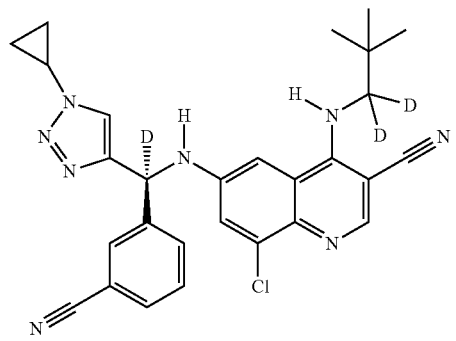 |
| 240 | 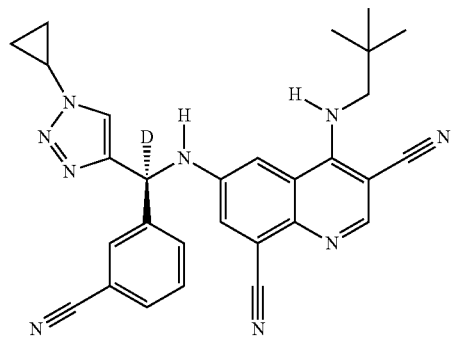 |
| 241 | 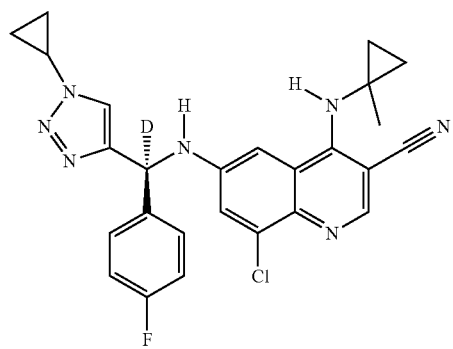 |

TABLE 1-continued

| Compound | Structure |
|---|---|
| 242 | |
| 243 | |
| 244 | |
| 245 | |

TABLE 1-continued

| Compound | Structure |
|---|---|
| 246 | |
| 247 | |
| 248 | |
| 249 | |

TABLE 1-continued

| Compound | Structure |
|---|---|
| 250 | |
| 251 | |
| 252 | |
| 253 | |

TABLE 1-continued
| Compound | Structure |
|---|---|
| 254 | 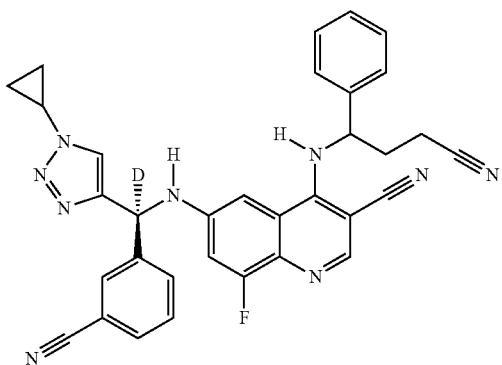 |
| 255 | 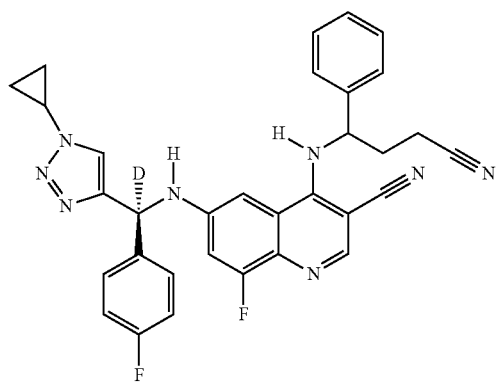 |
| 256 | 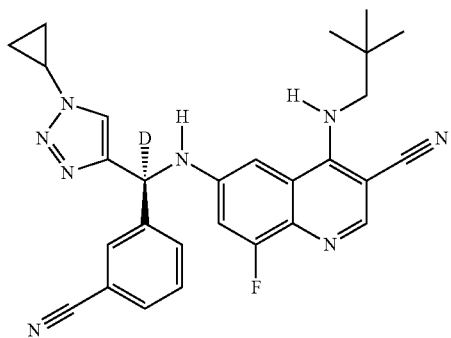 |
| 257 | 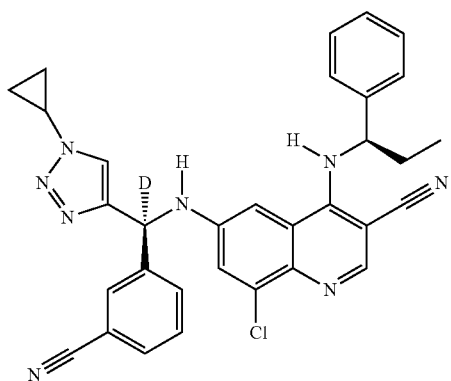 |

TABLE 1-continued
| Compound | Structure |
|---|---|
| 258 | 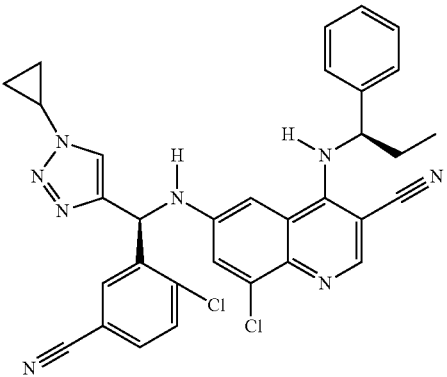 [SMILES: CC[C@@H](Nc1c(C#N)cnc2c(Cl)cc(N[C@H](c3cn(C4CC4)nn3)c3cc(C#N)ccc3Cl)cc12)c1ccccc1] |
| 259 | 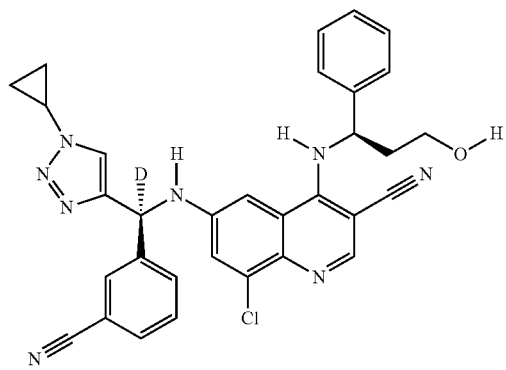 |
| 260 | 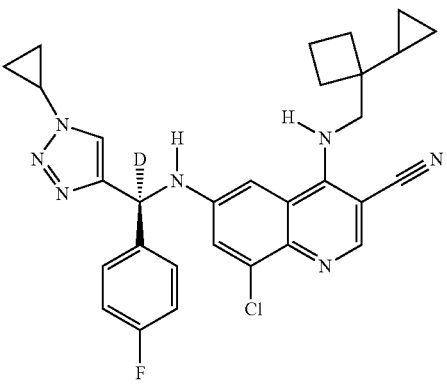 |
| 261 | 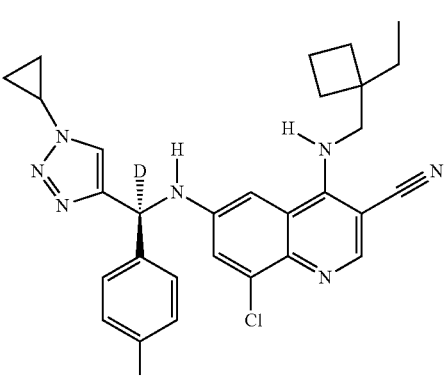 |

TABLE 1-continued

| Compound | Structure |
|---|---|
| 262 | |
| 263 | |
| 264 | |
| 265 | |

TABLE 1-continued
| Compound | Structure |
|---|---|
| 266 | 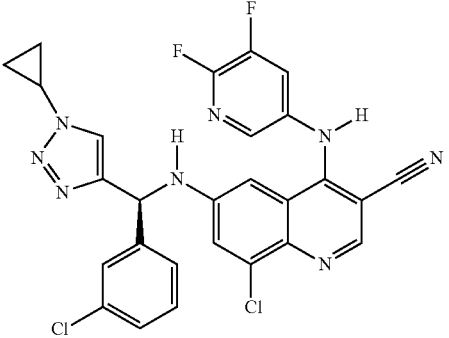 |
| 267 | 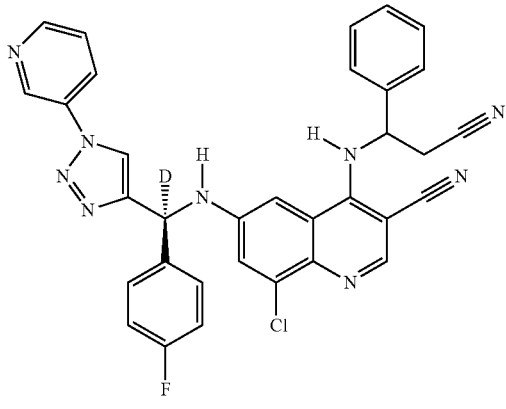 |
| 268 | 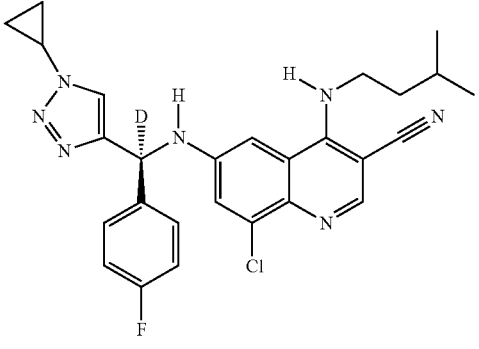 |
| 269 | 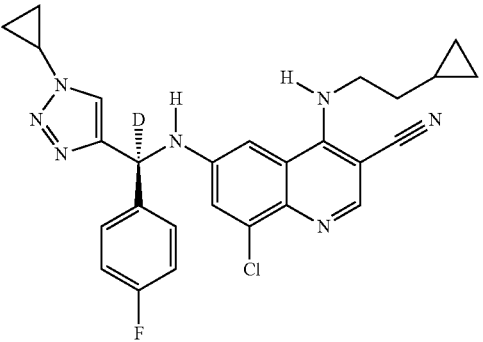 |

TABLE 1-continued

| Compound | Structure |
|---|---|
| 270 | |
| 271 | |
| 272 | |
| 273 | |

TABLE 1-continued

| Compound | Structure |
|---|---|
| 274 | |
| 275 | |
| 276 | |
| 277 | |

TABLE 1-continued

| Compound | Structure |
|---|---|
| 278 | |
| 279 | |
| 280 | |
| 281 | |

TABLE 1-continued

| Compound | Structure |
|---|---|
| 282 | |
| 283 | |
| 284 | |
| 285 | |

TABLE 1-continued

| Compound | Structure |
|---|---|
| 286 | |
| 287 | |
| 288 | |
| 289 | |

TABLE 1-continued

| Compound | Structure |
|---|---|
| 290 | |
| 291 | |
| 292 | |
| 293 | |

TABLE 1-continued
| Compound | Structure |
|---|---|
| 294 | 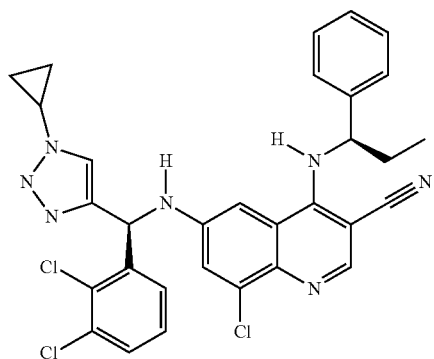 [SMILES: CC[C@@H](Nc1c(C#N)cnc2c(Cl)cc(N[C@H](C3=CN(C4CC4)NN3)c3cccc(Cl)c3Cl)cc12)c1ccccc1] |
| 295 | 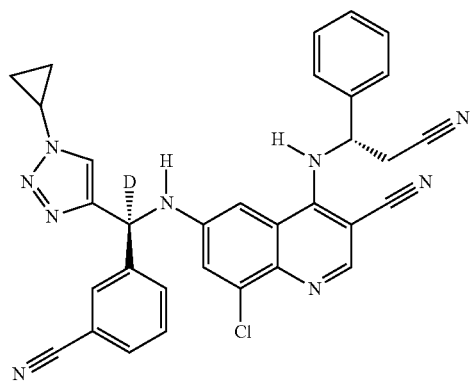 |
| 296 | 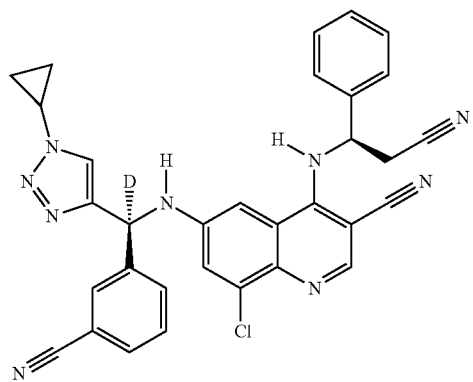 |
| 297 | 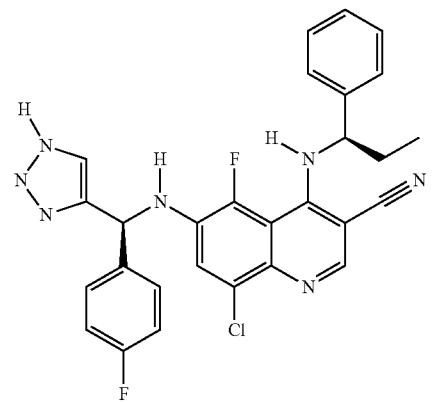 [SMILES: CC[C@@H](Nc1c(C#N)cnc2c(Cl)cc(N[C@H](C3=CNNN3)c3ccc(F)cc3)c(F)c12)c1ccccc1] |

TABLE 1-continued

| Compound | Structure |
|---|---|
| 298 | |
| 299 | |
| 300 | |
| 301 | |

TABLE 1-continued

| Compound | Structure |
|---|---|
| 302 | |
| 303 | |
| 304 | |
| 305 | |

TABLE 1-continued

| Compound | Structure |
|---|---|
| 306 | |
| 307 | |
| 308 | |
| 309 | |

TABLE 1-continued

| Compound | Structure |
|---|---|
| 310 | |
| 311 | |
| 312 | |
| 313 | |

TABLE 1-continued
| Compound | Structure |
|---|---|
| 314 | 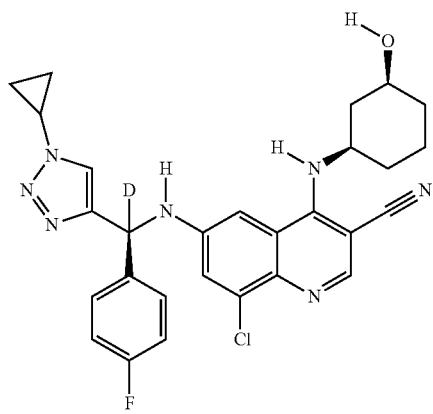 [SMILES: [2H][C@@](Nc1cc(Cl)c2ncc(C#N)c(N[C@@H]3CCC[C@H](O)C3)c2c1)(c1ccc(F)cc1)c1cn(C2CC2)nn1] |
| 315 | 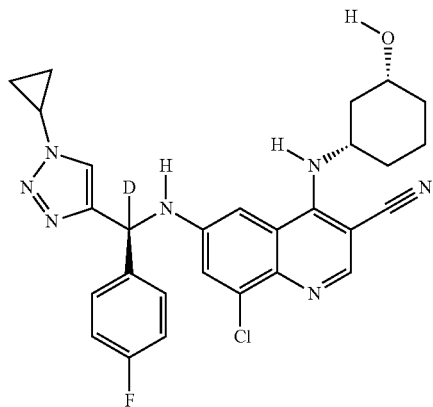 |
| 316 | 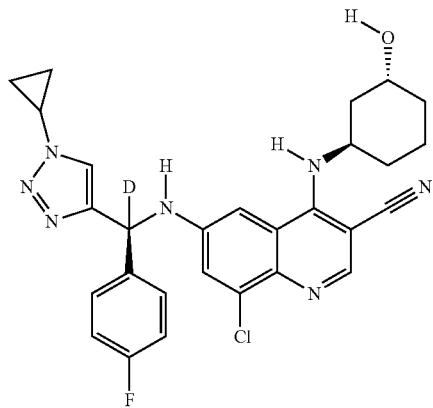 [SMILES: [2H][C@@](Nc1cc(Cl)c2ncc(C#N)c(N[C@@H]3CCC[C@@H](O)C3)c2c1)(c1ccc(F)cc1)c1cn(C2CC2)nn1] |
| 317 | 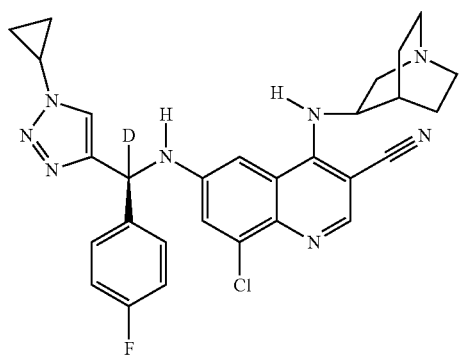 [SMILES: [2H][C@@](Nc1cc(Cl)c2ncc(C#N)c(NC3CN4CCC3CC4)c2c1)(c1ccc(F)cc1)c1cn(C2CC2)nn1] |

TABLE 1-continued

| Compound | Structure |
|---|---|
| 318 | |
| 319 | |
| 320 | |
| 321 | |

TABLE 1-continued
| Compound | Structure |
|---|---|
| 322 | 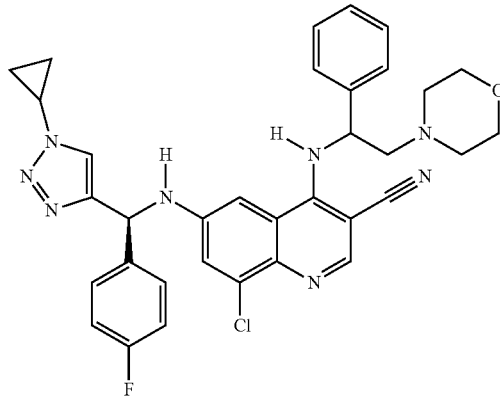 |
| 323 | 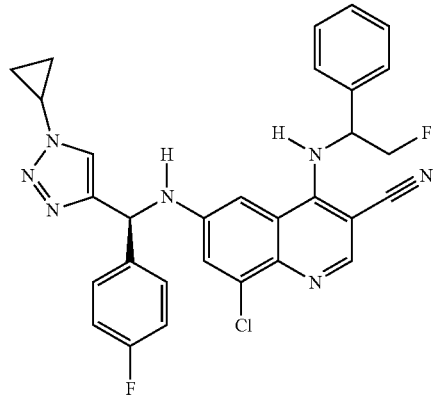 [SMILES: N#Cc1cnc2c(Cl)cc(N[C@@H](c3ccc(F)cc3)c3cn(C4CC4)nn3)cc2c1NC(CF)c1ccccc1] |
| 324 | 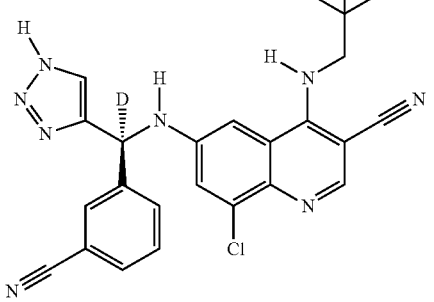 |
| 325 | 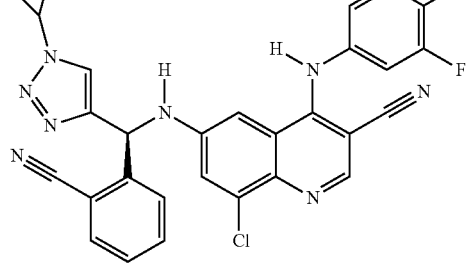 |

TABLE 1-continued
| Compound | Structure |
|---|---|
| 326 | 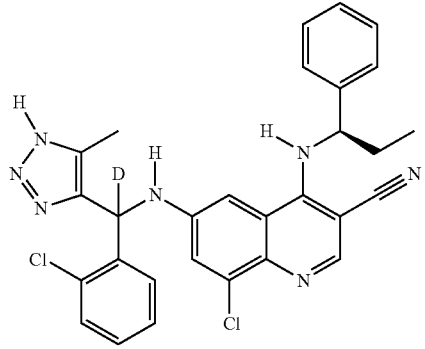 [SMILES: [2H]C(Nc1cc(Cl)c2ncc(C#N)c(N[C@H](CC)c3ccccc3)c2c1)(c1ccccc1Cl)c1nn[nH]c1C] |
| 327 | 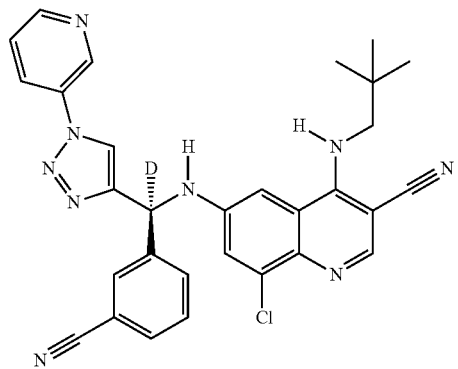 |
| 328 | 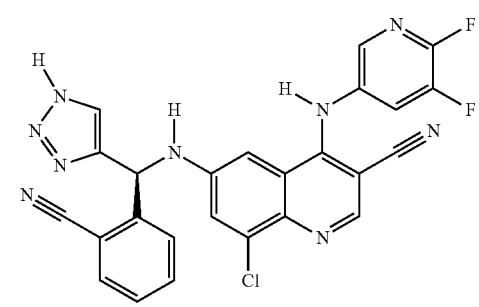 [SMILES: N#Cc1ccccc1[C@H](Nc1cc(Cl)c2ncc(C#N)c(Nc3cnc(F)c(F)c3)c2c1)c1c[nH]nn1] |
| 329 | 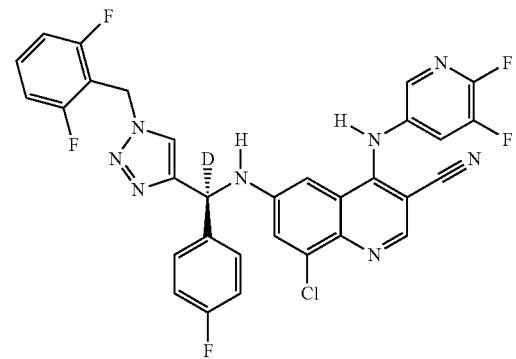 |

TABLE 1-continued

| Compound | Structure |
|---|---|
| 330 | |
| 331 | |
| 332 | |
| 333 | |

TABLE 1-continued
| Compound | Structure |
|---|---|
| 334 | 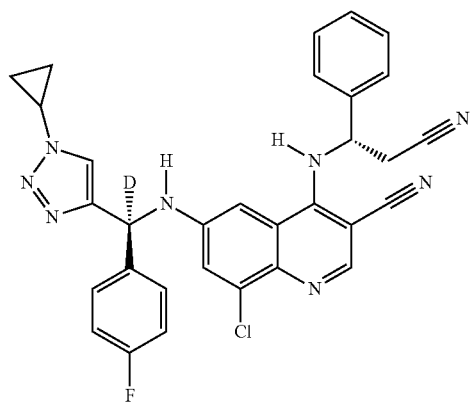 |
| 335 | 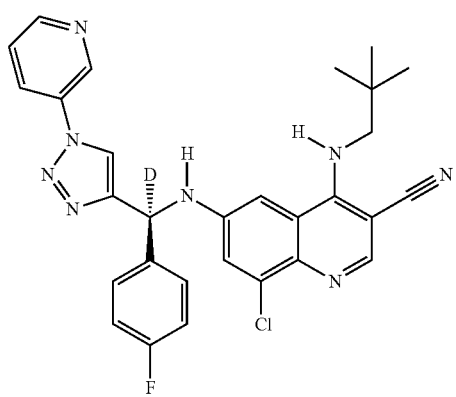 |
| 336 | 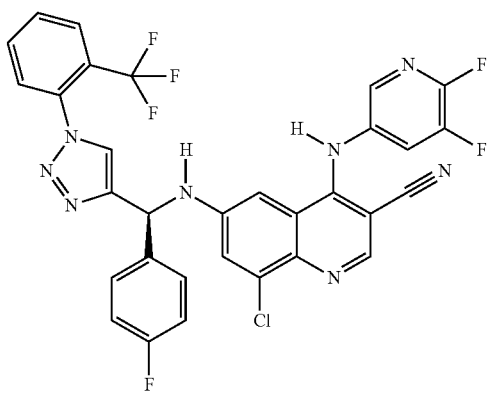 [SMILES: N#Cc1cnc2c(Cl)cc(N[C@@H](c3ccc(F)cc3)c3cn(-c4ccccc4C(F)(F)F)nn3)cc2c1Nc1cnc(F)c(F)c1] |
| 337 | 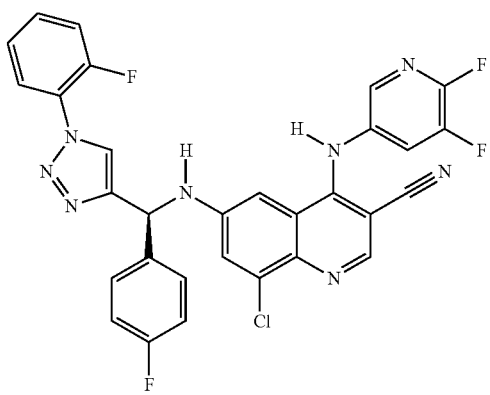 [SMILES: N#Cc1cnc2c(Cl)cc(N[C@@H](c3ccc(F)cc3)c3cn(-c4ccccc4F)nn3)cc2c1Nc1cnc(F)c(F)c1] |

TABLE 1-continued
| Compound | Structure |
|---|---|
| 338 | 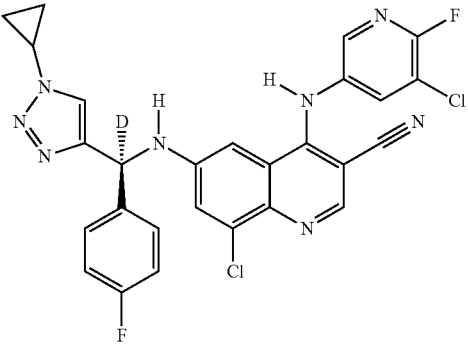 |
| 339 | 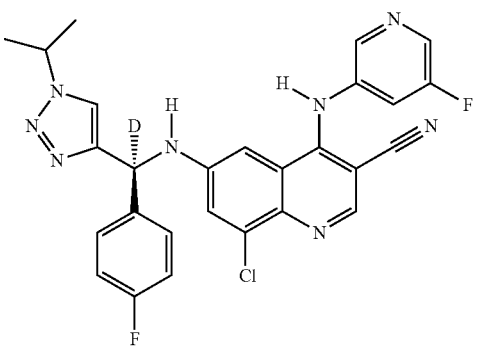 |
| 340 | 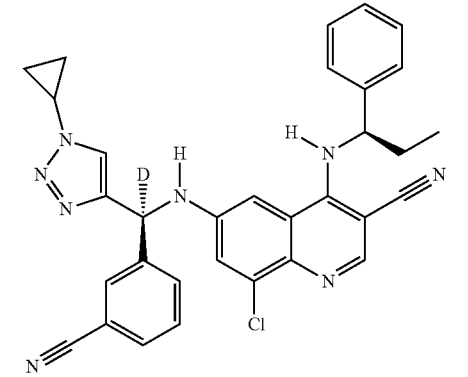 |
| 341 | 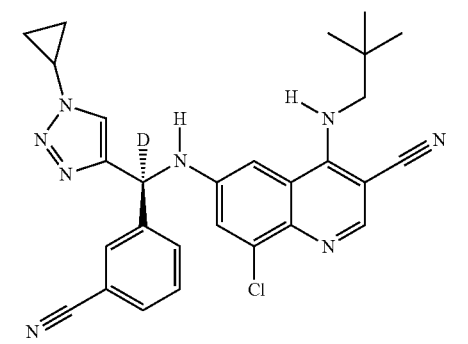 |

TABLE 1-continued
| Compound | Structure |
|---|---|
| 342 | 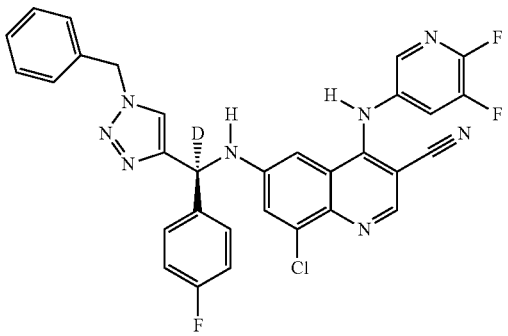 |
| 343 | 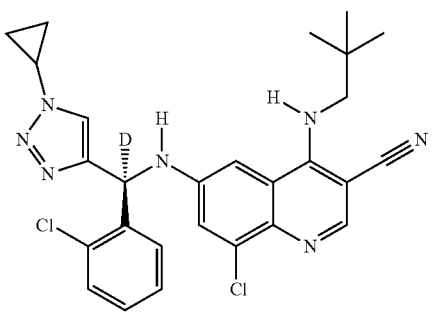 |
| 344 | 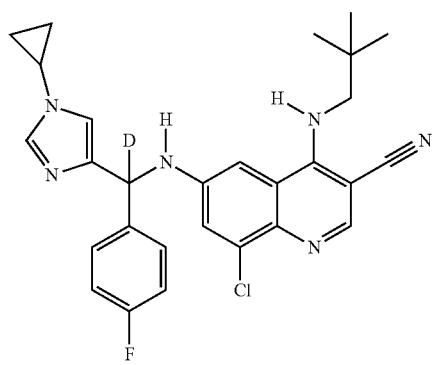 [SMILES: [2H]C(Nc1cc(Cl)c2ncc(C#N)c(NCC(C)(C)C)c2c1)(c1ccc(F)cc1)c1cn(C2CC2)cn1] |
| 345 | 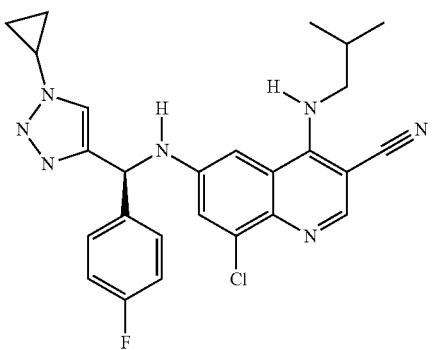 [SMILES: CC(C)CNc1c(C#N)cnc2c(Cl)cc(N[C@H](C3=CN(C4CC4)NN3)c3ccc(F)cc3)cc12] |

TABLE 1-continued
| Compound | Structure |
|---|---|
| 346 | 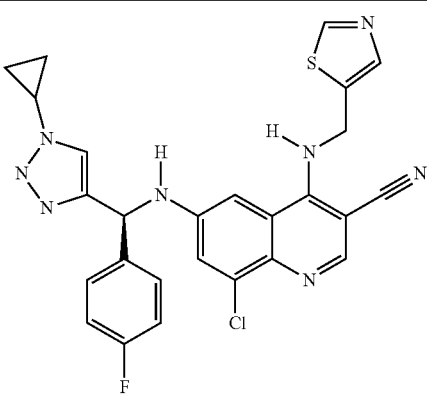 |
| 347 | 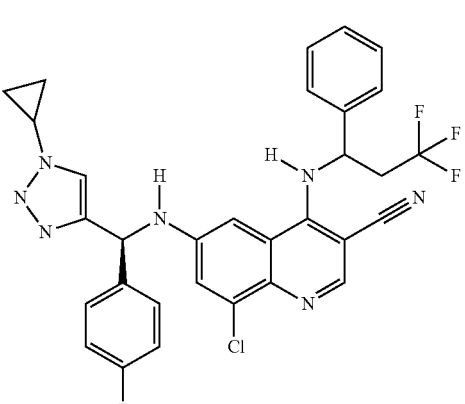 |
| 348 | 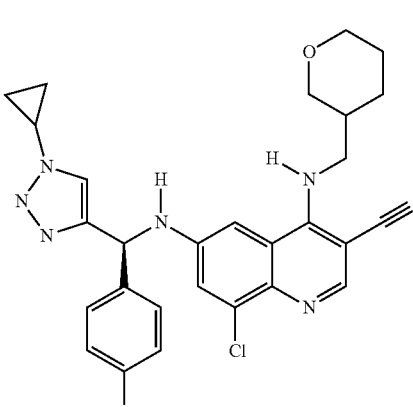 |
| 349 | 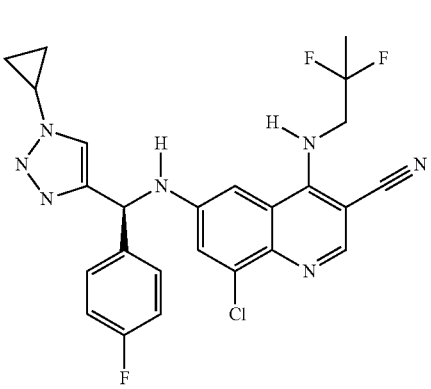 [SMILES: CC(F)(F)CNc1c(C#N)cnc2c(Cl)cc(N[C@H](C3=CN(C4CC4)NN3)c3ccc(F)cc3)cc12] |

TABLE 1-continued

| Compound | Structure |
|---|---|
| 350 | |
| 351 | |
| 352 | |
| 353 | |

TABLE 1-continued
| Compound | Structure |
|---|---|
| 354 | 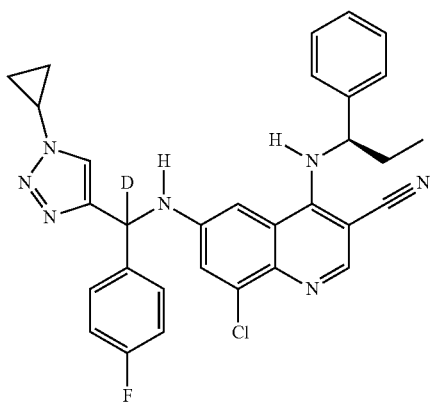 [SMILES: [2H]C(Nc1cc(Cl)c2ncc(C#N)c(N[C@H](CC)c3ccccc3)c2c1)(c1ccc(F)cc1)c1cn(C2CC2)nn1] |
| 355 | 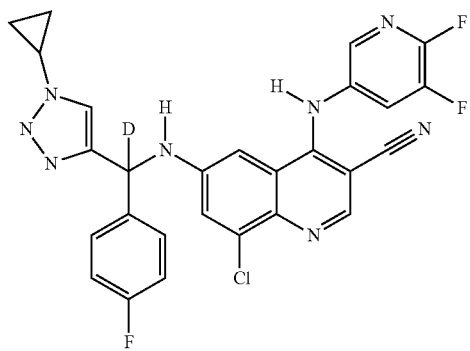 [SMILES: [2H]C(Nc1cc(Cl)c2ncc(C#N)c(Nc3cnc(F)c(F)c3)c2c1)(C1=CN(C2CC2)NN1)c1ccc(F)cc1] |
| 356 | 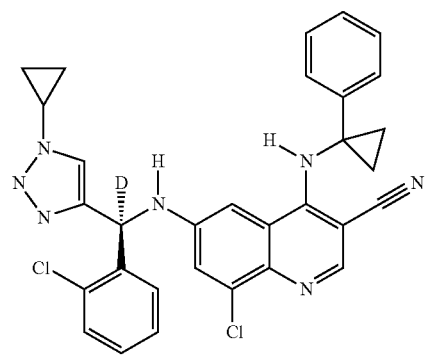 |
| 357 | 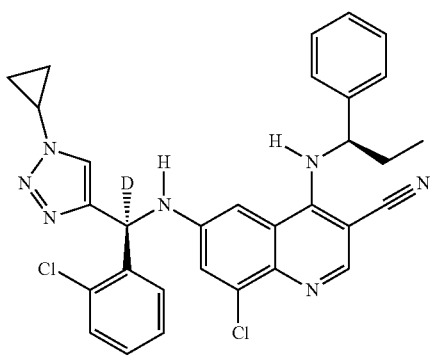 |

TABLE 1-continued

| Compound | Structure |
|---|---|
| 358 | |
| 359 | |
| 360 | |
| 361 | |

TABLE 1-continued
| Compound | Structure |
|---|---|
| 362 | 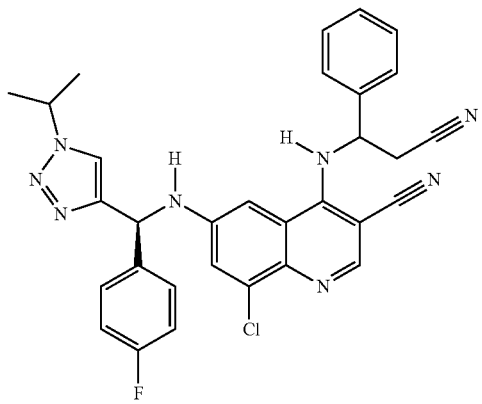 [SMILES: CC(C)n1cc([C@@H](Nc2cc(Cl)c3ncc(C#N)c(NC(CC#N)c4ccccc4)c3c2)c2ccc(F)cc2)nn1] |
| 363 | 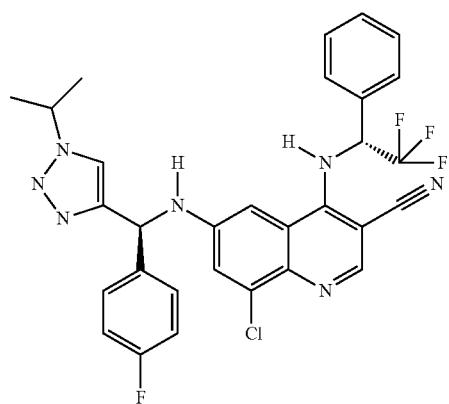 [SMILES: CC(C)N1C=C([C@@H](Nc2cc(Cl)c3ncc(C#N)c(N[C@H](c4ccccc4)C(F)(F)F)c3c2)c2ccc(F)cc2)NN1] |
| 364 | 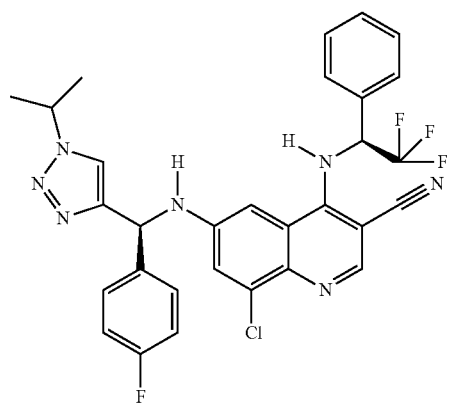 [SMILES: CC(C)n1cc([C@@H](Nc2cc(Cl)c3ncc(C#N)c(N[C@@H](c4ccccc4)C(F)(F)F)c3c2)c2ccc(F)cc2)nn1] |

TABLE 1-continued
| Compound | Structure |
|---|---|
| 365 | 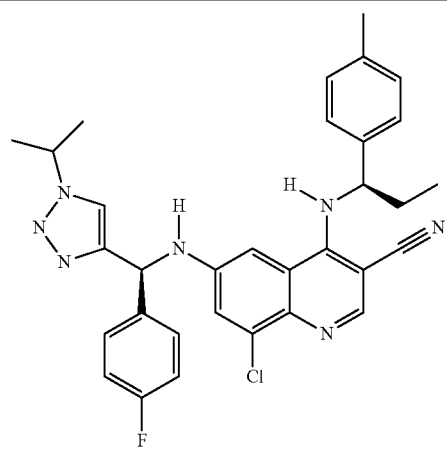 |
| 366 | 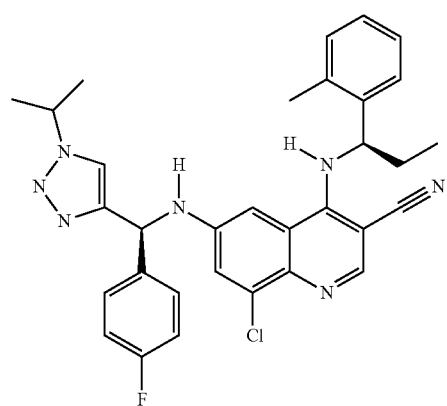 [SMILES: CC[C@@H](Nc1c(C#N)cnc2c(Cl)cc(N[C@H](C3=CN(C(C)C)NN3)c3ccc(F)cc3)cc12)c1ccccc1C] |
| 367 | 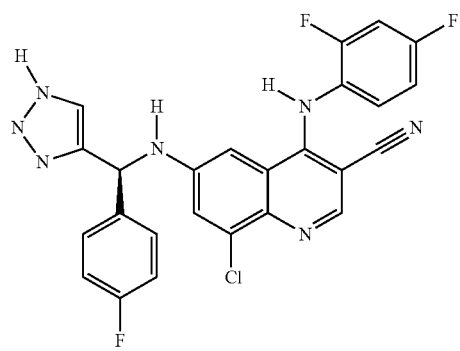 [SMILES: N#Cc1cnc2c(Cl)cc(N[C@H](C3=CNNN3)c3ccc(F)cc3)cc2c1Nc1ccc(F)cc1F] |
| 368 | 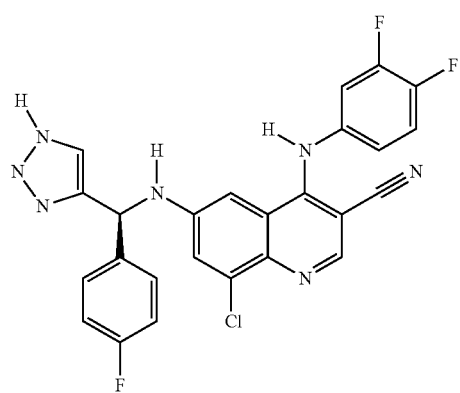 [SMILES: N#Cc1cnc2c(Cl)cc(N[C@H](C3=CNNN3)c3ccc(F)cc3)cc2c1Nc1ccc(F)c(F)c1] |

TABLE 1-continued

| Compound | Structure |
|---|---|
| 369 | |
| 370 | |
| 371 | |
| 372 | |

TABLE 1-continued
| Compound | Structure |
|---|---|
| 373 | 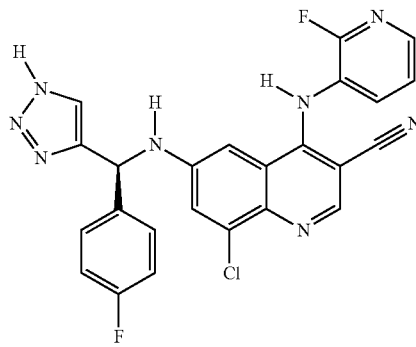 |
| 374 | 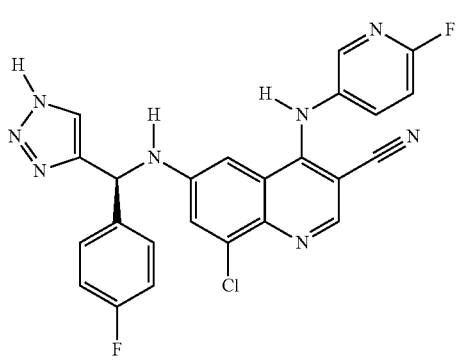 |
| 375 | 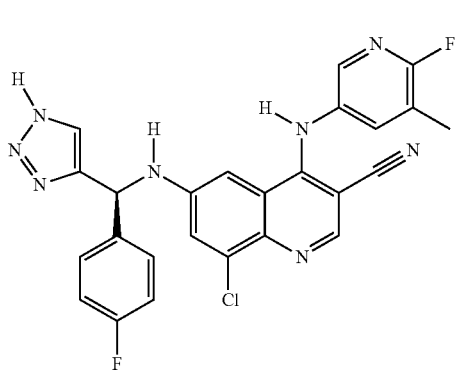 [SMILES: Cc1cc(Nc2c(C#N)cnc3c(Cl)cc(N[C@@H](c4ccc(F)cc4)c4c[nH]nn4)cc23)cnc1F] |
| 376 | 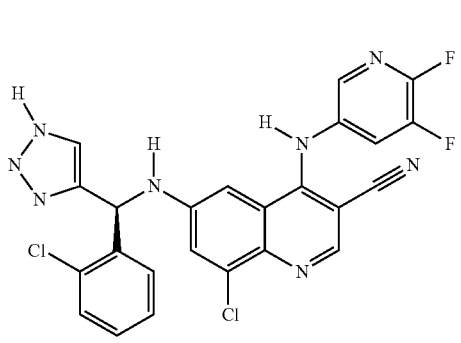 |

TABLE 1-continued

| Compound | Structure |
|---|---|
| 377 | |
| 378 | |
| 379 | |
| 380 | |

TABLE 1-continued

| Compound | Structure |
|---|---|
| 381 | |
| 382 | |
| 383 | |
| 384 | |

TABLE 1-continued

| Compound | Structure |
|---|---|
| 385 | |
| 386 | |
| 387 | |
| 388 | |

TABLE 1-continued

| Compound | Structure |
|---|---|
| 389 | |
| 390 | |
| 391 | |
| 392 | |

TABLE 1-continued

| Compound | Structure |
|---|---|
| 393 | |
| 394 | |
| 395 | |
| 396 | |

TABLE 1-continued

| Compound | Structure |
|---|---|
| 397 | |
| 398 | |
| 399 | |
| 400 | |

TABLE 1-continued
| Compound | Structure |
|---|---|
| 401 | 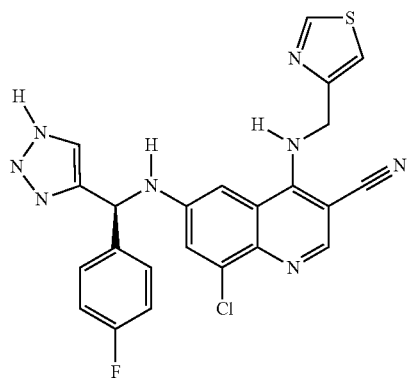 [SMILES: N#Cc1cnc2c(Cl)cc(N[C@H](C3=CNNN3)c3ccc(F)cc3)cc2c1NCc1cscn1] |
| 402 | 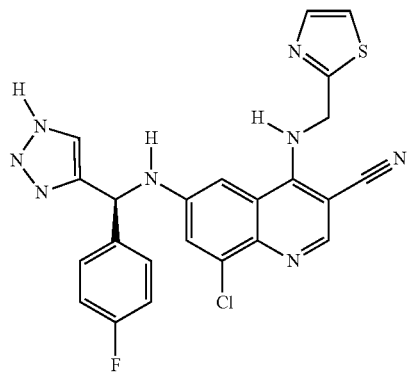 [SMILES: N#Cc1cnc2c(Cl)cc(N[C@H](C3=CNNN3)c3ccc(F)cc3)cc2c1NCc1nccs1] |
| 403 | 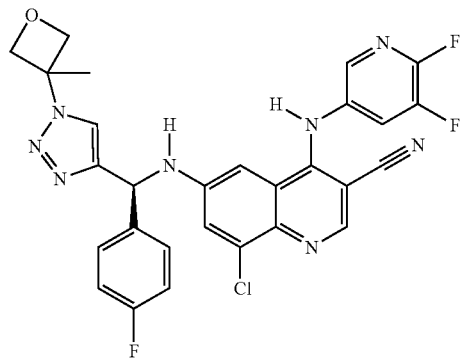 [SMILES: CC1(n2cc([C@@H](Nc3cc(Cl)c4ncc(C#N)c(Nc5cnc(F)c(F)c5)c4c3)c3ccc(F)cc3)nn2)COC1] |
| 404 | 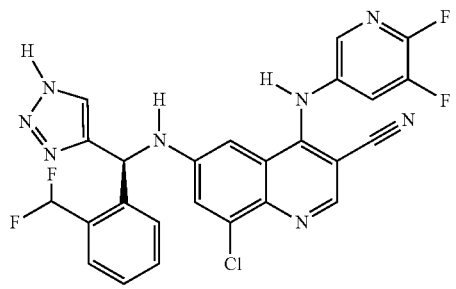 [SMILES: N#Cc1cnc2c(Cl)cc(N[C@H](c3c[nH]nn3)c3ccccc3C(F)F)cc2c1Nc1cnc(F)c(F)c1] |

TABLE 1-continued

| Compound | Structure |
|---|---|
| 405 | (structure) |
| 406 | (structure) |
| 407 | (structure) |
| 408 | (structure) |

TABLE 1-continued

| Compound | Structure |
|---|---|
| 409 | |
| 410 | |
| 411 | |
| 412 | |

TABLE 1-continued

| Compound | Structure |
|---|---|
| 413 | |
| 414 | |
| 415 | |
| 416 | |

TABLE 1-continued

| Compound | Structure |
|---|---|
| 417 | |
| 418 | |
| 419 | |
| 420 | |

TABLE 1-continued
| Compound | Structure |
|---|---|
| 421 | 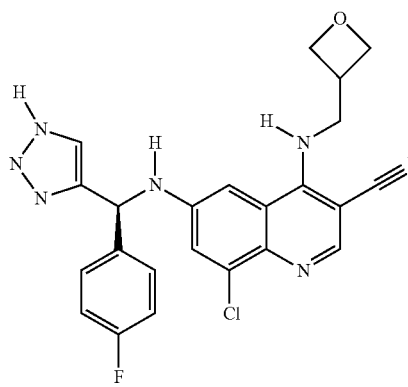 |
| 422 | 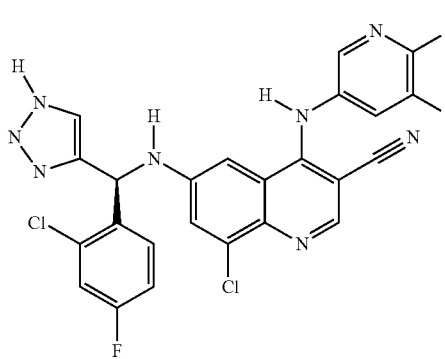 |
| 423 | 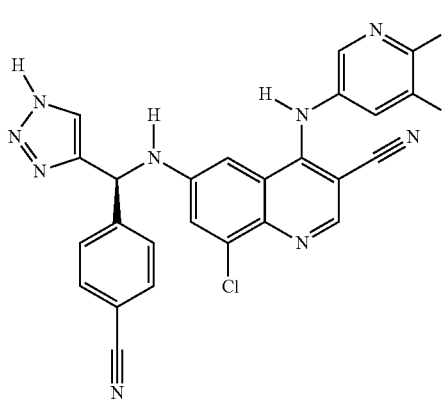 |
| 424 | 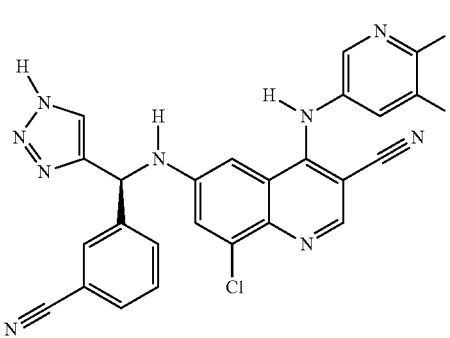 |

TABLE 1-continued
| Compound | Structure |
|---|---|
| 425 | 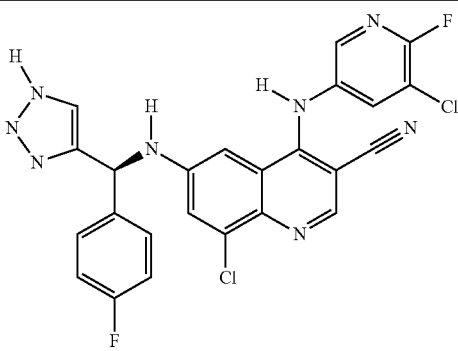 |
| 426 | 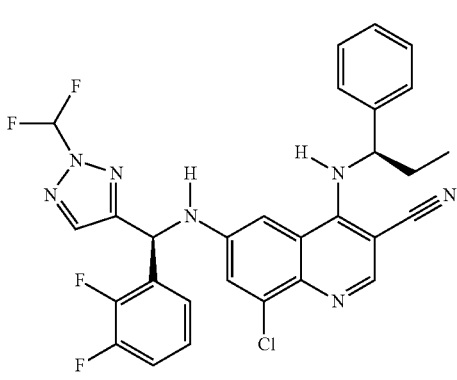 [SMILES: CC[C@@H](Nc1c(C#N)cnc2c(Cl)cc(N[C@H](c3cnn(C(F)F)n3)c3cccc(F)c3F)cc12)c1ccccc1] |
| 427 | 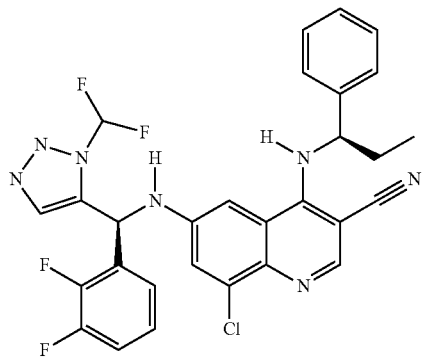 [SMILES: CC[C@@H](Nc1c(C#N)cnc2c(Cl)cc(N[C@H](C3=CNNN3C(F)F)c3cccc(F)c3F)cc12)c1ccccc1] |
| 428 | 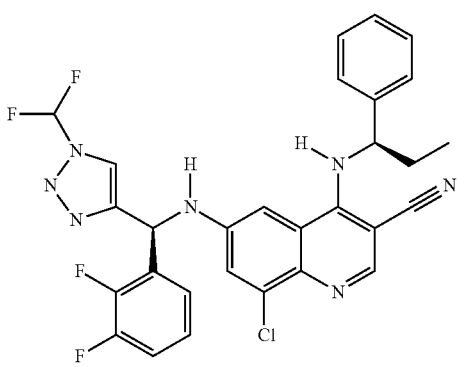 [SMILES: CC[C@@H](Nc1c(C#N)cnc2c(Cl)cc(N[C@H](C3=CN(C(F)F)NN3)c3cccc(F)c3F)cc12)c1ccccc1] |

TABLE 1-continued
| Compound | Structure |
|---|---|
| 429 | 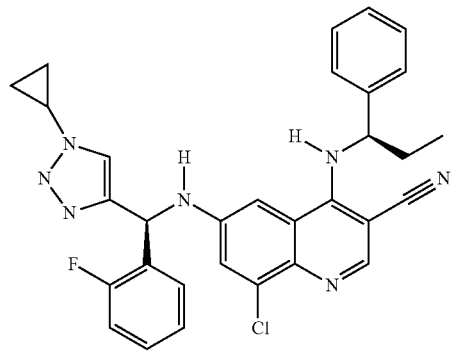 [SMILES: CC[C@@H](Nc1c(C#N)cnc2c(Cl)cc(N[C@H](C3=CN(C4CC4)NN3)c3ccccc3F)cc12)c1ccccc1] |
| 430 | 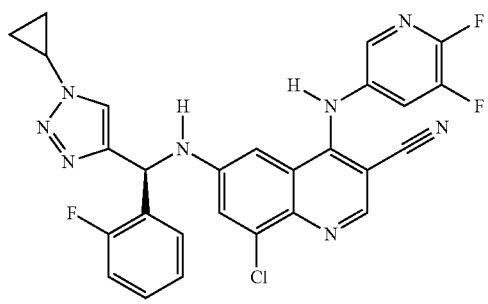 [SMILES: N#Cc1cnc2c(Cl)cc(N[C@H](c3cn(C4CC4)nn3)c3ccccc3F)cc2c1Nc1cnc(F)c(F)c1] |
| 431 | 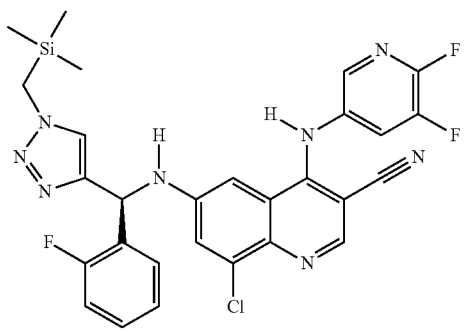 [SMILES: C[Si](C)(C)Cn1cc([C@@H](Nc2cc(Cl)c3ncc(C#N)c(Nc4cnc(F)c(F)c4)c3c2)c2ccccc2F)nn1] |
| 432 | 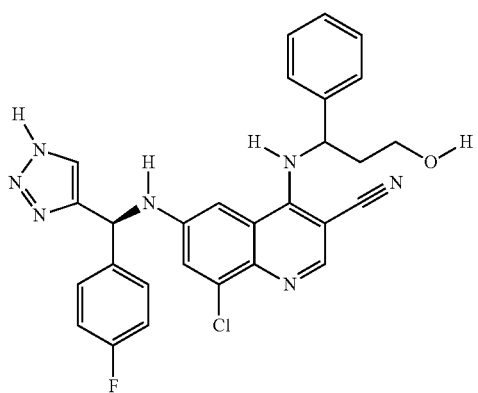 [SMILES: N#Cc1cnc2c(Cl)cc(N[C@@H](c3ccc(F)cc3)c3c[nH]nn3)cc2c1NC(CCO)c1ccccc1] |

TABLE 1-continued
| Compound | Structure |
|---|---|
| 433 | 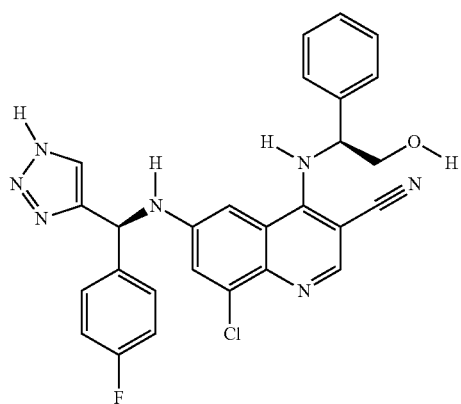 [SMILES: N#Cc1cnc2c(Cl)cc(N[C@@H](c3ccc(F)cc3)c3c[nH]nn3)cc2c1N[C@H](CO)c1ccccc1] |
| 434 | 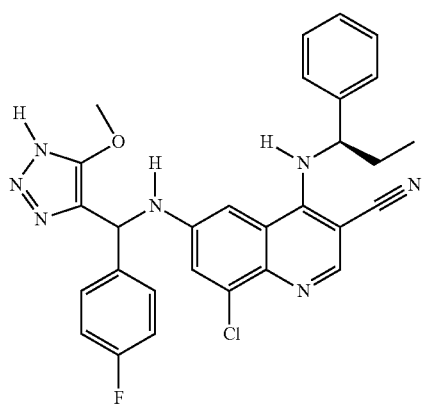 [SMILES: CC[C@@H](Nc1c(C#N)cnc2c(Cl)cc(NC(c3ccc(F)cc3)c3nn[nH]c3OC)cc12)c1ccccc1] |
| 435 | 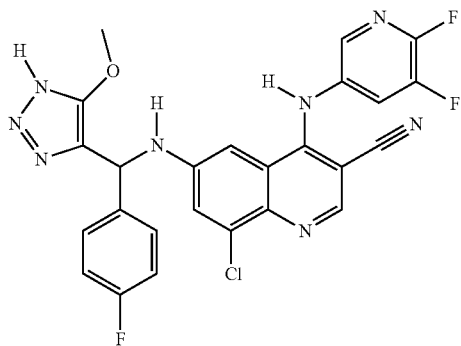 [SMILES: COc1[nH]nnc1C(Nc1cc(Cl)c2ncc(C#N)c(Nc3cnc(F)c(F)c3)c2c1)c1ccc(F)cc1] |
| 436 | 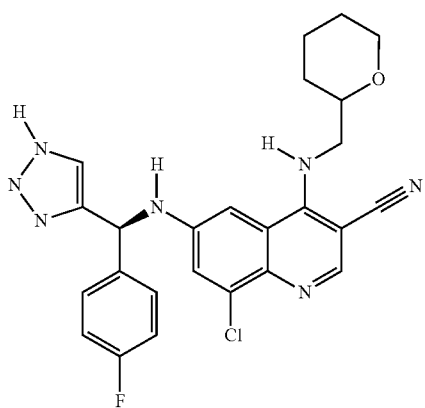 [SMILES: N#Cc1cnc2c(Cl)cc(N[C@H](C3=CNNN3)c3ccc(F)cc3)cc2c1NCC1CCCCO1] |

TABLE 1-continued
| Compound | Structure |
|---|---|
| 437 | 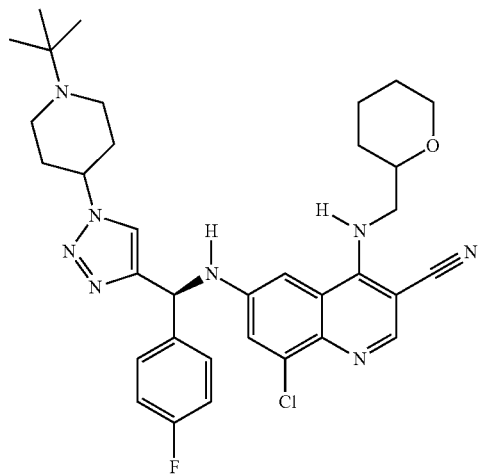 [SMILES: CC(C)(C)N1CCC(n2cc([C@@H](Nc3cc(Cl)c4ncc(C#N)c(NCC5CCCCO5)c4c3)c3ccc(F)cc3)nn2)CC1] |
| 438 | 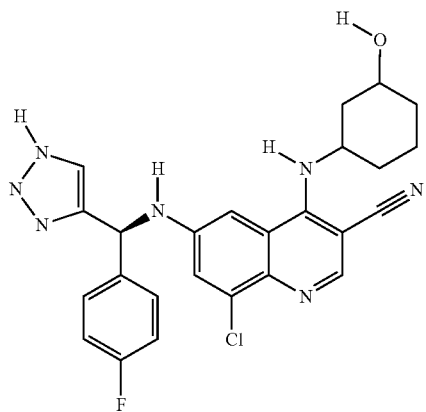 [SMILES: N#Cc1cnc2c(Cl)cc(N[C@H](C3=CNNN3)c3ccc(F)cc3)cc2c1NC1CCCC(O)C1] |
| 439 | 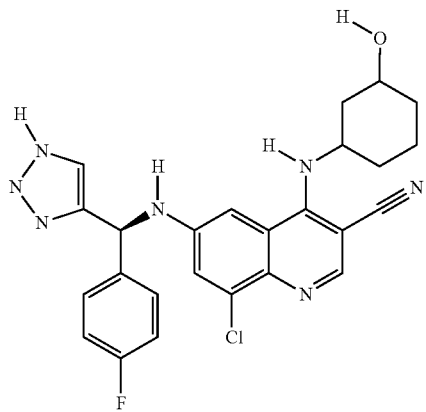 [SMILES: N#Cc1cnc2c(Cl)cc(N[C@H](C3=CNNN3)c3ccc(F)cc3)cc2c1NC1CCCC(O)C1] |

TABLE 1-continued
| Compound | Structure |
|---|---|
| 440 | 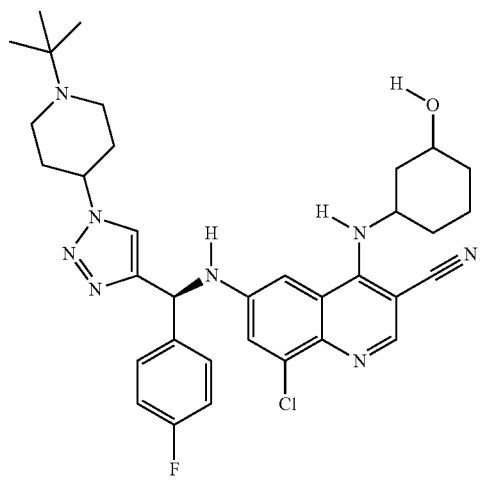 [SMILES: CC(C)(C)N1CCC(n2cc([C@@H](Nc3cc(Cl)c4ncc(C#N)c(NC5CCCC(O)C5)c4c3)c3ccc(F)cc3)nn2)CC1] |
| 441 | 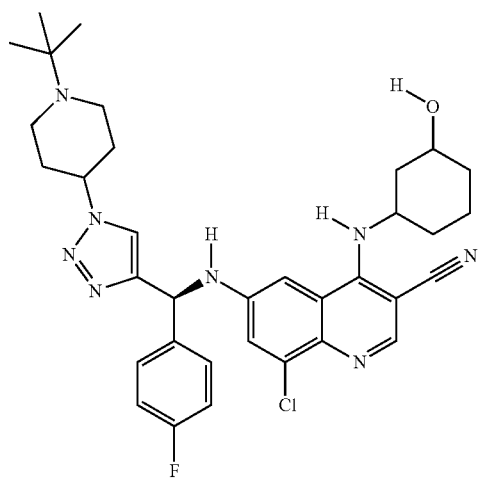 [SMILES: CC(C)(C)N1CCC(n2cc([C@@H](Nc3cc(Cl)c4ncc(C#N)c(NC5CCCC(O)C5)c4c3)c3ccc(F)cc3)nn2)CC1] |
| 442 | 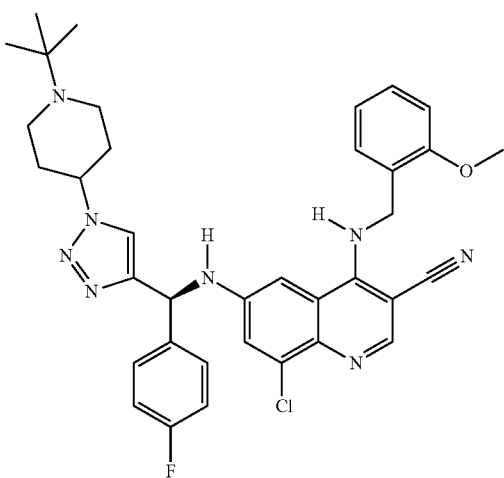 [SMILES: COc1ccccc1CNc1c(C#N)cnc2c(Cl)cc(N[C@@H](c3ccc(F)cc3)c3cn(C4CCN(C(C)(C)C)CC4)nn3)cc12] |

TABLE 1-continued
| Compound | Structure |
|---|---|
| 443 | 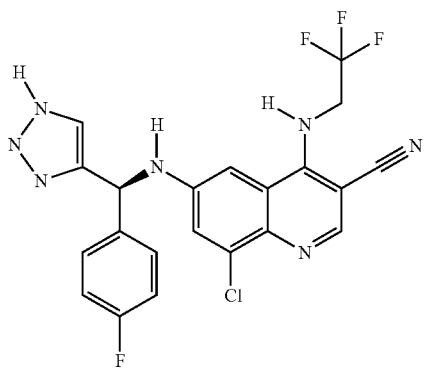 [SMILES: N#Cc1cnc2c(Cl)cc(N[C@H](C3=CNNN3)c3ccc(F)cc3)cc2c1NCC(F)(F)F] |
| 444 | 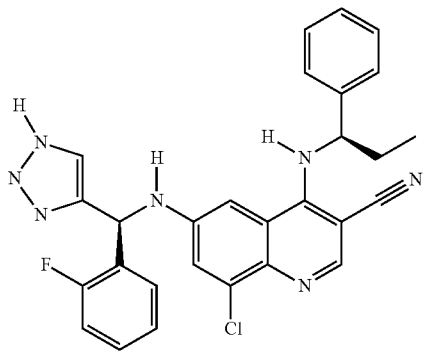 [SMILES: CC[C@@H](Nc1c(C#N)cnc2c(Cl)cc(N[C@H](C3=CNNN3)c3ccccc3F)cc12)c1ccccc1] |
| 445 | 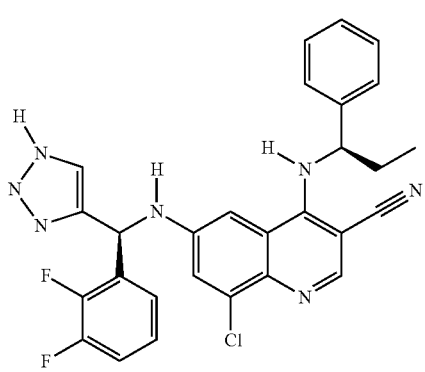 [SMILES: CC[C@@H](Nc1c(C#N)cnc2c(Cl)cc(N[C@H](C3=CNNN3)c3cccc(F)c3F)cc12)c1ccccc1] |
| 446 | 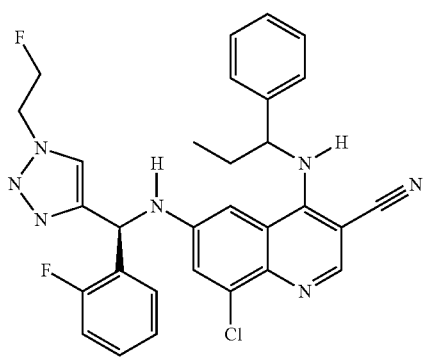 [SMILES: CCC(Nc1c(C#N)cnc2c(Cl)cc(N[C@H](C3=CN(CCF)NN3)c3ccccc3F)cc12)c1ccccc1] |

TABLE 1-continued

| Compound | Structure |
|---|---|
| 447 | |
| 448 | |
| 449 | |
| 450 | |

TABLE 1-continued
| Compound | Structure |
|---|---|
| 451 | 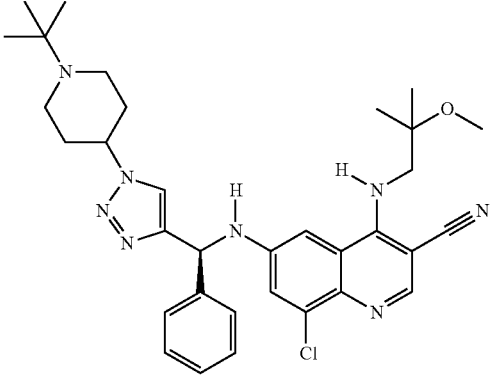 [SMILES: COC(C)(C)CNc1c(C#N)cnc2c(Cl)cc(N[C@@H](c3ccccc3)c3cn(C4CCN(C(C)(C)C)CC4)nn3)cc12] |
| 452 | 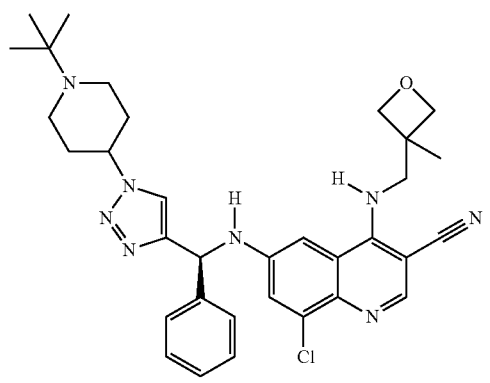 [SMILES: CC1(CNc2c(C#N)cnc3c(Cl)cc(N[C@@H](c4ccccc4)c4cn(C5CCN(C(C)(C)C)CC5)nn4)cc23)COC1] |
| 453 | 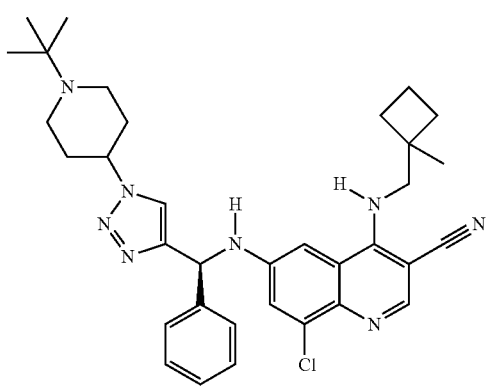 |
| 454 | 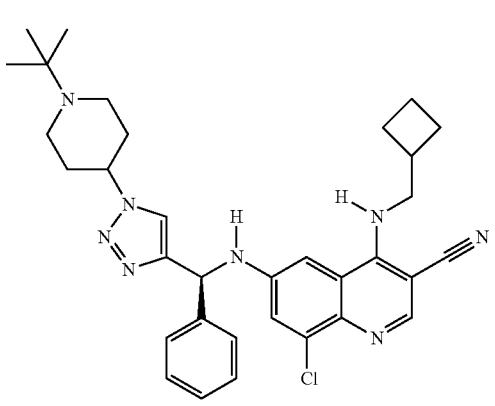 [SMILES: CC(C)(C)N1CCC(n2cc([C@@H](Nc3cc(Cl)c4ncc(C#N)c(NCC5CCC5)c4c3)c3ccccc3)nn2)CC1] |

TABLE 1-continued

| Compound | Structure |
|---|---|
| 455 | |
| 456 | |
| 457 | |
| 458 | |

TABLE 1-continued
| Compound | Stucture |
|---|---|
| 459 | 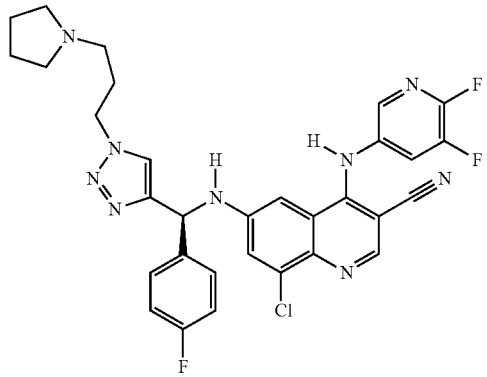 [SMILES: N#Cc1cnc2c(Cl)cc(N[C@@H](c3ccc(F)cc3)c3cn(CCCN4CCCC4)nn3)cc2c1Nc1cnc(F)c(F)c1] |
| 460 | 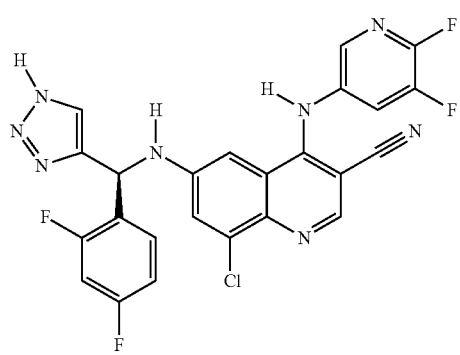 [SMILES: N#Cc1cnc2c(Cl)cc(N[C@H](c3c[nH]nn3)c3ccc(F)cc3F)cc2c1Nc1cnc(F)c(F)c1] |
| 461 | 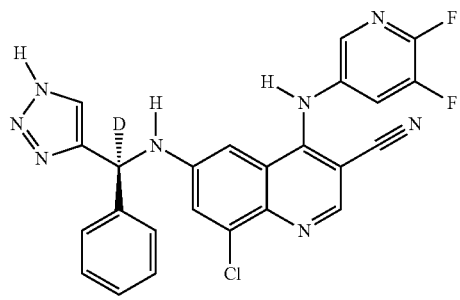 |
| 462 | 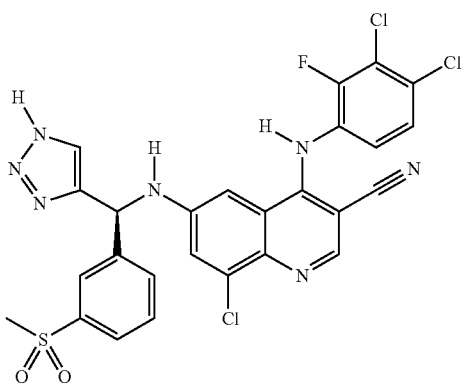 [SMILES: CS(=O)(=O)c1cccc([C@H](Nc2cc(Cl)c3ncc(C#N)c(Nc4ccc(Cl)c(Cl)c4F)c3c2)c2c[nH]nn2)c1] |

TABLE 1-continued

| Compound | Structure |
|---|---|
| 463 | |
| 464 | |
| 465 | |
| 466 | |

TABLE 1-continued

| Compound | Structure |
|---|---|
| 467 | |
| 468 | |
| 469 | |
| 470 | |

TABLE 1-continued
| Compound | Structure |
|---|---|
| 471 | 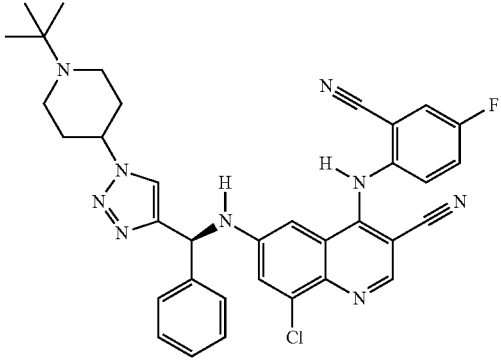 [SMILES: CC(C)(C)N1CCC(n2cc([C@@H](Nc3cc(Cl)c4ncc(C#N)c(Nc5ccc(F)cc5C#N)c4c3)c3ccccc3)nn2)CC1] |
| 472 | 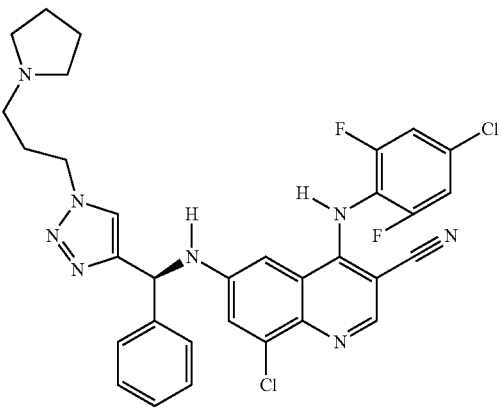 [SMILES: N#Cc1cnc2c(Cl)cc(N[C@@H](c3ccccc3)c3cn(CCCN4CCCC4)nn3)cc2c1Nc1c(F)cc(Cl)cc1F] |
| 473 | 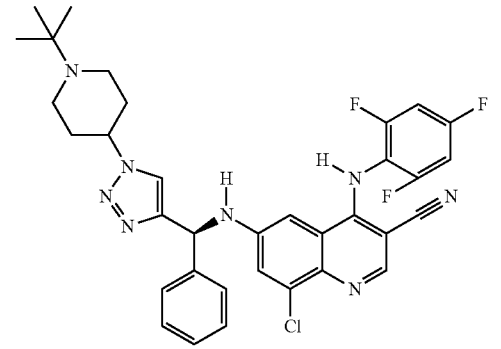 [SMILES: CC(C)(C)N1CCC(n2cc([C@@H](Nc3cc(Cl)c4ncc(C#N)c(Nc5c(F)cc(F)cc5F)c4c3)c3ccccc3)nn2)CC1] |
| 474 | 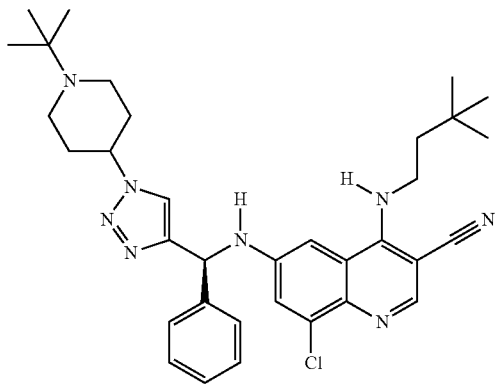 [SMILES: CC(C)(C)CCNc1c(C#N)cnc2c(Cl)cc(N[C@@H](c3ccccc3)c3cn(C4CCN(C(C)(C)C)CC4)nn3)cc12] |

TABLE 1-continued

| Compound | Structure |
|---|---|
| 475 | |
| 476 | |
| 477 | |
| 478 | |

TABLE 1-continued
| Compound | Structure |
|---|---|
| 479 | 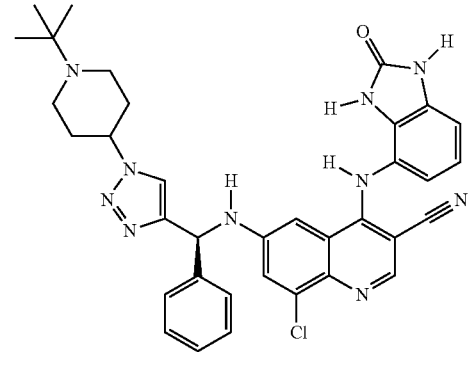 [SMILES: CC(C)(C)N1CCC(n2cc([C@@H](Nc3cc(Cl)c4ncc(C#N)c(Nc5cccc6[nH]c(=O)[nH]c56)c4c3)c3ccccc3)nn2)CC1] |
| 480 | 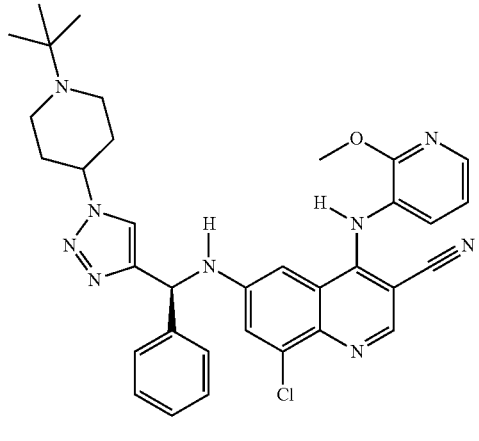 [SMILES: COc1ncccc1Nc1c(C#N)cnc2c(Cl)cc(N[C@@H](c3ccccc3)c3cn(C4CCN(C(C)(C)C)CC4)nn3)cc12] |
| 481 | 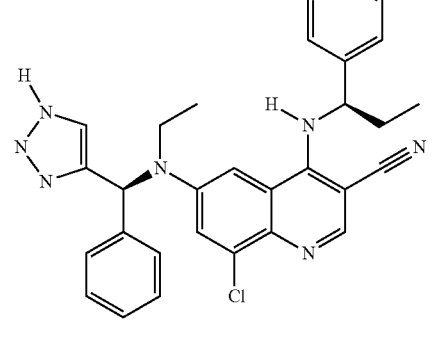 |
| 482 | 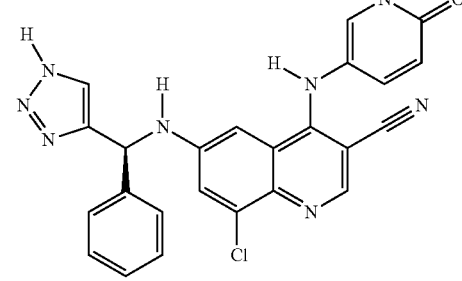 |

TABLE 1-continued

| Compound | Structure |
|---|---|
| 483 | |
| 484 | |
| 485 | |
| 486 | |

US 9,815,818 B2
1645 1646
TABLE 1-continued
| Compound | Stucture |
|---|---|
| 487 | 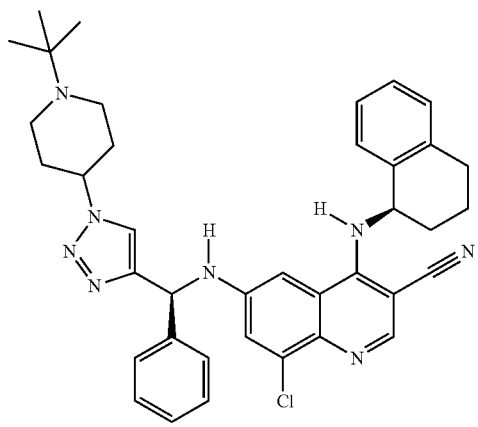 [SMILES: CC(C)(C)N1CCC(n2cc([C@@H](Nc3cc(Cl)c4ncc(C#N)c(N[C@@H]5CCCc6ccccc65)c4c3)c3ccccc3)nn2)CC1] |
| 488 | 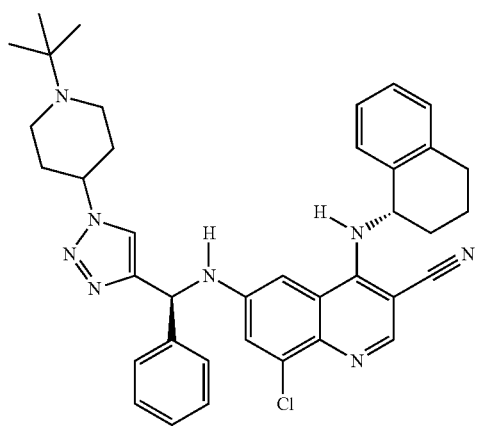 [SMILES: CC(C)(C)N1CCC(n2cc([C@@H](Nc3cc(Cl)c4ncc(C#N)c(N[C@H]5CCCc6ccccc65)c4c3)c3ccccc3)nn2)CC1] |
| 489 | 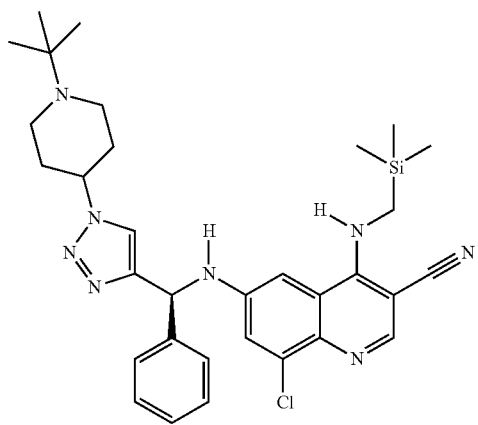 [SMILES: CC(C)(C)N1CCC(n2cc([C@@H](Nc3cc(Cl)c4ncc(C#N)c(NC[Si](C)(C)C)c4c3)c3ccccc3)nn2)CC1] |
| 490 | 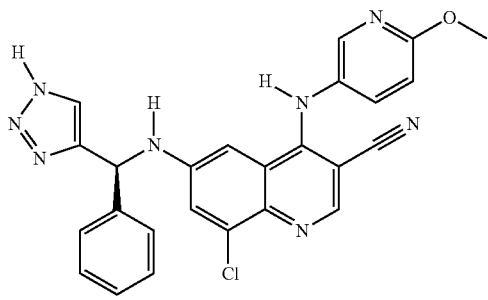 |

TABLE 1-continued

| Compound | Structure |
|---|---|
| 491 | |
| 492 | |
| 493 | |
| 494 | |

TABLE 1-continued

| Compound | Structure |
|---|---|
| 495 | |
| 496 | |
| 497 | |
| 498 | |

TABLE 1-continued

| Compound | Structure |
|---|---|
| 499 | |
| 500 | |
| 501 | |
| 502 | |
| 503 | |

TABLE 1-continued
| Compound | Structure |
|---|---|
| 504 | 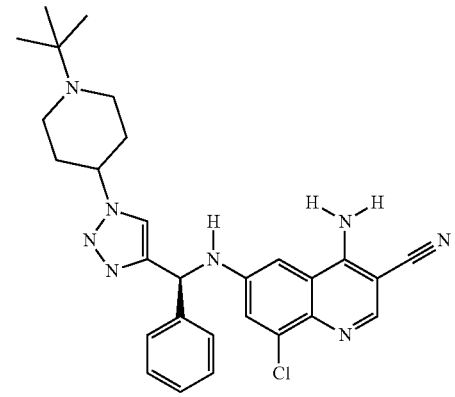 [SMILES: CC(C)(C)N1CCC(N2C=C([C@@H](Nc3cc(Cl)c4ncc(C#N)c(N)c4c3)c3ccccc3)NN2)CC1] |
| 505 | 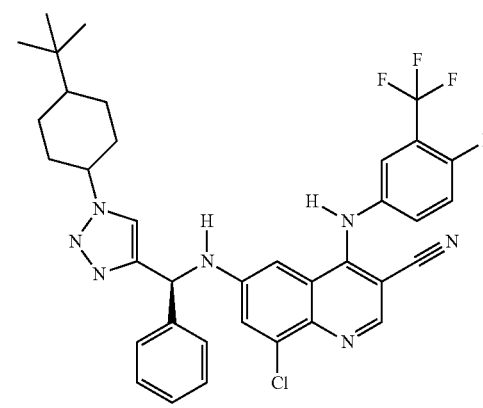 |
| 506 | 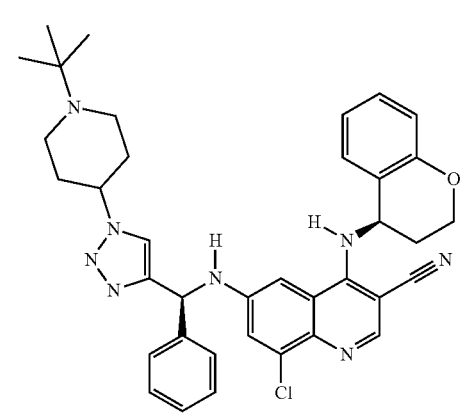 [SMILES: CC(C)(C)N1CCC(N2C=C([C@@H](Nc3cc(Cl)c4ncc(C#N)c(N[C@@H]5CCOc6ccccc65)c4c3)c3ccccc3)NN2)CC1] |
| 507 | 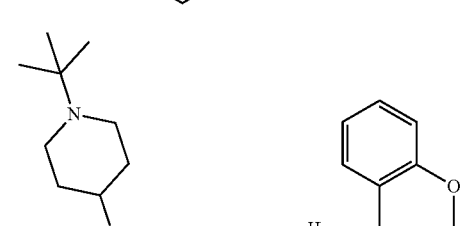 |

TABLE 1-continued

| Compound | Structure |
|---|---|
| 508 | |
| 509 | |
| 510 | |
| 511 | |

TABLE 1-continued

| Compound | Structure |
|---|---|
| 512 | |
| 513 | |
| 514 | |
| 515 | |

TABLE 1-continued

| Compound | Structure |
|---|---|
| 516 | |
| 517 | |
| 518 | |
| 519 | |

TABLE 1-continued
| Compound | Structure |
|---|---|
| 520 | 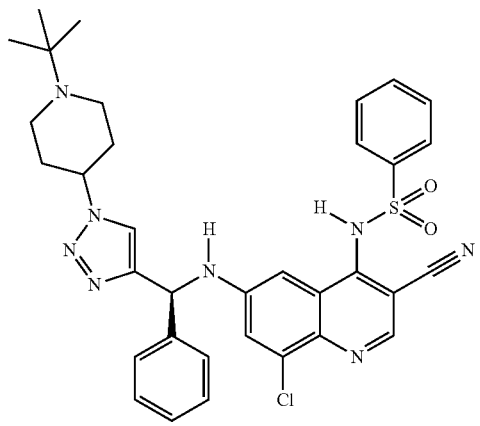 [SMILES: CC(C)(C)N1CCC(n2cc([C@@H](Nc3cc(Cl)c4ncc(C#N)c(NS(=O)(=O)c5ccccc5)c4c3)c3ccccc3)nn2)CC1] |
| 521 | 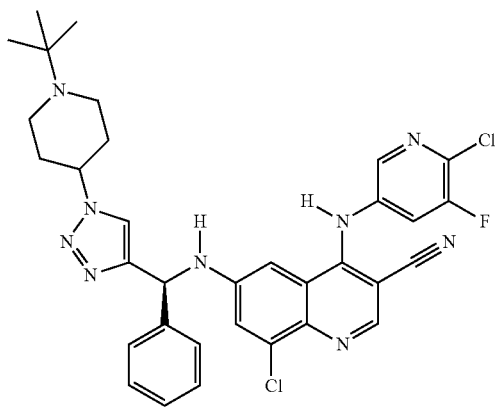 |
| 522 | 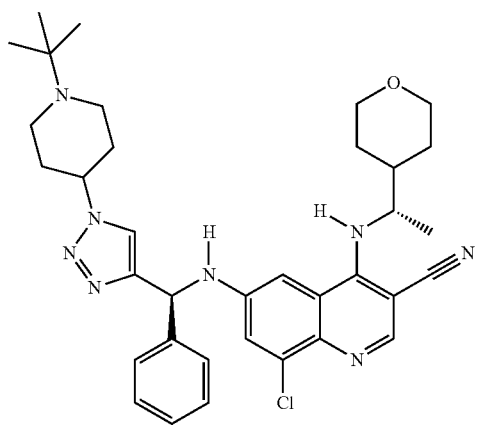 [SMILES: C[C@H](Nc1c(C#N)cnc2c(Cl)cc(N[C@@H](c3ccccc3)c3cn(C4CCN(C(C)(C)C)CC4)nn3)cc12)C1CCOCC1] |

TABLE 1-continued
| Compound | Structure |
|---|---|
| 523 | 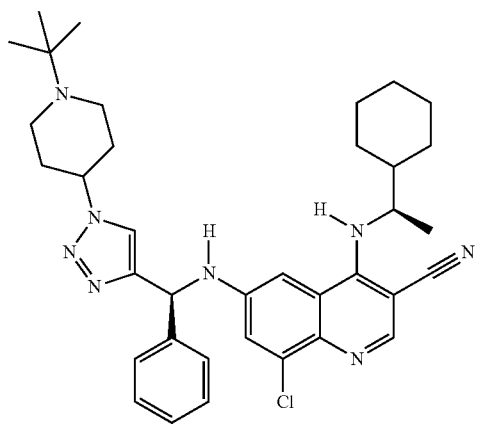 [SMILES: C[C@@H](Nc1c(C#N)cnc2c(Cl)cc(N[C@@H](c3ccccc3)c3cn(C4CCN(C(C)(C)C)CC4)nn3)cc12)C1CCCCC1] |
| 524 | 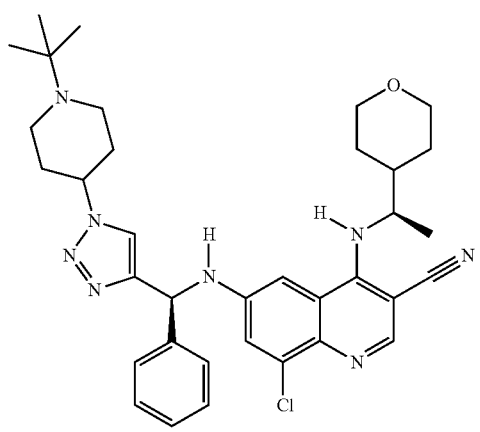 [SMILES: C[C@@H](Nc1c(C#N)cnc2c(Cl)cc(N[C@@H](c3ccccc3)c3cn(C4CCN(C(C)(C)C)CC4)nn3)cc12)C1CCOCC1] |
| 525 | 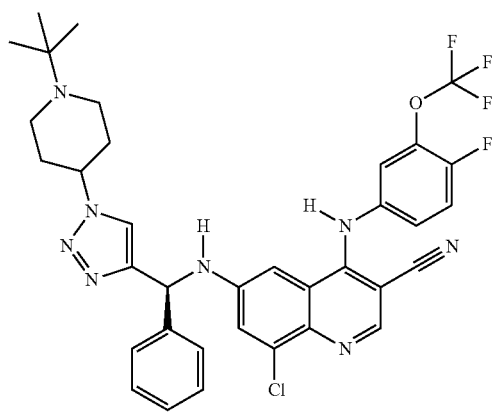 [SMILES: CC(C)(C)N1CCC(n2cc([C@@H](Nc3cc(Cl)c4ncc(C#N)c(Nc5ccc(F)c(OC(F)(F)F)c5)c4c3)c3ccccc3)nn2)CC1] |

TABLE 1-continued
| Compound | Structure |
|---|---|
| 526 | 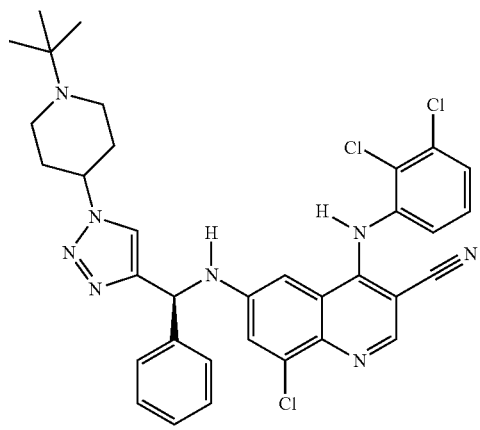 [SMILES: CC(C)(C)N1CCC(n2cc([C@@H](Nc3cc(Cl)c4ncc(C#N)c(Nc5cccc(Cl)c5Cl)c4c3)c3ccccc3)nn2)CC1] |
| 527 | 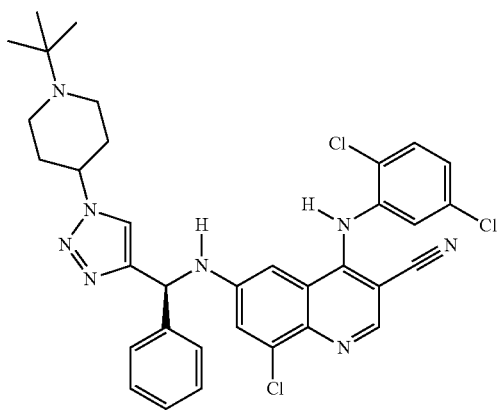 [SMILES: CC(C)(C)N1CCC(n2cc([C@@H](Nc3cc(Cl)c4ncc(C#N)c(Nc5cc(Cl)ccc5Cl)c4c3)c3ccccc3)nn2)CC1] |
| 528 | 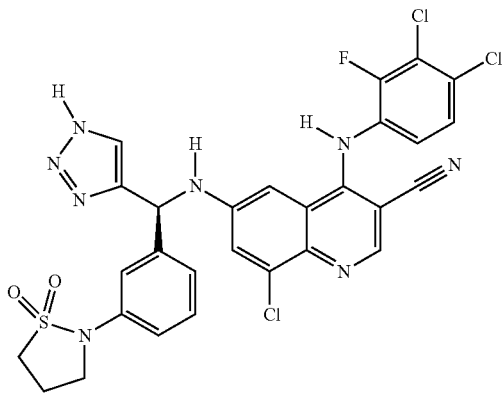 [SMILES: N#Cc1cnc2c(Cl)cc(N[C@@H](c3cccc(N4CCCS4(=O)=O)c3)c3c[nH]nn3)cc2c1Nc1ccc(Cl)c(Cl)c1F] |

TABLE 1-continued

| Compound | Structure |
|---|---|
| 529 | |
| 530 | |
| 531 | |
| 532 | |

TABLE 1-continued

| Compound | Structure |
|---|---|
| 533 | |
| 534 | |
| 535 | |
| 536 | |

TABLE 1-continued
| Compound | Structure |
|---|---|
| 537 | 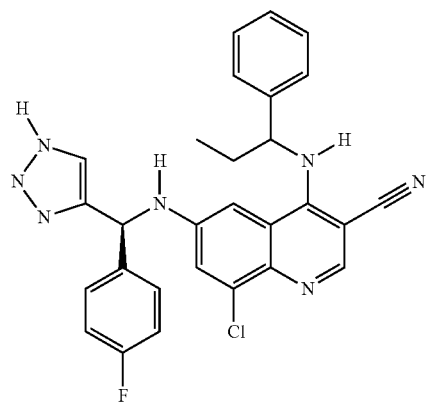 [SMILES: CCC(Nc1c(C#N)cnc2c(Cl)cc(N[C@H](C3=CNNN3)c3ccc(F)cc3)cc12)c1ccccc1] |
| 538 | 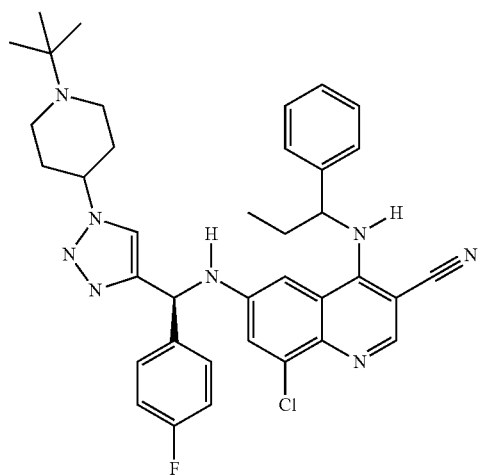 [SMILES: CCC(Nc1c(C#N)cnc2c(Cl)cc(N[C@H](C3=CN(C4CCN(C(C)(C)C)CC4)NN3)c3ccc(F)cc3)cc12)c1ccccc1] |
| 539 | 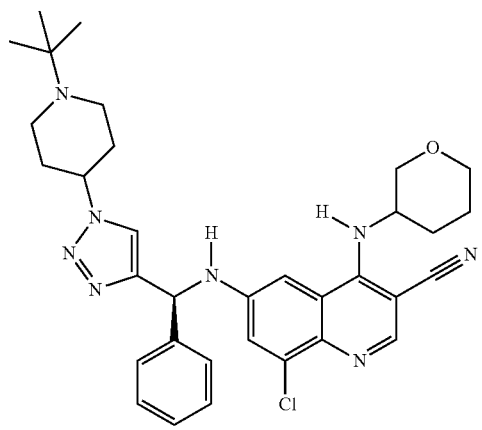 |

TABLE 1-continued
| Compound | Structure |
|---|---|
| 540 | 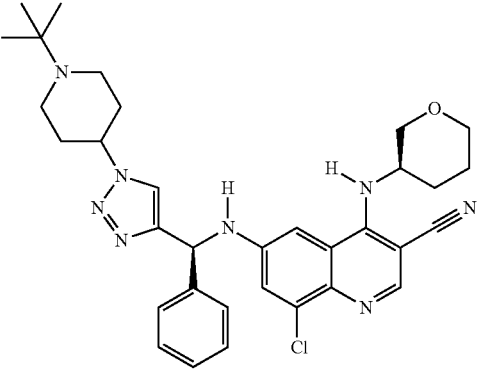 [SMILES: CC(C)(C)N1CCC(n2cc([C@@H](Nc3cc(Cl)c4ncc(C#N)c(N[C@@H]5CCCOC5)c4c3)c3ccccc3)nn2)CC1] |
| 541 | 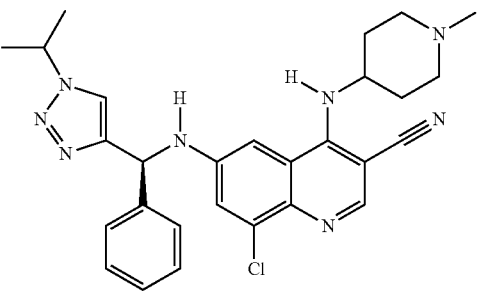 [SMILES: CC(C)n1cc([C@@H](Nc2cc(Cl)c3ncc(C#N)c(NC4CCN(C)CC4)c3c2)c2ccccc2)nn1] |
| 542 | 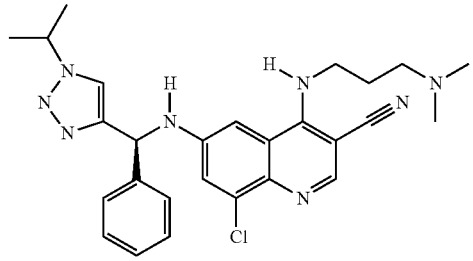 [SMILES: CC(C)N1C=C([C@@H](Nc2cc(Cl)c3ncc(C#N)c(NCCCN(C)C)c3c2)c2ccccc2)NN1] |
| 543 | 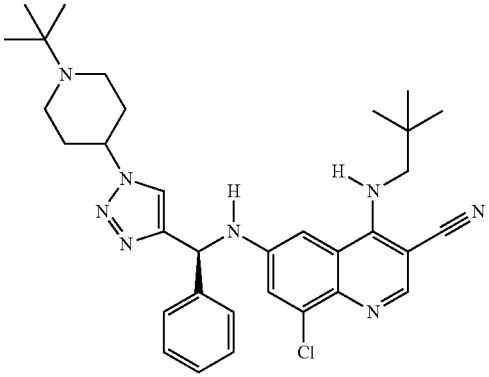 [SMILES: CC(C)(C)CNc1c(C#N)cnc2c(Cl)cc(N[C@@H](c3ccccc3)c3cn(C4CCN(C(C)(C)C)CC4)nn3)cc12] |

TABLE 1-continued
| Compound | Structure |
|---|---|
| 544 | 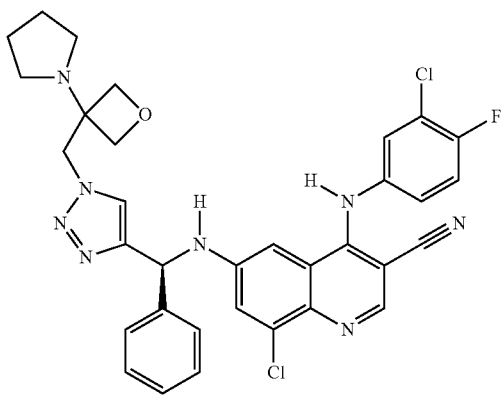 [SMILES: N#Cc1cnc2c(Cl)cc(N[C@@H](c3ccccc3)c3cn(CC4(N5CCCC5)COC4)nn3)cc2c1Nc1ccc(F)c(Cl)c1] |
| 545 | 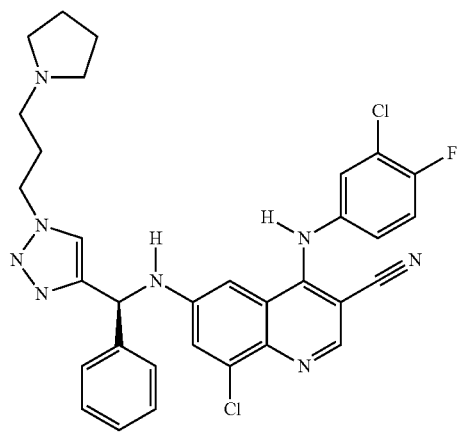 [SMILES: N#Cc1cnc2c(Cl)cc(N[C@H](C3=CN(CCCN4CCCC4)NN3)c3ccccc3)cc2c1Nc1ccc(F)c(Cl)c1] |
| 546 | 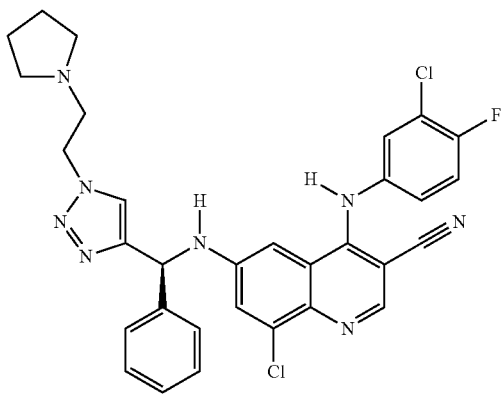 [SMILES: N#Cc1cnc2c(Cl)cc(N[C@@H](c3ccccc3)c3cn(CCN4CCCC4)nn3)cc2c1Nc1ccc(F)c(Cl)c1] |

TABLE 1-continued

| Compound | Structure |
|---|---|
| 547 | (structure) |
| 548 | (structure) |
| 549 | (structure) |
| 550 | (structure) |

TABLE 1-continued
| Compound | Structure |
|---|---|
| 551 | 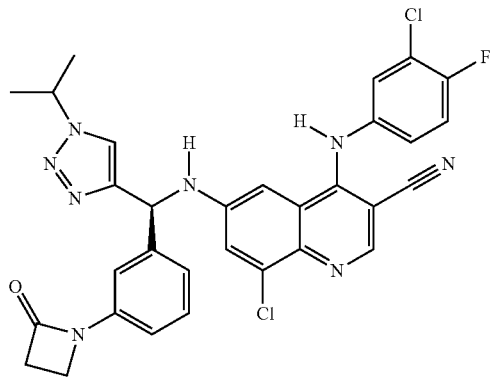 [SMILES: CC(C)n1cc([C@@H](Nc2cc(Cl)c3ncc(C#N)c(Nc4ccc(F)c(Cl)c4)c3c2)c2cccc(N3CCC3=O)c2)nn1] |
| 552 | 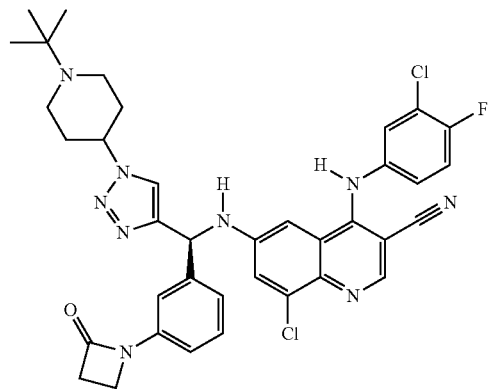 [SMILES: CC(C)(C)N1CCC(n2cc([C@@H](Nc3cc(Cl)c4ncc(C#N)c(Nc5ccc(F)c(Cl)c5)c4c3)c3cccc(N4CCC4=O)c3)nn2)CC1] |
| 553 | 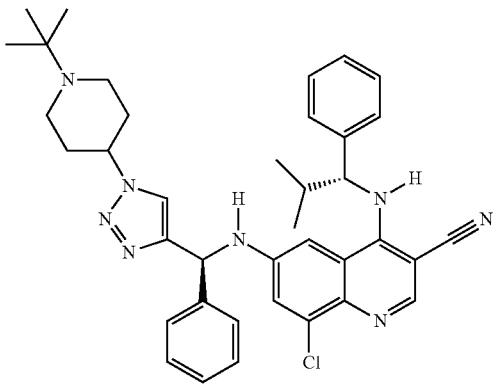 [SMILES: CC(C)[C@@H](Nc1c(C#N)cnc2c(Cl)cc(N[C@@H](c3ccccc3)c3cn(C4CCN(C(C)(C)C)CC4)nn3)cc12)c1ccccc1] |
| 554 | 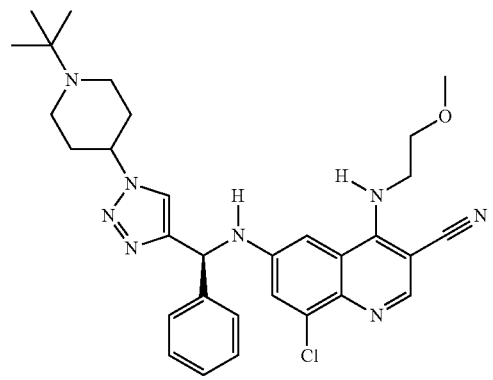 |

TABLE 1-continued
| Compound | Structure |
|---|---|
| 555 | 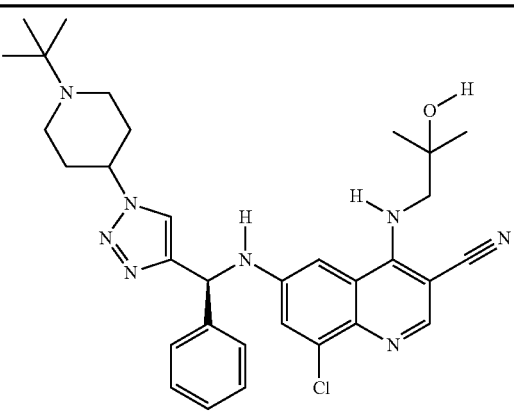 |
| 556 | 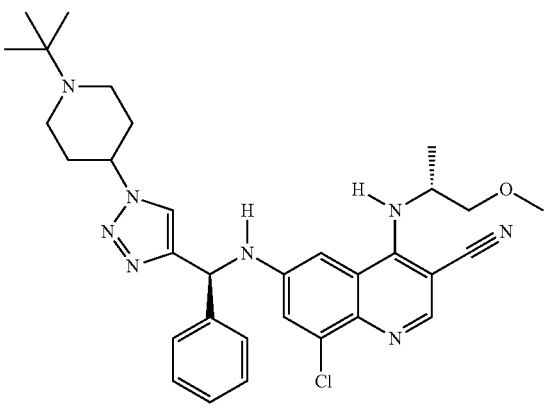 [SMILES: COC[C@@H](C)Nc1c(C#N)cnc2c(Cl)cc(N[C@@H](c3ccccc3)c3cn(C4CCN(C(C)(C)C)CC4)nn3)cc12] |
| 557 | 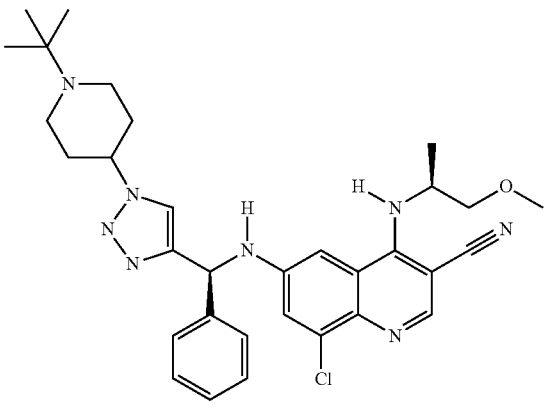 [SMILES: COC[C@H](C)Nc1c(C#N)cnc2c(Cl)cc(N[C@H](C3=CN(C4CCN(C(C)(C)C)CC4)NN3)c3ccccc3)cc12] |
| 558 | 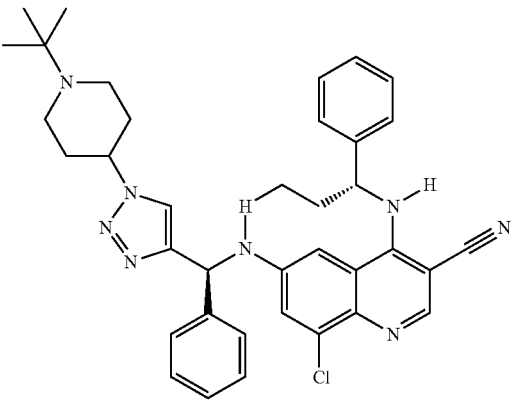 |

TABLE 1-continued

| Compound | Structure |
|---|---|
| 559 | |
| 560 | |
| 561 | |

TABLE 1-continued
| Compound | Structure |
|---|---|
| 562 | 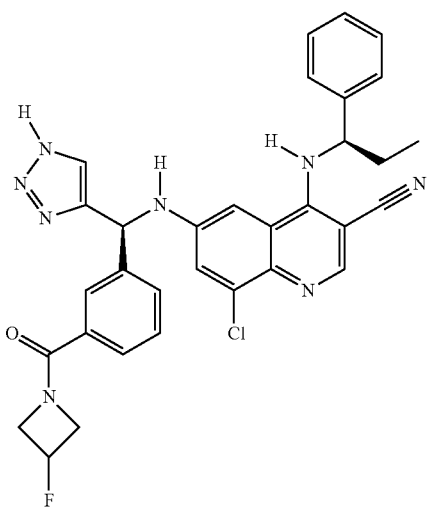 [SMILES: CC[C@@H](Nc1c(C#N)cnc2c(Cl)cc(N[C@@H](c3cccc(C(=O)N4CC(F)C4)c3)c3c[nH]nn3)cc12)c1ccccc1] |
| 563 | 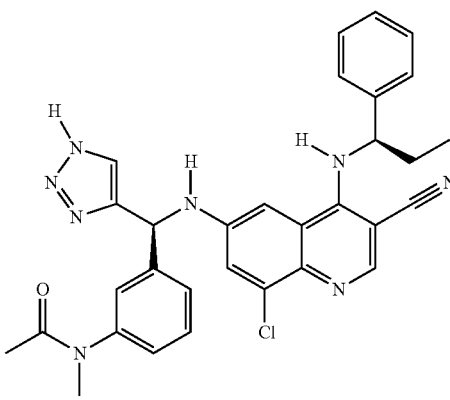 |
| 564 | 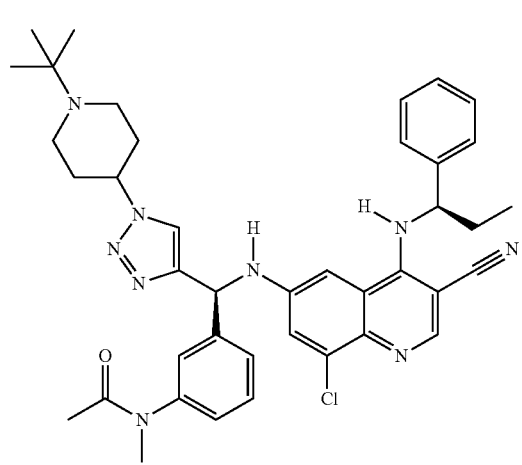 [SMILES: CC[C@@H](Nc1c(C#N)cnc2c(Cl)cc(N[C@@H](c3cccc(N(C)C(C)=O)c3)c3cn(C4CCN(C(C)(C)C)CC4)nn3)cc12)c1ccccc1] |

TABLE 1-continued
| Compound | Structure |
|---|---|
| 565 | 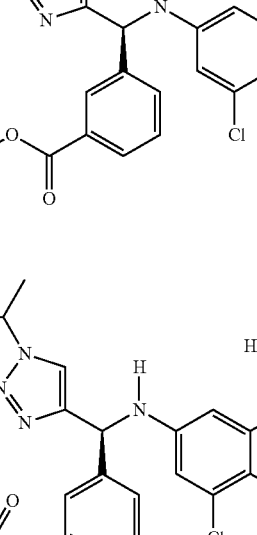 |
| 566 | 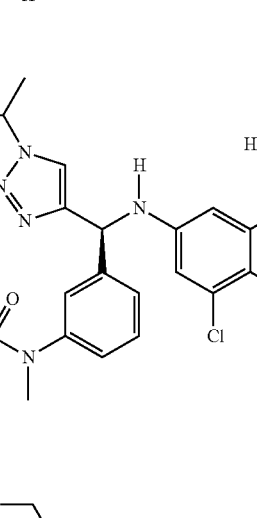 |
| 567 | 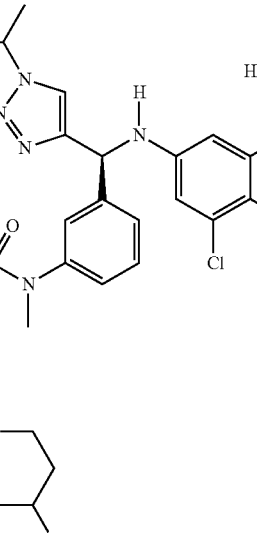 |
| 568 | 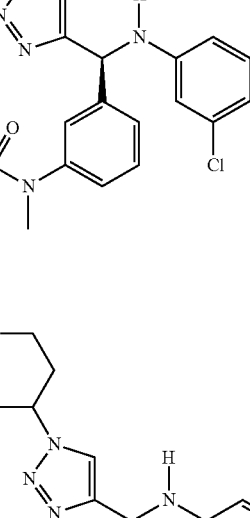 |

TABLE 1-continued
| Compound | Structure |
|---|---|
| 569 | 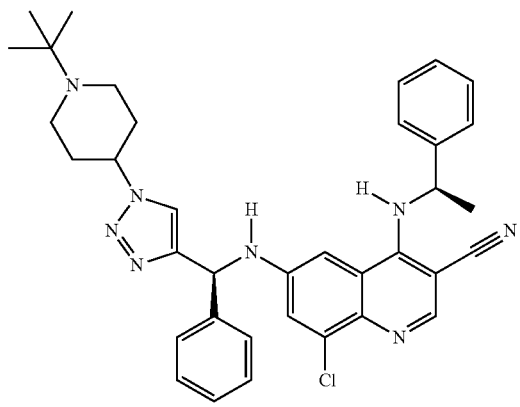 [SMILES: C[C@@H](Nc1c(C#N)cnc2c(Cl)cc(N[C@@H](c3ccccc3)c3cn(C4CCN(C(C)(C)C)CC4)nn3)cc12)c1ccccc1] |
| 570 | 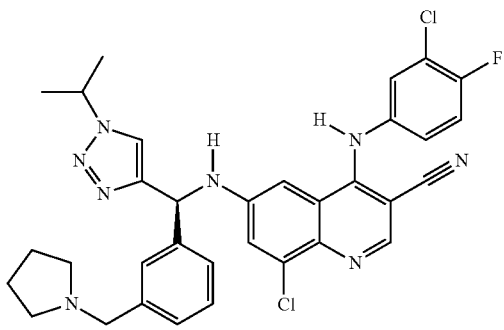 [SMILES: CC(C)n1cc([C@@H](Nc2cc(Cl)c3ncc(C#N)c(Nc4ccc(F)c(Cl)c4)c3c2)c2cccc(CN3CCCC3)c2)nn1] |
| 571 | 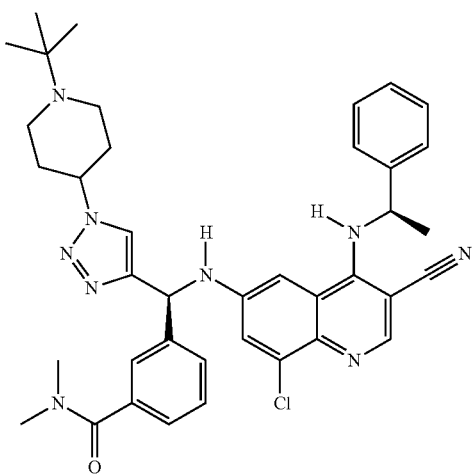 [SMILES: C[C@@H](Nc1c(C#N)cnc2c(Cl)cc(N[C@@H](c3cccc(C(=O)N(C)C)c3)c3cn(C4CCN(C(C)(C)C)CC4)nn3)cc12)c1ccccc1] |

TABLE 1-continued
| Compound | Structure |
|---|---|
| 572 | 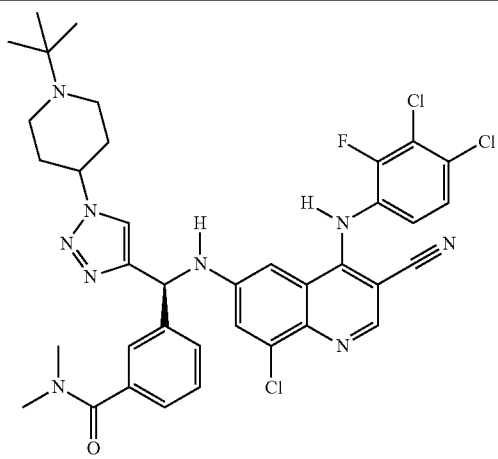 |
| 573 | 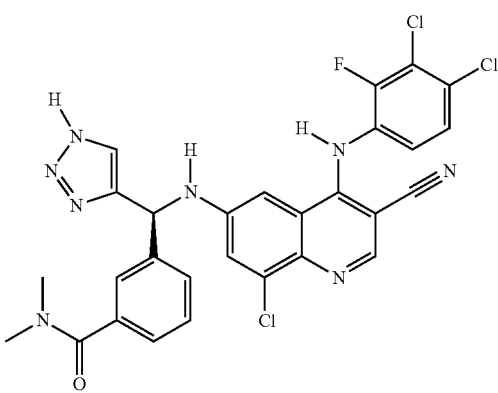 [SMILES: CN(C)C(=O)c1cccc([C@H](Nc2cc(Cl)c3ncc(C#N)c(Nc4ccc(Cl)c(Cl)c4F)c3c2)c2c[nH]nn2)c1] |
| 574 | 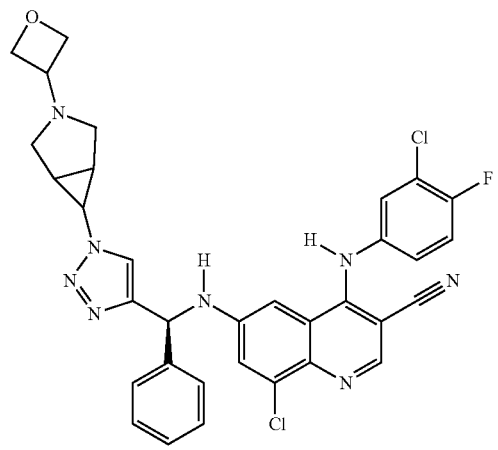 [SMILES: N#Cc1cnc2c(Cl)cc(N[C@@H](c3ccccc3)c3cn(C4C5CN(C6COC6)CC54)nn3)cc2c1Nc1ccc(F)c(Cl)c1] |
| 575 | 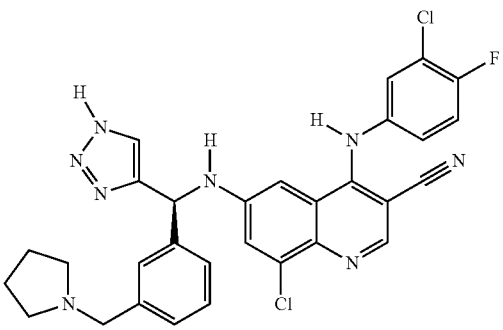 |

TABLE 1-continued
| Compound | Structure |
|---|---|
| 576 | 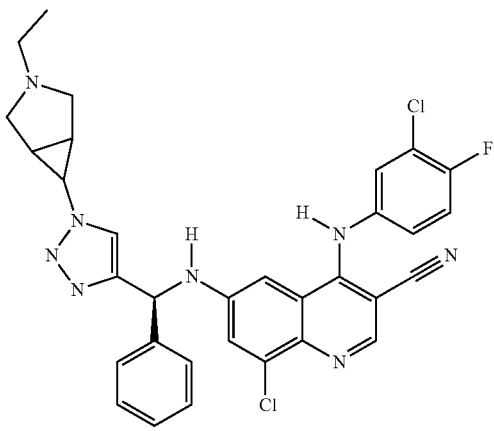 [SMILES: CCN1CC2C(C1)C2N1C=C([C@@H](Nc2cc(Cl)c3ncc(C#N)c(Nc4ccc(F)c(Cl)c4)c3c2)c2ccccc2)NN1] |
| 577 | 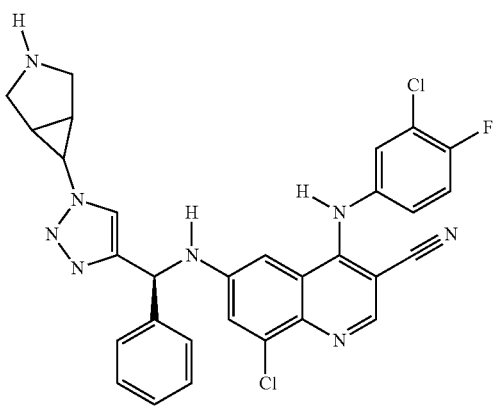 [SMILES: N#Cc1cnc2c(Cl)cc(N[C@H](C3=CN(C4C5CNCC54)NN3)c3ccccc3)cc2c1Nc1ccc(F)c(Cl)c1] |
| 578 | 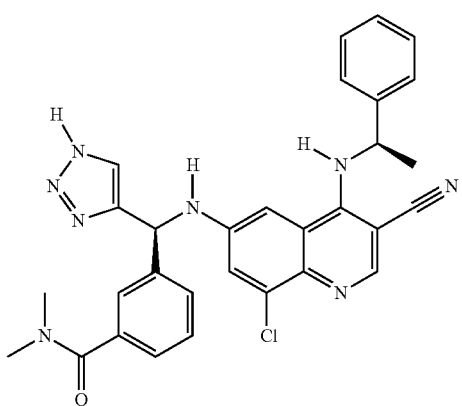 |

TABLE 1-continued
| Compound | Structure |
|---|---|
| 579 | 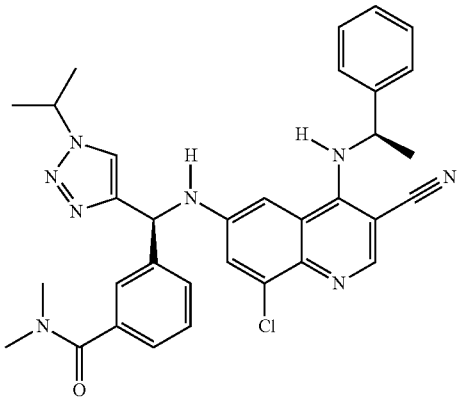 [SMILES: CC(C)n1cc([C@@H](Nc2cc(Cl)c3ncc(C#N)c(N[C@H](C)c4ccccc4)c3c2)c2cccc(C(=O)N(C)C)c2)nn1] |
| 580 | 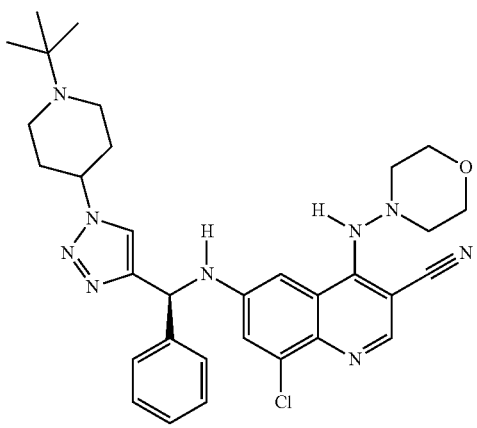 [SMILES: CC(C)(C)N1CCC(n2cc([C@@H](Nc3cc(Cl)c4ncc(C#N)c(NN5CCOCC5)c4c3)c3ccccc3)nn2)CC1] |
| 581 | 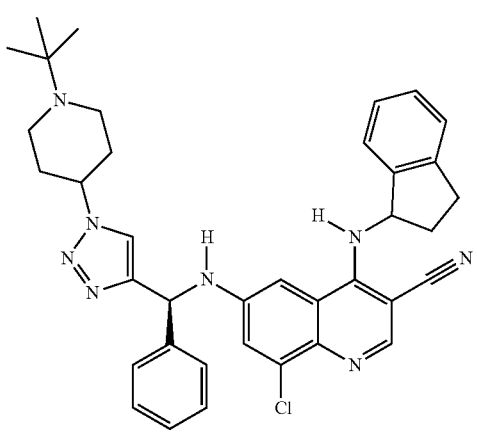 [SMILES: CC(C)(C)N1CCC(n2cc([C@@H](Nc3cc(Cl)c4ncc(C#N)c(NC5CCc6ccccc65)c4c3)c3ccccc3)nn2)CC1] |
| 582 | 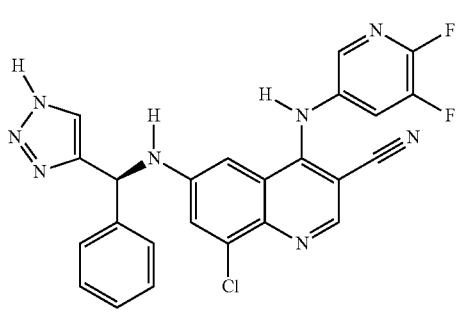 [SMILES: N#Cc1cnc2c(Cl)cc(N[C@@H](c3ccccc3)c3c[nH]nn3)cc2c1Nc1cnc(F)c(F)c1] |

TABLE 1-continued

| Compound | Structure |
|---|---|
| 583 | |
| 584 | |
| 585 | |
| 586 | |

TABLE 1-continued

| Compound | Structure |
|---|---|
| 587 | |
| 588 | |
| 589 | |
| 590 | |

TABLE 1-continued
| Compound | Structure |
|---|---|
| 591 | 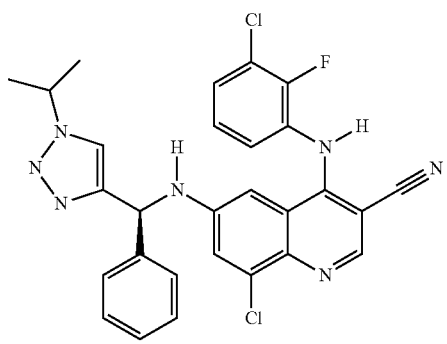 [SMILES: CC(C)N1C=C([C@@H](Nc2cc(Cl)c3ncc(C#N)c(Nc4cccc(Cl)c4F)c3c2)c2ccccc2)NN1] |
| 592 | 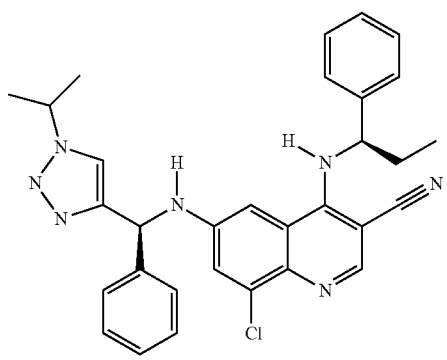 [SMILES: CC[C@@H](Nc1c(C#N)cnc2c(Cl)cc(N[C@H](C3=CN(C(C)C)NN3)c3ccccc3)cc12)c1ccccc1] |
| 593 | 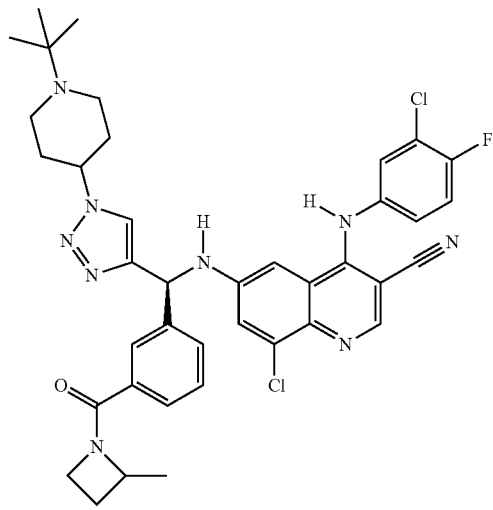 [SMILES: CC1CCN1C(=O)c1cccc([C@H](Nc2cc(Cl)c3ncc(C#N)c(Nc4ccc(F)c(Cl)c4)c3c2)c2cn(C3CCN(C(C)(C)C)CC3)nn2)c1] |

TABLE 1-continued
| Compound | Structure |
|---|---|
| 594 | 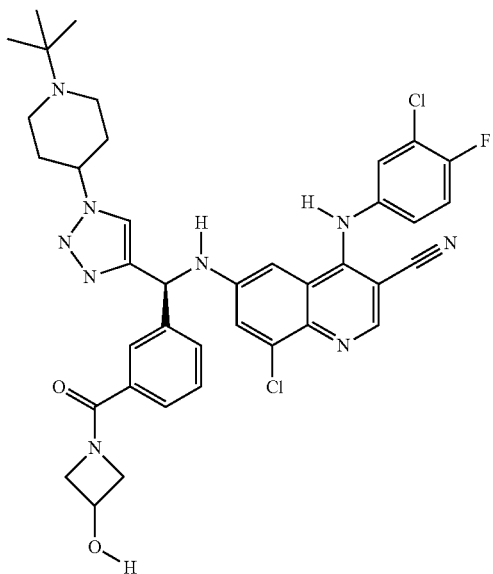 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)N4CC(O)C4)c3)NN2)CC1] |
| 595 | 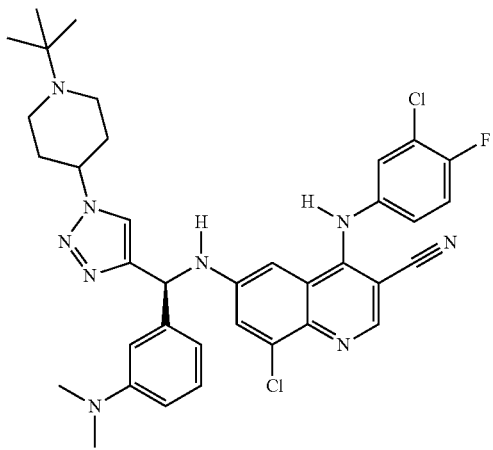 [SMILES: CN(C)c1cccc([C@H](Nc2cc(Cl)c3ncc(C#N)c(Nc4ccc(F)c(Cl)c4)c3c2)c2cn(C3CCN(C(C)(C)C)CC3)nn2)c1] |
| 596 | 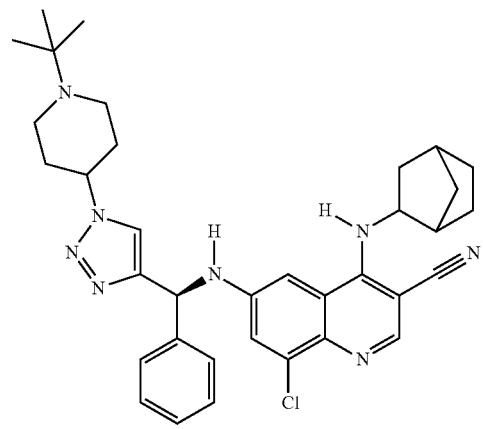 [SMILES: CC(C)(C)N1CCC(n2cc([C@@H](Nc3cc(Cl)c4ncc(C#N)c(NC5CC6CCC5C6)c4c3)c3ccccc3)nn2)CC1] |

TABLE 1-continued
| Compound | Structure |
|---|---|
| 597 | 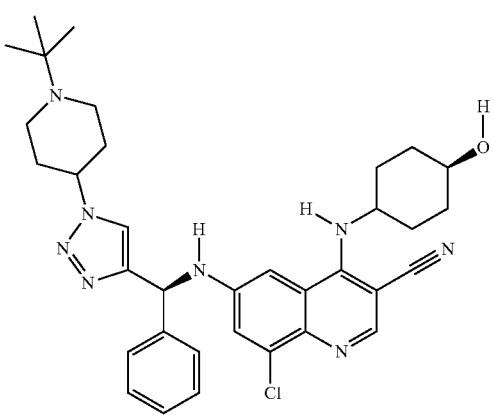 |
| 598 | 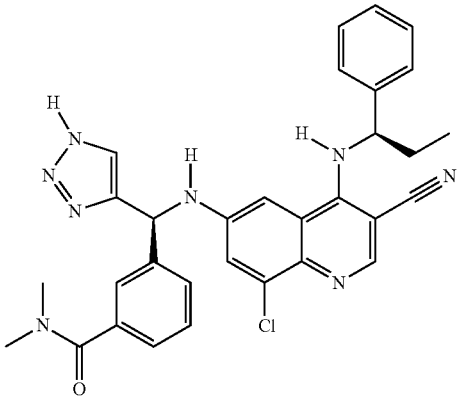 [SMILES: CC[C@@H](Nc1c(C#N)cnc2c(Cl)cc(N[C@@H](c3cccc(C(=O)N(C)C)c3)c3c[nH]nn3)cc12)c1ccccc1] |
| 599 | 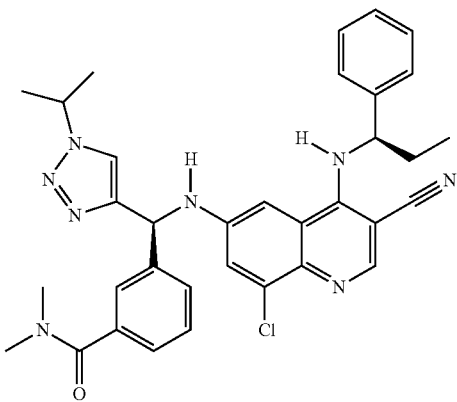 [SMILES: CC[C@@H](Nc1c(C#N)cnc2c(Cl)cc(N[C@@H](c3cccc(C(=O)N(C)C)c3)c3cn(C(C)C)nn3)cc12)c1ccccc1] |

TABLE 1-continued
| Compound | Structure |
|---|---|
| 600 | 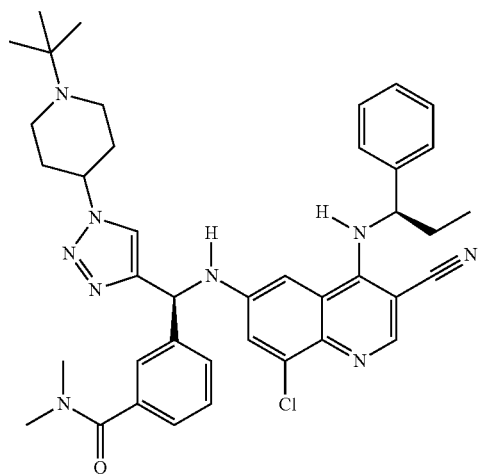 [SMILES: CC[C@@H](Nc1c(C#N)cnc2c(Cl)cc(N[C@@H](c3cccc(C(=O)N(C)C)c3)c3cn(C4CCN(C(C)(C)C)CC4)nn3)cc12)c1ccccc1] |
| 601 | 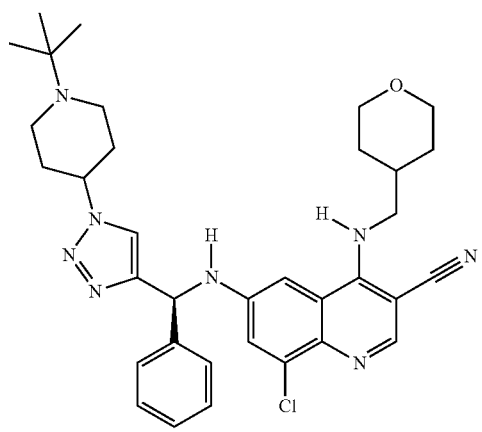 [SMILES: CC(C)(C)N1CCC(n2cc([C@@H](Nc3cc(Cl)c4ncc(C#N)c(NCC5CCOCC5)c4c3)c3ccccc3)nn2)CC1] |
| 602 | 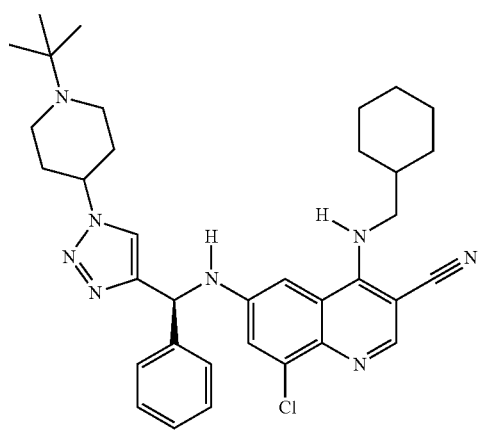 [SMILES: CC(C)(C)N1CCC(n2cc([C@@H](Nc3cc(Cl)c4ncc(C#N)c(NCC5CCCCC5)c4c3)c3ccccc3)nn2)CC1] |

TABLE 1-continued
| Compound | Structure |
|---|---|
| 603 | 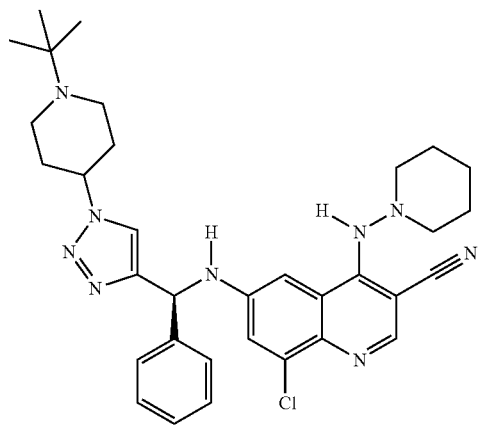 [SMILES: CC(C)(C)N1CCC(n2cc([C@@H](Nc3cc(Cl)c4ncc(C#N)c(NN5CCCCC5)c4c3)c3ccccc3)nn2)CC1] |
| 604 | 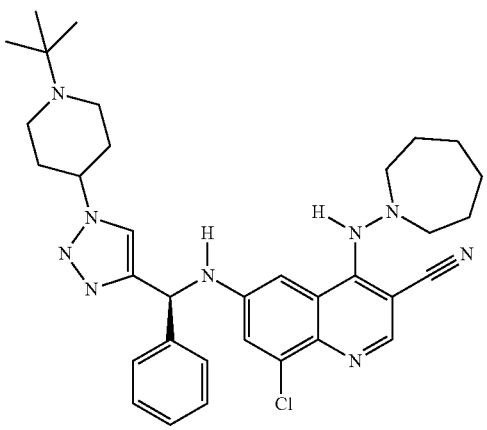 [SMILES: CC(C)(C)N1CCC(N2C=C([C@@H](Nc3cc(Cl)c4ncc(C#N)c(NN5CCCCCC5)c4c3)c3ccccc3)NN2)CC1] |
| 605 | 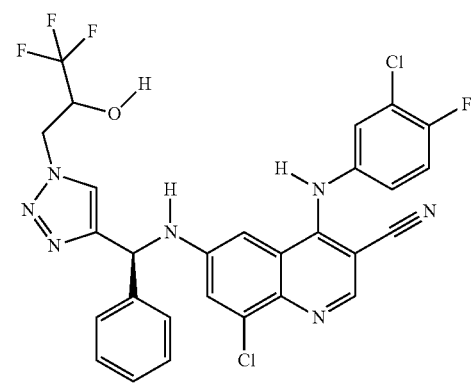 [SMILES: N#Cc1cnc2c(Cl)cc(N[C@@H](c3ccccc3)c3cn(CC(O)C(F)(F)F)nn3)cc2c1Nc1ccc(F)c(Cl)c1] |

TABLE 1-continued

| Compound | Structure |
|---|---|
| 606 | |
| 607 | |
| 608 | |

TABLE 1-continued

| Compound | Structure |
|---|---|
| 609 | |
| 610 | |
| 611 | |
| 612 | |

TABLE 1-continued

| Compound | Structure |
|---|---|
| 613 | |
| 614 | |
| 615 | |
| 616 | |

TABLE 1-continued
| Compound | Structure |
|---|---|
| 617 | 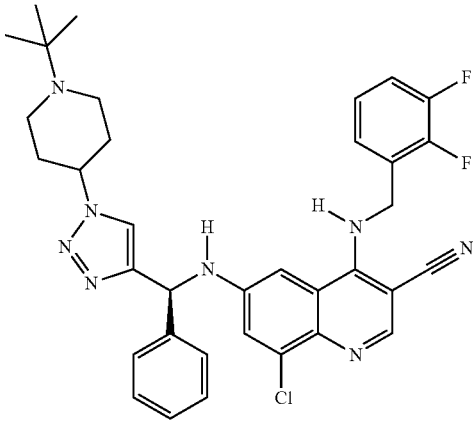 [SMILES: CC(C)(C)N1CCC(n2cc([C@@H](Nc3cc(Cl)c4ncc(C#N)c(NCc5cccc(F)c5F)c4c3)c3ccccc3)nn2)CC1] |
| 618 | 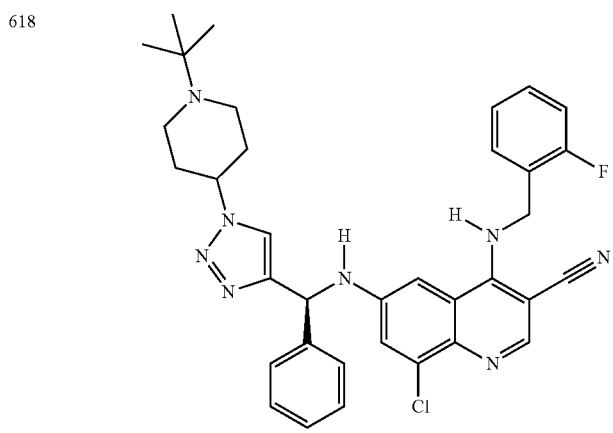 |
| 619 | 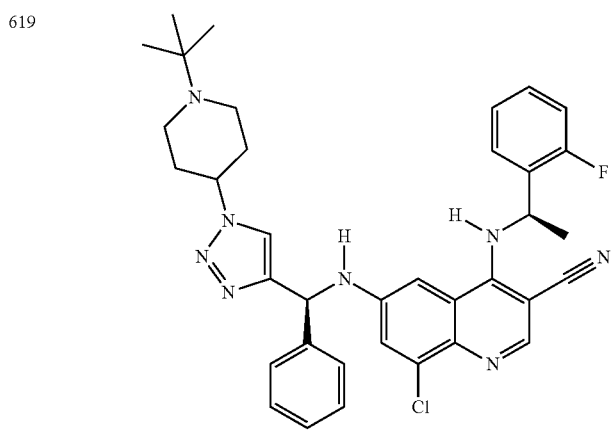 |

TABLE 1-continued
| Compound | Structure |
|---|---|
| 620 | 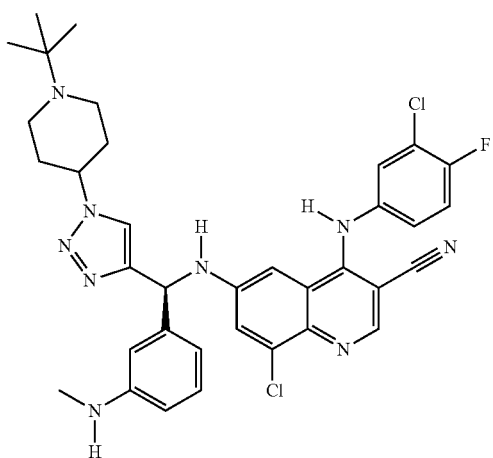 [SMILES: CNc1cccc([C@H](Nc2cc(Cl)c3ncc(C#N)c(Nc4ccc(F)c(Cl)c4)c3c2)c2cn(C3CCN(C(C)(C)C)CC3)nn2)c1] |
| 621 | 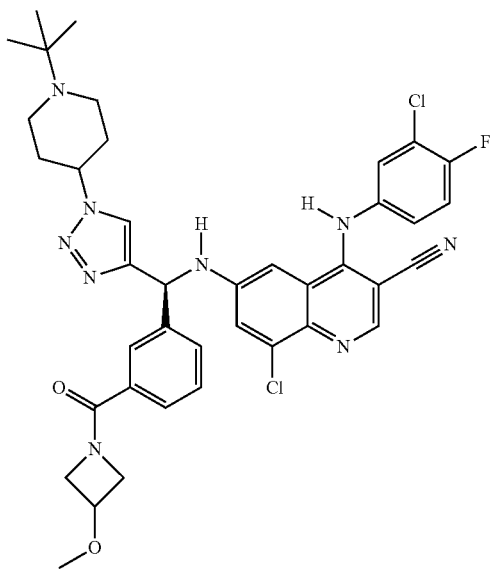 [SMILES: COC1CN(C(=O)c2cccc([C@H](Nc3cc(Cl)c4ncc(C#N)c(Nc5ccc(F)c(Cl)c5)c4c3)c3cn(C4CCN(C(C)(C)C)CC4)nn3)c2)C1] |
| 622 | 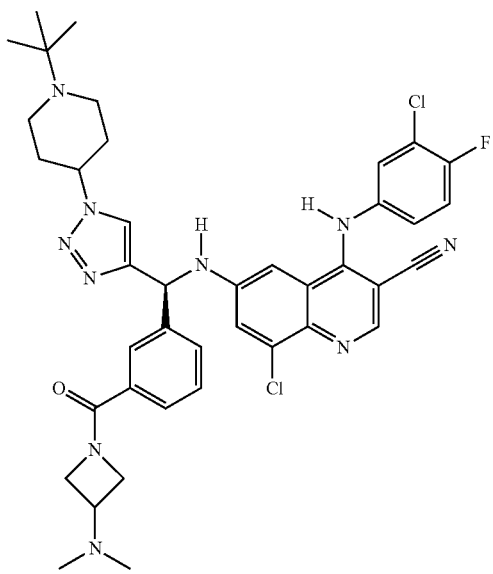 [SMILES: CN(C)C1CN(C(=O)c2cccc([C@H](Nc3cc(Cl)c4ncc(C#N)c(Nc5ccc(F)c(Cl)c5)c4c3)c3cn(C4CCN(C(C)(C)C)CC4)nn3)c2)C1] |

TABLE 1-continued

| Compound | Structure |
|---|---|
| 623 | |
| 624 | |
| 625 | |

TABLE 1-continued

| Compound | Structure |
|---|---|
| 626 | |
| 627 | |
| 628 | |
| 629 | |

TABLE 1-continued
| Compound | Structure |
|---|---|
| 630 | 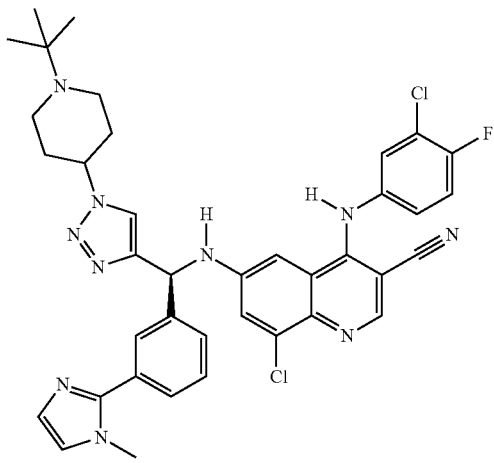 [SMILES: Cn1ccnc1-c1cccc([C@H](Nc2cc(Cl)c3ncc(C#N)c(Nc4ccc(F)c(Cl)c4)c3c2)c2cn(C3CCN(C(C)(C)C)CC3)nn2)c1] |
| 631 | 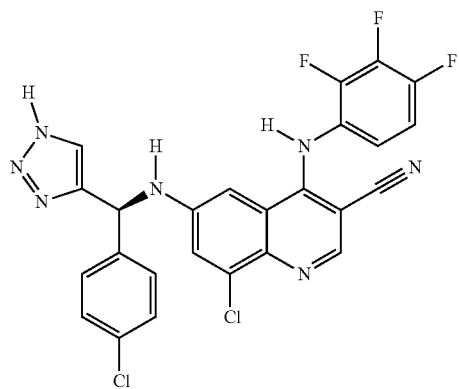 [SMILES: N#Cc1cnc2c(Cl)cc(N[C@@H](c3ccc(Cl)cc3)c3c[nH]nn3)cc2c1Nc1ccc(F)c(F)c1F] |
| 632 | 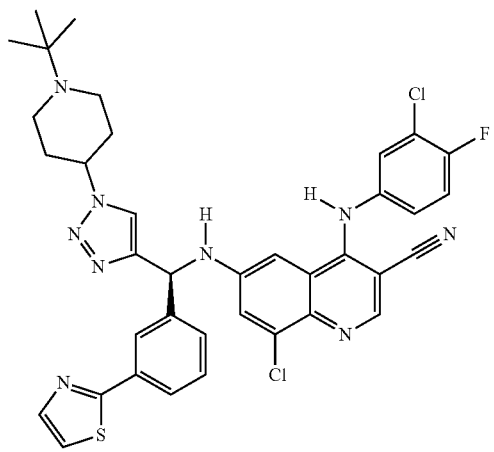 [SMILES: CC(C)(C)N1CCC(n2cc([C@@H](Nc3cc(Cl)c4ncc(C#N)c(Nc5ccc(F)c(Cl)c5)c4c3)c3cccc(-c4nccs4)c3)nn2)CC1] |

TABLE 1-continued
| Compound | Structure |
|---|---|
| 633 | 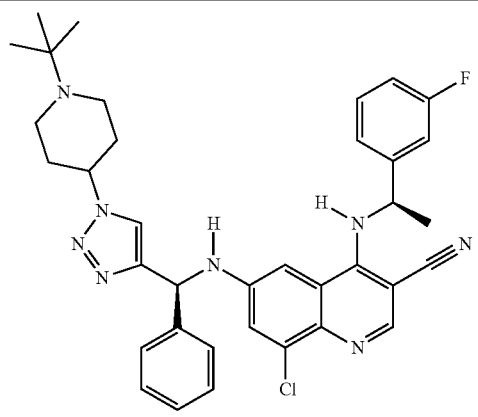 |
| 634 | 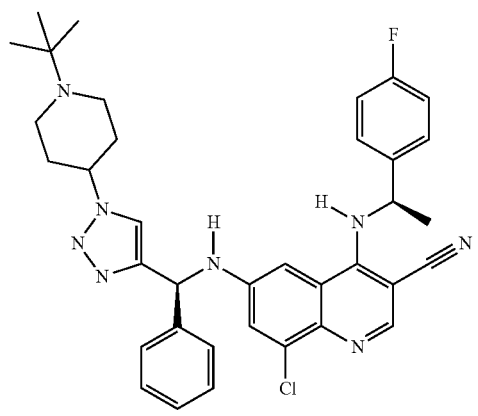 [SMILES: C[C@@H](Nc1c(C#N)cnc2c(Cl)cc(N[C@H](C3=CN(C4CCN(C(C)(C)C)CC4)NN3)c3ccccc3)cc12)c1ccc(F)cc1] |
| 635 | 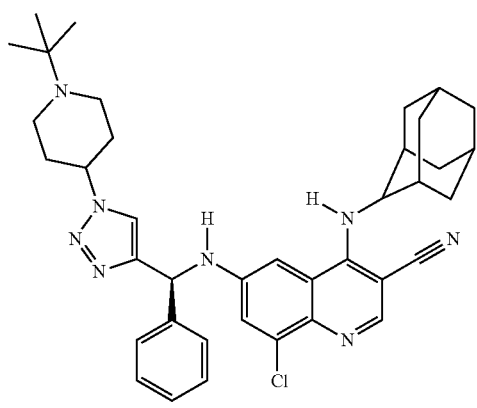 [SMILES: CC(C)(C)N1CCC(n2cc([C@@H](Nc3cc(Cl)c4ncc(C#N)c(NC5C6CC7CC(C6)CC5C7)c4c3)c3ccccc3)nn2)CC1] |

TABLE 1-continued

| Compound | Structure |
|---|---|
| 636 | |
| 637 | |
| 638 | |
| 639 | |

TABLE 1-continued
| Compound | Structure |
|---|---|
| 640 | 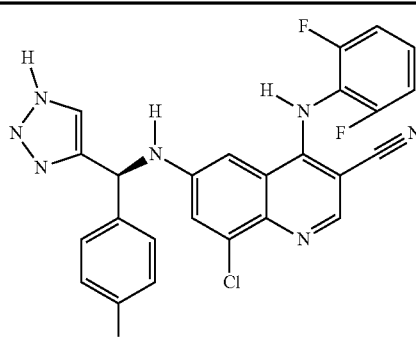 |
| 641 | 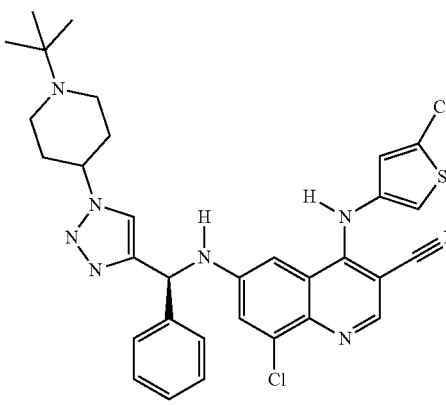 |
| 642 | 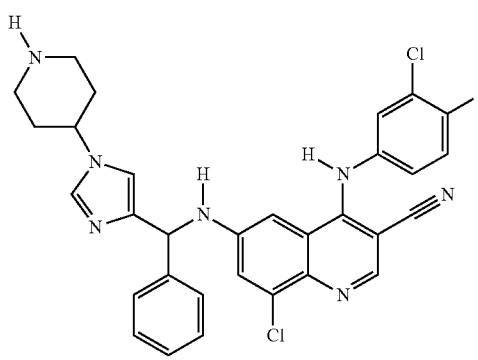 |
| 643 | 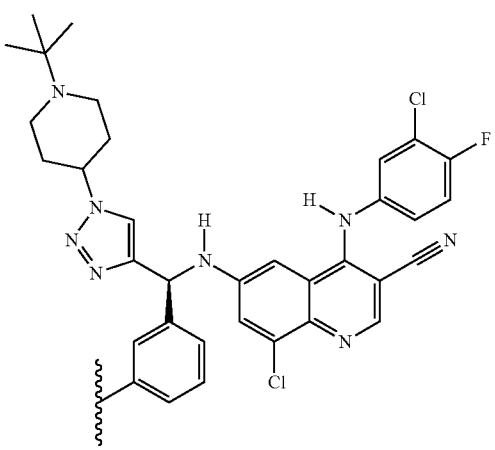 [SMILES: *c1cccc([C@H](Nc2cc(Cl)c3ncc(C#N)c(Nc4ccc(F)c(Cl)c4)c3c2)c2cn(C3CCN(C(C)(C)C)CC3)nn2)c1] |

TABLE 1-continued
| Compound | Structure |
|---|---|
| 644 | 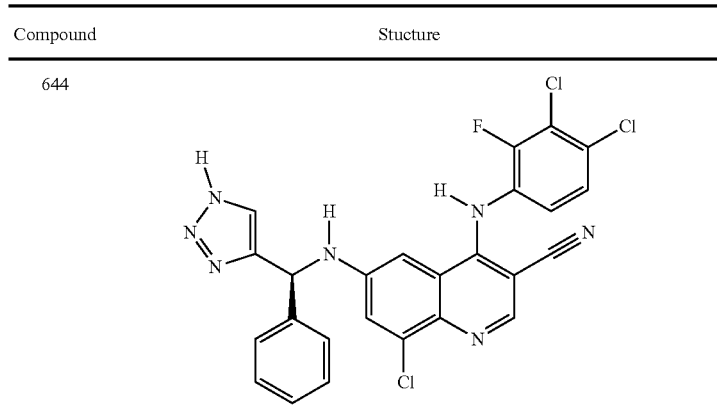 |
| 645 | 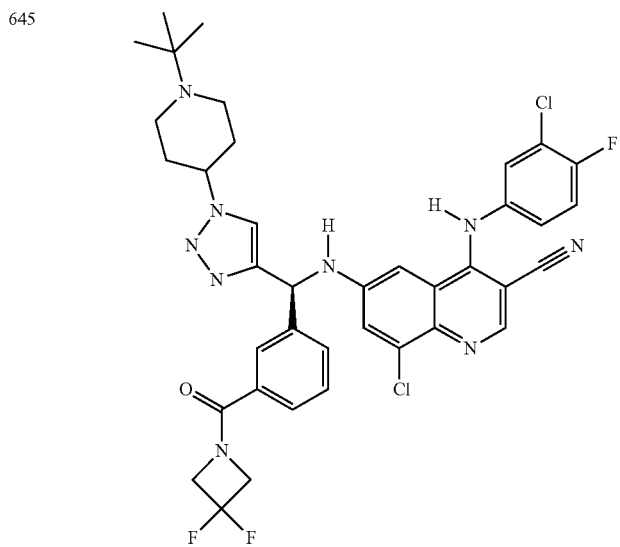 |
| 646 | 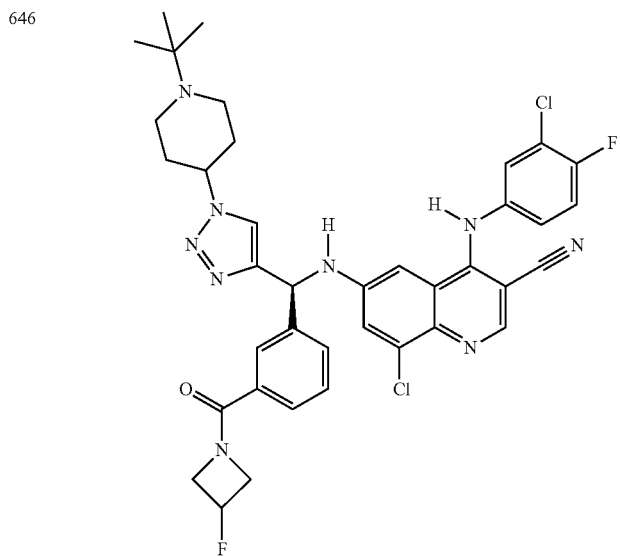 |

TABLE 1-continued

| Compound | Structure |
|---|---|
| 647 | |
| 648 | |
| 649 | |
| 650 | |

TABLE 1-continued
| Compound | Structure |
|---|---|
| 651 | 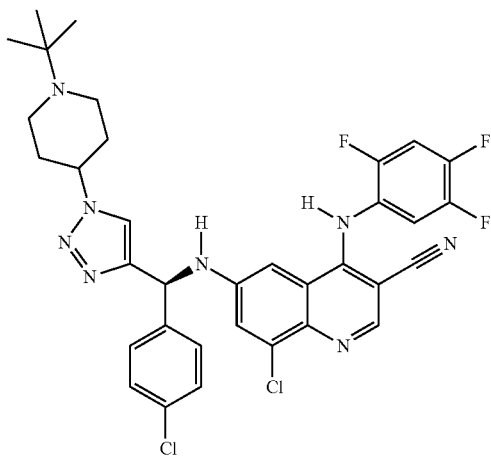 [SMILES: CC(C)(C)N1CCC(n2cc([C@@H](Nc3cc(Cl)c4ncc(C#N)c(Nc5cc(F)c(F)cc5F)c4c3)c3ccc(Cl)cc3)nn2)CC1] |
| 652 | 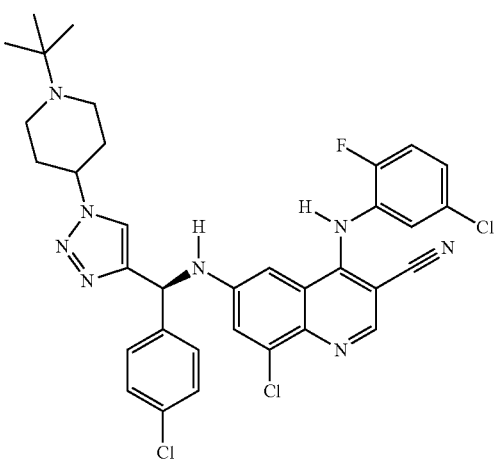 |
| 653 | 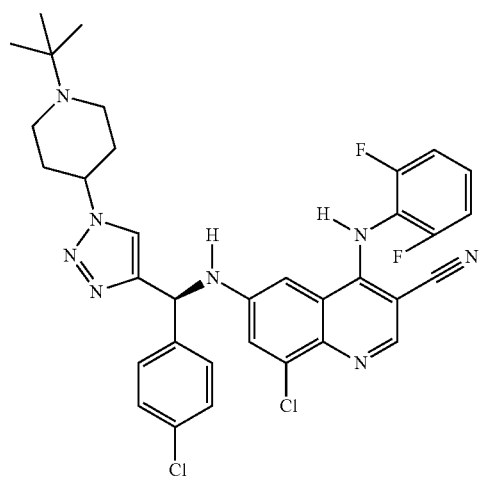 [SMILES: CC(C)(C)N1CCC(n2cc([C@@H](Nc3cc(Cl)c4ncc(C#N)c(Nc5c(F)cccc5F)c4c3)c3ccc(Cl)cc3)nn2)CC1] |

TABLE 1-continued

| Compound | Structure |
|---|---|
| 654 | |
| 655 | |
| 656 | |
| 657 | |

TABLE 1-continued
| Compound | Structure |
|---|---|
| 658 | 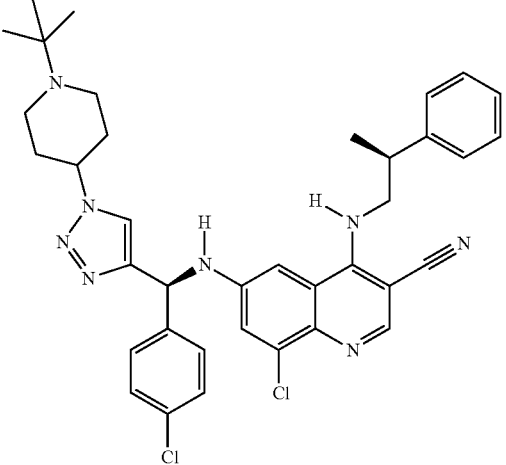 [SMILES: C[C@H](CNc1c(C#N)cnc2c(Cl)cc(N[C@@H](c3ccc(Cl)cc3)c3cn(C4CCN(C(C)(C)C)CC4)nn3)cc12)c1ccccc1] |
| 659 | 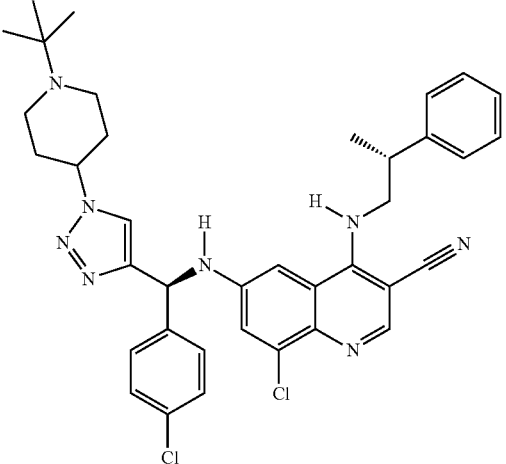 [SMILES: C[C@@H](CNc1c(C#N)cnc2c(Cl)cc(N[C@@H](c3ccc(Cl)cc3)c3cn(C4CCN(C(C)(C)C)CC4)nn3)cc12)c1ccccc1] |
| 660 | 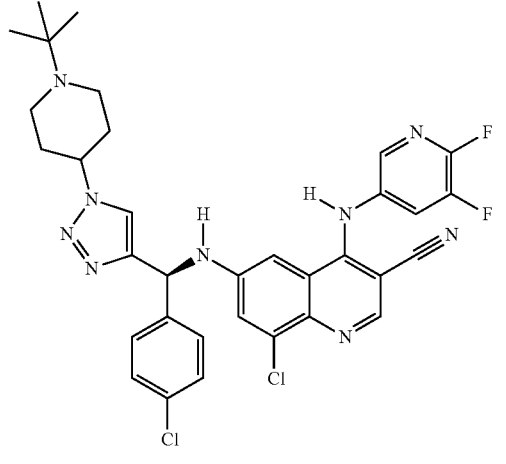 [SMILES: CC(C)(C)N1CCC(n2cc([C@@H](Nc3cc(Cl)c4ncc(C#N)c(Nc5cnc(F)c(F)c5)c4c3)c3ccc(Cl)cc3)nn2)CC1] |

TABLE 1-continued
| Compound | Structure |
|---|---|
| 661 | 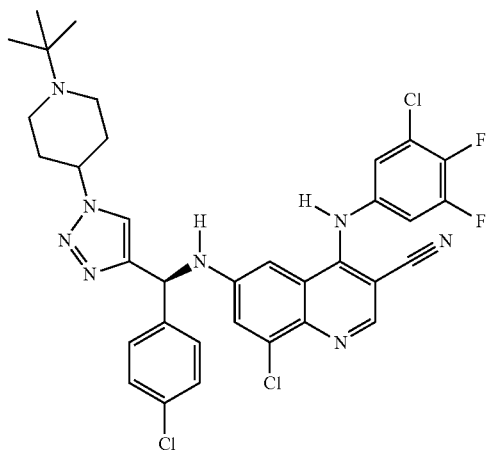 [SMILES: CC(C)(C)N1CCC(n2cc([C@@H](Nc3cc(Cl)c4ncc(C#N)c(Nc5cc(F)c(F)c(Cl)c5)c4c3)c3ccc(Cl)cc3)nn2)CC1] |
| 662 | 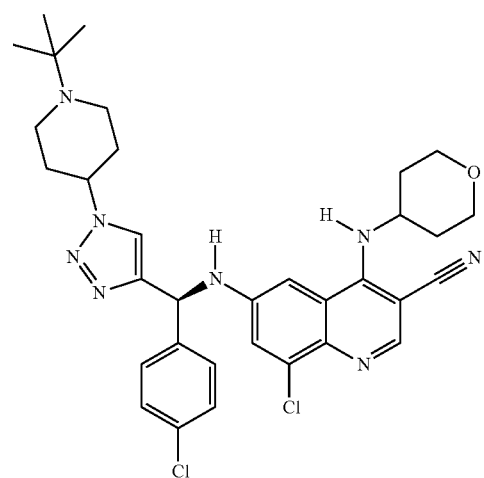 [SMILES: CC(C)(C)N1CCC(n2cc([C@@H](Nc3cc(Cl)c4ncc(C#N)c(NC5CCOCC5)c4c3)c3ccc(Cl)cc3)nn2)CC1] |
| 663 | 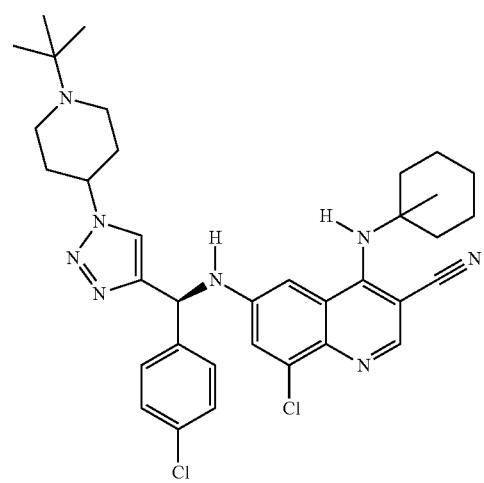 |

TABLE 1-continued

| Compound | Structure |
|---|---|
| 664 | |
| 665 | |
| 666 | |
| 667 | |

TABLE 1-continued

| Compound | Structure |
|---|---|
| 668 | |
| 669 | |
| 670 | |
| 671 | |

TABLE 1-continued
| Compound | Structure |
|---|---|
| 672 | 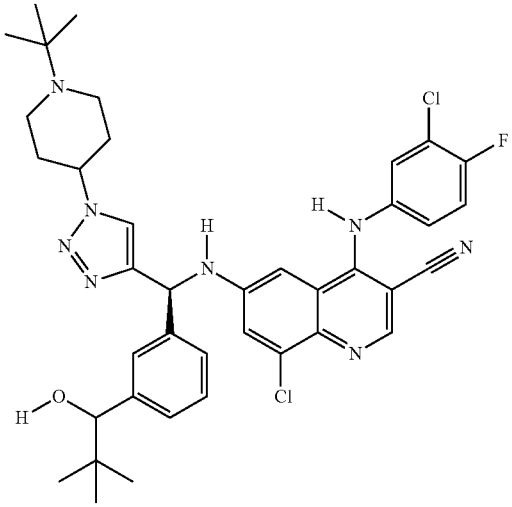 [SMILES: CC(C)(C)C(O)c1cccc([C@H](Nc2cc(Cl)c3ncc(C#N)c(Nc4ccc(F)c(Cl)c4)c3c2)c2cn(C3CCN(C(C)(C)C)CC3)nn2)c1] |
| 673 | 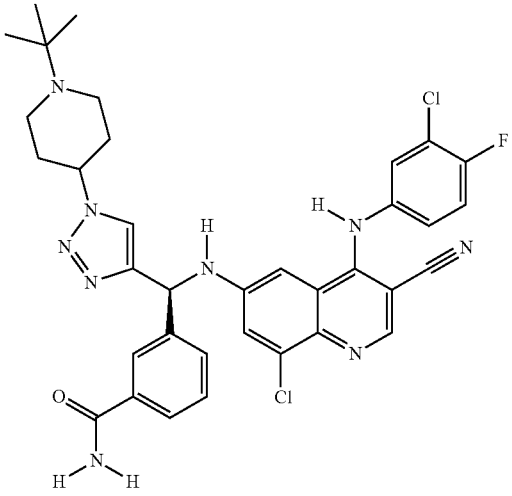 [SMILES: CC(C)(C)N1CCC(n2cc([C@@H](Nc3cc(Cl)c4ncc(C#N)c(Nc5ccc(F)c(Cl)c5)c4c3)c3cccc(C(N)=O)c3)nn2)CC1] |
| 674 | 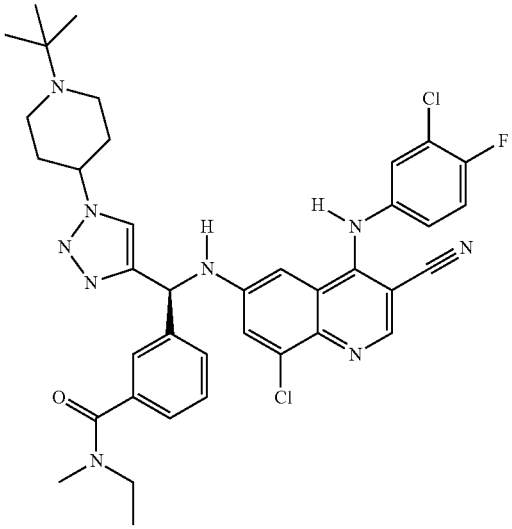 [SMILES: CCN(C)C(=O)c1cccc([C@H](Nc2cc(Cl)c3ncc(C#N)c(Nc4ccc(F)c(Cl)c4)c3c2)C2=CN(C3CCN(C(C)(C)C)CC3)NN2)c1] |

TABLE 1-continued
| Compound | Structure |
|---|---|
| 675 | 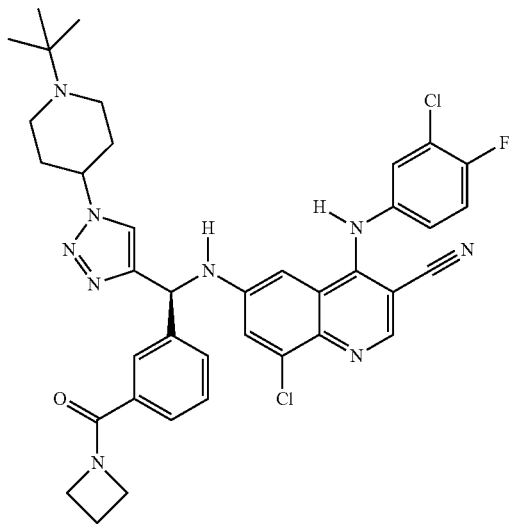 [SMILES: CC(C)(C)N1CCC(n2cc([C@@H](Nc3cc(Cl)c4ncc(C#N)c(Nc5ccc(F)c(Cl)c5)c4c3)c3cccc(C(=O)N4CCC4)c3)nn2)CC1] |
| 676 | 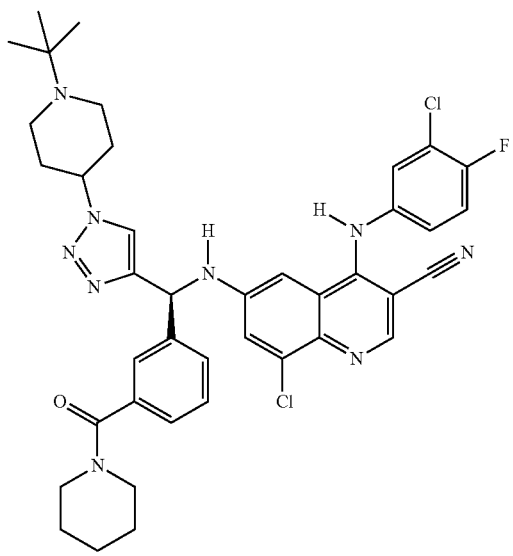 [SMILES: CC(C)(C)N1CCC(n2cc([C@@H](Nc3cc(Cl)c4ncc(C#N)c(Nc5ccc(F)c(Cl)c5)c4c3)c3cccc(C(=O)N4CCCCC4)c3)nn2)CC1] |
| 677 | 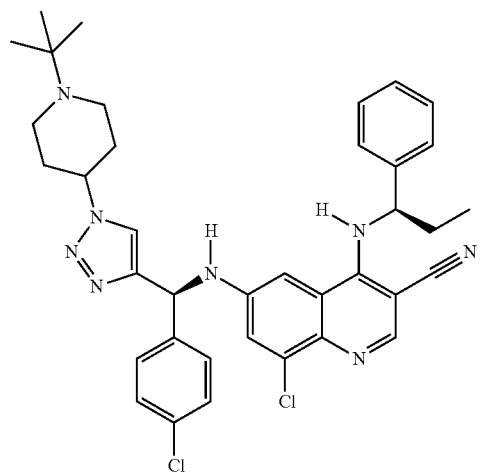 [SMILES: CC[C@@H](Nc1c(C#N)cnc2c(Cl)cc(N[C@@H](c3ccc(Cl)cc3)c3cn(C4CCN(C(C)(C)C)CC4)nn3)cc12)c1ccccc1] |

TABLE 1-continued
| Compound | Structure |
|---|---|
| 678 | 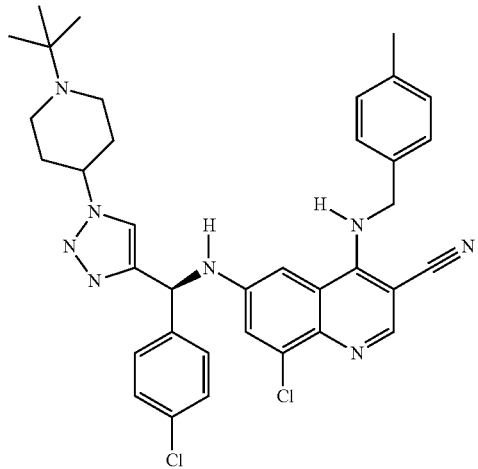 [SMILES: Cc1ccc(CNc2c(C#N)cnc3c(Cl)cc(N[C@H](C4=CN(C5CCN(C(C)(C)C)CC5)NN4)c4ccc(Cl)cc4)cc23)cc1] |
| 679 | 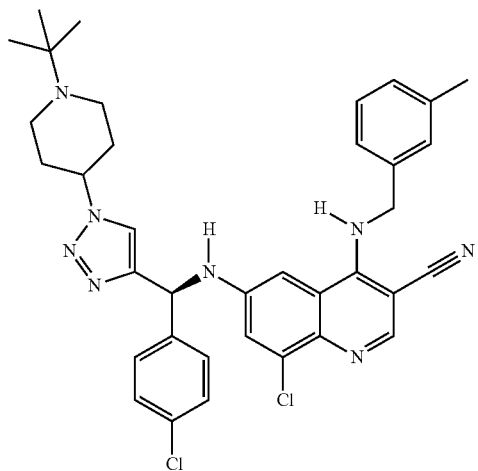 [SMILES: Cc1cccc(CNc2c(C#N)cnc3c(Cl)cc(N[C@@H](c4ccc(Cl)cc4)c4cn(C5CCN(C(C)(C)C)CC5)nn4)cc23)c1] |
| 680 | 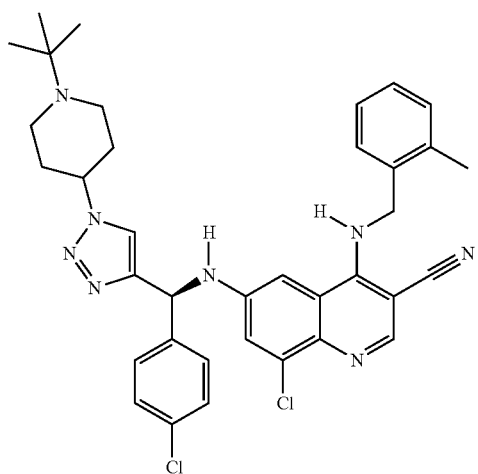 [SMILES: Cc1ccccc1CNc1c(C#N)cnc2c(Cl)cc(N[C@@H](c3ccc(Cl)cc3)c3cn(C4CCN(C(C)(C)C)CC4)nn3)cc12] |

TABLE 1-continued
| Compound | Structure |
|---|---|
| 681 | 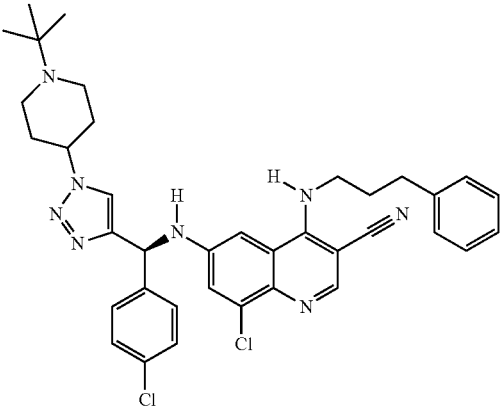 [SMILES: CC(C)(C)N1CCC(n2cc([C@@H](Nc3cc(Cl)c4ncc(C#N)c(NCCCc5ccccc5)c4c3)c3ccc(Cl)cc3)nn2)CC1] |
| 682 | 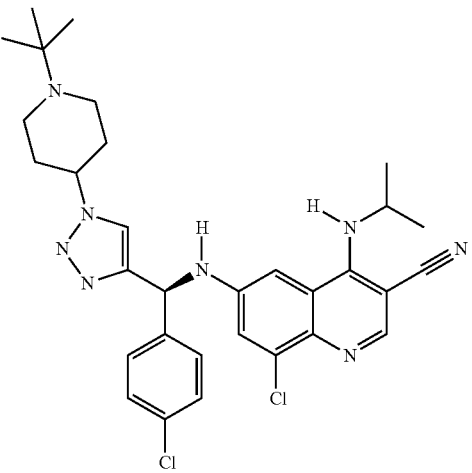 [SMILES: CC(C)Nc1c(C#N)cnc2c(Cl)cc(N[C@H](C3=CN(C4CCN(C(C)(C)C)CC4)NN3)c3ccc(Cl)cc3)cc12] |
| 683 | 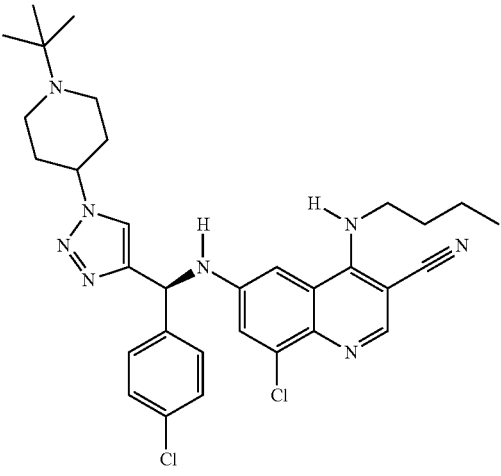 [SMILES: CCCCNc1c(C#N)cnc2c(Cl)cc(N[C@@H](c3ccc(Cl)cc3)c3cn(C4CCN(C(C)(C)C)CC4)nn3)cc12] |

TABLE 1-continued
| Compound | Stucture |
|---|---|
| 684 | 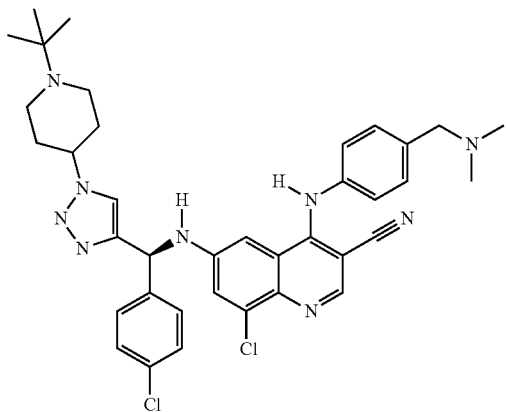 [SMILES: CN(C)Cc1ccc(Nc2c(C#N)cnc3c(Cl)cc(N[C@H](C4=CN(C5CCN(C(C)(C)C)CC5)NN4)c4ccc(Cl)cc4)cc23)cc1] |
| 685 | 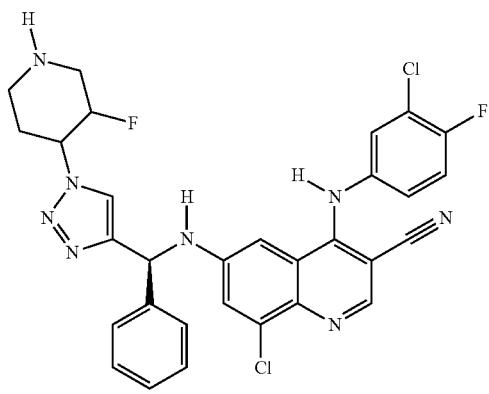 [SMILES: N#Cc1cnc2c(Cl)cc(N[C@@H](c3ccccc3)c3cn(C4CCNCC4F)nn3)cc2c1Nc1ccc(F)c(Cl)c1] |
| 686 | 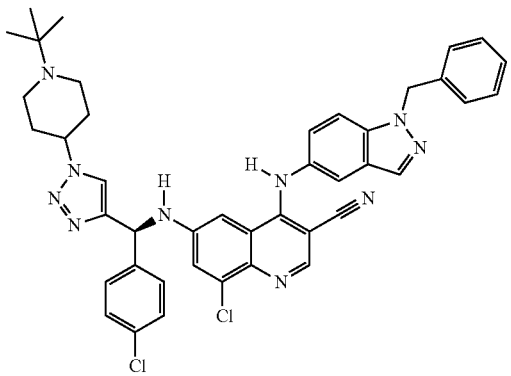 [SMILES: CC(C)(C)N1CCC(n2cc([C@@H](Nc3cc(Cl)c4ncc(C#N)c(Nc5ccc6c(cnn6Cc6ccccc6)c5)c4c3)c3ccc(Cl)cc3)nn2)CC1] |

TABLE 1-continued
| Compound | Structure |
|---|---|
| 687 | 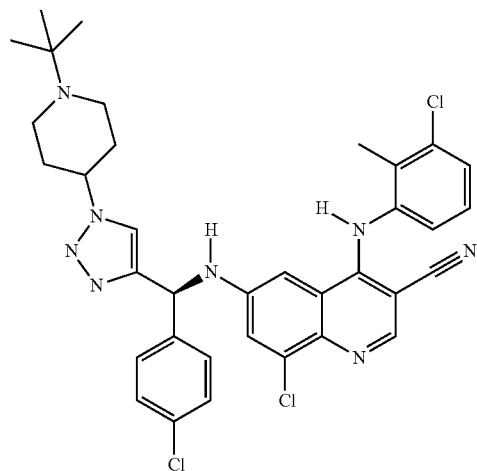 |
| 688 | 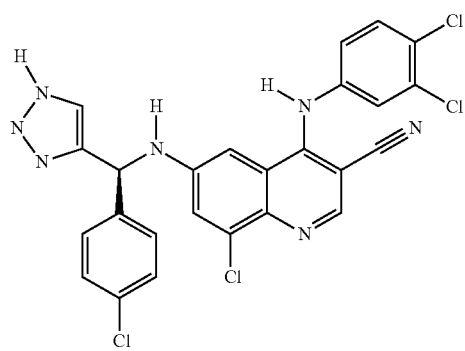 [SMILES: N#Cc1cnc2c(Cl)cc(N[C@H](C3=CNNN3)c3ccc(Cl)cc3)cc2c1Nc1ccc(Cl)c(Cl)c1] |
| 689 | 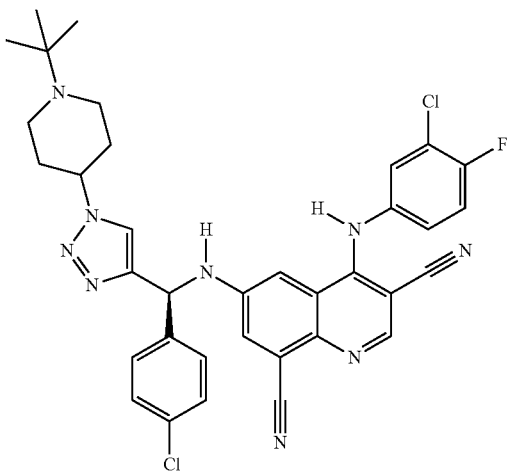 [SMILES: CC(C)(C)N1CCC(n2cc([C@@H](Nc3cc(C#N)c4ncc(C#N)c(Nc5ccc(F)c(Cl)c5)c4c3)c3ccc(Cl)cc3)nn2)CC1] |

TABLE 1-continued
| Compound | Structure |
|---|---|
| 690 | 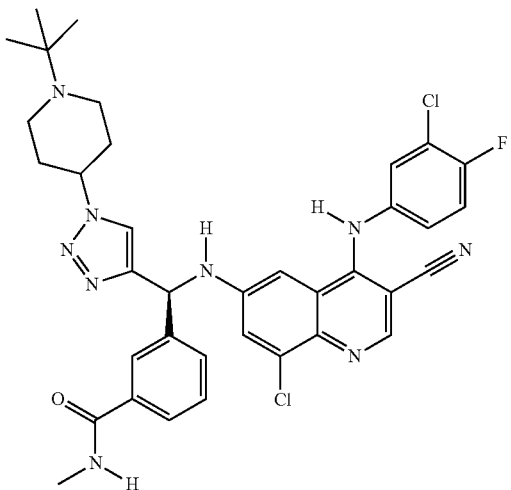 [SMILES: CNC(=O)c1cccc([C@H](Nc2cc(Cl)c3ncc(C#N)c(Nc4ccc(F)c(Cl)c4)c3c2)c2cn(C3CCN(C(C)(C)C)CC3)nn2)c1] |
| 691 | 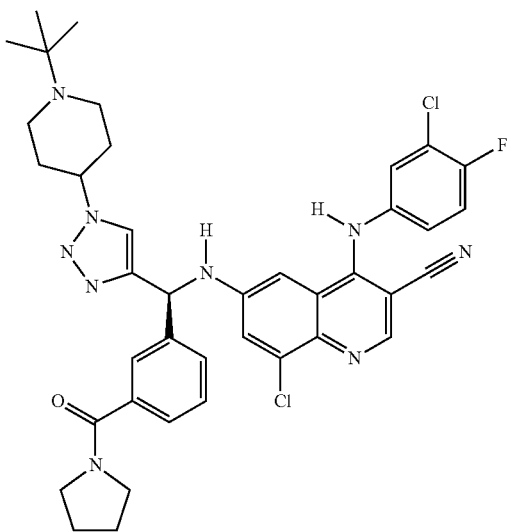 [SMILES: CC(C)(C)N1CCC(N2C=C([C@@H](Nc3cc(Cl)c4ncc(C#N)c(Nc5ccc(F)c(Cl)c5)c4c3)c3cccc(C(=O)N4CCCC4)c3)NN2)CC1] |
| 692 | 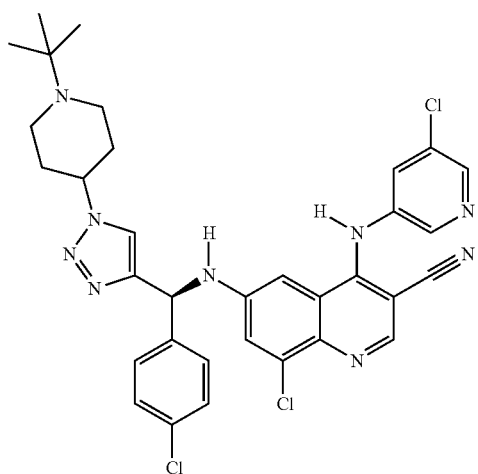 |

TABLE 1-continued
| Compound | Structure |
|---|---|
| 693 | 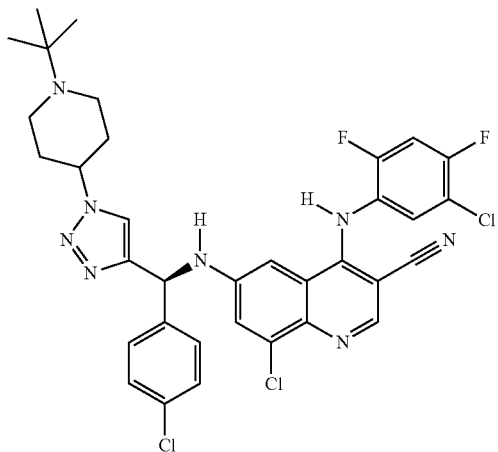 [SMILES: CC(C)(C)N1CCC(n2cc([C@@H](Nc3cc(Cl)c4ncc(C#N)c(Nc5cc(Cl)c(F)cc5F)c4c3)c3ccc(Cl)cc3)nn2)CC1] |
| 694 | 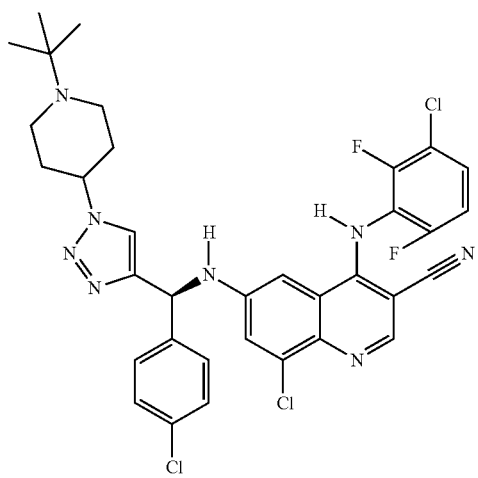 [SMILES: CC(C)(C)N1CCC(n2cc([C@@H](Nc3cc(Cl)c4ncc(C#N)c(Nc5c(F)ccc(Cl)c5F)c4c3)c3ccc(Cl)cc3)nn2)CC1] |
| 695 | 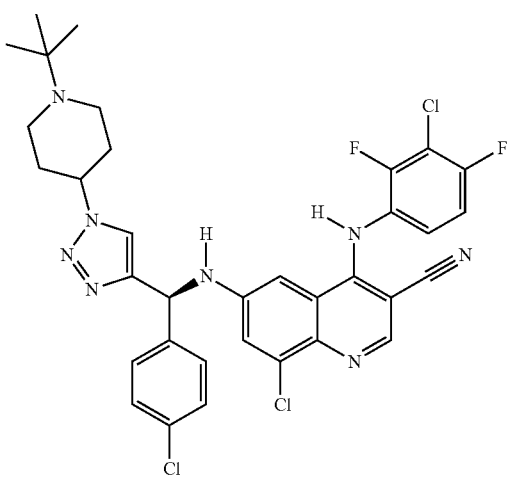 [SMILES: CC(C)(C)N1CCC(n2cc([C@@H](Nc3cc(Cl)c4ncc(C#N)c(Nc5ccc(F)c(Cl)c5F)c4c3)c3ccc(Cl)cc3)nn2)CC1] |

TABLE 1-continued
| Compound | Structure |
|---|---|
| 696 | 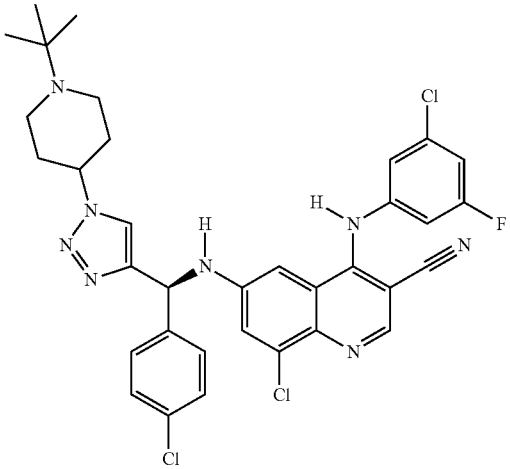 [SMILES: CC(C)(C)N1CCC(n2cc([C@@H](Nc3cc(Cl)c4ncc(C#N)c(Nc5cc(F)cc(Cl)c5)c4c3)c3ccc(Cl)cc3)nn2)CC1] |
| 697 | 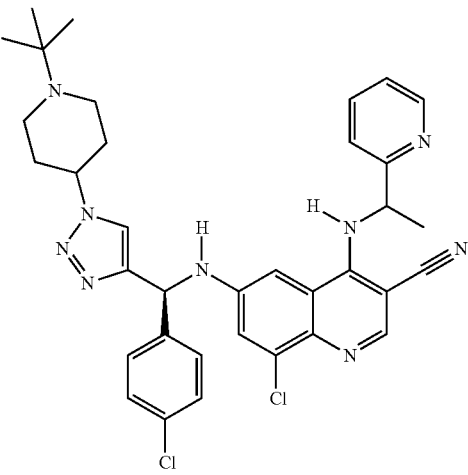 [SMILES: CC(Nc1c(C#N)cnc2c(Cl)cc(N[C@@H](c3ccc(Cl)cc3)c3cn(C4CCN(C(C)(C)C)CC4)nn3)cc12)c1ccccn1] |
| 698 | 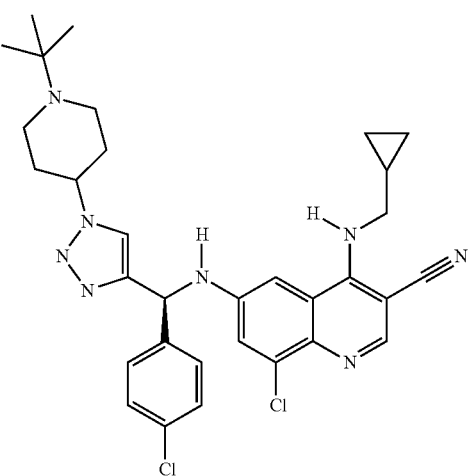 [SMILES: CC(C)(C)N1CCC(N2C=C([C@@H](Nc3cc(Cl)c4ncc(C#N)c(NCC5CC5)c4c3)c3ccc(Cl)cc3)NN2)CC1] |

TABLE 1-continued

| Compound | Structure |
|---|---|
| 699 | |
| 700 | |
| 701 | |

TABLE 1-continued
| Compound | Structure |
|---|---|
| 702 | 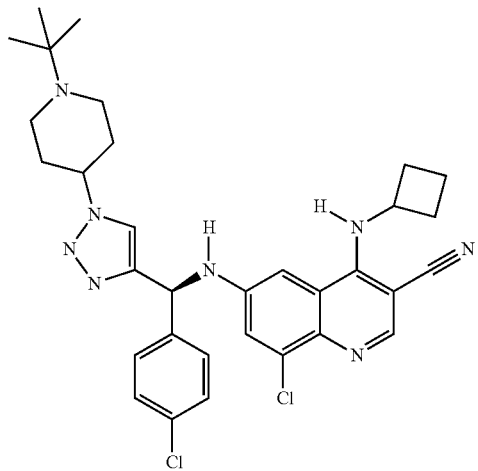 [SMILES: CC(C)(C)N1CCC(N2C=C([C@@H](Nc3cc(Cl)c4ncc(C#N)c(NC5CCC5)c4c3)c3ccc(Cl)cc3)NN2)CC1] |
| 703 | 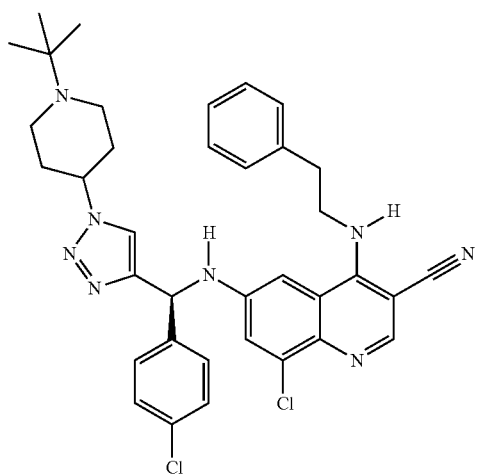 [SMILES: CC(C)(C)N1CCC(n2cc([C@@H](Nc3cc(Cl)c4ncc(C#N)c(NCCc5ccccc5)c4c3)c3ccc(Cl)cc3)nn2)CC1] |
| 704 | 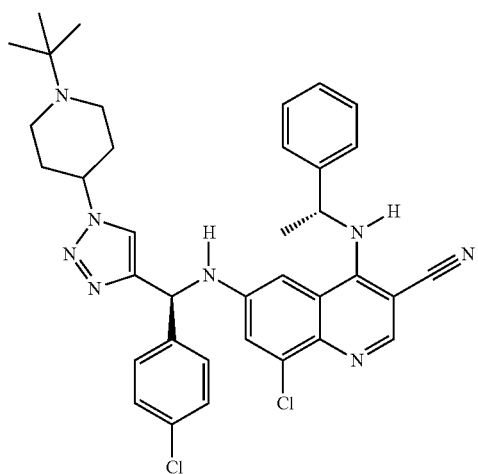 [SMILES: C[C@@H](Nc1c(C#N)cnc2c(Cl)cc(N[C@@H](c3ccc(Cl)cc3)c3cn(C4CCN(C(C)(C)C)CC4)nn3)cc12)c1ccccc1] |

TABLE 1-continued
| Compound | Structure |
|---|---|
| 705 | 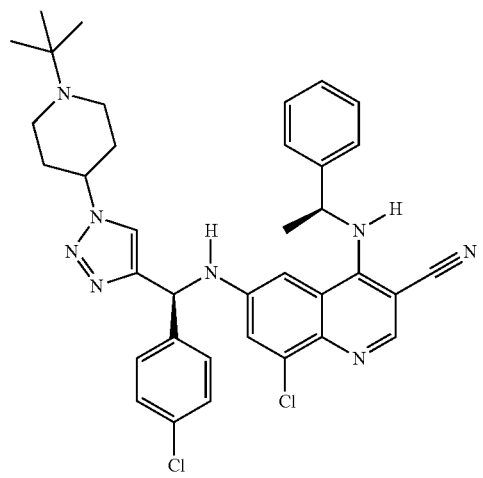 [SMILES: C[C@H](Nc1c(C#N)cnc2c(Cl)cc(N[C@@H](c3ccc(Cl)cc3)c3cn(C4CCN(C(C)(C)C)CC4)nn3)cc12)c1ccccc1] |
| 706 | 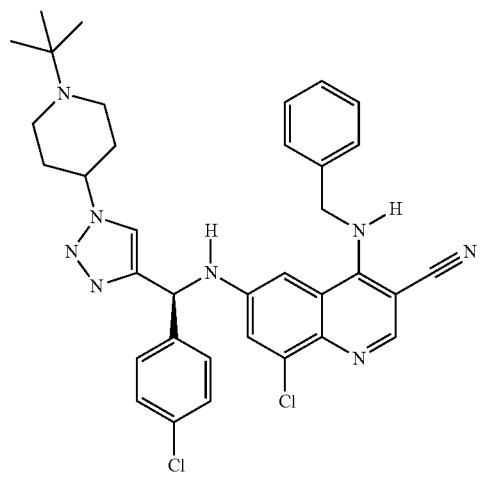 [SMILES: CC(C)(C)N1CCC(N2C=C([C@@H](Nc3cc(Cl)c4ncc(C#N)c(NCc5ccccc5)c4c3)c3ccc(Cl)cc3)NN2)CC1] |
| 707 | 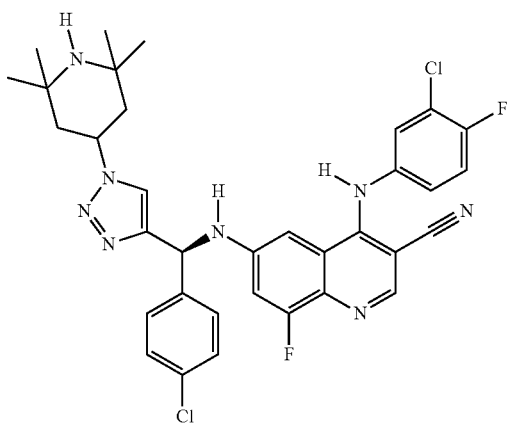 [SMILES: CC1(C)CC(n2cc([C@@H](Nc3cc(F)c4ncc(C#N)c(Nc5ccc(F)c(Cl)c5)c4c3)c3ccc(Cl)cc3)nn2)CC(C)(C)N1] |

TABLE 1-continued

| Compound | Stucture |
|---|---|
| 708 | |
| 709 | |
| 710 | |

TABLE 1-continued

| Compound | Structure |
|---|---|
| 711 | |
| 712 | |
| 713 | |
| 714 | |

TABLE 1-continued
| Compound | Structure |
|---|---|
| 715 | 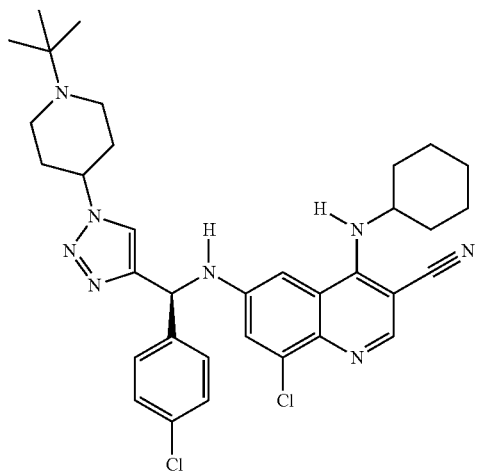 [SMILES: CC(C)(C)N1CCC(n2cc([C@@H](Nc3cc(Cl)c4ncc(C#N)c(NC5CCCCC5)c4c3)c3ccc(Cl)cc3)nn2)CC1] |
| 716 | 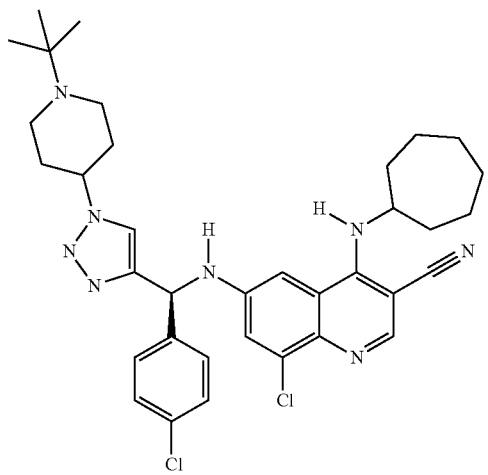 [SMILES: CC(C)(C)N1CCC(N2C=C([C@@H](Nc3cc(Cl)c4ncc(C#N)c(NC5CCCCCC5)c4c3)c3ccc(Cl)cc3)NN2)CC1] |
| 717 | 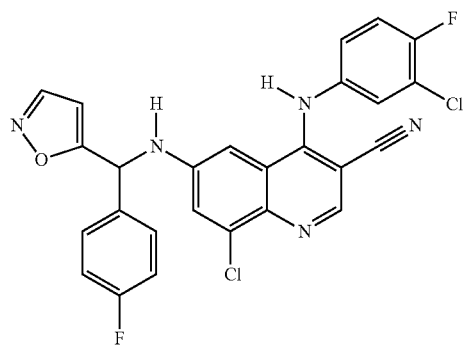 [SMILES: N#Cc1cnc2c(Cl)cc(NC(c3ccc(F)cc3)c3ccno3)cc2c1Nc1ccc(F)c(Cl)c1] |

TABLE 1-continued

| Compound | Structure |
|---|---|
| 718 | |
| 719 | |
| 720 | |
| 721 | |

TABLE 1-continued
| Compound | Structure |
|---|---|
| 722 | 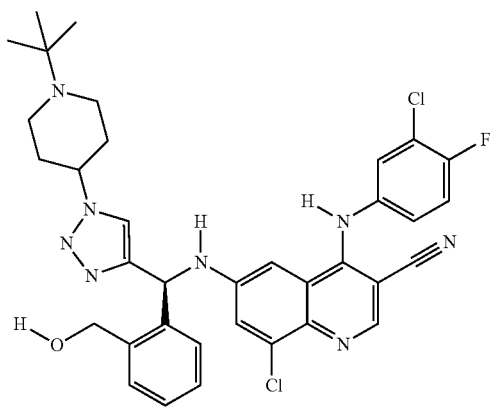 [SMILES: CC(C)(C)N1CCC(N2C=C([C@@H](Nc3cc(Cl)c4ncc(C#N)c(Nc5ccc(F)c(Cl)c5)c4c3)c3ccccc3CO)NN2)CC1] |
| 723 | 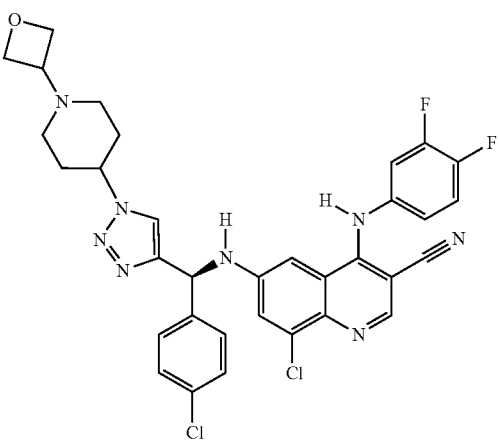 [SMILES: N#Cc1cnc2c(Cl)cc(N[C@@H](c3ccc(Cl)cc3)c3cn(C4CCN(C5COC5)CC4)nn3)cc2c1Nc1ccc(F)c(F)c1] |
| 724 | 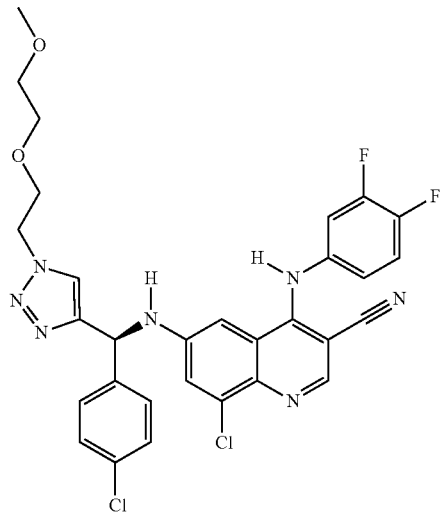 [SMILES: COCCOCCn1cc([C@@H](Nc2cc(Cl)c3ncc(C#N)c(Nc4ccc(F)c(F)c4)c3c2)c2ccc(Cl)cc2)nn1] |

TABLE 1-continued
| Compound | Structure |
| --- | --- |
| 725 | 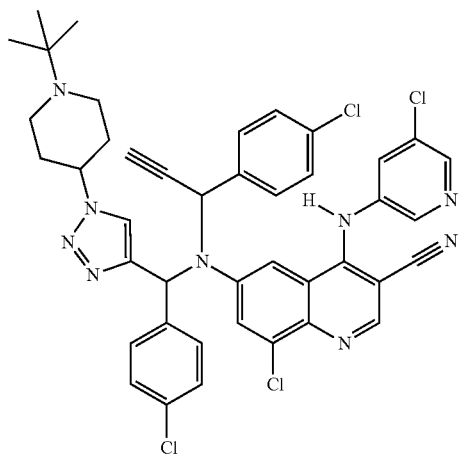 [SMILES: C#CC(c1ccc(Cl)cc1)N(c1cc(Cl)c2ncc(C#N)c(Nc3cncc(Cl)c3)c2c1)C(c1ccc(Cl)cc1)c1cn(C2CCN(C(C)(C)C)CC2)nn1] |
| 726 | 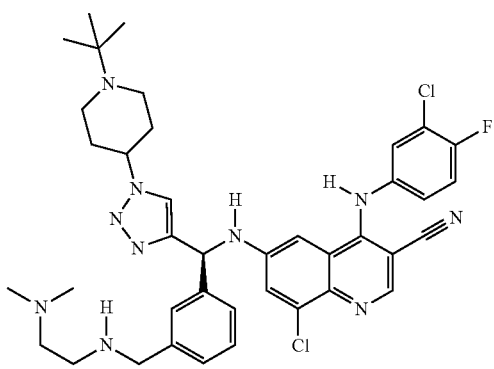 [SMILES: CN(C)CCNCc1cccc([C@H](Nc2cc(Cl)c3ncc(C#N)c(Nc4ccc(F)c(Cl)c4)c3c2)C2=CN(C3CCN(C(C)(C)C)CC3)NN2)c1] |
| 727 | 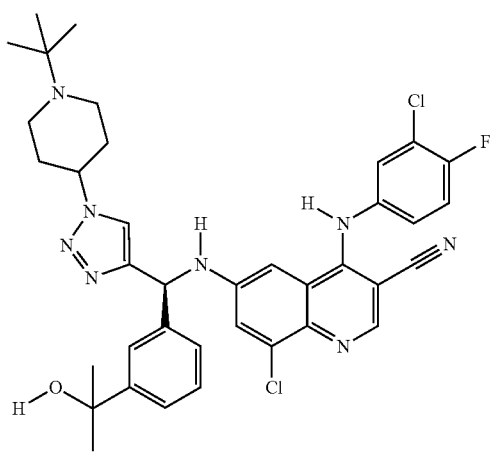 [SMILES: CC(C)(O)c1cccc([C@H](Nc2cc(Cl)c3ncc(C#N)c(Nc4ccc(F)c(Cl)c4)c3c2)c2cn(C3CCN(C(C)(C)C)CC3)nn2)c1] |

TABLE 1-continued
| Compound | Structure |
|---|---|
| 728 | 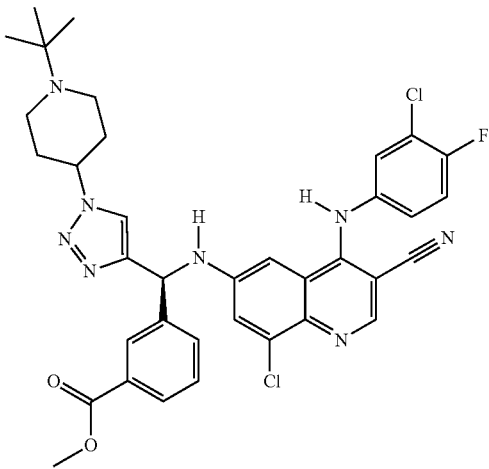 [SMILES: COC(=O)c1cccc([C@H](Nc2cc(Cl)c3ncc(C#N)c(Nc4ccc(F)c(Cl)c4)c3c2)c2cn(C3CCN(C(C)(C)C)CC3)nn2)c1] |
| 729 | 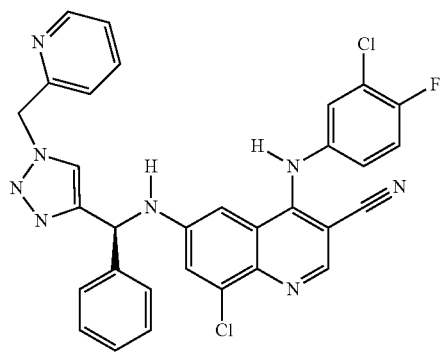 [SMILES: N#Cc1cnc2c(Cl)cc(N[C@H](C3=CN(Cc4ccccn4)NN3)c3ccccc3)cc2c1Nc1ccc(F)c(Cl)c1] |
| 730 | 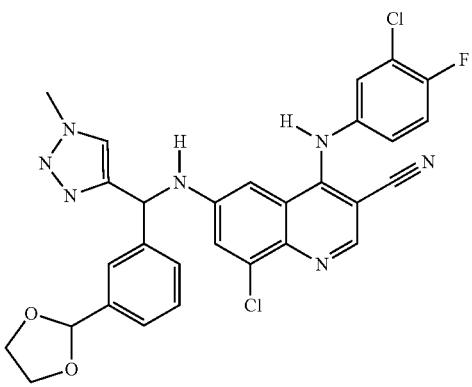 [SMILES: CN1C=C(C(Nc2cc(Cl)c3ncc(C#N)c(Nc4ccc(F)c(Cl)c4)c3c2)c2cccc(C3OCCO3)c2)NN1] |

TABLE 1-continued

| Compound | Structure |
|---|---|
| 731 | |
| 732 | |
| 733 | |

TABLE 1-continued

| Compound | Structure |
|---|---|
| 734 | |
| 735 | |
| 736 | |
| 737 | |

TABLE 1-continued
| Compound | Structure |
|---|---|
| 738 | 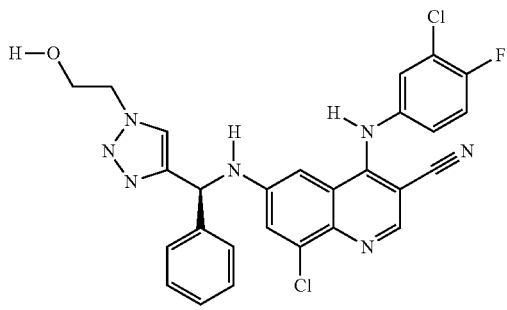 |
| 739 | 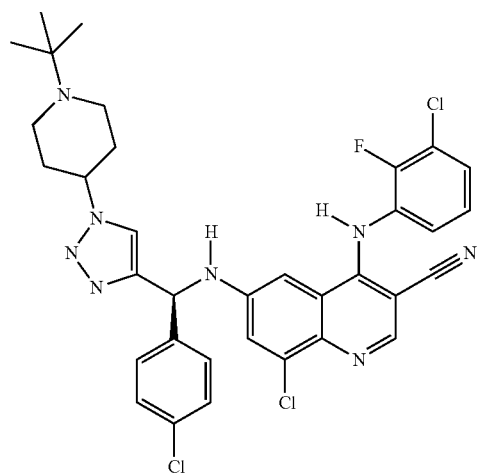 |
| 740 | 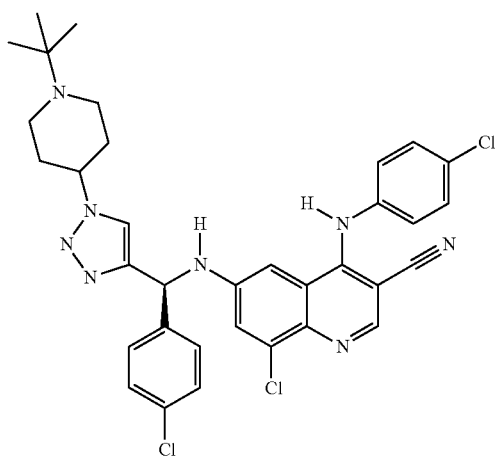 [SMILES: CC(C)(C)N1CCC(N2C=C([C@@H](Nc3cc(Cl)c4ncc(C#N)c(Nc5ccc(Cl)cc5)c4c3)c3ccc(Cl)cc3)NN2)CC1] |

TABLE 1-continued
| Compound | Structure |
|---|---|
| 741 | 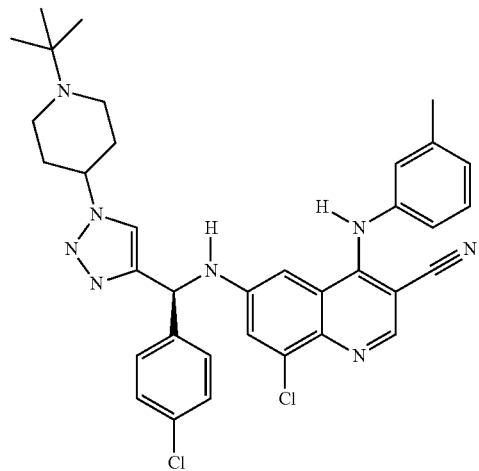 |
| 742 | 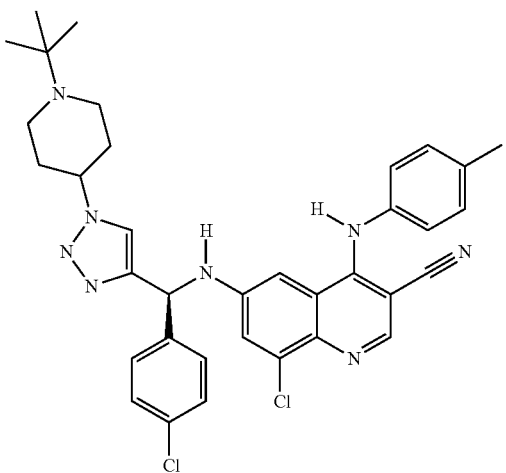 [SMILES: Cc1ccc(Nc2c(C#N)cnc3c(Cl)cc(N[C@H](C4=CN(C5CCN(C(C)(C)C)CC5)NN4)c4ccc(Cl)cc4)cc23)cc1] |
| 743 | 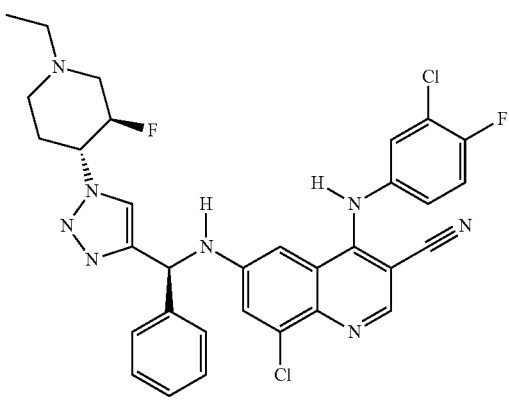 [SMILES: CCN1CC[C@@H](N2C=C([C@@H](Nc3cc(Cl)c4ncc(C#N)c(Nc5ccc(F)c(Cl)c5)c4c3)c3ccccc3)NN2)[C@H](F)C1] |

TABLE 1-continued

| Compound | Structure |
|---|---|
| 744 | |
| 745 | |
| 746 | |
| 747 | |

TABLE 1-continued
| Compound | Structure |
|---|---|
| 748 | 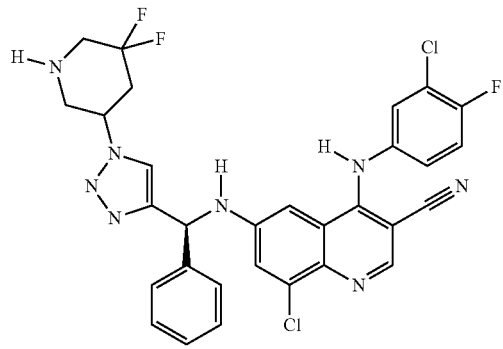 [SMILES: N#Cc1cnc2c(Cl)cc(N[C@H](C3=CN(C4CNCC(F)(F)C4)NN3)c3ccccc3)cc2c1Nc1ccc(F)c(Cl)c1] |
| 749 | 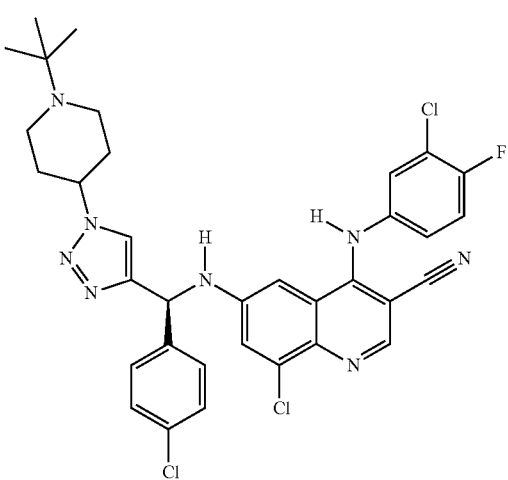 [SMILES: CC(C)(C)N1CCC(n2cc([C@@H](Nc3cc(Cl)c4ncc(C#N)c(Nc5ccc(F)c(Cl)c5)c4c3)c3ccc(Cl)cc3)nn2)CC1] |
| 750 | 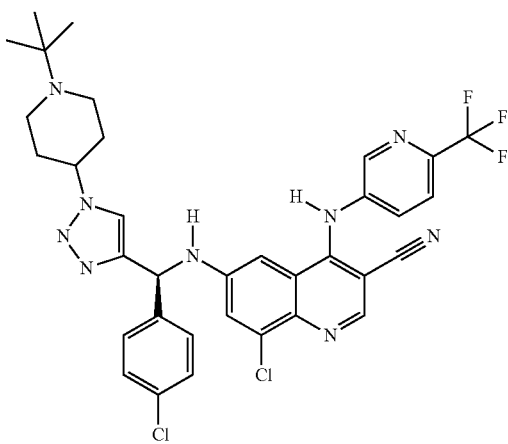 [SMILES: CC(C)(C)N1CCC(N2C=C([C@@H](Nc3cc(Cl)c4ncc(C#N)c(Nc5ccc(C(F)(F)F)nc5)c4c3)c3ccc(Cl)cc3)NN2)CC1] |

TABLE 1-continued
| Compound | Structure |
|---|---|
| 751 | 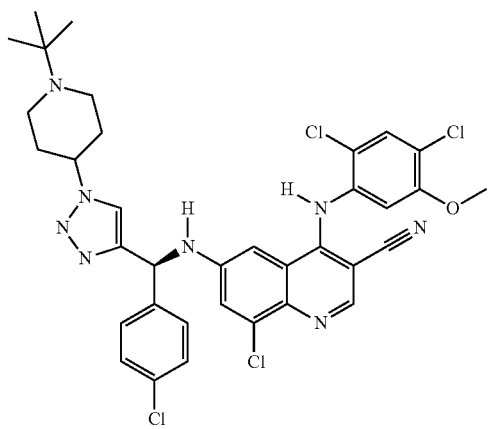 [SMILES: COc1cc(Nc2c(C#N)cnc3c(Cl)cc(N[C@H](C4=CN(C5CCN(C(C)(C)C)CC5)NN4)c4ccc(Cl)cc4)cc23)c(Cl)cc1Cl] |
| 752 | 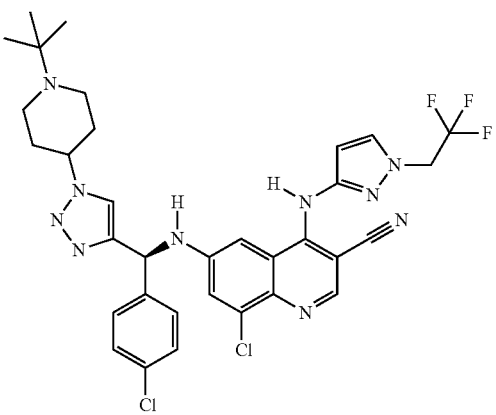 [SMILES: CC(C)(C)N1CCC(N2C=C([C@@H](Nc3cc(Cl)c4ncc(C#N)c(Nc5ccn(CC(F)(F)F)n5)c4c3)c3ccc(Cl)cc3)NN2)CC1] |
| 753 | 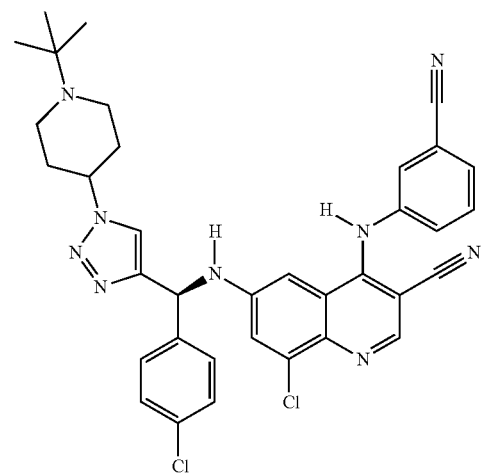 [SMILES: CC(C)(C)N1CCC(n2cc([C@@H](Nc3cc(Cl)c4ncc(C#N)c(Nc5cccc(C#N)c5)c4c3)c3ccc(Cl)cc3)nn2)CC1] |

TABLE 1-continued
| Compound | Structure |
|---|---|
| 754 | 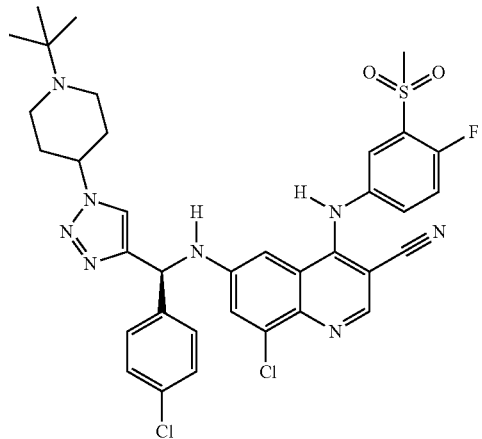 [SMILES: CC(C)(C)N1CCC(n2cc([C@@H](Nc3cc(Cl)c4ncc(C#N)c(Nc5ccc(F)c(S(C)(=O)=O)c5)c4c3)c3ccc(Cl)cc3)nn2)CC1] |
| 755 | 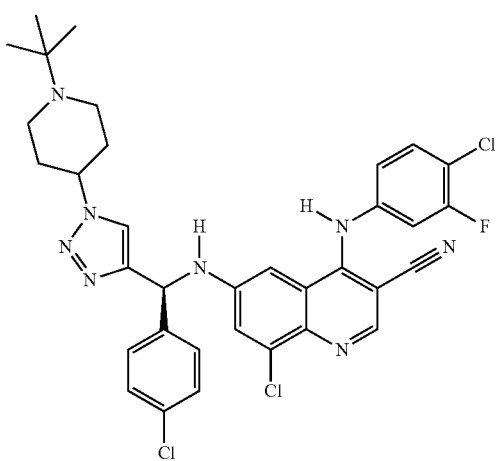 [SMILES: CC(C)(C)N1CCC(n2cc([C@@H](Nc3cc(Cl)c4ncc(C#N)c(Nc5ccc(Cl)c(F)c5)c4c3)c3ccc(Cl)cc3)nn2)CC1] |
| 756 | 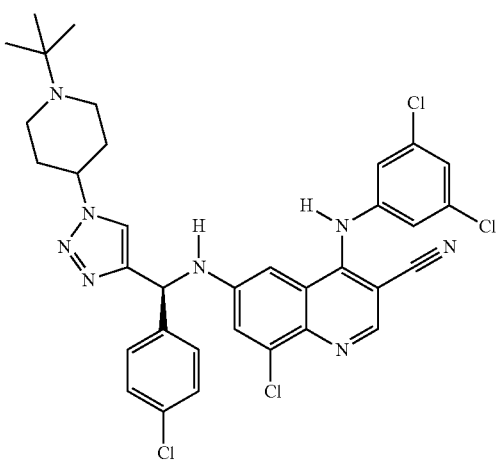 [SMILES: CC(C)(C)N1CCC(n2cc([C@@H](Nc3cc(Cl)c4ncc(C#N)c(Nc5cc(Cl)cc(Cl)c5)c4c3)c3ccc(Cl)cc3)nn2)CC1] |

TABLE 1-continued
| Compound | Structure |
|---|---|
| 757 | 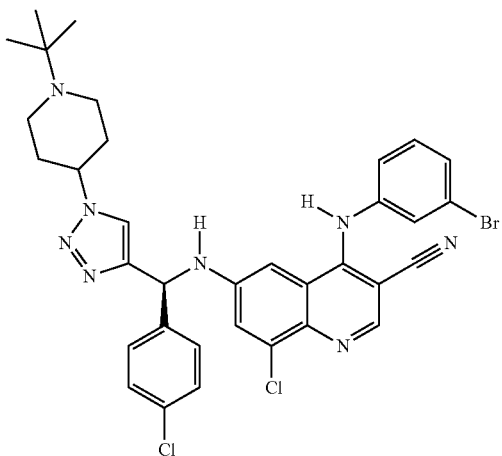 [SMILES: CC(C)(C)N1CCC(n2cc([C@@H](Nc3cc(Cl)c4ncc(C#N)c(Nc5cccc(Br)c5)c4c3)c3ccc(Cl)cc3)nn2)CC1] |
| 758 | 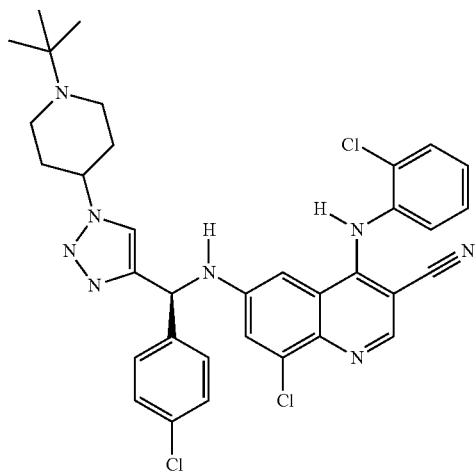 [SMILES: CC(C)(C)N1CCC(N2C=C([C@@H](Nc3cc(Cl)c4ncc(C#N)c(Nc5ccccc5Cl)c4c3)c3ccc(Cl)cc3)NN2)CC1] |
| 759 | 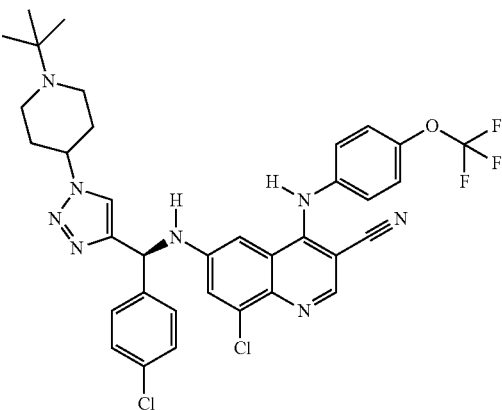 [SMILES: CC(C)(C)N1CCC(n2cc([C@@H](Nc3cc(Cl)c4ncc(C#N)c(Nc5ccc(OC(F)(F)F)cc5)c4c3)c3ccc(Cl)cc3)nn2)CC1] |

TABLE 1-continued
| Compound | Structure |
|---|---|
| 760 | 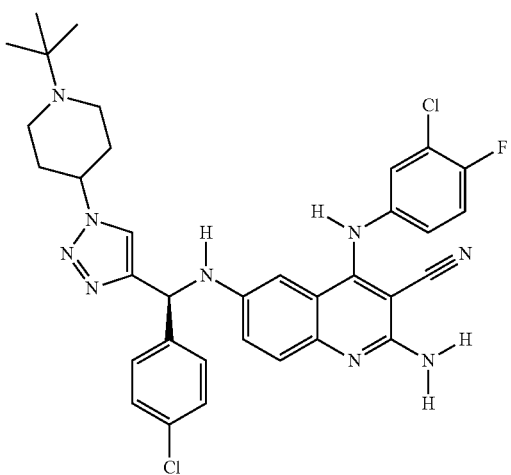 [SMILES: CC(C)(C)N1CCC(n2cc([C@@H](Nc3ccc4nc(N)c(C#N)c(Nc5ccc(F)c(Cl)c5)c4c3)c3ccc(Cl)cc3)nn2)CC1] |
| 761 | 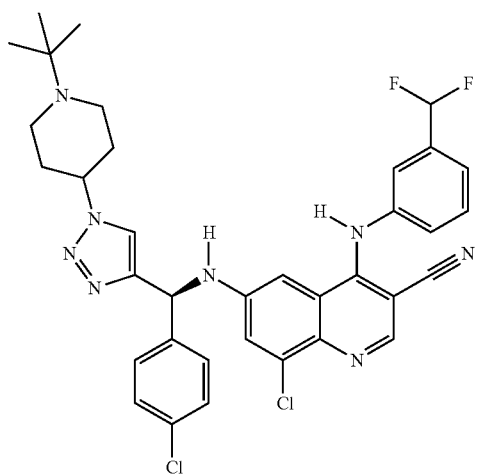 [SMILES: CC(C)(C)N1CCC(n2cc([C@@H](Nc3cc(Cl)c4ncc(C#N)c(Nc5cccc(C(F)F)c5)c4c3)c3ccc(Cl)cc3)nn2)CC1] |
| 762 | 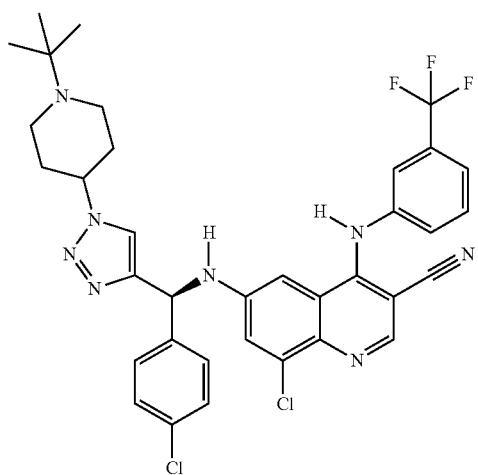 [SMILES: CC(C)(C)N1CCC(n2cc([C@@H](Nc3cc(Cl)c4ncc(C#N)c(Nc5cccc(C(F)(F)F)c5)c4c3)c3ccc(Cl)cc3)nn2)CC1] |

TABLE 1-continued
| Compound | Structure |
|---|---|
| 763 | 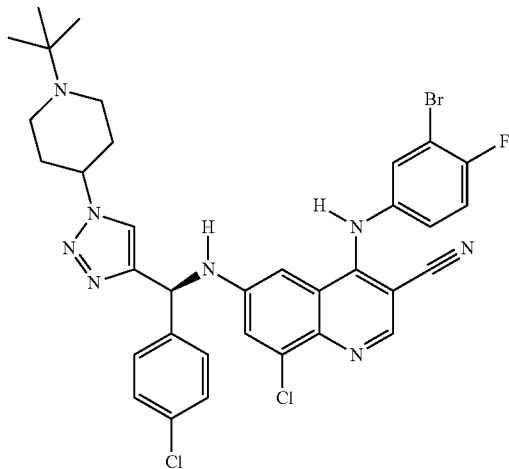 |
| 764 | 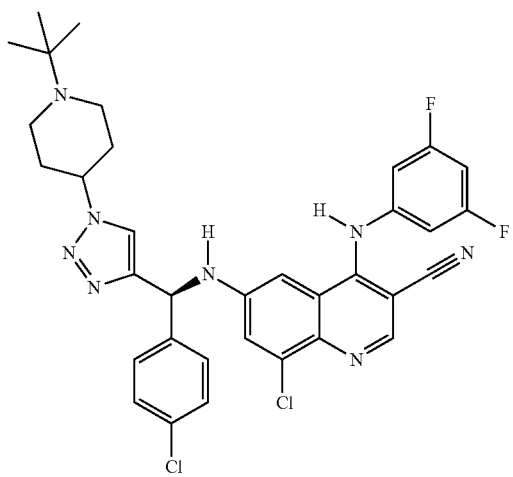 |
| 765 | 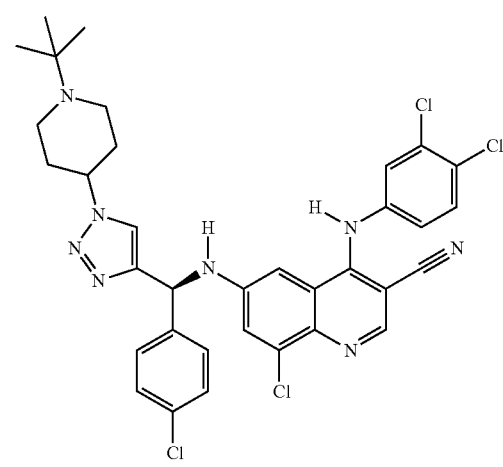 [SMILES: CC(C)(C)N1CCC(n2cc([C@@H](Nc3cc(Cl)c4ncc(C#N)c(Nc5ccc(Cl)c(Cl)c5)c4c3)c3ccc(Cl)cc3)nn2)CC1] |

TABLE 1-continued
| Compound | Structure |
|---|---|
| 766 | 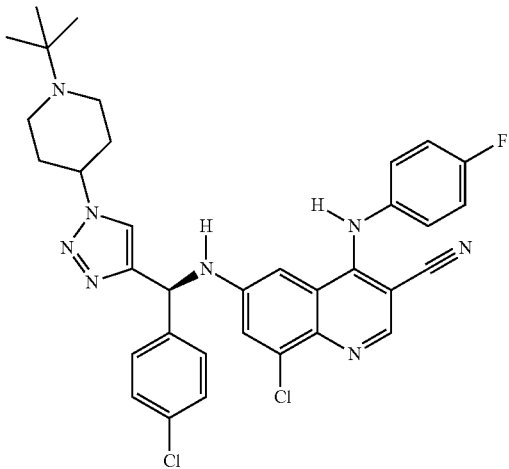 [SMILES: CC(C)(C)N1CCC(n2cc([C@@H](Nc3cc(Cl)c4ncc(C#N)c(Nc5ccc(F)cc5)c4c3)c3ccc(Cl)cc3)nn2)CC1] |
| 767 | 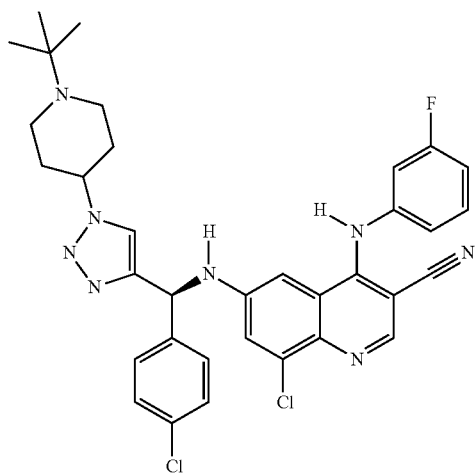 [SMILES: CC(C)(C)N1CCC(N2C=C([C@@H](Nc3cc(Cl)c4ncc(C#N)c(Nc5cccc(F)c5)c4c3)c3ccc(Cl)cc3)NN2)CC1] |
| 768 | 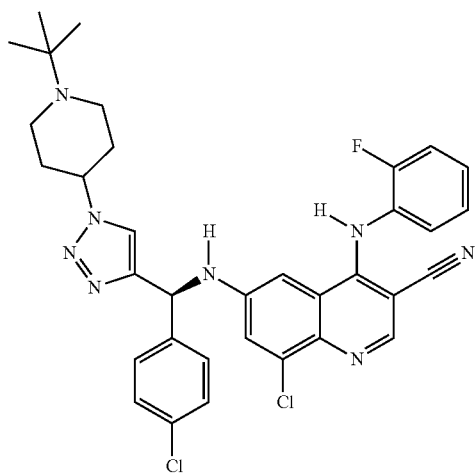 [SMILES: CC(C)(C)N1CCC(n2cc([C@@H](Nc3cc(Cl)c4ncc(C#N)c(Nc5ccccc5F)c4c3)c3ccc(Cl)cc3)nn2)CC1] |

TABLE 1-continued
| Compound | Structure |
|---|---|
| 769 | 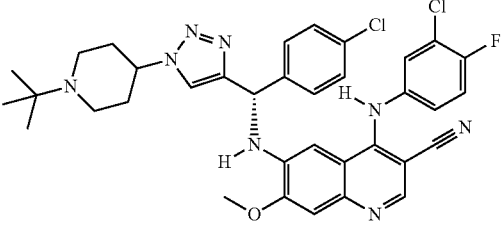 [SMILES: COc1cc2ncc(C#N)c(Nc3ccc(F)c(Cl)c3)c2cc1N[C@@H](c1ccc(Cl)cc1)c1cn(C2CCN(C(C)(C)C)CC2)nn1] |
| 770 | 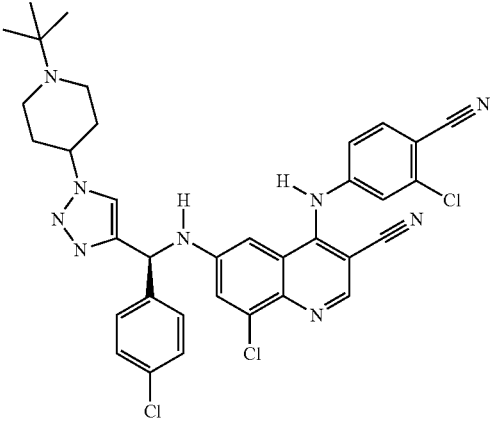 [SMILES: CC(C)(C)N1CCC(N2C=C([C@@H](Nc3cc(Cl)c4ncc(C#N)c(Nc5ccc(C#N)c(Cl)c5)c4c3)c3ccc(Cl)cc3)NN2)CC1] |
| 771 | 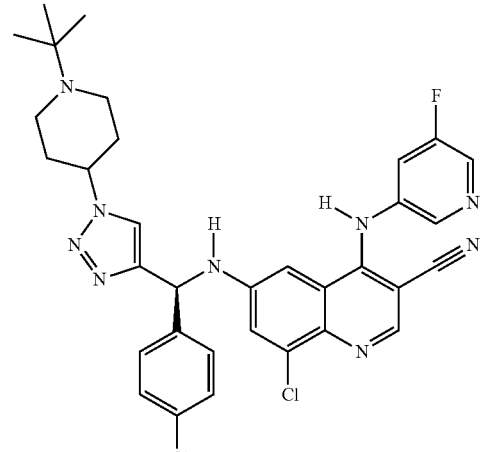 |
| 772 | 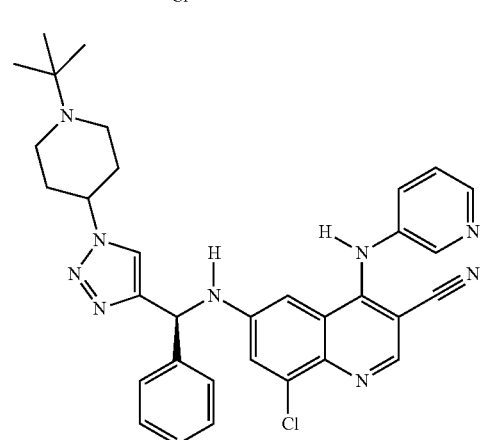 |

TABLE 1-continued
| Compound | Structure |
|---|---|
| 773 | 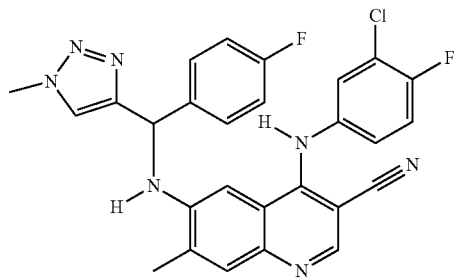 [SMILES: Cc1cc2ncc(C#N)c(Nc3ccc(F)c(Cl)c3)c2cc1NC(c1ccc(F)cc1)c1cn(C)nn1] |
| 774 | 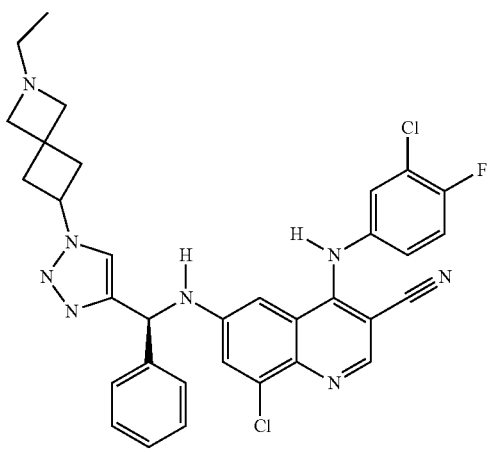 [SMILES: CCN1CC2(CC(N3C=C([C@@H](Nc4cc(Cl)c5ncc(C#N)c(Nc6ccc(F)c(Cl)c6)c5c4)c4ccccc4)NN3)C2)C1] |
| 775 | 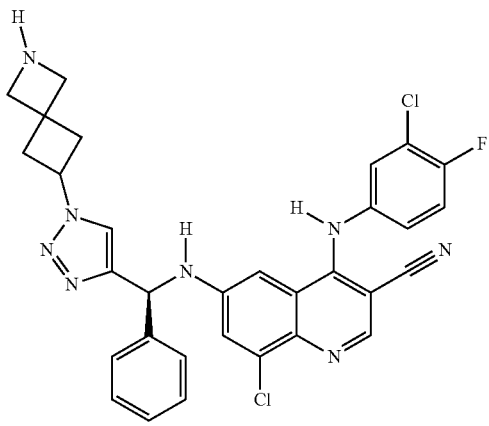 [SMILES: N#Cc1cnc2c(Cl)cc(N[C@@H](c3ccccc3)c3cn(C4CC5(CNC5)C4)nn3)cc2c1Nc1ccc(F)c(Cl)c1] |

TABLE 1-continued
| Compound | Structure |
|---|---|
| 776 | 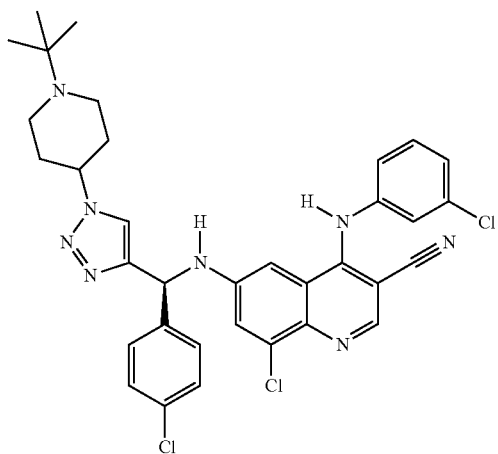 [SMILES: CC(C)(C)N1CCC(n2cc([C@@H](Nc3cc(Cl)c4ncc(C#N)c(Nc5cccc(Cl)c5)c4c3)c3ccc(Cl)cc3)nn2)CC1] |
| 777 | 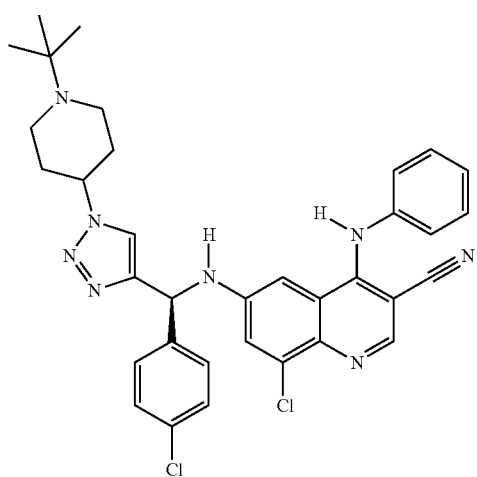 [SMILES: CC(C)(C)N1CCC(n2cc([C@@H](Nc3cc(Cl)c4ncc(C#N)c(Nc5ccccc5)c4c3)c3ccc(Cl)cc3)nn2)CC1] |
| 778 | 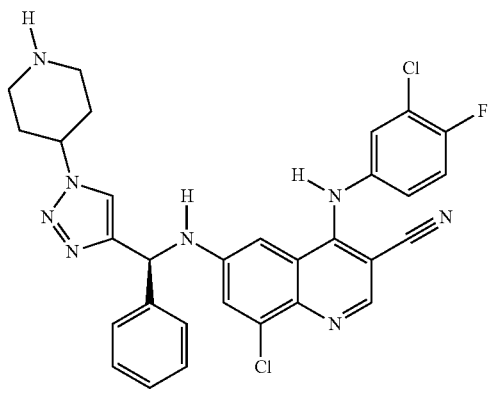 [SMILES: N#Cc1cnc2c(Cl)cc(N[C@@H](c3ccccc3)c3cn(C4CCNCC4)nn3)cc2c1Nc1ccc(F)c(Cl)c1] |

TABLE 1-continued

| Compound | Structure |
|---|---|
| 779 | |
| 780 | |
| 781 | |
| 782 | |

TABLE 1-continued

| Compound | Structure |
|---|---|
| 783 | |
| 784 | |
| 785 | |
| 786 | |

TABLE 1-continued
| Compound | Structure |
|---|---|
| 787 | 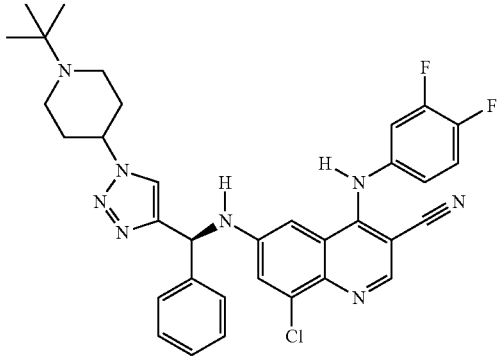 [SMILES: CC(C)(C)N1CCC(n2cc([C@@H](Nc3cc(Cl)c4ncc(C#N)c(Nc5ccc(F)c(F)c5)c4c3)c3ccccc3)nn2)CC1] |
| 788 | 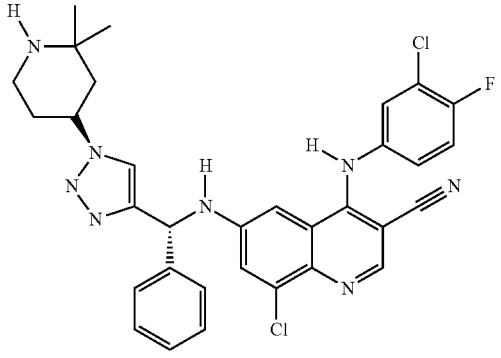 |
| 789 | 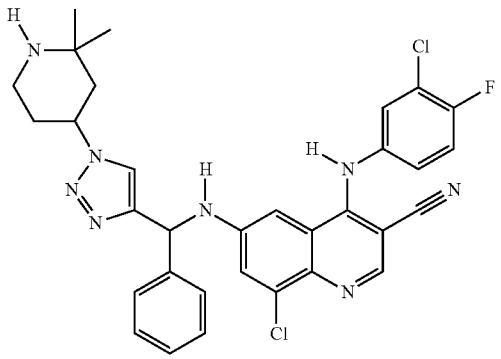 |
| 790 | 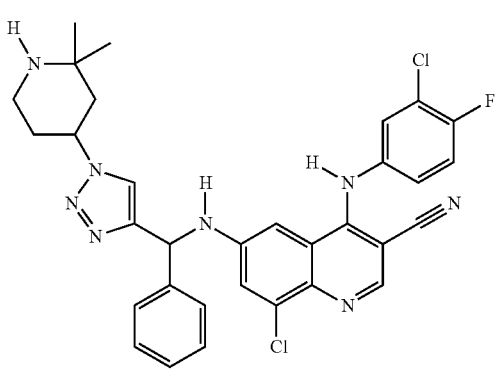 |

TABLE 1-continued

| Compound | Structure |
|---|---|
| 791 | |
| 792 | |
| 793 | |
| 794 | |

TABLE 1-continued

| Compound | Structure |
|---|---|
| 795 | |
| 796 | |
| 797 | |
| 798 | |

TABLE 1-continued
| Compound | Structure |
|---|---|
| 799 | 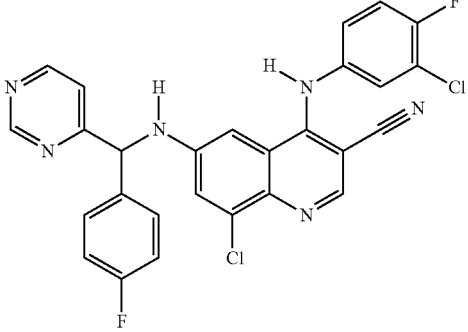 |
| 800 | 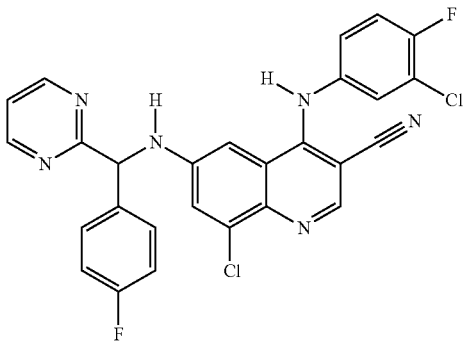 [SMILES: N#Cc1cnc2c(Cl)cc(NC(c3ccc(F)cc3)c3ncccn3)cc2c1Nc1ccc(F)c(Cl)c1] |
| 801 | 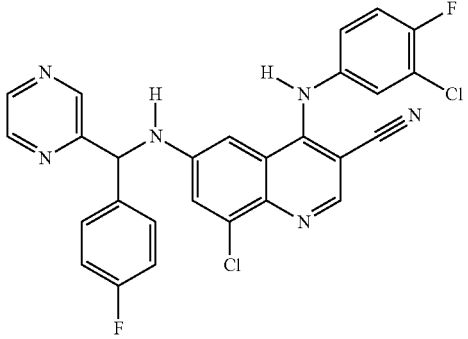 [SMILES: N#Cc1cnc2c(Cl)cc(NC(c3ccc(F)cc3)c3cnccn3)cc2c1Nc1ccc(F)c(Cl)c1] |
| 802 | 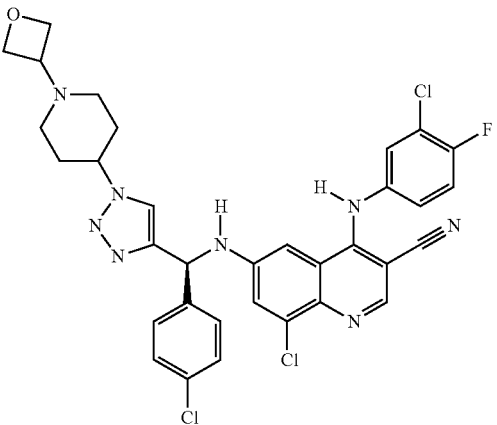 [SMILES: N#Cc1cnc2c(Cl)cc(N[C@H](C3=CN(C4CCN(C5COC5)CC4)NN3)c3ccc(Cl)cc3)cc2c1Nc1ccc(F)c(Cl)c1] |

TABLE 1-continued

| Compound | Structure |
|---|---|
| 803 | |
| 804 | |
| 805 | |
| 806 | |

TABLE 1-continued

| Compound | Structure |
|---|---|
| 807 | |
| 808 | |
| 809 | |
| 810 | |

TABLE 1-continued
| Compound | Structure |
|---|---|
| 811 | 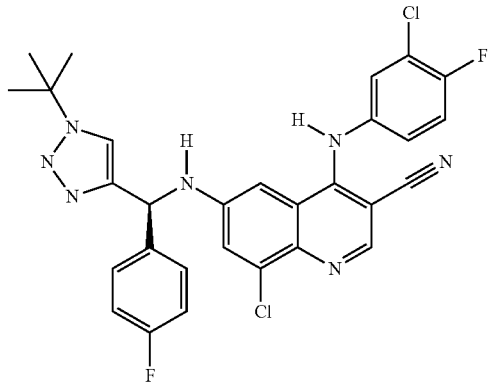 [SMILES: CC(C)(C)N1C=C([C@@H](Nc2cc(Cl)c3ncc(C#N)c(Nc4ccc(F)c(Cl)c4)c3c2)c2ccc(F)cc2)NN1] |
| 812 | 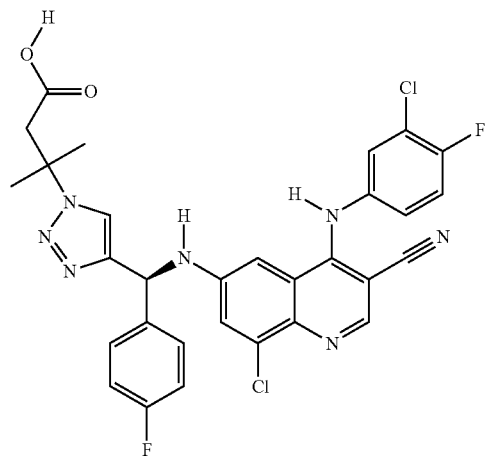 [SMILES: CC(C)(CC(=O)O)n1cc([C@@H](Nc2cc(Cl)c3ncc(C#N)c(Nc4ccc(F)c(Cl)c4)c3c2)c2ccc(F)cc2)nn1] |
| 813 | 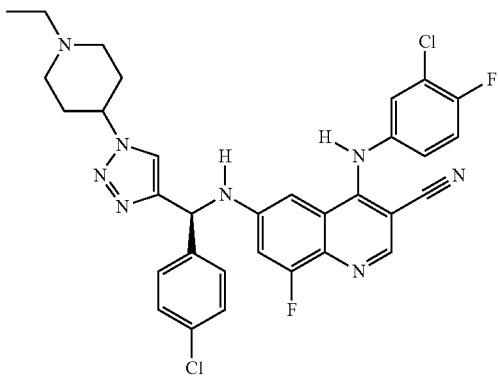 [SMILES: CCN1CCC(n2cc([C@@H](Nc3cc(F)c4ncc(C#N)c(Nc5ccc(F)c(Cl)c5)c4c3)c3ccc(Cl)cc3)nn2)CC1] |

TABLE 1-continued

| Compound | Structure |
|---|---|
| 814 | |
| 815 | |
| 816 | |
| 817 | |

TABLE 1-continued

| Compound | Structure |
|---|---|
| 818 | |
| 819 | |
| 820 | |
| 821 | |

TABLE 1-continued
| Compound | Structure |
|---|---|
| 822 | 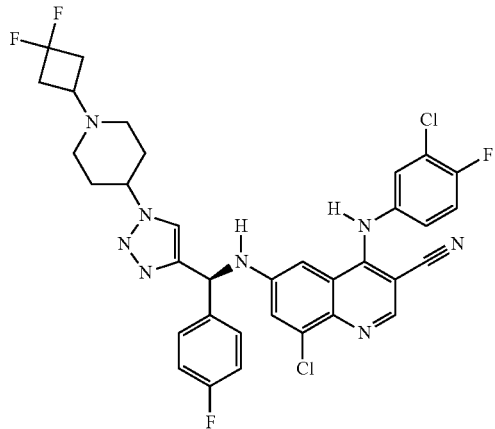 [SMILES: N#Cc1cnc2c(Cl)cc(N[C@H](C3=CN(C4CCN(C5CC(F)(F)C5)CC4)NN3)c3ccc(F)cc3)cc2c1Nc1ccc(F)c(Cl)c1] |
| 823 | 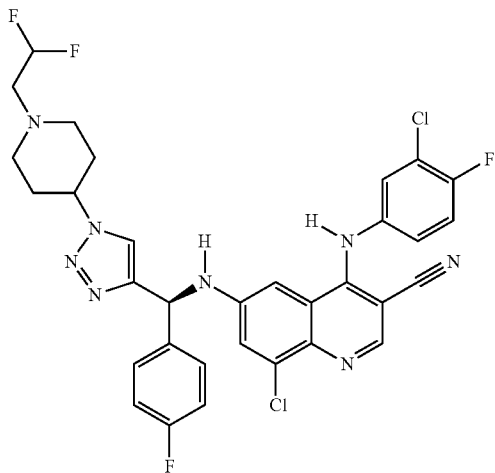 [SMILES: N#Cc1cnc2c(Cl)cc(N[C@@H](c3ccc(F)cc3)c3cn(C4CCN(CC(F)F)CC4)nn3)cc2c1Nc1ccc(F)c(Cl)c1] |
| 824 | 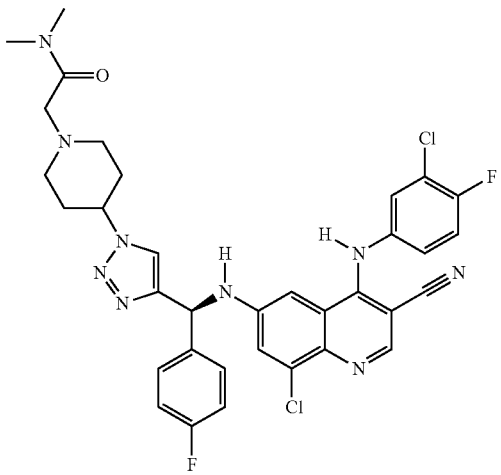 [SMILES: CN(C)C(=O)CN1CCC(n2cc([C@@H](Nc3cc(Cl)c4ncc(C#N)c(Nc5ccc(F)c(Cl)c5)c4c3)c3ccc(F)cc3)nn2)CC1] |

TABLE 1-continued
| Compound | Stucture |
|---|---|
| 825 | 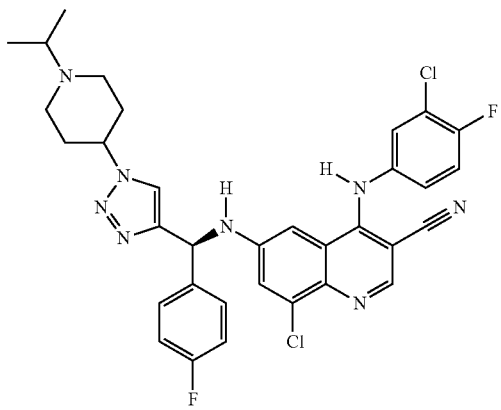 [SMILES: CC(C)N1CCC(n2cc([C@@H](Nc3cc(Cl)c4ncc(C#N)c(Nc5ccc(F)c(Cl)c5)c4c3)c3ccc(F)cc3)nn2)CC1] |
| 826 | 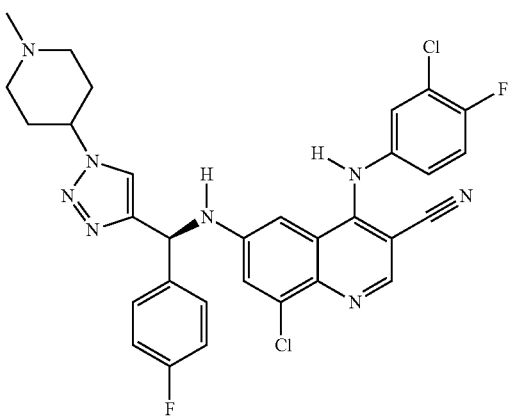 [SMILES: CN1CCC(n2cc([C@@H](Nc3cc(Cl)c4ncc(C#N)c(Nc5ccc(F)c(Cl)c5)c4c3)c3ccc(F)cc3)nn2)CC1] |
| 827 | 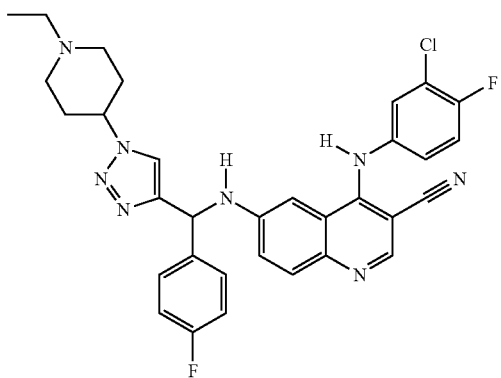 [SMILES: CCN1CCC(n2cc(C(Nc3ccc4ncc(C#N)c(Nc5ccc(F)c(Cl)c5)c4c3)c3ccc(F)cc3)nn2)CC1] |

TABLE 1-continued

| Compound | Structure |
|---|---|
| 828 | |
| 829 | |
| 830 | |

TABLE 1-continued

| Compound | Structure |
|---|---|
| 831 | |
| 832 | |
| 833 | |

TABLE 1-continued
| Compound | Structure |
|---|---|
| 834 | 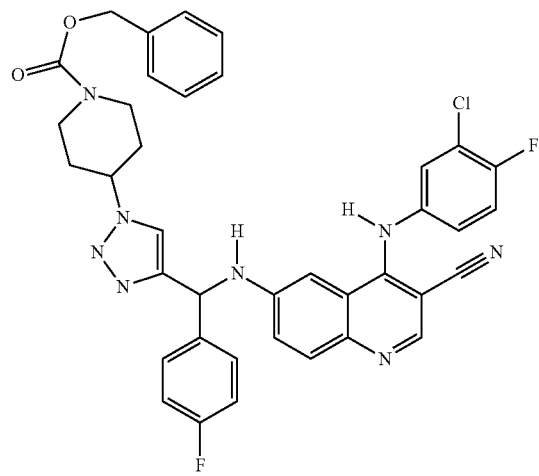 [SMILES: N#Cc1cnc2ccc(NC(C3=CN(C4CCN(C(=O)OCc5ccccc5)CC4)NN3)c3ccc(F)cc3)cc2c1Nc1ccc(F)c(Cl)c1] |
| 835 | 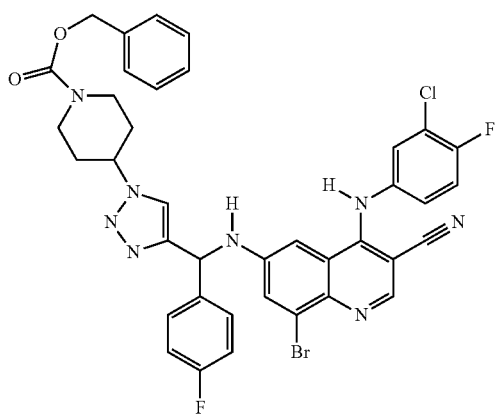 [SMILES: N#Cc1cnc2c(Br)cc(NC(C3=CN(C4CCN(C(=O)OCc5ccccc5)CC4)NN3)c3ccc(F)cc3)cc2c1Nc1ccc(F)c(Cl)c1] |
| 836 | 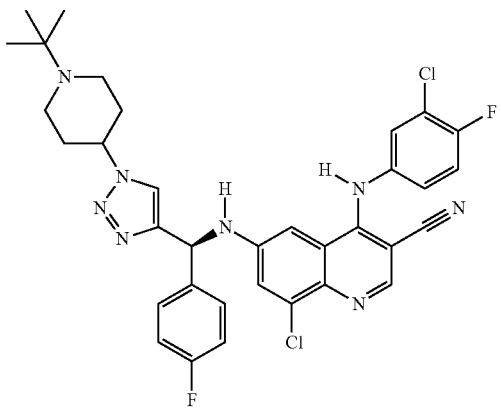 [SMILES: CC(C)(C)N1CCC(n2cc([C@@H](Nc3cc(Cl)c4ncc(C#N)c(Nc5ccc(F)c(Cl)c5)c4c3)c3ccc(F)cc3)nn2)CC1] |

TABLE 1-continued

| Compound | Structure |
|---|---|
| 837 | |
| 838 | |
| 839 | |

TABLE 1-continued
| Compound | Structure |
|---|---|
| 840 | 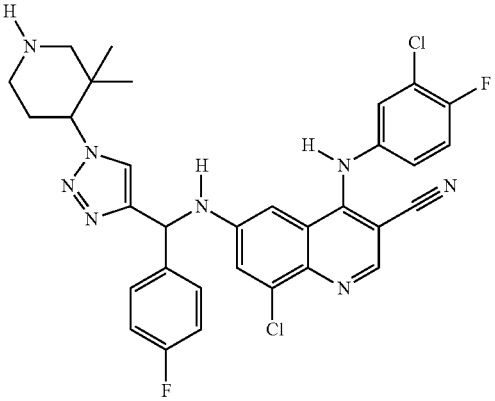 [SMILES: CC1(C)CNCCC1n1cc(C(Nc2cc(Cl)c3ncc(C#N)c(Nc4ccc(F)c(Cl)c4)c3c2)c2ccc(F)cc2)nn1] |
| 841 | 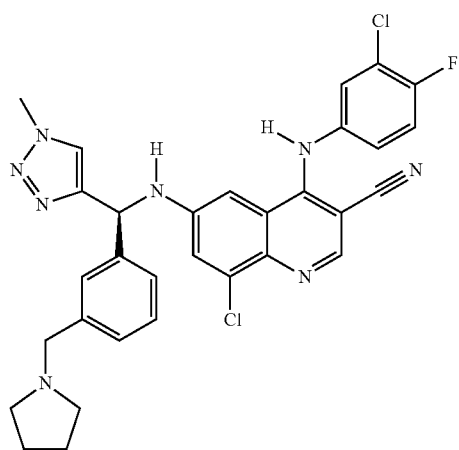 |
| 842 | 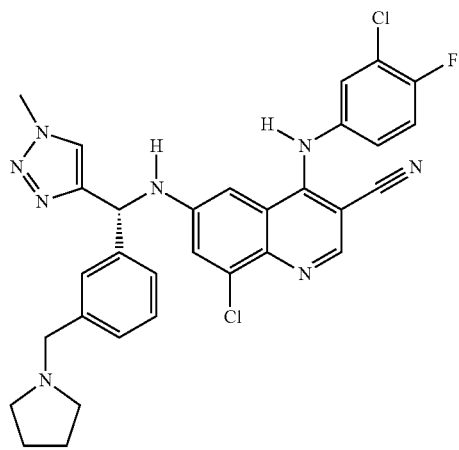 [SMILES: Cn1cc([C@H](Nc2cc(Cl)c3ncc(C#N)c(Nc4ccc(F)c(Cl)c4)c3c2)c2cccc(CN3CCCC3)c2)nn1] |

TABLE 1-continued
| Compound | Stucture |
|---|---|
| 843 | 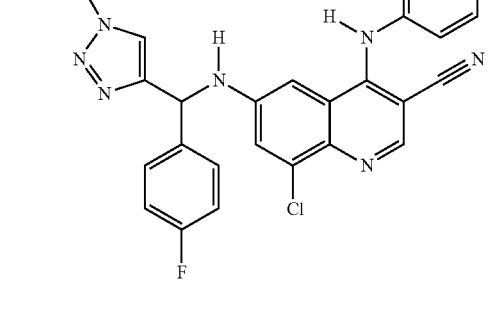 |
| 844 | 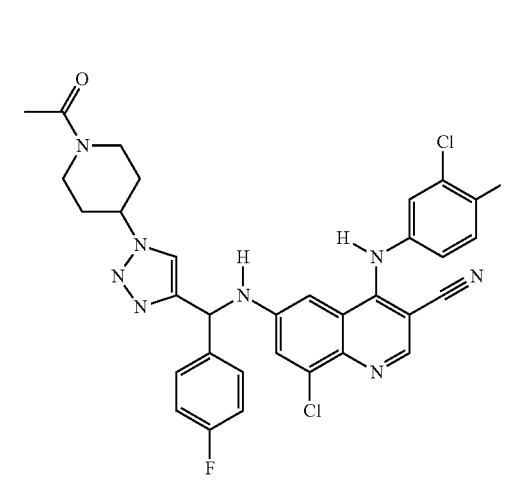 |
| 845 | 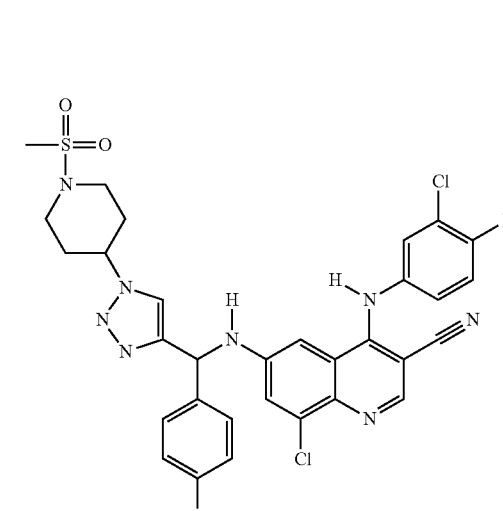 |

TABLE 1-continued
| Compound | Structure |
|---|---|
| 846 | 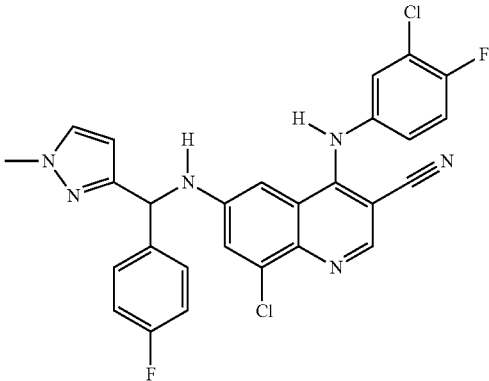 [SMILES: Cn1ccc(C(Nc2cc(Cl)c3ncc(C#N)c(Nc4ccc(F)c(Cl)c4)c3c2)c2ccc(F)cc2)n1] |
| 847 | 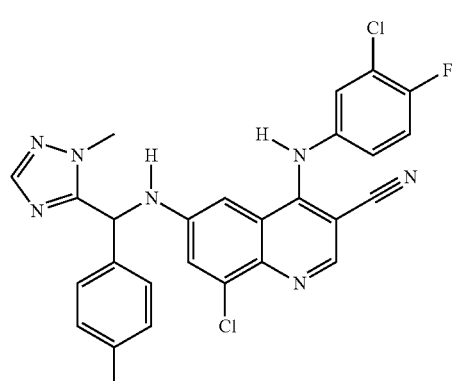 |
| 848 | 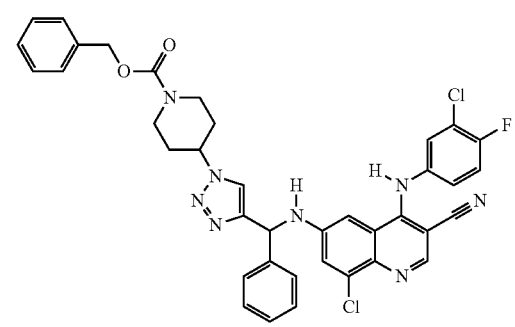 [SMILES: N#Cc1cnc2c(Cl)cc(NC(c3ccccc3)c3cn(C4CCN(C(=O)OCc5ccccc5)CC4)nn3)cc2c1Nc1ccc(F)c(Cl)c1] |
| 849 | 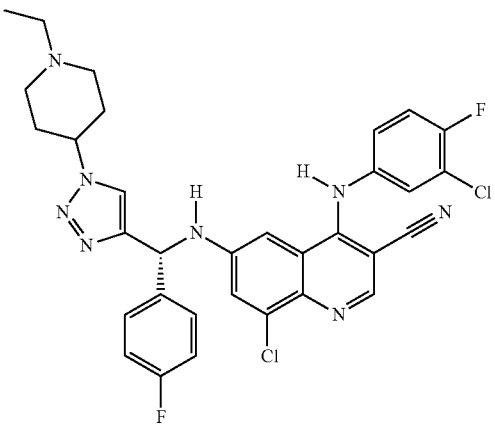 |

TABLE 1-continued

| Compound | Structure |
|---|---|
| 850 | (chemical structure) |
| 851 | (chemical structure) |
| 852 | (chemical structure) |

TABLE 1-continued
| Compound | Structure |
|---|---|
| 853 | 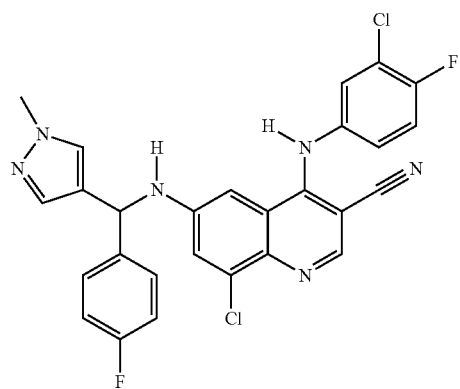 [SMILES: Cn1cc(C(Nc2cc(Cl)c3ncc(C#N)c(Nc4ccc(F)c(Cl)c4)c3c2)c2ccc(F)cc2)cn1] |
| 854 | 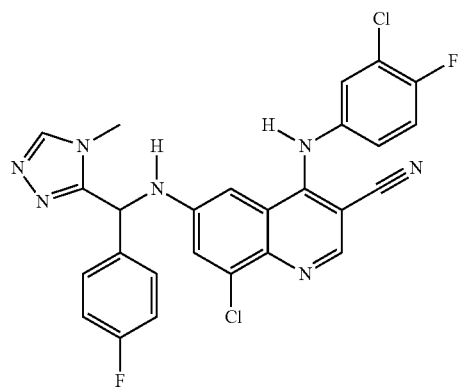 [SMILES: Cn1cnnc1C(Nc1cc(Cl)c2ncc(C#N)c(Nc3ccc(F)c(Cl)c3)c2c1)c1ccc(F)cc1] |
| 855 | 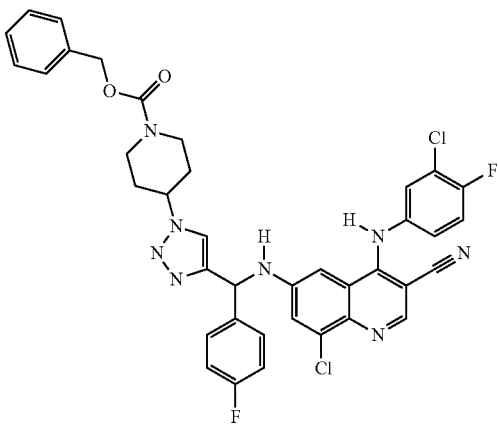 [SMILES: N#Cc1cnc2c(Cl)cc(NC(C3=CN(C4CCN(C(=O)OCc5ccccc5)CC4)NN3)c3ccc(F)cc3)cc2c1Nc1ccc(F)c(Cl)c1] |

TABLE 1-continued
| Compound | Structure |
|---|---|
| 856 | 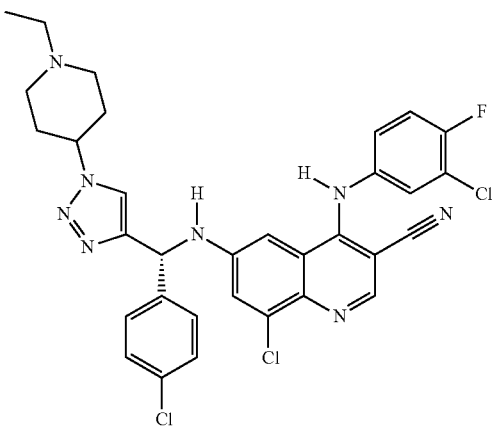 |
| 857 | 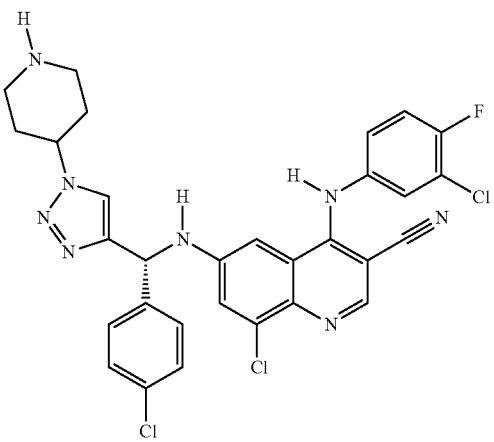 [SMILES: N#Cc1cnc2c(Cl)cc(N[C@H](c3ccc(Cl)cc3)c3cn(C4CCNCC4)nn3)cc2c1Nc1ccc(F)c(Cl)c1] |
| 858 | 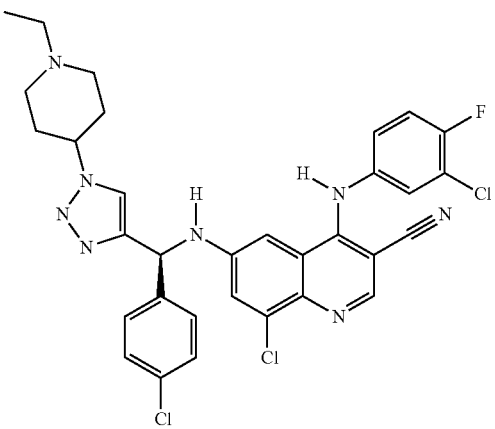 |

TABLE 1-continued
| Compound | Structure |
|---|---|
| 859 | 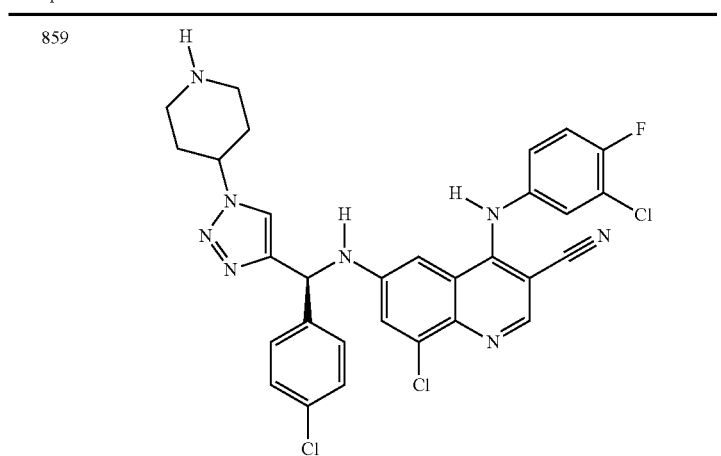 |
| 860 | 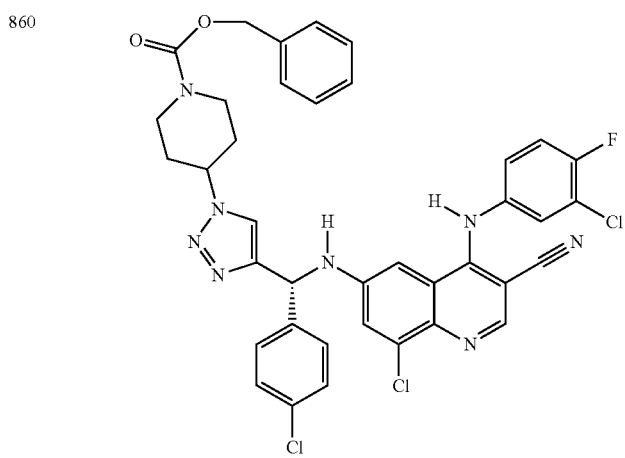 |
| 861 | 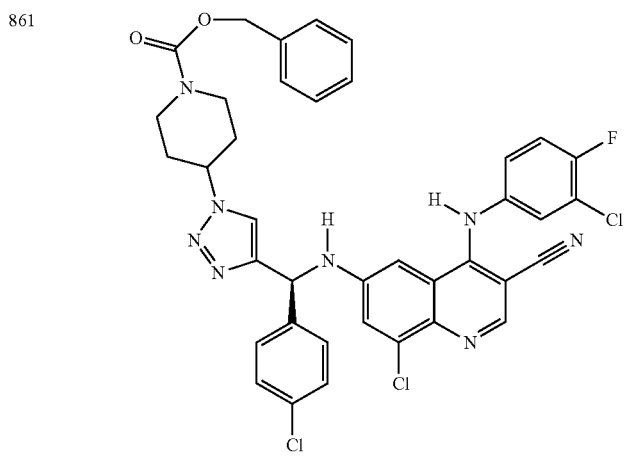 |

TABLE 1-continued
| Compound | Structure |
|---|---|
| 862 | 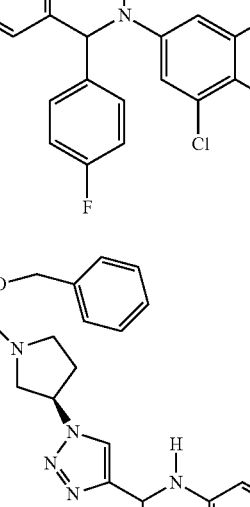 |
| 863 | 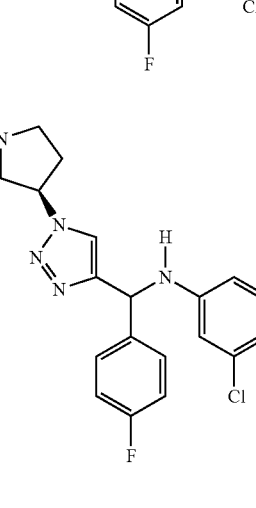 |
| 864 | 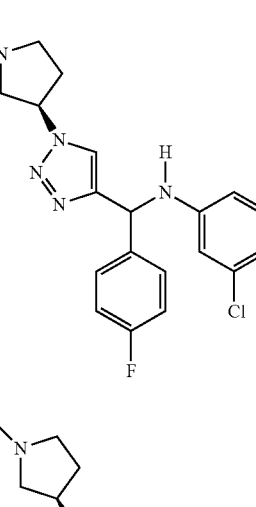 |
| 865 | 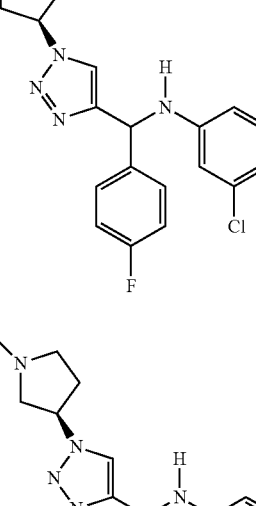 |

TABLE 1-continued

| Compound | Structure |
|---|---|
| 866 | |
| 867 | |
| 868 | |
| 869 | |

TABLE 1-continued
| Compound | Structure |
|---|---|
| 870 | 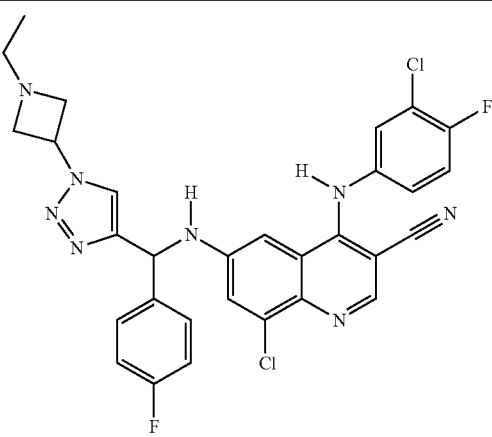 |
| 871 | 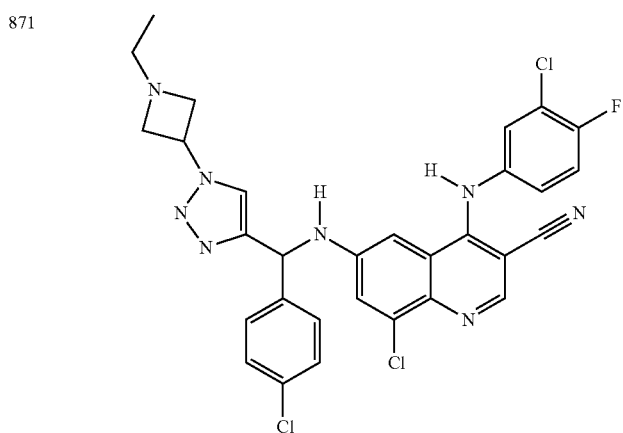 |
| 872 | 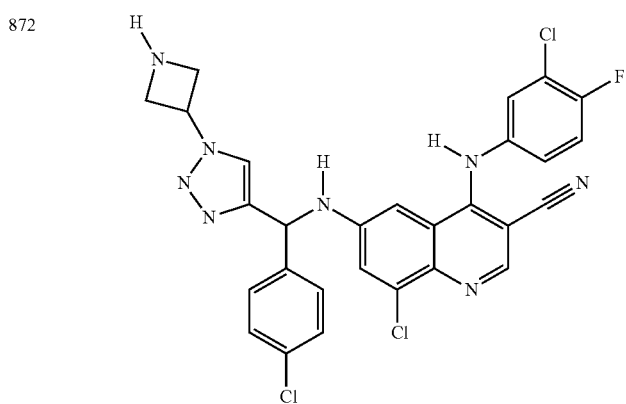 |

TABLE 1-continued
| Compound | Structure |
|---|---|
| 873 | 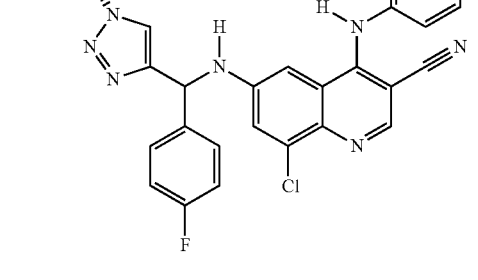 |
| 874 | 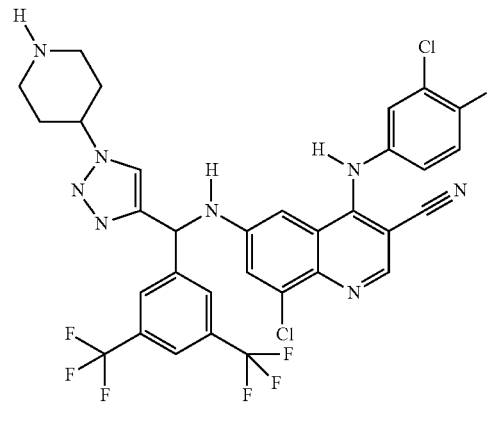 |
| 875 | 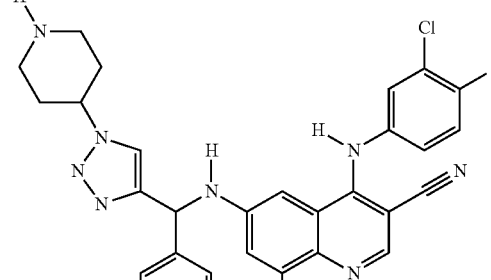 |

TABLE 1-continued
| Compound | Structure |
|---|---|
| 876 | 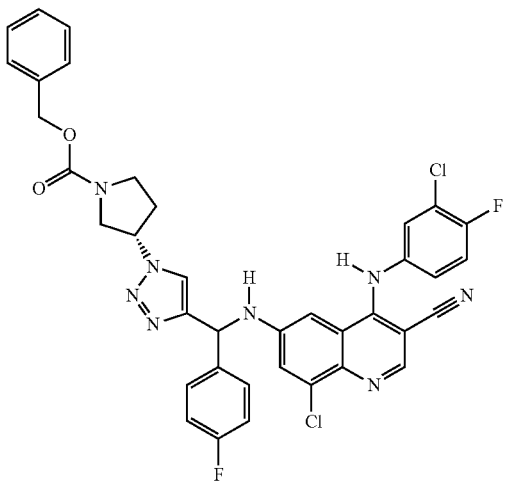 [SMILES: N#Cc1cnc2c(Cl)cc(NC(c3ccc(F)cc3)c3cn([C@H]4CCN(C(=O)OCc5ccccc5)C4)nn3)cc2c1Nc1ccc(F)c(Cl)c1] |
| 877 | 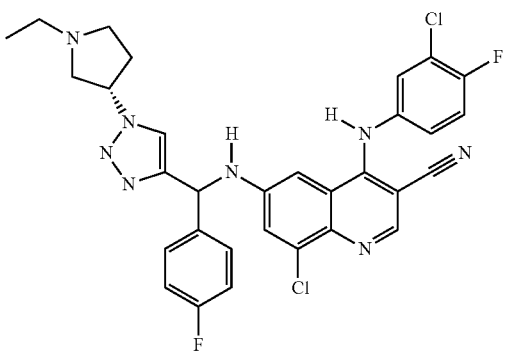 [SMILES: CCN1CC[C@H](N2C=C(C(Nc3cc(Cl)c4ncc(C#N)c(Nc5ccc(F)c(Cl)c5)c4c3)c3ccc(F)cc3)NN2)C1] |
| 878 | 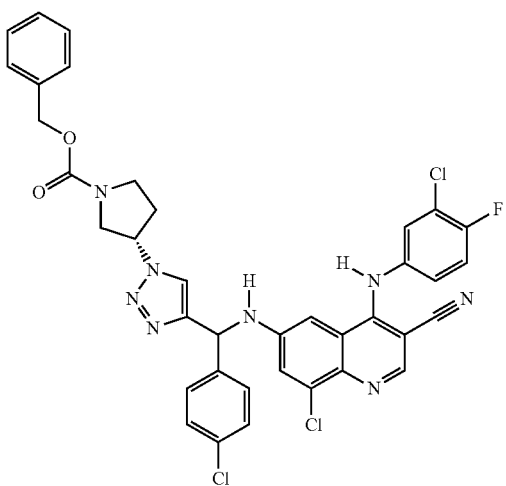 [SMILES: N#Cc1cnc2c(Cl)cc(NC(c3ccc(Cl)cc3)c3cn([C@H]4CCN(C(=O)OCc5ccccc5)C4)nn3)cc2c1Nc1ccc(F)c(Cl)c1] |

TABLE 1-continued

| Compound | Structure |
|---|---|
| 879 | |
| 880 | |
| 881 | |
| 882 | |

TABLE 1-continued
| Compound | Structure |
|---|---|
| 883 | 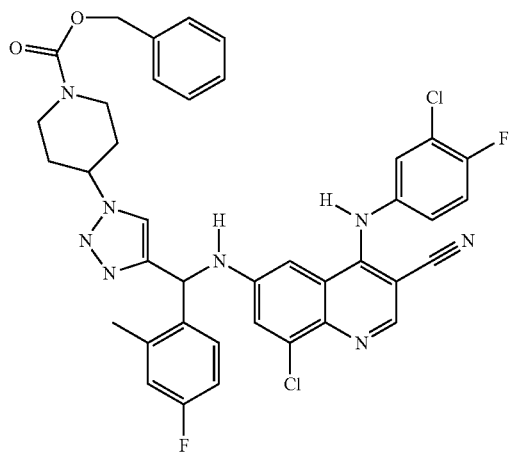 [SMILES: Cc1cc(F)ccc1C(Nc1cc(Cl)c2ncc(C#N)c(Nc3ccc(F)c(Cl)c3)c2c1)C1=CN(C2CCN(C(=O)OCc3ccccc3)CC2)NN1] |
| 884 | 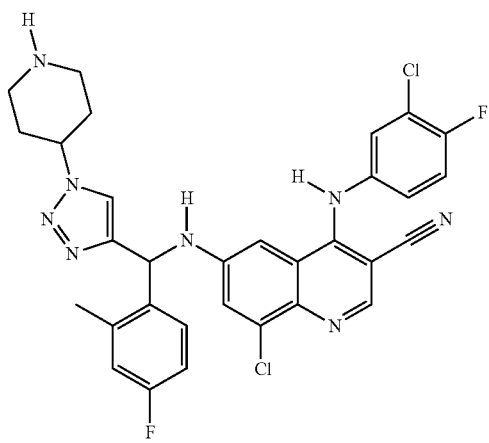 [SMILES: Cc1cc(F)ccc1C(Nc1cc(Cl)c2ncc(C#N)c(Nc3ccc(F)c(Cl)c3)c2c1)c1cn(C2CCNCC2)nn1] |
| 885 | 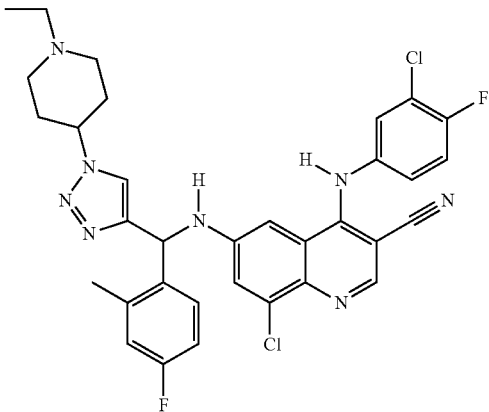 [SMILES: CCN1CCC(n2cc(C(Nc3cc(Cl)c4ncc(C#N)c(Nc5ccc(F)c(Cl)c5)c4c3)c3ccc(F)cc3C)nn2)CC1] |

TABLE 1-continued

| Compound | Structure |
|---|---|
| 886 | (structure) |
| 887 | (structure) |
| 888 | (structure) |
| 889 | (structure) |

TABLE 1-continued
| Compound | Structure |
|---|---|
| 890 | 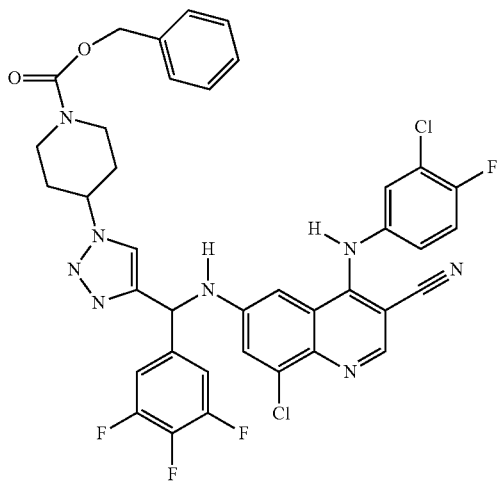 [SMILES: N#Cc1cnc2c(Cl)cc(NC(C3=CN(C4CCN(C(=O)OCc5ccccc5)CC4)NN3)c3cc(F)c(F)c(F)c3)cc2c1Nc1ccc(F)c(Cl)c1] |
| 891 | 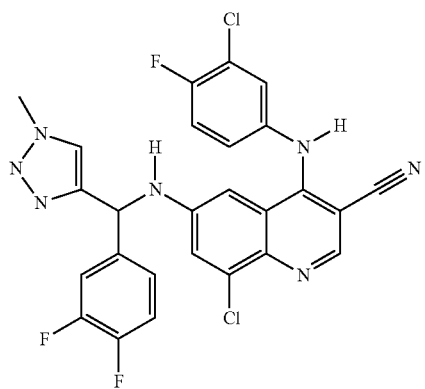 [SMILES: CN1C=C(C(Nc2cc(Cl)c3ncc(C#N)c(Nc4ccc(F)c(Cl)c4)c3c2)c2ccc(F)c(F)c2)NN1] |
| 892 | 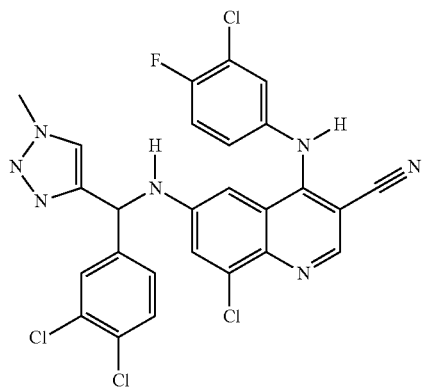 |

TABLE 1-continued
| Compound | Structure |
|---|---|
| 893 | 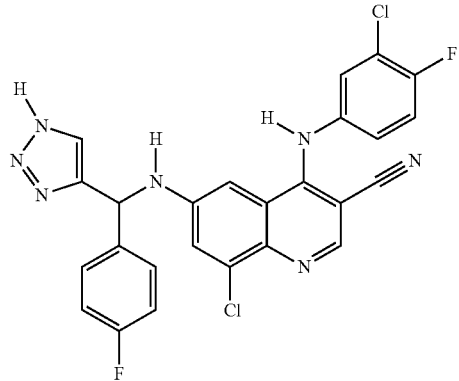 |
| 894 | 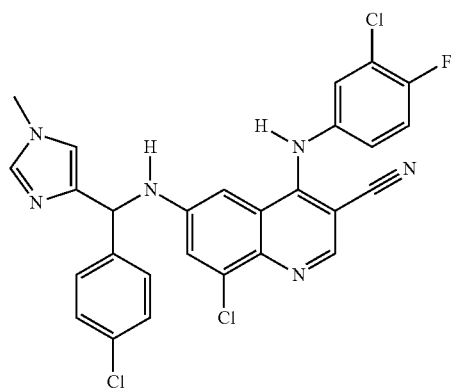 |
| 895 | 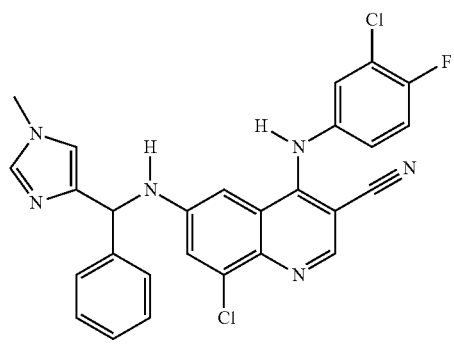 [SMILES: Cn1cnc(C(Nc2cc(Cl)c3ncc(C#N)c(Nc4ccc(F)c(Cl)c4)c3c2)c2ccccc2)c1] |

TABLE 1-continued
| Compound | Structure |
|---|---|
| 896 | 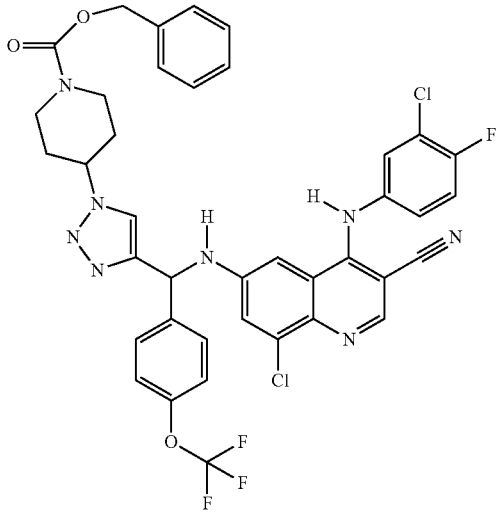 [SMILES: N#Cc1cnc2c(Cl)cc(NC(C3=CN(C4CCN(C(=O)OCc5ccccc5)CC4)NN3)c3ccc(OC(F)(F)F)cc3)cc2c1Nc1ccc(F)c(Cl)c1] |
| 897 | 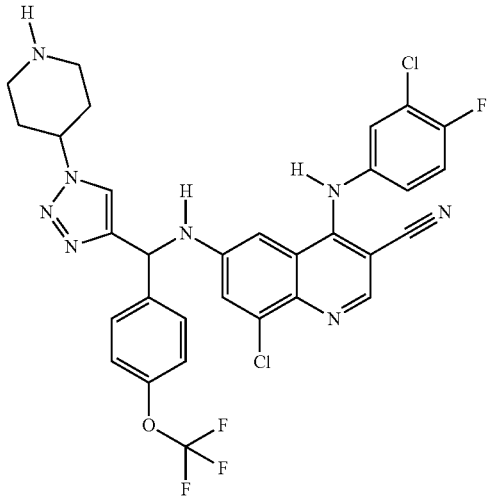 [SMILES: N#Cc1cnc2c(Cl)cc(NC(c3ccc(OC(F)(F)F)cc3)c3cn(C4CCNCC4)nn3)cc2c1Nc1ccc(F)c(Cl)c1] |
| 898 | 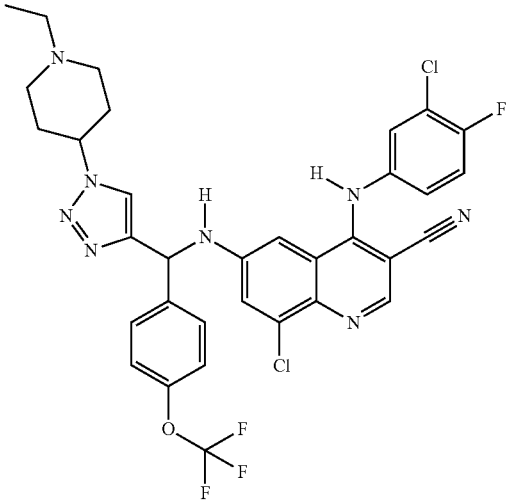 [SMILES: CCN1CCC(n2cc(C(Nc3cc(Cl)c4ncc(C#N)c(Nc5ccc(F)c(Cl)c5)c4c3)c3ccc(OC(F)(F)F)cc3)nn2)CC1] |

TABLE 1-continued
| Compound | Structure |
|---|---|
| 899 | 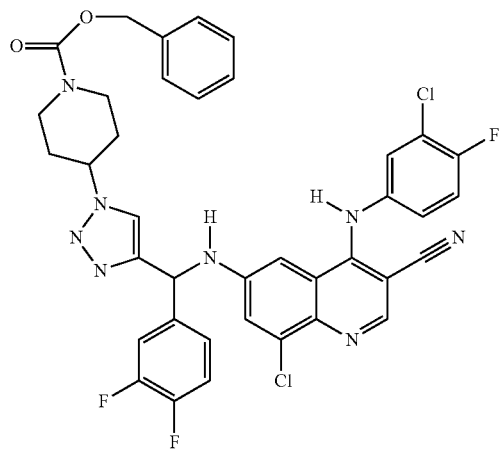 [SMILES: N#Cc1cnc2c(Cl)cc(NC(C3=CN(C4CCN(C(=O)OCc5ccccc5)CC4)NN3)c3ccc(F)c(F)c3)cc2c1Nc1ccc(F)c(Cl)c1] |
| 900 | 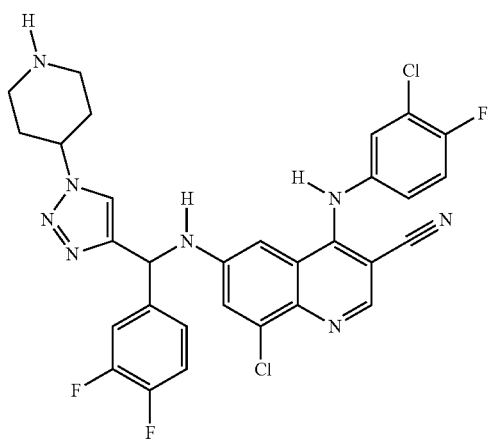 [SMILES: N#Cc1cnc2c(Cl)cc(NC(c3ccc(F)c(F)c3)c3cn(C4CCNCC4)nn3)cc2c1Nc1ccc(F)c(Cl)c1] |
| 901 | 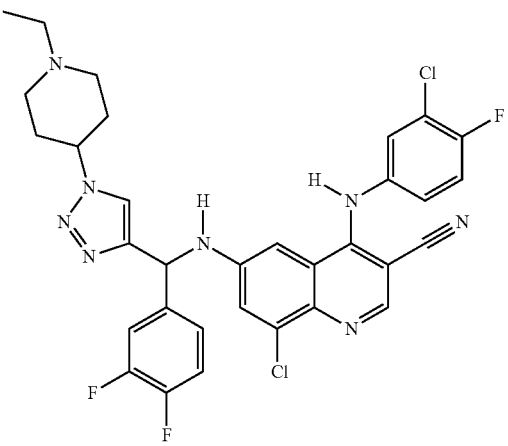 |

TABLE 1-continued

| Compound | Structure |
|---|---|
| 902 | |
| 903 | |
| 904 | |
| 905 | |

TABLE 1-continued
| Compound | Structure |
|---|---|
| 906 | 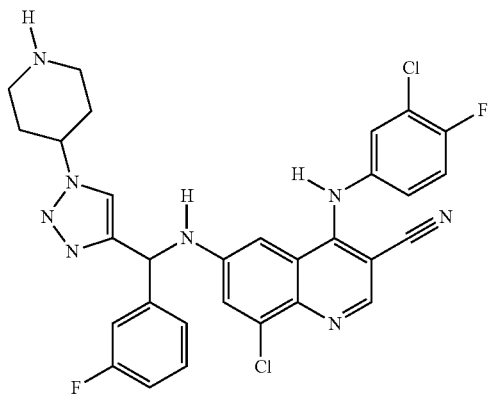 |
| 907 | 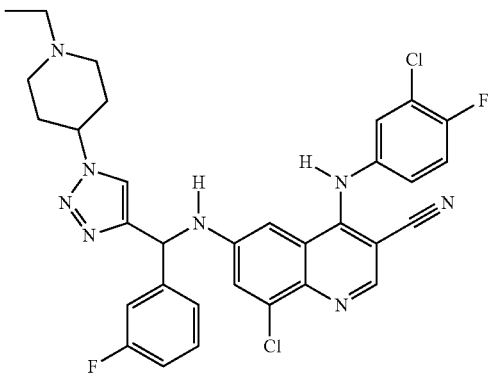 [SMILES: CCN1CCC(N2C=C(C(Nc3cc(Cl)c4ncc(C#N)c(Nc5ccc(F)c(Cl)c5)c4c3)c3cccc(OC)c3)NN2)CC1] |
| 908 | 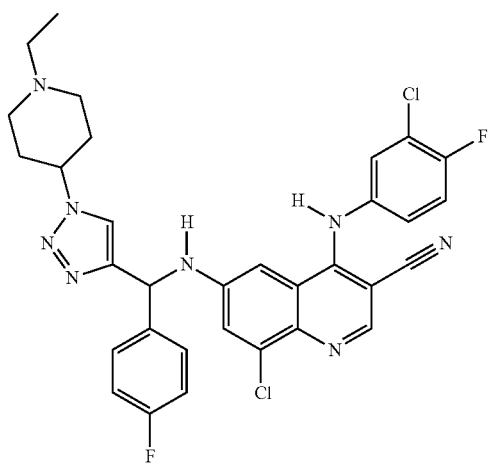 [SMILES: CCN1CCC(n2cc(C(Nc3cc(Cl)c4ncc(C#N)c(Nc5ccc(F)c(Cl)c5)c4c3)c3ccc(F)cc3)nn2)CC1] |

TABLE 1-continued
| Compound | Structure |
|---|---|
| 909 | 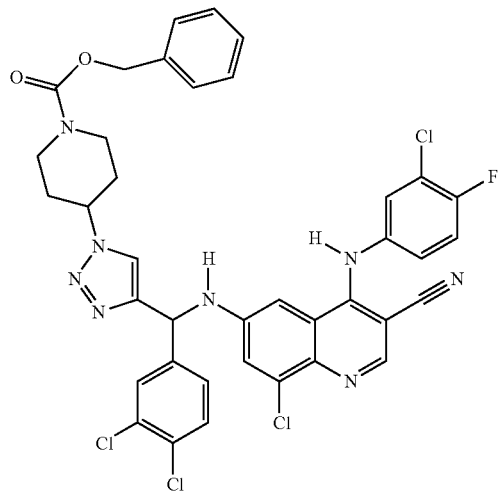 [SMILES: N#Cc1cnc2c(Cl)cc(NC(c3ccc(Cl)c(Cl)c3)c3cn(C4CCN(C(=O)OCc5ccccc5)CC4)nn3)cc2c1Nc1ccc(F)c(Cl)c1] |
| 910 | 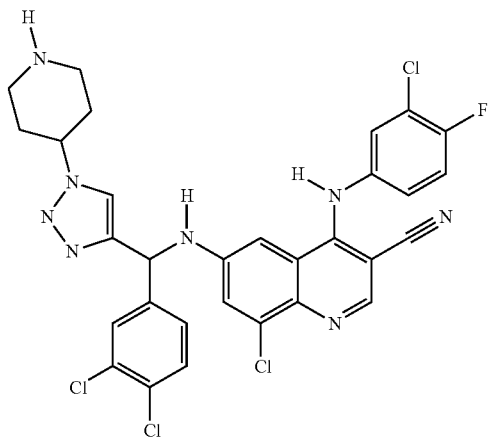 [SMILES: N#Cc1cnc2c(Cl)cc(NC(C3=CN(C4CCNCC4)NN3)c3ccc(Cl)c(Cl)c3)cc2c1Nc1ccc(F)c(Cl)c1] |
| 911 | 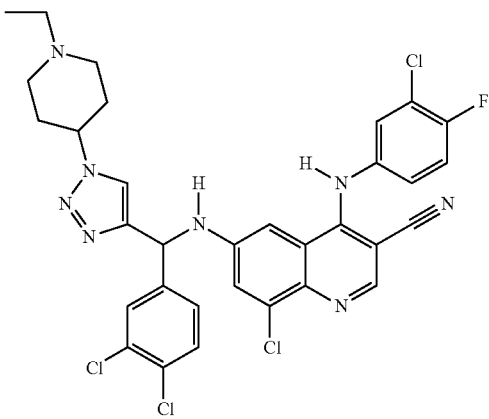 [SMILES: CCN1CCC(n2cc(C(Nc3cc(Cl)c4ncc(C#N)c(Nc5ccc(F)c(Cl)c5)c4c3)c3ccc(Cl)c(Cl)c3)nn2)CC1] |

TABLE 1-continued
| Compound | Structure |
|---|---|
| 912 | 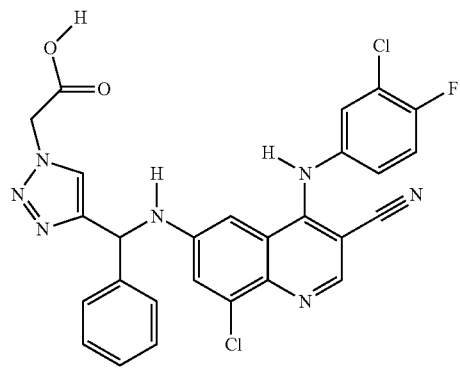 [SMILES: N#Cc1cnc2c(Cl)cc(NC(c3ccccc3)c3cn(CC(=O)O)nn3)cc2c1Nc1ccc(F)c(Cl)c1] |
| 913 | 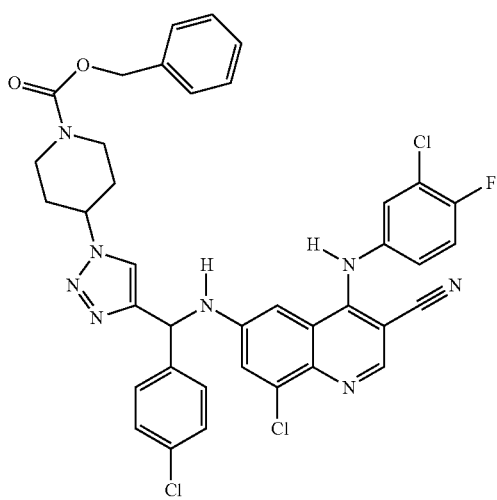 [SMILES: N#Cc1cnc2c(Cl)cc(NC(c3ccc(Cl)cc3)c3cn(C4CCN(C(=O)OCc5ccccc5)CC4)nn3)cc2c1Nc1ccc(F)c(Cl)c1] |
| 914 | 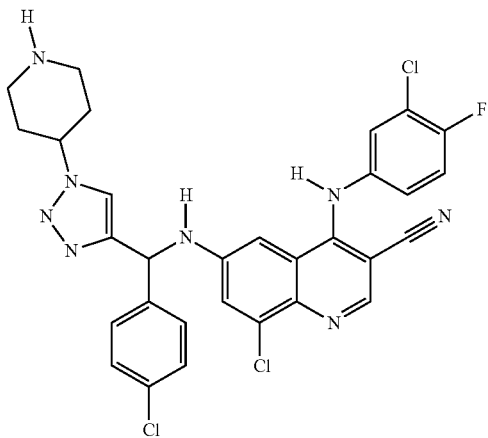 [SMILES: N#Cc1cnc2c(Cl)cc(NC(C3=CN(C4CCNCC4)NN3)c3ccc(Cl)cc3)cc2c1Nc1ccc(F)c(Cl)c1] |

TABLE 1-continued
| Compound | Structure |
|----------|-----------|
| 915 | 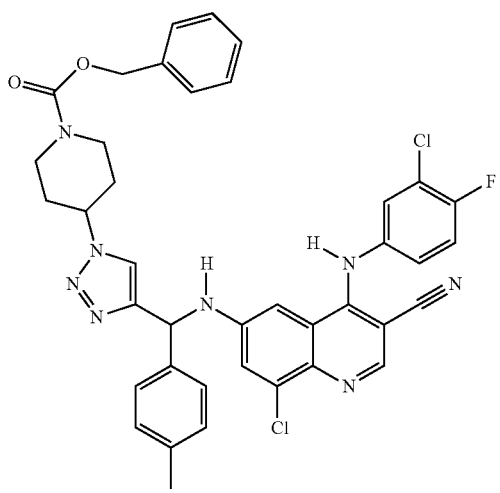 [SMILES: Cc1ccc(C(Nc2cc(Cl)c3ncc(C#N)c(Nc4ccc(F)c(Cl)c4)c3c2)c2cn(C3CCN(C(=O)OCc4ccccc4)CC3)nn2)cc1] |
| 916 | 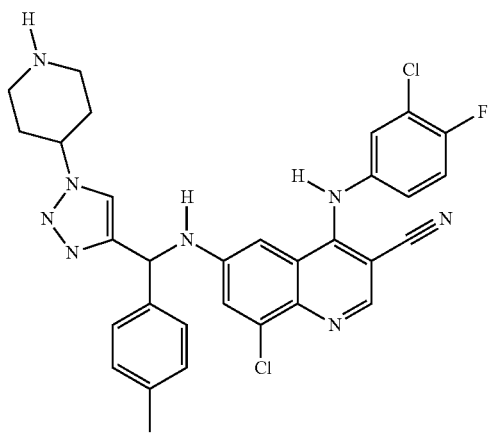 [SMILES: Cc1ccc(C(Nc2cc(Cl)c3ncc(C#N)c(Nc4ccc(F)c(Cl)c4)c3c2)C2=CN(C3CCNCC3)NN2)cc1] |
| 917 | 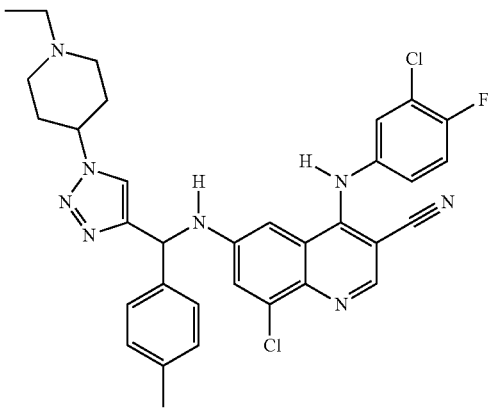 [SMILES: CCN1CCC(n2cc(C(Nc3cc(Cl)c4ncc(C#N)c(Nc5ccc(F)c(Cl)c5)c4c3)c3ccc(C)cc3)nn2)CC1] |

TABLE 1-continued

| Compound | Structure |
|---|---|
| 918 | |
| 919 | |
| 920 | |
| 921 | |

TABLE 1-continued

| Compound | Structure |
|---|---|
| 922 | |
| 923 | |
| 924 | |
| 925 | |

TABLE 1-continued
| Compound | Structure |
|---|---|
| 926 | 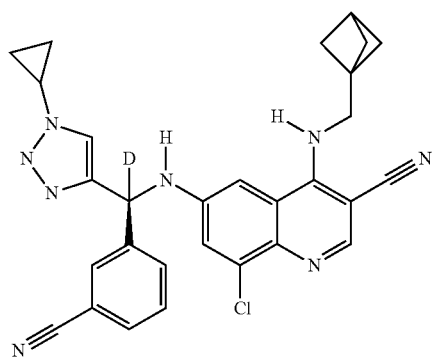 [SMILES: [2H][C@](Nc1cc(Cl)c2ncc(C#N)c(NCC34CC(C3)C4)c2c1)(C1=CN(C2CC2)NN1)c1cccc(C#N)c1] |
| 927 | 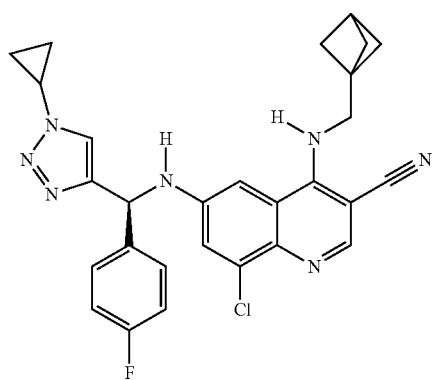 [SMILES: N#Cc1cnc2c(Cl)cc(N[C@@H](c3ccc(F)cc3)c3cn(C4CC4)nn3)cc2c1NCC12CC(C1)C2] |
| 928 | 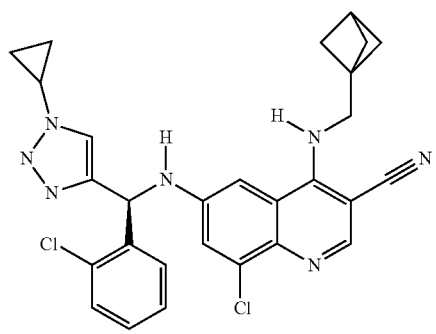 [SMILES: N#Cc1cnc2c(Cl)cc(N[C@H](C3=CN(C4CC4)NN3)c3ccccc3Cl)cc2c1NCC12CC(C1)C2] |
| 929 | 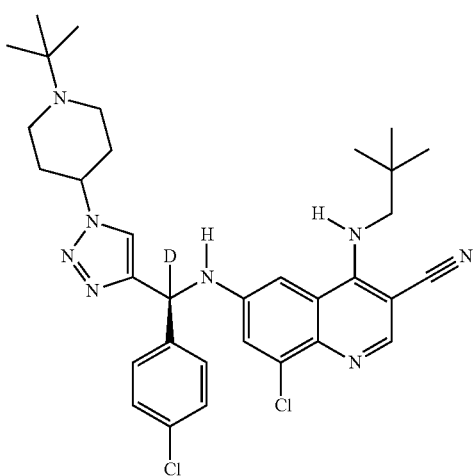 [SMILES: [2H][C@@](Nc1cc(Cl)c2ncc(C#N)c(NCC(C)(C)C)c2c1)(c1ccc(Cl)cc1)c1cn(C2CCN(C(C)(C)C)CC2)nn1] |

TABLE 1-continued

| Compound | Structure |
|---|---|
| 930 | |
| 931 | |
| 932 | |
| 933 | |

TABLE 1-continued

| Compound | Structure |
|---|---|
| 934 | |
| 935 | |
| 936 | |
| 937 | |

TABLE 1-continued

| Compound | Structure |
|---|---|
| 938 | |
| 939 | |
| 940 | |
| 941 | |

TABLE 1-continued
| Compound | Structure |
|---|---|
| 942 | 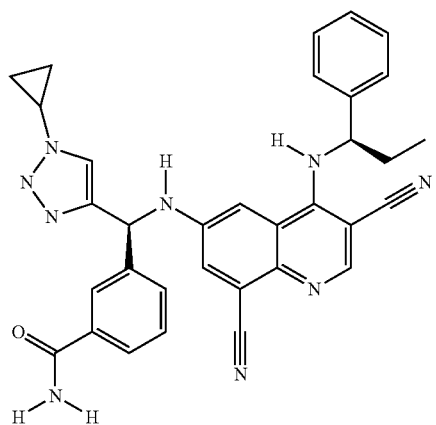 |
| 943 | 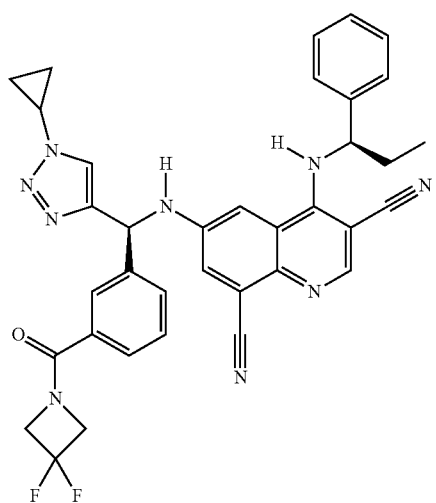 [SMILES: CC[C@@H](Nc1c(C#N)cnc2c(C#N)cc(N[C@@H](c3cccc(C(=O)N4CC(F)(F)C4)c3)c3cn(C4CC4)nn3)cc12)c1ccccc1] |
| 944 | 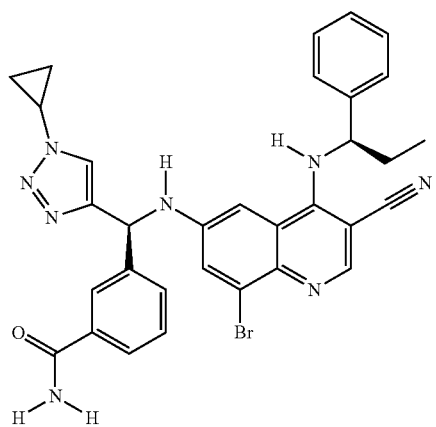 [SMILES: CC[C@@H](Nc1c(C#N)cnc2c(Br)cc(N[C@@H](c3cccc(C(N)=O)c3)c3cn(C4CC4)nn3)cc12)c1ccccc1] |

TABLE 1-continued
| Compound | Structure |
|---|---|
| 945 | 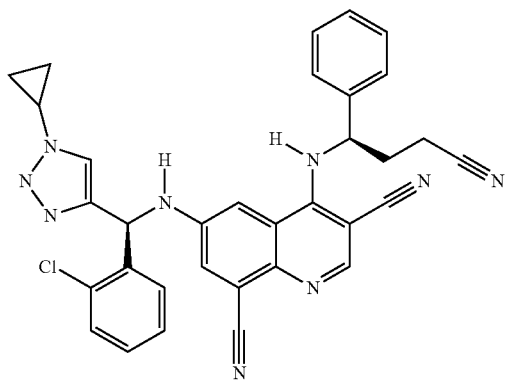 |
| 946 | 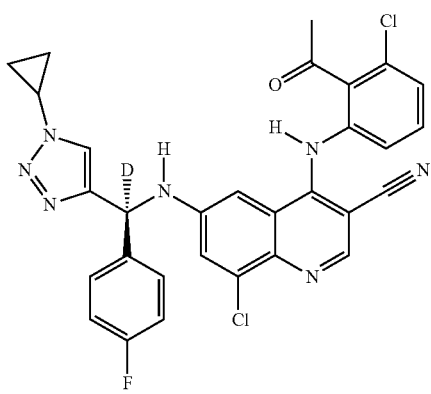 |
| 947 | 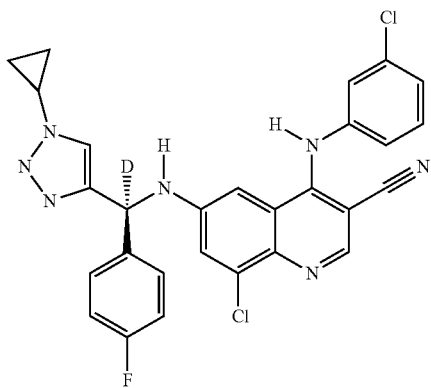 |
| 948 | 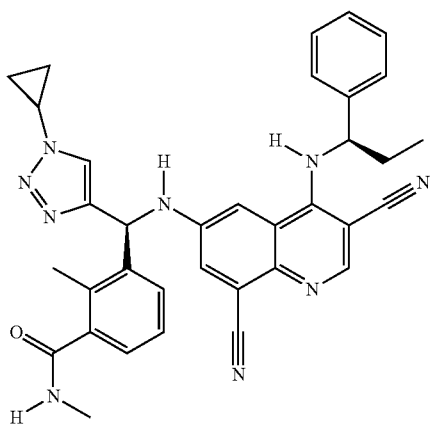 [SMILES: CC[C@@H](Nc1c(C#N)cnc2c(C#N)cc(N[C@H](c3cn(C4CC4)nn3)c3cccc(C(=O)NC)c3C)cc12)c1ccccc1] |

TABLE 1-continued

| Compound | Structure |
|---|---|
| 949 | |
| 950 | |
| 951 | |
| 952 | |

TABLE 1-continued

| Compound | Stucture |
| --- | --- |
| 953 | |
| 954 | |
| 955 | |
| 956 | |

TABLE 1-continued

| Compound | Structure |
|---|---|
| 957 | |
| 958 | |
| 959 | |
| 960 | |

TABLE 1-continued
| Compound | Structure |
|---|---|
| 961 | 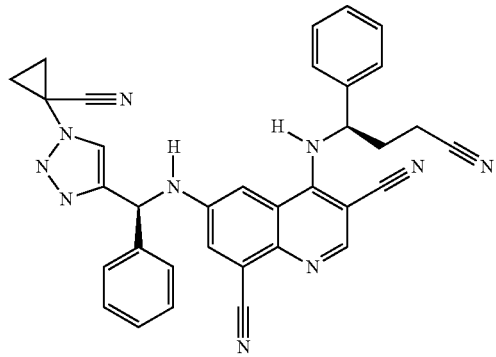 [SMILES: N#CCC[C@@H](Nc1c(C#N)cnc2c(C#N)cc(N[C@H](C3=CN(C4(C#N)CC4)NN3)c3ccccc3)cc12)c1ccccc1] |
| 962 | 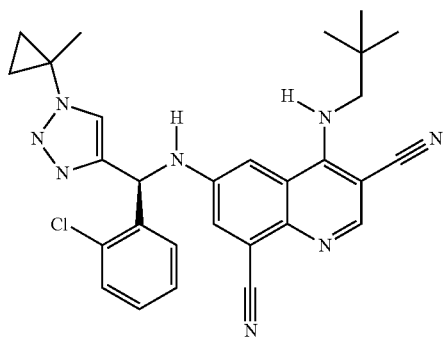 [SMILES: CC(C)(C)CNc1c(C#N)cnc2c(C#N)cc(N[C@H](C3=CN(C4(C)CC4)NN3)c3ccccc3Cl)cc12] |
| 963 | 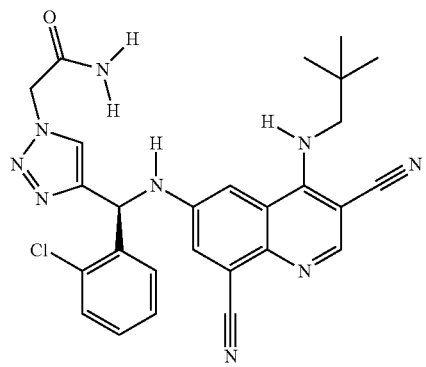 [SMILES: CC(C)(C)CNc1c(C#N)cnc2c(C#N)cc(N[C@H](c3cn(CC(N)=O)nn3)c3ccccc3Cl)cc12] |
| 964 | 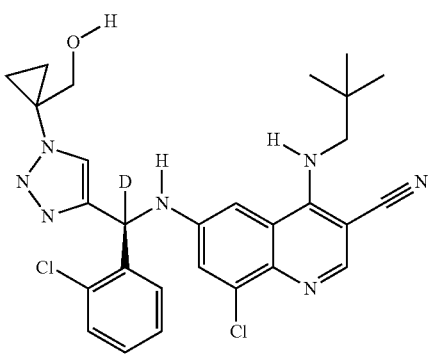 [SMILES: [2H][C@](Nc1cc(Cl)c2ncc(C#N)c(NCC(C)(C)C)c2c1)(C1=CN(C2(CO)CC2)NN1)c1ccccc1Cl] |

TABLE 1-continued

| Compound | Structure |
|---|---|
| 965 | |
| 966 | |
| 967 | |
| 968 | |

TABLE 1-continued

| Compound | Structure |
|---|---|
| 969 | (structure) |
| 970 | (structure) |
| 971 | (structure) |
| 972 | (structure) |

TABLE 1-continued
| Compound | Structure |
|---|---|
| 973 | 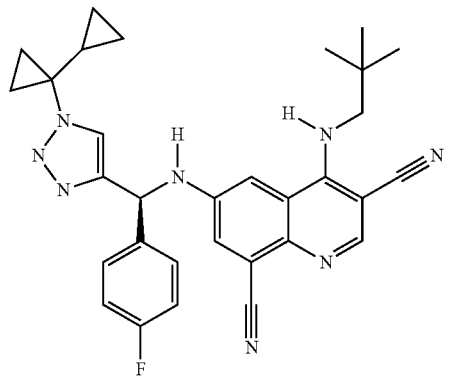 [SMILES: CC(C)(C)CNc1c(C#N)cnc2c(C#N)cc(N[C@H](C3=CN(C4(C5CC5)CC4)NN3)c3ccc(F)cc3)cc12] |
| 974 | 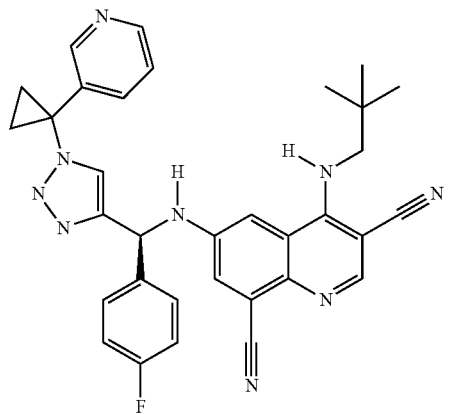 |
| 975 | 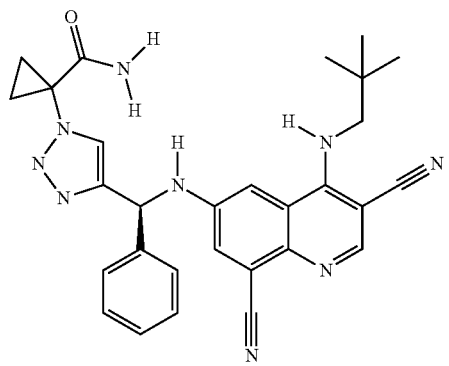 [SMILES: CC(C)(C)CNc1c(C#N)cnc2c(C#N)cc(N[C@H](C3=CN(C4(C(N)=O)CC4)NN3)c3ccccc3)cc12] |
| 976 | 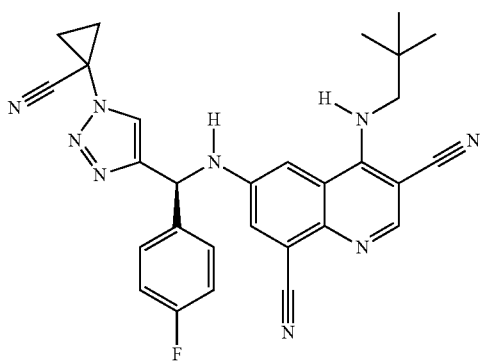 [SMILES: CC(C)(C)CNc1c(C#N)cnc2c(C#N)cc(N[C@@H](c3ccc(F)cc3)c3cn(C4(C#N)CC4)nn3)cc12] |

TABLE 1-continued
| Compound | Structure |
|---|---|
| 977 | 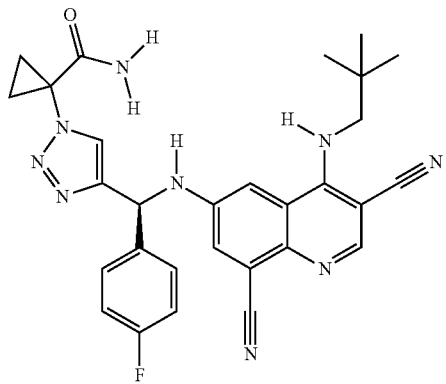 [SMILES: CC(C)(C)CNc1c(C#N)cnc2c(C#N)cc(N[C@@H](c3ccc(F)cc3)c3cn(C4(C(N)=O)CC4)nn3)cc12] |
| 978 | 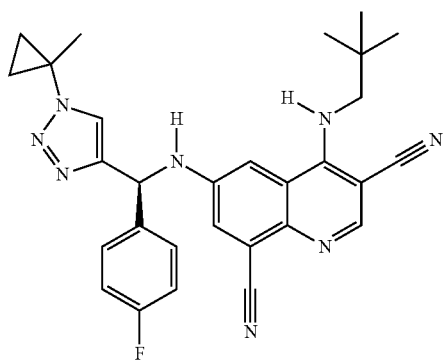 [SMILES: CC(C)(C)CNc1c(C#N)cnc2c(C#N)cc(N[C@@H](c3ccc(F)cc3)c3cn(C4(C)CC4)nn3)cc12] |
| 979 | 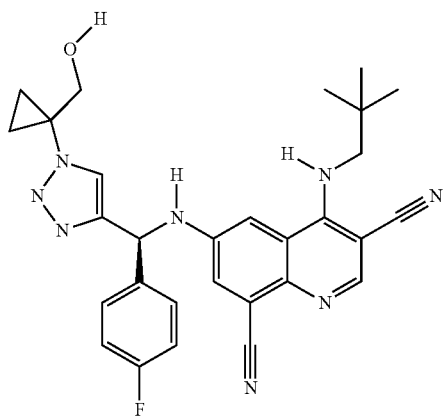 [SMILES: CC(C)(C)CNc1c(C#N)cnc2c(C#N)cc(N[C@H](C3=CN(C4(CO)CC4)NN3)c3ccc(F)cc3)cc12] |

TABLE 1-continued

| Compound | Structure |
|---|---|
| 980 | |
| 981 | |
| 982 | |

TABLE 1-continued

| Compound | Structure |
|---|---|
| 983 | |
| 984 | |
| 985 | |
| 986 | |

TABLE 1-continued

| Compound | Structure |
|---|---|
| 987 | |
| 988 | |
| 989 | |

TABLE 1-continued

| Compound | Structure |
|---|---|
| 990 | |
| 991 | |
| 992 | |
| 993 | |

TABLE 1-continued

| Compound | Stucture |
|---|---|
| 994 | |
| 995 | |
| 996 | |
| 997 | |

TABLE 1-continued

| Compound | Structure |
|---|---|
| 998 | |
| 999 | |
| 1000 | |
| 1001 | |

TABLE 1-continued
| Compound | Structure |
|---|---|
| 1002 | 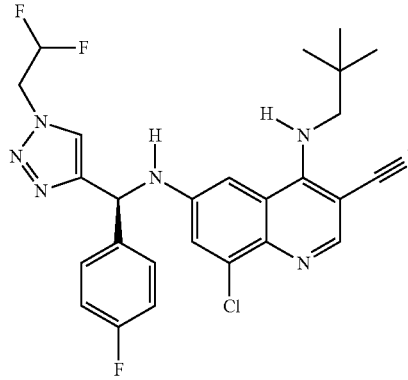 |
| 1003 | 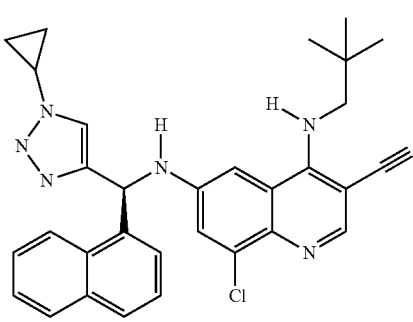 |
| 1004 | 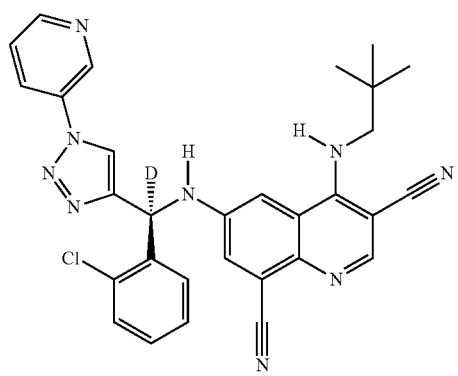 |
| 1005 | 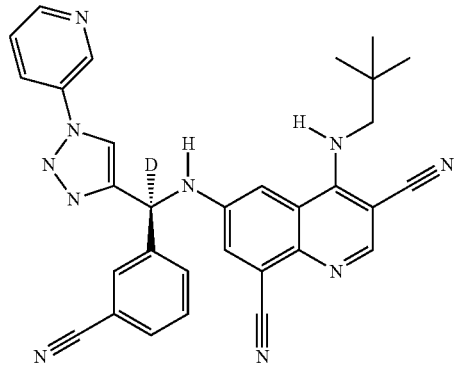 |

TABLE 1-continued

| Compound | Structure |
|---|---|
| 1006 | |
| 1007 | |
| 1008 | |
| 1009 | |

TABLE 1-continued

| Compound | Structure |
|---|---|
| 1010 | |
| 1011 | |
| 1012 | |
| 1013 | |

TABLE 1-continued

| Compound | Structure |
| --- | --- |
| 1014 | |
| 1015 | |
| 1016 | |
| 1017 | |

TABLE 1-continued
| Compound | Structure |
|---|---|
| 1018 | 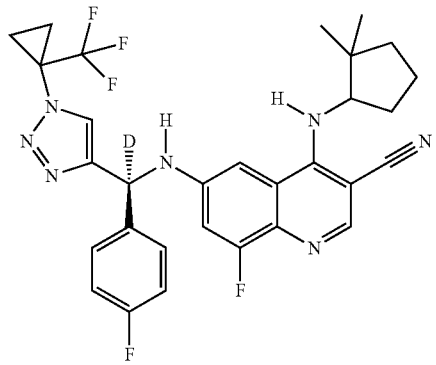 |
| 1019 | 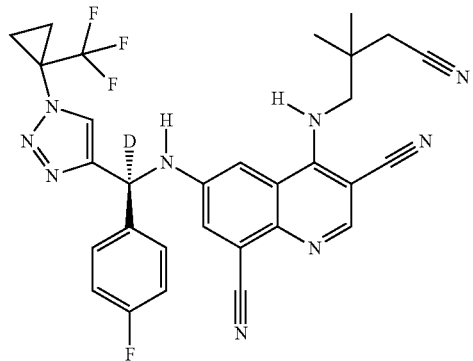 |
| 1020 | 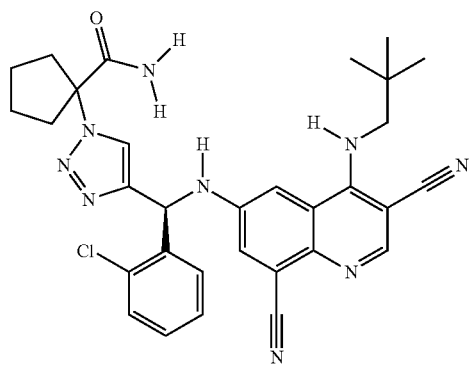 [SMILES: CC(C)(C)CNc1c(C#N)cnc2c(C#N)cc(N[C@H](c3cn(C4(C(N)=O)CCCC4)nn3)c3ccccc3Cl)cc12] |
| 1021 | 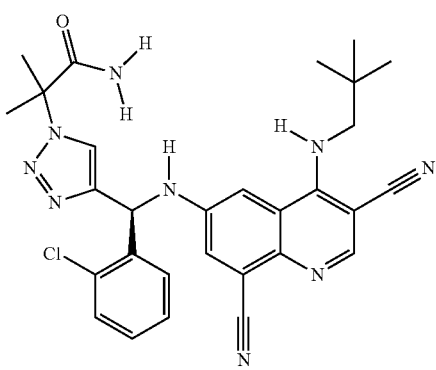 [SMILES: CC(C)(C)CNc1c(C#N)cnc2c(C#N)cc(N[C@H](c3cn(C(C)(C)C(N)=O)nn3)c3ccccc3Cl)cc12] |

TABLE 1-continued

| Compound | Structure |
|---|---|
| 1022 | |
| 1023 | |
| 1024 | |
| 1025 | |

TABLE 1-continued

| Compound | Structure |
|---|---|
| 1026 | |
| 1027 | |
| 1028 | |
| 1029 | |

TABLE 1-continued
| Compound | Structure |
|---|---|
| 1030 | 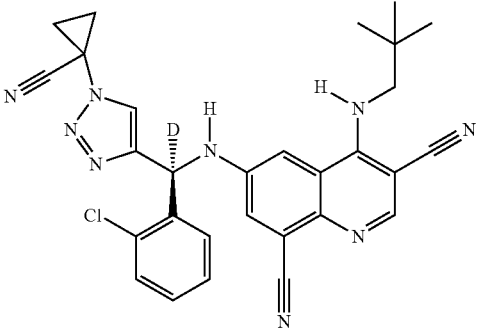 |
| 1031 | 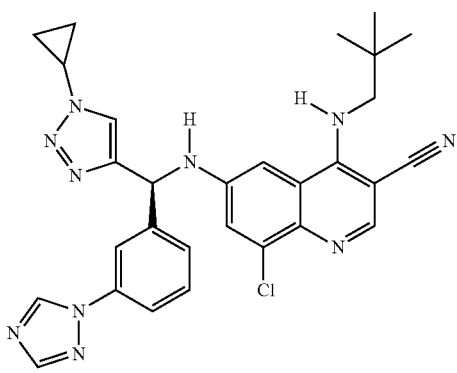 [SMILES: CC(C)(C)CNc1c(C#N)cnc2c(Cl)cc(N[C@@H](c3cccc(-n4cncn4)c3)c3cn(C4CC4)nn3)cc12] |
| 1032 | 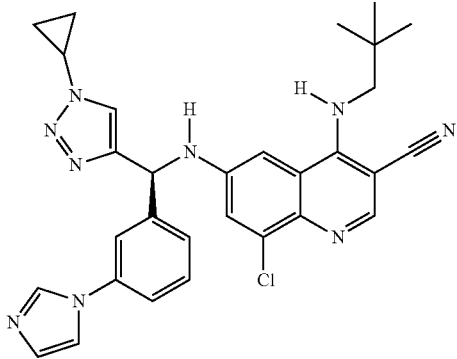 [SMILES: CC(C)(C)CNc1c(C#N)cnc2c(Cl)cc(N[C@@H](c3cccc(-n4ccnc4)c3)c3cn(C4CC4)nn3)cc12] |
| 1033 | 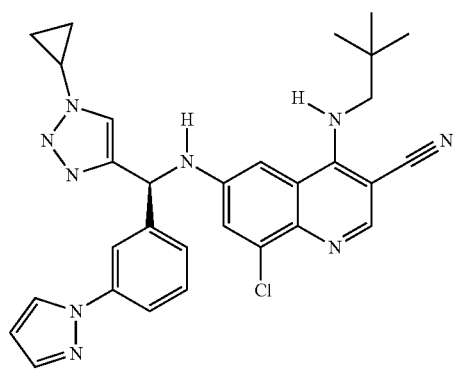 [SMILES: CC(C)(C)CNc1c(C#N)cnc2c(Cl)cc(N[C@H](C3=CN(C4CC4)NN3)c3cccc(-n4cccn4)c3)cc12] |

TABLE 1-continued
| Compound | Structure |
|---|---|
| 1034 | 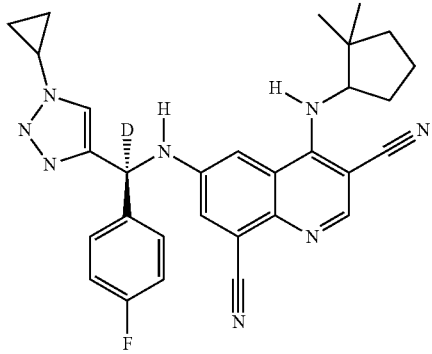 |
| 1035 | 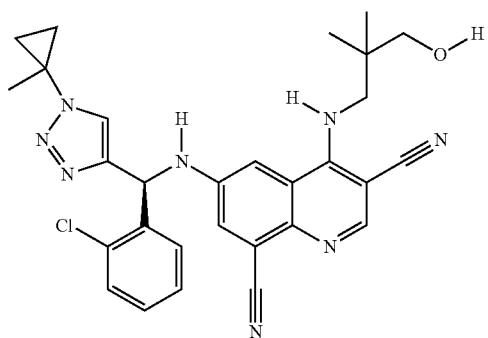 [SMILES: CC(C)(CO)CNc1c(C#N)cnc2c(C#N)cc(N[C@H](c3cn(C4(C)CC4)nn3)c3ccccc3Cl)cc12] |
| 1036 | 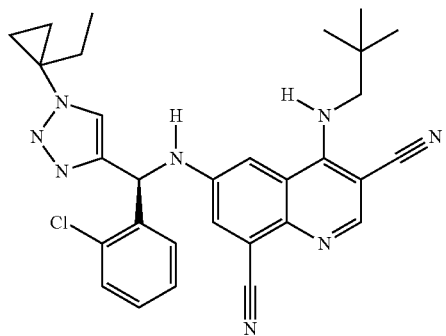 [SMILES: CCC1(N2C=C([C@@H](Nc3cc(C#N)c4ncc(C#N)c(NCC(C)(C)C)c4c3)c3ccccc3Cl)NN2)CC1] |
| 1037 | 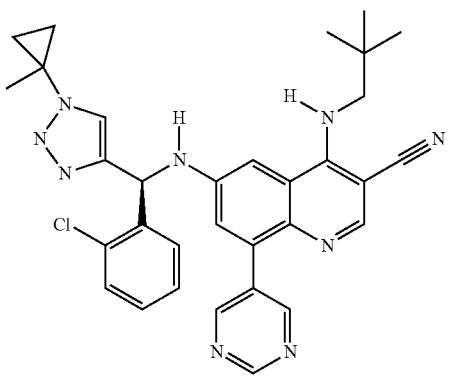 [SMILES: CC(C)(C)CNc1c(C#N)cnc2c(-c3cncnc3)cc(N[C@H](C3=CN(C4(C)CC4)NN3)c3ccccc3Cl)cc12] |

TABLE 1-continued

| Compound | Structure |
|---|---|
| 1038 | |
| 1039 | |
| 1040 | |
| 1041 | |

TABLE 1-continued
| Compound | Structure |
|---|---|
| 1042 | 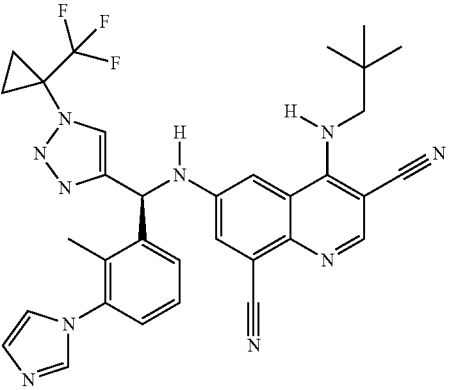 [SMILES: Cc1c([C@H](Nc2cc(C#N)c3ncc(C#N)c(NCC(C)(C)C)c3c2)C2=CN(C3(C(F)(F)F)CC3)NN2)cccc1-n1ccnc1] |
| 1043 | 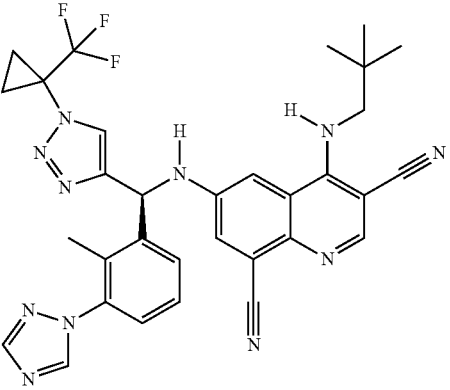 [SMILES: Cc1c([C@H](Nc2cc(C#N)c3ncc(C#N)c(NCC(C)(C)C)c3c2)c2cn(C3(C(F)(F)F)CC3)nn2)cccc1-n1cncn1] |
| 1044 | 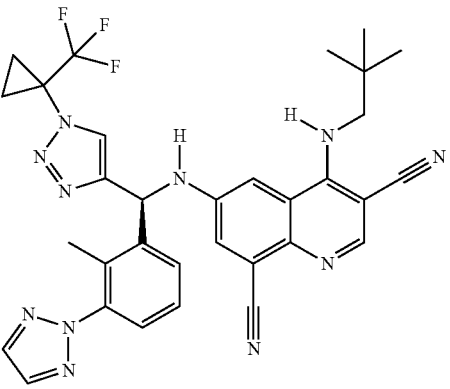 |
| 1045 | 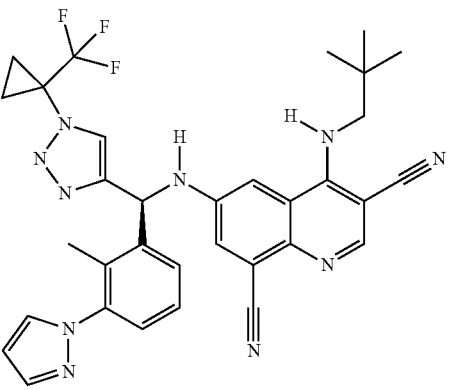 [SMILES: Cc1c([C@H](Nc2cc(C#N)c3ncc(C#N)c(NCC(C)(C)C)c3c2)C2=CN(C3(C(F)(F)F)CC3)NN2)cccc1-n1cccn1] |

TABLE 1-continued
| Compound | Structure |
|---|---|
| 1046 | 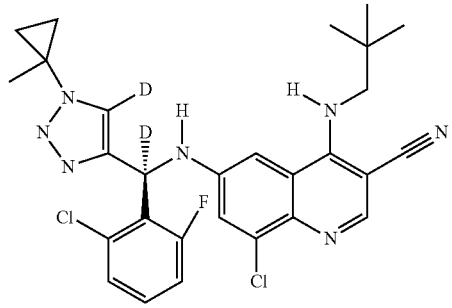 |
| 1047 | 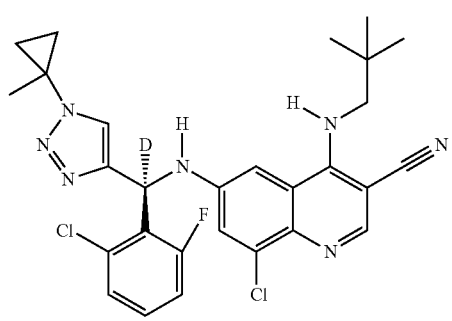 |
| 1048 | 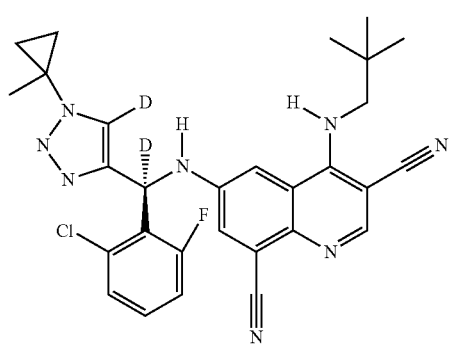 |
| 1049 | 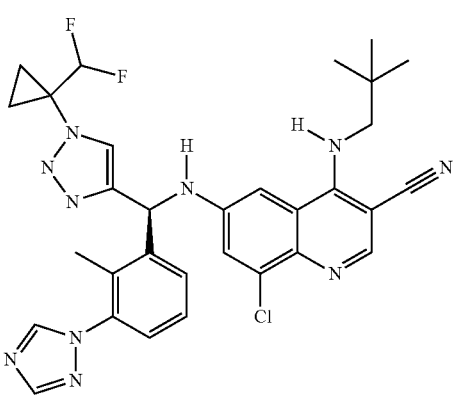 [SMILES: Cc1c([C@H](Nc2cc(Cl)c3ncc(C#N)c(NCC(C)(C)C)c3c2)C2=CN(C3(C(F)F)CC3)NN2)cccc1-n1cncn1] |

TABLE 1-continued

| Compound | Structure |
|---|---|
| 1050 | |
| 1051 | |
| 1052 | |
| 1053 | |

TABLE 1-continued

| Compound | Structure |
|---|---|
| 1054 | |
| 1055 | |
| 1056 | |
| 1057 | |

TABLE 1-continued
| Compound | Structure |
|---|---|
| 1058 | 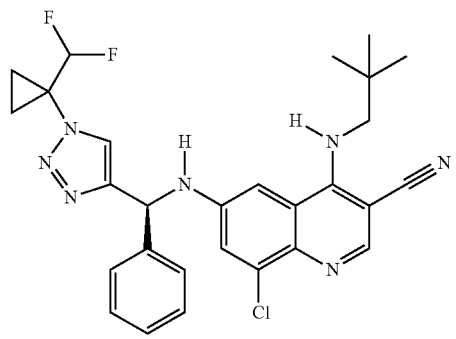 [SMILES: CC(C)(C)CNc1c(C#N)cnc2c(Cl)cc(N[C@@H](c3ccccc3)c3cn(C4(C(F)F)CC4)nn3)cc12] |
| 1059 | 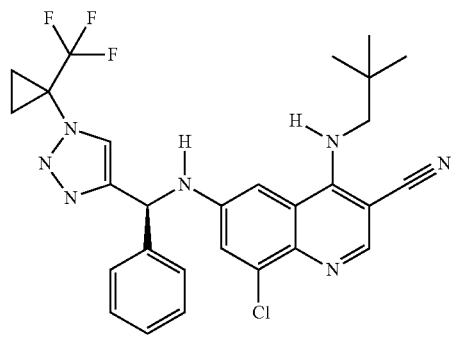 [SMILES: CC(C)(C)CNc1c(C#N)cnc2c(Cl)cc(N[C@H](C3=CN(C4(C(F)(F)F)CC4)NN3)c3ccccc3)cc12] |
| 1060 | 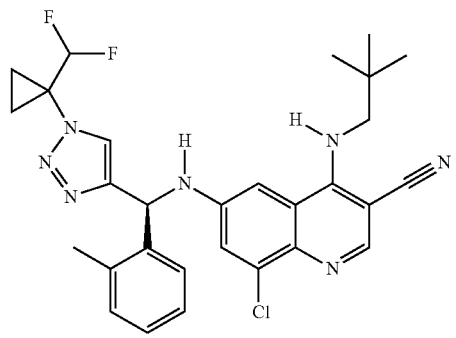 [SMILES: Cc1ccccc1[C@H](Nc1cc(Cl)c2ncc(C#N)c(NCC(C)(C)C)c2c1)c1cn(C2(C(F)F)CC2)nn1] |
| 1061 | 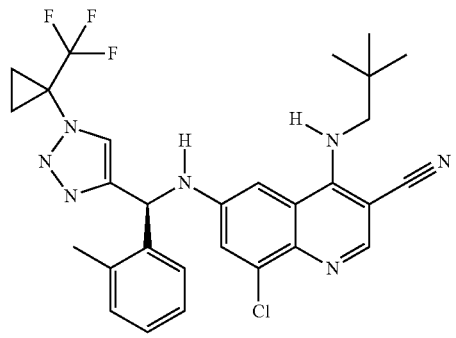 [SMILES: Cc1ccccc1[C@H](Nc1cc(Cl)c2ncc(C#N)c(NCC(C)(C)C)c2c1)C1=CN(C2(C(F)(F)F)CC2)NN1] |

TABLE 1-continued

| Compound | Structure |
|---|---|
| 1062 | |
| 1063 | |
| 1064 | |
| 1065 | |

TABLE 1-continued

| Compound | Structure |
|---|---|
| 1066 | |
| 1067 | |
| 1068 | |
| 1069 | |

TABLE 1-continued
| Compound | Structure |
|---|---|
| 1070 | 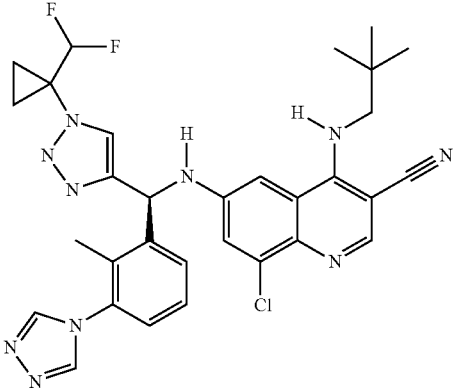 [SMILES: Cc1c([C@H](Nc2cc(Cl)c3ncc(C#N)c(NCC(C)(C)C)c3c2)C2=CN(C3(C(F)F)CC3)NN2)cccc1-n1cnnc1] |
| 1071 | 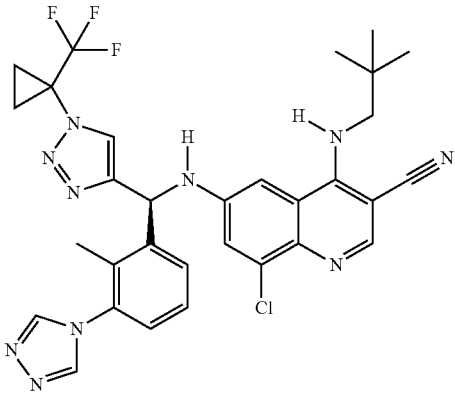 [SMILES: Cc1c([C@H](Nc2cc(Cl)c3ncc(C#N)c(NCC(C)(C)C)c3c2)c2cn(C3(C(F)(F)F)CC3)nn2)cccc1-n1cnnc1] |
| 1072 | 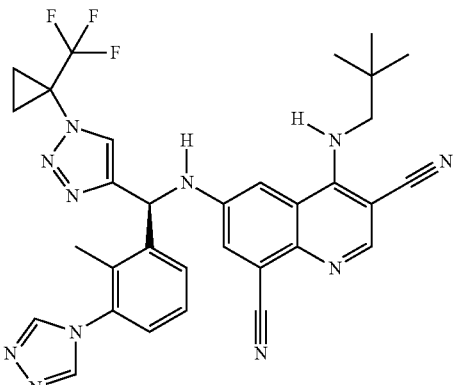 |
| 1073 | 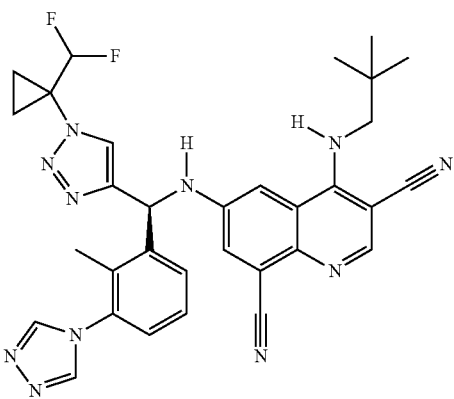 [SMILES: Cc1c([C@H](Nc2cc(C#N)c3ncc(C#N)c(NCC(C)(C)C)c3c2)c2cn(C3(C(F)F)CC3)nn2)cccc1-n1cnnc1] |

TABLE 1-continued
| Compound | Structure |
|---|---|
| 1074 | 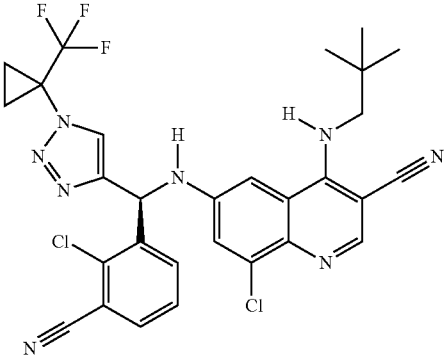 [SMILES: CC(C)(C)CNc1c(C#N)cnc2c(Cl)cc(N[C@H](c3cn(C4(C(F)(F)F)CC4)nn3)c3cccc(C#N)c3Cl)cc12] |
| 1075 | 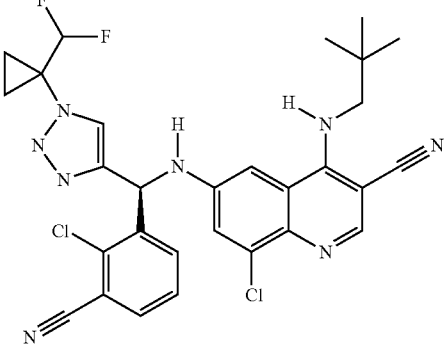 |
| 1076 | 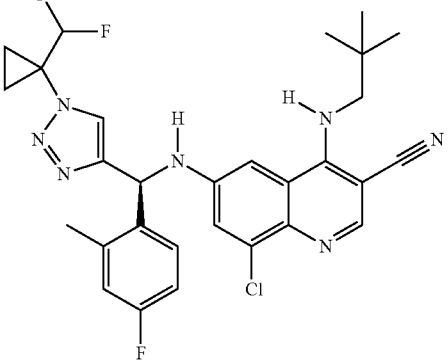 |
| 1077 | 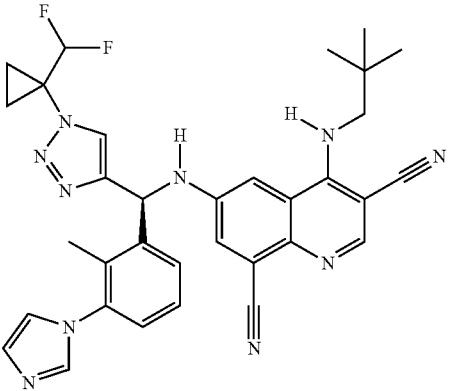 [SMILES: Cc1c([C@H](Nc2cc(C#N)c3ncc(C#N)c(NCC(C)(C)C)c3c2)c2cn(C3(C(F)F)CC3)nn2)cccc1-n1ccnc1] |

TABLE 1-continued

| Compound | Structure |
|---|---|
| 1078 | |
| 1079 | |
| 1080 | |
| 1081 | |

TABLE 1-continued

| Compound | Structure |
|---|---|
| 1082 | |
| 1083 | |
| 1084 | |
| 1085 | |

TABLE 1-continued
| Compound | Stucture |
|---|---|
| 1086 | 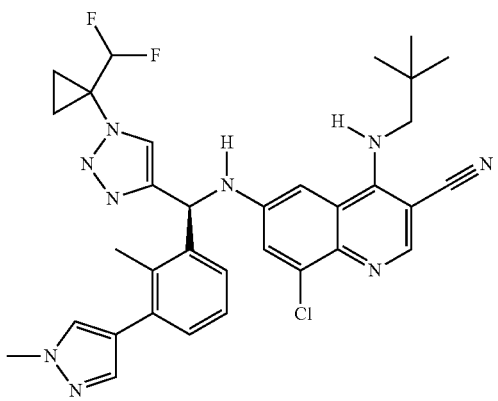 [SMILES: Cc1c(-c2cnn(C)c2)cccc1[C@H](Nc1cc(Cl)c2ncc(C#N)c(NCC(C)(C)C)c2c1)C1=CN(C2(C(F)F)CC2)NN1] |
| 1087 | 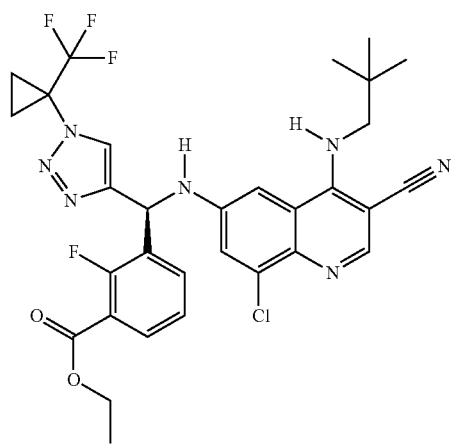 [SMILES: CCOC(=O)c1cccc([C@H](Nc2cc(Cl)c3ncc(C#N)c(NCC(C)(C)C)c3c2)c2cn(C3(C(F)(F)F)CC3)nn2)c1F] |
| 1088 | 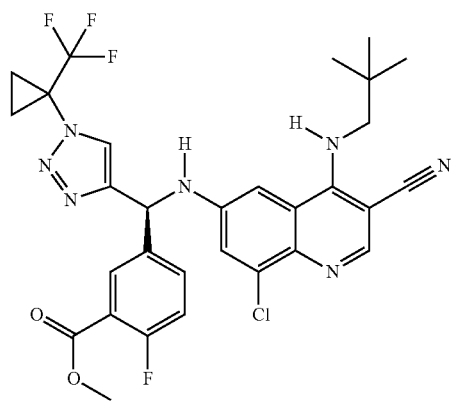 [SMILES: COC(=O)c1cc([C@H](Nc2cc(Cl)c3ncc(C#N)c(NCC(C)(C)C)c3c2)c2cn(C3(C(F)(F)F)CC3)nn2)ccc1F] |

TABLE 1-continued
| Compound | Structure |
|---|---|
| 1089 | 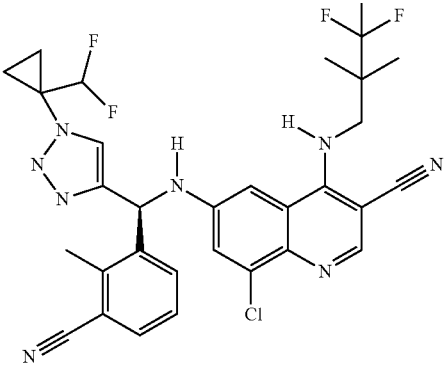 |
| 1090 | 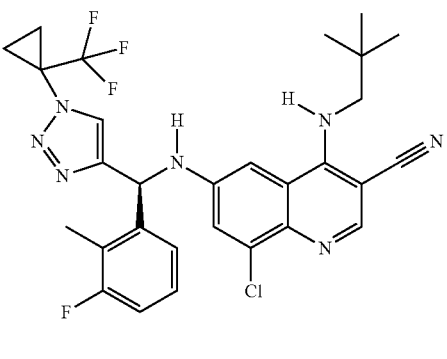 [SMILES: Cc1c(F)cccc1[C@H](Nc1cc(Cl)c2ncc(C#N)c(NCC(C)(C)C)c2c1)c1cn(C2(C(F)(F)F)CC2)nn1] |
| 1091 | 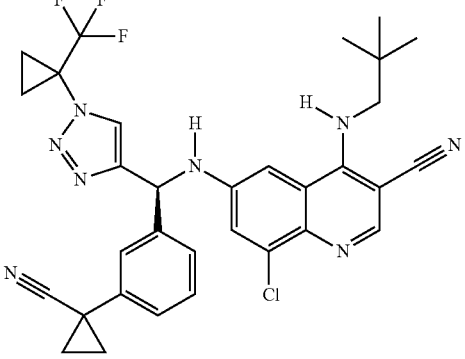 |
| 1092 | 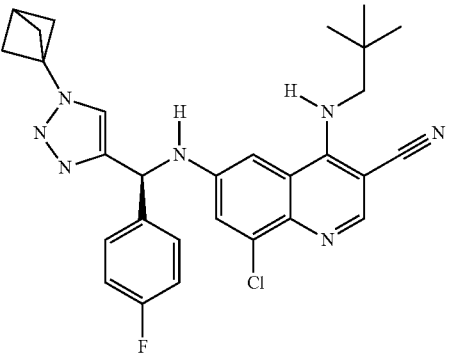 [SMILES: CC(C)(C)CNc1c(C#N)cnc2c(Cl)cc(N[C@H](C3=CN(C45CC(C4)C5)NN3)c3ccc(F)cc3)cc12] |

TABLE 1-continued

| Compound | Structure |
|---|---|
| 1093 | |
| 1094 | |
| 1095 | |
| 1096 | |

TABLE 1-continued
| Compound | Structure |
|---|---|
| 1097 | 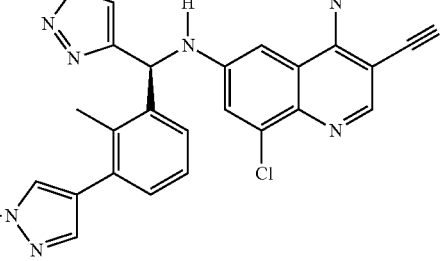 |
| 1098 | 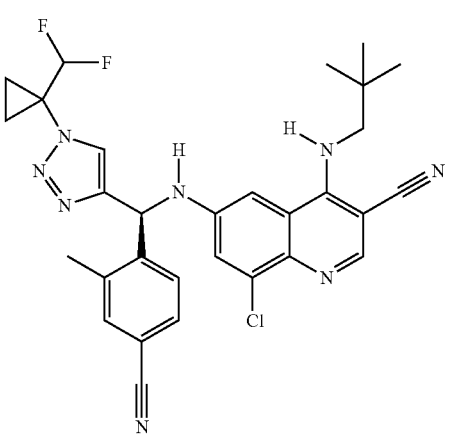 [SMILES: Cc1cc(C#N)ccc1[C@H](Nc1cc(Cl)c2ncc(C#N)c(NCC(C)(C)C)c2c1)c1cn(C2(C(F)F)CC2)nn1] |
| 1099 | 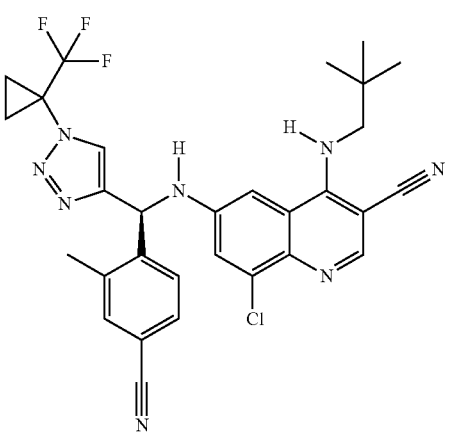 [SMILES: Cc1cc(C#N)ccc1[C@H](Nc1cc(Cl)c2ncc(C#N)c(NCC(C)(C)C)c2c1)c1cn(C2(C(F)(F)F)CC2)nn1] |
| 1100 | 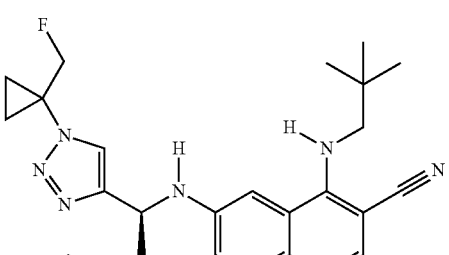 |

TABLE 1-continued

| Compound | Structure |
|---|---|
| 1101 | |
| 1102 | |
| 1103 | |
| 1104 | |

TABLE 1-continued
| Compound | Structure |
|---|---|
| 1105 | 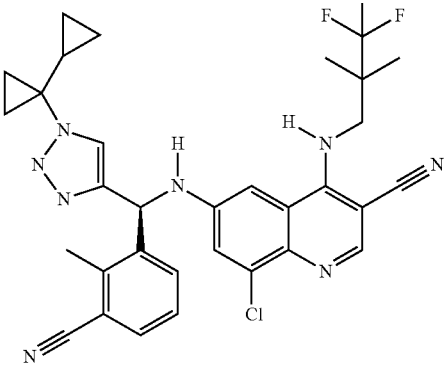 |
| 1106 | 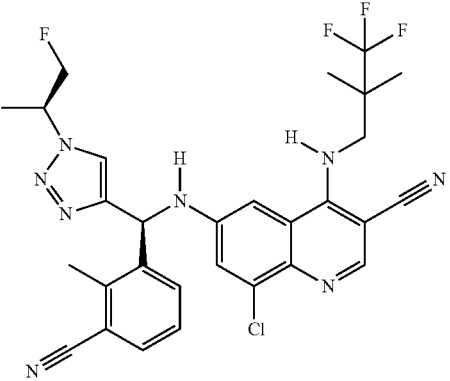 [SMILES: Cc1c(C#N)cccc1[C@H](Nc1cc(Cl)c2ncc(C#N)c(NCC(C)(C)C(F)(F)F)c2c1)c1cn([C@@H](C)CF)nn1] |
| 1107 | 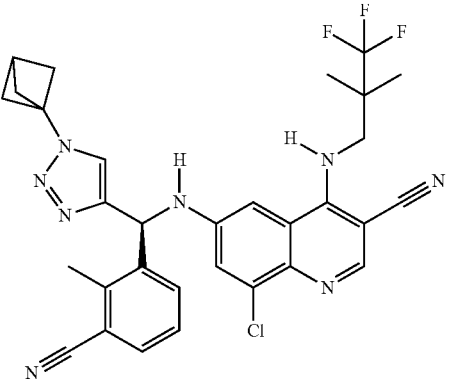 [SMILES: Cc1c(C#N)cccc1[C@H](Nc1cc(Cl)c2ncc(C#N)c(NCC(C)(C)C(F)(F)F)c2c1)c1cn(C23CC(C2)C3)nn1] |
| 1108 | 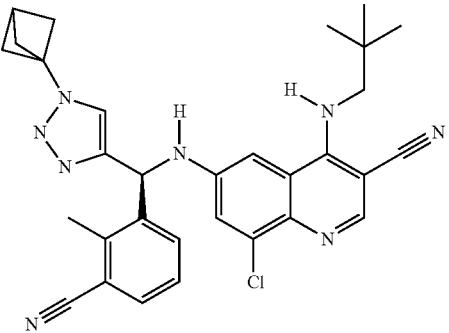 [SMILES: Cc1c(C#N)cccc1[C@H](Nc1cc(Cl)c2ncc(C#N)c(NCC(C)(C)C)c2c1)C1=CN(C23CC(C2)C3)NN1] |

TABLE 1-continued
| Compound | Structure |
|---|---|
| 1109 | 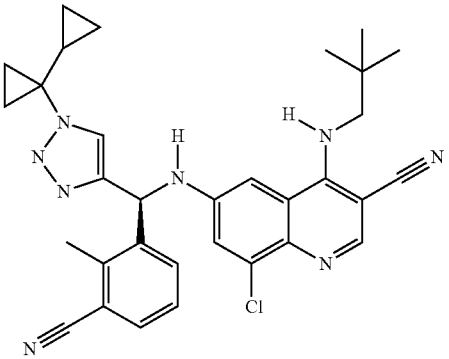 [SMILES: Cc1c(C#N)cccc1[C@H](Nc1cc(Cl)c2ncc(C#N)c(NCC(C)(C)C)c2c1)C1=CN(C2(C3CC3)CC2)NN1] |
| 1110 | 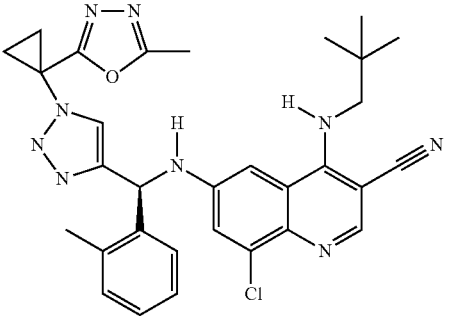 [SMILES: Cc1nnc(C2(N3C=C([C@@H](Nc4cc(Cl)c5ncc(C#N)c(NCC(C)(C)C)c5c4)c4ccccc4C)NN3)CC2)o1] |
| 1111 | 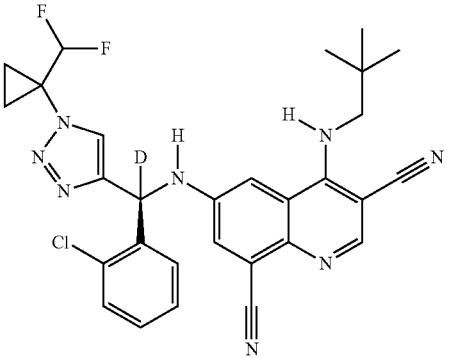 [SMILES: [2H][C@](Nc1cc(C#N)c2ncc(C#N)c(NCC(C)(C)C)c2c1)(c1cn(C2(C(F)F)CC2)nn1)c1ccccc1Cl] |
| 1112 | 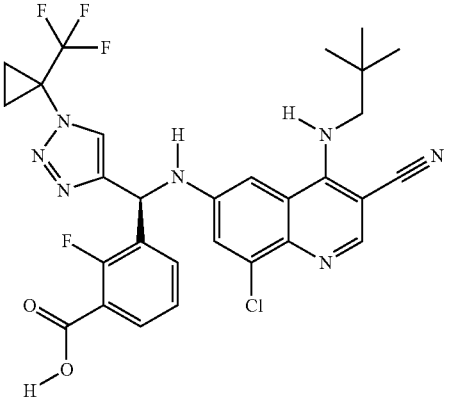 [SMILES: CC(C)(C)CNc1c(C#N)cnc2c(Cl)cc(N[C@H](c3cn(C4(C(F)(F)F)CC4)nn3)c3cccc(C(=O)O)c3F)cc12] |

TABLE 1-continued

| Compound | Stucture |
|---|---|
| 1113 | |
| 1114 | |
| 1115 | |
| 1116 | |

TABLE 1-continued

| Compound | Structure |
|---|---|
| 1117 | |
| 1118 | |
| 1119 | |
| 1120 | |

TABLE 1-continued
| Compound | Structure |
| --- | --- |
| 1121 | 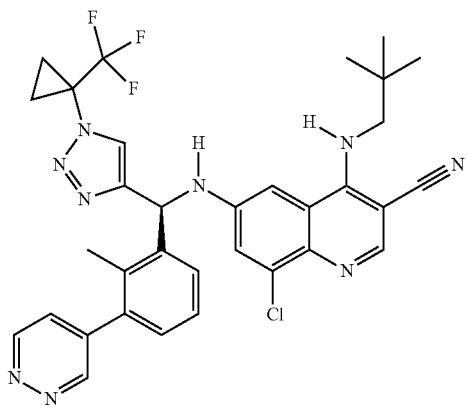 [SMILES: Cc1c(-c2ccnnc2)cccc1[C@H](Nc1cc(Cl)c2ncc(C#N)c(NCC(C)(C)C)c2c1)c1cn(C2(C(F)(F)F)CC2)nn1] |
| 1122 | 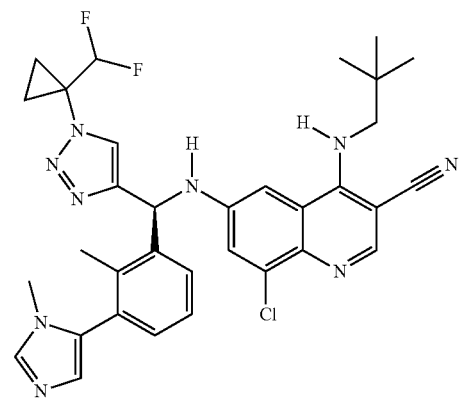 [SMILES: Cc1c(-c2cncn2C)cccc1[C@H](Nc1cc(Cl)c2ncc(C#N)c(NCC(C)(C)C)c2c1)c1cn(C2(C(F)F)CC2)nn1] |
| 1123 | 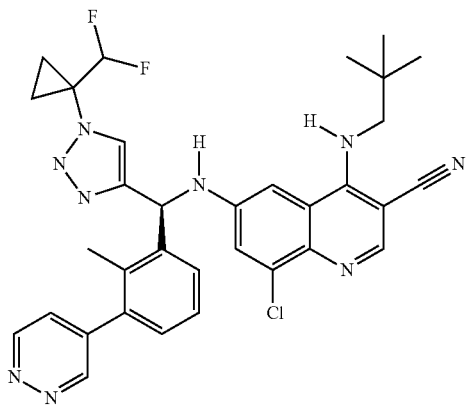 [SMILES: Cc1c(-c2ccnnc2)cccc1[C@H](Nc1cc(Cl)c2ncc(C#N)c(NCC(C)(C)C)c2c1)C1=CN(C2(C(F)F)CC2)NN1] |
| 1124 | 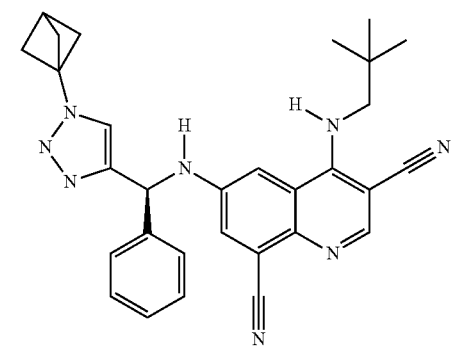 [SMILES: CC(C)(C)CNc1c(C#N)cnc2c(C#N)cc(N[C@H](C3=CN(C45CC(C4)C5)NN3)c3ccccc3)cc12] |

TABLE 1-continued

| Compound | Structure |
|---|---|
| 1125 | |
| 1126 | |
| 1127 | |
| 1128 | |

TABLE 1-continued

| Compound | Structure |
|---|---|
| 1129 | |
| 1130 | |
| 1131 | |
| 1132 | |

TABLE 1-continued

| Compound | Structure |
|---|---|
| 1133 | |
| 1134 | |
| 1135 | |
| 1136 | |

TABLE 1-continued
| Compound | Structure |
|---|---|
| 1137 | 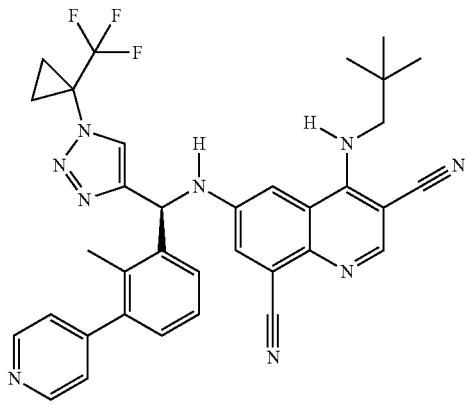 [SMILES: Cc1c(-c2ccncc2)cccc1[C@H](Nc1cc(C#N)c2ncc(C#N)c(NCC(C)(C)C)c2c1)c1cn(C2(C(F)(F)F)CC2)nn1] |
| 1138 | 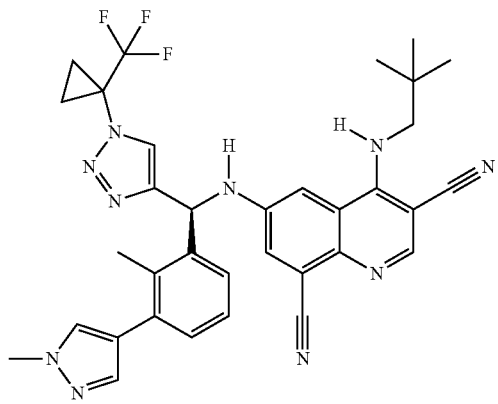 [SMILES: Cc1c(-c2cnn(C)c2)cccc1[C@H](Nc1cc(C#N)c2ncc(C#N)c(NCC(C)(C)C)c2c1)c1cn(C2(C(F)(F)F)CC2)nn1] |
| 1139 | 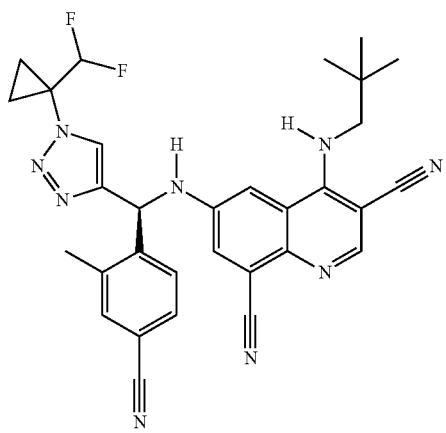 [SMILES: Cc1cc(C#N)ccc1[C@H](Nc1cc(C#N)c2ncc(C#N)c(NCC(C)(C)C)c2c1)c1cn(C2(C(F)F)CC2)nn1] |

TABLE 1-continued

| Compound | Structure |
|---|---|
| 1140 | |
| 1141 | |
| 1142 | |

TABLE 1-continued
| Compound | Structure |
|---|---|
| 1143 | 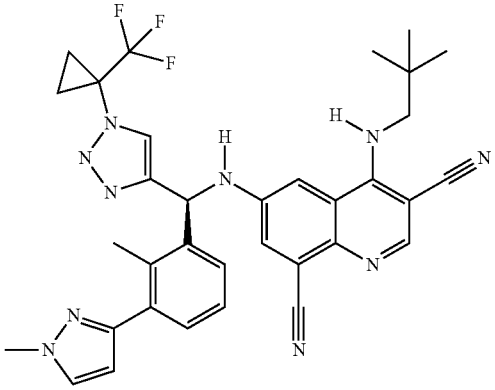 [SMILES: Cc1c(-c2cn(C)cn2)cccc1[C@H](Nc1cc(C#N)c2ncc(C#N)c(NCC(C)(C)C)c2c1)c1cn(C2(C(F)(F)F)CC2)nn1] |
| 1144 | 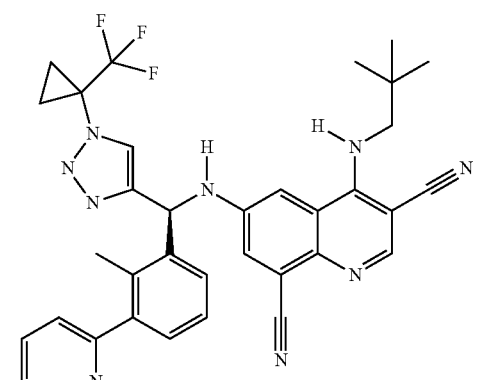 |
| 1145 | 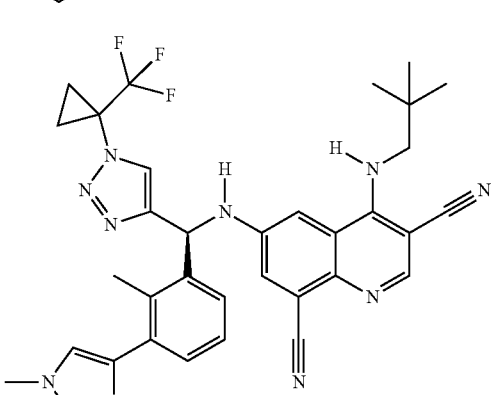 |
| 1146 | 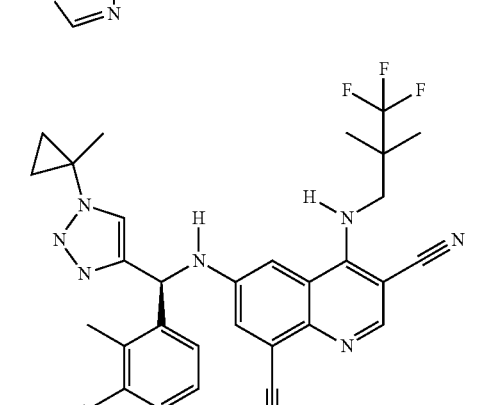 |

TABLE 1-continued

| Compound | Structure |
|---|---|
| 1147 | |
| 1148 | |
| 1149 | |
| 1150 | |

TABLE 1-continued

| Compound | Structure |
|---|---|
| 1151 | |
| 1152 | |
| 1153 | |
| 1154 | |

TABLE 1-continued

| Compound | Structure |
|---|---|
| 1155 | |
| 1156 | |
| 1157 | |
| 1158 | |

TABLE 1-continued

| Compound | Structure |
|---|---|
| 1159 | |
| 1160 | |
| 1161 | |
| 1162 | |

TABLE 1-continued

| Compound | Structure |
|---|---|
| 1163 | |
| 1164 | |
| 1165 | |
| 1166 | |

TABLE 1-continued

| Compound | Structure |
|---|---|
| 1167 | |
| 1168 | |
| 1169 | |
| 1170 | |

31. A composition comprising a compound according to claim 1 and a pharmaceutically acceptable carrier.

32. A composition comprising a mixture of stereoisomers of a compound of Formula I:

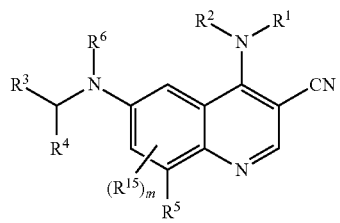

I wherein the mixture comprises compounds of Formula IA and IB in a ratio of at least about 3:1:

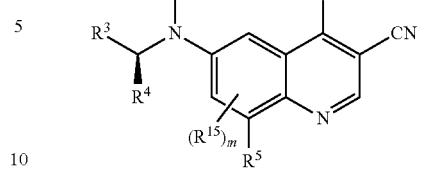

IA

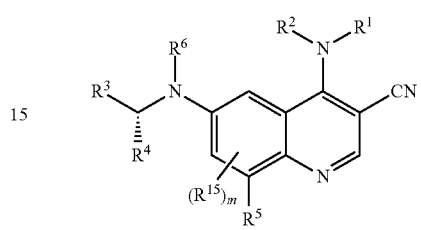

IB wherein m, $R^1$, $R^2$, $R^3$, $R^4$, $R^5$, $R^6$ and $R^{15}$ are as defined in claim 1, or a pharmaceutically acceptable salt thereof.

* * * * *